(12) United States Patent
Oslob et al.

(10) Patent No.: US 9,809,591 B2
(45) Date of Patent: Nov. 7, 2017

(54) HETEROCYCLIC MODULATORS OF LIPID SYNTHESIS

(71) Applicant: 3-V Biosciences, Inc., Menlo Park, CA (US)

(72) Inventors: Johan D. Oslob, Sunnyvale, CA (US); Robert S. McDowell, San Francisco, CA (US); Russell Johnson, San Mateo, CA (US); Hanbiao Yang, Sunnyvale, CA (US); Marc Evanchik, San Jose, CA (US); Cristiana A. Zaharia, Redwood City, CA (US); Haiying Cai, Cupertino, CA (US); Lily W. Hu, Palo Alto, CA (US)

(73) Assignee: 3-V Biosciences, Inc., Menlo Park, CA (US)

( * ) Notice: Subject to any disclaimer, the term of this patent is extended or adjusted under 35 U.S.C. 154(b) by 0 days.

(21) Appl. No.: 14/874,961

(22) Filed: Oct. 5, 2015

(65) Prior Publication Data

US 2016/0102091 A1 Apr. 14, 2016

Related U.S. Application Data

(60) Division of application No. 14/315,133, filed on Jun. 25, 2014, now abandoned, which is a continuation of
(Continued)

(51) Int. Cl.
*C07D 401/10* (2006.01)
*C07D 471/04* (2006.01)
(Continued)

(52) U.S. Cl.
CPC ......... *C07D 471/04* (2013.01); *C07D 401/10* (2013.01); *C07D 401/12* (2013.01);
(Continued)

(58) Field of Classification Search
CPC .. C07D 401/10; C07D 401/12; C07D 401/14; C07D 405/12; C07D 405/14;
(Continued)

(56) References Cited

U.S. PATENT DOCUMENTS 8,871,790 B2  10/2014  Oslob et al.
2008/0103208 A1  5/2008  Ossovskaya et al.
(Continued)

FOREIGN PATENT DOCUMENTS

WO  WO 2007/063012 A1  6/2007
WO  WO 2008/059214 A1  5/2008
(Continued)

OTHER PUBLICATIONS

Improper Markush Fed. Registry, vol. 76(27) p. 7162-75, slide 1, 64-67 (2011).*
(Continued)

*Primary Examiner* — David K O'Dell
(74) *Attorney, Agent, or Firm* — Cooley LLP; J. Dean Farmer

(57) ABSTRACT

Compounds that are fatty acid synthesis modulators are provided. The compounds may be used to treat disorders characterized by disregulation of the fatty acid synthase function by modulating the function and/or the fatty acid synthase pathway. Methods are provided for treating such disorders including viral infections, such as hepatitis C infection, cancer and metabolic disorders.

10 Claims, 1 Drawing Sheet

Related U.S. Application Data application No. 13/415,660, filed on Mar. 8, 2012, now Pat. No. 8,871,790.

(60) Provisional application No. 61/585,642, filed on Jan. 11, 2012, provisional application No. 61/508,611, filed on Jul. 16, 2011, provisional application No. 61/450,561, filed on Mar. 8, 2011.

(51) Int. Cl.

| | |
|---|---|
| *C07D 491/052* | (2006.01) |
| *C07D 405/14* | (2006.01) |
| *C07D 401/12* | (2006.01) |
| *C07D 401/14* | (2006.01) |
| *C07D 405/12* | (2006.01) |
| *C07D 491/107* | (2006.01) |
| *C07D 513/04* | (2006.01) |

(52) U.S. Cl.
CPC ......... *C07D 401/14* (2013.01); *C07D 405/12* (2013.01); *C07D 405/14* (2013.01); *C07D 491/052* (2013.01); *C07D 491/107* (2013.01); *C07D 513/04* (2013.01)

(58) Field of Classification Search
CPC  C07D 471/04; C07D 491/52; C07D 491/107; C07D 513/04
USPC ........ 514/210.21, 215, 217.04, 234.2, 235.5, 514/252.03, 253.04, 303, 321, 322, 326; 540/593, 597; 544/127, 130, 238, 331, 544/362; 546/118, 198, 199, 207, 210, 546/214
See application file for complete search history.

(56) References Cited

U.S. PATENT DOCUMENTS

| | | | |
|---|---|---|---|
| 2009/0105305 A1 | 4/2009 | Butlin et al. | |
| 2009/0118332 A1 | 5/2009 | Butlin et al. | |
| 2012/0264737 A1 | 10/2012 | Oslob et al. | |
| 2014/0322355 A1 | 10/2014 | Oslob et al. | |
| 2015/0259292 A1 | 9/2015 | Oslob et al. | |

FOREIGN PATENT DOCUMENTS

| | | |
|---|---|---|
| WO | WO 2008/075064 A1 | 6/2008 |
| WO | WO 2008/075077 A1 | 6/2008 |
| WO | WO 2012/122391 A1 | 9/2012 |
| WO | WO 2014/008197 A1 | 1/2014 |
| WO | WO2014008197 * | 1/2014 |

OTHER PUBLICATIONS

Acton, A., *Multiple Myeloma: New Insights for the Healthcare Professional*, p. 71 (2013).

Appel, L. et al., "Combination Therapy," Healthcommunities.com (Jul. 16, 2013).

Bentzien, J. M., et al., "Pyrrolidinyl and piperidinyl compounds useful as NHE-1 inhibitors and their preparation and pharmaceutical compositions," *CAPLUS* 152:144485, 2010.

Colombo, P. et al., "Novel Platforms for Oral Drug Delivery," *Pharmaceut. Res.*, vol. 26, No. 3, 602-611, 2009.

Cui, J. J., "Preparation of aminoheteroaryl compounds as protein kinase inhibitors," *CAPLUS* 141:260769, 2004.

Knust, H. et al., "Preparation of piperidine derivatives as NK-3 receptor antagonists," *CAPLUS* 153:456481, 2010.

Menet, C. J. M., et al., "Novel triazolopyridine compounds as JAK kinase inhibitors useful for the treatment of degenerative and inflammatory diseases and their preparation," *CAPLUS* 152:192130, 2010.

Rodon, J. et al., "Combining Targeted Therapies: Practical Issues to Consider at the Bench and Bedside", *The Oncologist*, vol. 15, p. 37-50, (2010).

Schneider, S. et al., "Preparation of 5-alkynyl-pyrimidines as kinase inhibitors," *CAPLUS* 155:271283, 2011.

* cited by examiner

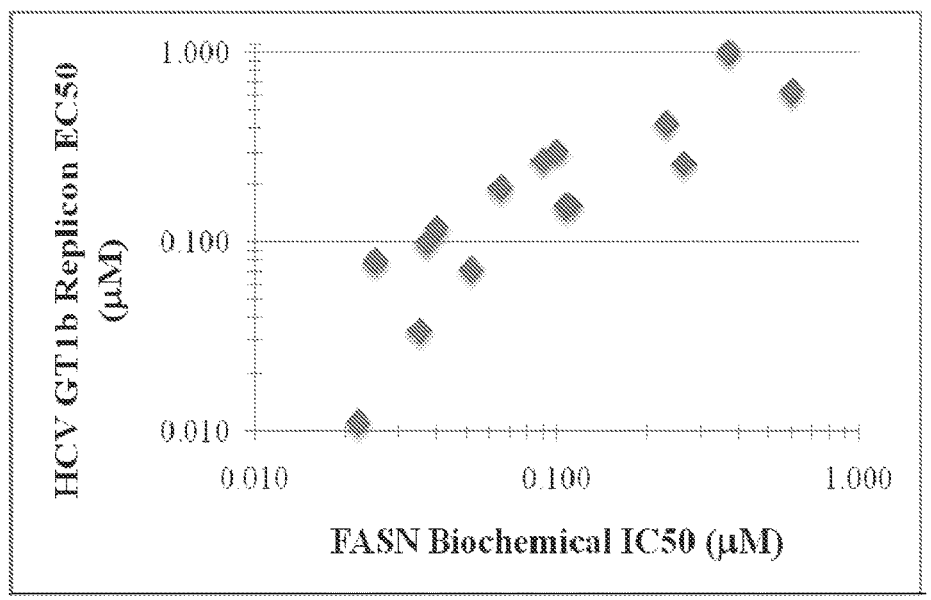

HETEROCYCLIC MODULATORS OF LIPID SYNTHESIS

RELATED APPLICATIONS

This application is a division of U.S. patent application Ser. No. 14/315,133, filed Jun. 25, 2014, which is a continuation of U.S. patent application Ser. No. 13/415,660, filed Mar. 8, 2012, now U.S. Pat. No. 8,871,790, which application claims the benefit of the earlier filed U.S. Application No. 61/450,561 filed Mar. 8, 2011, U.S. Application No. 61/508,611 filed Jul. 16, 2011 and U.S. Application 61/585,642 filed on Jan. 11, 2012, which applications are incorporated herein by reference in their entirety for all purposes.

FIELD

The present disclosure relates generally to heterocyclic modulators of lipid synthesis and methods of use thereof. The present heterocyclic modulators of lipid synthesis can be used for the treatment of disorders characterized by disregulation in the fatty acid synthase function in a subject by modulating the fatty acid synthase pathway and/or the fatty acid synthase function.

BACKGROUND

Viral disease is a significant health concern that threatens large segments of human populations. Some of the features related to viral infection which are of concern to health care professionals include its highly contagious nature (e.g., HIV, SARS, etc.) and high mutability. Some viruses are also oncogenic (such as HPV, EBV and HBV). While viruses are structurally amongst the simplest of organisms, they are regarded to be among the most difficult to control and present a formidable challenge for antiviral drug R&D.

Thus far, there have been a few antiviral drugs widely used in patients, such as Amantadine and Oseltamivir for influenza, Acyclovir for HSV-related infections, Ganciclovir for CMV infection, and multiple agents including co-formulated drugs (Efavirenz, emtricitabine, and tonfovir disoproxil fumarate) for AIDS treatments. These drugs possess a variety of undesirable neurological, metabolic and immunological side-effects. Therefore, development of new antiviral therapy has become a major focus of medical and pharmaceutical research and development.

Infection by hepatitis C virus (HCV) is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves combination therapy with interferon-alpha and ribavirin, often with the addition of a direct-acting protease inhibitor (Telaprevir or Boceprevir). The treatment is cumbersome and sometimes has debilitating and severe side effects. For this reason, many patients are not treated in early stages of the disease. Additionally, some patient populations do not durably respond to treatment. New and effective methods of treating HCV infection are urgently needed.

The dominant therapeutic approaches that are currently employed to treat cancer include surgical removal of primary tumors, tumor irradiation, and parenteral application of anti-mitotic cytotoxic agents. Unfortunately, only a relatively small cross-section of cancer patients have tumors that are "addicted" to a specific pathway, and can therefore be treated with newer targeted agents. The continued dominance of these long established therapies is mirrored by the lack of improvement in survival rates for most cancers. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established. Improved methods for the treatment of cancer are needed.

SUMMARY

The present disclosure addresses the deficiencies for antiviral and anticancer treatments by providing novel heterocyclic modulators of lipid synthesis having improved antiviral and anticancer activities.

In various aspects, the present disclosure provides for compounds of Structure (I):

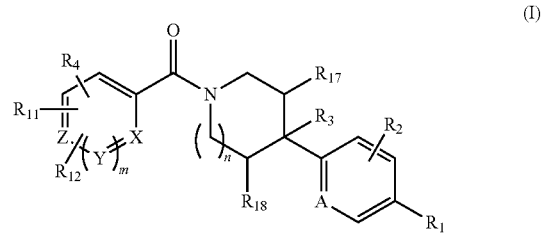

(I)

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and R$_{12}$ taken together with the atoms to which they are attached join together to form a heteroaryl;

R$_5$, R$_6$, R$_7$, R$_8$, R$_9$R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

n is 1 or 2; and m is 0 or 1.

In various aspects, the present disclosure provides for compounds of Structure (II):

(II)

or a pharmaceutically acceptable salt thereof, wherein:

X, Y, and Z are each independently CR or NR', wherein R is hydrogen or C$_{1-6}$ alkyl and R' is hydrogen, C$_{1-6}$ alkyl, or absent;

L and D are each independently C or N;

R$_1$ is hydrogen, cyano, halo, C$_{1-6}$ alkyl, C$_{1-6}$ alkoxy, —C(=O)N(R$_{13}$)(R$_{14}$), —(CH$_2$)$_q$C(=O)N(R$_{13}$)(R$_{14}$), CF$_3$, —OCF$_3$, or —S(=O)$_2$R$_{20}$;

q is 0, 1, 2, 3, or 4;

R$_{20}$ is hydrogen or C$_{1-6}$ alkyl, C$_{1-6}$ alkoxy, or —N(R$_{13}$R$_{14}$);

R$_2$ is hydrogen, halo, C$_{1-6}$ alkoxy, C$_{1-6}$ alkyl, or R$_2$ and R$_3$ taken together with the atoms to which they are attached form a 5 membered heterocyclyl;

R$_3$ is hydrogen, hydroxyl, halo, C$_{1-6}$ alkyl, C$_{1-6}$ alkoxy, or R$_2$ and R$_3$ taken together with the atoms to which they are attached form a 5-membered heterocyclyl;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, R$_4$ and R$_{11}$ taken together with the atoms to which they are attached join together to form a heteroaryl, or R$_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_5$, R$_6$, R$_7$, R$_8$, R$_9$R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

n is 1 or 2; and m is 0 or 1.

In various aspects, the present disclosure provides for compounds of Structure (III):

(III)

or a pharmaceutically acceptable salt thereof, wherein:

X, Y, and Z are each independently CR or NR', wherein R is hydrogen or C$_{1-6}$ alkyl and R' is hydrogen, C$_{1-6}$ alkyl, or absent;

Q is C or N;

R$_3$ is hydrogen, hydroxyl, halo, C$_{1-6}$ alkyl, C$_{1-6}$ alkoxy, or if Q is N then R$_3$ is absent;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, R$_4$ and R$_{11}$ taken together with the atoms to which they are attached join together to form a heteroaryl, or R$_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_{20}$ is hydrogen or C$_{1-6}$ alkyl, C$_{1-6}$ alkoxy, or —N(R$_{13}$)(R$_{14}$);

R$_5$, R$_6$, R$_7$, R$_8$, R$_9$R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino;

R$_{17}$ and R$_{18}$ are each independently hydrogen or alkyl or can optionally join together to form a bond;

R$_{19}$ is aryl, heteroaryl, cycloalkyl, or heterocyclyl;

n is 0, 1, or 2; and m is 0 or 1.

In various aspects, the present disclosure provides for compounds of Structures (IV-A), (IV-B), or (IV-C):

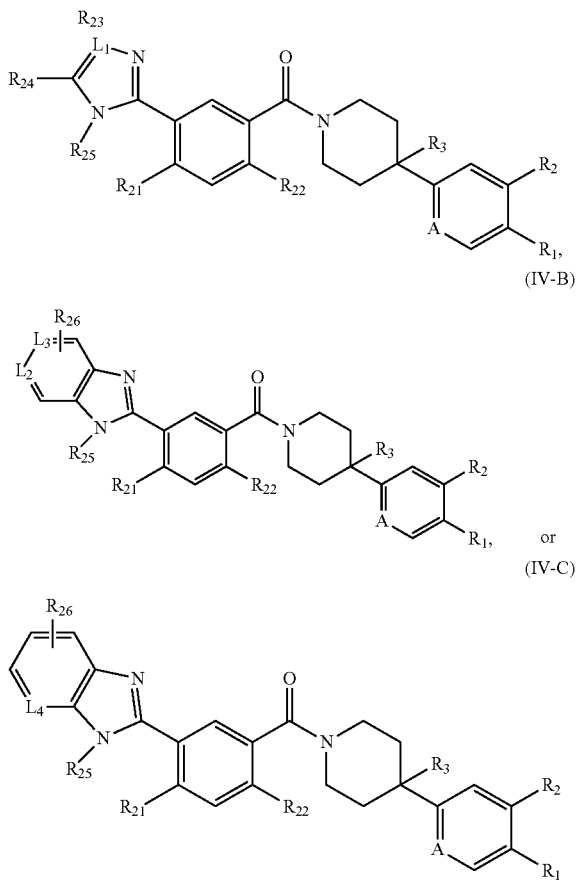

or a pharmaceutically acceptable salt thereof, wherein:
$L_1$, $L_2$, $L_3$, $L_4$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{23}$ is hydrogen, —N($R_{13}$)($R_{14}$), $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;
$R_{24}$ is hydrogen, —N($R_{13}$)($R_{14}$), $C_{1-6}$ alkyl, $C_{1-6}$ alkoxy, —($C_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl;
$R_{26}$ is hydrogen, heteroaryl, heterocycyl, —N($R_{13}$)($R_{14}$), or —S(=O)$_2$R$_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{25}$ is hydrogen, $C_{1-6}$ alkyl, or $C_{1-6}$ alkoxy; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In various aspects, the present disclosure provides for compounds of Structure (V):

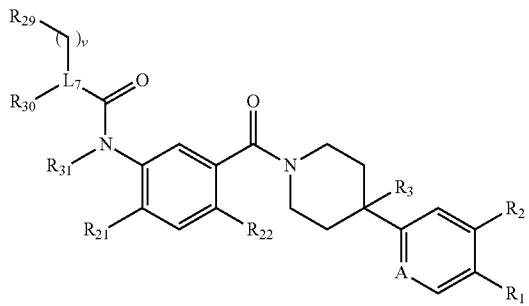

or a pharmaceutically acceptable salt thereof, wherein:
$L_7$ is N or O, wherein $R_{30}$ is absent if $L_7$ is O;
A is CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{29}$ and $R_{30}$ are each independently hydrogen, $C_{1-6}$ alkyl, $C_{1-6}$ alkoxy, hydroxyalkyl, heteroaryl, heterocyclyl, —N($R_{15}R_{16}$), —C(=O)R$_{46}$, —R$_{48}$C(=O)R$_{47}$, or $R_{29}$ and $R_{30}$ taken together with the atoms to which they are attached join together to form a heteroaryl or heterocyclyl, wherein $R_{30}$ is absent if $L_7$ is O;
$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;
$R_{48}$ is alkyl or is absent;
$R_{31}$ is hydrogen, $C_{1-6}$ alkyl, or $C_{1-6}$ alkoxy;
$R_{13}$ and $R_{14}$ are, each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, cycloalkyl, aryl, heterocyclyl, heteroaryl, hydroxyalkyl, or alkylamino; and
v is 0 or 1.

In various aspects, the present disclosure provides for compounds of Structures (VI-A) or (VI-B):

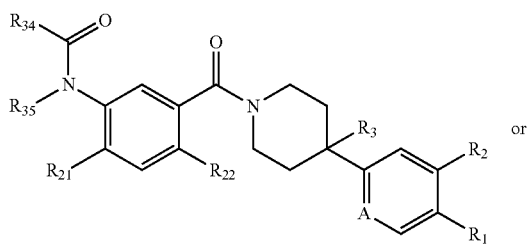

-continued (VI-B)

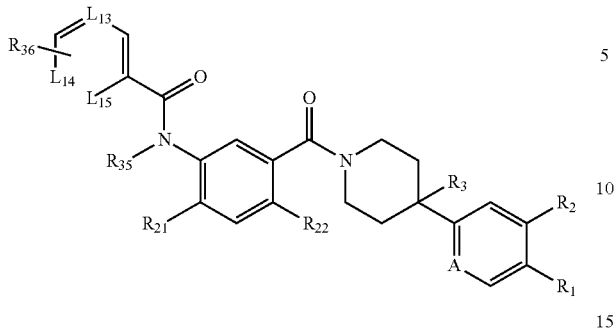

or a pharmaceutically acceptable salt thereof, wherein:
$L_{13}$, $L_{14}$, $L_{15}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, CF$_3$, —OCF$_3$, —S(=O)$_2$R$_{20}$, or —N($R_{15}R_{16}$);
$R_{35}$ is hydrogen; $C_{1-6}$ alkyl, or $C_{1-6}$ alkoxy;
$R_{36}$ is hydrogen, $C_{1-6}$ alkyl, $C_{1-6}$ alkoxy, —N($R_{15}R_{16}$), heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In various aspects, the present disclosure provides for compounds of Structure (VI-J):

(VI-J)

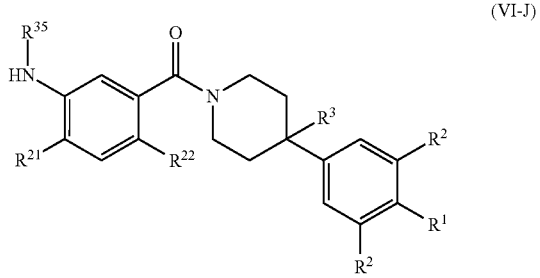

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
the $C_3$-$C_5$ cycloalkyl optionally includes an oxygen or nitrogen heteroatom; and when $R^1$ is not H, —CN or halogen, it is optionally substituted with one or more halogens;
each $R^2$ is independently H, halogen or $C_1$-$C_4$ straight or branched alkyl;
$R^3$ is H, —OH, or halogen;
$R^{21}$ is cyclobutyl, azetidin-1-yl, or cyclopropyl;
$R^{22}$ is H, halogen, or $C_1$-$C_2$ alkyl;
$R^{35}$ is —C(O)—R$^{351}$, —C(O)—NHR$^{351}$, —C(O)—O—R$^{351}$ or S(O)$_2$R$^{351}$; and
$R^{351}$ is $C_1$-$C_6$ straight or branched alkyl, cycloalkyl, heterocyclyl, aryl or heteroaryl.

In some aspects of Structure (VI-J), $R^3$ is H or halogen.
In some aspects of Structure (VI-J), $R^1$ is halogen, —CN or $C_1$-$C_2$ haloalkyl.
In some aspects of Structure (VI-J), $R^{22}$ is $C_1$-$C_2$ alkyl.
In some aspects of Structure (VI-J), $R^{21}$ is cyclobutyl and $R^{22}$ is $C_1$-$C_2$ alkyl.
In some aspects of Structure (VI-J), $R^{21}$ is cyclobutyl.
In some aspects of Structure (VI-J), $R^3$ is H or F.
In some aspects of Structure (VI-J), $R^1$ is —CN.
In some aspects of Structure (VI-J), $R^1$ is —CF$_3$.
In some aspects of Structure (VI-J), $R^{22}$ is H, methyl or ethyl.
In some aspects of Structure (VI-J), $R^{22}$ is H.
In some aspects of Structure (VI-J), $R^{22}$ is methyl.
In some aspects of Structure (VI-J), $R^{35}$ is —C(O)—NHR$^{351}$.
In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or (S)-tetrahydro-2H-pyran-3-yl.
In some aspects of Structure (VI-J), $R^{351}$ is (R)-(tetrahydrofuran-2-yl)methyl or (S)-(tetrahydrofuran-2-yl)methyl.
In some aspects of Structure (VI-J), $R^1$ is —CN, each $R^2$ is hydrogen, $R^3$ is H or F, $R^{21}$ is $C_3$-$C_4$ cycloalkyl, $R^{22}$ is H, $R^{35}$ is —C(O)—NHR$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.
In some aspects of Structure (VI-J), $R^{35}$ is —C(O)—O—R$^{351}$.
In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.
In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—R$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.
In some aspects of Structure (VI-J), $R^{351}$ is (R)-3-tetrahydrofuranyl or (S)-3-tetrahydrofuranyl.
In some aspects of Structure (VI-J), compounds have a structure selected from the group consisting of:

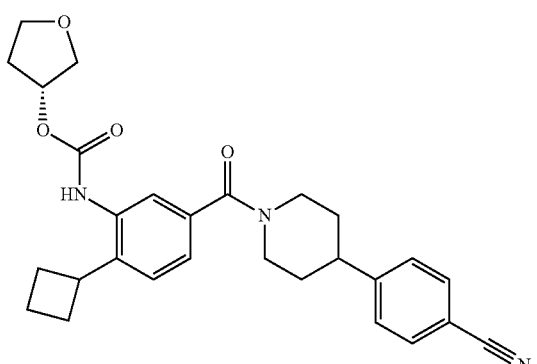
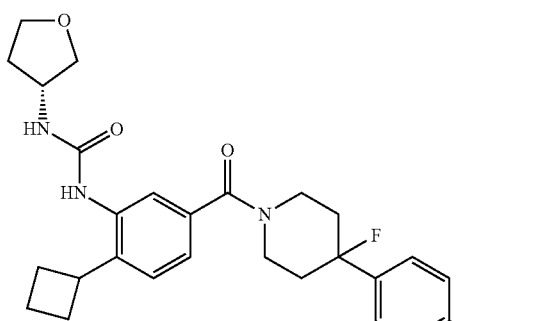
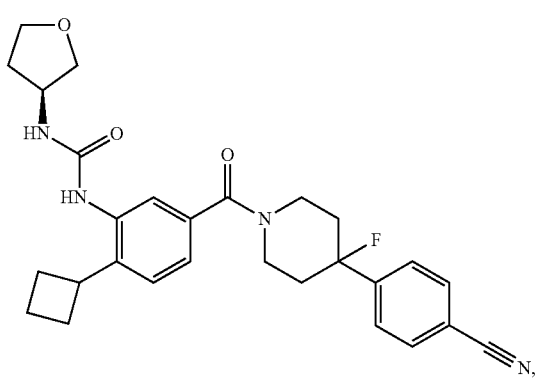
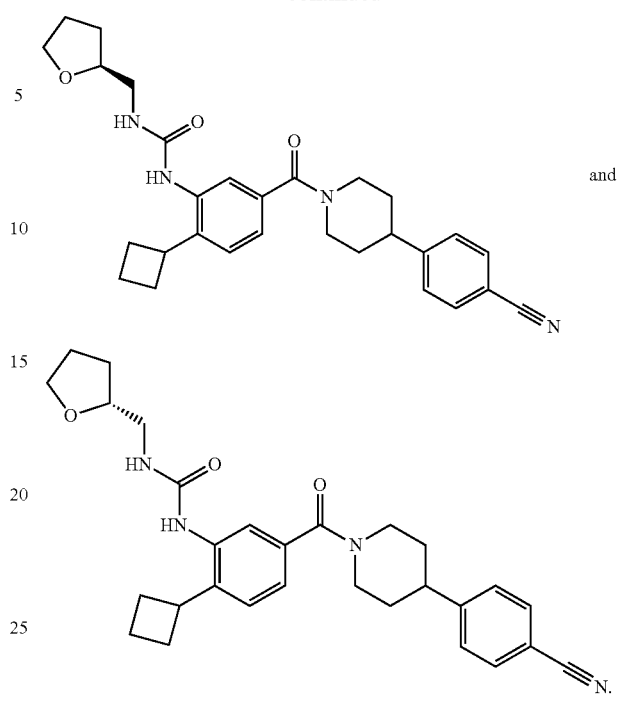
In various aspects, the present disclosure provides for compounds of Structures (VII-A) or (VII-B):
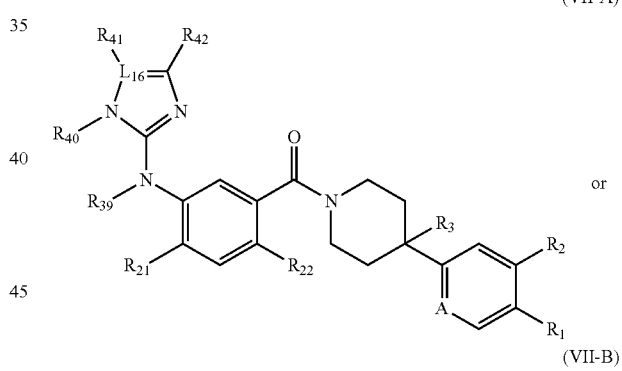
(VII-A)
(VII-B)
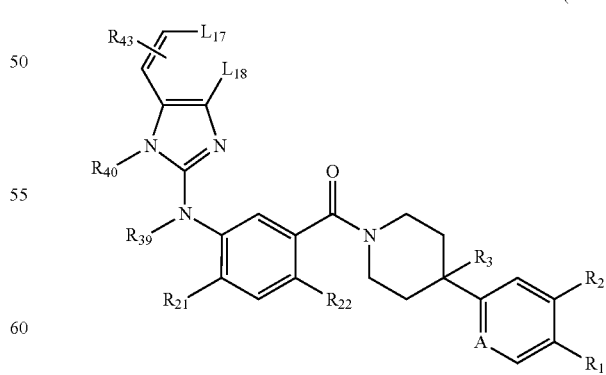
or a pharmaceutically acceptable salt thereof, wherein:
$L_{16}$ is C or N, wherein $R_{41}$ is absent if $L_{16}$ is N;
$L_{17}$, $L_{18}$, and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{40}$, $R_{42}$, and $R_{43}$ are each independently hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), or $R_{41}$ and $R_{42}$ taken together with the atoms to which they are attached join together to form a heteroaryl or heterocyclyl;

$R_{41}$ is hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), $R_{41}$ is absent if $L_{16}$ is N, or $R_{41}$ and $R_{42}$ taken together with the atoms to which they are attached join together to form a heteroaryl or heterocyclyl;

R is hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{39}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In various aspects, the present disclosure provides for compounds of Structures (VIII-A), (VIII-B), or (VIII-C):

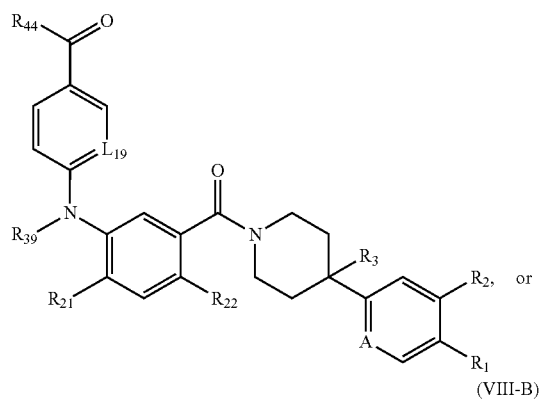

(VIII-A)

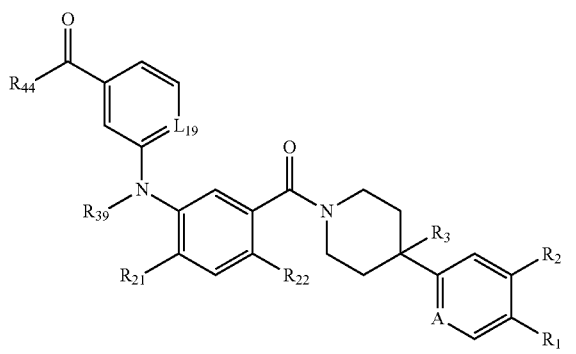

(VIII-B)

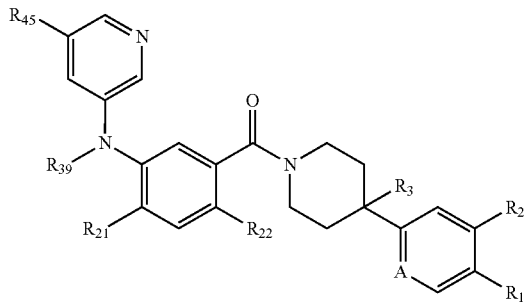

(VIII-C)

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(=O)$_2$R$_{20}$, —C(=O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In various aspects, compounds of Structure (IX) are provided:

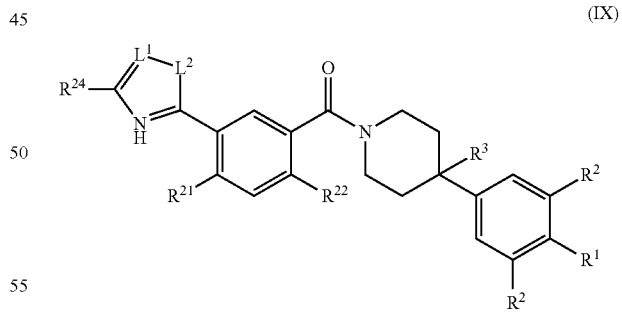

(IX)

or a pharmaceutically acceptable salt thereof, wherein:

$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:

$C_3$-$C_5$ cycloalkyl optionally includes an oxygen or nitrogen heteroatom; and when $R^1$ is not H, —CN or halogen, it is optionally substituted with one or more halogens;

each $R^2$ is independently hydrogen, halogen or $C_1$-$C_4$ straight or branched alkyl;

R³ is H, —OH, or halogen;
R²¹ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;
R²² is H, halogen, or $C_1$-$C_2$ alkyl;
R²⁴ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
  t is 0 or 1;
  the $C_3$-$C_5$ cycloalkyl optionally includes an oxygen or nitrogen heteroatom;
L¹ is CR²³ or N;
L² is CH or N;
at least one of L¹ or L² is N; and
R²³ is H or $C_1$-$C_4$ straight or branched alkyl.

In some aspects of Structure (IX), R²⁴ is $C_1$-$C_4$ straight or branched alkyl or —($C_1$-$C_4$ alkyl)$_t$-O—($C_1$-$C_4$ straight or branched alkyl) wherein t is 0 or 1.

In some aspects of Structure (IX), R²¹ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some aspects of Structure (IX), R³ is H or halogen.
In some aspects of Structure (IX), R¹ is halogen, —CN or $C_1$-$C_2$ haloalkyl.
In some aspects of Structure (IX), both L¹ and L² are N.
In some aspects of Structure (IX), R²¹ is $C_1$-$C_2$ alkyl or $C_3$-$C_5$ cycloalkyl and R²² is $C_1$-$C_2$ alkyl.
In some aspects of Structure (IX), R²¹ is $C_3$-$C_5$ cycloalkyl and R²² is $C_1$-$C_2$ alkyl.
In some aspects of Structure (IX), R²⁴ is —($C_1$-$C_2$ alkyl)$_t$-O—($C_1$-$C_2$ alkyl) wherein t is 0 or 1.
In some aspects of Structure (IX), R²¹ is $C_3$-$C_5$ cycloalkyl, R²² is $C_1$-$C_2$ alkyl and R²⁴ is $C_1$-$C_2$ alkyl.
In some aspects of Structure (IX), R²¹ is cyclobutyl, R²² is $C_1$-$C_2$ alkyl and R²⁴ is $C_1$-$C_2$ alkyl.
In some aspects of Structure (IX), R²¹ is cyclobutyl.
In some aspects of Structure (IX), R³ is H or F.
In some aspects of Structure (IX), R¹ is —CN.
In some aspects of Structure (IX), R¹ is —CF₃.
In some aspects of Structure (IX), R²² is H, methyl or ethyl.
In some aspects of Structure (IX), R²² is H.
In some aspects of Structure (IX), R²² is methyl.
In some aspects of Structure (IX), R¹ is —CN, each R² is H, R³ is H or F, R²¹ is $C_3$-$C_4$ cycloalkyl, R²² is methyl, L¹ and L² are N, and R²⁴ is methyl, ethyl, hydroxymethyl, methoxymethyl, 2-methoxyethyl.
In some aspects of Structure (IX), R¹ is —CN, each R² is H, R³ is H or F, R²¹ is $C_3$-$C_4$ cycloalkyl, R²² is methyl, L¹ and L² are N, and R²⁴ is methoxy or ethoxy.
In some aspects of Structure (IX), R¹ is —CN, each R² is H, R³ is H or F, R²¹ is $C_3$-$C_4$ cycloalkyl, R²² is methyl, L¹ is CH, L² is N, and R²⁴ is methyl, ethyl, hydroxymethyl, methoxymethyl, or 2-methoxyethyl.
In some aspects of Structure (IX), R¹ is —CN, each R² is H, R³ is H or F, R²¹ is $C_3$-$C_4$ cycloalkyl, R²² is methyl, L¹ is N, L² is CH, and R²⁴ is methyl, ethyl, hydroxymethyl, methoxymethyl, or 2-methoxyethyl.
In some aspects of Structure (IX), compounds have a structure selected from the group consisting of:

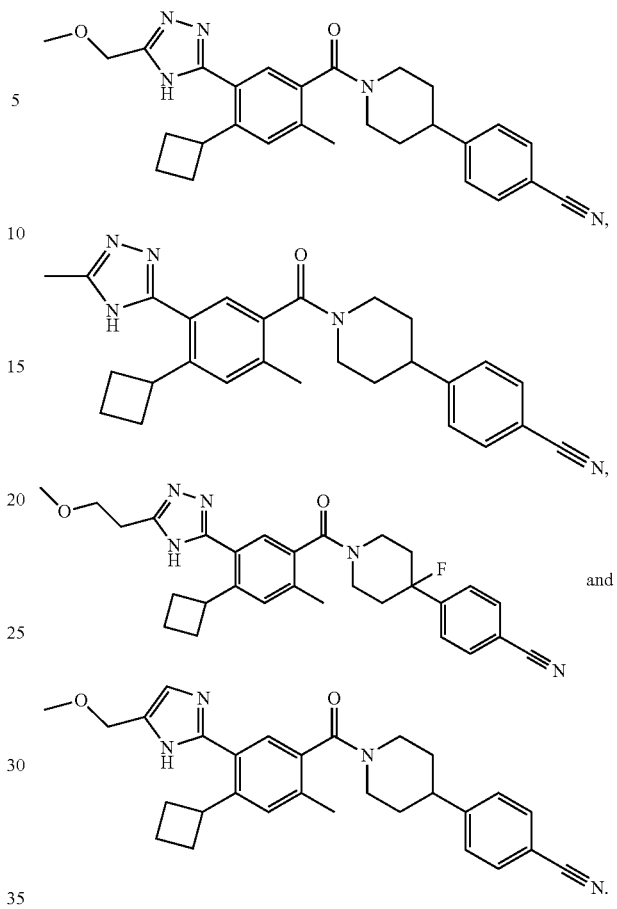

In various aspects, compounds of Structure (X) are provided:

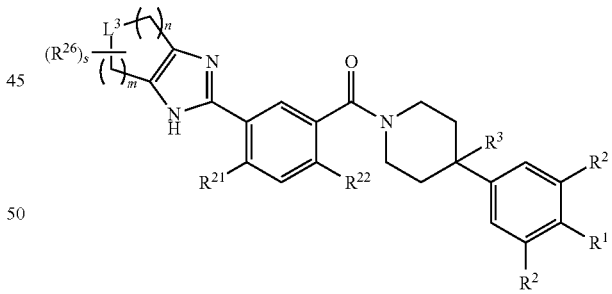

X or a pharmaceutically acceptable salt thereof, wherein:
R¹ is H, —CN, halogen, $C_1$-$C_4$ straight or branched alkyl, —O—($C_3$-$C_5$ cycloalkyl), —O—($C_1$-$C_4$ straight or branched alkyl) wherein:
  the $C_3$-$C_5$ cycloalkyl optionally includes an oxygen or nitrogen heteroatom; and
  when R¹ is not H, —CN or halogen, it is optionally substituted with one or more halogens;
each R² is independently hydrogen, halogen or $C_1$-$C_4$ straight or branched alkyl;
R³ is H, —OH or halogen;
L³ is C(R⁶⁰)₂, O or NR⁵⁰;

each $R^{60}$ is independently H, —OH, —CN, —O$_t$—(C$_3$-C$_5$ cycloalkyl), —O—(C$_1$-C$_4$ straight or branched alkyl), or —C(O)—N(R$^{601}$)$_2$ wherein:
  t is 0 or 1, and
  the C$_3$-C$_5$ cycloalkyl optionally includes an oxygen or nitrogen heteroatom;
each $R^{50}$ is independently H, —C(O)—O$_t$—(C$_1$-C$_4$ straight or branched alkyl), —C(O)—O$_t$—(C$_3$-C$_5$ cyclic alkyl), —C$_3$-C$_5$ cyclic alkyl optionally containing an oxygen or nitrogen heteroatom, —C(O)—N(R$^{501}$)$_2$, C$_1$-C$_4$ straight or branched alkyl wherein:
  t is 0 or 1, and
  the C$_3$-C$_5$ cycloalkyl optionally includes an oxygen or nitrogen heteroatom;
n is 1, 2 or 3;
m is 1 or 2;
$R^{21}$ is H, halogen, C$_1$-C$_4$ straight or branched alkyl, C$_3$-C$_5$ cycloalkyl wherein the C$_3$-C$_5$ cycloalkyl optionally includes an oxygen or nitrogen heteroatom
$R^{22}$ is H, halogen, C$_1$-C$_2$ alkyl;
each $R^{26}$ is independently —OH, —CN, halogen, C$_1$-C$_4$ straight or branched alkyl, —(C$_1$-C$_4$ alkyl)$_t$-O$_t$—(C$_3$-C$_5$ cycloalkyl), —(C$_1$-C$_4$ alkyl)$_t$-O—(C$_1$-C$_4$ straight or branched alkyl), —C(O)—O$_t$—(C$_1$-C$_4$ alkyl), or —C(O)—N(R$^{501}$)$_2$ wherein:
  t is 0 or 1, and
  the C$_3$-C$_5$ cycloalkyl optionally includes an oxygen or nitrogen heteroatom;
s is 0, 1 or 2;
each $R^{601}$ and $R^{501}$ is independently H or C$_1$-C$_4$ straight or branched alkyl; and
wherein two of $R^{26}$, $R^{60}$, $R^{50}$, $R^{501}$ and $R^{601}$ optionally join to form a ring wherein the two of $R^{26}$, $R^{60}$, $R^{50}$, $R^{501}$ and $R^{601}$ may be two $R^{26}$, two $R^{60}$, two $R^{50}$, two $R^{501}$ or two $R^{601}$.

In some aspects of Structure (X), $R^{21}$ is halogen, C$_1$-C$_4$ straight or branched alkyl or C$_3$-C$_5$ cycloalkyl.
In some aspects of Structure (X), $R^3$ is H or halogen.
In some aspects of Structure (X), $R^1$ is —CN or C$_1$-C$_2$ haloalkyl.
In some aspects of Structure (X), $R^3$ is H or F.
In some aspects of Structure (X), $R^1$ is —CN.
In some aspects of Structure (X), $R^1$ is —CF$_3$.
In some aspects of Structure (X), n is 1.
In some aspects of Structure (X), n is 2.
In some aspects of Structure (X), m is 1
In some aspects of Structure (X), m is 2.
In some aspects of Structure (X), $R^{21}$ is C$_1$-C$_2$ alkyl or C$_3$-C$_5$ cycloalkyl and $R^{22}$ is C$_1$-C$_2$ alkyl.
In some aspects of Structure (X), $R^{21}$ is C$_3$-C$_5$ cycloalkyl and $R^{22}$ is C$_1$-C$_2$ alkyl.
In some aspects of Structure (X), n is 2, m is 1, $L^3$ is —N—C(O)—O—(C$_1$-C$_2$ alkyl).
In some aspects of Structure (X), $L^3$ is NR$^{50}$; $R^{50}$ is C$_1$-C$_2$ alkyl; $R^{21}$ is cyclobutyl; $R^{22}$ is H or methyl; $R^3$ is H; $R^1$ is —CN; m is 2 and n is 1 or 2.
In some aspects of Structure (X), n is 2, m is 1, $L^3$ is O and s is 0.
In some aspects of Structure (X), $R^{22}$ is H, methyl or ethyl.
In some aspects of Structure (X), $R^{22}$ is methyl.
In some aspects of Structure (X), $R^{22}$ is H.
In some aspects of Structure (X), $R^1$ is —CN, each $R^2$ is H, $R^3$ is H or F, $R^{21}$ is C$_3$-C$_4$ cycloalkyl, $R^{22}$ is methyl, n is 2 and $L^3$ is NR$^{50}$ where $R^{50}$ is methyl or ethyl.

In some aspects of Structure (X), $R^1$ is —CN, each $R^2$ is H, $R^3$ is H or F, $R^{21}$ is C$_3$-C$_4$ cycloalkyl, $R^{22}$ is methyl, n is 2 and $L^3$ is O.

In some aspects of Structure (X), the compound has a structure selected from the group consisting of:

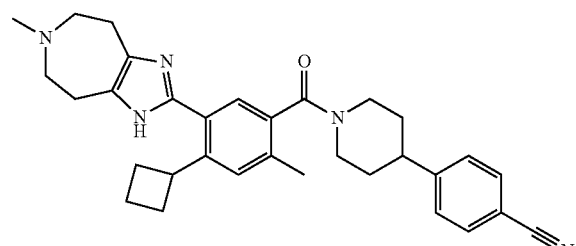

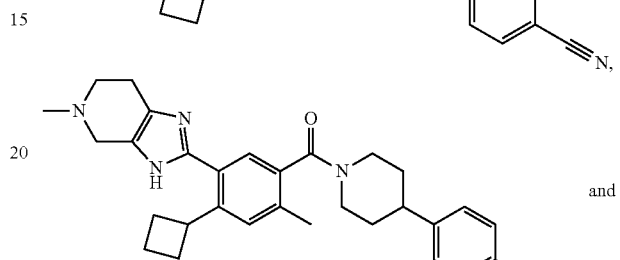

and

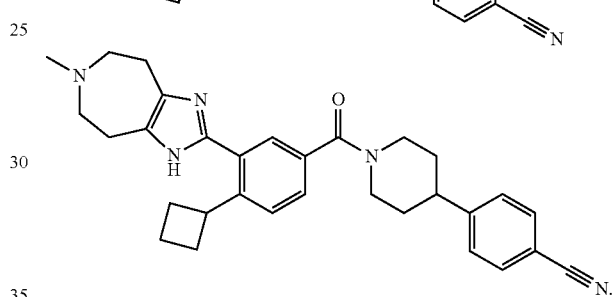

In various aspects, compounds of Structure (XI) are provided:

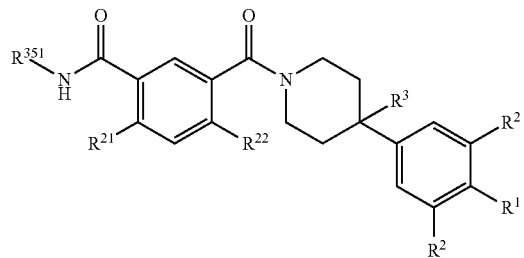

(XI)

or a pharmaceutically acceptable salt thereof, wherein:
  $R^1$ is H, —CN, halogen, C$_1$-C$_4$ straight or branched alkyl, —O—(C$_3$-C$_5$ cycloalkyl), —O—(C$_1$-C$_4$ straight or branched alkyl) wherein:
    the C$_3$-C$_5$ cycloalkyl optionally includes an oxygen or nitrogen heteroatom; and
    when $R^1$ is not H, —CN or halogen, it is optionally substituted with one or more halogens;
  each $R^2$ is independently H, halogen or C$_1$-C$_4$ straight or branched alkyl;
  $R^3$ is H, —OH, or halogen;
  $R^{21}$ is cyclobutyl, azetidin-1-yl, or cyclopropyl;
  $R^{22}$ is halogen, C$_1$-C$_2$ alkyl; and
  $R^{351}$ is C$_1$-C$_2$ alkyl or C$_2$—O—(C$_1$ or C$_2$ alkyl).

17

In some aspects of Structure (XI), $R^3$ is H or halogen.

In some aspects of Structure (XI), $R^1$ is halogen, —CN or $C_1$-$C_2$ haloalkyl.

In some aspects of Structure (XI), $R^{21}$ is $C_3$-$C_4$ cycloalkyl and $R^{22}$ is $C_1$-$C_2$ alkyl.

In some aspects of Structure (XI), $R^{21}$ is cyclobutyl and $R^{22}$ is $C_1$-$C_2$ alkyl.

In some aspects of Structure (XI), $R^{21}$ is cyclobutyl.

In some aspects of Structure (XI), $R^3$ is H or F.

In some aspects of Structure (XI), $R^1$ is —CN.

In some aspects of Structure (XI), $R^1$ is —$CF_3$.

In some aspects of Structure (XI), $R^{22}$ is H, methyl or ethyl.

In some aspects of Structure (XI), $R^{22}$ is H.

In some aspects of Structure (XI), $R^{22}$ is methyl.

In some aspects of Structure (XI), $R^1$ is —CN, each $R^2$ is H, $R^3$ is H or F, $R^{21}$ is cyclobutyl, $R^{22}$ is methyl and $R^{351}$ is methyl or ethyl.

In some aspects of Structure (XI), the compound has a structure selected from the group consisting of:

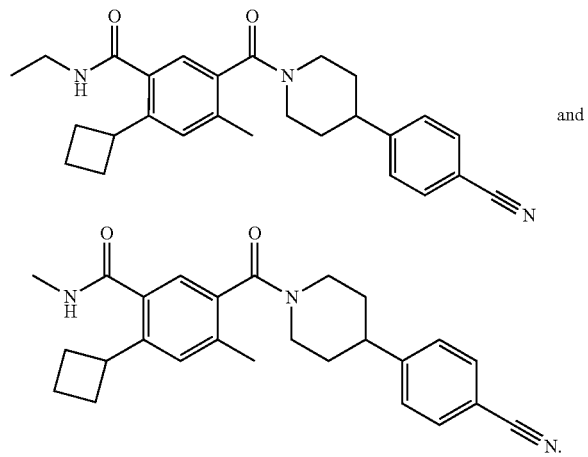

and

In various aspects, the present disclosure provides pharmaceutical compositions comprising any one of the compounds of Structures (I), (II), (III), (IV), (V), (VI), (VII), (VIII), (IX), (X) or (XI) and a pharmaceutically acceptable carrier, excipient, or diluent.

In various aspects, the present disclosure provides methods of treating a condition characterized by disregulation of a fatty acid synthase function in subject, the method comprising administering to the subject in need of such treatment an effective amount of a compound of any one of the Structures (I), (II), (III), (IV), (V), (VI), (VII), (VIII), (IX), (X) or (XI). In various aspects the condition characterized by disregulation of the fatty acid synthase function is a viral infection or cancer. In various aspects the viral infection is treated using a compound of any one of the Structures (I), (II), (III), (IV), (V), (VI), (VII), (VIII), (IX), (X) or (XI) in combination with one or more additional antiviral treatments. In various aspects the cancer is treated using a compound of any one of the Structures (I), (II), (III), (IV), (V), (VI), (VII), (VIII), (IX), (X) or (XI) in combination with one or more additional cancer treatments. In various aspects, the viral infection is hepatitis C.

BRIEF DESCRIPTION OF THE DRAWINGS

FIG. 1 illustrates a correlation between FASN inhibition and HCV inhibition.

18

DETAILED DESCRIPTION

The present disclosure addresses the deficiencies in treating conditions characterized by disregulation of the FASN function in a subject, such as viral infection, cancer and metabolic disorders, by providing novel heterocyclic modulators of lipid synthesis.

In certain aspects, the present disclosure provides compositions and methods for treatment of viral infections. In general, the compositions and methods for treatment of viral infections are directed toward modulation of the fatty acid synthesis pathway. The fatty acid synthesis pathway is involved in the replication of viruses into the host cells. The present invention embodies methods for the treatment of viral infection, such as hepatitis C infections, yellow fever infections, and human rhinovirus infections, or any virus that targets the fatty acid synthesis pathway.

In certain aspects, the present disclosure provides compositions and methods for the treatment of cancer. Fatty acid synthase is responsible for conversion of malonyl-CoA into long-chain fatty acids, which is an early reaction in fatty acid biosynthesis. Fatty acid synthase is overexpressed in many cancer cells. Without being bound by any particular theory, it is hypothesized that inhibition of fatty acid synthase expression or fatty acid synthase activity selectivity suppresses proliferation and induces cell death of cancer cells, with little toxicity towards normal cells.

Further, the present disclosure provides compounds and methods for modulating host cell targets that are targeted by viruses. Such modulation of host cell targets can include either activation or inhibition of the host cell targets. Accordingly, compounds that modulate, e.g., inhibit, the activity of a non-viral protein, e.g., a host cell protein, e.g., components of the fatty acid synthesis pathway, can be used as antiviral pharmaceutical agents.

Definitions

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—$OCH_3$, a $C_1$ alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkoxycarbonyl" refers to a carbonyl group with an alkoxy group as a substituent.

"Alkyl," "alkenyl," and "alkynyl," refer to optionally substituted, straight and branched chain aliphatic groups having from 1 to 30 carbon atoms, or preferably from 1 to 15 carbon atoms, or more preferably from 1 to 6 carbon atoms. Examples of alkyl groups include, without limitation, methyl, ethyl, propyl, isopropyl, butyl, tert-butyl, isobutyl, pentyl, hexyl, vinyl, allyl, isobutenyl, ethynyl, and propynyl. The term "heteroalkyl" as used herein contemplates an alkyl with one or more heteroatoms.

"Alkylene" refers to an optionally substituted divalent radical which is a branched or unbranched hydrocarbon fragment containing the specified number of carbon atoms, and having two points of attachment. An example is propylene [—$CH_2CH_2CH_2$—, a $C_3$alkylene].

"Amino" refers to the group —$NH_2$.

"Aryl" refers to optionally substituted aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Carbamoyl" as used herein contemplates a group of the structure

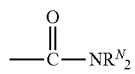

where in $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

"Carbonyl" refers to a group of the structure

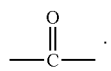

"Cycloalkyl" refers to an optionally substituted ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Heterocycle" refers to an optionally substituted 5- to 7-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to optionally substituted aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, benzothiadiazolyl, and the like.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, none of which are further substituted. Unless otherwise specified, when the substituent is on a nitrogen, it is selected from the group consisting of $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, sulfonyl, sulfonate and sulfonamide none of which are further substituted.

The term "sulfonamide" as used herein contemplates a group having the structure

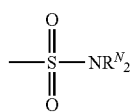

wherein $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide.

The term "sulfonate" as used herein contemplates a group having the structure

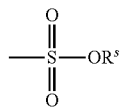

wherein $R^s$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

"Sulfonyl" as used herein alone or as part of another group, refers to an $SO_2$ group. The $SO_2$ moiety is optionally substituted.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

Individual atoms in the disclosed compounds may be any isotope of that element. For example hydrogen may be in the form of deuterium.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "treating" includes the administration of the compounds or agents of the present invention to a subject to prevent or delay, to alleviate, or to arrest or inhibit development of the symptoms or conditions associated with fatty acid synthase-associated disorders, e.g., tumor growth associated with cancer. A skilled medical practitioner will know how to use standard methods to determine whether a patient is suffering from a disease associated with activity of fatty acid synthase, e.g., by examining the patient and determining whether the patient is suffering from a disease known to be associated with fatty acid synthase activity or by assaying for fatty acid synthase levels in blood plasma or tissue of the individual suspected of suffering from fatty acid synthase associated disease and comparing fatty acid synthase levels in the blood plasma or tissue of the individual suspected of suffering from a fatty acid synthase associated disease fatty acid synthase levels in the blood plasma or tissue of a healthy individual. Increased securin levels are indicative of disease. Accordingly, the present invention provides, inter alia, methods of administering a compound of the present invention to a subject and determining fatty acid synthase activity in the subject. Fatty acid synthase activity in the subject can be determined before and/or after administration of the compound.

A "therapeutically effective amount" or "pharmaceutically effective amount" means the amount that, when administered to a subject, produces effects for which it is administered. For example, a "therapeutically effective amount," when administered to a subject to inhibit fatty acid synthase activity, is sufficient to inhibit fatty acid synthase activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

FASN Pathway Modulators

One aspect of the present disclosure includes a method of inhibiting viral infection or treating cancer by contacting a cell with an agent that modulates the fatty acid synthesis pathway. This method of inhibiting viral infection or treating cancer can be performed in vitro by contacting virally infected/cancerous cells with an agent that modulates the fatty acid synthesis pathway, or in vivo by administering an agent that modulates the fatty acid synthesis pathway to a subject infected with a virus/having cancer. In one aspect, an agent can be an inhibitor of the fatty acid synthesis pathway.

Examples of inhibitors of the fatty acid synthesis pathway that can be used in the methods and compositions of the present disclosure are described below.

Compounds of Structure (I)

In various aspects, the present disclosure provides for compounds of Structure (I):

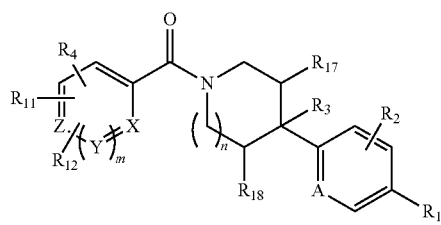

(I)

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$$R_{10}$, $R_{13}$, and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain aspects of Structure (I), $R_3$ is F.

In certain aspects of Structure (I), A is CH.

In certain aspects of Structure (I), A is N.

In certain aspects of Structure (I), X, Y, and Z are NR'.

In certain aspects of Structure (I), $R_4$ is heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, or $R_4$ and $R_{11}$ taken together with the atoms to which they are attached join together to form a heteroaryl.

In certain aspects of Structure (I), $R_5$ is hydrogen and $R_6$ is aryl or heteroaryl.

In certain aspects, the compounds of Structure (I) have one of the following Structures (I-A) or (I-B):

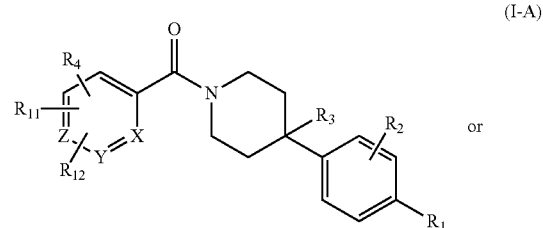

(I-A)

or

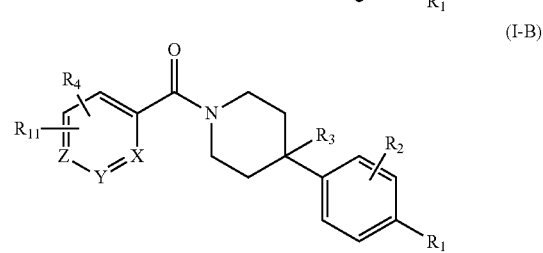

(I-B)

or a pharmaceutically acceptable salt thereof, wherein:

X, Y, and Z are each independently CR or NR', wherein R is hydrogen or $C_{1-6}$ alkyl and R' is hydrogen, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_5$, R$_6$, R$_7$, R$_8$, R$_9$R$_{10}$, R$_{13}$, and R$_{14}$ are each independently hydrogen, C$_{1-6}$ alkyl, cycloalkyl, aryl, heterocyclyl, heteroaryl, hydroxyalkyl, alkylamino, —N(R$_{15}$R$_{16}$), or —S(=O)$_2$R$_{20}$;

R$_{15}$ and R$_{16}$ are each independently hydrogen, C$_{1-6}$ alkyl, cycloalkyl, aryl, heterocyclyl, heteroaryl, or alkylamino; and R$_{17}$ and R$_{18}$ are each independently hydrogen or alkyl or can optionally join together to form a bond.

In certain aspects, the compounds of Structure (I) have one of the following Structures (I-C) or (I-D):

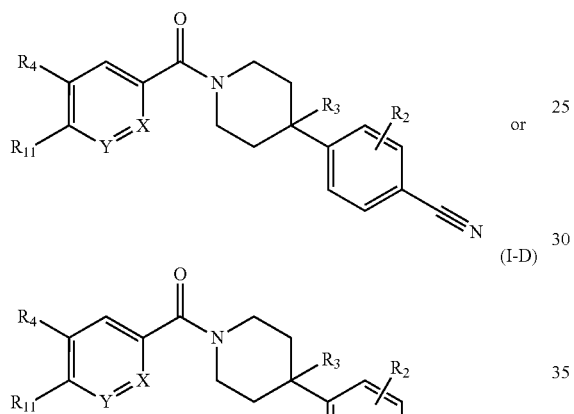

or a pharmaceutically acceptable salt thereof, wherein:

X, Y, and Z are each independently CR or NR', wherein R is hydrogen or C$_{1-6}$ alkyl and R' is hydrogen, C$_{1-6}$ alkyl, or absent;

R$_2$ is hydrogen, halo, C$_{1-6}$ alkoxy, C$_{1-6}$ alkyl, or R$_2$ and R$_3$ taken together with the atoms to which they are attached form a 5-membered heterocyclyl;

R$_3$ is hydrogen, hydroxyl, halo, C$_{1-6}$ alkyl, C$_{1-6}$ alkoxy, or R$_2$ and R$_3$ taken together with the atoms to which they are attached form a 5-membered heterocyclyl;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{20}$ is hydrogen or C$_{1-6}$ alkyl, C$_{1-6}$ alkoxy, or —N(R$_{13}$)(R$_{14}$);

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_4$ and R$_{11}$ taken together with the atoms to which they are attached join together to form a heteroaryl;

R$_5$, R$_6$, R$_7$, R$_8$, R$_9$, and R$_{10}$ are each independently H, C$_{1-6}$ alkyl, cycloalkyl, aryl, heterocyclyl, heteroaryl, alkylamino, or —N(R$_{15}$R$_{16}$); and R$_{15}$ and R$_{16}$ are each independently H, C$_{1-6}$ alkyl, cycloalkyl, aryl, heterocyclyl, heteroaryl, or alkylamino.

In certain aspects, the compounds of Structure (I) have one of the following Structures (I-E), (I-F), (I-G), (I-H):

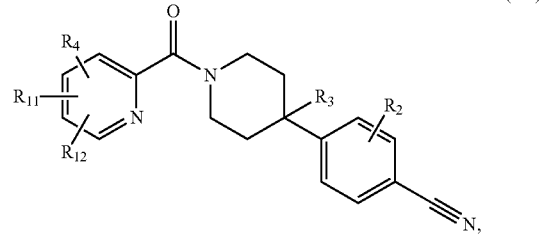
(I-E)

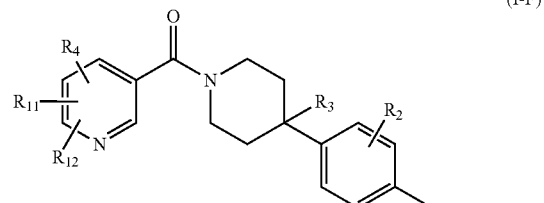
(I-F)

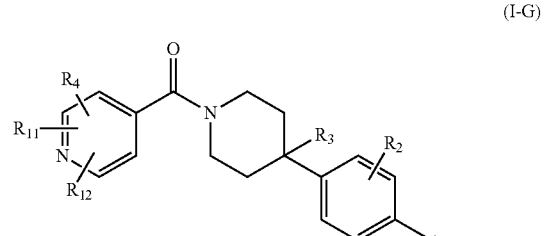
(I-G)

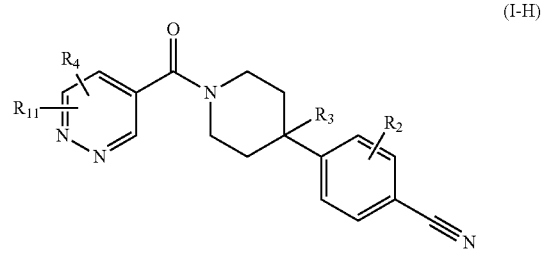
(I-H)

or a pharmaceutically acceptable salt thereof, wherein:

R$_2$ is hydrogen, halo, C$_{1-6}$ alkoxy, C$_{1-6}$ alkyl, or R$_2$ and R$_3$ taken together with the atoms to which they are attached form a 5-membered heterocyclyl;

R$_3$ is hydrogen, hydroxyl, halo, C$_{1-6}$ alkyl, C$_{1-6}$ alkoxy, or R$_2$ and R$_3$ taken together with the atoms to which they are attached form a 5-membered heterocyclyl;

R$_4$ is hydrogen, heteroaryl, heterocyclyl, —C(=O)N(R$_5$R$_6$), —N(R$_7$)C(=O)R$_8$, —N(R$_9$R$_{10}$), C$_{1-6}$ alkyl, C$_{1-6}$ alkoxy, —S(=O)$_2$R$_{20}$, or R$_4$ and R$_{11}$ taken together with the atoms to which they are attached join together to form a heteroaryl;

R$_{20}$ is hydrogen or C$_{1-6}$ alkyl, C$_{1-6}$ alkoxy, or —N(R$_{13}$)(R$_{14}$);

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, R$_4$ and R$_{11}$ taken together with the atoms to which they are attached join together to form a heteroaryl, or R$_{11}$ and R$_{12}$ taken together with the atoms to which they are attached join together to form a heteroaryl;

R$_{12}$ is hydrogen, halo, cyano, C$_{1-6}$ alkyl, C$_{1-6}$ alkoxy, —N(R$_{13}$R$_{14}$), CF$_3$, —OCF$_3$, —S(=O)$_2$R$_{20}$, or R$_{11}$ and R$_{12}$ taken together with the atoms to which they are attached join together to form a heteroaryl;

R$_5$, R$_6$, R$_7$, R$_8$, R$_9$, R$_{10}$, R$_{13}$, and R$_{14}$ are each independently H, alkyl, cycloalkyl, aryl, heterocyclyl, heteroaryl, alkylamino, or —N(R$_{15}$R$_{16}$); and R$_{15}$ and R$_{16}$ are each independently H, C$_{1-6}$ alkyl, cycloalkyl, aryl, heterocyclyl, heteroaryl, or alkylamino.

In certain aspects, the compounds of Structure (I) have one of the following Structures (I-I), (I-J), or (I-K):

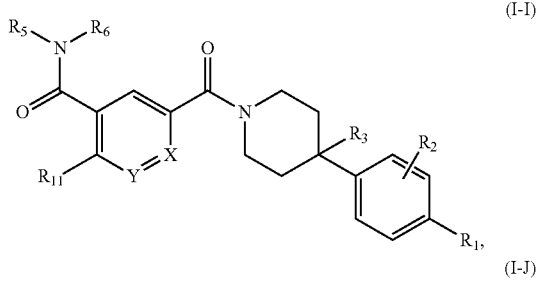

(I-I)

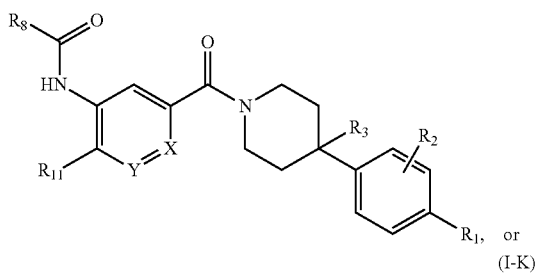

(I-J)

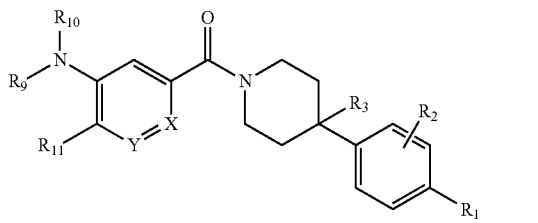

(I-K)

or a pharmaceutically acceptable salt thereof, wherein:

X and Y are each independently CR or NR'; wherein R is H or C$_{1-6}$ alkyl and R' is H, C$_{1-6}$ alkyl, or absent;

R$_1$ is hydrogen, cyano, halo, C$_{1-6}$ alkyl, C$_{1-6}$ alkoxy, —C(═O)N(R$_{13}$)(R$_{14}$), —(CH$_2$)$_q$C(═O)N(R$_{13}$)(R$_{14}$), CF$_3$, —OCF$_3$, or —S(═O)$_2$R$_{20}$;

q is 0, 1, 2, 3, or 4;

R$_{20}$ is hydrogen or C$_{1-6}$ alkyl, C$_{1-6}$ alkoxy, or —N(R$_{13}$)(R$_{14}$);

R$_2$ is hydrogen, halo, C$_{1-6}$ alkoxy, C$_{1-6}$ alkyl, or R$_2$ and R$_3$ taken together with the atoms to which they are attached form a 5-membered heterocyclyl;

R$_3$ is hydrogen, hydroxyl, halo, C$_{1-6}$ alkyl, C$_{1-6}$ alkoxy, or R$_2$ and R$_3$ taken together with the atoms to which they are attached form a 5-membered heterocyclyl;

R$_{11}$ is hydrogen, halo, cyano, C$_{1-6}$ alkyl, C$_{1-6}$ alkoxy, —N(R$_{13}$R$_{14}$), CF$_3$, —OCF$_3$, or —S(═O)$_2$R$_{20}$;

R$_5$, R$_6$, R$_7$, R$_8$, R$_9$, and R$_{10}$ are each independently H, C$_{1-6}$ alkyl, cycloalkyl, aryl, heterocyclyl, heteroaryl, alkylamino, or —N(R$_{15}$R$_{16}$); and R$_{15}$ and R$_{16}$ are each independently H, C$_{1-6}$ alkyl, cycloalkyl, aryl, heterocyclyl, heteroaryl, or alkylamino.

In certain aspects, the compounds of Structure (I) have one of the following Structures (I-L) or (I-M):

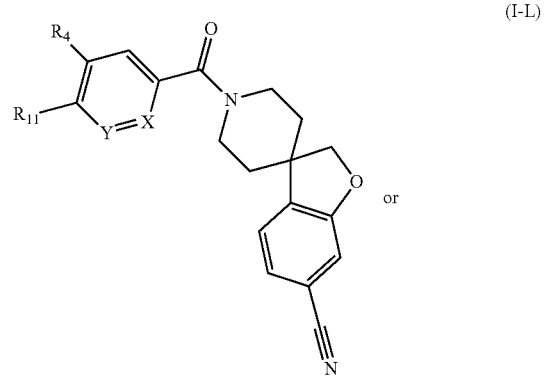

(I-L)

or

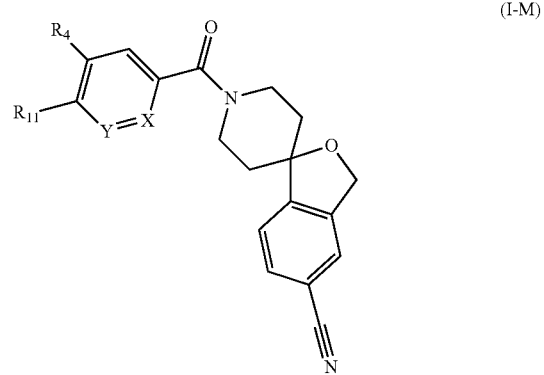

(I-M)

or a pharmaceutically acceptable salt thereof, wherein:

X and Y are each independently CR or NR'; wherein R is H or C$_{1-6}$ alkyl and R' is H, C$_{1-6}$ alkyl, or absent;

R$_4$ is hydrogen, heteroaryl, heterocyclyl, —C(═O)N(R$_5$R$_6$), —N(R$_7$)C(═O)R$_8$, —N(R$_9$R$_{10}$), C$_{1-6}$ alkyl, C$_{1-6}$ alkoxy, —S(═O)$_2$R$_{20}$, or R$_4$ and R$_{11}$ taken together with the atoms to which they are attached join together to form a heteroaryl;

R$_{20}$ is hydrogen or C$_{1-6}$ alkyl, C$_{1-6}$ alkoxy, or —N(R$_{13}$)(R$_{14}$);

R$_{11}$ is hydrogen, halo, cyano, C$_{1-6}$ alkyl, C$_{1-6}$ alkoxy, —N(R$_{13}$R$_{14}$), CF$_3$, —OCF$_3$, —S(═O)$_2$R$_{20}$, or R$_4$ and R$_{11}$ taken together with the atoms to which they are attached join together to form a heteroaryl;

R$_5$, R$_6$, R$_7$, R$_8$, R$_9$, and R$_{10}$ are each independently H, C$_{1-6}$ alkyl, cycloalkyl, aryl, heterocyclyl, heteroaryl, alkylamino, or —N(R$_{15}$R$_{16}$); and R$_{15}$ and R$_{16}$ are each independently H, C$_{1-6}$ alkyl, cycloalkyl, aryl, heterocyclyl, heteroaryl, or alkylamino.

In certain aspects, the compounds of Structure (I) have one of the following Structures (I-N) or (I-O):

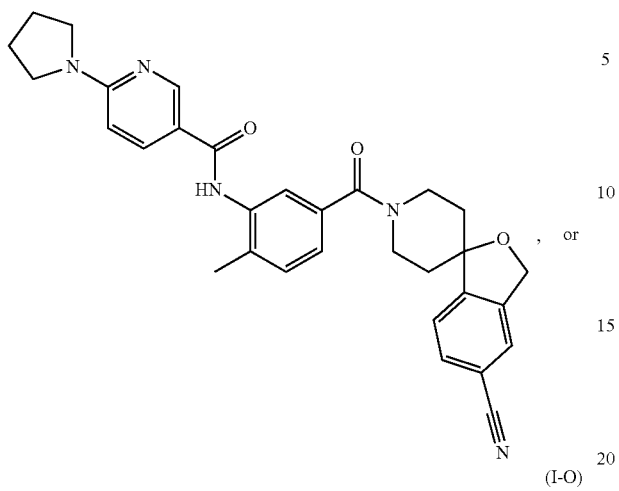

(I-N)

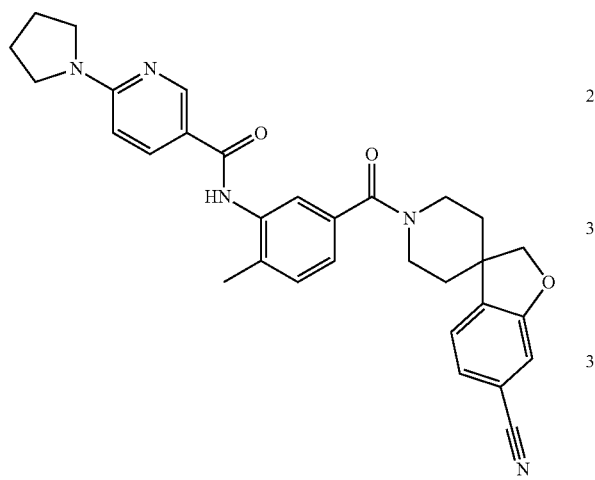

(I-O)

or a pharmaceutically acceptable salt thereof.

In certain aspects, the compounds of Structure (I) have the following Structure (I-P):

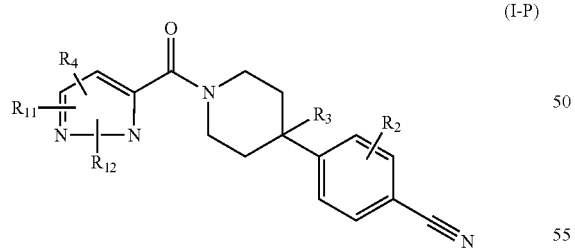

(I-P)

or a pharmaceutically acceptable salt thereof, wherein:

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —S(=O)$_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have one of the following Structures (I-Q), (I-R), or (I-S):

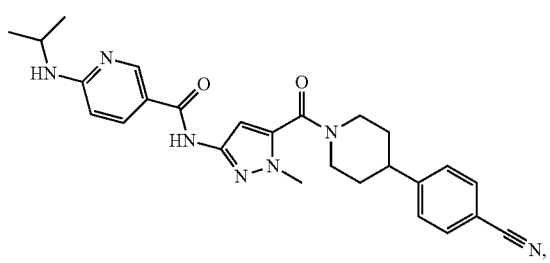

(I-Q)

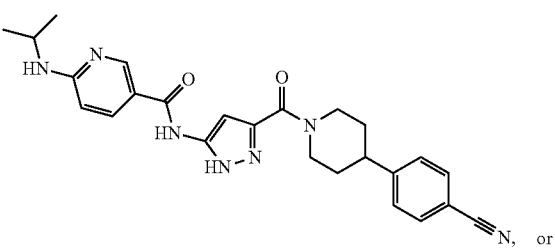

(I-R)

, or

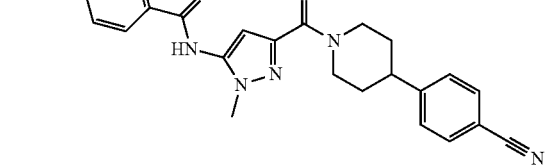

(I-S)

or a pharmaceutically acceptable salt thereof.

In certain aspects, the compounds of Structure (I) have the following Structure (I-T):

(I-T)

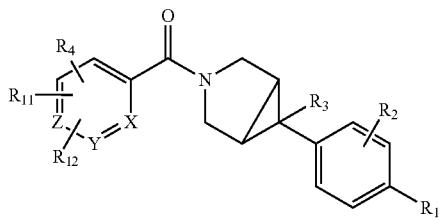

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (I) have the following Structure (I-U):

(I-U)

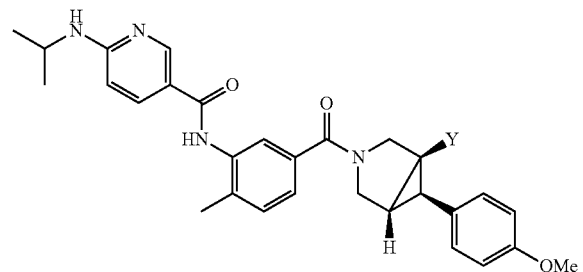

or a pharmaceutically acceptable salt thereof.

In certain aspects, the compounds of Structure (I) have one of the following Structures (I-V):

(I-V)

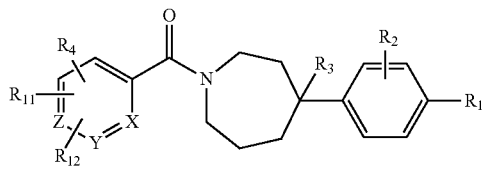

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compound of Structure (I) has the following Structure (I-W):

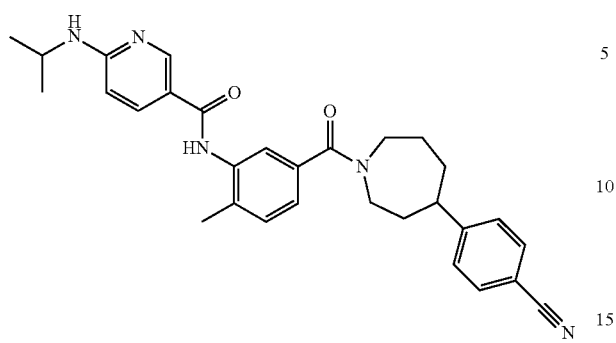
or a pharmaceutically acceptable salt thereof.
In certain aspects, the compounds of Structure (I) have one of the following Structures (I-X), (I-Y), (I-Z), (I-AA), (I-AB), (I-AC), (I-AD), (I-AF), (I-AG), or (I-AH):
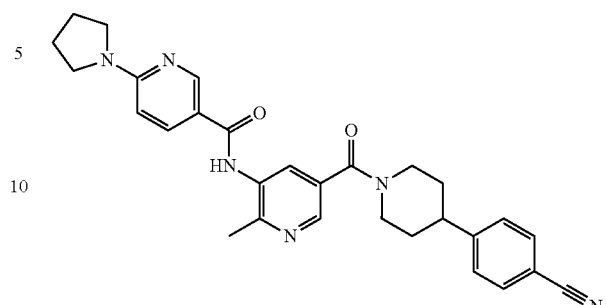
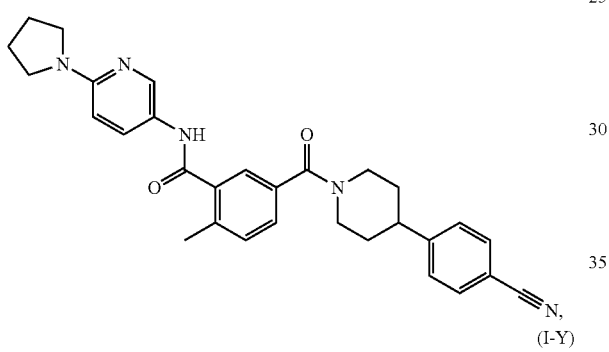
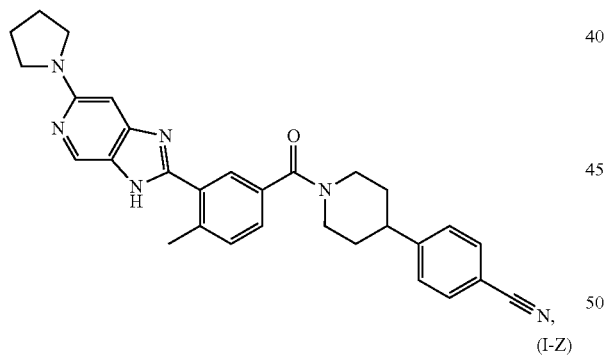
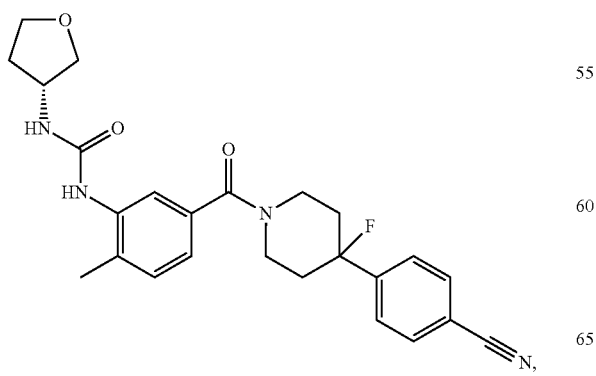

-continued (I-AE)

(I-AF)

(I-AG)

(I-AH)

or a pharmaceutically acceptable salt thereof.

Compounds of Structure (II)

In various aspects, the present disclosure provides for compounds of Structure (II):

(II)

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

L and D are each independently C or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{11}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), CF$_3$, —OCF$_3$, —S(=O)$_2$R$_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$);

$R_{15}$ and $R_{16}$ are each independently H, $C_{1-6}$ alkyl, cycloalkyl, aryl, heterocyclyl, heteroaryl, or alkylamino;

$R_{17}$ and $R_{18}$ are each independently hydrogen or alkyl or can optionally join together to form a bond;

n is 1 or 2; and m is 0 or 1.

In certain aspects, the compounds of Structure (II) have the following Structure (II-A):

(II-A)

or a pharmaceutically acceptable salt thereof, wherein:

X, Y, and Z are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2$R$_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —$S(=O)_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;

$R_{12}$ is hydrogen, halo, cyano, $C_{1-6}$ alkyl, $C_{1-6}$ alkoxy, —N($R_{13}R_{14}$), $CF_3$, —$OCF_3$, —$S(=O)_2R_{20}$, or $R_{11}$ and $R_{12}$ taken together with the atoms to which they are attached join together to form a heteroaryl;

$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (II) have the following Structure (II-B):

(II-B)

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_4$ is hydrogen, heteroaryl, heterocyclyl, —C(=O)N($R_5R_6$), —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;

$R_{20}$ is hydrogen or $C_{1-6}$ alkyl, $C_{1-6}$ alkoxy, or —N($R_{13}$)($R_{14}$);

$R_{11}$ is hydrogen, halo, cyano, $C_{1-6}$ alkyl, $C_{1-6}$ alkoxy, —N($R_{13}R_{14}$), $CF_3$, —$OCF_3$, —$S(=O)_2R_{20}$, or $R_4$ and $R_{11}$ taken together with the atoms to which they are attached join together to form a heteroaryl;

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compounds of Structure (II) have one of the following Structures (II-C), (II-D), or (II-E):

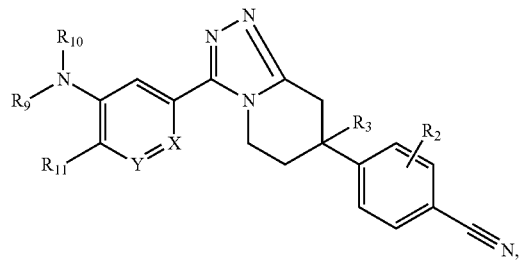

(II-C)

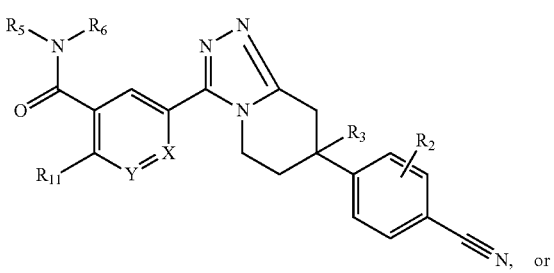

(II-D)

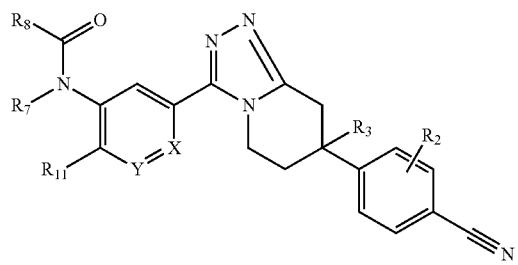

(II-E)

or a pharmaceutically acceptable salt thereof, wherein:

X and Y are each independently CR or NR', wherein R is H or $C_{1-6}$ alkyl and R' is H, $C_{1-6}$ alkyl, or absent;

$R_2$ is hydrogen, halo, $C_{1-6}$ alkoxy, $C_{1-6}$ alkyl, or $R_2$ and $R_3$ taken together with the atoms to which they are attached form a 5-membered heterocyclyl;

$R_3$ is hydrogen, hydroxyl, halo, $C_{1-6}$ alkyl, $C_{1-6}$ alkoxy, or $R_2$ and $R_3$ taken together with the atoms to which they are attached form a 5-membered heterocyclyl;

$R_{11}$ is hydrogen, halo, cyano, $C_{1-6}$ alkyl, $C_{1-6}$ alkoxy, —N($R_{13}R_{14}$), $CF_3$, —$OCF_3$, or —$S(=O)_2R_{20}$;

$R_{20}$ is hydrogen or $C_{1-6}$ alkyl, $C_{1-6}$ alkoxy, or —N($R_{13}$)($R_{14}$);

$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and $R_{15}$ and $R_{16}$ are each independently H, $C_{1-6}$ alkyl, cycloalkyl, aryl, heterocyclyl, heteroaryl, or alkylamino.

In certain aspects, the compound of Structure (II) has the following Structure (II-P):

(II-F)

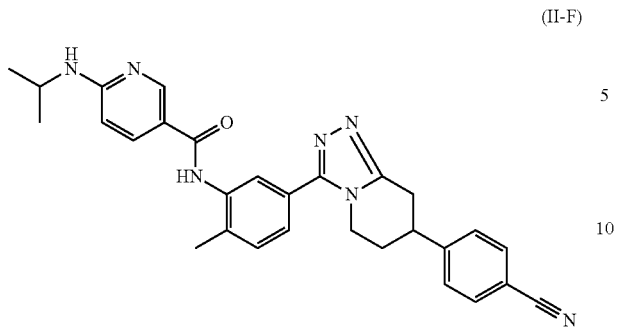

or a pharmaceutically acceptable salt thereof.

Compounds of Structure (III)

In various aspects, the present disclosure provides for compounds of Structure (III):

(III)

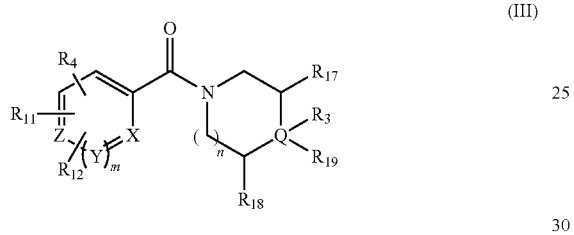

or a pharmaceutically acceptable salt thereof, wherein:
X, Y, and Z are each independently CR or NR', wherein R is H or $C_{1-6}$ alkyl and R' is H, $C_{1-6}$ alkyl, or absent;
Q is C or N;
$R_3$ is hydrogen, hydroxyl, halo, $C_{1-6}$ alkyl, $C_{1-6}$ alkoxy, or if Q is $NR_3$ is absent;
$R_4$ is hydrogen, heteroaryl, heterocyclyl, —C(=O)N$(R_5R_6)$, —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;
$R_{20}$ is hydrogen or $C_{1-6}$ alkyl, $C_{1-6}$ alkoxy, or —N($R_{13}$)($R_{14}$);
$R_{11}$ is hydrogen, halo, cyano, $C_{1-6}$ alkyl, $C_{1-6}$ alkoxy, —N($R_{13}R_{14}$), $CF_3$, —OCF$_3$, —S(=O)$_2R_{20}$, $R_4$ and $R_{11}$ taken together with the atoms to which they are attached join together to form a heteroaryl, or $R_{11}$ and $R_{12}$ taken together with the atoms to which they are attached join together to form a heteroaryl;
$R_{12}$ is hydrogen, halo, cyano, $C_{1-6}$ alkyl, $C_{1-6}$ alkoxy, —N($R_{13}R_{14}$), $CF_3$, —OCF$_3$, —S(=O)$_2R_{20}$, or $R_{11}$ and $R_{12}$ taken together with the atoms to which they are attached join together to form a heteroaryl;
$R_5$, $R_6$, $R_7$, $R_8$, $R_9$, $R_{10}$, $R_{13}$, and $R_{14}$ are each independently H, $C_{1-6}$ alkyl, cycloalkyl, aryl, heterocyclyl, heteroaryl, alkylamino, or —N($R_{15}R_{16}$);
$R_{15}$ and $R_{16}$ are each independently H, $C_{1-6}$ alkyl, cycloalkyl, aryl, heterocyclyl, heteroaryl, or alkylamino;
$R_{17}$ and $R_{18}$ are each independently hydrogen or alkyl or can optionally join together to form a bond;
$R_{19}$ is aryl, heteroaryl, cycloalkyl, or heterocyclyl;
n is 0, 1, or 2; and
m is 0 or 1.

In certain aspects, the compounds of Structure (III) have one of the following Structures (III-A), or (III-C):

(III-A)

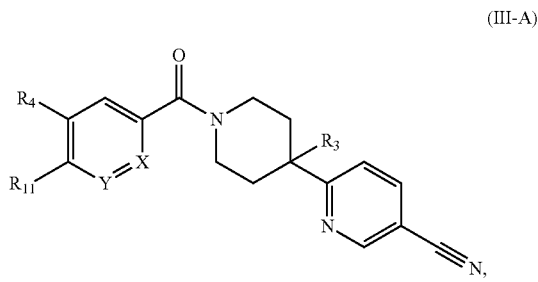

(III-B)

(III-C)

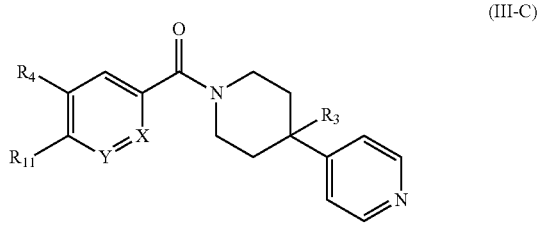

or a pharmaceutically acceptable salt thereof, wherein:
X and Y are each independently CR or NR', wherein R is H or $C_{1-6}$ alkyl and R' is H, $C_{1-6}$ alkyl, or absent;
$R_3$ is hydrogen, hydroxyl, halo, $C_{1-6}$ alkyl, or $C_{1-6}$ alkoxy;
$R_4$ is hydrogen, heteroaryl, heterocyclyl, —C(=O)N$(R_5R_6)$, —N($R_7$)C(=O)$R_8$, —N($R_9R_{10}$), $C_{1-6}$ alkyl, $C_{1-6}$ alkoxy, —S(=O)$_2R_{20}$, or $R_4$ and $R_{11}$ taken together with the atoms to which they are attached join together to form a heteroaryl;
$R_{11}$ is hydrogen, halo, cyano, $C_{1-6}$ alkyl, $C_{1-6}$ alkoxy, —N($R_{13}R_{14}$), $CF_3$, —OCF$_3$, —S(=O)$_2R_{20}$, or $R_4$ and $R_{11}$ taken together with the atoms to which they are attached join together to form a heteroaryl;
$R_5$, $R_6$, $R_7$, $R_8$, $R_9$, and $R_{10}$ are each independently H, $C_{1-6}$ alkyl, cycloalkyl, aryl, heterocyclyl, heteroaryl, alkylamino, or —N($R_{15}R_{16}$); and
$R_{15}$ and $R_{16}$ are each independently H, $C_{1-6}$ alkyl, cycloalkyl, aryl, heterocyclyl, heteroaryl, or alkylamino.

In certain aspects, the compounds of Structure (III) have one of the following Structures (III-D), (III-E), or (III-F):

(III-D)

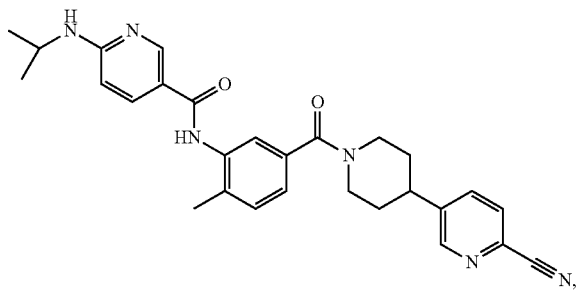

(III-E)

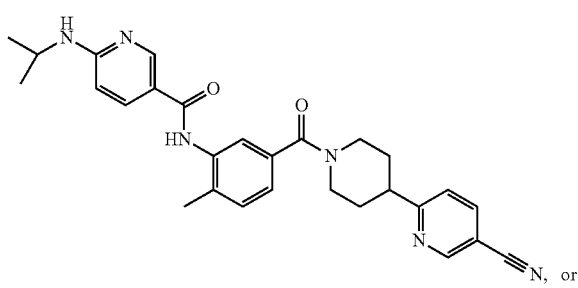

(III-F)

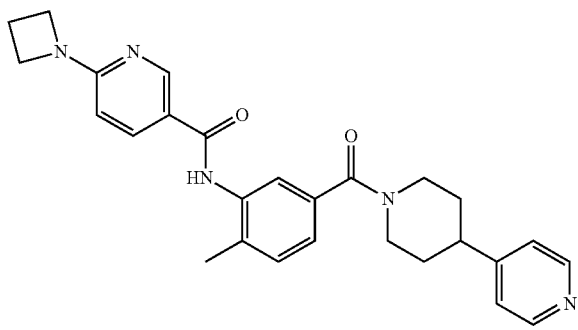

or a pharmaceutically acceptable salt thereof.

Compounds of Structure (IV)

In certain aspects, the compounds of Structure (IV) have one of the following Structures (IV-A), (IV-B), or (IV-C):

(IV-A)

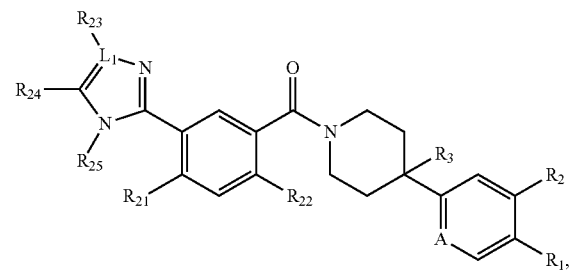

(IV-B)

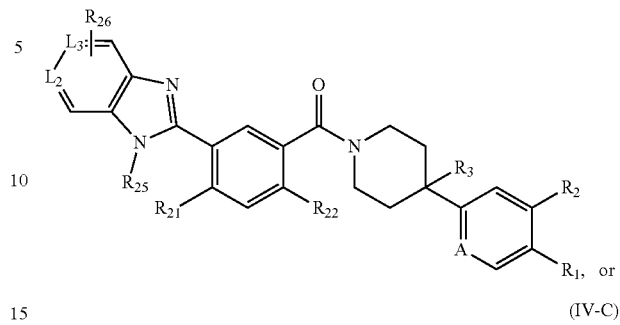

(IV-C)

or a pharmaceutically acceptable salt thereof, wherein:

$L_1$, $L_2$, $L_3$, $L_4$, and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{23}$ is hydrogen, —N($R_{13}$)($R_{14}$), $C_{1-6}$ alkyl, $C_{1-6}$ alkoxy, is absent if $L_1$ is N, or $R_{23}$ and $R_{24}$ taken together with the atoms to which they are attached join together to form a heterocyclyl, heteroaryl, or cycloalkyl;

$R_{24}$ is hydrogen, —N($R_{13}$)($R_{14}$), $C_{1-6}$ alkyl, $C_{1-6}$ alkoxy, —($C_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl;

$R_{26}$ is hydrogen, heteroaryl, heterocycyl, —N($R_{13}$)($R_{14}$), or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{25}$ is hydrogen, $C_{1-6}$ alkyl, or $C_{1-6}$ alkoxy; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain aspects, the compounds of Structure (IV) have one of the following Structures (IV-D) and (IV-E):

(IV-D)

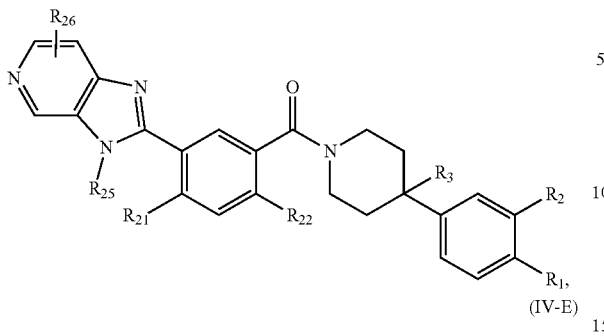

(IV-E)

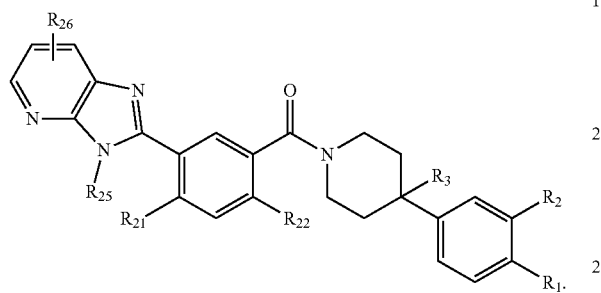

or a pharmaceutically acceptable salt thereof.

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{26}$ is hydrogen, heteroaryl, heterocycyl, —N($R_{13}$)($R_{14}$), or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxy-alkyl, alkylamino, —N($R_{15}R_{16}$), or —S(=O)$_2$R$_{20}$;

$R_{25}$ is hydrogen, $C_{1-6}$ alkyl, or $C_{1-6}$ alkoxy; and $R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain aspects, the compounds of Structure (IV) have one of the following Structures (IV-F) and (IV-G):

(IV-F)

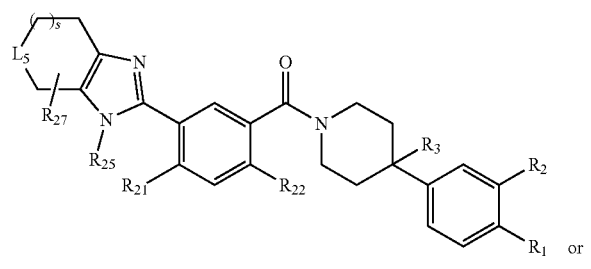

or (IV-G)

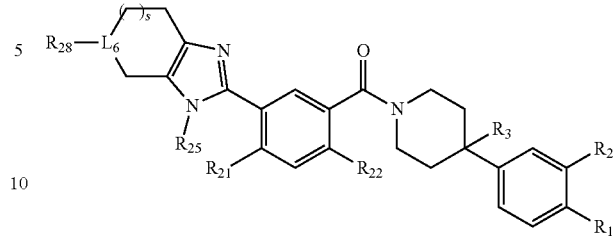

or a pharmaceutically acceptable salt thereof, wherein:

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxy-alkyl, alkylamino, —N($R_{15}R_{16}$), or —S(=O)$_2$R$_{20}$;

$R_{25}$ is hydrogen, $C_{1-6}$ alkyl, or $C_{1-6}$ alkoxy;

$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino;

s is 0, 1, or 2;

$L_5$ is CH$_2$, NH, S, or O;

$L_6$ is CH or N;

$R_{27}$ is hydrogen, —C(=O)R", —S(=O)$_2$R$_{20}$;

$R_{28}$ is hydrogen, —C(=O)R", —S(=O)$_2$R$_{20}$, or is absent if $L_6$ is O; and R" is hydrogen, $C_{1-6}$ alkyl, $C_{1-6}$ alkoxy, —C(=O)N($R_{13}$)($R_{14}$), or —N($R_{13}$)($R_{14}$).

In certain aspects of Structure (IV), $R_1$ is hydrogen, cyano, $C_{1-6}$ alkyl, $C_{1-6}$ alkoxy, or —C(=O)N($R_{13}$)($R_{14}$).

In certain aspects of Structure (IV), $R_1$ is cyano.

In certain aspects of Structure (IV), $R_2$ is hydrogen or halo; $R_2$ is hydrogen.

In certain aspects of Structure (IV), $R_3$ is hydrogen.

In certain aspects of Structure (IV), $R_{21}$ and $R_{22}$ are each independently hydrogen or $C_{1-6}$ alkyl.

In certain aspects of Structure (IV), $R_{21}$ and $R_{22}$ are each independently $C_{1-6}$ alkyl.

In certain aspects of Structure (IV), $R_{25}$ is hydrogen.

In certain aspects of Structure (IV), $L_2$ is N.

In certain aspects of Structure (IV), $L_1$ is CH.

In certain aspects of Structure (IV), $L_3$ is CH.

In certain aspects of Structure (IV), $L_4$ is CH.

In certain aspects of Structure (IV), A is N.

In certain aspects of Structure (IV), A is CH.

In certain aspects of Structure (IV), $R_{26}$ is heterocyclyl.

In certain aspects of Structure (IV), $R_{24}$ is —N($R_{13}$)($R_{14}$).

In certain aspects of Structure (IV), $L_5$ and $L_6$ are each independently N. In certain aspects of Structure (IV), s is 1.

In certain aspects of Structure (IV), s is 0.

In certain aspects, the compounds of Structure (IV) have one of the following Structures (IV-H), (IV-I), (IV-J), (IV-K), (IV-L), (IV-M), (IV-N), or (IV-O):

(IV-H)
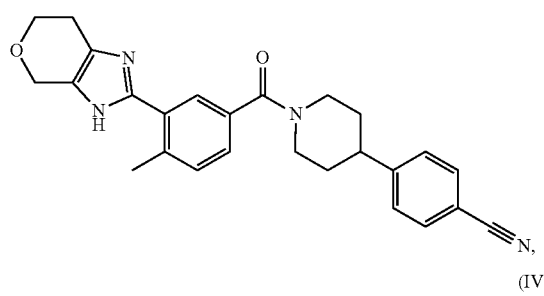
(IV-I)
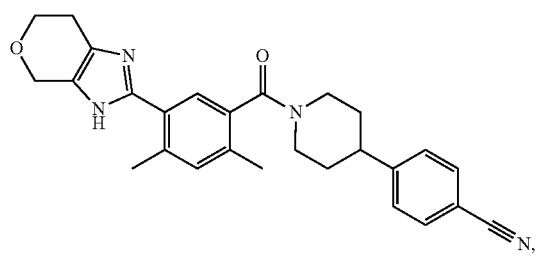
(IV-J)
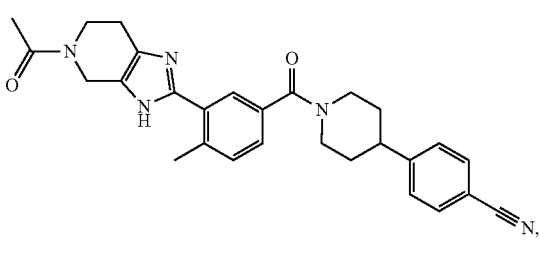
(IV-K)
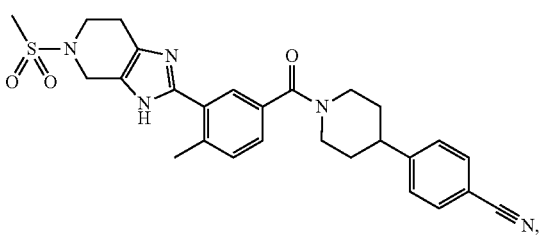
(IV-L)
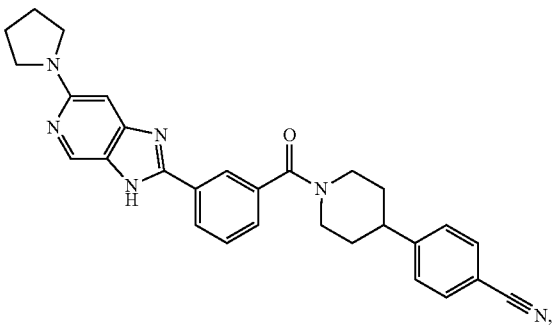
(IV-M)
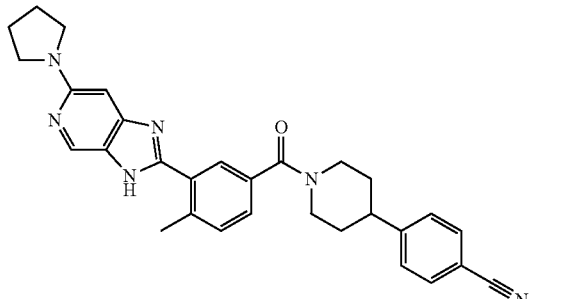
(IV-N)
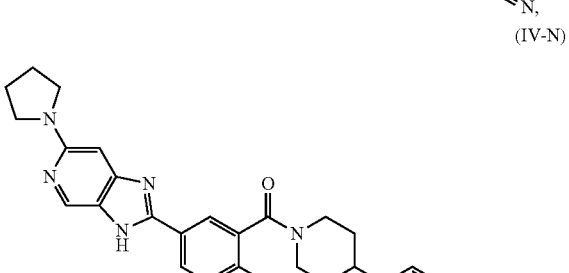
or
(IV-O)
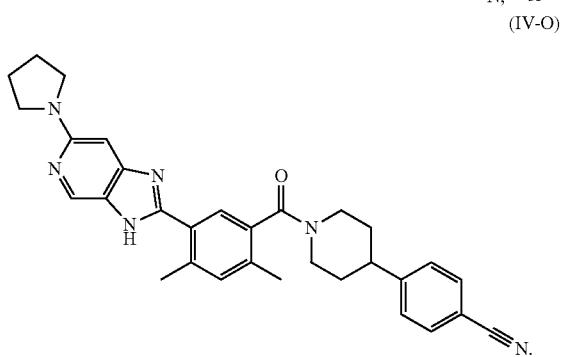
or a pharmaceutically acceptable salt thereof.
Compounds of Structure (V)
In various aspects, the present disclosure provides for compounds of Structure (V):
(V)
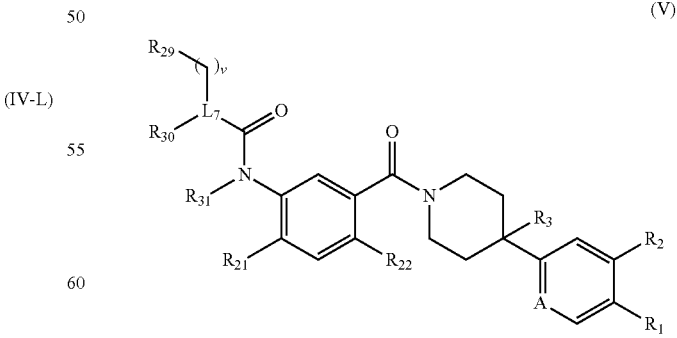
or a pharmaceutically acceptable salt thereof, wherein:
$L_7$ is N or O, wherein $R_{30}$ is absent if $L_7$ is O;
A is CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{29}$ and $R_{30}$ are each independently hydrogen, $C_{1-6}$ alkyl, $C_{1-6}$ alkoxy, hydroxyalkyl, heteroaryl, heterocyclyl, —N($R_{15}R_{16}$), —C(=O)$R_{46}$, —$R_{48}$C(=O)$R_{47}$, or $R_{29}$ and $R_{30}$ taken together with the atoms to which they are attached join together to form a heteroaryl or heterocyclyl, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and v is 0 or 1.

In certain aspects, the compounds of Structure (V) have one of the following Structures (V-A), (V-B), (V-C), or (V-D):

(V-A)

(V-B)

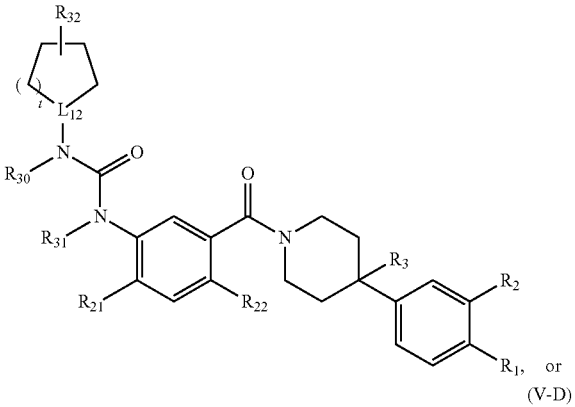

(V-C)

(V-D)

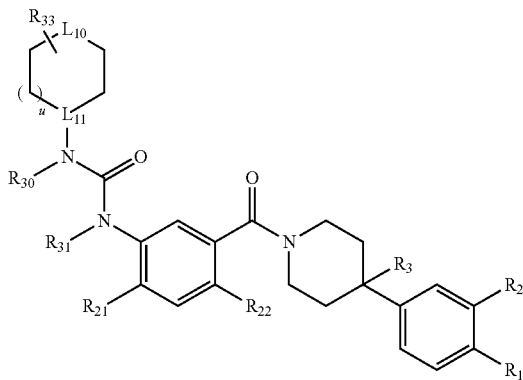

or a pharmaceutically acceptable salt thereof, wherein:

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{30}$ is hydrogen, $C_{1-6}$ alkyl, $C_{1-6}$ alkoxy, hydroxyalkyl, heteroaryl, heterocyclyl, —N($R_{15}R_{16}$), —C(=O)$R_{46}$, or —$R_{48}$C(=O)$R_{47}$, wherein $R_{30}$ is absent if $L_7$ is O;

$R_{46}$ and $R_{47}$ are each independently hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;

$R_{48}$ is alkyl or is absent;

$R_{31}$ is hydrogen, $C_{1-6}$ alkyl, or $C_{1-6}$ alkoxy;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$L_8$, $L_9$, and $L_{10}$ are each independently CH$_2$, NH, or O;

$L_{11}$ and $L_{12}$ are each independently CH or N;

$R_{32}$ and $R_{33}$ are each independently hydrogen, $C_{1-6}$ alkyl, $C_{1-6}$ alkoxy, —S(=O)$_2$R$_{20}$, —C(=O)$R_{46}$, hydroxyalkyl, hydroxyl, or are absent;

u is 0, 1, or 2; and t is 0, 1, or 2.

In certain aspects of Structure (V), $L_7$ is N.

In certain aspects of Structure (V), $L_7$ is O.

In certain aspects of Structure (V), A is N.

In certain aspects of Structure (V), A is CH.

In certain aspects of Structure (V), $R_1$ is hydrogen, cyano, $C_{1-6}$ alkyl, $C_{1-6}$ alkoxy, or —C(=O)N($R_{13}$)($R_{14}$).

In certain aspects of Structure (V), $R_1$ is cyano.

In certain aspects of Structure (V), $R_2$ is hydrogen or halo.

In certain aspects of Structure (V), $R_2$ is hydrogen.

In certain aspects of Structure (V), $R_3$ is fluorine.

In certain aspects of Structure (V), $R_{21}$ and $R_{22}$ are each independently hydrogen or $C_{1-6}$ alkyl.

In certain aspects of Structure (V), $R_{21}$ and $R_{22}$ are each independently $C_{1-6}$ alkyl.

In certain aspects of Structure (V), $R_{31}$ is hydrogen.

In certain aspects of Structure (V), $R_{30}$ is hydrogen.

In certain aspects of Structure (V), $L_8$ is O.

In certain aspects of Structure (V), $L_9$ is O.

In certain aspects of Structure (V), $L_{10}$ is O and $L_{11}$ is N.

In certain aspects of Structure (V), $L_{12}$ is N.

In certain aspects of Structure (V), $R_{32}$ and $R_{33}$ are each independently hydrogen.

In certain aspects, the compounds of Structure (V) have one of the following Structures (V-I), (V-J), (V-K), (V-L), (V-M), (V-N), or (V-O):

-continued (V-O)

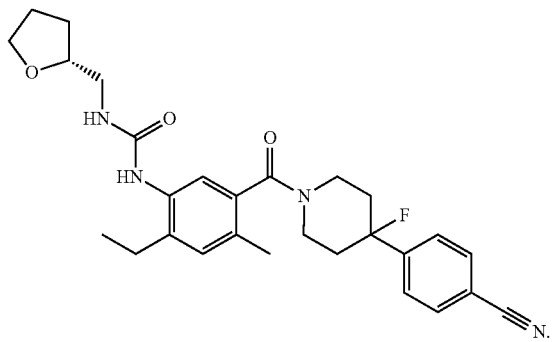

or a pharmaceutically acceptable salt thereof.

Compounds of Structure (VI)

In certain aspects, the compounds of Structure (VI) have one of the following Structures (VI-A) or (VI-B):

(VI-A)

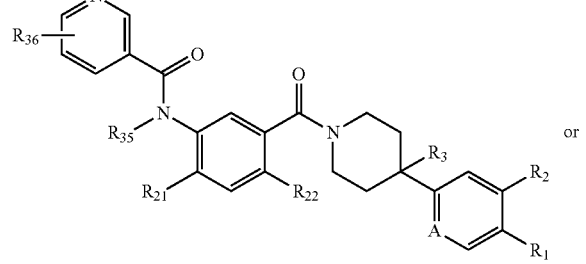

(VI-B)

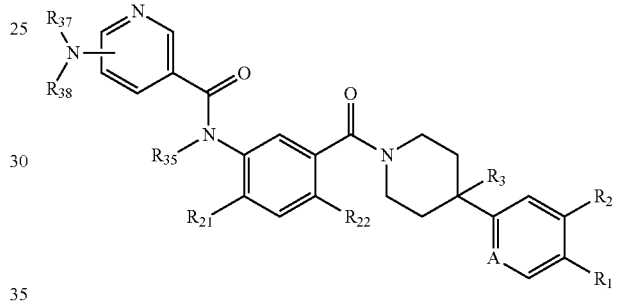

or a pharmaceutically acceptable salt thereof, wherein:
$L_{13}$, $L_{14}$, $L_{15}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, CF$_3$, —OCF$_3$, —S(=O)$_2$R$_{20}$, or —N($R_{15}R_{16}$);
$R_{35}$ is hydrogen, $C_{1-6}$ alkyl, or $C_{1-6}$ alkoxy;
$R_{36}$ is hydrogen, $C_{1-6}$ alkyl, $C_{1-6}$ alkoxy, —N($R_{15}R_{16}$), heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino.

In certain aspects, the compounds of Structure (VI) have one of the following Structures (VI-C) or (VI-D):

(VI-C)

(VI-D)

or a pharmaceutically acceptable salt thereof, wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{35}$ is hydrogen, $C_{1-6}$ alkyl, or $C_{1-6}$ alkoxy;
$R_{36}$ is hydrogen, $C_{1-6}$ alkyl, $C_{1-6}$ alkoxy, —N($R_{15}R_{16}$), heterocyclyl, or heteroaryl;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, $C_{1-6}$ alkoxy, cycloalkyl, aryl, heterocyclyl, heteroaryl, hydroxyalkyl, or alkylamino; and
$R_{37}$ and $R_{38}$ are each independently hydrogen, $C_{1-6}$ alkyl, $C_{1-6}$ alkoxy, hydroxyalkyl, heteroaryl, heterocyclyl, or $R_{37}$ and $R_{38}$ taken together with the atoms to which they are attached join together to form a heteroaryl or heterocyclyl.

In certain aspects of Structure (VI), $R_1$ is hydrogen, cyano, $C_{1-6}$ alkyl, $C_{1-6}$ alkoxy, or —C(=O)N($R_{13}$)($R_{14}$).

In certain aspects of Structure (VI), $R_1$ is cyano.

In certain aspects of Structure (VI), $R_2$ is hydrogen or halo.

In certain aspects of Structure (VI), $R_2$ is hydrogen.

In certain aspects of Structure (VI), $R_3$ is fluorine.

In certain aspects of Structure (VI), $R_{21}$ and $R_{22}$ are each independently hydrogen or $C_{1-6}$ alkyl.

In certain aspects of Structure (VI), $R_{21}$ and $R_{22}$ are each independently $C_{1-6}$ alkyl.

In certain aspects of Structure (VI), $R_{35}$ is hydrogen.

In certain aspects of Structure (VI), $R_{34}$ is heteroaryl;

In certain aspects of Structure (VI), $R_{34}$ is thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, or benzothiadiazolyl.

In certain aspects of Structure (VI), $L_{13}$ is N.

In certain aspects of Structure (VI), $L_{14}$ and $L_{15}$ are each independently CH.

In certain aspects of Structure (VI), A is N.

In certain aspects of Structure (VI), A is CH.

In certain aspects, the compounds of Structure (VI) have one of the following Structures (VI-E), (VI-F), (VI-G), (VI-H), or (VI-I):

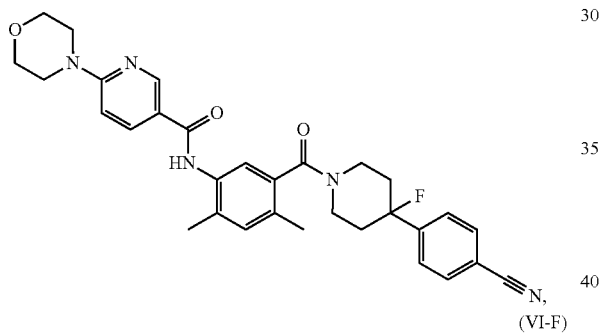

(VI-E)

(VI-F)

(VI-G)

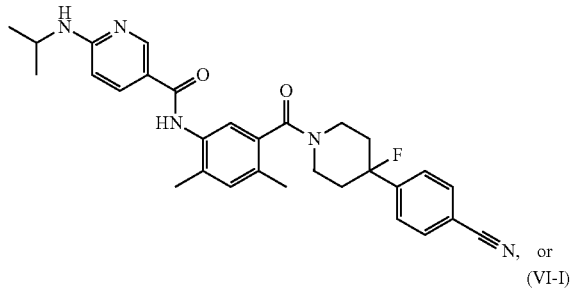

(VI-H)

(VI-I)

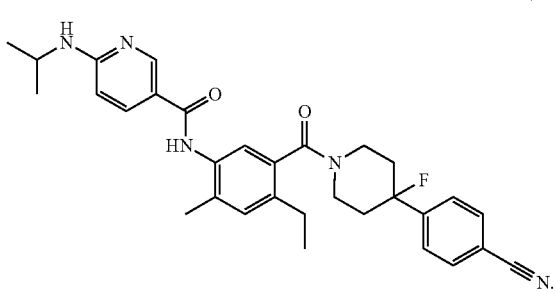

or a pharmaceutically acceptable salt thereof.

In various aspects, the present disclosure provides for compounds of Structure (VI-J):

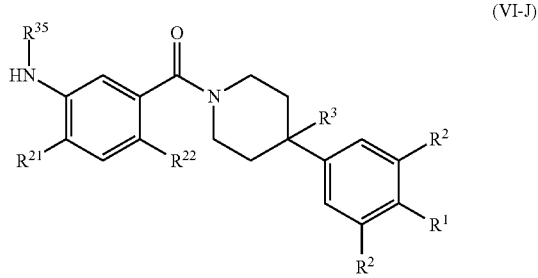

(VI-J)

or a pharmaceutically acceptable salt thereof, wherein:
  $R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
    the $C_3$-$C_5$ cycloalkyl optionally includes an oxygen or nitrogen heteroatom; and
    when $R^1$ is not H, —CN or halogen, it is optionally substituted with one or more halogens;
  each $R^2$ is independently H, halogen or $C_1$-$C_4$ straight or branched alkyl;
  $R^3$ is H, —OH, or halogen;
  $R^{21}$ is cyclobutyl, azetidin-1-yl, or cyclopropyl;
  $R^{22}$ is halogen, or $C_1$-$C_2$ alkyl;
  $R^{35}$ is —C(O)—$R^{351}$, —C(O)—NHR$^{351}$, —C(O)—O—$R^{351}$ or S(O)$_2$R$^{351}$; and
  $R^{351}$ is $C_1$-$C_6$ straight or branched alkyl, cycloalkyl, heterocyclyl, aryl or heteroaryl, each of which is optionally substituted.

In some aspects of Structure (VI-J), $R^3$ is H or halogen.

In some aspects of Structure (VI-J), $R^1$ is halogen, —CN or $C_1$-$C_2$ haloalkyl.

In some aspects of Structure (VI-J), $R^{22}$ is $C_1$-$C_2$ alkyl.

In some aspects of Structure (VI-J), $R^{21}$ is cyclobutyl and $R^{22}$ is $C_1$-$C_2$ alkyl.

In some aspects of Structure (VI-J), $R^{21}$ is cyclobutyl.

In some aspects of Structure (VI-I), $R^3$ is H or F.

In some aspects of Structure (VI-J), $R^1$ is —CN.

In some aspects of Structure (VI-J), $R^1$ is —CF$_3$.

In some aspects of Structure (VI-J), $R^{22}$ is H, methyl or ethyl.

In some aspects of Structure (VI-J), $R^{22}$ is H.

In some aspects of Structure (VI-J), $R^{22}$ is methyl.

In some aspects of Structure (VI-J), $R^{35}$ is —C(O)—NHR$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl or (S)-tetrahydro-2H-pyran-3-yl.

In some aspects of Structure (VI-J), $R^{351}$ is (R)-(tetrahydrofuran-2-yl)methyl or (S)-(tetrahydrofuran-2-yl)methyl.

In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—NHR$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{35}$ is —C(O)—O—R$^{351}$.

In some aspects of Structure (VI-J), $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^1$ is —CN, each $R^2$ is H, $R^3$ is H or F, $R^{21}$ is $C_3$-$C_4$ cycloalkyl, $R^{22}$ is H, $R^{35}$ is —C(O)—O—R$^{351}$ where $R^{351}$ is isopropyl, isobutyl, (R)-3-tetrahydrofuranyl, (S)-3-tetrahydrofuranyl, (R)-(tetrahydrofuran-2-yl)methyl, (S)-(tetrahydrofuran-2-yl)methyl, (R)-tetrahydro-2H-pyran-3-yl, or (S)-tetrahydro-2H-pyran-3-yl.

In some aspects of Structure (VI-J), $R^{351}$ is (R)-3-tetrahydrofuranyl or (S)-3-tetrahydrofuranyl.

In some aspects of Structure (VI-J), compounds have a structure selected from the group consisting of:

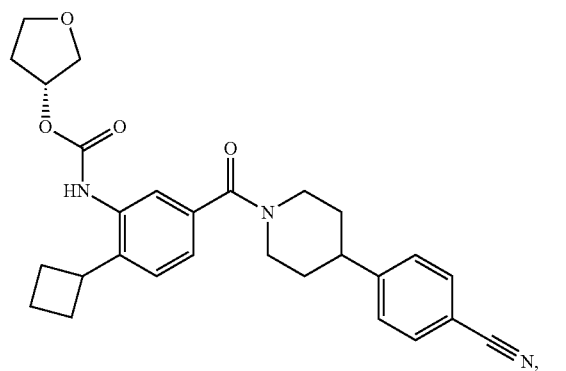

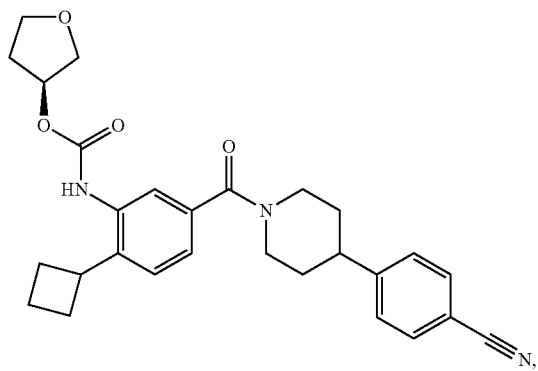

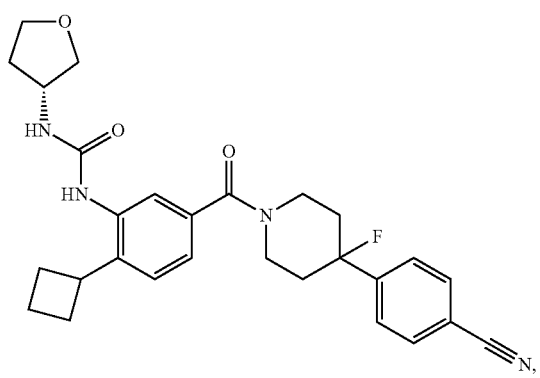

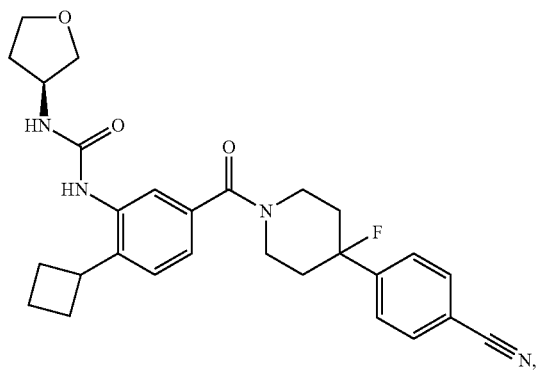

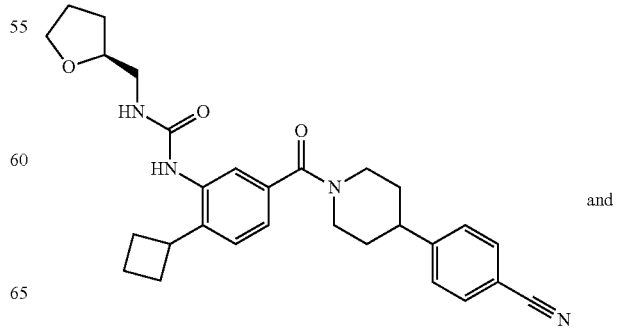

and

-continued

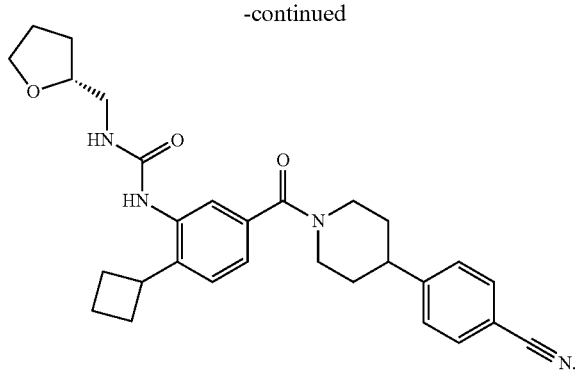

Compounds of Structure (VII)

In certain aspects, the compounds of Structure (VII) have one of the following Structures (VII-A) or (VII-B):

(VII-A)

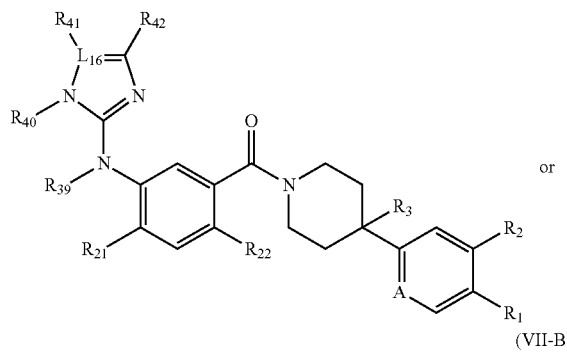

or (VII-B)

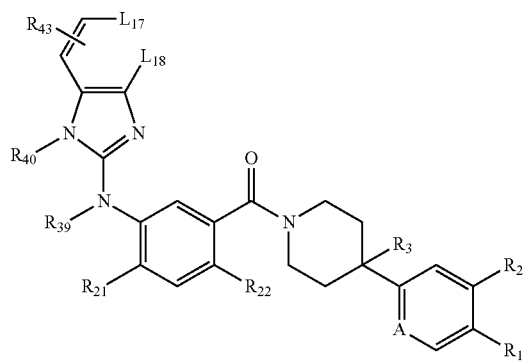

or a pharmaceutically acceptable salt thereof, wherein:
$L_{16}$ is C or N, wherein $R_{41}$ is absent if $L_{16}$ is N;
$L_{17}$, $L_{18}$, and A are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{40}$, $R_{42}$, and $R_{43}$ are each independently hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), or $R_{41}$ and $R_{42}$ taken together with the atoms to which they are attached join together to form a heteroaryl or heterocyclyl;
$R_{41}$ is hydrogen, $C_{1-6}$ alkyl, $C_{1-6}$ alkoxy, —S(=O)$_2$R$_{20}$, —C(=O)R, hydroxyalkyl, hydroxyl, —N($R_{13}R_{14}$), $R_{41}$ is absent if $L_{16}$ is N, or $R_{41}$ and $R_{42}$ taken together with the atoms to which they are attached join together to form a heteroaryl or heterocyclyl;
R is hydrogen, $C_{1-6}$ alkyl, cycloalkyl, aryl, heterocyclyl, heteroaryl, hydroxyalkyl, —N($R_{15}R_{16}$), or —S(=O)$_2$R$_{20}$;
$R_{39}$ is hydrogen, $C_{1-6}$ alkyl, or $C_{1-6}$ alkoxy;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and
$R_{15}$ and $R_{16}$ are each independently hydrogen, $C_{1-6}$ alkyl, cycloalkyl, aryl, heterocyclyl, heteroaryl, hydroxyalkyl, or alkylamino.

In certain aspects of Structure (VII), $R_1$ is hydrogen, cyano, $C_{1-6}$ alkyl, $C_{1-6}$ alkoxy, or —C(=O)N($R_{13}$)($R_{14}$).

In certain aspects of Structure (VII), $R_1$ is cyano.

In certain aspects of Structure (VII), $R_2$ is hydrogen or halo.

In certain aspects of Structure (VII), $R_2$ is hydrogen.

In certain aspects of Structure (VII), $R_3$ is hydrogen.

In certain aspects of Structure (VII), $R_{21}$ and $R_{22}$ are each independently hydrogen or $C_{1-6}$ alkyl.

In certain aspects of Structure (VII), $R_{21}$ and $R_{22}$ are each independently $C_{1-6}$ alkyl.

In certain aspects of Structure (VII), $R_{39}$ is hydrogen.

In certain aspects of Structure (VII), $R_{40}$ is hydrogen.

In certain aspects of Structure (VII), $L_{16}$ is N.

In certain aspects of Structure (VII), $L_{17}$ is N.

In certain aspects of Structure (VII), $L_{18}$ is CH.

In certain aspects of Structure (VII), $L_{18}$ is N.

In certain aspects of Structure (VII), A is N.

In certain aspects of Structure (VII), A is CH.

In certain aspects of Structure (VII), $R_{42}$ is $C_{1-6}$ alkyl.

In certain aspects of Structure (VII), $R_{41}$ is $C_{1-6}$ alkyl.

In certain aspects, the compounds of Structure (VII) have one of the following Structures (VII-C) or (VII-D):

(VII-C)

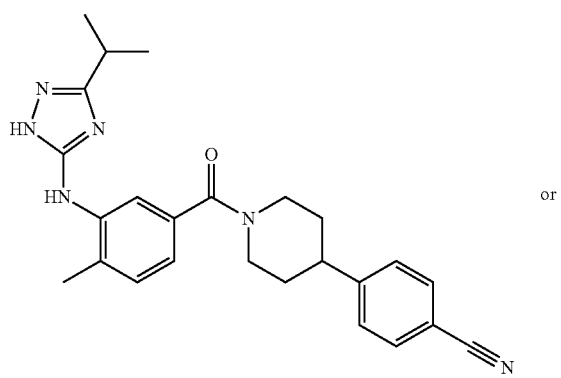

or or a pharmaceutically acceptable salt thereof.

Compounds of Structure (VIII)

In certain aspects, the compounds of Structure (VIII) have one of the following Structures (VIII-A), (VIII-B), or (VIII-C):

or a pharmaceutically acceptable salt thereof, wherein:

$L_{19}$ and A are each independently CH or N;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{39}$ is hydrogen, $C_{1-6}$ alkyl, or $C_{1-6}$ alkoxy;

$R_{44}$ and $R_{45}$ are each independently hydrogen, $C_{1-6}$ alkyl, $C_{1-6}$ alkoxy, cycloalkyl, hydroxyalkyl, aryl, heterocyclyl, heteroaryl, alkylamino, —S(=O)$_2$R$_{20}$, —C(=O)R, or —N($R_{13}R_{14}$); and $R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$; and $R_{15}$ and $R_{16}$ are each independently hydrogen, $C_{1-6}$ alkyl, cycloalkyl, aryl, heterocyclyl, heteroaryl, hydroxyalkyl, or alkylamino.

In certain aspects of Structure (VIII), $R_1$ is hydrogen, cyano, $C_{1-6}$ alkyl, $C_{1-6}$ alkoxy, or —C(=O)NN($R_{13}$)($R_{14}$).

In certain aspects of Structure (VIII), $R_1$ is cyano.

In certain aspects of Structure (VIII), $R_2$ is hydrogen or halo.

In certain aspects of Structure (VIII), $R_2$ is hydrogen.

In certain aspects of Structure (VIII), $R_3$ is hydrogen.

In certain aspects of Structure (VIII), $R_{21}$ and $R_{22}$ are each independently hydrogen or $C_{1-6}$ alkyl.

In certain aspects of Structure (VIII), $R_{21}$ and $R_{22}$ are each independently $C_{1-6}$ alkyl.

In certain aspects of Structure (VIII), $R_{39}$ is hydrogen.

In certain aspects of Structure (VIII), $L_{19}$ is N.

In certain aspects of Structure (VIII), A is N.

In certain aspects of Structure (VIII), A is CH.

In certain aspects, the compounds of Structure (VIII) have the following Structure (VIII-D):

or a pharmaceutically acceptable salt thereof.

In various aspects, compounds of formula IX are provided:

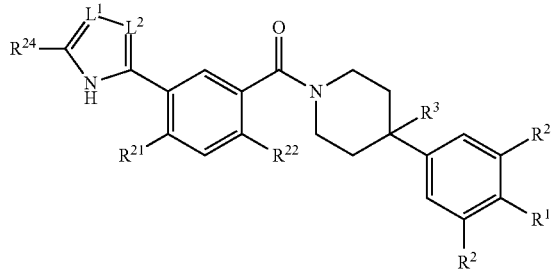

or a pharmaceutically acceptable salt thereof, wherein:
$R^1$ is H, —CN, halogen, $C_1$-$C_4$ straight or branched alkyl, —O—($C_3$-$C_5$ cycloalkyl) or —O—($C_1$-$C_4$ straight or branched alkyl) wherein:
  $C_3$-$C_5$ cycloalkyl optionally includes an oxygen or nitrogen heteroatom; and
  when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH, or halogen;
$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;
$R^{22}$ is H, halogen, or $C_1$-$C_2$ alkyl;
$R^{24}$ is H, $C_1$-$C_4$ straight or branched alkyl, —($C_1$-$C_4$ alkyl)$_t$-OH, —($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
  t is 0 or 1;
  the $C_3$-$C_5$ cycloalkyl optionally includes an oxygen or nitrogen heteroatom;
$L^1$ is $CR^{23}$ or N;
$L^2$ is CH or N;
at least one of $L^1$ or $L^2$ is N; and
$R^{23}$ is H or $C_1$-$C_4$ straight or branched alkyl.

In some aspects of Structure (IX), $R^{24}$ is $C_1$-$C_4$ straight or branched alkyl, —($C_1$-$C_4$ alkyl)$_t$-O—($C_1$-$C_4$ straight or branched alkyl) wherein t is 0 or 1.

In some aspects of Structure (IX), $R^{21}$ is halogen, $C_1$-$C_4$ straight or branched alkyl, $C_3$-$C_5$ cycloalkyl wherein the $C_3$-$C_5$ cycloalkyl optionally includes an oxygen or nitrogen heteroatom, —S(O)$_u$—($C_1$-$C_4$ straight or branched alkyl) wherein u is 0 or 2, or —S(O)$_u$—($C_3$-$C_5$ cycloalkyl) wherein u is 0 or 2;

In some aspects of Structure (IX), $R^3$ is H or halogen.

In some aspects of Structure (IX), $R^1$ is halogen, —CN or $C_1$-$C_2$ haloalkyl.

In some aspects of Structure (IX), both $L^1$ and $L^2$ are N.

In some aspects of Structure (IX), $R^{21}$ is $C_1$-$C_2$ alkyl or $C_3$-$C_5$ cycloalkyl and $R^{22}$ is $C_1$-$C_2$ alkyl.

In some aspects of Structure (IX), $R^{21}$ is $C_3$-$C_5$ cycloalkyl and $R^{22}$ is $C_1$-$C_2$ alkyl.

In some aspects of Structure (IX), $R^{24}$ is —($C_1$-$C_2$ alkyl)$_t$-O—($C_1$-$C_2$ alkyl) wherein t is 0 or 1.

In some aspects of Structure (IX), $R^{21}$ is $C_3$-$C_5$ cycloalkyl, $R^{22}$ is $C_1$-$C_2$ alkyl and $R^{24}$ is $C_1$-$C_2$ alkyl.

In some aspects of Structure (IX), $R^{21}$ is cyclobutyl, $R^{22}$ is $C_1$-$C_2$ alkyl and $R^{24}$ is $C_1$-$C_2$ alkyl.

In some aspects of Structure (IX), $R^{21}$ is cyclobutyl.
In some aspects of Structure (IX), $R^3$ is H or F.
In some aspects of Structure (IX), $R^1$ is —CN.
In some aspects of Structure (IX), $R^1$ is —CF$_3$.
In some aspects of Structure (IX), $R^{22}$ is H, methyl or ethyl.
In some aspects of Structure (IX), $R^{22}$ is H.
In some aspects of Structure (IX), $R^{22}$ is methyl.

In some aspects of Structure (IX), $R^1$ is —CN, each $R^2$ is hydrogen, $R^3$ is H or F, $R^{21}$ is $C_3$-$C_4$ cycloalkyl, $R^{22}$ is methyl, $L^1$ and $L^2$ are N, and $R^{24}$ is methyl, ethyl, hydroxymethyl, methoxymethyl, 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ and $L^2$ are N, and $R^{24}$ is methoxy or ethoxy.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is CH, $L^2$ is N, and $R^{24}$ is methyl, ethyl, hydroxymethyl, methoxymethyl, or 2-methoxyethyl.

In some aspects of Structure (IX), $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.

In some aspects of Structure (IX), compounds have a structure selected from the group consisting of:

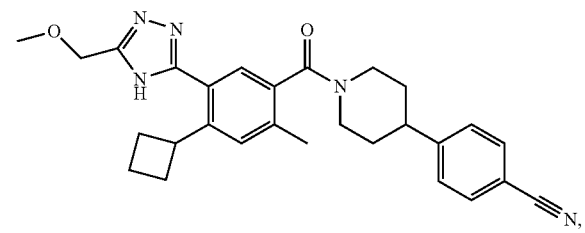

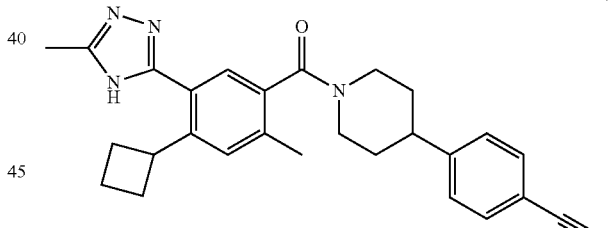

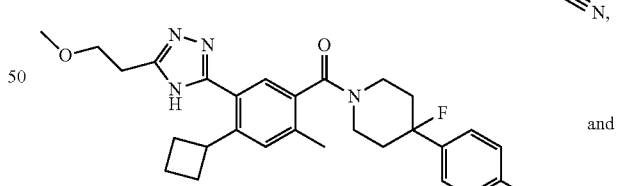

and

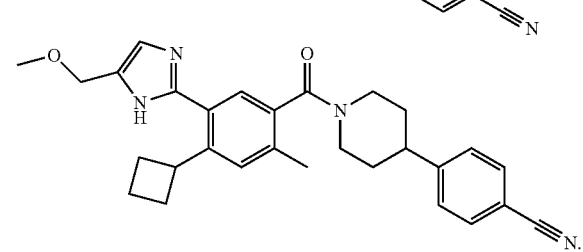

In various aspects, compounds of Structure (X) are provided:

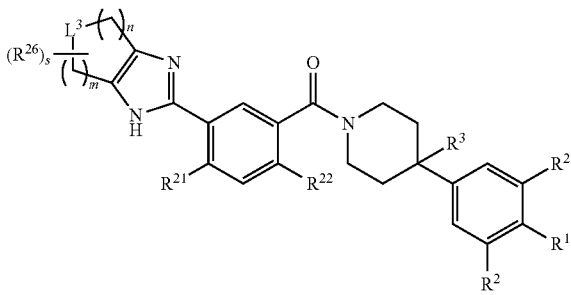

or a pharmaceutically acceptable salt thereof, wherein:
R$^1$ is H, —CN, halogen, C$_1$-C$_4$ straight or branched alkyl, —O—(C$_3$-C$_5$ cycloalkyl), —O—(C$_1$-C$_4$ straight or branched alkyl) wherein:
  the C$_3$-C$_5$ cycloalkyl optionally includes an oxygen or nitrogen heteroatom; and
  when R$^1$ is not H, —CN or halogen, it is optionally substituted with one or more halogens;
each R$^2$ is independently hydrogen, halogen or C$_1$-C$_4$ straight or branched alkyl;
R$^3$ is H, —OH or halogen;
L$^3$ is C(R$^{60}$)$_2$, O or NR$^{50}$;
each R$^{60}$ is independently H, —OH, —CN, —O$_t$—(C$_3$-C$_5$ cycloalkyl), —O—(C$_1$-C$_4$ straight or branched alkyl), or —C(O)—N(R$^{601}$)$_2$ wherein:
  t is 0 or 1, and
  the C$_3$-C$_5$ cycloalkyl optionally includes an oxygen or nitrogen heteroatom;
each R$^{50}$ is independently H, —C(O)—O$_t$—(C$_1$-C$_4$ straight or branched alkyl), —C(O)—O$_t$—(C$_3$-C$_5$ cyclic alkyl), —C$_3$-C$_5$ cyclic alkyl optionally containing an oxygen or nitrogen heteroatom, —C(O)—N(R$^{501}$)$_2$, C$_1$-C$_4$ straight or branched alkyl wherein:
  t is 0 or 1, and
  the C$_3$-C$_5$ cycloalkyl optionally includes an oxygen or nitrogen heteroatom;
n is 1, 2 or 3;
m is 1 or 2;
R$^{21}$ is H, halogen, C$_1$-C$_4$ straight or branched alkyl, C$_3$-C$_5$ cycloalkyl wherein the C$_3$-C$_5$ cycloalkyl optionally includes an oxygen or nitrogen heteroatom
R$^{22}$ is H, halogen, C$_1$-C$_2$ alkyl;
each R$^{26}$ is independently —OH, —CN, halogen, C$_1$-C$_4$ straight or branched alkyl, —(C$_1$-C$_4$ alkyl)$_t$-O$_t$—(C$_3$-C$_5$ cycloalkyl), —(C$_1$-C$_4$ alkyl)$_t$-O—(C$_1$-C$_4$ straight or branched alkyl), —C(O)—O$_t$—(C$_1$-C$_4$ alkyl), or —C(O)—N(R$^{501}$)$_2$ wherein:
  t is 0 or 1, and
  the C$_3$-C$_5$ cycloalkyl optionally includes an oxygen or nitrogen heteroatom;
s is 0, 1 or 2;
each R$^{601}$ and R$^{501}$ is independently H or C$_1$-C$_4$ straight or branched alkyl; and
wherein two of R$^{26}$, R$^{60}$, R$^{50}$, R$^{501}$ and R$^{601}$ optionally join to form a ring wherein the two of R$^{26}$, R$^{60}$, R$^{50}$, R$^{501}$ and R$^{601}$ may be two R$^{26}$, two R$^{60}$, two R$^{50}$, two R$^{501}$ or two R$^{601}$.

In some aspects of Structure (X), R$^{21}$ is halogen, C$_1$-C$_4$ straight or branched alkyl or C$_3$-C$_5$ cycloalkyl.
In some aspects of Structure (X), R$^3$ is H or halogen.
In some aspects of Structure (X), R$^1$ is —CN or C$_1$-C$_2$ haloalkyl.

In some aspects of Structure (X), R$^3$ is H or F.
In some aspects of Structure (X), R$^1$ is —CN.
In some aspects of Structure (X), R$^1$ is —CF$_3$.
In some aspects of Structure (X), n is 1.
In some aspects of Structure (X), n is 2.
In some aspects of Structure (X), m is 1
In some aspects of Structure (X), m is 2.
In some aspects of Structure (X), R$^{21}$ is C$_1$-C$_2$ alkyl or C$_3$-C$_5$ cycloalkyl and R$^{22}$ is C$_1$-C$_2$ alkyl.
In some aspects of Structure (X), R$^{21}$ is C$_3$-C$_5$ cycloalkyl and R$^{22}$ is C$_1$-C$_2$ alkyl.
In some aspects of Structure (X), n is 2, m is 1, L$^3$ is —N—C(O)—O—(C$_1$-C$_2$ alkyl).
In some aspects of Structure (X), L$^3$ is NR$^{50}$; R$^{50}$ is C$_1$-C$_2$ alkyl; R$^{21}$ is cyclobutyl; R$^{22}$ is H or methyl; R$^3$ is H; R$^1$ is —CN; m is 2 and n is 1 or 2.
In some aspects of Structure (X), n is 2, m is 1, L$^3$ is O and s is 0.
In some aspects of Structure (X), R$^{22}$ is H, methyl or ethyl.
In some aspects of Structure (X), R$^{22}$ is methyl.
In some aspects of Structure (X), R$^{22}$ is H.
In some aspects of Structure (X), R$^1$ is —CN, each R$^2$ is H, R$^3$ is H or F, R$^{21}$ is C$_3$-C$_4$ cycloalkyl, R$^{22}$ is methyl, n is 2 and L$^3$ is NR$^{50}$ where R$^{50}$ is methyl or ethyl.
In some aspects of Structure (X), R$^1$ is —CN, each R$^2$ is H, R$^3$ is H or F, R$^{21}$ is C$_3$-C$_4$ cycloalkyl, R$^{22}$ is methyl, n is 2 and L$^3$ is O.
In some aspects of Structure (X), the compound has a structure selected from the group consisting of:

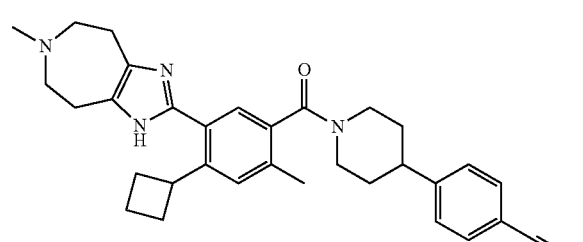

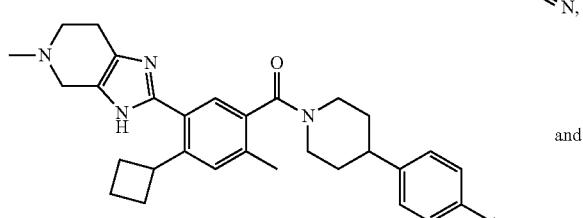

and

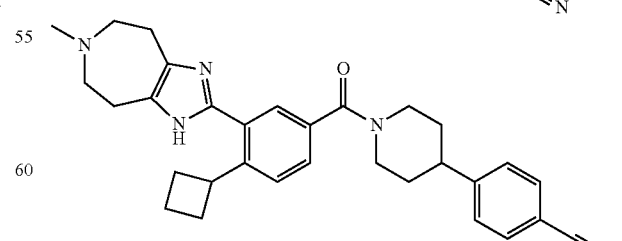

In various aspects, compounds of Structure (XI) are provided:

(XI)

[Structure XI shown]

or a pharmaceutically acceptable salt thereof, wherein:
  $R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
    the $C_3$-$C_5$ cycloalkyl optionally includes an oxygen or nitrogen heteroatom; and
    when $R^1$ is not H, —CN or halogen, it is optionally substituted with one or more halogens;
  each $R^2$ is independently H, halogen or $C_1$-$C_4$ straight or branched alkyl;
  $R^3$ is H, —OH, or halogen;
  $R^{21}$ is cyclobutyl, azetidin-1-yl, or cyclopropyl;
  $R^{22}$ is H, halogen, $C_1$-$C_2$ alkyl; and
  $R^{351}$ is $C_1$-$C_2$ alkyl or $C_2$—O—($C_1$ or $C_2$ alkyl).

In some aspects of Structure (XI), $R^3$ is H or halogen.
In some aspects of Structure (XI), $R^1$ is halogen, —CN or $C_1$-$C_2$ haloalkyl.
In some aspects of Structure (XI), $R^{21}$ is $C_3$-$C_4$ cycloalkyl and $R^{22}$ is $C_1$-$C_2$ alkyl.
In some aspects of Structure (XI), $R^{21}$ is cyclobutyl and $R^{22}$ is $C_1$-$C_2$ alkyl.
In some aspects of Structure (XI), $R^{21}$ is cyclobutyl.
In some aspects of Structure (XI), $R^3$ is H or F.
In some aspects of Structure (XI), $R^1$ is —CN.
In some aspects of Structure (XI), $R^1$ is —CF$_3$.
In some aspects of Structure (XI), $R^{22}$ is H, methyl or ethyl.
In some aspects of Structure (XI), $R^{22}$ is H.
In some aspects of Structure (XI), $R^{22}$ is methyl.

In some aspects of Structure (XI), $R^1$ is —CN, each $R^2$ is H, $R^3$ is H or F, $R^{21}$ is cyclobutyl, $R^{22}$ is methyl and $R^{351}$ is methyl or ethyl.

In some aspects of Structure (XI), the compound has a structure selected from the group consisting of:

[Two compound structures shown] and

In certain aspects, the present disclosure provides compounds having any one of the structures found in Table 1. According to the present disclosure, the compounds of Table 1 are inhibitors of fatty acid synthase.

Synthesis of Compounds

Also described herein are methods of synthesizing the compounds of the present disclosure. Compounds of the present disclosure can be synthesized as indicated in SYNTHETIC SCHEMES 1-13 below.

Scheme 1

[Reaction scheme showing: piperidinone with ArX, THF, BuLi → alcohol intermediate; then DAST or Deoxo-Fluor ($R_3$ = F) → fluoro intermediate; then Deprotection (TFA if P = Boc or H$_2$, Pd/C if P = Cbz) → HN intermediate; then coupling to final product. Alternative pathway with POCl$_3$ ($R_3$ = OH) and Deprotection.]

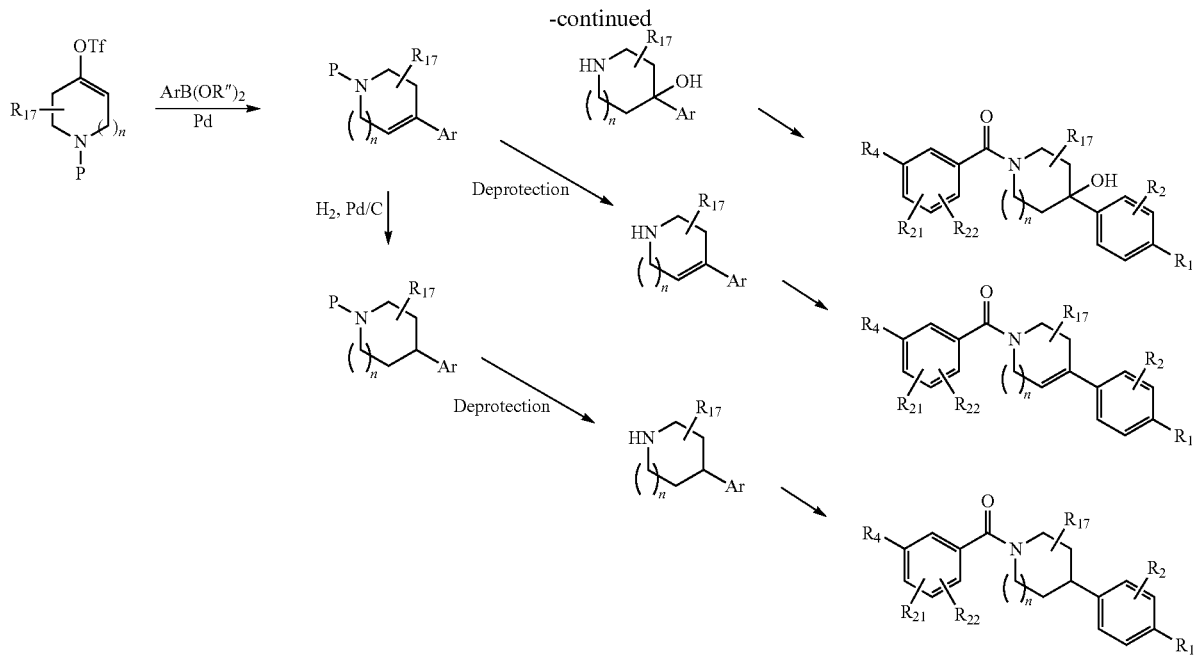

-continued

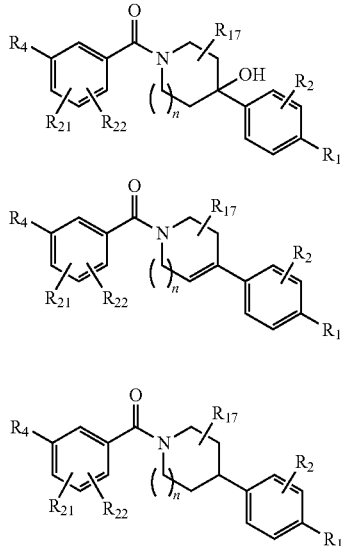

wherein:

R″ is hydrogen or alkyl;

$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;

q is 0, 1, 2, 3, or 4;

$R_{20}$ is hydrogen or $C_{1-6}$ alkyl, $C_{1-6}$ alkoxy, or —N($R_{13}$)($R_{14}$);

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino; and $R_{17}$ is hydrogen or alkyl.

Scheme 2

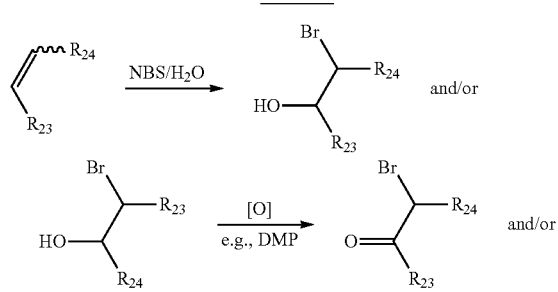

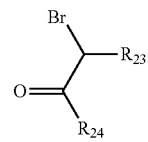

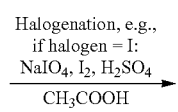

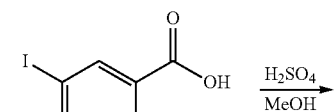

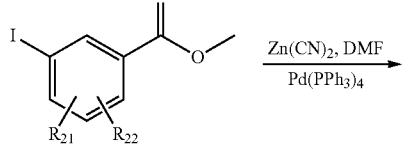

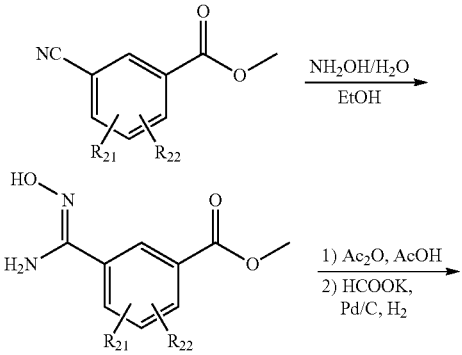

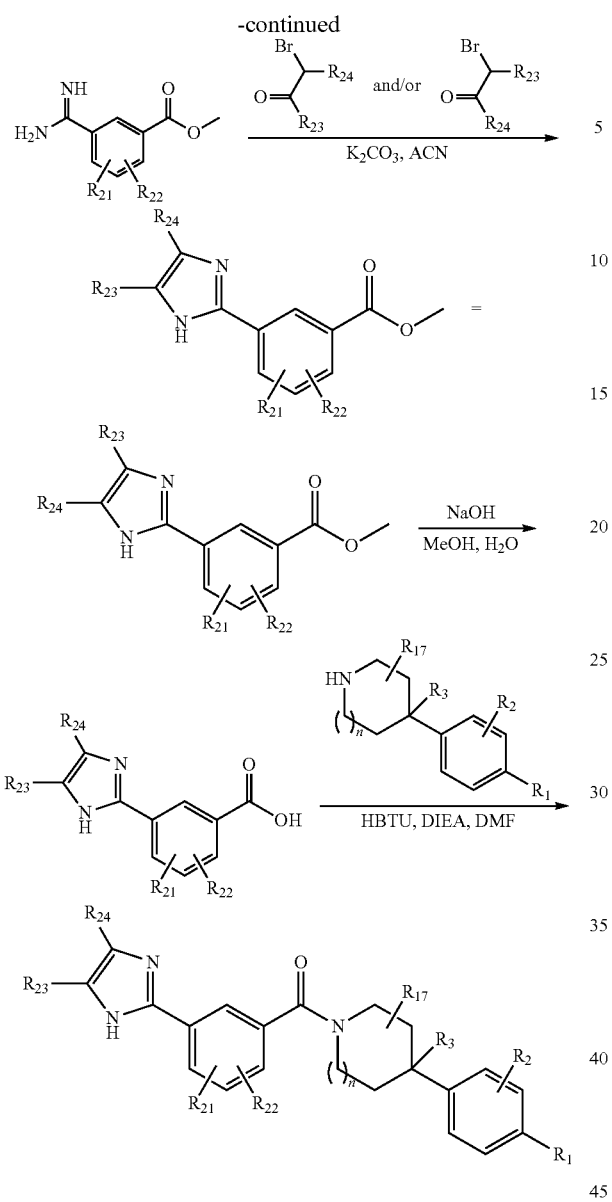

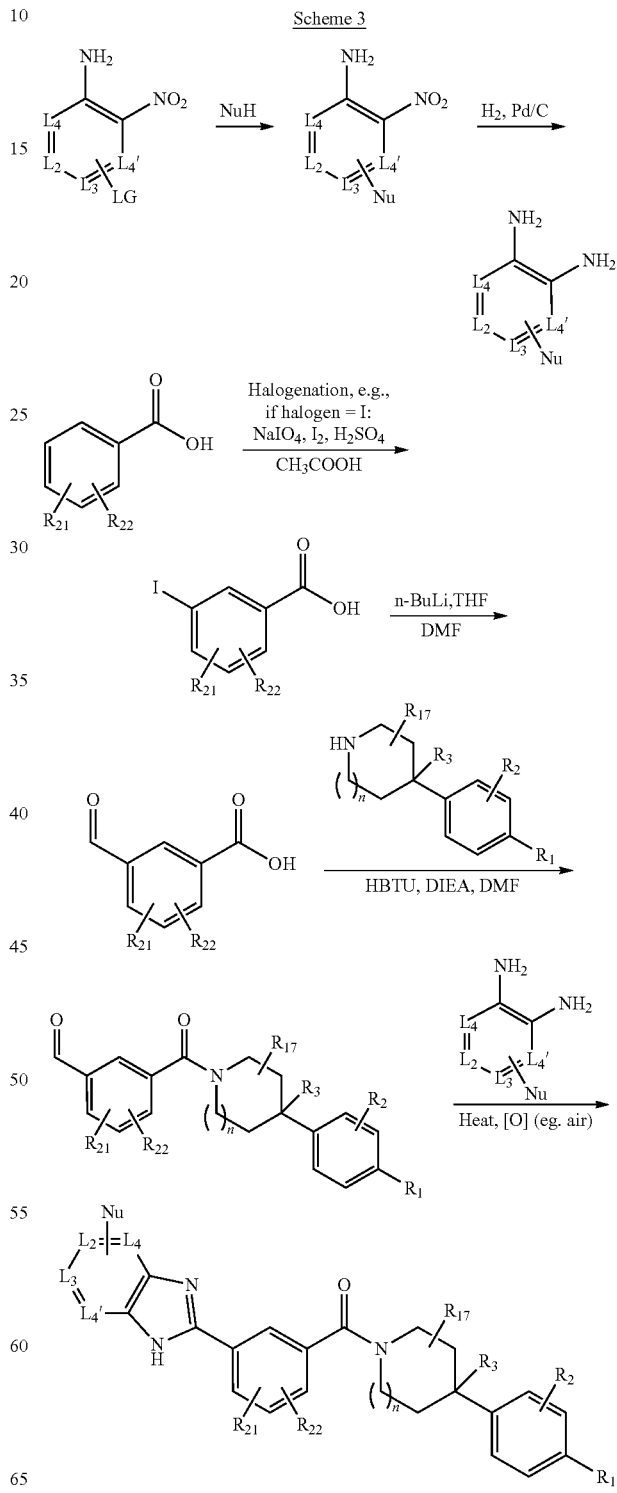

the atoms to which they are attached join together to form a heterocyclyl, heteroaryl, or cycloalkyl; and $R_{24}$ is hydrogen, $-N(R_{13})(R_{14})$, $C_{1-6}$ alkyl, $C_{1-6}$ alkoxy, $-(C_{1-6}$ alkoxy)(heterocyclyl), heterocyclyl, or $R_{23}$ and $R_{24}$ taken together with the atoms to which they are attached join together to form a heterocyclyl, heteroaryl, or cycloalkyl.

wherein:
$R_1$ is hydrogen, cyano, halo, $C_{1-6}$ alkyl, $C_{1-6}$ alkoxy, $-C(=O)N(R_{13})(R_{14})$, $-(CH_2)_qC(=O)N(R_{13})(R_{14})$, $CF_3$, $-OCF_3$, or $-S(=O)_2R_{20}$;

q is 0, 1, 2, 3, or 4;

$R_{20}$ is hydrogen or $C_{1-6}$ alkyl, $C_{1-6}$ alkoxy, or $-N(R_{13})(R_{14})$;

$R_2$ is hydrogen, halo, $C_{1-6}$ alkoxy, or $C_{1-6}$ alkyl;

$R_3$ is hydrogen, hydroxyl, halo, $C_{1-6}$ alkyl, or $C_{1-6}$ alkoxy;

$R_{21}$ and $R_{22}$ are each independently hydrogen, halo, cyano, $C_{1-6}$ alkyl, $C_{1-6}$ alkoxy, $CF_3$, $-OCF_3$, or $-S(=O)_2R_{20}$;

$R_{13}$ and $R_{14}$ are each independently hydrogen, $C_{1-6}$ alkyl, cycloalkyl, aryl, heterocyclyl, heteroaryl, hydroxyalkyl, alkylamino, $-N(R_{15}R_{16})$, or $-S(=O)_2R_{20}$;

$R_{15}$ and $R_{16}$ are each independently hydrogen, $C_{1-6}$ alkyl, cycloalkyl, aryl, heterocyclyl, heteroaryl, hydroxyalkyl, or alkylamino;

$R_{23}$ is hydrogen, $-N(R_{13})(R_{14})$, $C_{1-6}$ alkyl, $C_{1-6}$ alkoxy, is absent if $L_1$ is N, or $R_{23}$ and $R_{24}$ taken together with wherein:
LG is a leaving group;
Nu is a nucleophile;
$L_2$, $L_3$, $L_4$, and $L_{4'}$ are each independently CH or N;
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, cycloalkyl, aryl, heterocyclyl, heteroaryl, hydroxyalkyl, or alkylamino; and
$R_{17}$ is hydrogen or alkyl.

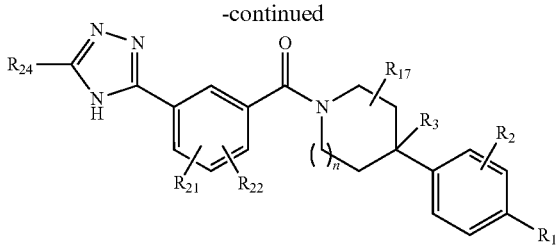

wherein:
$R_1$ is hydrogen, cyano, halo, $C_{1-6}$ alkyl, $C_{1-6}$ alkoxy, —C(=O)N($R_{13}$)($R_{14}$), —(CH$_2$)$_q$C(=O)N($R_{13}$)($R_{14}$), CF$_3$, —OCF$_3$, or —S(=O)$_2$R$_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, CF$_3$, —OCF$_3$, or —S(=O)$_2$R$_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)$_2$R$_{20}$;
$R_{15}$ and $R_{16}$ are each independently hydrogen, $C_{1-6}$ alkyl, cycloalkyl, aryl, heterocyclyl, heteroaryl, hydroxyalkyl, or alkylamino;
$R_{17}$ is hydrogen or alkyl; and
$R_{24}$ is hydrogen, —N($R_{13}$)($R_{14}$), $C_{1-6}$ alkyl, $C_{1-6}$ alkoxy, —(C$_{1-6}$ alkoxy)(heterocyclyl), or heterocyclyl.

Scheme 4

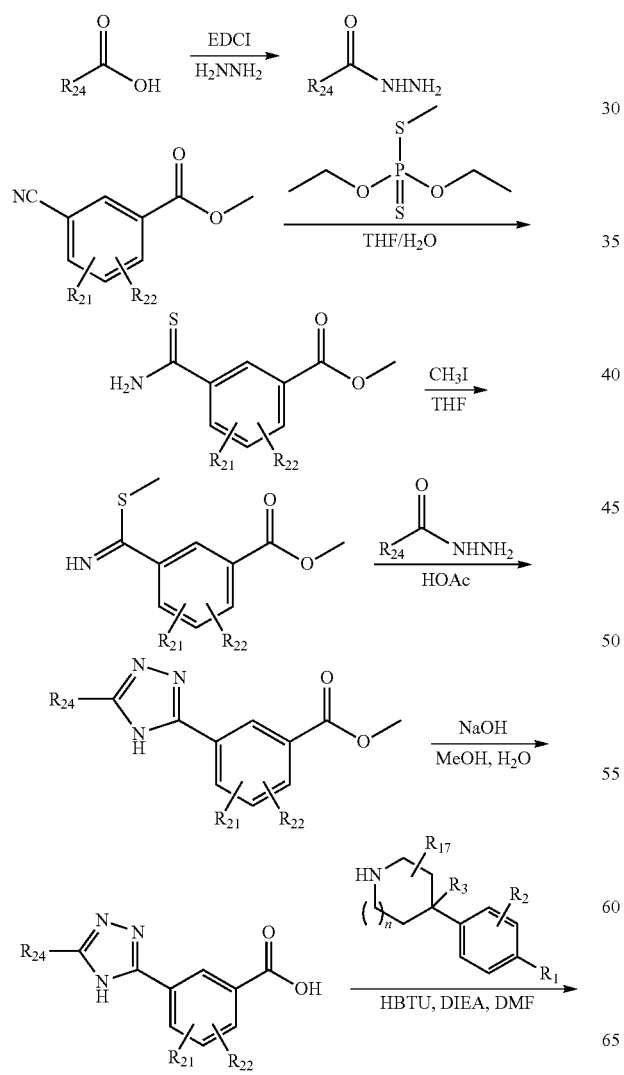

Scheme 5

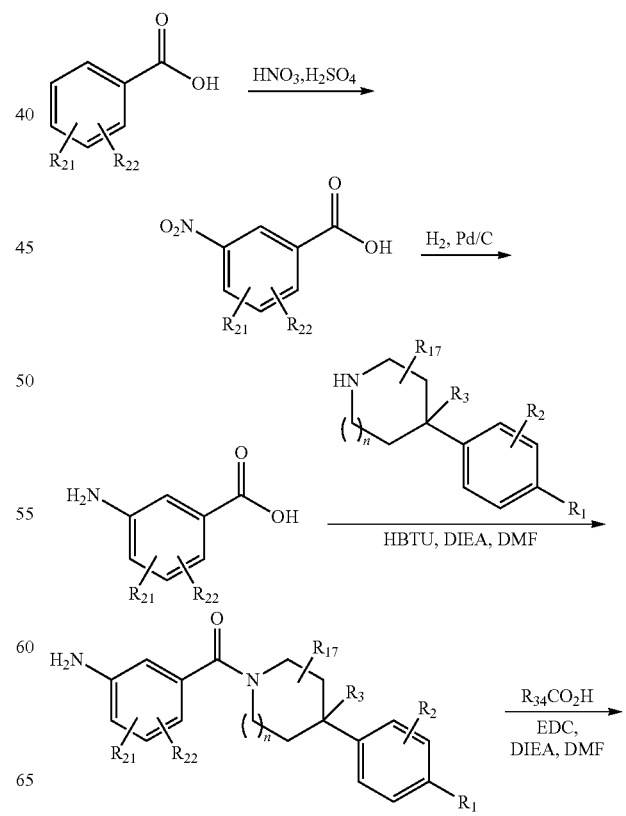

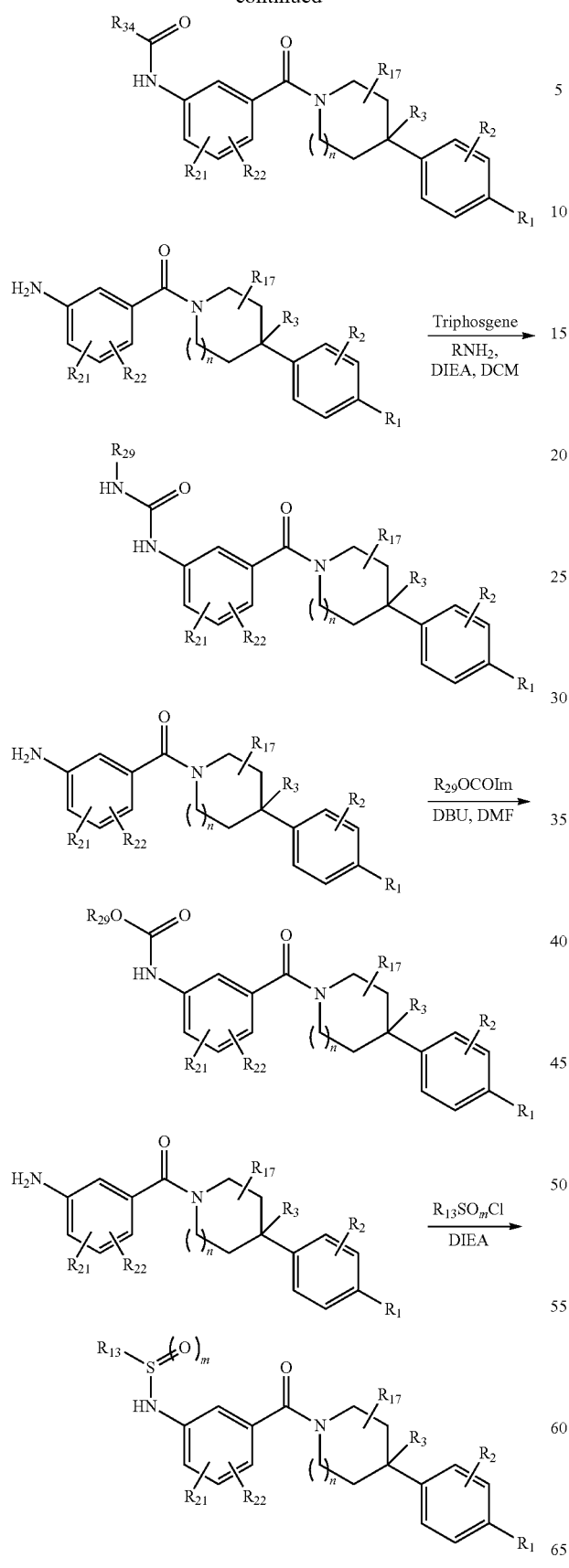
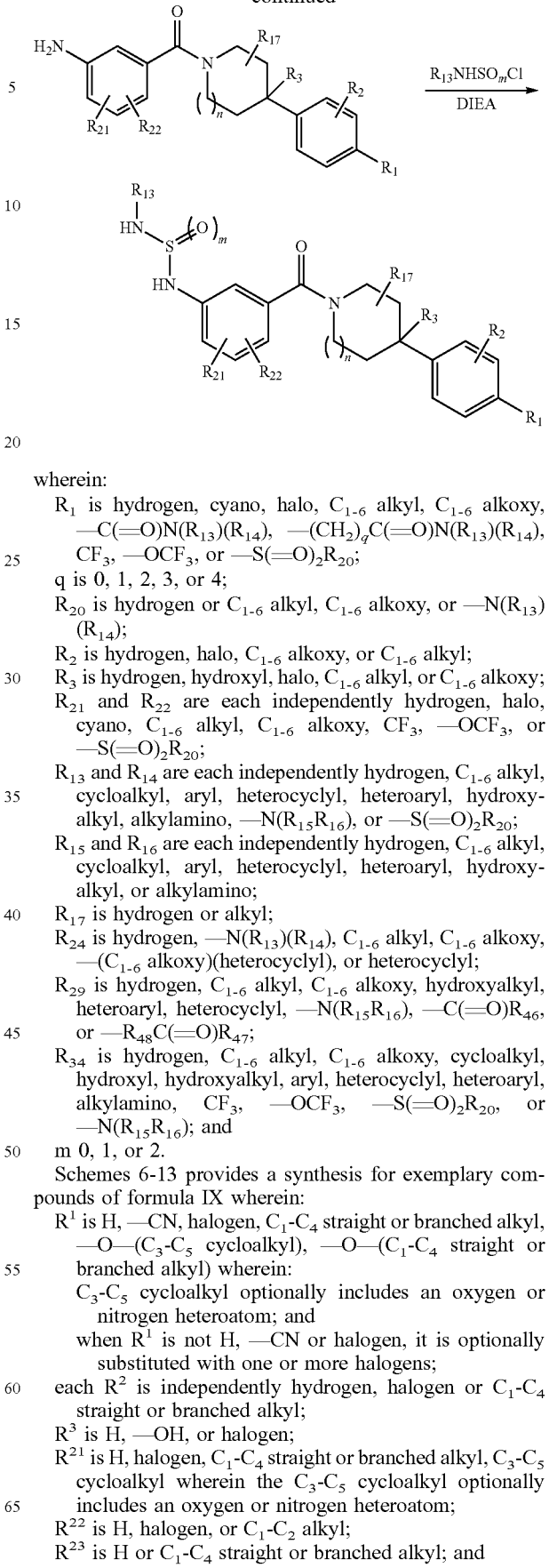

wherein:
R₁ is hydrogen, cyano, halo, $C_{1-6}$ alkyl, $C_{1-6}$ alkoxy, —C(=O)N($R_{13}$)($R_{14}$), —(CH₂)$_q$C(=O)N($R_{13}$)($R_{14}$), $CF_3$, —$OCF_3$, or —S(=O)₂$R_{20}$;
q is 0, 1, 2, 3, or 4;
$R_{20}$ is hydrogen or $C_{1-6}$ alkyl, $C_{1-6}$ alkoxy, or —N($R_{13}$)($R_{14}$);
$R_2$ is hydrogen, halo, $C_{1-6}$ alkoxy, or $C_{1-6}$ alkyl;
$R_3$ is hydrogen, hydroxyl, halo, $C_{1-6}$ alkyl, or $C_{1-6}$ alkoxy;
$R_{21}$ and $R_{22}$ are each independently hydrogen, halo, cyano, $C_{1-6}$ alkyl, $C_{1-6}$ alkoxy, $CF_3$, —$OCF_3$, or —S(=O)₂$R_{20}$;
$R_{13}$ and $R_{14}$ are each independently hydrogen, $C_{1-6}$ alkyl, cycloalkyl, aryl, heterocyclyl, heteroaryl, hydroxyalkyl, alkylamino, —N($R_{15}R_{16}$), or —S(=O)₂$R_{20}$;
$R_{15}$ and $R_{16}$ are each independently hydrogen, $C_{1-6}$ alkyl, cycloalkyl, aryl, heterocyclyl, heteroaryl, hydroxyalkyl, or alkylamino;
$R_{17}$ is hydrogen or alkyl;
$R_{24}$ is hydrogen, —N($R_{13}$)($R_{14}$), $C_{1-6}$ alkyl, $C_{1-6}$ alkoxy, —($C_{1-6}$ alkoxy)(heterocyclyl), or heterocyclyl;
$R_{29}$ is hydrogen, $C_{1-6}$ alkyl, $C_{1-6}$ alkoxy, hydroxyalkyl, heteroaryl, heterocyclyl, —N($R_{15}R_{16}$), —C(=O)$R_{46}$, or —$R_{48}$C(=O)$R_{47}$;
$R_{34}$ is hydrogen, $C_{1-6}$ alkyl, $C_{1-6}$ alkoxy, cycloalkyl, hydroxyl, hydroxyalkyl, aryl, heterocyclyl, heteroaryl, alkylamino, $CF_3$, —$OCF_3$, —S(=O)₂$R_{20}$, or —N($R_{15}R_{16}$); and
m 0, 1, or 2.

Schemes 6-13 provides a synthesis for exemplary compounds of formula IX wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
$C_3$-$C_5$ cycloalkyl optionally includes an oxygen or nitrogen heteroatom; and
when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH, or halogen;
$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;
$R^{22}$ is H, halogen, or $C_1$-$C_2$ alkyl;
$R^{23}$ is H or $C_1$-$C_4$ straight or branched alkyl; and $R^{24}$ is H, $C_1$-$C_4$ straight or branched alkyl, —($C_1$-$C_4$ alkyl)$_t$-OH—($C_1$-$C_4$ alkyl)$_t$-O$_t$—($C_3$-$C_5$ cycloalkyl), or —($C_1$-$C_4$ alkyl)$_t$-O—($C_1$-$C_4$ straight or branched alkyl) wherein:
t is 0 or 1; and
the $C_3$-$C_5$ cycloalkyl optionally includes an oxygen or nitrogen heteroatom.
Scheme 6
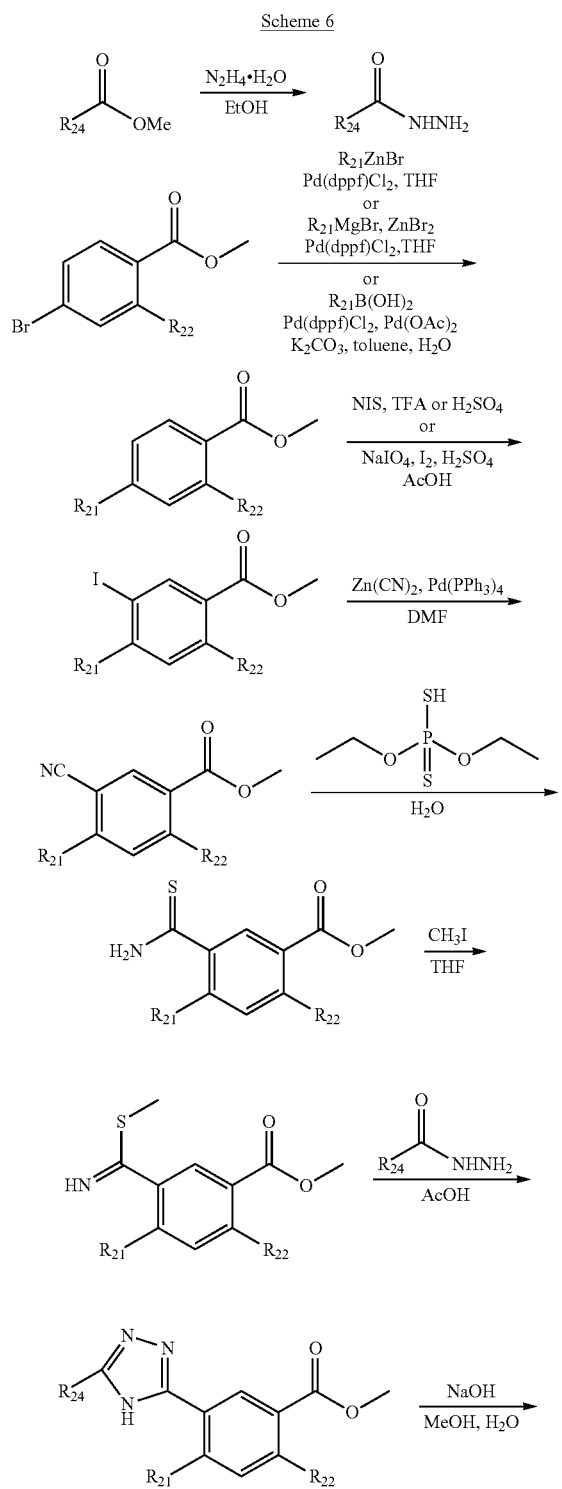
Scheme 7
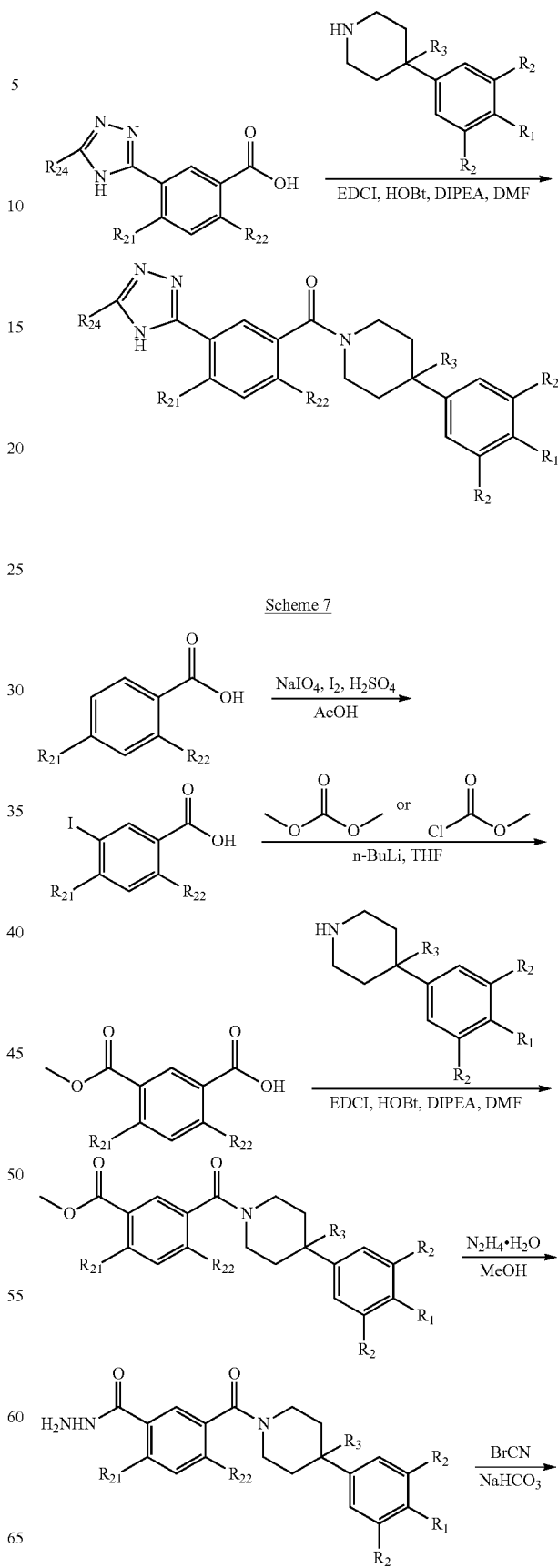

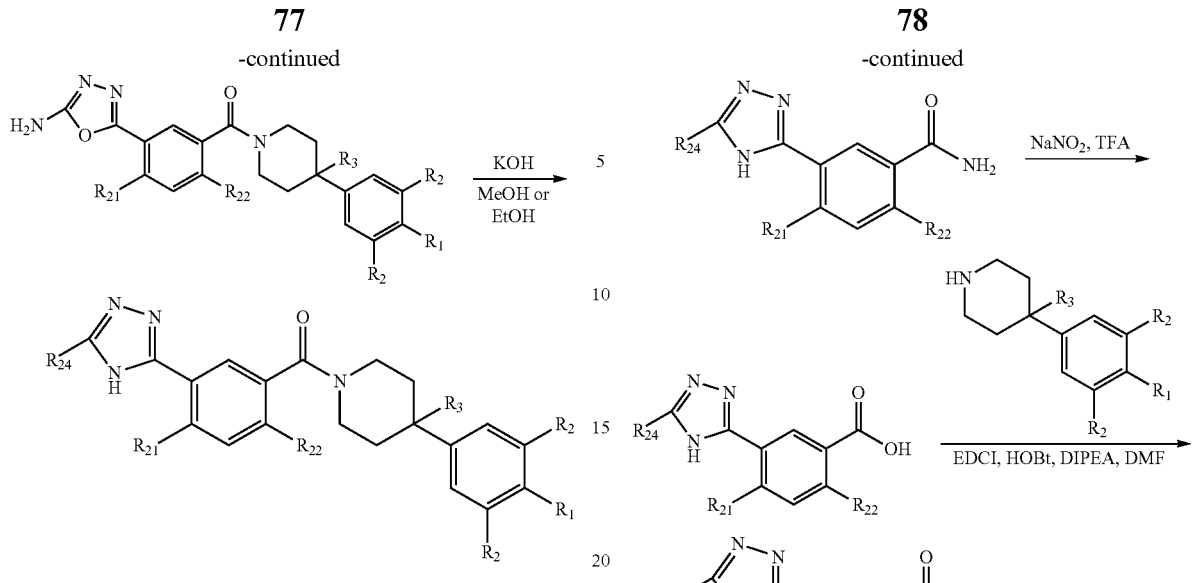
Scheme 8
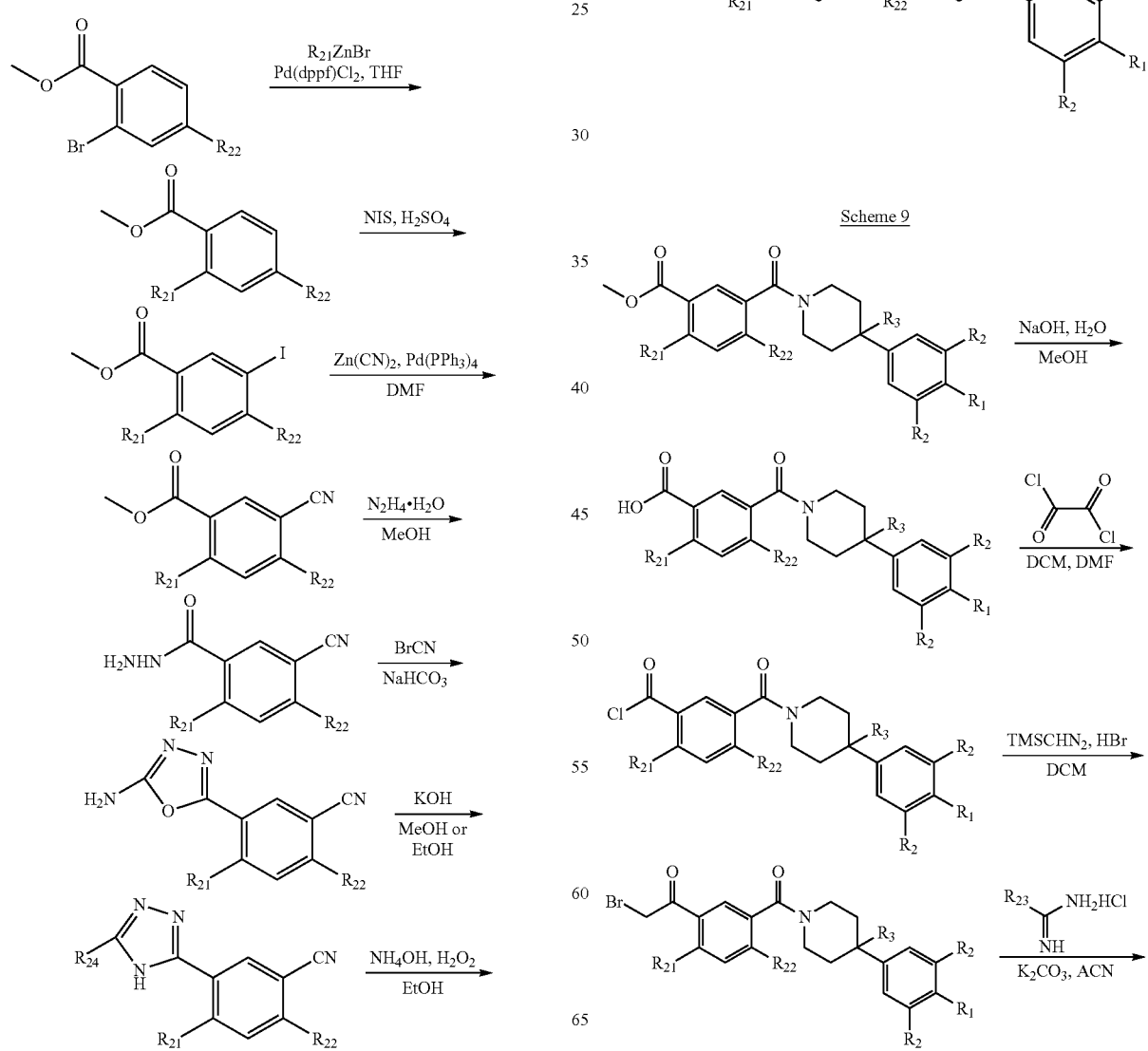
Scheme 9

79 80
-continued -continued
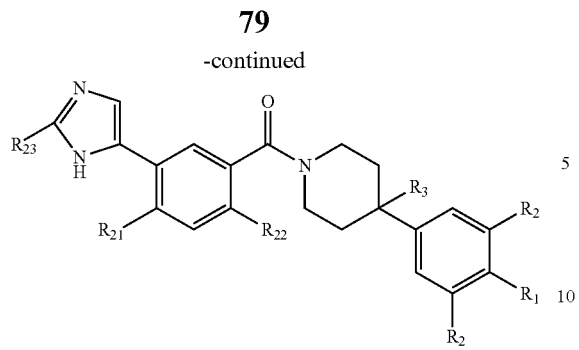
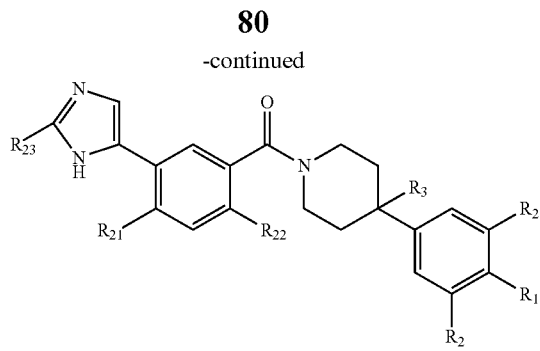
Scheme 10
Scheme 11
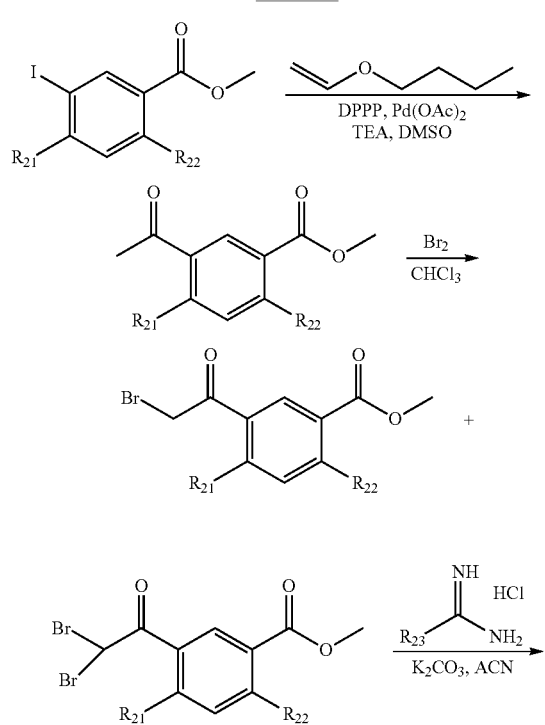
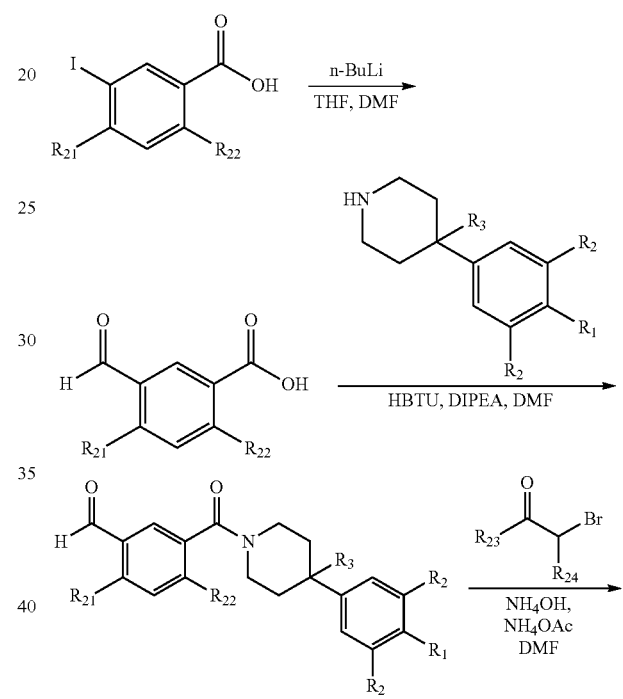
Scheme 12
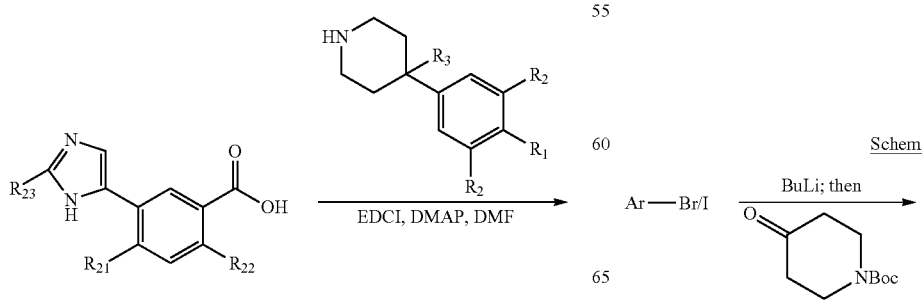

81

-continued

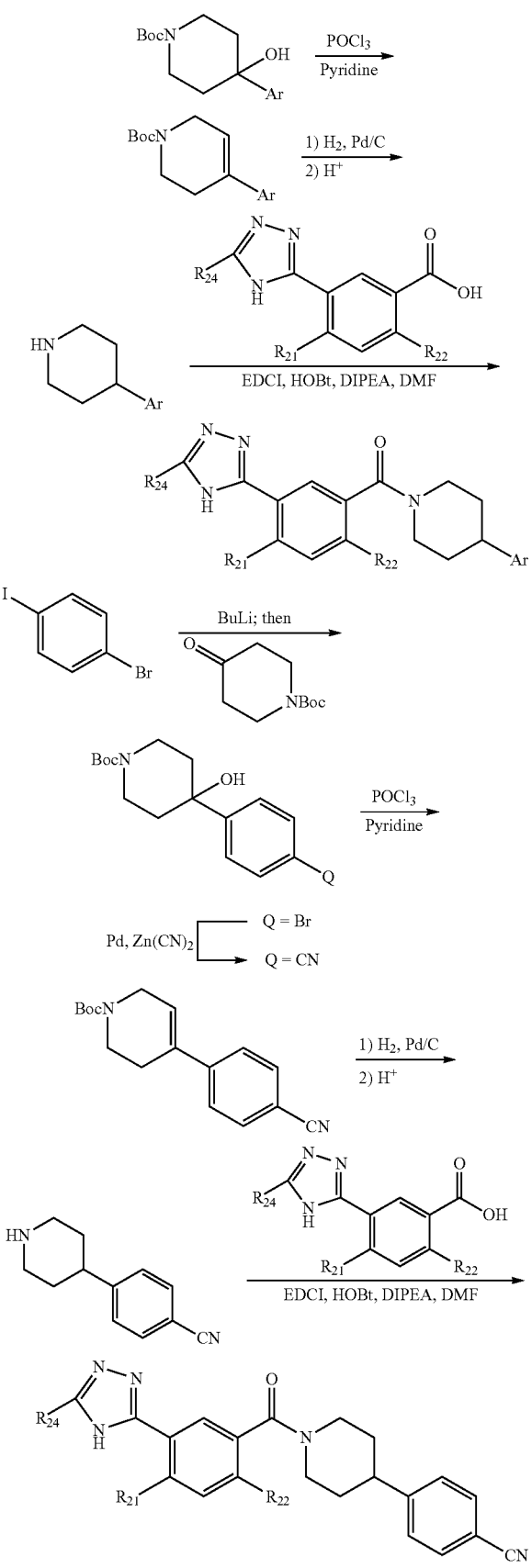

82

Scheme 13

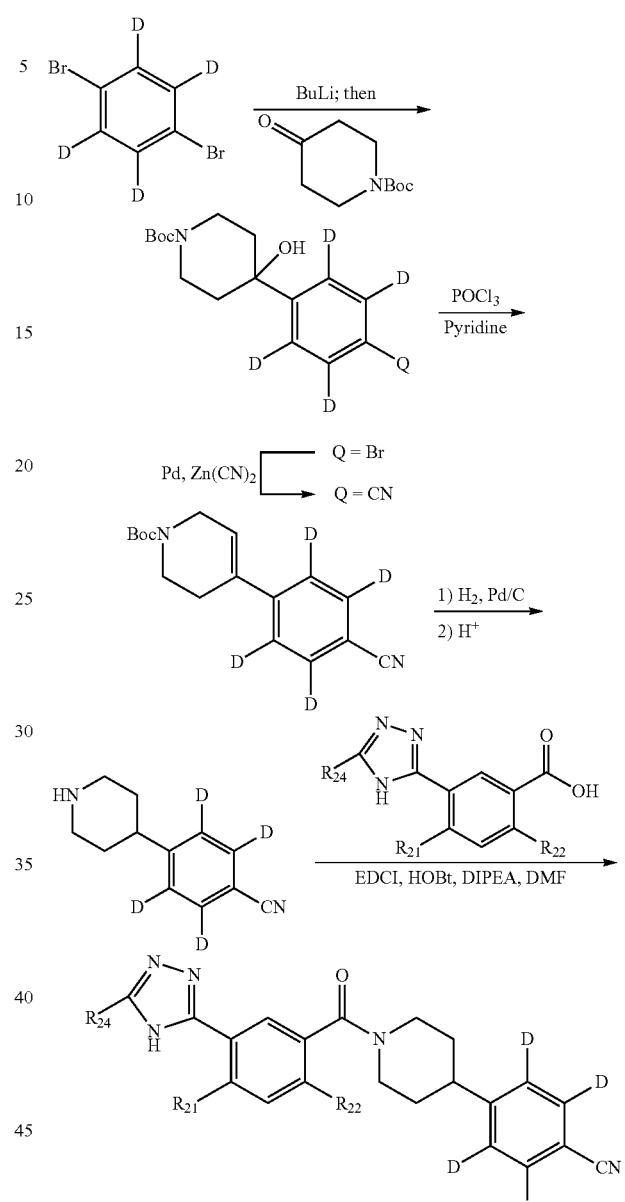

Additional methods for producing particular compounds according to the present disclosure are provided in the EXAMPLES. One skilled in the art will recognize that other compounds of structures can be made by modifications to the specifically disclosed schemes employing methods known to those of skill in the art. Additional examples can be found in Table 1.

Many such techniques are well known in the art. However, many of the known techniques are elaborated in Compendium of Organic Synthetic Methods (Vol. 1, 1971; Vol. 2, 1974; Vol. 3, 1977; Vol. 4, 1980; Vol. 5, 1984; and Vol. 6 as well as March in Advanced Organic Chemistry (1985); Comprehensive Organic Synthesis. Selectivity, Strategy & Efficiency in Modern Organic Chemistry. In 9 Volumes (1993); Advanced Organic Chemistry Part B: Reactions and Synthesis, Second Edition (1983); Advanced Organic Chemistry, Reactions, Mechanisms, and Structure, Second Edition (1977); Protecting Groups in Organic Synthesis, Second Edition; and Comprehensive Organic Transformations (1999).

Viral Infection Pathways

The host cell targets inhibited by the present compounds and methods play a role in the viral replication and/or infection pathways. Targeting of such host cell targets modulates the replication and/or infection pathways of the viruses. In preferred aspects the identified host cell targets are directly or indirectly modulated using the compositions of the present disclosure. The modulation of such host cell targets can also be performed by targeting entities in the upstream or downstream signaling pathways of the host cell targets.

According to the present disclosure, viral infection can be treated by targeting the fatty acid synthesis pathway, and in particular fatty acid synthase. HRV is representative of viruses that can be treated according to the present disclosure. Like other viruses, the replication of HRV involves six phases; transmission, entry, replication, biosynthesis, assembly, and exit. Entry occurs by endocytosis, replication and vRNP assembly takes place in the nucleus, and the virus buds from the plasma membrane. In the infected patient, the virus targets airway epithelial cells. The present compounds and methods target and modulate at least one host cell targets involved in such pathways.

For some viruses a great deal of progress has been made in the elucidation of the steps involved during infection of host cells. For example, experiments initiated in the early 1980s showed that influenza virus follows a stepwise, endocytic entry program with elements shared with other viruses such as alpha- and rhabdoviruses (Marsh and Helenius 1989; Whittaker 2006). The steps include: 1) Initial attachment to sialic acid containing glycoconjugates receptors on the cell surface; 2) signaling induced by the virus particle; 3) endocytosis by clathrin-dependent and clathrin-independent cellular mechanism; 4) acid-induced, hemaglutinin (HA)-mediated penetration from late endosomes; 5) acid-activated, M2 and matrix protein (M1) dependent uncoating of the capsid; and, 6) intra-cytosolic transport and nuclear import of vRNPs. These steps depend on assistance from the host cell in the form of sorting receptors, vesicle formation machinery, kinase-mediated regulation, organelle acidification, and, most likely, activities of the cytoskeleton.

Influenza attachment to the cells surface occurs via binding of the HA1 subunit to cell surface glycoproteins and glycolipids that carry oligosaccharide moieties with terminal sialic acid residues (Skehel and Wiley 2000). The linkage by which the sialic acid is connected to the next saccharide contributes to species specificity. Avian strains including H5N1 prefer an a-(2,3)-link and human strains a-(2,6)-link (Matrosovich 2006). In epithelial cells, binding occurs preferentially to microvilli on the apical surface, and endocytosis occurs at base of these extensions (Matlin 1982). Whether receptor binding induces signals that prepare the cell for the invasion is not yet known, but it is likely because activation of protein kinase C and synthesis of phosphatidylinositol-3-phosphate (PI3P) are required for efficient entry (Sieczkarski et al. 2003; Whittaker 2006).

Endocytic internalization occurs within a few minutes after binding (Matlin 1982; Yoshimura and Ohnishi 1984). In tissue culture cells influenza virus makes use of three different types of cellular processes; 1) preexisting clathrin coated pits, 2) virus-induced clathrin coated pits, and 3) endocytosis in vesicles without visible coat (Matlin 1982; Sieczkarski and Whittaker 2002; Rust et al. 2004). Video microscopy using fluorescent viruses showed the virus particles undergoing actin-mediated rapid motion in the cell periphery followed by minus end-directed, microtubule-mediated transport to the perinuclear area of the cell. Live cell imaging indicated that the virus particles first entered a subpopulation of mobile, peripheral early endosomes that carry them deeper into the cytoplasm before penetration takes place (Lakadamyali et al. 2003; Rust et al. 2004). The endocytic process is regulated by protein and lipid kinases, the proteasome, as well as by Rabs and ubiquitin-dependent sorting factors (Khor et al. 2003; Whittaker 2006).

The membrane penetration step is mediated by low pH-mediated activation of the trimeric, metastable HA, and the conversion of this Type I viral fusion protein to a membrane fusion competent conformation (Maeda et al. 1981; White et al. 1982). This occurs about 16 min after internalization, and the pH threshold varies between strains in the 5.0-5.6 range. The target membrane is the limiting membrane of intermediate or late endosomes. The mechanism of fusion has been extensively studied (Kielian and Rey 2006). Further it was observed that fusion itself does not seem to require any host cell components except a lipid bilayer membrane and a functional acidification system (Maeda et al. 1981; White et al. 1982). The penetration step is inhibited by agents such as lysosomotropic weak bases, carboxylic ionophores, and proton pump inhibitors (Matlin 1982; Whittaker 2006).

To allow nuclear import of the incoming vRNPs, the capsid has to be disassembled. This step involves acidification of the viral interior through the amantadine-sensitive M2-channels causes dissociation of M1 from the vRNPs (Bukrinskaya et al. 1982; Martin and Helenius 1991; Pinto et al. 1992). Transport of the individual vRNPs to the nuclear pore complexes and transfer into the nucleus depends on cellular nuclear transport receptors (O'Neill et al. 1995; Cros et al. 2005). Replication of the viral RNAs (synthesis of positive and negative strands), and transcription occurs in complexes tightly associated with the chromatin in the nucleus. It is evident that, although many of the steps are catalyzed by the viral polymerase, cellular factors are involved including RNA polymerase activating factors, a chaperone HSP90, hCLE, and a human splicing factor UAP56. Viral gene expression is subject to complex cellular control at the transcriptional level, a control system dependent on cellular kinases (Whittaker 2006).

The final assembly of an influenza particle occurs during a budding process at the plasma membrane. In epithelial cells, budding occurs at the apical membrane domain only (Rodriguez-Boulan 1983). First, the progeny vRNPs are transported within the nucleoplasm to the nuclear envelope, then from the nucleus to the cytoplasm, and finally they accumulate in the cell periphery. Exit from the nucleus is dependent on viral protein NEP and M1, and a variety of cellular proteins including CRM1 (a nuclear export receptor), caspases, and possibly some nuclear protein chaperones. Phosphorylation plays a role in nuclear export by regulating M1 and NEP synthesis, and also through the MAPK/ERK system (Bui et al. 1996; Ludwig 2006). G protein and protein kinase signaling is involved in influenza virus budding from infected host cells (Hui E. and Nayak D, 2002).

The three membrane proteins of the virus are synthesized, folded and assembled into oligomers in the ER (Doms et al. 1993). They pass through the Golgi complex; undergo maturation through modification of their carbohydrate moieties and proteolytic cleavage. After reaching the plasma membrane they associate with M1 and the vRNPs in a budding process that results in the inclusion of all eight vRNPs and exclusion of most host cell components except lipids.

Influenza infection is associated with activation of several signaling cascades including the MAPK pathway (ERK, JNK, p38 and BMK-1/ERK5), the IkB/NF-kB signaling module, the Raf/MEK/ERK cascade, and programmed cell death (Ludwig 2006). These result in a variety of effects that limit the progress of infection such as transcriptional activation of IFNb, apoptotic cell death, and a block in virus escape of from late endosomes (Ludwig 2006).

Most previous studies on virus-cell interactions were performed in tissue culture using tissue culture- or egg-adapted virus strains. The viruses in these examples were adapted in such as manner that changes were induced that affected receptor binding and tropism (Matrosovich 2006). Infection with wild-type pathogenic strains is provides a more natural picture of viral interaction with host proteins. It is known that in the human airways influenza A and B primarily infect non ciliated epithelial cells in the upper respiratory track carrying NeuSAc a-(2,6)-Gal, whereas avian strains infect ciliated epithelial cell with a-(2,3)-linked sialic acids deeper in the airways (Matrosovich et al. 2004a).

Additionally, progress has been made in the elucidation of the steps involved during infection by HRV of host cells. Selected events in rhinovirus infection of the normal human airway can be regarded as occurring sequentially. Initial steps in rhinovirus pathogenesis are believed to include viral entry through the nose, mucociliary transport of virus to the posterior pharynx, and initiation of infection in ciliated and non-ciliated epithelial cells of the upper airway. Viral replication peaks on average within 48 h of initiation of infection and persists for up to 3 wk. Infection is followed by activation of several inflammatory mechanisms, which can include release or generation of interleukins, bradykinins, prostaglandins, and possibly histamine and stimulation of parasympathetic reflexes. Pathophysiologic processes are initiated, which include vasodilatation of nasal blood vessels, transudation of plasma, glandular secretion, and stimulation of nerve fibers, causing pain and triggering sneeze and cough reflexes. The resultant clinical illness is a rhinosinusitis, pharyngitis, and bronchitis, which, on average, lasts one week.

Changes in gene expression profiles during in vivo rhinovirus infections have been identified (Proud D. et al. Am J Respir Crit Care Med Vol 178. pp 962-968, 2008). Nasal epithelial scrapings were obtained before and during experimental rhinovirus infection, and gene expression was evaluated by microarray. Viperin is identified as an antiviral protein induced by interferon (IFN), viral infections, and pathogen-associated molecules. Naturally acquired rhinovirus infections, cultured human epithelial cells, and short interfering RNA knockdown were used to further evaluate the role of viperin in rhinovirus infections. Symptom scores and viral titers were measured in subjects inoculated with rhinovirus or a sham control, and changes in gene expression were assessed 8 and 48 hours after inoculation. Rhinovirus-induced changes in gene expression were not observed 8 hours after viral infection, but 11,887 gene transcripts were significantly altered in scrapings obtained 2 days post-inoculation. Major groups of up-regulated genes include chemokines, signaling molecules, interferon-responsive genes, and antivirals. Rhinovirus infection significantly alters the expression of many genes associated with the immune response, including chemokines and antivirals. Some of the genes markedly induced by HRV-16 infection include but are not limited to CCL2, CCL8, CXCL11, CXCL10, CXCL13, CXCL9, CCL20, IFIT2, GBP1, IFIT1, GIP2, IFIT4, IL28B, IRF7, CIG5, NOS2A, OAS3, OASL, OAS2, OAS1, MX2, MX1, PLSCR1, SOCS1, SOCS2, MDA5, RIGI, SOCS3, ICAM-1, HAPLN3, MMP12, EPSTI1, and TNC.

Fatty Acid Synthesis Pathway

Various aspects of the present disclosure relate to compositions and methods that modulate the activity of the fatty acid synthesis pathway to treat a viral infection or treat cancer. The fatty acid synthesis pathway in humans can use four enzymes: 1) acetyl-CoA carboxylase (ACC), which can synthesize malonyl-CoA; 2) malic enzyme, which can produce NADPH; 3) citrate lyase, which can synthesize acetyl-CoA; and 4) fatty acid synthase, which can catalyze NADPH-dependent synthesis of fatty acids from acetyl-CoA and malonyl-CoA. In various aspects, the present disclosure relates to treatment of viral infections and cancer by modulating the activity of the fatty acid synthase protein.

The final products of fatty acid synthase are free fatty acids which can use separate enzymatic derivatization with coenzyme-A for incorporation into other products. In humans, fatty acid synthesis can occur in two sites: the liver, where palmitic acid can be made (Roncari, (1974) *Can. J. Biochem.*, 52:221-230) and lactating mammary gland, where $C_{10}$-$C_{14}$ fatty acids can be made (Thompson, et al., (1985) *Pediatr. Res.*, 19:139-143).

Fatty acids can be synthesized in the cytoplasm from acetyl-CoA. Acetyl-CoA can be generated from pyruvate by pyruvate dehydrodenase (PDH) and by β-oxidation of fatty acids in the mitochondria. A "citrate shuttle" can transport acetyl-CoA from the mitochondria to the cytoplasm. Acetyl-CoA can react with oxaloacetate to yield citrate, and a tricarboxylate translocase can transport citrate from the mitochondria to the cytosol. In the cytoplasm, citrate can be cleaved back to oxaloacetate and acetyl-CoA, a reaction that can be catalyzed by ATP-citrate lyase. Oxaloacetate can be converted back to pyruvate for re-entry into mitochondria.

Acetyl-CoA can be converted to malonyl-CoA. Acetyl-CoA carboxylase (ACC) is a complex multifunctional, biotin-containing, enzyme system that can catalyze carboxylation of acetyl-CoA to malonyl-CoA. This conversion is an irreversible, rate-limiting step in fatty acid synthesis. ACC can carry out three functions: biotin carboxyl carrier protein, biotin carboxylase and carboxyltransferase. ATP-dependent carboxylation of biotin, a prosthetic group (cofactor) can be followed by transfer of the carboxyl group to acetyl-CoA.

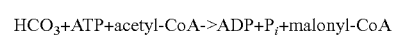

$HCO_3+ATP+acetyl\text{-}CoA \rightarrow ADP+P_i+malonyl\text{-}CoA$

There are two ACC forms, alpha and beta, encoded by two different genes ACC-alpha (also known as ACC, ACAC, ACC1, ACCA, and ACACA) can encode protein highly enriched in lipogenic tissues. Multiple alternatively spliced transcript variants divergent in the sequence and encoding distinct isoforms have been found for this gene. ACC-beta (also known as ACC2, ACCB, HACC275, and ACACB) can encode protein thought to control fatty acid oxidation by means of the ability of malonyl-CoA to inhibit carnitine-palmitoyl-CoA transferase I, the rate-limiting step in fatty acid uptake and oxidation by mitochondria. ACC-beta may be involved in the regulation of fatty acid oxidation, rather than fatty acid biosynthesis. There is evidence for the presence of two ACC-beta isoforms.

ACC can be regulated by the phosphorylation/dephosphorylation of targeted serine residues. For example, AMP-activated kinase (AMPK) can phosphorylate ACC, and this phosphorylation can inhibit the ability of ACC to produce malonyl-CoA. On ACACA, AMPK can phosphorylate Ser79, Ser1200, and Ser1215 (Park S. H. et al. (2002) *J. Appl. Physiol.* 92:2475-82). AMPK can phosphorylate Ser218 on ACACB (Hardie D. G. (1992) *Biochim. Biophys. Acta* 1123:231-8). Also, cAMP-dependent protein kinase (Protein Kinase A, or PKA) can phosphorylate ACC.

ACC can be regulated by allosteric transformation by citrate or palmitoyl-CoA. For example, citrate can be a positive effector (i.e. citrate can allosterically activate ACC). Citrate concentration can be high when there is adequate acetyl-CoA entering the Krebs Cycle. Excess aceytl-CoA can then be converted via malonyl-CoA to fatty acids. Palmitoyl-CoA can be a negative effector. Palmitoyl-CoA, which is the product of Fatty Acid Synthase (FASN), can promote the inactive conformation of ACC, which can reduce production of malonyl-CoA (a feedback inhibition process). AMP can regulate fatty acid synthesis by regulating the availability of malonyl-CoA. Insulin binding a receptor can activate a phosphatase to dephosphorylate ACC, which can remove the inhibitory effect.

The fatty acid synthase gene (also known as FAS, OA-519, SDR27X1; MGC14367; MGC15706; FASN) is involved in fatty acid synthesis. The enzyme encoded by this gene is a multifunctional protein of approximately 272 kDa with multiple domains, each with distinct enzyme activities that can play a role in fatty acid biosynthesis. FASN can catalyze the synthesis of palmitate from acetyl-CoA and malonyl-CoA, in the presence of NADPH, into long-chain saturated fatty acids. In some cancer cell lines, FASN protein has been found to be fused with estrogen receptor-alpha (ER-alpha), in which the N-terminus of FASN is fused in-frame with the C-terminus of ER-alpha.

FASN protein can exist in the cytosol as a dimer of identical subunits. FASN consists of three catalytic domains in the N-terminal section (-ketoacyl synthase (KS), malonyl/acetyltransferase (MAT), and dehydrase (DH)). The N-terminal section is separated by a core region of about 600 amino acids from four C-terminal domains (enoyl reductase (ER), -ketoacyl reductase (KR), acyl carrier protein (ACP), and thioesterase (TE)). The crystal structure of a mammalian fatty acid synthase has been reported (Maier T. et al. (2008) *Science* 321: 1315-1322). Each of the catalytic domains of FASN can be targeted in the methods of treating viral infection of the provided invention.

The enzymatic steps of fatty acid synthesis can involve decarboxylative condensation, reduction, dehydration, and another reduction and can result in a saturated acyl moiety. NADPH can be an electron donor in reductive reactions.

Antiviral Activity

In various aspects, the present disclosure provides methods for treating viral infection in a subject, the method comprising administering to a subject in need of such treatment an effective amount of a compound of Structures (I), (II), (III), (IV), (V), (VI), (VII), (VIII), (IX), (X), (XI) or as provided in Table 1.

In various aspects, the disclosure provides methods for treating a viral infection, the method comprising administering the compounds of the present disclosure to a subject in need thereof the agent.

The present disclosure contemplates the treatment of any viral infection that targets the fatty acid synthesis pathway in a host, and in particular by modulating the activity of fatty acid synthase. For example, the present methods can be used to treat influenza infection, adenovirus infection, respiratory syncytial virus infection, poxvirus infection, poliomyelitis infection, hepatitis C infection, yellow fever infection, dengue fever infection, rhinovirus infection, and the like.

In various aspects, the present disclosure provides methods for treating hepatitis C infection by administering to the subject one or more compounds disclosed herein. In modulating the FASN pathway in the subject, hepatitis C infection is treated. It has been shown that expression of FASN is upregulated in human hepatoma cell line Huh7 when these cells are infected with HCV. Inhibiting FASN production with a FASN inhibitor reduced the production of HCV. Thus administration to a subject of the compounds of the present disclosure. (Yang, W. et al. (2008) *Hepatology* 48(5):1396-1403). It is demonstrated in the EXAMPLES that FASN inhibition correlates to inhibition of HCV.

In certain aspects, the methods of inhibiting viral infection can be performed in vitro. In further aspects, the methods of inhibiting viral infection can be performed in vivo.

In certain aspects the compounds of the present disclosure may be used in combination with other antiviral treatments in the treating of viral infection.

In various aspects, the viral infection is a human yellow fever infection. In further aspects, the viral infection is a human hepatitis C infection. In yet further aspects, the viral infection is a human rhinoviral infection.

In various aspects the compounds of the present disclosure can be used for the treatment of infection of an animal subject, such as a human, by any of a plethora of viruses.

In certain aspects, the compounds of the present disclosure can be used for the inhibition of a host by a respiratory virus. Respiratory viruses are most commonly transmitted by airborne droplets or nasal secretions and can lead to a wide spectrum of illness. Respiratory viruses include the respiratory syncytial virus (RSV), influenza viruses, coronaviruses such as SARS, adenoviruses, parainfluenza viruses and rhinoviruses (HRV).

According to one aspect, the present disclosure can be used to treat infection by HRV. The genus of rhinoviruses is a member of the Picornaviridae family of viruses. Genera within the family include the Genus *Enterovirus, Rhinovirus, Cardiovirus, Aphthovirus, Hepatovirus, Parechovirus, Erbovirus, Kobuvirus, Teschovirus*. Human rhinoviruses (HRV) include the most common viruses that infect humans and can cause the common cold. HRV are lytic in nature. Rhinoviruses have single-stranded positive sense RNA genomes of between 7.2 and 8.5 kb in length. At the 5' end of these genomes is a virus-encoded protein, and like mammalian mRNA, there is also a 3' poly-A tail. The 5'-terminal UMP of the viral RNA is covalently linked to the small viral protein VPg (Paul A V, et al. *Nature* 1998, 393(6682):280-284). The 5'UTR contains two structural elements. One is the 5'-cloverleaf structure involved in the plus-strand RNA synthesis and in the process of switching from translation to replication (Huang H, et al. *Biochemistry* 2001, 40(27):8055-8064). The other is the internal ribosomal entry site (IRES) which promotes translation of the polyprotein. In addition, species-specific internal cis-acting replication elements (cre) have been identified in human enteroviruses (HEV), HRV-A and HRV-B (Gerber K, Wimmer E, Paul A V, *J Virol* 2001, 75(22):10979-10990). The viral particles themselves are not enveloped and are icosahedral in structure. Rhinoviruses also grow best in temperatures between 33-35° C. They are also sensitive to acidic environment.

HRV viral proteins are transcribed as a single long polypeptide, which is cleaved into the viral structural and non-structural proteins. Rhinoviruses are composed of a capsid that contains four viral proteins VP1, VP2, VP3 and VP4 (Rossmann M, et al. 1985 *Nature* 317 (6033): 145-53; Smith T, et al. 1986, *Science* 233 (4770): 1286-93). The isometric nucleocapsids are 22-40 nm in diameter. VP1, VP2, and VP3 form the major part of the protein capsid. The much smaller VP4 protein has a more extended structure and lies at interface between the capsid and the RNA genome. There are 60 copies of each of these proteins assembled as an icosahedron. Human antibodies that target epitopes lying on the exterior regions of VP1-VP3 play a role in the immune response to HRVs.

HRVs have two general modes of transmission: 1) via aerosols of respiratory droplets and 2) from contaminated surfaces, including direct person-to-person contact. The primary route of entry for rhinoviruses is the upper respiratory tract. Afterwards, an HRV binds to ICAM-1 (Inter-Cellular Adhesion Molecule 1) also known as CD54 (Cluster of Differentiation 54) receptors on respiratory epithelial cells. As the virus replicates and spreads, infected cells release chemokines and cytokines, which in turn activate inflammatory mediators. Infection occurs rapidly, with the rhinovirus adhering to surface receptors within 15 minutes of entering the respiratory tract. The incubation period is generally 8-10 hours before symptoms begin to occur. HRVs are the most frequent cause of infection across all age groups of the human population. Replication is often restricted to the upper respiratory tract leading to self-limited illnesses such as the common cold. However, HRV infections can also exacerbate pre-existing airway disorders, invade the lower respiratory tract and lead to serious complications.

In another aspect, the compounds of the present disclosure can be used for the treatment of infection by the influenza virus by targeting the pathways that the virus relies on for infection or replication. Influenza viruses belong to Orthomyxoviridae family of viruses. This family also includes Thogoto viruses and Dhoriviruses. There are several types and subtypes of influenza viruses known, which infect humans and other species. Influenza type A viruses infect people, birds, pigs, horses, seals and other animals, but wild birds are the natural hosts for these viruses. Influenza type A viruses are divided into subtypes and named on the basis of two proteins on the surface of the virus: hemagglutinin (HA) and neuraminidase (NA). For example, an "H7N2 virus" designates an influenza A subtype that has an HA 7 protein and an NA 2 protein. Similarly an "H5N1" virus has an HA 5 protein and an NA 1 protein. There are 16 known HA subtypes and 9 known NA subtypes. Many different combinations of HA and NA proteins are possible. Only some influenza A subtypes (i.e., H1N1, H1N2, and H3N2) are currently in general circulation among people. Other subtypes are found most commonly in other animal species. For example, H7N7 and H3N8 viruses cause illness in horses, and H3N8 also has recently been shown to cause illness in dogs (see www.cdc.gov/flu/avian/gen-info/flu-viruses.htm).

Antiviral agents which target host cell proteins involved in influenza infection can be used to protect high-risk groups (hospital units, institutes caring for elderly, immuno-suppressed individuals), and on a case by case basis. A potential use for antiviral agents is to limit the spread and severity of the future pandemics whether caused by avian H5N1 or other strains of influenza virus. Avian influenza A viruses of the subtypes H5 and H7, including H5N1, H7N7, and H7N3 viruses, have been associated with high pathogenicity, and human infection with these viruses have ranged from mild (H7N3, H7N7) to severe and fatal disease (H7N7, H5N1). Human illness due to infection with low pathogenicity viruses has been documented, including very mild symptoms (e.g., conjunctivitis) to influenza-like illness. Examples of low pathogenicity viruses that have infected humans include H7N7, H9N2, and H7N2 (see www.cdc.gov/flu/avian/gen-info/flu-viruses.htm).

Influenza B viruses are usually found in humans but can also infect seals. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics. (see www.cdc.gov/flu/avian/gen-info/flu-viruses.htm).

Influenza type C viruses cause mild illness in humans and do not cause epidemics or pandemics. These viruses can also infect dogs and pigs. These viruses are not classified according to subtype. (see www.cdc.gov/flu/avian/gen-info/flu-viruses.htm).

Influenza viruses differ from each other in respect to cell surface receptor specificity and cell tropism, however they use common entry pathways. The compounds of the present disclosure advantageously target pathways that are common to multiple viruses giving rise to broader antiviral activity. Thus, the present compounds can also prove useful against unrelated viruses that use similar pathways. For example, the agents can protect airway epithelial cells against a number of different viruses in addition to influenza viruses.

In certain aspects, the compounds of the present disclosure can be used for the treatment of infection by adenoviruses. Most adenoviruses commonly cause respiratory illness; symptoms of respiratory illness caused by adenovirus infection range from the common cold syndrome to pneumonia, croup, and bronchitis. Patients with compromised immune systems are especially susceptible to severe complications of adenovirus infection. Acute respiratory disease (ARD), first recognized among military recruits during World War II, can be caused by adenovirus infections during conditions of crowding and stress. Adenoviruses are medium-sized (90-100 nm), nonenveloped icosohedral viruses containing double-stranded DNA. There are 49 immunologically distinct types (6 subgenera: A through F) that can cause human infections. Adenoviruses are unusually stable to chemical or physical agents and adverse pH conditions, allowing for prolonged survival outside of the body. Some adenoviruses, such as AD2 and Ad5 (species C) use clathrin mediated endocytosis and macropinocytosis for infectious entry. Other adenoviruses, such as Ad3 (species B) use dynamin dependent endocytosis and macropinocytosis for infectious entry.

In certain aspects, the compounds of the present disclosure can be used for the treatment of infection by respiratory syncytial virus (RSV). RSV is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease can occur at any age, especially among the elderly or among those with compromised cardiac, pulmonary, or immune systems. RSV is a negative-sense, enveloped RNA virus. The virion is variable in shape and size (average diameter of between 120 and 300 nm), is unstable in the environment (surviving only a few hours on environmental surfaces), and is readily inactivated with soap and water and disinfectants.

In certain aspects, the compounds of the present disclosure can be used for the treatment of infection by human parainfluenza virus (HPIV). HPIVs are second to respiratory syncytial virus (RSV) as a common cause of lower respiratory tract disease in young children. Similar to RSV, HPIVs can cause repeated infections throughout life, usually manifested by an upper respiratory tract illness (e.g., a cold and/or sore throat). HPIVs can also cause serious lower respiratory tract disease with repeat infection (e.g., pneumonia, bronchitis, and bronchiolitis), especially among the elderly, and among patients with compromised immune systems. Each of the four HPIVs has different clinical and epidemiologic features. The most distinctive clinical feature of HPIV-1 and HPIV-2 is croup (i.e., laryngotracheobronchitis); HPIV-1 is the leading cause of croup in children, whereas HPIV-2 is less frequently detected. Both HPIV-1 and -2 can cause other upper and lower respiratory tract illnesses. HPIV-3 is more often associated with bronchiolitis and pneumonia. HPIV-4 is infrequently detected, possibly because it is less likely to cause severe disease. The incubation period for HPIVs is generally from 1 to 7 days. HPIVs are negative-sense, single-stranded RNA viruses that possess fusion and hemagglutinin-neuraminidase glycoprotein "spikes" on their surface. There are four serotypes types of HPIV (1 through 4) and two subtypes (4a and 4b). The virion varies in size (average diameter between 150 and 300 nm) and shape, is unstable in the environment (surviving a few hours on environmental surfaces), and is readily inactivated with soap and water.

In various aspects, the compounds of the present disclosure can be used for the treatment of infection by coronavirus. Coronavirus is a genus of animal virus belonging to the family Coronaviridae. Coronaviruses are enveloped viruses with a positive-sense single-stranded RNA genome and a helical symmetry. The genomic size of coronaviruses ranges from approximately 16 to 31 kilobases, extraordinarily large for an RNA virus. The name "coronavirus" is derived from the Latin corona, meaning crown, as the virus envelope appears under electron microscopy to be crowned by a characteristic ring of small bulbous structures. This morphology is actually formed by the viral spike peplomers, which are proteins that populate the surface of the virus and determine host tropism. Coronaviruses are grouped in the order Nidovirales, named for the Latin nidus, meaning nest, as all viruses in this order produce a 3' co-terminal nested set of subgenomic mRNA's during infection. Proteins that contribute to the overall structure of all coronaviruses are the spike, envelope, membrane and nucleocapsid. In the specific case of SARS a defined receptor-binding domain on S mediates the attachment of the virus to its cellular receptor, angiotensin-converting enzyme 2.

The present disclosure contemplates the treatment of any viral infection that targets the fatty acid synthesis pathway in a host, and in particular by modulating the activity of fatty acid synthase. For example, the present methods can be used to treat infections caused by Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, ETA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shiner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus *hominis*, Herpesvirus infection, Herpesvirus saimiri, Herpesvirus *suis*, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Pity virus, Pixuma virus, pneumonia virus of mice, Pneumovirus, poliomyelitis virus, poliovirus, Polydnavirus, polyhedral virus, polyoma virus, Polyomavirus, Polyomavirus *bovis*, Polyomavirus cercopitheci, Polyomavirus *hominis* 2, Polyomavirus maccacae 1, Polyomavirus *muris* 1, Polyomavirus *muris* 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Utility in Metabolic Disorders

In various aspects, the compounds of the present disclosure have utility in the treating of metabolic diseases. FASN has been demonstrated to be involved in regulation of glucose, lipids and cholesterol metabolism. Mice with a liver-specific inactivation of FASN have normal physiology unless fed a zero-fat diet, in which case they develop hypoglycemia and fatty liver, both of which are reversed with dietary fat. (Chakravarthy, M. V., et al. (2005) *Cell Metabolism* 1:309-322). Db/+ mice fed a high fructose diet exhibit reduced liver triglyceride levels and improved insulin sensitivity when treated for 28 days with platensimycin, a covealent inhibitor of FASN. (Wu, M. et al. (2011) *PNAS* 108(13):5378-5383). Ambient glucose levels are also reduced in db/db mice following treatment with platensimycin. These results provide evidence that inhibiting FASN can yield therapeutically relevant benefits in animal models of diabetes and related metabolic disorders. Thus the disclosed FASN inhibitors are useful in the treatment of disorders characterized by disregulation in these systems. Without limitation, examples include steatosis and diabetes.

Anticancer Activity

In various aspects, the present disclosure provides methods for treating cancer in subject, the method comprising administering to a subject in need of such treatment an effective amount of a compound of Structures (I), (II), (III), (IV), (V), (VI), (VII), (VIII), (IX), (X), (XI) or as provided in Table 1. In further aspects, compounds having Structure (I), (II), (III), (IV), (V), (VI), (VII), (VIII), (IX), (X), (XI) or as provided in Table 1 can be used for the manufacture of a medicament for treating cancer.

In certain aspects, the present disclosure provides a method for inhibiting tumor cell growth in a subject, the method comprising administering to a subject in need of such treatment an effective amount of a compound of Structure (I), (II), (III), (IV), (V), (VI), (VII), (VIII), (IX), (X), (XI) or as provided in Table 1. In further aspects, the tumor can be derived from ovary, breast, lung, thyroid, lymph node, kidney, ureter, bladder, ovary, teste, prostate, bone; skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue. In certain aspects, the present compounds can be administered concurrently with one or more additional anti-cancer treatments.

Rapidly proliferating cancer cells activate the fatty acid synthesis pathway to supply the high levels of lipids needed for membrane assembly and oxidative metabolism. (Flavin, R. et al. (2010) *Future Oncology.* 6(4):551-562) Inhibitors of fatty acid synthesis have demonstrated in vivo activity in preclinical cancer models. (Orita, H. et al. (2007) *Clinical Cancer Research.* 13(23):7139-7145 and Puig, T. et al. (2011) *Breast Cancer Research,* 13(6):R131) Additionally, fatty acid synthesis supports new blood vessel formation and inhibitors of this pathway have activity in in vitro models of angiogenesis. (Browne, C. D., et al. (2006) *The FASEB Journal,* 20(12):2027-2035). The presently disclosed compounds demonstrated the ability to selectively induce cell-cycle arrest in HUVEC cells without causing general cell death by apoptosis. See EXAMPLES.

The cancer treatment of the present invention includes an anti-tumor effect that may be assessed by conventional means such as the response rate, the time to disease progression and/or the survival rate. Anti-tumor effects of the present invention include, but are not limited to, inhibition of tumor growth, tumor growth delay, regression of tumor, shrinkage of tumor, increased time to regrowth of tumor on cessation of treatment and slowing of disease progression. For example, it is expected that when the combination of the present invention is administered to a warm-blooded animal such as a human, in need of treatment for cancer involving a solid tumor, such a method of treatment will produce an effect, as measured by, for example, one or more of: the extent of the anti-tumor effect, the response rate, the time to disease progression and the survival rate.

Methods of Treatment

Also provided herein are pharmaceutical compositions comprising the compounds of the present disclosure. The present compositions and methods have antiviral and/or anticancer activity.

In various aspects, the present disclosure provides pharmaceutical compositions comprising any one of the compounds of Structures (I), (II), (III), (IV), (V), (VI), (VII), (VIII), (IX), (X) or (XI) and a pharmaceutically acceptable carrier, excipient, or diluent.

In certain aspects, the present disclosure provides pharmaceutical compositions comprising any one of the compounds of Table 1 and a pharmaceutically acceptable carrier, excipient, or diluent.

Certain aspects of the present disclosure relates to methods of using pharmaceutical compositions and kits comprising one or more agents that inhibit the fatty acid synthesis pathway to inhibit or decrease a viral infection or for the treatment of cancer. Certain aspects of the present disclosure relates to methods of using pharmaceutical compositions and kits comprising one or more agents that inhibit fatty acid synthase to inhibit or decrease a viral infection or for the treatment of cancer. Another aspect of the present invention provides methods, pharmaceutical compositions, and kits for the treatment of animal subjects having a viral infection or cancer or at risk of developing a viral infection or cancer. The term "subject" as used herein includes humans as well as other mammals. The term "treating" as used herein includes achieving a therapeutic benefit and/or a prophylactic benefit. By therapeutic benefit is meant eradication or amelioration of the underlying viral infection. Also, a therapeutic benefit is achieved with the eradication or amelioration of one or more of the physiological symptoms associated with the underlying viral infection such that an improvement is observed in the animal subject, notwithstanding the fact that the subject can still be afflicted with the underlying virus.

For aspects where a prophylactic benefit is desired, a pharmaceutical composition of the invention can be administered to a patient at risk of developing viral infection such as HRV, or HIV, or to a patient reporting one or more of the physiological symptoms of a viral infection, even though a diagnosis of the condition may not have been made. Administration can prevent the viral infection from developing, or it can reduce, lessen, shorten and/or otherwise ameliorate the viral infection that develops. The pharmaceutical composition can modulate the fatty acid synthesis pathway, e.g., FASN gene expression or FASN protein activity. Wherein, the term modulate includes inhibition of the fatty acid synthesis pathway, e.g., FASN gene expression or FASN protein activity or alternatively activation of the fatty acid synthesis pathway, e.g., FASN gene expression or FASN protein activity.

Reducing the activity of the fatty acid synthesis pathway, e.g., FASN gene expression or FASN protein activity, is also referred to as "inhibiting" the fatty acid synthesis pathway, e.g., FASN gene expression or FASN protein activity. The term "inhibits" and its grammatical conjugations, such as "inhibitory," do not require complete inhibition, but refer to a reduction in fatty acid synthesis activity, e.g., FASN gene expression or FASN protein activity. In another aspect, such reduction is by at least 50%, at least 75%, at least 90%, and can be by at least 95% of the activity of the enzyme in the absence of the inhibitory effect, e.g., in the absence of an inhibitor. Conversely, the phrase "does not inhibit" and its grammatical conjugations refer to situations where there is less than 20%, less than 10%, and can be less than 5%, of reduction in enzyme activity in the presence of the agent. Further the phrase "does not substantially inhibit" and its grammatical conjugations refer to situations where there is less than 30%, less than 20%, and in some aspects less than 10% of reduction in enzyme activity in the presence of the agent.

Increasing the activity of the fatty acid synthesis pathway, e.g., FASN gene expression or FASN protein activity, is also referred to as "activating" the fatty acid synthesis pathway, e.g., FASN gene expression or FASN protein activity. The term "activated" and its grammatical conjugations, such as "activating," do not require complete activation, but refer to an increase in fatty acid synthesis pathway activity, e.g., FASN gene expression or FASN protein activity. In another aspect such increase is by at least 50%, at least 75%, at least 90%, and can be by at least 95% of the activity of the enzyme in the absence of the activation effect, e.g., in the absence of an activator. Conversely, the phrase "does not activate" and its grammatical conjugations refer to situations where there is less than 20%, less than 10%, and can be less than 5%, of an increase in enzyme activity in the presence of the agent. Further the phrase "does not substantially activate" and its grammatical conjugations refer to situations where there is less than 30%, less than 20%, and in another aspect less than 10% of an increase in enzyme activity in the presence of the agent.

The ability to reduce enzyme activity is a measure of the potency or the activity of an agent, or combination of agents, towards or against the enzyme. Potency can be measured by cell free, whole cell and/or in vivo assays in terms of IC50, $K_i$ and/or ED50 values. An IC50 value represents the concentration of an agent required to inhibit enzyme activity by half (50%) under a given set of conditions. A $K_i$ value represents the equilibrium affinity constant for the binding of an inhibiting agent to the enzyme. An ED50 value represents the dose of an agent required to effect a half-maximal response in a biological assay. Further details of these measures will be appreciated by those of ordinary skill in the art, and can be found in standard texts on biochemistry, enzymology, and the like.

The present invention also includes kits that can be used to treat viral infections or treat cancer. These kits comprise an agent or combination of agents that inhibit the fatty acid synthesis pathway, e.g., FASN gene expression or FASN protein activity, and optionally instructions teaching the use of the kit according to the various methods and approaches described herein. Such kits can also include information, such as scientific literature references, package insert materials, clinical trial results, and/or summaries of these and the like, which indicate or establish the activities and/or advantages of the agent. Such information can be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

Formulations, Routes of Administration, and Effective Doses

Yet another aspect of the present invention relates to formulations, routes of administration and effective doses for pharmaceutical compositions comprising an agent or combination of agents of the instant invention. Such pharmaceutical compositions can be used to treat viral infections as described above.

Compounds of the invention can be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various aspects, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another aspect, the pharmaceutical preparation is substantially free of preservatives. In another aspect, the pharmaceutical preparation can contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the compositions of this invention, the type of carrier will vary depending on the mode of administration.

Compounds can also be encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intravenous injection, as is well known in the art.

The compounds of the invention can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present invention, and which are not biologically or otherwise undesirable. For example, a pharmaceutically acceptable salt does not interfere with the beneficial effect of an agent of the invention in inhibiting the fatty acid synthesis pathway, e.g., inhibiting FASN gene expression or FASN protein activity.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present invention, and which are not biologically or otherwise undesirable. For example, the ester or amide does not interfere with the beneficial effect of an agent of the invention in inhibiting the fatty acid synthesis pathway, e.g., inhibiting FASN gene expression or FASN protein activity. Typical esters include ethyl, methyl, isobutyl, ethylene glycol, and the like. Typical amides include unsubstituted amides, alkyl amides, dialkyl amides, and the like.

In another aspect, an agent can be administered in combination with one or more other compounds, forms, and/or agents, e.g., as described above. Pharmaceutical compositions comprising combinations of a fatty acid synthesis pathway inhibitor e.g., an inhibitor or FASN gene expression or FASN protein activity with one or more other active agents can be formulated to comprise certain molar ratios. For example, molar ratios of about 99:1 to about 1:99 of a fatty acid synthesis pathway inhibitor e.g., an inhibitor of FASN gene expression or FASN protein activity, to the other active agent can be used. In some subset of the aspects, the range of molar ratios of fatty acid synthesis pathway inhibitor e.g., an inhibitor of FASN gene expression or FASN protein activity: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a fatty acid synthesis pathway inhibitor e.g., an inhibitor of FASN gene expression or FASN protein activity: other active agent can be about 1:9, and in another aspect can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant invention can depend, at least in part, on the condition being treated. Agents of particular use in the formulations of the present invention include, for example, any agent having a therapeutic effect for a viral infection, including, e.g., drugs used to treat inflammatory conditions. For example, in treatments for HRV, in some aspects formulations of the instant invention can additionally contain one or more conventional anti-inflammatory drugs, such as an NSAID, e.g., ibuprofen, naproxen, acetaminophen, ketoprofen, or aspirin. In some alternative aspects for the treatment of influenza formulations of the instant invention can additionally contain one or more conventional influenza antiviral agents, such as amantadine, rimantadine, zanamivir, and oseltamivir. In treatments for retroviral infections, such as HIV, formulations of the instant invention can additionally contain one or more conventional antiviral dmg, such as protease inhibitors (lopinavir/ritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), tipranavir (Aptivus)), reverse transcriptase inhibitors, including non-Nucleoside and Nucleoside/nucleotide inhibitors (AZT (zidovudine, Retrovir), ddI (didanosine, Videx), 3TC (lamivudine, Epivir), d4T (stavudine, Zerit), abacavir (Ziagen), FTC (emtricitabine, Emtriva), tenofovir (Viread), efavirenz (Sustiva) and nevirapine (Viramune)), fusion inhibitors T20 (enfuvirtide, Fuzeon), integrase inhibitors (MK-0518 and GS-9137), and maturation inhibitors (PA-457 (Bevirimat)). As another example, formulations can additionally contain one or more supplements, such as vitamin C, E or other antioxidants.

In certain aspects, the compounds of the present disclosure can be administered in combination with a known cancer therapeutic. For example, the compounds can be administered in combination with paclitaxel (commercially available as Taxol, Bristol-Myers Squibb), doxorubicin (also known under the trade name Adriamycin), vincristine (known under the trade names Oncovin, Vincasar PES, and Vincrex), actinomycin D, altretamine, asparaginase, bleomycin, busulphan, capecitabine, carboplatin, carmustine, chlorambucil, cisplatin, cyclophosphamide, cytarabine, dacarbazine, daunorubicin, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, UFT (uracil-tegufur), vinblastine, and vindesine, or the like.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present invention can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present invention, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, the agents can be formulated readily by combining the active agent(s) with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the agents of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain agent(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In another aspect, oils or non-aqueous solvents can be required to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this invention can also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration should be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Suitable fillers or carriers with which the compositions can be administered include agar, alcohol, fats, lactose, starch, cellulose derivatives, polysaccharides, poly vinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating compounds of the invention for oral administration, it can be desirable to utilize gastroretentive formulations to enhance absorption from the gastrointestinal (GI) tract. A formulation which is retained in the stomach for several hours can release compounds of the invention slowly and provide a sustained release that can be used in methods of the invention. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques can be utilized to maximize absorption of the compounds of the invention.

The compounds of the invention can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In a preferred aspect, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In another aspect, the pharmaceutical composition does not comprise an adjuvant or any other substance added to enhance the immune response stimulated by the peptide. In another aspect, the pharmaceutical composition comprises a substance that inhibits an immune response to the peptide.

Methods of formulation are known in the art, for example, as disclosed in Remington's Pharmaceutical Sciences, latest edition, Mack Publishing Co., Easton P.

In addition to the formulations described previously, the agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

In another aspect, pharmaceutical compositions comprising one or more agents of the present invention exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another aspect, local/topical formulations comprising a fatty acid synthesis pathway inhibitor e.g., an inhibitor of FASN gene expression or FASN protein activity, are used to treat epidermal or mucosal viral infections.

Pharmaceutical compositions of the present invention can contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents of the instant invention can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

Compositions of the present invention can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

In another aspect, ocular viral infections can be effectively treated with ophthalmic solutions, suspensions, ointments or inserts comprising an agent or combination of agents of the present invention. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the invention can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g. from 0.001% to 0.008%, preferably about 0.005% by weight. It has been found that a concentration of benzalkonium chloride of 0.005% can be sufficient to preserve the compositions of the present invention from microbial attack.

In another aspect, viral infections of the ear can be effectively treated with otic solutions, suspensions, ointments or inserts comprising an agent or combination of agents of the present invention.

In another aspect, the agents of the present invention are delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

In another aspect relating to topical/local application, the pharmaceutical compositions can include one or more penetration enhancers. For example, the formulations can comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In another aspect, the pharmaceutical compositions will include one or more such penetration enhancers.

In another aspect, the pharmaceutical compositions for local/topical application can include one or more antimicrobial preservatives such as quaternary ammonium compounds, organic mercurials, p-hydroxy benzoates, aromatic alcohols, chlorobutanol, and the like.

Gastrointestinal viral infections can be effectively treated with orally- or rectally delivered solutions, suspensions, ointments, enemas and/or suppositories comprising an agent or combination of agents of the present invention.

Respiratory viral infections can be effectively treated with aerosol solutions, suspensions or dry powders comprising an agent or combination of agents of the present invention. Administration by inhalation is particularly useful in treating viral infections of the lung, such as an HRV infection. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a fatty acid synthesis pathway inhibitor e.g., an inhibitor of FASN gene expression or FASN protein activity, can be dissolved, suspended or emulsified in a propellant or a mixture of solvent and propellant, e.g., for administration as a nasal spray or inhalant. Aerosol formulations can contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent of the invention such as a fatty acid synthesis pathway inhibitor e.g., an inhibitor of FASN gene expression or FASN protein activity, in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation can comprise a suspension of an agent or combination of agents of the instant invention, e.g., a fatty acid synthesis pathway inhibitor, e.g., an inhibitor of FASN gene expression or FASN protein activity, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents of the invention, e.g., a fatty acid synthesis pathway, e.g., an inhibitor of FASN gene expression or FASN protein activity. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The compounds of the invention can be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds of the invention can be formulated for vaginal administration. Pessaries, tampons, creams, gels, pastes, foams or sprays containing in addition to the active ingredient such carriers as are known in the art to be appropriate.

It is envisioned additionally, that the compounds of the invention can be attached releasably to biocompatible polymers for use in sustained release formulations on, in or attached to inserts for topical, intraocular, periocular, or systemic administration. The controlled release from a biocompatible polymer can be utilized with a water soluble polymer to form a instillable formulation, as well. The controlled release from a biocompatible polymer, such as for example, PLGA microspheres or nanospheres, can be utilized in a formulation suitable for intra ocular implantation or injection for sustained release administration, as well. Any suitable biodegradable and biocompatible polymer can be used.

Pharmaceutical compositions suitable for use in the present invention include compositions wherein the active ingredients are present in an effective amount, i.e., in an amount effective to achieve therapeutic and/or prophylactic benefit in a host with at least one viral infection or in a subject having cancer. The actual amount effective for a particular application will depend on the condition or conditions being treated, the condition of the subject, the formulation, and the route of administration, as well as other factors known to those of skill in the art. Determination of an effective amount of a fatty acid synthesis pathway inhibitor e.g., an inhibitor of FASN gene expression or FASN protein activity, is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present invention appropriate for humans.

The effective amount when referring to an agent or combination of agents of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Further, appropriate doses for a fatty acid synthesis pathway inhibitor e.g., an inhibitor of FASN gene expression or FASN protein activity, can be determined based on in vitro experimental results. For example, the in vitro potency of an agent in inhibiting a fatty acid synthesis pathway component, e.g., FASN gene expression or FASN protein activity, provides information useful in the development of effective in vivo dosages to achieve similar biological effects.

In another aspect, administration of agents of the present invention can be intermittent, for example administration once every two days, every three days, every five days, once a week, once or twice a month, and the like. In another aspect, the amount, forms, and/or amounts of the different forms can be varied at different times of administration.

A person of skill in the art would be able to monitor in a patient the effect of administration of a particular agent. For example, HIV viral load levels can be determined by techniques standard in the art, such as measuring CD4 cell counts, and/or viral levels as detected by PCR. Other techniques would be apparent to One of skill in the art.

Having now generally described various aspects and aspects of the invention, the same will be more readily understood through reference to the following examples which are provided by way of illustration. and are not intended to be limiting, unless specified.

EXAMPLES

Example—Synthesis of Compounds of the Present Disclosure

General: All reactions and manipulations described were carried out in well ventilated fume-hoods. Operations and reactions carried out at elevated or reduced pressure were carried out behind blast shields. Abbreviations: ACN, acetonitrile; AcOH, acetic acid; AIBN, azobisisobutyronitrile; BuLi, butyl lithium; CDI, 1,1'-Carbonyldiimidazole; DBU, 1,8-Diazabicyclo[5.4.0]undec-7-ene; DCE, 1,2-dichloroethane; DCM, dichloromethane or methylene chloride; DIEA, N,N-Diisopropylethylamine; DMAP, 4-dimethylaminopyridine; DMF, N,N-dimethylformamide; DMSO, dimethylsulfoxide; EDC, 1-ethyl-3-(3-dimethylaminopropyl)carbodiimide; EDCl, 1-ethyl-3-(3-dimethylaminopropyl)carbodiimide hydrochloride; EtOAc, ethyl acetate; EtOH, Ethanol; HATU, 2-(1H-7-Azabenzotriazol-1-yl)-1,1,3,3-tetramethyl uronium hexafluorophosphate; HBTU, O-Benzotriazole-N,N,N',N'-tetramethyl-uronium-hexafluoro-phosphate or 2-(1H-Benzotriazole-1-yl)-1,1,3,3-tetramethylaminium hexafluorophosphate; HMPA, hexamethylphosphoramide; HOAc, acetic acid; HOBT, 1-Hydroxybenzotriazole; LDA, lithium diisopropylamine; MeOH, methanol; MsCl, methanesulfonyl chloride; MsOH, methanesulfonic acid; NBS, N-bromosuccinimide; NIS, N-iodosuccinimide; PE, petroleum ether; PTAT, phenyltrimethylammonium tribromide; PTSA, p-toluenesulfonic acid; Py; pyridine; Pyr, pyridine; TEA, tdethylamine; TFA, trifluoroacetic acid; THF, tetrahydrofuran; TMSCl, chlorotrimethylsilane; TsOH, p-toluenesulfonic acid.

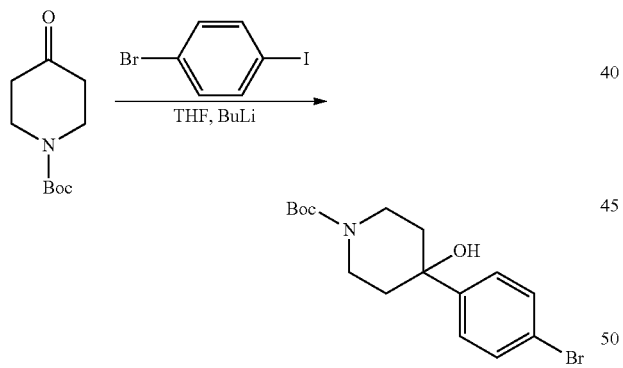

Compound 1.1. tert-Butyl 4-(4-bromophenyl)-4-hydroxypiperidine-1-carboxylate

To a stirred solution of 1-bromo-4-iodobenzene (93.7 g, 331.21 mmol, 1.10 equiv) in tetrahydrofuran (800 mL) under nitrogen at −78° C. was added dropwise of a solution of butyllithium (150 mL, 2.43 Min THF, 1.05 equiv) during 30 min. The resulting solution was stirred for 2 h at −78° C. To this was then added a solution of tert-butyl 4-oxopiperidine-1-carboxylate (60 g, 301.13 mmol, 1.00 equiv) in tetrahydrofuran (800 mL) dropwise with stirring at −78° C. during 30 min. After stirring for 1 h at −78° C., reaction was carefully quenched with 350 mL of H₂O. The resulting mixture was extracted with 2×400 mL of ethyl acetate and the combined organic layers were dried (Na₂SO₄) and concentrated under reduced pressure. The residue was purified using silica gel column chromatography with ethyl acetate/petroleum ether (1:200-1:10) as eluent to yield 91 g (85%) of the title compound as a yellow oil.

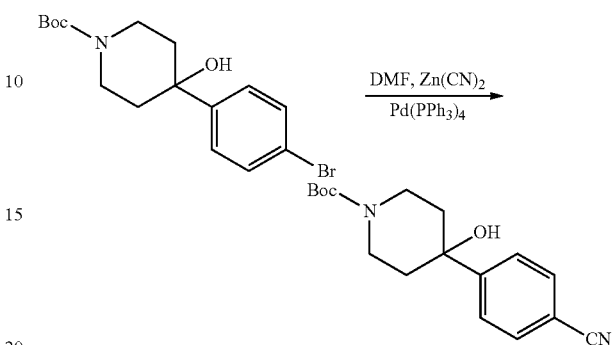

Compound 1.2. tert-Butyl 4-(4-cyanophenyl)-4-hydroxypiperidine-1-carboxylate

A solution of tort-butyl 4-(4-bromophenyl)-4-hydroxypiperidine-1-carboxylate (compound 1.1, 36 g, 101.05 mmol, 1.00 equiv), Pd(PPh₃)₄ (11.7 g, 10.12 mmol, 0.05 equiv), and Zn(CN)₂ (17.9 g, 152.44 mmol, 1.51 equiv) in DMF (400 mL) under nitrogen was stirred overnight at 80° C. After reaching ambient temperature, the reaction was then quenched by the addition of 600 mL of FeSO₄(aq., sat.) and diluted with ethyl acetate. The resulting mixture was stirred vigorously then filtered through celite and washed with 1 M FeSO₄, water, and ethyl acetate. The layers were separated and the aqueous phase was extracted with 2×300 mL of ethyl acetate. The combined organic layers were washed with 1×200 mL of potassium carbonate (aq., sat.) followed by 1×200 mL of brine, dried (Na₂SO₄), and concentrated under reduced pressure. The residue was purified using silica gel column chromatography with ethyl acetate/petroleum ether (1:200-1:5) as eluent to yield 23 g (75%) of the title compound as a white solid.

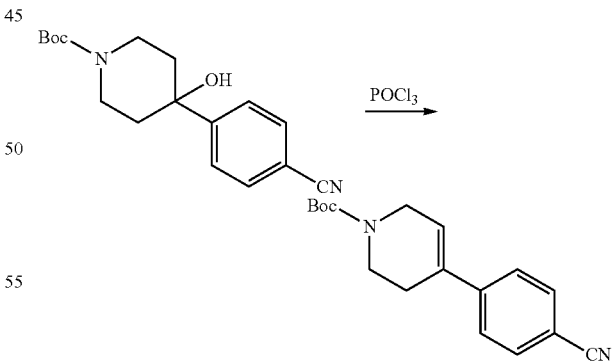

Compound 1.3. tert-Butyl 4-(4-cyanophenyl)-5,6-dihydropyridine-1(2H)-carboxylate Into a round-bottom flask, was placed a solution of tert-butyl 4-(4-cyanophenyl)-4-hydroxypiperidine-1-carboxylate (compound 1.2, 2 g, 6.61 mmol, 1.00 equiv) in pyridine (40 mL). POCl₃ (10.16 g, 66.26 mmol, 10.02 equiv)

was carefully added. The resulting mixture was stirred under nitrogen overnight at room temperature and then concentrated under vacuum. The residue was taken up in 20 mL of DCM, washed with 2×20 mL of sodium bicarbonate (aq), dried (Na$_2$SO$_4$), and concentrated under reduced pressure. The residue was purified using silica gel column chromatography with PE/EtOAc (100:1-30:1) as eluent to yield 1.4 g (74%) of the title compound as a white solid.

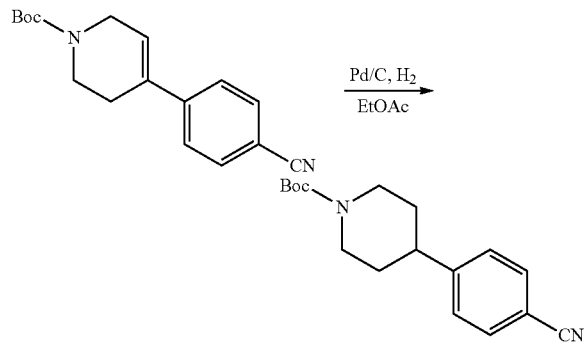

Compound 1.4. tert-Butyl 4-(4-cyanophenyl)piperidine-1-carboxylate

A round-bottom flask, containing a solution of tert-butyl 4-(4-cyanophenyl)-5,6-dihydropyridine-1(2H)-carboxylate (compound 1.3, 500 mg, 1.76 mmol, 1.00 equiv) in ethyl acetate (20 mL) was purged with nitrogen gas. To the solution was then added palladium on carbon (0.1 g, 10%, 60% water) and the flask was then further purged with nitrogen. The atmosphere was then changed to hydrogen and the mixture was stirred overnight at room temperature. After purging the system with nitrogen, the solids were removed by filtration and the filtrate was concentrated under reduced pressure to yield 0.2 g (40%) of the title compound as a yellow oil.

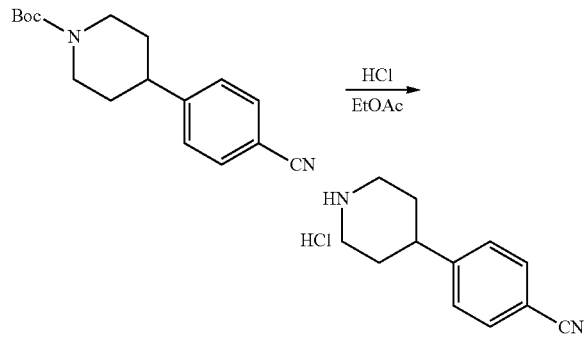

Compound 1.5. 4-(Piperidin-4-yl)benzonitrile hydrochloride

Into a 100-mL 3-necked round-bottom flask, was placed a solution of tert-butyl 4-(4-cyanophenyl)piperidine-1-carboxylate (compound 1.4, 4 g, 13.99 mmol, 1.00 equiv) in ethyl acetate (60 mL). Hydrogen chloride (gas) was bubbled through the solution and the resulting mixture was stirred for 1 h at room temperature. The formed precipitate was collected by filtration and dried to yield 2.2 g (71%) of the title compound as a white solid. m/z (ES+) 187 (M+H)$^+$. $^1$H NMR (300 MHz, CD$_3$OD): δ 7.72 (d, 1=8.4 Hz, 2H), 7.50 (d, J=8.4 Hz, 2H), 3.54 (d with fine structure, J=12.6 Hz, 2H), 3.18 (t with fine structure, J=12.2 Hz, 2H), 3.12-1.97 (m, 1H), 2.11 (d with fine structure, J=14.1 Hz, 2H), 2.04-1.84 (m, 2H).

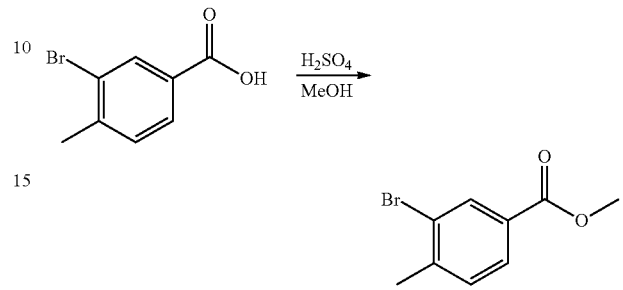

Compound 1.6. Methyl 3-bromo-4-methylbenzoate

A solution of 3-bromo-4-methylbenzoic acid (20 g, 93.00 mmol, 1.00 equiv) and sulfuric acid (20 mL) in methanol (100 mL) was stirred overnight at 80° C. The mixture was then concentrated under reduced pressure and the residue was diluted with 500 mL of ethyl acetate. The resulting mixture was washed with 3×200 mL of water, 1×200 mL of sodium bicarbonate (aq), followed by 1×200 mL of brine. The organic phase was dried over anhydrous sodium sulfate, concentrated under reduced pressure, and dried to yield 20 g (94%) of the title compound as a dark red oil.

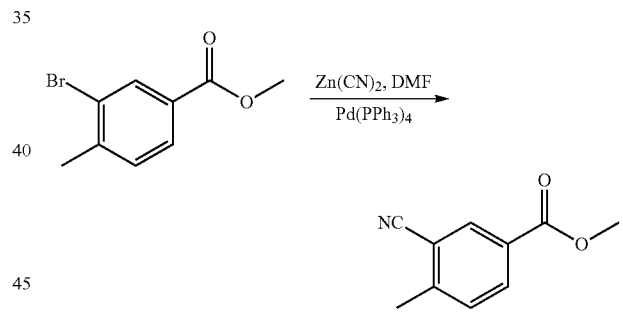

Compound 1.7. Methyl 3-cyano-4-methylbenzoate

A mixture of methyl 3-bromo-4-methylbenzoate (compound 1.6, 18 g, 78.58 mmol, 1.00 equiv), Zn(CN)$_2$ (11.1 g, 94.87 mmol, 1.20 equiv), and Pd(PPh$_3$)$_4$ (7.3 g, 6.32 mmol, 0.08 equiv) in N,N-dimethylformamide (250 mL) was stirred under a nitrogen atmosphere at 100° C. overnight. After cooling to room temperature, the reaction was then quenched by careful addition of 200 mL of FeSO$_4$(aq., sat.) and diluted with ethyl acetate. The resulting mixture was stirred vigorously then filtered through celite and washed with 1 M FeSO$_4$, water, and ethyl acetate. The layers were separated and the aqueous phase was extracted with 2×500 mL of ethyl acetate. The combined organic layers were washed with 3×200 mL of brine, dried over (Na$_2$SO$_4$), and concentrated under reduced pressure. The residue was purified using silica gel column chromatography with ethyl acetate/petroleum ether (1:50) as eluent to yield. 11 g (76%) of the title compound as an off-white solid.

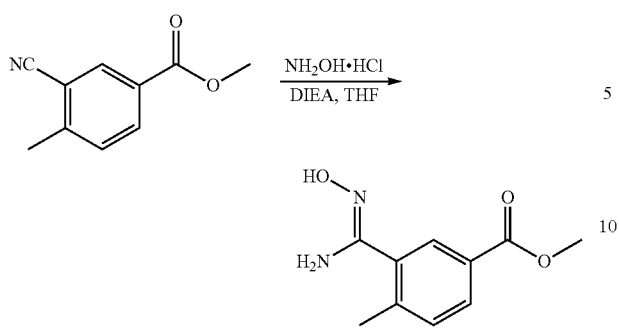

Compound 1.8. Methyl 3-(N'-hydroxycarbamimidoyl)-4-methylbenzoate

A mixture of methyl 3-cyano-4-methylbenzoate (compound 1.7, 8 g, 43.38 mmol, 1.00 equiv, 95%), NH₂OH.HCl (3.785 g, 54.86 mmol, 1.20 equiv), and N,N-Diisopropylethylamine (DIEA, 17.7 g, 136.95 mmol, 3.00 equiv) in tetrahydrofuran (100 mL) was stirred overnight at 70° C. After cooling to room temperature, the mixture was concentrated under reduced pressure. The residue was taken up in water and the pH was adjusted to 2-3 with hydrogen chloride (aqueous, 1 M). After washing the mixture with 3×40 mL of ethyl acetate, the pH of the aqueous layer was adjusted to 8-9 with NaOH (aqueous, 2 M) followed by extraction with 3×30 mL of ethyl acetate. The combined organic layers were dried over (Na₂SO₄) and concentrated under reduced pressure to yield 2.76 g (29%) of the title compound as a white solid.

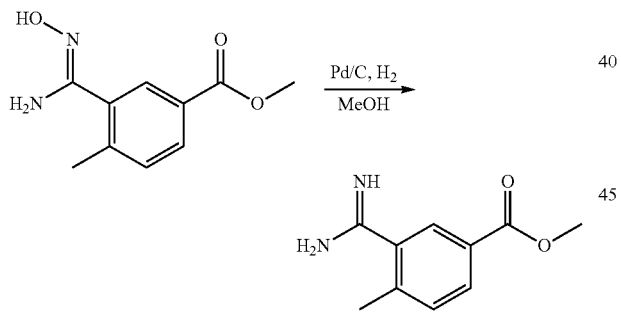

Compound 1.9. Methyl 3-carbamimidoyl-4-methylbenzoate

A round-bottom flask, containing a solution of methyl 3-(N'-hydroxycarbamimidoyl)-4-methylbenzoate (compound 1.8, 8 g, 36.50 mmol, 1.00 equiv, 95%) in methanol (150 mL) was purged with nitrogen gas. To the solution was added palladium on carbon (9 g, 10%, 60% water) and the flask was then further purged with nitrogen gas. The atmosphere was then changed to hydrogen and the mixture was stirred overnight at 25° C. under a balloon. After purging the system with nitrogen, the solids were removed by filtration and the filtrate was concentrated under reduced pressure to yield 4 g (54%) of the title compound as a brown solid.

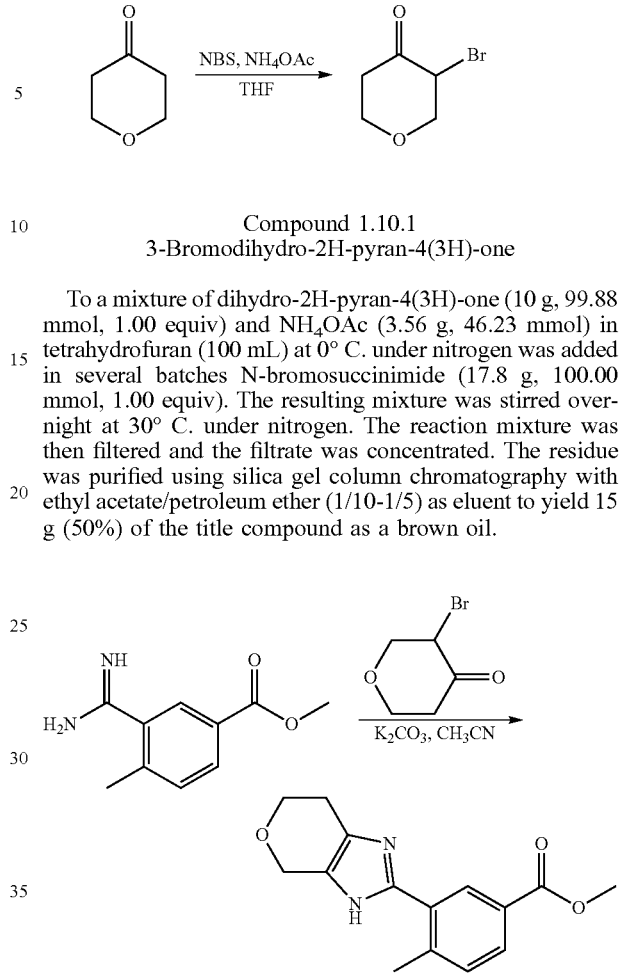

Compound 1.10.1 3-Bromodihydro-2H-pyran-4(3H)-one

To a mixture of dihydro-2H-pyran-4(3H)-one (10 g, 99.88 mmol, 1.00 equiv) and NH₄OAc (3.56 g, 46.23 mmol) in tetrahydrofuran (100 mL) at 0° C. under nitrogen was added in several batches N-bromosuccinimide (17.8 g, 100.00 mmol, 1.00 equiv). The resulting mixture was stirred overnight at 30° C. under nitrogen. The reaction mixture was then filtered and the filtrate was concentrated. The residue was purified using silica gel column chromatography with ethyl acetate/petroleum ether (1/10-1/5) as eluent to yield 15 g (50%) of the title compound as a brown oil.

Compound 1.10. Methyl 4-methyl-3-(3,4,6,7-tetrahydropyrano[3,4-d]imidazol-2-yl)benzoate A mixture of methyl 3-carbamimidoyl-4-methylbenzoate (compound 1.9, 400 mg, 1.98 mmol, 1.00 equiv, 95%), 3-bromodihydro-2H-pyran-4(3H)-one (compound 1.10.1, 750 mg, 2.09 mmol, 1.00 equiv), and potassium carbonate (580 mg, 4.20 mmol, 2.00 equiv) in CH₃CN (15 mL) was stirred overnight at 80° C. under nitrogen. After cooling to ambient temperature, the reaction mixture was concentrated under reduced pressure. The residue was dissolved in 50 mL of ethyl acetate and washed with 2×10 mL of H₂O. The organic phase was dried over (Na₂SO₄) and concentrated under reduced pressure. The residue was purified using silica gel column chromatography and purified using ethyl acetate/petroleum ether (1/3) to yield 0.21 g (37%) of the title compound as a white solid.

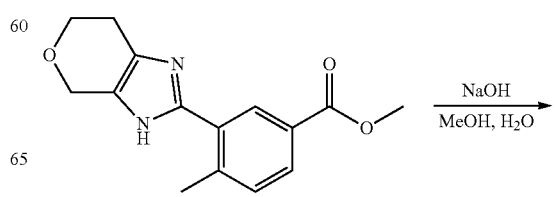

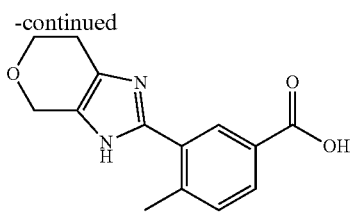

Compound 1.11. 4-Methyl-3-(3,4,6,7-tetrahydropyrano[3,4-d]imidazol-2-yl)benzoic acid A mixture of methyl 4-methyl-3-(3,4,6,7-tetrahydropyrano[3,4-d]imidazol-2-yl)benzoate (compound 1.10, 210 mg, 0.73 mmol, 1.00 equiv, 95%) and sodium hydroxide (92.65 mg, 2.32 mmol, 3.00 equiv) in 12 mL methanol/H$_2$O (2:1) stirred for at 60° C. in an oil bath. After 2 h, the reaction mixture was concentrated under reduced pressure and the residue was taken up in 5 mL of H$_2$O. The resulting mixture was washed with 3×10 mL of ethyl acetate and the pH of the aqueous layer was then adjusted to 2-3 using hydrogen chloride (aq., 2 M). The resulting mixture was extracted with 3×30 mL of ethyl acetate. The combined organic layers were dried (Na$_2$SO$_4$) and concentrated under reduced pressure to yield 0.21 g (89%) of the title compound as a white solid.

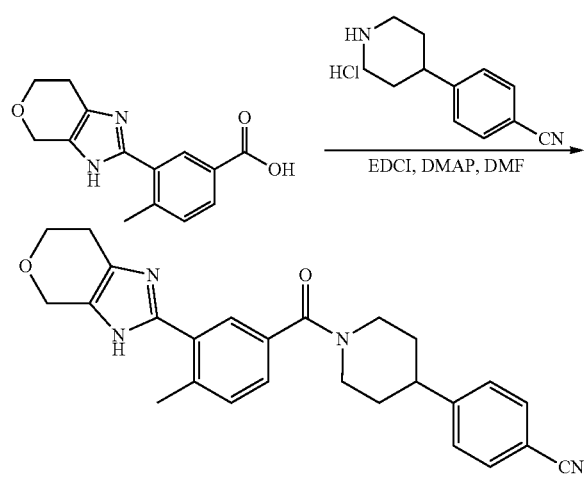

Compound 1. Methyl 4-(1-(4-methyl-3-(3,4,6,7-tetrahydropyrano[3,4-d]imidazol-2-yl)benzoyl)piperidin-4-yl)benzonitrile A mixture of 4-methyl-3-(3,4,6,7-tetrahydropyrano[3,4-d]imidazol-2-yl)benzoic acid (compound 1.11, 60 mg, 0.22 mmol, 1.00 equiv, 95%), EDCI (88.4 mg, 0.46 mmol, 2.00 equiv), DMAP (85.12 mg, 0.70 mmol, 3.00 equiv), and 4-(piperidin-4-yl)benzonitrile hydrochloride (compound 1.5, 52 mg, 0.23 mmol, 1.00 equiv) in DMF was stirred at room temperature. After 311, the reaction mixture was diluted with 40 mL of DCM and washed with 2×10 mL of NH$_4$Cl (aq.sat.) followed by 2×10 mL of brine. The organic layer was dried (Na$_2$SO$_4$) and concentrated under reduced pressure. The crude product (~100 mg) was purified by Prep-HPLC with the following conditions (1#-Pre-HPLC-006 (Waters)): Column, SunFire Prep C18, 19*150 mm 5 um; mobile phase, WATER WITH 0.05% TFA and CH3CN (15.0% CH3CN up to 42.0% in 12 min, up to 100.0% in 1 min); Detector, uv 254/220 nm. The fractions containing pure compound were combined and lyophilized to yield 32.9 mg (34%) of the title compound as a white solid. m/z (ES+) 427 (M+H)$^+$. $^1$H NMR (300 MHz, CD$_3$OD): δ 7.73-7.65 (m, 4H), 7.61 (d, J=5.7 Hz, 1H), 7.50 (d, J=6.0 Hz, 2H), 4.89-4.78 (1H partially obscured by water peak), 4.81 (s, 2H), 4.10 (t, J=4.1 Hz, 2H), 3.94-3.81 (m, 1H), ~3.35 (1H partially obscured by methanol solvent peak), 3.08-1.95 (m, 2H), 2.92 (t, J=4.1 Hz, 2H), 2.52 (s, 3H), 2.08-1.92 (m, 1H), 1.92-1.65 (m, 3H). $^1$H NMR (400 MHz, CDCl$_3$): δ 7.63 (d, J=8.3 Hz, 2H), 7.34 (d, J=8.3 Hz, 2H), 7.30 (s, 1H) 7.50 (m, 2H), 4.89 (d, J=13.0 Hz, 1H), 4.81 (s, 2H), 4.05 (t, J=5.2 Hz, 2H), 3.77 (d, J=13.2 Hz, 1H), 3.30 (t, J=13.0 Hz, 1H), 3.01-2.84 (m, 4H), 2.34 (s, 3H), 2.06 (d, J=13.7 Hz, 1H), 1.86 (d, J=12.9 Hz, 1H), 1.76 (q, J=12.8 Hz, 1H), 1.57 (q, J=11.7 Hz, 1H).

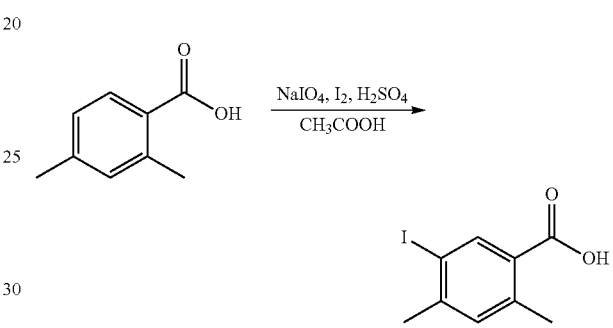

Compound 2.1. 5-Iodo-2,4-dimethylbenzoic acid

A solution of 2,4-dimethylbenzoic acid (20 g, 133.18 mmol, 1.00 equiv), sodium periodate (14.27 g, 66.72 mmol, 0.50 equiv), iodine (37.25 g, 146.76 mmol, 1.10 equiv), and sulfuric acid (1.96 g, 19.98 mmol, 0.15 equiv) in acetic acid (150 mL) was stirred at 110° C. in an oil bath. After 6 h, the reaction mixture was allowed to reach ambient temperature and was then diluted with 1.2 L of water. To this was carefully added 800 mL of aq Na$_2$S$_2$O$_3$ (aq., sat.). The resulting solids were collected by filtration, dissolved in 1.2 L of ethyl acetate, and washed with 1×300 mL of Na$_2$S$_2$O$_3$ (aq., sat.) followed by 1×400 mL of brine. The organic layer was dried (Na$_2$SO$_4$) and concentrated under reduced pressure. The crude residue was re-crystallized from ethanol:H$_2$O (2:1) to yield 30 g (82%) of the title compound as a white solid.

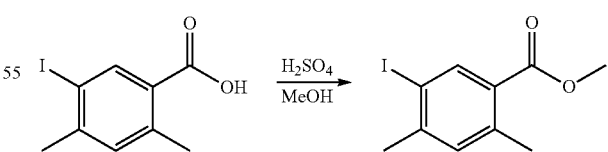

Compound 2.2. Methyl 5-iodo-2,4-dimethylbenzoate

A solution of 5-iodo-2,4-dimethylbenzoic acid (compound 2.1, 10 g, 32.60 mmol, 1.00 equiv, 90%) and sulfuric acid (10 mL) in methanol (100 mL) was stirred overnight at 80° C. After cooling to room temperature, the mixture was concentrated under reduced pressure and the residue was diluted with 200 mL of ethyl acetate. The resulting mixture was washed with 3×50 mL of water, 2×50 mL of sodium bicarbonate (aq. sat.), followed by 2×50 mL of brine. The organic phase was dried over anhydrous sodium sulfate and concentrated under reduced pressure to yield 9.2 g (88%) of the title compound as a yellow oil.

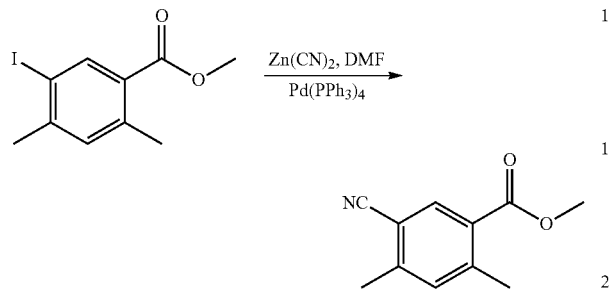

Compound 2.3. Methyl 5-cyano-2,4-dimethylbenzoate

A solution of methyl 5-iodo-2,4-dimethylbenzoate (compound 2.2, 9.2 g, 31.71 mmol, 1.00 equiv), Zn(CN)$_2$ (4.46 g, 38.12 mmol, 1.20 equiv), and Pd(PPh$_3$)$_4$ (2.93 g, 2.54 mmol, 0.08 equiv) in N,N-dimethylformamide (120 mL) was stirred under a nitrogen atmosphere at 100° C. overnight. After cooling to room temperature, the reaction was then quenched by careful addition of 100 mL of FeSO$_4$ (aq., sat.) and diluted with ethyl acetate. The resulting mixture was stirred vigorously then filtered through celite and washed with 1 M FeSO$_4$, water, and ethyl acetate. The layers were separated and the aqueous phase was extracted with 2×100 mL of ethyl acetate. The combined organic layers were washed with 2×20 mL of brine, dried (Na$_2$SO$_4$), and concentrated under reduced pressure. The residue was purified using silica gel column chromatography with ethyl acetate/petroleum ether (1:5) as eluent to yield 6.2 g (93%) of the title compound as a white solid.

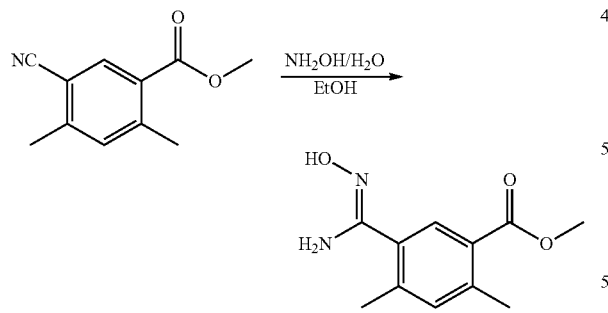

Compound 2.4. Methyl 5-(N'-hydroxycarbamimidoyl)-2,4-dimethylbenzoate

A solution of methyl 5-cyano-2,4-dimethylbenzoate (compound 2.3, 6 g, 28.54 mmol, 1.00 equiv, 90%) and NH$_2$OH (10 mL, 5.00 equiv, 50% in water) in EtOH (20 mL) was stirred at 100° C. in an oil bath. After 2 h, the mixture was cooled to room temperature and concentrated under reduced pressure. The residue was diluted with 100 mL of ethyl acetate, washed with 2×20 mL of brine, dried (Na$_2$SO$_4$), and concentrated under reduced pressure to yield 4.66 g (66%) of the title compound as a white solid.

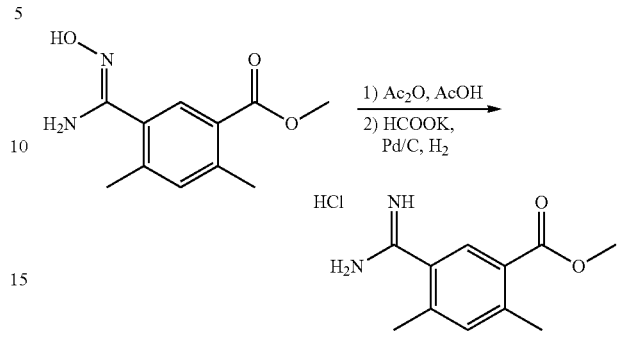

Compound 2.5. Methyl 5-carbamimidoyl-2,4-dimethylbenzoate hydrochloride

A solution of methyl 5-(N'-hydroxycarbamimidoyl)-2,4-dimethylbenzoate (compound 2.4, 4.66 g, 18.87 mmol, 1.00 equiv, 90%) and Ac$_2$O (2.36 g, 23.09 mmol, 1.10 equiv) in AcOH (21 mL) was stirred at room temperature. After 5 minutes, the flask was purged with nitrogen and HCOOK (8.8 g, 104.76 mmol, 5.00 equiv) and palladium on carbon (10%, 2.33 g) were added. The flask was purged with nitrogen followed by hydrogen. The mixture was stirred under a hydrogen atmosphere (balloon) at room temperature for 4 h. After purging the system with nitrogen, the solids were removed by filtration, and the filtrate was concentrated under reduced pressure. The residue was dissolved in 50 mL of ethanol and the pH was adjusted to 5-6 with hydrogen chloride (aq., 5 M). The resulting solids were removed by filtration and the filtrate was concentrated under reduced pressure to yield 4 g of the title compound as a white solid.

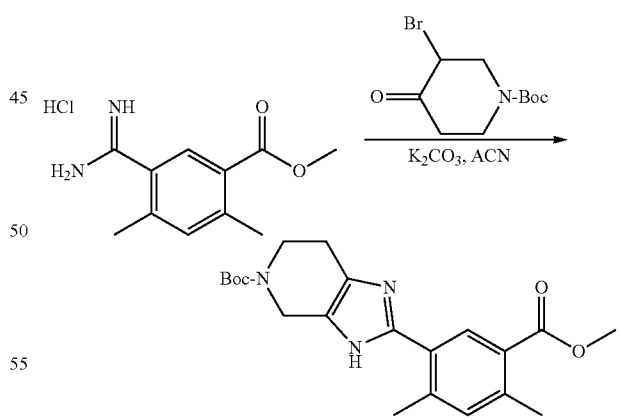

Compound 2.6. tert-Butyl 2-(5-(methoxycarbonyl)-2,4-dimethylphenyl)-6,7-dihydro-3H-imidazo[4,5-c]pyridine-5(4H)-carboxylate A mixture of methyl methyl 5-carbamimidoyl-2,4-dimethylbenzoate hydrochloride (compound 2.5, 500 mg, 90%), tert-butyl 3-bromo-4-oxopiperidine-1-carboxylate (860 mg, 2.78 mmol), and potassium carbonate (570 mg, 4.12 mmol)

in CH₃CN (15 mL) was stirred overnight under nitrogen at 80° C. After cooling to ambient temperature, the reaction mixture was concentrated under reduced pressure. The residue was dissolved in 25 mL of ethyl acetate and washed with 2×10 mL of H₂O. The organic phase was dried (Na₂SO₄) and concentrated under reduced pressure. The crude product thus obtained was purified using silica gel column chromatography with ethyl acetate/petroleum ether (1:3) as eluent to yield 0.3 g of the title compound as a white solid.

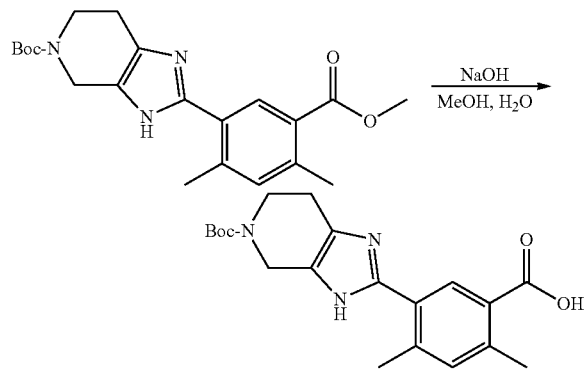

Compound 2.7. 5-(5-(tert-Butoxycarbonyl)-4,5,6,7-tetrahydro-3H-imidazo[4,5-c]pyridin-2-yl)-2,4-dimethylbenzoic acid A mixture of tert-butyl 2-(5-(methoxycarbonyl)-2,4-dimethylphenyl)-6,7-dihydro-3H-imidazo[4,5-c]pyridine-5(4H)-carboxylate (compound 2.6, 300 mg, 0.70 mmol, 1.00 equiv, 90%) and sodium hydroxide (62 mg, 1.55 mmol, 2.00 equiv) in 15 mL methanol/H₂O (2:1) was stirred for at 40° C. in an oil bath. After 2 h, the reaction mixture was concentrated to about ⅓ of the volume under reduced pressure. The pH value of the remaining mixture was adjusted to 3-4 with hydrogen chloride (aq., 1 M). The resulting solids were collected by filtration and dried in an oven under reduced pressure to yield 0.2 g (69%) of the title compound as a yellow solid.

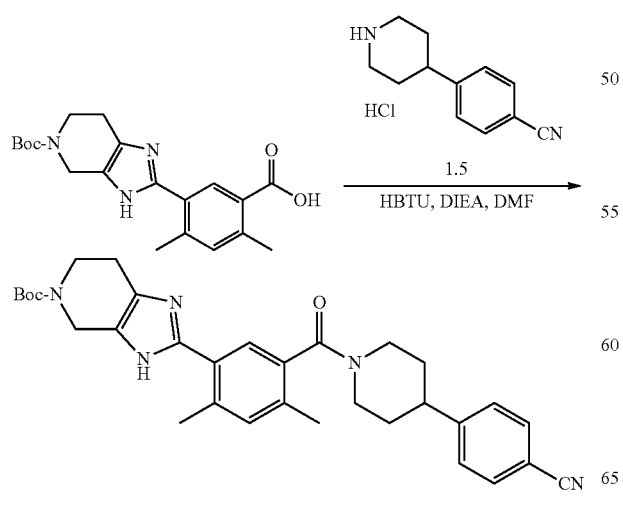

Compound 2.8. tert-Butyl 2-(5-(4-(4-cyanophenyl)piperidine-1-carbonyl)-2,4-dimethylphenyl)-6,7-dihydro-3H-imidazo[4,5-c]pyridine-5(4H)-carboxylate A solution of compound 2.7 (125 mg, 0.30 mmol, 1.00 equiv, 90%), DIEA (130.5 mg, 1.01 mmol, 3.00 equiv), HBTU (256.2 mg, 0.68 mmol, 2.00 equiv), and 4-(piperidin-4-yl)benzonitrile hydrochloride (compound 1.5, 75 mg, 0.30 mmol, 1.00 equiv) in DMF (5 mL) was stirred overnight at room temperature. The reaction mixture was then diluted with 50 mL of ethyl acetate, washed with 2×20 mL of brine, dried over anhydrous sodium sulfate, and concentrated under reduced pressure. The residue was purified using silica gel column chromatography and purified using ethyl acetate/petroleum ether (1:1) to yield 0.1 g (55%) of the title compound as a yellow solid.

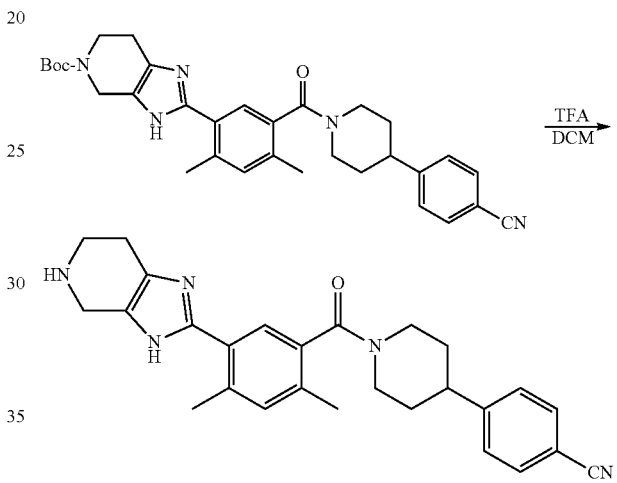

Compound 2.9. 4-(1-(2,4-Dimethyl-5-(4,5,6,7-tetrahydro-3H-imidazo[4,5-c]pyridin-2-yl)benzoyl)piperidin-4-yl)benzonitrile To a solution of tert-butyl 2-(5-(4-(4-cyanophenyl)piperidine-1-carbonyl)-2,4-dimethylphenyl)-6,7-dihydro-3H-imidazo[4,5-c]pyridine-5(4H)-carboxylate (compound 2.8, 100 mg, 0.17 mmol, 1.00 equiv, 90%) in dichloromethane (3 mL) was added trifluoroacetic acid (1 mL). The resulting mixture was stirred at room temperature. After 2 h, the reaction mixture was concentrated under reduced pressure. The residue was taken up in dichloromethane and washed with sodium bicarbonate (aq., sat.). The organic phase was dried (Na₂SO₄) and concentrated under reduced pressure to yield 0.1 g (68%) of the title compound as a yellow solid.

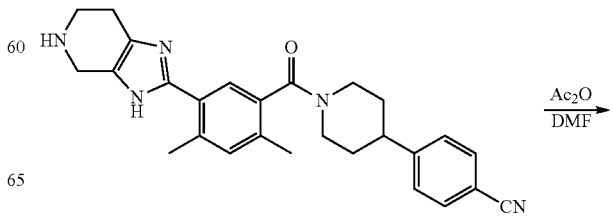

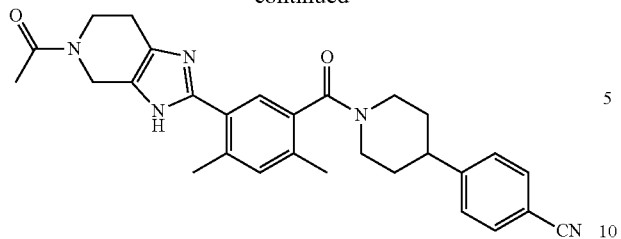

Compound 2. 4-(1-(5-(5-Acetyl-4,5,6,7-tetrahydro-3H-imidazo[4,5-c]pyridin-2-yl)-2,4-dimethylbenzoyl)piperidin-4-yl)benzonitrile To a stirred mixture of 4-(1-(2,4-dimethyl-5-(4,5,6,7-tetrahydro-3H-imidazo[4,5-c]pyridin-2-yl)benzoyl)piperidin-4-yl)benzonitrile (compound 2.9, 20 mg, 0.02 mmol, 1.00 equiv, 50%) in DMF (2 mL) under nitrogen was added a solution of $Ac_2O$ (2.4 mg, 0.02 mmol, 1.00 equiv) in DMF (0.2 mL) dropwise at 0° C. The resulting solution was stirred for 1 h at 0~3° C. in a water/ice bath. The reaction mixture was then diluted with 50 mL of ethyl acetate and washed with 2×20 mL of brine. The organic phase was dried ($Na_2SO_4$) and concentrated under reduced pressure. The crude residue (50 mg) was purified by Prep-HPLC with the following conditions (1#-Pre-HPLC-006 (Waters)): Column, xbridge C18; mobile phase, WATER WITH 0.05% $NH_3.H_2O$ and $CH_3CN$ (hold 5% $CH_3CN$ in 2 min, up to 20%-46% in 10 min, up to 100% in 12 min, down to 20% in 14 min); Detector, UV 254/220 nm. The fractions containing pure compound were combined and lyophilized to yield 5.5 mg of the title compound as a white solid. m/z (ES+) 482 (M+H)$^+$. $^1$H NMR (300 MHz, $CD_3OD$): δ 7.69 (d, J=8.1 Hz, 2H), 7.48 (d, J=8.1 Hz, 2H), 7.39-7.28 (m, 2H), 4.90 (m, 1H, partially obscured by the solvent peak), 4.67 and 4.62 (2 singlets, acetamide rotamers, $MeCONCH_2$-imidazole, 2H), 3.92 (m, 2H), 3.66 (m, 1H), 3.23 (m, 1H), 3.00 (m, 2H), 2.85-2.76 (m, 2H), 2.48 (s, 3H), 2.41 and 2.31 (2 singlets, aryl amide rotamers, $ArCH_3$, 3H), 2.25 and 2.22 (2 singlets, acetamide rotamers, $CH_3CON$, 3H), 2.04 (m, 1H), 1.92-1.20 (m, 3H).

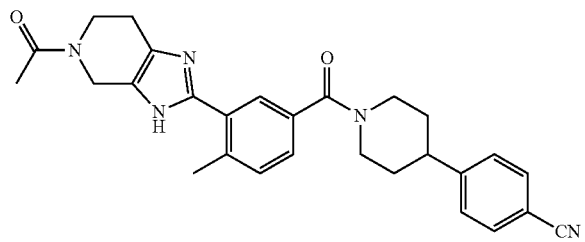 [SMILES: CC(=O)N1CCc2nc(-c3cc(C(=O)N4CCC(c5ccc(C#N)cc5)CC4)ccc3C)[nH]c2C1]

Compound 3. 4-(1-(3-(5-Acetyl-4,5,6,7-tetrahydro-3H-imidazo[4,5-c]pyridin-2-yl)-4-methylbenzoyl)piperidin-4-yl)benzonitrile The title compound was prepared using standard chemical manipulations and procedures similar to those used for the preparation of compounds 1 and 2. m/z (ES+) 468 (M+H)$^+$.

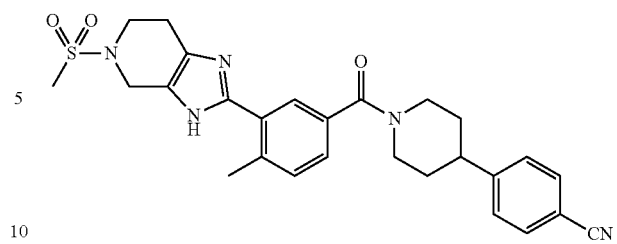

Compound 4. 4-(1-(4-Methyl-3-(5-(methylsulfonyl)-4,5,6,7-tetrahydro-3H-imidazo[4,5-c]pyridin-2-yl)benzoyl)piperidin-4-yl)benzonitrile The title compound was prepared using standard chemical manipulations and procedures similar to those used for the preparation of compounds 1 and 2. m/z (ES+) 504 (M+H)$^+$.

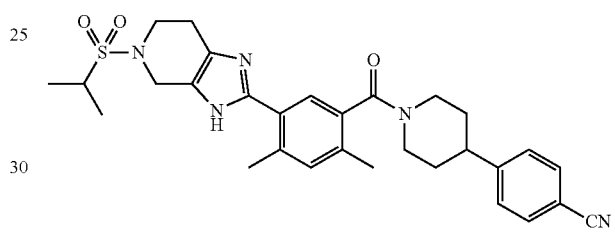

Compound 5. 4-(1-(5-(5-(Isopropylsulfonyl)-4,5,6,7-tetrahydro-3H-imidazo[4,5-c]pyridin-2-yl)-2,4-dimethylbenzoyl)piperidin-4-yl)benzonitrile The title compound was prepared using standard chemical manipulations and procedures similar to those used for the preparation of compounds 1 and 2. m/z (ES+) 546 (M+H)$^+$.

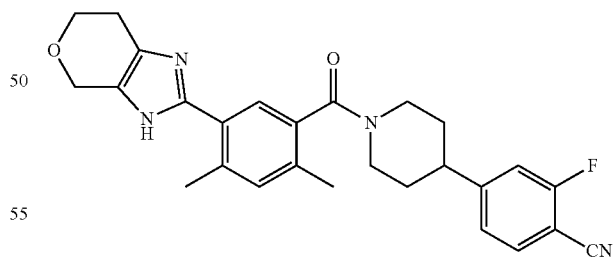

Compound 6. 4-(1-(2,4-Dimethyl-5-(3,4,6,7-tetrahydropyrano[3,4-d]imidazol-2-yl)benzoyl)piperidin-4-yl)-2-fluorobenzonitrile The title compound was prepared using standard chemical manipulations and procedures similar to those used for the preparation of compounds 1 and 2. m/z (ES+) 459 (M+H)$^+$.

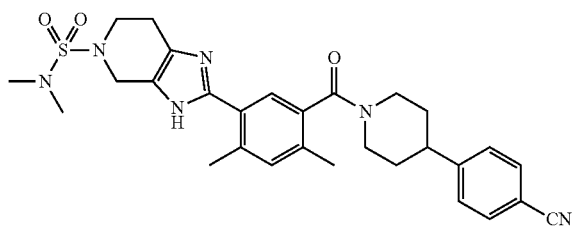 [SMILES: Cc1cc(C)c(-c2nc3c([nH]2)CN(S(=O)(=O)N(C)C)CC3)cc1C(=O)N1CCC(c2ccc(C#N)cc2)CC1]

Compound 7. 2-(5-(4-(4-Cyanophenyl)piperidine-1-carbonyl)-2,4-dimethylphenyl)-N,N-dimethyl-6,7-dihydro-3H-imidazo[4,5-c]pyridine-5(4H)-sulfonamide The title compound was prepared using standard chemical manipulations and procedures similar to those used for the preparation of compounds 1 and 2. m/z (ES+) 547 (M+H)+.

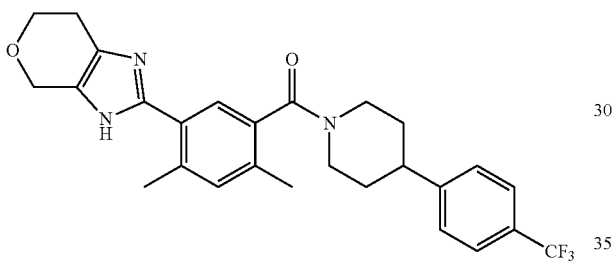

Compound 8. (2,4-Dimethyl-5-(3,4,6,7-tetrahydropyrano[3,4-d]imidazol-2-yl)phenyl)(4-(4-(trifluoromethyl)phenyl)piperidin-1-yl)methanone The title compound was prepared using standard chemical manipulations and procedures similar to those used for the preparation of compounds 1 and 2. m/z (ES+) 484 (M+H)+.

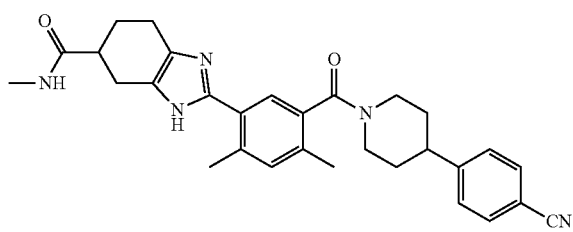 [SMILES: CNC(=O)C1CCc2nc(-c3cc(C(=O)N4CCC(c5ccc(C#N)cc5)CC4)c(C)cc3C)[nH]c2C1]

Compound 9. 2-(5-(4-(4-Cyanophenyl)piperidine-1-carbonyl)-2,4-dimethylphenyl)-N-methyl-4,5,6,7-tetrahydro-1H-benzo[d]imidazole-6-carboxamide The title compound was prepared using standard chemical manipulations and procedures similar to those used for the preparation of compounds 1 and 2. m/z (ES+) 496 (M+H)+.

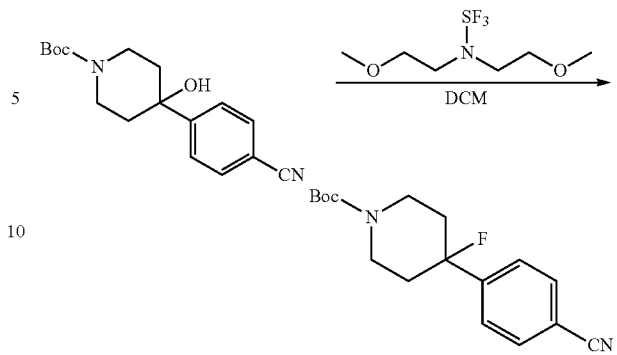

Compound 11.1. tert-Butyl 4-(4-cyanophenyl)-4-fluoropiperidine-1-carboxylate

To a stirred solution of compound 1.2 (5 g, 16.54 mmol, 1.00 equiv) in dichloromethane (250 mL) under nitrogen at −78° C. was added dropwise Deoxo-Fluor® (4.4 g, 19.89 mmol, 1.20 equiv). The resulting mixture was stirred for 1 h at −78° C. The reaction mixture was then carefully quenched by the addition of 50 mL of sodium bicarbonate (aq.sat.) and extracted with 3×100 mL of dichloromethane. The combined organic layers were washed with 150 mL of brine, dried over anhydrous magnesium sulfate, and concentrated under reduced pressure. The residue was purified using silica gel column chromatography with ethyl acetate/petroleum ether (1:30) as eluent to yield 2.5 g (35%) of the title compound as a white solid.

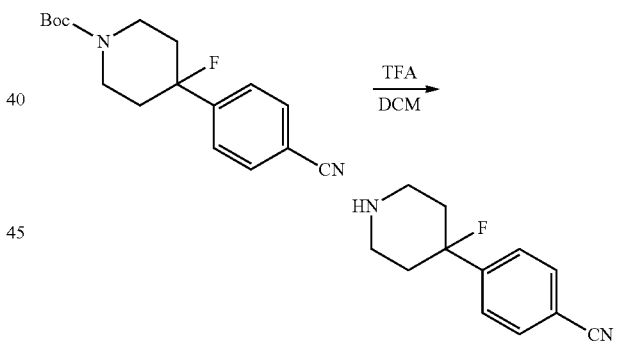

Compound 11.2. 4-(4-Fluoropiperidin-4-yl)benzonitrile

To a stirred solution of compound 11.1 (620 mg, 1.02 mmol, 1.00 equiv, 50%) in DCM (10 mL) was added dropwise trifluoroacetic acid (6 g, 52.62 mmol, 51.66 equiv). After stirring at ambient temperature for 2 h, the mixture was concentrated under reduced pressure. The residue was taken up in DCM and treated with aqueous sodium bicarbonate. The phases were separated and the aqueous layer was extracted with 2×50 mL DCM. The combined organic layers were dried over anhydrous magnesium sulfate and concentrated under reduced pressure to yield 0.4 g of the title compound as a light yellow solid. m/z (ES+) 205 (M+H)+.

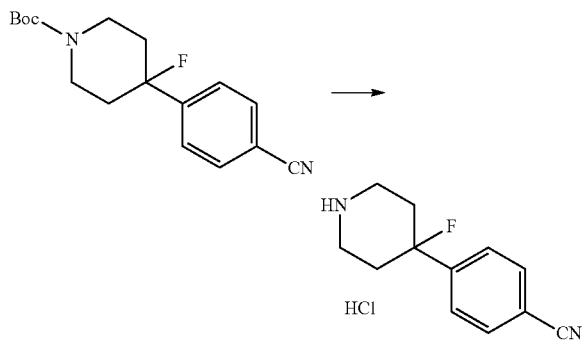

Compound 11.2 HCl salt.
4-(4-Fluoropiperidin-4-yl)benzonitrile hydrochloride The title compound was prepared using standard chemical manipulations and a procedure similar to that used for the preparation of compound 1.5 and using compound 11.1 in place of compound 1.4. m/z (ES+) 205 (M+H)⁺. ¹H NMR (300 MHz, CD₃OD): δ 7.83 (d, J=6.3 Hz, 2H), 7.68 (d, J=6.3 Hz, 2H), 3.55-3.32 (m, 4H), 2.58-2.40 (m, 2H), 2.28-2.22 (m, 2H).

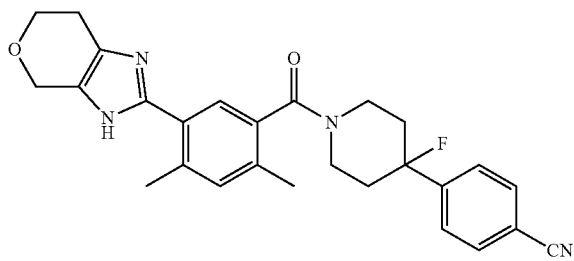 [SMILES: Cc1cc(C)c(-c2nc3c([nH]2)COCC3)cc1C(=O)N1CCC(F)(c2ccc(C#N)cc2)CC1]

Compound 11. 4-(1-(2,4-Dimethyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compounds 1 and 2 and using compound 11.2 in place of compound 1.5. m/z (ES+) 459 (M+H)⁺.

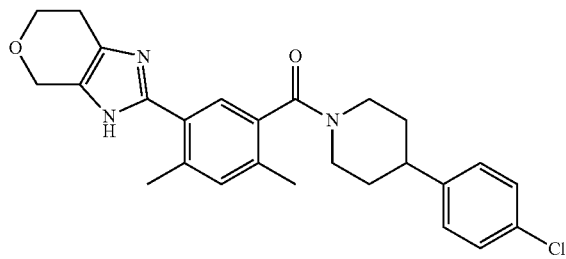 [SMILES: Cc1cc(C)c(-c2nc3c([nH]2)COCC3)cc1C(=O)N1CCC(c2ccc(Cl)cc2)CC1]

Compound 12. (4-(4-Chlorophenyl)piperidin-1-yl)(2,4-dimethyl-5-(3,4,6,7-tetrahydropyrano[3,4-d]imidazol-2-yl)phenyl)methanone The title compound was prepared using standard chemical manipulations and procedures similar to those used for the preparation of compounds 1 and 2. m/z (ES+) 450 (M+H)⁺.

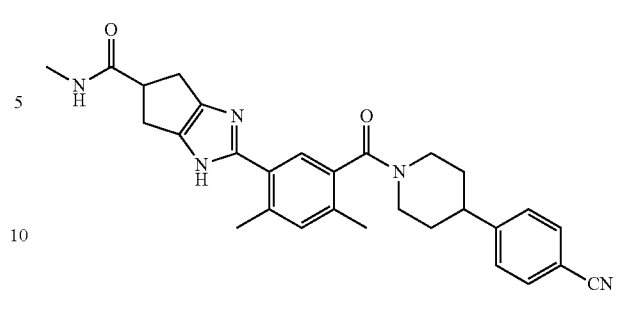

Compound 13. 2-(5-(4-(4-Cyanophenyl)piperidine-1-carbonyl)-2,4-dimethylphenyl)-N-methyl-1,4,5,6-tetrahydrocyclopenta[d]imidazole-5-carboxamide The title compound was prepared using standard chemical manipulations and procedures similar to those used for the preparation of compounds 1 and 2. m/z (ES+) 482 (M+H)⁺.

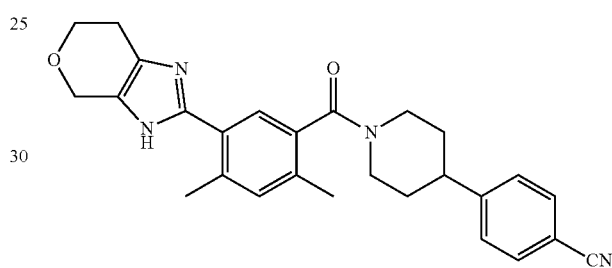

Compound 14. 4-(1-(2,4-Dimethyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compounds 1 and 2. m/z (ES+) 441 (M+H)⁺.

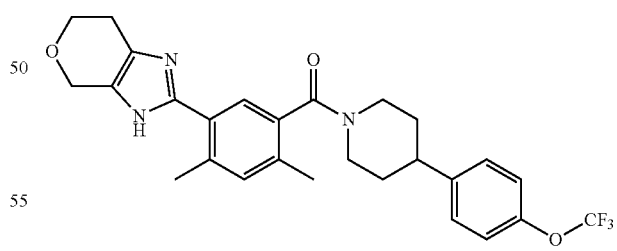

Compound 15. (2,4-Dimethyl-5-(3,4,6,7-tetrahydropyrano[3,4-d]imidazol-2-yl)phenyl)(4-(4-(trifluoromethoxy)phenyl)piperidin-1-yl)methanone The title compound was prepared using standard chemical manipulations and procedures similar to those used for the preparation of compounds 1 and 2. m/z (ES+) 500 (M+H)⁺.

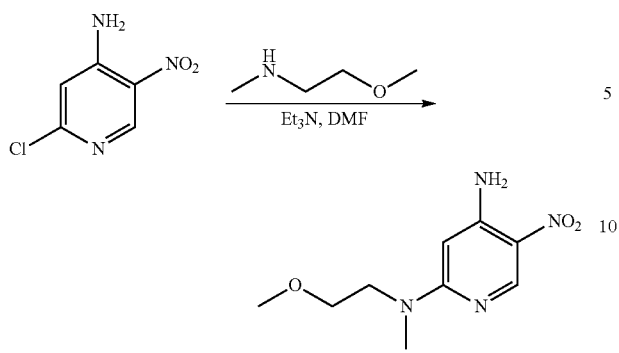

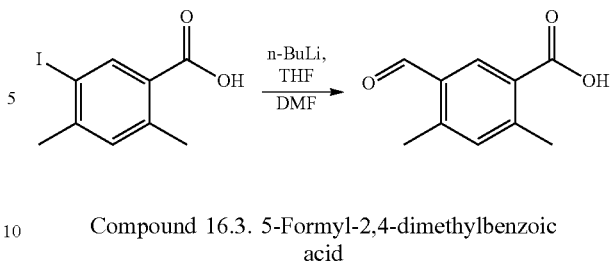

Compound 16.3. 5-Formyl-2,4-dimethylbenzoic acid

To a stirred solution of 5-iodo-2,4-dimethylbenzoic acid (compound 2.1, 5 g, 18.11 mmol, 1.00 equiv) in tetrahydrofuran (150 mL) under nitrogen at −78° C. was added n-BuLi (2.5 M in THF, 18 mL, 2.50 equiv) dropwise. After stirring at −78° C. for 1 h, DMF (5 g, 68.4 mmol, 3.80 equiv) was added dropwise. The resulting mixture was stirred at −78° C. for an additional 0.5 h and then carefully quenched by slow addition of 50 mL of water. The pH was then adjusted to ~3-4 using aqueous HCl (aq., 6 M). The mixture was extracted with 3×200 mL of ethyl acetate. The combined organic layers were dried (Na$_2$SO$_4$) and concentrated under reduced pressure. The residue thus obtained was purified using silica gel column chromatography with ethyl acetate/petroleum ether (1:10-1:5) as gradient to yield 2.4 g (74%) of the title compound as a white solid.

Compound 16.1. N$^2$-(2-Methoxyethyl)-N$^2$-methyl-5-nitropyridine-2,4-diamine A solution of 2-chloro-5-nitropyridin-4-amine (500 mg, 2.88 mmol, 1.00 equiv), triethylamine (1.167 g, 11.53 mmol, 4.00 equiv), and (2-methoxyethyl)(methyl)amine (514 mg, 5.77 mmol, 2.00 equiv) in DMF (20 mL) was stirred in a sealed tube at 55° C. behind a blast shield overnight. After cooling to room temperature, the mixture was diluted with 100 mL of water and extracted with 3×150 mL of ethyl acetate. The combined organic layers were dried (Na$_2$SO$_4$) and concentrated under reduced pressure to yield 723 mg (crude) of the title compound as a dark red oil.

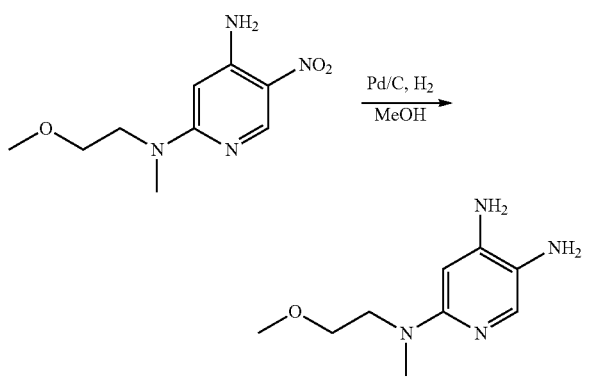

Compound 16.2. N$^2$-(2-Methoxyethyl)-N$^2$-methyl-pyridine-2,4,5-triamine

Around-bottom flask, containing a solution of compound 16.1 (400 mg, 1.77 mmol, 1.00 equiv)) in methanol (30 mL) was purged with nitrogen gas. To the solution was then added palladium on carbon (40 mg, 10%, 60% water). The flask was purged further with nitrogen and the atmosphere was then changed to hydrogen. The mixture was stirred at room temperature under a balloon with hydrogen for 4 h. After purging the system with nitrogen, the solids were removed by filtration and the filtrate was concentrated under reduced pressure to yield 300 mg (86%) of the title compound as a light brown solid. The crude product was found to be unstable and used immediately.

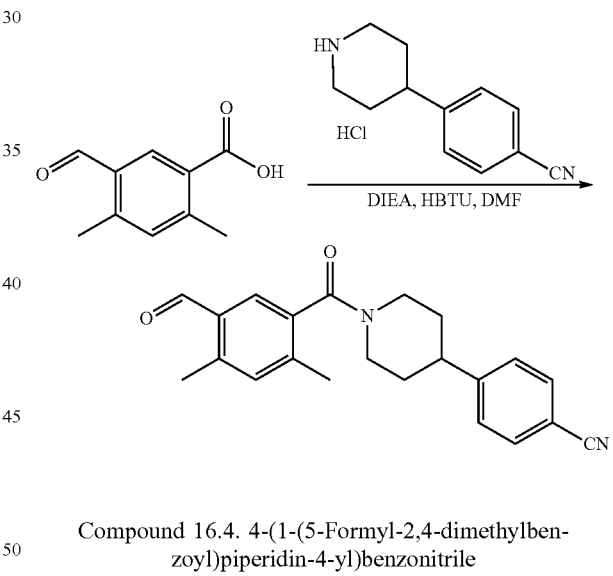

Compound 16.4. 4-(1-(5-Formyl-2,4-dimethylbenzoyl)piperidin-4-yl)benzonitrile To a stirred solution of 5-formyl-2,4-dimethylbenzoic acid (compound 16.3, 950 mg, 5.33 mmol, 1.10 equiv) in DMF (15 mL) was added DIEA (2.48 g, 19.19 mmol, 4.00 equiv) followed by HBTU (3.67 g, 9.68 mmol, 2.00 equiv), and 4-(piperidin-4-yl)benzonitrile hydrochloride (compound 1.5, 1.07 g, 4.80 mmol, 1.00 equiv). After stirring overnight at ambient temperature, the reaction was quenched by the addition of 60 mL of water. The resulting mixture was extracted with 3×150 mL of ethyl acetate and the organic layers were combined, dried over anhydrous sodium sulfate, and concentrated under reduced pressure. The residue was purified using silica gel column chromatography with ethyl acetate/petroleum ether (1:10-1:3) as eluent to yield 1.4 g (84%) of the title compound as a brown oil.

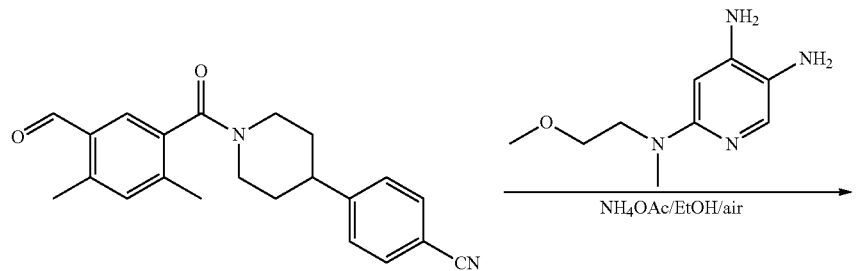

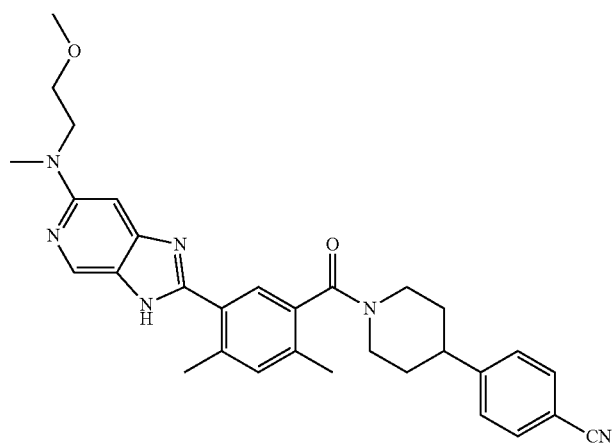

Compound 16. 4-(1-(5-(6-((2-Methoxyethyl)(methyl)amino)-3H-imidazo[4,5-c]pyridin-2-yl)-2,4-dimethylbenzoyl)piperidin-4-yl)benzonitrile A solution of compound 16.2 (300 mg, 1.53 mmol, 1.30 equiv), compound 16.4 (407 mg, 1.17 mmol, 1.00 equiv), and ammonium acetate (362 mg, 4.70 mmol, 4.00 equiv) in ethanol (20 mL) was stirred overnight at 70° C. in an oil bath. The resulting mixture was then concentrated under vacuum and the residue was purified using silica gel column chromatography with ethyl acetate/petroleum ether (1:10-2:1) as eluent to yield ~200 mg of product which was further purified by Prep-HPLC with the following conditions (1#-Pre-HPLC-006 (Waters)): Column, SunFire Prep C18, 19*150 mm 5 um; mobile phase, WATER WITH 0.05% TFA and CH3CN (hold 5.0% CH3CN in 2 min, up to 25.0% in 1 min, up to 55.0% in 12 min, up to 100.0% in 1 min); Detector, UV 254/220 nm. The fractions containing pure compound were combined and lyophilized to yield 150 mg (24%) of the title compound as a white solid. m/z (ES+) 523 (M+H)$^+$. $^1$H NMR (300 MHz, CDCl$_3$): δ 8.57-8.38 (m, 1H), 7.78-7.53 (m, 4H), 7.34 (d, J=7.5 Hz, 2H), 7.28-7.12 (m, 2H), 5.06-4.88 (m, 1H), 3.71 (app s, 5H), 3.50 (s, 3H), 3.41-3.05 (m, 4H), 3.01-2.75 (m, 2H), 2.68 (s, 3H), 2.42 & 2.31 (2 singlets, amide rotamers, ArCH$_3$, 3H), 2.12-1.93 (m, 1H), 1.93-1.39 (m, 3H).

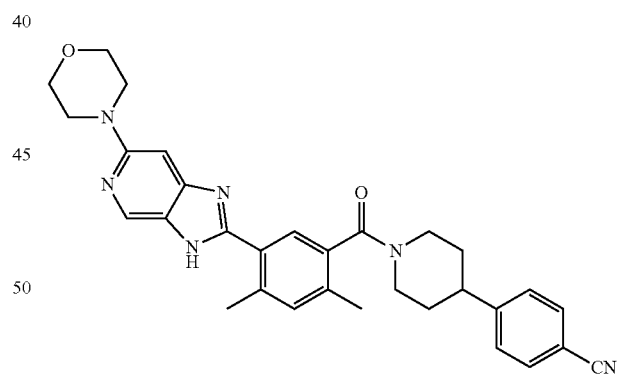

Compound 17. 4-(1-(2,4-Dimethyl-5-(6-morpholino-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 521 (M+H)$^+$.

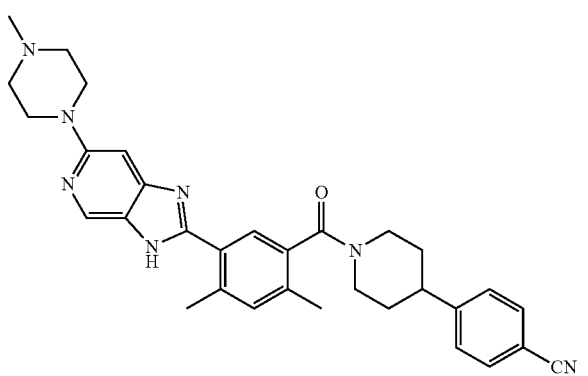 [SMILES: Cc1cc(C)c(-c2nc3cc(N4CCN(C)CC4)ncc3[nH]2)cc1C(=O)N1CCC(c2ccc(C#N)cc2)CC1]

Compound 18. 4-(1-(2,4-Dimethyl-5-(6-(4-methyl-piperazin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 534 (M+H)+. $^1$H NMR (300 MHz, DMSO-$d_6$): 8.73 (s, 1H), 7.76 (d, J=7.5 Hz, 2H), 7.66 & 7.56 (2 singlets, amide rotamers, Ar—H, 1H), 7.49 (d, J=8.1 Hz, 2H), 7.37 (s, 1H), 7.12 (s, 1H), 4.81-4.67 (m, 1H), 4.30 (br s, 2H), 3.70-3.37 (m, 3H), 3.37-3.05 (m, 5H), 3.05-1.80 (m, 5H), 2.60 (s, 3H), 2.37 & 2.27 (2 singlets, amide rotamers, Ar—CH$_3$, 3H), 2.02-1.87 (m, 1H), 1.87-2.40 (m, 3H).

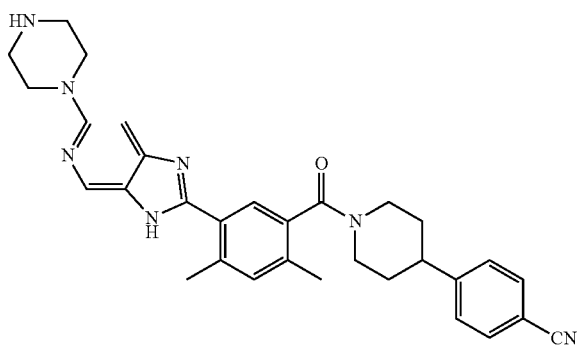 [SMILES: C=c1nc(-c2cc(C(=O)N3CCC(c4ccc(C#N)cc4)CC3)c(C)cc2C)[nH]/c1=C/N=C/N1CCNCC1]

Compound 19. 4-(1-(2,4-Dimethyl-5-(6-(piperazin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 519 (M+H)+.

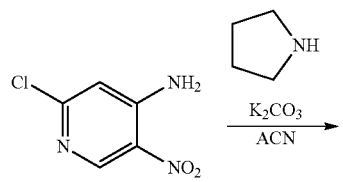

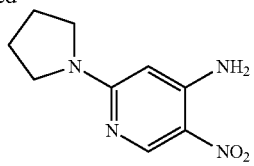

Compound 20.1. 5-Nitro-2-(pyrrolidin-1-yl)pyridin-4-amine

A 500 mL round bottom flask equipped with a reflux condenser was charged with 2-chloro-5-nitropyridin-4-amine (2.00 g, 11.5 mmol, 1.0 equiv), pyrrolidine (2.86 mL, 34.6 mmol, 3.0 equiv), potassium carbonate (4.78 g, 34.6 mmol, 3.0 equiv) and acetonitrile (50 mL). The mixture was heated at 70° C. overnight under nitrogen then cooled to room temperature. The yellow solids were collected by filtration and washed with acetonitrile, water and hexanes. The solids were dried to obtain the title compound as a bright yellow solid (1.43 g, 1$^{st}$ crop). The solvents from the filtrate were removed and the aqueous was extracted with ethyl acetate. The organic extracts was dried (Na$_2$SO$_4$), filtered and removed in vacuo to obtain additional product as an orange/yellow solid (820 mg, 2$^{nd}$ crop). The 2$^{nd}$ crop of product was triturated with ethyl acetate (3 mL) and then filtered and washed with ethyl acetate (2×1 mL) and diethyl ether (3 mL) to obtain a bright yellow solid (751 mg). The total yield of 5-nitro-2-(pyrrolidin-1-yl)pyridin-4-amine obtained was 2.18 g (91%). m/z (ES+) 209.1 (M+H)+. $^1$H NMR (400 MHz, DMSO-$d_6$): δ 8.79 (s, 1H), 7.39 (br s, 2H), 5.63 (s, 1H), 3.40 (br s, 4H), 1.93 (br s, 4H).

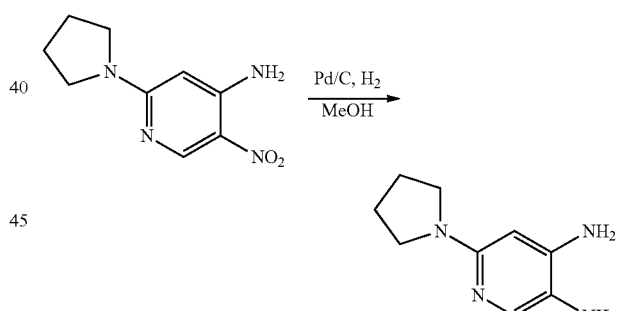

Compound 20.2. 6-(Pyrrolidin-1-yl)pyridine-3,4-diamine

To a 100 mL round bottom flask was added 5-nitro-2-(pyrrolidin-1-yl)pyridin-4-amine (compound 20.1, 800 mg, 3.84 mmol, 1.0 equiv) and Pd on carbon (10 wt % Pd, 400 mg, 0.38 mmol, 0.1 equiv). The system was purged with nitrogen and charged with methanol (19 mL) followed by hydrogen. The mixture was stirred at room temperature under hydrogen for 4 hours then purged with nitrogen. The mixture was filtered though celite and washed extensively with MeOH. The solvents were removed in vacuo to obtain the title compound as a purple solid (641 mg, 94%). m/z (ES+) 179.3 (M+H)+. $^1$H NMR (400 MHz, DMSO-$d_6$): δ 7.27 (s, 1H), 5.62 (s, 1H), 5.14 (br s, 2H), 3.67 (br s, 2H), 3.23-3.13 (m, 4H), 1.91-1.79 (m, 4H).

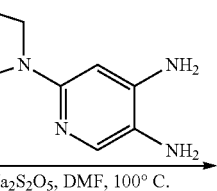
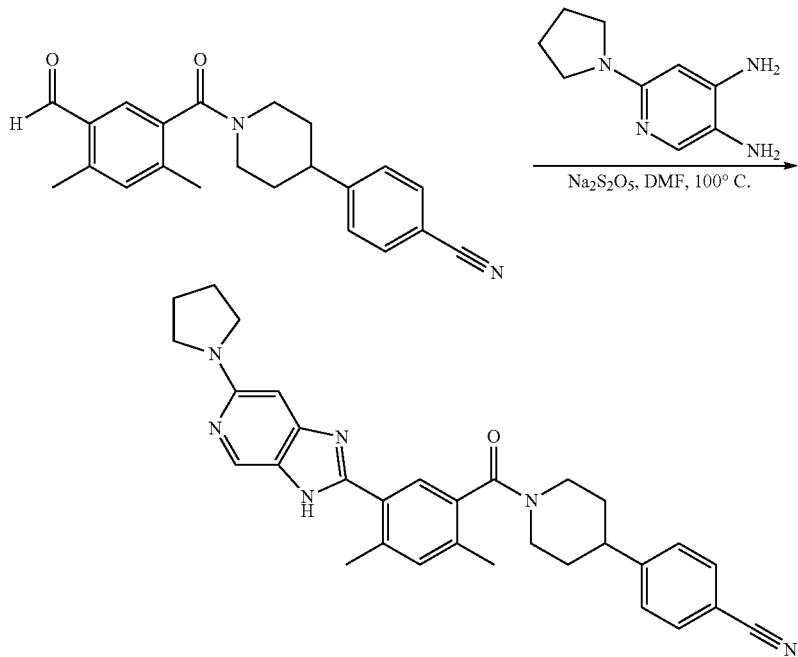

Compound 20. 4-(1-(2,4-Dimethyl-5-(6-(pyrrolidin-1-yl)-3H-imidazo[4,5-c]pyridin-2-yl)benzoyl)piperidin-4-yl)benzonitrile To a 100 mL round bottom flask was added 6-(pyrrolidin-1-yl)pyridine-3,4-diamine (compound 20.2, 641 mg, 3.60 mmol, 1.0 equiv), 4-(1-(5-formyl-2,4-dimethylbenzoyl)piperidin-4-yl)benzonitrile (compound 16.4, 1.25 g, 3.60 mmol, 1.0 equiv), sodium metabisulfite (890 mg, 4.68 mmol, 1.3 equiv) and DMF (36 mL). The mixture was heated at 100° C. under air for 22 hours then allowed to cool to room temperature. Water (80 mL) was added slowly to the stirred solution until no further product precipitated. The solids were filtered and washed with water (2×15 mL) and dried to a brown solid (1.42 g). Additional product precipitated from the filtrate upon standing which was filtered and washed with water (2×10 mL) to obtain an off white solid (241 mg). The above reaction was repeated a second time in the exact manner and quantities as described to yield additional product (1.26 g of brown solid upon initial precipitation, plus 288 mg of off white solid from additional precipitation). The aqueous filtrates from the two reactions were combined and aqueous NaHCO$_3$ was added to adjust the pH to 7. The aqueous was extracted with DCM/2% MeOH (300 mL), dried (Na$_2$SO$_4$), filtered and evaporated to obtain a brown solid (547 mg). All products obtained were combined and purified by silica gel chromatography (DCM/MeOH) to obtain the title compound as a yellow solid (2.37 g, 65% based on the theoretical yield for the two reactions). m/z (ES+) 505.1 (M+H)$^+$. $^1$H NMR (400 MHz, DMSO-d$_6$): δ 12.41 (br s, 1H), 8.52 (s, 1H), 7.77 (d, J=8.2 Hz, 2H), 7.66 & 7.56 (2 br singlets, amide rotamers, ArH, 1H), 7.49 (s, J=8.2 Hz, 2H), 7.29 (s, 1H), 6.31 (br s, 1H), 4.79-4.67 (m, 1H), 3.54-3.34 (m, 5H), 3.17 (app t, J=11.8, 1H), 2.99-2.82 (m, 2H), 2.63 (s, 3H), 2.33 & 2.24 (2 singlets, amide rotamers, ArCH$_3$, 3H), 2.03-1.87 (m, 5H), 1.82-1.38 (m, 3H). Elemental analysis (C$_{31}$H$_{32}$N$_6$O.1.3H$_2$O, 528.04); found (calcd), C, 70.66 (70.51); H, 6.54 (6.60); N, 15.78 (15.92).

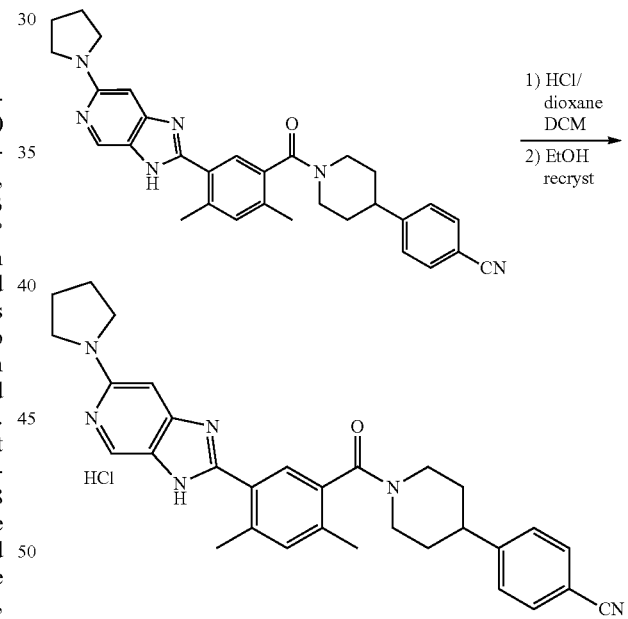

Compound 20 HCl salt. 4-(1-(2,4-Dimethyl-5-(6-(pyrrolidin-1-yl)-3H-imidazo[4,5-c]pyridin-2-yl)benzoyl)piperidin-4-yl)benzonitrile hydrochloride Dichloromethane (~50 mL) was added to 4-(1-(2,4-dimethyl-5-(6-(pyrrolidin-1-yl)-3H-imidazo[4,5-c]pyridin-2-yl)benzoyl)piperidin-4-yl)benzonitrile (compound 20 free base, 2.31 g, 4.58 mmol) until it completely dissolved and then 4M HCl in dioxane (5 mL, 20 mmol, 4.3 equiv) was added. The solvents were removed and the residue was dissolved in DCM and removed in vacuo. The resulting hydrochloride salt was recrystallized from boiling ethanol (180 mL) and allowed to cool to room temperature slowly. The mixture sat at room temperature, overnight and then placed in the freezer for 4 hours. The resulting solids were filtered and washed with cold ethanol (25 mL) followed by diethyl ether (25 mL). The solids were dried to obtain an off white to light grey solid (1.82 g, 73%). $^1$H NMR (400 MHz, DMSO-d$_6$): δ 13.59 & 13.46 (2 br singlets, imidazole NH tautomers, 1H), 13.29 (br s, 1H), 8.62 (br s, 1H), 7.83 & 7.67 (2 singlets, amide rotamers, ArH, 1H), 7.78 (d, J=7.8 Hz, 2H), 7.58-7.45 (m, 2H), 7.37 (s, 1H), 6.71 (br s, 1H), 4.80-4.68 (m, 1H), 3.65-3.38 (m, 5H), 3.25-3.12 (m, 1H), 3.00-2.82 (m, 2H), 2.66 (s, 3H), 2.37 & 2.27 (2 singlets, amide rotamers, ArCH$_3$, 3H), 2.13-2.01 (m, 4H), 1.98-1.87 (m, 1H), 1.82-1.40 (m, 3H). Elemental analysis (C$_{31}$H$_{32}$N$_6$O.1.0 HCl.2.4H$_2$O, 584.32). found (calcd), C, 63.80 (63.72); H, 6.32 (6.52); N, 14.25 (14.38).

aqueous methanesulfonic acid solution (3.33 mL, 3.33 mmol, 1.0 equiv) was added and mixed well. Additional water (6 mL) was added and the mixture was frozen and dried on the lyophilizer to obtain a yellow powder (1.99 g, 99%). m/z (ES+) 505.1 (M+H)$^+$. $^1$H NMR (400 MHz, DMSO-d$_6$): δ 13.29 (br s, 1H), 13.10 (br s, 1H), 8.65 (br s, 1H), 7.78 (d, J=8.2 Hz, 2H), 7.74 & 7.64 (2 singlets, amide rotamers, ArH, 1H), 7.50 (d, J=8.3 Hz, 2H), 7.37 (s, 1H), 6.74 (br s, 1H), 4.80-4.68 (m, 1H), 3.65-3.38 (m, 5H), 3.26-3.12 (m, 1H), 3.01-2.83 (m, 2H), 2.64 (s, 3H), 2.37 & 2.27 (2 singlets, amide rotamers, ArCH$_3$, 3H), 2.32 (s, 3H) 2.12-2.00 (m, 4H), 1.98-1.88 (m, 1H), 1.82-1.39 (m, 3H). Elemental analysis (C$_{31}$H$_{32}$N$_6$O.1.0MsOH.1.7H$_2$O, 631.36). found (calcd), C, 60.96 (60.88); H, 6.14 (6.29); N, 13.21 (13.31); S, 5.08 (5.08).

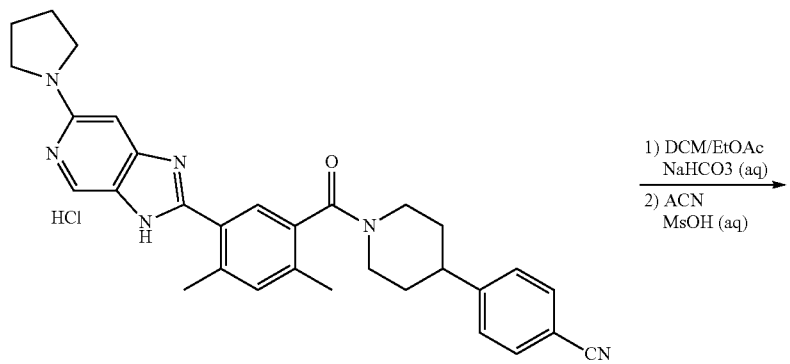

Compound 20 MsOH salt. 4-(1-(2,4-Dimethyl-5-(6-(pyrrolidin-1-yl)-3H-imidazo[4,5-c]pyridin-2-yl)benzoyl)piperidin-4-yl)benzonitrile methanesulfonate 4-(1-(2,4-Dimethyl-5-(6-(pyrrolidin-1-yl)-3H-imidazo[4,5-c]pyridin-2-yl)benzoyl)piperidin-4-yl)benzonitrile hydrochloride (compound 20 HCl salt, 1.82 g, 3.36 mmol) was added to water (100 mL) plus saturated NaHCO$_3$ (50 mL) and extracted with 1:1 DCM/EtOAc (500 mL) plus MeOH (25 mL). Once the entire product completely dissolved, the layers were separated and the aqueous was extracted with additional 1:1 DCM/EtOAc (100 mL). The combined organics was dried (Na$_2$SO$_4$), filtered and evaporated to a light yellow powder (1.68 g, 3.33 mmol). The free base material was dissolved in hot acetonitrile (10 mL), then a 1.0 M

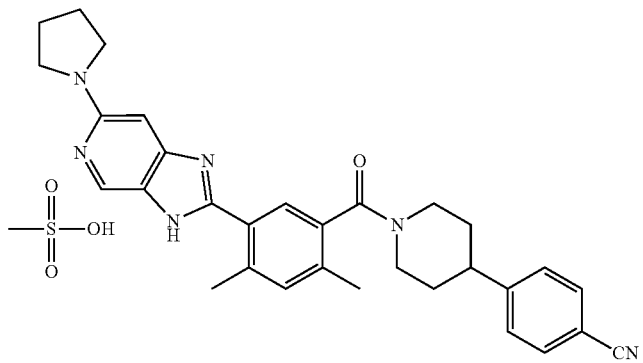

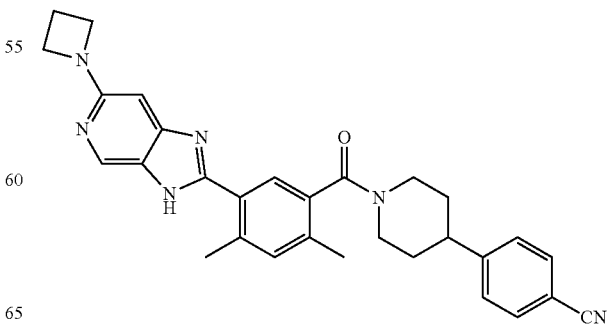

Compound 21. 4-(1-(5-(6-(Azetidin-1-yl)-3H-imidazo[4,5-c]pyridin-2-yl)-2,4-dimethylbenzoyl)piperidin-4-yl)benzonitrile The title compound was prepared using standard chemical manipulations and procedures similar to those used for preparation of compound 16. m/z (ES+) 491 (M+H)+.

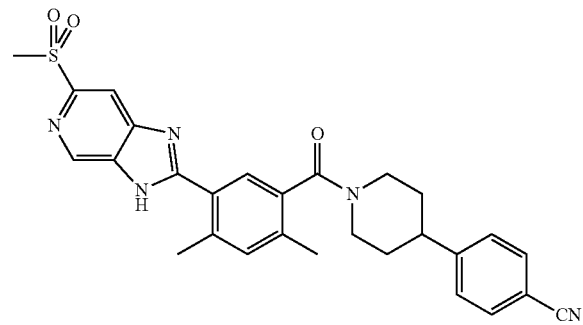 [SMILES: Cc1cc(C)c(-c2nc3cc(S(C)(=O)=O)ncc3[nH]2)cc1C(=O)N1CCC(c2ccc(C#N)cc2)CC1]

Compound 22. 4-(1-(2,4-Dimethyl-5-(6-(methylsulfonyl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 514 (M+H)+.

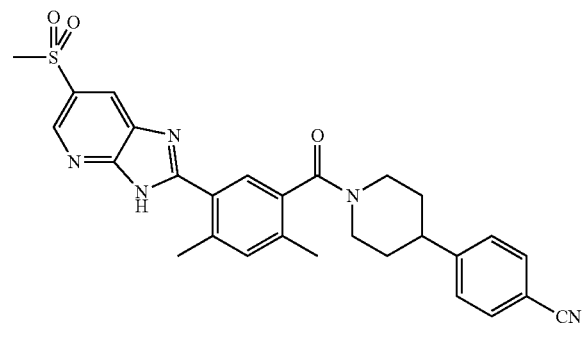 [SMILES: Cc1cc(C)c(-c2nc3cc(S(C)(=O)=O)cnc3[nH]2)cc1C(=O)N1CCC(c2ccc(C#N)cc2)CC1]

Compound 23. 4-(1-(2,4-Dimethyl-5-(6-(methylsulfonyl)-3H-imidazo[4,5-b]pyridin-2-yl)benzoyl)piperidin-4-yl)benzonitrile The title compound was prepared using standard chemical manipulations and procedures similar to those used for preparation of compound 16. m/z (ES+) 514 (M+H)+. $^1$H NMR (300 MHz, DMSO-$d_6$+$D_2O$): δ 8.87 (d, J=1.8 Hz, 1H), 8.52 (d, J=2.1 Hz, 1H), 7.74 (d, J=7.5 Hz, 2H), 7.66 & 7.56 (2 singlets, amide rotamers, Ar—H, 1H), 7.48 (d, J=8.4 Hz, 2H), 7.38 (br s, 1H), 4.76-4.63 (m, 1H), 3.57-3.38 (m, 1H), 3.31 (s, 3H), 3.28-3.13 (m, 1H), 3.03-2.85 (m, 2H), 2.60 (s, 3H), 2.35 & 2.27 (2 singlets, amide rotamers, Ar—CH$_3$, 3H), 2.00-1.85 (m, 1H), 1.85-1.32 (m, 3H).

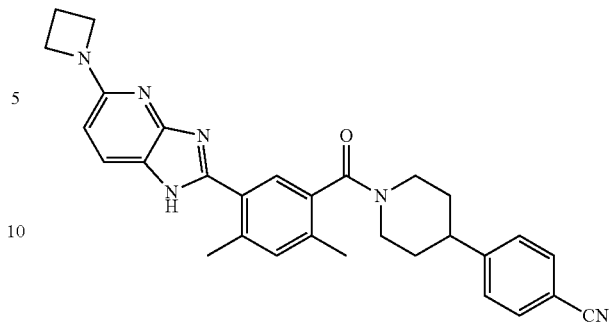

Compound 24. 4-(1-(5-(5-(Azetidin-1-yl)-1H-imidazo[4,5-b]pyridin-2-yl)-2,4-dimethylbenzoyl)piperidin-4-yl)benzonitrile The title compound was prepared using standard chemical manipulations and procedures similar to those used for preparation of compound 16 but using 6-chloro-3-nitropyridin-2-amine and azetidine hydrochloride in place of 2-chloro-5-nitropyridin-4-amine and (2-methoxyethyl)(methyl)amine respectively. m/z (ES+) 491 (M+H)+. $^1$H NMR (300 MHz, CD$_3$OD): δ 8.06 (d, J=9.0 Hz, 1H), 7.70-7.42 (m, 6H), 6.60 (d, J=9.0 Hz, 1H), 4.90 (m, 1H, partially obscured by the solvent peak), 4.32 (m, 4H), 3.65 (m, 1H), 3.03 (m, 1H), 2.62 (s, 3H), 2.57 (m, 3H), 2.48 and 2.38 (2 singlets, amide rotamers, ArCH$_3$, 3H), 2.04 (m, 1H), 1.96-1.68 (m, 4H).

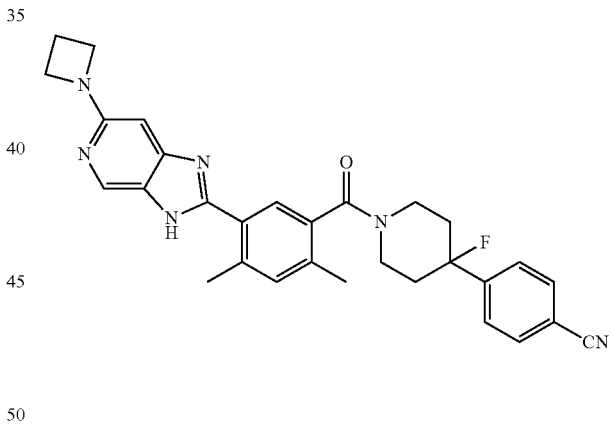

Compound 25. 4-(1-(5-(6-(Azetidin-1-yl)-3H-imidazo[4,5-c]pyridin-2-yl)-2,4-dimethylbenzoyl)-4-fluoropiperidin-4-yl)benzonitrile The title compound was prepared using standard chemical manipulations and procedures similar to those used for preparation of compound 16 and using compound 11.2 in place of compound 1.5. m/z (ES+) 509 (M+H)+.

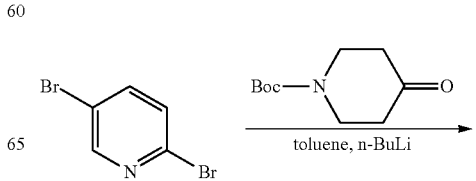

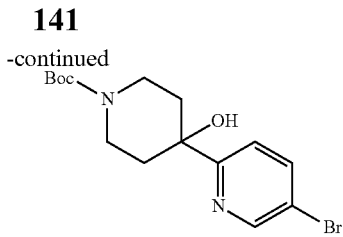

Compound 26.1. tert-Butyl 4-(5-bromopyridin-2-yl)-4-hydroxypiperidine-1-carboxylate To a stirred solution of 2,5-dibromopyridine (10 g, 42.19 mmol, 1.00 equiv) in toluene (1000 mL) under nitrogen at −78° C. was added dropwise n-BuLi (18 mL, 2.5 M in toluene). After 1 h at −78° C., a solution of tert-butyl 4-oxopiperidine-1-carboxylate (10 g, 50.25 mmol, 1.19 equiv) in toluene (200 mL) was added dropwise while stirring. After an additional 2 h of stirring at −78° C., the reaction was then carefully quenched by the addition of 300 mL of water. The resulting mixture was extracted with 3×500 mL of ethyl acetate. The combined organic layers were washed with 1×300 mL of brine, dried over anhydrous sodium sulfate, and concentrated under reduced pressure. The residue was purified using silica gel column chromatography with ethyl acetate/petroleum ether (1:100-1:5) to yield 6.5 g (42%) of the title compound as a yellow oil.

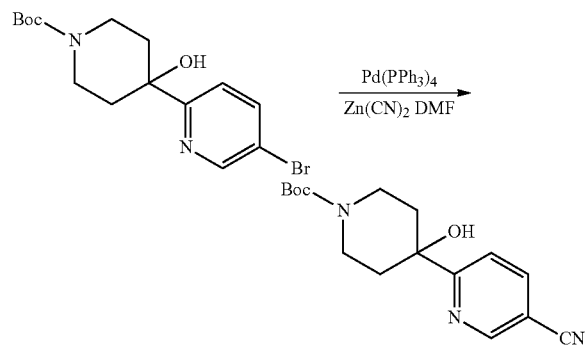

Compound 26.2. tert-Butyl 4-(5-cyanopyridin-2-yl)-4-hydroxypiperidine-1-carboxylate A mixture of tert-butyl 4-(5-bromopyridin-2-yl)-4-hydroxypiperidine-1-carboxylate (compound 26.1, 1 g, 2.80 mmol, 1.00 equiv), zinc cyanide (400 mg, 3.42 mmol, 1.22 equiv), Pd(PPh₃)₄ (200 mg, 0.17 mmol, 0.06 equiv) in DMF (50 mL) was stirred under nitrogen for 2 h at 100° C. After cooling to room temperature, the reaction was then quenched by careful addition of 300 mL of FeSO₄ (aq., sat.) and diluted with ethyl acetate. The resulting mixture was stirred vigorously then filtered through celite and washed with 1 M FeSO₄, water, and ethyl acetate. The layers were separated and the aqueous phase was extracted with 2×100 mL of ethyl acetate. The combined organic layers were washed with 1×100 mL of brine, dried over anhydrous sodium sulfate, and concentrated under reduced pressure. The residue was purified using silica gel column chromatography with ethyl acetate/petroleum ether (1:100-1:4) yield 0.5 g (58%) of the title compound as a yellow oil.

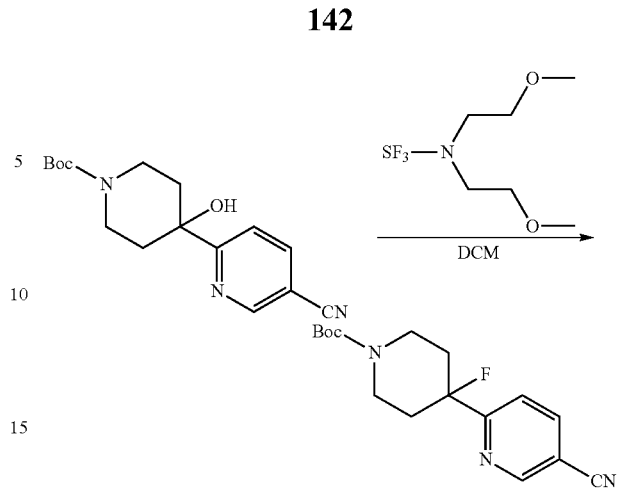

Compound 26.3. tert-Butyl 4-(5-cyanopyridin-2-yl)-4-fluoropiperidine-1-carboxylate To a solution of tert-butyl 4-(5-cyanopyridin-2-yl)-4-hydroxypiperidine-1-carboxylate (compound 26.2, 1 g, 3.13 mmol, 1.00 equiv, 95%) in dichloromethane (50 mL) under nitrogen at −78° C. was added dropwise a solution of bis(2-methoxyethyl)aminosulfur trifluoride (830 mg, 3.75 mmol, 1.20 equiv) in dichloromethane (10 mL) during the course of 1 min. The resulting mixture was stirred for 1 h at −78° C. The reaction was then carefully quenched by dropwise addition of water and washed with 2×20 mL of sodium bicarbonate (aq) followed by 3×20 mL of brine. The organic layer was dried over anhydrous sodium sulfate and concentrated under reduced pressure. The crude residue was purified using silica gel column chromatography with ethyl acetate/petroleum ether (1:10) to yield 0.38 g (38%) of the title compound as a white solid.

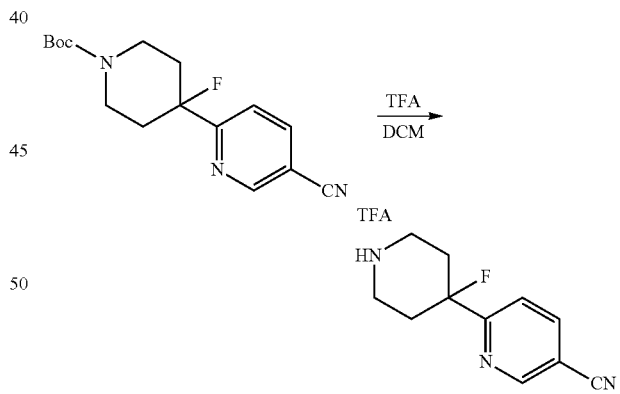

Compound 26.4. 6-(4-Fluoropiperidin-4-yl)nicotinonitrile trifluoroacetate

To a stirred solution of tert-butyl 4-(5-cyanopyridin-2-yl)-4-fluoropiperidine-1-carboxylate (compound 26.3, 1 g, 3.11 mmol, 1.00 equiv, 95%) in dichloromethane (20 mL) was added dropwise TFA (3.75 g, 32.89 mmol, 10.57 equiv). After stirring for 1 h at 25° C., the mixture was concentrated under reduced pressure to yield 0.5 g of the title compound as a brown oil.

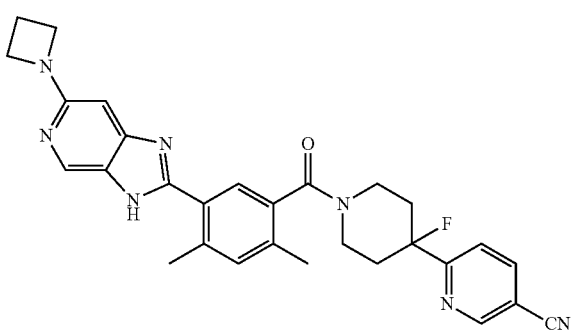 [SMILES: Cc1cc(C)c(-c2nc3cc(N4CCC4)ncc3[nH]2)cc1C(=O)N1CCC(F)(c2ccc(C#N)cn2)CC1]

Compound 26. 6-(1-(5-(6-(Azetidin-1-yl)-3H-imidazo[4,5-c]pyridin-2-yl)-2,4-dimethylbenzoyl)-4-fluoropiperidin-4-yl)nicotinonitrile The title compound was prepared using standard chemical manipulations and procedures similar to those used for preparation of compound 16 but using compound 26.4 in place of compound 1.5. m/z (ES+) 509 (M+H)+.

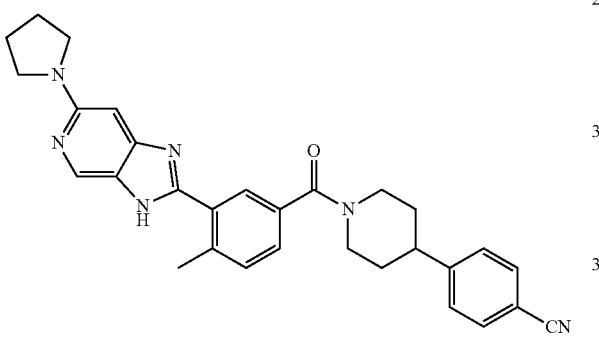

Compound 27. 4-(1-(4-Methyl-3-(6-(pyrrolidin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16 but using 3-bromo-4-methylbenzoic acid in place of 5-iodo-2,4-dimethylbenzoic acid. m/z (ES+) 491 (M+H)+.

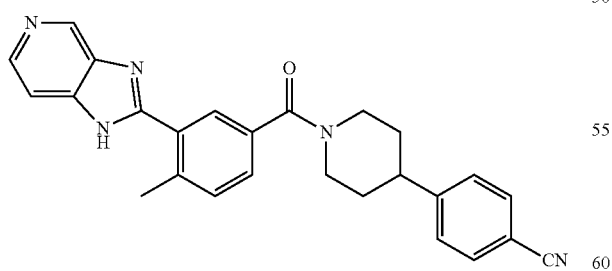

Compound 28. 4-(1-(3-(1H-Imidazo[4,5-c]pyridin-2-yl)-4-methylbenzoyl)piperidin-4-yl)benzonitrile The title compound was prepared using standard chemical manipulations and procedures similar to those used for preparation of compounds 16 and 27. m/z (ES+) 422 (M+H)+. 1H NMR (300 MHz, CD3OD): δ 9.35 (s, 1H), 8.60 (d, J=6.6 Hz, 1H), 8.19 (d, J=6.6 Hz, 1H), 7.92 (s, 1H), 7.73-7.58 (m, 4H), 7.50 (d, J=8.1 Hz, 1H), ~4.9 (1H, partially obscured by water peak), 4.06-3.87 (m, 1H), 3.13-2.95 (m, 3H), 2.73 (s, 3H), 2.11-1.63 (m, 4H).

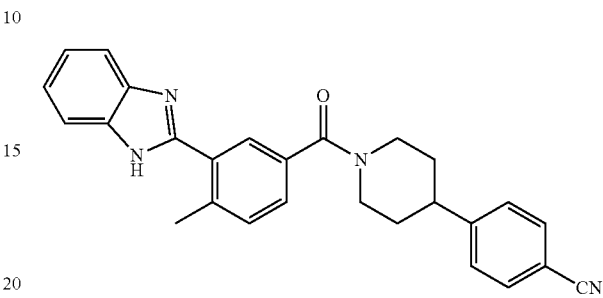

Compound 29. 4-(1-(3-(1H-Benzo[d]imidazol-2-yl)-4-methylbenzoyl)piperidin-4-yl)benzonitrile The title compound was prepared using standard chemical manipulations and procedures similar to those used for preparation of compounds 16 and 27. m/z (ES+) 421 (M+H)+. 1H NMR (300 MHz, CD3OD): δ 7.87-7.77 (m, 3H), 7.75-7.60 (m, 4H), 7.60-7.47 (m, 4H), ~4.85 (1H, partially obscured by water peak), 4.04-3.89 (m, 1H), 3.13-2.95 (m, 3H), 2.61 (s, 3H), 2.11-1.69 (m, 4H).

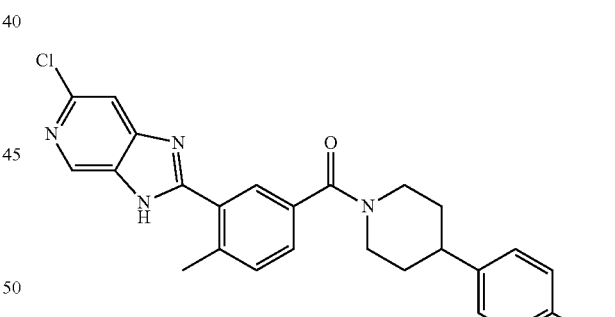

Compound 30. 4-(1-(3-(6-Chloro-3H-imidazo[4,5-c]pyridin-2-yl)-4-methylbenzoyl)piperidin-4-yl)benzonitrile The title compound was prepared using standard chemical manipulations and procedures similar to those used for preparation of compounds 16 and 27. m/z (ES+) 456 (M+H)+.

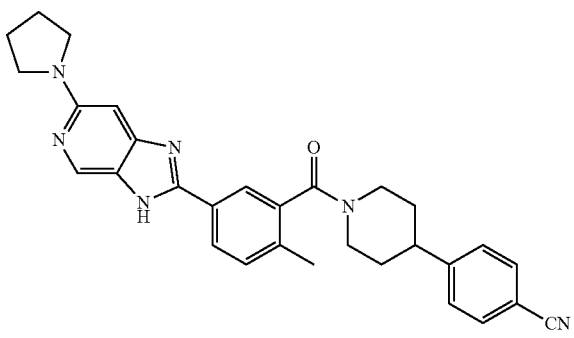 [SMILES: Cc1ccc(-c2nc3cc(N4CCCC4)ncc3[nH]2)cc1C(=O)N1CCC(c2ccc(C#N)cc2)CC1]

Compound 31. 4-(1-(2-Methyl-5-(6-(pyrrolidin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16 but using 5-bromo-2-methylbenzoic acid in place of 5-iodo-2,4-dimethylbenzoic acid (compound 2.1). m/z (ES+) 491 (M+H)$^+$. $^1$H NMR (300 MHz, DMSO-d6): δ 12.63 (br s, 1H), 8.06 (d, J=7.8 Hz, 1H), 8.01 & 7.91 (2 singlets, amide rotamers, Ar—H, 1H), 7.81 (d, J=6.6 Hz, 2H), 7.58-7.42 (m, 3H), 6.31 (s, 1H), 4.85 (m, 1H), 3.57-3.35 (m, 5H), 3.30-3.13 (m, 1H), 3.07-1.85 (m, 2H), 2.39 & 2.29 (2 singlets, amide rotamers, Ar—CH$_3$, 3H), 2.10-1.89 (m, 5H), 1.87-1.40 (m, 3H).

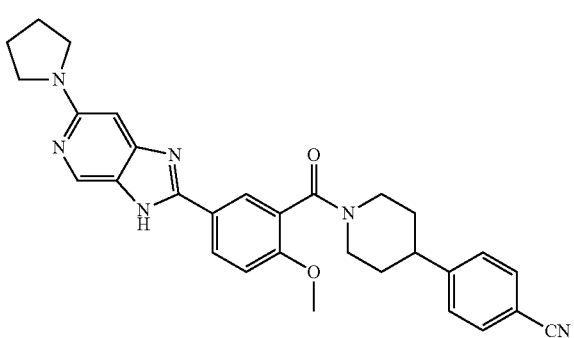 [SMILES: COc1ccc(-c2nc3cc(N4CCCC4)ncc3[nH]2)cc1C(=O)N1CCC(c2ccc(C#N)cc2)CC1]

Compound 32. 4-(1-(2-Methoxy-5-(6-(pyrrolidin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 507 (M+H)$^+$.

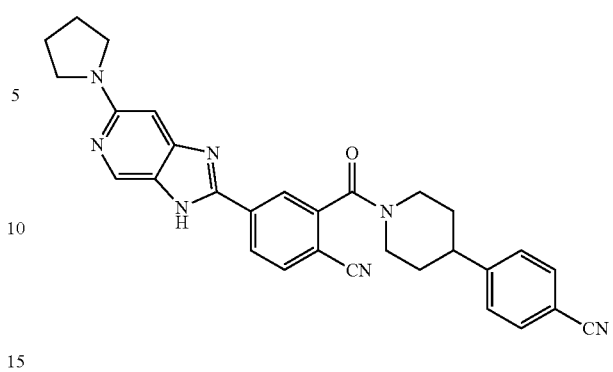

Compound 33. 2-(4-(4-Cyanophenyl)piperidine-1-carbonyl)-4-(6-(pyrrolidin-1-yl)-3H-imidazo[4,5-c]pyridin-2-yl)benzonitrile The title compound was prepared using standard chemical manipulations and procedures similar to those used for preparation of compound 16. m/z (ES+) 502 (M+H)$^+$.

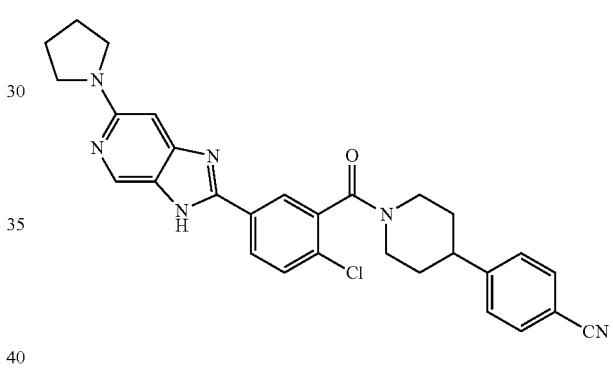

Compound 34. 4-(1-(2-Chloro-5-(6-(pyrrolidin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 511 (M+H)$^+$.

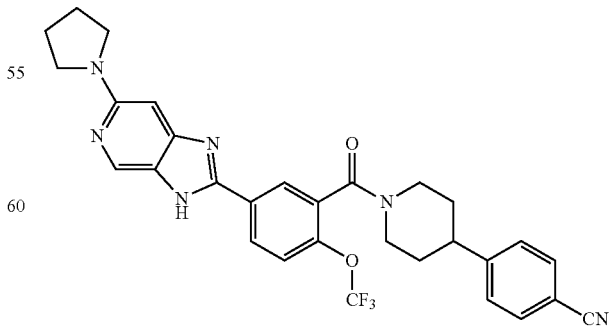

Compound 35. 4-(1-(5-(6-(Pyrrolidin-1-yl)-3H-imidazo[4,5-c]pyridin-2-yl)-2-(trifluoromethoxy)benzoyl)piperidin-4-yl)benzonitrile The title compound was prepared using standard chemical manipulations and procedures similar to those used for preparation of compound 16. m/z (ES+) 561 (M+H)+.

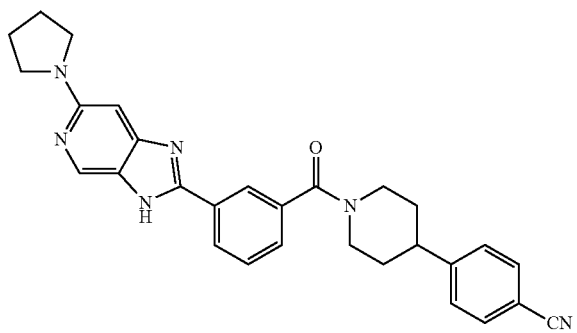 [SMILES: N#Cc1ccc(C2CCN(C(=O)c3cccc(-c4nc5cc(N6CCCC6)ncc5[nH]4)c3)CC2)cc1]

Compound 36. 4-(1-(3-(6-(Pyrrolidin-1-yl)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 477 (M+H)+. 1H NMR (300 MHz, CD3OD): δ 8.44 (s, 1H), 8.25-8.17 (m, 2H), 7.77-7.63 (m, 4H), 7.51 (d, J=8.1 Hz, 2H), 6.59 (s, 1H), ~4.85 (1H, partially obscured by water peak), 3.98-3.83 (m, 1H), 3.61-3.48 (m, 4H), ~3.4 (1H, partially obscured by methanol solvent peak), 3.12-2.96 (m, 2H), 2.22-2.09 (m, 4H), 2.09-1.95 (m, 1H), 1.95 (m, 3H).

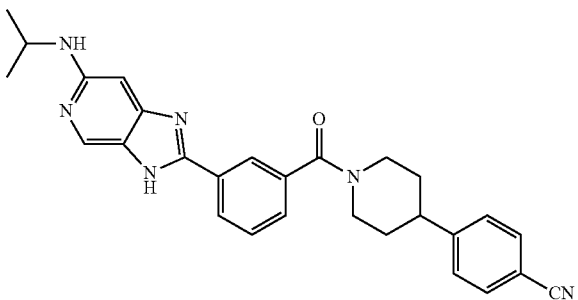 [SMILES: CC(C)Nc1cc2nc(-c3cccc(C(=O)N4CCC(c5ccc(C#N)cc5)CC4)c3)[nH]c2cn1]

Compound 37. 4-(1-(3-(6-(Isopropylamino)-3H-imidazo[4,5-c]pyridin-2-yl)benzoyl)piperidin-4-yl)benzonitrile The title compound was prepared using standard chemical manipulations and procedures similar to those used for preparation of compound 16. m/z (ES+) 465 (M+H)+.

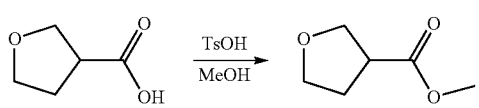

Compound 38.1. Methyl tetrahydrofuran-3-carboxylate

A solution of tetrahydrofuran-3-carboxylic acid (540 mg, 4.65 mmol, 1.00 equiv) and TsOH (10 mg, 0.06 mmol, 0.01 equiv) in methanol (40 mL) was stirred at 66° C. in an oil bath. After 16 h, the resulting mixture was cooled to room temperature and concentrated under reduced pressure. The residue was dissolved in 10 mL of ether, washed with 1×20 mL of NaHCO3 (aq., sat.) followed by 3×20 mL of brine, and concentrated under reduced pressure to yield 0.40 g (66%) of the title compound as a colorless oil.

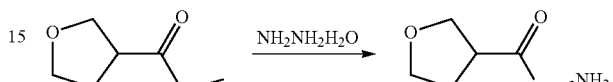

Compound 38.2. Tetrahydrofuran-3-carbohydrazide

Into around-bottom flask, was placed hydrazine hydrate (20 mL). To this was added methyl tetrahydrofuran-3-carboxylate (compound 38.1, 390 mg, 3.00 mmol, 1.00 equiv) dropwise with stirring. The resulting mixture was stirred at 50° C. in ah oil bath. After 3 h, the reaction mixture was concentrated and dried under reduced pressure to yield 0.29 g (74%) of the title compound as a colorless oil.

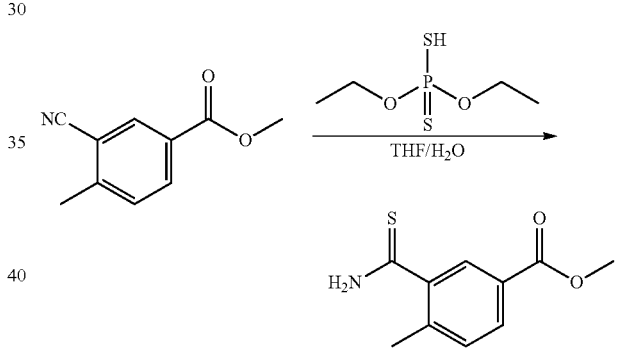

Compound 38.3. Methyl 3-carbamothioyl-4-methylbenzoate

A solution of methyl 3-cyano-4-methylbenzoate (compound 1.7, 880 mg, 5.02 mmol, 1.00 equiv) and O,O'-diethyl dithiophosphate (1.41 g, 8.29 mmol, 1.50 equiv) in THF/H2O (40 mL) was stirred at 80° C. (CAUTION: significant gas evolution occurs—this and all other reactions described herein should be carried out in well ventilated fume hoods). After 3 h, the organic solvent was removed under reduced pressure and the residual aqueous phase was extracted with 3×20 mL of ethyl acetate. The combined organic layers were concentrated under reduced pressure to yield 0.85 g (79%) of the title compound as a light yellow solid.

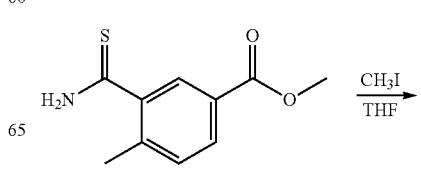

-continued

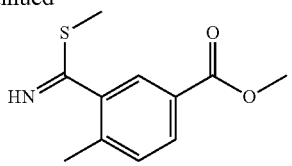

Compound 38.4. Methyl 3-(imino(methylthio)methyl)-4-methylbenzoate

To a stirred solution of methyl 3-carbamothioyl-4-methylbenzoate (compound 38.3, 2.10 g, 9.85 mmol, 1.00 equiv) in tetrahydrofuran (30 mL) was added iodomethane (2.8 g, 19.73 mmol, 2.00 equiv) dropwise. The resulting mixture was stirred at room temperature. After 3 h, the reaction mixture was concentrated under reduced pressure and the residue was dried under vacuum to yield 1.6 g (73%) of the title compound as a light yellow solid.

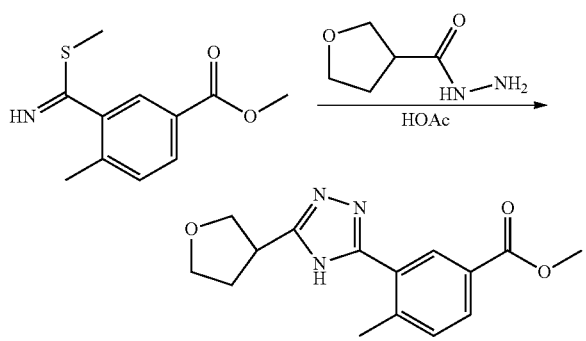

Compound 38.5. Methyl 4-methyl-3-(5-(tetrahydrofuran-3-yl)-4H-1,2,4-triazol-3-yl)benzoate A solution of tetrahydrofuran-3-carbohydrazide (compound 38.2, 195 mg, 1.50 mmol, 1.50 equiv) and compound 38.4 (223 mg, 1.00 mmol, 1.00 equiv) in AcOH (30 mL) was stirred at 80° C. After 4 h, the reaction mixture was concentrated under reduced pressure and the residue was dried under high-vacuum to yield 153 mg (53%) of the title compound as yellow oil.

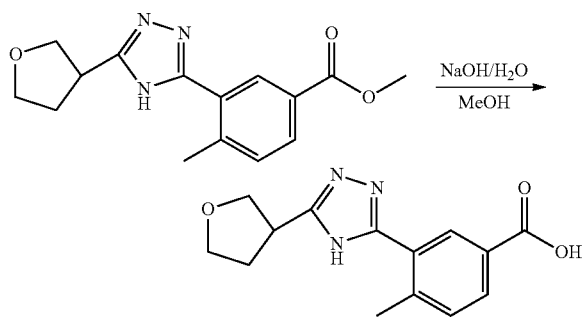

Compound 38.6. 4-Methyl-3-(5-(tetrahydrofuran-3-yl)-4H-1,2,4-triazol-3-yl)benzoic acid To a stirred solution of compound 38.5 (57 mg, 0.20 mmol, 1.00 equiv) in methanol (20 mL) was added sodium hydroxide (aqueous, 1 M, 0.2 mL) dropwise. The resulting mixture was stirred at room temperature. After 4 h, the organic solvent was removed under reduced pressure. The residual aqueous layer was washed with 2×20 mL of ethyl acetate. The pH of the aqueous phase was then adjusted to 4 with hydrogen chloride (aq., 1 M) and the resulting solids were collected by filtration and dried to yield 23 g (42%) of the title compound as a light yellow solid.

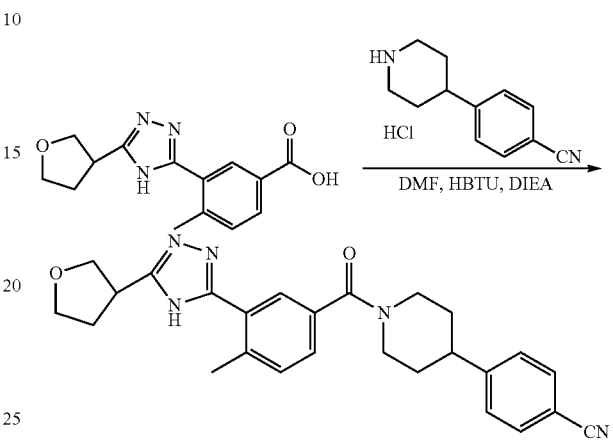

Compound 38. 4-(1-(4-Methyl-3-(5-(tetrahydrofuran-3-yl)-4H-1,2,4-triazol-3-yl)benzoyl)piperidin-4-yl)benzonitrile A mixture of compound 38.6 (137 mg, 0.50 mmol, 1.00 equiv), HBTU (228 mg, 0.60 mmol, 1.20 equiv), DIEA (162 mg, 1.25 mmol, 2.50 equiv), and 4-(piperidin-4-yl)benzonitrile hydrochloride (1.5, 111 mg, 0.50 mmol, 1.00 equiv) in DMF (20 mL) was stirred at room temperature. After 1 h, the reaction was quenched by the addition of 20 mL of water and resulting mixture was extracted with 3×20 mL of ethyl acetate. The combined organic phases were dried (Na$_2$SO$_4$) and concentrated under reduced pressure. The residue was purified using silica gel column chromatography with ethyl acetate/petroleum ether (1:100-1:3) to yield 35 mg (16%) of the title compound as a brown solid. m/z (ES+) 442 (M+H)$^+$.

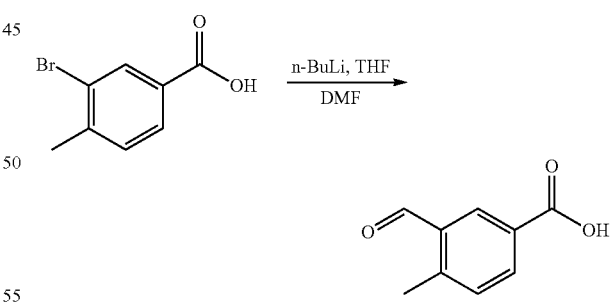

Compound 39.1. 3-Formyl-4-methylbenzoic acid

To a stirred solution of 3-bromo-4-methylbenzoic acid (2.14 g, 10.00 mmol, 1.00 equiv) in tetrahydrofuran (30 mL) under nitrogen at −78° C.: was added n-BuLi (10 mL, 2.5 M in THF, 2.50 equiv) dropwise. After stirring for 1 h below −70° C., DMF (5 mL) was slowly added. The resulting solution was warmed slowly to room temperature and stirred for 1 h. After carefully quenching the reaction by slowly adding 50 mL of water, the pH was adjusted to 3-4 using aqueous HCl (6 M). The resulting mixture was extracted with 2×50 mL of ethyl acetate and the combined organic layers were dried over anhydrous sodium sulfate and concentrated under reduced pressure to yield 1.6 g (98%) of the title compound as a yellow solid.

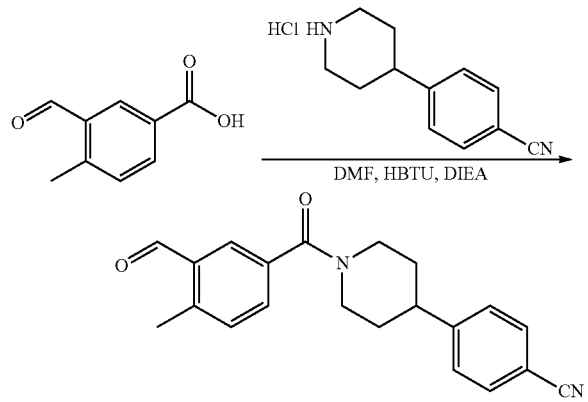

Compound 39.2. 4-(1-(3-Formyl-4-methylbenzoyl) piperidin-4-yl)benzonitrile

A mixture of 3-formyl-4-methylbenzoic acid (compound 39.1, 660 mg, 4.02 mmol, 1.00 equiv), HBTU (2 g, 5.28 mmol, 1.30 equiv) in N,N-dimethylformamide (20 mL) was stirred at room temperature. After 1 h, 4-(piperidin-4-yl) benzonitrile hydrochloride (1.5, 890 mg, 4.01 mmol, 1.00 equiv) and DIEA (1.03 g, 7.98 mmol, 2.00 equiv) were added. The resulting mixture was stirred for 5 h at room temperature and then overnight at 60° C. in. After cooling to ambient temperature, the reaction mixture was diluted with 100 mL of EtOAc and washed with 2×50 mL of NH$_4$Cl (aq., sat.) followed by 2×50 mL of sodium bicarbonate (aq., sat.). The organic layer was dried over anhydrous sodium sulfate and concentrated under reduced pressure to yield 1 g (75%) of the title compound as a brown oil.

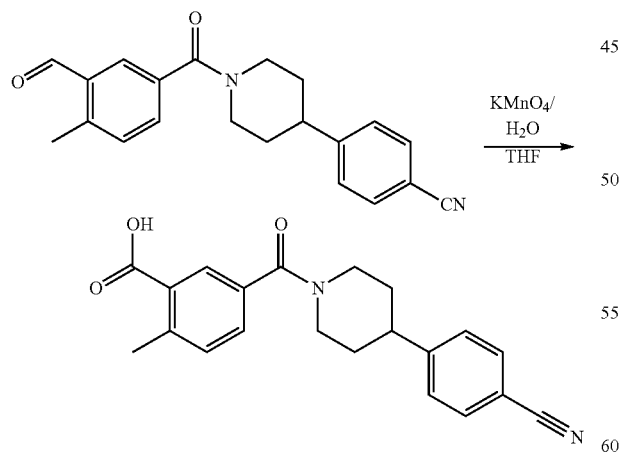

Compound 39.3. 5-(4-(4-Cyanophenyl)piperidine-1-carbonyl)-2-methylbenzoic acid

To a stirred mixture of 4-(1-(3-formyl-4-methylbenzoyl) piperidin-4-yl)benzonitrile (compound 39.2, 600 mg, 1.81 mmol, 1.00 equiv) in THF (5 mL) was added dropwise a solution of KMnO$_4$ (1 g) in water (10 mL). The resulting mixture was stirred overnight at 60° C. in an oil bath. After cooling to ambient temperature, the solids were removed by filtration and the pH of the filtrate was adjusted to ≥10 with sodium hydroxide (aqueous, 1 M). The resulting mixture was washed with 20 mL of ethyl acetate. Aqueous 1 M HCl was then employed to adjust the pH of the aqueous layer to ~4. The resulting aqueous phase was extracted with 2×100 mL of ethyl acetate and the combined organic layers were dried over anhydrous sodium sulfate and concentrated under reduced pressure to yield 500 mg (80%) of the title compound as light yellow oil.

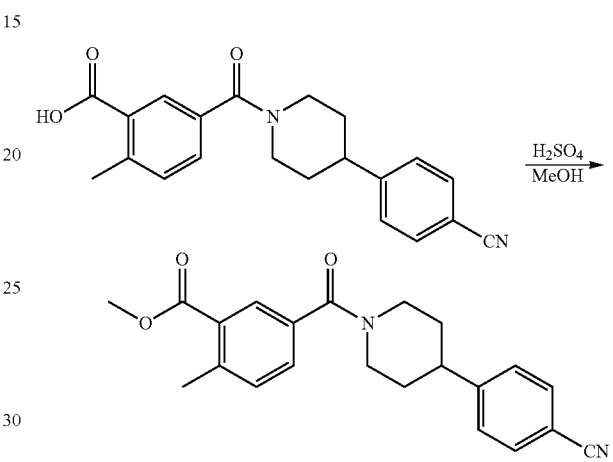

Compound 39.4. Methyl 5-(4-(4-cyanophenyl)piperidine-1-carbonyl)-2-methylbenzoate To a stirred mixture of 5-(4-(4-cyanophenyl)piperidine-1-carbonyl)-2-methylbenzoic acid (compound 39.3, 1.392 g, 4.00 mmol, 1.00 equiv) in methanol (50 mL) was added sulfuric acid (784 mg, 7.99 mmol, 2.00 equiv), dropwise. The resulting mixture was heated to reflux overnight in an oil bath. After cooling to ambient temperature, the organic solvent was removed under reduced pressure. The residue was diluted with 20 mL of EtOAc and was washed with 1×100 mL of saturated sodium bicarbonate(aq) followed by 1×100 mL of brine. The organic layer was dried (Na$_2$SO$_4$) and concentrated under reduced pressure to yield 1.303 g (90%) of the title compound as a white solid.

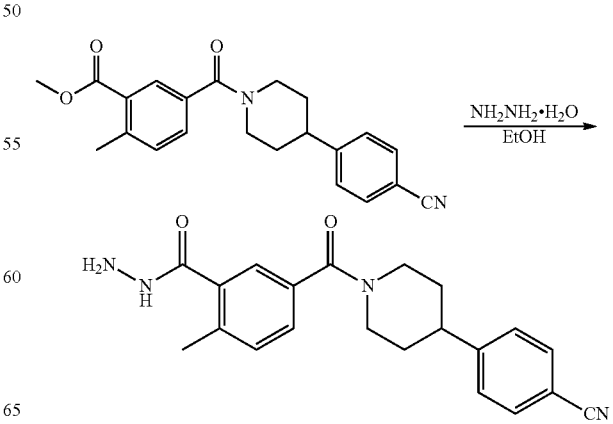

Compound 39.5. 5-(4-(4-Cyanophenyl)piperidine-1-carbonyl)-2-methylbenzohydrazide A solution of compound 39.4 (1.503 g, 4.15 mmol, 1.00 equiv) and hydrazine hydrate (10 mL) in ethanol (50 mL) was heated at reflux in an oil bath. After 2 h, the mixture was concentrated under reduced pressure and the residue was dissolved in 20 mL of EtOAc. The resulting mixture was washed with 1×50 mL of H₂O and 1×50 mL of brine. The organic layer was dried (Na₂SO₄) and concentrated under reduced pressure to yield 1.353 g (90%) of the title compound as a white solid

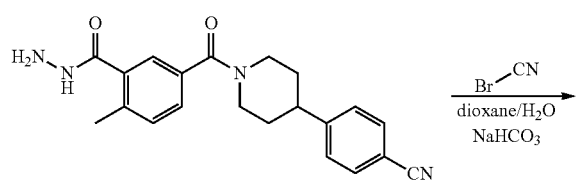

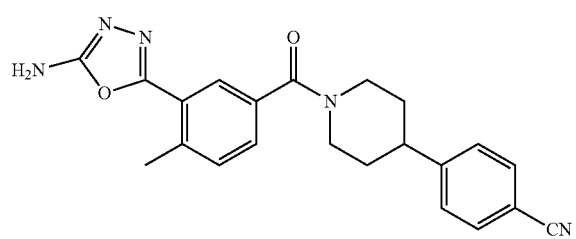

Compound 39.6. 4-(1-(3-(5-Amino-1,3,4-oxadiazol-2-yl)-4-methylbenzoyl)piperidin-4-yl)benzonitrile A mixture of compound 39.5 (380 mg, 1.05 mmol, 1.00 equiv) and sodium bicarbonate (105.8 mg, 1.26 mmol, 1.20 equiv) in dioxane/H₂O (1:1) (50 mL) was stirred at room temperature. After 5 minutes, cyanogen bromide (212 mg, 2.00 mmol, 2.00 equiv) was added. The resulting mixture was stirred for 3 h at room temperature. The resulting solution was stirred for 3 h at room temperature, then quenched with 30 mL of FeSO₄ (aq., sat.) and diluted with ethyl acetate. The resulting mixture was stirred vigorously then filtered through celite and washed with 1 M FeSO₄, water, and ethyl acetate. The layers were separated and the aqueous phase was extracted with 2×50 mL of ethyl acetate. The combined organic layers were washed with 2×50 mL of brine, dried over anhydrous sodium sulfate, and concentrated in vacuo. This resulted in 397 mg (98%) of an off-white solid.

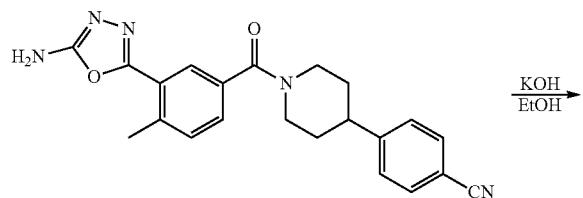

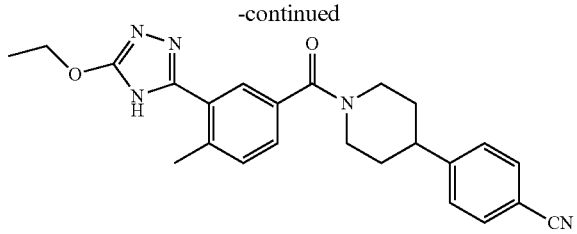

Compound 39. 4-(1-(3-(5-Ethoxy-4H-1,2,4-triazol-3-yl)-4-methylbenzoyl)piperidin-4-yl)benzonitrile A mixture of compound 39.6 (397 mg, 1.02 mmol, 1.00 equiv) and potassium hydroxide (287 mg, 5.12 mmol, 5.00 equiv) in ethanol (25 mL) was heated at reflux overnight. After cooling the reaction mixture to room temperature with a water bath, the pH was adjusted to ~7 with acetic acid. The resulting mixture was concentrated under reduced pressure. The residue was taken up in ethyl acetate and washed with water. The organic layer was dried (Na₂SO₄) and concentrated. The crude residue was purified using silica gel column chromatography with ethyl acetate/petroleum ether (1:5-1:0). The product was further purified by Prep-HPLC with the following conditions (1#-Pre-HPLC-006 (Waters)): Column, SunFire Prep C18, 5 um, 19*150 mm; mobile phase, WATER WITH 0.05% TFA and CH₃CN (hold 5.0% CH₃CN in 2 min, up to 30.0% in 1 min, up to 59.0% in 12 min, up to 100.0% in 2 min); Detector, UV 254/220 nm. The fractions containing pure compound were combined and lyophilized to yield 51.9 mg (12%) of the title compound as a white solid. m/z (ES+) 416 (M+H)⁺.

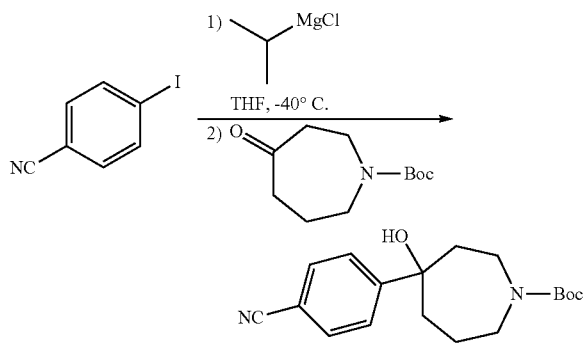

Compound 40.1. tert-Butyl 4-(4-cyanophenyl)-4-hydroxyazepane-1-carboxylate

A solution of 4-iodobenzonitrile (510 mg, 2.22 mmol, 1.1 equiv) in THF (3 mL) was added to a 10 mL round-bottom flask and the system purged with nitrogen. The mixture was cooled to −40° C. then isopropylmagnesium chloride (1.16 mL of a 2.0 M soln in THF, 2.32 mmol, 1.15 equiv) was added dropwise over 20 minutes. The resulting mixture was stirred at −40° C. for 2 hours then tert-butyl 4-oxoazepane-1-carboxylate (431 mg, 2.02 mmol, 1.0 equiv) in THF (0.5 mL) was added dropwise over 15 minutes. The resulting mixture was stirred at −40° C. for 1 hour then diluted into ethyl acetate (15 mL) and washed with 0.2 M HCl (10 mL), 0.1 M HCl (5 mL), saturated sodium bicarbonate (5 mL) then brine (5 mL). The organics were dried (Na₂SO₄), filtered and evaporated. To remove remaining ketone and aldol by-product, the residue was dissolved in acetonitrile (3 mL) then hydrazine (0.2 mL) was added and heated at 60° C. for 4 hours. The mixture was diluted with EtOAc (20 mL) and washed with water (20 mL), followed by 0.5 M phosphoric acid (3×20 mL), saturated sodium bicarbonate (10 mL) and brine (10 mL). The organics were dried ($Na_2SO_4$), filtered and evaporated. The residue was purified by silica column chromatography (hexanes/ethyl acetate) to obtain the title compound as a pink oil which solidified upon standing (303 mg, 47%). m/z (ES+) 317 (M+H)+.

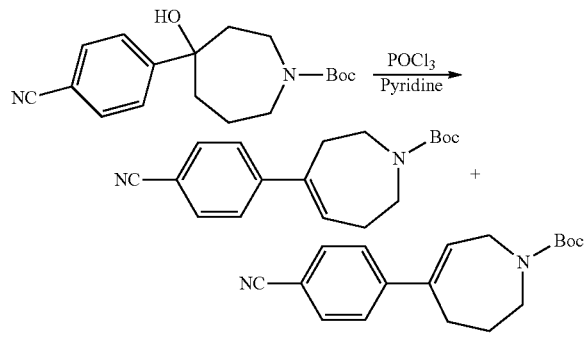

Compound 40.2. tert-Butyl 4-(4-cyanophenyl)-2,3,6,7-tetrahydro-1H-azepine-1-carboxylate and tert-butyl 5-(4-cyanophenyl)-2,3,4,7-tetrahydro-1H-azepine In a vial containing tert-butyl 4-(4-cyanophenyl)-4-hydroxyazepane-1-carboxylate (compound 40.1, 200 mg, 0.63 mmol, 1.0 equiv) was added pyridine (3 mL) and phosphorus oxychloride (438 µL, 4.7 mmol, 7.5 equiv) and the mixture was stirred at room temperature for 45 hours. The solvents were removed in vacuo and the residue was dissolved in DCM (5 mL) and washed with water (10 mL). The aqueous layer was extracted with DCM (5 mL) and the combined organics were washed with saturated sodium bicarbonate (2×10 mL), dried ($Na_2SO_4$), filtered and concentrated to obtain a mixture of the title compounds as a pale yellow oil (167 mg, 89%). m/z (ES+) 299 (M+H)+.

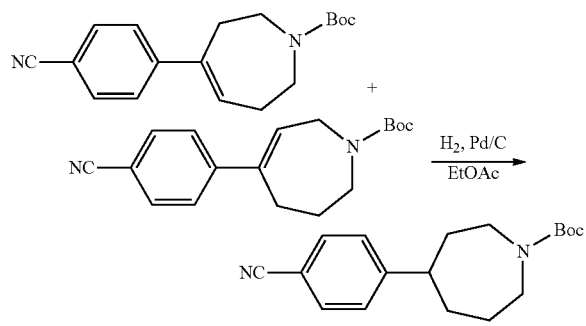

Compound 40.3. tert-Butyl 4-(4-cyanophenyl)azepane-1-carboxylate

To a 25 mL round bottom flask containing a mixture of tert-butyl 4-(4-cyanophenyl)-2,3,6,7-tetrahydro-1H-azepine- and tert-butyl 5-(4-cyanophenyl)-2,3,4,7-tetrahydro-1H-azepine-1-carboxylate (compound 40.2, 167 mg, 0.56 mmol) was added 10% palladium on carbon (40 mg) and ethyl acetate (6 mL). The system was purged with nitrogen then charged with hydrogen and stirred at room temperature. After purging the system with nitrogen, the mixture was filtered through celite and the filtrate was concentrated. The residue was purified by preparative TLC to obtain a colorless wax (77 mg, 45%). m/z (ES+) 245 (M minus t-butyl+H)+.

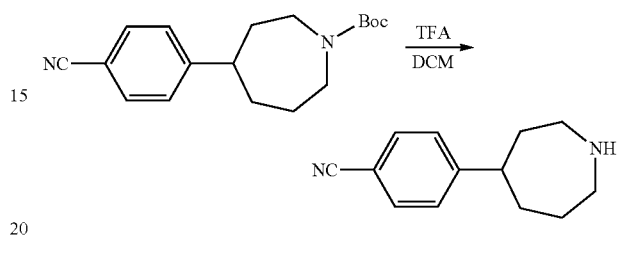

Compound 40.4. 4-(Azepan-4-yl)benzonitrile

To a vial containing tert-butyl 4-(4-cyanophenyl)azepane-1-carboxylate (compound 40.3, 77 mg, 0.257 mmol, 1.0 equiv) was added DCM (500 µL) and trifluoroacetic acid (198 µL, 2.57 mmol, 10 equiv) and the mixture was stirred vented for 90 min. The mixture was diluted into ethyl acetate (5 mL) and washed with saturated sodium bicarbonate (5 mL). The aqueous was adjusted to pH 10-11 and extracted with addition ethyl acetate until no product remained. The combined organics were dried ($Na_2SO_4$), filtered and concentrated to obtain the title compound as a yellow oil (51 mg, theoretical). m/z (ES+) 201 (M+H)+.

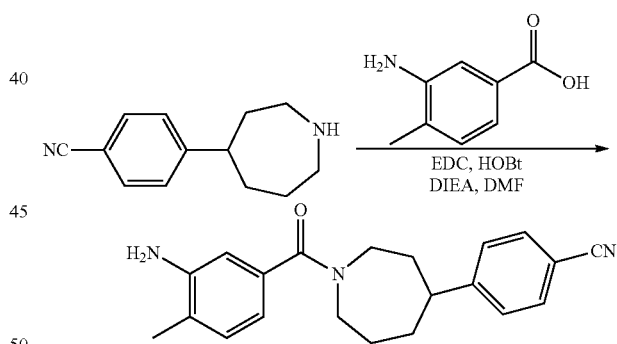

Compound 40.5. 4-(1-(3-Amino-4-methylbenzoyl)azepan-4-yl)benzonitrile

To a 4-mL vial was added 3-amino-4-methylbenzoic acid (27 mg, 0.18 mmol, 1.0 equiv), 4-(azepan-4-yl)benzonitrile (compound 40.4, 40 mg, 0.2 mmol, 1.1 equiv), hydroxybenzotriazole (39 mg of 20 wt % H2O, 0.23 mmol, 1.3 equiv), 1-ethyl-3-(3-dimethylaminopropyl) carbodiimide (44 mg, 0.23 mmol, 1.3 equiv), DMF (1 mL) and N,N-diisopropylethylamine (93 µL, 0.54 mmol, 3.0 equiv). The mixture was stirred at room temperature for 4 hours then diluted into ethyl acetate (10 mL) and washed with brine (10 mL). The aqueous was extracted with ethyl acetate (3 mL) and the combined organics were washed with brine (10 mL), 1 M $NaH_2PO_4$ (5 mL) and brine (10 mL). The organics were dried (Na$_2$SO$_4$), filtered and concentrated to obtain the title compound as a brown solid (45 mg, 74%). m/z (ES+) 334 (M+H)$^+$.

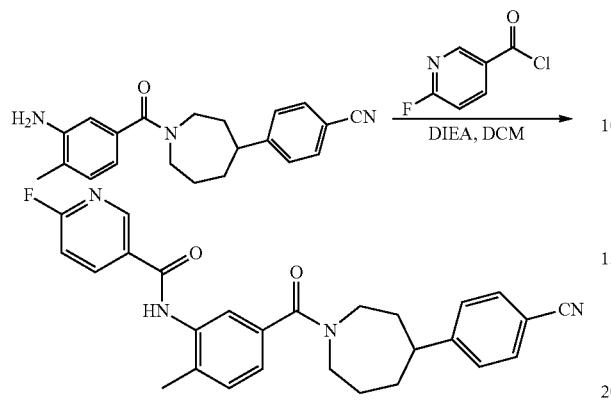

Compound 40.6. N-(5-(4-(4-Cyanophenyl)azepane-1-carbonyl)-2-methylphenyl)-6-fluoronicotinamide To a 4-mL vial containing 4-(1-(3-amino-4-methylbenzoyl)azepan-4-yl)benzonitrile (compound 40.5, 44 mg, 0.13 mmol, 1.0 equiv) was added dichloromethane (1 mL) and N,N-diisopropylethylamine (35 μL, 0.20 mmol, 1.5 equiv). A solution of 6-fluoronicotinoyl chloride (22 mg, 0.14 mmol, 1.05 equiv) in dichloromethane (1 mL) was added dropwise over about 2 minutes. The resulting mixture was stirred at room temperature for 19 hours then diluted with dichloromethane (5 mL) and washed with 1 M NaH$_2$PO$_4$ (3 mL), saturated sodium bicarbonate (3 mL) and brine (3 mL). The organics were dried (Na$_2$SO$_4$), filtered and concentrated to obtain the title compound as a brown wax (64 mg, theoretical). m/z (ES+) 457 (M+H)$^+$.

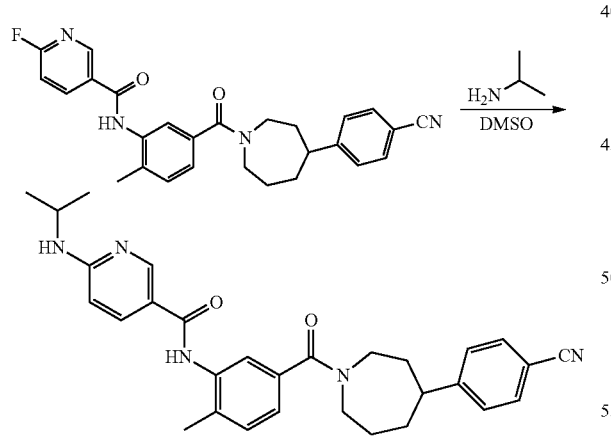

Compound 40. N-(5-(4-(4-Cyanophenyl)azepane-1-carbonyl)-2-methylphenyl)-6-(isopropylamino)nicotinamide To a vial containing N-(5-(4-(4-cyanophenyl)azepane-1-carbonyl)-2-methylphenyl)-6-fluoronicotinamide (compound 40.6, 61 mg, 0.13 mmol) was added dimethylsulfoxide (1 mL) and isopropylamine (1 mL). The mixture was stirred at 35° C. for 2 hours then at room temperature for 16 hours followed by 35° C. for an additional 4 hours. The excess isopropyl amine was removed in vacuo and the remaining solution was purified by preparative HPLC to yield the product as an off white powder (TFA salt, 39 mg, 49%). m/z (ES+) 496 (M+H)$^+$.

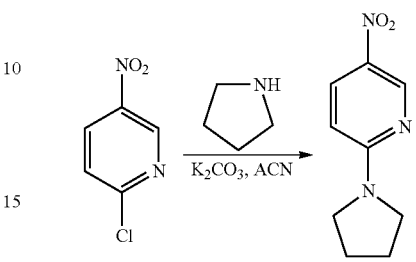

Compound 41.1. 5-Nitro-2-(pyrrolidin-1-yl)pyridine

A mixture of 2-chloro-5-nitropyridine (1.58 g, 10.00 mmol, 1.00 equiv), pyrrolidine (710 mg, 10.00 mmol, 1.00 equiv) and potassium carbonate (2.76 g, 20.00 mmol, 2.00 equiv) in CH$_3$CN (20 mL) was stirred at 60° C. in an oil bath. After 2 h, the reaction mixture was allowed to reach ambient temperature. The solids were filtered off and the filtrate was concentrated under reduced pressure. The residue was triturated with 1×20 mL of petroleum ether to yield 1.8 g (93%) of the title compound as a yellow solid.

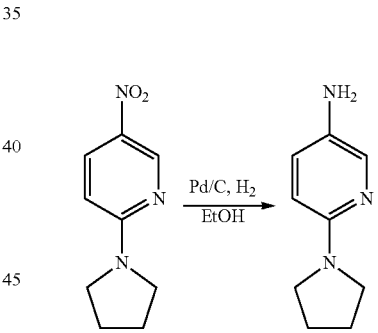

Compound 41.2. 6-(Pyrrolidin-1-yl)pyridin-3-amine

A round-bottom flask, containing a solution of 5-nitro-2-(pyrrolidin-1-yl)pyridine (compound 40.1, 1.93 g, 10.00 mmol, 1.00 equiv) in ethanol (30 mL) was purged with nitrogen. Palladium on carbon (0.4 g, 10%, 60% water) was added. After further purging the system with nitrogen, the atmosphere was changed to hydrogen and the resulting mixture was stirred overnight at room temperature. After purging the system with nitrogen, the solids were filtered off and the filtrate was concentrated under reduced pressure and dried to yield 1.6 g (98%) of the title compound as a brown solid.

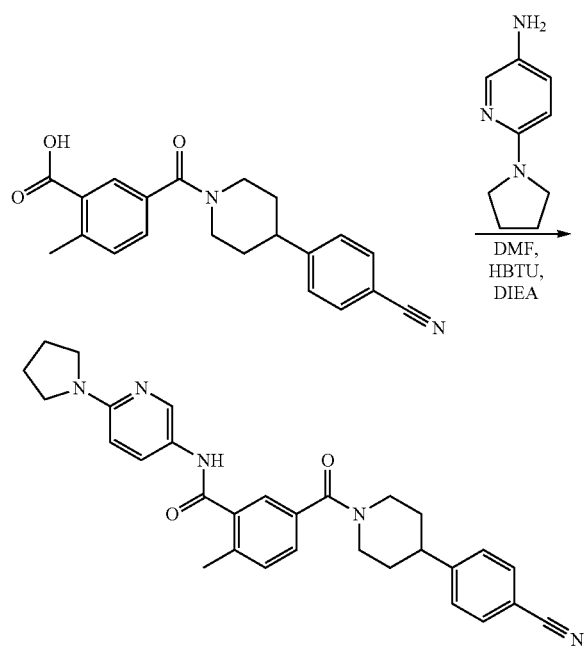

Compound 41. 5-(4-(4-Cyanophenyl)piperidine-1-carbonyl)-2-methyl-N-(6-(pyrrolidin-1-yl)pyridin-3-yl)benzamide A mixture of compound 39.3 (528 mg, 1.52 mmol, 1.00 equiv) and HBTU (635 mg, 2.28 mmol, 1.50 equiv) in DMF (30 mL) was stirred for 30 min at room temperature. To this was added 6-(pyrrolidin-1-yl)pyridin-3-amine (compound 41.2, 299 rag, 1.82 mmol, 1.20 equiv) and DIEA (50 mg). The resulting mixture was stirred overnight at 60° C. in an oil bath. After cooling to room temperature, the reaction mixture was diluted with 50 mL of EtOAc and washed with 2×30 mL of NH$_4$Cl (aq., sat.) followed by 2×30 mL of sodium bicarbonate (aq., sat.). The organic layer was dried over anhydrous sodium sulfate and concentrated under reduced pressure. The crude product was purified by Prep-HPLC with the following conditions (1#-Pre-HPLC-016 (Waters)): Column, SunFire Prep C18, 19*150 mm 5 um; mobile phase, Water with 50 mmol NH$_4$HCO$_3$ and CH$_3$CN (10% CH$_3$CN up to 32% in 3 min, up to 51% in 20 min, up to 100% in 1 min, down to 10% in 1 min); Detector, UV 220NMnm. The fractions containing pure compound were combined and lyophilized to yield 50 mg (7%) of the title compound as a solid. m/z (ES+) 494 (M+H)$^+$.

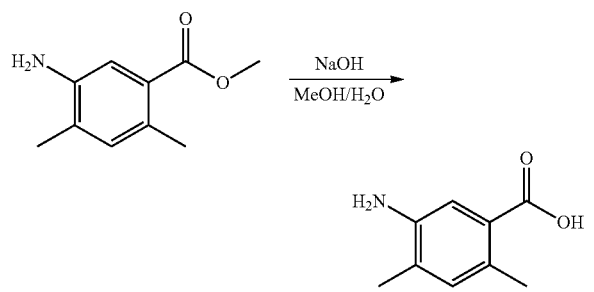

Compound 42.1. 5-Amino-2,4-dimethylbenzoic acid

A mixture of methyl 5-amino-2,4-dimethylbenzoate (1.2 g, 6.70 mmol, 1.00 equiv) and sodium hydroxide (1.5 g, 37.50 mmol, 5.60 equiv) in methanol/FLO (20/20 mL) was stirred overnight at 50° C. After cooling to ambient temperature, the organic phase was removed under reduced pressure. The pH of the remaining aqueous layer was adjusted to ~4-5 with hydrogen chloride (aq., 2 M). The resulting solids were collected by filtration and dried to yield 1.0 g of a yellow solid.

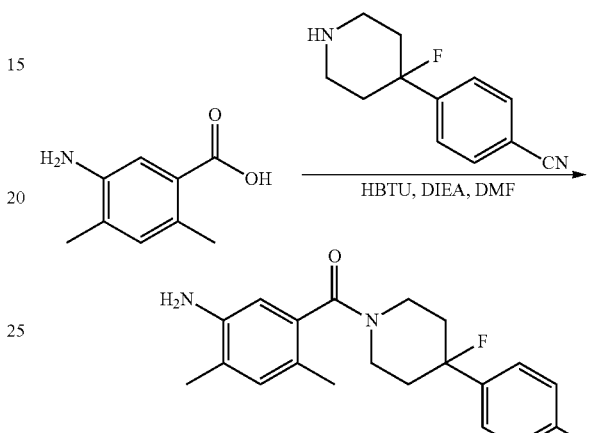

Compound 42.2. 4-(1-(5-Amino-2,4-dimethylbenzoyl)-4-fluoropiperidin-4-yl)benzonitrile A mixture of 5-amino-2,4-dimethylbenzoic acid (compound 42.1, 2.264 g, 13.71 mmol, 1.00 equiv), HBTU (7.803 g, 20.59 mmol, 1.50 equiv), 4-(4-fluoropiperidin-4-yl)benzonitrile (compound 11.2, 2.8 g, 13.71 mmol, 1.00 equiv), and DMA (3.541 g, 27.45 mmol, 2.00 equiv) in DMF (50 mL) was stirred at room temperature. After 1 h, the mixture was diluted with 100 mL of EtoAc and washed with 1×100 mL of water followed by 1×100 mL of brine. The organic layer was dried over anhydrous sodium sulfate and concentrated under reduced pressure to yield 3.51 g (73%) of the title compound as a white solid.

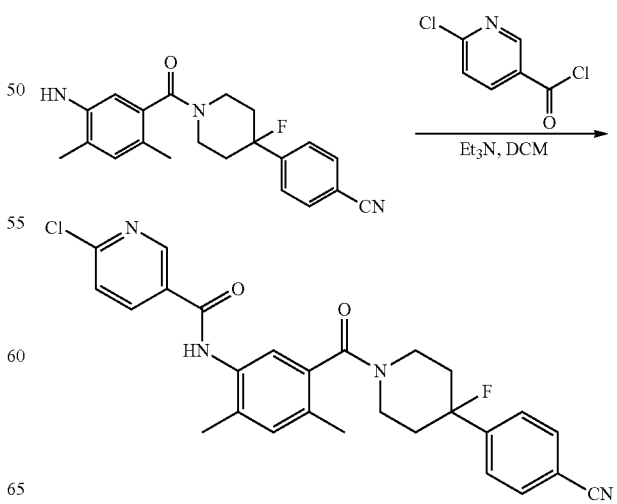

Compound 42.3. 6-Chloro-N-(5-(4-(4-cyanophenyl)-4-fluoropiperidine-1-carbonyl)-2,4-dimethylphenyl)nicotinamide To a mixture of compound 42.2 (3.51 g, 9.99 mmol, 1.00 equiv) and triethylamine (2.02 g, 19.96 mmol, 2.00 equiv) in DCM (50 mL) under nitrogen at 0° C. was added dropwise a solution of 6-chloropyridine-3-carbonyl chloride (1.936 g, 11.00 mmol, 1.10 equiv) in DCM (50 mL). After stirring for 1 h at 0° C., the reaction mixture was quenched by careful addition of 50 mL of water and extracted with 2×50 mL of dichloromethane. The combined organic layers were washed with 2×50 mL of brine, dried over anhydrous sodium sulfate, and concentrated under reduced pressure to yield 4.41 g (90%) of the title compound as a yellow solid.

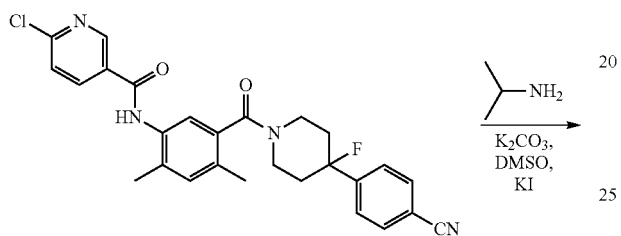

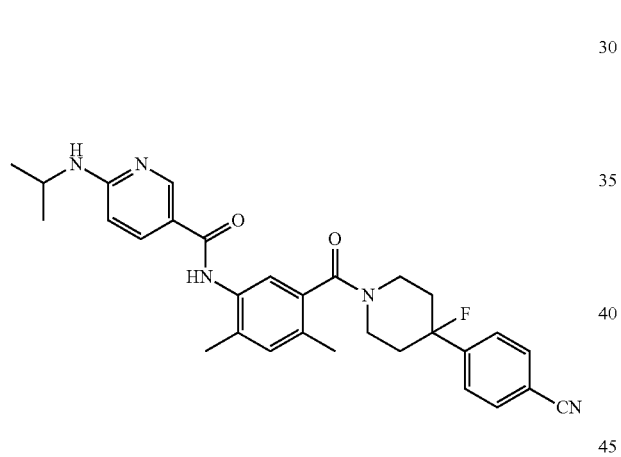

Compound 42. N-(5-(4-(4-Cyanophenyl)-4-fluoropiperidine-1-carbonyl)-2,4-dimethylphenyl)-6-(isopropylamino)nicotinamide A mixture of compound 42.3 (392 mg, 0.80 mmol, 1.00 equiv), propan-2-amine (472 mg, 7.99 mmol, 10.00 equiv), potassium carbonate (221 mg, 1.60 mmol, 2.01 equiv), KI (66.4 mg, 0.40 mmol, 0.50 equiv) in DMSO (10 mL) was heated at 100° C. in a sealed tube behind a blast shield. After 48, the mixture was allowed to reach ambient temperature and was then diluted with 20 mL of EtOAc. The mixture was washed with 1×20 mL of water followed by 1×20 mL of brine. The organic phase was dried over anhydrous sodium sulfate and concentrated under reduced pressure. The crude product (~300 mg) was purified by Prep-HPLC with the following conditions (1#-Pre-HPLC-002(Agilent)): Column, SunFire Prep C18, 19*150 mm 5 um; mobile phase, WATER WITH 0.05% TFA and CH3CN (15.0% CH3CN up to 40.0% in 6 min, up to 100.0% in 2 min, down to 15.0% in 2 min); Detector, uv 220 & 254 nm. The fractions containing pure compound were combined and lyophilized to yield 158 mg (39%) of the title compound as an off-white solid. m/z (ES+) 514 (M+H)+. $^1$H NMR (300 MHz, CD$_3$OD, ppm): δ 8.49 (s, 1H), 8.32 (d, J=9.9 Hz, 1H), 7.79 (d, J=8.1 Hz, 2H), 7.67 (d, J=7.5 Hz, 2H), 7.40-7.22 (m, 2H), 7.07 (d, J=9.6 Hz, 1H), 4.85 (m, 1H), 4.03 (m, 1H), 3.80-3.42 (m, 2H), 3.29 (m, 1H), 2.48-2.03 (m, 9H), 1.95 (m, 1H), 1.39 (d, J=6.3 Hz, 6H).

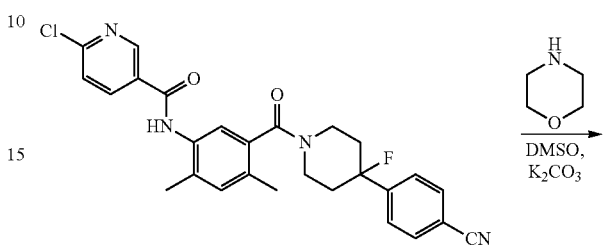

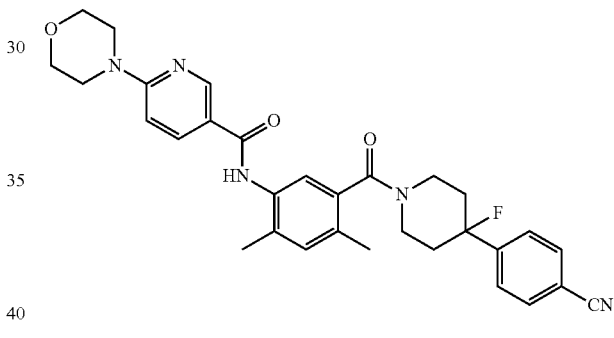

Compound 43. N-(5-(4-(4-Cyanophenyl)-4-fluoropiperidine-1-carbonyl)-2,4-dimethylphenyl)-6-morpholinonicotinamide A mixture of compound 42.3 (392 mg, 0.80 mmol, 1.00 equiv), morpholine (348 mg, 3.99 mmol, 5.00 equiv), and potassium carbonate (221 mg, 1.60 mmol, 2.01 equiv) in DMSO (10 mL) was stirred overnight at 100° C. in a sealed tube behind a blast shield. After cooling to ambient temperature, the reaction mixture was diluted with 20 mL of EtOAc and was washed with 1×20 mL of water followed by 1×20 mL of brine. The organic layer was dried over anhydrous sodium sulfate and concentrated under reduced pressure. The crude product (300 mg) was purified by Prep-HPLC with the following conditions (1#-Pre-HPLC-002 (Agilent)): Column, 1#-PrepC-005 (XBridge C18 19*150 186002979 170130047113 03), n; mobile phase, WATER WITH 0.05% TFA and CH$_3$CN (15.0% CH$_3$CN up to 50.0% in 10 min, up to 100.0% in 1 min, hold 100.0% in 1 min, down to 15.0% in 2 min); Detector, uv 220 & 254 nm. The fractions containing pure compound were combined and lyophilized to yield 106 mg (25%) of the title compound as a white solid. m/z (ES+) 542 (M+H)+.

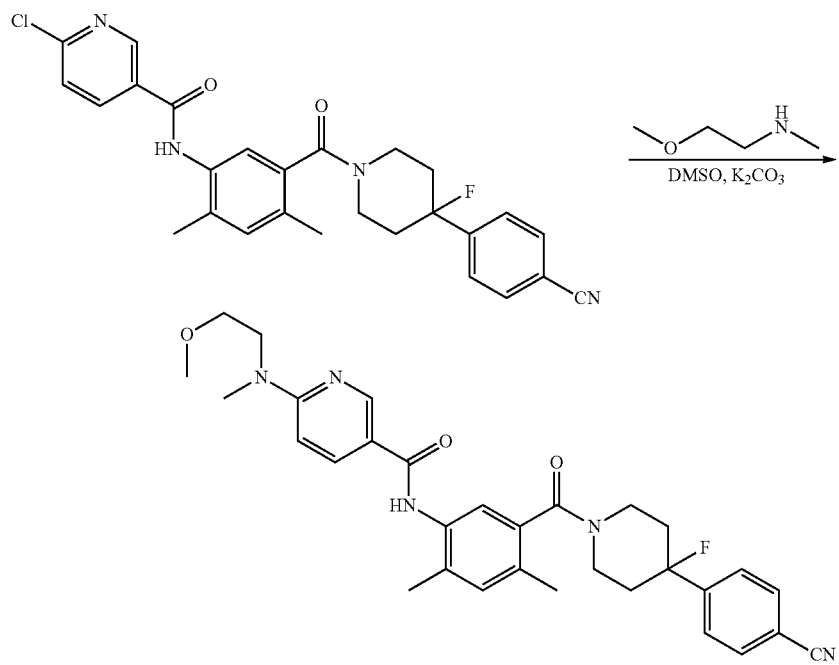

Compound 44. N-(5-(4-(4-Cyanophenyl)-4-fluoropiperidine-1-carbonyl)-2,4-dimethylphenyl)-6-((2-methoxyethyl)(methyl)amino)nicotinamide The title compound was synthesized in a similar manner to that described for compound 43 to yield a white solid (219 mg, 50%). m/z (ES+) 544 (M+H)$^+$. $^1$H NMR (300 MHz, CD$_3$OD): b 8.56 (s with fine structure, 1H), 8.41 (d with fine structure, J=9.9 Hz, 1H), 7.79 d (br d, J=8.1 Hz, 2H), 7.67 (br d, J 6.9 Hz, 2H), 7.44-7.19 (m, 3H), 4.88-4.73 (m, 1H), 3.94 (1, J=5.0 Hz, 2H), 3.73 (t, J=5.0 Hz, 2H), 3.70-3.47 (m, 2H), 3.39 (s, 3H), 3.36 (s, 3H), 3.36-3.21 (m, 1H), 2.46-2.22 (m, 6H), 2.22-1.85 (m, 4H).

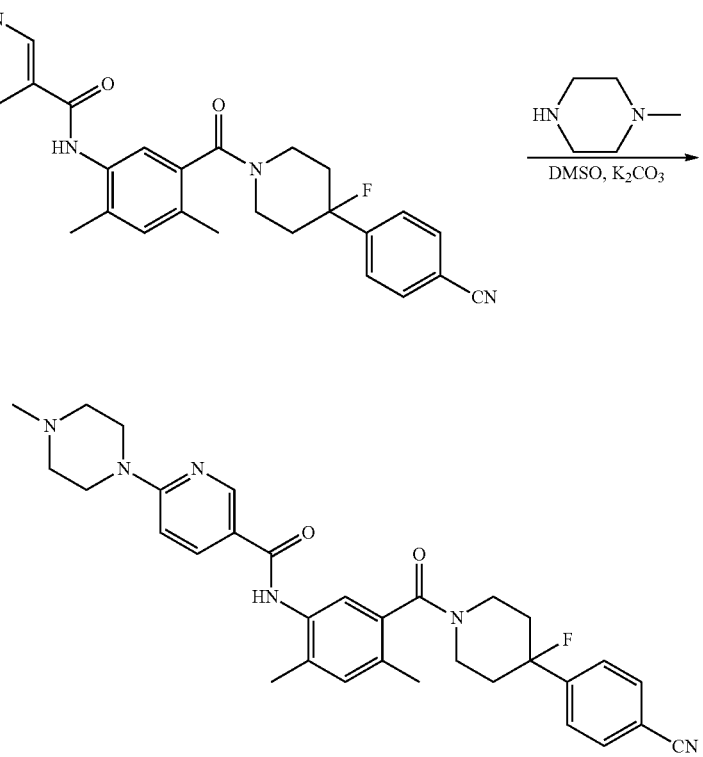

Compound 45. N-(5-(4-(4-Cyanophenyl)-4-fluoropiperidine-1-carbonyl)-2,4-dimethylphenyl)-6-(4-methylpiperazin-1-yl)nicotinamide The title compound was synthesized in a similar manner to that described for compound 43 to yield a white solid (180 mg, 44%). m/z (ES+) 555 (M+H)+.

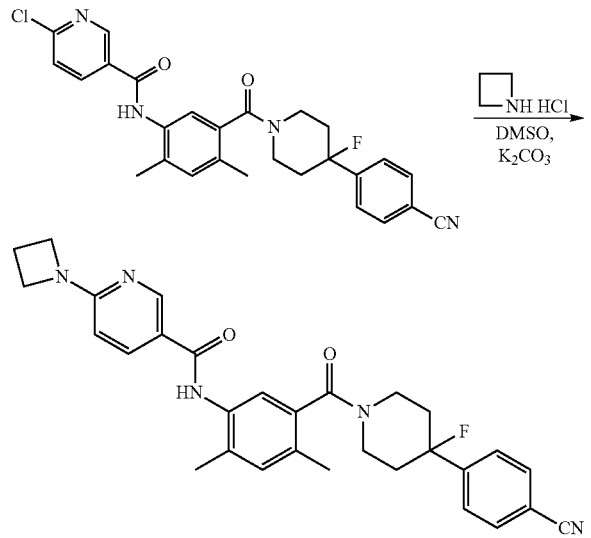

Compound 46. 6-(Azetidin-1-yl)-N-(5-(4-(4-cyanophenyl)-4-fluoropiperidine-1-carbonyl)-2,4-dimethylphenyl)nicotinamide The title compound was synthesized in a similar manner to that described for compound 43 to yield a white solid (180 mg, 44%). m/z (ES+) 512 (M+H)+.

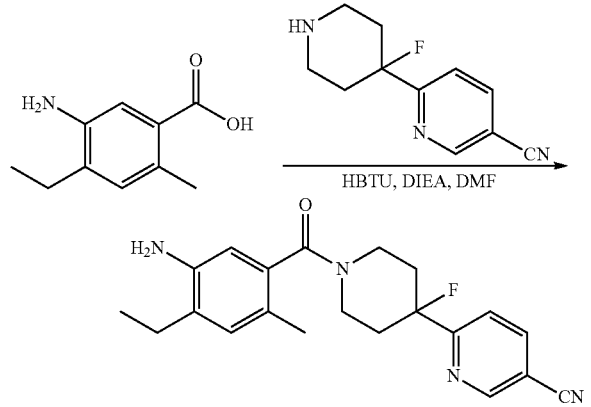

Compound 47.1. 6-(1-(5-Amino-4-ethyl-2-methylbenzoyl)-4-fluoropiperidin-4-yl)nicotinonitrile The title compound was synthesized in a similar manner to that described for 42.2 and using compound 26.4 in place of compound 1.5 to yield a brown oil (280 mg, 89%).

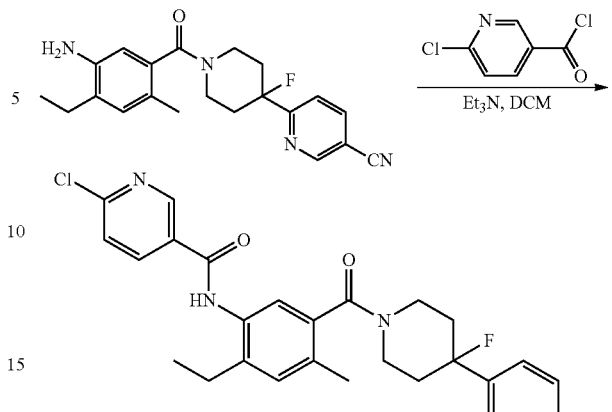

Compound 47.2. 6-Chloro-N-(5-(4-(5-cyanopyridin-2-yl)-4-fluoropiperidine-1-carbonyl)-2-ethyl-4-methylphenyl)nicotinamide The title compound was synthesized in a similar manner to that described for compound 42.3 to yield a brown oil (350 mg, 91%).

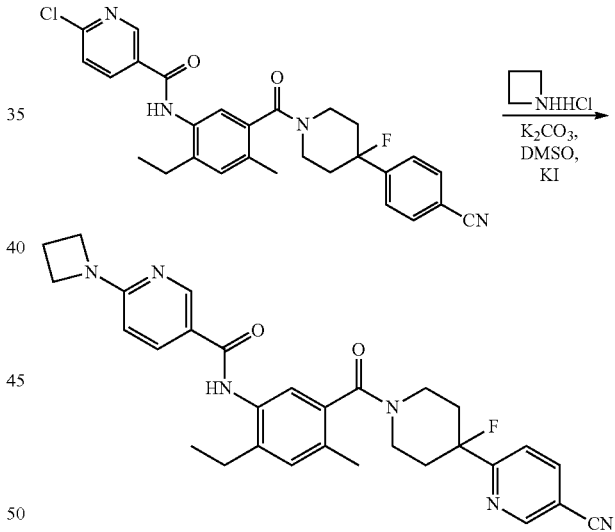

Compound 47. 6-(Azetidin-1-yl)-N-(5-(4-(5-cyanopyridin-2-yl)-4-fluoropiperidine-1-carbonyl)-2-ethyl-4-methylphenyl)nicotinamide The title compound was synthesized in a similar manner to that described for compound 43 to yield a white solid (187 mg, 54%). m/z (ES+) 527 (M+H)+. $^1$H NMR (300 MHz, DMSO-$d_6$): δ 9.88 (s, 1H), 9.06 (s, 1H), 8.59 (d, J=1.8 Hz, 1H), 8.43 (dd, J=8.4 Hz, J=2.1 Hz, 1H), 8.23 (d, J=9.3 Hz, 1H), 7.81 (d, J=8.1 Hz, 1H), 7.22 (s, 1H), 7.17 (br s, 1H), 6.74 (d, J=9.0 Hz, 1H), 4.68-4.53 (m, 1H), 4.23 (t, J=7.7 Hz, 4H), 3.54-3.32 (m, 2H), 3.22-3.05 (m, 1H), 2.59 (q, J=7.5 Hz, 2H), 2.50-2.38 (m, 2H), 2.35-1.80 (m, 7H), 1.14 (t, 3H).

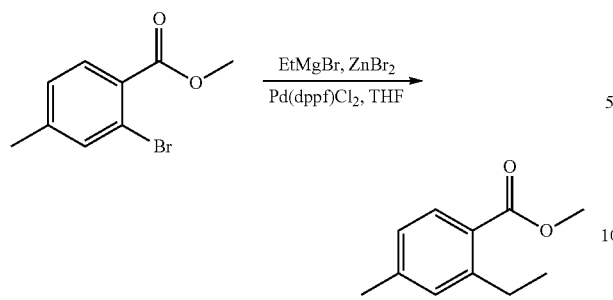

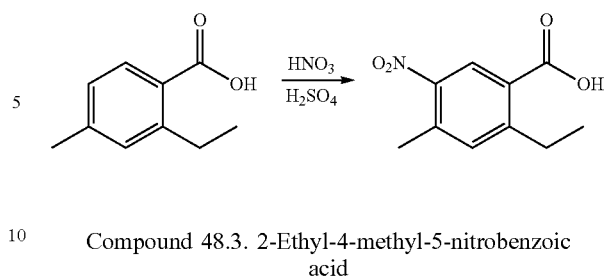

Compound 48.3. 2-Ethyl-4-methyl-5-nitrobenzoic acid

Compound 48.1. Methyl 2-ethyl-4-methylbenzoate

To a stirred mixture of $ZnBr_2$ (13 g, 57.72 mmol, 2.00 equiv) in THF (230 mL) under nitrogen at 0° C. was added dropwise EtMgBr (19.5 mL, 3 M in THF). After 30 minutes at 0° C., the temperature was lowered to −78° C. and Pd(dppf)Cl$_2$ (2 g, 2.73 mmol, 0.09 equiv) was added followed by dropwise addition of a solution of methyl 2-bromo-4-methylbenzoate (6.6 g, 28.81 mmol, 1.00 equiv) in tetrahydrofuran (200 mL). The resulting mixture was allowed to slowly reach ambient temperature and stirred under nitrogen overnight. The reaction mixture was quenched by the careful addition of 20 mL $NH_4Cl$ (aq., sat.) and extracted with 3×100 mL of ethyl acetate. The combined organic layers were washed with 1×200 mL of brine, dried over anhydrous sodium sulfate, and concentrated under reduced pressure. The residue was purified using silica gel column chromatography with ethyl acetate/petroleum ether (1:30) as eluent to yield 3.7 g (72%) of the title compound as a colorless oil.

To a stirred mixture of 2-ethyl-4-methylbenzoic acid (compound 48.2, 2 g, 12.18 mmol, 1.00 equiv) in sulfuric acid (30 mL) at −10° C. was added dropwise a solution of nitric acid (1.6 g, 16.50 mmol, 2.08 equiv) in sulfuric acid (10 mL). After stirring for 30 min at −10° C., 200 mL of $H_2O$/ice was carefully added and the resulting mixture was extracted with 50 mL of ethyl acetate. The organic phase was washed with 2×50 mL of brine, dried over sodium sulfate, and concentrated under reduced pressure. The crude product was purified by re-crystallization from ethyl acetate/petroleum ether in the ratio 1:10 to yield 1.0 g (37%) of 2-ethyl-4-methyl-5-nitrobenzoic acid as a light-yellow solid.

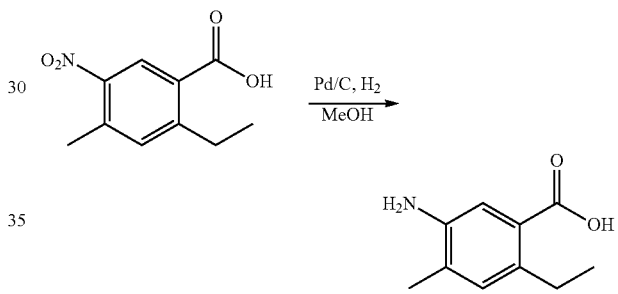

Compound 48.4. 5-Amino-2-ethyl-4-methylbenzoic acid

The title compound was synthesized from 48.3 (1 g, 4.78 mmol) using a procedure similar to that described for the preparation of 1.9 to yield the title compound as a light pink solid (900 mg, 97%).

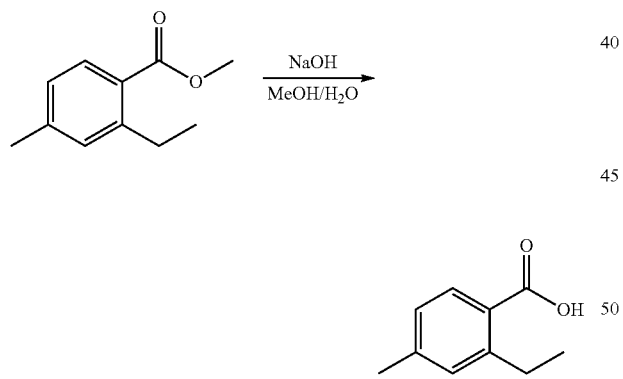

Compound 48.2. 2-Ethyl-4-methylbenzoic acid

A mixture of compound 48.1, 3.7 g, 20.76 mmol, 1.00 equiv) and sodium hydroxide (4 g, 100.01 mmol, 4.82 equiv) in methanol/$H_2O$ (30/20 mL was stirred overnight at 50° C. After cooling to ambient temperature, the organic solvent was removed under reduced pressure. The pH of the residual aqueous layer was adjusted to 3-4 with hydrogen chloride (aq., 1 M). The resulting precipitate was collected by filtration and dried to yield in 3.0 g (83%) of the title compound as a white solid.

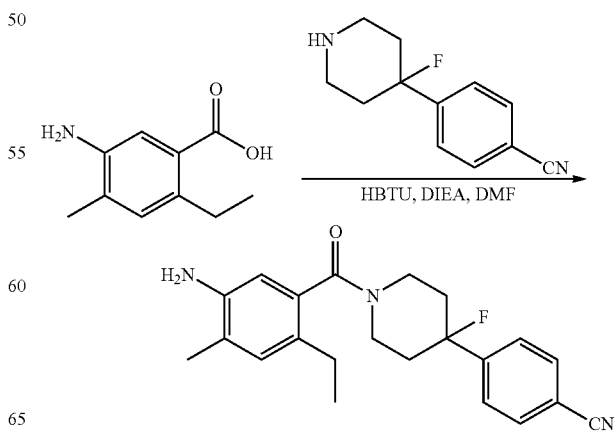

Compound 48.5. 4-(1-(5-Amino-2-ethyl-4-methyl-benzoyl)-4-fluoropiperidin-4-yl)benzonitrile A mixture of 5-amino-2-ethyl-4-methylbenzoic acid (compound 48.4, 100 mg, 0.56 mmol, 1.00 equiv), 4-(4-fluoropiperidin-4-yl) benzonitrile (compound 11.2, 140 mg, 0.69 mmol, 1.23 equiv), HBTU (320 mg, 0.84 mmol, 1.51 equiv), and DIEA (150 mg, 1.16 mmol, 2.08 equiv) in DMF (20 mL) was stirred for 48 h at room temperature. Water (30 mL) was added and the resulting mixture was extracted with 3×20 mL of ethyl acetate. The combined organic layers were washed with 1×50 mL of brine, dried over Na$_2$SO$_4$, and concentrated under reduced pressure. The residue was purified using silica gel column chromatography with PE:EtOAc (1:1) to yield 130 mg (38%) of the title compound as a light yellow solid.

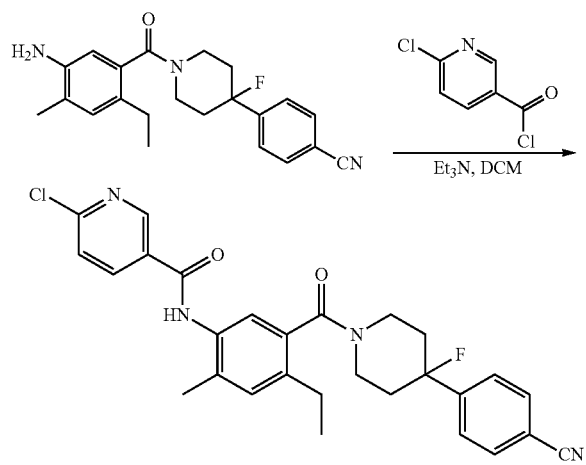

Compound 48.6. 6-Chloro-N-(5-(4-(4-cyanophenyl)-4-fluoropiperidine-1-carbonyl)-4-ethyl-2-methylphenyl)nicotinamide The title compound was synthesized in a similar manner to that described for compound 42.3 and using compound 48.5 in place of compound 42.2 to yield a light yellow solid (200 mg, 87%).

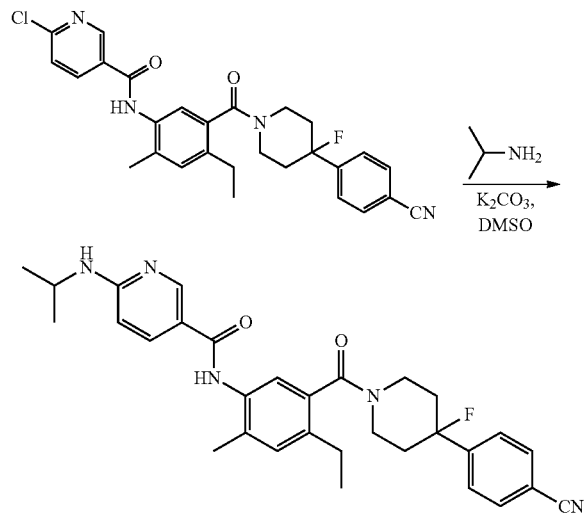

Compound 48. N-(5-(4-(4-Cyanophenyl)-4-fluoropiperidine-1-carbonyl)-4-ethyl-2-methylphenyl)-6-(isopropylamino)nicotinamide The title compound was synthesized in a similar manner to that described for compound 43 and using compound 48.6 in place of compound 42.3 to yield an off-white solid (32 mg, 30%). m/z (ES+) 528 (M+H)$^-$.

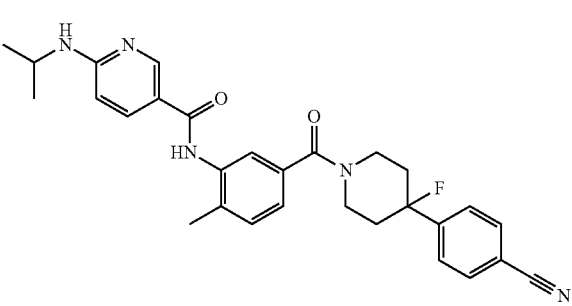 [SMILES: Cc1ccc(C(=O)N2CCC(F)(c3ccc(C#N)cc3)CC2)cc1NC(=O)c1ccc(NC(C)C)nc1]

Compound 49. N-(5-(4-(4-Cyanophenyl)-4-fluoropiperidine-1-carbonyl)-2-methylphenyl)-6-(isopropylamino)nicotinamide The title compound was synthesized using readily available reagents and procedures similar to those described for compound 43. m/z (ES+) 500 (M+H)$^+$.

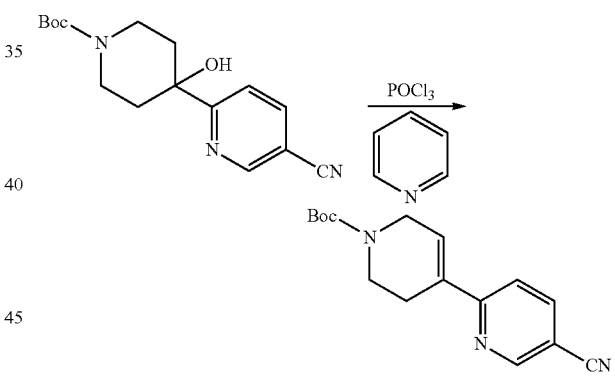

Compound 50.1. tert-Butyl 5-cyano-5',6'-dihydro-[2,4'-bipyridine]-1'(2'H)-carboxylate To a stirred mixture of tert-butyl 4-(5-cyanopyridin-2-yl)-4-hydroxypiperidine-1-carboxylate (compound 26.2, 500 mg, 1.65 mmol, 1.00 equiv) in pyridine (20 mL) was added dropwise phosphoryl trichloride (2.5 g, 16.34 mmol, 9.90 equiv) at 10-15° C. The resulting solution was stirred for 18 h at 15~20° C. The reaction was then carefully quenched by the addition of 20 mL of water and extracted with 3×100 mL of ethyl acetate. The combined organic phases were washed with 2×50 mL of aqueous HCl (1 M) followed by 1×100 mL of brine. The organic layer was dried over anhydrous sodium sulfate and concentrated under reduced pressure. The residue was purified using silica gel column chromatography with ethyl acetate/petroleum ether (1:100 to 1:7) as eluent to yield 0.3 g (64%) of the title compound as a yellow solid.

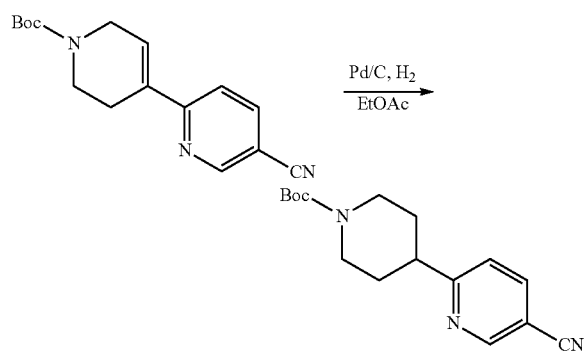

Compound 50.2. tert-butyl 4-(5-cyanopyridin-2-yl)piperidine-1-carboxylate

Around-bottom flask, containing a solution of compound 50.1 (300 mg, 1.05 mmol, 1.00 equiv) in ethyl acetate (20 mL), was purged with nitrogen gas. To the solution was then added palladium on carbon (40 mg, 10%) and the flask was purged further with nitrogen gas. The atmosphere was then changed to hydrogen and the mixture was stirred for 16 h at 15~20° C. After purging the system with nitrogen, the solids were removed by filtration and the filtrate was concentrated under reduced pressure to yield 0.2 g (66%) of the title compound as a yellow oil.

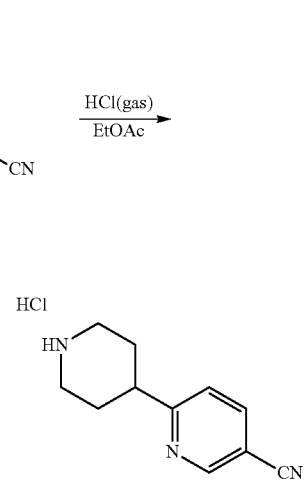

Compound 50.3. 6-(Piperidin-4-yl)nicotinonitrile hydrochloride

Through a solution of tert-butyl 4-(5-cyanopyridin-2-yl)piperidine-1-carboxylate (compound 50.2, 200 mg, 0.70 mmol, 1.00 equiv) in ethyl acetate (20 mL) was bubbled HCl gas. The resulting mixture was stirred for 40 min at 5-10° C. The resulting precipitate was collected by filtration and dried to yield 150 mg (97%) of the title compound as a white solid.

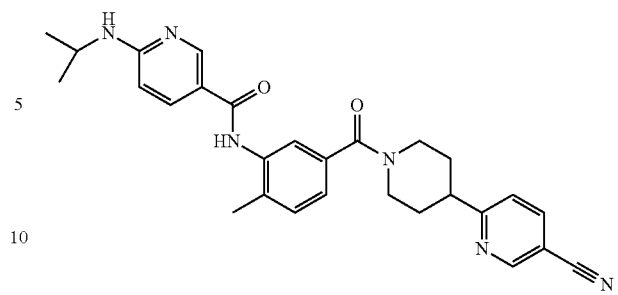

Compound 50. N-(5-(4-(5-Cyanopyridin-2-yl)piperidine-1-carbonyl)-2-methylphenyl)-6-(isopropylamino)nicotinamide The title compound was synthesized using readily available reagents and procedures similar to those described for compound 43 but using compound 50.3 in place of compound 11.2. m/z (ES+) 483 (M+H)$^+$.

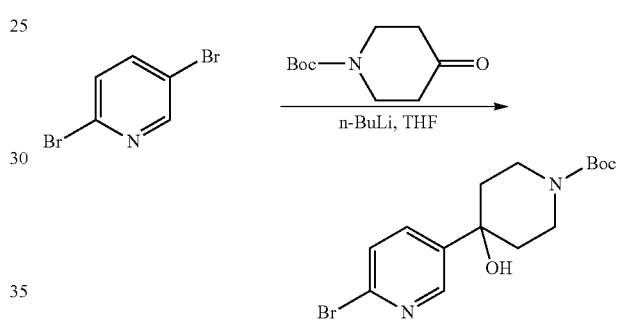

Compound 51.1. tert-Butyl 4-(6-bromopyridin-3-yl)-4-hydroxypiperidine-1-carboxylate To a solution of 2,5-dibromopyridine (10 g, 42.55 mmol, 1.00 equiv) in tetrahydrofuran (400 mL) under nitrogen at −78° C. was added dropwise n-BuLi (19 mL, 2.4 M in THF). After 1 h at −78° C., a solution of tert-butyl 4-oxopiperidine-1-carboxylate (9.5 g, 47.74 mmol, 1.12 equiv) in tetrahydrofuran (100 mL) was added dropwise. The resulting mixture was stirred for an additional hour at −78° C. The reaction was then warmed to −30° C. and carefully quenched by the addition of 300 mL of water. The resulting mixture was extracted with 3×200 mL of ethyl acetate and the combined organic layers were washed with 1×200 mL of brine, dried over anhydrous sodium sulfate, and concentrated under reduced pressure. The residue was purified using silica gel column chromatography with ethyl acetate/petroleum ether (1:3) as eluent to yield 5 g (33%) of the title compound as a yellow solid.

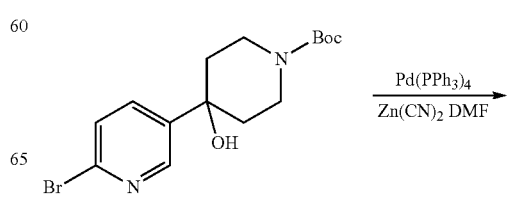

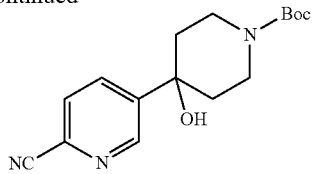

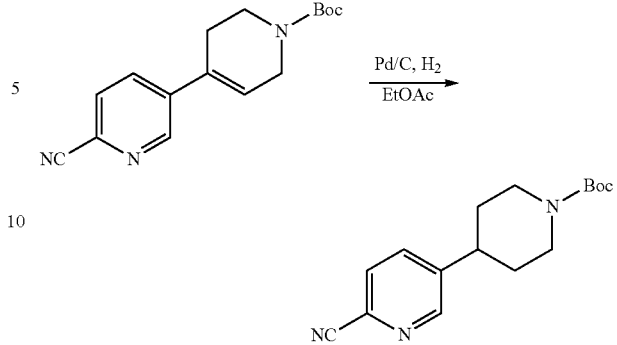

Compound 51.2. tert-Butyl 4-(6-cyanopyridin-3-yl)-4-hydroxypiperidine-1-carboxylate To a mixture of tert-butyl 4-(6-bromopyridin-3-yl)-4-hydroxypiperidine-1-carboxylate (compound 51.1, 1 g, 2.81 mmol, 1.00 equiv) in DMF (50 mL) under nitrogen at 50° C. was added. $Zn(CN)_2$ (400 mg, 3.42 mmol, 1.22 equiv) at 50° C. followed by $Pd(PPh_3)_4$ (200 mg, 0.17 mmol, 0.06 equiv) at 80° C. The resulting mixture was then stirred for 1 h at 120° C. After cooling to ambient temperature, the reaction was quenched by the addition of 200 mL of $FeSO_4$(aq., sat.) and diluted with ethyl acetate. The resulting mixture was stirred vigorously then filtered through celite and washed with 1 M $FeSO_4$, water, and ethyl acetate. The layers were separated and the aqueous phase was extracted with 2×100 mL of ethyl acetate. The combined organic layers were washed with 1×200 mL of brine, dried over anhydrous sodium sulfate, and concentrated under reduced pressure. The residue was purified using silica gel column chromatography with ethyl acetate/petroleum ether (1:5-1:3) as eluent to yield 0.6 g (70%) of the title compound as a light yellow oil.

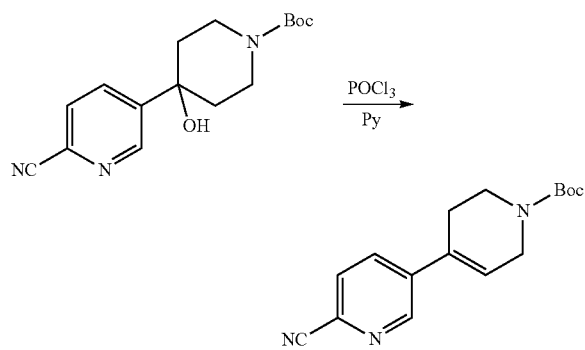

Compound 51.3. tert-Butyl 6-cyano-5',6'-dihydro-[3,4'-bipyridine]-1'(2'H)-carboxylate To solution of tert-butyl 4-(6-cyanopyridin-3-yl)-4-hydroxypiperidine-1-carboxylate (compound 51.2, 600 mg, 1.98 mmol, 1.00 equiv) in pyridine (15 mL) under nitrogen at 10-15° C. was carefully added $POCl_3$ (3 g, 19.74 mmol, 9.97 equiv). After stirring overnight under nitrogen in a water/ice bath, the mixture was concentrated and the residue was dissolved in 50 mL of ethyl acetate. The organic phase was washed with 1×50 mL of hydrogen chloride (aq. 1M) followed by 1×50 mL of sodium bicarbonate (aq.sat.). The organic layer was then dried over anhydrous sodium sulfate and concentrated under reduced pressure. The residue was purified using silica gel column chromatography with ethyl acetate/petroleum ether (1:10) as the eluent to yield 0.26 g (46%) of the title compound as a white solid.

Compound 51.4. tert-Butyl 4-(6-cyanopyridin-3-yl)piperidine-1-carboxylate

A round-bottom flask, containing a solution of compound 51.3 (260 mg, 0.91 mmol, 1.00 equiv) in ethyl acetate (40 mL) was purged with nitrogen gas. To the solution was then added palladium on carbon (0.1 g, 10%, 60% water) and the flask was purged further with nitrogen gas. The atmosphere was then changed to hydrogen and the mixture was stirred for 16 h at 15-20° C. After purging the system with nitrogen, the solids were removed by filtration and the filtrate was concentrated under reduced pressure. The crude residue was purified using silica gel column chromatography with ethyl acetate/petroleum ether (1:5). This resulted in 0.18 g (69%) of the title compound as a colorless oil.

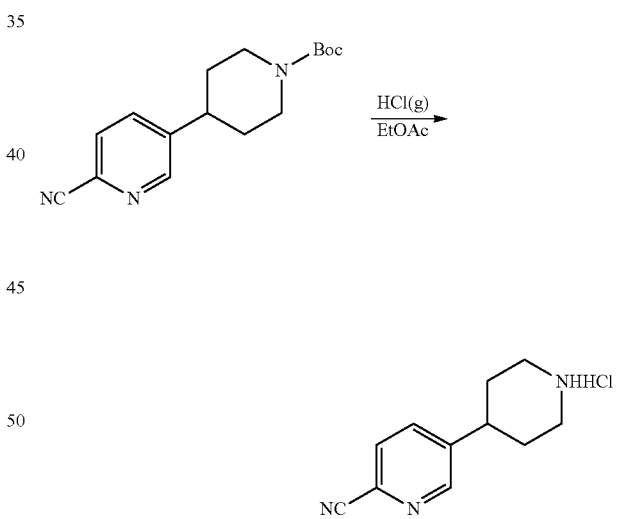

Compound 51.5. 5-(Piperidin-4-yl)picolinonitrile hydrochloride

Into a cooled (5-10° C.) solution of tert-butyl 4-(6-cyanopyridin-3-yl)piperidine-1-carboxylate (51.4, 180 mg, 0.63 mmol, 1.00 equiv) in ethyl acetate (30 mL) was bubbled hydrogen chloride gas. The mixture was stirred for 30 min at 5-10° C. and the resulting solids were collected by filtration and dried to yield 0.11 g (78%) of 5-(piperidin-4-yl)picolinonitrile hydrochloride as a white solid.

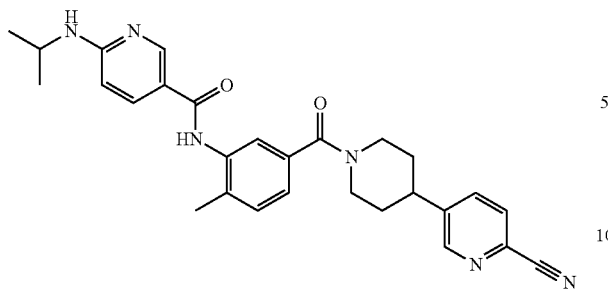

Compound 51. N-(5-(4-(6-Cyanopyridin-3-yl)piperidine-1-carbonyl)-2-methylphenyl)-6-(isopropylamino)nicotinamide The title compound was synthesized using readily available reagents and procedures similar to those described for compound 43 but using compound 51.5 in place of compound 11.2. m/z (ES+) 483 (M+H)+.

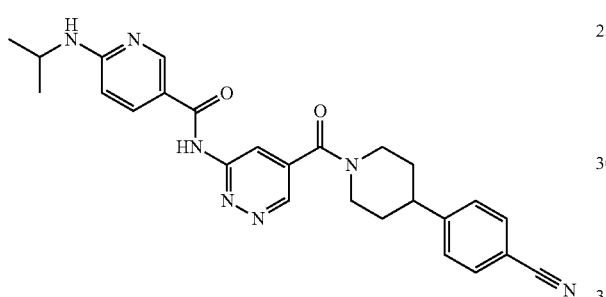

Compound 52. N-(5-(4-(4-Cyanophenyl)piperidine-1-carbonyl)pyridazin-3-yl)-6-(isopropylamino)nicotinamide The title compound was synthesized using readily available reagents and procedures similar to those described for compound 43. m/z (ES+) 470 (M+H)+.

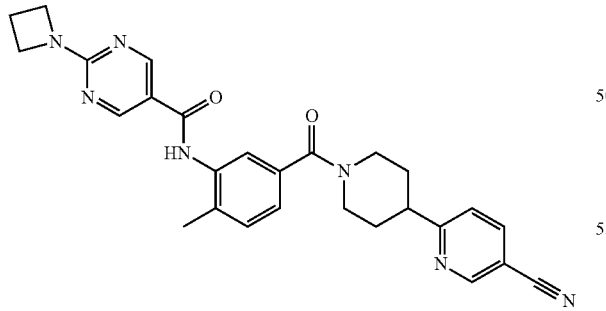

Compound 53. 2-(Azetidin-1-yl)-N-(5-(4-(5-cyanopyridin-2-yl)piperidine-1-carbonyl)-2-methylphenyl)pyrimidine-5-carboxamide The title compound was synthesized using readily available reagents and procedures similar to those described for compound 50. m/z (ES+) 482 (M+H)+.

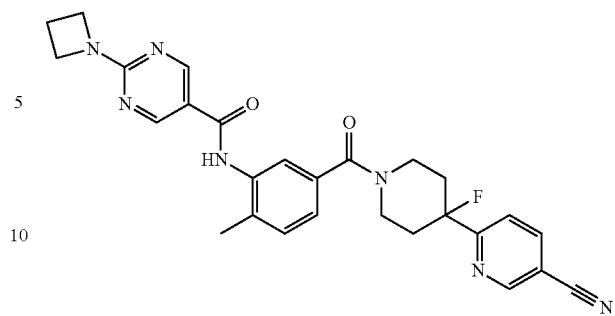

Compound 54. 2-(Azetidin-1-yl)-N-(5-(4-(5-cyanopyridin-2-yl)-4-fluoropiperidine-1-carbonyl)-2-methylphenyl)pyrimidine-5-carboxamide The title compound was synthesized using readily available reagents and procedures similar to those described for compound 47. m/z (ES+) 500 (M+H)+.

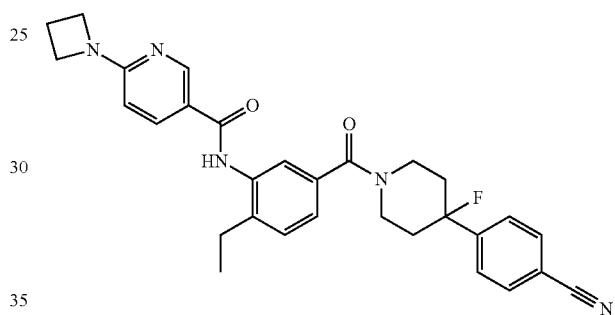

Compound 55. 6-(Azetidin-1-yl)-N-(5-(4-(4-cyanophenyl)-4-fluoropiperidine-1-carbonyl)-2-ethylphenyl)nicotinamide The title compound was synthesized using readily available reagents and procedures similar to those described for compound 43. m/z (ES+) 512 (M+H)+.

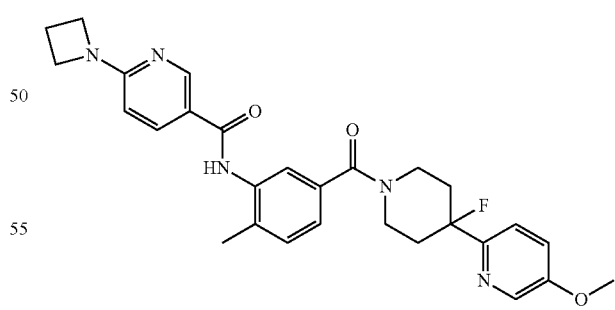

Compound 56. 6-(Azetidin-1-yl)-N-(5-(4-fluoro-4-(5-methoxypyridin-2-yl)piperidine-1-carbonyl)-2-methylphenyl)nicotinamide The title compound was synthesized using readily available reagents and procedures similar to those described for compound 43. m/z (ES+) 504 (M+H)+.

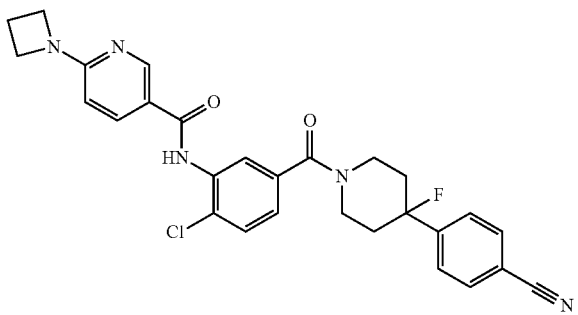 [SMILES: N#Cc1ccc(C2(F)CCN(C(=O)c3ccc(Cl)c(NC(=O)c4ccc(N5CCC5)nc4)c3)CC2)cc1]

Compound 57. 6-(Azetidin-1-yl)-N-(2-chloro-5-(4-(4-cyanophenyl)-4-fluoropiperidine-1-carbonyl)phenyl)nicotinamide The title compound was synthesized using readily available reagents and procedures similar to those described for compound 43. m/z (ES+) 518 (M+H)$^+$.

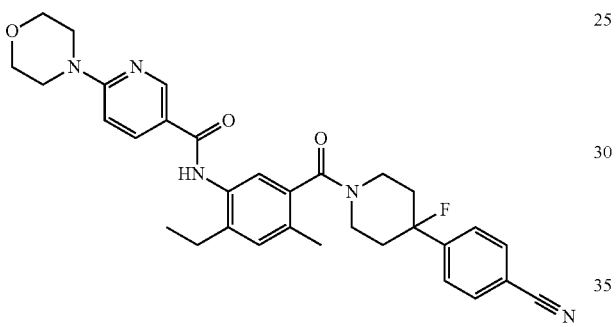

Compound 58. N-(5-(4-(4-Cyanophenyl)-4-fluoropiperidine-1-carbonyl)-2-ethyl-4-methylphenyl)-6-morpholinonicotinamide The title compound was synthesized using readily available reagents and procedures similar to those described for compound 43. m/z (ES+) 556 (M+H)$^+$.

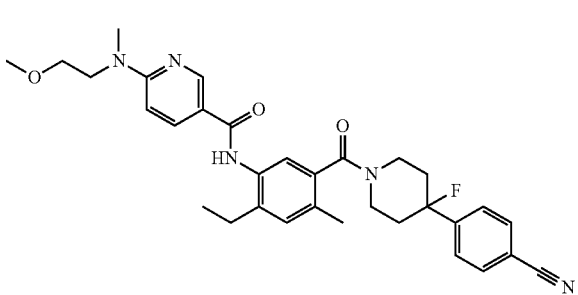 [SMILES: CCc1cc(C)c(C(=O)N2CCC(F)(c3ccc(C#N)cc3)CC2)cc1NC(=O)c1ccc(N(C)CCOC)nc1]

Compound 60. N-(5-(4-(4-Cyanophenyl)-4-fluoropiperidine-1-carbonyl)-2-ethyl-4-methylphenyl)-6-((2-methoxyethyl)(methyl)amino)nicotinamide The title compound was synthesized using readily available reagents and procedures similar to those described for compound 43. m/z (ES+) 558 (M+H)$^+$.

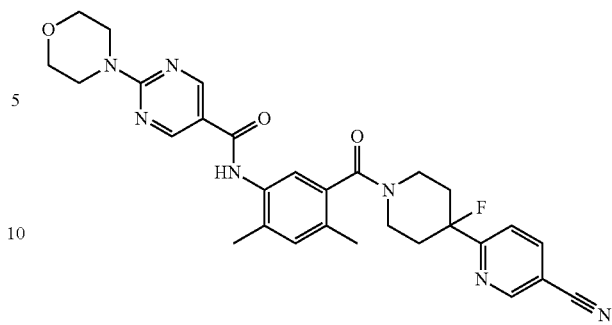

Compound 61. N-(5-(4-(5-Cyanopyridin-2-yl)-4-fluoropiperidine-1-carbonyl)-2,4-dimethylphenyl)-2-morpholinopyrimidine-5-carboxamide The title compound was synthesized using readily available reagents and procedures similar to those described for compound 47. m/z (ES+) 544 (M+H)$^+$.

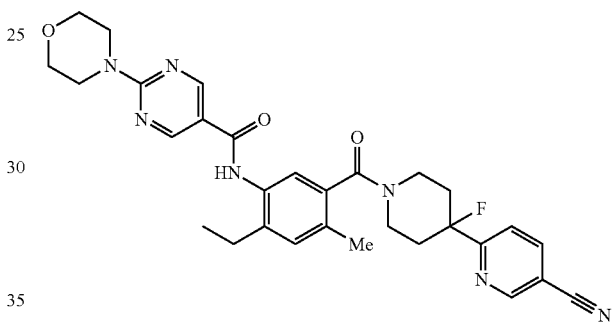

Compound 62. N-(5-(4-(5-Cyanopyridin-2-yl)-4-fluoropiperidine-1-carbonyl)-2-ethyl-4-methylphenyl)-2-morpholinopyrimidine-5-carboxamide The title compound was synthesized using readily available reagents and procedures similar to those described for compound 47. m/z (ES+) 558 (M+H)$^+$.

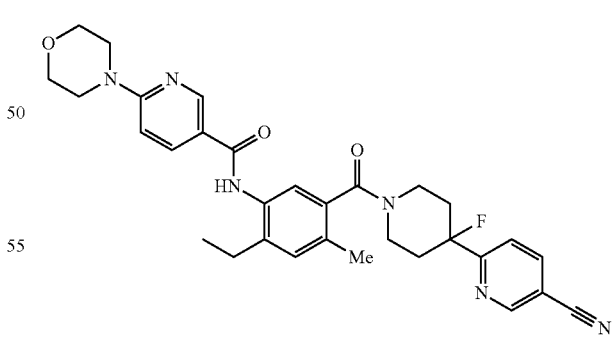

Compound 63. N-(5-(4-(5-Cyanopyridin-2-yl)-4-fluoropiperidine-1-carbonyl)-2-ethyl-4-methylphenyl)-6-morpholinonicotinamide The title compound was synthesized using readily available reagents and procedures similar to those described for compound 47. m/z (ES+) 557 (M+H)$^+$.

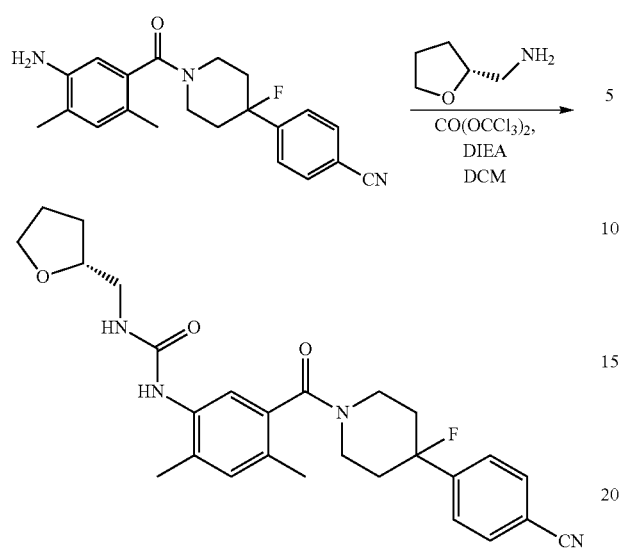

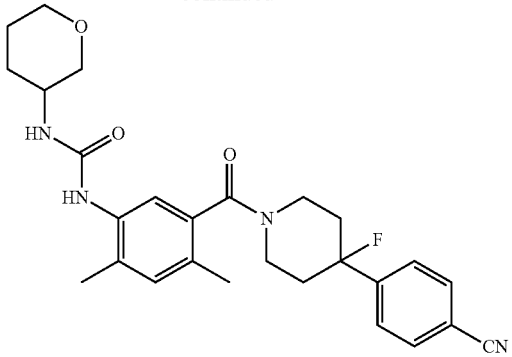 [SMILES: CCc1cc(C)c(NC(=O)NC2CCCOC2)cc1C(=O)N1CCC(F)(c2ccc(C#N)cc2)CC1]

Compound 64. (R)-1-(5-(4-(4-Cyanophenyl)-4-fluoropiperidine-1-carbonyl)-2,4-dimethylphenyl)-3-((tetrahydrofuran-2-yl)methyl)urea A mixture of 4-(1-(5-amino-2,4-dimethylbenzoyl)-4-fluoropiperidin-4-yl)benzonitrile (compound 42.2, 150 mg, 0.43 mmol, 1.00 equiv), DIEA (560 mg, 4.33 mmol, 10.15 equiv), and CO(OCCl3)2 (160 mg, 0.54 mmol, 1.26 equiv) in DCM (50 mL) was stirred under nitrogen at room temperature. After 0.5 h, (R)-(tetrahydrofuran-2-yl)methanamine (52 mg, 0.51 mmol, 1.20 equiv) was added. After stirring for 2 h at room temperature, the mixture was washed with 2×50 mL of water and 1×50 mL of brine. The organic phase was concentrated under reduced pressure and the residue (~200 mg) was purified by prep-HPLC with the following conditions (1#-Pre-HPLC-006(Waters)): Column, SunFire Prep C18, 19*150 mm 5 um; mobile phase, WATER WITH 0.05% TFA and CH3CN (hold 5.0% CH3CN in 2 min, up to 35.0% in 1 min, up to 65.0% in 12 min, up to 100.0% in 1 min); Detector, UV 254/220 nm. The fractions containing pure compound were combined and lyophilized to yield 110 mg (54%) of the title compound as a light yellow solid. m/z (ES+) 479 (M+H)+. $^1$H NMR (300 MHz, DMSO, ppm): δ 7.91 (d, J=8.1 Hz, 2H), 7.77-7.69 (m, 4H), 7.04 (s, 1H), 6.68 (s, 1H), 4.64 (m, 1H), 3.89-3.82 (m, 2H), 3.71 (m, 1H), 3.33-3.23 (m, 3H), 3.11-3.09 (m, 2H), 2.18-2.03 (m, 8H), 1.97-1.84 (m, 4H), 1.57 (m, 1H).

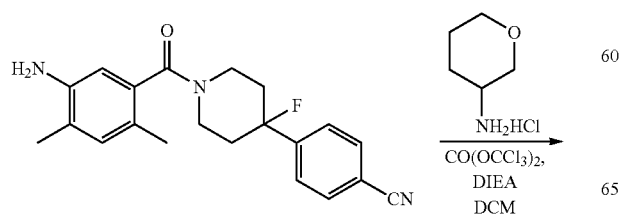

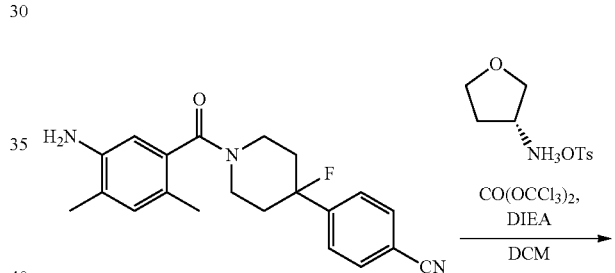

Compound 65. 1-(5-(4-(4-Cyanophenyl)-4-fluoropiperidine-1-carbonyl)-2,4-dimethylphenyl)-3-(tetrahydro-2H-pyran-3-yl)urea The title compound was synthesized in a similar manner to that described for compound 64 to yield a yellow solid (111 mg, 53%). m/z (ES+) 479 (M+H)+ $^1$H NMR (300 MHz, CD3OD): δ 7.80 (d, J=8.1 Hz, 2H), 7.78-7.50 (m, 3H), 7.13 (s, 1H), 4.88-4.72 (m, 1H), 3.94-8.82 (m, 1H), 3.82-3.68 (m, 2H), 3.68-3.33 (m, 3H), 3.33-3.19 (m, 2H), 2.42-2.08 (m, 8H), 2.08-1.74 (m, 4H), 1.74-1.54 (m, 2H).

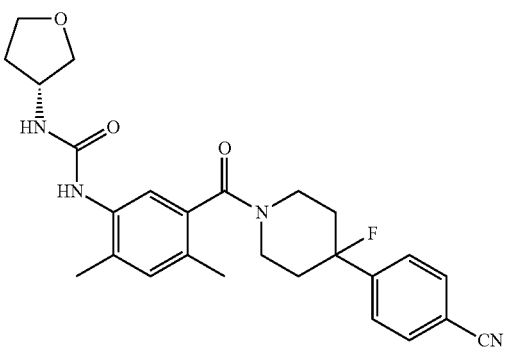

Compound 66. (R)-1-(5-(4-(4-Cyanophenyl)-4-fluoropiperidine-1-carbonyl)-2,4-dimethylphenyl)-3-(tetrahydrofuran-3-yl)urea The title compound was synthesized in a similar manner to that described for compound 64 to yield a light yellow solid (105 mg, 53%). m/z (ES+) 465 (M+H)+.

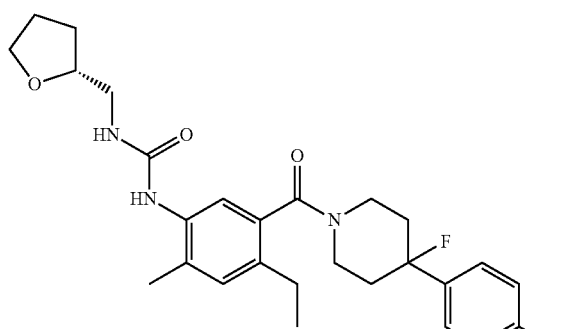

Compound 67. (R)-1-(5-(4-(4-Cyanophenyl)-4-fluoropiperidine-1-carbonyl)-4-ethyl-2-methylphenyl)-3-((tetrahydrofuran-2-yl)methyl)urea The title compound was synthesized in a similar manner to that described for compound 64 but using compound 48.5 in place of compound 42.2. m/z (ES+) 493 (M+H)$^+$.

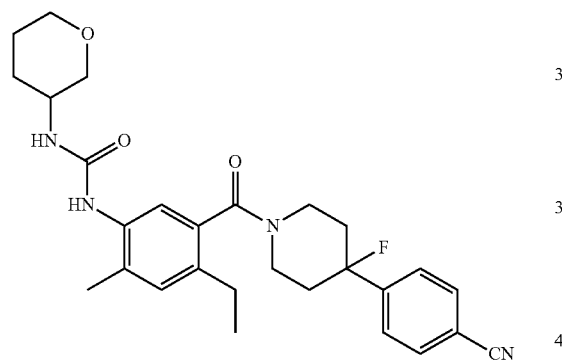

Compound 68. 1-(5-(4-(4-Cyanophenyl)-4-fluoropiperidine-1-carbonyl)-4-ethyl-2-methylphenyl)-3-(tetrahydro-2H-pyran-3-yl)urea The title compound was synthesized in a similar manner to that described for compound 64 but using compound 48.5 in place of compound 42.2. m/z (ES+) 493 (M+H)$^+$.

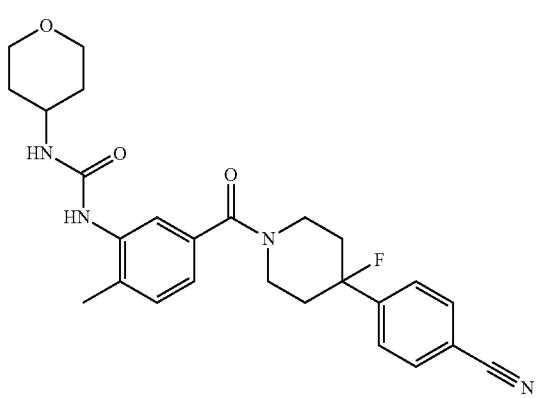 [SMILES: Cc1ccc(C(=O)N2CCC(F)(c3ccc(C#N)cc3)CC2)cc1NC(=O)NC1CCOCC1]

Compound 69. 1-(5-(4-(4-Cyanophenyl)-4-fluoropiperidine-1-carbonyl)-2-methylphenyl)-3-(tetrahydro-2H-pyran-4-yl)urea The title compound was synthesized using readily available reagents and procedures similar to those described for compound 64. m/z (ES+) 465 (M+H)$^+$.

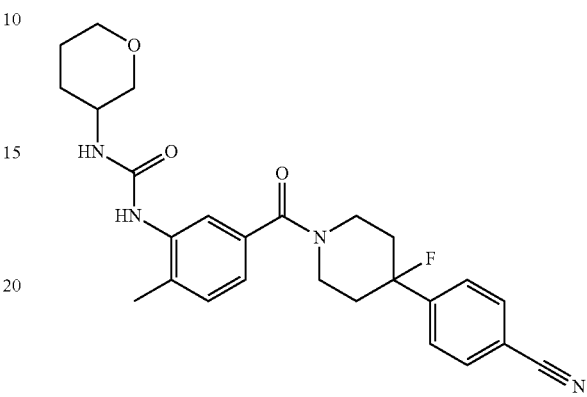

Compound 70. 1-(5-(4-(4-Cyanophenyl)-4-fluoropiperidine-1-carbonyl)-2-methylphenyl)-3-(tetrahydro-2H-pyran-3-yl)urea The title compound was synthesized using readily available reagents and procedures similar to those described for compound 64. m/z (ES+) 465 (M+H)$^+$.

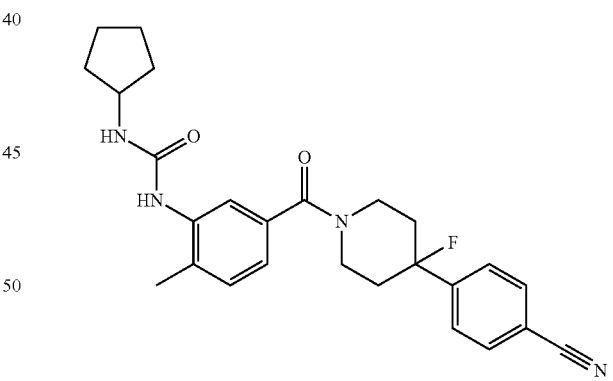

Compound 71. 1-(5-(4-(4-Cyanophenyl)-4-fluoropiperidine-1-carbonyl)-2-methylphenyl)-3-cyclopentylurea The title compound was synthesized using readily available reagents and procedures similar to those described for compound 64. m/z (ES+) 449 (M+H)$^+$.

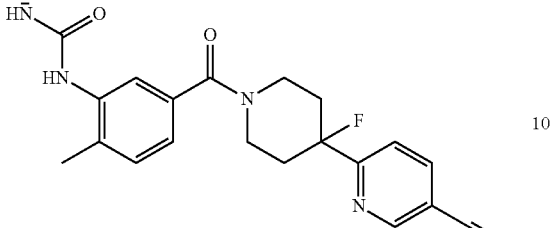

Compound 72. (R)-1-(5-(4-(5-Cyanopyridin-2-yl)-4-fluoropiperidine-1-carbonyl)-2-methylphenyl)-3-(tetrahydrofuran-3-yl)urea The title compound was synthesized using readily available reagents and procedures similar to those described for compound 64. m/z (ES+) 452 (M+H)+.

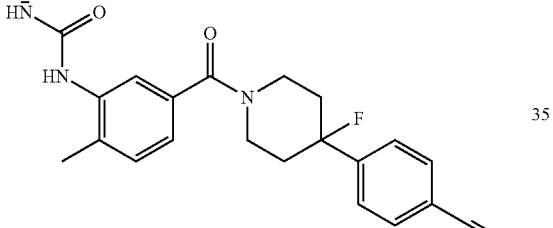

Compound 73. (R)-1-(5-(4-(4-Cyanophenyl)-4-fluoropiperidine-1-carbonyl)-2-methylphenyl)-3-(tetrahydrofuran-3-yl)urea The title compound was synthesized using readily available reagents and procedures similar to those described for compound 64. m/z (ES+) 451 (M+H)+.

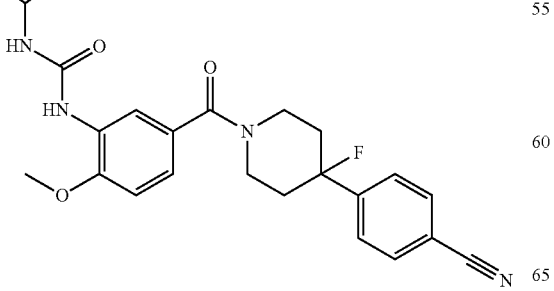

Compound 74. 1-(5-(4-(4-Cyanophenyl)-4-fluoropiperidine-1-carbonyl)-2-methoxyphenyl)-3-(tetrahydrofuran-3-yl)urea The title compound was synthesized using readily available reagents and procedures similar to those described for compound 64. m/z (ES+) 467 (M+H)+.

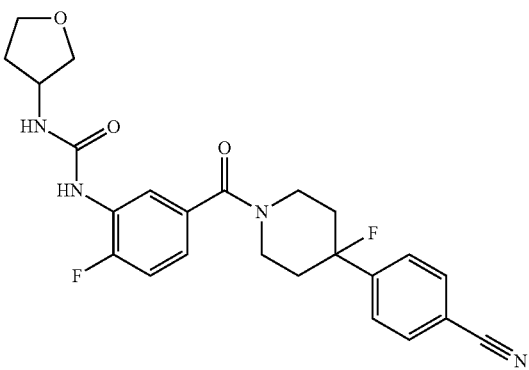

Compound 75. 1-(5-(4-(4-Cyanophenyl)-4-fluoropiperidine-1-carbonyl)-2-fluorophenyl)-3-(tetrahydrofuran-3-yl)urea The title compound was synthesized using readily available reagents and procedures similar to those described for compound 64, m/z (ES+) 455 (M+H)+.

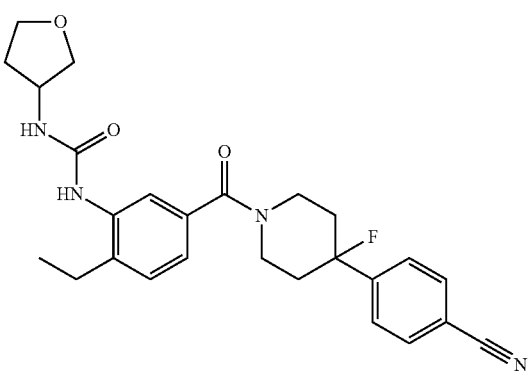

Compound 76. 1-(5-(4-(4-Cyanophenyl)-4-fluoropiperidine-1-carbonyl)-2-ethylphenyl)-3-(tetrahydrofuran-3-yl)urea The title compound was synthesized using readily available reagents and procedures similar to those described for compound 64. m/z (ES+) 465 (M+H)+.

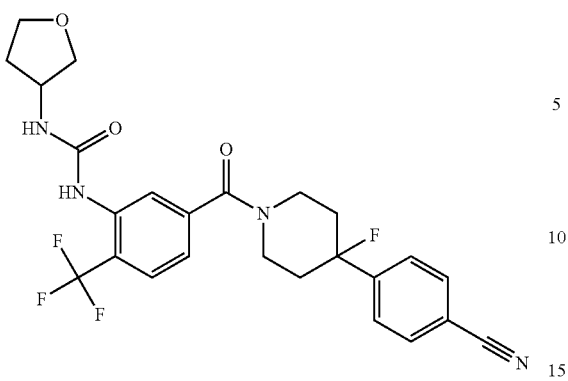

Compound 77. 1-(5-(4-(4-Cyanophenyl)-4-fluoropiperidine-1-carbonyl)-2-(trifluoromethyl)phenyl)-3-(tetrahydrofuran-3-yl)urea The title compound was synthesized using readily available reagents and procedures similar to those described for compound 64. m/z (ES+) 505 (M+H)+.

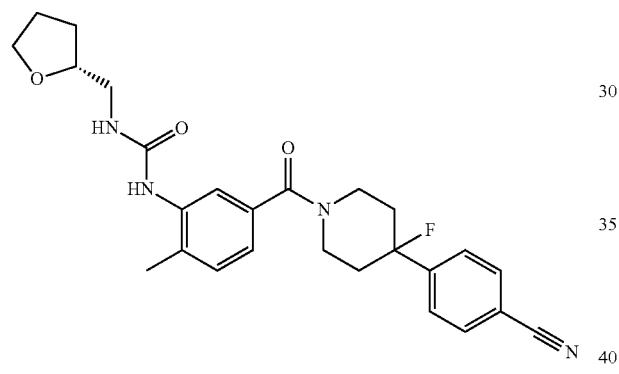

Compound 78. (R)-1-(5-(4-(4-Cyanophenyl)-4-fluoropiperidine-1-carbonyl)-2-methylphenyl)-3-((tetrahydrofuran-2-yl)methyl)urea The title compound was synthesized using readily available reagents and procedures similar to those described for compound 64. m/z (ES+) 465 (M+H)+.

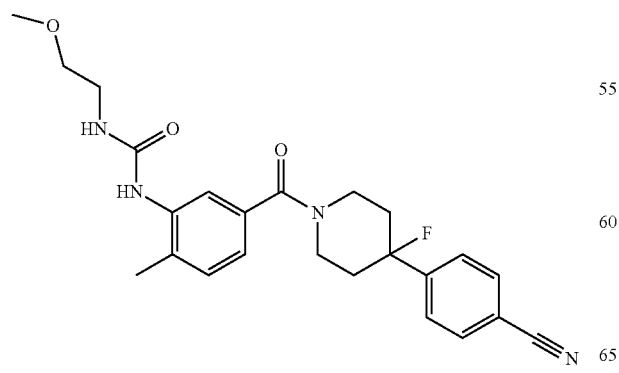

Compound 79. 1-(5-(4-(4-Cyanophenyl)-4-fluoropiperidine-1-carbonyl)-2-methylphenyl)-3-(2-methoxyethyl)urea The title compound was synthesized using readily available reagents and procedures similar to those described for compound 64. m/z (ES+) 439 (M+H)+.

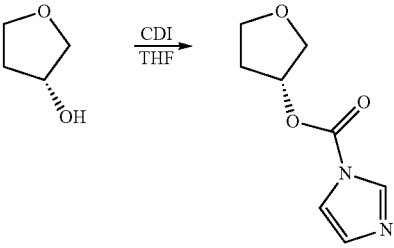

Compound 80.1. (R)-Tetrahydrofuran-3-yl 1H-imidazole-1-carboxylate

A solution of (R)-tetrahydrofuran-3-ol (500 mg, 5.68 mmol, 1.00 equiv) and CDI (2 g, 12.33 mmol, 2.17 equiv) in tetrahydrofuran (50 mL) was stirred overnight under nitrogen at 60° C. After cooling to room temperature, the mixture was concentrated under reduced pressure. The residue was dissolved in 30 mL of DCM and washed with 1×50 mL of H₂O. The organic layer was dried (Na₂SO₄) and concentrated under reduced pressure. The crude residue was purified using silica gel column chromatography with ethyl acetate/petroleum ether (1:1) to yield 0.95 g (92%) of the title compound as a white solid.

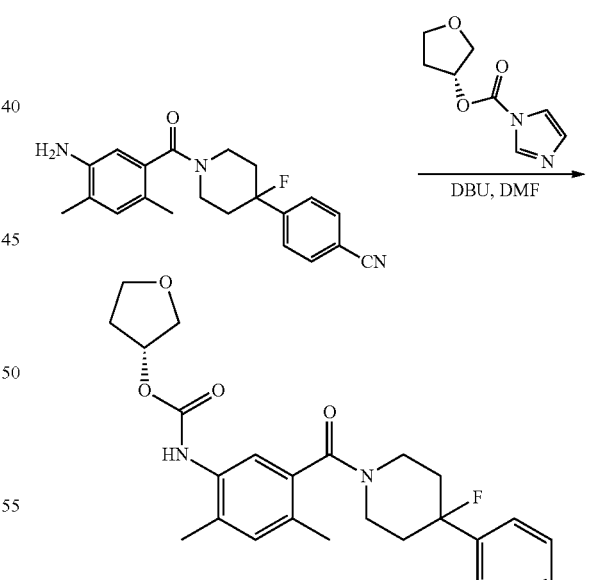

Compound 80. (R)-Tetrahydrofuran-3-yl (5-(4-(4-cyanophenyl)-4-fluoropiperidine-1-carbonyl)-2,4-dimethylphenyl)carbamate A mixture of compound 42.2 (200 mg, 0.57 mmol, 1.00 equiv), (R)-tetrahydrofuran-3-yl 1H-imidazole-1-carboxylate (80.1, 124 mg, 0.68 mmol, 1.20 equiv), and DBU (2.6 mg, 0.02 mmol. 0.03 equiv) in DMF (50 mL) was stirred for 16 h under nitrogen at 120° C. After cooling to ambient temperature, the reaction was quenched by the addition of 200 mL of water. The resulting mixture was extracted with 3×100 mL of ethyl acetate. The combined organic layers were washed with 1×100 mL of brine, dried over anhydrous sodium sulfate, and concentrated under reduced pressure. The residue (200 mg) was purified by Prep-HPLC with the following conditions (1#-Pre-HPLC-002(Agilent)): Column, SunFire Prep C18, 19*150 mm 5 um; mobile phase, WATER WITH 0.05% TFA and CH$_3$CN (40.0% CH$_3$CN up to 45.0% in 8 min, hold 45.0% in 2 min, up to 100.0% in 1 min, down to 40.0% in 2 min); Detector, uv 220 254 nm. 47.4 mg product was obtained. The fractions containing pure compound were combined and lyophilized to yield 47.4 mg (18%) of the title compound as a white solid. m/z (ES+) 466 (M+H)$^+$.

Compound 81. 1-Acetylpyrrolidin-3-yl(5-(4-(4-cyanophenyl)-4-fluoropiperidine-1-carbonyl)-2,4-dimethylphenyl)carbamate The title compound was synthesized in a similar manner to that described for compound 80 to yield a white solid (113 mg, 39%). m/z (ES+) 507 (M+H)$^+$. $^1$H NMR (300 MHz, CD$_3$OD): δ 7.80 (d, J=8.1 Hz, 2H), 7.77-7.61 (m, 2H), 7.52 & 7.33 (2 br singlets, amide rotamers, Ar—H, 1H), 7.17 (s, 1H), 5.41-5.28 (m, 1H), 4.87-4.72 (m, 1H), 3.88-3.42 (m, 6H), 3.33-3.19 (m, 1H), 2.42-1.82 (m, 15H).

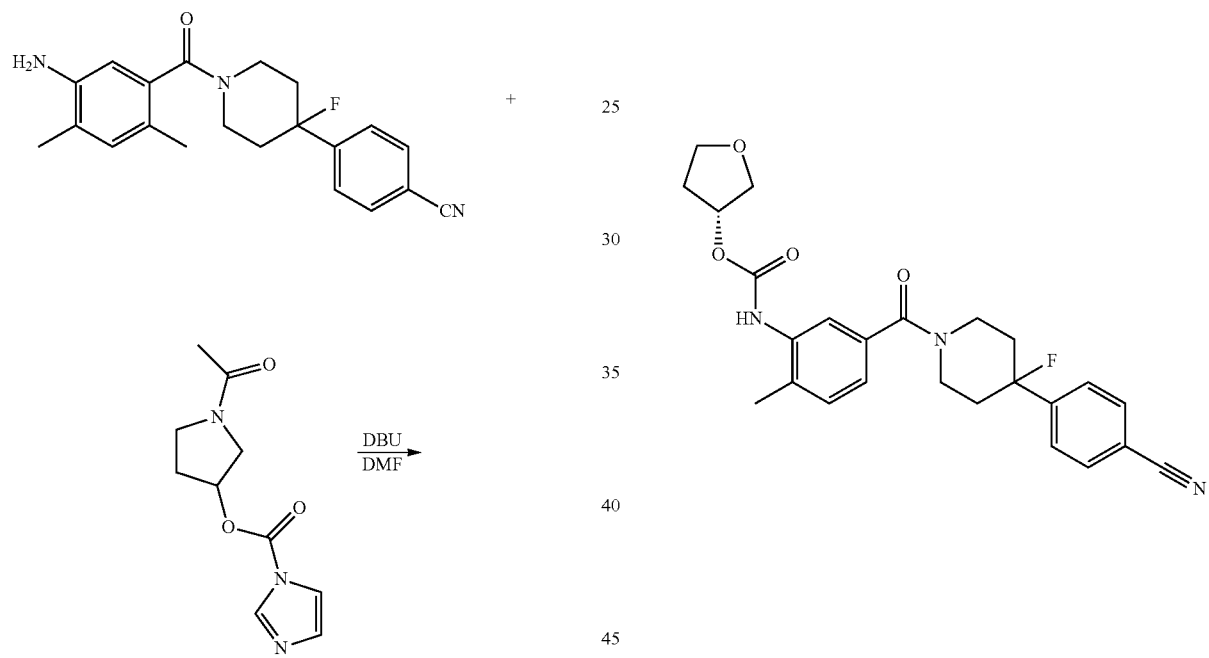

Compound 82. (R)-Tetrahydrofuran-3-yl(5-(4-(4-cyanophenyl)-4-fluoropiperidine-1-carbonyl)-2-methylphenyl)carbamate The title compound was synthesized using readily available reagents and procedures similar to those described for compound 80. m/z (ES+) 452 (M+H)$^+$.

The compounds in the following table were prepared using standard chemical manipulations, readily available starting materials, and procedures similar to those used for the preparation of compounds 1 and 2:

| Cmpnd # | Compound Name | Compound Structure | m/z (ES+) |
|---|---|---|---|
| 83 | 2-(5-(4-(4-cyanophenyl)piperidine-1-carbonyl)-2,4-dimethylphenyl)-N,N-dimethyl-6,7-dihydro-3H-imidazo[4,5-c]pyridine-5(4H)-carboxamide | 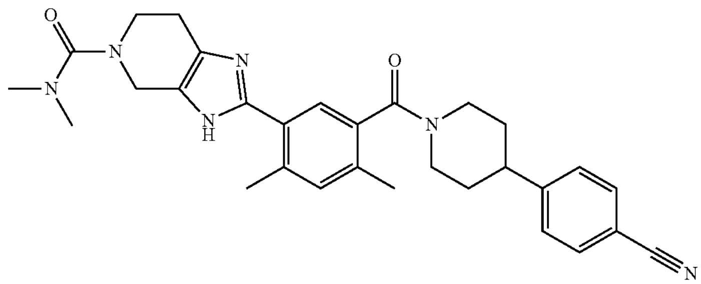 [SMILES: Cc1cc(C)c(-c2nc3c([nH]2)CN(C(=O)N(C)C)CC3)cc1C(=O)N1CCC(c2ccc(C#N)cc2)CC1] | 511 (M + H)+ |
| 84 | 4-(1-(2,4-dimethyl-5-(3,4,6,7-tetrahydropyrano[3,4-d]imidazol-2-yl)benzoyl)piperidin-4-yl)-N,N-dimethylbenzamide | 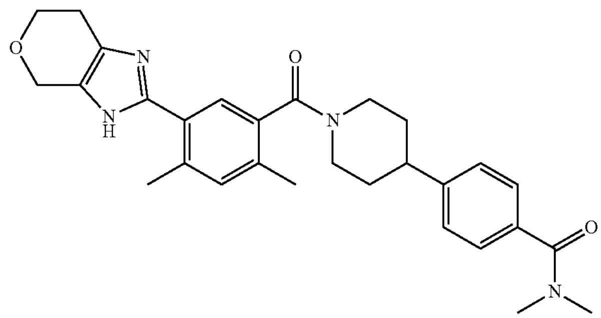 [SMILES: Cc1cc(C)c(-c2nc3c([nH]2)COCC3)cc1C(=O)N1CCC(c2ccc(C(=O)N(C)C)cc2)CC1] | 487 (M + H)+ |
| 85 | (2,4-dimethyl-5-(3,4,6,7-tetrahydropyrano[3,4-d]imidazol-2-yl)phenyl)(4-(4-fluorophenyl)piperidin-1-yl)methanone | 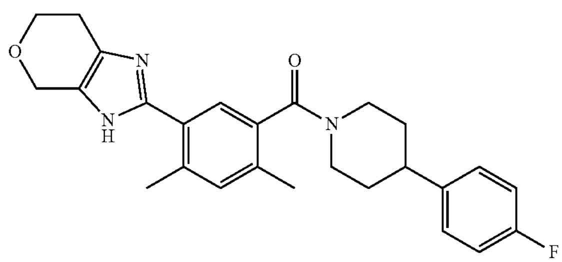 [SMILES: Cc1cc(C)c(-c2nc3c([nH]2)COCC3)cc1C(=O)N1CCC(c2ccc(F)cc2)CC1] | 434 (M + H)+ |
| 86 | (2,4-dimethyl-5-(3,4,6,7-tetrahydropyrano[3,4-d]imidazol-2-yl)phenyl)(4-(4-(methylsulfonyl)phenyl)piperidin-1-yl)methanone | 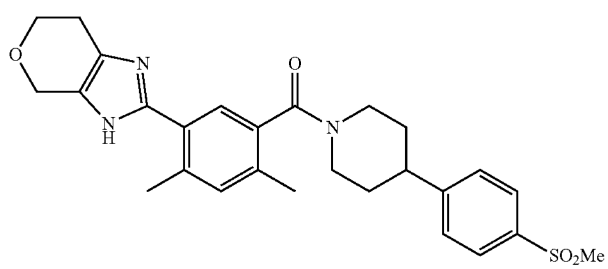 [SMILES: Cc1cc(C)c(-c2nc3c([nH]2)COCC3)cc1C(=O)N1CCC(c2ccc(S(C)(=O)=O)cc2)CC1] | 494 (M + H)+ |
| 87 | (2,4-dimethyl-5-(3,4,6,7-tetrahydropyrano[3,4-d]imidazol-2-yl)phenyl)(4-(4-methoxyphenyl)piperidin-1-yl)methanone | 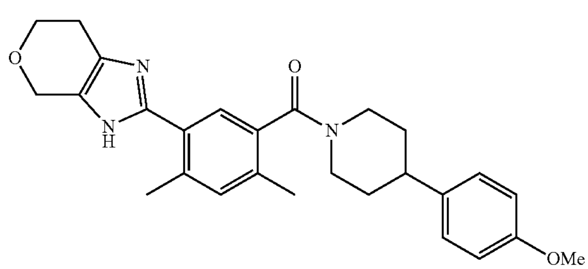 [SMILES: COc1ccc(C2CCN(C(=O)c3cc(-c4nc5c([nH]4)COCC5)c(C)cc3C)CC2)cc1] | 446 (M + H)+ |

-continued

| Cmpnd # | Compound Name | Compound Structure | m/z (ES+) |
|---|---|---|---|
| 88 | 1-(2-(2,4-dimethyl-5-(4-(4-(trifluoromethyl)phenyl)piperidine-1-carbonyl)phenyl)-6,7-dihydro-3H-imidazo[4,5-c]pyridin-5(4H)-yl)ethanone | 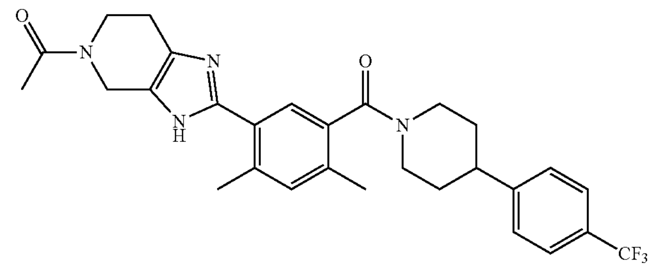 [SMILES: CC(=O)N1CCc2nc(-c3cc(C(=O)N4CCC(c5ccc(C(F)(F)F)cc5)CC4)c(C)cc3C)[nH]c2C1] | 525 (M + H)+ |
| 89 | 4-(1-(5-(5-(cyclopropanecarbonyl)-4,5,6,7-tetrahydro-3H-imidazo[4,5-c]pyridin-2-yl)-2,4-dimethylbenzoyl)piperidin-4-yl)benzonitrile | 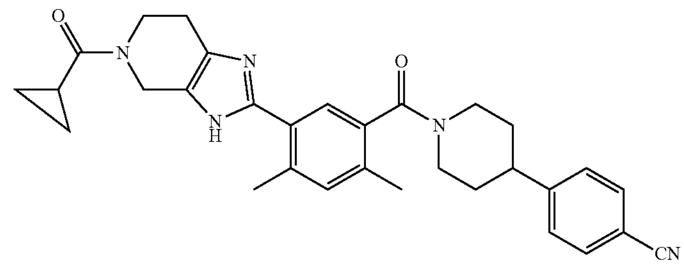 [SMILES: Cc1cc(C)c(-c2nc3c([nH]2)CN(C(=O)C2CC2)CC3)cc1C(=O)N1CCC(c2ccc(C#N)cc2)CC1] | 508 (M + H)+ |
| 90 | 1-(2-(5-(4-(4-fluorophenyl)piperidin-1-carbonyl)-2,4-dimethylphenyl)-6,7-dihydro-3H-imidazo[4,5-c]pyridin-5(4H)-yl)ethanone | 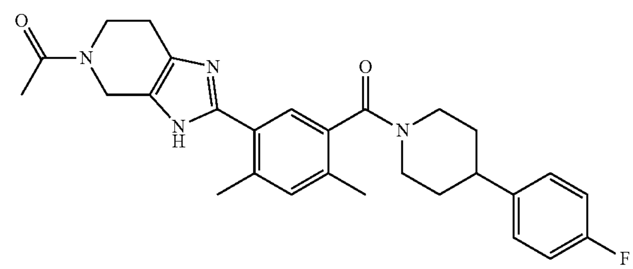 [SMILES: CC(=O)N1CCc2nc(-c3cc(C(=O)N4CCC(c5ccc(F)cc5)CC4)c(C)cc3C)[nH]c2C1] | 475 (M + H)+ |
| 91 | 4-(1-(4-methoxy-2-methyl-5-(3,4,6,7-tetrahydropyrano[3,4-d]imidazol-2-yl)benzoyl)piperidin-4-yl)benzonitrile | 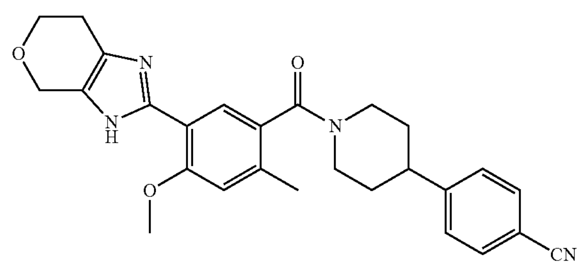 [SMILES: COc1cc(C)c(C(=O)N2CCC(c3ccc(C#N)cc3)CC2)cc1-c1nc2c([nH]1)COCC2] | 457 (M + H)+ |
| 92 | (4-(4-fluorophenyl)piperidin-1-yl)(5-(5-(isopropylsulfonyl)-4,5,6,7-tetrahydro-3H-imidazo[4,5-c]pyridin-2-yl)-2,4-dimethylphenyl)methanone | 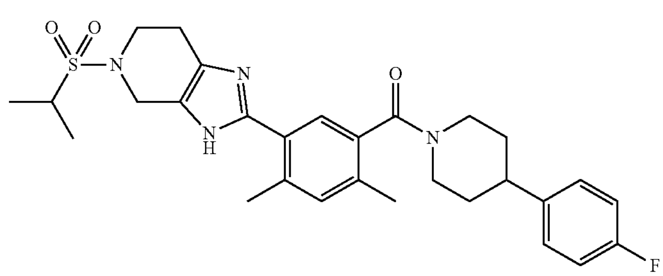 [SMILES: Cc1cc(C)c(-c2nc3c([nH]2)CN(S(=O)(=O)C(C)C)CC3)cc1C(=O)N1CCC(c2ccc(F)cc2)CC1] | 539 (M + H)+ |

-continued

| Cmpnd # | Compound Name | Compound Structure | m/z (ES+) |
|---|---|---|---|
| 93 | 1-(2-(5-(4-(4-fluorophenyl)piperidine-1-carbonyl)-2,4-dimethylphenyl)-6,7-dihydro-3H-imidazo[4,5-c]pyridin-5(4H)-yl)-2-methylpropan-1-one | 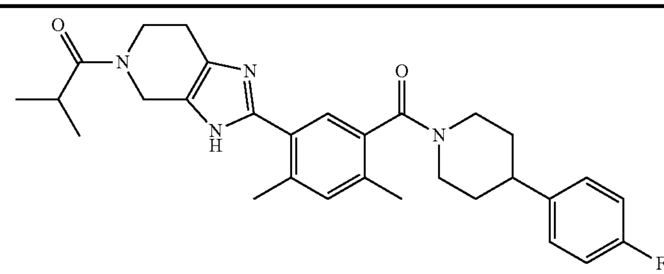 | 503 (M + H)+ |
| 94 | (2,4-dimethyl-5-(3,4,6,7-tetrahydropyrano[3,4-d]imidazol-2-yl)phenyl)(4-phenylpiperidin-1-yl)methanone | 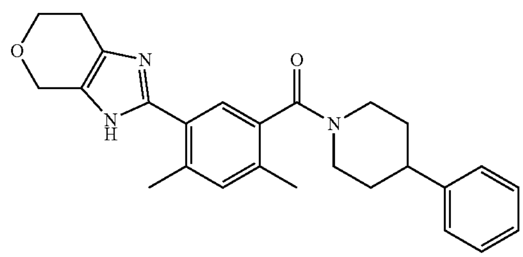 [SMILES: Cc1cc(C)c(-c2nc3c([nH]2)COCC3)cc1C(=O)N1CCC(c2ccccc2)CC1] | 416 (M + H)+ |
| 95 | methyl 2-(5-(4-(4-cyanophenyl)piperidin-1-carbonyl)-2,4-dimethylphenyl)-6,7-dihydro-3H-imidazo[4,5-c]pyridin-5(4H)-carboxylate | 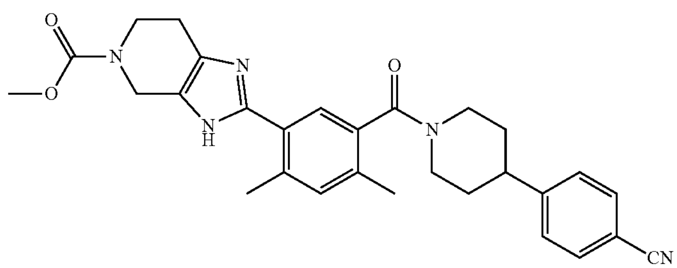 [SMILES: COC(=O)N1CCc2nc(-c3cc(C(=O)N4CCC(c5ccc(C#N)cc5)CC4)c(C)cc3C)[nH]c2C1] | 498 (M + H)+ |
| 96 | 4-(1-(2,4-dimethyl-5-(5-propionyl-4,5,6,7-tetrahydro-3H-imidazo[4,5-c]pyridin-2-yl)benzoyl)piperidin-4-yl)benzonitrile | 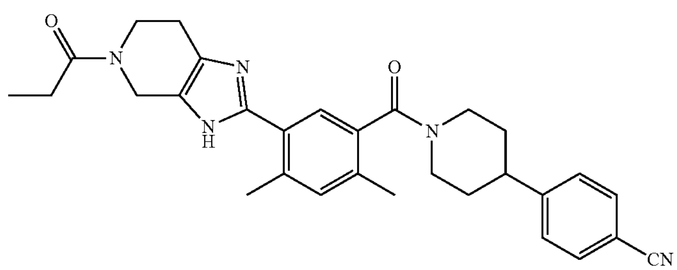 | 496 (M + H)+ |
| 97 | 4-(1-(5-(5-isobutyryl-4,5,6,7-tetrahydro-3H-imidazo[4,5-c]pyridin-2-yl)-2,4-dimethylbenzoyl)piperidin-4-yl)benzonitrile | 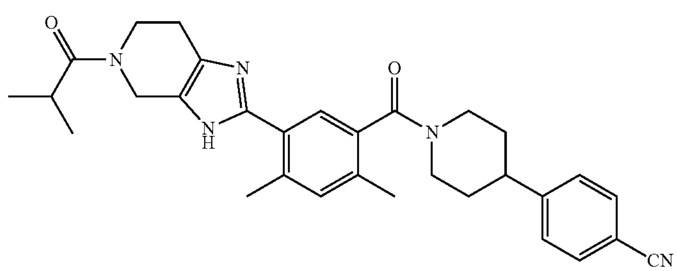 [SMILES: Cc1cc(C)c(-c2nc3c([nH]2)CN(C(=O)C(C)C)CC3)cc1C(=O)N1CCC(c2ccc(C#N)cc2)CC1] | 510 (M + H)+ |
| 98 | (2,4-dimethyl-5-(3,4,6,7-tetrahydropyrano[3,4-d]imidazol-2-yl)phenyl)(4-(p-tolyl)piperidin-1-yl)methanone | 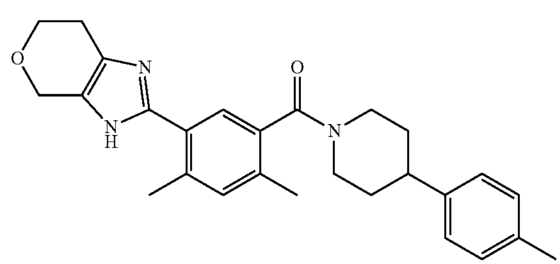 [SMILES: Cc1ccc(C2CCN(C(=O)c3cc(-c4nc5c([nH]4)COCC5)c(C)cc3C)CC2)cc1] | 430 (M + H)+ |

-continued

| Cmpnd # | Compound Name | Compound Structure | m/z (ES+) |
|---|---|---|---|
| 99 | 4-(1-(2,4-dimethyl-5-(4,5,6,7-tetrahydro-1H-benzo[d]imidazol-2-yl)benzoyl)piperidin-4-yl)benzonitrile | 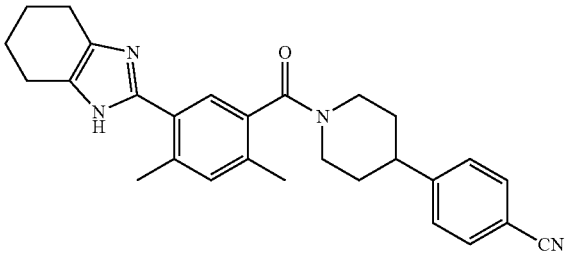 [SMILES: Cc1cc(C)c(-c2nc3c([nH]2)CCCC3)cc1C(=O)N1CCC(c2ccc(C#N)cc2)CC1] | 439 (M + H)+ |
| 100 | 4-(1-(2,3-dimethyl-5-(3,4,6,7-tetrahydropyrano[3,4-d]imidazol-2-yl)benzoyl)piperidin-4-yl)benzonitrile | 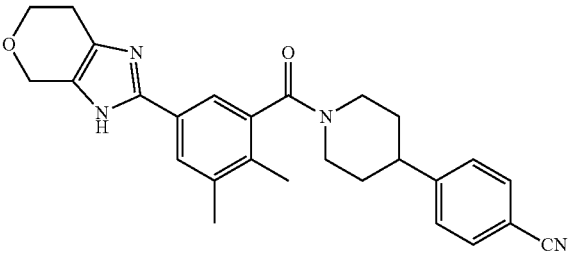 [SMILES: Cc1cc(-c2nc3c([nH]2)COCC3)cc(C(=O)N2CCC(c3ccc(C#N)cc3)CC2)c1C] | 441 (M + H)+ |
| 101 | 4-(1-(2-chloro-3-(3,4,6,7-tetrahydropyrano[3,4-d]imidazol-2-yl)benzoyl)piperidin-4-yl)benzonitrile | 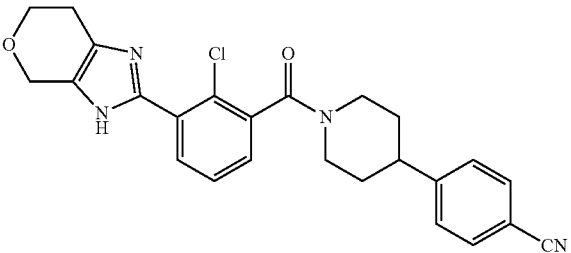 [SMILES: N#Cc1ccc(C2CCN(C(=O)c3cccc(-c4nc5c([nH]4)COCC5)c3Cl)CC2)cc1] | 447 (M + H)+ |
| 102 | 4-(1-(3-(5-isopropyl-4,5,6,7-tetrahydro-3H-imidazo[4,5-c]pyridin-2-yl)-4-methylbenzoyl)piperidin-4-yl)benzonitrile | 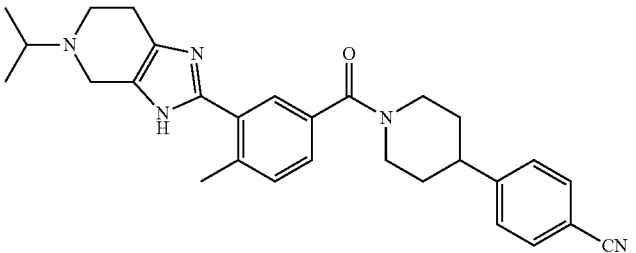 [SMILES: Cc1ccc(C(=O)N2CCC(c3ccc(C#N)cc3)CC2)cc1-c1nc2c([nH]1)CN(C(C)C)CC2] | 468 (M + H)+ |

| Cmpnd # | Compound Name | Compound Structure | m/z (ES+) |
|---|---|---|---|
| 103 | methyl 2-(5-(4-(4-cyanophenyl)piperidin-1-carbonyl)-2-methylphenyl)-6,7-dihydro-3H-imidazo[4,5-c]pyridine-5(4H)-carboxylate | 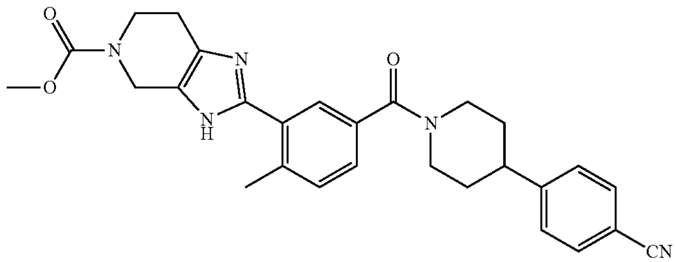 [SMILES: COC(=O)N1CCc2nc(-c3cc(C(=O)N4CCC(c5ccc(C#N)cc5)CC4)ccc3C)[nH]c2C1] | 484 (M + H)+ |
| 104 | (2,4-dimethyl-5-(5-methyl-4,5,6,7-tetrahydro-3H-imidazo[4,5-c]pyridin-2-yl)phenyl)(4-(4-(trifluoromethyl)phenyl)piperidin-1-yl)methanone | 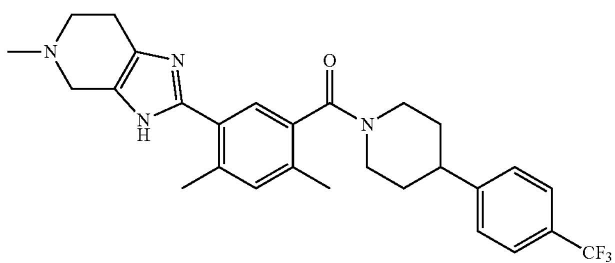 [SMILES: Cc1cc(C)c(-c2nc3c([nH]2)CN(C)CC3)cc1C(=O)N1CCC(c2ccc(C(F)(F)F)cc2)CC1] | 497 (M + H)+ |

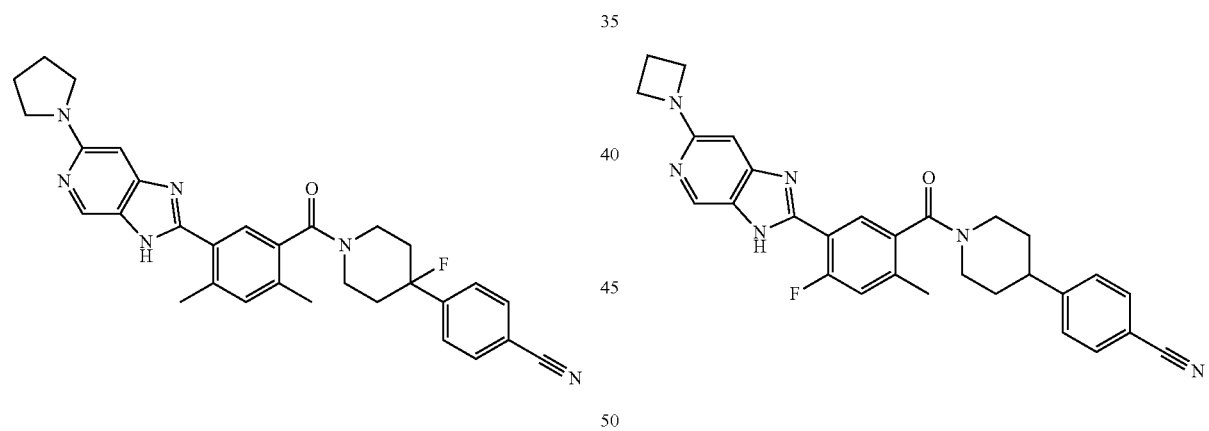

Compound 105. 4-(1-(2,4-Dimethyl-5-(6-(pyrrolidin-1-yl)-3H-imidazo[4,5-c]pyridin-2-yl)benzoyl)-4-fluoropiperidin-4-yl)benzonitrile The title compound was prepared using standard chemical manipulations and procedures similar to those used for the preparation of compound 20, except compound 11.2 HCl salt was used in place of compound 1.5. m/z (ES+) 523 (M+H)+.

Compound 106. 4-(1-(5-(6-(Azetidin-1-yl)-3H-imidazo[4,5-c]pyridin-2-yl)-4-fluoro-2-methylbenzoyl)piperidin-4-yl)benzonitrile The title compound was prepared using standard chemical manipulations and procedures similar to those used for the preparation of compound 20, except 4-fluoro-2-methylbenzoic acid and azetidine were used in place of 2,4-dimethylbenzoic acid and pyrrolidine respectively. m/z (ES+) 495 (M+H)+.

The compounds in the following table were prepared using standard chemical manipulations, readily available starting materials, and procedures similar to those used for the preparation of compound 20:

| Cmpnd # | Compound Name | Compound Structure | m/z (ES+) |
|---|---|---|---|
| 107 | 2-(5-(4-(4-cyanophenyl)piperidine-1-carbonyl)-2,4-dimethylphenyl)-1H-benzo[d]imidazole-5-carboxylic acid | 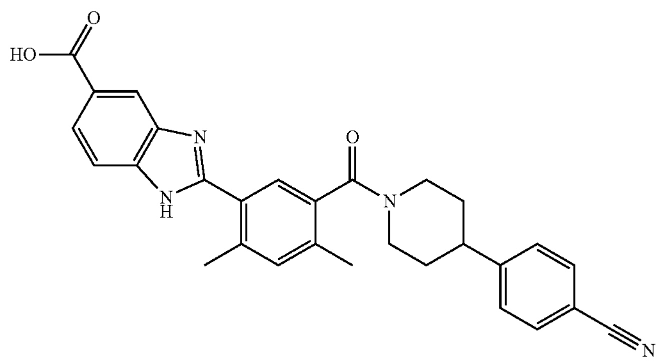 [SMILES: Cc1cc(C)c(-c2nc3cc(C(=O)O)ccc3[nH]2)cc1C(=O)N1CCC(c2ccc(C#N)cc2)CC1] | 479 (M + H)+ |
| 108 | 4-(1-(5-(3H-imidazo[4,5-c]pyridin-2-yl)-2,4-dimethylbenzoyl)piperidin-4-yl)benzonitrile | 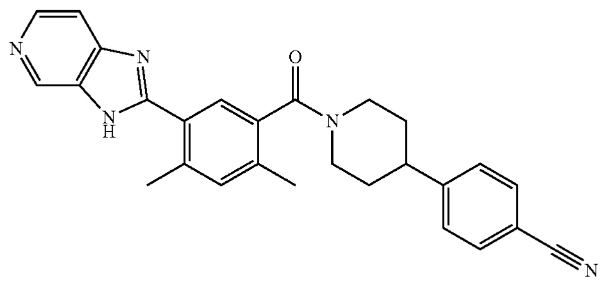 [SMILES: Cc1cc(C)c(-c2nc3ccncc3[nH]2)cc1C(=O)N1CCC(c2ccc(C#N)cc2)CC1] | 436 (M + H)+ |
| 109 | 2-(5-(4-(4-cyanophenyl)piperidine-1-carbonyl)-2,4-dimethylphenyl)-N,N-dimethyl-1H-benzo[d]imidazole-5-carboxamide | 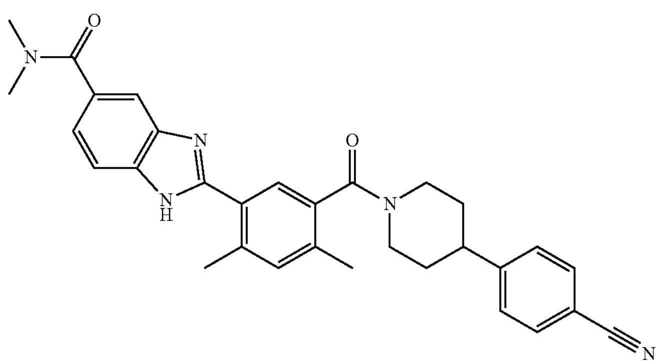 [SMILES: Cc1cc(C)c(-c2nc3cc(C(=O)N(C)C)ccc3[nH]2)cc1C(=O)N1CCC(c2ccc(C#N)cc2)CC1] | 506 (M + H)+ |
| 110 | 2-(5-(4-(4-cyanophenyl)piperidine-1-carbonyl)-2,4-dimethylphenyl)-1H-benzo[d]imidazole-5-carboxamide | 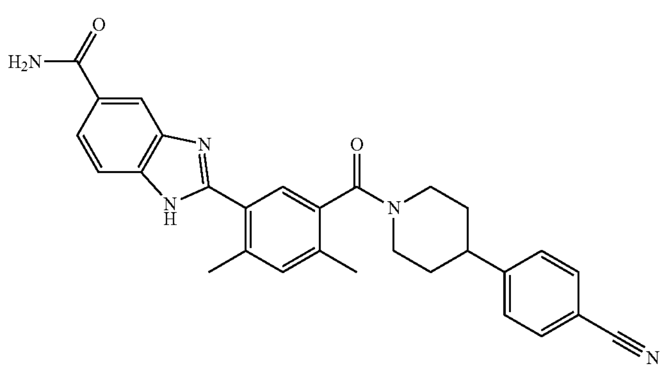 [SMILES: Cc1cc(C)c(-c2nc3cc(C(N)=O)ccc3[nH]2)cc1C(=O)N1CCC(c2ccc(C#N)cc2)CC1] | 478 (M + H)+ |

-continued

| Cmpnd # | Compound Name | Compound Structure | m/z (ES+) |
|---|---|---|---|
| 111 | 2-(5-(4-(4-cyanophenyl)piperidine-1-carbonyl)-2,4-dimethylphenyl)-1H-benzo[d]imidazole-5-carbonitrile | 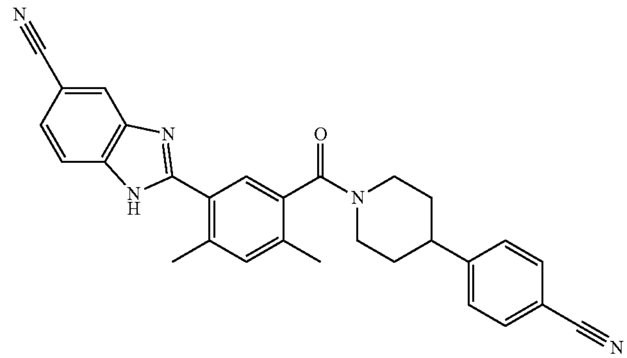 [SMILES: Cc1cc(C)c(-c2nc3cc(C#N)ccc3[nH]2)cc1C(=O)N1CCC(c2ccc(C#N)cc2)CC1] | 460 (M + H)+ |
| 112 | 4-(1-(2,4-dimethyl-5-(4-(oxetan-3-yl)-3H-imidazo[4,5-c]pyridin-2-yl)benzoyl)piperidin-4-yl)benzonitrile | 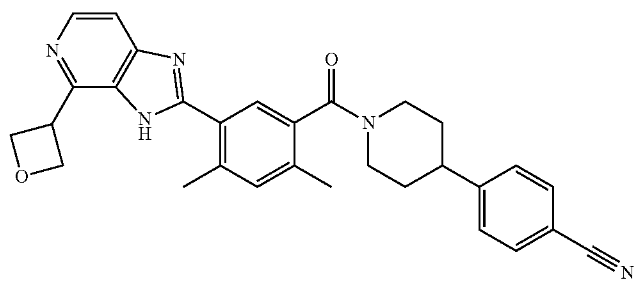 [SMILES: Cc1cc(C)c(-c2nc3ccnc(C4COC4)c3[nH]2)cc1C(=O)N1CCC(c2ccc(C#N)cc2)CC1] | 492 (M + H)+ |
| 113 | 4-(1-(5-(4-methoxy-3H-imidazo[4,5-c]pyridin-2-yl)-2,4-dimethylbenzoyl)piperidin-4-yl)benzonitrile | 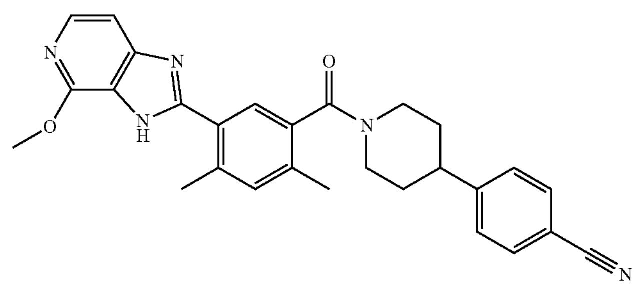 [SMILES: COc1nccc2nc(-c3cc(C(=O)N4CCC(c5ccc(C#N)cc5)CC4)c(C)cc3C)[nH]c12] | 466 (M + H)+ |
| 114 | 4-(1-(2,4-dimethyl-5-(4-oxo-4,5-dihydro-3H-imidazo[4,5-c]pyridin-2-yl)benzoyl)piperidin-4-yl)benzonitrile | 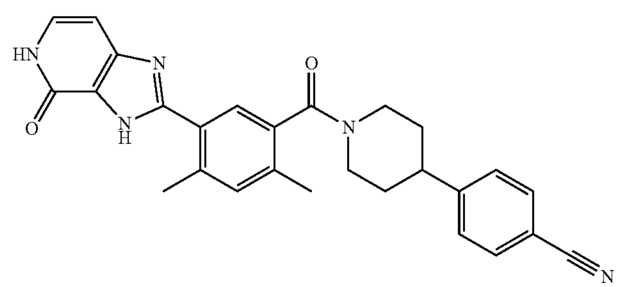 [SMILES: Cc1cc(C)c(-c2nc3cc[nH]c(=O)c3[nH]2)cc1C(=O)N1CCC(c2ccc(C#N)cc2)CC1] | 452 (M + H)+ |
| 115 | 4-(1-(5-(4-(azetidin-1-yl)-3H-imidazo[4,5-c]pyridin-2-yl)-2,4-dimethylbenzoyl)piperidin-4-yl)benzonitrile | 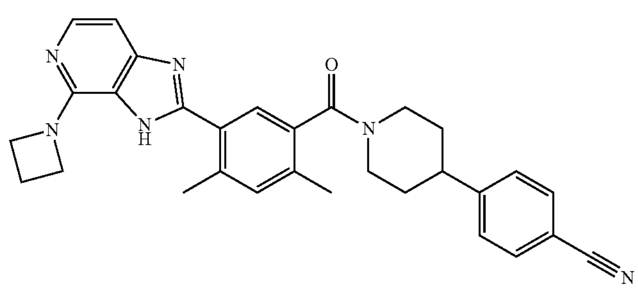 [SMILES: Cc1cc(C)c(-c2nc3ccnc(N4CCC4)c3[nH]2)cc1C(=O)N1CCC(c2ccc(C#N)cc2)CC1] | 491 (M + H)+ |

| Cmpnd # | Compound Name | Compound Structure | m/z (ES+) |
|---|---|---|---|
| 116 | 4-(1-(2,4-dimethyl-5-(6-(oxetan-3-yloxy)-3H-imidazo[4,5-c]pyridin-2-yl)benzoyl)piperidin-4-yl)benzonitrile | 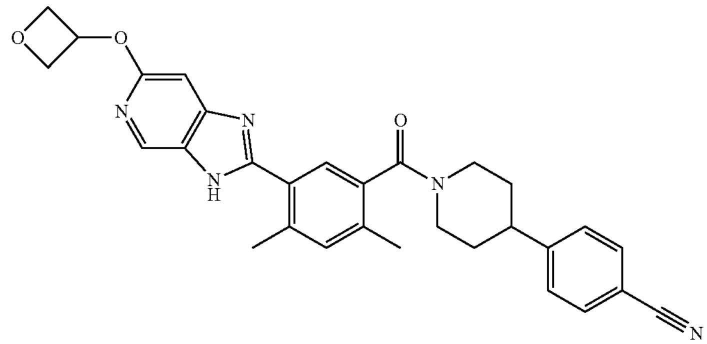 [SMILES: Cc1cc(C)c(-c2nc3cc(OC4COC4)ncc3[nH]2)cc1C(=O)N1CCC(c2ccc(C#N)cc2)CC1] | 508 (M + H)+ |
| 117 | 4-(1-(2,4-dimethyl-5-(4-(pyrrolidin-1-yl)-3H-imidazo[4,5-c]pyridin-2-yl)benzoyl)piperidin-4-yl)benzonitrile | 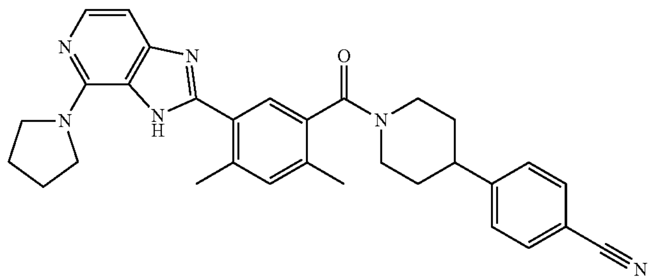 [SMILES: Cc1cc(C)c(-c2nc3ccnc(N4CCCC4)c3[nH]2)cc1C(=O)N1CCC(c2ccc(C#N)cc2)CC1] | 505 (M + H)+ |

Compound 118.1. Tetramethyl 2-(4-methoxyphenyl)propane-1,1,3,3-tetracarboxylate A mixture of (E)-N-(4-methoxybenzylidene)-4-methyl-benzenesulfonamide (2.89 g, 10 mmol), dimethyl malonate (3.43 mL, 30 mmol), BuOK (2.24 g, 20 mmol) in anhydrous t-BuOH (20 mL) was heated at 50° C. for 4 h. After cooling to room temperature, the reaction mixture was poured into saturated aqueous NH$_4$Cl and extracted with CH$_7$Cl$_2$ (3×). The combined organic layer was dried over MgSO$_4$, filtered, and then concentrated. The residue was purified by flash column chromatography with EtOAc in hexane (10%, 20%, 30%, then 40%) to give the title compound as a clear oil (3.255 g, 85% yield).

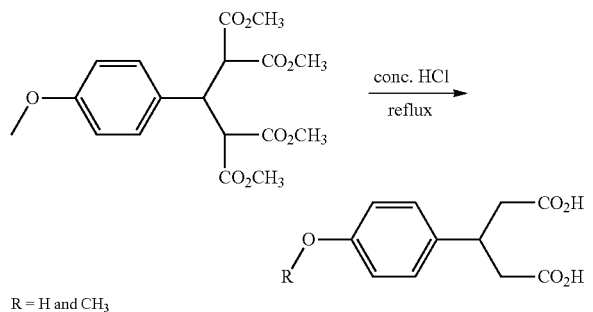

Compound 118.2. 3-(4-Methoxyphenyl)pentanedioic acid and 3-(4-hydroxyphenyl)pentanedioic acid A mixture of tetramethyl 2-(4-methoxyphenyl)propane-1,1,3,3-tetracarboxylate (compound 118.1, 6.0 g, 15.7 mmol) in concentrated HCl (37%, 80 mL) was heated under reflux overnight. After cooling to room temperature, the suspension was filtered. The filtrate was washed with water and dried under vacuum to give 2.66 g product as a mixture of 3-(4-methoxyphenyl)pentanedioic acid (major, LCMS observed [M–H]− 237) and 3-(4-hydroxyphenyl)pentanedioic acid (minor, LCMS observed [M–H]− 223).

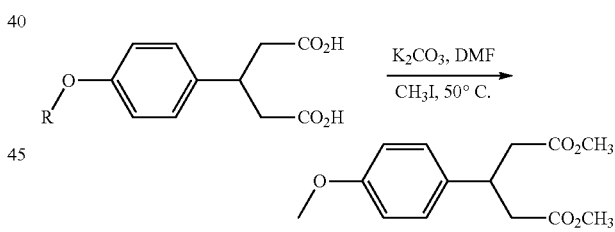

Compound 118.3. Dimethyl 3-(4-methoxyphenyl)pentanedioate

A mixture of the product (compound 118.2) obtained from the previous step (2.66 g), K$_2$CO$_3$ (6.56 g, 47.5 mmol) and CH$_3$I (3 mL, 47.5 mmol) in DMF (10 mL) was heated at 50° C. in a pressure tube overnight. After cooling to room temperature, the reaction mixture was poured into saturated aqueous NaHCO$_3$ and extracted with EtOAc (3×). The combined organic extract was dried over MgSO$_4$, filtered and concentrated. The residue was purified by flash column chromatography with EtOAc in hexane (20%, 30%, 40%, then 50%) to give the title compound as a clear oil (2.0 g, 48% yield over two steps).

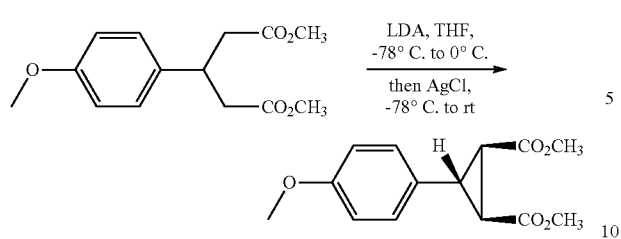

Compound 118.4. Dimethyl 3-(4-methoxyphenyl)cyclopropane-1,2-dicarboxylate

To a solution of LDA (18.8 mmol) in THF (60 mL) at −78° C. was added a solution of dimethyl 3-(4-methoxyphenyl)pentanedioate (2.0 g, 7.52 mmol) in THF (10 mL) dropwise. After stirring at −78° C. for 1 h, the dry ice-acetone bath was removed. The reaction mixture was stirred for 30 min before being cooled to −78° C. Solid AgCl (2.2 g, 15.4 mmol) was added all at once. The reaction mixture was stirred at −78° C. for 1 h and then room temperature overnight. Saturated aqueous $NH_4Cl$ was added. The mixture was vigorously stirred for 10 min. The suspension was filtered through celite. The filtrate was extracted with EtOAc (3×). The combined organic extract was dried over $MgSO_4$, filtered, and concentrated. The residue was purified by flash column chromatography with EtOAc in hexane (10%, 15%, 20%, then 30%) to give the title compound as a pale yellow solid (0.87 g, 44% yield). $^1$HNMR ($CDCl_3$, 400 Hz) δ 7.09 (d, J=8.8 Hz, 2H), 6.86 (d, J=8.8 Hz, 2H), 3.82 (s, 3H), 3.77 (s, 6H), 3.17 (t, J=7.6 Hz, 1H), 2.36 (d, J=7.6 Hz, 2H).

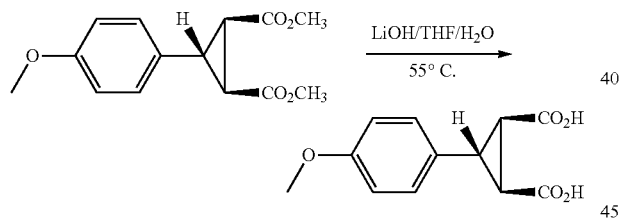

Compound 118.5. 3-(4-Methoxyphenyl)cyclopropane-1,2-dicarboxylic acid

A mixture of dimethyl 3-(4-methoxyphenyl)cyclopropane-1,2-dicarboxylate (0.88 g, 3.33 mmol) and LiOH (2M in $H_2O$, 10 mL) in THF (30 mL) was stirred at 55° C. overnight. After cooling to room temperature, the reaction mixture was poured into 1N HCl and extracted with EtOAc (3×). The combined organic extract was dried over $MgSO_4$, filtered, and concentrated to give the title compound as a light yellow solid.

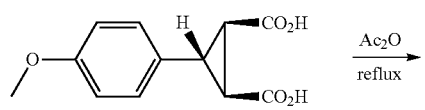

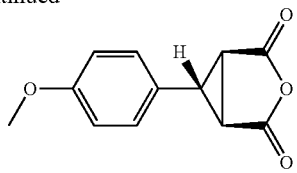

Compound 118.6. 6-(4-Methoxyphenyl)-3-oxabicyclo[3.1.0]hexane-2,4-dione

A mixture of 3-(4-methoxyphenyl)cyclopropane-1,2-dicarboxylic acid (crude product from the previous step) in $Ac_2O$ (20 mL) was heated under reflux for 1 h. Excess $Ac_2O$ was removed under reduced pressure. The crude product was used in the next step without further purification.

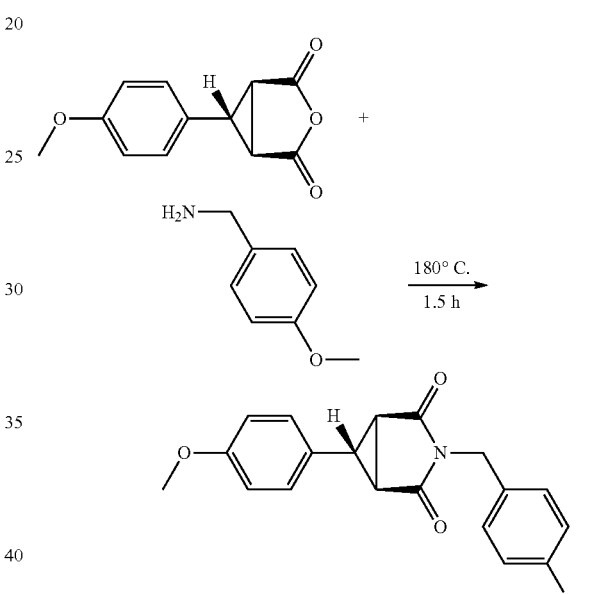

Compound 118.7. 3-(4-Methoxybenzyl)-6-(4-methoxyphenyl)-3-azabicyclo[3.1.0]hexane-2,4-dione A mixture of 6-(4-Methoxyphenyl)-3-oxabicyclo[3.1.0]hexane-2,4-dione (crude product from the previous step) and (4-methoxyphenyl)methanamine was heated at 180° C. for 1.5 h. After cooling to room temperature, the reaction mixture was dissolved in $CH_2Cl_2$ and purified by flash column chromatography with EtOAc in hexane (20%, 30%, then 40%) to give the title compound as a yellow solid (0.71 a, 63% yield over three steps). MS [M+H]$^+$: 338.

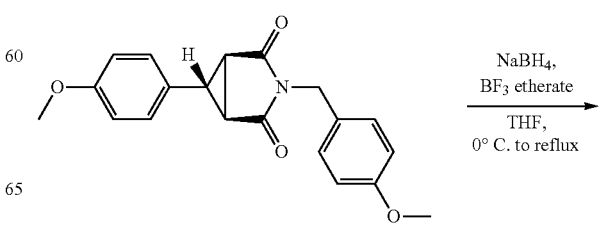

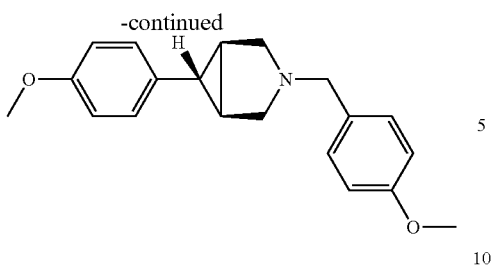

Compound 118.8. 3-(4-Methoxybenzyl)-6-(4-methoxyphenyl)-3-azabicyclo[3.1.0]hexane A mixture of 3-(4-methoxybenzyl)-6-(4-methoxyphenyl)-3-azabicyclo[3.1.0]hexane-2,4-dione (0.86 g, 2.6 mmol), NaBH$_4$ (0.296 g, 7.8 mmol) and BF; etherate (1.0 mL, 7.8 mmol) in THF was heated under reflux overnight. After cooling to 0° C., a solution of piperazine (2 g) in H$_2$O (20 mL) was added. The mixture was stirred at room temperature for 2 h, poured into H$_2$O and extracted with EtOAc (3×). The combined organic extract was dried over MgSO$_4$, filtered and then concentrated. The residue was purified by flash column chromatography with EtOAc in hexane (10%, 20%, then 30%) to give a white solid. To a suspension of the solid in THF (20 mL) and H$_2$O (10 mL) was added piperazine (3 g). After heating the mixture under reflux overnight, it was poured into brine and extracted with EtOAc (3×). The combined organic extract was dried over MgSO$_4$, filtered and concentrated to give the title compound as white solid (0.51 n. 65% yield). MS [M+H]$^+$: 310.

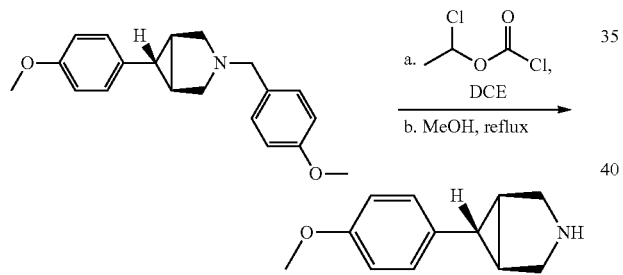

Compound 118.9. 6-(4-Methoxyphenyl)-3-azabicyclo[3.1.0]hexane

To a solution of (1R,5S,6S)-3-(4-Methoxybenzyl)-6-(4-methoxyphenyl)-3-azabicyclo[3.1.0]hexane (0.5 g, 1.6 mmol) in DCE (30 mL) at 0° C. was added 1-chloroethyl chloroformate (0.21 mL, 1.9 mmol, 1.2 equiv). The reaction mixture was stirred at 0° C. for 30 min, heated under reflux for 1 h and then concentrated under reduced pressure. MeOH (20 mL) was added. The resulting mixture was heated under reflux for 40 min and then concentrated. The residue was purified by preparative TLC to give the title compound as a white crystalline solid (155 mg, 51% yield). MS [M+H]$^+$: 190.

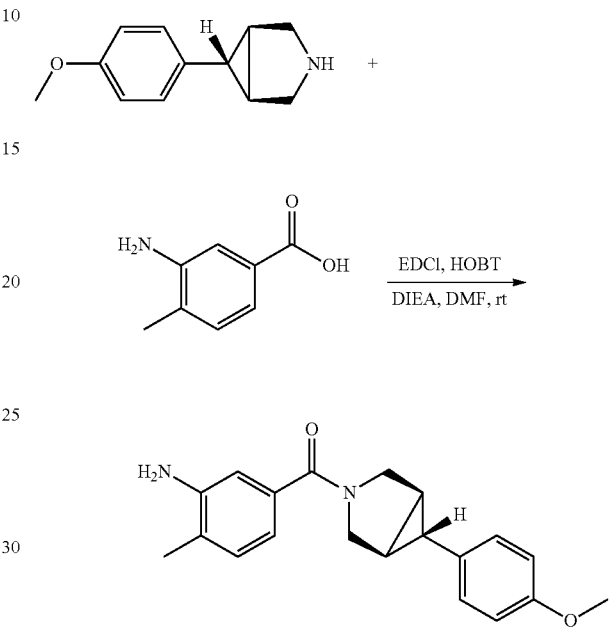

Compound 118.10. (3-Amino-4-methylphenyl)(6-(4-methoxyphenyl)-3-azabicyclo[3.1.0]hexan-3-yl)methanone A mixture of 6-(4-Methoxyphenyl)-3-azabicyclo[3.1.0]hexane (0.124 g, 0.82 mmol), 3-amino-4-methylbenzoic acid (0.155 g, 0.82 mmol), 1-ethyl-3-(3-dimethylaminopropyl)carbodiimide hydrochloride (EDCI, 0.172 g, 0.90 mmol), 1-hydroxybenzotriazole (~20% H$_2$O, 0.122 g, 0.90 mmol) and diisopropylethylamine (0.71 mL, 4.1 mmol) in DMF (3 mL) was stirred at room temperature overnight. The reaction mixture was poured into saturated aqueous NaHCO$_3$ and extracted with EtOAc (3×). The combined organic extract was dried over MgSO$_4$, filtered and concentrated. The residue was purified by flash column chromatography with EtOAc in hexane (60%, then 100%) to give the title compound as a white foam (0.15 g, 57% yield).

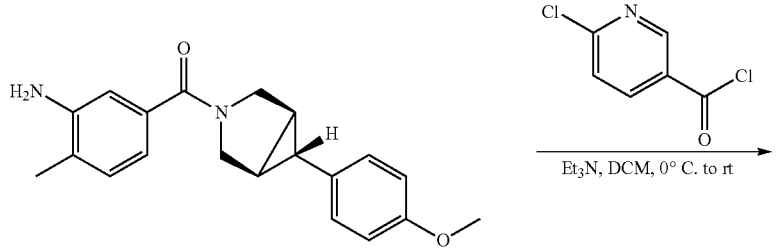

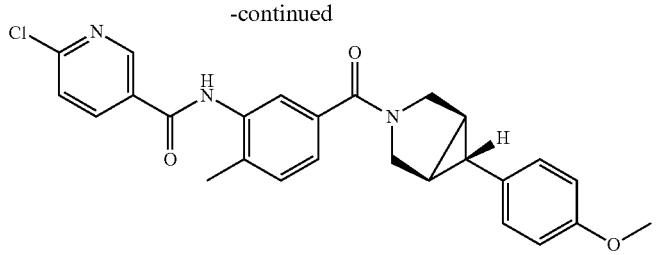

Compound 118.11. 6-Chloro-N-(5-(6-(4-methoxyphenyl)-3-azabicyclo[3.1.0]hexane-3-carbonyl)-2-methylphenyl)nicotinamide To a solution of (3-Amino-4-methylphenyl)(6-(4-methoxyphenyl)-3-azabicyclo[3.1.0]hexan-3-yl)methanone (150 mg, 0.47 mmol) and Et$_3$N (0.25 mL, 1.8 mmol) in CH$_2$Cl$_2$ (4 mL) at 0 was added 6-chloronicotinoyl chloride (106 mg, 0.6 mmol). The ice bath was removed after the addition. The reaction mixture was stirred at room temperature for 1.5 h and then purified by flash column chromatography with EtOAc in hexane (60%, then 100%) to give the title compound as a white foam (0.172 g, 80% yield). MS [M+H]$^+$: 462, 464.

room temperature, the reaction mixture was poured into saturated aqueous NaHCO$_3$ and extracted with EtOAc (3×). The combined organic extract was dried over MgSO$_4$, filtered and concentrated. The residue was triturated with hexane to give the title compound as a white powder (40 mg, 36% yield). MS [M+H]$^+$: 485. $^1$H-NMR (DMSO-d6, 400 Hz) δ 9.63 (s, 1H), 8.69 (d, J=3 Hz, 1H), 7.95-7.90 (m, 1H), 7.55-7.51 (m, 1H), 7.39-7.30 (m, 2H), 7.10-7.03 (m, 3H), 6.84 (d, J=9.2 Hz, 2H), 6.52 (d, J=9.2 Hz, 1H), 4.17-4.07 (m, 2H), 3.85-3.77 (m, 1H), 3.74 (s, 3H), 3.65-3.51 (m, 2H), 2.30 (s, 3H), 1.87 (s, 2H), 1.69 (t, J=3.7 Hz, 1H), 1.20 (d, J=7.2 Hz, 6H).

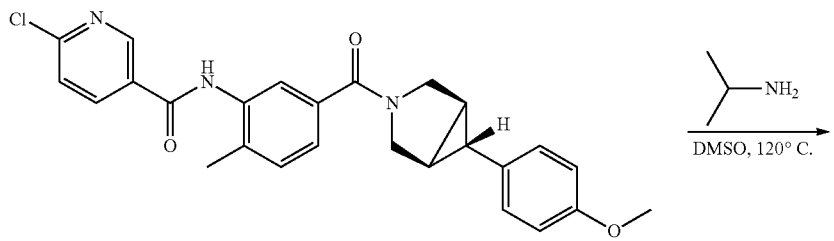

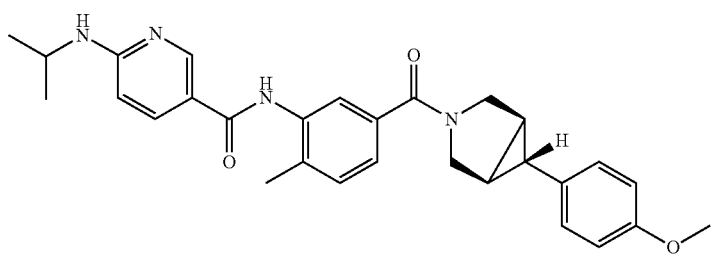

Compound 118. 6-(Isopropylamino)-N-(5-(6-(4-methoxyphenyl)-3-azabicyclo[3.1.0]hexane-3-carbonyl)-2-methylphenyl)nicotinamide A mixture of 6-chloro-N-(5-(6-(4-methoxyphenyl)-3-azabicyclo[3.1.0]hexane-3-carbonyl)-2-methylphenyl)nicotinamide (compound 118.11, 0.107 g, 0.23 mmol) and isopropylamine (1.5 mL) in DMSO (1.5 mL) was heated at 120° C. in a sealed pressure tube overnight. After cooling to

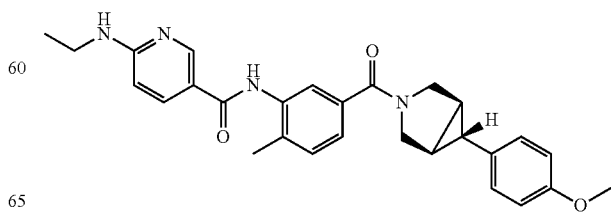

Compound 119. 6-(Ethylamino)-N-(5-(6-(4-methoxyphenyl)-3-azabicyclo[3.1.0]hexane-3-carbonyl)-2-methylphenyl)nicotinamide The title compound was prepared using standard chemical manipulations and procedures similar to those used for the preparation of compound 118. MS [M+H]⁺: 471. ¹HNMR (DMSO-d6, 400 Hz) δ 9.62 (s, 1H), 8.66 (d, J=2.4 Hz, 1H), 7.91 (dd, J=2.4, 9.0 Hz, 1H), 7.50 (s, 1H), 7.34-7.24 (m, 2H), 7.18 (t, J=6.0 Hz, 1H), 7.02 (d, J=8.8 Hz, 2H), 6.81 (d, J=8.8 Hz, 2H), 6.50 (d, J=9.2 Hz, 1H), 4.08 (d, J=12.4 Hz, 1H), 3.81-3.75 (m, 1H), 3.70 (s, 3H), 3.59 (d, J=11.2 Hz, 1H), 3.52 (d, J=13.2 Hz, 1H), 3.37-3.30 (m, 2H), 2.26 (s, 3H), 1.84 (s, 2H), 1.66 (t, J=3.2 Hz, 1H), 1.16 (t, J=8.4 Hz, 3H).

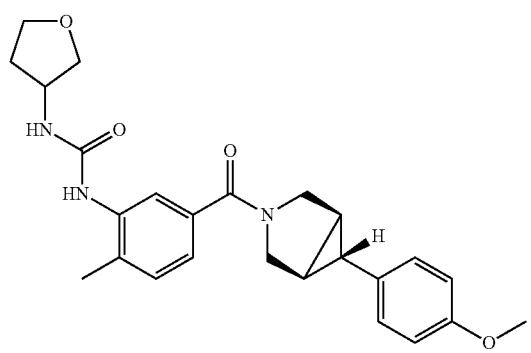 [SMILES: COc1ccc([C@H]2[C@@H]3CN(C(=O)c4ccc(C)c(NC(=O)NC5CCOC5)c4)C[C@@H]32)cc1]

Compound 120. 1-(5-(6-(4-Methoxyphenyl)-3-azabicyclo[3.1.0]hexane-3-carbonyl)-2-methylphenyl)-3-(tetrahydrofuran-3-yl)urea The title compound was prepared using readily available reagents and procedures similar to those used for the preparation of compounds 64 and 118. m/z (ES-F) 436 (M+H)⁺.

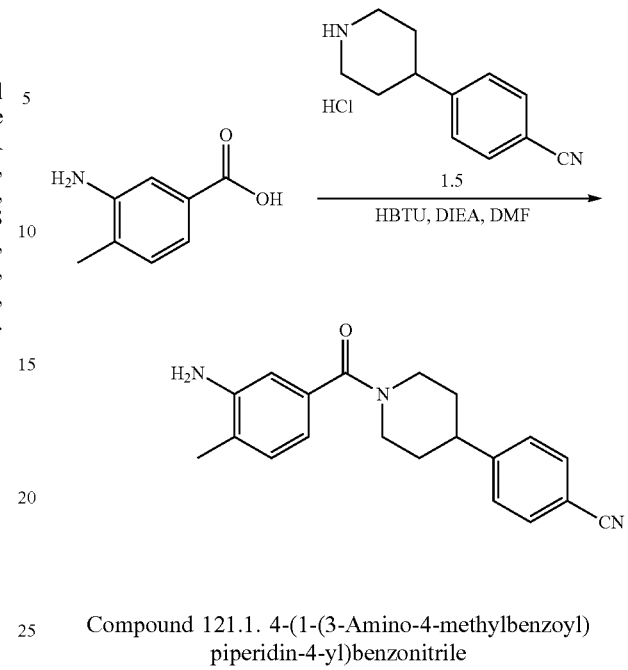

Compound 121.1. 4-(1-(3-Amino-4-methylbenzoyl)piperidin-4-yl)benzonitrile

A solution of 3-amino-4-methylbenzoic acid (1.362, 9.0 mmol), (4-(piperidin-4-yl)benzonitrile HCl salt (compound 1.5, 2.0 g, 9.0 mmol), EDCI (1.89 g, 9.9 mmol), HOBT (1.66 g, 9.9 mmol, with 20% H₂O) and DIEA (3.13 ml, 18.0 mmol) in DMF (50 ml) was stirred at room temperature overnight. The reaction mixture was poured into cold water (300 ml) and off white solids precipitated. The precipitate was filtered, washed with water and dried under reduced pressure in an oven to yield 2.88 g (100%) of the title compound. m/z (ES+) 320 (M+H)⁺.

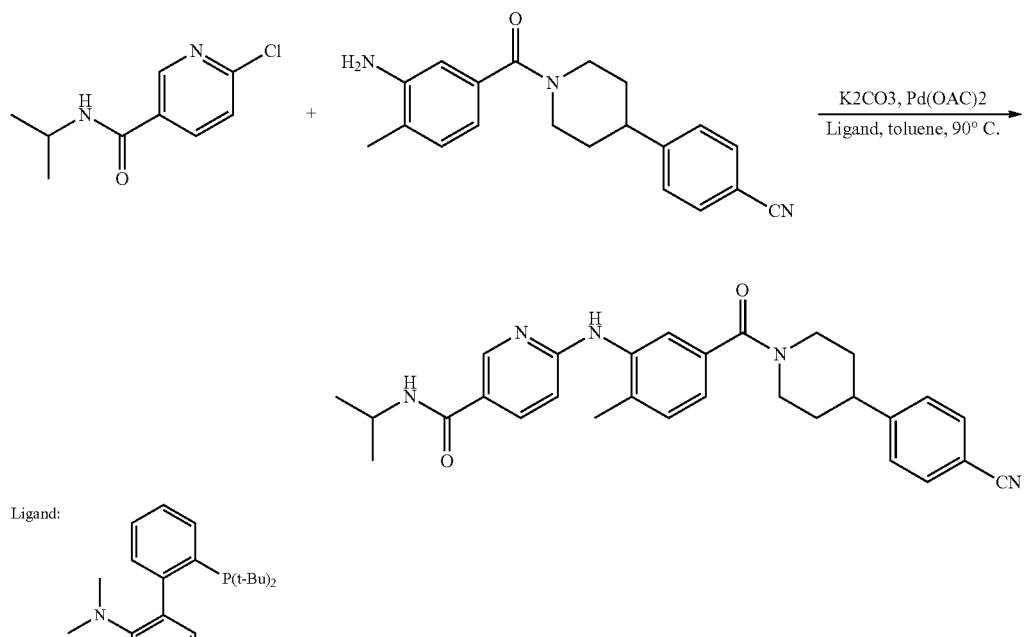

Compound 121. 6-((5-(4-(4-Cyanophenyl)piperidine-1-carbonyl)-2-methylphenyl)amino)-N-isopropylnicotinamide A mixture of 6-chloro-N-isopropylnicotinamide (0.055 g, 0.26 mmol), 4-(1-(3-amino-4-methylbenzoyl)piperidin-4-yl)benzonitrile (121.1, 0.1 g, 0.31 mmol), $K_2CO_3$ (0.171 g, 1.24 mmol), Pd(OAc)$_2$ (6.7 mg, 0.03 mmol) and the ligand (10.2 mg, 0.03 mmol) in toluene (5 mL) was heated at 90° C. under argon for 3 h. After cooling to room temperature, the reaction mixture was diluted with $H_2O$ and extracted with EtOAc. The combined organic extract was dried over $MgSO_4$, filtered, and concentrated. The residue was purified by flash column chromatography with EtOAc in hexane (60%, 80%, then 100%) to give the title compound as an off-white powder after lyophilization from $CH_3CN/H_2O$ (11.2 mg, 9% yield). m/z (ES+) 482 (M+H)$^+$.

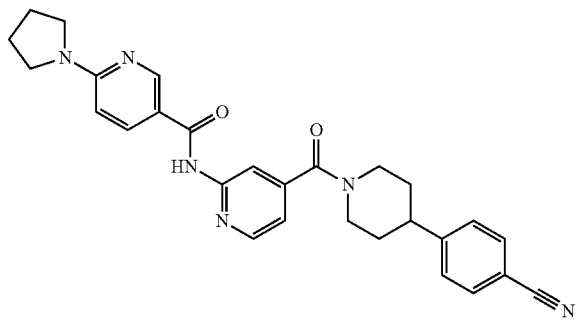 [SMILES: N#Cc1ccc(C2CCN(C(=O)c3ccnc(NC(=O)c4ccc(N5CCCC5)nc4)c3)CC2)cc1]

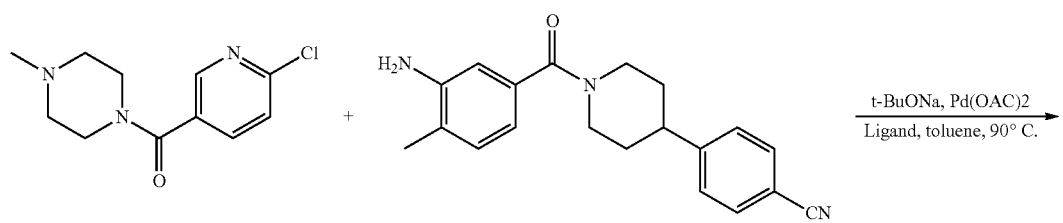

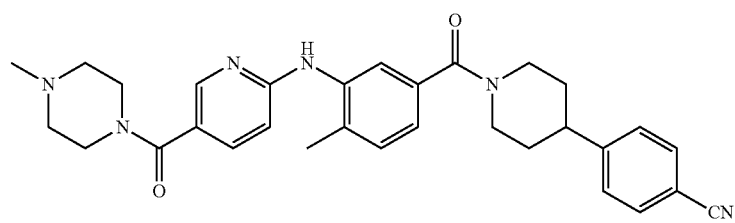

Ligand:

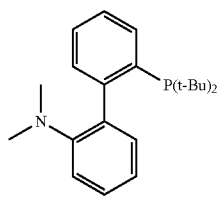

Compound 122. 4-(1-(4-Methyl-3-((5-(4-methylpiperazine-1-carbonyl)pyridin-2-yl)amino)benzoyl)piperidin-4-yl)benzonitrile The title compound was prepared using standard chemical manipulations and procedures similar to those used for the preparation of compound 121 replacing $K_2CO_3$ with t-BuONa. m/z (ES+) 524 (M+H)$^+$.

Compound 123. N-(4-(4-(4-Cyanophenyl)piperidine-1-carbonyl)pyridin-2-yl)-6-(pyrrolidin-1-yl)nicotinamide The title compound was prepared using standard chemical manipulations and procedures similar to those used for the preparation of compound 43 and using 2-aminoisonicotinic acid in place of 3-amino-4-methylbenzoic acid. m/z (ES+) 481 (M+H)$^+$.

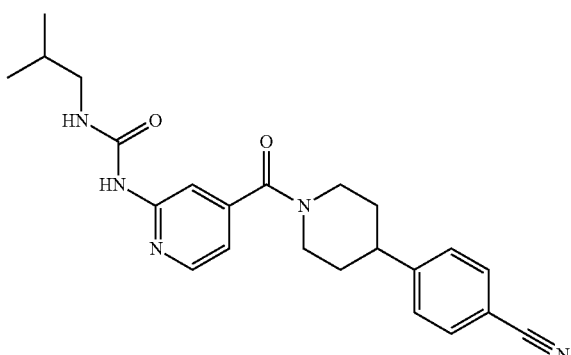

Compound 124. 1-(4-(4-(4-Cyanophenyl)piperidine-1-carbonyl)pyridin-2-yl)-3-isobutylurea The title compound was prepared using standard chemical manipulations and procedures similar to those used for the preparation of compound 64 and using 2-aminoisonicotinic acid in place of 3-amino-4-methylbenzoic acid. m/z (ES+) 406 (M+H)

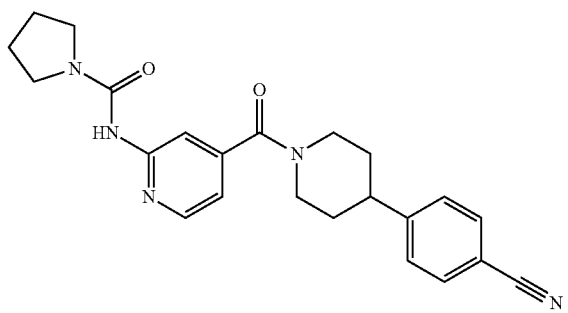 [SMILES: N#Cc1ccc(C2CCN(C(=O)c3ccnc(NC(=O)N4CCCC4)c3)CC2)cc1]

Compound 125. N-(4-(4-(4-Cyanophenyl)piperidine-1-carbonyl)pyridin-2-yl)pyrrolidine-1-carboxamide The title compound was prepared using standard chemical manipulations and procedures similar to those used for the preparation of compound 64 and using 2-aminoisonicotinic acid m place of 3-amino-4-methylbenzoic acid. m/z (ES+) 404 (M+H)$^+$.

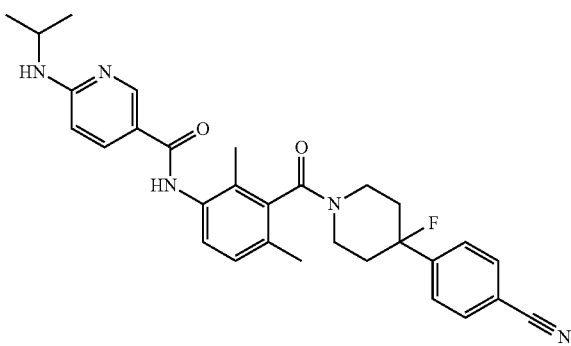 [SMILES: Cc1ccc(NC(=O)c2ccc(NC(C)C)nc2)c(C)c1C(=O)N1CCC(F)(c2ccc(C#N)cc2)CC1]

Compound 126. N-(3-(4-(4-Cyanophenyl)-4-fluoropiperidine-1-carbonyl)-2,4-dimethylphenyl)-6-(isopropylamino)nicotinamide The title compound was prepared using readily available reagents and procedures similar to those used for the preparation of compound 43 and using 3-amino-2,6-dimethylbenzoic acid in place of 3-amino-4-methylbenzoic acid. m/z (ES+) 514 (M+H)$^+$.

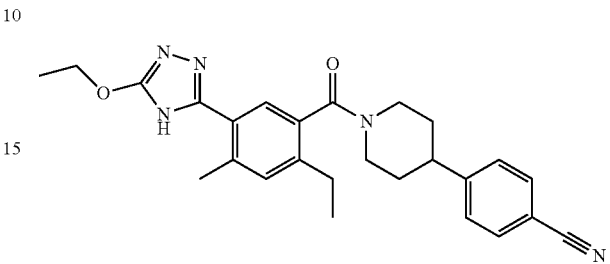

Compound 127. 4-(1-(5-(5-Ethoxy-4H-1,2,4-triazol-3-yl)-2-ethyl-4-methylbenzoyl)piperidin-4-yl)benzonitrile The title compound was prepared using standard chemical manipulations and procedures similar to those used for the preparation of compound 39. m/z (ES+) 445 (M+H)$^+$.

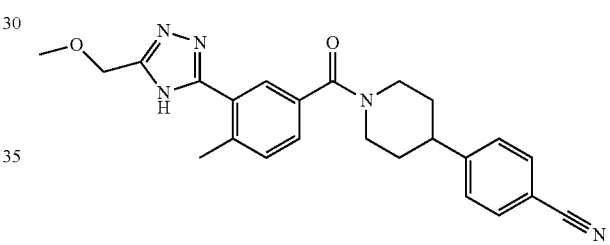

Compound 128. 4-(1-(3-(5-(Methoxymethyl)-4H-1,2,4-triazol-3-yl)-4-methylbenzoyl)piperidin-4-yl)benzonitrile The title compound was prepared using standard chemical manipulations and procedures similar to those used for the preparation of 4-(1-(4-methyl-3-(5-(tetrahydrofuran-3-yl)-4H-1,2,4-triazol-3-yl)benzoyl)piperidin-4-yl)benzonitrile (compound 38). m/z (ES+) 416 (M+H)$^+$.

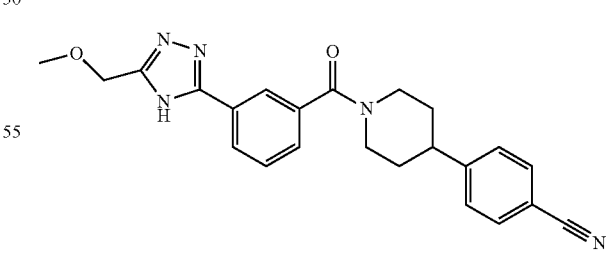

Compound 129. 4-(1-(3-(5-(Methoxymethyl)-4H-1,2,4-triazol-3-yl)benzoyl)piperidin-4-yl)benzonitrile The title compound was prepared using standard chemical manipulations and procedures similar to those used for the preparation of compound 38. m/z (ES+) 402 (M+H)$^+$.

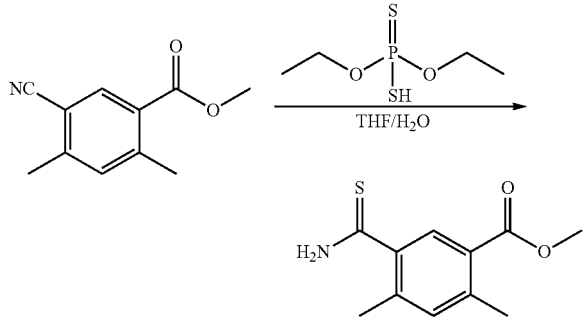

Compound 130.1. Methyl 5-carbamothioyl-2,4-dimethylbenzoate

To a round-bottom flask was added a solution of methyl 5-cyano-2,4-dimethylbenzoate (compound 2.3, 1.78 g, 9.41 mmol, 1.00 equiv) in tetrahydrofuran/H70 (30/3 mL). O,O'-diethyl dithiophosphate (3.30 g, 17.7 mmol, 2.00 equiv) was added and the resulting mixture was stirred for 2 days at 85° C. (CAUTION: significant gas evolution occurs—this and all other reactions described herein should be carried out in well ventilated fume hoods). After cooling to ambient temperature, the mixture was extracted with 2×50 mL of ethyl acetate. The combined organic layers were dried over sodium sulfate and concentrated in vacuo. The crude residue was purified using silica gel column chromatography with ethyl acetate/petroleum ether (1:10) as eluent to furnish 1.20 g (57%) of the title compound as a yellow solid.

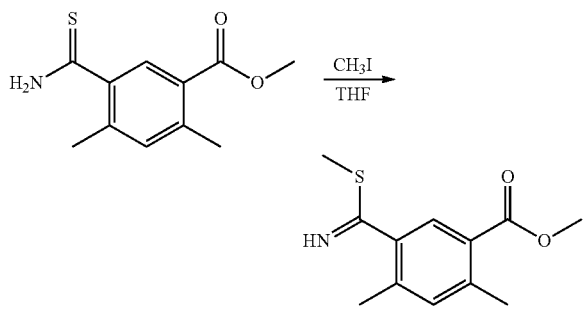

Compound 130.2. Methyl 5-(imino(methylthio)methyl)-2,4-dimethylbenzoate

To a solution of methyl 5-carbamothioyl-2,4-dimethylbenzoate (compound 130.1, 3.10 g, 12.5 mmol, 1.00 equiv, 90%) in tetrahydrofuran (30 mL) was added CH$_3$I (3.95 g, 27.8 mmol, 2.00 equiv) and the resulting mixture was stirred overnight at 25° C. The organic layer was washed with 2×30 mL of Na$_2$S$_2$O$_4$(aq.) and 1×30 mL of brine, dried over anhydrous sodium sulfate, and concentrated in vacuo. This resulted in 2.10 g (64%) of methyl 5-(imino(methylthio)methyl)-2,4-dimethylbenzoate as a yellow oil.

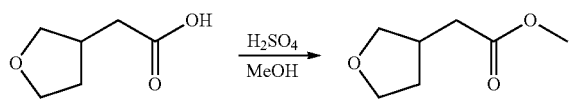

Compound 130.3. Methyl 2-(tetrahydrofuran-3-yl)acetate

A mixture of 2-(tetrahydrofuran-3-yl)acetic acid (2.00 g, 15.4 mmol, 1.00 equiv) and sulfuric acid (2 mL) in methanol (20 mL) was stirred for 3 h at 80° C. in an oil bath. After cooling to ambient temperature, the mixture was diluted with 50 mL of ether and washed with 2×20 mL of water, 2×20 mL of sodium bicarbonate (aq., sat. Note: gas evolution), and 2×20 mL of brine. The organic phase was then dried over anhydrous sodium sulfate and concentrated in vacuo to yield 1.50 g (68%) of the title compound as a yellow oil.

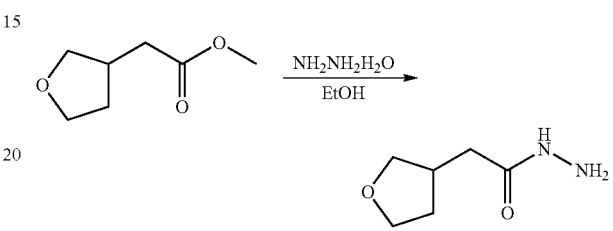

Compound 130.4. 2-(Tetrahydrofuran-3-yl)acetohydrazide

To a round-bottom flask was added a solution of methyl 2-(tetrahydrofuran-3-yl)acetate (compound 130.3, 1.50 g, 10.4 mmol, 1.00 equiv) and NH$_2$NH$_2$—H$_2$O (1.04 g, 20.8 mmol, 2.00 equiv) in methanol (15 mL). The resulting mixture was stirred overnight at 80° C. in an oil bath. After cooling to ambient temperature, the mixture was concentrated in vacuo to yield 1.20 g (80%) of the title compound as a yellow oil.

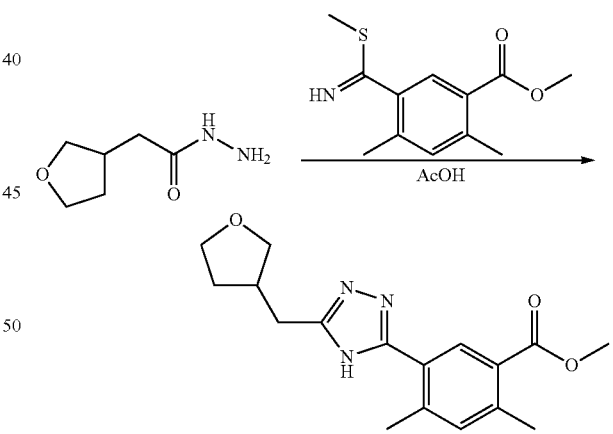

Compound 130.5. Methyl 2,4-dimethyl-5-(5-((tetrahydrofuran-3-yl)methyl)-4H-1,2,4-triazol-3-yl)benzoate To a round-bottom flask was added a solution of 2-(tetrahydrofuran-3-yl)acetohydrazide (compound 130.4, 1.20 g, 8.32 mmol, 1.50 equiv) in acetic acid (4 mL). Methyl 2,4-dimethyl-5-(methylsulfanyl)carboximidoylbenzoate (compound 130.2, 1.30 g, 5.48 mmol, 1.00 equiv) was added and the resulting mixture was stirred overnight at 100° C. in an oil bath. After cooling to ambient temperature, the mixture was concentrated in vacuo. The residue was diluted with 50 mL of ethyl acetate, then washed with 2×20 mL of water and 2×20 mL of brine. The organic phase was dried over anhydrous sodium sulfate and concentrated in vacuo. The residue was purified using silica gel column chromatography with ethyl acetate/petroleum ether (0:1-1:10-1:1) as eluent to furnish 0.600 g (35%) of the title compound as a yellow solid.

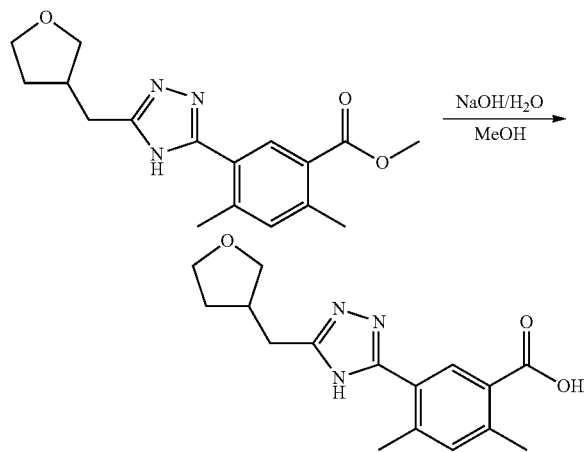

Compound 130.6. 2,4-Dimethyl-5-(5-((tetrahydrofuran-3-yl)methyl)-4H-1,2,4-triazol-3-yl)benzoic acid To a round-bottom flask was added a solution of methyl 2,4-dimethyl-5-(5-((tetrahydrofuran-3-yl)methyl)-4H-1,2,4-triazol-3-yl)benzoate (compound 130.5, 600 mg, 1.90 mmol, 1.00 equiv) in methanol (10 mL). A solution of sodium hydroxide (381 mg, 9.53 mmol, 5.00 equiv) in water (5 mL) was added and the resulting mixture was stirred for 3 h at 70° C. in an oil bath. After cooling to room temperature, the organic solvent was then removed under reduced pressure and the pH of the remaining aqueous phase was adjusted to 3-4 with hydrogen chloride (aq., 1 M). The resulting solids were collected via filtration and dried in an oven under reduced pressure to yield 0.500 g (87%) of the title compound as a yellow solid.

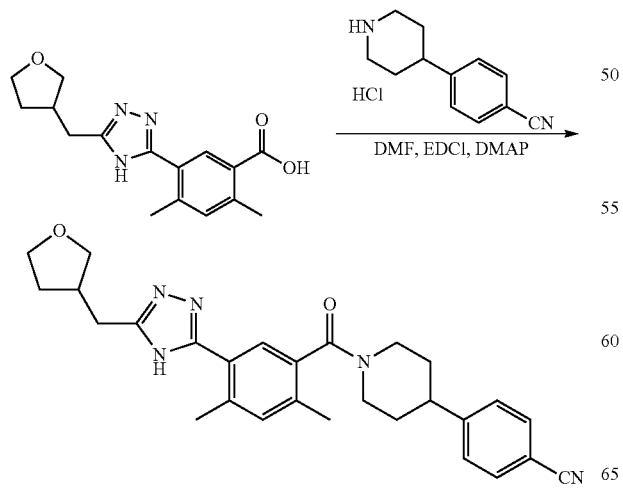

Compound 130. 4-(1-(2,4-Dimethyl-5-(5-((tetrahydrofuran-3-yl)methyl)-4H-1,2,4-triazol-3-yl)benzoyl)piperidin-4-yl)benzonitrile A mixture of compound 130.6 (200 mg, 0.660 mmol, 1.00 equiv), EDCI (253 mg, 1.32 mmol, 2.00 equiv), DMAP (243 mg, 1.99 mmol, 3.00 equiv), and 4-(piperidin-4-yl)benzonitrile hydrochloride (compound 1.5, 148 mg, 0.660 mmol, 1.00 equiv) in DMF (5 mL) was stirred for 3 h at 25° C., then diluted with 50 mL of ethyl acetate. The organic layer was washed with 2×10 mL of water, 2×10 mL of brine, dried over anhydrous sodium sulfate and concentrated in vacuo. The crude product (~300 mg) was purified by Prep-HPLC with the following conditions (1 #-Pre-HPLC-001 (SHIMADZU)): Column, SunFire Prep C18, 19*150 mm 5 um; mobile phase, water with 0.05% TFA and $CH_3CN$ (28% $CH_3CN$ up to 52% in 8 min, up to 100% in 1 min, down to 28% in 1 min); Detector, Waters 2489 254 & 220 nm. The fractions containing pure compound were combined and lyophilized to yield 168 mg (52%) of the title compound as a white solid. m/z (ES+) 470 (M+H)$^+$. $^1$H-NMR (400 Hz, CD3OD): δ 7.68 (d, J=8.0 Hz, 2H), 7.61 (s, 1H), 7.50-7.49 (m, 2H), 7.33-7.31 (m, 1H), 4.90-4.88 (m, 1H), 3.95-3.92 (m, 2H), 3.90-3.81 (m, 1H), 3.79-3.77 (m, 1H), 3.69-3.55 (m, 1H), 3.28-3.25 (m, 1H), 3.03-2.94 (m, 4H), 2.81-2.73 (m, 1H), 2.53 (s, 3H), 2.43 and 2.33 (2s, amide rotamers, $ArCH_3$, 3H), 2.19-2.15 (m, 1H), 113-2.05 (m, 1H), 1.94-1.68 (m, 4H).

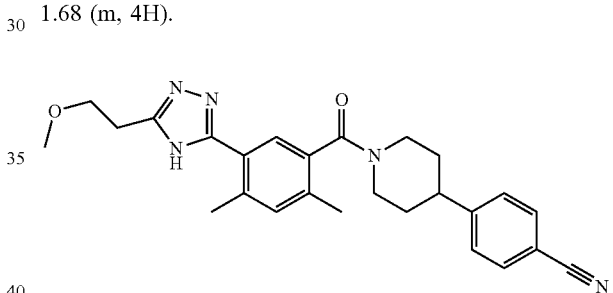

Compound 131. 4-(1-(5-(5-(2-Methoxyethyl)-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 3-methoxypropanehydrazide (compound 143.1) instead of 2-(tetrahydrofuran-3-yl)acetohydrazide (compound 130.4). m/z (ES+) 444 (M+H)$^+$.

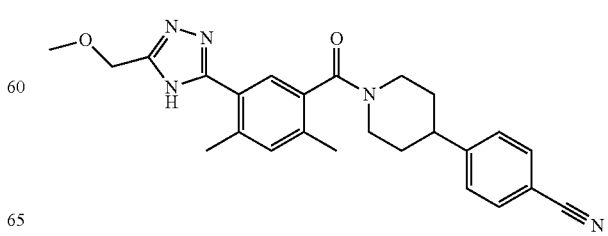

Compound 132. 4-(1-(5-(5-(Methoxymethyl)-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 2-methoxyacetohydrazide (compound 190.6) instead of 2-(tetrahydrofuran-3-yl)acetohydrazide (compound 130.4). m/z (ES+) 430 (M+H)+.

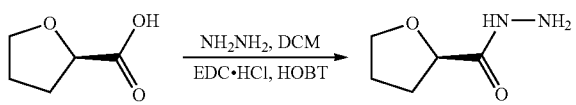

Compound 133.1. (R)-Tetrahydrofuran-2-carbohydrazide

A mixture of (R)-tetrahydrofuran-2-carboxylic acid (5.00 g, 43.1 mmol, 1.00 equiv), EDCI (12.4 g, 64.6 mmol, 1.50 equiv) and HOBt (8.70 g, 64.4 mmol, 1.50 equiv) in dichloromethane (100 mL) was stirred for 30 min at 25° C. To the mixture was then added hydrazine (2.00 g, 62.4 mmol, 1.50 equiv) dropwise. The resulting mixture was stirred overnight at 25° C. The solids were removed by filtration, and the filtrate was concentrated in vacuo to furnish 25.0 g (crude) of (R)-tetrahydrofuran-2-carbohydrazide as a yellow oil.

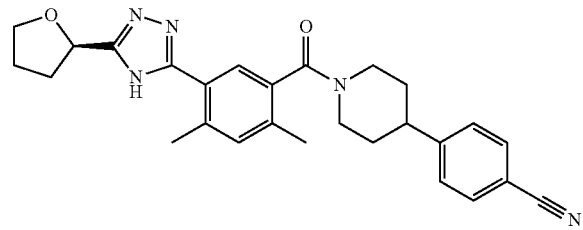 [SMILES: Cc1cc(C)c(-c2nnc([C@H]3CCCO3)[nH]2)cc1C(=O)N1CCC(c2ccc(C#N)cc2)CC1]

Compound 133. (R)-4-(1-(2,4-Dimethyl-5-(5-(tetrahydrofuran-2-yl)-4H-1,2,4-triazol-3-yl)benzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using (R)-tetrahydrofuran-2-carbohydrazide (compound 133.1) instead of 2-(tetrahydrofuran-3-yl)acetohydrazide (compound 130.4). m/z (ES+) 446 (M+H)+.

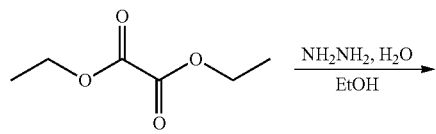

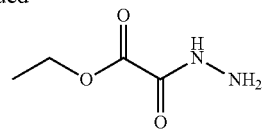

Compound 134.1. Ethyl 2-hydrazinyl-2-oxoacetate

To a round-bottom flask was added a solution of diethyl oxalate (10.0 g, 68.4 mmol, 1.00 equiv) in ethanol (100 mL). Hydrazine hydrate (2.75 g, 85.8 mmol, 1.00 equiv) was added and the resulting mixture was stirred for 3 h at 80° C. After cooling to ambient temperature, the solids were removed via filtration and the filtrate was concentrated in vacuo to yield 8.00 g (80%) of the title compound as a colorless oil.

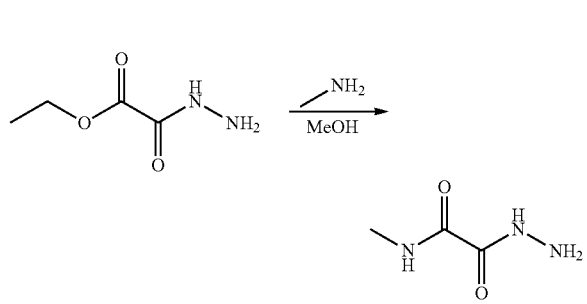

Compound 134.2. 2-Hydrazinyl-N-methyl-2-oxoacetamide

To a round-bottom flask was added a solution of ethyl 2-hydrazinyl-2-oxoacetate (compound 134.1, 300 rug, 2.04 mmol, 1.00 equiv, 90%) in methanol (10 mL). Methyl amine (10 mL, 40% in water) was added and the resulting mixture was stirred overnight at 70° C. After cooling to ambient temperature, the solids were collected by filtration and dried to yield 250 mg (94%) of the title compound as a white solid.

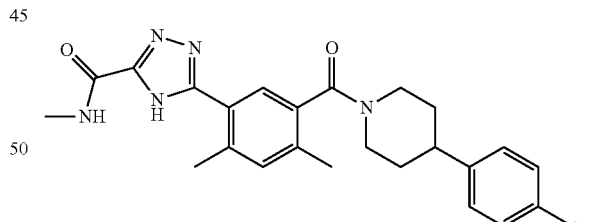

Compound 134. 5-(5-(4-(4-Cyanophenyl)piperidine-1-carbonyl)-2,4-dimethylphenyl)-N-methyl-4H-1,2,4-triazole-3-carboxamide The title compound was prepared using standard chemical manipulations and procedures similar to those used for the preparation of compound 130, using compound 134.2 instead of compound 130.4. m/z (ES+) 443 (M+H)+. 1H NMR (300 MHz, CD3OD): δ 7.69 (d, J=8.1 Hz, 2H), 7.62-7.43 (m, 3H), 7.32 (s, 1H), ~4.9 (1H partially obscured by water peak), 3.73-3.58 (m, 1H), 3.32-3.18 (m, 1H partially obscured by methanol solvent peak), 3.07-1.91 (m, 5H), 2.58 (s, 3H), 2.43 & 2.33 (2 singlets, amide rotamers, Ar—CH₃, 3H), 2.10-1.93 (m, 1H), 1.93-1.52 (m, 3H).

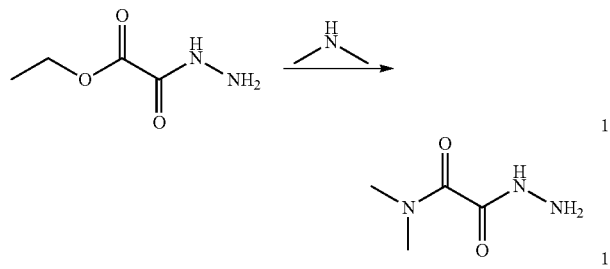

Compound 135.1.
2-Hydrazinyl-N,N-dimethyl-2-oxoacetamide

To a round-bottom flask was added ethyl 2-hydrazinyl-2-oxoacetate (compound 134.1, 2.00 g, 13.6 mmol, 1.00 equiv, 90%). Dimethylamine (10 mL) was added to the reaction, and then the reaction was stirred overnight at 70° C. in an oil bath. The mixture was cooled to room temperature and concentrated in vacuo to yield 1.50 g (76%) of the title compound as a colorless oil.

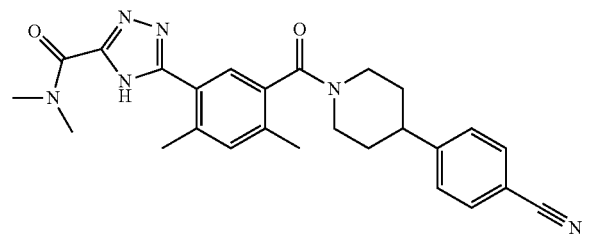 [SMILES: Cc1cc(C)c(-c2nnc(C(=O)N(C)C)[nH]2)cc1C(=O)N1CCC(c2ccc(C#N)cc2)CC1]

Compound 135. 5-(5-(4-(4-Cyanophenyl)piperidine-1-carbonyl)-2,4-dimethylphenyl)-N,N-dimethyl-4H-1,2,4-triazole-3-carboxamide The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 2-hydrazinyl-N,N-dimethyl-2-oxoacetamide (compound 135.1) instead of 2-(tetrahydrofuran-3-yl)acetohydrazide (compound 130.4). m/z (ES+) 457 (M+H)⁺.

Compound 136.1.
(S)-Tetrahydrofuran-2-carbohydrazide

To a round-bottom flask was added a solution of (S)-tetrahydrofuran-2-carboxylic acid (3.00 g, 23.3 mmol, 1.00 equiv, 90%) in dichloromethane (40 mL). NH₂NH₂ (2 mL, 2.00 equiv), HOBt (5.20 g, 38.5 mmol, 1.50 equiv), and EDCI (7.50 g, 39.1 mmol, 1.50 equiv) were added and the resulting mixture was stirred overnight at 25° C. The solids were removed by filtration, and the filtrate was concentrated in vacuo to furnish 2.50 g (74%) of (S)-tetrahydrofuran-2-carbohydrazide as a yellow oil.

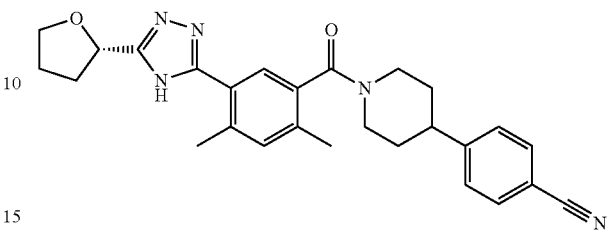

Compound 136. (S)-4-(1-(2,4-Dimethyl-5-(5-(tetrahydrofuran-2-yl)-4H-1,2,4-triazol-3-yl)benzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using (S)-tetrahydrofuran-2-carbohydrazide (compound 136.1) instead of 2-(tetrahydrofuran-3-yl)acetohydrazide (compound 130.4). m/z (ES+) 456 (M+H)⁺.

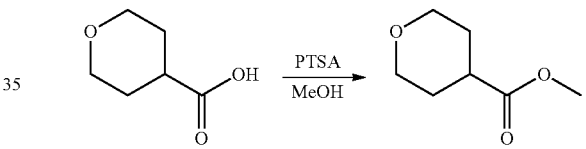

Compound 137.1. Methyl tetrahydro-2H-pyran-4-carboxylate

To a solution of tetrahydro-2H-pyran-4-carboxylate acid (520 mg, 4.00 mmol, 1.00 equiv) in methanol (50 mL) was added PTSA (35.0 mg, 0.200 mmol). The resulting mixture was stirred overnight at 80° C. in an oil bath, then cooled to ambient temperature and concentrated in vacuo. The residue was diluted with 30 mL of water and extracted with 3×30 mL of DCM. The combined organic layers were dried over anhydrous magnesium sulfate and concentrated in vacuo. This resulted in 500 mg (87%) of methyl tetrahydro-2H-pyran-4-carboxylate as a colorless oil.

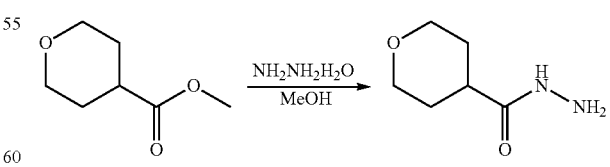

Compound 137.2.
Tetrahydro-2H-pyran-4-carbohydrazide

To a round-bottom flask was added a solution of methyl tetrahydro-2H-pyran-4-carboxylate (compound 137.1, 5.00 g, 31.2 mmol, 1.00 equiv, 90%) in methanol (50 mL). Hydrazine hydrate (5.20 g, 83.2 mmol, 3.00 equiv) was added and the resulting mixture was stirred overnight at 40° C. in an oil bath. After cooling to ambient temperature, the mixture was concentrated in vacuo to yield 4.00 g (80%) of tetrahydro-2H-pyran-4-carbohydrazide as a white solid.

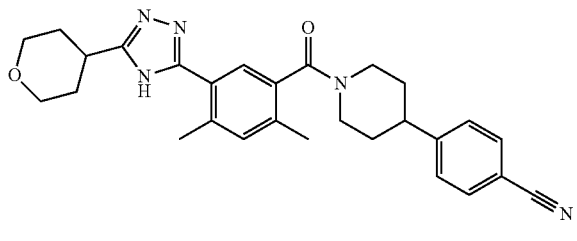 [SMILES: Cc1cc(C)c(-c2nnc(C3CCOCC3)[nH]2)cc1C(=O)N1CCC(c2ccc(C#N)cc2)CC1]

Compound 137. 4-(1-(2,4-Dimethyl-5-(5-(tetrahydro-2H-pyran-4-yl)-4H-1,2,4-triazol-3-yl)benzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using tetrahydro-2H-pyran-4-carbohydrazide (compound 137.2) instead of 2-(tetrahydrofuran-3-yl)acetohydrazide (compound 130.4). m/z (ES+) 470 (M+H)⁺.

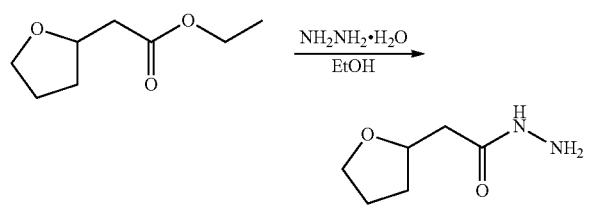

Compound 138.1. 2-(Tetrahydrofuran-2-yl)acetohydrazide

To a round-bottom flask was added a solution of ethyl 2-(tetrahydrofuran-2-yl)acetate (2.00 g, 12.6 mmol, 1.00 equiv) in ethanol (20 mL). NH$_2$NH$_2$.H$_2$O (1.27 g, 25.4 mmol, 2.00 equiv) was added to the reaction. The resulting solution was stirred overnight at 80° C. in an oil bath, then cooled to room temperature and concentrated in vacuo. This resulted in 2.10 g (92%) of 2-(tetrahydrofuran-2-yl)acetohydrazide as a yellow oil.

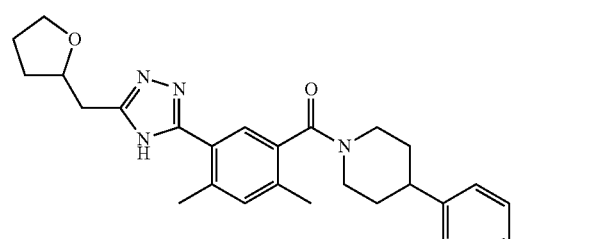

Compound 138. 4-(1-(2,4-Dimethyl-5-(5-((tetrahydrofuran-2-yl)methyl)-4H-1,2,4-triazol-3-yl)benzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 2-(tetrahydrofuran-2-yl)acetohydrazide (compound 138.1) instead of 2-(tetrahydrofuran-3-yl)acetohydrazide (compound 130.4). m/z (ES+) 470 (M+H)⁺.

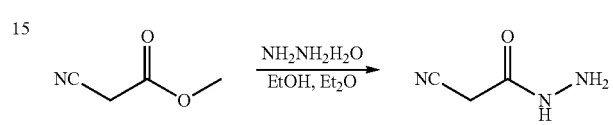

Compound 139.1. 2-Cyanoacetohydrazide

To a solution of NH$_2$NH$_2$.H$_2$O (3.50 g, 70.0 mmol, 1.00 equiv) in a solvent mixture of ethanol and Et$_2$O (35/35 mL) at 0° C. was added dropwise a solution of methyl 2-cyanoacetate (7.00 g, 70.6 mmol, 1.00 equiv) in ethanol (5 mL). The resulting mixture was stirred for 3 h at room temperature, then washed with 2×30 mL of ether. The solids were collected by filtration to yield 5.00 g (68%) of 2-cyanoacetohydrazide as a white solid.

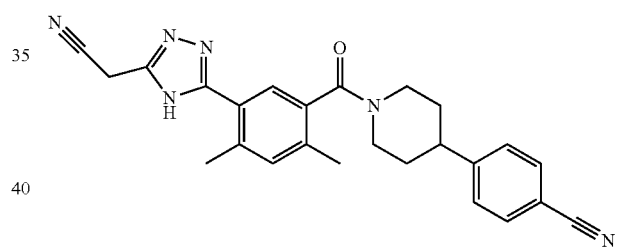

Compound 139. 4-(1-(5-(5-(cyanomethyl)-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 2-cyanoacetohydrazide (compound 139.1) instead of 2-(tetrahydrofuran-3-yl)acetohydrazide (compound 130.4). m/z (ES+) 425 (M+H)⁺. ¹H-NMR (300 Hz, CD$_3$OD): δ 7.70 (d, J=8.4 Hz, 2H), 7.54-7.42 (m, 3H), 7.35 (s, 1H), 4.87-4.80 (m, 1H), 4.12 (s, 2H), 3.77-3.65 (m, 1H), 3.27-3.23 (m, 1H), 3.09-2.99 (m, 2H), 2.55 (s, 3H), 2.43 and 2.33 (2 singlets, amide rotamers, ArCH$_3$, 3H), 2.05-2.00 (m, 1H), 1.83-1.76 (m, 3H).

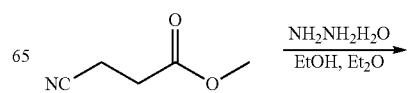

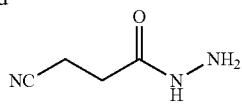

Compound 140.1. 3-cyanopropanehydrazide

To a round-bottom flask was added a solution of NH$_2$NH$_2$.H$_2$O (1.25 g, 25.1 mmol, 1.00 equiv) in ether/EtOH (8/8 mL). To this was added methyl 3-cyanopropanoate (2.84 g, 25.1 mmol, 1.00 equiv) dropwise. The resulting solution was stirred for 2 h at room temperature, then concentrated in vacuo. This resulted in 1.40 g (49%) of 3-cyanopropanehydrazide as a colorless oil.

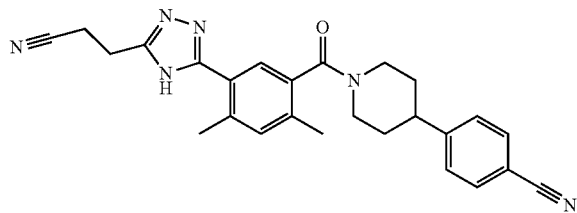 [SMILES: Cc1cc(C)c(-c2nnc(CCC#N)[nH]2)cc1C(=O)N1CCC(c2ccc(C#N)cc2)CC1]

Compound 140. 4-(1-(5-(5-(2-cyanoethyl)-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130), using 3-cyanopropanehydrazide (compound 140.1) instead of 2-(tetrahydrofuran-3-yl)acetohydrazide (compound 130.4). m/z (ES+) 439 (M+H)$^+$. $^1$H-NMR (300 Hz, CD$_3$OD): δ 7.68 (d, 2H), 7.58-4.47 (m, 3H), 7.30 (s, 1H), 4.89-4.80 (m, 1H), 3.65-3.62 (m, 1H), 3.32-3.30 (m, 1H), 3.15 (t, 2H), 3.03-2.95 (m, 4H), 2.50 (s, 3H), 2.42 and 2.32 (2 singlets, amide rotamers, ArCH$_3$, 3H), 2.03-2.00 (m, 1H), 1.83-1.78 (m, 3H).

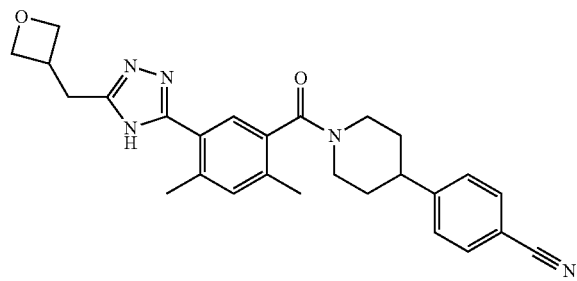 [SMILES: Cc1cc(C)c(-c2nnc(CC3COC3)[nH]2)cc1C(=O)N1CCC(c2ccc(C#N)cc2)CC1]

Compound 141. 4-(1-(2,4-Dimethyl-5-(5-(oxetan-3-ylmethyl)-4H-1,2,4-triazol-3-yl)benzoyl)piperidin-4-yl)benzonitrile The title compound was prepared using standard chemical manipulations and procedures similar to those used for the preparation of 4-(1-(2,4-dimethyl-5-(5-((tetrahydrofuran-3-yl)methyl)-4H-1,2,4-triazol-3-yl)benzoyl)piperidin-4-yl)benzonitrile (compound 130). m/z (ES+) 456 (M+H)$^+$.

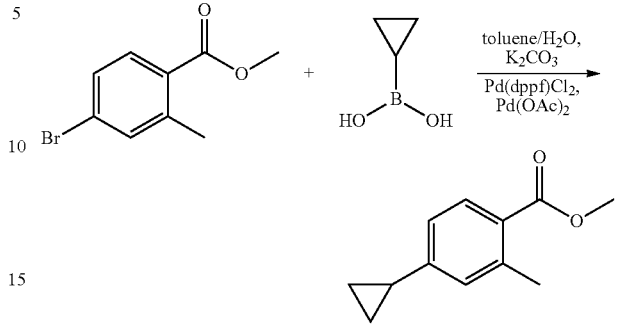

Compound 142.1. Methyl 4-cyclopropyl-2-methylbenzoate

To a solution of methyl 4-bromo-2-methylbenzoate (5.00 g, 20.7 mmol, 1.00 equiv, 95%) in a mixture of toluene and H$_2$O (20 mL/1 mL) were added potassium carbonate (6.10 g, 44.1 mmol, 2.00 equiv), cyclopropylboronic acid (2.30 g, 26.8 mmol, 1.20 equiv), Pd(dppf)Cl$_2$ (900 mg, 1.23 mmol, 0.05 equiv), and Pd(OAc)$_2$ (250 mg, 1.12 mmol, 0.05 equiv). The reaction mixture was purged with nitrogen and stirred at 80° C. overnight. After cooling to room temperature, the mixture was then concentrated in vacuo. The resulting residue was purified via silica gel column chromatography with ethyl acetate/petroleum ether (1:50) as eluent to yield 2.68 g (61%) of methyl 4-cyclopropyl-2-methylbenzoate as a colorless oil.

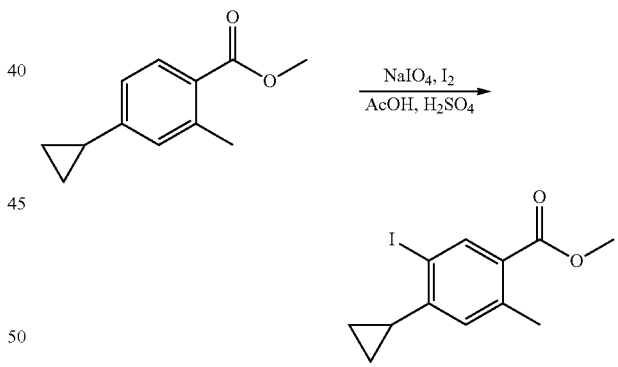

Compound 142.2. Methyl 4-cyclopropyl-5-iodo-2-methylbenzoate

To a solution of methyl 4-cyclopropyl-2-methylbenzoate (compound 142.1, 2.68 g, 13.4 mmol, 1.00 equiv, 95%) in AcOH (50 mL) were added NaIO$_4$ (1.51 g, 7.08 mmol, 0.50 equiv), (3.58 g, 14.1 mmol, 1.00 equiv), and sulfuric acid (201 mg, 2.01 mmol, 0.15 equiv, 98%). The reaction mixture was stirred at 110° C. overnight. After cooling to ambient temperature, 100 mL of water was added. The resulting mixture was diluted with 100 mL of ethyl acetate, then washed with 3×30 mL of Na$_2$S$_2$O$_3$ (aq., sat.) and 1×30 mL of brine. The organic phase was dried over anhydrous sodium sulfate and concentrated in vacuo. The residue was purified via silica gel column chromatography with ethyl acetate/petroleum ether (1/50) as eluent to yield 2.00 g (45%) of methyl 4-cyclopropyl-5-iodo-2-methylbenzoate as a colorless oil.

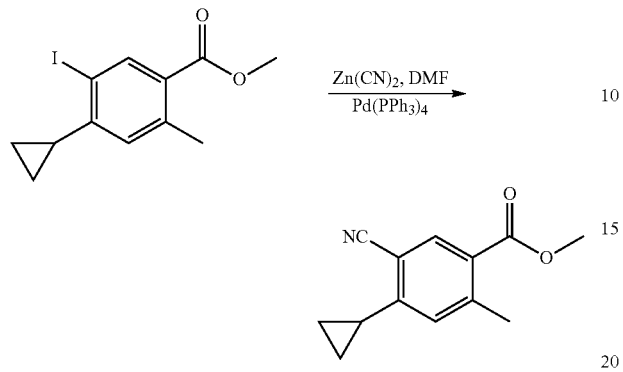

Compound 142.3. Methyl 5-cyano-4-cyclopropyl-2-methylbenzoate

To a solution of methyl 4-cyclopropyl-5-iodo-2-methylbenzoate (compound 142.2, 2.00 g, 6.01 mmol, 1.00 equiv, 95%) in DMF (16 mL) was added $Zn(CN)_2$ (890 mg, 7.58 mmol, 1.27 equiv) and $Pd(PPh_3)_4$ (731 mg, 0.630 mmol, 0.11 equiv). The resulting solution was stirred at 100° C. under nitrogen overnight. After cooling to ambient temperature, the reaction was then quenched by the addition of 100 mL of $FeSO_4$ (aq., sat.) and diluted with ethyl acetate. The resulting mixture was stirred vigorously then filtered through celite and washed with 1 M $FeSO_4$, water, and ethyl acetate. The layers were separated and the aqueous phase was extracted with 2×100 mL of ethyl acetate. The combined organic phases were dried over anhydrous sodium sulfate and concentrated in vacuo. The residue was purified via silica gel column chromatography with ethyl acetate/petroleum ether (1/50) as eluent to yield 1.10 g (81%) of methyl 5-cyano-4-cyclopropyl-2-methylbenzoate as a light yellow oil.

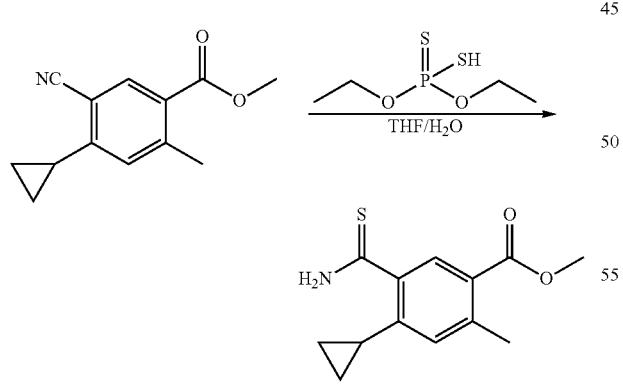

Compound 142.4. Methyl 5-carbamothioyl-4-cyclopropyl-2-methylbenzoate

To a solution of methyl 5-cyano-4-cyclopropyl-2-methylbenzoate (compound 142.3, 1.65 g, 7.28 mmol, 1.00 equiv, 95%) in a mixture of tetrahydrofuran and $H_2O$ (20 mL/5 mL) was added O,O'-diethylphosphorodithioate (3.79 g, 22.3 mmol, 2.00 equiv). The resulting mixture was stirred at 80° C. overnight (CAUTION: significant gas evolution occurs—this and all other reactions described herein should be carried out in well ventilated fume hoods). After cooling to ambient temperature, the reaction was quenched with 100 mL of water. The resulting solution was extracted with 100 mL of ethyl acetate. The combined organic layers were washed with 3×30 mL of brine, dried over anhydrous sodium sulfate, and concentrated in vacuo. The residue was purified via silica gel column chromatography with ethyl acetate/petroleum ether (1/5) as eluent to furnish 0.880 g (46%) of methyl 5-carbamothioyl-4-cyclopropyl-2-methylbenzoate as a white solid.

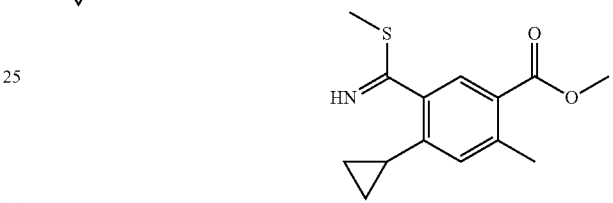

Compound 142.5. Methyl 4-cyclopropyl-2-methyl-5-(methylsulfanyl)carboximidoylbenzoate To a round-bottom flask was added a solution of methyl 5-carbamothioyl-4-cyclopropyl-2-methylbenzoate (compound 142.4, 880 mg, 3.35 mmol, 1.00 equiv, 95%) in tetrahydrofuran (10 mL). Iodomethane (1.00 g, 7.05 mmol, 2.00 equiv) was added and the resulting mixture and stirred at room temperature overnight. The mixture was then concentrated in vacuo to yield 0.800 g (86%) of methyl 4-cyclopropyl-2-methyl-5-(methylsulfanyl)carboximidoylbenzoate as a colorless liquid.

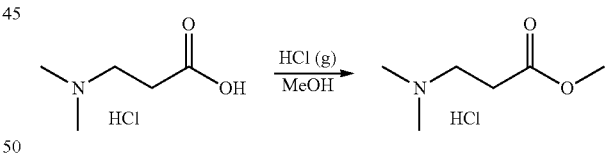

Compound 142.6. Methyl 3-(dimethylamino)propanoate hydrochloride

To a round-bottom flask was added a solution of 3-(dimethylamino)propanoic acid (2.00 g, 17.1 mmol, 1.00 equiv) in methanol (60 mL). Hydrogen chloride (g) was bubbled into the reaction mixture and the resulting solution was stirred for 4 h at 25° C. Concentration of the reaction mixture in vacuo afforded 2.00 g of title compound as a colorless oil.

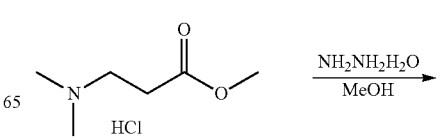

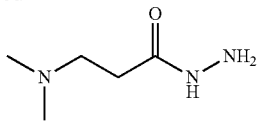

Compound 142.7. 3-(Dimethylamino)propanehydrazide

To a solution of methyl 3-(dimethylamino)propanoate hydrochloride (compound 142.6, 2.00 g, 15.3 mmol, 1.00 equiv) in methanol (40 mL) was added hydrazine hydrate (6 mL, 6.00 equiv). The reaction mixture was stirred at 70° C. for 3 h. The mixture was concentrated in vacuo and then dissolved in 50 mL of H$_2$O and washed with 2×10 mL of ethyl acetate. The aqueous layers were combined and concentrated in vacuo to afford 1.30 g (65%) of 3-(dimethylamino)propanehydrazide as a colorless oil.

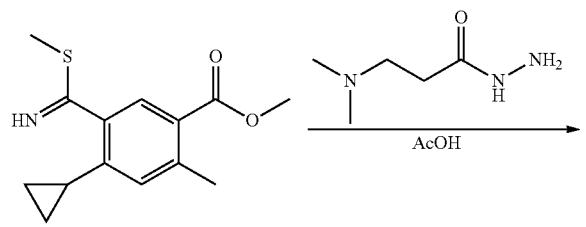

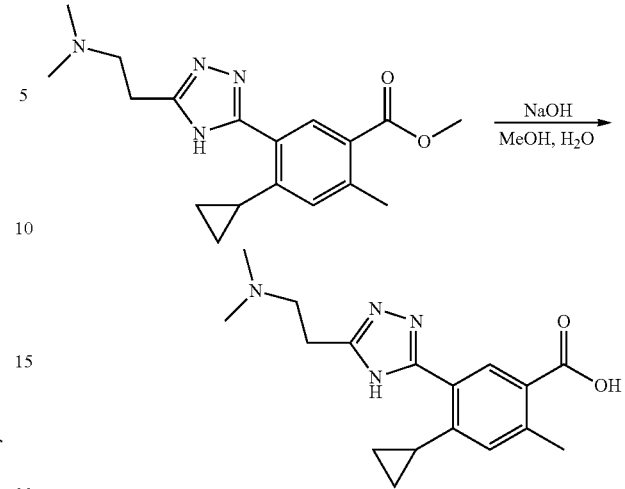

Compound 142.9. 4-Cyclopropyl-5-(5-(2-(dimethylamino)ethyl)-4H-1,2,4-triazol-3-yl)-2-methylbenzoic acid To a solution of compound 142.8 (200 mg, 0.610 mmol, 1.00 equiv) in a mixture of methanol and H$_2$O (6 mL/3 mL) was added sodium hydroxide (97.6 mg, 2.44 mmol, 4.00 equiv) in water (1 mL). After stirring at 60° C. overnight, the organic solvent was removed under reduced pressure. The residual aqueous layer was washed with 20 mL of ethyl acetate. The pH was then adjusted to 4-5 with HCl (aq., 3 M), and the resulting mixture was extracted with ethyl acetate (3×20 mL). The combined organic layers were dried (Na$_2$SO$_4$) and concentrated in vacuo to afford 280 mg (73%) of the title compound as a brown solid.

Compound 142.8. Methyl 4-cyclopropyl-5-(5-(2-(dimethylamino)ethyl)-4H-1,2,4-triazol-3-yl)-2-methylbenzoate A solution of 3-(dimethylamino)propanehydrazide (compound 142.7, 1.20 g, 9.15 mmol, 5.00 equiv) and methyl 4-cyclopropyl-2-methyl-5-(methylsulfanyl)carboximidoylbenzoate (compound 142.5, 600 mg, 2.28 mmol, 1.00 equiv) in AcOH (30 mL) was stirred at 80° C. overnight. After cooling to ambient temperature, the pH was adjusted to 8-9 with sodium hydroxide (aq., 1 M). The resulting mixture was extracted with 2×100 mL of ethyl acetate and the combined organic layers were concentrated in vacuo. The residue was purified via silica column chromatography with dichloromethane/methanol (10/1) as eluent to give 504 mg (67%) of the title compound as a white solid.

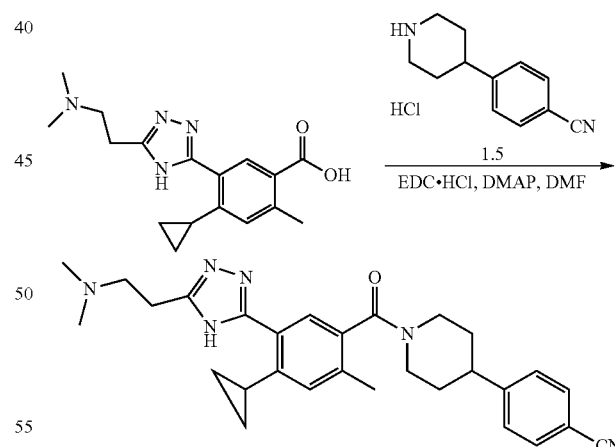

Compound 142. 4-(1-(4-Cyclopropyl-5-(5-(2-(dimethylamino)ethyl)-4H-1,2,4-triazol-3-yl)-2-methylbenzoyl)piperidin-4-yl)benzonitrile To a solution of compound 2661.9 (250 mg, 0.800 mmol, 1.00 equiv) in N,N-dimethylformamide (3 mL) were added 4-(piperidin-4-yl)benzonitrile hydrochloride (compound 1.5, 175 mg, 0.790 mmol, 1.00 equiv), EDCI (302 mg, 1.58 mmol, 2.00 equiv), and DMAP (194 mg, 1.59 mmol, 2.00 equiv). The resulting mixture was stirred at 25° C. overnight and then diluted with water. The mixture was extracted with 3×50 mL of ethyl acetate. The combined organic layers were washed with 2×20 mL of NH₄Cl (aq) and 2×20 mL of brine, dried over anhydrous sodium sulfate and concentrated in vacuo. The residue was purified via silica gel column chromatography with dichloromethane/methanol (10/1) as eluent. The product (~150 mg) was further purified by Prep-HPLC with the following conditions [(1#-Pre-HPLC-001 (SHIMADZU)): Column, Xbridge Prep C18, 5 um, 19*150 mm; mobile phase, water with 0.03% NH₃.H₂O and CH₃CN (32.0% CH₃CN up to 47.0% in 7 min, up to 100.0% in 1 min, down to 32.0% in 1 min); Detector, Waters 2489 254 & 220 nm]. The fractions containing pure compound were combined and lyophilized to yield 70.3 mg (18%) of the title compound as a white solid. m/z (ES+) 483 (M+H)⁺.

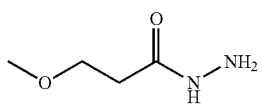

Compound 143.1. 3-Methoxypropanehydrazide

A mixture of methyl 3-methoxypropanoate (5.0 g, 42.33 mmol) and hydrazine (1.36 g, 42.33 mmol) was heated at 50° C. for two hours. The mixture was concentrated and dried under reduced pressure to give the product as a clear oil. Yield: 5.0 g, 100%. m/z (ES+) 119 (M+H)⁺. ¹H NMR (400 MHz, Chloroform-d) δ 7.86 (br, 1H), 4.05-3.71 (m, 2H), 3.63 (t, 2H), 3.34 (s, 3H), 2.42 (t, 2H).

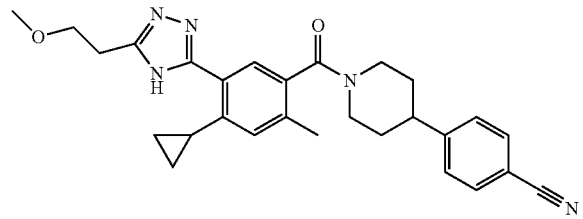 [SMILES: COCCc1nnc(-c2cc(C(=O)N3CCC(c4ccc(C#N)cc4)CC3)c(C)cc2C2CC2)[nH]1]

Compound 143. 4-(1-(4-Cyclopropyl-5-(5-(2-methoxyethyl)-4H-1,2,4-triazol-3-yl)-2-methylbenzoyl)piperidin-4-yl)benzonitrile The title compound was prepared using standard chemical manipulations and procedures similar to those used for the preparation of compound 142 and using compound 143.1 in place of 142.7. m/z (ES+) 471 (M+H)⁺.

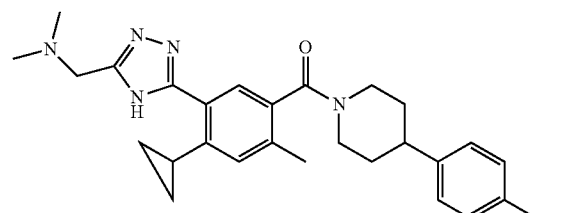

Compound 144. 4-(1-(4-Cyclopropyl-5-(5-((dimethylamino)methyl)-4H-1,2,4-triazol-3-yl)-2-methylbenzoyl)piperidin-4-yl)benzonitrile The title compound was prepared using standard chemical manipulations and procedures similar to those used for the preparation of compound 142. m/z (ES+) 469 (M+H)⁺. ¹H NMR (300 MHz, CD₃OD): δ 7.69 (d, J=6.3 Hz, 2H), 7.49 (d, J=6.0 Hz, 2H), 7.47 & 7.39 (2 singlets, amide rotamers, Ar—H, 1H), 7.03 (s, 1H), ~4.9 (1H partially obscured by water peak), 3.74 (s, 2H), 3.72-3.57 (m, 1H), 3.32-3.22 (m, 1H partially obscured by methanol solvent peak), 3.00 (t with fine structure, J=8.9 Hz, 2H), 2.49-2.27 (m, 2H), 2.10-1.98 (m, 2H), 1.93-1.51 (m, 3H), 1.05-0.90 (m, 2H), 0.79-0.64 (m, 2H).

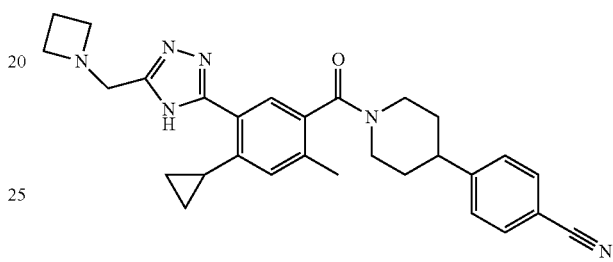

Compound 145. 4-(1-(5-(5-(Azetidin-1-ylmethyl)-4H-1,2,4-triazol-3-yl)-4-cyclopropyl-2-methylbenzoyl)piperidin-4-yl)benzonitrile The title compound was prepared using standard chemical manipulations and procedures similar to those used for the preparation of compound 142. m/z (ES+) 481 (M+H)⁺.

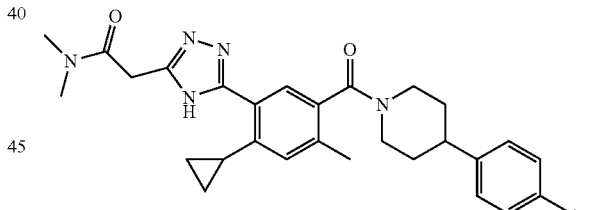

Compound 146. 2-(5-(5-(4-(4-Cyanophenyl)piperidine-1-carbonyl)-2-cyclopropyl-4-methylphenyl)-4H-1,2,4-triazol-3-yl)-N,N-dimethylacetamide The title compound was prepared using standard chemical manipulations and procedures similar to those used for the preparation of compound 142. m/z (ES+) 497 (M+H)⁺.

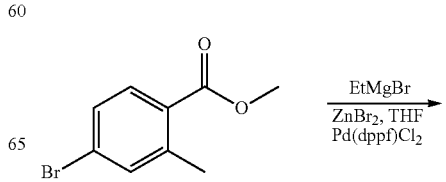

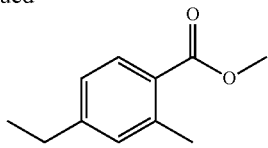

Compound 147.1. Methyl 4-ethyl-2-methylbenzoate

To a stirred mixture of ZnBr$_2$ (4.50 g, 20.0 mmol, 2.00 equiv) in tetrahydrofuran (50 mL) under nitrogen at 0° C. was added EtMgBr (6.6 mL, 2.00 equiv, 3M in THF) dropwise. After stirring for 30 min at 0° C., the temperature was lowered to −78° C. and Pd(dppf)Cl$_2$ (1.08 g, 1.48 mmol, 0.30 equiv) was added followed by a solution of methyl 4-bromo-2-methylbenzoate (compound 152.1, 2.30 g, 10.0 mmol, 1.00 equiv) in tetrahydrofuran (20 mL). The resulting mixture was stirred for 30 min at −78° C., warmed to room temperature, and stirred overnight. The reaction mixture was carefully quenched with 60 mL of NH$_4$Cl (aq.) and extracted with 3×50 mL of ethyl acetate. The combined organic phases were dried (Na$_2$SO$_4$) and concentrated in vacuo. The residue was purified using silica gel column chromatography with ethyl acetate/petroleum ether (1:100-1:5) as eluent to furnish 1.50 g (84%) of methyl 4-ethyl-2-methylbenzoate as a brown oil.

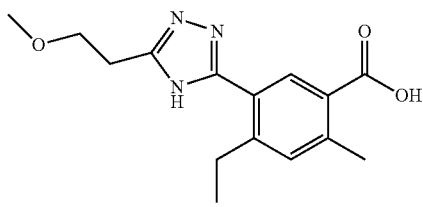 [SMILES: CCc1cc(C)c(C(=O)O)cc1-c1nnc(CCOC)[nH]1]

Compound 147.2. 4-Ethyl-5-(5-(2-methoxyethyl)-4H-1,2,4-triazol-3-yl)-2-methylbenzoic acid The title compound was prepared using standard chemical manipulations and procedures similar to those used for the preparation of compound 142.9 and using compounds 147.1 and 143.1 instead of compounds 142.1. and 142.7.

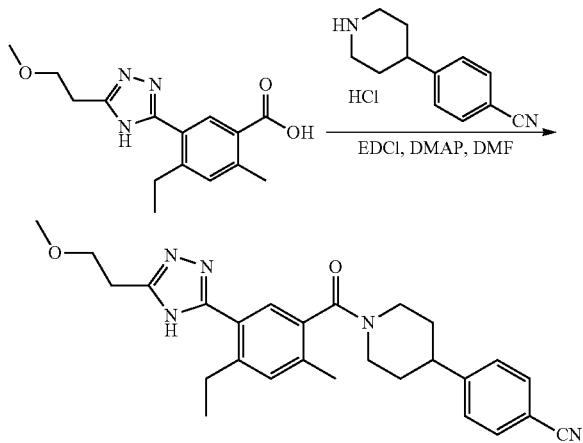

Compound 147. 4-(1-(4-Ethyl-5-(5-(2-methoxyethyl)-4H-1,2,4-triazol-3-yl)-2-methylbenzoyl)piperidin-4-yl)benzonitrile To a solution of compound (147.2, 100 mg, 0.350 mmol, 1.00 equiv) in DMF (10 mL) under nitrogen were added EDCI (132 mg, 0.690 mmol, 2.00 equiv) and DMAP (85.0 mg, 0.700 mmol, 2.00 equiv). The resulting mixture was stirred 30 min at 25° C. followed by the addition of 4-(piperidin-4-yl)benzonitrile (compound 1.5, 129 mg, 2.77 mmol, 2.00 equiv). The reaction mixture was stirred for 25 h at 25° C., then quenched with 40 mL of ice water, and extracted with 3×50 mL of ethyl acetate. The combined organic layers were washed with 1×50 mL of brine, dried over anhydrous sodium sulfate, and concentrated in vacuo. The residue was purified using silica gel column chromatography with ethyl acetate/petroleum ether (1:100-1:1) as eluent. The crude product (50 mg) was purified by Prep-HPLC with the following conditions (1#-Pre-HPLC-001 (SHIMADZU)): Column, Xbridge Prep C18, 5 um, 19*150 mm; mobile phase, water with 0.03% NH$_3$H$_2$O and CH$_3$CN (33% CH$_3$CN up to 52% in 10 min, up to 100% in 1 min, down to 33% in 1 min); Detector, Waters 2489 254 & 220 nm. The fractions containing pure compound were combined and lyophilized to yield 20.2 mg (12%) of the title compound as a white solid. m/z (ES+) 458 (M+H)$^+$.

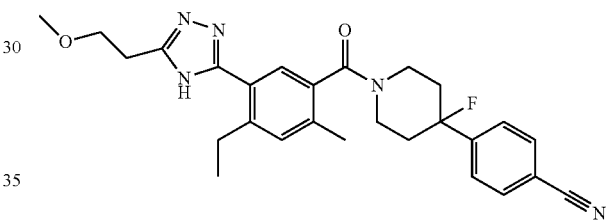

Compound 148. 4-(1-(4-ethyl-5-(5-(2-methoxyethyl)-4H-1,2,4-triazol-3-yl)-2-methylbenzoyl)-4-fluoropiperidin-4-yl)benzonitrile The title compound was prepared using standard chemical manipulations and procedures similar to those used for the preparation compound 147 and using compound 11.2 HCl salt instead compound 1.5. m/z (ES+) 476 (M+H)$^+$.

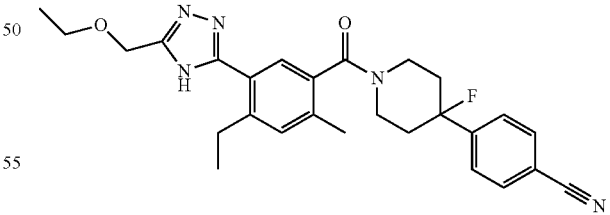

Compound 149. 4-(1-(5-(5-(Ethoxymethyl)-4H-1,2,4-triazol-3-yl)-4-ethyl-2-methylbenzoyl)-4-fluoropiperidin-4-yl)benzonitrile The title compound was prepared using standard chemical manipulations and procedures similar to those used for the preparation of compounds 147 and 148. m/z (ES+) 476 (M+H)$^+$.

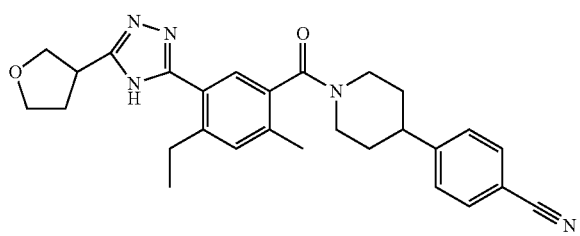 [SMILES: CCc1cc(C)c(C(=O)N2CCC(c3ccc(C#N)cc3)CC2)cc1-c1nnc(C2CCOC2)[nH]1]

Compound 150. 4-(1-(4-Ethyl-2-methyl-5-(5-(tetra-hydrofuran-3-yl)-4H-1,2,4-triazol-3-yl)benzoyl)piperidin-4-yl)benzonitrile The title compound was prepared using standard chemical manipulations and procedures similar to those used for the preparation of 4-(1-(4-ethyl-5-(5-(2-methoxyethyl)-4H-1,2,4-triazol-3-yl)-2-methylbenzoyl)piperidin-4-yl)benzonitrile (compound 147). m/z (ES+) 470 (M+H)+.

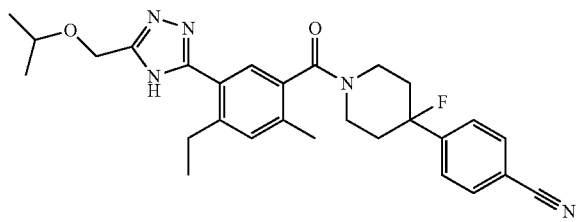 [SMILES: CCc1cc(C)c(C(=O)N2CCC(F)(c3ccc(C#N)cc3)CC2)cc1-c1nnc(COC(C)C)[nH]1]

Compound 151. 4-(1-(4-Ethyl-5-(5-(isopropoxymethyl)-4H-1,2,4-triazol-3-yl)-2-methylbenzoyl)-4-fluoropiperidin-4-yl)benzonitrile The title compound was prepared using standard chemical manipulations and procedures similar to those used for the preparation of compounds 147 and 148. m/z (ES+) 490 (M+H)+. 1H-NMR (300 MHz, CD3OD): δ 7.78 (d, 2H), 7.69-7.34 (m, 4H), 4.82-4.78 (m, 1H), 4.72 (s, 2H), 3.80 (quintet, 1H), 3.57-3.55 (m, 2H), 3.30-3.25 (m, 1H), 2.94 (q, 2H), 2.46 and 2.35 (2 singlets, amide rotamers, ArCH3, 3H), 2.35-2.1 (m, 3H), 2.0-1.95 (m, 1H), 1.30 (d, 6H), 1.14 (t, 3H).

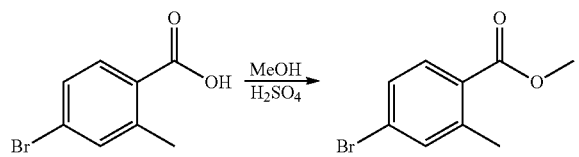

Compound 152.1. Methyl 4-bromo-2-methylbenzoate

To a solution of 4-bromo-2-methylbenzoic acid (5.11 g, 23.8 mmol, 1.0 equiv) in methanol (25 mL) was added dropwise sulfuric acid (2.0 mL) over about 3 minutes (mildly exothermic). The resulting mixture was refluxed for 4 hours. After cooling to room temperature, the reaction mixture was carefully quenched into saturated aqueous NaHCO3 (100 mL) (note—significant gas evolution) and extracted with dichloromethane (200 mL×1 then 50 mL×1). The combined organic phases were washed with a mixture of brine/saturated NaHCO3 (9:1)(50 mL), dried (Na2SO4), and concentrated under reduced pressure to obtain the title compound as a colorless oil (5.28 g, 97%). 1H NMR (400 MHz, CDCl3): δ 7.78 (d, J=8.0 Hz, 1H), 7.42 (d, J=1.6 Hz, 1H), 7.38 (dd, J=1.6 Hz, 1H), 3.89 (s, 3H), 2.58 (s, 3H).

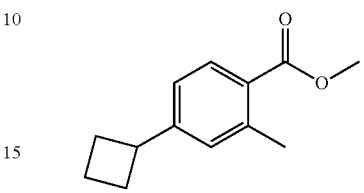

Compound 152.2. Methyl 4-cyclobutyl-2-methylbenzoate

Cyclobutylzinc(II) bromide (50 ml, 0.5 M in THF, 25.0 mmol) was added to a mixture of methyl 4-bromo-2-methylbenzoate (compound 152.1, 5.2 g, 22.7 mmol) and PdCl2(dppf)CH2Cl2 (1.85 g, 2.27 mmol). The mixture was degassed and the flask was filled with argon through a balloon. The mixture was heated at 65° C. under argon for 24 hours. The mixture was cooled to 0° C. and quenched with water (10 ml). The mixture was diluted with EtOAc (200 ml), washed with water then with brine. The EtOAc layer was dried (Na2SO4), concentrated under reduced pressure, and purified using column (silica gel) chromatography (hexanes:EtOAc 30:1 to 20:1). Yield: 4.1 g, clear oil, 89.1%. 1H NMR (400 MHz, Chloroform-d) δ 7.86 (d, 1H), 7.12-7.02 (m, 2H), 3.88 (s, 3H), 3.59-3.48 (m, 1H), 2.59 (s, 3H), 2.35 (m, 2H), 2.22-1.96 (m, 3H), 1.86-1.84 (m, 1H).

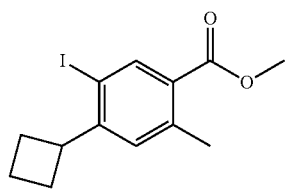 [SMILES: COC(=O)c1cc(I)c(C2CCC2)cc1C]

Compound 152.3. Methyl 4-cyclobutyl-5-iodo-2-methylbenzoate

N-Iodosuccinimide (3.52 g, 15.6 mmol) was added portionwise to a solution of methyl cyclobutyl-2-methylbenzoate (compound 152.2, 3.2 g, 15.6 mmol) in concentrated sulfuric acid (25 ml) at 0° C. The mixture was stirred at 0° C. for 30 min and at RT for 2 hours. The mixture turned very thick. The mixture was cooled to 0° C. again and MeOH (30 ml) was added. The mixture was heated at 60° C. for 2 hours. The methanol was removed under reduced pressure and the residue was poured into ice water (100 ml). The mixture was extracted with EtOAc (2×). The combined organic layers were washed with brine, then aq. 1N NaHCO3 (note-significant gas evolution), dried (Na2SO4) and concentrated. The residue was purified using column (silica gel) chromatography (hexanes:EtOAc 30:1 to 20:1). Yield: 4.17 g, light yellow oil, 81%. 1H NMR (400 MHz, Chloroform-d) δ 8.33

(s, 1H), 7.14 (s, 1H), 3.87 (s, 3H), 3.67-3.54 (m, 1H), 2.57 (s, 3H), 2.51-2.40 (m, 2H), 2.14-1.97 (m, 3H), 1.82-1.79 (m, 1H).

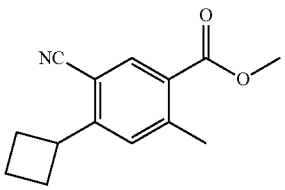 [SMILES: COC(=O)c1cc(C#N)c(C2CCC2)cc1C]

Compound 152.4. Methyl 5-cyano-4-cyclobutyl-2-methylbenzoate

A mixture of methyl 4-cyclobutyl-5-iodo-2-methylbenzoate (compound 152.3, 4.17 g, 12.64 mmol), Zn(CN)$_2$ (2.96 g, 25.21 mmol) and Pd(PPh$_3$)$_4$ (0.73 g, 0.63 mmol) in DMF (30 ml) was degassed and the flask was filled with argon through a balloon. The mixture was heated at 100° C. under argon overnight. After cooling to ambient temperature, the mixture was quenched with saturated aq. FeSO$_4$ (20 ml) and diluted with EtOAc (200 ml). The greenish solid was removed by filtration through celite. The filtrate was partitioned between water and EtOAc. The EtOAc layer was washed with brine, dried (Na$_2$SO$_4$), and concentrated. The residue was purified using column (silica gel) chromatography (hexanes:EtOAc 30:1 to 20:1). Yield: 2.55 g, white solid, 88%. $^1$H NMR (400 MHz, Chloroform-d) δ 8.16 (s, 1H), 7.28 (s, 1H), 3.90 (s, 3H), 3.86-3.82 (m, 1H), 2.68 (s, 3H), 2.55-2.45 (m, 2H), 2.27-2.04 (m, 3H), 1.89-1.87 (m, 1H).

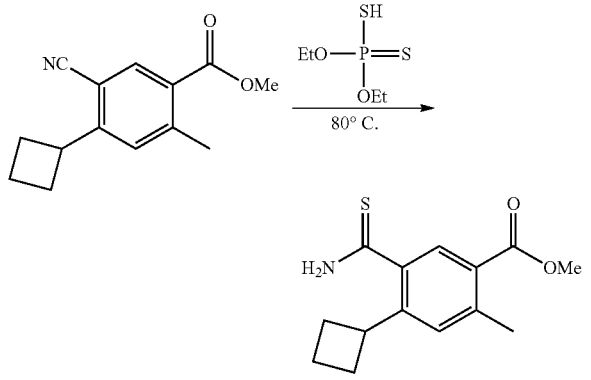

Compound 152.5. Methyl 5-carbamothioyl-4-cyclobutyl-2-methylbenzoate

To a round-bottom flask were added methyl 5-cyano-1-cyclobutyl-2-methylbenzoate (compound 152.4, 3.63 g, 0.015 mol), O,O'-diethyl dithiophosphate (10 mL) and water (1 mL). The reaction mixture was heated to 80° C. for 3 hours (CAUTION: significant gas evolution occurs—this and all other reactions described herein should be carried out in well ventilated fume hoods). After cooling to room temperature, the reaction mixture was partitioned between ethyl acetate (50 mL) and water (50 mL). The combined organic layers were washed successively with saturated aqueous NaHCO$_3$ (50 mL) and brine (50 mL), dried over Na$_2$SO$_4$, and concentrated in vacuo. Purification by SiO$_2$ flash chromatography (hexanes/ethyl acetate=80/20 to 50/50) afforded methyl 5-carbamothioyl-4-cyclobutyl-2-methylbenzoate as a yellow solid (3:06 g, 78% yield). m/z (ES+) 264 (M+H)$^+$. $^1$H NMR (400 MHz, CDCl$_3$): δ 7.93 (s, 1H), 7.82 (s, 1H), 7.26 (s, 1H), 6.92 (s, 1H), 4.19 (m, 1H), 3.89 (s, 3H), 2.64 (s, 3H), 2.40 (m, 2H), 2.29-2.15 (m, 2H), 2.12-2.00 (m, 1H), 1.95-1.84 (m, 1H).

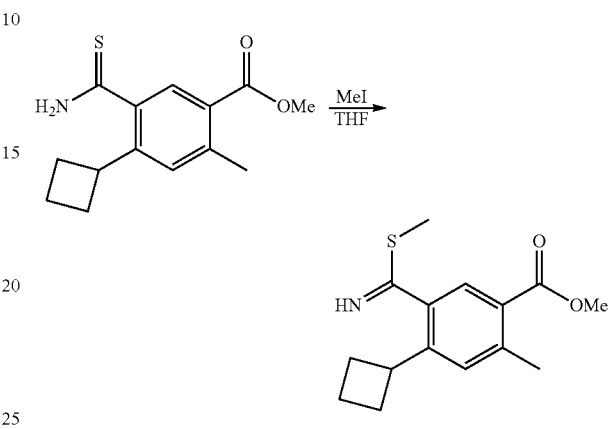

Compound 152.6. Methyl 4-cyclobutyl-5-(imino (methylthio)methyl)-2-methylbenzoate To a round-bottom flask was added methyl 5-carbamothioyl-4-cyclobutyl-2-methylbenzoate (compound 152.5, 861 mg, 3.27 mmol) in THF (10 mL). Iodomethane (912 mg, 6.42 mmol) was added dropwise and the reaction mixture was stirred at room temperature for 7 hours. The reaction mixture was concentrated in vacuo and purified by SiO$_2$ flash chromatography (ethyl acetate to ethyl acetate/methanol=95/5) to afford methyl 4-cyclobutyl-5-(imino(methylthio)methyl)-2-methylbenzoate as a yellowish oil (807 mg, 89% yield). m/z (ES+) 278 (M+H)$^+$. $^1$H NMR (400 MHz, DMSO-d$_6$): δ 7.67 (s, 1H), 7.40 (s, 1H), 3.88-3.71 (m, 4H), 2.57 (s, 3H), 2.44 (s, 3H), 2.22-2.19 (m, 2H), 2.12 (m, 2H), 1.98-1.86 (m, 1H), 1.82-1.70 (m, 1H).

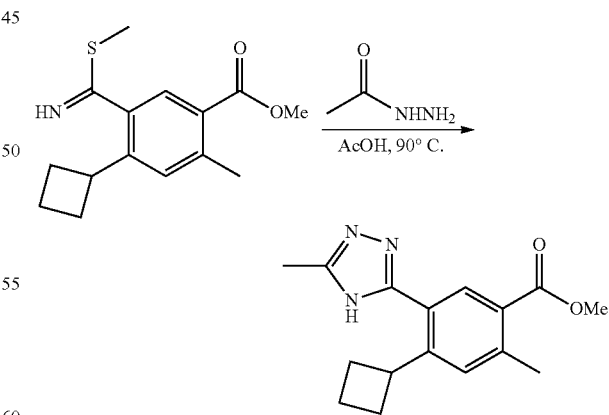

Compound 152.7. Methyl 4-cyclobutyl-2-methyl-5-(5-methyl-4H-1,2,4-triazol-3-yl)benzoate To a round-bottom flask were added methyl 4-cyclobutyl-5-(imino(methylthio)methyl)-2-methylbenzoate (compound 152.6, 556 mg, 0.002 mol) and acetohydrazide (223 mg, 0.003 mol) in 6 mL acetic acid. The reaction mixture was heated to 90° C. for 3 hours. After cooling to room temperature, the reaction mixture was partitioned between water (50 mL) and ethyl acetate (50 mL). The organic layer was washed with brine (2×50 mL), dried over Na$_2$SO$_4$, and concentrated in vacuo. Purification via SiO$_2$ flash chromatography (hexanes/ethyl acetate=50/50 to 30/70) afforded the title compound as a white solid (243 mg, 43% yield). m/z (ES+) 286 (M+H)$^+$. $^1$H NMR (400 MHz, CDCl$_3$): δ 8.23 (s, 1H), 7.32 (s, 1H), 4.24-4.05 (m, 1H), 3.89 (s; 3H), 2.69 (s, 3H), 2.54 (s, 3H), 2.23-2.20 (m, 2H), 2.16-2.05 (m, 2H), 2.05-1.88 (m, 1H), 1.88-1.71 (m, 1H).

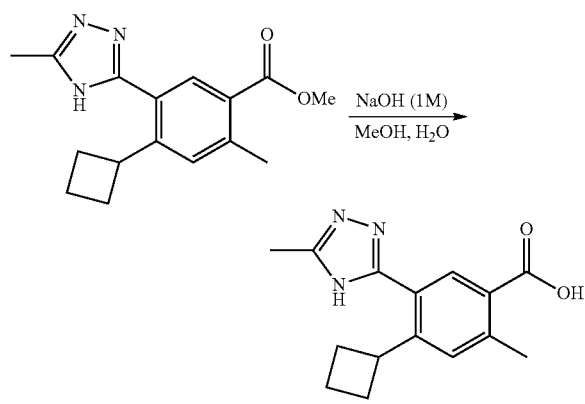

Compound 152.8. 4-Cyclobutyl-2-methyl-5-(5-methyl-4H-1,2,4-triazol-3-yl)benzoic acid To a solution of methyl 4-cyclobutyl-2-methyl-5-(5-methyl-4H-1,2,4-triazol-3-yl)benzoate (compound 152.7, 240 mg, 0.842 mmol) in methanol (5 mL) was added aqueous NaOH (6 mL, 1M). The resulting mixture was heated to 50° C. for 6 hours. After cooling to ambient temperature, the reaction mixture was acidified with 1N HCl to pH 2 and extracted with ethyl acetate (3×50 mL). The combined organic layers were washed with brine (50 mL), dried over Na$_2$SO$_4$, and concentrated in vacuo to afford 4-cyclobutyl-2-methyl-5-(5-methyl-4H-1,2,4-triazol-3-yl) benzoic acid (260 mg, quantitative) as a white solid. m/z (ES+) 272 (M+H)$^+$.

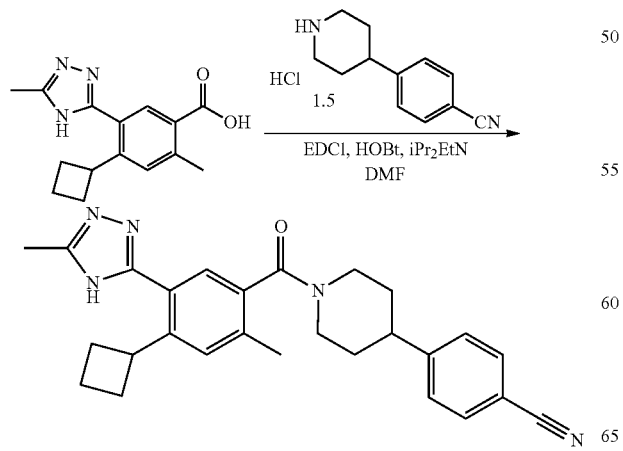

Compound 152. 4-(1-(4-Cyclobutyl-2-methyl-5-(5-methyl-4H-1,2,4-triazol-3-yl)benzoyl)piperidin-4-yl)benzonitrile To a solution of 4-cyclobutyl-2-methyl-5-(5-methyl-1,2,4-triazol-3-yl)benzoic acid (compound 152.8, 260 mg, 0.95 mmol) in DMF (4 mL) were added 4-(piperidin-4-yl) benzonitrile hydrochloride salt (compound 1.5, 232 mg, 1.045 mmol), EDC (272 mg, 1.425 mmol), HOBt (39 mg, 0.285 mmol), and DIEA (367.7 mg, 2.85 mmol). The resulting mixture was stirred at room temperature for 16 hours. The mixture was quenched with saturated aqueous NaHCO$_3$ (20 mL) and extracted with ethyl acetate (2×50 mL). The combined organic layers were washed with brine (50 mL), dried over Na$_2$SO$_4$, filtered, and concentrated in vacuo. Purification via SiO$_2$ column chromatography (dichloromethane/methanol=95/5) afforded 4-(1-(4-cyclobutyl-2-methyl-5-(5-methyl-4H-1,2,4-triazol-3-yl)benzoyl)piperidin-4-yl)benzonitrile as a white solid (193 mg, 44% yield). m/z (ES+) 440 (M+H)$^+$. $^1$H NMR (300 MHz, CD$_3$OD): δ 7.69 (d, J=5.4 Hz, 2H), 7.56-7.30 (m, 4H), 1 proton obscured by methanol solvent peak, 4.10-3.98 (m, 1H), 3.64 (t, J=10.7 Hz, 1H), 3.33-3.21 (m, 1H), 3.00 (t, J=8.9 Hz, 2H), 2.58 (s, 3H), 2.48 and 2.38 (2 singlets, amide rotamers, ArCH$_3$, 3H), 2.28-1.92 (m, 6H), 1.92-1.55 (m, 4H). $^1$H NMR (400 MHz, DMSO-d$_6$): δ 13.66 (s, 1H), 7.77 (d, J=8.0 Hz, 2H), 7.62-7.34 (m, 4H), 4.78-4.63 (m, 1H), 4.31 (br s, 1H), 3.45 (br s, 1H), 3.15 (app t, J=12.3 Hz, 1H), 2.99-2.78 (m, 2H), 2.44-1.80 (m, 12H), 1.80-1.37 (m, 4H).

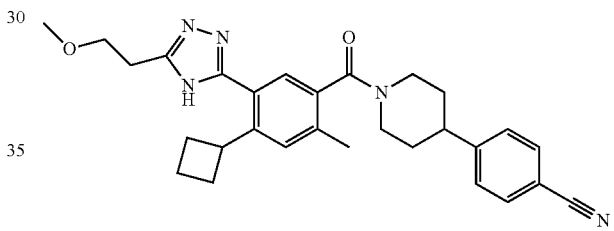

Compound 153. 4-(1-(4-Cyclobutyl-5-(5-(2-methoxyethyl)-4H-1,2,4-triazol-3-yl)-2-methylbenzoyl)piperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152), but using 3-methoxypropanehydrazide (compound 143.1) in place of acetohydrazide. m/z (ES+) 484 (M+H)$^+$, 967 (2M+H)$^+$. $^1$H NMR (400 MHz, Chloroform-d) δ 11.50-11.33 (br s, 1H), 7.66-7.44 (m, 3H), 7.33-7.27 (m, 3H), 4.98 (d, 1H), 4.24-4.12 (m, 1H), 3.78 (t, 2H), 3.70 (d, 1H), 3.44 (s, 3H), 3.14-3.03 (m, 3H), 2.90-2.75 (m, 2H), 2.42 and 2.34 (2 singlets, amide rotamers, ArCH$_3$, 3H), 2.17 (d, 2H), 2.08-1.88 (m, 3H), 1.84-1.51 (m, 5H).

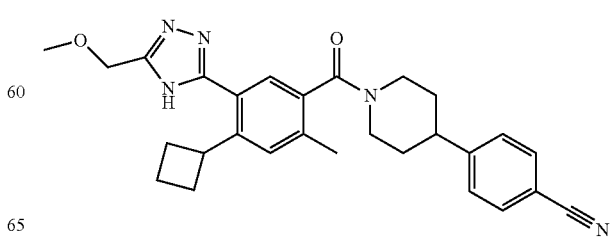

Compound 154. 4-(1-(4-Cyclobutyl-5-(5-(methoxymethyl)-4H-1,2,4-triazol-3-yl)-2-methyl-benzoyl)piperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152) but using 2-methoxyacetohydrazide (compound 190.6) in place of acetohydrazide. m/z (ES+) 470 (M+H)$^+$. $^1$H NMR (400 MHz, CDCl$_3$): δ 12.15 (br s, 1H), 7.64-7.57 (m, 2H), 7.43 & 7.33 (2 singlets, amide rotamers, Ar—H, 1H), 7.30 (d, J=8.4 Hz, 2H), 7.20 (s, 1H), 5.04-4.92 (m, 1H), 4.65 (s, 2H), 4.18-4.03 (m, 1H), 3.63 (br d, J=13.2 Hz, 1H), 3.51 (s, 3H), 3.08 (t with fine structure, J=12.8 Hz, 1H), 2.93-2.77 (m, 2H), 2.38 & 2.30 (2 singlets, amide rotamers, ArCH$_3$, 3H), 2.25-1.84 (m, 6H), 1.84-1.43 (m, 4H).

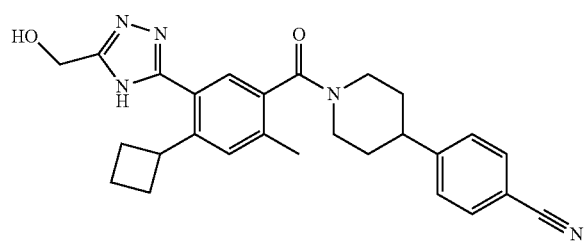 [SMILES: Cc1cc(C2CCC2)c(-c2nnc(CO)[nH]2)cc1C(=O)N1CCC(c2ccc(C#N)cc2)CC1]

Compound 155. 4-(1-(4-Cyclobutyl-5-(5-(hydroxymethyl)-4H-1,2,4-triazol-3-yl)-2-methylbenzoyl)piperidin-4-yl)benzonitrile The title compound was prepared using standard chemical manipulations and procedures similar to those used for the preparation of compound 152 but using 2-hydroxyacetohydrazide in place of acetohydrazide. m/z (ES+) 456 (M+H)$^+$.

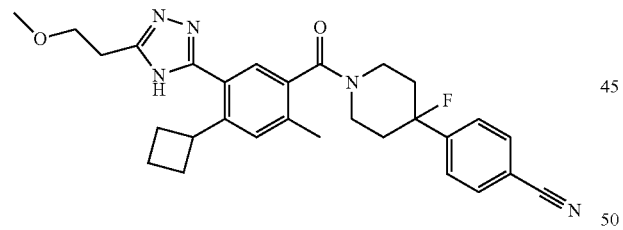

Compound 156. 4-(1-(4-Cyclobutyl-5-(5-(2-methoxyethyl)-4H-1,2,4-triazol-3-yl)-2-methylbenzoyl)-4-fluoropiperidin-4-yl)benzonitrile The title compound was prepared using standard chemical manipulations and procedures similar to those used for the preparation of 4-(1-(4-cyclobutyl-5-(5-(2-methoxyethyl)-4H-1,2,4-triazol-3-yl)-2-methylbenzoyl)piperidin-4-yl)benzonitrile (compound 153), using 4-(4-fluoropiperidin-4-yl)benzonitrile hydrochloride salt (compound 11.2 HCl salt) instead of 4-(piperidin-4-yl)benzonitrile hydrochloride salt (compound 1.5). m/z (ES+) 501.8 (M+H)$^+$. $^1$H NMR (400 MHz, CDCl$_3$): δ 11.46 (br s, 1H), 7.75-7.45 (m, 3H), 7.49 (d, J=8.4 Hz, 2H), 7.32 (s, 1H), 4.89 (br d, J=13.2 Hz, 1H), 4.28-4.15 (m, 1H), 3.79 (t, J=6.0 Hz, 2H), 3.70-3.45 (m, 2H), 3.46 (s, 3H), 3.31-3.17 (m, 1H), 3.13 (t, J=6.0 Hz, 2H), 2.45 & 2.38 (2 br singlets, amide rotamers, Ar—CH$_3$, 3H), 2.30-1.68 (m, 10H).

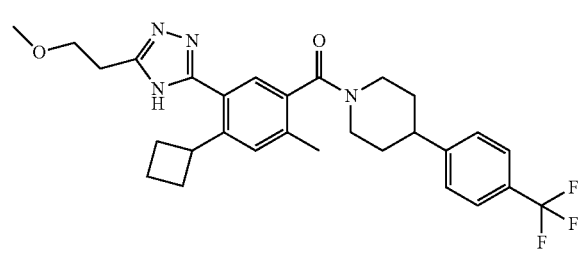 [SMILES: COCCc1nnc(-c2cc(C(=O)N3CCC(c4ccc(C(F)(F)F)cc4)CC3)c(C)cc2C2CCC2)[nH]1]

Compound 157. (4-Cyclobutyl-5-(5-(2-methoxyethyl)-4H-1,2,4-triazol-3-yl)-2-methylphenyl)(4-(4-(trifluoromethyl)phenyl)piperidin-1-yl)methanone The title compound was prepared using standard chemical manipulations and procedures similar to those used for the preparation of 4-(1-(4-cyclobutyl-5-(5-(2-methoxyethyl)-4H-1,2,4-triazol-3-yl)-2-methylbenzoyl)piperidin-4-yl)benzonitrile (compound 153), using 4-(4-(trifluoromethyl)phenyl)piperidine hydrochloride salt instead of 4-(piperidin-4-yl)benzonitrile hydrochloride salt (compound 1.5). m/z (ES+) 527 (M+H)$^+$. $^1$H NMR (400 MHz, Chloroform-d) δ 11.30-11.10 (br, 1H), 7.60-7.47 (m, 3H), 7.35-7.28 (m, 3H), 5.10-4.93 (m, 1H), 4.24-4.13 (m, 1H), 3.78 (t, 2H), 3.70 (d, 1H), 3.45 (s, 3H), 3.12 t, 2H), 3.15-3.05 (m, 1H), 2.90-2.75 (m, 2H), 2.44 and 2.35 (2 singlets, amide rotamers, ArCH$_3$, 3H), 2.25-2.13 (m, 2H), 2.13-1.85 (m, 4H), 1.87-1.66 (m, 4H).

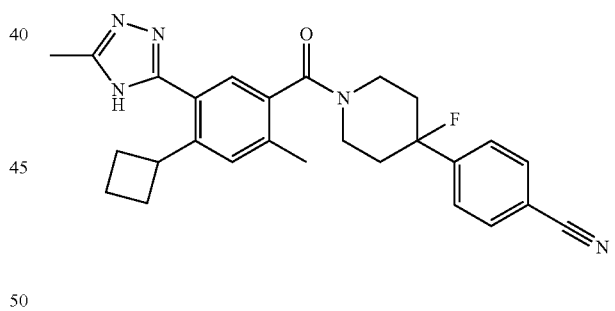

Compound 158. 4-(1-(4-Cyclobutyl-2-methyl-5-(5-methyl-4H-1,2,4-triazol-3-yl)benzoyl)-4-fluoropiperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152), using compound 11.2 HCl salt instead of compound 1.5. m/z (ES+) 458 (M+H)$^+$. $^1$H NMR (400 MHz, DMSO-d$_6$) δ 13.66 (s, 1H), 7.66 (d, 2H), 7.51 (d, 3H), 7.38 (s, 1H), 4.72 (d, 1H), 4.30 (br s, 1H), 3.46 (br s, 1H), 3.16 (dd, 1H), 3.04-2.78 (m, 2H), 2.38 and 2.36 (2 singlets, amide rotamers, ArCH$_3$, 3H), 2.35-2.27 (m, 3H), 2.22-1.82 (m, 6H), 1.81-1.56 (m, 3H).

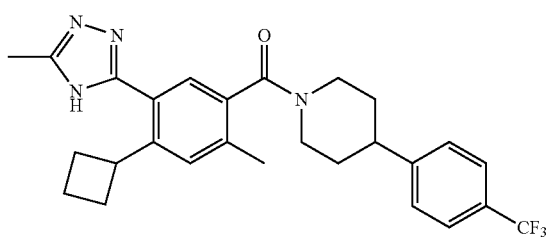 [SMILES: Cc1nnc(-c2cc(C(=O)N3CCC(c4ccc(C(F)(F)F)cc4)CC3)c(C)cc2C2CCC2)[nH]1]

Compound 159. (4-Cyclobutyl-2-methyl-5-(5-methyl-4H-1,2,4-triazol-3-yl)phenyl)(4-(4-(trifluoromethyl)phenyl)piperidin-1-yl)methanone The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 483 (M+H)$^+$.

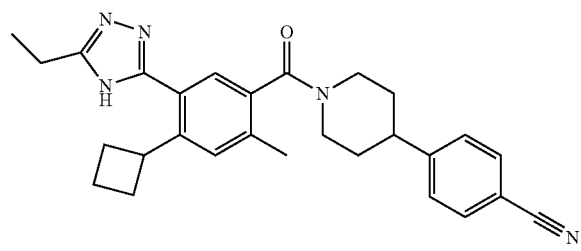 [SMILES: CCc1nnc(-c2cc(C(=O)N3CCC(c4ccc(C#N)cc4)CC3)c(C)cc2C2CCC2)[nH]1]

Compound 160. 4-(1-(4-Cyclobutyl-5-(5-ethyl-4H-1,2,4-triazol-3-yl)-2-methylbenzoyl)piperidin-4-yl)benzonitrile The title compound was prepared using standard chemical manipulations and procedures similar to those used for the preparation of compound 152 and using propionohydrazide instead of acetohydrazide. m/z (ES+) 454 (M+H)$^+$. $^1$H NMR (400 MHz, Chloroform-d) δ 7.75-7.43 (m, 3H), 7.40-7.17 (m, 3H), 5.18-4.81 (m, 1H), 4.30-3.91 (m, 1H), 3.84-3.55 (m, 1H), 3.21-2.99 (m, 1H), 2.92-2.69 (m, 4H), 2.40 and 2.32 (2 singlets, amide rotamers, ArCH$_3$, 3H), 2.25-1.84 (m, 7H), 1.83-1.42 (m, 3H), 1.32 (t, 3H).

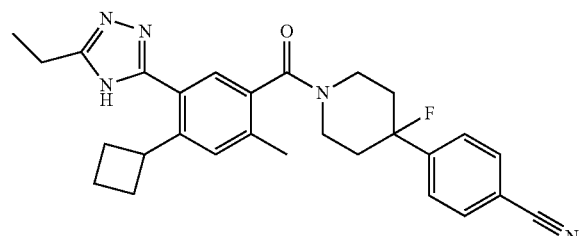

Compound 161. 4-(1-(4-Cyclobutyl-5-(5-ethyl-4H-1,2,4-triazol-3-yl)-2-methylbenzoyl)-4-fluoropiperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 472 (M+H)$^+$. $^1$H NMR (400 MHz, Chloroform-d) δ 7.79-7.57 (m, 2H), 7.57-7.18 (m, 4H), 4.86 (dd, 1H), 4.14 (s, 1H), 3.62-3.40 (m, 4H), 3.22 (t, 1H), 2.77 (q, 2H), 2.31 & 2.41 (2 singlets, amide rotamers, 3H), 2.29-1.47 (m, 8H), 1.30 (t, 3H).

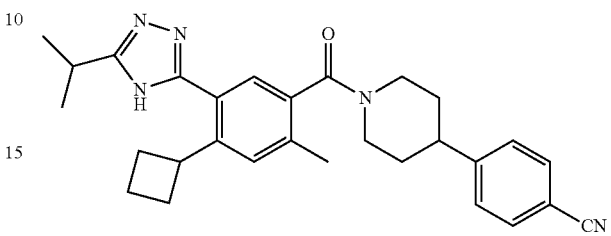

Compound 162. 4-(1-(4-Cyclobutyl-5-(5-isopropyl-4H-1,2,4-triazol-3-yl)-2-methylbenzoyl)piperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 468 (M+H)$^+$. $^1$H NMR (400 MHz, DMSO-d$^6$) δ 13.67 (s, 1H), 7.77 (d, 2H), 7.49-7.47 (m, 3H), 7.36 (s, 1H), 4.72 (d, 1H), 4.29 (s, 1H), 3.46 (d, 1H), 3.12 (m, 2H), 2.98-2.75 (m, 2H), 2.31 (d, 3H), 2.23-1.81 (m, 6H), 1.83-1.36 (m, 4H), 1.31 (d, 6H).

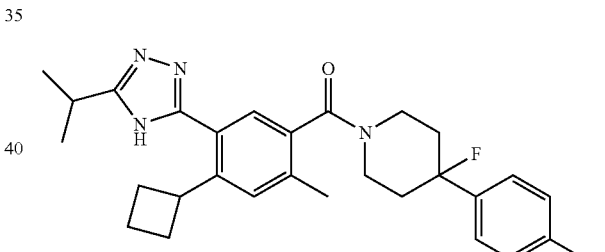

Compound 163. 4-(1-(4-Cyclobutyl-5-(5-isopropyl-4H-1,2,4-triazol-3-yl)-2-methylbenzoyl)-4-fluoropiperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 486 (M+H)$^+$.

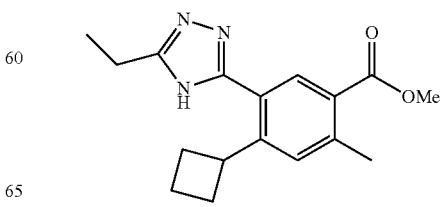

Compound 164.1. 4-(1-(4-Cyclobutyl-5-(5-isopropyl-4H-1,2,4-triazol-3-yl)-2-methylbenzoyl)-4-fluoropiperidin-4-yl)benzonitrile The title compound was prepared using standard chemical manipulations and procedures similar to those used for the preparation of compound 152.7 and using propionohydrazide instead of acetohydrazide.

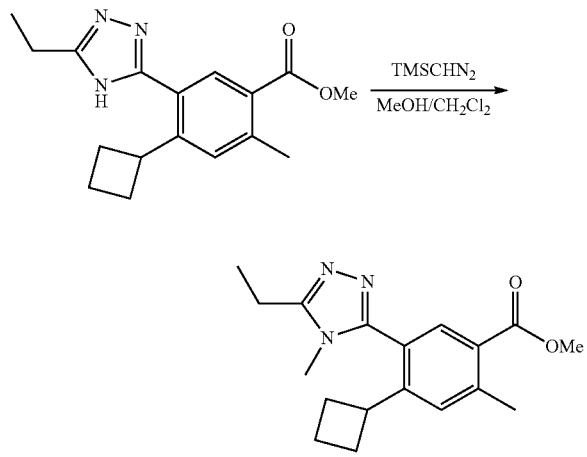 [SMILES: CCc1nnc(-c2cc(C(=O)OC)c(C)cc2C2CCC2)[nH]1 ; CCc1nnc(-c2cc(C(=O)OC)c(C)cc2C2CCC2)n1C]

Compound 164.2. Methyl 4-cyclobutyl-5-(5-ethyl-N-methyl-4H-1,2,4-triazol-3-yl)-2-methylbenzoate Methyl 4-cyclobutyl-5-(5-ethyl-4H-1,2,4-triazol-3-yl)-2-methylbenzoate (compound 164.1, 87 mg, 0.29 mmol) was dissolved in methanol and dichloromethane (1:1 v/v) (6 ml). ((Trimethylsilyl)methyl)diazomethane (2.0 M in ether) (220 ul, 0.44 mmol) was added. The mixture was stirred for 16 hours and quenched with HOAc (300 ul). The volatiles were removed in vacuo to afford an oil (85 mg). The residue was carried as crude onto the next step without further purification. m/z (ES+) 314 (M+H)+.

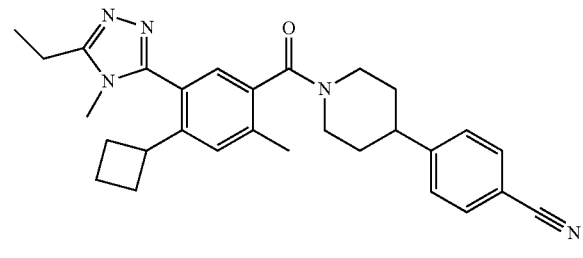 [SMILES: CCc1nnc(-c2cc(C(=O)N3CCC(c4ccc(C#N)cc4)CC3)c(C)cc2C2CCC2)n1C]

Compound 164. 4-(1-(4-Cyclobutyl-5-(5-ethyl-N-methyl-4H-1,2,4-triazol-3-yl)-2-methylbenzoyl)piperidin-4-yl)benzonitrile The title compound (mixture of N-methyl isomers) was prepared using standard chemical manipulations and procedures similar to those used for preparation of compound 152 and using compound 164.2 instead of compound 152.7. m/z (ES+) 468 (M+)+.

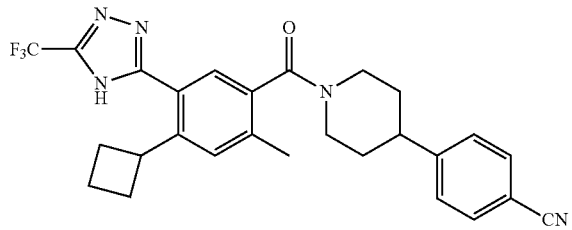 [SMILES: Cc1cc(C2CCC2)c(-c2nnc(C(F)(F)F)[nH]2)cc1C(=O)N1CCC(c2ccc(C#N)cc2)CC1]

Compound 165. 4-(1-(4-Cyclobutyl-2-methyl-5-(5-(trifluoromethyl)-4H-1,2,4-triazol-3-yl)benzoyl)piperidin-4-yl)benzonitrile The title compound was prepared using standard chemical manipulations and procedures similar to those used for preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 494.0 (M+H)+.

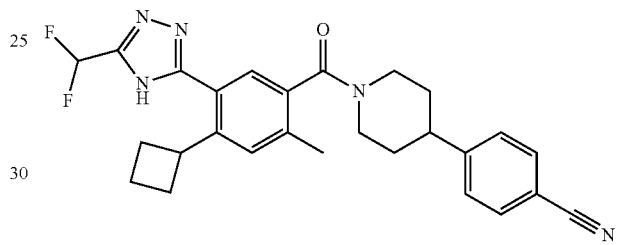

Compound 166. 4-(1-(4-Cyclobutyl-5-(5-(difluoromethyl)-4H-1,2,4-triazol-3-yl)-2-methylbenzoyl)piperidin-4-yl)benzonitrile The title compound was prepared using standard chemical manipulations and procedures similar to those used for preparation of 4-(1-(4-cyclobutyl-2-methyl-5-(5-methyl-4H-1,2,4-triazol-3-yl)benzoyl)piperidin-4-yl)benzonitrile (compound 152). m/z (ES+) 476 (M+H)+.

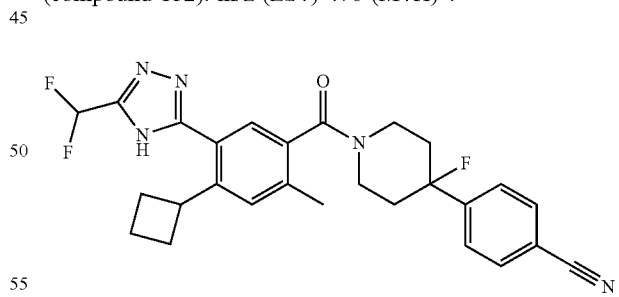

Compound 167. 4-(1-(4-Cyclobutyl-5-(5-(difluoromethyl)-4H-1,2,4-triazol-3-yl)-2-methylbenzoyl)-4-fluoropiperidin-4-yl)benzonitrile The title compound was prepared using standard chemical manipulations and procedures similar to those used for preparation of 4-[1-[4-cyclobutyl-2-methyl-5-(5-methyl-4H-1,2,4-triazol-3-yl)benzoyl]-4-piperidyl]benzonitrile (compound 152). m/z (ES+) 494 (M+H)+.

Compound 168.1. Methyl 4-cyclobutylbenzoate

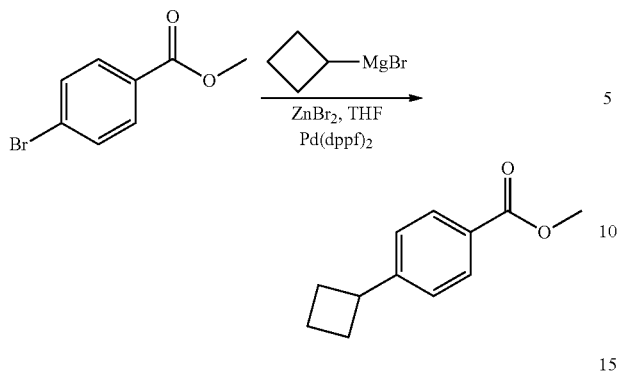

To a stirred mixture of ZnBr$_2$ (83.0 g, 368.53 mmol, 4.00 equiv) in THF (500 mL) under nitrogen at 0° C. was added a solution of bromo(cyclobutyl)magnesium (242 mL, 364 mmol, 1.5 M in THF) dropwise during 20 min. To the resulting mixture were added Pd(dppf)Cl$_2$ (2.00 g, 0.10 equiv) and methyl 4-bromobenzoate (20 g, 93.00 mmol, 1.00 equiv) at −40° C. The resulting mixture was stirred at −40° C. for 1 h under nitrogen, and then carefully quenched with 500 mL of NH$_4$Cl (aq., sat.). The mixture was extracted with 3×500 mL of ethyl acetate. The combined organic layers were washed with 3×500 mL of brine, then dried over anhydrous sodium sulfate, and concentrated under reduced pressure to yield 18.0 g (crude) of the title compound as a light yellow oil.

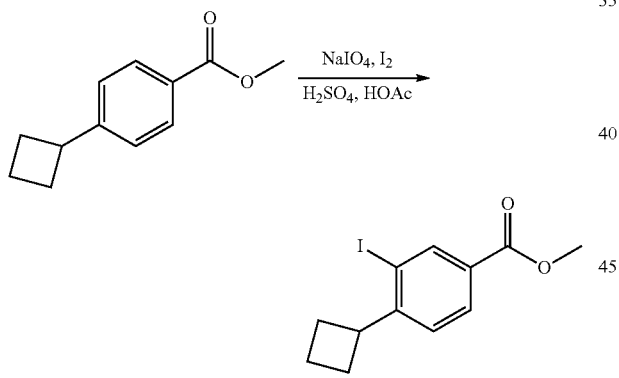

Compound 168.2. Methyl 4-cyclobutyl-3-iodobenzoate

To a solution of methyl 4-cyclobutylbenzoate (168.1, 2.00 g, 10.5 mmol, 1.00 equiv) in acetic acid (30 mL) were carefully added sodium periodate (1.00 g, 4.68 mmol, 0.50 equiv), iodine (3.00 g, 11.8 mmol, 1.10 equiv) and sulfuric acid (0.15 g, 0.15 equiv). The resulting mixture was stirred overnight at 100° C. After cooling to room temperature, the reaction was then quenched by carefully adding 30 mL of Na$_2$S$_2$O$_3$ (aq., sat.) and the resulting mixture was extracted with 3×20 mL of ethyl acetate. The combined organic layers were washed with 3×20 mL of brine, dried over anhydrous sodium sulfate, and concentrated under reduced pressure to yield 1.50 g (45%) of the title compound as a yellow oil.

Compound 168.3. Methyl 3-cyano-4-cyclobutylbenzoate

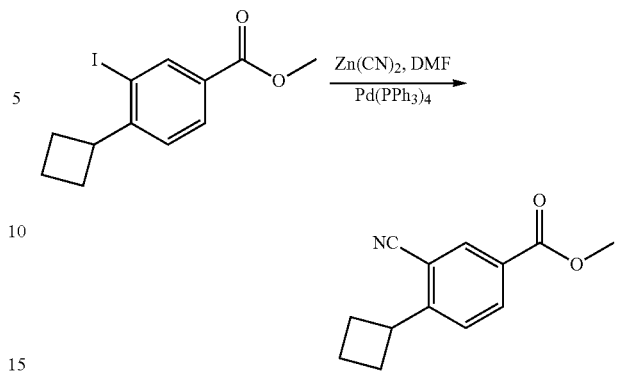

The title compound (2.60 g (95%), white solid) was prepared using standard chemical manipulations and a procedure similar to that used for the preparation of compound 152.4 and using compound 168.2 (4.00 g, 12.7 mmol) in place of compound 152.3.

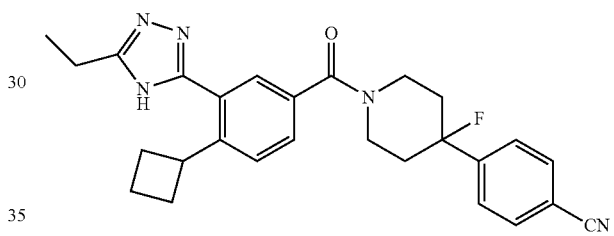

Compound 168. 4-(1-(4-Cyclobutyl-3-(5-ethyl-4H-1,2,4-triazol-3-yl)benzoyl)-4-fluoropiperidin-4-yl)benzonitrile The title compound was prepared using procedures similar to those used for preparation of compound 152 and using 168.3 in place of 152.4. m/z (ES+) 458 (M+H)$^+$.

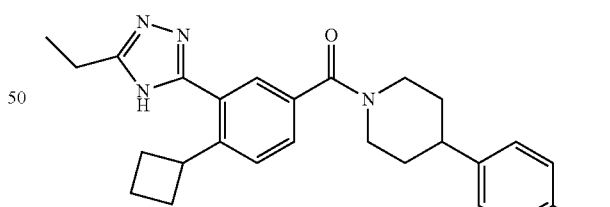

Compound 169. 4-(1-(4-Cyclobutyl-3-(5-ethyl-4H-1,2,4-triazol-3-yl)benzoyl)piperidin-4-yl)benzonitrile The title compound was prepared using procedures similar to those used for preparation of compound 152 and using 168.3 in place of 152.4. m/z (ES+) 440 (M+H)$^+$. $^1$H NMR (300 MHz, CD$_3$OD) δ 7.88 (d, 2H), 7.67-7.50 (m, 3H), 7.47 (d, 2H), 4.89-4.75 (m, 1H), 4.25-3.73 (m, 2H), 3.35-3.25 (m, 1H), 3.16-2.75 (m, 4H), 2.30-1.94 (m, 6H), 1.93-1.56 (m, 4H), 1.51-1.32 (m, 3H).

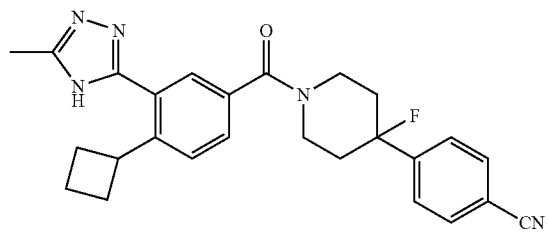 [SMILES: Cc1nnc(-c2cc(C(=O)N3CCC(F)(c4ccc(C#N)cc4)CC3)ccc2C2CCC2)[nH]1]

Compound 170. 4-(1-(4-Cyclobutyl-3-(5-methyl-4H-1,2,4-triazol-3-yl)benzoyl)-4-fluoropiperidin-4-yl)benzonitrile The title compound was prepared using procedures similar to those used for preparation of compound 152 and using compounds 168.3 and 11.2 HCl salt in place of compounds 152.4 and 1.5 respectively. m/z (ES+) 444 (M+H)+.

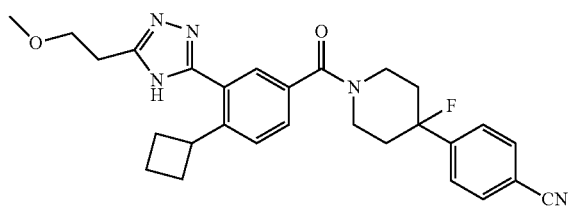 [SMILES: COCCc1nnc(-c2cc(C(=O)N3CCC(F)(c4ccc(C#N)cc4)CC3)ccc2C2CCC2)[nH]1]

Compound 171. 4-(1-(4-Cyclobutyl-3-(5-(2-methoxyethyl)-4H-1,2,4-triazol-3-yl)benzoyl)-4-fluoropiperidin-4-yl)benzonitrile The title compound was prepared using procedures similar to those used for preparation of compounds 152 and 156 and using 168.3 in place of 152.4. m/z (ES+) 488 (M+H)+.

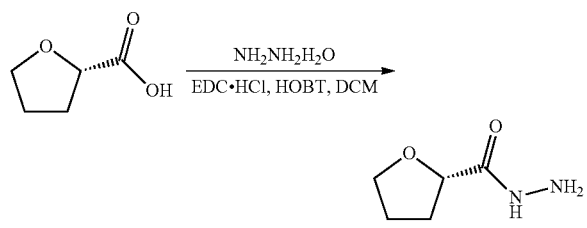

Compound 172.1.
(S)-Tetrahydrofuran-2-carbohydrazide

To a round-bottom flask was added a solution of (S)-tetrahydrofuran-2-carboxylic acid (3.00 g, 25.8 mmol, 1.00 equiv) in dichloromethane (40 mL). EDC·HCl (7.50 g, 39.1 mmol, 1.50 equiv), HOBT (5.20 g, 38.5 mmol, 1.50 equiv), and hydrazine hydrate (2 mL, 2.00 equiv, 99%) were added to the reaction. The resulting solution was stirred overnight at room temperature. The solids were removed by filtration and the filtrate was concentrated in vacuo to furnish 5.38 g (80%) of the title compound as a yellow oil.


Compound 172. (S)-4-(1-(4-Cyclobutyl-2-methyl-5-(5-(tetrahydrofuran-2-yl)-4H-1,2,4-triazol-3-yl)benzoyl)piperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152), using (S)-tetrahydrofuran-2-carbohydrazide (compound 172.1) in place of acetohydrazide. m/z (ES+) 496 (M+H)+.


Compound 173. (S)-4-(1-(4-Cyclobutyl-2-methyl-5-(5-(tetrahydrofuran-2-yl)-4H-1,2,4-triazol-3-yl)benzoyl)-4-fluoropiperidin-4-yl)benzonitrile The title compound was prepared using procedures similar to those used for the preparation of compound 172 and using compound 11.2 HCl salt in place of compound 1.5. m/z (ES+) 514 (M+H)+.

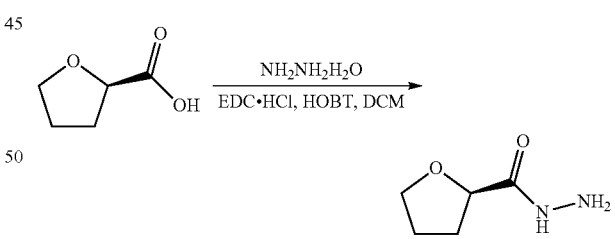

Compound 174.1.
(R)-Tetrahydrofuran-2-carbohydrazide

To a round-bottom flask was added a solution of (R)-tetrahydrofuran-2-carboxylic acid (3.00 g, 25.8 mmol, 1.00 equiv) in dichloromethane (60 mL). EDC·HCl (7.37 g, 38.5 mmol, 1.50 equiv), HOBt (5.24 g, 38.8 mmol, 1.50 equiv), and hydrazine hydrate (2.60 g, 51.9 mmol, 2.00 equiv) were added to the reaction. The resulting solution was stirred overnight at 25° C. The solids were removed with filtration. The filtrate was concentrated in vacuo to yield 2.00 g (59%) of (R)-tetrahydrofuran-2-carbohydrazide as a yellow oil.

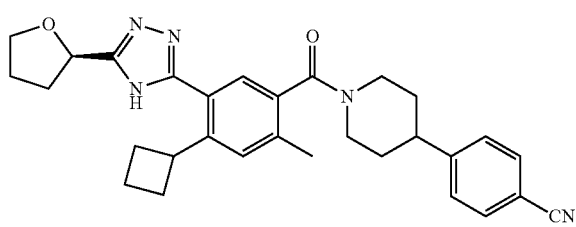 [SMILES: Cc1cc(C2CCC2)c(-c2nnc([C@H]3CCCO3)[nH]2)cc1C(=O)N1CCC(c2ccc(C#N)cc2)CC1]

Compound 174, (R)-4-(1-(4-Cyclobutyl-2-methyl-5-(5-(tetrahydrofuran-2-yl)-4H-1,2,4-triazol-3-yl)benzoyl)piperidin-4-yl)benzonitrile The title compound was prepared using standard chemical manipulations and procedures similar to those used for the preparation of 4-(1-(4-cyclobutyl-2-methyl-5-(5-methyl-4H-1,2,4-triazol-3-yl)benzoyl)piperidin-4-yl)benzonitrile (compound 152), using (R)-tetrahydrofuran-2-carbohydrazide (compound 174.1) in place of acetohydrazide. m/z (ES+) 496 (M+H)+. $^1$H NMR (300 MHz, CD$_3$OD) δ 7.70 (d, 2H), 7.49-7.41 (m, 4H), 5.15 (t, 1H), 4.89-4.80 (m, 1H), 4.14-3.92 (m, 3H), 3.65-3.51 (m, 1H), 3.33-3.27 (m, 1H), 3.03-2.95 (m, 2H), 2.47-2.37 (m, 4H), 2.24-1.91 (m, 9H), 1.83-1.71 (m, 4H).

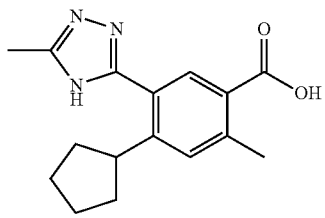 [SMILES: Cc1nnc(-c2cc(C(=O)O)c(C)cc2C2CCCC2)[nH]1]

Compound 175.1. 4-Cyclopentyl-2-methyl-5-(5-methyl-4H-1,2,4-triazol-3-yl)benzoic acid The title compound was synthesized using standard chemical manipulations and procedures similar to those used for the preparation of compound 152.8 and using bromo(cyclopentyl)magnesium in place of bromo(cyclobutyl)magnesium.

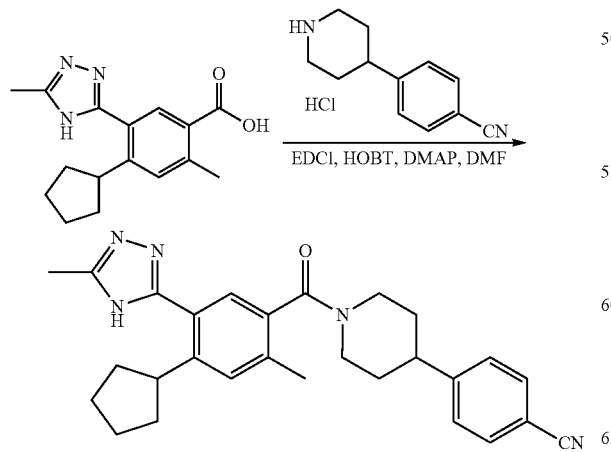

Compound 175. 4-(1-(4-Cyclopentyl-2-methyl-5-(5-methyl-4H-1,2,4-triazol-3-yl)benzoyl)piperidin-4-yl)benzonitrile The title compound was synthesized using a procedure similar to that used for the preparation of compound 152 and using compound 175.1 in place of compound 152.8. m/z (ES+) 495 (M+H)+.

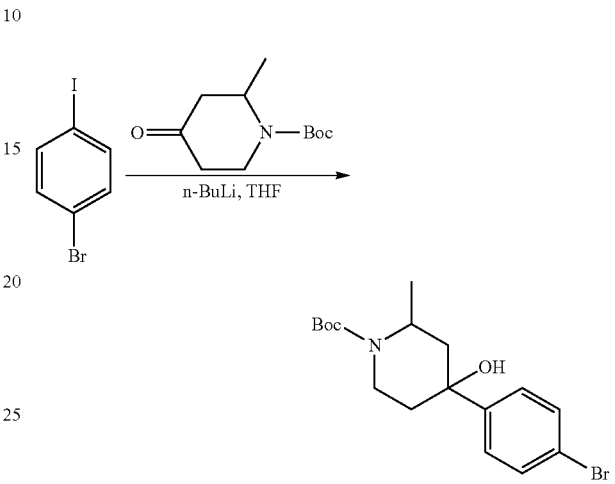

Compound 176.1. tert-Butyl 4-(4-bromophenyl)-4-hydroxy-2-methylpiperidine-1-carboxylate The title compound was synthesized using a procedure similar to that used for the preparation of compound 1.1 and using tert-butyl 2-methyl-4-oxopiperidine-1-carboxylate in place of tert-butyl 4-oxopiperidine-1-carboxylate.

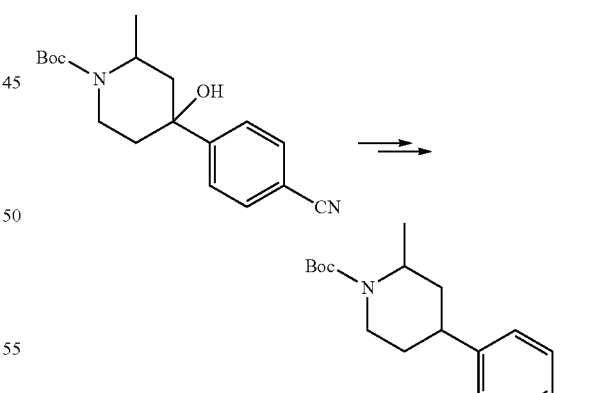

Compound 176.2. tert-Butyl 4-(4-cyanophenyl)-2-methylpiperidine-1-carboxylate

The title compound was synthesized using procedures similar to those used for the preparation of compound 1.4 and using compound 176.1 in place of compound 1.1.

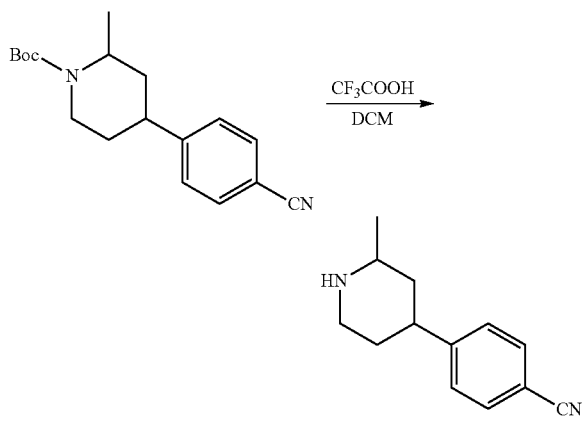

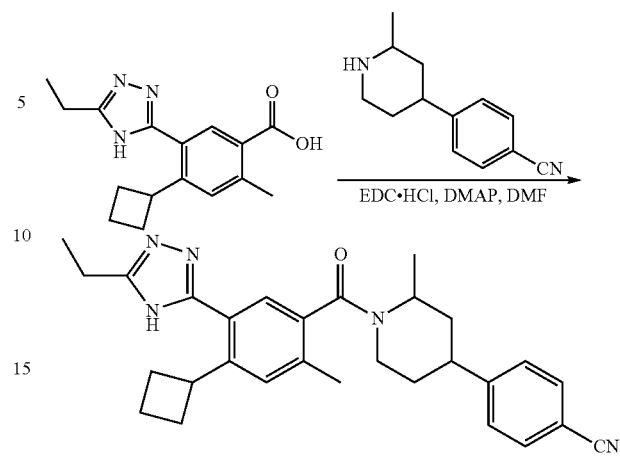

Compound 176.3.
4-(2-Methylpiperidin-4-yl)benzonitrile

To a solution of tert-butyl 4-(4-cyanophenyl)-2-methyl-piperidine-1-carboxylate (compound 176.2, 500 mg, 1.50 mmol, 1.00 equiv, 90%) in dichloromethane (3 mL) was added TFA dropwise (1 mL). The resulting mixture was stirred for 1.5 h at room temperature, then diluted with 30 mL of dichloromethane. The resulting mixture was washed with sodium bicarbonate (aq., 1 M. Note: significant gas evolution). The aqueous phase was extracted with 2×50 mL of dichloromethane and the combined organic layers were dried ($Na_2SO_4$), and concentrated in vacuo. The residue was purified using silica gel column chromatography with methanol/dichloromethane (1:50-1:20) as eluent to yield 280 mg (93%) of 4-(2-methylpiperidin-4-yl)benzonitrile as a colorless oil.

Compound 176. 4-(1-(4-Cyclobutyl-5-(5-ethyl-4H-1,2,4-triazol-3-yl)-2-methylbenzoyl)-2-methylpiperidin-4-yl)benzonitrile To a round-bottom flask was added a solution of 4-(2-methylpiperidin-4-yl)benzonitrile (compound 176.3, 210 mg, 0.940 mmol, 1.00 equiv, 90%) in N,N-dimethylformamide (2 mL). EDC·HCl (404 mg, 2.11 mmol, 2.00 equiv), 4-dimethylaminopyridine (257 mg, 2.10 mmol, 2.00 equiv), and 4-cyclobutyl-5-(5-ethyl-4H-1,2,4-triazol-3-yl)-2-methylbenzoic acid (compound 176.4, 300 mg, 1.05 mmol, 1.00 equiv) were added to the reaction mixture. The resulting solution was stirred for 4 h at 25° C., then diluted with 50 mL of ethyl acetate. The resulting mixture was washed with 2×30 mL of $NH_4Cl$ (aq., sat.) and 2×30 mL of brine, dried over anhydrous sodium sulfate, and concentrated in vacuo. The residue was purified using silica gel column chromatography with dichloromethane/methanol (20:1) as eluent. The crude product (~20 mg) was further purified by Prep-HPLC with the following conditions (1#-Pre-HPLC-001 (SHIMADZU)): Column, SunFire Prep C18, 19*150 mm 5 um; mobile phase, water with 0.05% TFA and $CH_3CN$ (48% $CH_3CN$ up to 49% in 8 min, up to 100% in 3 min, down to 48% in 2 min); Detector, Waters 2489 254 & 220 nm. The fractions containing pure compound were combined and lyophilized to yield 3.8 mg (1%) of the title compound as a white solid. m/z (ES+) 468 (M+H)+.

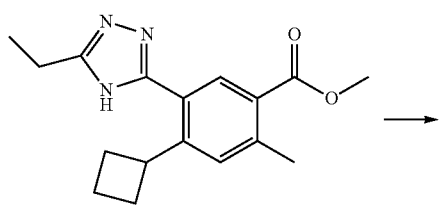

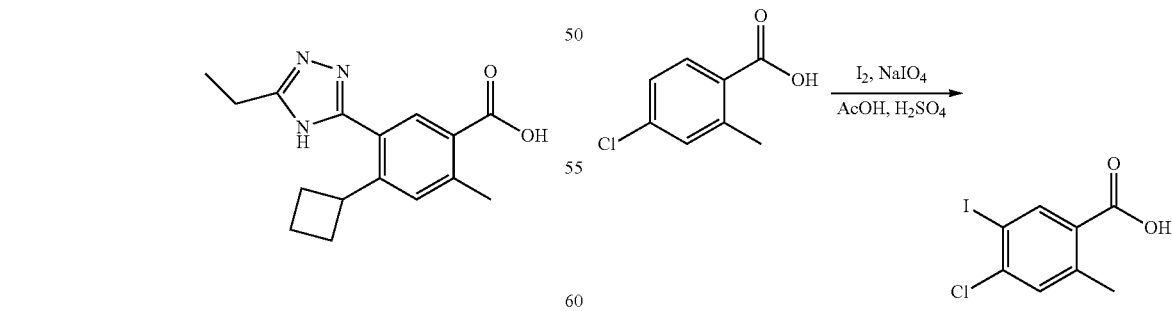

Compound 176.4. tert-Butyl 4-(4-cyanophenyl)-2-methylpiperidine-1-carboxylate The title compound was synthesized using a procedure similar to that used for the preparation of compound 152.8 and using compound 164.1 in place of compound 152.7.

Compound 177.1. 4-Chloro-5-iodo-2-methylbenzoic acid

To a round-bottom flask was added a solution of 4-chloro-2-methylbenzoic acid (30.0 g, 176 mmol, 1.00 equiv) in acetic acid (300 mL). NaIO₄ (19.0 g, 88.8 mmol, 0.50 equiv), I₂ (49.0 g, 193 mmol, 1.10 equiv), and sulfuric acid (3 mL) were added to the reaction. The resulting mixture was stirred overnight at 110° C. After cooling to ambient temperature, the reaction was carefully quenched with 500 mL of Na₂S₂O₃ (aq., sat.). The resulting solids were collected by filtration and then dissolved in 500 mL of ethyl acetate. The organic phase was washed with 2×200 mL of brine, dried over anhydrous sodium sulfate, and concentrated under reduced pressure. This resulted in 20.0 g (38%) of 4-chloro-5-iodo-2-methylbenzoic acid as a white solid.

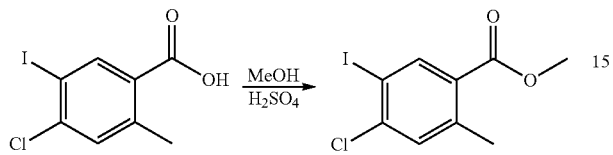

Compound 177.2. Methyl 4-chloro-5-iodo-2-methylbenzoate

To a solution of 4-chloro-5-iodo-2-methylbenzoic acid (compound 177.1, 20.0 g, 67.5 mmol, 1.00 equiv) in methanol (100 mL) was added sulfuric acid (5 mL) dropwise. The resulting mixture was stirred overnight at 75° C. After cooling to ambient temperature, the methanol was removed under reduced pressure. The pH value of the remaining aqueous layer was carefully adjusted to 7 with sodium bicarbonate (aq., 1 M. Note: significant gas evolution). The aqueous phase was extracted with 2×200 mL of ethyl acetate and the combined organic layers were washed with 2×100 mL of brine, dried over anhydrous sodium sulfate and concentrated under vacuum. The residue was purified using silica gel column chromatography with ethyl acetate/petroleum ether (1:50) as eluent to furnish 20.0 g (95%) of methyl 4-chloro-5-iodo-2-methylbenzoate as a light yellow liquid.

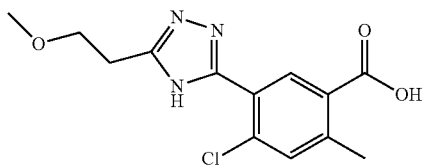 [SMILES: COCCc1nnc(-c2cc(C(=O)O)c(C)cc2Cl)[nH]1]

Compound 177.3. 4-Chloro-5-(5-(2-methoxyethyl)-4H-1,2,4-triazol-3-yl)-2-methylbenzoic acid The title compound was prepared using standard chemical manipulations and procedures similar to those used for the preparation of compound 152.8 but using compounds 177.2 and 143.1 instead of compound 152.3 and acetohydrazide respectively.

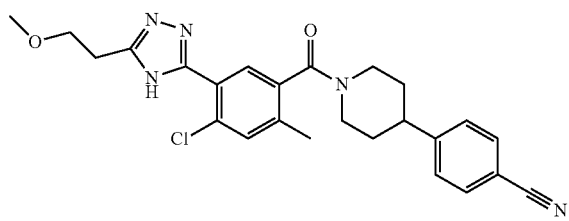 [SMILES: COCCc1nnc(-c2cc(C(=O)N3CCC(c4ccc(C#N)cc4)CC3)c(C)cc2Cl)[nH]1]

Compound 177. 4-(1-(4-Chloro-5-(5-(2-methoxyethyl)-4H-1,2,4-triazol-3-yl)-2 methylbenzoyl)piperidin-4-yl)benzonitrile The title compound was prepared using standard chemical manipulations and procedures similar to those used for the preparation of compound 152 but using compound 177.3 instead of compound 152.8. m/z (ES+) 464 (M+H)⁺.

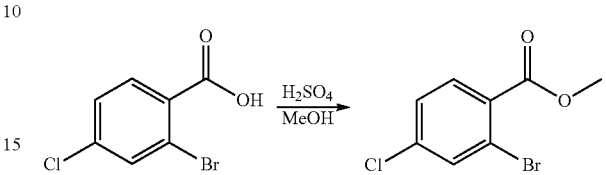

Compound 178.1. 2-Bromo-4-chlorobenzoate

The title compound (17.0 g light yellow solid, 80%) was prepared using a procedure similar to that used for the preparation of compound 177.2 but using 2-bromo-4-chlorobenzoic acid (20.0 g) in place of compound 177.1.

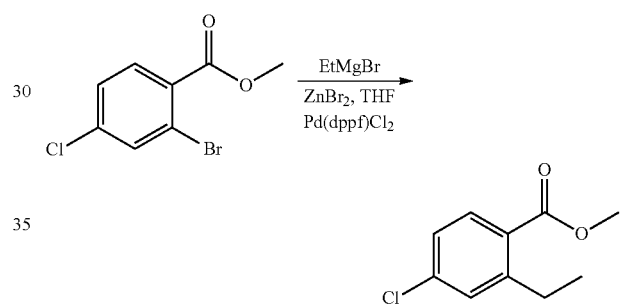

Compound 178.2. Methyl 4-chloro-2-ethylbenzoate

The title compound (2.20 g light colorless liquid, 55%) was prepared using a procedure similar to that used for the preparation of compound 48.1 but using compound 178.1 (5.00 g) in place of methyl 2-bromo-4-methylbenzoate.

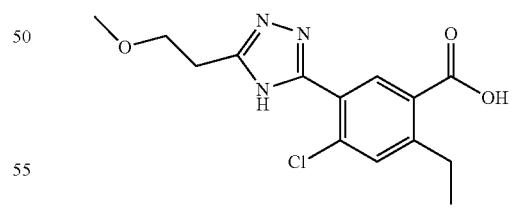

Compound 178.3. 4-Chloro-2-ethyl-5-(5-(2-methoxyethyl)-4H-1,2,4-triazol-3-yl)benzoic acid The title compound was prepared using standard chemical manipulations and procedures similar to those used for the preparation of compound 152.8 using compound 178.2 and 3-methoxypropanehydrazide (compound 143.1) instead of compound 152.2 and acetohydrazide respectively.

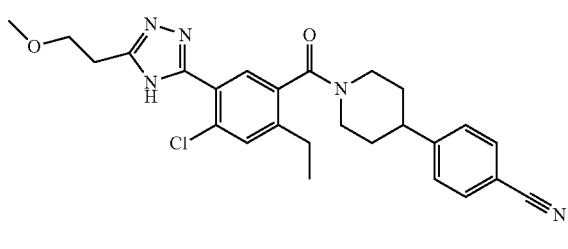 [SMILES: CCc1cc(Cl)c(-c2nnc(CCOC)[nH]2)cc1C(=O)N1CCC(c2ccc(C#N)cc2)CC1]

Compound 178. 4-(1-(4-Chloro-2-ethyl-5-(5-(2-methoxyethyl)-4H-1,2,4-triazol-3-yl)benzoyl)piperidin-4-yl)benzonitrile The title compound was prepared using a procedure similar to that used for the preparation of compound 152 but using compound 178.3 in place of compound 152.8. m/z (ES+) 478 (M+H)⁺.

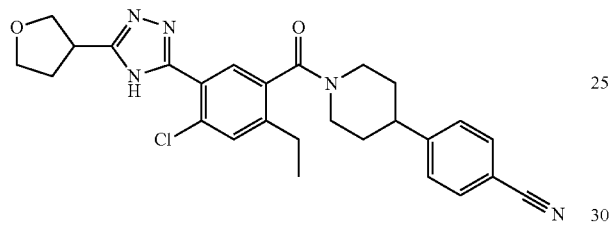

Compound 179. 4-(1-(4-Chloro-2-ethyl-5-(5-(tetrahydrofuran-3-yl)-4H-1,2,4-triazol-3-yl)benzoyl)piperidin-4-yl)benzonitrile The title compound was prepared using standard chemical manipulations and procedures similar to those used for the preparation of compounds 38 and 178. m/z (ES+) 490 (M+H)⁺.

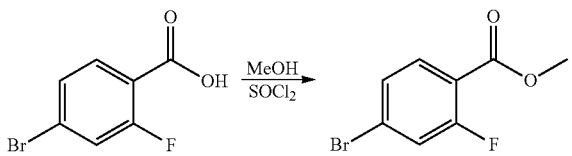

Compound 180.1. Methyl 4-bromo-2-fluorobenzoate

To a 500-mL three neck round-bottom flask was added a solution of 4-bromo-2-fluorobenzoic acid (30.0 g, 137 mmol, 1.00 equiv) in methanol (200 mL). SOCl₂ (24.0 g, 202 mmol, 1.50 equiv) was added dropwise at 0° C. The resulting solution was stirred for 10 min at 0° C., for 30 min at 25° C., and then for 3 h at 50° C. After cooling to room temperature, the resulting mixture was concentrated under reduced pressure. The residue was partitioned between water (100 mL) and ethyl acetate (100 mL). The aqueous phase was extracted with 100 mL of ethyl acetate. The combined organic layers were washed with 1×100 mL of water, 1×100 mL of sodium bicarbonate (aq. sat.) and 1×100 mL of brine. The organic layer was dried over anhydrous sodium sulfate and concentrated under reduced pressure to yield 30.0 g (94%) of the title compound as a light yellow solid.

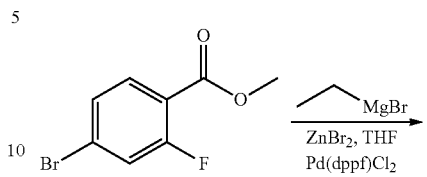

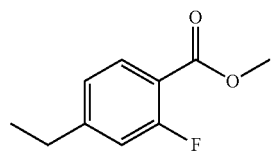

Compound 180.2. Methyl 4-ethyl-2-fluorobenzoate

The title compound (3.80 g light colorless oil, 97%) was prepared using a procedure similar to that used for the preparation of compound 48.1 but using compound 180.1 (5.00 g) in place of methyl 2-bromo-4-methylbenzoate.

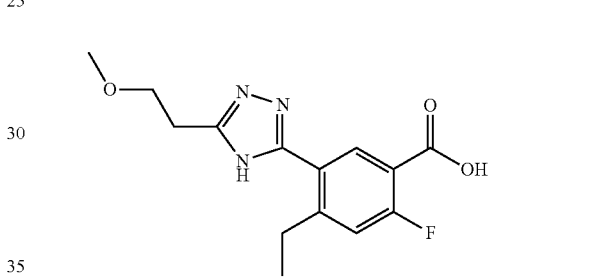

Compound 180.3. 4-Ethyl-2-fluoro-5-(5-(2-methoxyethyl)-4H-1,2,4-triazol-3-yl)benzoic acid The title compound was prepared using standard chemical manipulations and procedures similar to those used for the preparation of compound 152.8 using compounds 180.2 and 143.1 instead of compound 152.2 and acetohydrazide respectively.

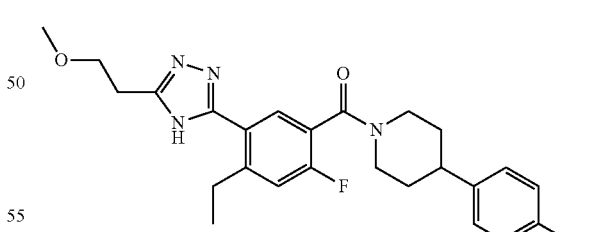

Compound 180. 4-(1-(4-Ethyl-2-fluoro-5-(5-(2-methoxyethyl)-4H-1,2,4-triazol-3-yl)benzoyl)piperidin-4-yl)benzonitrile The title compound was prepared using standard chemical manipulations and procedures similar to those used for the preparation of compound 152 but using compound 180.3 in place of compound 152.8. m/z (ES+) 462 (M+H)⁺.

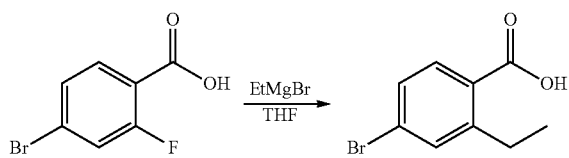

Compound 181.1. 4-Bromo-2-ethylbenzoic acid

To a 1 L three neck round-bottom flask, which was purged and maintained with a nitrogen atmosphere, was added 4-bromo-2-fluorobenzoic acid (50.0 g, 228 mmol, 1.00 equiv) in tetrahydrofuran (500 mL). A solution of ethylmagnesium bromide (250 mL, 3 M in THF) was added dropwise at 0° C. The resulting solution was stirred for 3-4 h at 0° C. The mixture was then carefully quenched by dropwise addition of water at 0° C. After complete quench of the reaction, additional water was added and the pH was adjusted to 2-3 with hydrogen chloride (aqueous, 2 M). The mixture was extracted with 2×200 mL of ethyl acetate and the organic layers were combined. Sodium hydroxide (2N, aq.) was employed to adjust the pH to 7-8. The resulting mixture was washed with 2×200 mL of ethyl acetate. The pH value of the aqueous solution was adjusted to 2-3 with 2N hydrogen chloride, then extracted with 2×200 mL of ethyl acetate. The combined organic layers were dried over anhydrous sodium sulfate and concentrated in vacuo. This resulted in 30.0 g (57%) of 4-bromo-2-ethylbenzoic acid as a yellow solid.

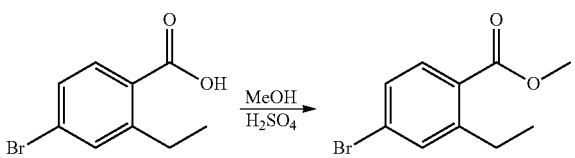

Compound 181.2. Methyl 4-bromo-2-ethylbenzoate

The title compound (25.0 g light yellow liquid, 79%) was prepared using a procedure similar to that used for the preparation of compound 177.2 but using compound 181.1 (30.0 g) in place of compound 177.1.

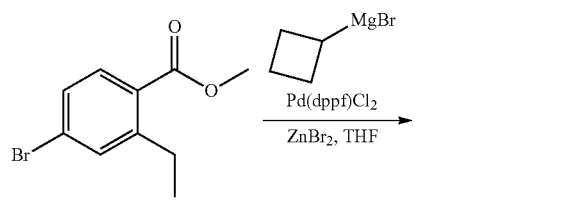

Compound 181.3. Methyl 4-cyclobutyl-2-ethylbenzoate

To a stirred mixture of ZnBr$_2$ (33.5 g, 149 mmol, 4.00 equiv) in THF (350 mL) under nitrogen at 0° C. was added dropwise a solution of cyclobutylmagnesium bromide (148 mmol in 50 mL THF). After stirring at 0° C. for 0.5 h, the temperature was lowered to −78° C. and Pd(dppf)Cl$_2$ (2.00 g, 2.73 mmol, 0.07 equiv) was added followed by the addition of a solution of methyl 4-bromo-2-ethylbenzoate (compound 181.2, 9.00 g, 37.0 mmol, 1.00 equiv) in tetrahydrofuran (10 mL) dropwise at the same temperature. The reaction mixture was slowly allowed to reach ambient temperature and then stirred overnight. The reaction was carefully quenched with a saturated NH$_4$Cl aqueous solution (100 mL). The resulting mixture was extracted with 500 mL of ethyl acetate. The organic layer was dried over anhydrous sodium sulfate and concentrated in vacuo. The residue was purified by silica gel chromatography with ethyl acetate/petroleum ether (1:50) to furnish 8.00 g (99%) of the desired product as a light yellow oil.

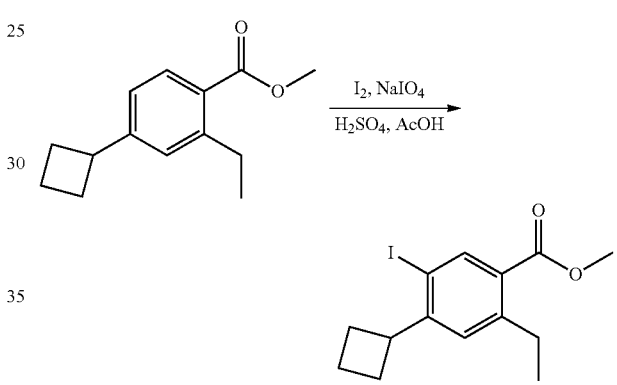

Compound 181.4. Methyl 4-cyclobutyl-2-ethyl-5-iodobenzoate

To a solution of methyl 4-cyclobutyl-2-ethylbenzoate (compound 181.3, 7.70 g, 35.3 mmol, 1.00 equiv) in acetic acid (80 mL) was added iodine (8.98 g, 35.4 mmol, 1.00 equiv), NaIO$_4$ (3.78 g, 17.7 mmol, 0.50 equiv), and sulfuric acid (0.870 g, 8.87 mmol, 0.25 equiv). The reaction mixture was stirred at 60° C. overnight. After cooling to room temperature, the reaction was slowly quenched with Na$_2$S$_2$O$_3$ (aq., sat.). The mixture was extracted with 200 mL of ethyl acetate and the organic layer was dried over anhydrous sodium sulfate and concentrated in vacuo. The residue was purified by silica gel chromatography with ethyl acetate/petroleum ether (1:50) to furnish 10.5 g (86%) of the desired product as a colorless solid.

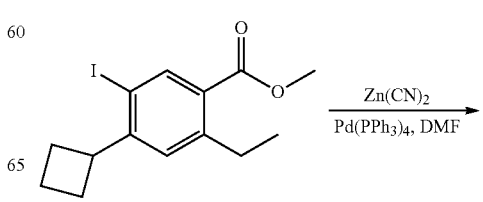

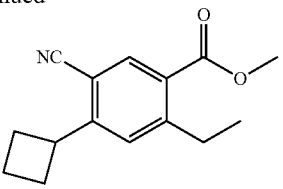

Compound 181.5. Methyl 5-cyano-4-cyclobutyl-2-ethylbenzoate

To a round-bottom flask, which was purged and maintained with a nitrogen atmosphere, was added a solution of methyl 4-cyclobutyl-2-ethyl-5-iodobenzoate (compound 181.4, 5.50 g, 16.0 mmol, 1.00 equiv) in N,N-dimethylformamide (150 mL). Zinc cyanide (2.78 g, 23.7 mmol, 1.50 equiv) and Pd(PPh₃)₄ (1.83 g, 1.59 mmol, 0.10 equiv) were added to the reaction mixture. The resulting solution was stirred at 100° C. for 15 h under nitrogen. After cooling to ambient temperature, the reaction was carefully quenched with 300 mL of FeSO₄ (aq., sat.) and diluted with ethyl acetate. The resulting mixture was stirred vigorously then filtered through celite and washed with 1 M FeSO₄, water, and ethyl acetate. The layers were separated and the aqueous phase was extracted with 2×300 mL of ethyl acetate. The combined organic layers were washed with 2×300 mL of brine, dried over anhydrous sodium sulfate, and concentrated in vacuo. The residue was purified using silica gel column chromatography with ethyl acetate/petroleum ether (1:100-1:50) as eluent to furnish 3.20 g (82%) of methyl 5-cyano-4-cyclobutyl-2-ethylbenzoate as a light yellow oil.

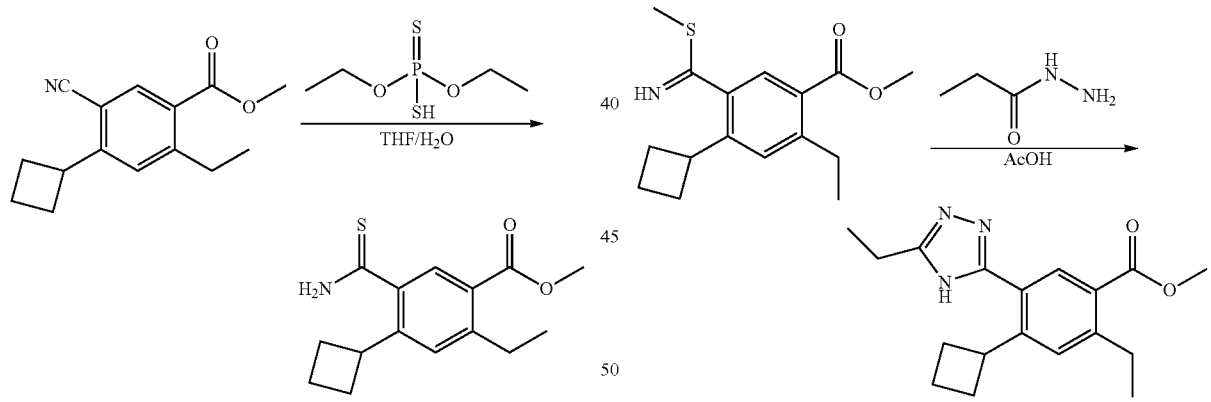

Compound 181.6. Methyl 5-carbamothioyl-4-cyclobutyl-2-ethylbenzoate

To a round-bottom flask was added a solution of methyl 5-cyano-4-cyclobutyl-2-ethylbenzoate (compound 181.5, 3.00 g, 12.3 mmol, 1.00 equiv) in a solvent mixture of tetrahydrofuran and H₂O (80 mL/40 mL). To this was added O,O'-diethyl dithiophosphate (6.69 g, 35.9 mmol, 3.00 equiv) dropwise with stirring. The resulting solution was stirred at 85° C. for 48 h (CAUTION: significant gas evolution occurs—this and all other reactions described herein should be carried out in well ventilated fume hoods). After cooling to ambient temperature, the mixture was then concentrated in vacuo. The crude product was purified by re-crystallization from petroleum ether to furnish 1.30 g (38%) of methyl 5-carbamothioyl-4-cyclobutyl-2-ethylbenzoate as a light yellow solid.

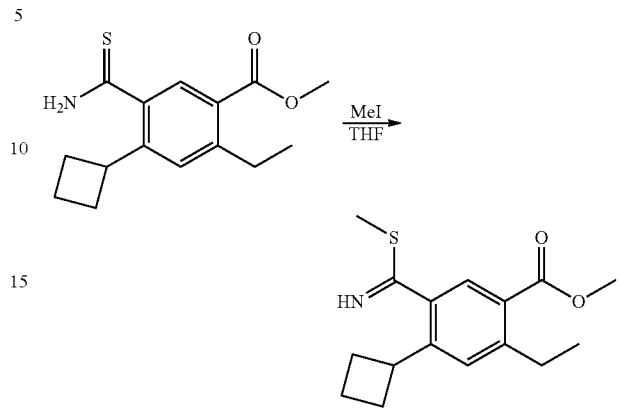

Compound 181.7. Methyl 4-cyclobutyl-2-ethyl-5-(imino(methylthio)methyl)benzoate To a round-bottom flask was added a solution of methyl 5-carbamothioyl-4-cyclobutyl-2-ethylbenzoate (compound 181.6, 1.50 g, 5.41 mmol, 1.00 equiv) in tetrahydrofuran (30 mL). This was followed by the addition of iodomethane (3.80 g, 26.8 mmol, 5.00 equiv) dropwise with stirring. The resulting solution was stirred at for 15 h, then concentrated in vacuo. This resulted in 1.80 g (97%) of the title compound as a yellow oil.

Compound 181.8. Methyl 4-cyclobutyl-2-ethyl-5-(5-ethyl-4H-1,2,4-triazol-3-yl)benzoate To a round-bottom flask was added a solution of methyl 4-cyclobutyl-2-ethyl-5-(methylsulfanyl)carboximidoylbenzoate (compound 181.7, 900 mg, 3.09 mmol, 1.00 equiv) in AcOH (20 mL). Propionohydrazide (880 mg, 9.99 mmol, 3.00 equiv) was added and the resulting mixture was stirred at 90° C. for 2 h. After cooling to ambient temperature, the mixture was then concentrated in vacuo. The residue was purified using silica gel column chromatography with ethyl acetate/petroleum ether (1:50-1:3) as eluent to give 0.360 g (37%) of the title compound as a clear oil.

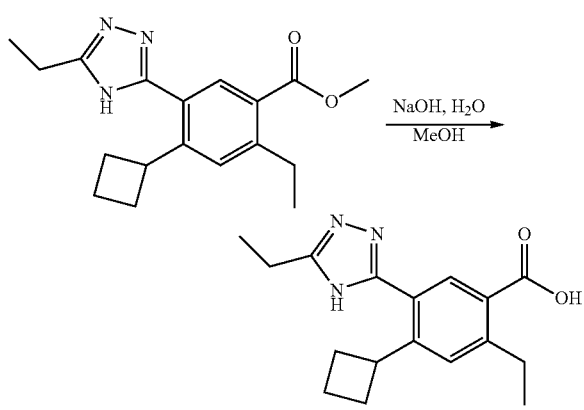

Compound 181.9. 4-Cyclobutyl-2-ethyl-5-(5-ethyl-4H-1,2,4-triazol-3-yl)benzoic acid To a round-bottom flask was added a solution of methyl 4-cyclobutyl-2-ethyl-5-(5-ethyl-4H-1,2,4-triazol-3-yl)benzoate (compound 181.8, 360 mg, 1.15 mmol, 1.00 equiv) in methanol (20 mL). A solution of sodium hydroxide (460 mg, 11.5 mmol, 10.0 equiv) in water (10 mL) was added to the reaction mixture. The resulting solution was stirred at 25° C. for 15 h. The organic solvent was then removed under reduced pressure. The pH value of the remaining aqueous phase was adjusted to 2-3 with hydrogen chloride (aq., 2 M). The resulting precipitate was collected by filtration and dried under high-vacuum to yield 320 mg (93%) of the title compound as a white solid.

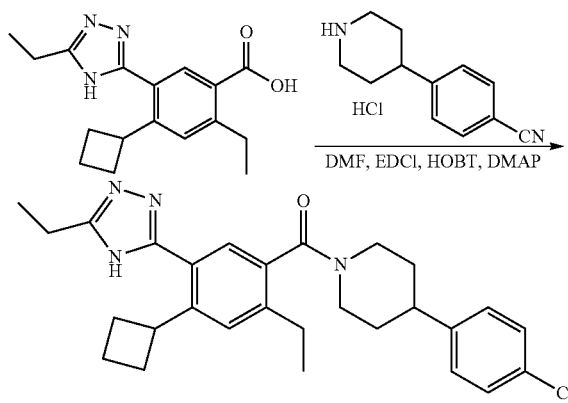

Compound 181. 4-(1-(4-Cyclobutyl-2-ethyl-5-(5-ethyl-4H-1,2,4-triazol-3-yl)benzoyl)piperidin-4-yl)benzonitrile To a solution of 4-cyclobutyl-2-ethyl-5-(5-ethyl-4H-1,2,4-triazol-3-yl)benzoic acid (compound 181.9, 160 mg, 0.530 mmol, 1.00 equiv) in N,N-dimethylformamide (20 mL) were added EDCI (113 mg, 0.590 mmol, 1.11 equiv), DMAP (197 mg, 1.62 mmol, 3.03 equiv), and HOBT (87.5 mg, 0.650 mmol, 1.21 equiv). After 5 min, 4-(piperidin-4-yl)benzonitrile hydrochloride (compound 1.5, 110 mg, 0.590 mmol, 1.10 equiv) was added. The resulting mixture was stirred at 25° C. for 15 h, then quenched with 100 mL of ice water. The mixture was extracted with 2×150 mL of ethyl acetate. The combined organic layers were washed with 3×150 mL of brine, dried over anhydrous sodium sulfate, and concentrated. The crude product (~150 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (47% CH$_3$CN up to 61% in 6 min, up to 100% in 1.5 min, down to 47% in 1.5 min); Detector, Waters 2489 254 & 220 nm. The fractions containing pure compound were combined and lyophilized to yield 99.5 mg (40%) of the title compound as a white solid m/z (ES+) 468 (M+H)$^+$. $^1$H-NMR (300 MHz, CD$_3$OD): δ 7.71-7.69 (m, 2H), 7.50-7.32 (m, 4H), 4.03-3.99 (m, 1H), 3.65-3.5 (m, 1H), 3.32-3.20 (m, 1H), 2.90-2.95 (m, 4H), 2.70-2.74 (m, 2H), 2.20-1.98 (m, 6H), 1.98-1.79 (m, 4H), 1.41 (t, 3H), 1.39-1.28 (m, 3H).

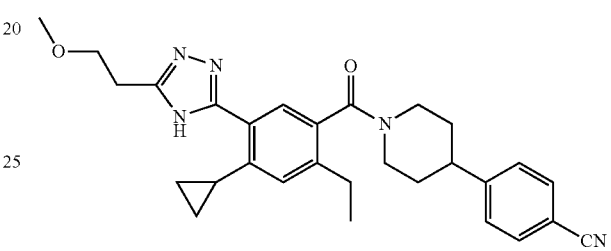

Compound 182. 4-(1-(4-Cyclopropyl-2-ethyl-5-(5-(2-methoxyethyl)-4H-1,2,4-triazol-3-yl)benzoyl)piperidin-4-yl)benzonitrile The title compound was prepared using standard chemical manipulations and procedures similar to those used for the preparation of compounds 143 and 181. m/z (ES+) 484 (M+H)$^+$. $^1$H-NMR (300 MHz, CD$_3$OD): δ 7.67 (d, 2H), 7.49-7.37 (m, 3H), 7.11-7.05 (m, 1H), 4.89-4.80 (m, 1H), 3.81 (t, 2H), 3.77-3.60 (m, 1H), 3.4 (s, 3H), 3.37-3.32 (m, 1H), 3.14 (t, 2H), 3.15-2.9 (m, 2H), 2.92-2.5 (m, 2H), 2.39-2.36 (m, 1H), 2.02-1.85 (m, 1H), 1.85-1.69 (m, 3H), 1.32-1.21 (m, 3H), 1.0-0.95 (m, 2H), 0.77-0.69 (m, 2H).

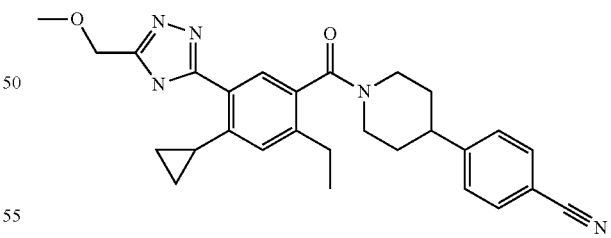

Compound 183. 4-(1-(4-Cyclopropyl-2-ethyl-5-(5-(methoxymethyl)-4H-1,2,4-triazol-3-yl)benzoyl)piperidin-4-yl)benzonitrile The title compound was prepared using standard chemical manipulations and procedures similar to those used for the preparation of compounds 143 and 181. m/z (ES+) 470 (M+H)$^+$.

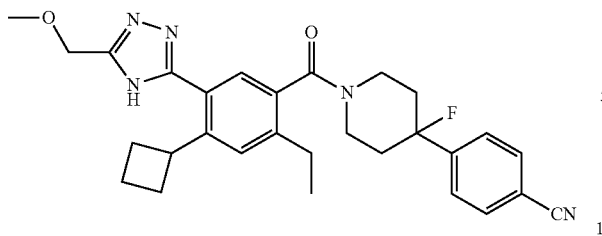

Compound 184. 4-(1-(4-Cyclobutyl-2-ethyl-5-(5-(methoxymethyl)-4H-1,2,4-triazol-3-yl)benzoyl)-4-fluoropiperidin-4-yl)benzonitrile The title compound was prepared using standard chemical manipulations and procedures similar to those used for the preparation of compounds 143 and 181 and using compound 11.2 HCl salt in place of compound 1.5. m/z (ES+) 502 (M+H)+.

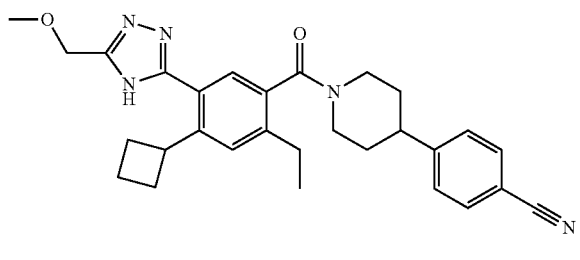 [SMILES: CCc1cc(C2CCC2)c(-c2nnc(COC)[nH]2)cc1C(=O)N1CCC(c2ccc(C#N)cc2)CC1]

Compound 185. 4-(1-(4-Cyclobutyl-2-ethyl-5-(5-(methoxymethyl)-4H-1,2,4-triazol-3-yl)benzoyl)piperidin-4-yl)benzonitrile The title compound was prepared using standard chemical manipulations and procedures similar to those used for the preparation of compounds 143 and 181. m/z (ES+) 484 (M+H)+.

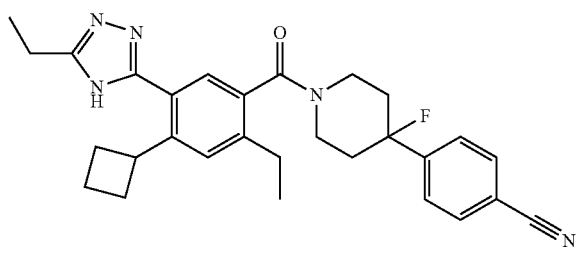 [SMILES: CCc1nnc(-c2cc(C(=O)N3CCC(F)(c4ccc(C#N)cc4)CC3)c(CC)cc2C2CCC2)[nH]1]

Compound 186. 4-(1-(4-Cyclobutyl-2-ethyl-5-(5-ethyl-4H-1,2,4-triazol-3-yl)benzoyl)-4-fluoropiperidin-4-yl)benzonitrile The title compound was prepared using standard chemical manipulations and procedures similar to those used for the preparation of compound 181 and using compound 11.2 HCl salt in place of compound 1.5. m/z (ES+) 486 (M+H)+.

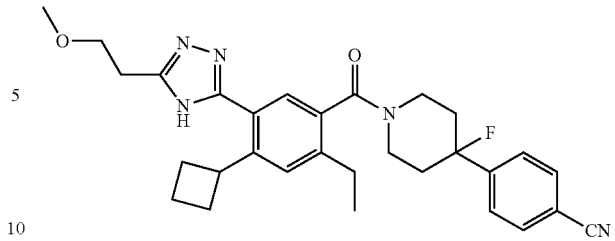

Compound 187. 4-(1-(4-Cyclobutyl-2-ethyl-5-(5-(2-methoxyethyl)-4H-1,2,4-triazol-3-yl)benzoyl)-4-fluoropiperidin-4-yl)benzonitrile The title compound was prepared using standard chemical manipulations and procedures similar to those used for the preparation of compounds 143 and 181 and using compound 11.2 HCl salt in place of compound 1.5. m/z (ES+) 516 (M+H)+. $^1$H-NMR (300 MHz, CD$_3$OD): δ 7.77 (d, 2H), 7.66-7.47 (m, 2H), 7.47-7.35 (m, 2H), 4.89-4.83 (m, 1H), 4.08-4.03 (t, 1H), 3.79 (t, 2H), 3.55 (t, 2H), 3.33 (s, 3H), 3.28-3.20 (m, 1H), 3.12 (t, 2H), 2.80-2.68 (m, 2H), 2.27-1.68 (m, 10H), 1.27 (t, 3H).

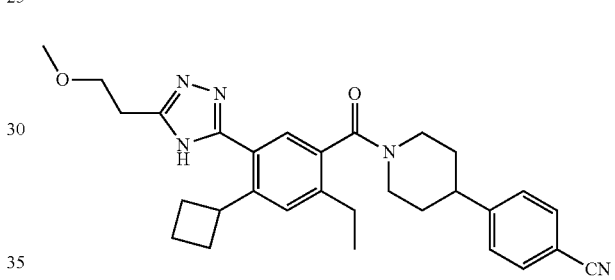

Compound 188. 4-(1-(4-Cyclobutyl-2-ethyl-5-(5-(2-methoxyethyl)-4H-1,2,4-triazol-3-yl)benzoyl)piperidin-4-yl)benzonitrile The title compound was prepared using standard chemical manipulations and procedures similar to those used for the preparation of compounds 143 and 181. m/z (ES+) 498 (M+H)+. $^1$H-NMR (300 MHz, CD$_3$OD): δ 7.67 (d, 2H), 7.44-7.31 (m, 4H), 4.89 (s, 1H), 4.04-3.98 (m, 1H), 3.79 (t, 2H), 3.66-3.60 (m, 1H), 3.33 (s, 3H), 3.23-3.12 (m, 1H), 3.10 (t, 2H), 3.02 (t, 2H), 2.77-2.66 (m, 2H), 2.19-2.04 (m, 6H), 1.80-1.68 (m, 4H), 1.31-1.26 (m, 3H).

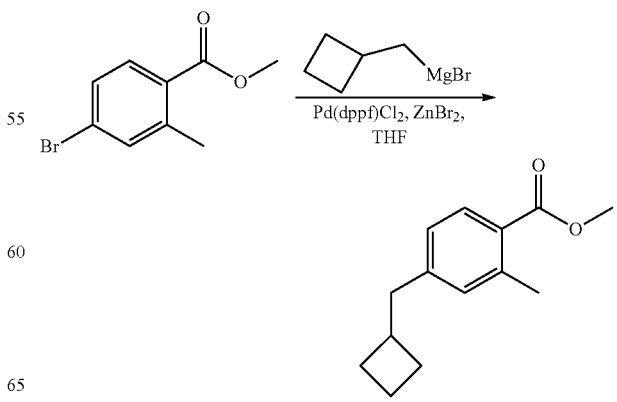

Compound 189.1. Methyl 4-(cyclobutylmethyl)-2-methylbenzoate

The title compound (4.00 g, yellow oil, 84%) was prepared using a procedure similar to that used for the preparation of compound 181.3 using compound 152.1 (5.00 g) and cyclobutylmethylmagnesium bromide in place of compound 181.2 and cyclobutylmagnesium bromide respectively.

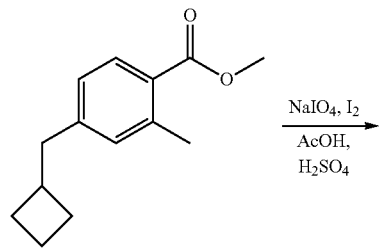

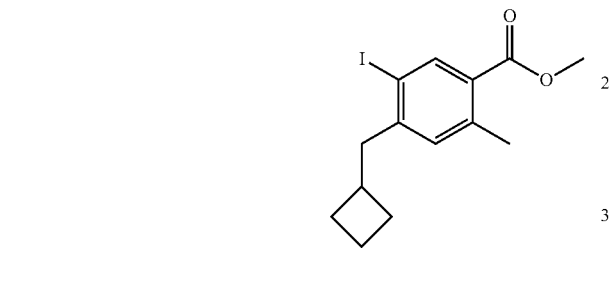

Compound 189.2. Methyl 4-(cyclobutylmethyl)-5-iodo-2-methylbenzoate

To a round-bottom flask was added a solution of methyl 4-(cyclobutylmethyl)-2-methylbenzoate (compound 189.1, 8.40 g, 38.5 mmol, 1.00 equiv) in AcOH (150 mL). NaIO$_4$ (5.00 g, 23.4 mmol, 0.50 equiv), iodine (10.0 g, 39.4 mmol, 1.00 equiv), and sulfuric acid (0.3 mL) were added to the reaction mixture. The resulting solution was stirred at 60° C. for 12 h. After cooling to room temperature, the reaction was quenched with 200 mL of NaHSO$_3$ (aq). The mixture was extracted with 2×200 mL of ethyl acetate, and the combined organic layers were dried over anhydrous sodium sulfate and concentrated in vacuo. The residue was purified using silica gel column chromatography with ethyl acetate/petroleum ether (20:1) as eluent to furnish 8.00 g (60%) of methyl 4-(cyclobutylmethyl)-5-iodo-2-methylbenzoate as a white solid.

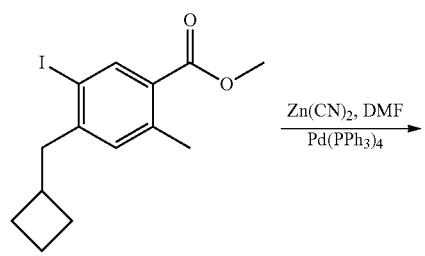

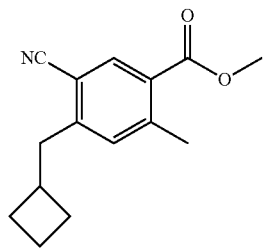

Compound 189.3. methyl 5-cyano-4-(cyclobutylmethyl)-2-methylbenzoate

The title compound (5.0 g, light yellow oil, 88%) was prepared using a procedure similar to that used for the preparation of compound 181.5 using compound 189.2 (8.00 g) in place of compound 181.4.

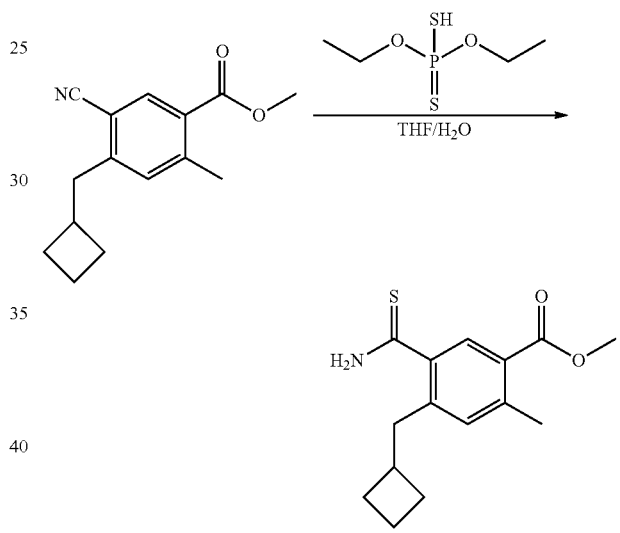

Compound 189.4. Methyl 5-carbamothioyl-4-(cyclobutylmethyl)-2-methylbenzoate To a round-bottom flask was added a solution of methyl 5-cyano-4-(cyclobutylmethyl)-2-methylbenzoate (compound 189.3, 5.00 g, 20.6 mmol, 1.00 equiv) in a solvent mixture of THF and H$_2$O (50 mL/25 mL). O,O'-diethyl dithiophosphate (15.0 g, 80.5 mmol, 4.00 equiv) was added to the reaction flask. The resulting solution was stirred at 80° C. for 48 h (CAUTION: significant gas evolution occurs—this and all other reactions described herein should be carried out in well ventilated fume hoods). After cooling to ambient temperature, the reaction was carefully quenched with 50 mL of brine. The mixture was extracted with 3×50 mL of ethyl acetate and the combined organic layers were dried over anhydrous sodium sulfate and concentrated in vacuo. The residue was purified using silica gel column chromatography with ethyl acetate/petroleum ether (1:4) as eluent to furnish 1.20 g (21%) of the title compound as a yellow oil.

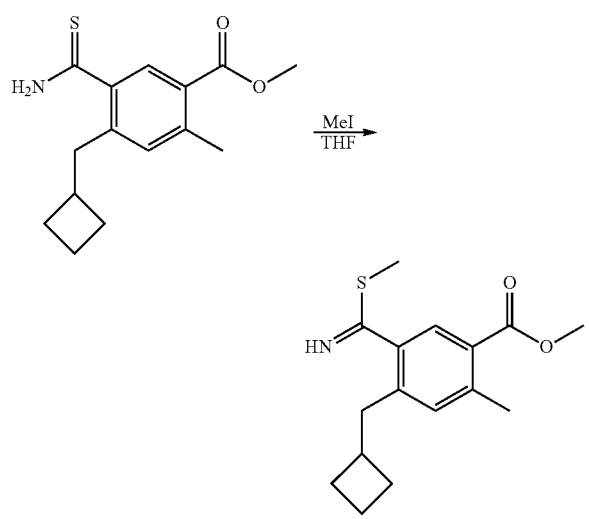

Compound 189.5. Methyl 4-(cyclobutylmethyl)-2-methyl-5-(methylsulfanyl)carboximidoylbenzoate To a round-bottom flask was added a solution of methyl 5-carbamothioyl-4-(cyclobutylmethyl)-2-methylbenzoate (compound 189.4, 1.20 g, 4.33 mmol, 1.00 equiv) in tetrahydrofuran (25 mL). Iodomethane (5.00 g, 35.2 mmol, 8.00 equiv) was added to the reaction mixture. The resulting solution was stirred at 20° C. for 12 h, and then concentrated in vacuo. This resulted in 1.10 g (87%) of methyl 4-(cyclobutylmethyl)-2-methyl-5-(methylsulfanyl)carboximidoylbenzoate as a yellow oil.

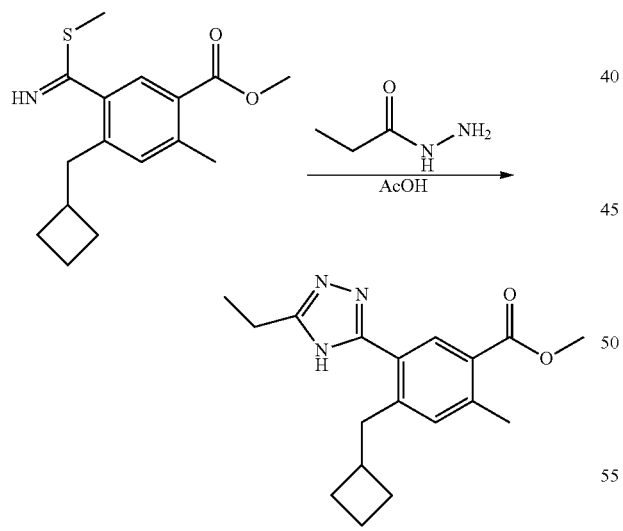

Compound 189.6. Methyl 4-(cyclobutylmethyl)-5-(5-ethyl-4H-1,2,4-triazol-3-yl)-2-methylbenzoate To a round-bottom flask was added a solution of methyl 4-(cyclobutylmethyl)-2-methyl-5-(methylsulfanyl)carboximidoylbenzoate (compound 189.5, 1.00 g, 3.43 mmol, 1.00 equiv) in AcOH (25 mL). Propionohydrazide (1.20 g, 13.6 mmol, 4.00 equiv) was added and the resulting mixture was stirred at 100° C. for 1 h. After cooling to ambient temperature, the mixture was concentrated in vacuo. The residue was purified using silica gel column chromatography with ethyl acetate/petroleum ether (1:5) as eluent to furnish 300 mg (28%) of the title compound as a white solid.

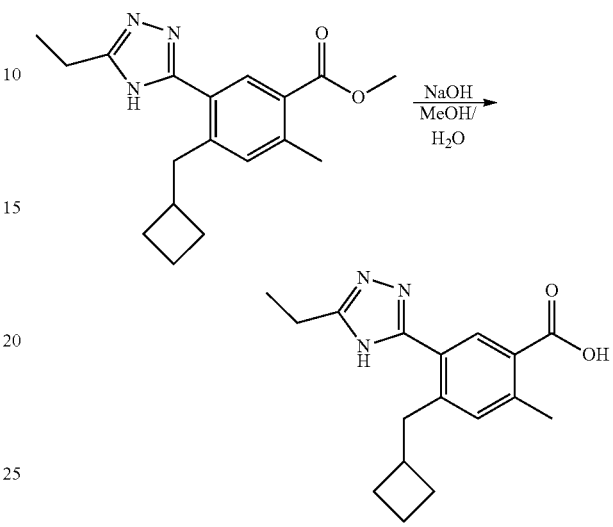

Compound 189.7. 4-(Cyclobutylmethyl)-5-(5-ethyl-4H-1,2,4-triazol-3-yl)-2-methylbenzoic acid The title compound (260 mg, white solid, 91%) was prepared using a procedure similar to that used for the preparation of compound 181.9 using compound 189.6 (300 mg) in place of compound 181.8.

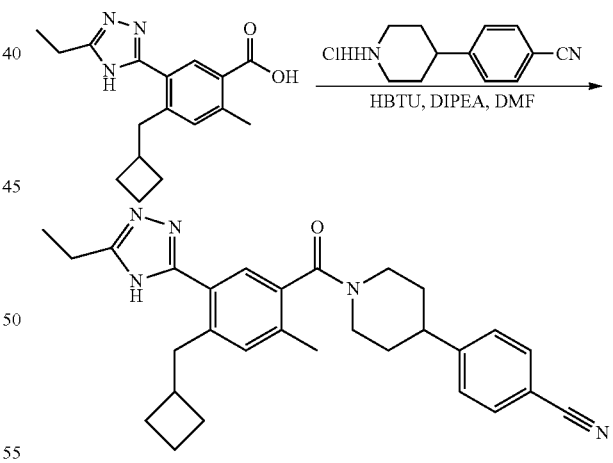

Compound 189. 4-(1-(4-(Cyclobutylmethyl)-5-(5-ethyl-4H-1,2,4-triazol-3-yl)-2-methylbenzoyl)piperidin-4-yl)benzonitrile The title compound (28 mg, white solid, 18%) was prepared using a procedure similar to that used for the preparation of compound 181 using compound 189.7 (100 mg) in place of compound 181.9. m/z (ES+) 468 (M+H)$^+$. $^1$H-NMR (300 MHz, CD$_3$OD): δ 7.67 (d, 2H), 7.52-7.47 (m, 3H), 7.26 (s, 1H), 3.66-3.22 (m, 1H), 3.33-3.22 (m, 1H), 3.05-2.99 (m, 4H), 2.97 (q, 2H), 2.53-2.47 (m, 1H), 2.47 and 2.45 (2 singlets, amide rotamers, ArCH₃, 3H) 2.00-1.50 (m, 10H), 1.41 (t, 3H).

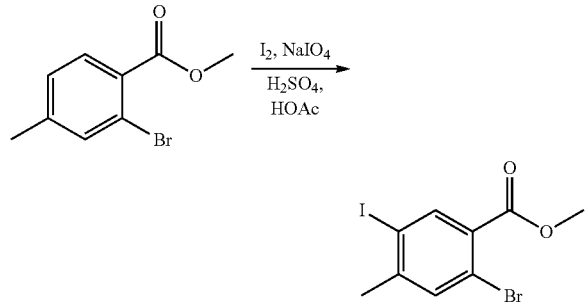

Compound 190.1. Methyl 2-bromo-5-iodo-4-methylbenzoate

To a round-bottom flask was added a mixture of methyl 2-bromo-4-methylbenzoate (2.00 g, 7.86 mmol, 1.00 equiv) in AcOH (20 mL). I₂ (2.45 g, 9.65 mmol, 1.10 equiv), NaIO₄ (950 mg, 4.42 mmol, 0.50 equiv), and sulfuric acid (0.1 mL, 0.15 equiv) were added and the resulting mixture was stirred at 100° C. overnight. After cooling to ambient temperature, the reaction was carefully quenched with Na₂S₂O₃ (aq., sat.). The resulting mixture was extracted with 2×50 mL of ethyl acetate. The combined organic layers were dried (Na₂SO₄) and concentrated in vacuo to yield 2.50 g (81%) of the title compound as an off-white solid.

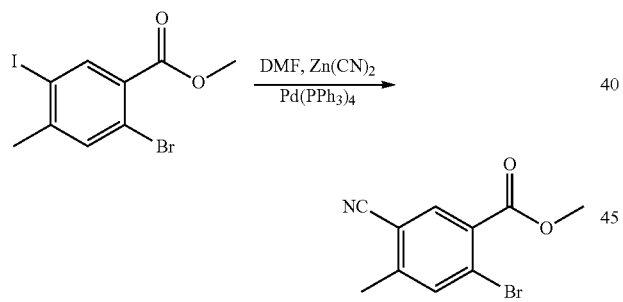

Compound 190.2. Methyl 2-bromo-5-cyano-4-methylbenzoate

The title compound (1.10 g, white solid, 61%) was prepared using a procedure similar to that used for the preparation of compound 181.5 using compound 190.1 (2.50 g) in place of compound 181.4.

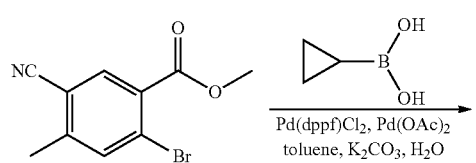

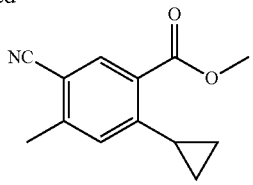

Compound 190.3. Methyl 5-cyano-2-cyclopropyl-4-methylbenzoate

To a solution of methyl 2-bromo-5-cyano-4-methylbenzoate (compound 190.2, 600 mg, 2.1.3 mmol, 1.00 equiv, 90%) in toluene (20 mL) under nitrogen were added cyclopropylboronic acid (552 mg, 6.43 mmol, 2.00 equiv), a solution of potassium carbonate (876 mg, 6.34 mmol, 2.00 equiv) in water (1 mL), Pd(dppf)Cl₂ (252 mg, 0.10 equiv), and Pd(OAc)₂ (70 mg, 0.10 equiv). The resulting mixture was stirred under nitrogen at 100° C. overnight. After cooling to ambient temperature, the mixture was diluted with 20 mL of H₂O, then extracted with 3×50 mL of ethyl acetate. The combined organic layers were dried (Na₂SO₄) and concentrated in vacuo to furnish 450 mg (89%) of methyl 5-cyano-2-cyclopropyl-4-methylbenzoate as a white solid.

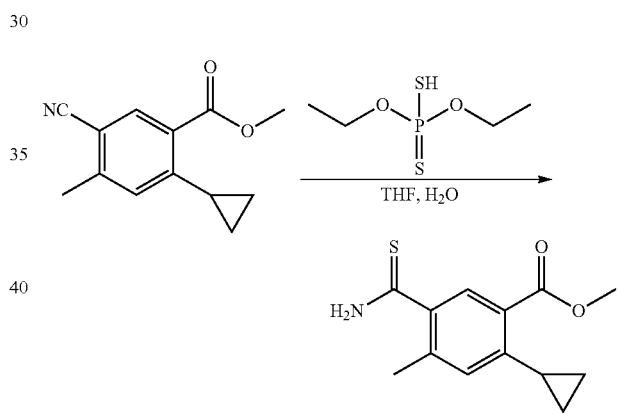

Compound 190.4. Methyl 5-carbamothioyl-2-cyclopropyl-4-methylbenzoate

To a round-bottom flask, was added a solution of methyl 5-cyano-2-cyclopropyl-4-methylbenzoate (compound 190.3, 220 mg, 0.920 mmol, 1.00 equiv, 90%) in tetrahydrofuran (6 mL). A solution of O,O'-diethyl dithiophosphate (300 mg, 1.61 mmol, 2.00 equiv) in water (1.5 mL) was added to the solution, and the resulting mixture was stirred overnight at 80° C. in an oil bath (CAUTION: significant gas evolution occurs—this and all other reactions described herein should be carried out in well ventilated fume hoods). After cooling to ambient temperature, the mixture was concentrated in vacuo. The residue was purified using silica gel column chromatography with ethyl acetate/petroleum ether (5:1) as eluent. The collected fractions were combined and concentrated in vacuo to furnish 100 mg (39%) of methyl 5-carbamothioyl-2-cyclopropyl-4-methylbenzoate as a yellow solid.

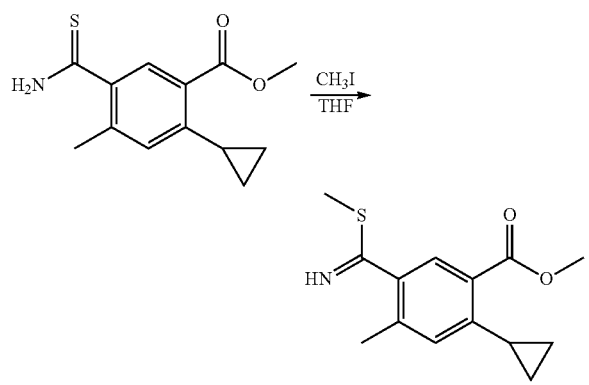

Compound 190.5. Methyl 2-cyclopropyl-4-methyl-5-(methylsulfanyl)carboximidoylbenzoate To a solution of methyl 5-carbamothioyl-2-cyclopropyl-4-methylbenzoate (compound 190.4, 600 mg, 2.17 mmol, 1.00 equiv, 90%) in THF (55 mL) was added dropwise iodomethane (1 mL). The resulting mixture was stirred overnight at 25° C., then concentrated and dried under reduced pressure to yield 400 mg (56%) of the title compound as a yellow solid.

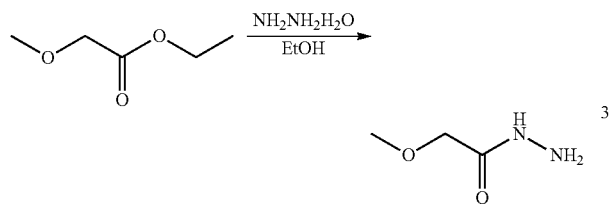

Compound 190.6. 2-Methoxyacetohydrazide

To a round-bottom flask, was added a solution of ethyl 2-methoxyacetate (10.0 g, 76.2 mmol, 1.00 equiv, 90%) and NH$_2$NH$_2$.H$_2$O (12 mL, 3.00 equiv) in ethanol (100 mL). The resulting solution was stirred for 3 h at 80° C. in an oil bath, then concentrated and dried under reduced pressure to yield 6 g (68%) of 2-methoxyacetohydrazide as a white solid.

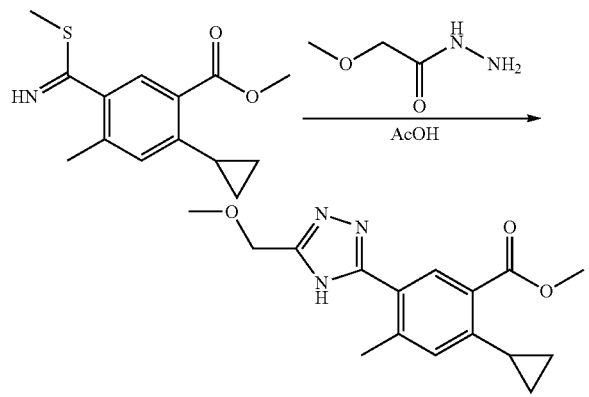

Compound 190.7. Methyl 2-cyclopropyl-5-(5-(methoxymethyl)-4H-1,2,4-triazol-3-yl)-4-methylbenzoate A solution of methyl 2-cyclopropyl-4-methyl-5-(methylsulfanyl)carboximidoylbenzoate (compound 190.5, 400 mg, 1.37 mmol, 1.00 equiv, 90%) and 2-methoxyacetohydrazide (compound 190.6, 889 mg, 7.69 mmol, 5.00 equiv) in AcOH (25 mL) was stirred overnight at 90° C. After cooling to room temperature, the mixture was concentrated in vacuo. The residue was purified using silica gel column chromatography with ethyl acetate/petroleum ether (2:1) as eluent. The collected fractions were combined and concentrated in vacuo to furnish 200 mg (44%) of methyl 2-cyclopropyl-5-(5-(methoxymethyl)-4H-1,2,4-triazol-3-yl)-4-methylbenzoate as a white solid.

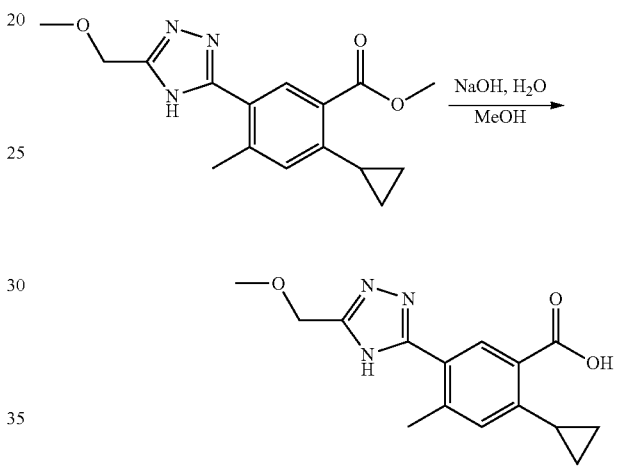

Compound 190.8. 2-Cyclopropyl-5-(5-(methoxymethyl)-4H-1,2,4-triazol-3-yl)-4-methylbenzoic acid To a round-bottom flask was added a solution of methyl 2-cyclopropyl-5-(5-(methoxymethyl)-4H-1,2,4-triazol-3-yl)-4-methylbenzoate (compound 190.7, 200 mg, 0.600 mmol, 1.00 equiv, 90%) in methanol (4 mL). A solution of sodium hydroxide (106 mg, 2.65 mmol, 4.00 equiv) in water (2 mL) was added to the reaction mixture. The resulting solution was stirred for 2 h at 60° C. After cooling to ambient temperature, the organic solvent was removed under reduced pressure and the pH the remaining aqueous layer was adjusted to 2-3 with hydrogen chloride (aq, 6 M). The resulting solids were collected by filtration and dried to yield 170 mg (89%) of the title compound as a white solid.

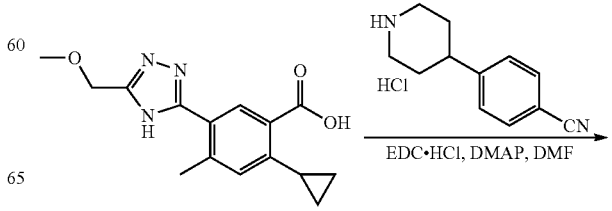

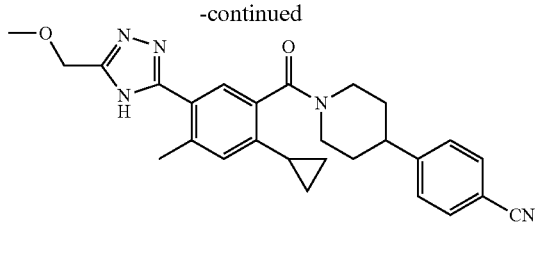

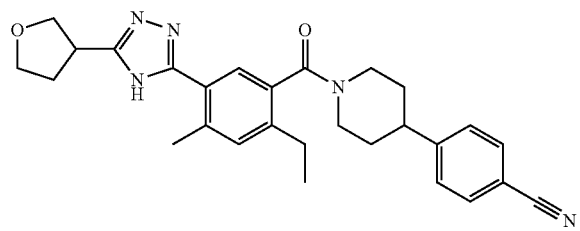

Compound 190. 4-(1-(2-Cyclopropyl-5-(5-(methoxymethyl)-4H-1,2,4-triazol-3-yl)-4-methyl-benzoyl)piperidin-4-yl)benzonitrile The title compound (115.5 mg, white solid, 51%) was prepared using a procedure similar to that used for the preparation of compound 181 using compound 190.8 (150 mg) in place of compound 181.9. m/z (ES+) 456 (M+H)+.

Compound 192. 4-(1-(2-Ethyl-4-methyl-5-(5-(tetra-hydrofuran-3-yl)-4H-1,2,4-triazol-3-yl)benzoyl)piperidin-4-yl)benzonitrile The title compound was prepared using standard chemical manipulations and procedures similar to those used for the preparation of compound 191. m/z (ES+) 470 (M+H)+.

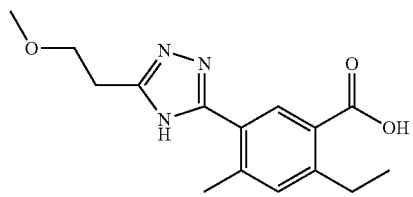 [SMILES: CCc1cc(C)c(-c2nnc(CCOC)[nH]2)cc1C(=O)O]

Compound 191.1. 2-Ethyl-5-(5-(2-methoxyethyl)-4H-1,2,4-triazol-3-yl)-4-methylbenzoic acid The title compound was prepared using standard chemical manipulations and procedures similar to those used for the preparation of compound 190.8.

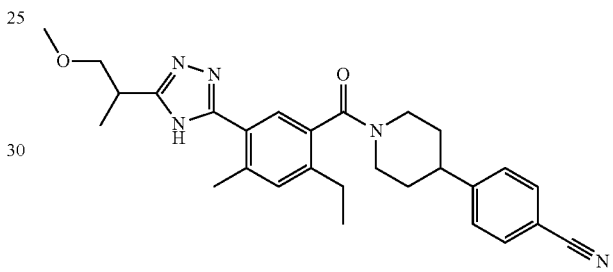

Compound 193. 4-(1-(2-Ethyl-5-(5-(1-methoxypropan-2-yl)-4H-1,2,4-triazol-3-yl)-4-methylbenzoyl)piperidin-4-yl)benzonitrile The title compound was prepared using standard chemical manipulations and procedures similar to those used for the preparation of compound 191. m/z (ES+) 472 (M+H)+.

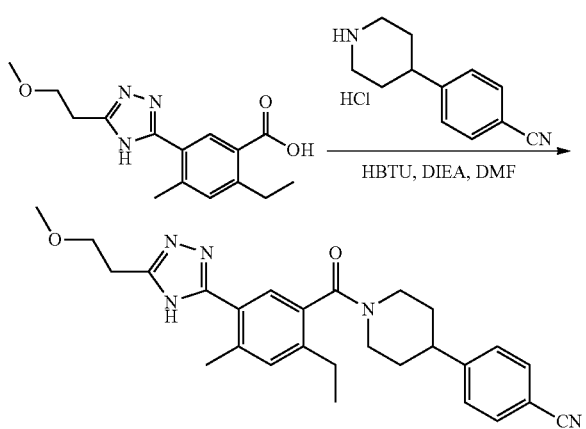

Compound 191. 4-(1-(2-Ethyl-5-(5-(2-methoxyethyl)-4H-1,2,4-triazol-3-yl)-4-methylbenzoyl)piperidin-4-yl)benzonitrile The title compound (74.8 mg, white solid, 33%) was prepared using a procedure similar to that used for the preparation of compound 181 using compound 191.1 (145 mg) in place of compound 181.9. m/z (ES+) 458 (M+H)+.

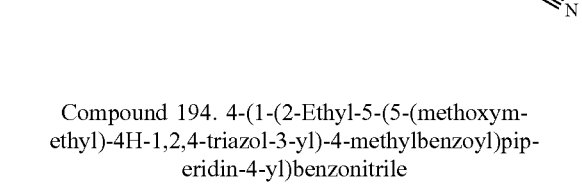

Compound 194. 4-(1-(2-Ethyl-5-(5-(methoxymethyl)-4H-1,2,4-triazol-3-yl)-4-methylbenzoyl)piperidin-4-yl)benzonitrile The title compound was prepared using standard chemical manipulations and procedures similar to those used for the preparation of compound 191. m/z (ES+) 444 (M+H)+.

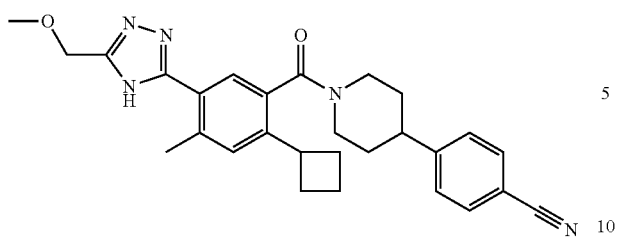

Compound 195. 4-(1-(2-Cyclobutyl-5-(5-(methoxymethyl)-4H-1,2,4-triazol-3-yl)-4-methyl-benzoyl)piperidin-4-yl)benzonitrile The title compound was prepared using standard chemical manipulations and procedures similar to those used for the preparation of compound 190. m/z (ES+) 470 (M+H)+.

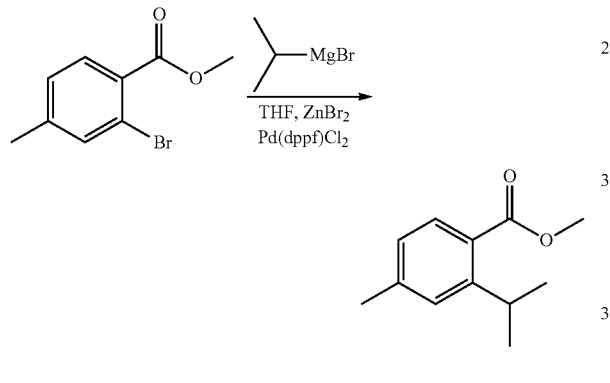

Compound 196.1. Methyl 2-isopropyl-4-methylbenzoate

To a stirred mixture of dibromozinc (39.0 g, 173 mmol, 4.00 equiv) in THF (500 mL) under nitrogen at −48° C. was added dropwise isopropylmagnesium bromide (3 M in THF, 170 mmol) over a period of 30 min. Pd(dppf)Cl₂ (0.5 g, 0.05 equiv) and methyl 2-bromo-4-methylbenzoate (10.0 g, 43.7 mmol, 1.00 equiv) were added to the above reaction mixture. After stirring for 1 h at −48° C., the reaction mixture was quenched by the careful addition of 500 mL of NH₄Cl (aq.). The resulting mixture was extracted with 3×500 mL of ethyl acetate. The combined organic layers were washed with 3×500 mL of brine and concentrated in vacuo. The residue was purified using silica gel column chromatography with petroleum ether (1:1) as eluent. This resulted in 6.50 g (77%) of methyl 2-isopropyl-4-methylbenzoate as a yellow oil.

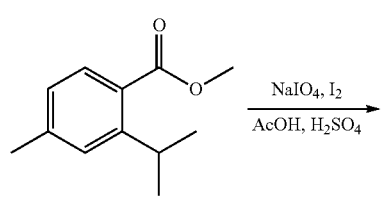

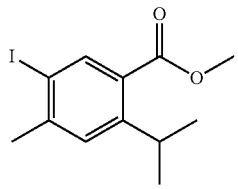

Compound 196.2. Methyl 5-iodo-2-isopropyl-4-methylbenzoate

To a round-bottom flask, was added a solution of methyl 2-isopropyl-4-methylbenzoate (compound 196.1, 6.50 g, 33.8 mmol, 1.00 equiv) in acetic acid (60 mL). Iodide (9.50 g, 37.4 mmol, 1.10 equiv), sodium periodate (3.60 g, 16.8 mmol, 0.50 equiv), and sulfuric acid (0.500 g, 0.15 equiv) were added to the reaction mixture. The resulting solution was stirred overnight at 100° C. After cooling to room temperature, the reaction was quenched with Na₂S₂O₃(aq, sat.). The mixture extracted with 3×100 mL of ethyl acetate. The combined organic layers were washed with 3×100 mL of brine, dried over anhydrous sodium sulfate, and concentrated in vacuo. This resulted in 6.00 g (56%) of methyl 5-iodo-2-isopropyl-4-methylbenzoate as a yellow oil.

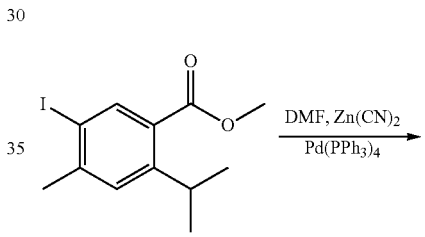

Compound 196.3. Methyl 5-cyano-2-isopropyl-4-methylbenzoate

The title compound (0.8 g, white solid, 37%) was prepared using a procedure similar to that used for the preparation of compound 181.5 using compound 196.2 (3.20 g) in place of compound 181.4,

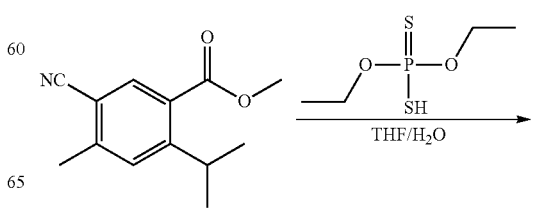

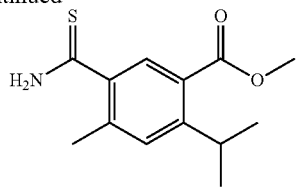

Compound 196.4. Methyl 5-carbamothioyl-2-isopropyl-4-methylbenzoate

To a round-bottom flask was added a solution of methyl 5-cyano-2-isopropyl-4-methylbenzoate (compound 196.3, 800 mg, 3.68 mmol, 1.00 equiv) in tetrahydrofuran/H$_2$O (10/5 mL). O,O'-diethyl dithiophosphate (2.05 g, 11.0 mmol, 3.00 equiv) was added to the reaction mixture. The resulting solution was stirred for 15 h at 85° C. in an oil bath (CAUTION: significant gas evolution occurs—this and all other reactions described herein should be carried out in well ventilated fume hoods). After cooling to ambient temperature, the mixture was extracted with 2×100 mL of ethyl acetate. The combined organic layers were dried (Na$_2$SO$_4$) and concentrated in vacuo. The residue was purified using silica gel column chromatography with ethyl acetate/petroleum ether (1:100-1:50-1:0) as eluent to furnish 0.800 g (86%) of methyl 5-carbamothioyl-2-isopropyl-4-methylbenzoate as a yellow oil.

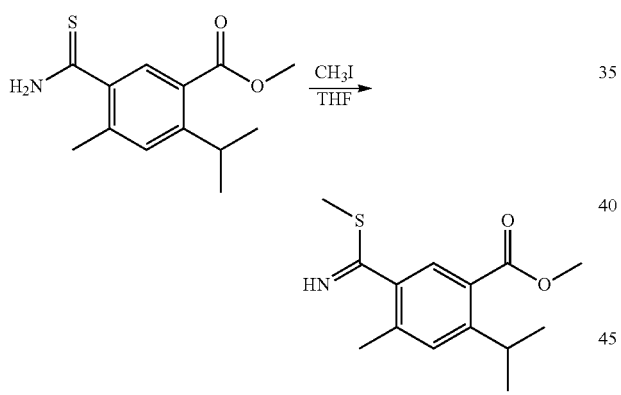

Compound 196.5. Methyl 5-(imino(methylthio)methyl)-2-isopropyl-4-methylbenzoate The title compound (0.800 g, yellow oil, 92%) was prepared using a procedure similar to that used for the preparation of compound 181.7 using compound 196.4 (820 mg) in place of compound 181.6.

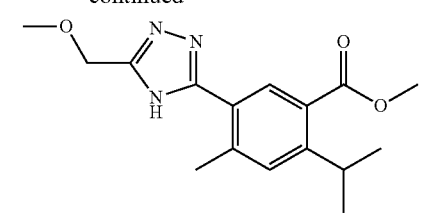

Compound 196.6

Methyl 2-isopropyl-5-(5-(methoxymethyl)-4H-1,2,4-triazol-3-yl)-4-methylbenzoate A solution of methyl 5-(imino(methylthio)methyl)-2-isopropyl-4-methylbenzoate (compound 196.5, 800 mg, 3.01 mmol, 1.00 equiv) and 2-methoxyacetohydrazide (compound 190.6, 1.90 g, 18.3 mmol, 5.00 equiv) in acetic acid (30 mL) was stirred for 2 h at 80 in an oil bath, then concentrated in vacuo. The residue was purified using silica gel column chromatography with ethyl acetate/petroleum ether (1:50-1:2) as eluent to yield 250 mg (27%) of methyl 2-isopropyl-5-(5-(methoxymethyl)-4H-1,2,4-triazol-3-yl)-4-methylbenzoate as a clear oil.

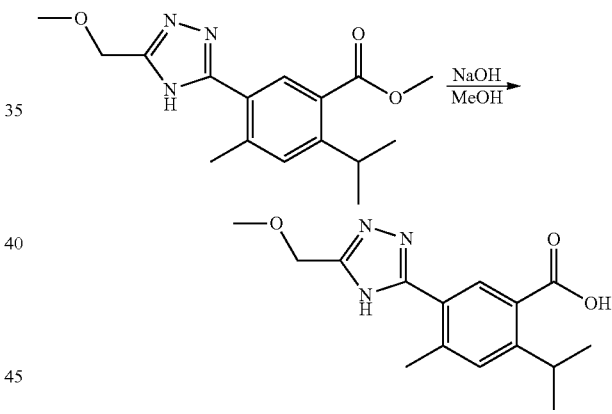

Compound 196.7. 2-Isopropyl-5-(5-(methoxymethyl)-4H-1,2,4-triazol-3-yl)-4-methylbenzoic acid The title compound (0.20 g, white solid, 84%) was prepared using a procedure similar to that used for the preparation of compound 181.9 using compound 196.6 (250 mg) in place of compound 181.8.

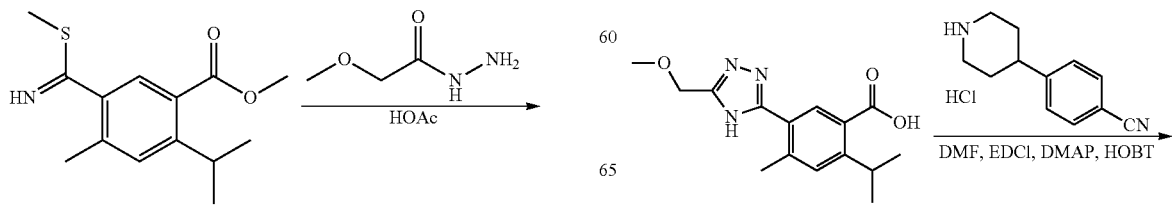

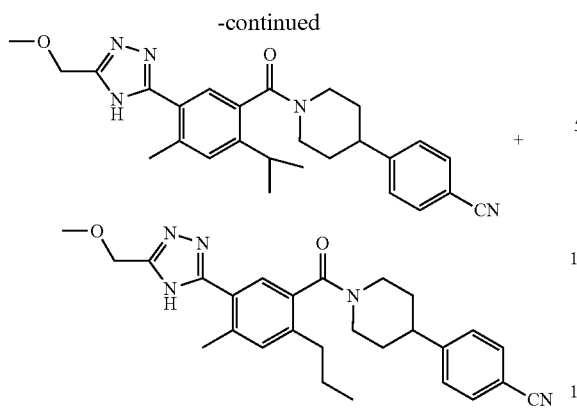

Compound 196. 4-(1-(2-Isopropyl-5-(5-(methoxymethyl)-4H-1,2,4-triazol-3-yl)-4-methylbenzoyl)piperidin-4-yl)benzonitrile and Compound 197. 4-(1-(5-(5-(methoxymethyl)-4H-1,2,4-triazol-3-yl)-4-methyl-2-propylbenzoyl)piperidin-4-yl)benzonitrile To a solution of 2-isopropyl-5-(5-(methoxymethyl)-4H-1,2,4-triazol-3-yl)-4-methylbenzoic acid (compound 196.7, 200 mg, 0.690 mmol, 1.00 equiv) in DMF (20 mL) were added EDCI (200 mg, 1.04 mmol, 1.51 equiv), DMAP (250 mg, 2.05 mmol, 2.96 equiv), and HOBT (110 mg, 0.810 mmol, 1.18 equiv). After stirring for 30 min at room temperature compound 1.5, 142 mg, 0.640 mmol, 0.92 equiv was added and the resulting solution was stirred for 15 h at 25° C., then quenched with 100 mL of ice water. The resulting mixture was extracted with 2×200 mL of ethyl acetate. The combined organic layers were washed with 2×100 mL of brine, then dried over anhydrous sodium sulfate and concentrated in vacuo. The residue was purified using silica gel column chromatography with ethyl acetate/petroleum ether (1:50-1:1-1:0) as eluent. The crude product (~120 mg) was further purified by Prep-HPLC with the following conditions (1#-Pre-HPLC-001(SHIMADZU)): Column, SunFire Prep C18, 19*150 mm 5 um; mobile phase, water with 0.05% TFA and CH$_3$CN (40.0% CH$_3$CN up to 55.0% in 8 min, up to 100.0% in 1 min, down to 40.0% in 1 min); Detector, Waters 2489 254 & 220 nm. The fractions containing pure compound were combined and lyophilized to yield 57.4 mg (18%) of compound 196 and 11.7 mg (4%) of compound 197 as white solids. Compound 196. m/z (ES+) 458 (M+H)$^+$. $^1$H-NMR (300 MHz, CD$_3$OD): δ 7.65-7.62 (m, 2H), 7.55-7.28 (m, 4H), 4.61 (s, 2H), 3.67-3.62 (m, 1H), 3.44 (s, 3H), 3.27-3.20 (m, 1H), 3.04-2.86 (m, 3H), 2.51 (s, 3H), 1.99-1.68 (m, 5H), 1.31-1.26 (m, 6H). Compound 197. m/z (ES+) 458 (M+H)$^+$. $^1$H-NMR (300 MHz, CD$_3$OD): δ 7.66-7.63 (m, 2H), 7.55 (s, 1H), 7.46-7.37 (m, 2H), 7.28 (m, 1H), 4.61 (s, 2H), 3.62-3.58 (m, 1H), 3.44 (s, 3H), 3.19-3.05 (m, 2H), 3.04-2.91 (m, 2H), 2.73-2.45 (m, 5H), 1.98-1.54 (m, 6H), 1.05-0.85 (m, 3H).

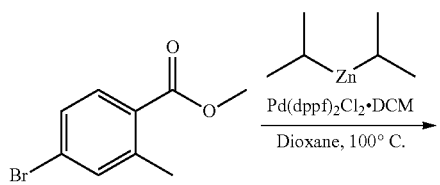

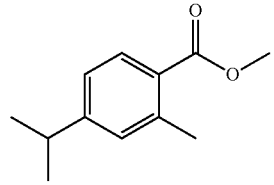

Compound 198.1. Methyl 4-isopropyl-2-methylbenzoate

A dried round bottom flask with stir bar was purged with nitrogen and charged with diisopropyl zinc (25 mL of a 1 M solution in THF, 25 mmol, 2.0 equiv). Methyl 4-bromo-2-methylbenzoate (compound 152.1, 2.86 g, 12.5 mmol, 1.0 equiv) in 1,4-dioxane (25 mL) was added followed by addition of Pd(dppf)$_2$Cl$_2$.DCM (1.02 g, 1.25 mmol, 0.1 equiv) (exothermic upon catalyst addition). The system was purged with additional nitrogen then argon and heated to 100° C. for 4 hours then stirred at room temperature for 12 hours. The mixture was carefully quenched with 1M HCl (aq., 12 mL) (some bubbling) and then diluted with water (100 mL) and ethyl acetate (150 mL) and mixed. The mixture was filtered through celite and washed with water and ethyl acetate (2×25 mL each). The layers were separated and the aqueous was extracted with addition ethyl acetate (50 mL). The combined organics were washed with brine (50 mL), dried (Na$_2$SO$_4$), and concentrated under reduced pressure. The crude product was purified by silica gel column chromatography (hexanes to 6% ethyl acetate) to obtain the title compound as a colorless oil (2.31 g, 96%). $^1$H NMR (400 MHz, CDCl$_3$): δ 7.86 (d with fine str, J=8.8 Hz, 1H), 7.12-7.07 (m, 2H), 3.87 (s, 3H), 2.90 (septet, J=6.8 Hz, 1H), 2.59 (s, 3H), 1.25 (d, J=6.8 Hz, 6H).

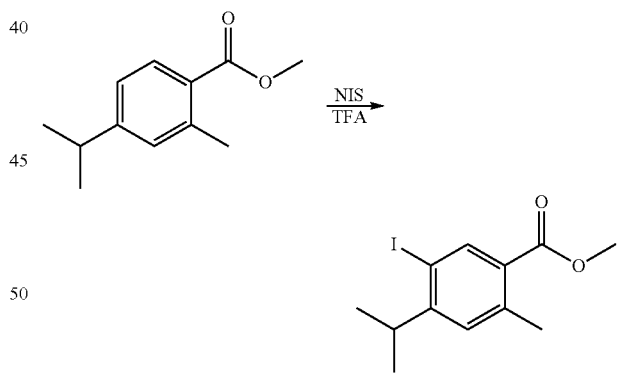

Compound 198.2. Methyl 5-iodo-4-isopropyl-2-methylbenzoate

To methyl 4-isopropyl-2-methylbenzoate (compound 198.1, 2.31 g, 12.0 mmol, 1.0 equiv) in a 100 mL round bottom flask was carefully added TFA (24 mL) and the mixture was cooled to 0° C. N-Iodosuccinimide (2.70 g, 12.0 mmol, 1.0 equi) was added portionwise over 2 minutes and the resulting mixture was added under nitrogen and stirred at 0° C. for 20 min then at room temperature for 15 hours. The mixture was carefully diluted To a mixture of dichloromethane (50 mL) and added to saturated aqueous disodium phosphate to maintain a pH above 3 (total disodium phosphate about 500 mL). The mixture was shaken well, separated and the aqueous was extracted with additional DCM (5×25 mL). The combined organics was washed with a mix of saturated sodium sulfite (10 mL) plus water (40 mL) followed by brine (50 mL), dried (Na$_2$SO$_4$), filtered and removed in vacuo. The crude product was purified by silica column chromatography (hexanes to 3% ethyl acetate) to obtain the title compound as a light tan oil (3.59 g, 94%). $^1$H NMR (400 MHz, CDCl$_3$): δ 8.35 (s, 1H), 7.08 (s, 1H), 3.87 (s, 3H), 3.17 (septet, J=6.8 Hz, 1H), 2.59 (s, 3H), 1.23 (d, J=6.8 Hz, 6H).

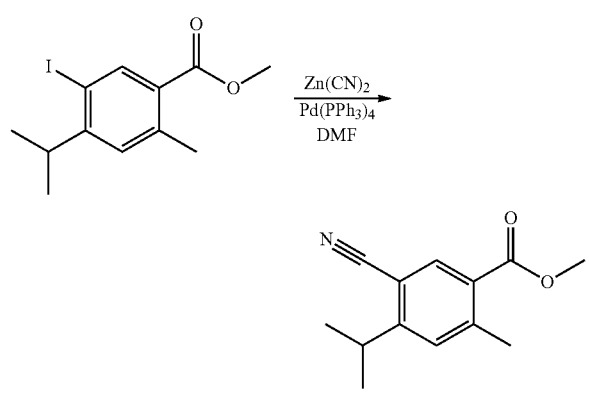

Compound 198.3. Methyl 5-cyano-4-isopropyl-2-methylbenzoate

To a dried round bottom flask was added methyl 5-iodo-4-isopropyl-2-methylbenzoate (compound 198.2, 2.00 g, 6.29 mmol, 1.0 equiv), zinc cyanide (1.48 g, 12.6 mmol, 2.0 equiv), DMF (20 mL) and Pd(PPh$_3$)$_4$ (364 mg, 0.315 mmol, 0.05 equiv). The system was purged with nitrogen followed by argon and the mixture was heated at 100° C. for 15 hours. The reaction was allowed to cool to room temperature then diluted with ethyl acetate (50 mL) and quenched with 1 M FeSO$_4$ (25 mL). The mixture was stirred vigorously for 40 minutes then filtered through celite and washed with 1 M FeSO$_4$ (15 mL), water (50 mL) and ethyl acetate (150 mL). The layers were separated and the aqueous phase was extracted with ethyl acetate (50 mL). The combined organic layers were washed with brine (4×100 mL), dried (Na$_2$SO$_4$), filtered, and concentrated in vacuo. The product was purified by silica column chromatography (hexanes to 8% ethyl acetate) to obtain the title compound (1.14 g, 83%). $^1$H NMR (400 MHz, CDCl$_3$): δ 8.19 (s, 1H), 7.25 (s, 1H), 3.91 (s, 3H), 3.37 (septet, J=6.8 Hz, 1H), 2.67 (s, 3H), 1.32 (d, I=6.8 Hz, 6H).

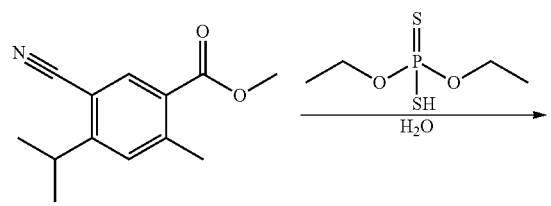

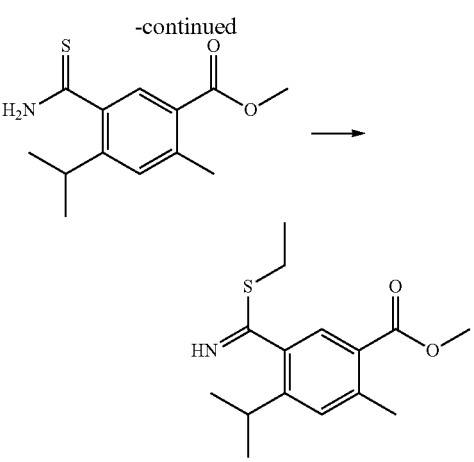

Compound 198.4. Methyl 5-((ethylthio)(imino)methyl)-4-isopropyl-2-methylbenzoate Methyl 5-cyano-4-isopropyl-2-methylbenzoate (compound 198.3, 1.12 g, 5.16 mmol, 1.0 equiv), O,O'-diethyl dithiophosphate (90%) (2.0 mL, 10.7 mmol, 2.1 equiv) and water (200 µL) were added to a 16 mL vial and the mixture was heated with the cap loose at 80° C. for 85 hours (CAUTION: significant gas evolution occurs—this and all other reactions described herein should be carried out in well ventilated fume hoods). Note that additional O,O'-diethyl dithiophosphate (0.5 mL, 2.7 mmol, 0.5 equiv) and water (50 µL) was added at 6 hours and 14 hours. The intermediate thioamide is also observed by LC/MS during the reaction and is heated until the conversion to the desired product is complete. The reaction mixture was diluted with ethyl acetate (75 mL) and washed with saturated aqueous NaHCO$_3$ (20 mL) followed by 1 M NaH$_2$PO$_4$ (10 mL) and brine (10 mL). The organics were dried (Na$_2$SO$_4$), filtered and removed in vacuo. The crude product was purified by silica column chromatography (hexanes to 25% ethyl acetate) to obtain a colorless oil (1.12 g, 78%). m/z (ES+) 280 (M+H)$^+$.

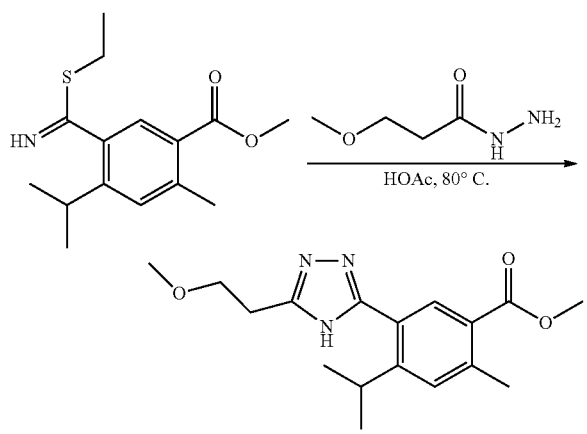

Compound 198.5. Methyl 4-isopropyl-5-(5-(2-methoxyethyl)-4H-1,2,4-triazol-3-yl)-2-methylbenzoate Methyl 5-((ethylthio)(imino)methyl)-4-isopropyl-2-methylbenzoate (compound 198.4, 33 mg, 0.12 mmol, 1.0 equiv), 3-methoxypropanehydrazide (compound 143.1, 21 mg, 0.18 mmol, 1.5 equiv) and acetic acid (1.2 mL) were added to a 4-mL vial and heated at 80° C. with a loose cap for 4 hours. The solvent was removed in vacuo and the residue was dissolved in DCM (10 mL) and washed with saturated NaHCO₃ (5 mL) then brine (5 mL), dried (Na₂SO₄), filtered and evaporated to a colorless oil (theoretical yield). m/z (ES+) 318 (M+H)⁺.

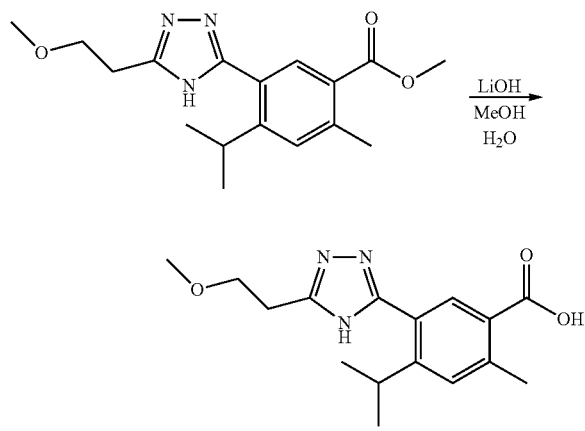

Compound 198.6. 4-Isopropyl-5-(5-(2-methoxyethyl)-4H-1,2,4-triazol-3-yl)-2-methylbenzoic acid To crude methyl 4-isopropyl-5-(5-(2-methoxyethyl)-4H-1,2,4-triazol-3-yl)-2-methylbenzoate (compound 198.5, 0.12 mmol, 1.0 equiv) from the previous step in a 4-mL vial was added lithium hydroxide monohydrate (10.1 mg, 0.24 mmol, 2.0 equiv), methanol (0.9 mL) and water (0.3 mL). The resulting mixture was stirred at room temperature for 3 hours followed by 50° C. for 3 hours and 40° C. for 17 hours. The solvents were removed in vacuo and the residue was diluted with water (7 mL) plus saturated NaHCO₃ (1 mL) and the aqueous was washed with diethyl ether (2 mL). The organic was back extracted with a mix of water (2 mL) plus saturated NaHCO₃ (0.5 mL). The combined aqueous was acidified to pH=3 with 1 M H₃PO₄ and extracted with dichlormethane (3×5 mL). The organics were dried (Na₂SO₄), filtered and removed in vacuo to obtain the title compound as a white waxy solid (31.5 mg, 88% over 2 steps). (ES+) 304 (M+H)⁺.

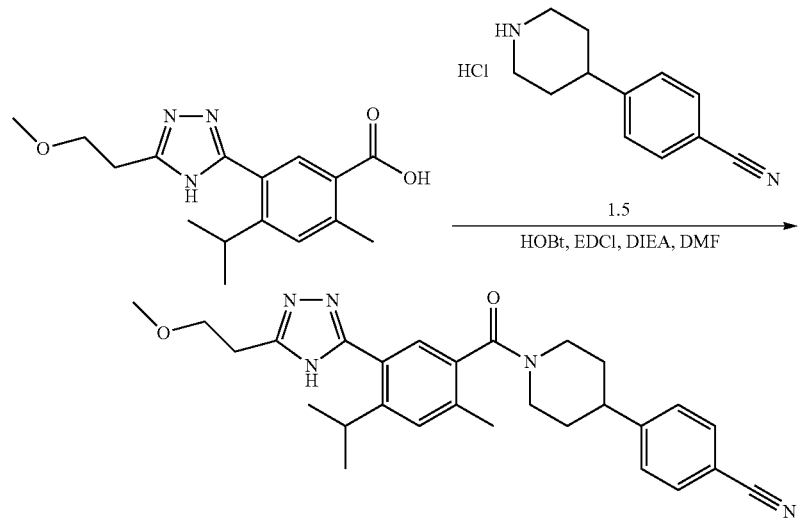

Compound 198. 4-(1-(4-Isopropyl-5-(5-(2-methoxyethyl)-4H-1,2,4-triazol-3-yl)-2-methylbenzoyl)piperidin-4-yl)benzonitrile To a 4-mL vial was added 4-Isopropyl-5-(5-(2-methoxyethyl)-4H-1,2,4-triazol-3-yl)-2-methylbenzoic acid (compound 198.6, 31 mg, 0.10 mmol, 1.0 equiv), 4-(piperidin-4-yl)benzonitrile hydrochloride (compound 1.5, 23 mg, 0.10 mmol, 1.0 equiv), 1-hydroxybenzotriazole hydrate (20 wt % water) (22 mg, 0.13 mmol, 1.25 equiv), 1-ethyl-3-(3-dimethylaminopropyl) carbodiimide hydrochloride (21.5 mg, 0.11 mmol, 1.1 equiv), DMF (1 mL) and DIEA (71 µL, 0.41 mmol, 4 equiv). The mixture was stirred at room temperature for 24 hours then diluted with ethyl acetate (10 mL) and washed with brine (10 mL). The aqueous was back extracted with ethyl acetate (3 mL) and the combined organics was washed with saturated NaHCO₃ (5 mL), 1 M NaH₂PO₄ (5 mL), and brine (5 mL). The organics were dried (Na₂SO₄), filtered and removed in vacuo. The crude residue was purified by preparative TLC (DCM/8% MeOH) to obtain the title compound as an off white solid (23 mg, 48%). m/z (ES+) 472 (M+H)⁺.

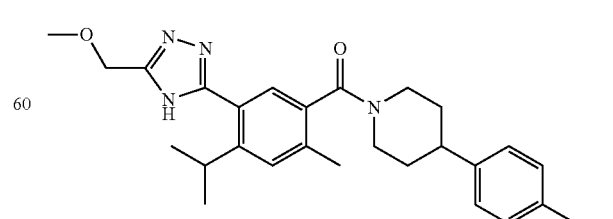

Compound 199. 4-(1-(4-Isopropyl-5-(5-(methoxymethyl)-4H-1,2,4-triazol-3-yl)-2-methylbenzoyl)piperidin-4-yl)benzonitrile The title compound was prepared using standard chemical manipulations and procedures similar to those used for the preparation of 4-(1-(4-isopropyl-5-(5-(2-methoxyethyl)-4H-1,2,4-triazol-3-yl)-2-methylbenzoyl)piperidin-4-yl)benzonitrile (compound 198). m/z (ES+) 458 (M+H)+.

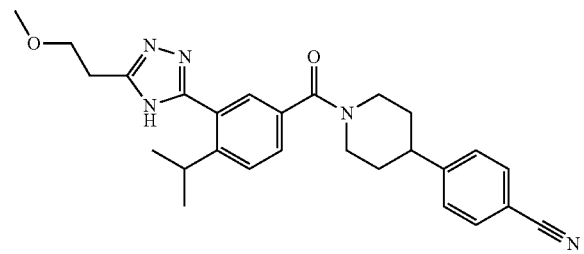 [SMILES: COCCc1nnc(-c2cc(C(=O)N3CCC(c4ccc(C#N)cc4)CC3)ccc2C(C)C)[nH]1]

Compound 200. 4-(1-(4-Isopropyl-3-(5-(2-methoxyethyl)-4H-1,2,4-triazol-3-yl)benzoyl)piperidin-4-yl)benzonitrile The title compound was prepared using standard chemical manipulations and procedures similar to those used for the preparation of 4-(1-(4-isopropyl-5-(5-(2-methoxyethyl)-4H-1,2,4-triazol-3-yl)-2-methylbenzoyl)piperidin-4-yl)benzonitrile (compound 198). m/z (ES+) 458 (M+H)+.

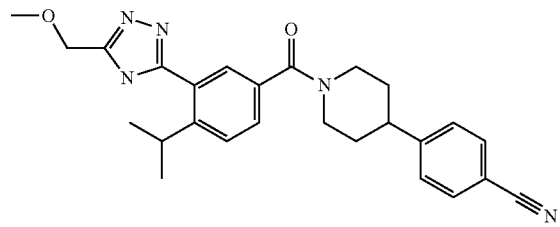 [SMILES: COCc1nnc(-c2cc(C(=O)N3CCC(c4ccc(C#N)cc4)CC3)ccc2C(C)C)[nH]1]

Compound 201. 4-(1-(4-Isopropyl-3-(5-(methoxymethyl)-4H-1,2,4-triazol-3-yl)benzoyl)piperidin-4-yl)benzonitrile The title compound was prepared using standard chemical manipulations and procedures similar to those used for the preparation of 4-(1-(4-isopropyl-5-(5-(2-methoxyethyl)-4H-1,2,4-triazol-3-yl)-2-methylbenzoyl)piperidin-4-yl)benzonitrile (compound 198). m/z (ES+) 444 (M+H)+.

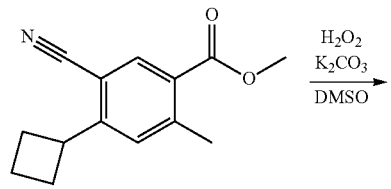

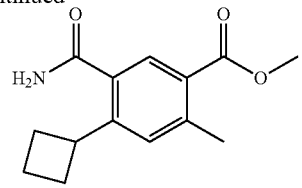

Compound 202.1. Methyl 5-carbamoyl-4-cyclobutyl-2-methylbenzoate

To an 8-mL vial was added methyl 5-cyano-4-cyclobutyl-2-methylbenzoate (152.4, 100 mg, 0.436 mmol, 1.0 equiv), potassium carbonate (181 mg, 1.31 mmol, 3.0 equiv) and DMSO (2.2 mL) and stirring was initiated. Hydrogen peroxide (50 wt %) (176 µL, 3.05 mmol, 7.0 equiv) was added over about 1 minute. The mixture was stirred at room temperature for 29 hours then diluted into brine (10 mL) plus 1 M $H_3PO_4$ (1.5 mL). The mixture was extracted with ethyl acetate (10 mL×1, 3 mL×1). The combined organic layers were washed with brine (10 mL) plus a few drops of 1 M $H_3PO_4$ followed by a mixture of water (10 plus saturated $NaHCO_3$ (1 mL) and finally brine (5 mL). The organics was dried ($Na_2SO_4$), filtered and evaporated to obtain the title compound as a white solid (59 mg, 55%). m/z (ES+) 248.0 (M+H)+.

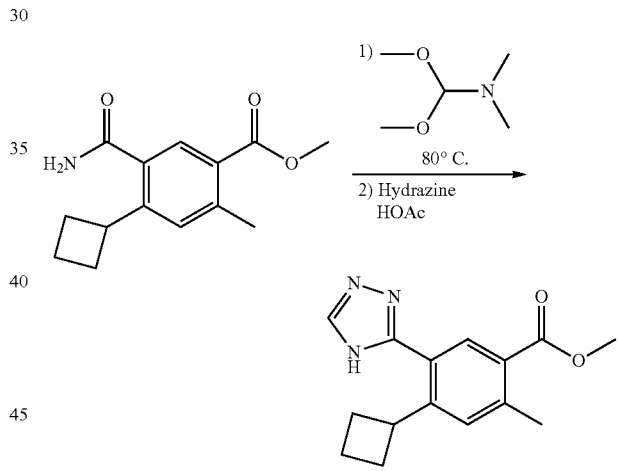

Compound 202.2. Methyl 4-cyclobutyl-2-methyl-5-(4H-1,2,4-triazol-3-yl)benzoate To a vial was added methyl 5-carbamoyl-4-cyclobutyl-2-methylbenzoate (compound 202.1, 59 mg, 0.24 mmol, 1.0 equiv) and N,N-dimethylformamide dimethyl acetal (1 mL) was added. The mixture was heated at 80° C. for 5 hours then the solvents were removed in vacuo. To the residue was added acetic acid (400 µl) and a solution of anhydrous hydrazine (8.2 µL, 0.26 mmol, 1.1 equiv) in acetic acid (100 µL). To the resulting thick suspension was added additional acetic acid (500 µL) and the mixture was stirred at 80° C. for 1.5 hours then the solvents removed in vacuo. Ethyl acetate (5 mL) and DCM (5 mL) was added (some undissolved solids). The organics was washed with saturated $NaHCO_3$ (10 mL) and brine (5 mL) and removed in vacuo to obtain the title compound as a white solid (theoretical yield). m/z (ES+) 272 (M+H)+.

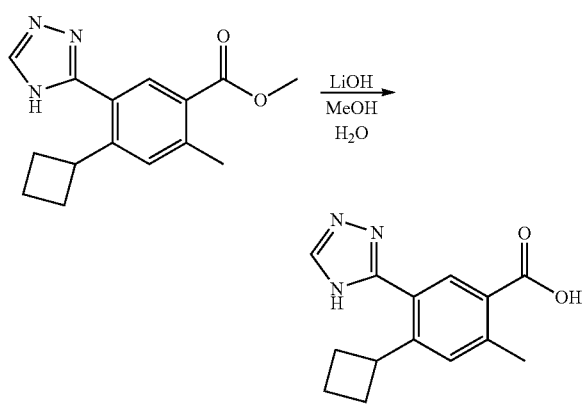

Compound 202.3. 4-Cyclobutyl-2-methyl-5-(4H-1,2,4-triazol-3-yl)benzoic acid

To crude methyl 4-cyclobutyl-2-methyl-5-(4H-1,2,4-triazol-3-yl)benzoate (compound 202.2, 0.24 mmol, 1.0 equiv) from the previous step in a 4-mL vial was added methanol (1.5 mL) and water (0.5 mL) and lithium hydroxide monohydrate (20 mg, 0.48 mmol, 2.0 equiv), The resulting mixture was stirred at 40° C. for 42 hours. The reaction mixture was diluted into water (5 mL), acidified to pH 3 with 1M $H_3PO_4$ and extracted with DCM (3×5 mL). The organics were dried ($Na_2SO_4$), filtered and concentrated in vacuo to obtain the title compound as a white solid (61 mg, 98% over 2 steps). m/z (ES+) 258 (M+H)$^+$.

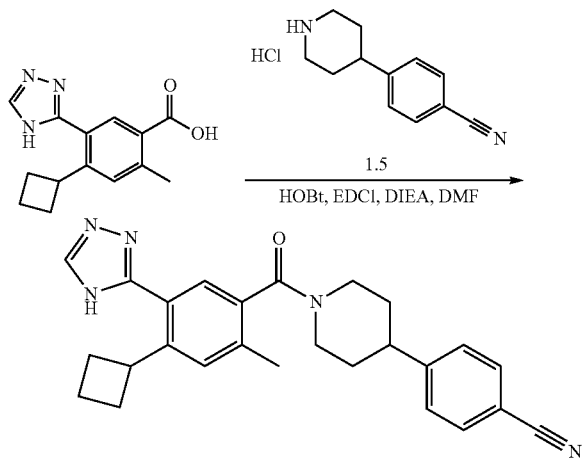

Compound 202. 4-(1-(4-Cyclobutyl-2-methyl-5-(4H-1,2,4-triazol-3-yl)benzoyl)piperidin-4-yl)benzonitrile To a 4-mL vial was added 4-cyclobutyl-2-methyl-5-(4H-1,2,4-triazol-3-yl)benzoic acid (compound 202.3, 31 mg, 0.12 mmol, 1.0 equiv), 4-(piperidin-4-yl)benzonitrile hydrochloride (compound 1.5, 27 mg, 0.12 mmol, 1.0 equiv), 1-hydroxybenzotriazole hydrate (20 wt % water) (25 mg, 0.15 mmol, 1.25 equiv), 1-ethyl-3-(3-dimethylaminopropyl) carbodiimide hydrochloride (25 mg, 0.13 mmol, 1.1 equiv), DMF (0.6 mL) and DIEA (83 µL, 0.48 mmol, 4 equiv). The mixture was stirred at room temperature for 4 hours then diluted with ethyl acetate (10 mL) and washed with 1 M $NaH_2PO_4$ (5 mL). The aqueous was back extracted with ethyl acetate (3 mL) and the combined organics was washed with brine (5 mL), saturated $NaHCO_3$ (5 mL) and brine (5 mL). The organics were dried ($Na_2SO_4$), filtered and removed in vacuo. The crude residue was purified by preparative TLC (DCM/8% MeOH) to obtain the title compound as a white solid (23 mg, 46%). m/z (ES+) 426 (M+H)$^+$.

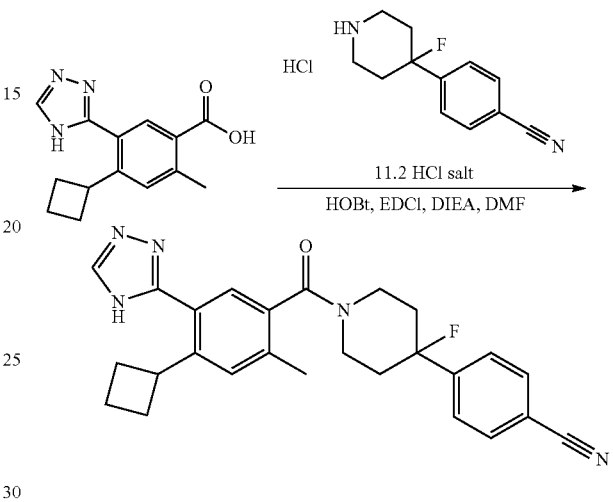

Compound 203. 4-(1-(4-Cyclobutyl-2-methyl-5-(4H-1,2,4-triazol-3-yl)benzoyl)-4-fluoropiperidin-4-yl)benzonitrile To a 4-mL vial was added 4-cyclobutyl-2-methyl-5-(4H-1,2,4-triazol-3-yl)benzoic acid (compound 202.3, 31 mg, 0.12 mmol, 1.0 equiv), 4-(4-fluoropiperidin-4-yl)benzonitrile (compound 11.2, 31 mg, 0.13 mmol, 1.1 equiv), 1-hydroxybenzotriazole hydrate (20 wt % water) (25 mg, 0.15 mmol, 1.25 equiv), 1-ethyl-3-(3-dimethylaminopropyl) carbodiimide hydrochloride (25 mg, 0.13 mmol, 1.1 equiv), DMF (0.6 mL) and DIEA (83 µL, 0.48 mmol, 4 equiv). The mixture was stirred at room temperature for 4 hours then diluted with ethyl acetate (10 mL) and washed with 1 M $NaH_2PO_4$ (5 mL). The aqueous was hack extracted with ethyl acetate (3 mL) and the combined organics was washed with brine (5 mL), saturated $NaHCO_3$ (5 mL) and brine (5 mL). The organics were dried ($Na_2SO_4$), filtered and removed in vacuo. The crude residue was purified by preparative TLC (DCM/8% MeOH) to obtain the title compound as a white solid (30 mg, 56%). m/z (ES+) 444 (M+H)$^+$.

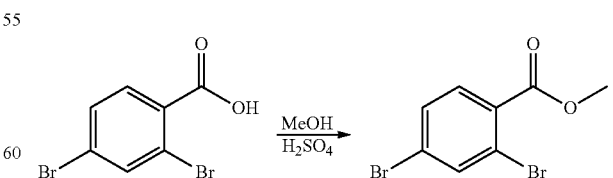

Compound 204.1. Methyl 2,4-dibromobenzoate

A solution of 2,4-dibromobenzoic acid (52.0 g, 176 mmol, 1.00 equiv, 95%) and sulfuric acid (20 mL) in methanol (400 mL) was stirred at 90° C. overnight. After cooling to room temperature, the mixture was concentrated under reduced pressure. The residue was diluted with 500 mL of ethyl acetate and washed with 3×100 mL of H₂O followed by 1×100 mL of NaHCO₃ (aq., sat. Note: gas evolution occurs). The organic layer was dried over anhydrous sodium sulfate and concentrated in vacuo. This resulted in 45.0 g (78%) of methyl 2,4-dibromobenzoate as a yellow oil.

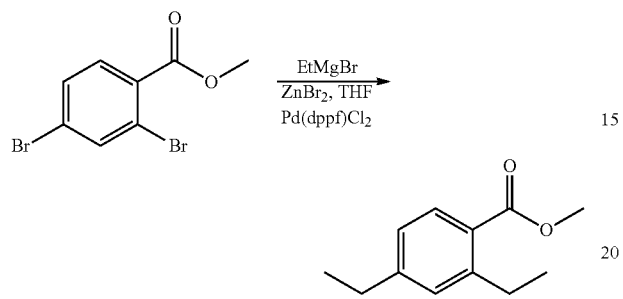

Compound 204.2. Methyl 2,4-diethylbenzoate

To stirred mixture of ZnBr₂ (40.0 g, 176 mmol, 5.44 equiv, 99%) in THF (100 mL) under nitrogen at 0° C. was added dropwise EtMgBr (60 mL, 3 M in THF). After 0.5 h at 0° C., the temperature was lowered to −78° C. and PdCl₂(dppf) (3.72 g, 5.03 mmol, 0.16 equiv, 99%) was added followed by the dropwise addition of a solution of methyl 2,4-dibromobenzoate (compound 204.1, 10.0 g, 32.3 mmol, 1.00 equiv, 95%) in THF (200 mL). The reaction was stirred overnight at room temperature, then carefully quenched with water followed by HCl (aq., 1 M). The resulting mixture was extracted with 3×500 mL of ethyl acetate, and the combined organic layers were washed with 3×50 mL of brine, dried over anhydrous sodium sulfate, and concentrated ire vacuo. The residue was purified using silica gel column chromatography with ethyl acetate/petroleum ether (1:60) as eluent to furnish 6.30 g (96%) of methyl 2,4-diethylbenzoate as a colorless oil

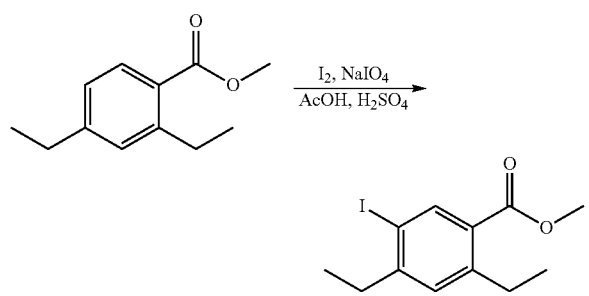

Compound 204.3. Methyl 2,4-diethyl-5-iodobenzoate

The title compound (4.0 g, light yellow oil, 69%) was prepared using a procedure similar to that used for the preparation of compound 181.4 using compound 204.2 (3.50 g) in place of compound 181.3.

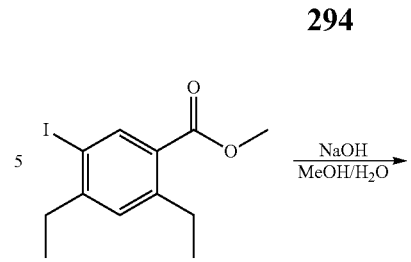

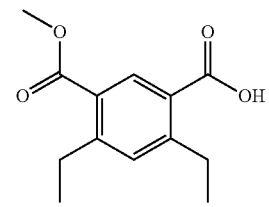

Compound 204.4. 2,4-Diethyl-5-iodobenzoic acid

The title compound (3.24 g, white solid, 85%) was prepared using a procedure similar to that used for the preparation of compound 181.9 using compound 204.3 (4.00 g) in place of compound 181.8.

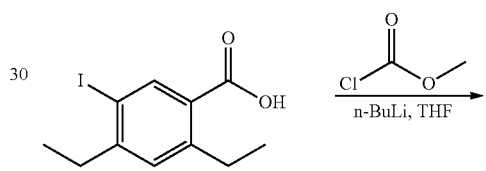

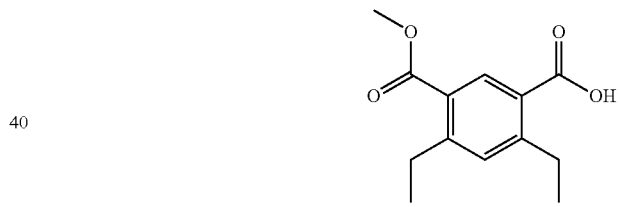

Compound 204.5. 2,4-Diethyl-5-(methoxycarbonyl)benzoic acid

To a stirred solution of 2,4-diethyl-5-iodobenzoic acid (compound 204.4., 500 mg, 1.64 mmol, 1.00 equiv, 90%) in tetrahydrofuran (20 mL) at −78° C. under nitrogen was added dropwise a solution of n-BuLi (1.73 mL, 4.10 mmol, 2.36 M in THF). After 5 minutes, a solution of methyl chloroformate (0.315 mL, 4.10 mmol, 2.50 equiv) in THF (5 mL) was added dropwise to the reaction at −78° C. over 5 minutes. The reaction was stirred for another 5 min at −78° C., and then carefully quenched with 10 mL of water. The pH was adjusted to 1-2 with hydrochloric acid (6 M) and the resulting mixture was extracted with ethyl acetate (2×30 mL). The combined organic layers were washed with 20 mL of brine, then dried over anhydrous sodium sulfate, and concentrated in mean. The residue was purified by silica gel column chromatograph with ethyl acetate-petroleum ether (1:20) as eluent to yield 96 mg (25%) of the title compound as an off-white solid.

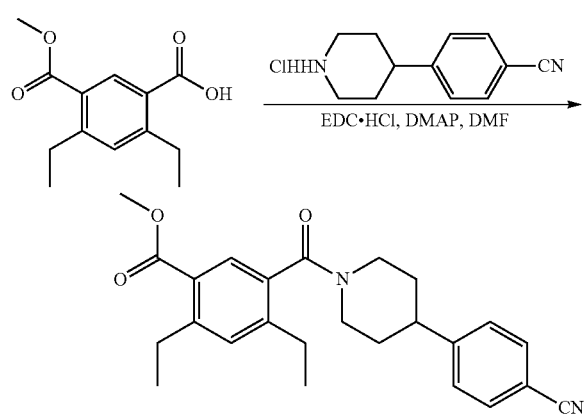

Compound 204.6. Methyl 5-(4-(4-cyanophenyl)piperidine-1-carbonyl)-2,4-diethylbenzoate

To a round-bottom flask, were added a solution of 2,4-diethyl-5-(methoxycarbonyl)benzoic acid (compound 204.5, 500 mg, 2.12 mmol, 1.00 equiv), 4-(piperidin-4-yl)benzonitrile hydrochloride (compound 1.5, 470 mg, 2.12 mmol, 1 equiv), EDC.HCl (810 mg, 4.24 mmol, 2.00 equiv), and 4-dimethylaminopyridine (520 mg, 4.24 mmol, 2 equiv) in N,N-dimethylformamide (15 mL). The reaction was stirred overnight at 25° C. Upon reaction completion, the reaction mixture was diluted with 30 mL of ethyl acetate, then washed with 1×20 mL of NH₄Cl (aq.) and 1×20 mL of brine. The organic phase was dried over anhydrous sodium sulfate and concentrated in vacuo. The residue was purified by silica gel chromatography with a solvent mixture of ethyl acetate and petroleum ether (1:1) to yield 500 mg (60%) of the title compound as a pale yellow solid.

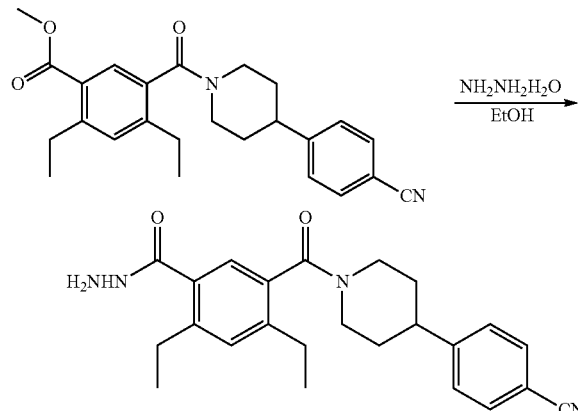

Compound 204.7. 5-(4-(4-Cyanophenyl)piperidine-1-carbonyl)-2,4-diethylbenzohydrazide

To a solution of compound 204.6 (500 mg, 1.05 mmol, 1.00 equiv, 85%) in ethanol (6 mL) was added hydrazine hydrate (3 mL). The resulting solution was stirred overnight at 90° C. After cooling to ambient temperature, the mixture was concentrated in vacuo. The residue was diluted with 20 mL of ethyl acetate, then washed with 1×5 mL of brine, dried over anhydrous sodium sulfate, and concentrated in vacuo. The residue was purified by silica gel column chromatography with dichloromethane-methanol (20:1) as eluent to yield 260 mg (55%) of the desired compound as a yellow solid.

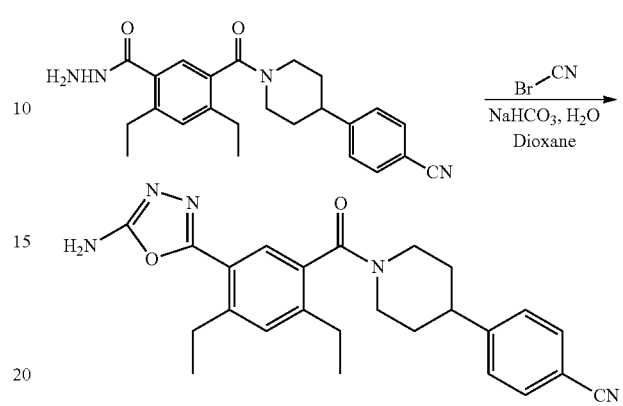

Compound 204.8. 4-(1-(5-(5-Amino-1,3,4-oxadiazol-2-yl)-2,4-diethylbenzoyl)piperidin-4-yl)benzonitrile

To a round-bottom flask was added a solution of 5-(4-(4-cyanophenyl)piperidine-1-carbonyl)-2,4-diethylbenzohydrazide (compound 204.7, 100 mg, 0.220 mmol, 1.00 equiv, 90%) in a solvent mixture of water (2 mL) and dioxane (3 mL). Sodium bicarbonate (62 mg, 0.740 mmol, 3.00 equiv) was added to the reaction mixture at room temperature, and stirred for 5 minutes. BrCN (75 mg, 0.740 mmol, 3.00 equiv) was then added to the reaction at room temperature. The resulting solution was stirred for 2 h at room temperature, then quenched with 30 mL of FeSO₄ (aq., sat.) and diluted with ethyl acetate. The resulting mixture was stirred vigorously then filtered through celite and washed with 1 M FeSO₄, water, and ethyl acetate. The layers were separated and the aqueous phase was extracted with 2×50 mL of ethyl acetate. The combined organic layers were washed with 2×50 mL of brine, dried over anhydrous sodium sulfate, and concentrated in vacuo. This resulted in 100 mg (89%) of the title compound as a yellow solid. The compound was used in the next step reaction without further purification.

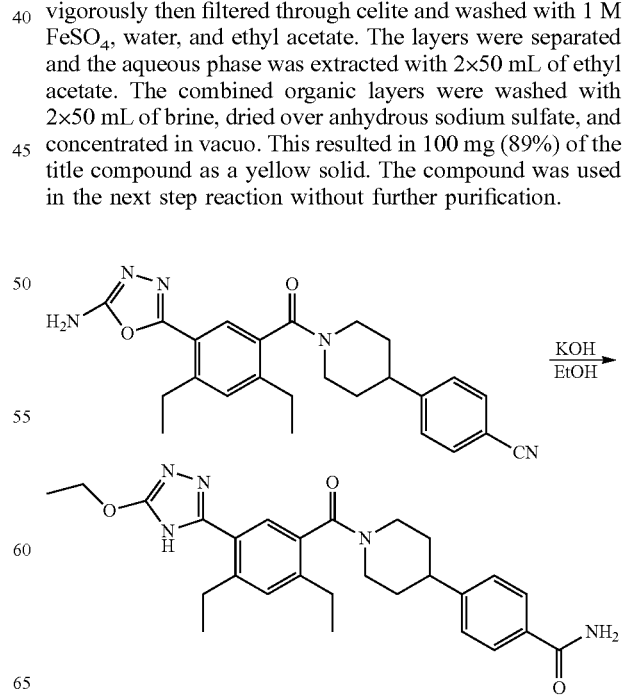

Compound 204.9. 4-(1-(5-(5-Ethoxy-4H-1,2,4-tri-azol-3-yl)-2,4-diethylbenzoyl)piperidin-4-yl)benzamide A mixture of compound 204.8 (100 mg, 0.200 mmol, 1.00 equiv, 85%) and potassium hydroxide (132 mg, 2.35 mmol, 10.0 equiv) in ethanol (10 mL) was stirred at 85° C. overnight. After cooling to ambient temperature, the pH was adjusted to 7 with acetic acid and the resulting solution was concentrated in vacuo. The residue was diluted with 50 mL of ethyl acetate, washed with 2×20 mL of brine, then concentrated in vacuo. The crude product was dried in a vacuum oven, before it was charged onto a silica gel column, and purified with dichloromethane-methanol (20:1) to afford 100 mg (85%) of the title compound as a yellow solid.

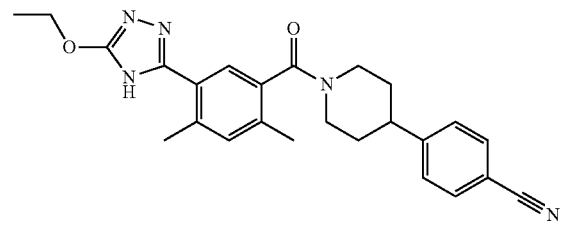 [SMILES: CCOc1nnc(-c2cc(C(=O)N3CCC(c4ccc(C#N)cc4)CC3)c(C)cc2C)[nH]1]

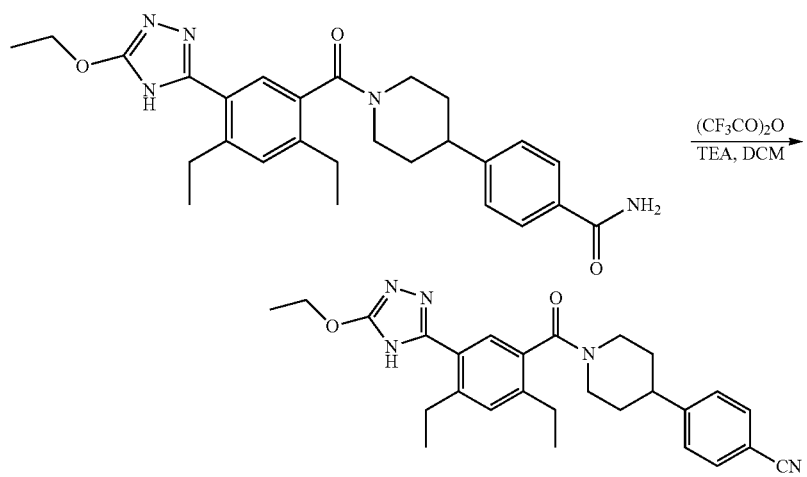

Compound 204. 4-(1-(5-(5-Ethoxy-4H-1,2,4-triazol-3-yl)-2,4-diethylbenzoyl)piperidin-4-yl)benzonitrile To a round-bottom flask was added a solution of 4-(1-(5-(5-ethoxy-4H-1,2,4-triazol-3-yl)-2,4-diethylbenzoyl)piperidin-4-yl)benzamide (compound 204.9, 100 mg, 0.170 mmol, 1.00 equiv) in dichloromethane (10 mL). Triethylamine (170 mg, 1.68 mmol, 8.00 equiv) was added to the reaction at room temperature, followed by dropwise addition of a solution of $(CF_3CO)_2O$ (160 mg, 0.760 mmol, 4.50 equiv) in dichloromethane (0.5 mL) at 0 to 5° C. The resulting solution was stirred at room temperature for another 2 hours. The mixture was diluted with 60 mL of ethyl acetate, then washed with 3×20 mL of brine. The organic layer was dried over anhydrous sodium sulfate, and concentrated in vacuo. The residue was purified by prep-HPLC (SunFire Prep C18, 19*1.50 mm 5 um, water with 0.05% TFA and $CH_3CN$ (53.0% $CH_3CN$ up to 65.0% in 8 min, up to 100.0% in 2 min, down to 53.0% in 1 min). The fractions containing pure compound were combined and lyophilized to yield 50 mg (50%) of the title compound as a white solid. m/z (ES+) 458 (M+H)$^+$. $^1$H NMR (300 MHz, $CD_3OD$): δ 7.63 (d, 2H), 7.45-7.30 (m, 4H), 4.89-4.80 (m, 1H, overlapped), 4.36 (q, 2H), 3.60-3.57 (m, 1H), 3.29-3.23 (m, 1H), 3.19-2.85 (m, 4H), 2.74-2.56 (m, 2H), 2.00-1.82 (m, 1H), 1.77-1.66 (m, 3H), 1.40 (t, 3H), 1.30-1.21 (m, 3H), 1.11 (t, 3H).

Compound 205. 4-(1-(5-(5-Ethoxy-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(5-(5-ethoxy-4H-1,2,4-triazol-3-yl)-2,4-diethylbenzoyl)piperidin-4-yl)benzonitrile (compound 204). m/z (ES+) 430 (M+H)$^+$. $^1$H NMR (300 MHz, $CD_3OD$): δ 7.69 (d, 2H), 7.52-7.47 (m, 3H), 7.29 (s, 1H), 4.89-4.80 (m, 1H, overlapped), 4.42-4.40 (m, 2H), 3.64-3.61 (m, 1H), 3.02-2.96 (m, 2H), 2.51 (s, 3H), 2.41 and 2.31 (2 singlets, amide rotamers, $ArCH_3$, 3H), 2.05-2.02 (m, 1H), 1.77-1.46 (m, 3H), 1.45 (t, 3H).

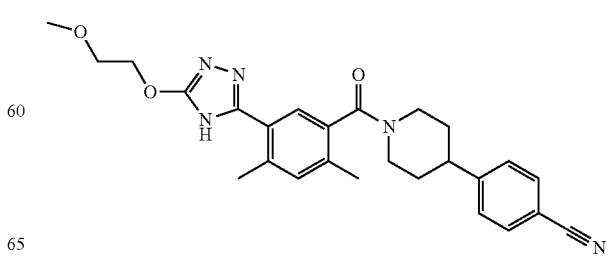

Compound 206. 4-(1-(5-(5-(2-Methoxyethoxy)-4H-1,2,4-triazol-3-yl)-2,4-dimethylbenzoyl)piperidin-4-yl)benzonitrile The title compound was prepared using standard chemical manipulations and procedures similar to those used for the preparation 4-(1-(5-(5-ethoxy-4H-1,2,4-triazol-3-yl)-2,4-diethylbenzoyl)piperidin-4-yl)benzonitrile (compound 204). m/z (ES+) 460 (M+H)+.

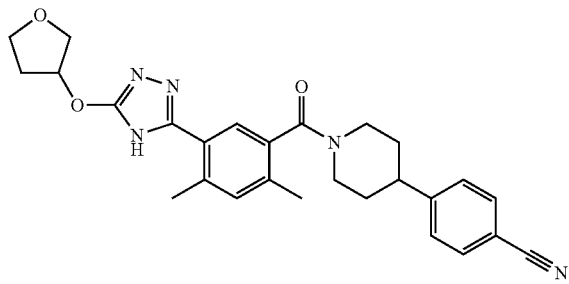 [SMILES: Cc1cc(C)c(-c2nnc(OC3CCOC3)[nH]2)cc1C(=O)N1CCC(c2ccc(C#N)cc2)CC1]

Compound 207. 4-(1-(2,4-Dimethyl-5-(5-((tetrahydrofuran-3-yl)oxy)-4H-1,2,4-triazol-3-yl)benzoyl)piperidin-4-yl)benzonitrile The title compound was prepared using standard chemical manipulations and procedures similar to those used for the preparation of 4-(1-(5-(5-ethoxy-4H-1,2,4-triazol-3-yl)-2,4-diethylbenzoyl)piperidin-4-yl)benzonitrile (compound 204). m/z (ES+) 472 (M+H)+. 1H NMR (300 MHz, CD3OD): δ 7.69 (d, J=6.0 Hz, 2H), 7.58-7.37 (m, 3H), 7.30 (br s, 1H), 5.40 (br s, 1H), ~4.9 (1H partially obscured by water peak), 4.08-3.96 (m, 3H), 3.96-3.88 (m, 1H), 3.71-3.58 (m, 1H), 3.33-3.22 (m, 1H), 3.00 (t with fine structure, J=9.0 Hz, 2H), 2.52 (s, 3H), 2.42 & 2.32 (2 singlets, amide rotamers, Ar—CH3, 3H), 2.38-2.20 (m, 2H), 2.08-1.97 (m, 1H), 1.93-1.55 (m, 3H).

Compound 208. 4-(1-(2,4-Diethyl-5-(5-methoxy-4H-1,2,4-triazol-3-yl)benzoyl)piperidin-4-yl)benzonitrile To a round-bottom flask was added a solution of 4-(1-(5-(5-amino-1,3,4-oxadiazol-2-yl)-2,4-diethylbenzoyl)piperidin-4-yl)benzonitrile (compound 204.8, 80.0 mg, 0.150 mmol, 1.00 equiv, 80%) and potassium hydroxide (104 mg, 1.85 mmol, 10.00 equiv) in methanol (10 mL). The resulting mixture was stirred at room temperature overnight, then concentrated in vacuo. The residue was purified using silica gel column chromatography with dichloromethane/methanol (20:1) as eluent. The crude product (50 mg) was further purified by Prep-HPLC with the following conditions (1#-Pre-HPLC-001(SHIMADZU)): Column, SunFire Prep C18, 19*150 mm 5 um; mobile phase, water with 0.05% TFA and CH3CN (40% CH3CN up to 64% in 8 min, up to 100% in 1 min, down to 40% in 1 min); Detector, Waters 2489 254 & 220 nm. The fractions containing pure compound were combined and lyophilized to yield 1.7 mg (3%) of the title compound as a white solid. m/z (ES+) 444 (M+H)+. 1H NMR (300 MHz, CD3OD): δ 7.63 (d, J=5.7 Hz, 2H), 7.45-7.30 (m, 4H), 4.85-4.80 (m, 1H), 4.02 (s, 3H), 3.65-3.62 (m, 1H), 3.15-3.10 (m, 1H), 2.90-2.84 (m, 4H), 2.72-2.60 (On, 2H), 2.02-2.00 (m, 1H), 1.72-1.65 (m, 3H), 1.30-1.25 (m, 3H), 1.11 (t, 3H).

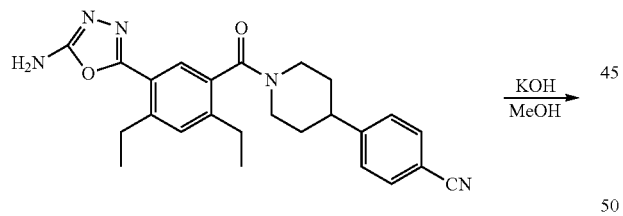

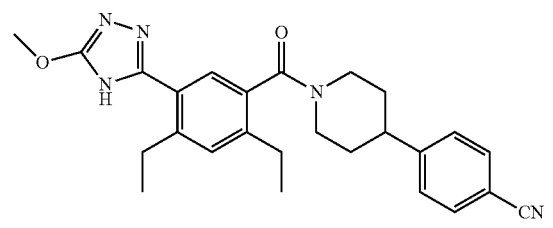

Compound 209.1. 2,4-Diethyl-5-(5-(2-methoxyethyl)-4H-1,2,4-triazol-3-yl)benzoic acid The title compound was prepared using standard chemical manipulations and procedures similar to those used for the preparation of compound 198.6, but using methyl 2,4-diethyl-5-iodobenzoate (compound 204.3) instead compound 198.2 as the starting material.

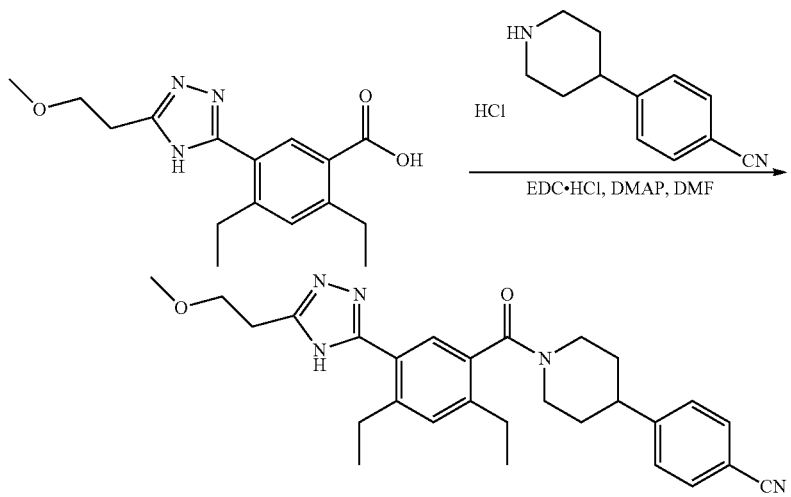

Compound 209. 4-(1-(2,4-Diethyl-5-(5-(2-methoxyethyl)-4H-1,2,4-triazol-3-yl)benzoyl)piperidin-4-yl)benzonitrile To a round-bottom flask was added a solution of 2,4-diethyl-5-(5-(2-methoxyethyl)-4H-1,2,4-triazol-3-yl)benzoic acid (compound 209.1, 300 mg, 0.940 mmol, 1.00 equiv, 95%) in N,N-dimethylformamide (20 mL). 4-(Piperidin-4-yl)benzonitrile hydrochloride (compound 1.5, 243 mg, 1.09 mmol, 1.10 equiv), EDC.HCl (380 mg, 1.98 mmol, 2.00 equiv), and 4-dimethylaminopyridine (240 mg, 1.96 mmol, 2.09 equiv) were added to the reaction mixture. The resulting solution was stirred overnight at room temperature, then diluted with 100 mL of ethyl acetate. The organic layer was washed with 3×15 mL of brine, dried over anhydrous sodium sulfate and concentrated in vacuo. The residue was purified using silica gel column chromatography with ethyl acetate as eluent. The crude product (300 mg) was purified by Prep-HPLC with the following conditions (1#-Pre-HPLC-001 (SHIMADZU)): Column, SunFire Prep C18, 19*150 mm 5 um; mobile phase, water with 0.05% TFA and $CH_3CN$ (35% $CH_3CN$ up to 60% in 8 min, up to 100% in 1 min, down to 35% in 1 min); Detector, Waters 2489 254 & 220 nm. The fractions containing pure compound were combined and lyophilized to yield 188 mg (42%) of the title compound as a white solid. m/z (ES+) 472 (M+H)$^+$.

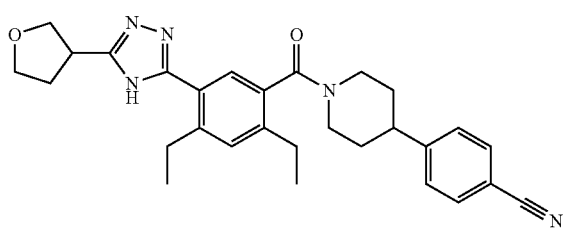

Compound 210. 4-(1-(2,4-Diethyl-5-(5-(tetrahydrofuran-3-yl)-4H-1,2,4-triazol-3-yl)benzoyl)piperidin-4-yl)benzonitrile The title compound was prepared using standard chemical manipulations and procedures similar to those used for the preparation of 4-(1-(2,4-diethyl-5-(5-(2-methoxyethyl)-4H-1,2,4-triazol-3-yl)benzoyl)piperidin-4-yl)benzonitrile (compound 209) but using tetrahydrofuran-3-carbohydrazide (compound 38.2) instead of 3-methoxypropanehydrazide (compound 143.1). m/z (ES+) 484.05 (M+H)$^+$.

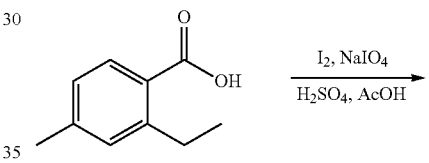

Compound 211.2. Methyl 2-ethyl-5-iodo-4-methylbenzoate

To a round-bottom flask was added a solution of methyl 2-ethyl-4-methylbenzoate (compound 48.1, 12.5 g, 70.1 mmol, 1.00 equiv) in AcOH (100 mL). $NaIO_4$ (7.51 g, 35.1 mmol, 0.50 equiv) and $I_2$ (21.4 g, 84.3 mmol, 1.20 equiv) were added in portions at 25° C. Sulfuric acid (1.60 g, 16.3 mmol, 0.20 equiv) was then added to the reaction mixture dropwise at 25° C. The resulting solution was stirred for 12 h at 110° C. in an oil bath, and then cooled to ambient temperature. The reaction was quenched with 150 mL of $Na_2S_2O_3$ (aq., sat.). The aqueous phase was extracted with 2×200 mL of ethyl acetate. The combined organic layers were washed with 3×300 mL of sodium bicarbonate (aq.) and 1×150 mL of brine. The mixture was dried over anhydrous sodium sulfate and concentrated in vacuo. This resulted in 20.0 g (94%) of methyl 2-ethyl-5-iodo-4-methylbenzoate as a yellow oil.

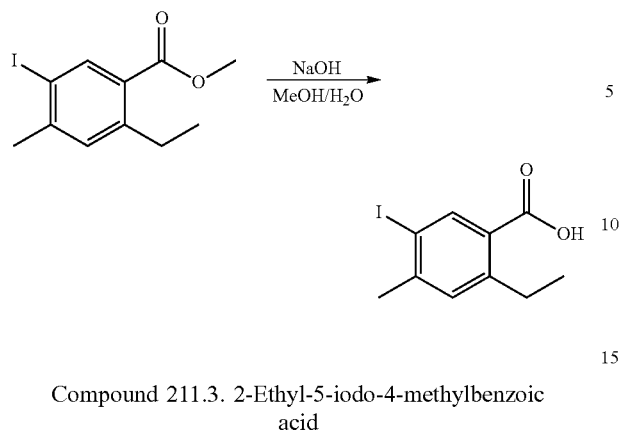

Compound 211.3. 2-Ethyl-5-iodo-4-methylbenzoic acid

To a round-bottom flask, was added a solution of methyl 2-ethyl-5-iodo-4-methylbenzoate (compound 211.2, 10.0 g, 32.9 mmol, 1.00 equiv) in methanol (40 mL). A solution of NaOH (5.26 g, 132 mmol, 4.00 equiv) in water (20 mL) was added dropwise. After stirring for 12 h at 40° C., the organic solvent was removed under reduced pressure. The pH of the remaining aqueous phase was adjusted to 4 with hydrogen chloride (aq., 6 M), then extracted with 2×100 mL of ethyl acetate. The combined organic layers were dried over anhydrous sodium sulfate and concentrated in vacuo. This resulted in 9.30 g (97%) of 2-ethyl-5-iodo-4-methylbenzoic acid as a white solid.

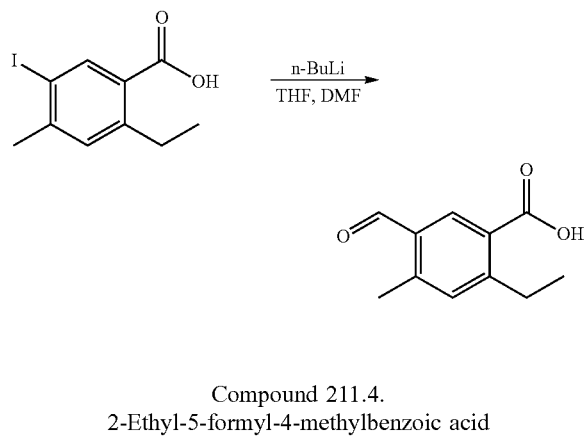

Compound 211.4. 2-Ethyl-5-formyl-4-methylbenzoic acid

To a stirred solution of 2-ethyl-5-iodo-4-methylbenzoic acid (compound 211.3, 5.00 g, 17.2 mmol, 1.00 equiv) in tetrahydrofuran (100 mL) at −78° C. under nitrogen was added dropwise n-BuLi (17 mL, 2 M in THF, 2.00 equiv). After 1 h at −78° C., DMF (7.00 g, 95.8 mmol, 3.00 equiv) was added dropwise at −78° C. The resulting solution was slowly warmed up to 25° C., then carefully quenched with water followed by the addition of 10 mL of HCl (aq., 6 M). The aqueous phase was extracted with 3×100 mL of ethyl acetate. The combined organic layers were dried over anhydrous sodium sulfate and concentrated in vacuo. The residue was purified using silica gel column chromatography with ethyl acetate/petroleum ether (2:1) as eluent to furnish 450 mg (14%) of 2-ethyl-5-formyl-4-methylbenzoic acid as a yellow solid.

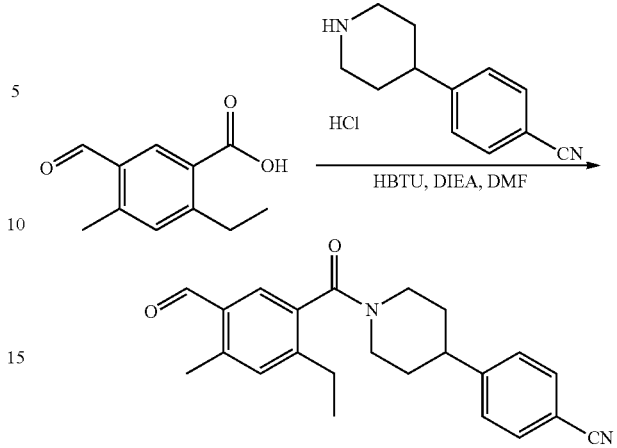

Compound 211.5. 4-(1-(2-Ethyl-5-formyl-4-methylbenzoyl)piperidin-4-yl)benzonitrile To a round-bottom flask was added a solution of 2-ethyl-5-formyl-4-methylbenzoic acid (compound 211.4, 450 mg, 2.34 mmol, 1.00 equiv) in N,N-dimethylformamide (5 mL). DIEA (907 mg, 7.02 mmol, 3.00 equiv) and HBTU (1.30 g, 3.43 mmol, 1.50 equiv) were added to the reaction mixture. The resulting solution was stirred for 30 min at 25° C. A solution of 4-(piperidin-4-yl)benzonitrile hydrochloride (compound 1.5, 624 mg, 2.80 mmol, 1.20 equiv) in DIEA (2 mL) was added dropwise. The resulting solution was stirred for 30 min at 25° C., then quenched with 20 mL of water. The aqueous phase was extracted with 3×30 mL of ethyl acetate. The combined organic layers were washed with 1×50 mL of brine, dried over anhydrous sodium sulfate and concentrated ire vacuo. The residue was purified using silica gel column chromatography with ethyl acetate/petroleum ether (5:1) as eluent to furnish 720 mg (85%) of the title compound as a yellow solid.

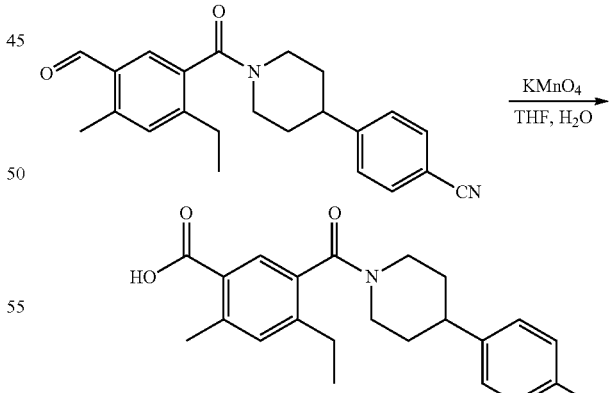

Compound 211.6. 5-(4-(4-Cyanophenyl)piperidine-1-carbonyl)-4-ethyl-2-methylbenzoic acid To a round-bottom flask was added a solution of 4-(1-(2-ethyl-5-formyl-4-methylbenzoyl)piperidin-4-yl)benzonitrile (compound 211.5, 720 mg, 2.00 mmol, 1.00 equiv) in tetrahydrofuran (20 mL). A solution of KMnO$_4$ (640 mg, 4.05 mmol, 2.00 equiv) in water (20 mL) was added dropwise. The resulting solution was stirred for 15 h at 60° C. then cooled to rt with a water bath. The solids were removed with filtration. The filtrate was extracted with 3×30 mL of ethyl acetate. The combined organic layers were dried over anhydrous sodium sulfate and concentrated in vacuo. This resulted in 600 mg (80%) of 5-(4-(4-cyanophenyl)piperidine-1-carbonyl)-4-ethyl-2-methylbenzoic acid as a light yellow solid.

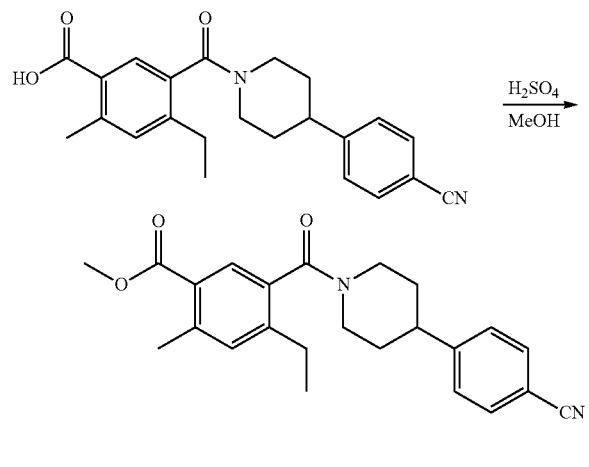

Compound 211.7. Methyl 5-(4-(4-cyanophenyl)piperidine-1-carbonyl)-4-ethyl-2-methylbenzoate To a round-bottom flask was added a solution of 5-(4-(4-cyanophenyl)piperidine-1-carbonyl)-4-ethyl-2-methylbenzoic acid (compound 211.6, 600 mg, 1.59 mmol, 1.00 equiv) in methanol (30 mL). To this was added sulfuric acid (500 mg, 5.10 mmol, 3.20 equiv) dropwise. The resulting solution was stirred for 15 h at 60° C. After cooling to ambient temperature, the mixture was concentrated in vacuo. The residue was diluted with 20 mL of H$_2$O. The aqueous phase was extracted with 3×20 mL of ethyl acetate. The combined organic layers were dried over anhydrous sodium sulfate and concentrated in vacuo. This resulted in 500 mg (80%) of methyl 5-(4-(4-cyanophenyl)piperidine-1-carbonyl)-4-ethyl-2-methylbenzoate as a yellow oil.

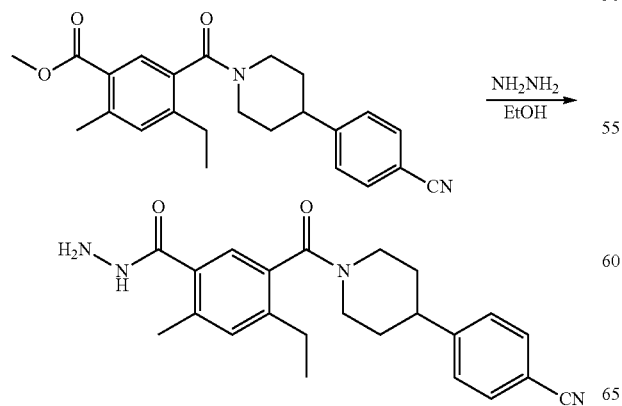

Compound 211.8. 5-(4-(4-Cyanophenyl)piperidine-1-carbonyl)-4-ethyl-2-methylbenzohydrazide To a round-bottom flask was added a solution of methyl 5-(4-(4-cyanophenyl)piperidine-1-carbonyl)-4-ethyl-2-methylbenzoate (compound 211.7, 500 mg, 1.28 mmol, 1.00 equiv) in ethanol (20 mL). Hydrazine (4 mL) was added to the reaction mixture. The resulting solution was stirred for 15 h at 80° C., then concentrated in vacuo. The residue was partitioned between water and ethyl acetate. The aqueous layer was extracted with ethyl acetate (2×). The combined organic layers were dried over anhydrous sodium sulfate and concentrated in vacuo to yield 400 mg (80%) of 5-(4-(4-cyanophenyl)piperidine-1-carbonyl)-4-ethyl-2-methylbenzohydrazide as a light yellow solid.

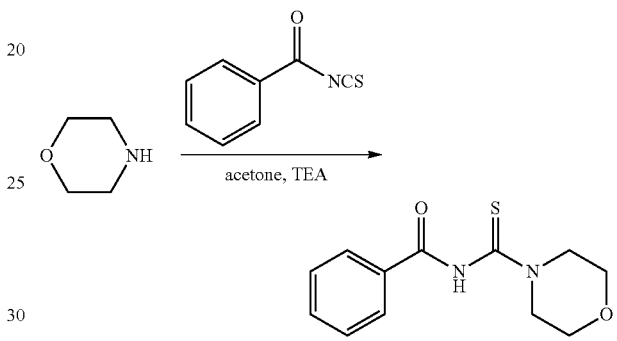

Compound 211.9. N-(Morpholine-4-carbonothioyl)benzamide

To a 50-mL three neck round-bottom flask, which was purged and maintained with an inert atmosphere of nitrogen, was added a solution of morpholine (1.00 g, 11.5 mmol, 1.00 equiv) in acetone (10 mL). TEA (1.74 g, 17.2 mmol, 1.50 equiv) was added to the reaction, and the resulting solution was stirred for 30 min at 25° C. Benzoyl isothiocyanate (1.87 g, 11.5 mmol, 2.00 equiv) was added dropwise to the reaction at 0° C. The resulting solution was stirred for 30 min at 0° C., then quenched with 20 mL of water. The mixture was extracted with 2×30 mL of ethyl acetate. The combined organic layers were dried (Na$_2$SO$_4$) and concentrated in vacuo. The residue was purified using silica gel column chromatography with ethyl acetate/petroleum ether (1:10-1:3) as eluent to furnish 2.30 g (80%) of N-(morpholine-4-carbonothioyl)benzamide as a yellow solid.

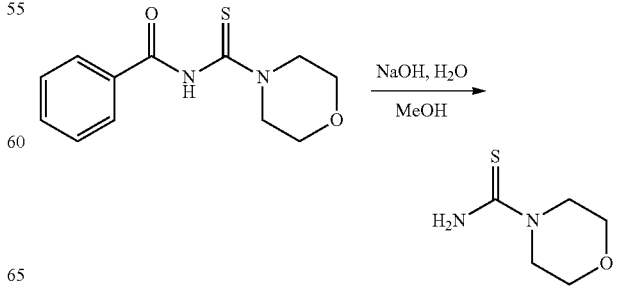

Compound 211.10. Morpholine-4-carbothioamide

To a round-bottom flask was added a solution of N-(morpholine-4-carbonothioyl)benzamide (compound 211.9, 3.00 g, 12.0 mmol, 1.00 equiv) in methanol (20 mL). A solution of sodium hydroxide (1.44 g, 36.0 mmol, 3.00 equiv) in water (20 mL) was added to the reaction. The resulting solution was stirred overnight at 60° C. After cooling to ambient temperature, the organic solvent was removed under reduced pressure. The residue was extracted with 2×20 mL of ethyl acetate/petroleum ether (1:1). The combined organic layers were dried over anhydrous sodium sulfate and concentrated in vacuo. This resulted in 430 mg (25%) of morpholine-4-carbothioamide as a yellow solid.

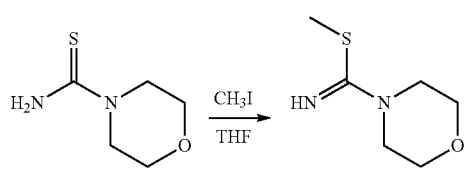

Compound 211.11. 4-(Methylsulfanyl)carboximidoylmorpholine

A solution of morpholine-4-carbothioamide (compound 211.10, 430 mg, 2.94 mmol, 1.00 equiv) and iodomethane (1.25 g, 8.81 mmol, 3.00 equiv) in tetrahydrofuran (10 mL) was stirred for 4 h at 25° C., then concentrated in vacuo. This resulted in 471 mg (100%) of 4-(methylsulfanyl)carboximidoylmorpholine as a yellow solid.

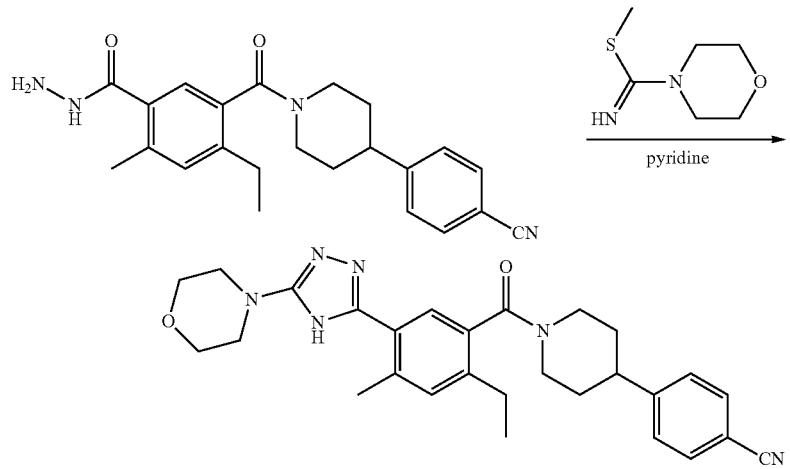

Compound 211. 4-(1-(2-Ethyl-4-methyl-5-(5-morpholino-4H-1,2,4-triazol-3-yl)benzoyl)piperidin-4-yl)benzonitrile To a 20-mL sealed tube was added solution of 5-(4-(4-cyanophenyl)piperidine-1-carbonyl)-4-ethyl-2-methylbenzohydrazide (compound 211.8, 225 mg, 0.580 mmol, 1.00 equiv) in pyridine (10 mL). 4-(Methylsulfanyl) carboximidoylmorpholine (compound 211.11, 200 mg, 1.25 mmol, 1.00 equiv) was added to the reaction mixture. The resulting solution was stirred for 3 days at 100° C. behind a blast shield. After cooling to room temperature, the mixture was then concentrated in vacuo. The residue was purified using silica gel column chromatography with chloroform/methanol (30:1) as eluent. The crude product (~100 mg) was purified by Prep-HPLC with the following conditions (1#-Pre-HPLC-001(SHIMADZU)): Column, Xbridge Prep C18, Sum, 19*150 mm; mobile phase, water with 0.03% $NH_3H_2O$ and $CH_3CN$ (32% $CH_3CN$ up to 55% in 8 min, up to 100% in 2 min, down to 32% in 1 min); Detector, Waters 2489 254 & 220 nm. The fractions containing pure compound were combined and lyophilized to yield 67.7 mg (24%) of the title compound as a white solid. m/z (ES+) 485 $(M+H)^+$. $^1$H-NMR (300 MHz, $CD_3OD$): δ 7.69 (d, 2H), 7.49-7.31 (m, 4H), 4.90-4.80 (m, 1H), 3.83-3.81 (m, 4H), 3.79-3.65 (m, 1H), 3.60-3.41 (m, 4H), 3.40-3.31 (m, 1H), 3.08-2.97 (m, 2H), 2.76-2.71 (m, 2H), 2.51 (s, 3H), 2.02-1.98 (m, 1H), 1.85-1.80 (m, 3H), 1.33-1.30 (m, 3H).

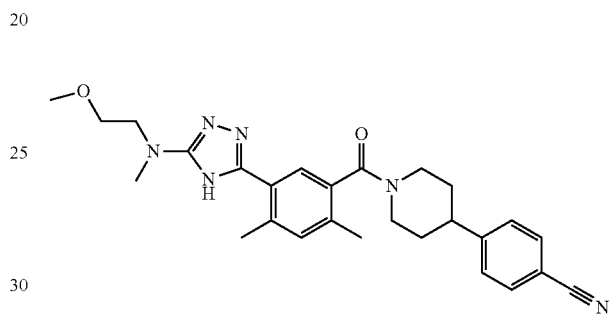

Compound 212. 4-(1-(5-(5-((2-Methoxyethyl)(methyl)amino)-4H-1,2,4-triazol-3-yl)-2,4-dimethylbenzoyl)piperidin-4-yl)benzonitrile The title compound was prepared using standard chemical manipulations and procedures similar to those used for the preparation of 4-(1-(2-ethyl-4-methyl-5-(5-morpholino-4H-1,2,4-triazol-3-yl)benzoyl)piperidin-4-yl)benzonitrile (compound 211). m/z (ES+) 473 $(M+H)^+$.

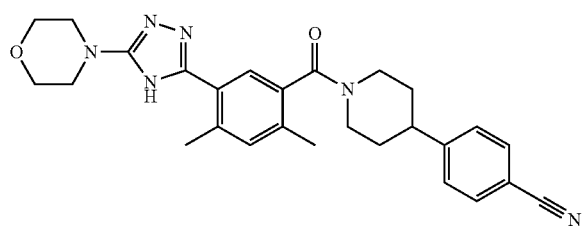 [SMILES: Cc1cc(C)c(-c2nnc(N3CCOCC3)[nH]2)cc1C(=O)N1CCC(c2ccc(C#N)cc2)CC1]

Compound 213. 4-(1-(2,4-Dimethyl-5-(5-morpholino-4H-1,2,4-triazol-3-yl)benzoyl)piperidin-4-yl)benzonitrile The title compound was prepared using standard chemical manipulations and procedures similar to those used for the preparation of 4-(1-(2-ethyl-4-methyl-5-(5-morpholino-4H-1,2,4-triazol-3-yl)benzoyl)piperidin-4-yl)benzonitrile (compound 211). m/z (ES+) 471 (M+H)$^+$.

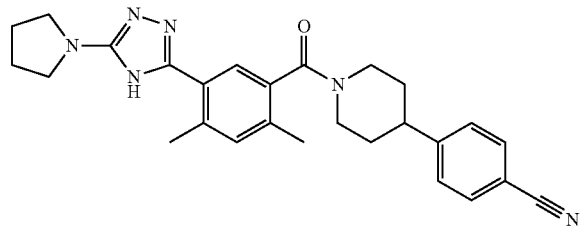 [SMILES: Cc1cc(C)c(-c2nnc(N3CCCC3)[nH]2)cc1C(=O)N1CCC(c2ccc(C#N)cc2)CC1]

Compound 214. 4-(1-(2,4-Dimethyl-5-(5-(pyrrolidin-1-yl)-4H-1,2,4-triazol-3-yl)benzoyl)piperidin-4-yl)benzonitrile The title compound was prepared using standard chemical manipulations and procedures similar to those used for the preparation of 4-(1-(2-ethyl-4-methyl-5-(5-morpholino-4H-1,2,4-triazol-3-yl)benzoyl)piperidin-4-yl)benzonitrile (compound 211). m/z (ES+) 455 (M+H)$^+$.

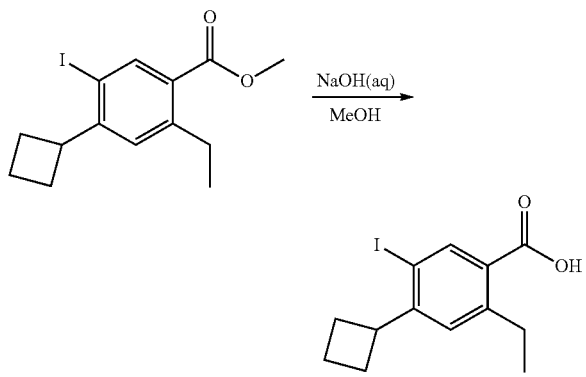

Compound 215.3.
4-Cyclobutyl-2-ethyl-5-iodobenzoic acid

To a round-bottom flask, was added a solution of methyl 4-cyclobutyl-2-ethyl-5-iodobenzoate (compound 181.4, 10.3 g, 30.0 mmol, 1.00 equiv) in methanol (100 mL). A solution of sodium hydroxide (3.60 g, 3.00 equiv) in water (10 mL) was added dropwise to the stirred reaction mixture. The resulting mixture was stirred for 2 h at 60° C. After cooling to ambient temperature, the volatiles were removed under reduced pressure. The pH of the remaining aqueous mixture was adjusted to ~4 using HCl (aq., 1 M). The resulting precipitate was collected by filtration and dried to yield 9.00 g (91%) of 4-cyclobutyl-2-ethyl-5-iodobenzoic acid as a white solid.

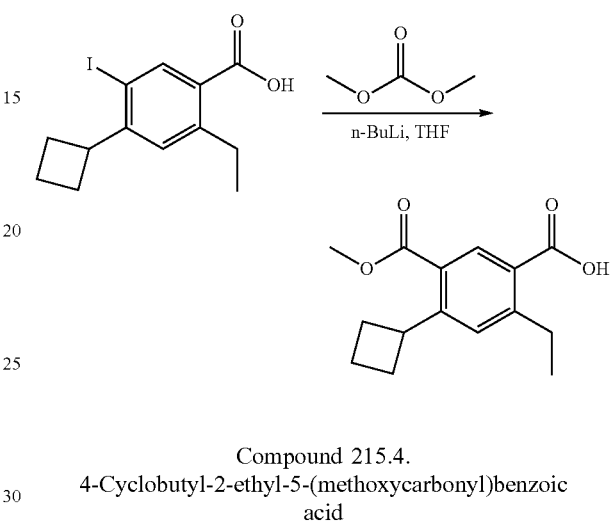

Compound 215.4.
4-Cyclobutyl-2-ethyl-5-(methoxycarbonyl)benzoic acid

To a solution of 4-cyclobutyl-2-ethyl-5-iodobenzoic acid (compound 215.3, 3.30 g, 10.0 mmol, 1.00 equiv) in THF (40 mL) was added n-BuLi (2.5 M, 9.50 mL, 2.38 equiv) dropwise at −78° C. under nitrogen atmosphere. The resulting solution was stirred for another 20 min at the same temperature, followed by the addition of a solution of dimethyl carbonate (2.70 g, 30.0 mmol, 3.00 equiv) in tetrahydrofuran (2 mL) dropwise. The reaction temperature was slowly raised to 25° C. and stirred for another 1 h, then slowly quenched with 50 mL of water. The pH was adjusted to ~4 with HCl (aq., 1 M) and the resulting mixture was extracted with 100 mL of ethyl acetate. The combined organic layers were dried over anhydrous sodium sulfate and concentrated in vacuo. The residue was purified by silica gel chromatography with ethyl acetate/petroleum ether (1:3) as eluent to furnish 1.80 g (69%) of the desired product as a white solid.

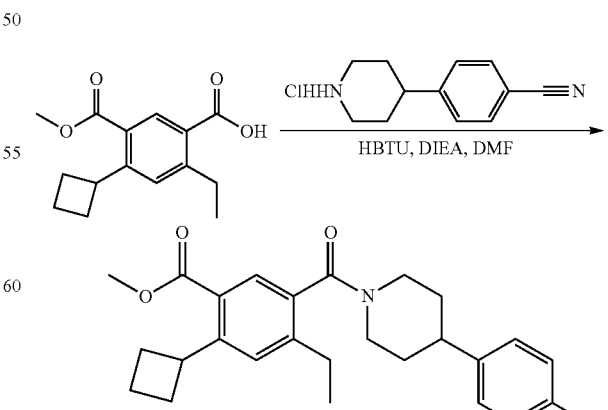

Compound 215.5. Methyl 5-(4-(4-cyanophenyl)piperidine-1-carbonyl)-2-cyclobutyl-4-ethylbenzoate To a round-bottom flask were added a solution of 4-cyclobutyl-2-ethyl-5-(methoxycarbonyl)benzoic acid (compound 215.4, 1.15 g, 4.38 mmol, 1.00 equiv), 4-(piperidin-4-yl)benzonitrile hydrochloride (compound 1.5, 1.07 g, 4.80 mmol, 1.10 equiv), HBTU (2.50 g, 6.59 mmol, 1.50 equiv), and DIEA (1.07 g, 8.28 mmol, 3.00 equiv) in N,N-dimethylformamide (10 mL). The resulting solution was stirred for 1 h at 25° C. The reaction was then quenched by the addition of 20 mL of water. The resulting mixture was extracted with 2×50 mL of ethyl acetate. The combined organic layers were dried over anhydrous sodium sulfate and concentrated in vacuo. The residue was purified using silica gel column chromatography with ethyl acetate/petroleum ether (1:3) to yield 1.80 g (95%) of methyl 5-(4-(4-cyanophenyl)piperidine-1-carbonyl)-2-cyclobutyl-4-ethylbenzoate as a yellow solid.

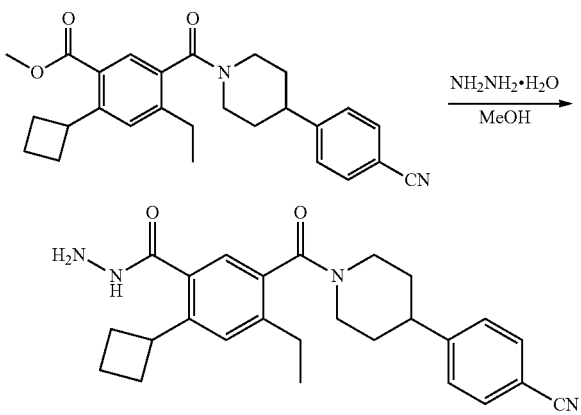

Compound 215.6. 5-(4-(4-Cyanophenyl)piperidine-1-carbonyl)-2-cyclobutyl-4-ethylbenzohydrazide To a solution of methyl 5-(4-(4-cyanophenyl)piperidine-1-carbonyl)-2-cyclobutyl-4-ethylbenzoate (compound 215.5, 2.15 g, 4.99 mmol, 1.00 equiv) in methanol (20 mL), was added hydrazine hydrate (80%, 15 mL) batchwise. The reaction was stirred at 80° C. overnight. After cooling to ambient temperature, the mixture was concentrated under reduced pressure. The residue was extracted with dichloromethane (2×100 mL). The combined organic layers were dried over anhydrous magnesium sulfate, and concentrated in vacuo. The residue was purified by silica gel chromatography with dichloromethane/methanol (100:1) to furnish 1.13 g (53%) of the desired product as a pinkish solid.

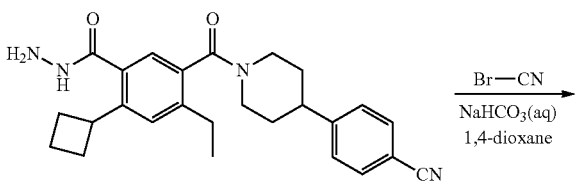

Compound 215.7. 4-(1-(5-(5-Amino-1,3,4-oxadiazol-2-yl)-4-cyclobutyl-2-ethylbenzoyl)piperidin-4-yl)benzonitrile To a solution of 5-(4-(4-cyanophenyl)piperidine-1-carbonyl)-2-cyclobutyl-4-ethylbenzohydrazide (compound 215.6, 600 mg, 1.39 mmol, 1.00 equiv) in 1,4-dioxane (10 mL) was added 10 mL of an aqueous solution of sodium bicarbonate (350 mg, 4.17 mmol, 1.00 equiv). Cyanogen bromide (220 mg, 2.08 mmol, 1.50 equiv) was added to the reaction mixture dropwise. The reaction mixture was stirred at 25° C. for 2 h, then quenched with 20 mL of FeSO₄ (aq., sat.) and diluted with DCM. The resulting mixture was stirred vigorously then filtered through celite and washed with 1 M FeSO₄, water, and ethyl acetate. The layers were separated and the aqueous phase was extracted with 2×50 mL of DCM. The combined organic layers were dried over anhydrous sodium sulfate and concentrated in vacuo. This resulted in 600 mg (95%) of 4-(1-(5-(5-amino-1,3,4-oxadiazol-2-yl)-4-cyclobutyl-2-ethylbenzoyl)piperidin-4-yl)benzonitrile as an off-white solid.

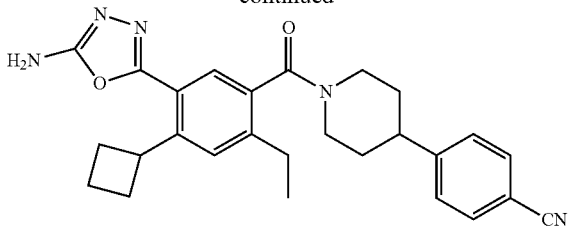

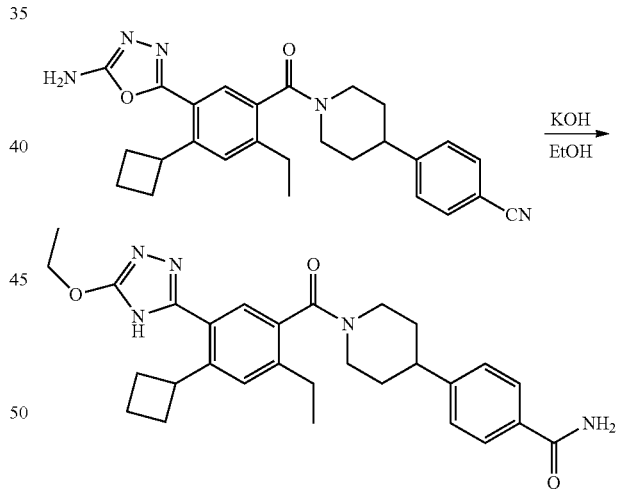

Compound 215.8. 4-(1-(4-Cyclobutyl-5-(5-ethoxy-4H-1,2,4-triazol-3-yl)-2-ethylbenzoyl)piperidin-4-yl)benzamide To a 10-mL sealed tube, which was purged and maintained with an inert atmosphere of nitrogen, was added a solution of 4-(1-(5-(5-amino-1,3,4-oxadiazol-2-yl)-4-cyclobutyl-2-ethylbenzoyl)piperidin-4-yl)benzonitrile (compound 215.7, 228 mg, 0.500 mmol, 1.00 equiv) in ethanol (5 mL). This was followed by the addition of potassium hydroxide (280 mg, 4.99 mmol, 10.0 equiv) in portions. The resulting solution was stirred for 511 at 80° C. behind a blast shield. After cooling to ambient temperature, the reaction was then quenched by the addition of 15 mL of water and extracted with 2×20 mL of ethyl acetate. The combined organic layers were dried over anhydrous sodium sulfate and concentrated in vacuo. This resulted in 200 mg (80%) of 4-(1-(4-cyclobutyl-5-(5-ethoxy-4H-1,2,4-triazol-3-yl)-2-ethylbenzoyl)piperidin-4-yl)benzamide as a yellow solid.

taining pure compound were combined and lyophilized to yield 60 mg (25%) of the title compound as a white solid. m/z (ES+) 484 (M+H)⁻. ¹H-NMR (300 MHz, CD₃OD): δ 7.64 (d, 2H), 7.45-7.21 (m, 4H), 4.37 (q, 2H), 4.02-3.96 (m, 1H), 3.60-3.53 (m, 1H), 3.29-3.19 (m, 2H), 2.98-2.90 (m, 2H), 2.76-2.61 (m, 2H), 2.15-2.12 (m, 2H), 2.07-1.92 (m, 4H), 1.80-1.68 (m, 4H), 1.35 (t, 3H), 1.29-1.20 (m, 3H).

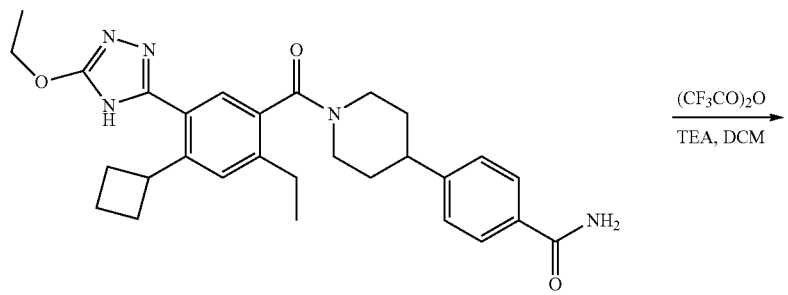

Compound 215. 4-(1-(4-Cyclobutyl-5-(5-ethoxy-4H-1,2,4-triazol-3-yl)-2-ethylbenzoyl)piperidin-4-yl)benzonitrile

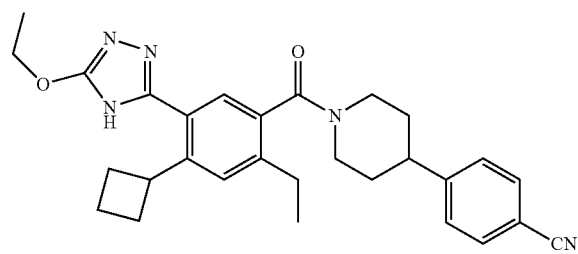

To a round-bottom flask was added a solution of compound 215.8 (251 mg, 0.500 mmol, 1.00 equiv) in dichloromethane (5 mL). This was followed by the addition of (CF₃CO)₂O (158 mg, 1.50 equiv) dropwise with stirring. Triethylamine (101 mg, 1.00 mmol, 2.00 equiv) was added dropwise with stirring. The resulting mixture was stirred at 25° C. for 1 h, then concentrated in vacuo. The residue was purified using silica gel column chromatography with dichloromethane/methanol (20:1) as eluent. The crude product (120 mg) was purified by Prep-HPLC with the following conditions (1#-Pre-HPLC-001 (SHIMADZU)): Column, SunFire Prep C18, 19*150 mm Sum; mobile phase, water with 0.05% TFA and CH₃CN (54.0% CH₃CN up to 64.0% in 6 min, up to 100.0% in 1 min, down to 54.0% in 1 min); Detector, Waters 2489 254 & 220 nm. The fractions con-

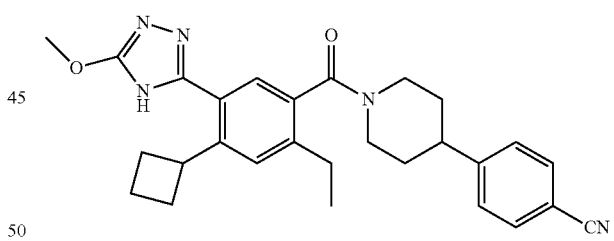

Compound 216. 4-(1-(4-Cyclobutyl-2-ethyl-5-(5-methoxy-4H-1,2,4-triazol-3-yl)benzoyl)piperidin-4-yl)benzonitrile The title compound was prepared using standard chemical manipulations and procedures similar to those used for the preparation of 4-(1-(4-cyclobutyl-5-(5-ethoxy-4H-1,2,4-triazol-3-yl)-2-ethylbenzoyl)piperidin-4-yl)benzonitrile (compound 215). m/z (ES+) 470 (M+H)⁺. ¹H-NMR (300 MHz, CD₃OD): δ 7.64 (d, 2H), 7.45-7.38 (m, 3H), 7.32 and 7.21 (2 singlets, amide rotamers, 1H), 4.0 (s, 3H), 4.00-3.95 (m, 1H), 3.63-3.56 (m, 1H), 3.29-3.19 (m, 2H), 2.98 (app t, 2H), 2.76-2.61 (m, 2H), 2.17-1.89 (m, 6H), 1.80-1.64 (m, 4H), 1.32-1.20 (m, 3H).

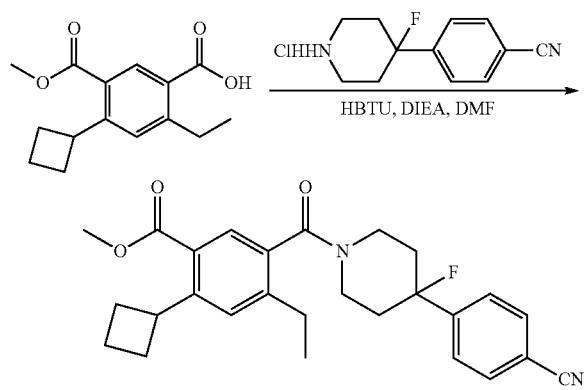

Compound 217.1. Methyl 5-(4-(4-cyanophenyl)-4-fluoropiperidine-1-carbonyl)-2-cyclobutyl-4-ethylbenzoate To a round-bottom flask was added a solution of 4-cyclobutyl-2-ethyl-5-(methoxycarbonyl)benzoic acid (compound 215.4, 70.0 mg, 0.270 mmol, 1.00 equiv) in N,N-dimethylformamide (5 mL). HBTU (210 mg, 0.550 mmol, 2.07 equiv), DIEA (150 mg, 1.16 mmol, 4.35 equiv) were added to the reaction mixture at 0° C., and stirred for 30 min. This was followed by the addition of 4-(4-fluoropiperidin-4-yl)benzonitrile hydrochloride (compound 11.2 HCl salt, 80.0 mg, 0.330 mmol, 1.20 equiv). The resulting solution was stirred for 15 h at 25° C., and then quenched with 20 mL of ice-water. The mixture was extracted with 2×50 mL of ethyl acetate. The combined organic layers were washed with 1×50 mL of brine, dried over anhydrous sodium sulfate, and concentrated in vacuo. The residue was purified using silica gel column chromatography with ethyl acetate/petroleum ether (1:100-1:5) as eluent to yield 100 mg (84%) of methyl 5-(4-(4-cyanophenyl)-4-fluoropiperidine-1-carbonyl)-2-cyclobutyl-4-ethylbenzoate as a white solid.

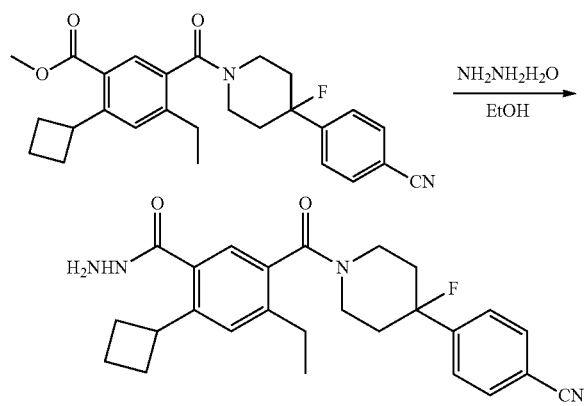

Compound 217.2. 5-(4-(4-Cyanophenyl)-4-fluoropiperidine-1-carbonyl)-2-cyclobutyl-4-ethylbenzohydrazide To a round-bottom flask was added a solution of methyl 5-(4-(4-cyanophenyl)-4-fluoropiperidine-1-carbonyl)-2-cyclobutyl-4-ethylbenzoate (compound 217.1, 1.10 g, 2.45 mmol, 1.00 equiv) in ethanol (40 mL). Hydrazine hydrate (20 mL) was added to the reaction mixture, and the reaction was stirred 80° C. for 15 h. After cooling to ambient temperature, the mixture was concentrated in vacuo, then diluted with 50 mL of H$_2$O. The resulting mixture was extracted with 3×50 mL of dichloromethane. The combined organic layers were washed with 2×50 mL of brine, dried over anhydrous sodium sulfate, and concentrated in vacuo. The residue was purified using silica gel column chromatography with ethyl acetate/petroleum ether (1:1-1:0) as eluent to yield 900 mg (82%) of 5-(4-(4-cyanophenyl)-4-fluoropiperidine-1-carbonyl)-2-cyclobutyl-4-ethylbenzohydrazide as a white solid.

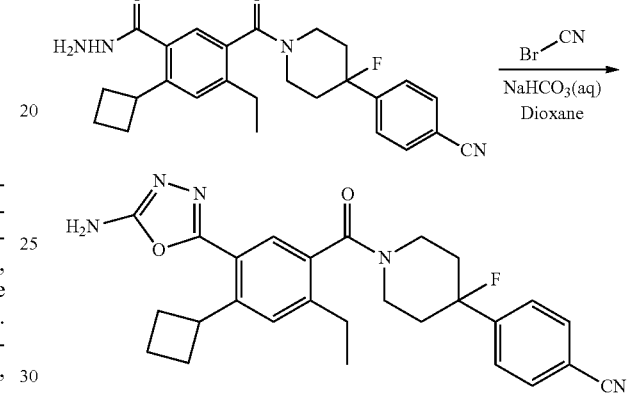

Compound 217.3. 4-(1-(5-(5-Amino-1,3,4-oxadiazol-2-yl)-4-cyclobutyl-2-ethylbenzoyl)-4-fluoropiperidin-4-yl)benzonitrile To a round-bottom flask was added a solution of 5-(4-(4-cyanophenyl)-4-fluoropiperidine-1-carbonyl)-2-cyclobutyl-4-ethylbenzohydrazide (compound 217.2, 450 mg, 1.00 mmol, 1.00 equiv) in 1,4-dioxane (10 mL), A solution of sodium bicarbonate (252 mg, 3.00 mmol, 2.99 equiv) in water (10 mL) and BrCN (128 mg, 1.21 mmol, 1.20 equiv) were added to the reaction mixture. The resulting solution was stirred for 3 h at room temperature, then quenched with 30 mL of FeSO$_4$ (aq., sat.) and diluted with ethyl acetate. The resulting mixture was stirred vigorously then filtered through celite and washed with 1 M FeSO$_4$, water, and ethyl acetate. The layers were separated and the aqueous phase was extracted with 2×50 mL of ethyl acetate. The combined organic layers were washed with 2×50 mL of brine, dried over anhydrous sodium sulfate, and concentrated in metro. This resulted in 400 mg (84%) of 4-(1-(5-(5-amino-1,3,4-oxadiazol-2-yl)-4-cyclobutyl-2-ethylbenzoyl)-4-fluoropiperidin-4-yl)benzonitrile as a light brown solid.

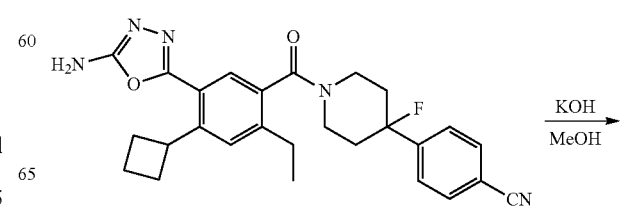

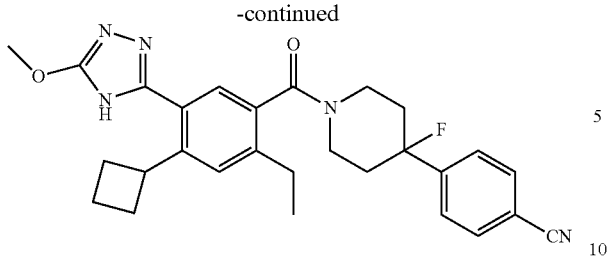

Compound 217. 4-(1-(4-Cyclobutyl-2-ethyl-5-(5-methoxy-4H-1,2,4-triazol-3-yl)benzoyl)-4-fluoropiperidin-4-yl)benzonitrile To a round-bottom flask, which was purged and maintained with a nitrogen atmosphere, was added a solution of 4-(1-(5-(5-amino-1,3,4-oxadiazol-2-yl)-4-cyclobutyl-2-ethylbenzoyl)-4-fluoropiperidin-4-yl)benzonitrile (compound 217.3, 200 mg, 0.420 mmol, 1.00 equiv) in methanol (20 mL). Potassium hydroxide (237 mg, 4.22 mmol, 10.0 equiv) was added to the reaction mixture. The resulting solution was stirred for 15 h at 70° C. After cooling to ambient temperature, the organic solvent was removed under reduced pressure. The residue was diluted with 30 mL of H$_2$O, then extracted with 2×50 mL of ethyl acetate. The combined organic layers were washed with 2×50 mL of brine, dried over anhydrous sodium sulfate and concentrated in vacuo. The crude product (50 mg) was purified by Prep-HPLC with the following conditions (1#-Pre-HPLC-001(SHIMADZU)): Column, SunFire Prep C18, 19*150 mm 5 um; mobile phase, water with 0.05% TFA and CH$_3$CN (49.0% CH$_3$CN up to 63.0% in 8 min, up to 100.0% in 1 min, down to 49.0% in 1 min); Detector, Waters 2489 254 & 220 nm. The fractions containing pure compound were combined and lyophilized to yield 20 mg (10%) of the title compound as a white. m/z (ES+) 488 (M+H)$^+$. $^1$H-NMR (300 MHz, CD$_3$OD): δ 7.72 (d, 2H), 7.64-7.61 (m, 2H), 7.39-7.25 (m, 2H), 4.85-4.78 (m, 1H), 4.00-3.93 (m, 4H), 3.54-3.49 (m, 2H), 3.28-3.22 (m, 1H), 2.80-2.65 (m, 2H), 2.26-1.84 (m, 10H), 1.45-1.27 (m, 3H).

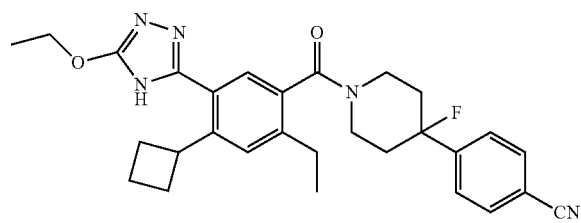 [SMILES: CCOc1nnc(-c2cc(C(=O)N3CCC(F)(c4ccc(C#N)cc4)CC3)c(CC)cc2C2CCC2)[nH]1]

Compound 218. 4-(1-(4-Cyclobutyl-5-(5-ethoxy-4H-1,2,4-triazol-3-yl)-2-ethylbenzoyl)-4-fluoropiperidin-4-yl)benzonitrile The title compound was prepared using standard chemical manipulations and procedures similar to those used for the preparation of 4-(1-(4-cyclobutyl-5-(5-ethoxy-4H-1,2,4-triazol-3-yl)-2-ethylbenzoyl)piperidin-4-yl)benzonitrile (compound 215) and using compound 11.2 HCl salt in place of compound 1.5. m/z (ES+) 502 [M+H]$^+$, 543 [M+CH$_3$CN+H]$^+$. $^1$H-NMR (300 MHz, CD$_3$OD): δ 7.73 (d, 2H), 7.64-7.58 (m, 2H), 7.39-7.26 (m, 2H), 4.89-4.82 (m, 1H), 4.35 (q, 2H), 4.10-3.95 (m, 1H), 3.50-3.38 (m, 2H), 3.30-3.27 (m, 1H), 2.75-2.65 (m, 2H), 2.22-1.86 (m, 10H), 1.41 (t, 3H), 1.35-1.20 (m, 3H).

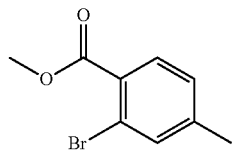

Compound 219.1 Methyl 2-bromo-4-methylbenzoate

To a solution of 2-bromo-4-methylbenzoic acid (10 g) in MeOH (50 ml) was added dropwise concentrated sulfuric acid (10 ml) at 0° C. The mixture was heated at 70° C. for 2 hours. After cooling to ambient temperature, the methanol was removed under reduced pressure. The residue was poured into ice-water (100 ml). The mixture was extracted with EtOAc (×2). The combined organic layers were washed with NaHCO$_3$ (aq. sat. Note: gas evolution), brine, dried over MgSO$_4$, filtered, and concentrated to give the product as a clear oil. Yield: 10.5 g, 99%. $^1$H NMR (400 MHz, Chloroform-d) δ 7.73 (d, 1H), 7.50 (d, 1H), 7.19-7.11 (m, 1H), 3.92 (s, 3H), 2.36 (s, 3H).

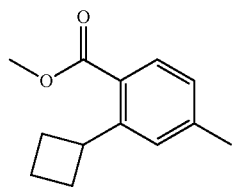

Compound 219.2 Methyl 2-cyclobutyl-4-methylbenzoate

Cyclobutylzinc(II) bromide (50 ml, 0.5M in THF, 25.0 mmol) was added to a mixture of methyl 2-bromo-4-methylbenzoate (219.1, 5.0 g, 21.8 mmol) and PdCl$_2$(dppf)CH$_2$Cl$_2$ (1.78 g, 2.20 mmol). The mixture was degassed and the flask was filled with argon through a balloon. After the mixture was heated at 65° C. under argon for 24 hours, it was cooled to 0° C. and quenched with water (10 ml). The mixture was diluted with EtOAc (200 ml), washed with water then with brine. The EtOAc layer was dried (Na$_2$SO$_4$), concentrated, and purified using column (silica gel) chromatography (hexanes:EtOAc 30:1 to 20:1). Yield: 3.6 g, 81%. $^1$H NMR (400 MHz, Chloroform-d) δ 7.68 (d, 1H), 7.23-7.17 (s, 1H), 7.03 (d, 1H), 4.16 (m, 1H), 3.86 (s, 3H), 2.39 (s, 3H), 2.34 (m, 2H), 2.16-1.96 (m, 3H), 1.80 (m, 1H).

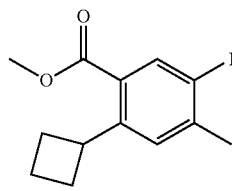

Compound 219.3 Methyl 2-cyclobutyl-5-iodo-4-methylbenzoate

N-Iodosuccinimide (5.25 g, 23.3 mmol) was added portionwise to a solution of methyl 2-cyclobutyl-4-methylbenzoate (219.2, 4.77 g, 23.3 mmol) in concentrated sulfuric acid (100 ml) at 0° C. The mixture turned very thick after it was stirred at 0° C. for 30 min and at RT for 2 hours. The mixture was cooled to 0° C. again and MeOH (100 ml) was added. The mixture was heated at 60° C. for 2 hours. The methanol was removed under reduced pressure and the residue was poured into ice water (200 ml). The mixture was extracted with EtOAc (2×). The combined organic layers were washed with brine, then aq. 1N NaHCO$_3$, dried (Na$_2$SO$_4$), and concentrated. The residue was purified using column (silica gel) chromatography (hexanes:EtOAc 30:1 to 20:1). Yield: 5.0 g, clear oil, 65%. $^1$H NMR (400 MHz, Chloroform-d) δ 8.19 (s, 1H), 7.24 (s, 1H), 4.17-4.04 (m, 1H), 3.86 (s, 3H), 2.48-2.44 (s, 3H), 2.40-2.28 (m, 2H), 2.13-1.92 (m, 3H), 1.85-1.75 (m, 1H).

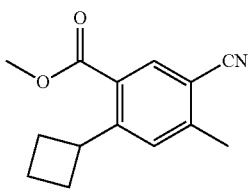 [SMILES: COC(=O)c1cc(C#N)c(C)cc1C1CCC1]

Compound 219.4 Methyl 5-cyano-2-cyclobutyl-4-methylbenzoate

A mixture of methyl 2-cyclobutyl-5-iodo-4-methylbenzoate (219.3, 3.0 g, 9.1 mmol), Zn(CN)$_2$ (2.3 g, 19.6 mmol) and Pd(PPh$_3$)$_4$ (0.55 g, 0.47 mmol) in DMF (50 ml) was degassed and the flask was filled with argon through a balloon. The mixture was heated at 100° C. under argon overnight. After cooling to ambient temperature, the reaction was quenched with saturated aq. FeSO$_4$ (20 ml) and diluted with EtOAc (200 ml). The mixture was stirred vigorously then filtered through celite and washed with 1 M FeSO$_4$, water and ethyl acetate. The layers were separated and the aqueous phase was extracted with ethyl acetate. The combined organic layers were washed with brine, dried (Na$_2$SO$_4$), and concentrated. The residue was purified using column (silica gel) chromatography (hexanes:EtOAc 30:1 to 20:1). Yield: 2.0 g, 96%. $^1$H NMR (400 MHz, Chloroform-d) δ 8.03 (s, 1H), 7.34 (s, 1H), 4.26-4.13 (m, 1H), 3.89 (s, 3H), 2.59 (s, 3H), 2.46-2.32 (m, 2H), 2.16-1.98 (m, 3H), 1.90-1.78 (m, 1H).

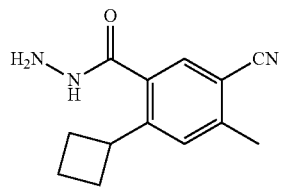 [SMILES: Cc1cc(C2CCC2)c(C(=O)NN)cc1C#N]

Compound 219.5. 5-Cyano-2-cyclobutyl-4-methylbenzohydrazide

To a solution of methyl 5-cyano-2-cyclobutyl-4-methylbenzoate (219.4, 2.0 g, 8.73 mmol) in EtOH (10 ml) was added anhydrous hydrazine (2 ml, excess) at room temperature. The mixture was heated at 90° C. overnight. After cooling to ambient temperature, the mixture was partitioned between water (60 ml) and EtOAc (200 ml). The EtOAc layer was washed with water (×2), brine, dried with Na$_2$SO$_4$, and concentrated to give the product as a white solid. Yield: 1.9 g, 95%. m/z (ES+) 230 (M+H)$^+$. $^1$H NMR (400 MHz, Chloroform-d) δ 7.52 (s, 1H), 7.32 (s, 1H), 6.91 (br, 1H), 4.08 (br, 2H), 3.89 (m, 1H), 2.61-2.52 (m, 3H), 2.42-2.28 (m, 2H), 2.18-1.98 (m, 3H), 1.91-1.78 (m, 1H).

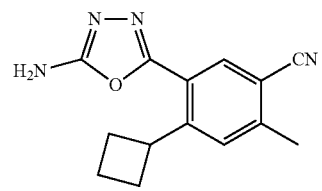 [SMILES: Cc1cc(C2CCC2)c(-c2nnc(N)o2)cc1C#N]

Compound 219.6. 5-(5-Amino-1,3,4-oxadiazol-2-yl)-4-cyclobutyl-2-methylbenzonitrile The title compound (0.55 g, white solid, 100%) was prepared using a procedure similar to that used for the preparation of compound 217.3 and using compound 219.5 (0.50 g) in place of compound 217.2. m/z (ES+) 255 (M+H)$^+$. $^1$H NMR (400 MHz, Chloroform-d) δ 7.93 (s, 1H), 7.45 (s, 1H), 5.10 (br, 2H), 4.38 (m, 1H), 2.61 (s, 3H), 2.48-2.34 (m, 2H), 2.17-1.98 (m, 3H), 1.91-1.79 (m, 1H).

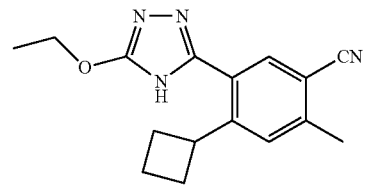 [SMILES: CCOc1nnc(-c2cc(C#N)c(C)cc2C2CCC2)[nH]1]

Compound 219.7. 4-Cyclobutyl-5-(5-ethoxy-4H-1,2,4-triazol-3-yl)-2-methylbenzonitrile To a solution of 5-(5-amino-1,3,4-oxadiazol-2-yl)-4-cyclobutyl-2-methylbenzonitrile (219.6, 0.5 g, 2.0 mmol) in EtOH (40 ml) was added KOH (1.11 g, 20.0 mmol). The mixture was heated at 85° C. overnight. After cooling to ambient temperature, the mixture was neutralized to pH 7 with 1N HCl at 0° C. and then extracted with EtOAc (×2). The combined organic layers were dried (Na$_2$SO$_4$) and concentrated. The residue was purified using column (silica gel) chromatography (hexanes:EtOAc 1:1 to EtOAc). Yield: 0.2 g, white solid, 34%. 777/Z (ES+) 283 (M+H)$^+$. $^1$H NMR (400 MHz, Chloroform-d) δ 7.84 (s, 1H), 7.35 (s, 1H), 4.48 (t, 2H), 4.19-4.10 (m, 1H), 2.58 (s, 3H), 2.30-2.19 (m, 2H), 2.11-1.95 (m, 3H), 1.85-1.76 (m, 1H), 1.45 (t, 3H).

Compound 219.8. 4-Cyclobutyl-5-(5-ethoxy-4H-1,2,4-triazol-3-yl)-2-methylbenzamide To a solution of 4-cyclobutyl-5-(5-ethoxy-4H-1,2,4-triazol-3-yl)-2-methylbenzonitrile (219.7, 0.15 g, 0.53 mmol) in EtOH (10 ml) was added NH₄OH (0.18 ml, 2.66 mmol, 14.8 N in H₂O) followed by H₂O₂ (1.8 ml, 26.6 mmol, 50% in H₂O). The mixture was stirred at room temperature overnight. The mixture was cooled to 0° C. and quenched carefully with 1N Na₂S₂O₃ solution (26 ml). The mixture was extracted with EtOAc (×2) and the combined organic layers were dried over Na₂SO₄, filtered, and concentrated. The residue was purified with prep-TLC (5% MeOH in CH₂Cl₂). Yield: 0.1 g, white solid, 62.5%. m/z (ES−) 299 (M−H)⁻.

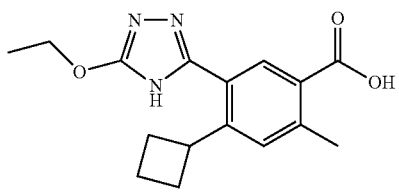 [SMILES: CCOc1nnc(-c2cc(C(=O)O)c(C)cc2C2CCC2)[nH]1]

Compound 219.9. 4-Cyclobutyl-5-(5-ethoxy-4H-1,2,4-triazol-3-yl)-2-methylbenzoic acid To a solution of 4-cyclobutyl-5-(5-ethoxy-4H-1,2,4-triazol-3-yl)-2-methylbenzamide (219.8, 0.1 g, 0.33 mmol) in TEA (5 ml) was added NaNO₂ (0.046 g, 0.66 mmol) at 0° C. The mixture was stirred at 0° C. for 1 hour then at room temperature for 2 hours. The mixture was concentrated under reduced pressure. The residue was partitioned between EtOAc and brine. The aqueous layer was extracted with EtOAc. The combined organic layers were dried (Na₂SO₄) and concentrated to give a clear oil. Yield: 0.1 g, 100%. m/z (ES−) 300 (M−H)⁻.

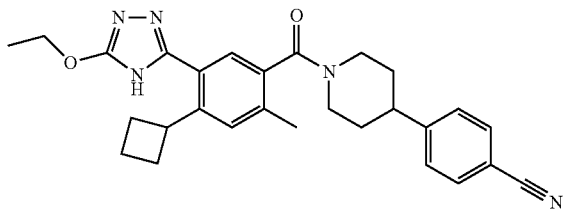 [SMILES: CCOc1nnc(-c2cc(C(=O)N3CCC(c4ccc(C#N)cc4)CC3)c(C)cc2C2CCC2)[nH]1]

Compound 219. 4-(1-(4-Cyclobutyl-5-(5-ethoxy-4H-1,2,4-triazol-3-yl)-2-methylbenzoyl)piperidin-4-yl)benzonitrile A solution of 4-cyclobutyl-5-(5-ethoxy-4H-1,2,4-triazol-3-yl)-2-methylbenzoic acid (compound 219.9, 40 mg, 0.13 mmol), DIEA (0.07 ml, 0.39 mmol), HOBT (34 mg, 0.19 mmol, with 20% water), EDCI (38 mg, 0.19 mmol), and 4-(piperidin-4-yl)benzonitrile hydrochloride (compound 1.5, 36 mg, 0.16 mmol) in N,N-dimethylformamide (3 mL) was stirred overnight at room temperature. The reaction mixture was then diluted with 50 mL of ethyl acetate and washed with 2×20 mL of brine. The mixture was dried over anhydrous sodium sulfate and concentrated under reduced pressure. The residue was applied onto a silica gel prep-TLC plate and developed using ethyl acetate/hexanes (1:1) to yield 0.1 g (68%) of the title compound as a white solid. m/z (ES+) 470 (M+H)⁺.

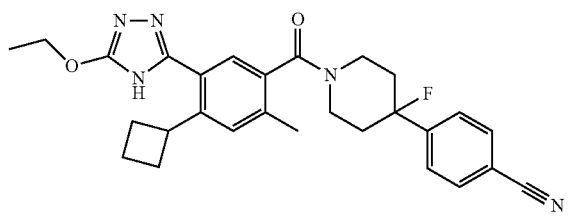 [SMILES: CCOc1nnc(-c2cc(C(=O)N3CCC(F)(c4ccc(C#N)cc4)CC3)c(C)cc2C2CCC2)[nH]1]

Compound 220. 4-(1-(4-Cyclobutyl-5-(5-ethoxy-4H-1,2,4-triazol-3-yl)-2-methylbenzoyl)-4-fluoropiperidin-4-yl)benzonitrile The title compound was prepared using standard chemical manipulations and procedures similar to those used for the preparation of 4-(1-(4-cyclobutyl-5-(5-ethoxy-4H-1,2,4-triazol-3-yl)-2-methylbenzoyl)piperidin-4-yl)benzonitrile (compound 219), using compound 11.2 HCl salt in place of compound 1.5. m/z (ES+) 488 (M+H)⁺. ¹H NMR (400 MHz, CDCl₃): δ 11.10 (br s, 1H), 7.72-7.63 (m, 2H), 7.47 (d, J=8.4 Hz, 2H), 7.42 & 7.33 (2 singlets, amide rotamers, Ar—H, 1H), 7.25 (s, 1H), 4.86 (br d, J=11.2 Hz, 1H), 4.41 (q, J=7.1 Hz, 2H), 4.17-4.03 (m, 1H), 3.61-3.38 (m, 2H), 3.29-3.14 (m, 1H), 2.46-1.70 (m, 13H), 1.45 (t, J=7.2 Hz, 3H).

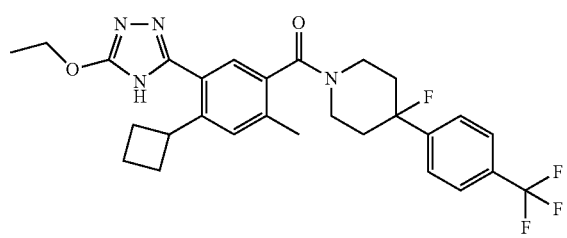 [SMILES: CCOc1nnc(-c2cc(C(=O)N3CCC(F)(c4ccc(C(F)(F)F)cc4)CC3)c(C)cc2C2CCC2)[nH]1]

Compound 221. (4-Cyclobutyl-5-(5-ethoxy-4H-1,2,4-triazol-3-yl)-2-methylphenyl)(4-fluoro-4-(4-(trifluoromethyl)phenyl)piperidin-1-yl)methanone The title compound was prepared using standard chemical manipulations and procedures similar to those used for the preparation of 4-(1-(4-cyclobutyl-5-(5-ethoxy-4H-1,2,4-triazol-3-yl)-2-methylbenzoyl)piperidin-4-yl)benzonitrile (compound 219). m/z (ES+) 531 (M+H)⁺.

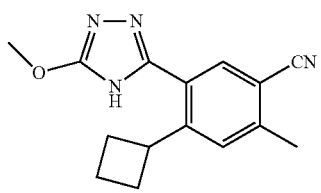 [SMILES: COc1nnc(-c2cc(C#N)c(C)cc2C2CCC2)[nH]1]

Compound 222.1. 4-Cyclobutyl-5-(5-methoxy-4H-1,2,4-triazol-3-yl)-2-methylbenzonitrile The title compound was prepared using standard chemical manipulations and procedures similar to those used for the preparation of compound 4-cyclobutyl-5-(5-ethoxy-4H-1,2,4-triazol-3-yl)-2-methylbenzonitrile (compound 219.7), except MeOH was used as the solvent instead of EtOH. m/z (ES+) 269 (M+H)+. $^1$H NMR (400 MHz, Chloroform-d) δ 10.96 (br, 1H), 7.82 (s, 1H), 7.35 (s, 1H), 4.11 (s, 3H), 4.15-4.05 (m, 1H), 2.59 (s, 3H), 2.31-2.16 (m, 2H), 2.14-1.89 (m, 3H), 1.87-1.71 (m, 1H).

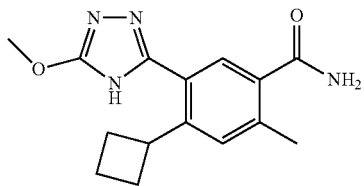 [SMILES: COc1nnc(-c2cc(C(N)=O)c(C)cc2C2CCC2)[nH]1]

Compound 222.2. 4-Cyclobutyl-5-(5-methoxy-4H-1,2,4-triazol-3-yl)-2-methylbenzamide The title compound was prepared using standard chemical manipulations and procedures similar to those used for the preparation of 4-cyclobutyl-5-(5-ethoxy-4H-1,2,4-triazol-3-yl)-2-methylbenzamide (compound 219.8) but using compound 222.1 in place of compound 219.7. m/z (ES+) 287 (M+H)+. $^1$H NMR (400 MHz, Methanol-d$_4$) δ 7.50 (s, 1H), 7.33 (s, 1H), 4.03 (s, 3H), 3.95-4.05 (m, 1H), 2.51 (s, 3H), 2.23-2.11 (m, 2H), 2.11-1.88 (m, 3H), 1.83-1.71 (m, 1H).

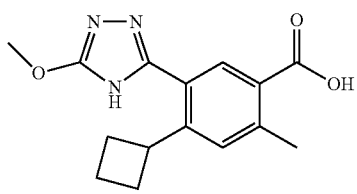 [SMILES: COc1nnc(-c2cc(C(=O)O)c(C)cc2C2CCC2)[nH]1]

Compound 222.3. 4-Cyclobutyl-5-(5-methoxy-4H-1,2,4-triazol-3-yl)-2-methylbenzoic acid The title compound was prepared using standard chemical manipulations and procedures similar to those used for the preparation of 4-cyclobutyl-5-(5-ethoxy-4H-1,2,4-triazol-3-yl)-2-methylbenzoic acid (compound 219.9) but using compound 222.2 in place of compound 219.8. m/z (ES+) 287 (M+H)+.

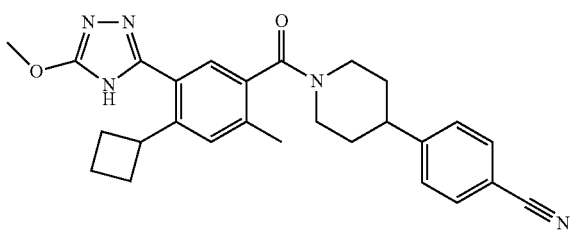 [SMILES: COc1nnc(-c2cc(C(=O)N3CCC(c4ccc(C#N)cc4)CC3)c(C)cc2C2CCC2)[nH]1]

Compound 222. 4-(1-(4-Cyclobutyl-5-(5-methoxy-4H-1,2,4-triazol-3-yl)-2-methylbenzoyl)piperidin-4-yl)benzonitrile A solution of 4-cyclobutyl-5-(5-methoxy-4H-1,2,4-triazol-3-yl)-2-methylbenzoic acid (compound 222.3, 60 mg, 0.21 mmol), DIEA (0.11 ml, 0.63 mmol), HOBT (53 mg, 0.32 mmol, with 20% water), EDCI (60 mg, 0.32 mmol) and 4-(piperidin-4-yl)benzonitrile hydrochloride (compound 1.5, 47 mg, 0.21 mmol) in N,N-dimethylformamide (3 mL) was stirred overnight at room temperature. The reaction mixture was then diluted with 50 mL of ethyl acetate and washed with 2×20 mL of brine. The mixture was dried over anhydrous sodium sulfate and concentrated under reduced pressure. The residue was applied onto a silica gel prep-TLC plate and developed using ethyl acetate/hexanes (1:1) to yield 21.0 mg (22%) of the title compound as a white solid. m/z (ES+) 456 (M+H)+. $^1$H NMR (400 MHz, Chloroform-d) δ 11.54-10.86 (br s, 1H), 7.60 (d, 2H), 7.38-7.20 (m, 4H), 5.04-4.92 (m, 1H), 4.06 (s, 3H), 4.14-4.00 (m, 1H), 3.62 (d, 1H), 3.15-3.03 (m, 1H), 2.93-2.76 (m, 2H), 2.38 and 2.30 (2 singlets, amide rotamers, ArCH$_3$, 3H), 2.34-2.22 (m, 1H), 2.20-2.06 (m, 2H), 2.05-1.84 (m, 3H), 1.61-1.45 (m, 1H).

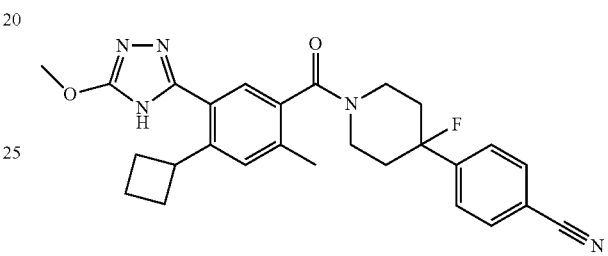

Compound 223. 4-(1-(4-Cyclobutyl-5-(5-methoxy-4H-1,2,4-triazol-3-yl)-2-methylbenzoyl)-4-fluoropiperidin-4-yl)benzonitrile The title compound was prepared using standard chemical manipulations and procedures similar to those used for the preparation of 4-(1-(4-cyclobutyl-5-(5-methoxy-4H-1,2,4-triazol-3-yl)-2-methylbenzoyl)piperidin-4-yl)benzonitrile (compound 222) but using compound 11.2 HCl salt in place of compound 1.5. m/z (ES+) 474 (M+H)+.

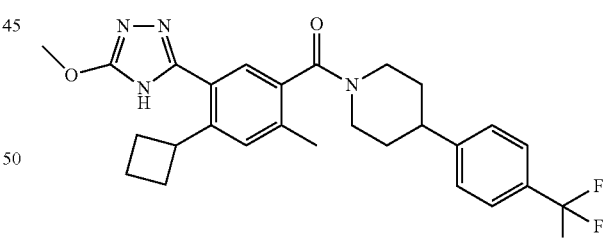

Compound 224. (4-Cyclobutyl-5-(5-methoxy-4H-1,2,4-triazol-3-yl)-2-methylphenyl)(4-(4-(trifluoromethyl)phenyl)piperidin-1-yl)methanone The title compound was prepared using standard chemical manipulations and procedures similar to those used for the preparation of 4-(1-(4-cyclobutyl-5-(5-methoxy-4H-1,2,4-triazol-3-yl)-2-methylbenzoyl)piperidin-4-yl)benzonitrile (222). m/z (ES+) 499 (M+H)+.

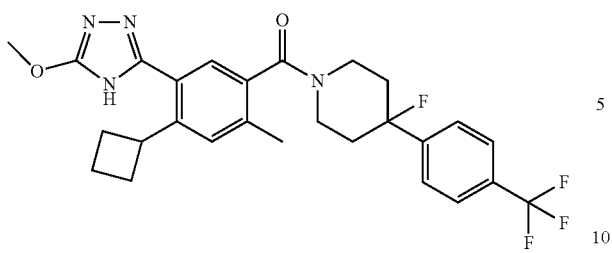

Compound 225. (4-Cyclobutyl-5-(5-methoxy-4H-1,2,4-triazol-3-yl)-2-methylphenyl)(4-fluoro-4-(4-(trifluoromethyl)phenyl)piperidin-1-yl)methanone The title compound was prepared using standard chemical manipulations and procedures similar to those used for the preparation of 4-(1-(4-cyclobutyl-5-(5-methoxy-4H-1,2,4-triazol-3-yl)-2-methylbenzoyl)piperidin-4-yl)benzonitrile (Compound 222). m/z (ES+) 517 (M+H)$^+$.

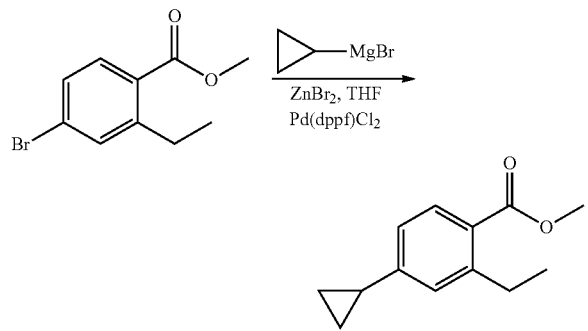

Compound 226.3. Methyl 4-cyclopropyl-2-ethylbenzoate

To a stirred mixture of ZnBr$_2$ (37.0 g, 164 mmol, 3.99 equiv) in tetrahydrofuran (150 mL) under nitrogen was added bromo(cyclopropyl)magnesium (3.28 M in THF, 50 mL, 4.00 equiv) dropwise at 0° C. After stirring at 15 minutes at 0° C., the temperature was lowered to −30° C. followed by the dropwise addition of a solution of Pd(dppf)Cl$_2$ (2.00 g, 2.73 mmol, 0.07 equiv) in tetrahydrofuran (50 mL) and a solution of methyl 4-bromo-2-ethylbenzoate (compound 181.2, 10.0 g, 41.1 mmol, 1.00 equiv) in tetrahydrofuran (50 mL). The resulting solution was warmed slowly to 25° C. and stirred for 15 h, then carefully quenched by slow addition of 100 mL of NH$_4$Cl (aq.sat.). The mixture was extracted with 2×100 mL of ethyl acetate and the combined organic layers were dried over anhydrous sodium sulfate and concentrated in vacuo. The residue was purified using silica gel column chromatography with ethyl acetate/petroleum ether (1:30) as eluent to yield 7.50 g (89%) of methyl 4-cyclopropyl-2-ethylbenzoate as a light yellow oil.

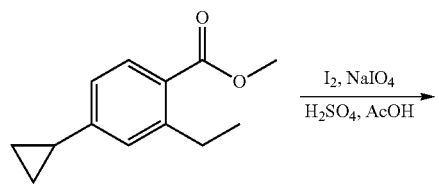

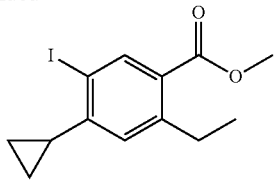

Compound 226.4. Methyl 4-cyclopropyl-2-ethyl-5-iodobenzoate

To a round-bottom flask was added a solution of methyl 4-cyclopropyl-2-ethylbenzoate (compound. 226.3, 5.00 g, 24.5 mmol, 1.00 equiv) in AcOH (40 mL). I$_2$ (6.80 g, 26.8 mmol, 1.10 equiv), NaIO$_4$ (2.60 g, 12.2 mmol, 0.50 equiv), and sulfuric acid (400 mg, 4.08 mmol, 0.15 equiv) were added to the reaction. The resulting solution was stirred for 2 h at 50° C. After cooling to ambient temperature, the reaction was carefully quenched with Na$_2$S$_2$O$_3$(aq., sat.). The mixture was extracted with 2×100 mL of ethyl acetate, and the combined organic layers were dried over sodium sulfate and concentrated in vacuo. The residue was purified using silica gel column chromatography with petroleum ether/ethyl acetate (20:1) as eluent to furnish 4.00 g (49%) of methyl 4-cyclopropyl-2-ethyl-5-iodobenzoate as a yellow oil.

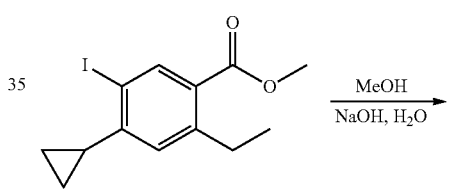

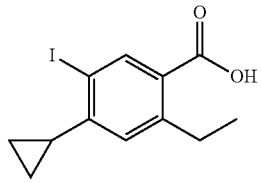

Compound 226.5. 4-Cyclopropyl-2-ethyl-5-iodobenzoic acid

To a solution of methyl 4-cyclopropyl-2-ethyl-5-iodobenzoate (compound 226.4, 2.50 g, 7.57 mmol, 1.00 equiv) in methanol (40 mL) was added aqueous sodium hydroxide (3.10 g, 77.5 mmol, 10.0 equiv, in 10 mL water). The resulting mixture was stirred for 15 h at 60° C. in an oil bath. After cooling to ambient temperature, the organic solvent was removed under reduced pressure and pH of the remaining aqueous layer was adjusted to 4 with hydrogen chloride (aq, 1 M). The solids were collected by filtration and dried in an oven under reduced pressure to yield 2.20 g (92%) of 4-cyclopropyl-2-ethyl-5-iodobenzoic acid as a white solid.

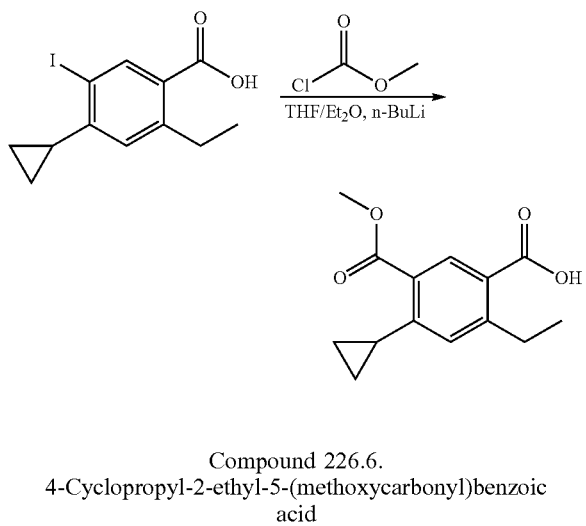

Compound 226.6.
4-Cyclopropyl-2-ethyl-5-(methoxycarbonyl)benzoic acid

To a solution of 4-cyclopropyl-2-ethyl-5-iodobenzoic acid (compound 226.5, 500 mg, 1.58 mmol, 1.00 equiv) in THF/Et$_2$O (10/10 mL) under nitrogen at −78° C. was added dropwise 17-butyllithium (2.5 M, 1.88 mL, 3.00 equiv) over 3 min. After stirring for 10 min at −78° C., methyl chloroformate (230 mg, 2.43 mmol, 1.50 equiv) was added dropwise at −78° C. The resulting solution was stirred for 40 min at −78° C., then warmed slowly to −35° C. The reaction was carefully quenched with 2 mL of water. The pH was adjusted to −4-5 with hydrogen chloride (aq., 1 M). The resulting mixture was extracted with 3×20 mL of ethyl acetate and the combined organic layers were dried (Na$_2$SO$_4$) and concentrated under reduced pressure to yield 400 mg the title compound as a yellow solid.

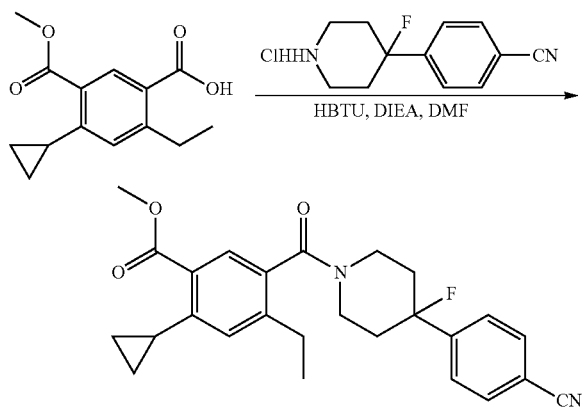

Compound 226.7. Methyl 5-(4-(4-cyanophenyl)-4-fluoropiperidine-1-carbonyl)-2-cyclopropyl-4-ethylbenzoate To a solution of 4-cyclopropyl-2-ethyl-5-(methoxycarbonyl)benzoic acid (compound 226.6, 150 mg, 0.600 mmol, 1.00 equiv) in N,N-dimethylformamide (15 mL) were added 4-(4-fluoropiperidin-4-yl)benzonitrile hydrochloride (compound 11.2, 150 mg, 0.620 mmol, 1.00 equiv), DIPEA (450 mg, 3.49 mmol, 6.00 equiv), and HBTU (300 mg, 0.790 mmol, 1.30 equiv). The resulting solution was stirred for 4 h at 20° C., then quenched by the addition of 20 mL of brine.

The resulting mixture was extracted with 4×30 mL of ethyl acetate. The combined organic layers were dried over anhydrous sodium sulfate and concentrated in vacuo. The residue was purified via silica gel column with ethyl acetate/petroleum ether (1:3) as eluent. This resulted in 0.200 g (76%) of methyl 5-(4-(4-cyanophenyl)-4-fluoropiperidine-1-carbonyl)-2-cyclopropyl-4-ethylbenzoate as a light yellow solid.

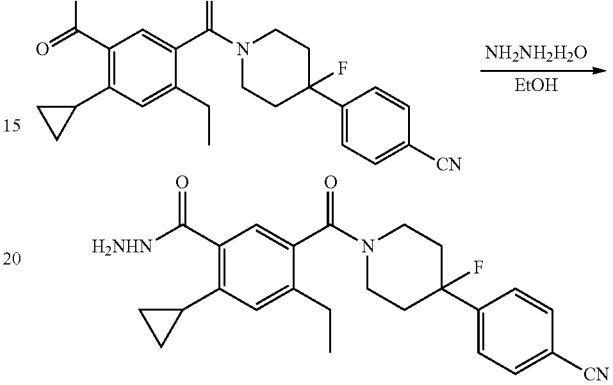

Compound 226.8. 5-(4-(4-Cyanophenyl)-4-fluoropiperidine-1-carbonyl)-2-cyclopropyl-4-ethylbenzohydrazide To a solution of methyl 5-(4-(4-cyanophenyl)-4-fluoropiperidine-1-carbonyl)-2-cyclopropyl-4-ethylbenzoate (compound 226.7, 200 mg, 0.460 mmol, 1.00 equiv) in ethanol (15 mL) was added hydrazine hydrate (80%, 5 mL). The resulting solution was stirred at 80° C. for 15 h. After cooling to ambient temperature, the reaction was quenched with 50 mL of water, then extracted with 3×50 mL of dichloromethane. The combined organic layers were dried over anhydrous sodium sulfate and concentrated in vacuo to yield 150 mg (75%) of 5-(4-(4-cyanophenyl)-4-fluoropiperidine-1-carbonyl)-2-cyclopropyl-4-ethylbenzohydrazide as a colorless oil.

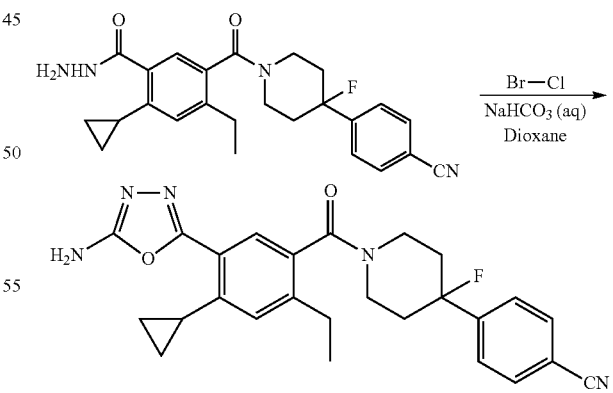

Compound 226.9. 4-(1-(5-(5-Amino-1,3,4-oxadiazol-2-yl)-4-cyclopropyl-2-ethylbenzoyl)-4-fluoropiperidin-4-yl)benzonitrile The title compound (50 mg, white solid, 95%) was prepared using a procedure similar to that used for the preparation of compound 217.3 and using compound 226.8 (50 mg) in place of compound 217.2.

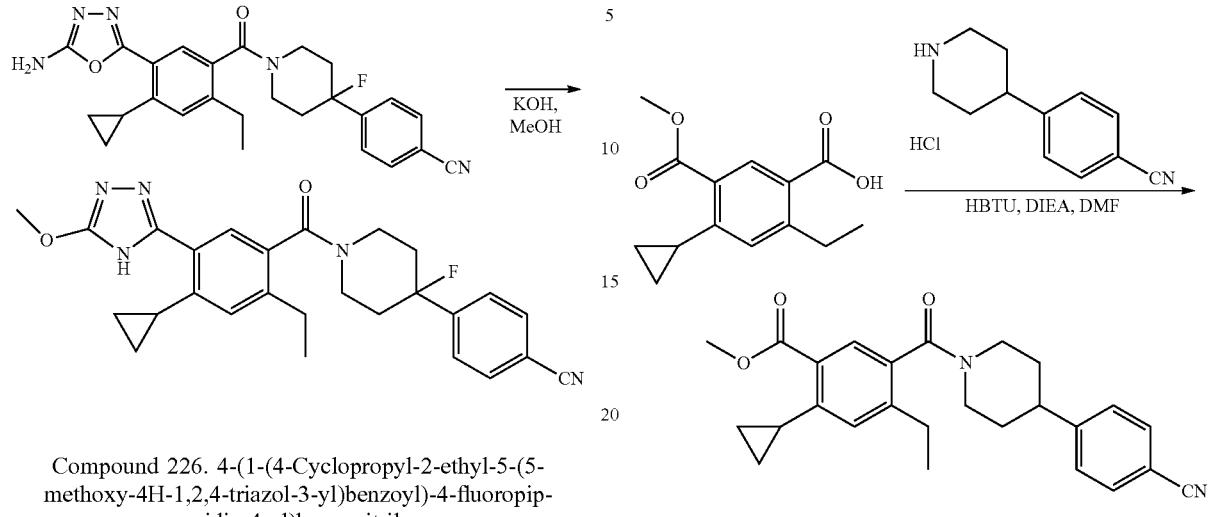

Compound 226. 4-(1-(4-Cyclopropyl-2-ethyl-5-(5-methoxy-4H-1,2,4-triazol-3-yl)benzoyl)-4-fluoropiperidin-4-yl)benzonitrile The title compound (50 mg, white solid, 95%) was prepared using a procedure similar to that used for the preparation of compound 219.7 and using compound 226.9 (300 mg) in place of compound 219.6. The crude product (~30 mg) was purified by Prep-HPLC with the following conditions (1#-Pre-HPLC-001(SHIMADZU)): Column, SunFire Prep C18, 19*150 mm 5 um; mobile phase, water with 0.05% TFA and CH$_3$CN (46.0% CH$_3$CN up to 57.0% in 8 min, up to 100.0% in 1 min, down to 46.0% in 1 min); Detector, Waters 2489 254 & 220 nm. The fractions containing pure compound were combined and lyophilized to yield 15 mg of the title compound as a white solid. m/z (ES+) 474 (M+H)$^+$. $^1$H-NMR (300 MHz, CD$_3$OD, ppm): δ 7.73 (d, 2H), 7.65-7.57 (m, 2H), 7.46-7.32 (m, 1H), 7.03 (s, 1H), 4.85-4.73 (m, 1H), 4.00 (s, 3H), 3.48-3.32 (m, 2H), 3.28-3.21 (m, 1H), 2.71-2.62 (m, 2H), 2.28-2.14 (m, 2H), 2.10-1.80 (m, 3H), 1.28-1.20 (m, 3H), 0.97-0.94 (m, 2H), 0.75-0.50 (m, 2H).

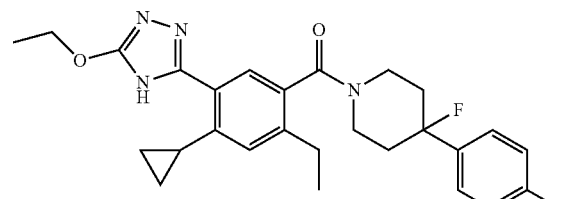

Compound 227. 4-(1-(4-Cyclopropyl-5-(5-ethoxy-4H-1,2,4-triazol-3-yl)-2-ethylbenzoyl)-4-fluoropiperidin-4-yl)benzonitrile The title compound was prepared using standard chemical manipulations and procedures similar to those used for the preparation of 4-(1-(4-cyclopropyl-2-ethyl-5-(5-methoxy-4H-1,2,4-triazol-3-yl)benzoyl)-4-fluoropiperidin-4-yl)benzonitrile (compound 226). m/z (ES+) 488 (M+H)$^+$. $^1$H-NMR (300 MHz, CD$_3$OD): δ7.80-7.78 (m, 2H), 7.70-7.63 (m, 2H), 7.51 (m, 1H), 7.07 (s, 1H), 4.89-4.82 (m, 1H), 4.40 (app t, 2H), 3.57-3.52 (m, 2H), 3.28-3.25 (m, 1H), 2.80-2.50 (m, 2H), 2.40-2.10 (m, 4H), 1.95-1.80 (m, 1H), 1.45 (t, 3H), 1.32-1.22 (m, 3H), 1.01-0.99 (m, 2H), 0.73-0.73 (m, 2H).

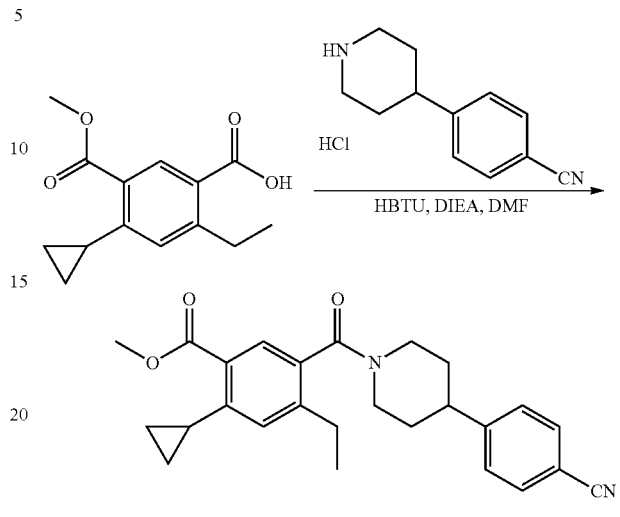

Compound 228.1. Methyl 5-(4-(4-cyanophenyl) piperidine-1-carbonyl)-2-cyclopropyl-4-ethylbenzoate To a round-bottom flask, which was purged and maintained with a nitrogen atmosphere, was added a solution of 4-cyclopropyl-2-ethyl-5-(methoxycarbonyl)benzoic acid (compound 226.6., 500 mg, 2.01 mmol, 1.00 equiv) in NA-dimethylformamide (20 mL). HBTU (1.53 g, 4.03 mmol, 2.00 equiv), DIEA (780 mg, 6.04 mmol, 3.00 equiv) were added to the reaction solution, and it was stirred for 5 min at 25° C. 4-(piperidin-4-yl)benzonitrile (compound 1.5, 410 mg, 2.20 mmol, 1.10 equiv) was added to the above mixture. After stirring for 15 h at 25° C., the reaction was quenched by the addition of water. The mixture was extracted with 100 mL of ethyl acetate and the combined organic layers were washed with 4×40 mL of brine, dried over anhydrous sodium sulfate and concentrated in vacuo. The residue was purified using silica gel column chromatography with ethyl acetate/petroleum ether (4:1) as eluent to furnish 0.830 g (99%) of methyl 5-(4-(4-cyanophenyl) piperidine-1-carbonyl)-2-cyclopropyl-4-ethylbenzoate as a colorless oil.

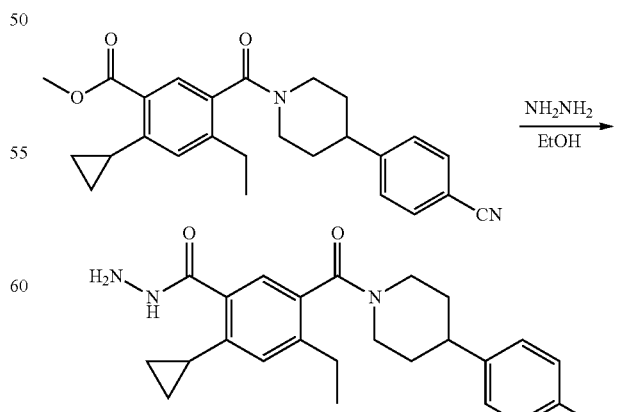

Compound 228.2. 5-(4-(4-Cyanophenyl)piperidine-1-carbonyl)-2-cyclopropyl-4-ethylbenzohydrazide To a round-bottom flask was added a solution of methyl 5-(4-(4-cyanophenyl)piperidine-1-carbonyl)-2-cyclopropyl-4-ethylbenzoate (compound 228.1, 830 mg, 1.99 mmol, 1.00 equiv) in ethanol (15 mL). Hydrazine (5 mL, 100 equiv) was added to the reaction. The resulting solution was stirred for 15 h at 100° C., then concentrated in vacuo. The residue was extracted with 100 mL of dichloromethane and the combined organic layers were washed with 1×30 mL of brine, dried over anhydrous sodium sulfate and concentrated in vacuo. This resulted in 0.800 g (96%) of 5-(4-(4-cyanophenyl)piperidine-1-carbonyl)-2-cyclopropyl-4-ethylbenzohydrazide as a white solid.

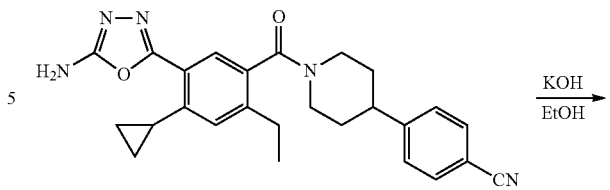

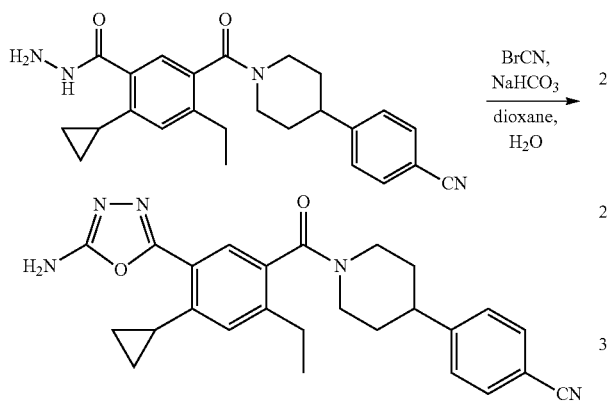

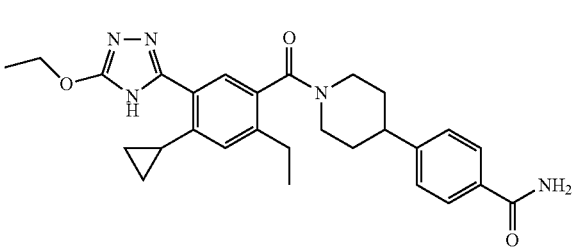

Compound 228.4. 4-(1-(4-Cyclopropyl-5-(5-ethoxy-4H-1,2,4-triazol-3-yl)-2-ethylbenzoyl)piperidin-4-yl)benzamide The title compound (80 mg, yellow solid, 36%) was prepared using a procedure similar to that used for the preparation of compound 219.7 and using compound 228.3 (200 mg) in place of compound 219.6.

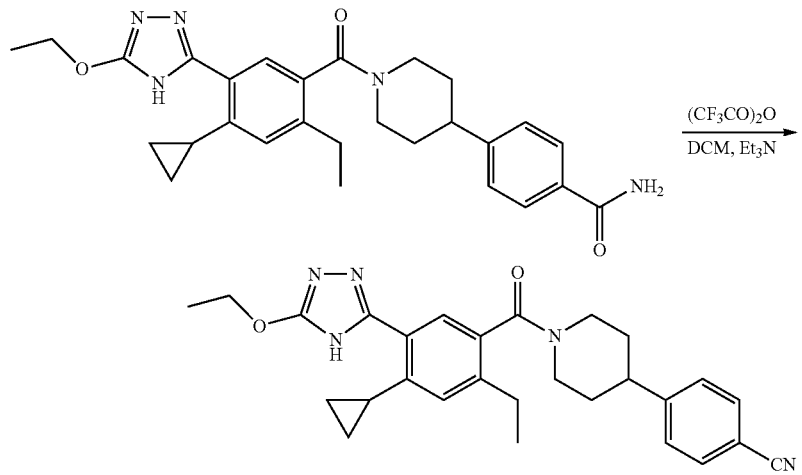

Compound 228.3. 4-(1-(5-(5-Amino-1,3,4-oxadiazol-2-yl)-4-cyclopropyl-2-ethylbenzoyl)piperidin-4-yl)benzonitrile The title compound (750 mg, light brown solid, 94%) was prepared using a procedure similar to that used for the preparation of compound 217.3 and using compound 228.2 (750 mg) in place of compound 217.2.

Compound 228. 4-(1-(4-Cyclopropyl-5-(5-ethoxy-4H-1,2,4-triazol-3-yl)-2-ethylbenzoyl)piperidin-4-yl)benzonitrile To a round-bottom flask, which was purged and maintained with a nitrogen atmosphere, was added a solution of 4-(1-(4-cyclopropyl-5-(5-ethoxy-4H-1,2,4-triazol-3-yl)-2-ethylbenzoyl)piperidin-4-yl)benzamide (compound 228.4, 80.0 mg, 0.160 mmol, 1.00 equiv) in dichloromethane (10 mL). Trifluoroacetic anhydride (34.0 mg, 0.160 mmol, 1.00 equiv) and triethylamine (33.0 mg, 0.330 mmol, 2.00 equiv) were added dropwise to the stirred mixture. The resulting solution was stirred for 2 h at 25 then washed with 1×10 mL of brine. The aqueous layer was extracted with 2×20 mL of dichloromethane and the combined organic layers were dried over anhydrous sodium sulfate and concentrated in mew. The crude product (30 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (42% CH$_3$CN up to 57% in 8 min, up to 100% in 1.5 min, down to 42% in 1 min); Detector, Waters 2489 254 & 220 nm. The fractions containing pure compound were combined and lyophilized to yield 15 mg (20%) of the title compound as a an off-white solid. m/z (ES+) 470 (M+H)$^+$. $^1$H-NMR (300 MHz, CD$_3$OD, ppm): δ 7.64 (d, 2H), 7.46-7.28 (m, 3H), 7.02-7.01 (m, 1H), 4.89-4.80 (m, 1H), 4.40-4.33 (m, 2H), 3.58-3.56 (m, 1H), 3.27-3.25 (m, 1H), 3.04-2.90 (m, 2H), 2.73-2.58 (m, 2H), 2.31-2.29 (m, 1H), 1.94-1.96 (m, 1H), 1.82-1.78 (m, 3H), 1.45 (t, 3H), 1.32-1.12 (m, 3H), 0.98-0.88 (m, 2H), 0.71-0.68 (m, 2H).

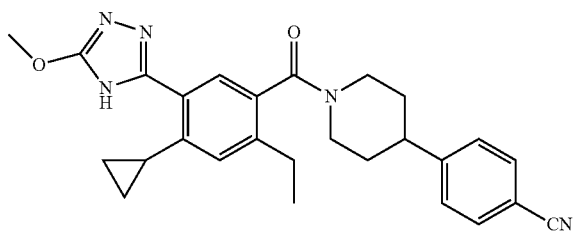 [SMILES: CCc1cc(C2CC2)c(-c2nnc(OC)[nH]2)cc1C(=O)N1CCC(c2ccc(C#N)cc2)CC1]

Compound 229. 4-(1-(4-Cyclopropyl-2-ethyl-5-(5-methoxy-4H-1,2,4-triazol-3-yl)benzoyl)piperidin-4-yl)benzonitrile The title compound was prepared using standard chemical manipulations and procedures similar to those used for the preparation of compound 228. m/z (ES+) 456 (M+H)$^+$. $^1$H-NMR (300 MHz, CD$_3$OD, ppm): δ 7.64 (d, 2H), 7.43-7.27 (m, 3H), 7.03-7.02 (m, 1H), 4.0 (s, 3H), 3.59-3.55 (m, 1H), 3.28-3.27 (m, 1H), 3.04-2.98 (m, 2H), 2.97-2.56 (m, 2H), 2.53-2.29 (m, 1H), 2.0-1.98 (m, 1H), 1.76-1.42 (m, 3H), 1.30-1.16 (m, 3H), 0.99-0.94 (m, 2H), 0.70-0.64 (m, 2H).

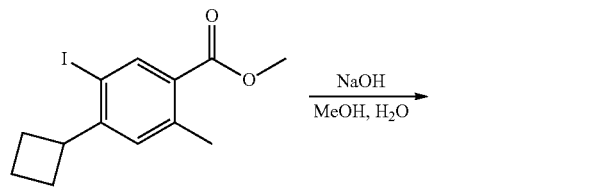

Compound 230.1.
4-Cyclobutyl-5-iodo-2-methylbenzoic acid

To a solution of methyl 4-cyclobutyl-5-iodo-2-methylbenzoate (compound 152.3, 35.0 g, 106 mmol, 1.00 equiv) in methanol (200 mL) at 0-5° C. was added dropwise aqueous sodium hydroxide (12.7 g, 318 mmol, 3.00 equiv in 100 mL water). The resulting mixture was stirred for 3 h at 60° C. After cooling to ambient temperature, the organic solvent was then removed under reduced pressure. The pH of the remaining aqueous phase was adjusted to ~4 with hydrogen chloride (aqueous, 2 M). The resulting solids were collected by filtration and dried in an oven under reduced pressure to yield 31.0 g (93%) of the title compound as a white solid.

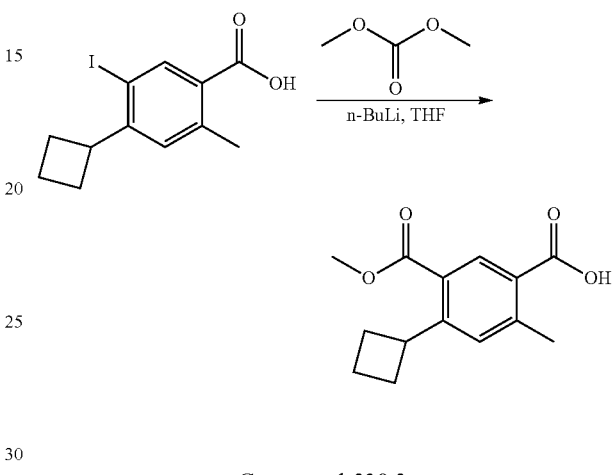

Compound 230.2.
4-Cyclobutyl-5-(methoxycarbonyl)-2-methylbenzoic acid

To a solution of 4-cyclobutyl-5-iodo-2-methylbenzoic acid (compound 230.1, 3.00 g, 9.49 mmol, 1.00 equiv) in THF (40 mL) under nitrogen at −78° C. was added dropwise n-BuLi (9.5 mL, 2.50 equiv, 2.5 M in THF). After 10 minutes, a solution of dimethyl carbonate (2.56 g, 28.4 mmol, 3.00 equiv) in THF (10 mL) was added dropwise at −78° C. The resulting solution was stirred for 1 h at −78° C., then carefully quenched by slow addition of 50 mL of water. The pH was adjusted to ~4 with hydrogen chloride (aq., 1 M). The resulting mixture was extracted with 2×80 mL of ethyl acetate, the combined organic layers were dried over anhydrous sodium sulfate and concentrated in vacuo. The residue was purified using silica gel column chromatography with ethyl acetate/petroleum ether (1:10-1:2) as eluent to furnish 1.30 g (55%) of 4-cyclobutyl-5-(methoxycarbonyl)-2-methylbenzoic acid as a white solid.

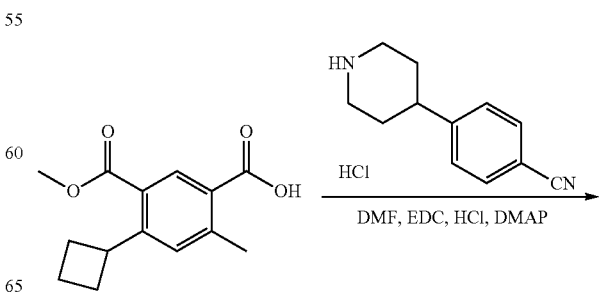

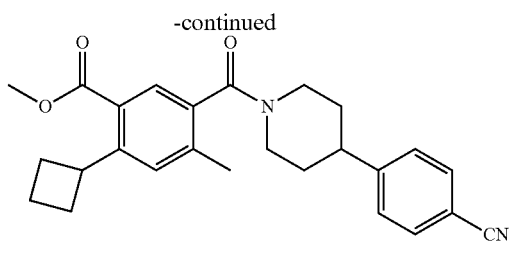
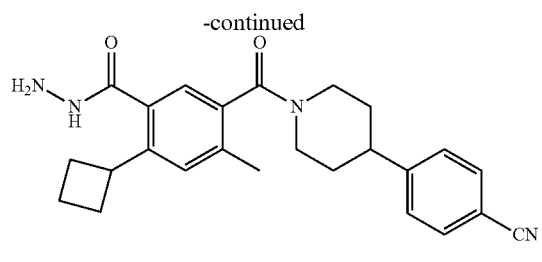

Compound 230.3. Methyl 5-(4-(4-cyanophenyl) piperidine-1-carbonyl)-2-cyclobutyl-4-methylbenzoate To a round-bottom flask was added a solution of 4-cyclobutyl-5-(methoxycarbonyl)-2-methylbenzoic acid (compound 230.2, 2.10 g, 8.46 mmol, 1.00 equiv) in N,N-dimethylformamide (10 mL). 4-(Piperidin-4-yl)benzonitrile hydrochloride (compound 1.5, 1.88 g, 8.44 mmol, 1.00 equiv), EDC.HCl (3.22 g, 16.8 mmol, 2.00 equiv), and 4-dimethylaminopyridine (3.10 g, 25.4 mmol, 3.00 equiv) were added to the reaction. The resulting solution was stirred overnight at 25° C., then diluted with 100 mL of ethyl acetate. The mixture was washed with 2×30 mL of NH₄Cl (aq., sat.) and 2×30 mL of brine, dried over anhydrous sodium sulfate and concentrated in vacuo. The residue was purified using silica gel column chromatography with ethyl acetate/petroleum ether (0:1-1:3) as eluent to yield 3.20 g (91%) of methyl 5-(4-(4-cyanophenyl)piperidine-1-carbonyl)-2-cyclobutyl-4-methylbenzoate as a white solid.

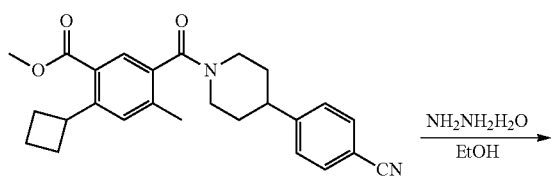

Compound 230.4. 5-(4-(4-Cyanophenyl)piperidine-1-carbonyl)-2-cyclobutyl-4-methylbenzohydrazide The title compound (660 mg, white solid, 66%) was prepared using a procedure similar to that used for the preparation of compound 219.5 and using compound 230.3 (1.00 g) in place of compound 219.4.

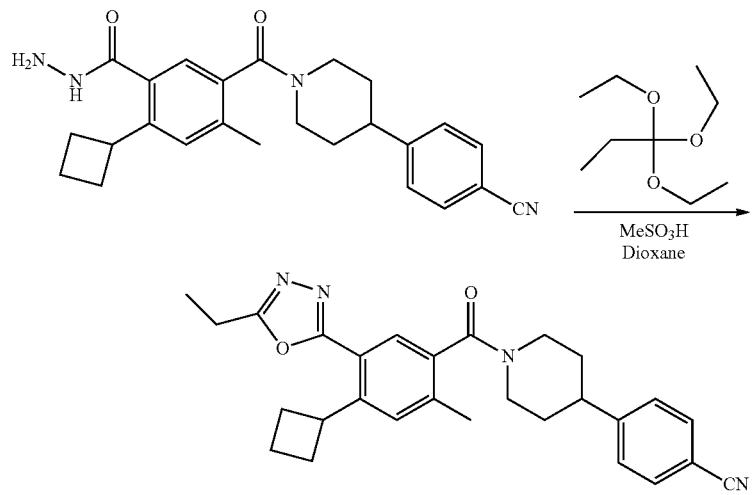

Compound 230. 4-(1-(4-Cyclobutyl-5-(5-ethyl-1,3,4-oxadiazol-2-yl)-2-methylbenzoyl)piperidin-4-yl)benzonitrile To a round-bottom flask was added a solution of 5-(4-(4-cyanophenyl)piperidine-1-carbonyl)-2-cyclobutyl-4-methylbenzohydrazide (compound 230.4, 150 mg, 0.360 mmol, 1.00 equiv) in dioxane (5 mL). MeSO₃H (7 mg, 0.07 mmol, 0.20 equiv), and 1,1,1-triethoxypropane (190 mg, 1.08 mmol, 3.00 equiv) were added to the reaction. The resulting solution was stirred for 20 min at 110° C., then cooled to room temperature and diluted with 50 mL of ethyl acetate. The organic layer was washed with 2×20 mL of water, dried over anhydrous sodium sulfate and concentrated in vacuo. The crude product (200 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH₃CN (64.0% CH₃CN up to 76.0% in 6 min, up to 100.0% in 4 min, down to 64.0% in 1 min); Detector, Waters 2489 254 & 220 nm. The fractions containing pure compound were combined and lyophilized to yield 129 mg (79%) of the title compound as a white solid. m/z (ES+) 455 (M+H)⁺. ¹H-NMR (300 MHz, CD₃OD, ppm): δ 7.73-7.67 (m, 3H), 7.52-7.48 (m, 3H), 5-4.94 (m, 1H), 4.25-4.20 (m, 1H), 3.60-3.58 (m, 1H), 3.33-3.24 (m, 1H), 3.05-2.97 (m, 4H), 2.49 and 2.30 (2 singlets, amide rotamers, CH₃, 3H), 2.39-2.34 (m, 2H), 2.19-1.91 (m, 4H), 1.88-1.66 (m, 4H), 1.49-1.42 (t, 3H).

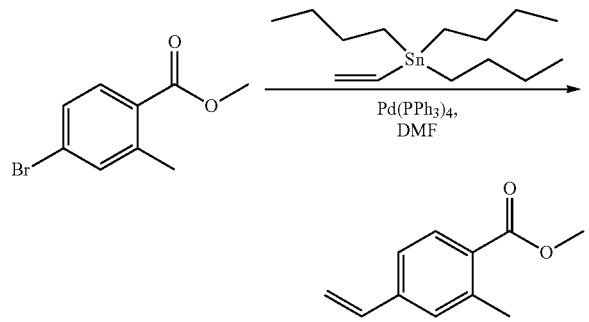

Compound 231.1. Methyl 4-ethenyl-2-methylbenzoate

To a round-bottom flask, which was purged and maintained with a nitrogen atmosphere, was added a solution of methyl 4-bromo-2-methylbenzoate (compound 152.1, 14.0 g, 61.1 mmol, 1.00 equiv) in N,N-dimethylformamide (150 mL). Tributyl(ethenyl)stannane (29.3 g, 92.4 mmol, 2.00 equiv) and Pd(PPh₃)₄ (7.10 g, 6.14 mmol, 0.10 equiv) were added to the reaction. The resulting mixture was stirred overnight at 100° C. in an oil bath. After cooling to room temperature, the mixture was diluted with 400 mL of ethyl acetate. The organic layer was washed with 2×400 mL of NH₄Cl (aq.) and 2×400 mL of brine, dried over anhydrous sodium sulfate, then concentrated in vacuo. The crude product was purified by CombiFlash with the following conditions (IntelFlash-1): mobile phase, petroleum ether/ethyl acetate=1:0 increasing to petroleum ether/ethyl acetate=100:1 within 20 min; Detector, UV 254 nm. This resulted in 6.81 g (63%) of methyl 4-ethenyl-2-methylbenzoate as a colorless oil.

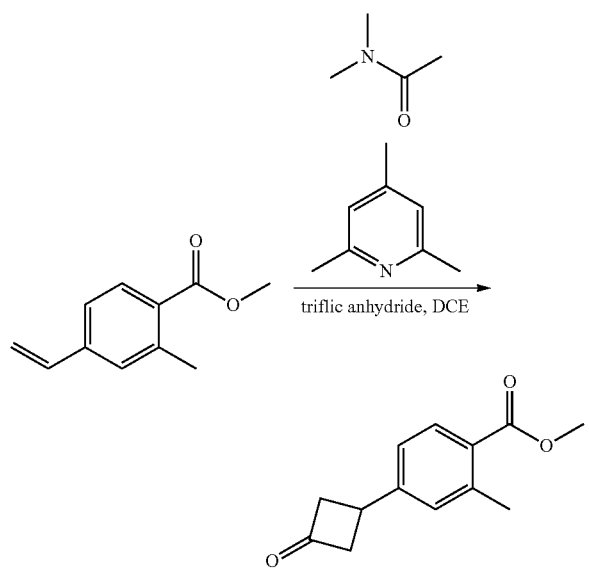

Compound 231.2. Methyl 2-methyl-4-(3-oxocyclobutyl)benzoate

To a solution of N,N-dimethylacetamide (5.5 mL) in DCE (20 mL) under nitrogen at −15° C. was added a solution of trifluoromethanesulfonic anhydride (10 mL) in DCE (50 mL) dropwise. The mixture was then stirred for 10 min at −15° C. to make solution A. To another flask was added methyl 4-ethenyl-2-methylbenzoate (compound 231.1, 5.30 g, 0.03 mol, 1.00 equiv). A solution of 2,4,6-trimethylpyridine (5.5 mL) in DCE (80 mL) was added dropwise at −15° C. The resulting mixture was added into solution A dropwise under an inert atmosphere of nitrogen. The resulting solution was stirred overnight at 80° C. After cooling to ambient temperature, the mixture was carefully quenched with water. The resulting mixture was extracted with 2×200 mL of ethyl acetate, and the combined organic layers were washed with 3×400 mL of brine, dried over anhydrous sodium sulfate and concentrated in vacuo. The residue was purified using silica gel column chromatography with ethyl acetate/petroleum ether (1:50-1:5) as eluent to furnish 2.95 g (45%) of methyl 2-methyl-4-(3-oxocyclobutyl)benzoate as a brown oil.

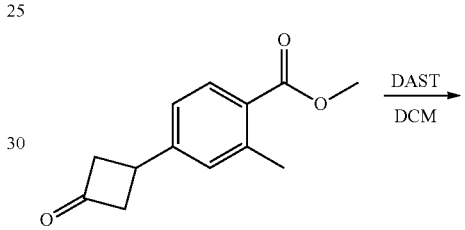

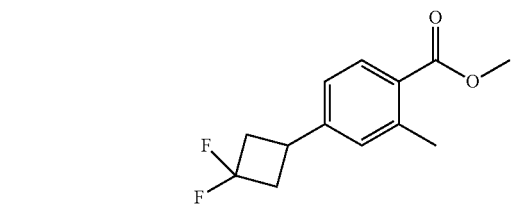

Compound 231.3. Methyl 4-(3,3-difluorocyclobutyl)-2-methylbenzoate

To a round-bottom flask, which was purged and maintained with an inert atmosphere of nitrogen, was added a solution of methyl 2-methyl-4-(3-oxocyclobutyl)benzoate (compound 231.2, 3.00 g, 13.8 mmol, 1.00 equiv) in dichloromethane (100 mL). DAST (22.2 g, 137 mmol, 10.00 equiv) was added to the reaction mixture. The resulting solution was stirred overnight at 25° C., then carefully quenched by slowly adding (dropwise at first) 500 mL of sodium bicarbonate (aq.) and ice. The mixture was extracted with 300 mL of ethyl acetate and the combined organic layers were washed with 2×300 mL of sodium bicarbonate (aq.) and 2×300 mL of brine, dried over anhydrous sodium sulfate, and concentrated in vacuo. The residue was purified using silica gel column chromatography with ethyl acetate/petroleum ether (1:20) as eluent to furnish 3.00 g (91%) of methyl 4-(3,3-difluorocyclobutyl)-2-methylbenzoate as a brown oil.

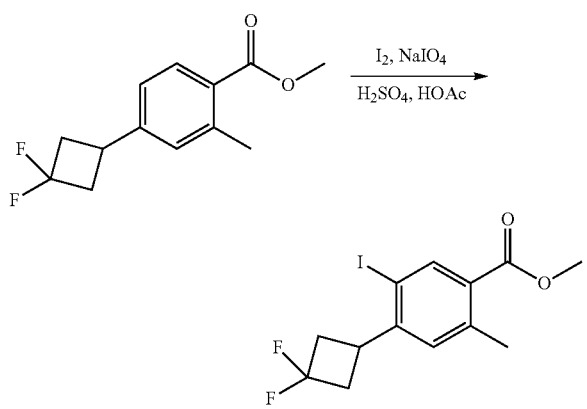

Compound 231.4. Methyl 4-(3,3-difluorocyclobutyl)-5-iodo-2-methylbenzoate

The title compound (3.02 g, yellow solid, 66%) was prepared using a procedure similar to that used for the preparation of compound 181.4 and using compound 231.3 (3.00 g) in place of compound 181.3.

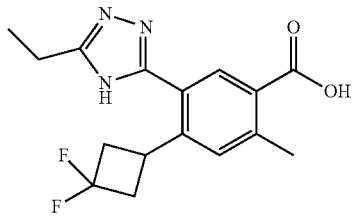 [SMILES: CCc1nnc(-c2cc(C(=O)O)c(C)cc2C2CC(F)(F)C2)[nH]1]

Compound 231.5. 4-(3,3-Difluorocyclobutyl)-5-(5-ethyl-4H-1,2,4-triazol-3-yl)-2-methylbenzoic acid The title compound was synthesized using standard chemical manipulations and procedures similar to those used for the preparation of compound 164.1 using compound 231.4 in place of compound 152.3.

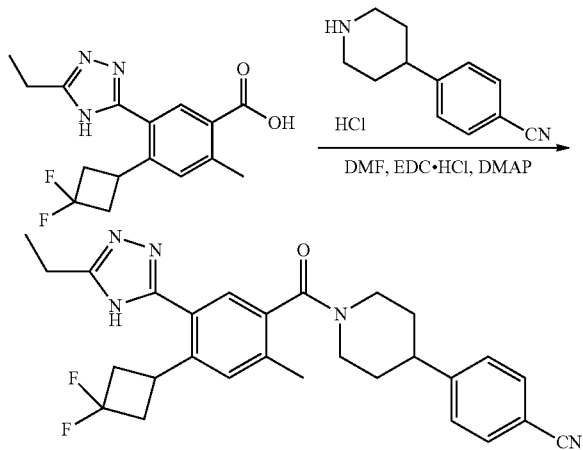

Compound 231. 4-(1-(4-(3,3-Difluorocyclobutyl)-5-(5-ethyl-4H-1,2,4-triazol-3-yl)-2-methylbenzoyl)piperidin-4-yl)benzonitrile To a round-bottom flask was added a solution of 4-(3,3-difluorocyclobutyl)-5-(5-ethyl-4H-1,2,4-triazol-3-yl)-2-methylbenzoic acid (compound 231.5, 211 mg, 0.660 mmol, 1.00 equiv) in N,N-dimethylformamide (5 mL). 4-(Piperidin-4-yl)benzonitrile hydrochloride (compound 1.5, 146 mg, 0.660 mmol, 1.00 equiv), EDC.HCl (252 mg, 1.31 mmol, 2.00 equiv) and 4-dimethylaminopyridine (160 mg, 1.31 mmol, 2.00 equiv) were added to the reaction. The resulting solution was stirred for 3 h at 30° C. in an oil bath, then diluted with 30 mL of ethyl acetate. The mixture was washed with 3×40 mL of brine, dried over anhydrous sodium sulfate and concentrated in vacuo. The crude product (448 mg) was purified by Prep-HPLC with the following conditions (1#-Pre-HPLC-001 (SHIMADZU)): Column, SunFire Prep C18, 19*150 mm 5 um; mobile phase, water with 0.05% TFA and $CH_3CN$ (48.0% $CH_3CN$ up to 62.0% in 6 min, up to 100.0% in 4 min, down to 48.0% in 2 min); Detector, Waters 2489 254 & 220 nm. The fractions containing pure compound were combined and lyophilized to yield 186 mg (58%) of the title compound as a white solid. m/z (ES+) 490 (M+H)$^+$. $^1$H-NMR (300 MHz, $CD_3OD$, ppm): δ 7.68 (d, J=8 Hz, 2H), 7.59-7.44 (m, 4H), 4.89-4.80 (m, 1H), 4.03-3.98 (m, 1H), 3.67-3.61 (m, 1H), 3.28-3.24 (m, 1H), 3.04-3.00 (m, 2H), 2.97-2.89 (m, 2H), 2.87-2.83 (m, 2H), 2.62-2.60 (m, 2H), 2.48 and 2.38 (2 singlets, amide rotamers, $ArCH_3$, 3H), 2.05-2.00 (m, 1H), 1.88-1.58 (m, 3H), 1.41 (t, 3H).

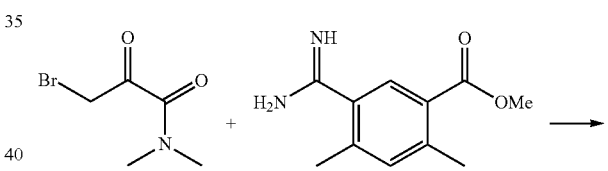

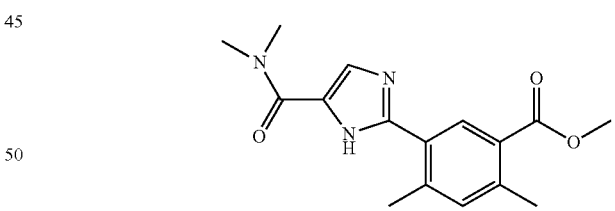

Compound 232.1. Methyl 5-(5-(dimethylcarbamoyl)-1H-imidazol-2-yl)-2,4-dimethylbenzoate A mixture of 3-bromo-N,N-dimethyl-2-oxopropanamide (246 mg), methyl 5-carbamimidoyl-2,4-dimethylbenzoate hydrochloride (compound 2.5, 237 mg), and potassium carbonate (311 mg) in acetonitrile (12 ml) was heated to reflux for 48 hours. After cooling to ambient temperature the mixture was concentrated. The residue was dissolved in EtOAc and washed with brine, dried over $MgSO_4$, concentrated, and purified by flash chromatography ($SiO_2$; EtOAc) to give 88 mg of the title compound. m/z (ES+) 302 (M+H)$^+$.

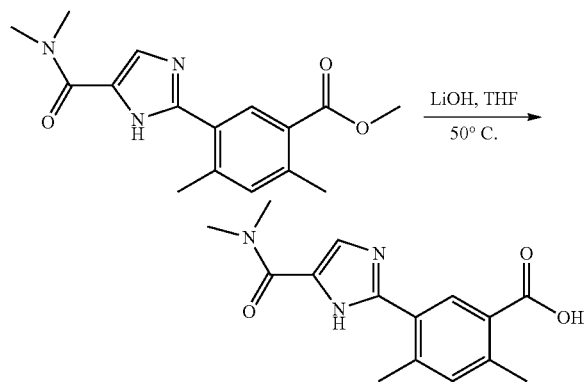

Compound 232.2. 5-(5-(Dimethylcarbamoyl)-1H-imidazol-2-yl)-2,4-dimethylbenzoic acid Methyl 5-(5-(dimethylcarbamoyl)-1H-imidazol-2-yl)-2,4-dimethylbenzoate (compound 232.1, 113 mg, 0.37 mmol) was dissolved in 2N LiOH aqueous (1 ml) and tetrahydrofuran (THF) (5 ml) and heated to 50° C. for 16 hours. After cooling to ambient temperature, the organic solvent was removed in vacuo. The pH of the remaining aqueous layer was adjusted with 2N HCl to pH 3-4. The resulting precipitate was collected by filtration and dried to afford 56 mg of 5-(5-(dimethylcarbamoyl)-1H-imidazol-2-yl)-2,4-dimethylbenzoic acid (53%). m/z (ES+) 288 (M+H)$^+$.

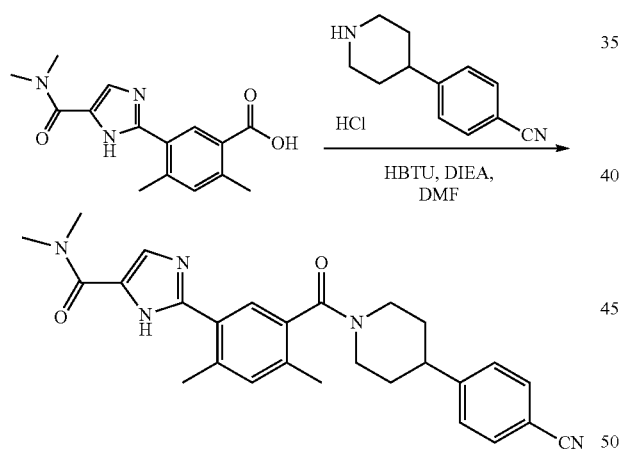

Compound 232. 2-(5-(4-(4-Cyanophenyl)piperidine-1-carbonyl)-2,4-dimethylphenyl)-N,N-dimethyl-1H-imidazole-5-carboxamide A mixture of above acid (compound 232.2, 56 mg, 0.2 mmol), 4-(piperidin-4-yl)benzonitrile hydrochloride (compound 1.5, 45 mg, 0.2 mmol), HBTU (152 mg, 0.4 mmol), and DIEA (105 ul, 0.6 mmol) in DMF (2 ml) was stirred at room temperature for 16 hours. The reaction was diluted with brine and extracted with EtOAc. The organic layer was washed with brine, dried over MgSO$_4$ and concentrated. The residue was purified by flash chromatography (SiO$_2$; 4% Methanol in EtOAc) to yield 44 mg of a foam (48%). m/z (ES+) 456 (M+H)$^+$.

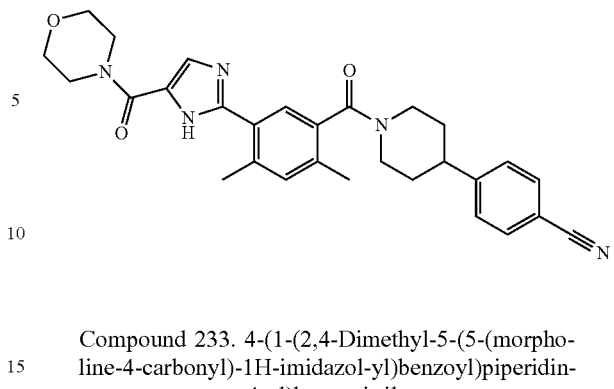

Compound 233. 4-(1-(2,4-Dimethyl-5-(5-(morpholine-4-carbonyl)-1H-imidazol-yl)benzoyl)piperidin-4-yl)benzonitrile The title compound was prepared using standard chemical manipulations and procedures similar to those used for preparation of 2-(5-(4-(4-cyanophenyl)piperidine-1-carbonyl)-2,4-dimethylphenyl)-N,N-dimethyl-1H-imidazole-5-carboxamide (compound 232). m/z (ES+) 498 (M+H)+.

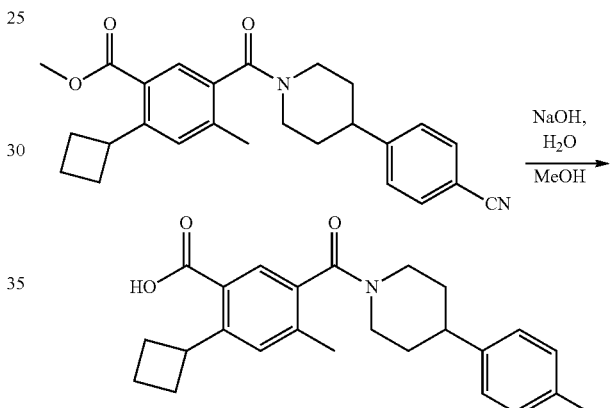

Compound 234. 5-(4-(4-Cyanophenyl)piperidine-1-carbonyl)-2-cyclobutyl-4-methylbenzoic acid To a solution of methyl 5-(4-(4-cyanophenyl)piperidine-1-carbonyl)-2-cyclobutyl-4-methylbenzoate (compound 230.3, 1.50 g, 3.60 mmol, 1.00 equiv) in methanol (10 mL) was added aqueous sodium hydroxide (577 mg, 14.4 mmol, in 5 mL water) dropwise at 0° C. The resulting solution was stirred for 2 h at 60° C. in an oil bath. After cooling to ambient temperature, the organic solvent was removed under reduced pressure. The pH of the remaining aqueous layer was adjusted to 3-4 with hydrogen chloride (aq., 2 M). The resulting solids were collected by filtration and dried in an oven under reduced pressure to yield 1.20 g (83%) of the title compound as a white solid. m/z (ES+) 403 (M+H)$^+$.

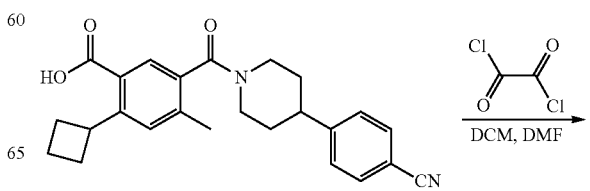

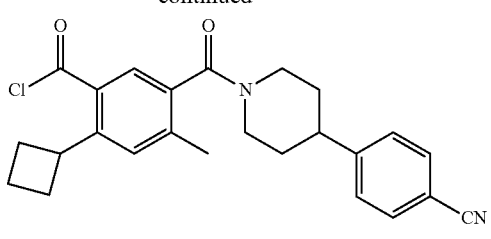

Compound 235.1. 5-(4-(4-Cyanophenyl)piperidine-1-carbonyl)-2-cyclobutyl-4-methylbenzoyl chloride To a round-bottom flask was added a solution of 5-(4-(4-cyanophenyl)piperidine-1-carbonyl)-2-cyclobutyl-4-methylbenzoic acid (compound 234, 500 mg, 1.24 mmol, 1.00 equiv) in dichloromethane (5 mL). Oxalyl chloride (317 mg, 2.50 mmol, 2.00 equiv) and N,N-dimethylformamide (~5 mg) were added dropwise to the mixture. The resulting solution was stirred for 1 h at 40° C., then concentrated and dried under reduced pressure to yield 480 mg (92%) of the title compound as a light yellow oil.

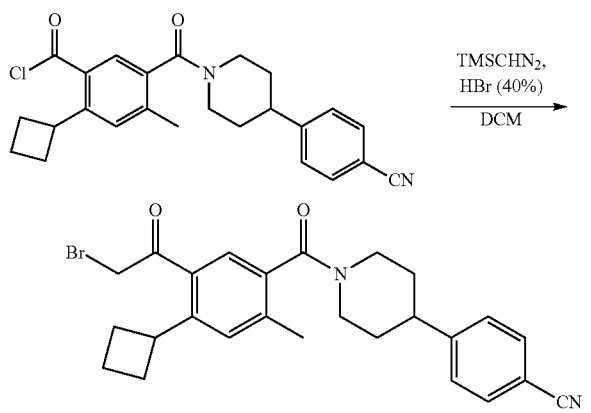

Compound 235.2. 4-(1-(5-(2-Bromoacetyl)-4-cyclobutyl-2-methylbenzoyl)piperidin-4-yl)benzonitrile To a solution of TMSCHN$_2$ (2 M in hexane) (0.476 mL, 2.00 equiv) in dichloromethane (10 mL) under nitrogen at 0° C. was added dropwise a solution of 5-(4-(4-cyanophenyl)piperidine-1-carbonyl)-2-cyclobutyl-4-methylbenzoyl chloride (compound 235.1, 200 mg, 0.480 mmol, 1.00 equiv) in dichloromethane (3 mL). The resulting mixture was stirred overnight at 25° C. HBr (40%) (0.154 mL, 1.50 equiv) was then added dropwise at 0° C. and the mixture was stirred for another 2 h at 0° C., then diluted with 50 mL of dichloromethane. The organic layer was washed with 2×20 mL of water and 1×20 mL of brine, dried over anhydrous sodium sulfate and concentrated in vacuo. The residue was purified using silica gel column chromatography with ethyl acetate/petroleum ether (0:1-1:50-1:5) as eluent to furnish 200 mg (88%) of 4-(1-(5-(2-bromoacetyl)-4-cyclobutyl-2-methylbenzoyl)piperidin-4-yl)benzonitrile as a yellow oil.

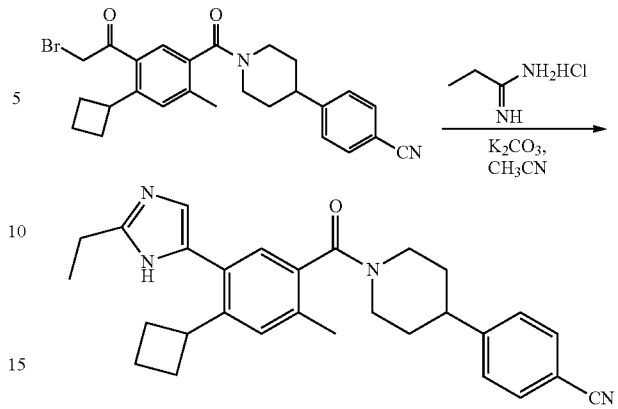

Compound 235. 4-(1-(4-Cyclobutyl-5-(2-ethyl-1H-imidazol-5-yl)-2-methylbenzoyl)piperidin-4-yl)benzonitrile To a round-bottom flask, which was purged and maintained with an inert atmosphere of nitrogen, was added a solution of 4-(1-(5-(2-bromoacetyl)-4-cyclobutyl-2-methylbenzoyl)piperidin-4-yl)benzonitrile (compound 235.2, 100 mg, 0.210 mmol, 1.00 equiv) in CH$_3$CN (5 mL). Propionimidamide hydrochloride (22.8 mg, 1.00 equiv) and potassium carbonate (86.6 mg, 0.63 mmol, 3.00 equiv) were added to the reaction. The resulting solution was stirred for 3 h at 80° C., then cooled to room temperature and concentrated in vacuo. The residue was dissolved in 20 mL of water. The mixture was extracted with 2×20 mL of ethyl acetate and the combined organic layers were dried over anhydrous sodium sulfate and concentrated in vacuo. The crude product (~100 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (29.0% CH$_3$CN up to 43.0% in 7 min, up to 100.0% in 3 min, down to 29.0% in 2 min); Detector, Waters 2489 254 & 220 nm. The fractions containing pure compound were combined and lyophilized to yield 43 mg (44%) of the title compound as a white solid, m/z (ES+) 453 (M+H)$^+$. $^1$H NMR (300 MHz, CD$_3$OD): δ 7.68 (d with fine structure, J=7.8 Hz, 2H), 7.56-7.53 (m, 4H), 7.30 and 7.20 (2 singlets, amide rotamers, Ar—H, 1H), ~4.9 (1H partially obscured by water peak), 3.84-3.70 (m, 1H), 3.70-3.53 (m, 1H), 3.33-3.19 (m, 1H partially obscured by methanol solvent peak), 3.13-2.92 (m, 4H), 2.48 & 2.38 (2 singlets, amide rotamers, Ar—CH$_3$, 3H), 2.29-2.11 (m, 4H), 2.11-1.93 (m, 2H), 1.93-1.72 (m, 3H), 1.72-1.53 (m, 1H), 1.45 (t, 3H).

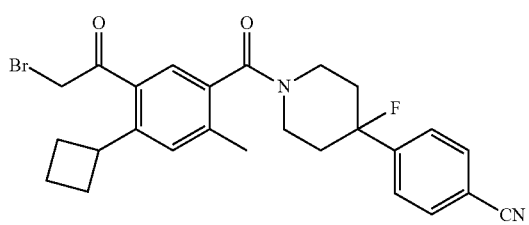 [SMILES: Cc1cc(C2CCC2)c(C(=O)CBr)cc1C(=O)N1CCC(F)(c2ccc(C#N)cc2)CC1]

Compound 236.1. 4-(1-(5-(2-Bromoacetyl)-4-cyclobutyl-2-methylbenzoyl)-4-fluoropiperidin-4-yl)benzonitrile The title compound was prepared using standard chemical manipulations and procedures similar to those used for preparation of 4-(1-(5-(2-bromoacetyl)-4-cyclobutyl-2-methylbenzoyl)piperidin-4-yl)benzonitrile (compound 235.2) but using compound 11.2 HCl salt instead of compound 1.5.

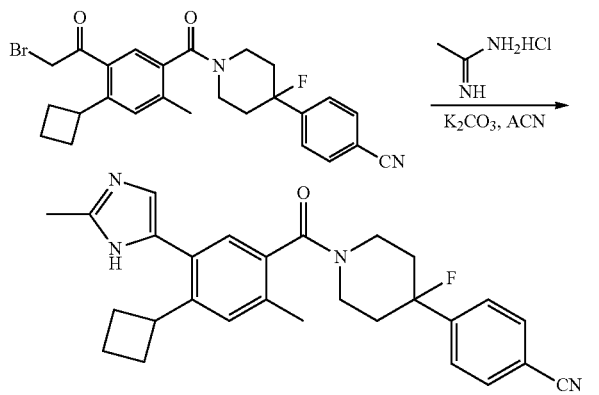

Compound 236. 4-(1-(4-Cyclobutyl-2-methyl-5-(2-methyl-1H-imidazol-5-yl)benzoyl)-4-fluoropiperidin-4-yl)benzonitrile To a round-bottom flask, which was purged and maintained with an inert atmosphere of nitrogen, was added a solution of 4-(1-(5-(2-bromoacetyl)-4-cyclobutyl-2-methylbenzoyl)-4-fluoropiperidin-4-yl)benzonitrile (compound 236.1, 40 mg, 0.08 mmol, 1.00 equiv) in CH$_3$CN (10 mL). Acetimidamide hydrochloride (7.6 mg, 0.08 mmol, 1.00 equiv) and potassium carbonate (33.4 mg, 0.24 mmol, 3.00 equiv) were added to the reaction. The resulting solution was stirred for 2 h at 80° C. in an oil bath, then cooled to ambient temperature and concentrated under reduced pressure. The residue was dissolved in 50 mL of ethyl acetate. The organic layer was washed with 2×20 mL of water, 2×20 mL of brine, dried over anhydrous sodium sulfate and concentrated under vacuum. The crude product (~50 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (29.0% CH$_3$CN up to 43.0% in 8 min, up to 100.0% in 2 min, down to 29.0% in 2 min); Detector, Waters 2489 254 & 220 nm. The fractions containing pure compound were combined and lyophilized to yield 13 mg (35%) of the title compound as a white solid. m/z (ES+) 457 (M+H)$^+$. $^1$H NMR (400 MHz, CD$_3$OD): δ 7.78 (d, 2H), 7.65 (d, 2H), 7.50-7.46 (m, 2H), 7.35 and 7.23 (2 s, amide rotamers, 1H), 4.91-4.83 (m, 1H), 3.76-3.63 (m, 1H), 3.54-3.49 (m, 2H), 3.32-3.30 (m, 1H), 2.70 (s, 3H), 2.49 and 2.39 (2 singlets, amide rotamers, ArCH$_3$, 3H), 2.34-2.28 (m, 7H), 1.98-1.80 (m, 3H).

Compound 237.1. N'-Hydroxy-3-methoxypropanimidamide

Into a round-bottom flask, was placed a solution of 3-methoxypropanenitrile (10.0 g, 118 mmol, 1.00 equiv) in ethanol (20 mL). NH$_2$OH (50% in H$_2$O) (10 mL) was added to the reaction. The resulting solution was stirred overnight at 90° C. in an oil bath, then cooled to ambient temperature and concentrated under reduced pressure. The residue was diluted with 30 mL of H$_2$O and washed with 2×20 mL of ethyl acetate. The aqueous layers were combined and concentrated under reduced pressure to yield 10.0 g (65%) of the title compound as a colorless oil.

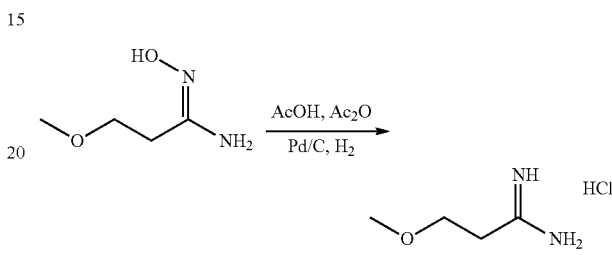

Compound 237.2. 3-Methoxypropanimidamide hydrochloride

Into a round-bottom flask, was placed a solution of N'-hydroxy-3-methoxypropanamidine (compound 237.1, 10.0 g, 76.2 mmol, 1.00 equiv, 90%) in AcOH (50 mL). Acetic anhydride (9.50 g, 93.1 mmol, 1.10 equiv) was added dropwise and the resulting mixture was stirred for 30 min at room temperature. After purging the flask with nitrogen, palladium on carbon (10%, 60% water, 5 g) was added. The flask was carefully purged with nitrogen again and the atmosphere was then changed to hydrogen. The mixture was stirred overnight at 20° C. under atmospheric pressure of hydrogen. After purging the system with nitrogen, the solids were then removed by filtration and the filtrate was concentrated under reduced pressure. The residue was diluted with 50 mL of H$_2$O. The pH value of the solution was adjusted to 2-3 with hydrogen chloride (12 mol/L), then washed with 2×30 mL of ethyl acetate. The aqueous layers were combined and concentrated under reduced pressure to furnish 5.00 g (40%) of the title compound as an off-white solid.

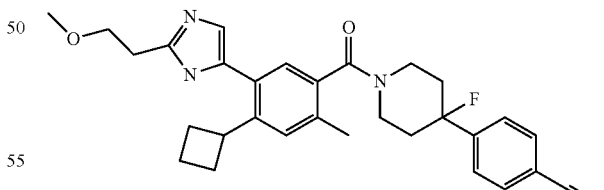

Compound 237. 4-(1-(4-Cyclobutyl-5-(2-(2-methoxyethyl)-1H-imidazol-5-yl)-2-methylbenzoyl)-4-fluoropiperidin-4-yl)benzonitrile The title compound was prepared using standard chemical manipulations and procedures similar to those used for preparation of 4-(1-(4-cyclobutyl-2-methyl-5-(2-methyl-1H-imidazol-5-yl)benzoyl)-4-fluoropiperidin-4-yl)benzoni-

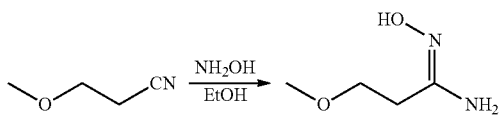

trile (compound 236) and using 237.2 in place of acetimidamide hydrochloride. m/z (ES+) 501 (M+H)+.

Compound 238.1. Methyl 5-acetyl-4-cyclobutyl-2-methylbenzoate

To a solution of methyl 4-cyclobutyl-5-iodo-2-methylbenzoate (152.3, 5.00 g, 15.1 mmol, 1.00 equiv) in DMSO (50 mL) under nitrogen were added 1-(ethenyloxy)butane (3.03 g, 30.3 mmol, 2.00 equiv), DPPP (624 mg, 1.51 mmol, 0.10 equiv), Pd(OAc)$_2$ (324 mg, 1.51 mmol, 0.10 equiv), and TEA (3.06 g, 30.2 mmol, 2.00 equiv). The resulting mixture was stirred overnight at 120° C. under nitrogen, then cooled to ambient temperature and diluted with water. The pH was adjusted to 1 with hydrogen chloride (aq., 6 M). The resulting mixture was diluted with 200 mL of ethyl acetate, washed with brine (3×200 mL), dried (Na$_2$SO$_4$), and concentrated under reduced pressure. The residue was purified using silica gel column chromatography with ethyl acetate/petroleum ether (1:30) as eluent to furnish 2.28 g (61%) of the title compound as a yellow oil.

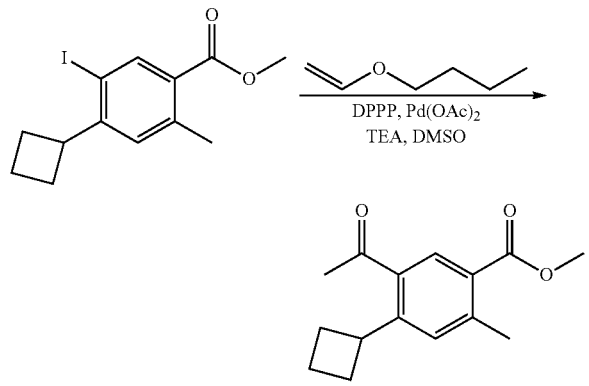

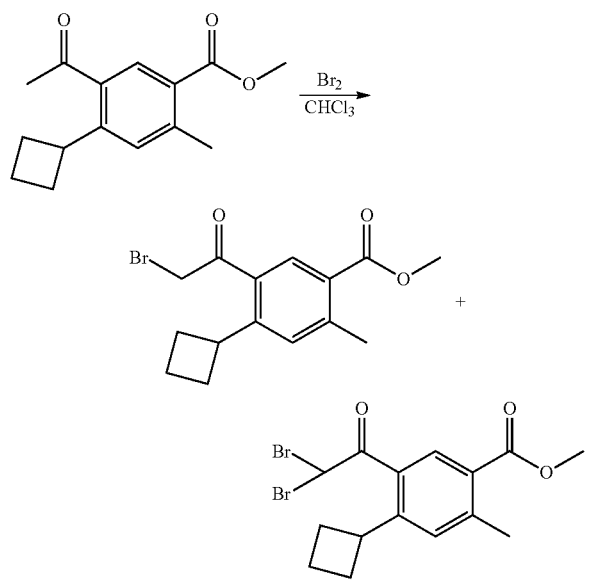

Compounds 238.2 and 238.3. Methyl 5-(2-bromoacetyl)-4-cyclobutyl-2-methylbenzoate and methyl 4-cyclobutyl-5-(2,2-dibromoacetyl)-2-methylbenzoate To a solution of methyl 5-acetyl-4-cyclobutyl-2-methylbenzoate (238.1, 500 mg, 1.83 mmol, 1.00 equiv, 90%) in chloroform (5 mL) was added dropwise Br) (325 mg, 2.03 mmol, 1.00 equiv) (CAUTION: exotherm reaction with significant evolution of HBr). The resulting mixture was stirred for 3 h at 25° C., and then quenched by the addition of 5 mL of H$_2$O. The mixture was then extracted with 50 mL of ethyl acetate. The organic phase was washed with 2×10 mL of Na$_2$S$_2$O$_3$ (aq., sat.) followed by 1×20 mL of brine, dried over anhydrous sodium sulfate, and concentrated under reduced pressure to yield 500 mg of a mixture of the title compounds as a yellow oil.

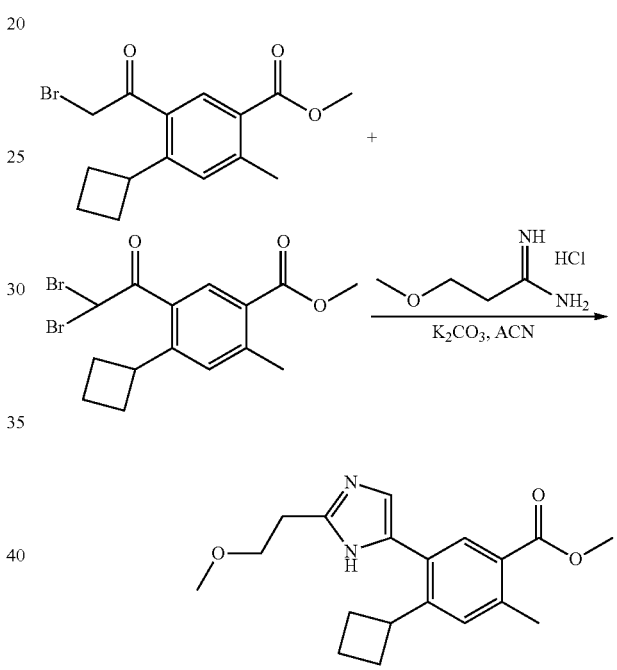

Compound 238.4. Methyl 4-cyclobutyl-5-(2-(2-methoxyethyl)-1H-imidazol-5-yl)-2-methylbenzoate Into around-bottom flask, which was purged and maintained with an inert atmosphere of nitrogen, was placed a solution of a mixture of compounds 238.2 and 238.3 (500 mg, ~0.6 mmol, 80%), potassium carbonate (640 mg, 3.00 equiv), 3-methoxypropanimidamide hydrochloride (compound 237.2, 213 mg, 1.54 mmol) in acetonitrile. The resulting solution was stirred overnight at 80° C. in an oil bath, then cooled to ambient temperature and concentrated under reduced pressure. The residue was diluted with 60 mL of ethyl acetate. The organic layer was washed with 2×25 mL of water, 2×25 mL of brine, dried over anhydrous sodium sulfate, and concentrated under reduced pressure. The residue was purified using silica gel column chromatography with ethyl acetate/petroleum ether (2:1) as eluent to furnish 90 mg (43%) of the title compound as a yellow solid.

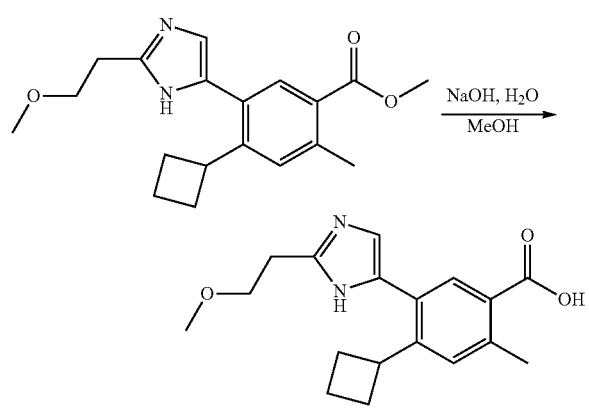

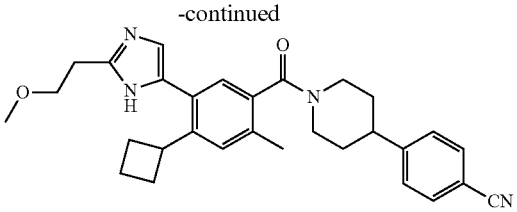

Compound 238. 4-(1-(4-Cyclobutyl-5-(2-(2-methoxyethyl)-1H-imidazol-5-yl)-2-methylbenzoyl)piperidin-4-yl)benzonitrile Into around-bottom flask, which was purged and maintained with an inert atmosphere of nitrogen, was placed a solution of compound 238.5 (80 mg, 0.23 mmol, 1.00 equiv, 90%) in N,N-dimethylformamide (2 mL). 4-(piperidin-4-yl)benzonitrile hydrochloride (compound 1.5, 54 mg, 0.24 mmol, 1.00 equiv), EDC.HCl (93 mg, 0.49 mmol, 2.00 equiv), and 4-dimethylaminopyridine (59 mg, 0.48 mmol, 2.00 equiv) were added to the solution. The resulting mixture was stirred for 3 h at 30° C., then diluted with 50 mL of ethyl acetate. The organic layer was washed with 2×20 mL of water, 2×20 mL of brine, dried over anhydrous sodium sulfate, and concentrated under reduced pressure. The residue was purified using silica gel column chromatography with chloroform/methanol (20:1) as eluent. The product (~50 mg) was further purified by Prep-HPLC with the following conditions (1#-Pre-HPLC-001 (SHIMADZU)): Column, SunFire Prep C18, 19*150 mm 5 um; mobile phase, water with 0.05% TFA and $CH_3CN$ (29% $CH_3CN$ up to 43% in 8 min, up to 100% in 6 min, down to 29% in 1 min); Detector, Waters 2489 254 & 220 nm. The fractions containing pure compound were combined and lyophilized to yield 20.6 mg (19%) of the title compound as a white solid. m/z (ES+) 483 (M+H)+.

Compound 238.5. 4-Cyclobutyl-5-(2-(2-methoxyethyl)-1H-imidazol-5-yl)-2-methylbenzoic acid A mixture of compound 238.4, 90 mg, 0.25 mmol, 1.00 equiv, 90%) and aqueous sodium hydroxide (44 mg, 1.10 mmol, 4.00 equiv in 1 mL of water) in methanol (3 mL) was stirred for 2 h at 60° C. After cooling to ambient temperature, the methanol was removed under reduced pressure. The pH of the residual aqueous layer was adjusted to 3-4 with hydrogen chloride (aqueous, 2 M). The resulting mixture was concentrated under reduced pressure to yield 80 mg (crude) of the title compound as a yellow solid.

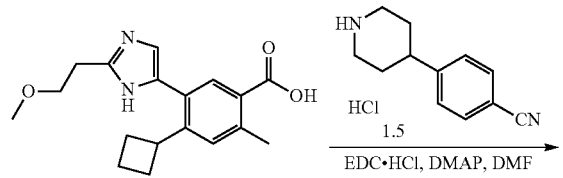

The compounds in the following table were prepared using standard chemical manipulations, readily available starting materials, and procedures similar to those used for the preparation of compounds 236, 237, and 238:

| Cmpnd # | Compound Name | Compound Structure | m/z (ES+) |
|---|---|---|---|
| 239 | 4-(1-(4-cyclobutyl-5-(2-(methoxymethyl)-1H-imidazol-5-yl)-2-methylbenzoyl)-4-fluoropiperidin-4-yl)benzonitrile | 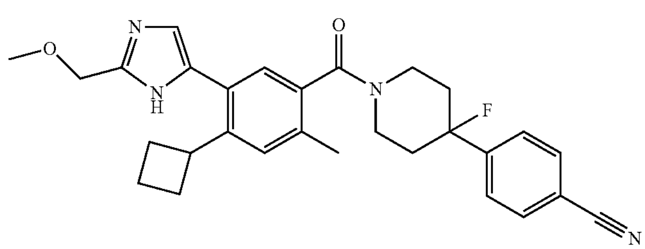 [SMILES: COCc1ncc(-c2cc(C(=O)N3CCC(F)(c4ccc(C#N)cc4)CC3)c(C)cc2C2CCC2)[nH]1] | 487 (M + H)+ |
| 240 | 4-(1-(4-cyclobutyl-5-(2-(methoxymethyl)-1H-imidazol-5-yl)-2-methylbenzoyl)piperidin-4-yl)benzonitrile | 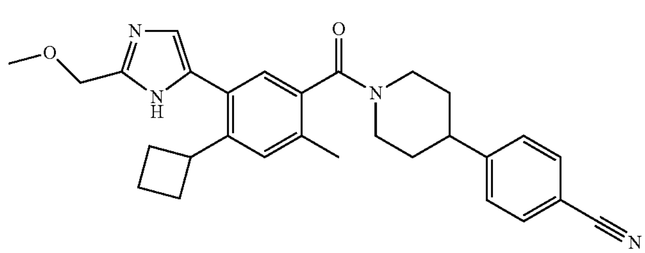 [SMILES: COCc1ncc(-c2cc(C(=O)N3CCC(c4ccc(C#N)cc4)CC3)c(C)cc2C2CCC2)[nH]1] | 469 (M + H)+ |

| Cmpnd # | Compound Name | Compound Structure | m/z (ES+) |
|---|---|---|---|
| 241 | 4-(1-(4-cyclobutyl-3-(2-methyl-1H-imidazol-5-yl)benzoyl)piperidin-4-yl)benzonitrile | 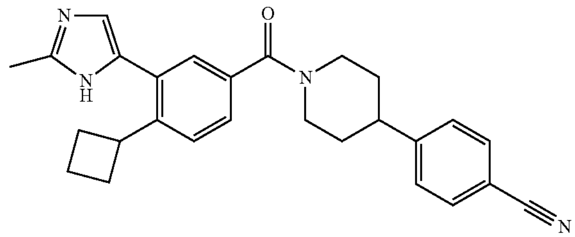 [SMILES: Cc1ncc(-c2cc(C(=O)N3CCC(c4ccc(C#N)cc4)CC3)ccc2C2CCC2)[nH]1] | 425 (M + H)+ |
| 242 | 4-(1-(4-cyclobutyl-2-methyl-5-(2-methyl-1H-imidazol-5-yl)benzoyl)piperidin-4-yl)benzonitrile | 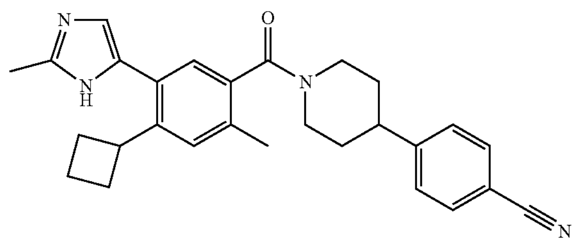 [SMILES: Cc1ncc(-c2cc(C(=O)N3CCC(c4ccc(C#N)cc4)CC3)c(C)cc2C2CCC2)[nH]1] | 439 (M + H)+ |
| 243 | 4-(1-(4-cyclobutyl-3-(2-(2-methoxyethyl)-1H-imidazol-5-yl)benzoyl)-4-fluoropiperidin-4-yl)benzonitrile | 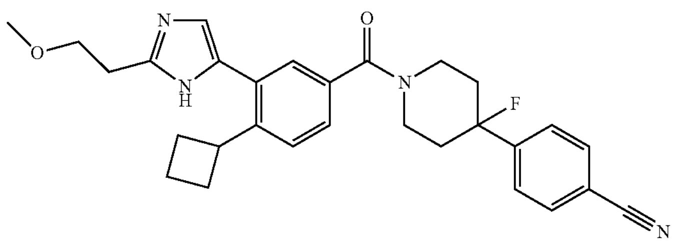 [SMILES: COCCc1ncc(-c2cc(C(=O)N3CCC(F)(c4ccc(C#N)cc4)CC3)ccc2C2CCC2)[nH]1] | 487 (M + H)+ |
| 244 | 4-(1-(4-cyclobutyl-3-(2-(2-methoxyethyl)-1H-imidazol-5-yl)benzoyl)piperidin-4-yl)benzonitrile | 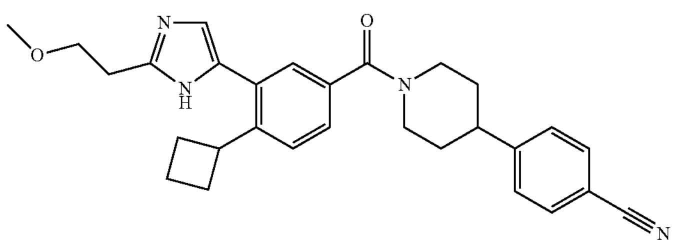 [SMILES: COCCc1ncc(-c2cc(C(=O)N3CCC(c4ccc(C#N)cc4)CC3)ccc2C2CCC2)[nH]1] | 469 (M + H)+ |

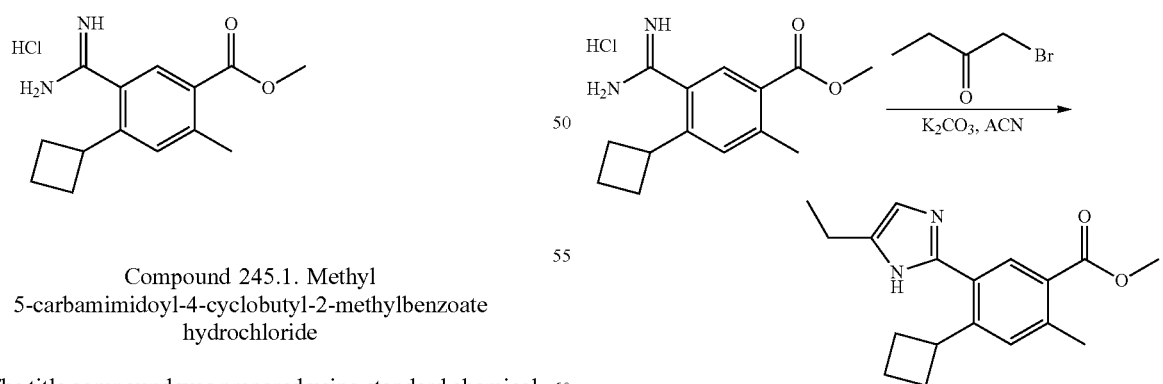

Compound 245.1. Methyl 5-carbamimidoyl-4-cyclobutyl-2-methylbenzoate hydrochloride The title compound was prepared using standard chemical manipulations and procedures similar to those used for preparation of methyl 5-(N'-hydroxycarbamimidoyl)-2,4-dimethylbenzoate (compound 2.4) and methyl 5-carbamimidoyl-2,4-dimethylbenzoate hydrochloride (compound 2.5) using methyl 5-cyano-4-cyclobutyl-2-methylbenzoate (compound 152.4) instead of methyl 5-cyano-2,4-dimethylbenzoate (compound 2.3).

Compound 245.2. Methyl 4-cyclobutyl-5-(5-ethyl-1H-imidazol-2-yl)-2-methylbenzoate To a round-bottom flask, which was purged and maintained with an inert atmosphere of nitrogen, was added a solution of methyl 5-carbamimidoyl-4-cyclobutyl-2-methylbenzoate hydrochloride (compound 245.1, 350 mg, 1.11 mmol, 1.00 equiv, 90%) in ACN (50 mL). 1-Bromobutan-2-one (186 mg, 1.23 mmol, 1.00 equiv) and potassium carbonate (513 mg, 3.53 mmol, 3.00 equiv, 95%) were added to the reaction. The resulting solution was stirred overnight at 80° C. After cooling to ambient temperature, the mixture was diluted with ethyl acetate and washed with 3×30 mL of brine, dried over anhydrous sodium sulfate, and concentrated in vacuo. The residue was purified using silica gel column chromatography with ethyl acetate/petroleum ether (1:5) as eluent to furnish 290 mg (83%) of methyl 4-cyclobutyl-5-(5-ethyl-1H-imidazol-2-yl)-2-methylbenzoate as a yellow solid.

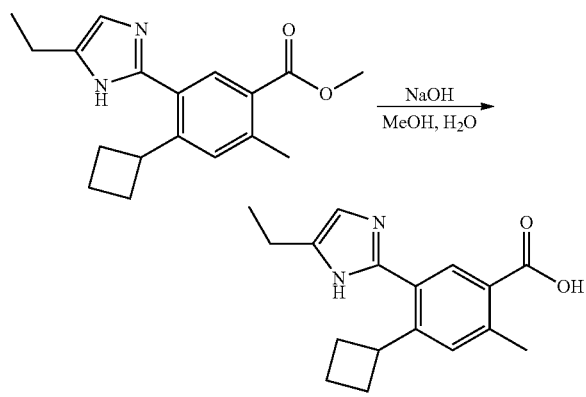

Compound 245.3. 4-Cyclobutyl-5-(5-ethyl-1H-imidazol-2-yl)-2-methylbenzoic acid

A mixture of methyl 4-cyclobutyl-5-(5-ethyl-1H-imidazol-2-yl)-2-methylbenzoate (compound 245.2, 200 mg, 0.600 mmol, 1.00 equiv, 90%) and sodium hydroxide (107 mg, 2.68 mmol, 4.00 equiv) in a solvent mixture of methanol and water (4/2 mL) was stirred for 3 h at 60° C. After cooling to ambient temperature, the pH was adjusted to 3-4 with hydrogen chloride (aq., 6 M). The resulting mixture was concentrated in vacuo to yield 150 mg of a white solid.

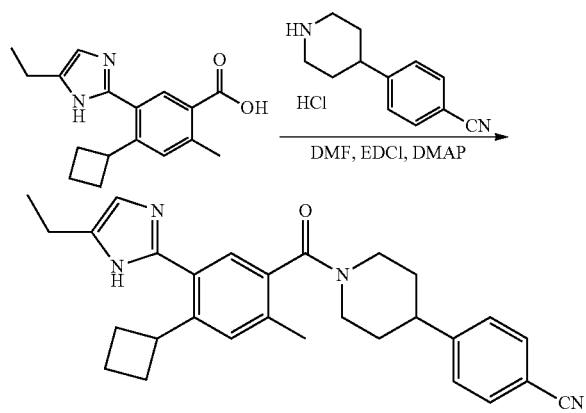

Compound 245. 4-(1-(4-Cyclobutyl-5-(5-ethyl-1H-imidazol-2-yl)-2-methylbenzoyl)piperidin-4-yl)benzonitrile To a round-bottom flask was added a solution of 4-cyclobutyl-5-(5-ethyl-1H-imidazol-2-yl)-2-methylbenzoic acid (compound 245.3, 153 mg, 0.480 mmol, 1.00 equiv, 90%) in N,N-dimethylformamide (5 mL). 4-(Piperidin-4-yl)benzonitrile hydrochloride (compound 1.5, 132 mg, 0.590 mmol, 1.10 equiv), EDC.HCl (204 mg, 1.01 mmol, 2.00 equiv, 95%) and 4-dimethylaminopyridine (131 mg, 1.02 mmol, 2.00 equiv, 95%) were added to the reaction. The resulting solution was stirred overnight at room temperature, then concentrated in vacuo. The residue was purified using silica gel column chromatography with ethyl acetate/petroleum ether (2:1) as eluent. The crude product (~150 mg) was further purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (28% CH$_3$CN up to 43% in 7 min, up to 100% in 2 min, down to 28% in 2 min); Detector, Waters 2489 254 & 220 nm. The fractions containing pure compound were combined and lyophilized to yield 62 mg, (29%) of the title compound as a white solid. m/z (ES+) 453 (M+H)$^+$. $^1$H NMR (400 MHz, CD$_3$OD) δ 7.75-7.67 (m, 2H), 7.49-7.34 (m, 5H), 4.89-4.80 (m, 1H), 3.75-3.72 (m, 1H), 3.64-3.59 (m, 1H), 3.27-3.23 (m, 1H), 3.05-2.90 (m, 2H), 2.83 (q, 2H), 2.40 and 2.30 (2 singlets, amide rotamers, ArCH$_3$, 3H), 2.27-1.97 (m, 6H), 1.90-1.70 (m, 4H), 1.40 (t, 3H).

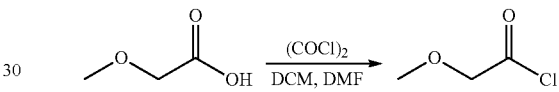

Compound 246.1. 2-Methoxyacetyl chloride

To a solution of 2-methoxyacetic acid (2.00 g, 22.2 mmol, 1.00 equiv) in dichloromethane (20 mL) was added dropwise (COCl)$_2$ (5.65 g, 2.00 equiv) in N,N-dimethylformamide (0.1 mL) (gas evolution observed). The reaction was stirred for 1 h at 40° C. The resulting mixture was then concentrated under reduced pressure to yield 2.10 g (70%) of 2-methoxyacetyl chloride as a yellow oil.

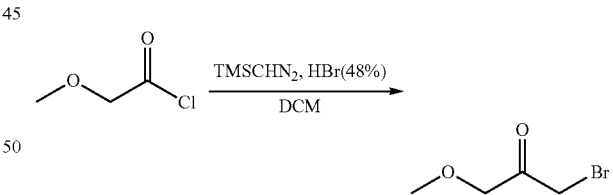

Compound 246.2. 1-Bromo-3-methoxypropan-2-one

To a solution of TMSCHN$_2$(2 M in hexane) (16 mL, 2.00 equiv) in dichloromethane (40 mL) was added 2-methoxyacetyl chloride (compound 246.1, 2.10 g, 15.5 mmol, 1.00 equiv, 80%) dropwise at 0° C. After stirring for 20 min, HBr (48%, 2 mL) was added to the reaction. The resulting solution was stirred for 30 min at 25° C. The mixture was washed with 1×20 mL of brine, dried over anhydrous sodium sulfate and concentrated in vacuo. This resulted in 2.30 g (71%) of 1-bromo-3-methoxypropan-2-one as a yellow oil.

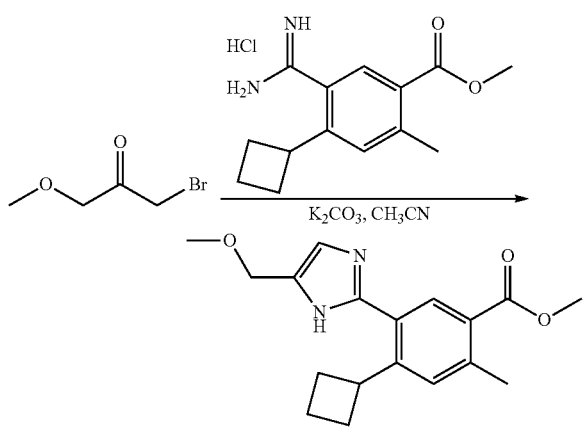

Compound 246.3. Methyl 4-cyclobutyl-5-(5-(methoxymethyl)-1H-imidazol-2-yl)-2-methylbenzoate To a round-bottom flask was added a solution of 1-bromo-3-methoxypropan-2-one (compound 246.2, 505 mg, 1.81 mmol, 1.00 equiv, 60%) in CH₃CN (16 mL). Methyl 5-carbamimidoyl-4-cyclobutyl-2-methylbenzoate hydrochloride (compound 245.1, 450 me, 1.59 mmol, 1.00 equiv) and potassium carbonate (554 mg, 3.61 mmol, 3.00 equiv, 90%) were added to the reaction. The resulting solution was stirred overnight at 80° C. under nitrogen. After cooling to ambient temperature, the reaction was carefully quenched by the addition of water. The resulting mixture was extracted with 2×50 mL of ethyl acetate. The combined organic layers were dried (Na₂SO₄), and concentrated in vacuo. The residue was purified using silica gel column chromatography with ethyl acetate/petroleum ether (1:2) as eluent to furnish 170 mg (24%) of methyl 4-cyclobutyl-5-(5-(methoxymethyl)-1H-imidazol-2-yl)-2-methylbenzoate as a white solid.

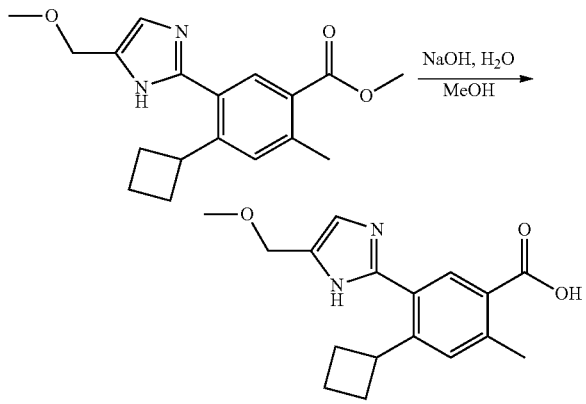

Compound 246.4. 4-Cyclobutyl-5-(5-(methoxymethyl)-1H-imidazol-2-yl)-2-methylbenzoic acid A solution of methyl 4-cyclobutyl-5-(5-(methoxymethyl)-1H-imidazol-2-yl)-2-methylbenzoate (compound 246.3, 150 mg, 0.430 mmol, 1.00 equiv, 90%) and aqueous sodium hydroxide (76.0 mg, 1.90 mmol, 4.00 equiv in 2 mL water) in methanol (4 mL) was stirred for 2 h at 60° C. After cooling to ambient temperature, the organic solvent was removed under reduced pressure. The pH value of the remaining aqueous phase was adjusted to ~4 with hydrogen chloride (aq., 4 M). The resulting mixture was extracted with 2×50 mL of ethyl acetate, and the combined organic layers were dried (Na₂SO₄) and concentrated in vacuo. This resulted in 120 mg (84%) of 4-cyclobutyl-5-(5-(methoxymethyl)-1H-imidazol-2-yl)-2-methylbenzoic acid as a white solid.

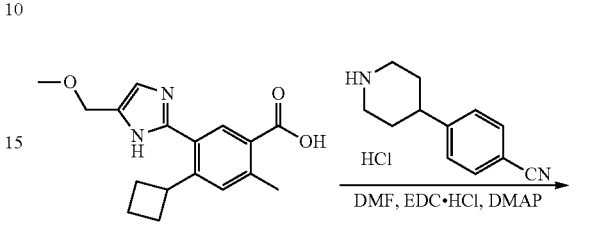

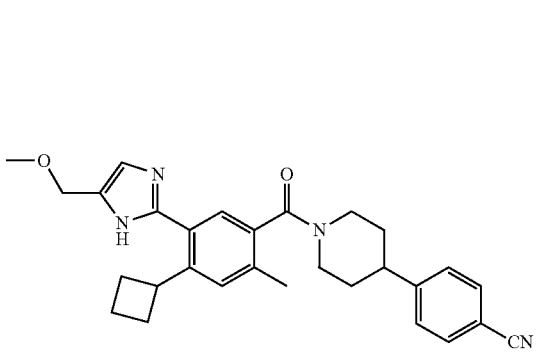

Compound 246. 4-(1-(4-Cyclobutyl-5-(5-(methoxymethyl)-1H-imidazol-2-yl)-2-methylbenzoyl)piperidin-4-yl)benzonitrile To a round-bottom flask was added a solution of 4-cyclobutyl-5-(5-(methoxymethyl)-1H-imidazol-2-yl)-2-methylbenzoic acid (compound 246.4, 50.0 mg, 0.150 mmol, 1.00 equiv, 90%) in N,N-dimethylformamide (3 mL). 4-(Piperidin-4-yl)benzonitrile hydrochloride (compound 1.5, 41.0 mg, 0.170 mmol, 1.10 equiv), EDC.HCl (64.0 mg, 0.330 mmol, 2.00 equiv), and 4-dimethylaminopyridine (41.0 mg, 0.340 mmol, 2.00 equiv) were added to the reaction. The resulting solution was stirred for 3 h at 25° C., then quenched with water and extracted with 2×30 mL of ethyl acetate. The combined organic layers were concentrated in vacuo. The crude product (~50 mg) was purified by Prep-HPLC with the following conditions (1#-Pre-HPLC-001(SHIMADZU)): Column, SunFire Prep C18, 19*150 mm 5 um; mobile phase, water with 0.05% TFA and CH3CN (26.0% CH3CN up to 42.0% in 7 min, up to 100.0% in 2 min, down to 26.0% in 1 min); Detector, Waters 2489 254 & 220 nm. The fractions containing pure compound were combined and lyophilized to yield 18 mg (25%) of the title compound as a white solid. m/z (ES+) 469 (M+H)⁺. ¹H NMR (300 MHz, CD₃OD): δ 7.73-7.64 (m, 3H), 7.52-7.32 (m, 4H), ~4.9 (1H partially obscured by water peak), 4.60 (s, 2H), 3.81-3.68 (m, 1H), 3.68-3.52 (m, 1H), 3.16 (s, 3H), 3.35 3.22 (m, 1H partially obscured by methanol solvent peak), 3.09-2.95 (m, 2H), 2.52 & 2.41 (2 singlets, amide rotamers, Ar—CH₃, 3H), 2.16-1.97 (m, 6H), 1.94-1.58 (m, 4H).

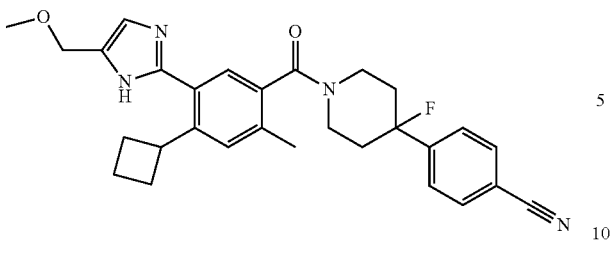

Compound 247. 4-(1-(4-Cyclobutyl-5-(5-(methoxymethyl)-1H-imidazol-2-yl)-2-methylbenzoyl)-4-fluoropiperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246), using 4-(4-fluoropiperidin-4-yl)benzonitrile hydrochloride (compound 11.2 HCl salt) instead of 4-(piperidin-4-yl)benzonitrile hydrochloride (compound 1.5). m/z (ES+) 487 (M+H)$^+$. $^1$H NMR (400 MHz, CD$_3$OD): δ 7.79-7.67 (m, 2H), 7.66 (d, 3H), 7.53-7.39 (m, 2H), 4.99-4.93 (m, 1H), 4.85 (s, 2H), 3.76-3.56 (m, 3H), 3.50 (s, 3H), 2.42 and 2.34 (2 singlets, amide rotamers, ArCH$_3$, 3H), 2.27-1.97 (m, 8H), 1.92-1.81 (m, 2H), 1.35-1.26 (m, 1H).

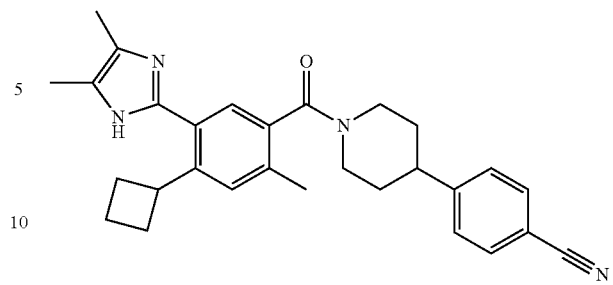

Compound 249. 4-(1-(4-Cyclobutyl-5-(4,5-dimethyl-1H-imidazol-2-yl)-2-methylbenzoyl)piperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246). m/z (ES+) 453 (M+H)$^+$. $^1$H NMR (400 MHz, CD$_3$OD): δ 7.68 (d, 2H), 7.51 (d, 2H), 7.31 (d, 1H), 7.32 and 7.30 (2 singlets, amide rotamers, ArH, 1H), 4.90-4.88 (m, 1H), 3.96-3.87 (m, 1H), 3.70-3.62 (m, 1H), 3.32-3.29 (m, 1H), 3.02 (t, 2H), 2.44 and 2.33 (2 singlets, amide rotamers, ArCH$_3$, 3H), 2.20 (s, 6H), 2.18-1.90 (m, 7H), 1.88-1.78 (m, 3H).

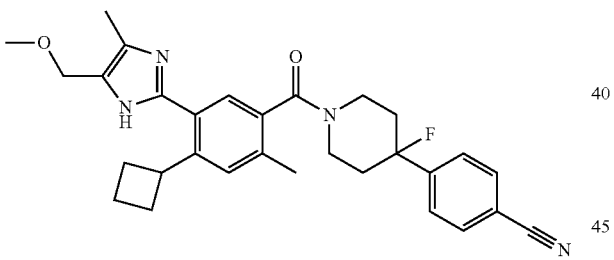

Compound 248. 4-(1-(4-Cyclobutyl-5-(5-(methoxymethyl)-4-methyl-1H-imidazol-2-yl)-2-methylbenzoyl)-4-fluoropiperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246). m/z (ES+) 501 (M+H)$^+$. $^1$H NMR (400 MHz, CD$_3$OD): δ 7.79-7.77 (m, 2H), 7.66 (d, 2H), 7.52-7.38 (m, 2H), 4.87-4.80 (m, 1H), 4.55 (s, 2H), 3.78-3.74 (m, 1H), 3.62-3.56 (m, 2H), 3.50 (s, 3H), 3.44-3.32 (m, 1H), 2.52 and 2.42 (2 singlets, amide rotamers, ArCH$_3$, 3H), 2.44 (s, 3H), 2.11-1.99 (m, 8H), 1.93-1.83 (m, 2H).

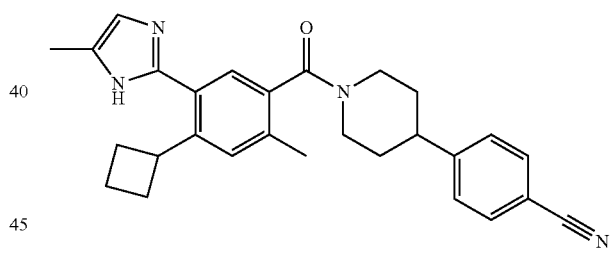

Compound 250. 4-(1-(4-Cyclobutyl-2-methyl-5-(5-methyl-1H-imidazol-2-yl)benzoyl)piperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246). m/z (ES+) 439 (M+H)$^+$. $^1$H NMR (400 MHz, CD$_3$OD): δ 7.68 (d, 2H), 7.49-7.39 (m, 4H), 7.36 and 7.34 (2 singlets, amide rotamers, ArH, 1H), 4.90-4.86 (m, 1H), 3.75-3.70 (m, 1H), 3.63-3.55 (m, 1H), 3.33-3.24 (m, 1H), 3.04-2.99 (m, 2H), 2.51 and 2.41 (2 singlets, amide rotamers, ArCH$_3$, 3H), 2.44 (s, 3H), 2.28-1.96 (m, 6H), 1.89-1.81 (m, 3H), 1.77-1.74 (m, 1H).

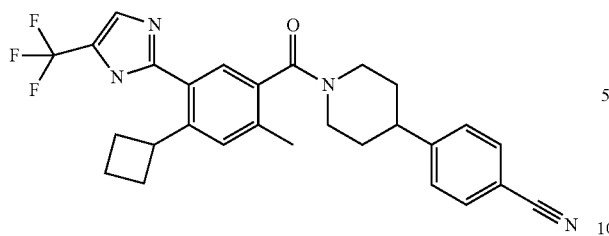

Compound 251. 4-(1-(4-Cyclobutyl-2-methyl-5-(5-(trifluoromethyl)-1H-imidazol-2-yl)benzoyl)piperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246). m/z (ES+) 493 (M+H)+.

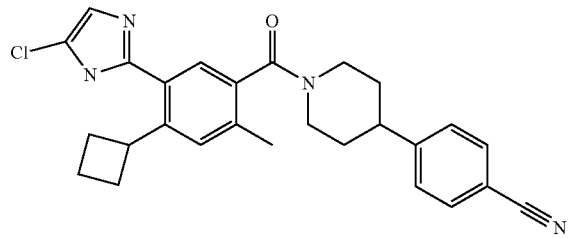 [SMILES: Cc1cc(C2CCC2)c(-c2ncc(Cl)[nH]2)cc1C(=O)N1CCC(c2ccc(C#N)cc2)CC1]

Compound 252. 4-(1-(5-(5-Chloro-1H-imidazol-2-yl)-4-cyclobutyl-2-methylbenzoyl)piperidin-4-yl)benzonitrile The title compound was prepared using standard chemical manipulations and procedures similar to those used for preparation of 4-(1-(4-cyclobutyl-5-(5-(methoxymethyl)-1H-imidazol-2-yl)-2-methylbenzoyl)piperidin-4-yl)benzonitrile (compound 246). m/z (ES+) 459 (M+H)+.

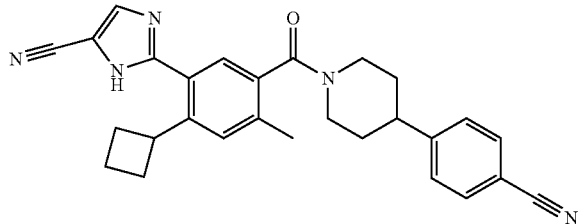 [SMILES: Cc1cc(C2CCC2)c(-c2ncc(C#N)[nH]2)cc1C(=O)N1CCC(c2ccc(C#N)cc2)CC1]

Compound 253. 2-(5-(4-(4-Cyanophenyl)piperidine-1-carbonyl)-2-cyclobutyl-4-methylphenyl)-1H-imidazole-5-carbonitrile The title compound was prepared using standard chemical manipulations and procedures similar to those used for preparation of compound 246. m/z (ES+) 450 (M+H)+.

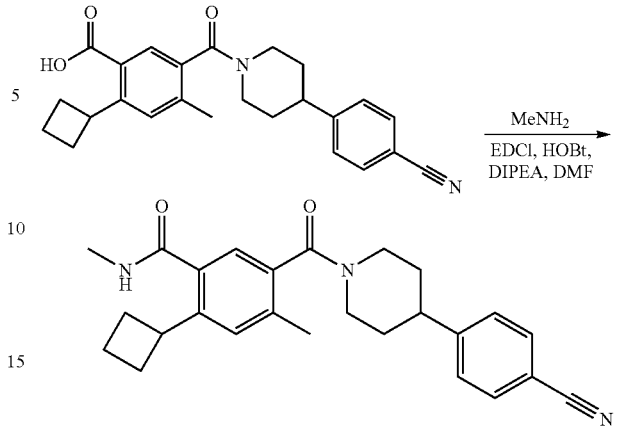

Compound 254. 5-(4-(4-Cyanophenyl)piperidine-1-carbonyl)-2-cyclobutyl-N,4-dimethylbenzamide To a solution of 5-(4-(4-cyanophenyl)piperidine-1-carbonyl)-2-cyclobutyl-4-methylbenzoic acid (compound 234, 50 mg, 0.124 mmol) in DMF (2 mL) were added EDCI (36 mg, 0.186 mmol), HOBt (10 mg, 0.5 mmol), diisopropylethyl amine (54 mg, 0.434 mmol), and methyl, amine (125 ul, 2.5 M in THF). The reaction mixture was stirred for 12 hours at room temperature and quenched with saturated aqueous NaHCO₃ (50 mL). After extraction with ethyl acetate (2×50 mL), the combined organic layers were dried over Na₂SO₄, filtered, and concentrated in vacuo. Purification via SiO2 flash chromatography with ethyl acetate to ethyl acetate/methanol=98/2 afforded 5-(4-(4-cyanophenyl)piperidine-1-carbonyl)-2-cyclobutyl-N,4-dimethylbenzamide (28.3 mg, 55% yield) as a white solid. m/z (ES+) 416 (M+H)+. ¹H NMR (400 MHz, DMSO-d₆): δ 8.13 (q, J=4.5 Hz, 1H), 7.77 (d, J=8.3 Hz, 2H), 7.55-7.45 (m, 2H), 7.26 (br s, 1H), 7.12 & 6.99 (2 singlets, amide rotamers, Ar—H, 1H), 4.70 (br d, J=11.9 Hz, 1H), 3.86-3.72 (m, 1H), 3.50-3.35 (m, 1H), 3.13 (t with fine structure, J=12.3 Hz, 1H), 2.99-2.78 (m, 2H), 2.72 (d, J=4.6 Hz, 3H), 2.39-2.17 (m, 5H), 2.17-1.98 (m, 2H), 1.98-1.81 (m, 2H), 1.81-1.35 (m, 4H).

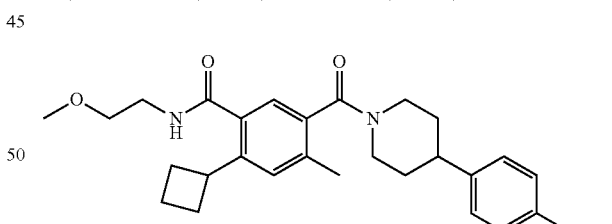

Compound 255. 5-(4-(4-Cyanophenyl)piperidine-1-carbonyl)-2-cyclobutyl-N-(2-methoxyethyl)-4-methylbenzamide The title compound was prepared using standard chemical manipulations and procedures similar to those used for preparation of 5-(4-(4-cyanophenyl)piperidine-1-carbonyl)-2-cyclobutyl-N,4-dimethylbenzamide (compound 254). m/z (ES+) 460 (M+H)+. ¹H NMR (400 MHz, DMSO-d₆) δ 8.27 (t, 1H), 7.78 (d, 2H), 7.49 (d, 2H), 7.26 (s, 1H), 7.12 and 6.98 (2 singlets, amide rotamers, 1H), 4.70 (d, 1H), 3.85-

3.75 (m, 1H), 3.44 (t, 3H), 3.39-3.33 (m, 2H), 3.30 (s, 3H), 3.19-3.03 (m, 1H), 3.02-2.71 (m, 2H), 2.32 and 2.2.6 (2 singlets, amide rotamers, ArCH₃, 3H), 2.38-2.17 (m, 2H), 2.15-2.00 (m, 2H), 1.98-1.81 (m, 2H), 1.83-1.47 (m, 4H).

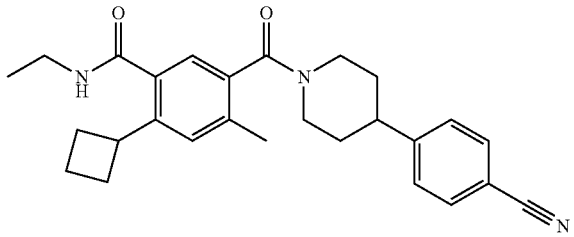 [SMILES: CCNC(=O)c1cc(C(=O)N2CCC(c3ccc(C#N)cc3)CC2)c(C)cc1C1CCC1]

Compound 256. 5-(4-(4-Cyanophenyl)piperidine-1-carbonyl)-2-cyclobutyl-N-ethyl-4-methylbenzamide The title compound was prepared using standard chemical manipulations and procedures similar to those used for preparation of 5-(4-(4-cyanophenyl)piperidine-1-carbonyl)-2-cyclobutyl-N,4-dimethylbenzamide (compound 254). m/z (ES+) 430 (M+H)⁺. ¹H NMR (400 MHz, DMSO-d₆) δ 8.21 (t, 1H), 7.78 (d, 2H), 7.56-7.45 (m, 2H), 7.31-7.20 (m, 1H), 7.11 and 6.98 (2 singlets, amide rotamers, 1H), 4.74-4.65 (m, 1H), 3.85-3.74 (m, 1H), 3.50-3.37 (m, 1H), 3.22 (q, 2H), 3.20-3.05 (m, 2H), 2.32 and 2.22 (2 singlets, amide rotamers, ArCH₃, 3H), 3.01-2.76 (m, 2H), 2.38-2.17 (m, 2H), 2.18-1.97 (m, 2H), 1.98-1.84 (m, 2H), 1.81-1.38 (m, 3H), 1.10 (t, 3H).

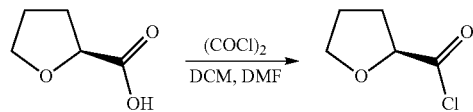 [SMILES: O=C(O)[C@@H]1CCCO1 ; "(COCl)2" ; O=C(Cl)[C@@H]1CCCO1]

Compound 257.1. (S)-Tetrahydrofuran-2-carbonyl chloride

To a round-bottom flask was added a solution of (S)-tetrahydrofuran-2-carboxylic acid (4.64 g, 40.0 mmol, 1.00 equiv) in dichloromethane (25 mL). N,N-dimethylformamide (0.05 mL, 0.05 equiv) and (COCl)₂ (5.2 mL, 1.50 equiv) were added dropwise to the reaction. The resulting solution was stirred for 1 h at 25° C., then concentrated in vacuo to yield 5.00 g (93%) of (S)-tetrahydrofuran-2-carbonyl chloride as a yellow oil.

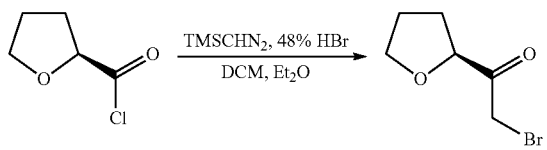

Compound 257.2. (S)-2-Bromo-1-(tetrahydrofuran-2-yl)ethanone

To a 250-mL three neck round-bottom flask, which was purged and maintained with an inert atmosphere of nitrogen, was added a solution of (diazomethyl)trimethylsilane (20 mL, 2 M in hexane) in ether (150 mL). A solution of (S)-tetrahydrofuran-2-carbonyl chloride (compound 257.1, 5.00 g, 37.2 mmol, 1.00 equiv) in ether/DCM (25/10 mL) was added dropwise at 0° C. and stirred for 20 min at 0° C. Hydrogen bromide (48%) (8 mL, 1.50 equiv) was added dropwise. The resulting solution was stirred for 30 min at 10° C., then washed with 2×100 mL of water and 1×50 mL of brine. The mixture was dried over anhydrous sodium sulfate and concentrated in vacuo. The residue was purified using silica gel column chromatography with ethyl acetate/petroleum ether (1:50) as eluent to furnish 2.50 g (35%) of (S)-2-bromo-1-(tetrahydrofuran-2-yl)ethanone as a yellow oil.

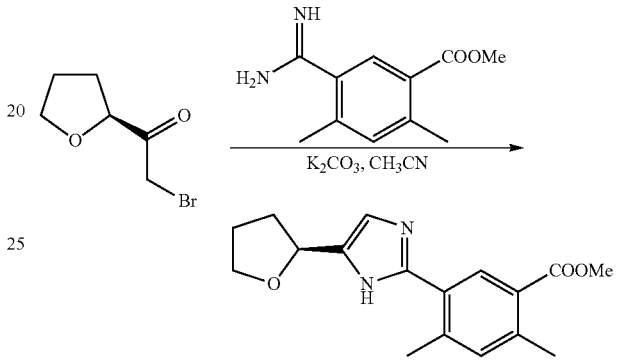

Compound 257.3. (S)-Methyl 2,4-dimethyl-5-(5-(tetrahydrofuran-2-yl)-1H-imidazol-2-yl)benzoate To a round-bottom flask was added a solution of methyl 5-carbamimidoyl-2,4-dimethylbenzoate hydrochloride (compound 2.5, 1.30 g) in CH₃CN (30 mL). (S)-2-bromo-1-(tetrahydrofuran-2-yl)ethanone (compound 257.2, 1.92 g, 9.95 mmol) and potassium carbonate (4.20 g, 30.4 mmol) were added to the reaction. The resulting solution was stirred for 3 days at 75° C. under nitrogen. After cooling to ambient temperature, the solids were removed by filtration. The filtrate was concentrated in vacuo and diluted with 30 mL of H₂O. The aqueous phase was extracted with 3×50 mL of ethyl acetate and the combined organic layers were dried over anhydrous sodium sulfate, then concentrated in vacuo. The mixture was purified using silica gel column chromatography with ethyl acetate/petroleum ether (1:2) as eluent to yield 400 mg (25%) of (S)-methyl 2,4-dimethyl-5-(5-(tetrahydrofuran-2-yl)-1H-imidazol-2-yl)benzoate as a light yellow solid.

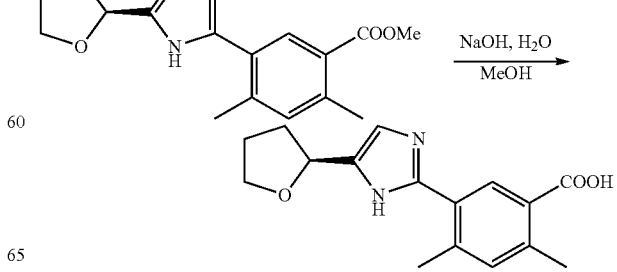

Compound 257.4. (S)-2,4-Dimethyl-5-(5-(tetrahydrofuran-2-yl)-1H-imidazol-2-yl)benzoic acid To a round-bottom flask was added a solution of (S)-methyl 2,4-dimethyl-5-(5-(tetrahydrofuran-2-yl)-1H-imidazol-2-yl)benzoate (compound 257.3, 400 mg, 1.33 mmol, 1.00 equiv) and sodium hydroxide (300 mg, 7.50 mmol, 5.63 equiv) in a solvent mixture of methanol and H$_2$O (20/10 mL). The resulting solution was stirred for 2 h at 70° C. After cooling to ambient temperature, the organic solvent was removed under reduced pressure. The residual aqueous layer was washed with 2×50 mL of ethyl acetate. The pH of the aqueous layer was adjusted to 5-6 with hydrogen chloride (aq., 6 M), then extracted with 3×50 mL of ethyl acetate. The combined organic layers were dried over anhydrous sodium sulfate and concentrated in vacuo. This resulted in 340 mg (90%) of (S)-methyl 2,4-dimethyl-5-(5-(tetrahydrofuran-2-yl)-1H-imidazol-2-yl)benzoate as a yellow solid.

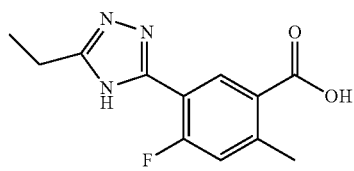 [SMILES: CCc1nnc(-c2cc(C(=O)O)c(C)cc2F)[nH]1]

Compound 258.1. 5-(5-Ethyl-4H-1,2,4-triazol-3-yl)-4-fluoro-2-methylbenzoic acid

The title compound was synthesized using standard chemical manipulations and procedures similar to those used for the preparation of compound 152.8 using 4-fluoro-2-methylbenzoic acid instead of 4-bromo-2-methylbenzoic acid and propionohydrazide instead of acetohydrazide.

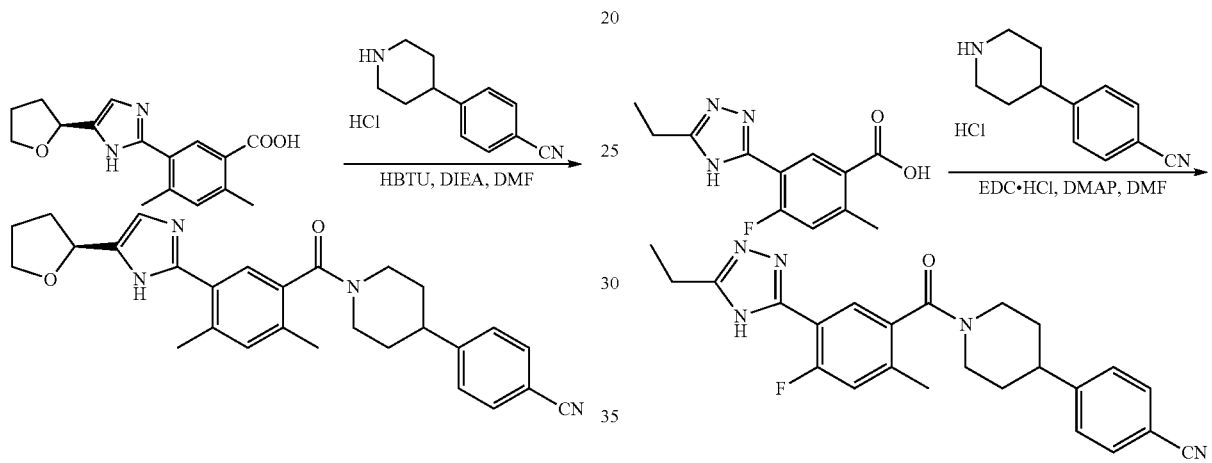

Compound 257. (S)-4-(1-(2,4-Dimethyl-5-(5-(tetrahydrofuran-2-yl)-1H-imidazol-2-yl)benzoyl)piperidin-4-yl)benzonitrile To a round-bottom flask was added a solution of (S)-methyl 2,4-dimethyl-5-(5-(tetrahydrofuran-2-yl)-1H-imidazol-2-yl)benzoate (compound 257.4, 143 mg, 0.500 mmol, 1.00 equiv) in N,N-dimethylformamide (10 mL). HBTU (285 mg, 0.750 mmol, 1.50 equiv) was added to the reaction, and it was stirred for 30 min at 25° C. To this was added 4-(piperidin-4-yl)benzonitrile hydrochloride (compound 1.5, 133 mg, 0.600 mmol, 1.20 equiv) and DIEA (390 mg, 3.02 mmol, 6.04 equiv) dropwise. The resulting solution was stirred for 30 min at 25° C., then quenched with 20 mL of water. The mixture was extracted with 3×25 mL of ethyl acetate and the combined organic layers were dried over anhydrous sodium sulfate and concentrated in vacuo. The residue was purified using silica gel column chromatography with methanol/ethyl acetate (1:30) as eluent. The product (~100 mg) was further purified by Prep-HPLC with the following conditions (1#-Pre-HPLC-001 (SHIMADZU)): Column, Xbridge Prep C18, 5 um, 19*150 mm; mobile phase, water with 0.03% NH$_3$H$_2$O and CH$_3$CN (35% CH$_3$CN up to 52% in 8 min, up to 100% in 1 min, down to 35% in 1 min); Detector, Waters 2489 254 & 220 nm. The fractions containing pure compound were combined and lyophilized to yield 34.6 mg (15%) of the title compound as a white solid. m/z (ES+) 455 (M+H)$^+$.

Compound 258.2. 4-(1-(5-(5-Ethyl-4H-1,2,4-triazol-3-yl)-4-fluoro-2-methylbenzoyl)piperidin-4-yl)benzonitrile To a round-bottom flask was added a solution of 5-(5-ethyl-4H-1,2,4-triazol-3-yl)-4-fluoro-2-methylbenzoic acid (compound 258.1, 125 mg, 0.500 mmol, 1.00 equiv) in DMF (10 mL). EDC.HCl (143 mg, 0.750 mmol, 1.50 equiv), 4-(piperidin-4-yl)benzonitrile hydrochloride (compound 1.5, 122 mg, 0.550 mmol, 1.10 equiv), and 4-dimethylaminopyridine (183 mg, 1.50 mmol, 3.00 equiv) were added in portions. The resulting solution was stirred for 1 h at 40° C. in an oil bath, then quenched with 50 mL of NH$_4$Cl (aq.sat.). The mixture was extracted with 40 mL of ethyl acetate and the combined organic layers were washed with 3×30 mL of NH$_4$Cl (aq.sat.), dried over anhydrous sodium sulfate and concentrated under vacuum. This resulted in 180 mg (86%) of 4-(I-(5-(5-ethyl-4H-1,2,4-triazol-3-yl)-4-fluoro-2-methylbenzoyl)piperidin-4-yl)benzonitrile as a white solid.

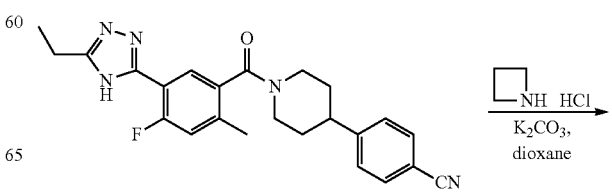

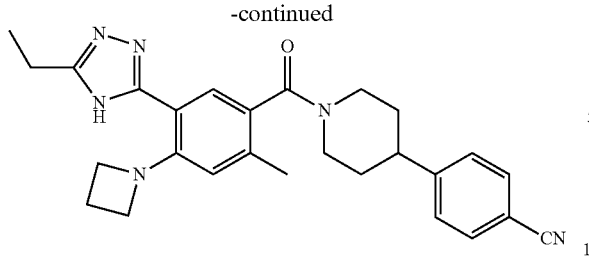

Compound 258. 4-(1-(4-(Azetidin-1-yl)-5-(5-ethyl-4H-1,2,4-triazol-3-yl)-2-methylbenzoyl)piperidin-4-yl)benzonitrile To a 10-mL sealed tube was added a solution of 4-(1-[[5-(5-ethyl-4H-1,2,4-triazol-3-yl)-4-fluoro-2-methylphenyl]carbonyl]piperidin-4-yl)benzonitrile (compound 258.2, 83.5 mg, 0.200 mmol, 1.00 equiv) in 1,4-dioxane (5 mL). Azetidine hydrochloride (93.0 mg, 0.990 mmol, 5.00 equiv) was added to the reaction in portions. Potassium carbonate (276 mg, 2.00 mmol, 10.0 equiv) was also added to the above mixture. The resulting solution was stirred overnight at 105° C. behind a blast shield, then cooled to rt. The reaction was quenched with 20 mL of water. The mixture was extracted with 30 ml, of ethyl acetate and the organic layer was dried over anhydrous sodium sulfate and concentrated under reduced pressure. The product (80 mg) was further purified by Prep-HPLC with the following conditions (1#-Pre-HPLC-001 (SHIMADZU)): Column, SunFire Prep C18, 19*150 mm 5 um; mobile phase, water with 50 mL NH$_4$CO$_3$ and CH$_3$CN (41.0% CH$_3$CN up to 43.0% in 8 min, up to 100.0% in 2 min, down to 41.0% in 2 min); Detector, Waters 2489 254 & 220 nm. The fractions containing pure compound were combined and lyophilized to yield 18.0 mg (20%) of the title compound as a white solid. m/z (ES+) 455 (M+H)$^+$. $^1$H NMR (300 MHz, CD$_3$OD): δ 7.68 (d, J=6.3 Hz, 2H), 7.48 (d, J=5.7 Hz, 2H), 7.24 & 7.13 (2 singlets, amide rotamers, Ar—H, 1H), 6.52 (s, 1H), 4.91-7.77 (m, 1H partially obscured by water peak), 3.81-3.67 (m, 1H), 3.68 (t, J=5.6 Hz, 4H), 3.32-3.18 (m, 1H), 3.05-1.91 (m, 2H), 2.84 (q, J=5.8 Hz, 2H), 2.45-2.19 (m, 5H), 2.09-1.91 (m, 1H), 1.91-1.49 (m, 3H), 1.39 (t, J=5.7 Hz, 3H).

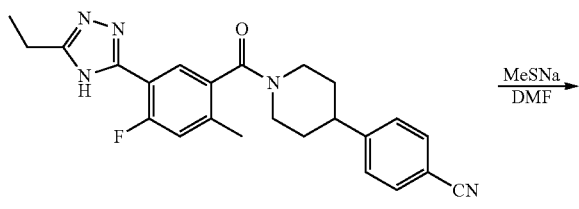

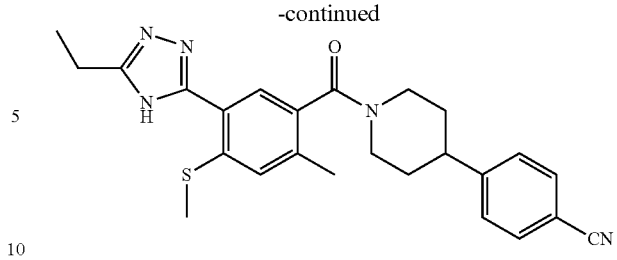

Compound 259. 4-(1-(5-(5-Ethyl-4H-1,2,4-triazol-3-yl)-2-methyl-4-(methylthio)benzoyl)piperidin-4-yl)benzonitrile To a round-bottom flask was added a solution of 4-(1-(5-(5-ethyl-4H-1,2,4-triazol-3-yl)-4-fluoro-2-methylbenzoyl)piperidin-4-yl)benzonitrile (compound 258.2, 20 mg, 0.050 mmol, 1.0 equiv) in N,N-dimethylformamide (3 mL). Sodium thiomethoxide (70 mg, 0.10 mmol, 2.0 equiv) was added to the reaction. The resulting mixture was stirred for 15 h at 110° C. in an oil bath, and then cooled to ambient temperature and quenched with 100 mL of ice water. The mixture was extracted with 50 mL of ethyl acetate and the combined organic layers were washed with 2×50 mL of brine, dried over anhydrous sodium sulfate, and concentrated under reduced pressure. The product (50 mg) was further purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (37% CH$_3$CN up to 49% in 7 min, up to 100% in 3 min, down to 37% in 2 min); Detector, Waters 2489 254 & 220 nm. The fractions containing pure compound were combined and lyophilized to yield 4 mg (19%) of the title compound as a white solid. m/z (ES+) 446 (M+H)$^+$. $^1$H NMR (300 MHz, CD$_3$OD): δ 7.69 (d, J=8.4 Hz, 2H), 7.61-7.43 (m, 3H), 7.35 (br s, 1H), ~4.85 (1H partially obscured by water peak), 3.77-3.60 (m, 1H), ~3.3 (1H partially obscured by methanol solvent peak), 3.08-2.94 (m, 2H), 2.91 (q, J=7.7 Hz, 2H), 2.51 (s, 3H), 2.47 & 2.37 (2 singlets, amide rotamers, Ar—CH$_3$, 3H), 2.10-1.97 (m, 1H), 1.88-1.55 (m, 3H), 1.40 (t, 3H).

The compounds in the following table were prepared using standard chemical manipulations, readily available starting materials, and procedures similar to those used for the preparation of compound 5-(4-(4-cyanophenyl)piperidine-1-carbonyl)-2-cyclobutyl-N,4-dimethylbenzamide (compound 254):

| Cmpnd # | Compound Name | Compound Structure | m/z (ES+) |
|---|---|---|---|
| 260 | 5-(4-(4-methoxyphenyl)piperidine-1-carbonyl)-2-methyl-N-(6-(pyrrolidin-1-yl)pyridin-3-yl)benzamide | 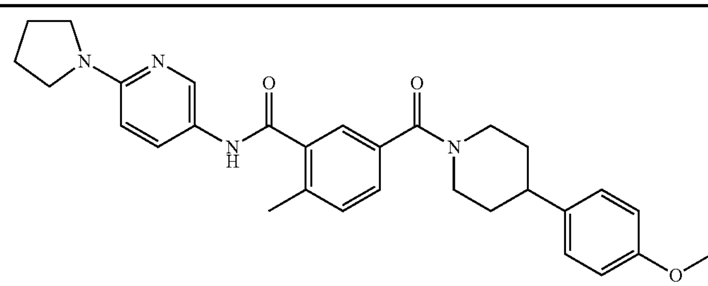 | 499 (M + H)$^+$ |

| Cmpnd # | Compound Name | m/z (ES+) |
|---|---|---|
| 261 | 5-(4-(4-cyanophenyl)piperidine-1-carbonyl)-2-methyl-N-((tetrahydrofuran-2-yl)methyl)benzamide | 432 (M + H)+ |
| 262 | 5-(4-(4-cyanophenyl)piperidine-1-carbonyl)-2-methyl-N-(tetrahydrofuran-3-yl)benzamide | 418 (M + H)+ |
| 263 | 3-(4-(4-cyanophenyl)piperidine-1-carbonyl)-N-(6-(pyrrolidin-1-yl)pyridin-3-yl)benzamide | 480 (M + H)+ |
| 264 | 5-(4-(4-cyanophenyl)piperidine-1-carbonyl)-2-methyl-N-(piperidin-4-ylmethyl)benzamide | 445 (M + H)+ |
| 265 | 5-(4-(4-cyanophenyl)piperidine-1-carbonyl)-2-methyl-N-((1-methylpiperidin-4-yl)methyl)benzamide | 459 (M + H)+ |
| 266 | 5-(4-(4-cyanophenyl)piperidin-1-carbonyl)-2-methyl-N-((tetrahydrofuran-3-yl)methyl)benzamide | 432 (M + H)+ |

| Cmpnd # | Compound Name | m/z (ES+) |
|---|---|---|
| 267 | 2-methyl-5-(4-(pyridin-4-yl)piperidine-1-carbonyl)-N-(6-(pyrrolidin-1-yl)pyridin-3-yl)benzamide | 470 (M + H)+ |
| 268 | 5-(4-(4-cyanophenyl)piperidin-1-carbonyl)-N-(6-((2-hydroxyethyl)(methyl)amino)pyridin-3-yl)-2-methylbenzamide | 499 (M + H)+ |
| 269 | 5-(4-(4-cyanophenyl)piperidine-1-carbonyl)-N-(6-(3-hydroxyazetidin-1-yl)pyridin-3-yl)-2-methylbenzamide | 497 (M + H)+ |
| 270 | 5-(4-(4-cyanophenyl)piperidine-1-carbonyl)-2-methyl-N-(6-(4-methylpiperazin-1-yl)pyridin-3-yl)benzamide | 524 (M + H)+ |

The compounds in the following table were prepared using standard chemical manipulations, readily available starting materials, and procedures similar to those used for the preparation of compounds 27, 38, and 211:

| Cmpnd # | Compound Name | Compound Structure | Preparation similar to compound #(s) [m/z (ES+)] |
|---|---|---|---|
| 271 | 4-(1-(4-methyl-3-(6-(4-methylpiperazin-1-yl)-3H-imidazo[4,5-c]pyridin-2-yl)benzoyl)piperidin-4-yl)benzonitrile | 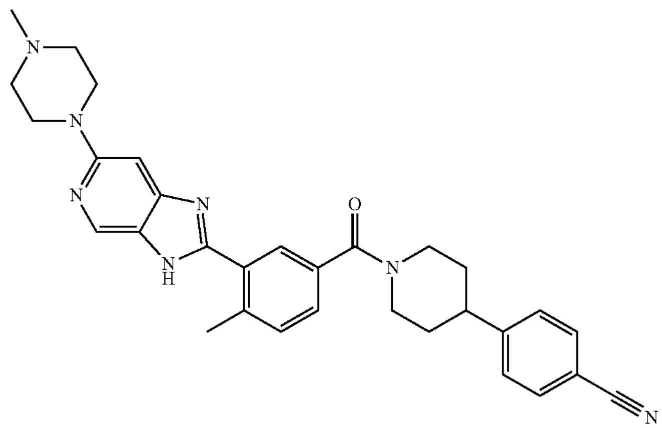 [SMILES: Cc1ccc(C(=O)N2CCC(c3ccc(C#N)cc3)CC2)cc1-c1nc2cc(N3CCN(C)CC3)ncc2[nH]1] | 27 [520 (M + H)+] |
| 272 | 4-(1-(3-(6-(3-hydroxyazetidin-1-yl)-3H-imidazo[4,5-c]pyridin-2-yl)-4-methylbenzoyl)piperidin-4-yl)benzonitrile | 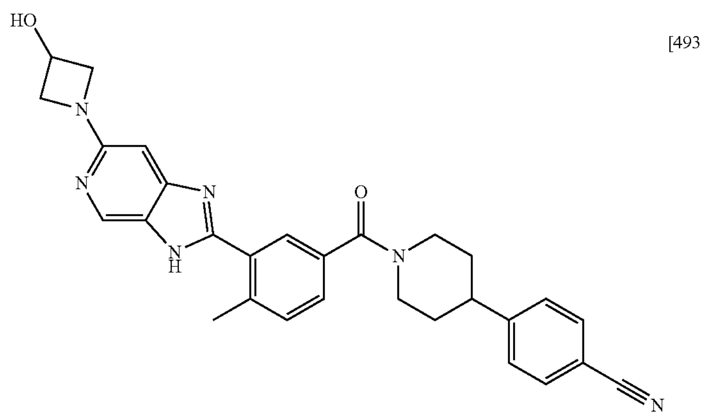 | 27 [493 (M + H)+] |
| 273 | 4-(1-(3-(6-((2-hydroxyethyl)(methyl)amino)-3H-imidazo[4,5-c]pyridin-2-yl)-4-methylbenzoyl)piperidin-4-yl)benzonitrile | 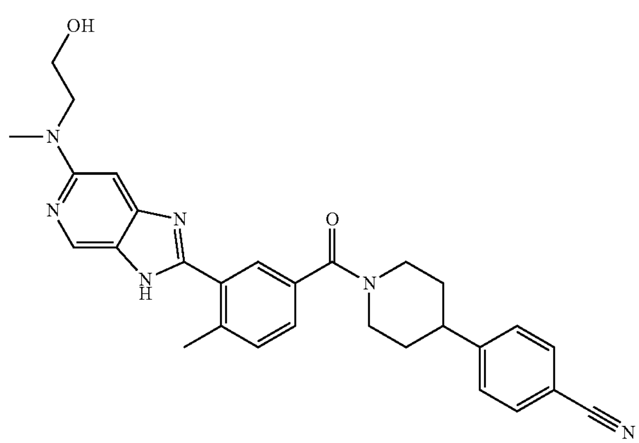 [SMILES: Cc1ccc(C(=O)N2CCC(c3ccc(C#N)cc3)CC2)cc1-c1nc2cc(N(C)CCO)ncc2[nH]1] | 27 [495 (M + H)+] |

| Cmpnd # | Compound Name | Compound Structure | Preparation similar to compound #(s) [m/z (ES+)] |
|---|---|---|---|
| 274 | 4-(1-(3-(5-isopropyl-4H-1,2,4-triazol-3-yl)-4-methylbenzoyl)piperidin-4-yl)benzonitrile | 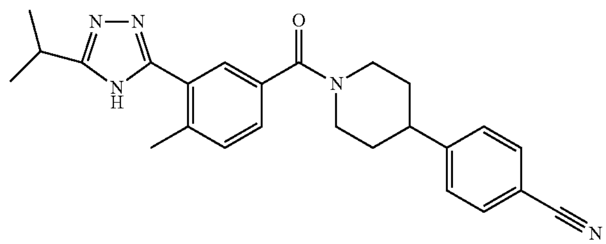 [SMILES: Cc1ccc(C(=O)N2CCC(c3ccc(C#N)cc3)CC2)cc1-c1nnc(C(C)C)[nH]1] | 38<br>[414 (M + H)+] |
| 275 | 4-(1-(3-(5-ethyl-4H-1,2,4-triazol-3-yl)-4-methylbenzoyl)piperidin-4-yl)benzonitrile | 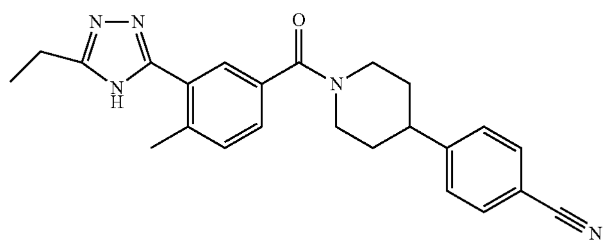 [SMILES: CCc1nnc(-c2cc(C(=O)N3CCC(c4ccc(C#N)cc4)CC3)ccc2C)[nH]1] | 38<br>[400 (M + H)+] |
| 276 | (S)-4-(1-(4-methyl-3-(5-((tetrahydrofuran-3-yl)amino)-4H-1,2,4-triazol-3-yl)benzoyl)piperidin-4-yl)benzonitrile | 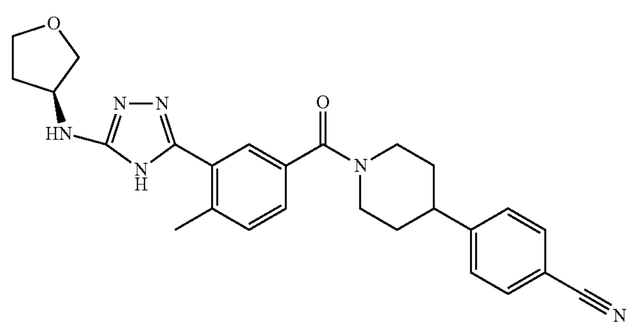 [SMILES: Cc1ccc(C(=O)N2CCC(c3ccc(C#N)cc3)CC2)cc1-c1nnc(N[C@H]2CCOC2)[nH]1] | 211<br>[457 (M + H)+] |
| 277 | (R)-4-(1-(4-methyl-3-(5-((tetrahydrofuran-3-yl)amino)-4H-1,2,4-triazol-3-yl)benzoyl)piperidin-4-yl)benzonitrile | 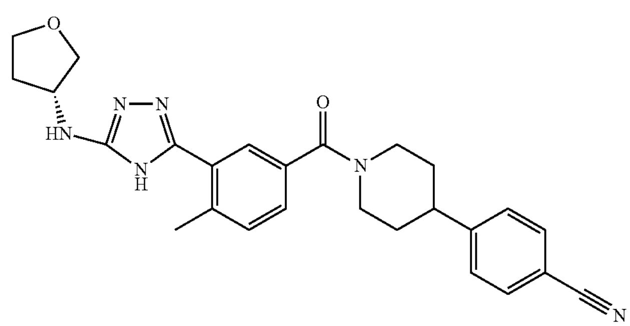 [SMILES: Cc1ccc(C(=O)N2CCC(c3ccc(C#N)cc3)CC2)cc1-c1nnc(N[C@@H]2CCOC2)[nH]1] | 211<br>[457 (M + H)+] |
| 278 | (R)-4-(4-fluoro-1-(4-methyl-3-(5-((tetrahydrofuran-3-yl)amino)-4H-1,2,4-triazol-3-yl)benzoyl)piperidin-4-yl)benzonitrile | 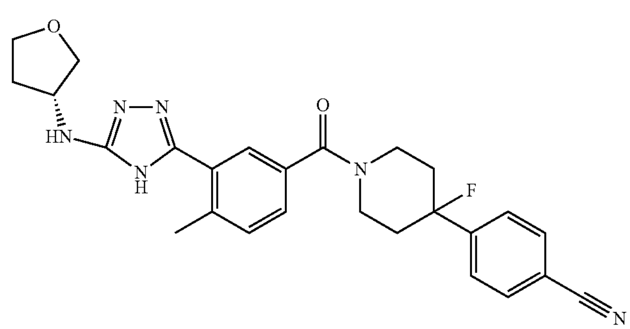 [SMILES: Cc1ccc(C(=O)N2CCC(F)(c3ccc(C#N)cc3)CC2)cc1-c1nnc(N[C@@H]2CCOC2)[nH]1] | 211<br>[475 (M + H)+] |

| Cmpnd # | Compound Name | Compound Structure | Preparation similar to compound #(s) [m/z (ES+)] |
|---|---|---|---|
| 279 | 4-(1-(2,4-dimethyl-5-(5-((tetrahydrofuran-3-yl)amino)-4H-1,2,4-triazol-3-yl)benzoyl)piperidin-4-yl)benzonitrile | 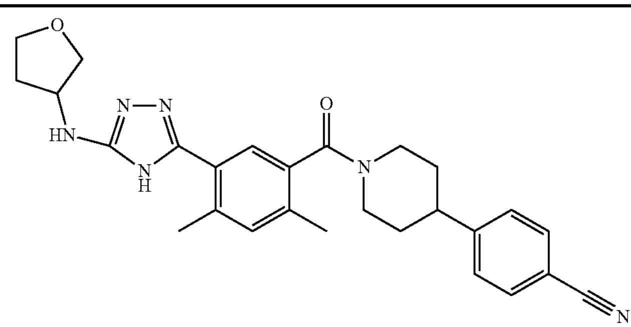 | 211 [471 (M + H)+] |

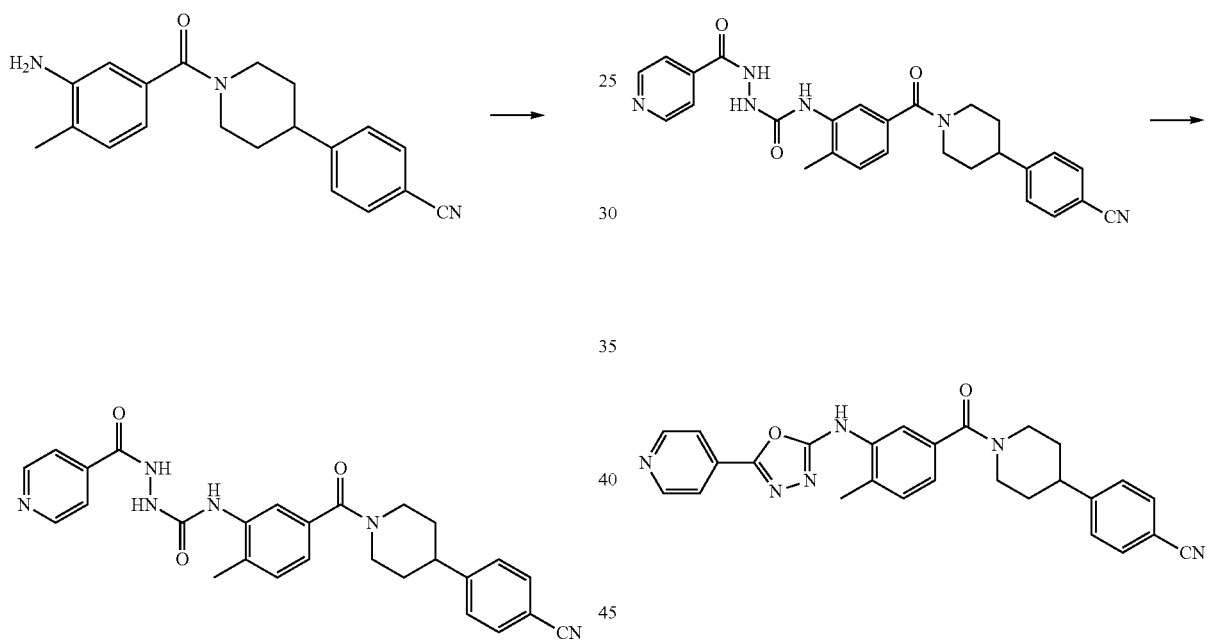

Compound 280.1. N-(5-(4-(4-Cyanophenyl)piperidine-1-carbonyl)-2-methylphenyl)-2-isonicotinoylhydrazinecarboxamide A solution of 4-(1-(3-Amino-4-methylbenzoyl)piperidin-4-yl)benzonitrile (compound 121.1, 0.1 g, 0.31 mmol) and triethyl amine (0.09 ml, 0.62 mmol) in DCM (5 ml) was added to a solution of phosgene (20% in toluene, 0.31 ml, 0.62 mmol) in DCM (5 ml) at 0° C. After the resulting reaction mixture was stirred at room temperature for 1.5 hours, all solvents were removed under reduced pressure. The residue was dried under high-vacuum for 30 minutes then was re-dissolved in EtOH (5 ml). Isonicotinohydrazide (0.05 g, 0.34 mmol) was added. The mixture was heated at 80° C. over night. The ethanol was removed and the residue was purified using prep.-TLC (10% MeOH in DCM) to give the product as a light brown solid. Yield: 0.14 g, 93%. m/z (ES+) 483.2 (M+H)+.

Compound 280. 4-(1-(4-Methyl-3-(5-(pyridin-4-yl)-1,3,4-oxadiazol-2-yl)benzoyl)piperidin-4-yl)benzonitrile To a solution of N-(5-(4-(4-Cyanophenyl)piperidine-1-carbonyl)-2-methylphenyl)-2-isonicotinoylhydrazinecarboxamide (compound 280.1, 0.14 g, 0.29 mmol) and PPh$_3$ (0.09 g, 0.35 mmol) in DCM (10 ml) was added triethyl amine (0.061 ml, 0.43 mmol) followed with CCl$_4$ (0.08 ml, 0.87 mmol). The mixture was refluxed for 3 hours. TLC and LCMS showed that the reaction was complete. The mixture was cooled to room temperature, diluted with DCM (100 ml), and washed with water (20 ml). The organic layer was dried with Na$_2$SO$_4$, concentrated and purified using prep.-TLC (5% MeOH in CH$_2$Cl$_2$) to yield 54 mg (42%) of a white solid. m/z (ES+) 465.0 (M+H)+. $^1$H NMR (400 MHz, DMSO-d$_6$) δ 10.00 (br, 1H), 8.77 (d, 2H), 7.92 (s, 1H), 7.81-7.73 (m, 4H), 7.50 (d, 2H), 7.33 (d, 1H), 7.14 (d, 1H), 4.64 (m, 1H), 3.81 (m, 1H), 3.17 (m, 1H), 3.00-2.80 (m, 2H), 2.35 (s, 3H), 1.95-1.57 (m, 4H).

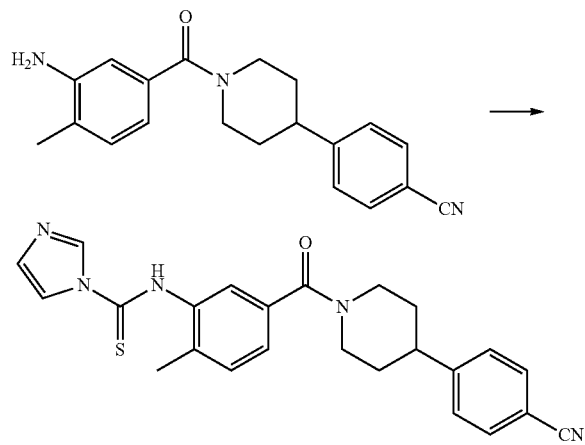

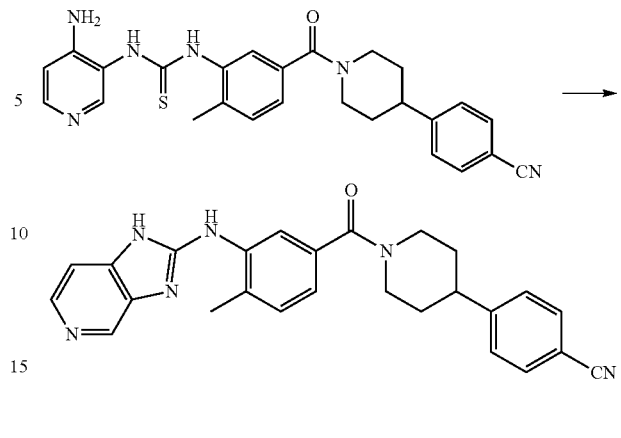

Compound 281. 4-(1-(3-(((1H-Imidazo[4,5-c]pyridin-2-yl)amino)-4-methylbenzoyl)piperidin-4-yl)benzonitrile To a solution of 1-(4-aminopyridin-3-yl)-3-(5-(4-(4-cyanophenyl)piperidine-1-carbonyl)-2-methylphenyl)thiourea (281.2) in DMF continued from the prior step was added EDCI (0.12 g, 0.64 mmol). The mixture was stirred at room temperature overnight. The DMF was removed under high vacuum and the residue was purified using prep.-TLC (5% MeOH in EtOAc) to yield 76 mg (56% for 3 steps) of a white powder. m/z (ES+) 437 (M+H)$^+$. $^1$H NMR (400 MHz, DMSO-d$_6$) δ 8.84 (br, 1H), 8.48 (s, 1H), 8.40 (s, 1H), 8.08 (d, 1H), 7.78 (d, 2H), 7.53 (d, 2H), 7.29 (d, 2H), 7.05 (d, 1H), 4.65 (m, 1H), 3.91 (m, 1H), 3.17 (m, 1H), 3.04-3.72 (m, 2H), 2.36 (s, 3H), 1.97-1.60 (m, 4H).

Compound 281.1. N-(5-(4-(4-Cyanophenyl)piperidine-1-carbonyl)-2-methylphenyl)-1H-imidazole-1-carbothioamide To a solution of 4-(1-(3-amino-4-methylbenzoyl)piperidin-4-yl)benzonitrile (121.1, 0.1 g, 0.32 mmol) in DMF (3 ml) was added 1,1'-thio-CDI (0.056 g, 0.32 mmol). The mixture was stirred at room temperature for 3 hours. LCMS showed the reaction was complete. The mixture was carried to the next step in one pot without work up or purification. m/z (ES+) 430 (M+H)$^+$.

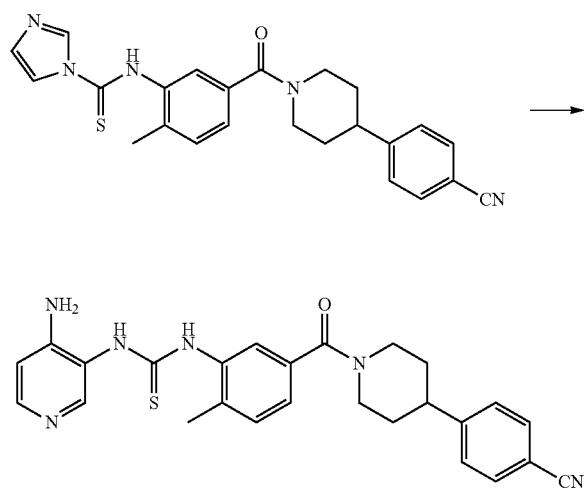 [SMILES: Cc1ccc(C(=O)N2CCC(c3ccc(C#N)cc3)CC2)cc1NC(=S)n1ccnc1 ; Cc1ccc(C(=O)N2CCC(c3ccc(C#N)cc3)CC2)cc1NC(=S)Nc1cnccc1N]

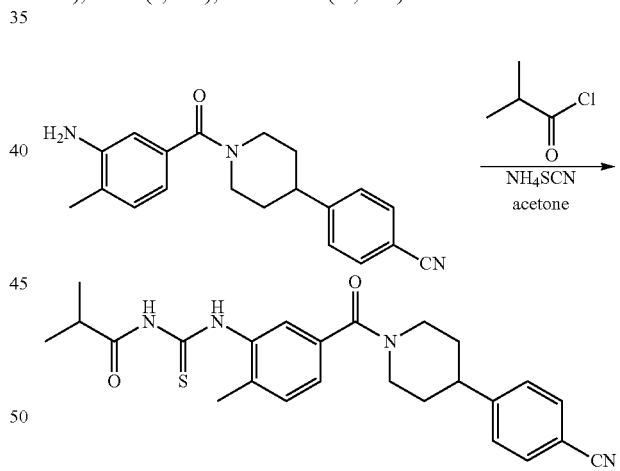

Compound 282.1. N-((5-(4-(4-Cyanophenyl)piperidine-1-carbonyl)-2-methylphenyl)carbamothioyl)isobutyramide Into a round-bottom flask, was placed a solution of NH$_4$SCN (72 mg, 0.95 mmol, 2.00 equiv) in acetone (10 mL). A solution of 2-methylpropanoyl chloride (50 mg, 0.47 mmol, 1.00 equiv) in acetone was added (5 mL) dropwise at 25° C. and the reaction was stirred overnight at 40° C. in an oil bath. To this was added 4-(1-(3-amino-4-methylbenzoyl)piperidin-4-yl)benzonitrile (compound 121.1, 150 mg, 0.42 mmol, 1.00 equiv) at 25° C. The resulting solution was stirred for 2 h at 25° C., then concentrated under reduced

Compound 281.2. 1-(4-Aminopyridin-3-yl)-3-(5-(4-(4-cyanophenyl)piperidine-1-carbonyl)-2-methylphenyl)thiourea To a solution of N-(5-(4-(4-cyanophenyl)piperidine-1-carbonyl)-2-methylphenyl)-1H-imidazole-1-carbothioamide (281.1) in DMF continued from the prior step was added pyridine-3,4-diamine (0.034, 0.32 mmol). The mixture was stirred at room temperature for 3 hours. LCMS showed the reaction was complete. The reaction was carried to the next step without workup or purification. m/z (ES+) 471 (M+H)$^+$.

pressure. The residue was diluted with 100 mL of ethyl acetate. The organic layer was washed with 2×30 mL of brine, dried over anhydrous sodium sulfate and concentrated under reduced pressure. The residue was purified using silica gel column chromatography with dichloromethane/methanol (20:1) as eluent to furnish 150 mg (64%) of the title compound as a brown oil.

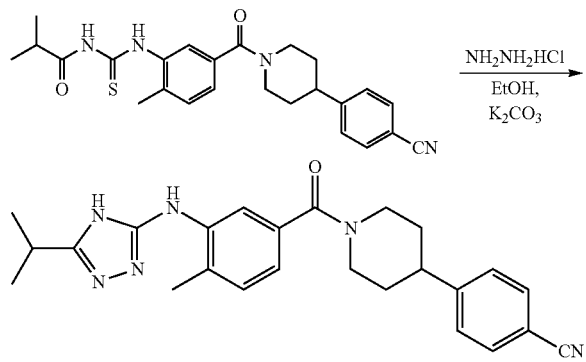

Compound 282. 4-(1-(3-((5-Isopropyl-4H-1,2,4-triazol-3-yl)amino)-4-methylbenzoyl)piperidin-4-yl)benzonitrile Into a 10-mL sealed tube, was placed a solution of N-((5-(4-(4-cyanophenyl)piperidine-1-carbonyl)-2-methylphenyl)carbamothioyl)isobutyramide (compound 282.1, 200 mg, 0.40 mmol, 1.00 equiv, 90%) in ethanol (3 mL). NH$_2$NH$_2$HCl (234 mg, 2.23 mmol, 5.00 equiv) and potassium carbonate (185 mg, 1.34 mmol, 3.00 equiv) were added to the reaction. The resulting solution was stirred overnight at 80° C. in an oil bath behind a blast shield. After cooling to ambient temperature, the mixture was concentrated under reduced pressure. The residue was partitioned between ethyl acetate and water. The organic phase was washed with brine, dried (Na$_2$SO$_4$), and concentrated. The crude product (~50 mg) was purified by Prep-HPLC with the following conditions (1#-Pre-HPLC-006 (Waters)): Column, SunFire Prep C18, 5 um, 19*150 mm; mobile phase, water with 0.05% TFA and CH$_3$CN (hold 5.0% CH$_3$CN in 2 min, up to 30.0% in 1 min, up to 60.0% in 12 min, up to 100.0% in 1 min); Detector, UV 254/220 nm. The fractions containing pure compound were combined and lyophilized to yield 10.3 mg (6%) of the title compound as a white solid. m/z (ES+) 429 (M+H)$^+$.

The compounds in the following table were prepared using standard chemical manipulations, readily available starting materials, and procedures similar to those used for the preparation of compounds 280, 121, 281, and 282:

| Cmpnd # | Compound Name | Compound Structure | Preparation similar to compound #(s) [m/z (ES+)] |
|---|---|---|---|
| 283 | 4-(1-(4-methyl-3-((5-(pyridin-3-yl)-1,3,4-oxadiazol-2-yl)amino)benzoyl)piperidin-4-yl)benzonitrile | 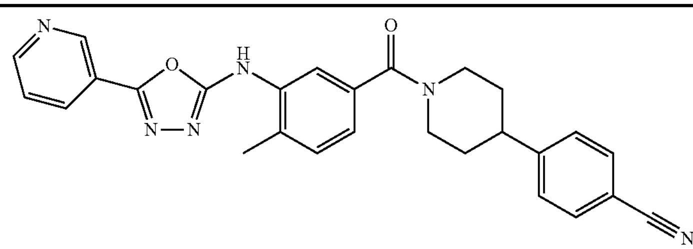 | 280 [465 (M + H)$^+$] |
| 284 | 4-(1-(3-((5-ethyl-1,3,4-oxadiazol-2-yl)amino)-4-methylbenzoyl)piperidin-4-yl)benzonitrile | 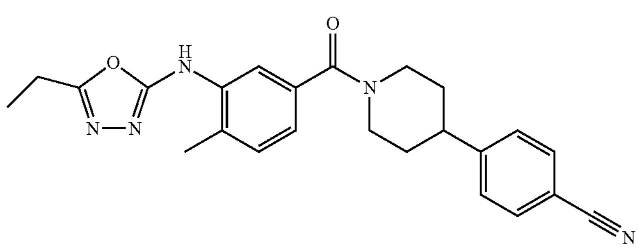 [SMILES: CCc1nnc(Nc2cc(C(=O)N3CCC(c4ccc(C#N)cc4)CC3)ccc2C)o1] | 280 [416 (M + H)$^+$] |
| 285 | 4-(1-(3-((1H-imidazo[4,5-b]pyridin-2-yl)amino)-4-methylbenzoyl)piperidin-4-yl)benzonitrile | 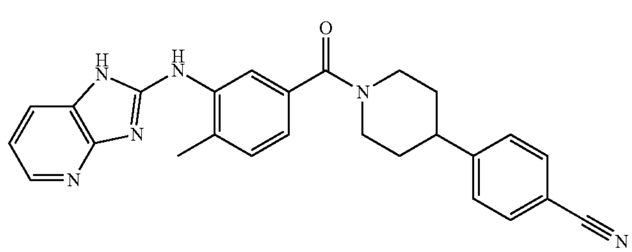 [SMILES: Cc1ccc(C(=O)N2CCC(c3ccc(C#N)cc3)CC2)cc1Nc1nc2ncccc2[nH]1] | 281 [437 (M + H)$^+$] |

| Cmpnd # | Compound Name | Compound Structure | Preparation similar to compound #(s) [m/z (ES+)] |
|---|---|---|---|
| 286 | 4-(1-(3-((1H-imidazol-2-yl)amino)-4-methylbenzoyl)piperidin-4-yl)benzonitrile | 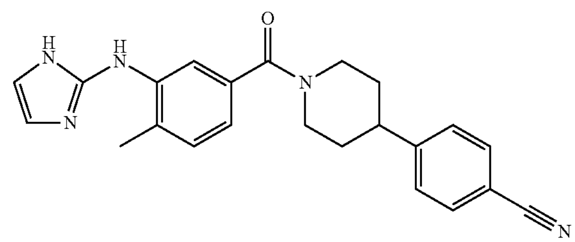 [SMILES: Cc1ccc(C(=O)N2CCC(c3ccc(C#N)cc3)CC2)cc1Nc1ncc[nH]1] | 281 [386 (M + H)+] |
| 287 | 4-(1-(3-((5-(dimethylamino)-1H-imidazo[4,5-b]pyridin-2-yl)amino)-4-methylbenzoyl)piperidin-4-yl)benzonitrile | 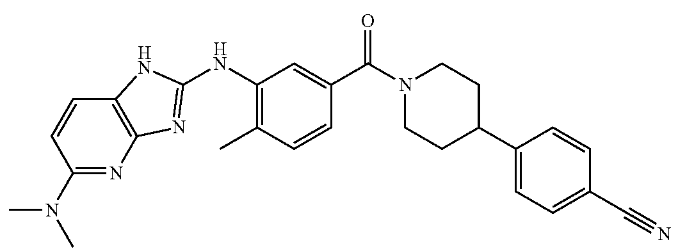 [SMILES: Cc1ccc(C(=O)N2CCC(c3ccc(C#N)cc3)CC2)cc1Nc1nc2nc(N(C)C)ccc2[nH]1] | 281 [480 (M + H)+] |
| 288 | 4-(1-(3-((5-(isobutylamino)-1H-imidazo[4,5-b]pyridin-2-yl)amino)-4-methylbenzoyl)piperidin-4-yl)benzonitrile | 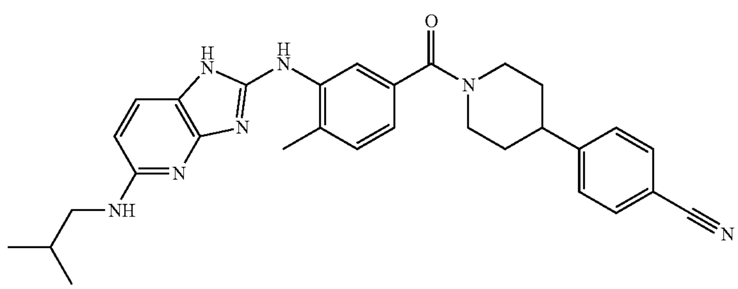 [SMILES: Cc1ccc(C(=O)N2CCC(c3ccc(C#N)cc3)CC2)cc1Nc1nc2nc(NCC(C)C)ccc2[nH]1] | 281 [508 (M + H)+] |
| 289 | 4-(1-(3-((5-(isopropylamino)-1H-imidazo[4,5-b]pyridin-2-yl)amino)-4-methylbenzoyl)piperidin-4-yl)benzonitrile | 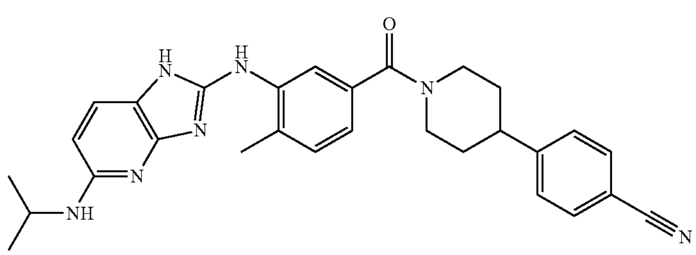 [SMILES: Cc1ccc(C(=O)N2CCC(c3ccc(C#N)cc3)CC2)cc1Nc1nc2nc(NC(C)C)ccc2[nH]1] | 281 [494 (M + H)+] |
| 290 | 5-((5-(4-(4-cyanophenyl)piperidin-1-carbonyl)-2-methylphenyl)amino)-N-isopropylnicotinamide | 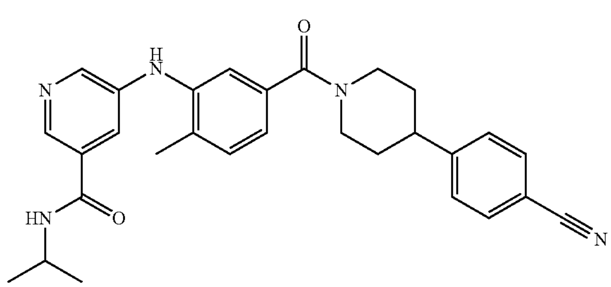 [SMILES: Cc1ccc(C(=O)N2CCC(c3ccc(C#N)cc3)CC2)cc1Nc1cncc(C(=O)NC(C)C)c1] | 121 [482 (M + H)+] |

-continued

| Cmpnd # | Compound Name | Compound Structure | Preparation similar to compound #(s) [m/z (ES+)] |
|---|---|---|---|
| 291 | 2-((5-(4-(4-cyanophenyl)piperidine-1-carbonyl)-2-methylphenyl)amino)-N-cyclopropyl-isonicotinamide | 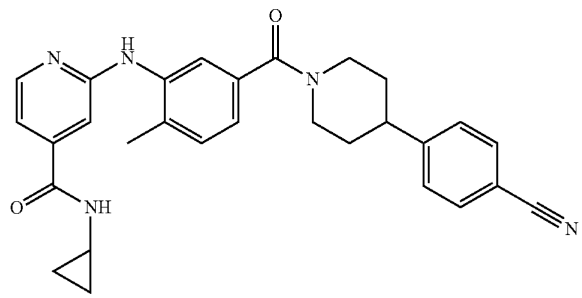 [SMILES: Cc1ccc(C(=O)N2CCC(c3ccc(C#N)cc3)CC2)cc1Nc1cc(C(=O)NC2CC2)ccn1] | 121 [480 (M + H)+] |
| 292 | 6-((5-(4-(4-cyanophenyl)piperidine-1-carbonyl)-2-methylphenyl)amino)-N-cyclopropyl-nicotinamide | 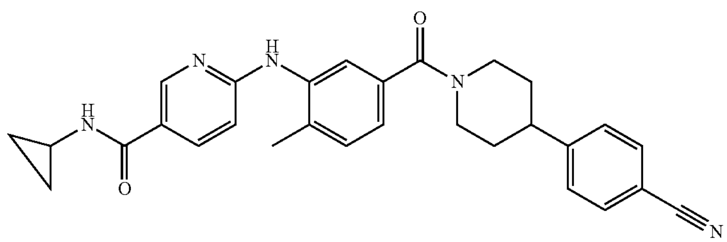 [SMILES: Cc1ccc(C(=O)N2CCC(c3ccc(C#N)cc3)CC2)cc1Nc1ccc(C(=O)NC2CC2)cn1] | 121 [480 (M + H)+] |
| 293 | 2-((5-(4-(4-cyanophenyl)piperidine-1-carbonyl)-2-methylphenyl)amino)-N-ethylisonicotinamide | 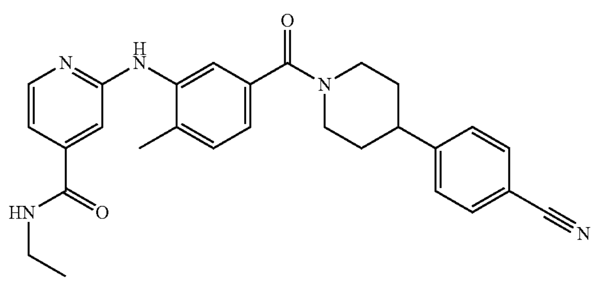 [SMILES: CCNC(=O)c1ccnc(Nc2cc(C(=O)N3CCC(c4ccc(C#N)cc4)CC3)ccc2C)c1] | 121 [468 (M + H)+] |
| 294 | 6-((5-(4-(4-cyanophenyl)piperidine-1-carbonyl)-2-methylphenyl)amino)-N-ethylnicotinamide | 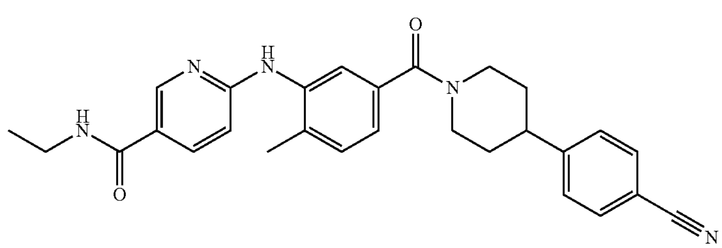 [SMILES: CCNC(=O)c1ccc(Nc2cc(C(=O)N3CCC(c4ccc(C#N)cc4)CC3)ccc2C)nc1] | 121 [468 (M + H)+] |
| 295 | 4-(1-(4-methyl-3-((4-(4-methylpiperazine-1-carbonyl)pyridin-2-yl)amino)benzoyl)piperidin-4-yl)benzonitrile | 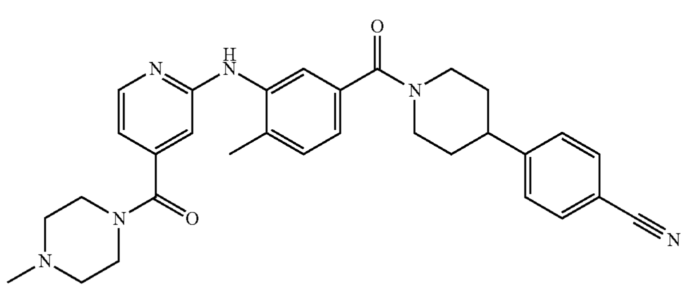 [SMILES: Cc1ccc(C(=O)N2CCC(c3ccc(C#N)cc3)CC2)cc1Nc1cc(C(=O)N2CCN(C)CC2)ccn1] | 121 [523 (M + H)+] |

| Cmpnd # | Compound Name | Compound Structure | Preparation similar to compound #(s) [m/z (ES+)] |
|---|---|---|---|
| 296 | 4-(1-(3-((5-ethyl-4H-1,2,4-triazol-3-yl)amino)-4-methylbenzoyl)piperidin-4-yl)benzonitrile | 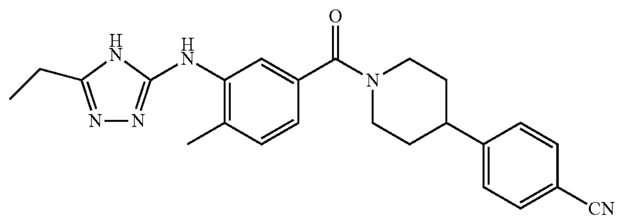 [SMILES: CCc1nnc(Nc2cc(C(=O)N3CCC(c4ccc(C#N)cc4)CC3)ccc2C)[nH]1] | 282 [415 (M + H)+] |

The compounds in the following table were prepared using standard chemical manipulations, readily available starting materials, and procedures similar to those used for the preparation of compounds 26, 43, 48, 50, 51, 64, and 80:

| Cmpnd # | Compound Name | Compound Structure | Preparation similar to compound #(s) [m/z (ES+)] |
|---|---|---|---|
| 297 | 1-(5-(4-(4-cyanophenyl)-4-fluoropiperidine-1-carbonyl)-2-methylphenyl)-3-isobutylurea | 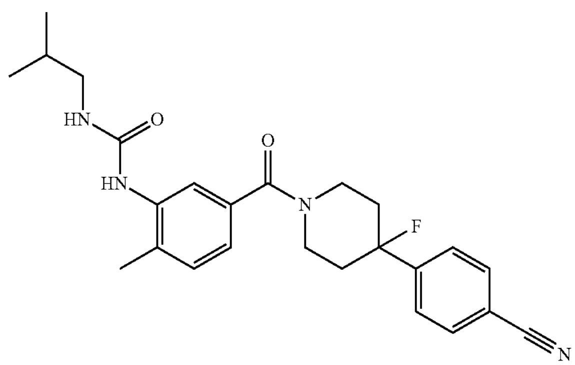 [SMILES: Cc1ccc(C(=O)N2CCC(F)(c3ccc(C#N)cc3)CC2)cc1NC(=O)NCC(C)C] | 64 [437 (M + H)+] |
| 298 | N-(5-(4-(5-cyanopyridin-2-yl)piperidine-1-carbonyl)-2-methylphenyl)pyrrolidine-1-carboxamide | 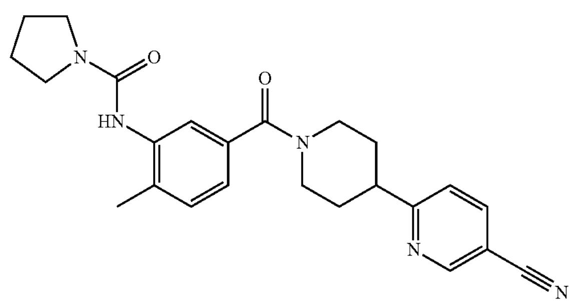 [SMILES: Cc1ccc(C(=O)N2CCC(c3ccc(C#N)cn3)CC2)cc1NC(=O)N1CCCC1] | 50 and 64 [418 (M + H)+] |
| 299 | N-(5-(4-(6-cyanopyridin-3-yl)piperidine-1-carbonyl)-2-methylphenyl)pyrrolidine-1-carboxamide | 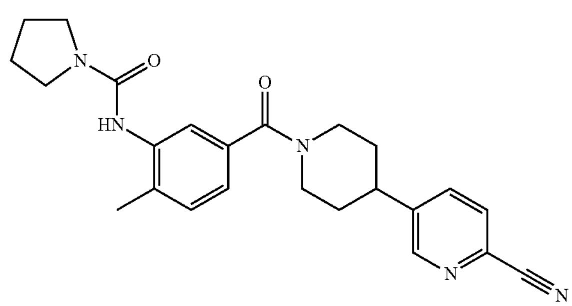 [SMILES: Cc1ccc(C(=O)N2CCC(c3ccc(C#N)nc3)CC2)cc1NC(=O)N1CCCC1] | 51 and 64 [418 (M + H)+] |

-continued

| Cmpnd # | Compound Name | Compound Structure | Preparation similar to compound #(s) [m/z (ES+)] |
|---|---|---|---|
| 300 | 1-(5-(4-(6-cyanopyridin-3-yl)piperidine-1-carbonyl)-2-methylphenyl)-3-(2-methoxyethyl)urea | 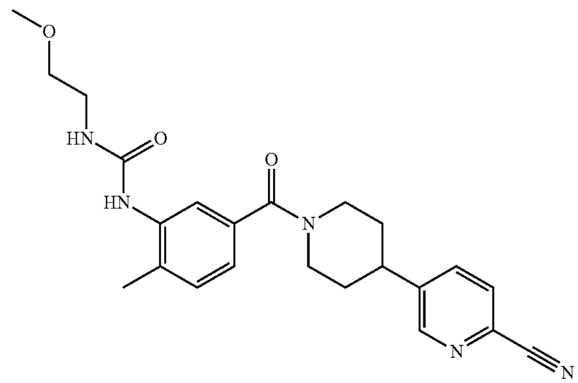 [SMILES: COCCNC(=O)Nc1cc(C(=O)N2CCC(c3ccc(C#N)nc3)CC2)ccc1C] | 51 and 64 [422 (M + H)+] |
| 301 | 1-(5-(4-(5-cyanopyridin-2-yl)piperidine-1-carbonyl)-2-methylphenyl)-3-(2-methoxyethyl)urea | 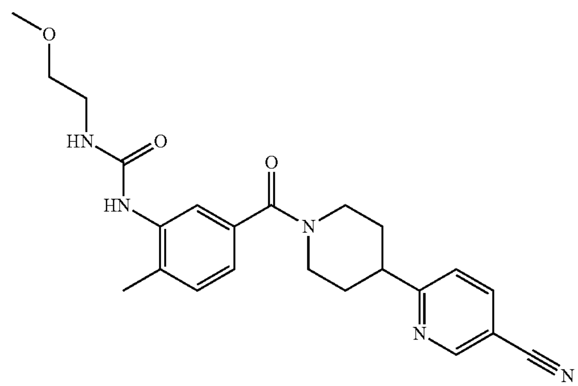 [SMILES: COCCNC(=O)Nc1cc(C(=O)N2CCC(c3ccc(C#N)cn3)CC2)ccc1C] | 50 and 64 [422 (M + H)+] |
| 302 | 1-(5-(4-(4-cyanophenyl)piperidine-1-carbonyl)pyridazin-3-yl)-3-(2-methoxyethyl)urea | 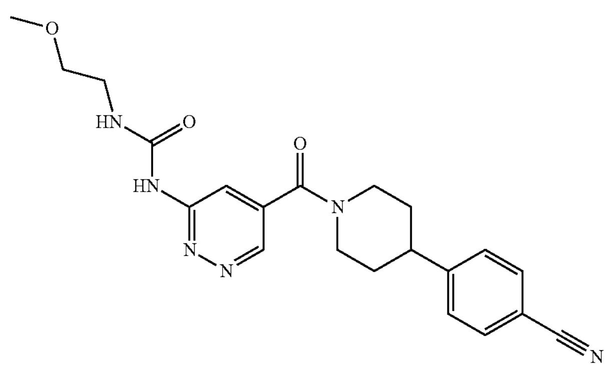 [SMILES: COCCNC(=O)Nc1cc(C(=O)N2CCC(c3ccc(C#N)cc3)CC2)cnn1] | 64 [409 (M + H)+] |
| 303 | N-(5-(4-(5-cyanopyridin-2-yl)piperidine-1-carbonyl)-2-methylphenyl)-6-(ethylamino)nicotinamide | 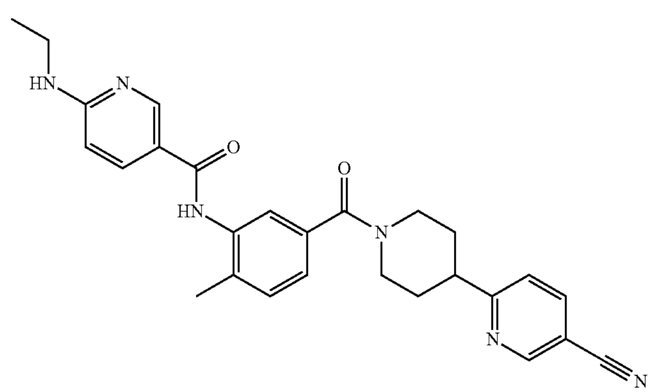 [SMILES: CCNc1ccc(C(=O)Nc2cc(C(=O)N3CCC(c4ccc(C#N)cn4)CC3)ccc2C)cn1] | 50 [469 (M + H)+] |

| Cmpnd # | Compound Name | Compound Structure | Preparation similar to compound #(s) [m/z (ES+)] |
|---|---|---|---|
| 304 | 6-(azetidin-1-yl)-N-(5-(4-(5-cyanopyridin-2-yl)piperidine-1-carbonyl)-2-methylphenyl)nicotinamide | 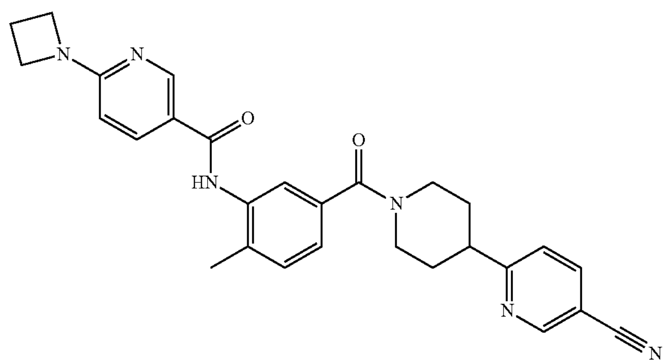 [SMILES: Cc1ccc(C(=O)N2CCC(c3ccc(C#N)cn3)CC2)cc1NC(=O)c1ccc(N2CCC2)nc1] | 50 [481 (M + H)+] |
| 305 | 1-(5-(4-(4-cyanophenyl)piperidine-1-carbonyl)pyridazin-3-yl)-3-isobutylurea | 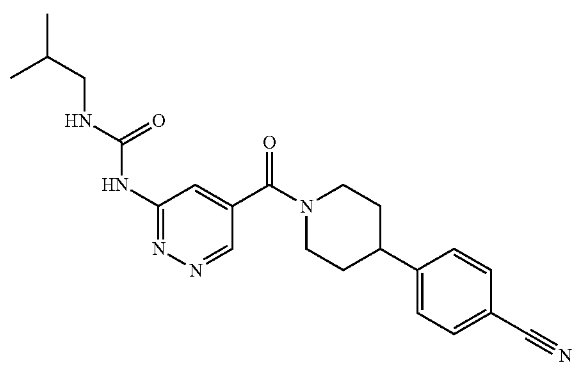 [SMILES: CC(C)CNC(=O)Nc1cc(C(=O)N2CCC(c3ccc(C#N)cc3)CC2)cnn1] | 64 [407 (M + H)+] |
| 306 | 1-(5-(4-(5-cyanopyridin-2-yl)piperidine-1-carbonyl)-2-methylphenyl)-3-isopropylurea | 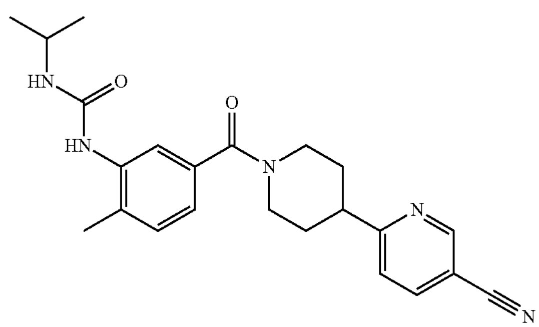 [SMILES: Cc1ccc(C(=O)N2CCC(c3ccc(C#N)cn3)CC2)cc1NC(=O)NC(C)C] | 50 and 64 [406 (M + H)+] |
| 307 | 1-(5-(4-(5-cyanopyridin-2-yl)piperidine-1-carbonyl)-2-methylphenyl)-3-cyclobutylurea | 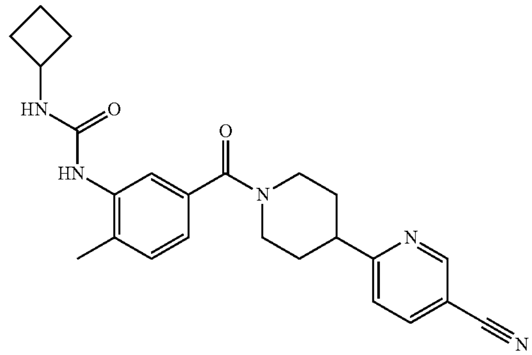 [SMILES: Cc1ccc(C(=O)N2CCC(c3ccc(C#N)cn3)CC2)cc1NC(=O)NC1CCC1] | 50 and 64 [418 (M + H)+] |

-continued

| Cmpnd # | Compound Name | Compound Structure | Preparation similar to compound #(s) [m/z (ES+)] |
|---|---|---|---|
| 308 | 1-(5-(4-(5-cyanopyridin-2-yl)piperidine-1-carbonyl)-2-methylphenyl)-3-cyclopentylurea | 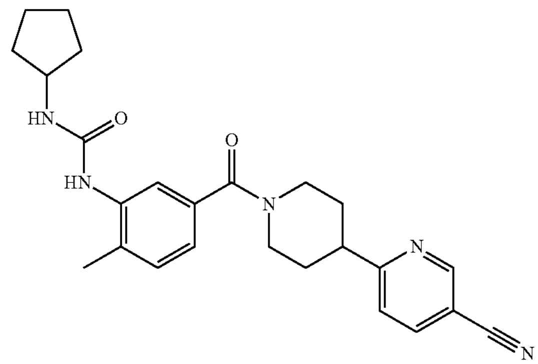 [SMILES: Cc1ccc(C(=O)N2CCC(c3ccc(C#N)cn3)CC2)cc1NC(=O)NC1CCCC1] | 50 and 64 [432 (M + H)+] |
| 309 | 1-(5-(4-(5-cyanopyridin-2-yl)piperidine-1-carbonyl)-2-methylphenyl)-3-(oxetan-3-yl)urea | 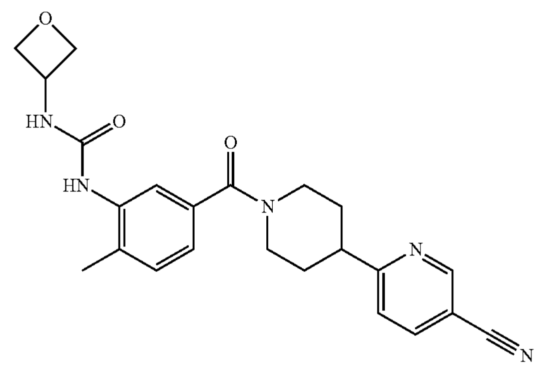 [SMILES: Cc1ccc(C(=O)N2CCC(c3ccc(C#N)cn3)CC2)cc1NC(=O)NC1COC1] | 50 and 64 [420 (M + H)+] |
| 310 | 1-(5-(4-(5-cyanopyridin-2-yl)piperidine-1-carbonyl)-2-methylphenyl)-3-(tetrahydro-2H-pyran-4-yl)urea | 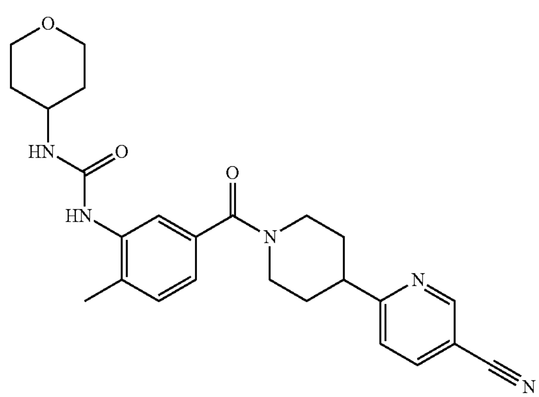 [SMILES: Cc1ccc(C(=O)N2CCC(c3ccc(C#N)cn3)CC2)cc1NC(=O)NC1CCOCC1] | 50 and 64 [448 (M + H)+] |
| 311 | 1-(5-(4-(5-cyanopyridin-2-yl)piperidine-1-carbonyl)-2-methylphenyl)-3-(tetrahydro-2H-pyran-3-yl)urea | 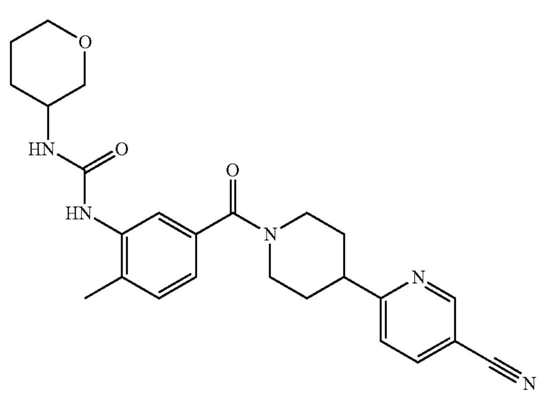 [SMILES: Cc1ccc(C(=O)N2CCC(c3ccc(C#N)cn3)CC2)cc1NC(=O)NC1CCCOC1] | 50 and 64 [448 (M + H)+] |

| Cmpnd # | Compound Name | Compound Structure | Preparation similar to compound #(s) [m/z (ES+)] |
|---|---|---|---|
| 312 | 6-(azetidin-1-yl)-N-(5-(4-(4-cyanophenyl)-4-fluoropiperidine-1-carbonyl)-2-methylphenyl)nicotinamide | 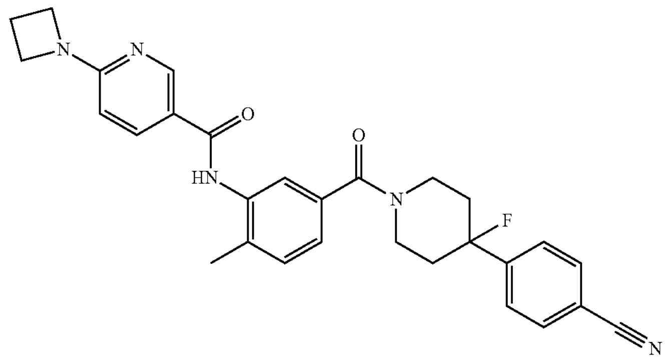 [SMILES: Cc1ccc(C(=O)N2CCC(F)(c3ccc(C#N)cc3)CC2)cc1NC(=O)c1ccc(N2CCC2)nc1] | 43<br>[498 (M + H)⁺] |
| 313 | 1-(5-(4-(5-cyanopyridin-2-yl)piperidine-1-carbonyl)-2-methylphenyl)-3-(tetrahydrofuran-3-yl)urea | 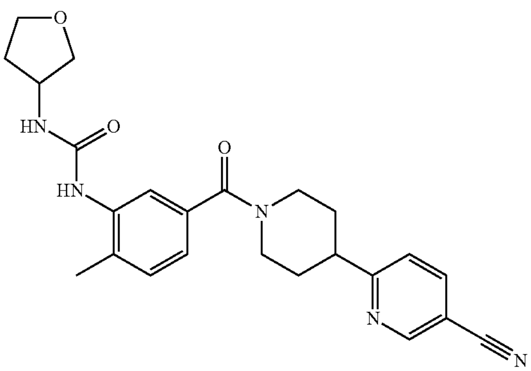 [SMILES: Cc1ccc(C(=O)N2CCC(c3ccc(C#N)cn3)CC2)cc1NC(=O)NC1CCOC1] | 50 and 64<br>[434 (M + H)⁺] |
| 314 | 2-(azetidin-1-yl)-N-(5-(4-(4-cyanophenyl)-4-fluoropiperidine-1-carbonyl)-2-methylphenyl)pyrimidine-5-carboxamide | 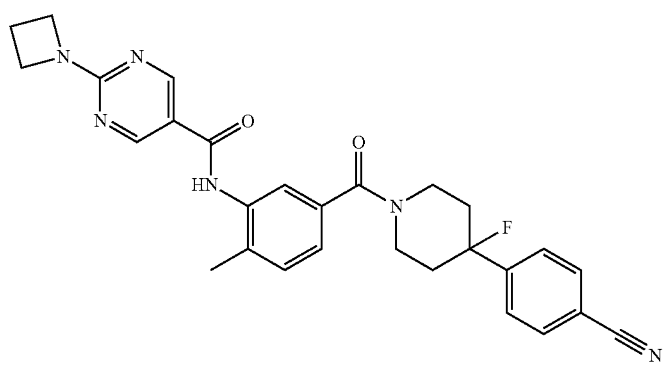 | 43<br>[499 (M + H)⁺] |
| 315 | 1-(5-(4-(5-cyanopyridin-2-yl)-4-fluoropiperidine-1-carbonyl)-2-methylphenyl)-3-(tetrahydrofuran-3-yl)urea | 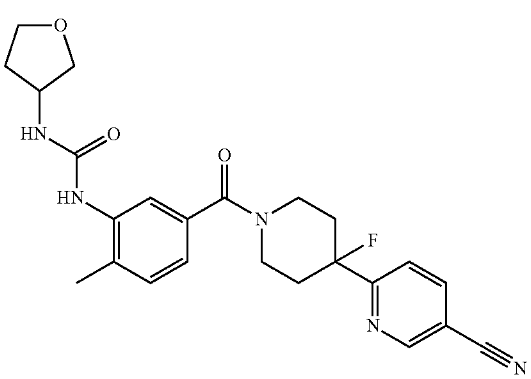 | 26 and 64<br>[452 (M + H)⁺] |

-continued

| Cmpnd # | Compound Name | Compound Structure | Preparation similar to compound #(s) [m/z (ES+)] |
|---|---|---|---|
| 316 | (S)-1-(5-(4-(5-cyanopyridin-2-yl)-4-fluoropiperidine-1-carbonyl)-2-methylphenyl)-3-(tetrahydrofuran-3-yl)urea | 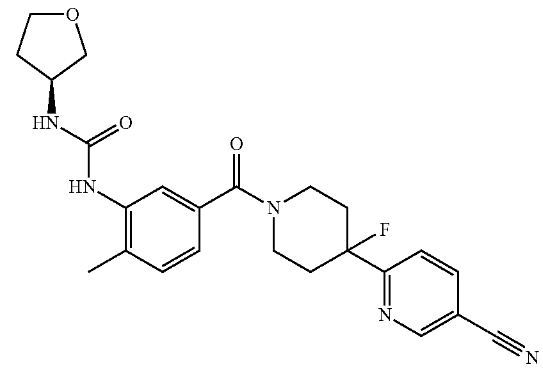 [SMILES: Cc1ccc(C(=O)N2CCC(F)(c3ccc(C#N)cn3)CC2)cc1NC(=O)N[C@H]1CCOC1] | 26 and 64 [452 (M + H)+] |
| 317 | 1-(5-(4-(5-cyanopyridin-2-yl)-4-fluoropiperidine-1-carbonyl)-2-methylphenyl)-3-(tetrahydro-2H-pyran-4-yl)urea | 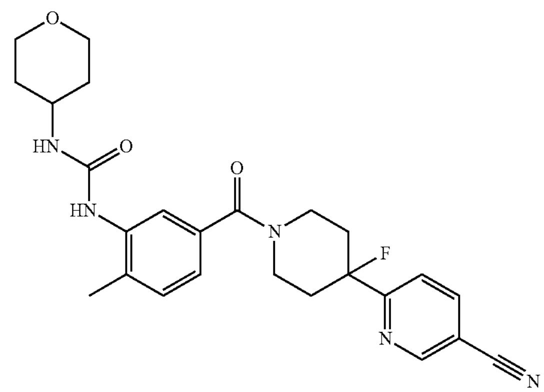 | 26 and 64 [466 (M + H)+] |
| 318 | 1-(5-(4-(4-cyanophenyl)-4-fluoropiperidine-1-carbonyl)-2-methylphenyl)-3-(tetrahydrofuran-3-yl)urea | 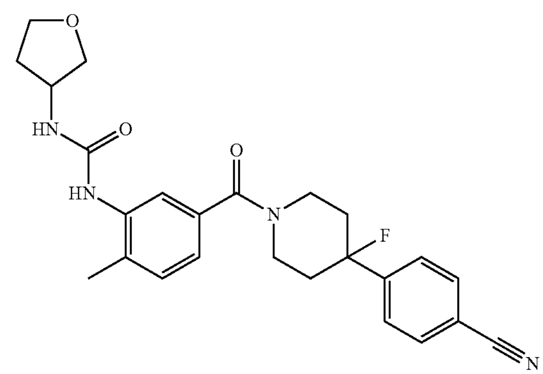 [SMILES: Cc1ccc(C(=O)N2CCC(F)(c3ccc(C#N)cc3)CC2)cc1NC(=O)NC1CCOC1] | 64 [451 (M + H)+] |
| 319 | (S)-1-(5-(4-(4-cyanophenyl)-4-fluoropiperidine-1-carbonyl)-2-methylphenyl)-3-(tetrahydrofuran-3-yl)urea | 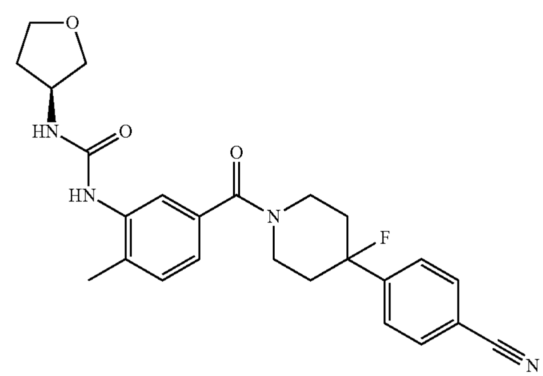 [SMILES: Cc1ccc(C(=O)N2CCC(F)(c3ccc(C#N)cc3)CC2)cc1NC(=O)N[C@H]1CCOC1] | 64 [451 (M + H)+] |

| Cmpnd # | Compound Name | Compound Structure | Preparation similar to compound #(s) [m/z (ES+)] |
|---|---|---|---|
| 320 | 1-(5-(4-(5-cyanopyridin-2-yl)-4-fluoropiperidine-1-carbonyl)-2-methylphenyl)-3-(oxetan-3-yl)urea | 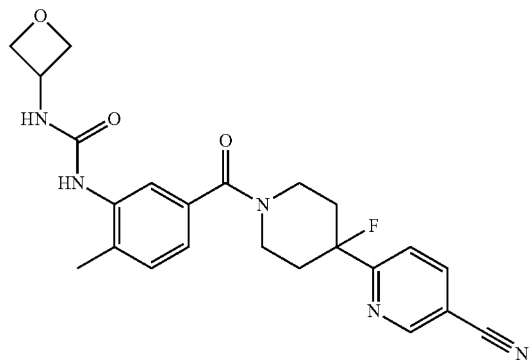 | 26 and 64 [438 (M + H)+] |
| 321 | 1-(2-chloro-5-(4-(4-cyanophenyl)-4-fluoropiperidine-1-carbonyl)phenyl)-3-(tetrahydrofuran-3-yl)urea | 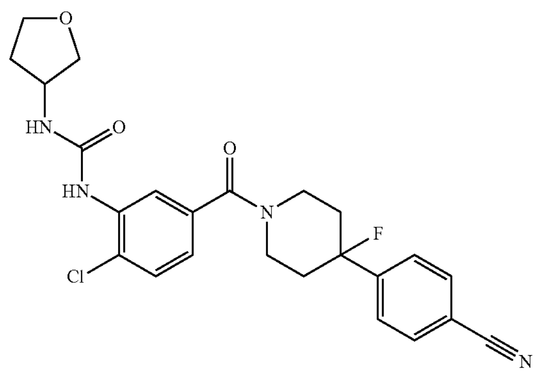 [SMILES: N#Cc1ccc(C2(F)CCN(C(=O)c3ccc(Cl)c(NC(=O)NC4CCOC4)c3)CC2)cc1] | 26 and 64 [471 (M + H)+] |
| 322 | 6-(azetidin-1-yl)-N-(5-(4-(5-cyanopyridin-2-yl)-4-fluoropiperidine-1-carbonyl)-2-methylphenyl)nicotinamide | 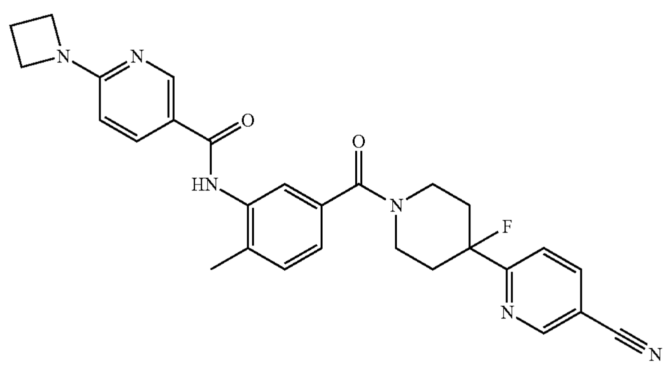 [SMILES: Cc1ccc(C(=O)N2CCC(F)(c3ccc(C#N)cn3)CC2)cc1NC(=O)c1ccc(N2CCC2)nc1] | 26 and 43 [499 (M + H)+] |
| 323 | N-(5-(4-(5-cyanopyridin-2-yl)-4-fluoropiperidine-1-carbonyl)-2-methylphenyl)-6-(isopropylamino)nicotinamide | 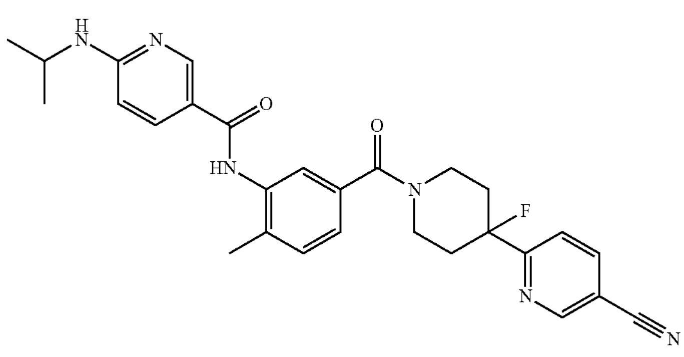 [SMILES: Cc1ccc(C(=O)N2CCC(F)(c3ccc(C#N)cn3)CC2)cc1NC(=O)c1ccc(NC(C)C)nc1] | 26 and 43 [501 (M + H)+] |

-continued

| Cmpnd # | Compound Name | Compound Structure | Preparation similar to compound #(s) [m/z (ES+)] |
|---|---|---|---|
| 324 | 1-(5-(4-fluoro-4-(5-methoxypyridin-2-yl)piperidine-1-carbonyl)-2-methylphenyl)-3-(tetrahydrofuran-3-yl)urea | 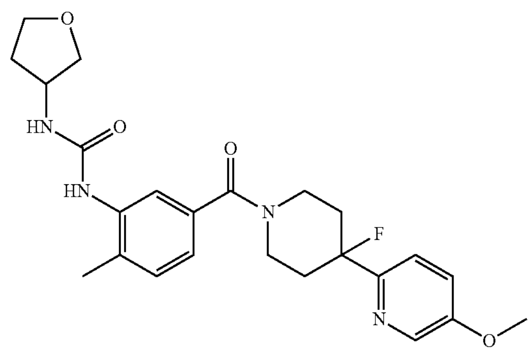 [SMILES: COc1ccc(C2(F)CCN(C(=O)c3ccc(C)c(NC(=O)NC4CCOC4)c3)CC2)nc1] | 1, 11, and 64 [457 (M + H)+] |
| 325 | 1-(5-(4-(4-cyanophenyl)-4-fluoropiperidine-1-carbonyl)-2-methylphenyl)-3-((1-methylpiperidin-4-yl)methyl)urea | 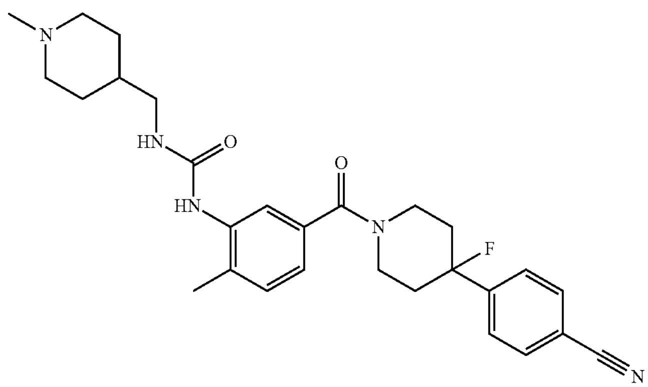 [SMILES: Cc1ccc(C(=O)N2CCC(F)(c3ccc(C#N)cc3)CC2)cc1NC(=O)NCC1CCN(C)CC1] | 64 [492 (M + H)+] |
| 326 | 6-(azetidin-1-yl)-N-(2-methyl-5-(4-(pyridin-4-yl)piperidine-1-carbonyl)phenyl)nicotinamide | 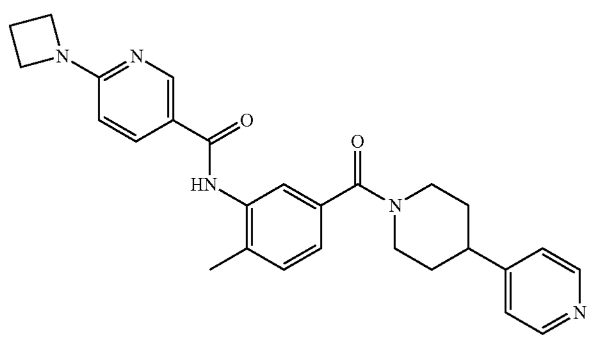 | 43 [492 (M + H)+] |
| 327 | 1-(5-(4-(4-cyanophenyl)-4-fluoropiperidine-1-carbonyl)-2-methylphenyl)-3-(piperidin-4-ylmethyl)urea | 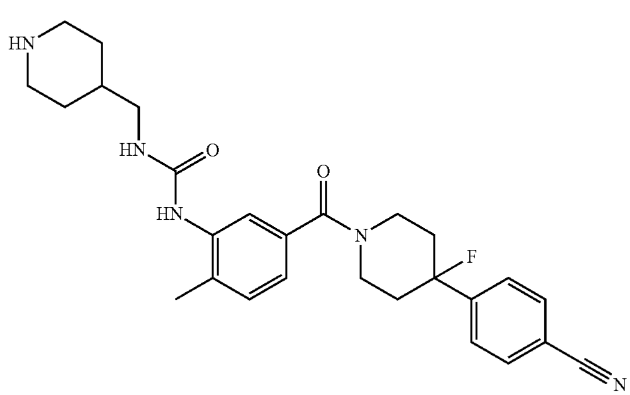 | 64 [492 (M + H)+] |

-continued

| Cmpnd # | Compound Name | Compound Structure | Preparation similar to compound #(s) [m/z (ES+)] |
|---|---|---|---|
| 328 | 6-(azetidin-1-yl)-N-(5-(4-(4-cyanophenyl)-4-fluoropiperidine-1-carbonyl)-2-fluorophenyl)nicotinamide | 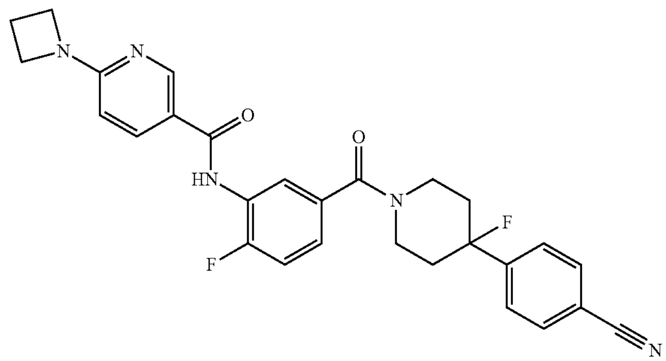 | 43 [502 (M + H)+] |
| 329 | 3-(5-(4-(4-cyanophenyl)-4-fluoropiperidine-1-carbonyl)-2-methylphenyl)-1-(2-methoxyethyl)-1-methylurea | 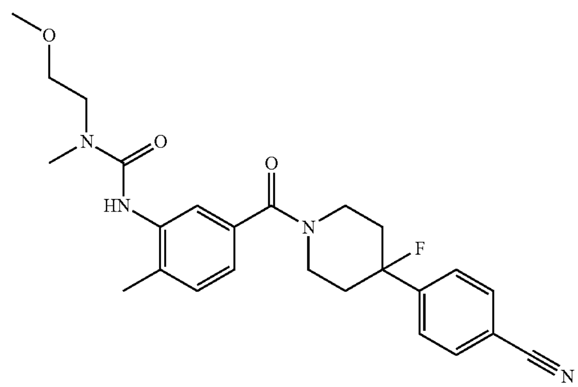 [SMILES: COCCN(C)C(=O)Nc1cc(C(=O)N2CCC(F)(c3ccc(C#N)cc3)CC2)ccc1C] | 64 [453 (M + H)+] |
| 330 | 6-(azetidin-1-yl)-N-(5-(4-(4-cyanophenyl)-4-fluoropiperidine-1-carbonyl)-2-(trifluoromethyl)phenyl)nicotinamide | 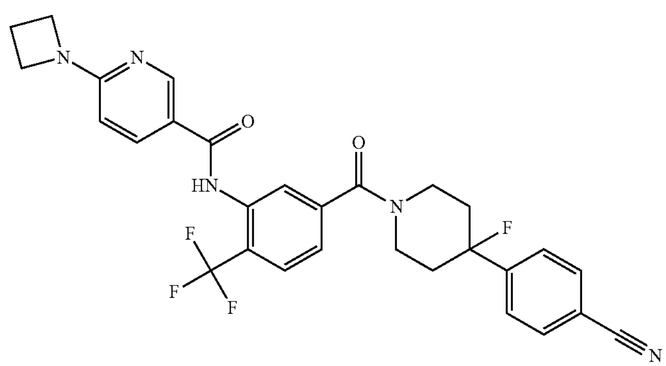 [SMILES: N#Cc1ccc(C2(F)CCN(C(=O)c3ccc(C(F)(F)F)c(NC(=O)c4ccc(N5CCC5)nc4)c3)CC2)cc1] | 43 [552 (M + H)+] |
| 331 | 6-(azetidin-1-yl)-N-(5-(4-(4-cyanophenyl)-4-fluoropiperidine-1-carbonyl)-2-methoxyphenyl)nicotinamide | 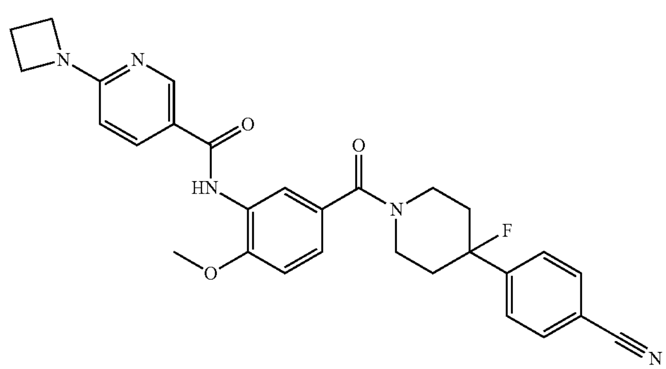 | 43 [514 (M + H)+] |

| Cmpnd # | Compound Name | Compound Structure | Preparation similar to compound #(s) [m/z (ES+)] |
|---|---|---|---|
| 332 | (S)-1-(5-(4-(4-cyanophenyl)-4-fluoropiperidine-1-carbonyl)-2-methylphenyl)-3-((tetrahydrofuran-2-yl)methyl)urea | 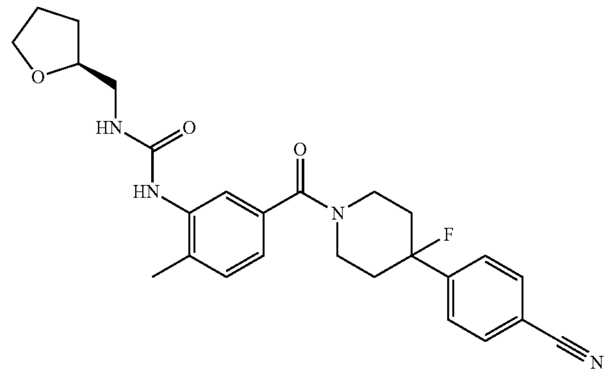 [SMILES: Cc1ccc(C(=O)N2CCC(F)(c3ccc(C#N)cc3)CC2)cc1NC(=O)NC[C@@H]1CCCO1] | 64 [465 (M + H)+] |
| 333 | (R)-1-(2-chloro-5-(4-(4-cyanophenyl)-4-fluoropiperidine-1-carbonyl)phenyl)-3-(tetrahydrofuran-3-yl)urea | 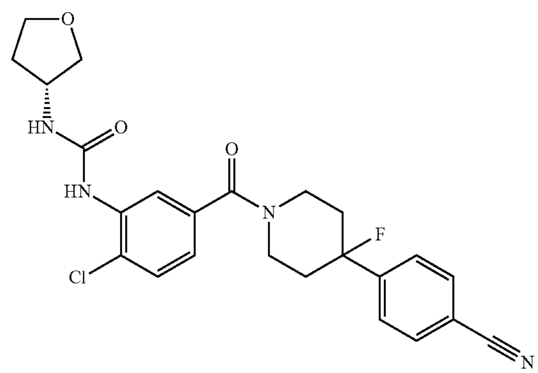 [SMILES: N#Cc1ccc(C2(F)CCN(C(=O)c3ccc(Cl)c(NC(=O)N[C@@H]4CCOC4)c3)CC2)cc1] | 64 [471 (M + H)+] |
| 334 | N-(5-(4-(4-cyanophenyl)-4-fluoropiperidine-1-carbonyl)-2,4-dimethylphenyl)-6-(piperazin-1-yl)nicotinamide | 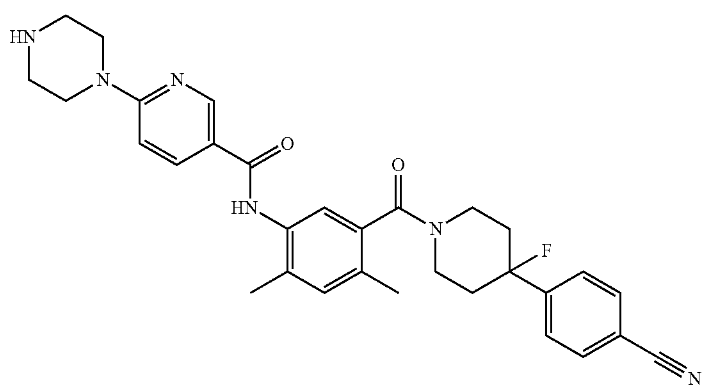 [SMILES: Cc1cc(C)c(C(=O)N2CCC(F)(c3ccc(C#N)cc3)CC2)cc1NC(=O)c1ccc(N2CCNCC2)nc1] | 43 [541 (M + H)+] |
| 335 | (R)-1-(5-(4-(4-cyanophenyl)-4-fluoropiperidine-1-carbonyl)-2-ethyl-4-methylphenyl)-3-(tetrahydrofuran-3-yl)urea | 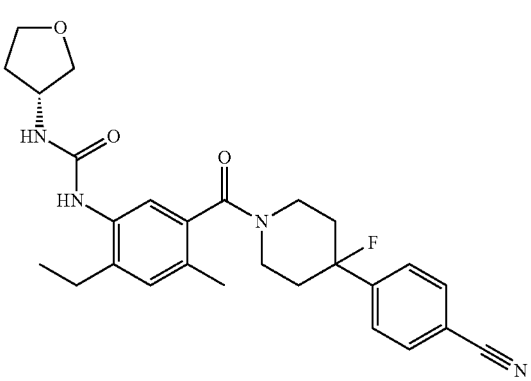 [SMILES: CCc1cc(C)c(C(=O)N2CCC(F)(c3ccc(C#N)cc3)CC2)cc1NC(=O)N[C@@H]1CCOC1] | 64 [479 (M + H)+] |

| Cmpnd # | Compound Name | Compound Structure | Preparation similar to compound #(s) [m/z (ES+)] |
|---|---|---|---|
| 336 | (R)-tetrahydrofuran-3-yl (3-(4-(4-cyanophenyl)-4-fluoropiperidine-1-carbonyl)-4-methylphenyl)carbamate | 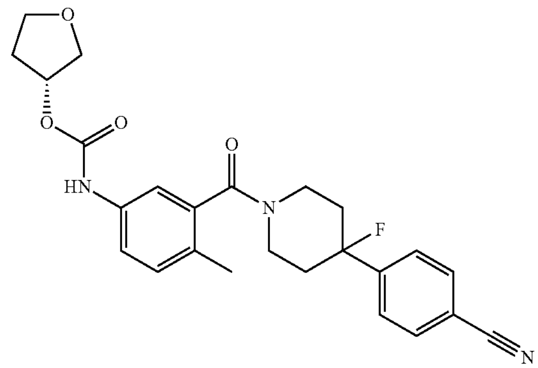 [SMILES: Cc1ccc(NC(=O)O[C@@H]2CCOC2)cc1C(=O)N1CCC(F)(c2ccc(C#N)cc2)CC1] | 80 [452 (M + H)+] |
| 337 | 1-acetylpyrrolidin-3-yl (3-(4-(4-cyanophenyl)-4-fluoropiperidine-1-carbonyl)-4-methylphenyl)carbamate | 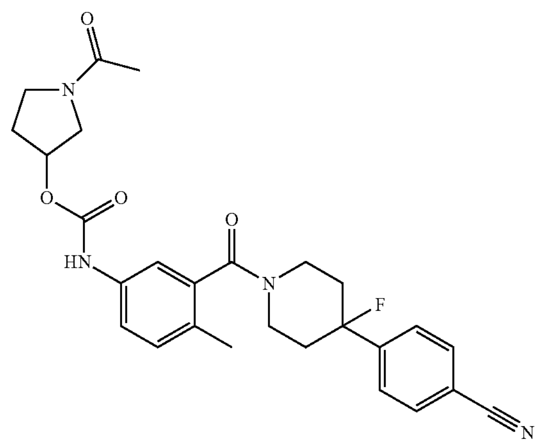 [SMILES: CC(=O)N1CCC(OC(=O)Nc2ccc(C)c(C(=O)N3CCC(F)(c4ccc(C#N)cc4)CC3)c2)C1] | 80 [493 (M + H)+] |
| 338 | (R)-1-(5-(4-(4-cyanophenyl)-4-fluoropiperidine-1-carbonyl)-2-ethyl-4-methylphenyl)-3-((tetrahydrofuran-2-yl)methyl)urea | 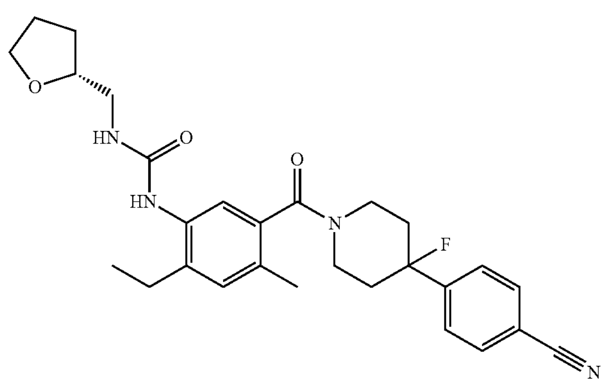 [SMILES: CCc1cc(C)c(C(=O)N2CCC(F)(c3ccc(C#N)cc3)CC2)cc1NC(=O)NC[C@H]1CCCO1] | 64 [493 (M + H)+] |

-continued

| Cmpnd # | Compound Name | Compound Structure | Preparation similar to compound #(s) [m/z (ES+)] |
|---|---|---|---|
| 339 | (S)-tetrahydrofuran-3-yl (5-(4-(4-cyanophenyl)-4-fluoropiperidine-1-carbonyl)-2-methylphenyl) carbamate | 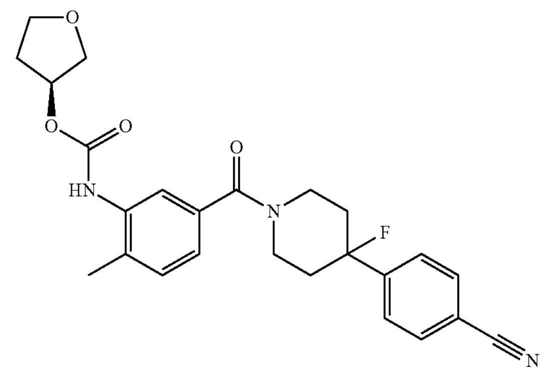 [SMILES: Cc1ccc(C(=O)N2CCC(F)(c3ccc(C#N)cc3)CC2)cc1NC(=O)O[C@H]1CCOC1] | 80 [452 (M + H)+] |
| 340 | 6-(azetidin-1-yl)-N-(5-(4-(4-cyanophenyl)-4-fluoropiperidine-1-carbonyl)-2-ethyl-4-methylphenyl) nicotinamide | 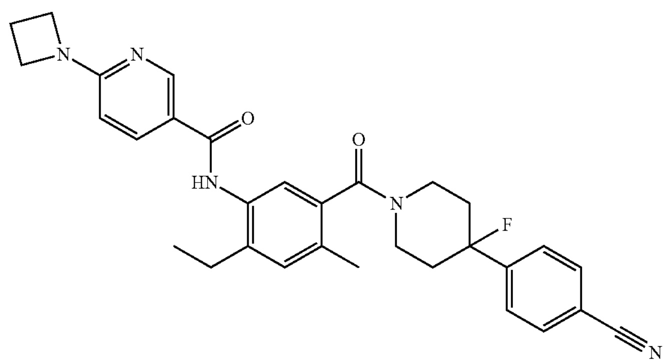 | 43 [526 (M + H)+] |
| 341 | N-(5-(4-(4-cyanophenyl)-4-fluoropiperidine-1-carbonyl)-4-ethyl-2-methylphenyl)-6-((2-methoxyethyl)(methyl)amino) nicotinamide | 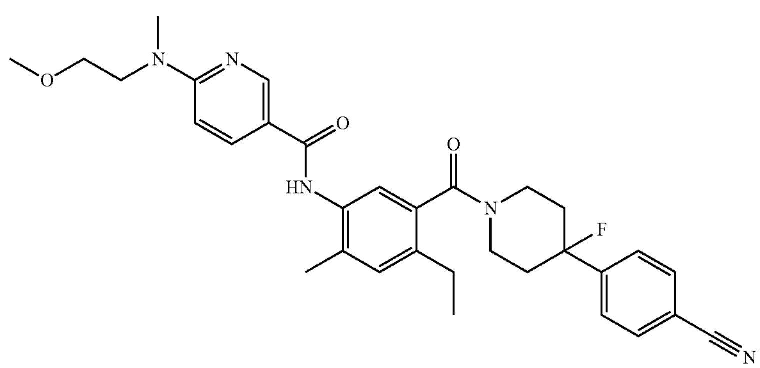 [SMILES: CCc1cc(C)c(NC(=O)c2ccc(N(C)CCOC)nc2)cc1C(=O)N1CCC(F)(c2ccc(C#N)cc2)CC1] | 43 and 48 [558 (M + H)+] |
| 342 | N-(5-(4-(4-cyanophenyl)-4-fluoropiperidine-1-carbonyl)-2-ethyl-4-methylphenyl)-6-(isopropylamino) nicotinamide | 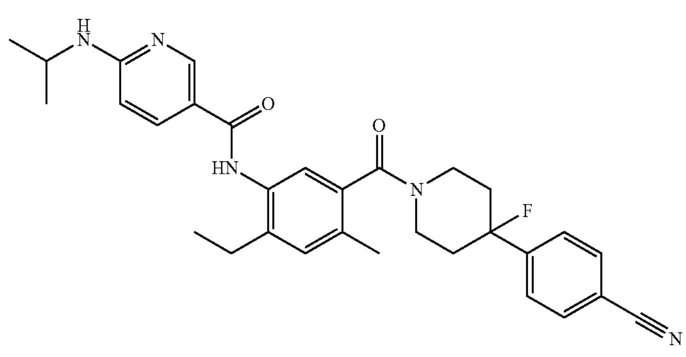 [SMILES: CCc1cc(C)c(C(=O)N2CCC(F)(c3ccc(C#N)cc3)CC2)cc1NC(=O)c1ccc(NC(C)C)nc1] | 43 [528 (M + H)+] |

-continued

| Cmpnd # | Compound Name | Compound Structure | Preparation similar to compound #(s) [m/z (ES+)] |
|---|---|---|---|
| 343 | N-(5-(4-(5-cyanopyridin-2-yl)-4-fluoropiperidine-1-carbonyl)-2,4-dimethylphenyl)-6-morpholinonicotinamide | 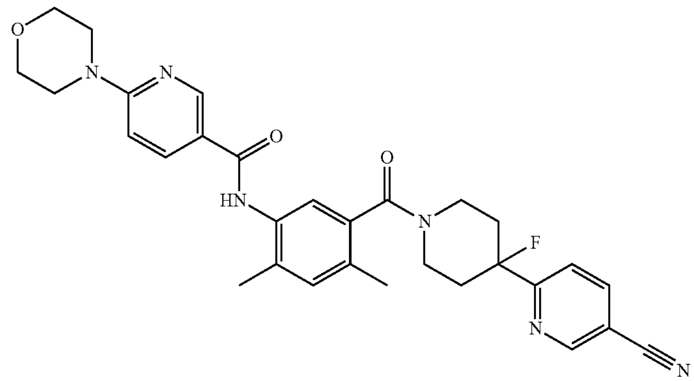 [SMILES: Cc1cc(C)c(C(=O)N2CCC(F)(c3ccc(C#N)cn3)CC2)cc1NC(=O)c1ccc(N2CCOCC2)nc1] | 26 and 43 [543 (M + H)+] |
| 344 | (R)-tetrahydrofuran-3-yl (5-(4-(4-cyanophenyl)-4-fluoropiperidine-1-carbonyl)-4-ethyl-2-methylphenyl) carbamate | 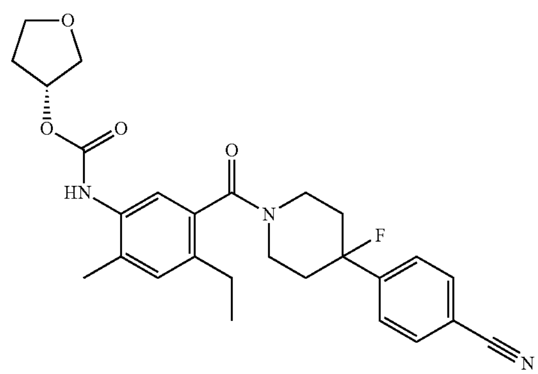 [SMILES: CCc1cc(C)c(NC(=O)O[C@@H]2CCOC2)cc1C(=O)N1CCC(F)(c2ccc(C#N)cc2)CC1] | 48 and 80 [480 (M + H)+] |
| 345 | (S)-tetrahydrofuran-3-yl (5-(4-(4-cyanophenyl)-4-fluoropiperidine-1-carbonyl)-4-ethyl-2-methylphenyl) carbamate | 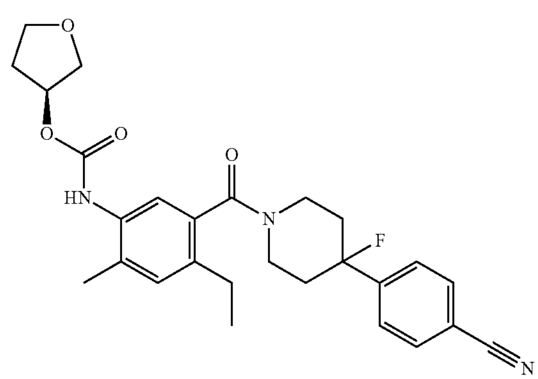 [SMILES: CCc1cc(C)c(NC(=O)O[C@H]2CCOC2)cc1C(=O)N1CCC(F)(c2ccc(C#N)cc2)CC1] | 48 and 80 [480 (M + H)+] |

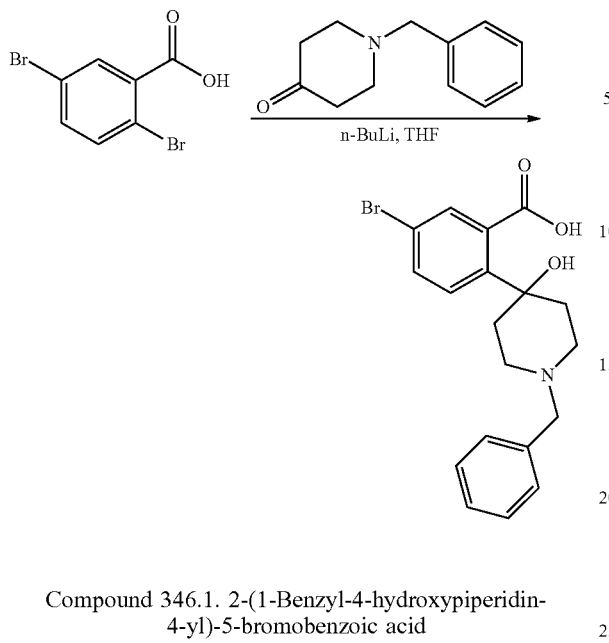

Compound 346.1. 2-(1-Benzyl-4-hydroxypiperidin-4-yl)-5-bromobenzoic acid

To a stirred solution of 2,5-dibromobenzoic acid (27.8 g, 100 mmol, 1.00 equiv) in THF/Et$_2$O (450/50 mL) under nitrogen at −78° C. was added dropwise n-BuLi (2.5M) (88 mL, 2.20 equiv). After 2 h at −78° C., was added 1-benzylpiperidin-4-one (26.5 g, 140 mmol, 1.40 equiv). The resulting solution was stirred for 0.5 h at −78° C. and then warmed to room temperature, and stirred overnight. The reaction was quenched by carefully adding 200 mL of water. The pH of the mixture was adjusted to 2~3 with hydrogen chloride (aq., 2 M). The aqueous phase was extracted with 3×500 mL of ethyl acetate and 3×500 mL of tetrahydrofuran. The combined organic layers were dried over anhydrous sodium sulfate and concentrated under reduced pressure to yield 38.9 g (crude) of the title compound as a yellow solid.

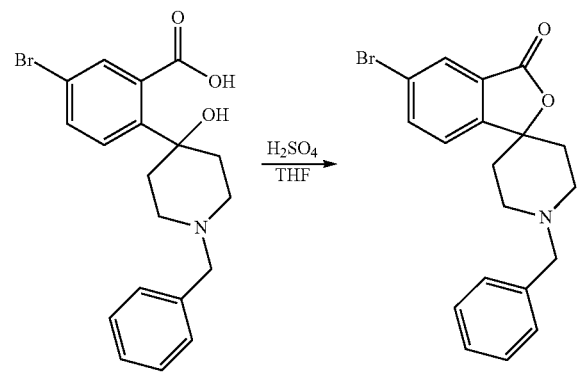

Compound 346.2. 1'-Benzyl-5-bromo-3H-spiro[isobenzofuran-1,4'-piperidin]-3-one Into a round-bottom flask, was placed a solution of crude compound 346.1 (38.9 g, 100 mmol, 1.00 equiv) in tetrahydrofuran (800 mL). To this was added sulfuric acid (8 mL) dropwise. The resulting solution was stirred overnight at reflux in an oil bath. The pH value of the solution was slowly adjusted to 10 with LiOH (aq.sat.). The aqueous phase was extracted with 3×500 mL of ethyl acetate and the combined organic layers were dried over anhydrous sodium sulfate and concentrated under vacuum. The residue was purified using silica gel column chromatography with ethyl acetate/petroleum ether (1:8~1:5) as eluent to furnish 8.00 g (22%) of the title compound as a white solid.

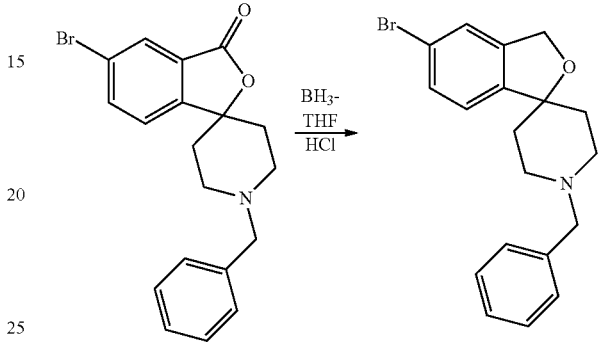

Compound 346.3. 1'-Benzyl-5-bromo-3H-spiro[isobenzofuran-1,4'-piperidine]

To a solution of compound 346.2 (10.0 g, 26.9 mmol, 1.00 equiv) in tetrahydrofuran (150 mL) under nitrogen at −10° C. was added dropwise BH$_3$-THF (135 mL, 5.00 equiv). The resulting solution was stirred for 30 min at room temperature and then heated at reflux temperature overnight. After cooling to −10° C., hydrogen chloride (aq., 6 M, 60 mL) was added dropwise at −10° C. The resulting solution was heated to reflux for 5 h in an oil bath. The reaction mixture was cooled and the pH of the solution was adjusted to 10 with potassium hydroxide (aq., 1 M). The aqueous phase was extracted with 2×200 mL of ethyl acetate and the combined organic layers were washed with 2×300 mL of brine, dried over sodium sulfate, and concentrated under reduced pressure to yield 15.0 g (crude) of the tile compound as a yellow oil.

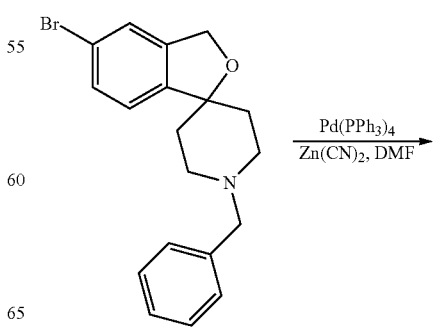

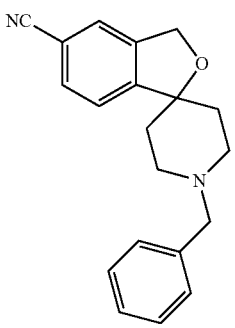

Compound 346.4. 1'-Benzyl-3H-spiro[isobenzofuran-1,4'-piperidine]-5-carbonitrile Into a three neck round-bottom flask, which was purged and maintained with an inert atmosphere of nitrogen, was placed a solution of compound 346.3 (12.0 g, 33.6 mmol, 1.00 equiv) in N,N-dimethylformamide (150 mL). Zn(CN)$_2$ (4.50 g, 38.5 mmol, 1.14 equiv) and Pd(PPh$_3$)$_4$ (4.00 g) were added to the reaction. The resulting solution was stirred overnight at 90° C. in an oil bath. The reaction mixture was cooled to rt, then quenched with 200 mL of FeSO$_4$ (aq. sat.) and diluted with ethyl acetate. The resulting mixture was stirred vigorously then filtered through celite and washed with 1 M FeSO$_4$, water, and ethyl acetate. The layers were separated and the aqueous phase was extracted with 2×200 mL of ethyl acetate. The combined organic layers were washed with 2×100 mL of sodium chloride (aq. sat.), dried over sodium sulfate, and concentrated under reduced pressure. The residue was purified using silica gel column chromatography with petroleum ether/ethyl acetate (10:1~5:1) as eluent to yield 9.12 g (89%) of the title compound as a yellow oil.

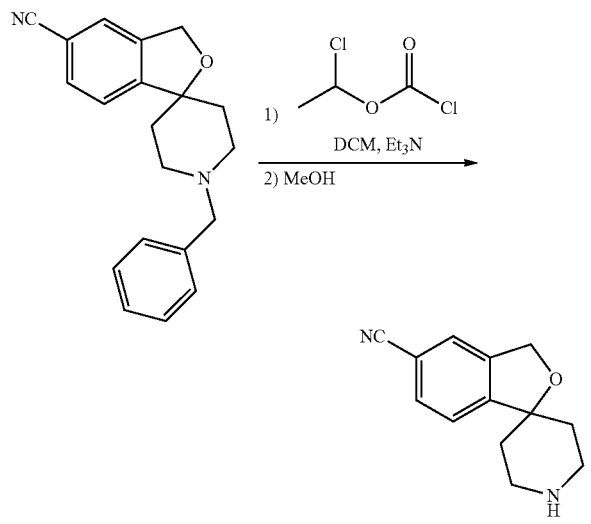

Compound 346.5. 3H-Spiro[isobenzofuran-1,4'-piperidine]-5-carbonitrile

To a solution of 346.4 (9.12 g, 30.0 mmol, 1.00 equiv) in DCE (150 mL) 0° C. was added dropwise 1-chloroethyl chloroformate (8.52 g, 60.0 mmol, 2.00 equiv). After stirring at ambient temperature for 30 min, triethylamine (9.09 g, 3.00 equiv) was carefully added to the mixture. The resulting solution was heated to reflux for 2 h in an oil bath, then concentrated under reduced pressure. The residue was dissolved in 100 mL of methanol and then heated to reflux for 1 h in an oil bath. The resulting mixture was concentrated under reduced pressure and the residue was taken up in water (100 mL). The pH of the mixture was adjusted to 10 with sodium hydroxide (aqueous, 1 M). The aqueous phase was extracted with 3×200 mL of ethyl acetate and the combined organic layers were washed with 2×100 mL of brine, dried over anhydrous sodium sulfate, and concentrated under reduced pressure. The residue was purified using silica gel column chromatography with ethyl acetate/methanol (100:0 to 3:1) as eluent to furnish 3.50 g (46%) of the title compound as a yellow solid.

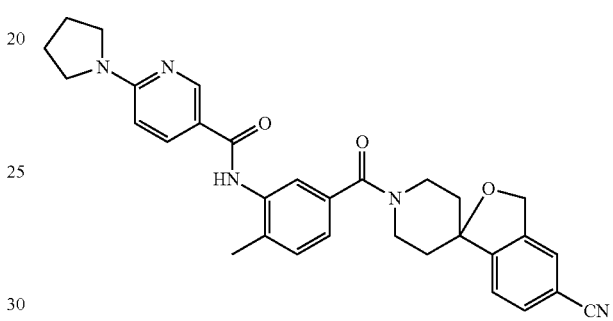

Compound 346. N-(5-(5-Cyano-3H-spiro[isobenzofuran-1,4'-piperidin]-1'-ylcarbonyl)-2-methylphenyl)-6-(pyrrolidin-1-yl)nicotinamide The title compound was prepared using procedures similar to those used for the preparation of compound 43 and using compound 346.5 was in place of compound 11.2. m/z (ES+) 522 (M+H)$^+$.

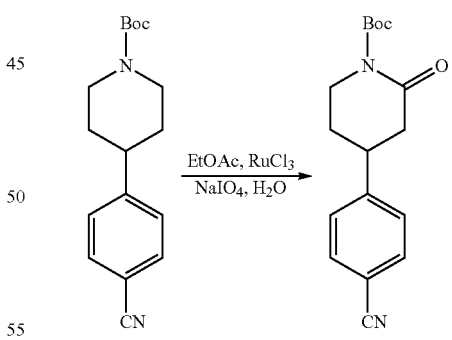

Compound 347.1. tert-Butyl 4-(4-cyanophenyl)-2-oxopiperidine-1-carboxylate

Into a round-bottom flask, was placed a solution of tert-butyl 4-(4-cyanophenyl)piperidine-1-carboxylate (compound 1.4, 515 mg, 1.80 mmol, 1.00 equiv) in ethyl acetate (5 mL). A solution of NaIO$_4$ (963 mg, 4.50 mmol, 2.50 equiv) in water (5 mL) and RuCl$_3$ (74.7 mg, 0.36 mmol, 0.20 equiv) was carefully added. The resulting mixture was stirred overnight at room temperature. The solids were removed by filtration and the filtrate was washed with 2×20 mL of water, dried over anhydrous sodium sulfate, and concentrated under reduced pressure to yield 432 mg (80%) of the title compound as a light yellow oil.

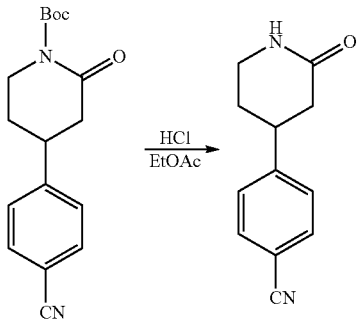 [SMILES: "EtOAc" ; CC(C)(C)OC(=O)N1CCC(c2ccc(C#N)cc2)CC1=O ; Cl ; N#Cc1ccc(C2CCNC(=O)C2)cc1]

Compound 347.2.
4-(2-Oxopiperidin-4-yl)benzonitrile

Into a round-bottom flask, was placed a solution of compound 347.1 (432 mg, 1.44 mmol, 1.00 equiv) in ethyl acetate (10 mL). Hydrogen chloride gas was bubbled through the solution and the resulting mixture was stirred for 0.5 h at room temperature. The solids were collected by filtration, then dissolved in 50 mL of ethyl acetate. The organic layer was dried over anhydrous sodium sulfate and concentrated under reduced pressure to yield 254 mg (88%) of the title compound as a white solid.

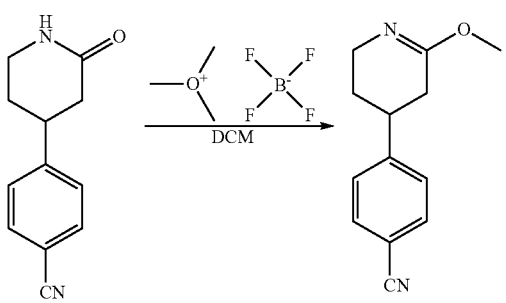

Compound 347.3. 4-(6-Methoxy-2,3,4,5-tetrahydro-pyridin-4-yl)benzonitrile

Into a round-bottom flask, was placed a solution of 4-(2-oxopiperidin-4-yl)benzonitrile (347.2, 220 mg, 1.10 mmol, 1.00 equiv) in dichloromethane (10 mL). Trimethyloxonium tetrafluoroborate (244.2 mg, 1.65 mmol, 1.50 equiv) was slowly added and the resulting mixture was stirred for 2 h at room temperature. The pH was carefully adjusted to 8 with sodium bicarbonate (aq.). The organic layer was washed with 2×20 mL of H$_2$O, dried over anhydrous sodium sulfate and concentrated under reduced pressure to yield 212 mg (90%) of the title compound as a white solid.

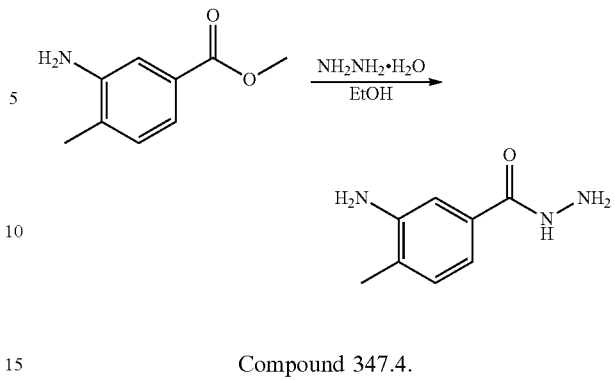

Compound 347.4.
3-Amino-4-methylbenzohydrazide

Into a round-bottom flask, was placed a solution of methyl 3-amino-4-methylbenzoate (6.60 g, 40.0 mmol, 1.00 equiv) in ethanol (100 mL). Hydrazine hydrate (10.0 g, 200 mmol, 5.00 equiv) was added to the reaction. The resulting solution was stirred for 2 h at 100° C. in an oil bath. After cooling to ambient temperature, the mixture was concentrated under reduced pressure. The residue was partitioned between water and ethyl acetate (20 mL). The aqueous layer was extracted with 4×20 mL of ethyl acetate and the combined organic layers were dried over anhydrous sodium sulfate, concentrated under reduced pressure, and dried under high-vacuum to yield 4.60 g (70%) of the title compound as a brown solid.

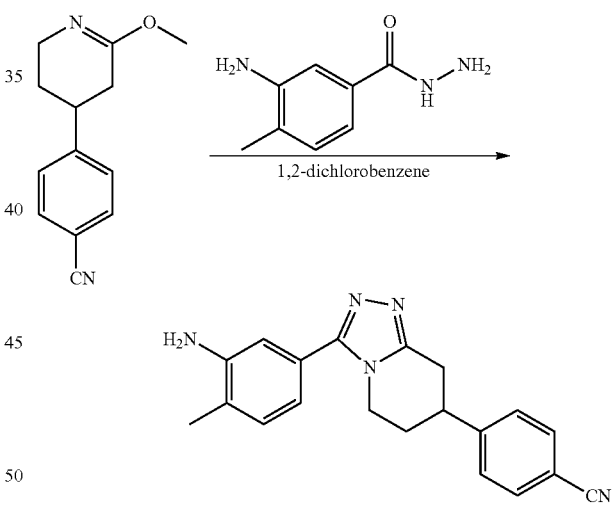

Compound 347.5. 4-(3-(3-Amino-4-methylphenyl)-5,6,7,8-tetrahydro-[1,2,4]triazolo[4,3-a]pyridin-7-yl)benzonitrile To a solution of 4-(6-methoxy-2,3,4,5-tetrahydropyridin-4-yl)benzonitrile (compound 347.3, 5.00 g, 23.36 mmol, 1.00 equiv) in 1,2-dichlorobenzene (100 mL) was added 3-amino-4-methylbenzohydrazide (compound 347.4, 4.63 g, 28.0 mmol, 1.20 equiv). The resulting solution was stirred overnight at 150° C. in an oil bath. After cooling to ambient temperature, the resulting mixture was purified using silica gel column chromatography with dichloromethane/methanol (1:0~100:1) as eluent to furnish 2.40 g (31%) of the title compound as a white solid.

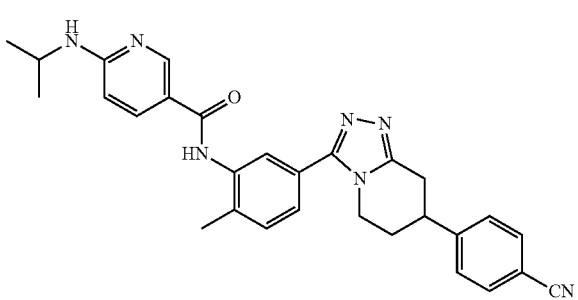 [SMILES: Cc1ccc(-c2nnc3n2CCC(c2ccc(C#N)cc2)C3)cc1NC(=O)c1ccc(NC(C)C)nc1]

Compound 347. N-(5-(7-(4-Cyanophenyl)-5,6,7,8-tetrahydro-[1,2,4]triazolo[4,3-a]pyridin-3-yl)-2-methylphenyl)-6-(isopropylamino)nicotinamide The title compound was prepared using procedures similar to those used for the preparation of compound 43 and using compound 347.5 was in place of compound 42.2. m/z (ES+) 492 (M+H)+.

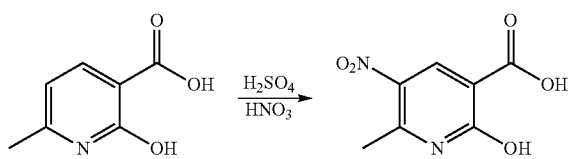

Compound 348.1. 2-Hydroxy-6-methyl-5-nitronicotinic acid

To a solution of 2-hydroxy-6-methylnicotinic acid (14.0 g, 91.5 mmol, 1.00 equiv) in sulfuric acid (conc.) (140 mL) at 0° C. was added dropwise a solution of HNO$_3$ (12.0 g, 190 mmol, 2.00 equiv) in sulfuric acid (conc.) (10 mL). The resulting mixture was then stirred for 2 h at 90° C., cooled to ambient temperature, and then quenched with 250 mL of ice water. The resulting solids were collected by filtration and dried in an oven under reduced pressure to yield 15.8 g (87%) of the title compound as a yellow solid.

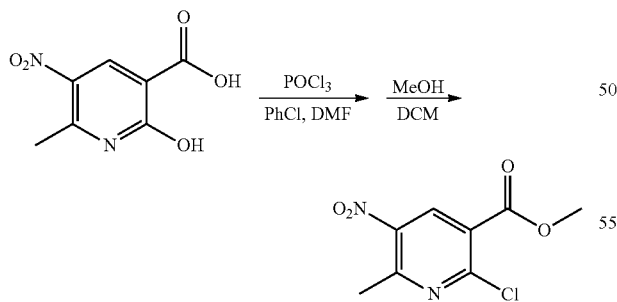

Compound 348.2. Methyl 2-chloro-6-methyl-5-nitronicotinate

To a solution of 2-hydroxy-6-methyl-5-nitronicotinic acid (compound 348.1, 15.0 g, 75.8 mmol, 1.00 equiv) in chlorobenzene (150 mL) were carefully added phosphoryl trichloride (45.0 g, 296 mmol, 4.00 equiv) and N,N-dimethylformamide (1.5 mL, 0.10 equiv). The resulting mixture was stirred for 2 h at 135° C., and then concentrated under reduced pressure. The residue was dissolved in 20 mL of DCM. To this was added methanol (20 mL) dropwise. The resulting solution was stirred for 3 h at 25° C., and then concentrated under reduced pressure. To the residue was carefully added 100 mL of water and the pH of the resulting mixture was slowly adjusted to 8 with sodium bicarbonate (aq.). The aqueous phase was extracted with 2×200 mL of ethyl acetate. The combined organic layers were dried over anhydrous sodium sulfate and concentrated under reduced pressure to yield 17.6 g (crude) of the title compound as a yellow solid.

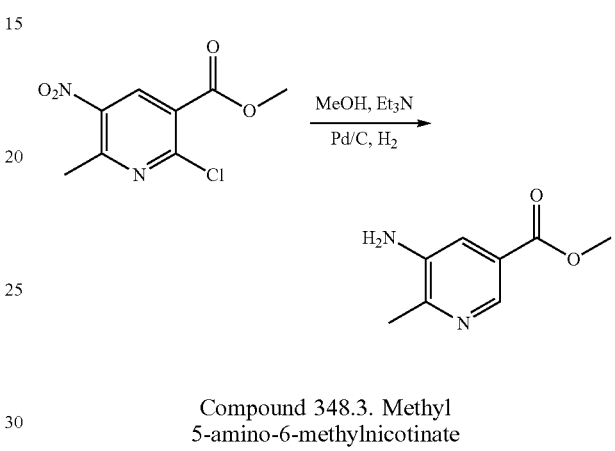

Compound 348.3. Methyl 5-amino-6-methylnicotinate

A round-bottom flask, containing a solution of methyl 2-chloro-6-methyl-5-nitronicotinate (12.8 g, 55.5 mmol, 1.00 equiv) in methanol (120 mL) was purged with nitrogen. Triethylamine (15.0 g, 149 mmol, 2.68 equiv) and palladium on carbon (1.30 g) were added. After further purging the flask with nitrogen, the atmosphere was changed to hydrogen and the resulting solution was stirred for 2 days at room temperature under atmospheric pressure. After purging the system with nitrogen, the solids were removed by filtration and the filtrate was concentrated under reduced pressure. The residue was purified using silica gel column chromatography with ethyl acetate/petroleum ether (1:50~1:5) as eluent to furnish 3.50 g (38%) of the title compound as a yellow solid.

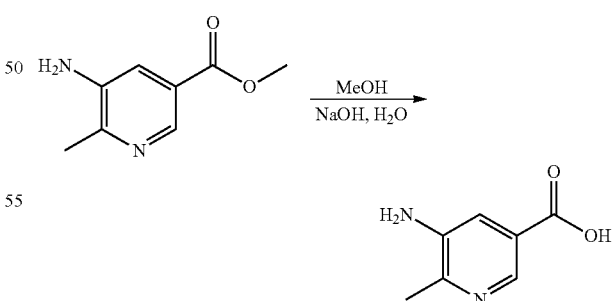

Compound 348.4. 5-Amino-6-methylnicotinic acid

Into a round-bottom flask, was placed a solution of methyl 5-amino-6-methylnicotinate (5.00 g, 30.1 mmol, 1.00 equiv) and sodium hydroxide (20 g) in MeOH/H$_2$O (80/200 mL). The resulting solution was heated at reflux overnight. After cooling to ambient temperature, the methanol was removed under reduced pressure. The pH of the remaining aqueous phase was adjusted to 4 with aqueous hydrogen chloride (2 M). The resulting mixture was then concentrated under reduced pressure to yield 5.00 g (crude) of the title compound as a yellow solid.

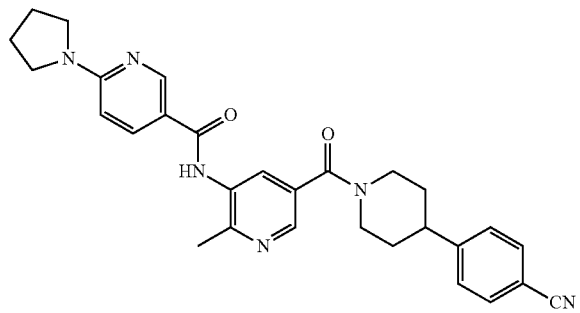 [SMILES: Cc1ncc(C(=O)N2CCC(c3ccc(C#N)cc3)CC2)cc1NC(=O)c1ccc(N2CCCC2)nc1]

Compound 348. N-(5-(4-(4-Cyanophenyl)piperidine-1-carbonyl)-2-methylpyridin-3-yl)-6-(pyrrolidin-1-yl)nicotinamide The title compound was prepared using procedures similar to those used for the preparation of compound 43 and using compounds 348.4 and 1.5 in place of 5-amino-2,4-dimethylbenzoic acid and compound 11.2 respectively. m/z (ES+) 495 (M+H)+.

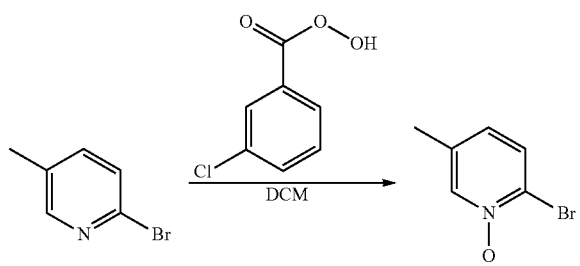

Compound 349.1. 2-Bromo-5-methylpyridine 1-oxide

Into a round-bottom flask, was placed a solution of 2-bromo-5-methylpyridine (10.0 g, 58.1 mmol, 1.00 equiv) in dichloromethane (250 mL). mCPBA (15.0 g, 86.9 mmol, 1.50 equiv) was added in several batches at room temperature. The resulting solution was stirred overnight at 30° C., then diluted with 50 mL of 2N sodium hydroxide (aq.). The pH value of the solution was adjusted to 10 with 2N sodium hydroxide (aq.). The aqueous phase was extracted with 3×100 mL of dichloromethane and the combined organic layers were dried over anhydrous magnesium sulfate and concentrated under reduced pressure to yield 11.0 g (91%) of 2-bromo-5-methylpyridin-1-ium-1-olate as a yellow solid.

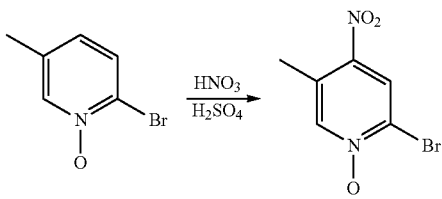

Compound 349.2. 2-Bromo-5-methyl-4-nitropyridine 1-oxide

Into a round-bottom flask, was placed HNO$_3$ (15 mL), sulfuric acid (20 mL). To this was added compound 349.1 (11.0 g, 52.7 mmol, 1.00 equiv, 90%) in several batches at room temperature. The resulting mixture was stirred overnight at 100° C., then cooled to ambient temperature and quenched with 50 mL of ice water. The pH was slowly adjusted to 2-3 with sodium hydroxide (aq. 2 M) and the resulting mixture was extracted with 3×50 mL of dichloromethane. The combined organic layers were dried over anhydrous magnesium sulfate and concentrated under reduced pressure. The residue was purified using silica gel column chromatography with ethyl acetate/petroleum ether (1:2) as eluent to furnish 3.00 g (23%) of the title compound as a yellow solid.

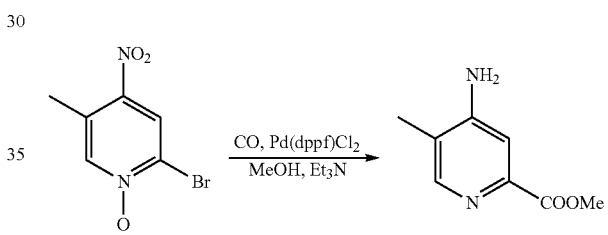

Compound 349.3. Methyl 4-amino-5-methylpicolinate

Into a 250-mL autoclave (30 atm, CAUTION: Carry out behind a blast shield) purged and maintained with an inert atmosphere of nitrogen, was placed a solution of 2-bromo-5-methyl-4-nitropyridine 1-oxide (compound 349.2, 3.00 g, 12.9 mmol, 1.00 equiv) in methanol (120 mL). Triethylamine (2.60 g, 25.7 mmol, 2.00 equiv) and Pd(dppf)Cl$_2$ (600 mg, 0.82 mmol, 0.06 equiv) were added to the reaction. The autoclave was purged and the mixture was then stirred overnight under 30 atm of CO (g) at 90° C. After cooling to ambient temperature, the mixture was concentrated under reduced pressure. The residue was purified using silica gel column chromatography with ethyl acetate:methanol (20:1) as eluent to furnish 1.50 g (67%) of methyl 4-amino-5-methylpyridine-2-carboxylate as a yellow solid.

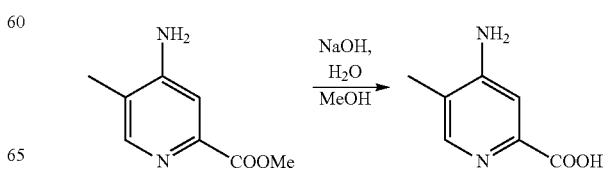

Compound 349.4. 4-Amino-5-methylpicolinic acid

A solution of methyl 4-amino-5-methylpicolinate (compound 349.3, 1.50 g, 8.12 mmol, 1.00 equiv, 90%) and 5N sodium hydroxide (aq., 15 mL) in methanol (15 mL) was stirred overnight at room temperature, then concentrated under reduced pressure. The residue was diluted with 20 mL of H$_2$O and the pH was adjusted to 3-4 with 2 M aqueous hydrogen chloride. The resulting precipitate was collected by filtration and dried to yield 0.8 g (58%) of the title compound as a yellow solid.

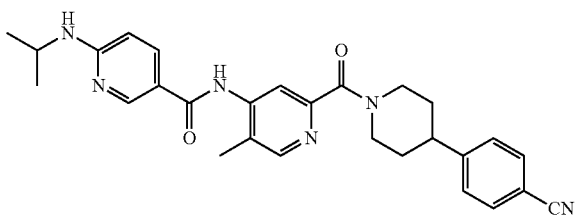 [SMILES: Cc1cnc(C(=O)N2CCC(c3ccc(C#N)cc3)CC2)cc1NC(=O)c1ccc(NC(C)C)nc1]

Compound 349. N-(2-(4-(4-Cyanophenyl)piperidine-1-carbonyl)-5-methylpyridin-4-yl)-6-(isopropylamino)nicotinamide The title compound was prepared using procedures similar to those used for the preparation of compound 43 and using compounds 349.4 and 1.5 in place of 5-amino-2,4-dimethylbenzoic acid and compound 11.2 respectively. 777/Z (ES+) 483 (M+H)$^+$.

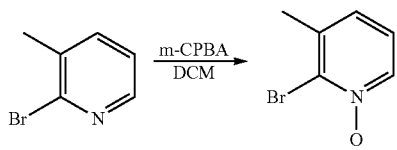

Compound 350.1. 2-Bromo-3-methylpyridine 1-oxide

The title compound was prepared (8.00 g, 85%) using a procedure similar to that used for the preparation of compound 349.1 and using 2-bromo-3-methylpyridine (8.60 g) in place of 2-bromo-5-methylpyridine.

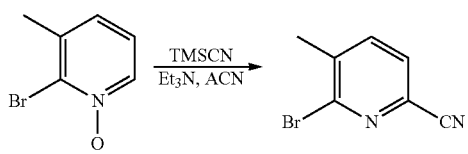

Compound 350.2. 6-Bromo-5-methylpicolinonitrile

To a solution of 2-bromo-3-methylpyridine 1-oxide (compound 350.1, 5.65 g, 30.1 mmol, 1.00 equiv) in acetonitrile (50 mL) were added triethylamine (6.10 g, 60.3 mmol, 2.00 equiv) and TMSCN (8.90 g, 3.00 equiv). The resulting solution was heated to reflux and stirred overnight in an oil bath, then cooled to ambient temperature and concentrated under reduced pressure. The residue was purified using silica gel column chromatography with ethyl acetate/petroleum ether (1:5) as eluent to yield 2.00 g (34%) of the title compound as a yellow solid.

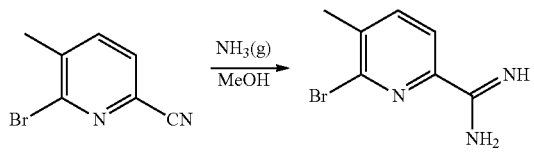

Compound 350.3. 6-Bromo-5-methylpicolinimidamide

Into a 50-mL sealed tube, was placed a solution of 6-bromo-5-methylpicolinonitrile (compound 350.2, 900 mg, 4.57 mmol, 1.00 equiv) in methanol (40 mL). NH$_3$ (g) was bubbled through the solution and the resulting solution was stirred overnight at 95° C. in an oil bath behind a blast shield. After cooling to ambient temperature, the mixture concentrated under reduced pressure to yield 800 mg (82%) of the title compound as a light brown solid.

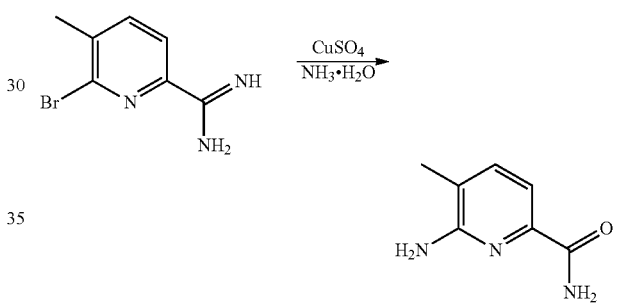

Compound 350.4. 6-Amino-5-methylpicolinamide

Into a 50-mL sealed tube, was placed a solution of 6-bromo-5-methylpicolinimidamide (compound 350.3, 800 mg, 3.74 mmol, 1.00 equiv) and CuSO$_4$ (80 mg) in NH$_3$.H$_2$O (40 mL). The resulting mixture was stirred overnight at 80° C. behind a blast shield. After cooling to ambient temperature, the mixture was then extracted with 2×50 mL of ethyl acetate. The combined organic layers were dried over anhydrous sodium sulfate and concentrated under reduced pressure to yield 750 mg (crude) of the title compound as a brown solid.

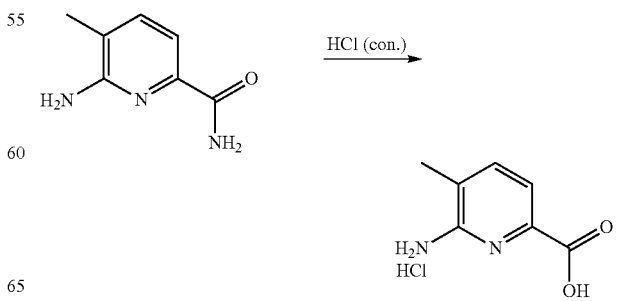

Compound 350.5. 6-Amino-5-methylpicolinic acid hydrochloride

Into a round-bottom flask was placed a solution of 6-amino-5-methylpicolinamide (compound 350.4, 500 mg, 3.31 mmol, 1.00 equiv) in hydrogen chloride (conc., 15 mL). The resulting solution was heated to reflux overnight in an oil bath, then concentrated under reduced pressure to yield 600 mg (crude) of the title compound as a light yellow solid.

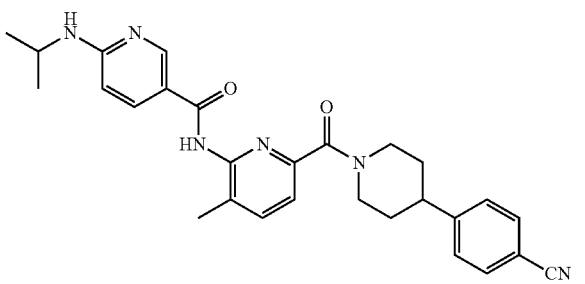 [SMILES: Cc1ccc(C(=O)N2CCC(c3ccc(C#N)cc3)CC2)nc1NC(=O)c1ccc(NC(C)C)nc1]

Compound 350. N-(6-(4-(4-Cyanophenyl)piperidine-1-carbonyl)-3-methylpyridin-2-yl)-6-(isopropylamino)nicotinamide The title compound was prepared using procedures similar to those used for the preparation of compound 43 and using compounds 350.5 and 1.5 in place of 5-amino-2,4-dimethylbenzoic acid and compound 11.2 respectively. m/z (ES+) 483 (M+H)+.

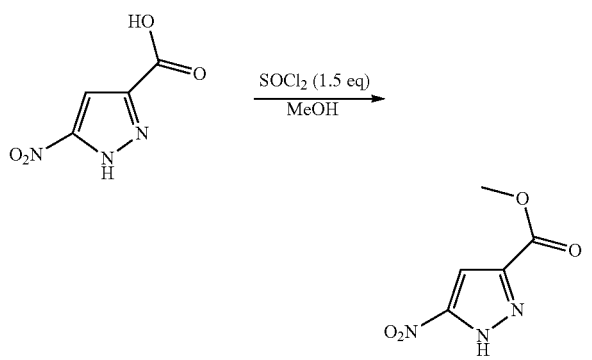

Compound 351.1. Methyl 5-nitro-1H-pyrazole-3-carboxylate

Into a round-bottom flask, which was purged and maintained with an inert atmosphere of nitrogen, was placed a solution of 5-nitro-1H-pyrazole-3-carboxylic acid (5.00 g, 31.9 mmol, 1.00 equiv) in methanol (150 mL). To this was added thionyl chloride (5.60 g, 47.8 mmol, 1.50 equiv) dropwise at 0° C. The resulting solution was stirred for 18 h at 30° C. in an oil bath, then concentrated under reduced pressure. The residue was purified using silica gel column chromatography with ethyl acetate/petroleum ether (1:30-1:10) as eluent to furnish 5.00 g (78%) of the title compound as a brown solid.

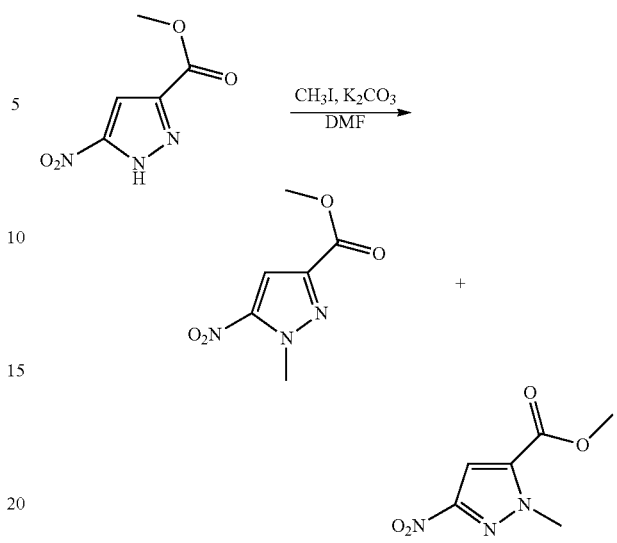

Compound 351.2 and 351.3. Methyl 1-methyl-5-nitro-1H-pyrazole-3-carboxylate and methyl 1-methyl-3-nitro-1H-pyrazole-5-carboxylate Into a round-bottom flask, which was purged and maintained with an inert atmosphere of nitrogen, was placed a solution of methyl 5-nitro-1H-pyrazole-3-carboxylate (3.00 g, 17.5 mmol, 1.00 equiv) in N,N-dimethylformamide (30 mL). Potassium carbonate (4.84 g, 35.0 mmol, 2.00 equiv) and CH₃I (2.98 g, 21.0 mmol, 1.20 equiv) were added at 0° C. The resulting solution was stirred for 2 h at 40° C. in an oil bath. After cooling to ambient temperature, the solids were removed by filtration followed by the addition of 120 mL of ice water. The mixture was extracted with 3×100 mL of ethyl acetate and the combined organic layers were dried over anhydrous sodium sulfate and concentrated under vacuum. The crude product was purified by re-crystallization from ether. This resulted in 1.10 g (34%) of methyl 1-methyl-3-nitro-1H-pyrazole-5-carboxylate as a white solid. m/z (ES+) 186 (M+H)+. ¹H-NMR, (300 MHz, DMSO-d₆, ppm): □ 7.57 (s, 1H), 4.22 (s, 3H), 3.91 (s, 3H). The filtrate was concentrated under vacuum and the crude product (2 g) was purified by Prep-HPLC with the following conditions (1#-Pre-HPLC-001(SHIMADZU)): Column. SunFire Prep C18, 19*150 mm 5 um; mobile phase, water with 0.05% TFA and CH₃CN (10% CH₃CN up to 56.5% in 10 min); Detector, uv 254 nm. The fractions containing pure compound were combined and concentrated to yield 470 mg (15%) of methyl 1-methyl-5-nitro-1H-pyrazole-3-carboxylate as a white solid. m/z (ES+) 186 (M+H)+. ¹H-NMR, (300 MHz, DMSO-d₆, ppm): □□7.64 (1H, s), 4.24 (3H, s), 3.87 (3H, s).

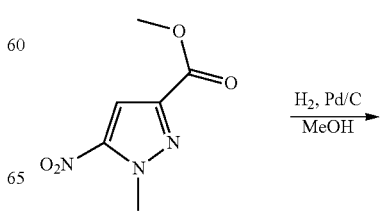

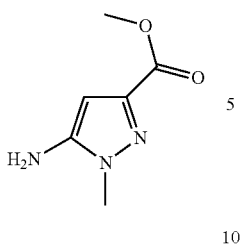

Compound 351.4. Methyl 5-amino-1-methyl-1H-pyrazole-3-carboxylate

To a solution of methyl 1-methyl-5-nitro-1H-pyrazole-3-carboxylate (351.2, 0.48 g, 2.60 mmol) in MeOH (15 ml) under nitrogen was added palladium on carbon (10%, 0.25 g). The flask was further degassed with nitrogen and filled with $H_2$ through a balloon. The mixture was stirred at room temperature for 1.5 hours. After purging the system with nitrogen, the reaction mixture was filtered through a Celite cake and concentrated to give 363 mg (90%) of a white solid. m/z (ES+) 156 (M+H)$^+$.

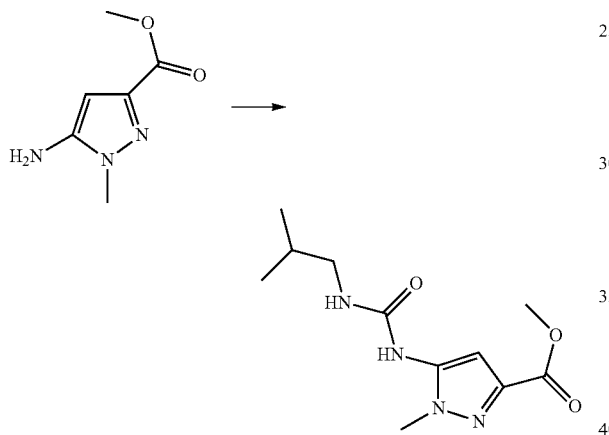

Compound 351.5. Methyl 5-(3-isobutylureido)-1-methyl-1H-pyrazole-3-carboxylate To a solution of methyl 5-amino-1-methyl-1H-pyrazole-3-carboxylate (compound 351.4, 0.088 g, 0.57 mmol) in THF (5 ml) was added triphosgene (0.084 g, 0.28 mmol) followed by DIEA (0.2 ml, 1.14 mmol). After the mixture was stirred at room temperature for 2 hours, isobutyl amine (0.225 ml, 2.28 mmol) was added. The resulting mixture was stirred at room temperature over night. The mixture was partitioned between water and EtOAc. The EtOAc layer was washed with 1 M aqueous $NaH_2PO_4$ solution followed by brine, dried with $Na_2SO_4$, and concentrated to give 120 mg (83%) of a light yellow solid. m/z (ES+) 255 (M+H)$^+$.

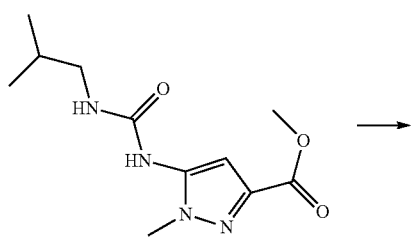

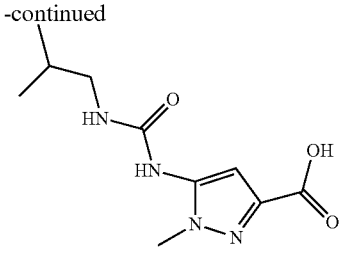

Compound 351.6. 5-(3-Isobutylureido)-1-methyl-1H-pyrazole-3-carboxylic acid

To a solution of methyl 5-(3-isobutylureido)-1-methyl-1H-pyrazole-3-carboxylate (compound 351.5, 0.12 g, 0.47 mmol) in MeOH (5 ml) was added 1 M LiOH in $H_2O$ (1.42 ml, 1.42 mmol). The mixture was stirred at room temperature for 5 hours. TLC showed the reaction was complete. The mixture was acidified to pH 3-4 at 0° C. and then was extracted with EcOAc (2×50 ml). The combined organic layers were dried with $Na_2SO_4$, filtered, and concentrated to give 110 mg (100%) of a clear oil. m/z (ES+) 241 (M+H)$^+$.

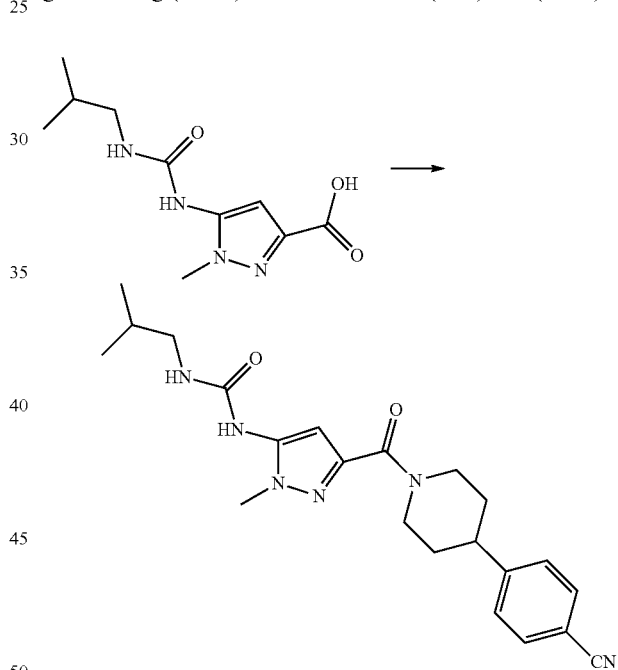

Compound 351. 1-(3-(4-(4-Cyanophenyl)piperidine-1-carbonyl)-1-methyl-1H-pyrazol-5-yl)-3-isobutylurea A solution of 5-(3-Isobutylureido)-1-methyl-1H-pyrazole-3-carboxylic acid (compound 351.6, 0.11 g, 0.46 mmol), 4-(piperidin-4-yl)benzonitrile HCl salt (compound 1.5, 0.097 g, 0.46 mmol), EDCI (0.090 g, 0.51 mmol), HOBT (0.065 g, 0.51 mmol, with 20% $H_2O$) and DIEA (0.22 ml, 1.38 mmol) in DMF (5 ml) was stirred at room temperature overnight. The reaction mixture was then diluted with 50 ml of ethyl acetate and washed with 2×20 ml of brine. The organic phase was dried over anhydrous sodium sulfate and concentrated under reduced pressure. The residue was purified using prep.-TLC and developed using neat ethyl acetate to yield 25 mg of the title compound as an off-white solid. m/z (ES+) 409 (M+H)+. $^1$H NMR (400 MHz, DMSO-d$_6$) δ8.46 (s, 1H), 7.76 (d, 2H), 7.49 (d, 2H), 6.48 (t, 1H), 6.37 (s, 1H), 4.84 (d, 1H), 4.63 (d, 1H), 3.65 (s, 3H), 3.14 (m, 1H), 2.92 (t, 3H), 2.79 (m, 2H), 1.85 (m, 1H), 1.67 (m, 1H), 1.57 (m, 2H), 0.87 (d, 6H).

The compounds in the following table were prepared using standard chemical manipulations, readily available starting materials, and procedures similar to those used for the preparation of compounds 346, 347, 348, 349, 350, and 351:

| Cmpnd # | Compound name | Compound Structure | Preparation similar to compound #(s) [m/z (ES+)] |
|---|---|---|---|
| 352 | 1-(5-(5-cyano-3H-spiro[isobenzofuran-1,4'-piperidin]-1'-ylcarbonyl)-2-methylphenyl)-3-isobutylurea | 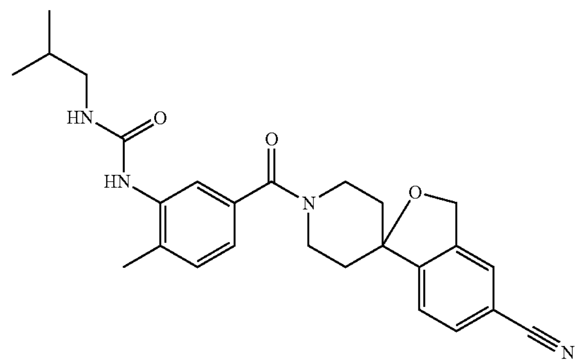 [SMILES: Cc1ccc(C(=O)N2CCC3(CC2)OCc2cc(C#N)ccc23)cc1NC(=O)NCC(C)C] | 346 and 64 [447 (M + H)+] |
| 353 | N-(5-(5-cyano-3H-spiro[isobenzofuran-1,4'-piperidin]-1'-ylcarbonyl)-2-methylphenyl)pyrrolidine-1-carboxamide | 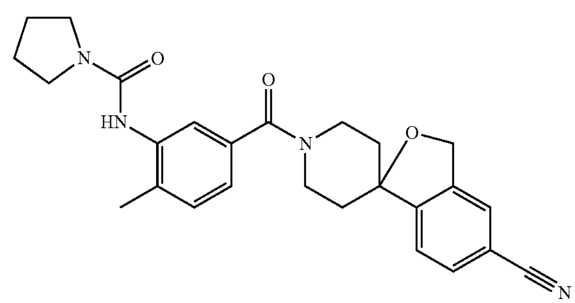 [SMILES: Cc1ccc(C(=O)N2CCC3(CC2)OCc2cc(C#N)ccc23)cc1NC(=O)N1CCCC1] | 346 and 64 [445 (M + H)+] |
| 354 | 1-(5-(5-cyano-3H-spiro[isobenzofuran-1,4'-piperidin]-1'-ylcarbonyl)-2-methylphenyl)-3-(2-methoxyethyl)urea | 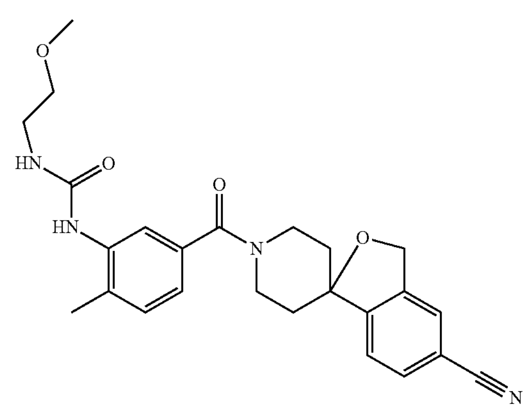 [SMILES: COCCNC(=O)Nc1cc(C(=O)N2CCC3(CC2)OCc2cc(C#N)ccc23)ccc1C] | 346 and 64 [449 (M + H)+] |

| Cmpnd # | Compound name | Compound Structure | Preparation similar to compound #(s) [m/z (ES+)] |
|---|---|---|---|
| 355 | N-(5-(5-cyano-3H-spiro[isobenzofuran-1,4'-piperidin]-1'-ylcarbonyl)-2-methylphenyl)-6-(isopropylamino)nicotinamide | 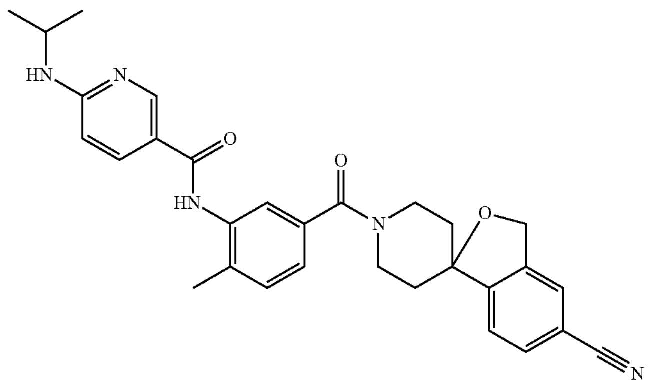 [SMILES: Cc1ccc(C(=O)N2CCC3(CC2)OCc2cc(C#N)ccc23)cc1NC(=O)c1ccc(NC(C)C)nc1] | 346 [510 (M + H)+] |
| 356 | 3-(5-(5-cyano-3H-spiro[isobenzofuran-1,4'-piperidin]-1'-ylcarbonyl)-2-methylphenyl)-1-(2-methoxyethyl)-1-methylurea | 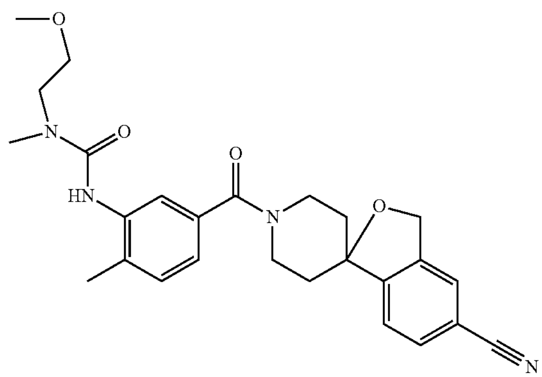 [SMILES: COCCN(C)C(=O)Nc1cc(C(=O)N2CCC3(CC2)OCc2cc(C#N)ccc23)ccc1C] | 346 and 64 [463 (M + H)+] |
| 357 | N-(5-(5-cyano-3H-spiro[isobenzofuran-1,4'-piperidin]-1'-ylcarbonyl)-2-methylphenyl)-6-(4-methylpiperazin-1-yl)nicotinamide | 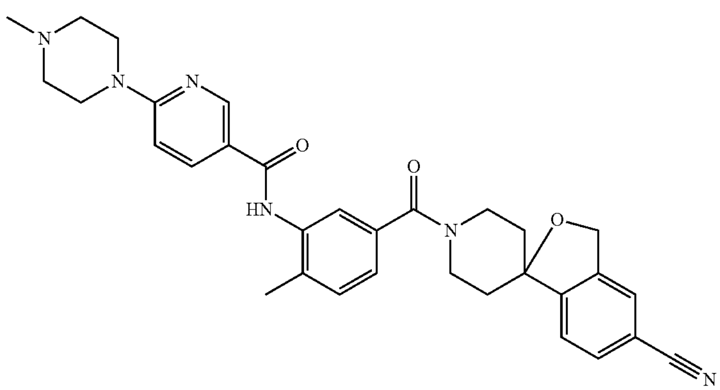 [SMILES: Cc1ccc(C(=O)N2CCC3(CC2)OCc2cc(C#N)ccc23)cc1NC(=O)c1ccc(N2CCN(C)CC2)nc1] | 346 [551 (M + H)+] |
| 358 | N-(5-(5-cyano-3H-spiro[isobenzofuran-1,4'-piperidin]-1'-ylcarbonyl)-2-methylphenyl)-6-(piperazin-1-yl)nicotinamide | 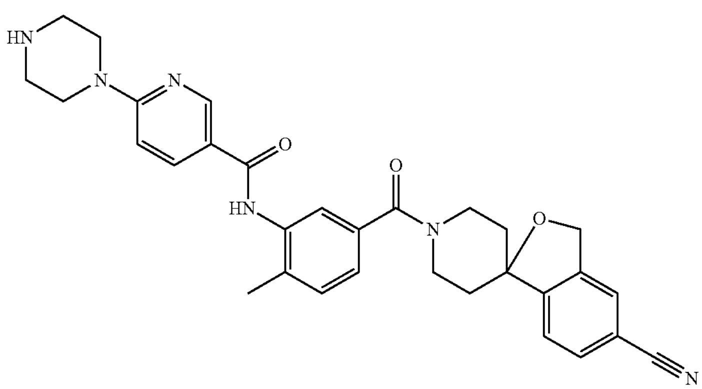 [SMILES: Cc1ccc(C(=O)N2CCC3(CC2)OCc2cc(C#N)ccc23)cc1NC(=O)c1ccc(N2CCNCC2)nc1] | 346 [537 (M + H)+] |

-continued

| Cmpnd # | Compound name | Compound Structure | Preparation similar to compound #(s) [m/z (ES+)] |
|---|---|---|---|
| 359 | N-(5-(5-cyano-3H-spiro[isobenzofuran-1,4'-piperidin]-1'-ylcarbonyl)-2-methylphenyl)-6-((2-methoxyethyl)(methyl)amino)nicotinamide | 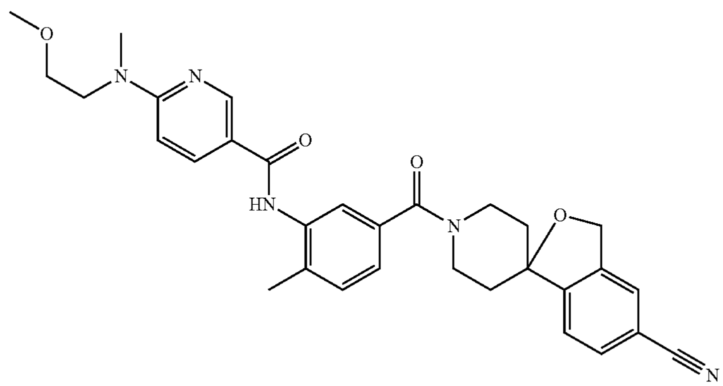 [SMILES: COCCN(C)c1ccc(C(=O)Nc2cc(C(=O)N3CCC4(CC3)OCc3cc(C#N)ccc34)ccc2C)cn1] | 346 [540 (M + H)+] |
| 360 | N-(5-(5-cyano-3H-spiro[isobenzofuran-1,4'-piperidin]-1'-ylcarbonyl)-2-methylphenyl)-6-((2-methoxyethyl)amino)nicotinamide | 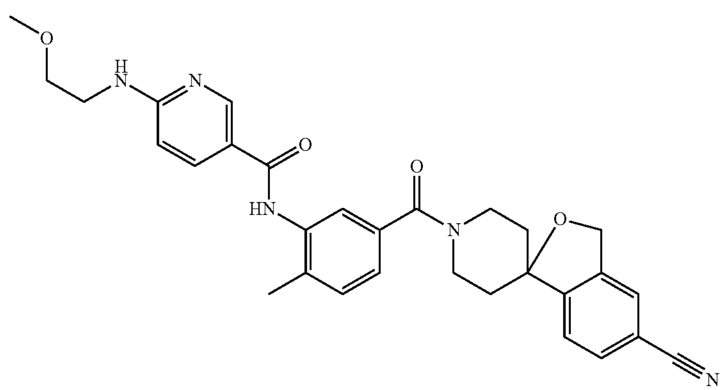 [SMILES: COCCNc1ccc(C(=O)Nc2cc(C(=O)N3CCC4(CC3)OCc3cc(C#N)ccc34)ccc2C)cn1] | 346 [526 (M + H)+] |
| 361 | N-(5-(5-cyano-3H-spiro[isobenzofuran-1,4'-piperidin]-1'-ylcarbonyl)-2-methylphenyl)-6-((2-hydroxyethyl)amino)nicotinamide | 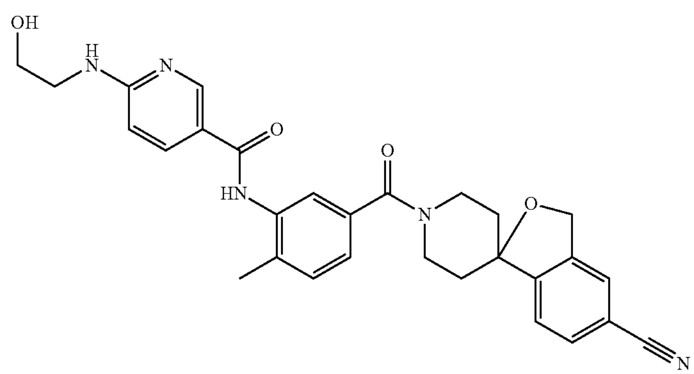 [SMILES: Cc1ccc(C(=O)N2CCC3(CC2)OCc2cc(C#N)ccc23)cc1NC(=O)c1ccc(NCCO)nc1] | 346 [512 (M + H)+] |
| 362 | N-(5-(5-cyano-3H-spiro[isobenzofuran-1,4'-piperidin]-1'-ylcarbonyl)-2-methylphenyl)-6-((2-hydroxyethyl)(methyl)amino)nicotinamide | 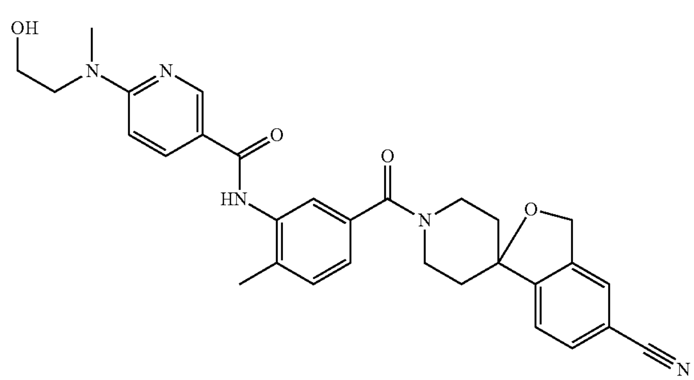 [SMILES: Cc1ccc(C(=O)N2CCC3(CC2)OCc2cc(C#N)ccc23)cc1NC(=O)c1ccc(N(C)CCO)nc1] | 346 [526 (M + H)+] |

| Cmpnd # | Compound name | Compound Structure | Preparation similar to compound #(s) [m/z (ES+)] |
|---|---|---|---|
| 363 | (S)-1-(5-(5-cyano-3H-spiro[isobenzofuran-1,4'-piperidin]-1'-ylcarbonyl)-2-methylphenyl)-3-((tetrahydrofuran-2-yl)methyl)urea | 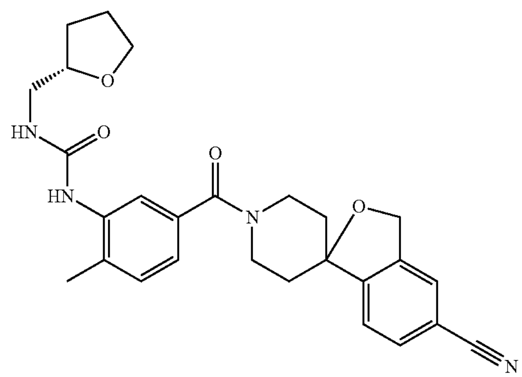 [SMILES: Cc1ccc(C(=O)N2CCC3(CC2)OCc2cc(C#N)ccc23)cc1NC(=O)NC[C@@H]1CCCO1] | 346 and 64 [475 (M + H)+] |
| 364 | 1-(5-(5-cyano-3H-spiro[isobenzofuran-1,4'-piperidin]-1'-ylcarbonyl)-2-methylpyridin-3-yl)-3-isobutylurea | 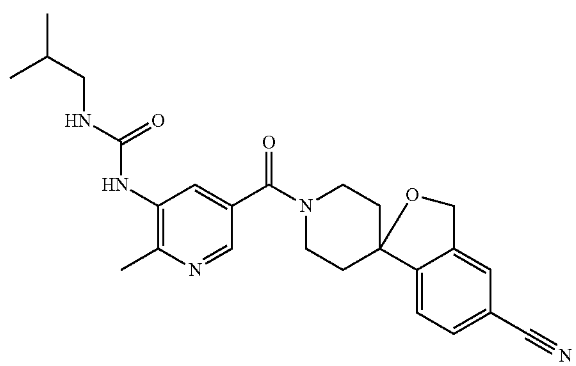 [SMILES: Cc1ncc(C(=O)N2CCC3(CC2)OCc2cc(C#N)ccc23)cc1NC(=O)NCC(C)C] | 346, 348, and 64 [448 (M + H)+] |
| 365 | 1-(5-(5-cyano-3H-spiro[isobenzofuran-1,4'-piperidin]-1'-ylcarbonyl)-2-methylphenyl)-3-(1-methylpiperidin-4-yl)urea | 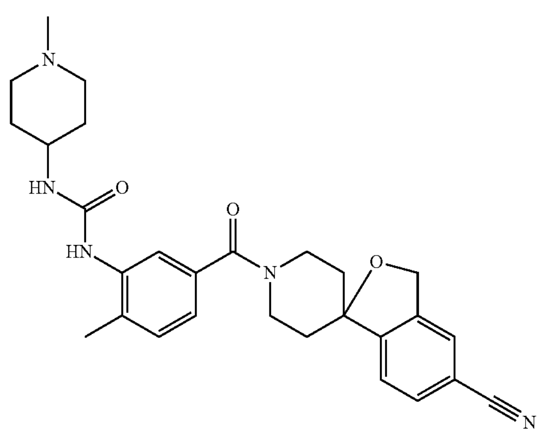 [SMILES: Cc1ccc(C(=O)N2CCC3(CC2)OCc2cc(C#N)ccc23)cc1NC(=O)NC1CCN(C)CC1] | 346 and 64 [488 (M + H)+] |

-continued

| Cmpnd # | Compound name | Compound Structure | Preparation similar to compound #(s) [m/z (ES+)] |
|---|---|---|---|
| 366 | N-(5-(5-cyano-3H-spiro[isobenzofuran-1,4'-piperidin]-1'-ylcarbonyl)-2-methylpyridin-3-yl)-6-(pyrrolidin-1-yl)nicotinamide | 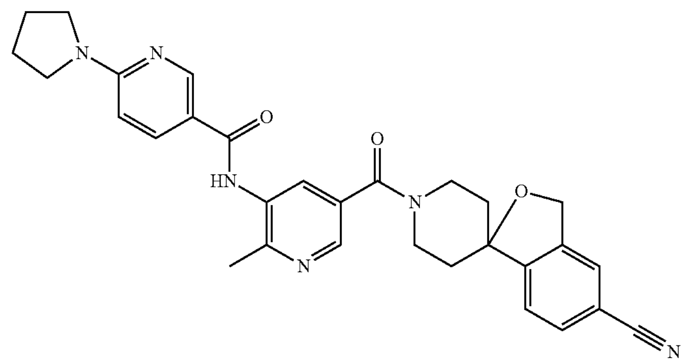 | 346 and 348 [523 (M + H)+] |
| 367 | 1-(5-(5-cyano-3H-spiro[isobenzofuran-1,4'-piperidin]-1'-ylcarbonyl)-2-methylpyridin-3-yl)-3-(2-methoxyethyl)urea | 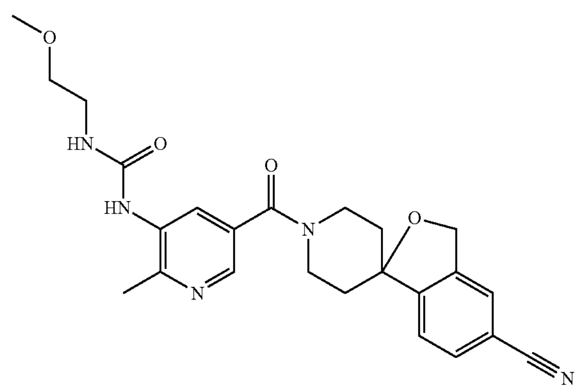 [SMILES: COCCNC(=O)Nc1cc(C(=O)N2CCC3(CC2)OCc2cc(C#N)ccc23)cnc1C] | 346, 348, and 64 [450 (M + H)+] |
| 368 | 1-(5-(5-cyano-3H-spiro[isobenzofuran-1,4'-piperidin]-1'-ylcarbonyl)-2-methylphenyl)-3-((tetrahydrofuran-3-yl)methyl)urea | 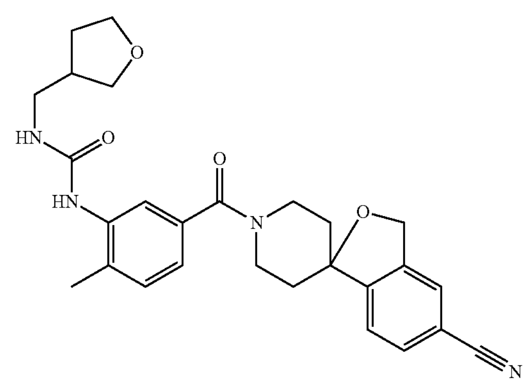 [SMILES: Cc1ccc(C(=O)N2CCC3(CC2)OCc2cc(C#N)ccc23)cc1NC(=O)NCC1CCOC1] | 346 and 64 [475 (M + H)+] |
| 369 | N-(5-(5-cyano-3H-spiro[isobenzofuran-1,4'-piperidin]-1'-ylcarbonyl)-2-methylpyridin-3-yl)-6-(isopropylamino)nicotinamide | 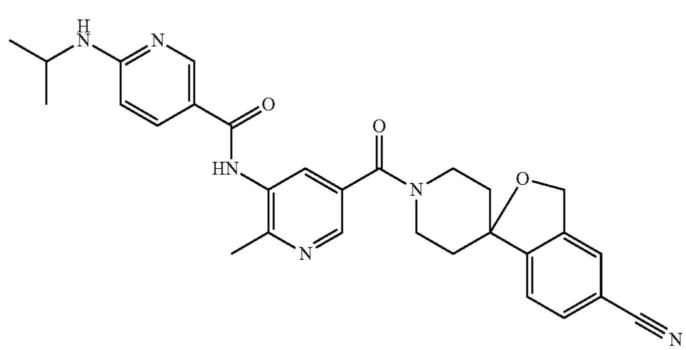 [SMILES: Cc1ncc(C(=O)N2CCC3(CC2)OCc2cc(C#N)ccc23)cc1NC(=O)c1ccc(NC(C)C)nc1] | 346 and 348 [511 (M + H)+] |

| Cmpnd # | Compound name | Compound Structure | Preparation similar to compound #(s) [m/z (ES+)] |
|---|---|---|---|
| 370 | N-(5-(5-cyano-3H-spiro[isobenzofuran-1,4'-piperidin]-1'-ylcarbonyl)-2-methylpyridin-3-yl)-6-(dimethylamino)nicotinamide | 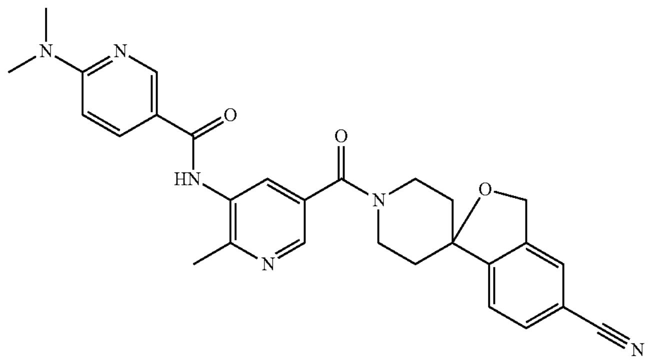 [SMILES: Cc1ncc(C(=O)N2CCC3(CC2)OCc2cc(C#N)ccc23)cc1NC(=O)c1ccc(N(C)C)nc1] | 346 and 348 [497 (M + H)+] |
| 371 | 6-(azetidin-1-yl)-N-(5-(5-cyano-3H-spiro[isobenzofuran-1,4'-piperidin]-1'-ylcarbonyl)-2-methylpyridin-3-yl)nicotinamide | 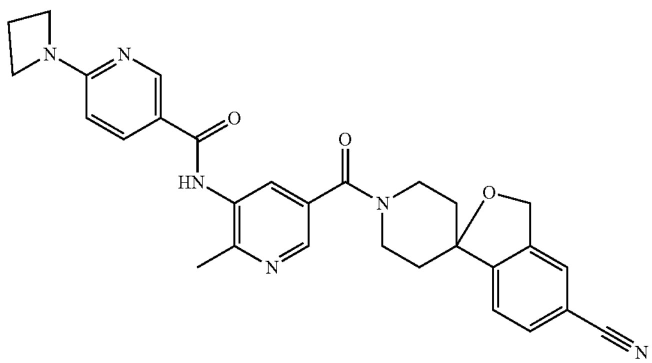 [SMILES: Cc1ncc(C(=O)N2CCC3(CC2)OCc2cc(C#N)ccc23)cc1NC(=O)c1ccc(N2CCC2)nc1] | 346 and 348 [509 (M + H)+] |
| 372 | N-(5-(5-cyano-3H-spiro[isobenzofuran-1,4'-piperidin]-1'-ylcarbonyl)-2-methylpyridin-3-yl)-6-((2-methoxyethyl)amino)nicotinamide | 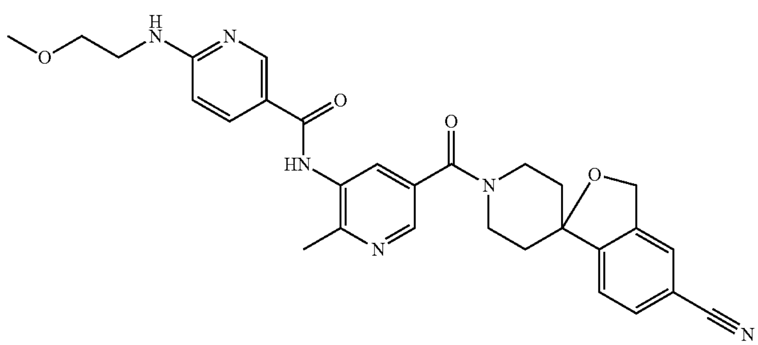 [SMILES: COCCNc1ccc(C(=O)Nc2cc(C(=O)N3CCC4(CC3)OCc3cc(C#N)ccc34)cnc2C)cn1] | 346 and 348 [527 (M + H)+] |
| 373 | N-(5-(7-(4-cyanophenyl)-5,6,7,8-tetrahydro-[1,2,4]triazolo[4,3-a]pyridin-3-yl)-2-methylphenyl)pyrrolidine-1-carboxamide | 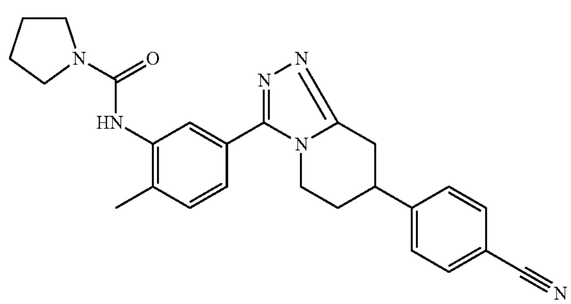 [SMILES: Cc1ccc(-c2nnc3n2CCC(c2ccc(C#N)cc2)C3)cc1NC(=O)N1CCCC1] | 347 and 64 [427 (M + H)+] |

| Cmpnd # | Compound name | Compound Structure | Preparation similar to compound #(s) [m/z (ES+)] |
|---|---|---|---|
| 374 | 1-(5-(7-(4-cyanophenyl)-5,6,7,8-tetrahydro-[1,2,4]triazolo[4,3-a]pyridin-3-yl)-2-methylphenyl)-3-(2-methoxyethyl)urea | 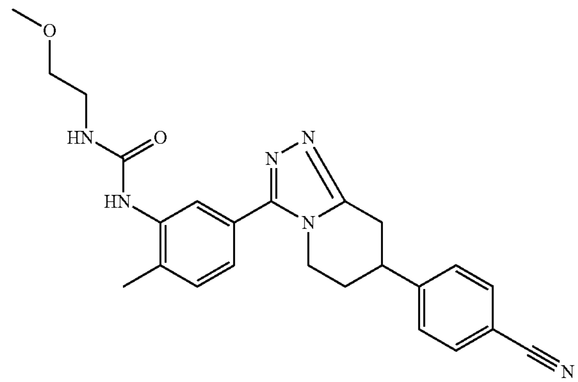 [SMILES: COCCNC(=O)Nc1cc(-c2nnc3n2CCC(c2ccc(C#N)cc2)C3)ccc1C] | 347 and 64 [431 (M + H)+] |
| 375 | 1-(5-(7-(4-cyanophenyl)-5,6,7,8-tetrahydro-[1,2,4]triazolo[4,3-a]pyridin-3-yl)-2-methylphenyl)-3-isobutylurea | 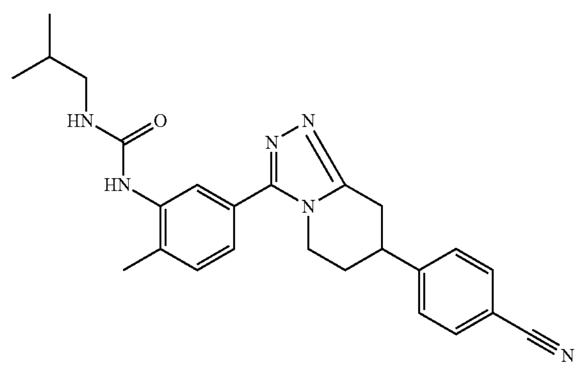 [SMILES: Cc1ccc(-c2nnc3n2CCC(c2ccc(C#N)cc2)C3)cc1NC(=O)NCC(C)C] | 347 and 64 [429 (M + H)+] |
| 376 | 1-(5-(4-(4-cyanophenyl)piperidine-1-carbonyl)-2-methylpyridin-3-yl)-3-isobutylurea | 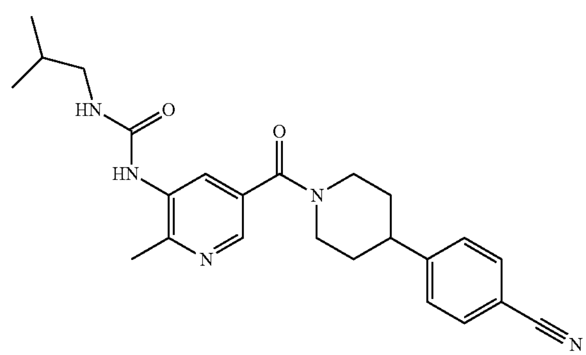 [SMILES: Cc1ncc(C(=O)N2CCC(c3ccc(C#N)cc3)CC2)cc1NC(=O)NCC(C)C] | 348 and 64 [420 (M + H)+] |
| 377 | 1-(5-(4-(4-cyanophenyl)piperidine-1-carbonyl)-2-methylpyridin-3-yl)-3-(2-methoxyethyl)urea | 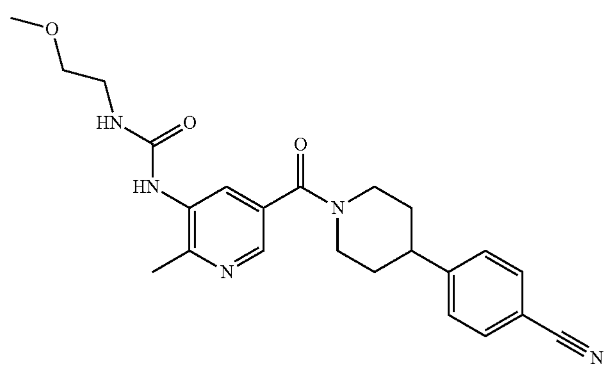 [SMILES: COCCNC(=O)Nc1cc(C(=O)N2CCC(c3ccc(C#N)cc3)CC2)cnc1C] | 348 and 64 [422 (M + H)+] |

| Cmpnd # | Compound name | Compound Structure | Preparation similar to compound #(s) [m/z (ES+)] |
|---|---|---|---|
| 378 | N-(5-(4-(4-cyanophenyl)piperidine-1-carbonyl)-2-methylpyridin-3-yl)pyrrolidine-1-carboxamide | 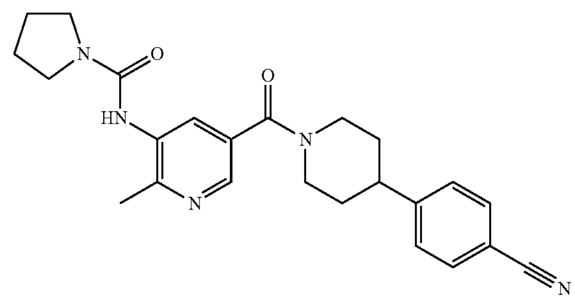 [SMILES: Cc1ncc(C(=O)N2CCC(c3ccc(C#N)cc3)CC2)cc1NC(=O)N1CCCC1] | 348 and 64 [418 (M + H)+] |
| 379 | N-(5-(4-(4-cyanophenyl)piperidine-1-carbonyl)-2-methylpyridin-3-yl)-6-(isopropylamino)nicotinamide | 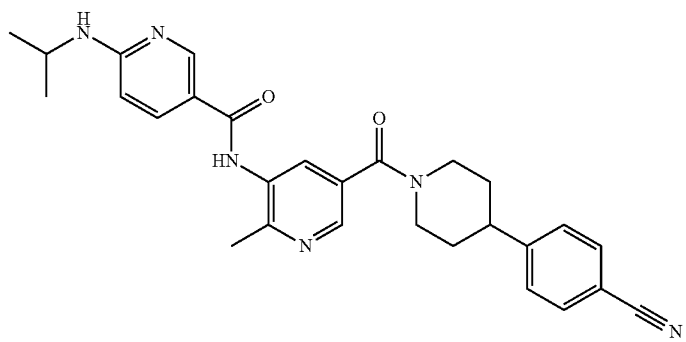 [SMILES: Cc1ncc(C(=O)N2CCC(c3ccc(C#N)cc3)CC2)cc1NC(=O)c1ccc(NC(C)C)nc1] | 348 [483 (M + H)+] |
| 380 | 1-(5-(5-cyano-3H-spiro[isobenzofuran-1,4'-piperidin]-1'-ylcarbonyl)-2-methylphenyl)-3-(piperidin-4-yl)urea | 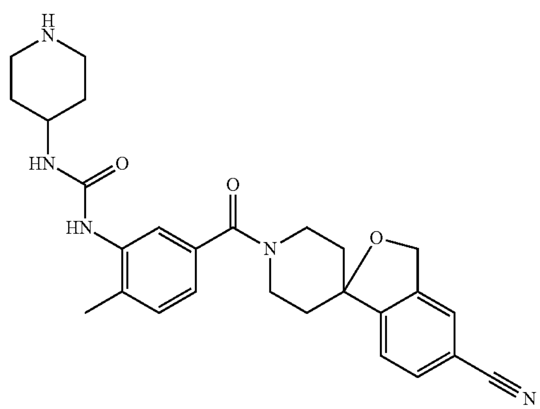 [SMILES: Cc1ccc(C(=O)N2CCC3(CC2)OCc2cc(C#N)ccc23)cc1NC(=O)NC1CCNCC1] | 348 and 64 [474 (M + H)+] |
| 381 | 3-(5-(5-cyano-3H-spiro[isobenzofuran-1,4'-piperidin]-1'-ylcarbonyl)-2-methylphenyl)-1-methyl-1-((tetrahydrofuran-3-yl)methyl)urea | 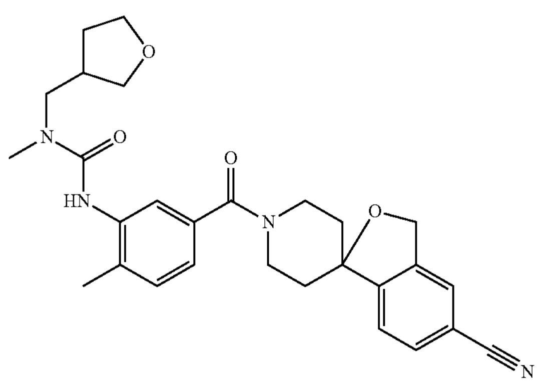 [SMILES: Cc1ccc(C(=O)N2CCC3(CC2)OCc2cc(C#N)ccc23)cc1NC(=O)N(C)CC1CCOC1] | 348 and 64 [489 (M + H)+] |

-continued

| Cmpnd # | Compound name | Compound Structure | Preparation similar to compound #(s) [m/z (ES+)] |
|---|---|---|---|
| 382 | 1-(2-(4-(4-cyanophenyl)piperidine-1-carbonyl)-5-methylpyridin-4-yl)-3-(tetrahydrofuran-3-yl)urea | 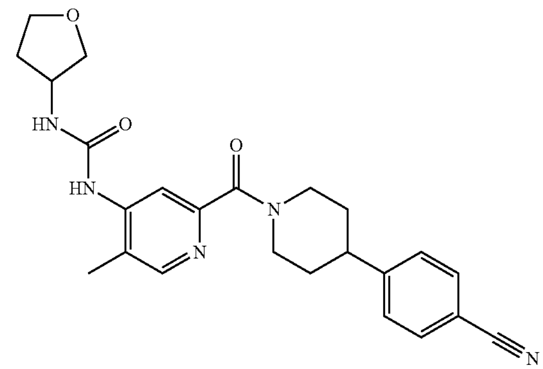 [SMILES: Cc1cnc(C(=O)N2CCC(c3ccc(C#N)cc3)CC2)cc1NC(=O)NC1CCOC1] | 349 and 64 [434 (M + H)+] |
| 383 | 1-(6-(4-(4-cyanophenyl)piperidine-1-carbonyl)-3-methylpyridin-2-yl)-3-(tetrahydrofuran-3-yl)urea | 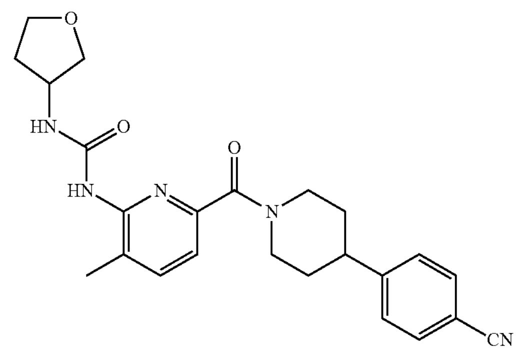 [SMILES: Cc1ccc(C(=O)N2CCC(c3ccc(C#N)cc3)CC2)nc1NC(=O)NC1CCOC1] | 321 and 64 [434 (M + H)+] |
| 384 | N-(5-(4-(4-cyanophenyl)piperidine-1-carbonyl)-1-methyl-1H-pyrazol-3-yl)-6-(isobutylamino)nicotinamide | 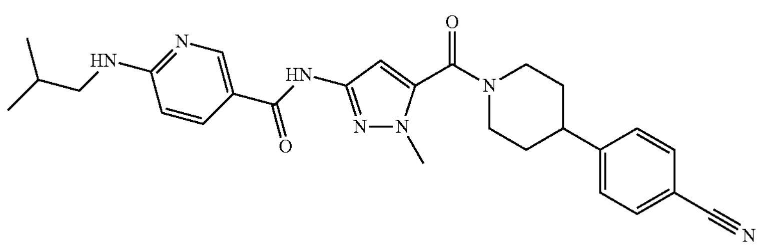 [SMILES: CC(C)CNc1ccc(C(=O)Nc2cc(C(=O)N3CCC(c4ccc(C#N)cc4)CC3)n(C)n2)cn1] | 351 and 43 [486 (M + H)+] |
| 385 | N-(5-(4-(4-cyanophenyl)piperidine-1-carbonyl)-1-methyl-1H-pyrazol-3-yl)-6-(isopropylamino)nicotinamide | 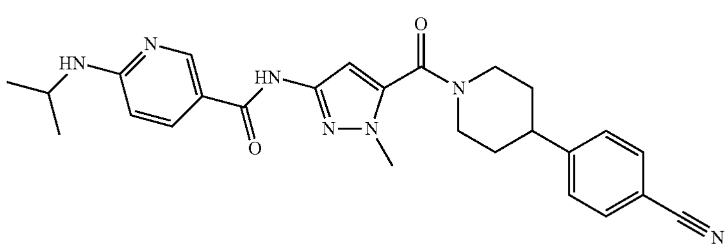 [SMILES: CC(C)Nc1ccc(C(=O)Nc2cc(C(=O)N3CCC(c4ccc(C#N)cc4)CC3)n(C)n2)cn1] | 351 and 43 [472 (M + H)+] |
| 386 | N-(3-(4-(4-cyanophenyl)piperidine-1-carbonyl)-1H-pyrazol-5-yl)-6-(isobutylamino)nicotinamide | 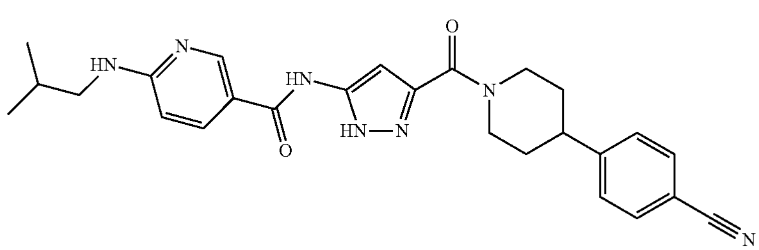 [SMILES: CC(C)CNc1ccc(C(=O)Nc2cc(C(=O)N3CCC(c4ccc(C#N)cc4)CC3)n[nH]2)cn1] | 351 and 43 [472 (M + H)+] |

-continued

| Cmpnd # | Compound name | Compound Structure | Preparation similar to compound #(s) [m/z (ES+)] |
|---|---|---|---|
| 387 | N-(3-(4-(4-cyanophenyl)piperidine-1-carbonyl)-1H-pyrazol-5-yl)-6-(isopropylamino)nicotinamide | 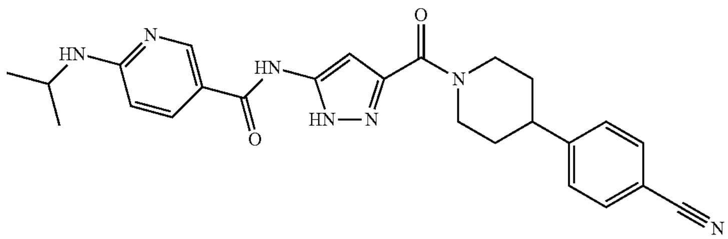 [SMILES: CC(C)Nc1ccc(C(=O)Nc2cc(C(=O)N3CCC(c4ccc(C#N)cc4)CC3)n[nH]2)cn1] | 351 and 43 [458 (M + H)+] |
| 388 | 1-(5-(4-(4-cyanophenyl)piperidine-1-carbonyl)-1-methyl-1H-pyrazol-3-yl)-3-isobutylurea | 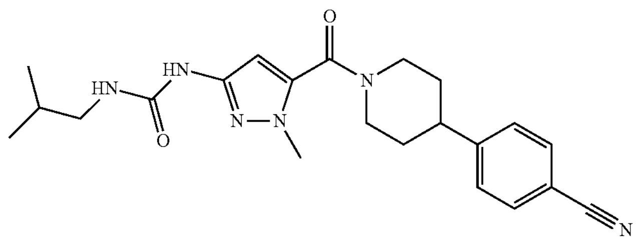 [SMILES: CC(C)CNC(=O)Nc1cc(C(=O)N2CCC(c3ccc(C#N)cc3)CC2)n(C)n1] | 351 and 64 [409 (M + H)+] |
| 389 | 1-(5-(4-(4-cyanophenyl)piperidine-1-carbonyl)-1-methyl-1H-pyrazol-3-yl)-3-isopropylurea | 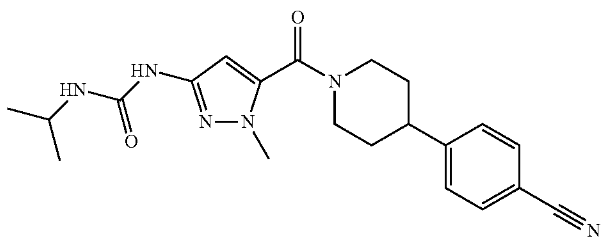 [SMILES: CC(C)NC(=O)Nc1cc(C(=O)N2CCC(c3ccc(C#N)cc3)CC2)n(C)n1] | 351 and 64 [395 (M + H)+] |
| 390 | 1-(3-(4-(4-cyanophenyl)piperidine-1-carbonyl)-1-methyl-1H-pyrazol-5-yl)-3-isopropylurea | 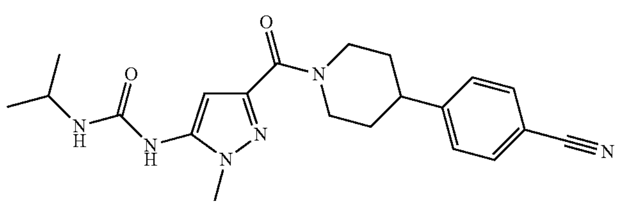 [SMILES: CC(C)NC(=O)Nc1cc(C(=O)N2CCC(c3ccc(C#N)cc3)CC2)nn1C] | 351 and 64 [395 (M + H)+] |
| 391 | N-(3-(4-(4-cyanophenyl)piperidine-1-carbonyl)-1-methyl-1H-pyrazol-5-yl)-6-(isobutylamino)nicotinamide | 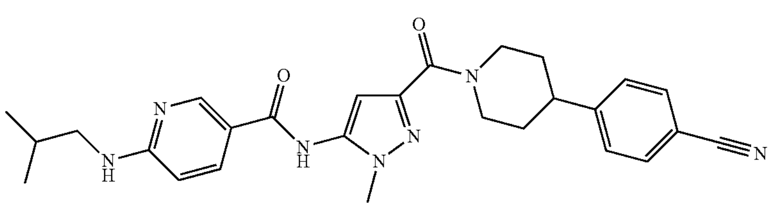 [SMILES: CC(C)CNc1ccc(C(=O)Nc2cc(C(=O)N3CCC(c4ccc(C#N)cc4)CC3)nn2C)cn1] | 351 and 43 [486 (M + H)+] |

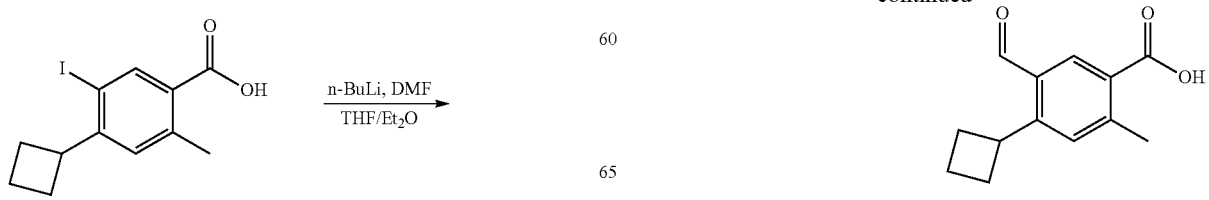

Compound 392.1.
4-Cyclobutyl-5-formyl-2-methylbenzoic acid

Into a three neck round-bottom flask, which was purged and maintained with an inert atmosphere of nitrogen, was placed a solution of 4-cyclobutyl-5-iodo-2-methylbenzoic acid (compound 230.1, 5.00 g, 12.7 mmol, 1.00 equiv, 80%) in a solvent mixture of tetrahydrofuran and Et$_2$O (50/50 mL). This was followed by the addition of butyllithium (15 mL, 2.50 equiv, 95%) dropwise with stirring at −78° C. To this was added N,N-dimethylformamide (2.50 g, 32.5 mmol, 2.00 equiv). The resulting solution was stirred for 1 h at −78° C. and then carefully quenched by slow addition of 50 mL of NH$_4$Cl (aq.). The pH was adjusted to 1-2 with hydrogen chloride (6 M). The resulting solution was diluted with 100 mL of ethyl acetate, then washed with 4×50 mL of brine. The organic layer was dried over anhydrous sodium sulfate and concentrated under vacuum. The residue was purified using silica gel column chromatography with ethyl acetate/petroleum ether (1:1) as eluent to furnish 1.62 g (41%) of 4-cyclobutyl-5-formyl-2-methylbenzoic acid as a white solid.

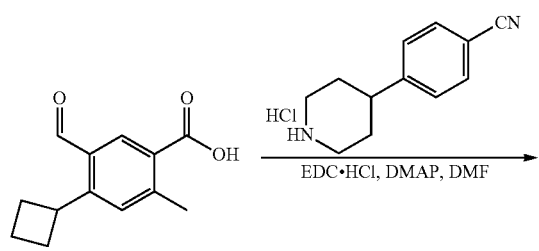

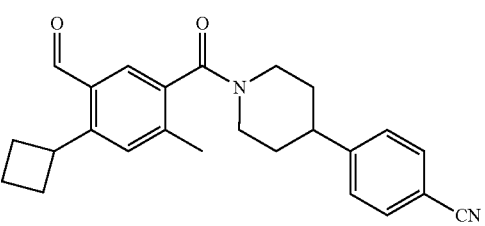

Compound 392.2. 4-(1-(4-Cyclobutyl-5-formyl-2-methylbenzoyl)piperidin-4-yl)benzonitrile Into a round-bottom flask, was placed a solution of 4-cyclobutyl-5-formyl-2-methylbenzoic acid (compound 392.1, 490 mg, 1.57 mmol, 1.00 equiv, 70%) in N,N-dimethylformamide (8 mL). Compound 1.5 (500 mg, 1.57 mmol, 1.00 equiv), EDC.HCl (860 mg, 4.26 mmol, 2.00 equiv, 95%) and 4-dimethylaminopyridine (550 mg, 4.28 mmol, 2.00 equiv, 95%) were added to the reaction mixture. The resulting solution was stirred overnight at room temperature, and then diluted with 30 mL of ethyl acetate. The resulting mixture was washed with 4×30 mL of brine, then dried over anhydrous sodium sulfate and concentrated under reduced pressure. The residue was purified using silica gel column chromatography with ethyl acetate/petroleum ether (1:2) as eluent to yield 560 mg (74%) of the title compound as a white solid.

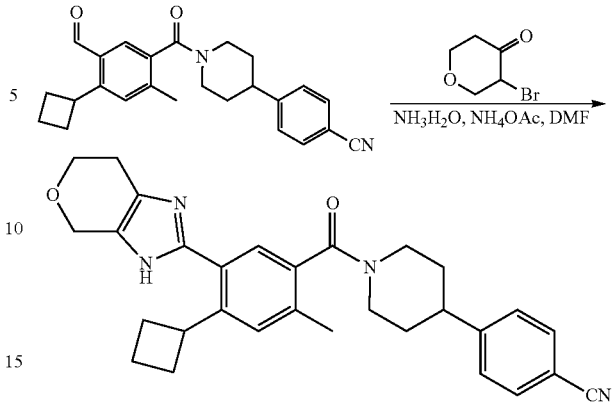

Compound 392. 4-(1-(4-Cyclobutyl-5-formyl-2-methylbenzoyl)piperidin-4-yl)benzonitrile Into around-bottom flask, was placed a solution of 4-[1-[(4-cyclobutyl-5-formyl-2-methylphenyl)carbonyl]piperidin-4-yl]benzonitrile (392.2, 300 mg, 0.74 mmol, 1.00 equiv, 95%) in N,N-dimethylformamide (10 mL). 3-Bromo-dihydro-2H-pyran-4(3H)-one (compound 1.10.1, 210 mg, 1.17 mmol, 1.00 equiv), ammonia (82 mg, 0.59 mmol, 3.00 equiv, 25% aq.), and NH$_4$OAc (270 mg, 2.81 mmol, 4.50 equiv, 80%) were added and the resulting mixture was stirred overnight at 130° C. under nitrogen. After cooling to room temperature, the mixture was diluted with 50 mL of ethyl acetate, washed with 4×50 mL of brine, dried over anhydrous sodium sulfate, and concentrated under reduced pressure. The residue was purified using silica gel column chromatography with ethyl acetate as eluent. The crude product (~80 mg) was further purified by Prep-HPLC with the following conditions (1#-Pre-HPLC-001(SHIMADZU)): Column, SunFire Prep C18, 19*150 min 5 um; mobile phase, water with 0.05% TFA and CH$_3$CN (26% CH$_3$CN up to 41% in 7 min, up to 100% in 3 min, down to 26% in 2 min); Detector, Waters 2489 254 & 220 nm. The fractions containing pure compound were combined and lyophilized to yield 24.6 mg (7%) of the title compound as a white solid. m/z (ES+) 481 (M+H)$^+$. $^1$H NMR (300 MHz, CD$_3$OD): δ 7.67 (d, J=7.8 Hz, 2H), 4.47 (d, J=8.1 Hz, 2H), 7.33 (br s, 1H), 7.26 & 7.15 (2 singlets, amide rotamers, Ar—H, 1H), ~4.9 (1H partially obscured by water peak), 4.68 (s, 2H), 4.06-3.88 (m, 3H), 3.73-3.58 (m, 1H), 3.33-3.18 (m, 1H), 3.07-2.92 (m, 2H), 2.83-2.73 (m, 2H), 2.44 & 2.34 (2 singlets, amide rotamers, Ar—CH$_3$, 3H), 2.25-1.91 (m, 6H), 1.91-1.50 (m, 4H). $^1$H NMR (400 MHz, CDCl$_3$): δ 7.64 (m, 2H), 7.34 (m, 2H), 7.13-6.93 (m, 2H), 4.99 (m, 1H), 4.75 (s, 2H), 3.98 (m, 2H), 3.73 (m, 1H), 3.53 (m, 1H), 3.31-2.83 (m, 5H), 2.41 (m, 1H), 2.37-1.61 (m, 11H), 1.44 (m, 1H).

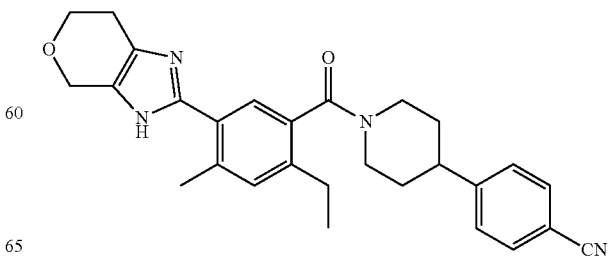

Compound 393. 4-(1-(2-Ethyl-4-methyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compounds 1 and 2 but compound 211.2 was used in place of compound 2.2. m/z (ES+) 455 (M+H)$^+$.

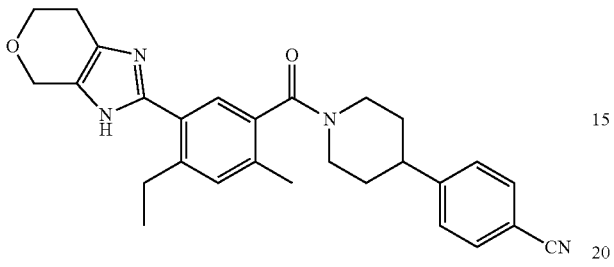

Compound 394. 4-(1-(4-Ethyl-2-methyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 393 but compound 152.1 was used in place of methyl 2-bromo-4-methylbenzoate. m/z (ES+) 455 (M+H)$^+$.

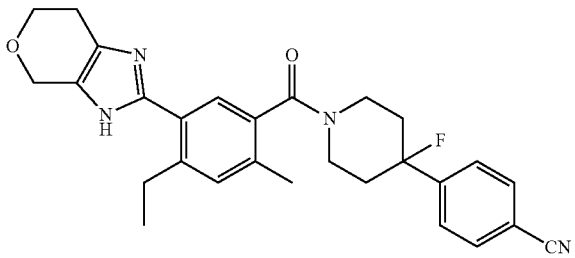

Compound 395. 4-(1-(4-Ethyl-2-methyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 394 but compound 11.2 HCl salt was used in place of compound 1.5. m/z (ES+) 473 (M+H)$^+$.

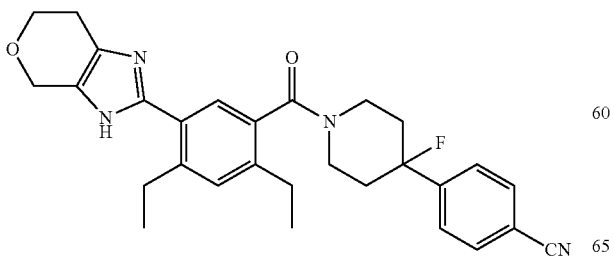

Compound 396. 4-(1-(2,4-Diethyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compounds 1 and 2 except compounds 204.3 and 11.2 were used in place of compounds 2.2 and 1.5 respectively. m/z (ES+) 487 (M+H)$^+$.

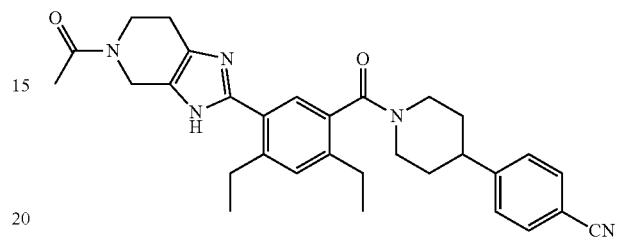

Compound 397. 4-(1-(5-(5-Acetyl-4,5,6,7-tetrahydro-3H-imidazo[4,5-c]pyridin-2-yl)-2,4-diethylbenzoyl)piperidin-4-yl)benzonitrile The title compound was prepared using standard chemical manipulations and procedures similar to those used for the preparation of compounds 1 and 2 except compound 204.3 was used in place of compound 2.2. m/z (ES+) 510 (M+H)$^+$.

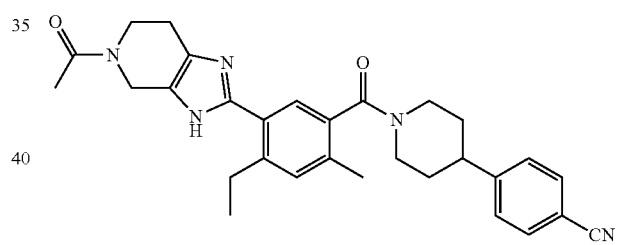

Compound 398. 4-(1-(5-(5-Acetyl-4,5,6,7-tetrahydro-3H-imidazo[4,5-c]pyridin-2-yl)-4-ethyl-2-methylbenzoyl)piperidin-4-yl)benzonitrile The title compound was prepared using standard chemical manipulations and procedures similar to those used for the preparation of compounds 1, 2, and 394. m/z (ES+) 496 (M+H)$^+$.

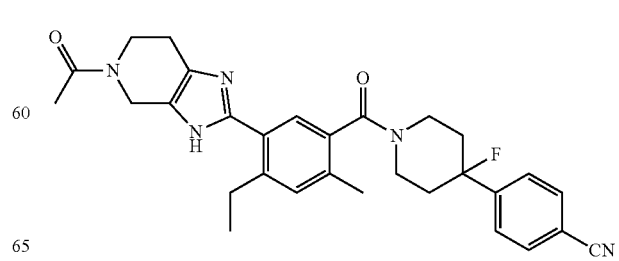

Compound 399. 4-(1-(5-(5-Acetyl-4,5,6,7-tetra-hydro-3H-imidazo[4,5-c]pyridin-2-yl)-4-ethyl-2-methylbenzoyl)-4-fluoropiperidin-4-yl)benzonitrile The title compound was prepared using standard chemical manipulations and procedures similar to those used for the preparation of compounds 1, 2, and 394, but using compound 11.2 HCl salt in place of compound 1.5. m/z (ES+) 514 (M+H)+.

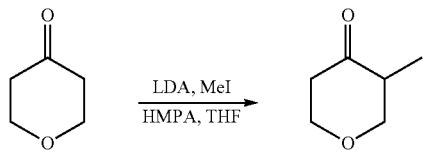

Compound 400.1.
3-Methyldihydro-2H-pyran-4(3H)-one

A 1-L three neck round-bottom flask was purged and maintained with a nitrogen atmosphere and a solution of LDA (2 M 132 mL, 1.20 equiv) in tetrahydrofuran (300 mL). The mixture was cooled to −78° C., then a solution of dihydro-2H-pyran-4(3H)-one (22.0 g, 220 mmol, 1.00 equiv) in hexamethylphosphoramide (40 mL, 230 mmol, 1.05 equiv) was added drop-wise followed by drop-wise addition of methyliodide (34 mL, 550 mmol, 2.5 equiv) at −78° C. The resulting solution was stirred at −78° C. for 5 min, then at 25° C. for 5 min. The reaction was carefully quenched with saturated aqueous NH$_4$Cl (80 mL) and extracted with ether (2×100 mL). The combined organics was dried (Na$_2$SO$_4$), filtered and concentrated in vacuo. The residue was purified by silica gel chromatography with PE/Et$_2$O (5:1) as the eluent to obtain the title compound as a yellow oil (6.00 g, 24%).

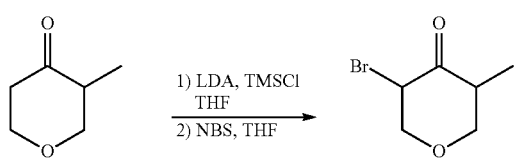

Compound 400.2.
3-Bromo-5-methyldihydro-2H-pyran-4(3H)-one

A 250-mL three neck round-bottom flask was purged and maintained with a nitrogen atmosphere. LDA (2.0 M in THF) (6 mL, 12 mmol, 1.20 equiv) and tetrahydrofuran (30 mL) were added. The solution was cooled to −78° C. and then TMSCl (7 mL, 55 mmol) was added drop-wise and stirred at −78° C. for 5 min. A solution of 3-methyldihydro-2H-pyran-4(3H)-one (compound 400.1, 1.14 g, 9.99 mmol, 1.00 equiv) in tetrahydrofuran (20 mL) was added drop-wise and the resulting mixture was stirred at −78° C. for 10 min. The mixture was carefully quenched with a mixture of triethylamine (15 mL) and saturated aqueous NaHCO$_3$ (100 mL). The aqueous was extracted with ether (2×50 mL), and the combined organics was washed with aqueous citric acid (3×100 mL), dried (K$_2$CO$_3$), filtered and concentrated in vacuo to obtain the intermediate enol silyl ether as a colorless oil. The enol silyl ether was dissolved in tetrahydrofuran (20 mL) and the system was purged with nitrogen. The mixture was cooled to 0° C., and then N-bromosuccinimide (1.95 g, 11.0 mmol, 1.10 equiv) was added portion-wise. The resulting mixture was stirred at 25° C. for 1 h, then quenched with saturated aqueous NaHCO$_3$ (30 mL). The aqueous was extracted with ether (2×30 mL), and the combined organics was dried (Na$_2$SO$_4$), filtered and concentrated in vacuo. The residue was purified by silica gel chromatography with PE/Et$_2$O (5:1) as the eluent to obtain the title compound as a colorless oil (1.00 g, 52%).

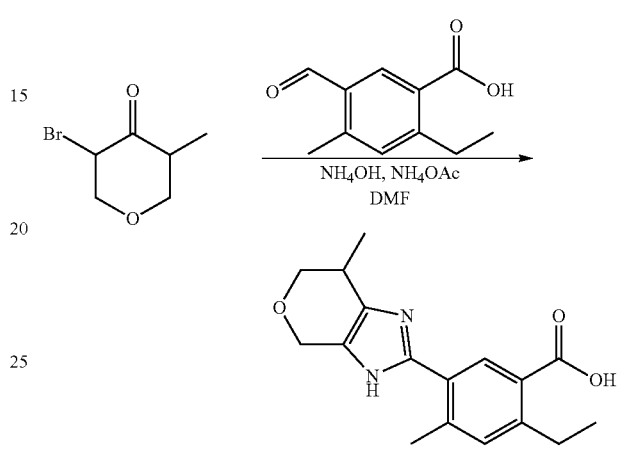

Compound 400.3. 2-Ethyl-4-methyl-5-(7-methyl-3,4,6,7-tetrahydropyrano[3,4-d]imidazol-2-yl)benzoic acid Into around-bottom flask, was placed a solution of 3-bromo-5-methyldihydro-2H-pyran-4(3H)-one (compound 400.2, 800 mg, 4.14 mmol, 1.6 equiv) in N,N-dimethylformamide (5 mL). Ammonium hydroxide (25% NH$_3$ in H$_2$O) (530 mg, 7.8 mmol, 3.0 equiv), NH$_4$OAc (904 mg, 11.7 mmol, 4.50 equiv) and 2-ethyl-5-formyl-4-methylbenzoic acid (compound 211.4, 500 mg, 2.60 mmol, 1.00 equiv) were added to the flask. The resulting mixture was stirred at 130° C. for 2 h, then concentrated in vacuo. The residue was purified by silica gel chromatography with dichloromethane/methanol (70/1) as the eluent to obtain the title compound as a white solid (30.0 mg, 2%).

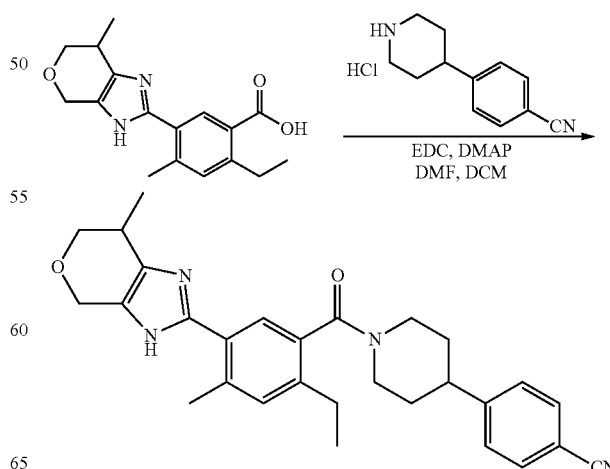

Compound 400. 4-[1-(2-Ethyl-4-methyl-5-(7-methyl-3,4,6,7-tetrahydropyrano[3,4-d]imidazol-2-yl]benzoyl)piperidin-4-yl)benzonitrile Into around-bottom flask, was placed a solution of 2-ethyl-4-methyl-5-(7-methyl-3,4,6,7-tetrahydropyrano[3,4-c]imidazol-2-yl)benzoic acid (compound 400.3, 30 mg, 0.10 mmol, 1.0 equiv) in DMF/DCM (5/5 mL). 4-(Piperidin-4-yl)benzonitrile hydrochloride (compound 1.5, 50 mg, 0.22 mmol, 2.2 equiv), EDC (40 mg, 2.0 equiv) and 4-dimethylaminopyridine (28 mg, 2.0 equiv) were added. The resulting solution was stirred overnight at 25° C., then quenched with water (10 mL). The mixture was extracted with ethyl acetate (3×5 mL), and the combined organic layers was dried (Na$_2$SO$_4$), filtered and concentrated in vacuo. The residue was purified by silica gel chromatography with ethyl acetate/petroleum ether (2:1) as the eluent to obtain the title compound as a light yellow solid (3.2 mg, 7%). m/z (ES+) 469 (M+H)$^+$.

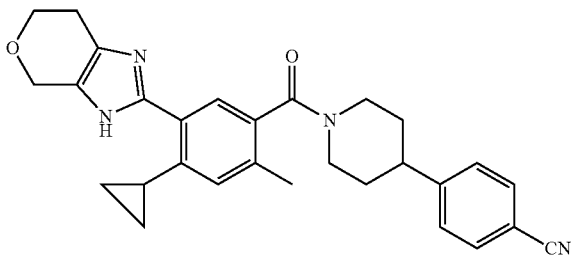 [SMILES: Cc1cc(C2CC2)c(-c2nc3c([nH]2)COCC3)cc1C(=O)N1CCC(c2ccc(C#N)cc2)CC1]

Compound 401. 4-(1-(4-Cyclopropyl-2-methyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 392 but compound 142.2 was used in place of compound 152.3. (ES+) 467 (M+H)$^+$.

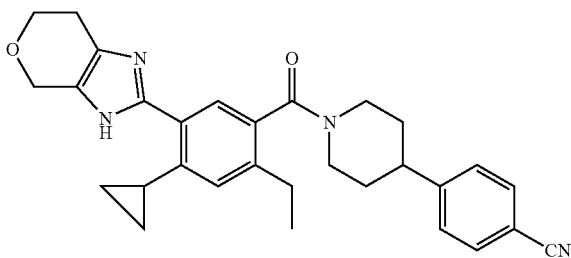 [SMILES: CCc1cc(C2CC2)c(-c2nc3c([nH]2)COCC3)cc1C(=O)N1CCC(c2ccc(C#N)cc2)CC1]

Compound 402. 4-(1-(4-Cyclopropyl-2-ethyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 392 but compound 226.5 was used in place of compound 230.1. m/z (ES+) 481 (M+H)$^+$.

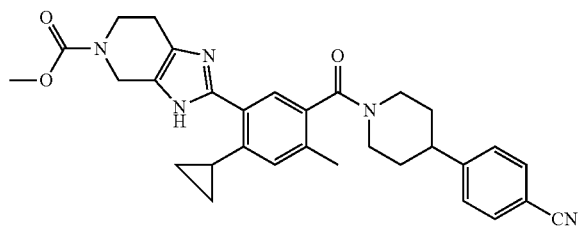 [SMILES: COC(=O)N1CCc2nc(-c3cc(C(=O)N4CCC(c5ccc(C#N)cc5)CC4)c(C)cc3C3CC3)[nH]c2C1]

Compound 403. Methyl 2-(5-(4-(4-cyanophenyl)piperidine-1-carbonyl)-2-cyclopropyl-4-methylphenyl)-6,7-dihydro-3H-imidazo[4,5-c]pyridine-5(4H)-carboxylate The title compound was prepared using standard chemical manipulations and procedures similar to those used for the preparation of compounds 1 and 2 but compound 142.2 and dimethyl dicarbonate/DIEA were used in place of compound 2.2. and acetic anhydride respectively. m/z (ES+) 524 (M+H)$^+$.

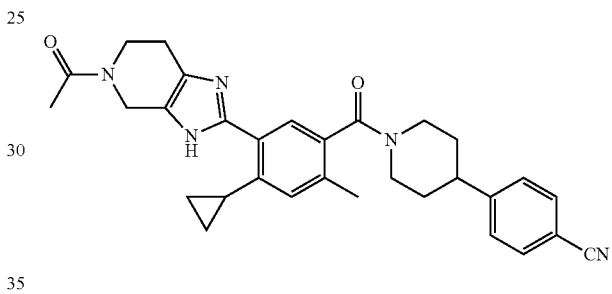

Compound 404. 4-(1-(5-(5-Acetyl-4,5,6,7-tetrahydro-3H-imidazo[4,5-c]pyridin-2-yl)-4-cyclopropyl-2-methylbenzoyl)piperidin-4-yl)benzonitrile The title compound was prepared using standard chemical manipulations and procedures similar to those used for the preparation of compounds 1 and 2 but using compound 142.2 was used in place of compound 2.2. m/z (ES+) 508 (M+H)$^+$.

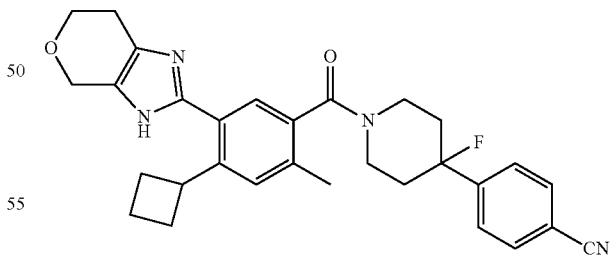

Compound 405. 4-(1-(4-Cyclobutyl-2-methyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 392, except compound 11.2 HCl salt was used in place of compound 1.5. m/z (ES+) 499

(M+H)⁺. ¹H NMR (300 MHz, CD₃OD) δ 7.97 (m, 2H), 7.97 (m, 2H), 7.67-7.53 (m, 2H), 4.80 (s, 2H), 4.10 (m, 2H), 3.75 (m, 1H), 3.55 (m, 2H), 3.27 (m, 1H), 2.90 (m, 2H), 2.53 and 2.43 (2 singlets, amide rotamers, ArCH₃, 3H), 2.38-1.80 (m, 10H).

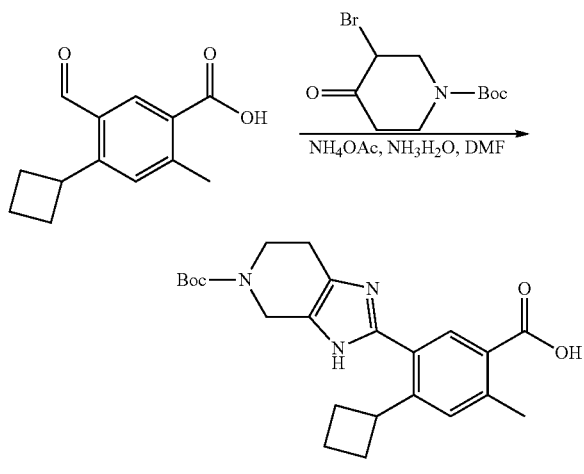

Compound 406.1. 5-(5-(tert-Butoxycarbonyl)-4,5,6,7-tetrahydro-3H-imidazo[4,5-c]pyridin-2-yl)-4-cyclobutyl-2-methylbenzoic acid To a solution of 4-cyclobutyl-5-formyl-2-methylbenzoic acid (compound 392.1, 2.00 g, 9.16 mmol, 1.00 equiv) in N,N-dimethylformamide (15 mL) were added tert-butyl 3-bromo-4-oxopiperidine-1-carboxylate (9.00 g, 16.2 mmol, 2.00 equiv), ammonium hydroxide (3.84 g, 27.4 mmol, 3.00 equiv, 25%), and NH₄OAc (3.18 g, 41.3 mmol, 4.50 equiv). The resulting mixture was stirred overnight at 130° C. under nitrogen. After cooling to ambient temperature, the mixture was diluted with 50 mL of ethyl acetate, washed with 3×30 mL of brine, dried over anhydrous sodium sulfate, and concentrated under reduced pressure. The residue was purified using silica gel column chromatography with dichloromethane/methanol (20:1) as eluent to furnish 2.00 g (27%) of the title compound as a brown solid.

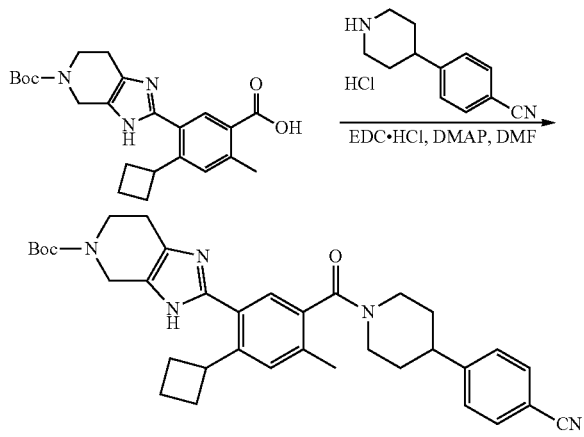

Compound 406.2. tert-Butyl 2-(5-(4-(4-cyanophenyl)piperidine-1-carbonyl)-2-cyclobutyl-4-methylphenyl)-6,7-dihydro-3H-imidazo[4,5-c]pyridine-5(4H)-carboxylate To a solution of 5-(5-(tert-butoxycarbonyl)-4,5,6,7-tetrahydro-3H-imidazo[4,5-c]pyridin-2-yl)-4-cyclobutyl-2-methylbenzoic acid (compound 406.1, 1.00 g, 1.22 mmol, 1.00 equiv, 50%) in N,N-dimethylformamide (5 mL) were added 4-(piperidin-4-yl)benzonitrile hydrochloride salt (compound 1.5, 270 mg, 1.21 mmol, 1.00 equiv), EDC.HCl (460 mg, 2.40 mmol, 2.00 equiv), and 4-dimethylaminopyridine (296 mg, 2.42 mmol, 2.00 equiv). The resulting mixture was stirred at 25° C. overnight. The mixture was then diluted with 30 mL of ethyl acetate, washed with 3×30 mL of brine, dried over anhydrous sodium sulfate, and concentrated under reduced pressure to yield 890 mg (63%) of the title compound as a brown solid.

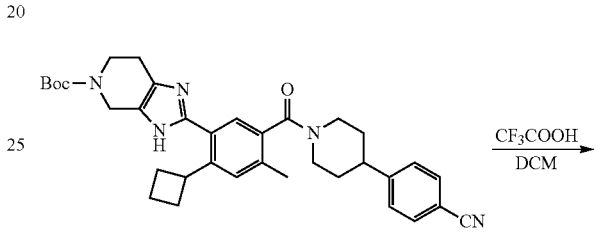

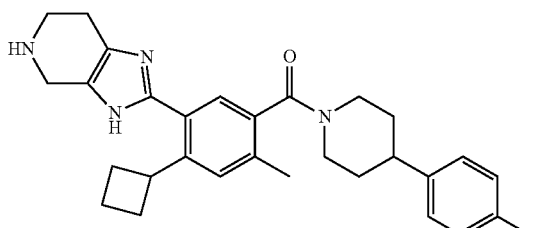

Compound 406.3. 4-(1-(4-Cyclobutyl-2-methyl-5-(4,5,6,7-tetrahydro-3H-imidazo[4,5-c]pyridin-2-yl)benzoyl)piperidin-4-yl)benzonitrile A solution of tert-butyl 2-(5-(4-(4-cyanophenyl)piperidine-1-carbonyl)-2-cyclobutyl-4-methylphenyl)-6,7-dihydro-3H-imidazo[4,5-c]pyridine-5(4H)-carboxylate (406.2, 600 mg, 0.620 mmol, 1.00 equiv, 60%) in dichloromethane (3 mL) and trifluoroacetic acid (1.5 mL) was stirred for 3 h at 25° C., then diluted with 5 mL of hydrochloric acid (3 mol/L) and 10 mL of water. The resulting mixture was washed with 3×20 mL of ethyl acetate and the pH was then adjusted to ~9 with sodium hydroxide (aq, 3 M). The resulting mixture was extracted with 4×20 mL of dichloromethane. The combined organic layers were dried (Na₂SO₄) and concentrated under reduced pressure to yield 140 mg (37%) of the title compound as a brown solid.

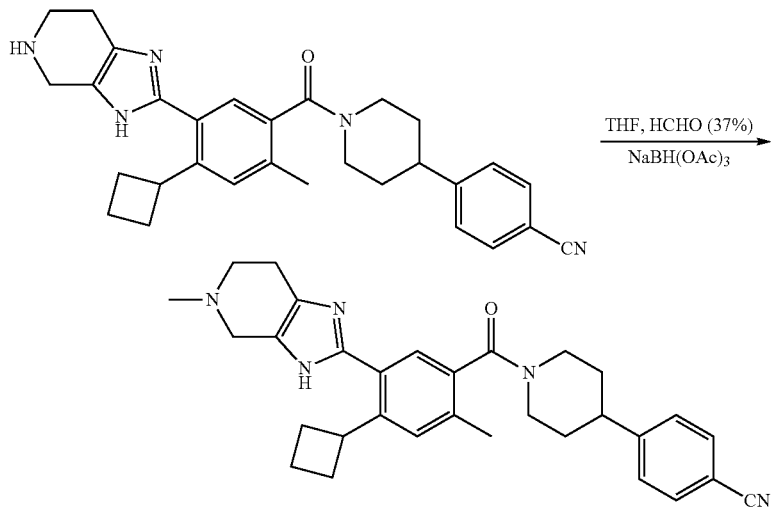

Compound 406. 4-(1-(4-Cyclobutyl-2-methyl-5-(5-methyl-4,5,6,7-tetrahydro-3H-imidazo[4,5-c]pyridin-2-yl)benzoyl)piperidin-4-yl)benzonitrile To a solution of 4-(1-(4-cyclobutyl-2-methyl-5-(4,5,6,7-tetrahydro-3H-imidazo[4,5-c]pyridin-2-yl)benzoyl)piperidin-4-yl)benzonitrile (406.3, 190 mg, 0.30 mmol, 1.00 equiv, 75%) in tetrahydrofuran (10 mL) were added NaBH(OAc)$_3$ (252 mg, 1.13 mmol, 3.00 equiv, 95%) and HCHO (37%) (2.2 mL, 2.00 equiv). The resulting mixture was stirred for 2 h at 40° C. in an oil bath and then concentrated under reduced pressure. The residue was diluted with dichloromethane and washed with aqueous saturated sodium bicarbonate and brine. The organic layer was dried (Na$_2$SO$_4$) and concentrated. The crude product (~80 mg) was purified by Prep-HPLC with the following conditions (1#-Pre-HPLC-001(SHIMADZU)): Column, Xbridge Prep C18, 5 um, 19*150 mm; mobile phase, water with 0.03% NH$_3$H$_2$O and CH$_3$CN (36% CH$_3$CN up to 48% in 8 min, up to 100% in 1 min, down to 36% in 1.5 min); Detector, Waters 2489 254 & 220 nm. The fractions containing pure compound were combined and lyophilized to yield 23.4 mg (16%) of the title compound as a white solid. m/z (ES+) 494 (M+H)$^+$. $^1$H NMR (300 MHz, CD$_3$OD): δ 7.69 (d, J=6.0 Hz, 2H), 7.48 (d, J=6.0 Hz, 2H), 7.37-7.31 (m, 1H), 7.26 & 7.15 (2 singlets, amide rotamers, Ar—H, 1H), ~4.9 (1H partially obscured by water peak), 4.02-3.90 (m, 1H), 3.73-3.57 (m, 1H), 3.57 (s, 2H), 3.34-3.21 (m, 1H), 3.06-2.94 (m, 2H), 2.90-2.77 (m, 4H), 2.54 (s, 3H), 2.45 & 2.34 (2 singlets, amide rotamers, ArCH$_3$, 3H), 2.11-1.86 (m, 6H), 1.86-1.54 (m, 4H).

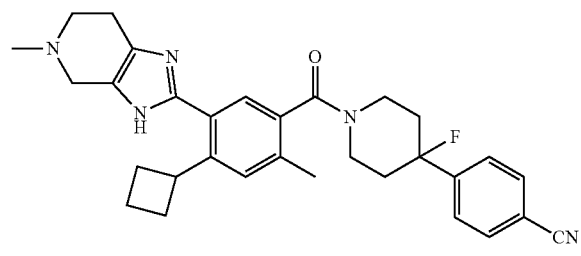 [SMILES: Cc1cc(C2CCC2)c(-c2nc3c([nH]2)CN(C)CC3)cc1C(=O)N1CCC(F)(c2ccc(C#N)cc2)CC1]

Compound 407. 4-(1-(4-Cyclobutyl-2-methyl-5-(5-methyl-4,5,6,7-tetrahydro-3H-imidazo[4,5-c]pyridin-2-yl)benzoyl)-4-fluoropiperidin-4-yl)benzonitrile The title compound was prepared using standard chemical manipulations and procedures similar to those used for the preparation of compound 406, except compound 11.2 HCl salt was used in place of compound 1.5. m/z (ES+) 512 (M+H)$^+$.

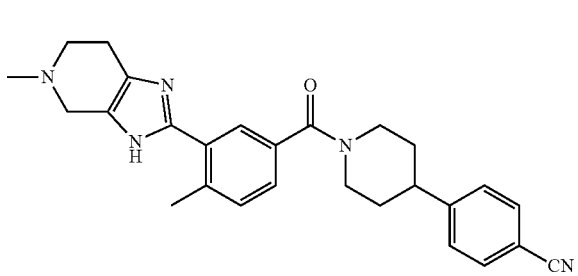 [SMILES: Cc1ccc(C(=O)N2CCC(c3ccc(C#N)cc3)CC2)cc1-c1nc2c([nH]1)CN(C)CC2]

Compound 408. 4-(1-(4-Methyl-3-(5-methyl-4,5,6,7-tetrahydro-3H-imidazo[4,5-c]pyridin-2-yl)benzoyl)piperidin-4-yl)benzonitrile The title compound was prepared using standard chemical manipulations and procedures similar to those used for the preparation of compound 406 except 3-iodo-4-methylbenzoic acid was used in place of compound 230.1. m/z (ES+) 440 (M+H)$^+$.

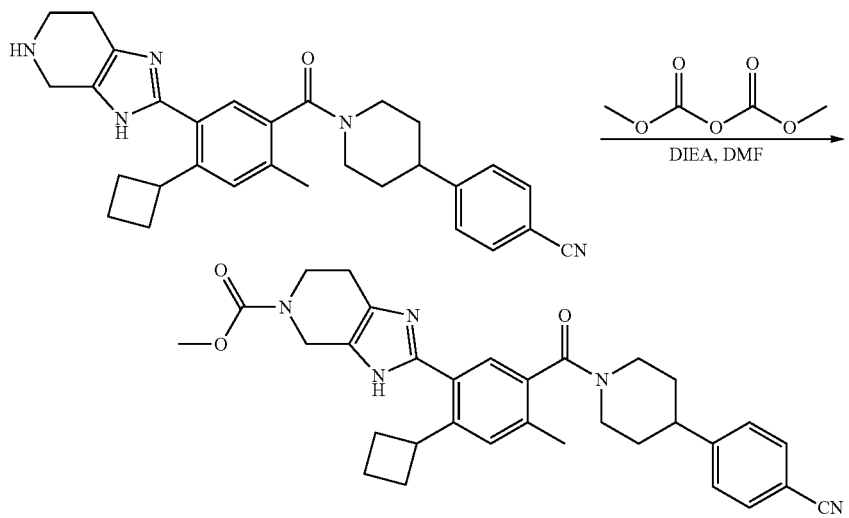

Compound 409. 4-(1-(4-Cyclobutyl-2-methyl-5-(5-methyl-4,5,6,7-tetrahydro-3H-imidazo[4,5-c]pyridin-2-yl)benzoyl)piperidin-4-yl)benzonitrile To a solution of 4-(1-(4-cyclobutyl-2-methyl-5-(4,5,6,7-tetrahydro-3H-imidazo[4,5-c]pyridin-2-yl)benzoyl)piperidin-4-yl)benzonitrile (406.3, 180 mg, 0.300 mmol, 1.00 equiv, 80%) in N,N-dimethylformamide (5 mL) were added dimethyl dicarbonate (176 mg, 1.31 mmol, 5.00 equiv) and DIEA (169 mg, 1.31 mmol, 5.00 equiv). The resulting solution was stirred overnight at 25° C. and then quenched with 20 mL of methanol. The resulting mixture was concentrated under reduced pressure and the crude product was purified by Prep-HPLC using the following conditions (1#-Pre-HPLC-001(SHIMADZU)): Column, SunFire Prep C18, 19*150 mm 5 um; mobile phase, water with 0.05% TFA and CH3CN (28% CH3CN up to 43% in 8 min, up to 100% in 3 min, down to 28% in 2 min); Detector, Waters 2489 254 & 220 nm. The fractions containing pure compound were combined and lyophilized to yield 29.9 mg (19%) of the title compound as a white solid. m/z (ES+) 538 (M+H)+. $^1$H NMR (400 MHz, CD$_3$OD): δ 7.70 (m, 2H), 7.50-7.35 (m, 4H), 4.90 (m, 1H), 4.70 (s, 2H), 4.00 (m, 2H), 3.80 (m, 4H), 3.60 (m, 1H), 3.25 (m, 1H), 3.05 (m, 2H), 2.85 (m, 2H), 2.50 and 2.40 (2 singlets, amide rotamers, ArCH$_3$, 3H), 2.16-2.00 (m, 6H), 1.86-1.64 (m, 4H).

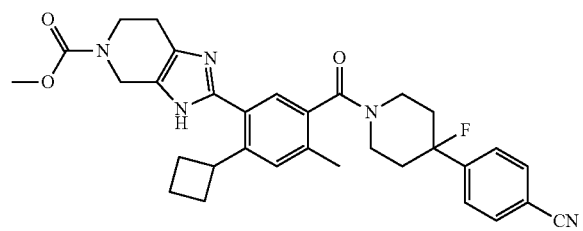 [SMILES: COC(=O)N1CCc2nc(-c3cc(C(=O)N4CCC(F)(c5ccc(C#N)cc5)CC4)c(C)cc3C3CCC3)[nH]c2C1]

Compound 410. Methyl 2-(5-(4-(4-cyanophenyl)-4-fluoropiperidine-1-carbonyl)-2-cyclobutyl-4-methylphenyl)-6,7-dihydro-3H-imidazo[4,5-c]pyridine-5(4H)-carboxylate The title compound was prepared using standard chemical manipulations and procedures similar to those used for the preparation of compound 409, except compound 11.2 was used in place of compound 1.5. m/z (ES+) 556 (M+H)+. $^1$H NMR (400 MHz, CD$_3$OD) δ 7.78 (m, 2H), 7.67 (m, 2H), 7.35-7.20 (m, 2H), 4.80 (m, 1H), 4.55 (s, 2H), 4.00 (m, 1H), 4.84 (m, 2H), 3.77 (s, 3H), 3.60 (m, 1H), 3.28 (m, 1H), 2.80 (s, 2H), 2.47 and 2.36 (2 singlets, amide rotamers, ArCH$_3$, 3H), 2.30-1.80 (m, 9H), 1.62 (m, 1H), 1.32 (m, 1H).

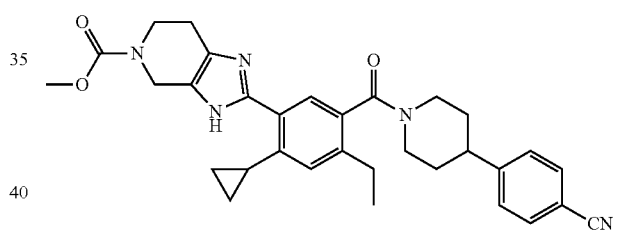

Compound 411. Methyl 2-(5-(4-(4-cyanophenyl)piperidine-1-carbonyl)-2-cyclopropyl-4-ethylphenyl)-6,7-dihydro-3H-imidazo[4,5-c]pyridine-5(4H)-carboxylate The title compound was prepared using standard chemical manipulations and procedures similar to those used for the preparation of compound 409, except compound 226.5 was used in place of compound 230.1. m/z (ES+) 538 (M+H)+.

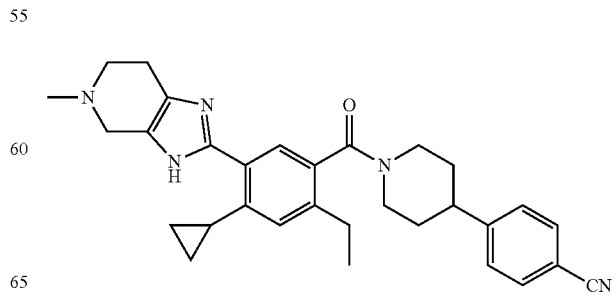

Compound 412. 4-(1-(4-Cyclopropyl-2-ethyl-5-(5-methyl-4,5,6,7-tetrahydro-3H-imidazo[4,5-c]pyridin-2-yl)benzoyl)piperidin-4-yl)benzonitrile The title compound was prepared using standard chemical manipulations and procedures similar to those used for the preparation of compound 406, except compound 226.5 was used in place of compound 230.1. m/z (ES+) 494 (M+H)+.

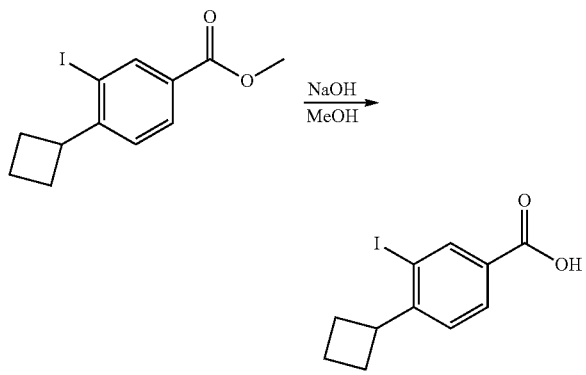

Compound 413.1. 4-Cyclobutyl-3-iodobenzoic acid

A solution of compound 168.2 (11.0 g, 34.8 mmol, 1.00 equiv) and sodium hydroxide (4.00 g, 100 mmol, 3.00 equiv) in methanol (~100 mL) was stirred at 50° C. overnight. After cooling to ambient temperature, the mixture was concentrated to dryness. The residue was taken up in water (50 mL) equiv and washed with ethyl acetate. The pH of the aqueous layer was adjusted to 3-4 with 6 M aqueous hydrogen chloride. The resulting precipitate was collected by filtration and dried to yield 8.60 g (82%) of the title compound as a white solid.

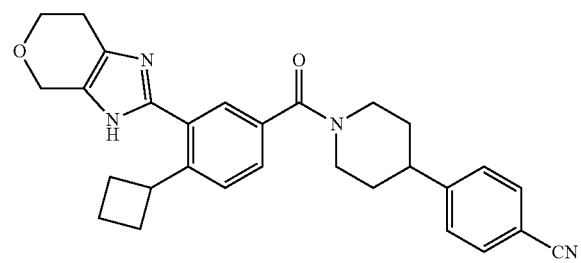 [SMILES: N#Cc1ccc(C2CCN(C(=O)c3ccc(C4CCC4)c(-c4nc5c([nH]4)COCC5)c3)CC2)cc1]

Compound 413. 4-(1-(4-Cyclobutyl-3-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 392, except compound 413.1 was used as in place of compound 230.1. m/z (ES+) 477 (M+H)+. 1H NMR (300 MHz, CD3OD) δ 7.76-7.65 (m, 5H), 7.48 (m, 2H), 5.00 (m, 1H), 4.80 (s, 2H), 4.10 (m, 2H), 3.80 (m, 2H), 3.45 (m, 1H), 3.04 (m, 2H), 2.90 (m, 2H), 2.18-1.95 (m, 6H), 1.85-1.77 (m, 4H).

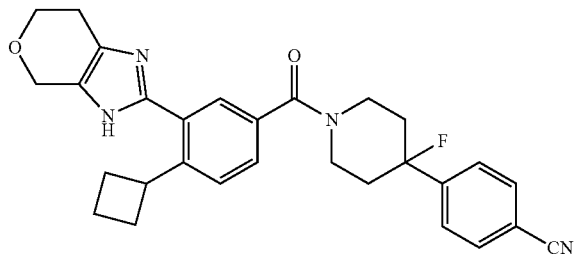 [SMILES: N#Cc1ccc(C2(F)CCN(C(=O)c3ccc(C4CCC4)c(-c4nc5c([nH]4)COCC5)c3)CC2)cc1]

Compound 414. 4-(1-(4-Cyclobutyl-3-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 413, except compound 11.2 HCl salt was used in place of compound 1.5. m/z (ES+) 485 (M+H)+. 1H NMR (300 MHz, CD3OD) δ 7.82-7.77 (m, 3H), 7.68-7.65 (m, 4H), 4.80 (m, 3H), 4. 90 (m, 2H), 3.83-3.46 (m, 3H), 2.90 (m, 2H), 2.29 (m, 1H), 2.18-1.83 (m, 10H).

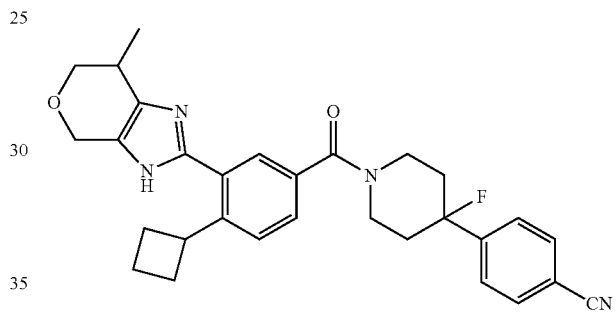

Compound 415. 4-(1-(4-Cyclobutyl-3-(7-methyl-3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 414, except 3-methyldihydro-2H-pyran-4(3H)-one was used in place of dihydro-2H-pyran-4(3H)-one. m/z (ES+) 499 (M+H)+.

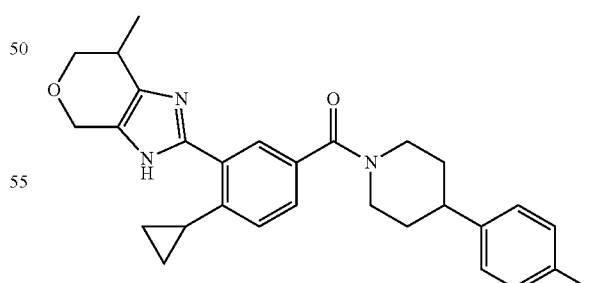

Compound 416. 4-(1-(4-Cyclopropyl-3-(7-methyl-3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 413, except bromo(cyclopropyl)magnesium and 3-methyldihydro-2H-pyran-4(3H)-one were used in place of bromo(cyclobutyl)magnesium and dihydro-2H-pyran-4(3H)-one respectively. m/z (ES+) 467 (M+H)+.

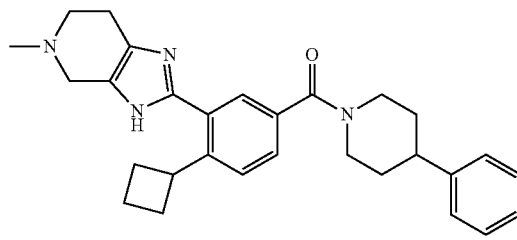

Compound 417. 4-(1-(4-Cyclobutyl-3-(5-methyl-4,5,6,7-tetrahydro-3H-imidazo[4,5-c]pyridin-2-yl)benzoyl)piperidin-4-yl)benzonitrile The title compound was prepared using standard chemical manipulations and procedures similar to those used for the preparation of compound 406, except compound 413.1 was used in place of compound 230.1. m/z (ES+) 480 (M+H)+. $^1$H NMR (300 MHz, CD$_3$OD) δ 7.72-7.63 (m, 4H), 7.56 (s, 1H), 7.49 (m, 2H), 4.82 (m, 1H), 4.56 (s, 2H), 3.89 (m, 2H), 3.80 (m, 2H), 3.08 (m, 2H), 3.04 (s, 3H), 2.99 (m, 2H), 2.18-1.66 (m, 11H).

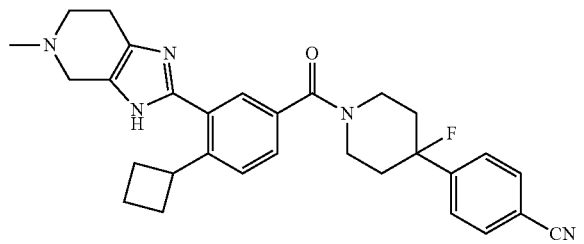 [SMILES: CN1CCc2nc(-c3cc(C(=O)N4CCC(F)(c5ccc(C#N)cc5)CC4)ccc3C3CCC3)[nH]c2C1]

Compound 418. 4-(1-(4-Cyclobutyl-3-(5-methyl-4,5,6,7-tetrahydro-3H-imidazo[4,5-c]pyridin-2-yl)benzoyl)-4-fluoropiperidin-4-yl)benzonitrile The title compound was prepared using standard chemical manipulations and procedures similar to those used for the preparation of compound 417, except compound 11.2 HCl salt was used in place of compound 1.5. m/z (ES+) 498 (M+H)+. $^1$H NMR (300 MHz, CD$_3$OD) δ 7.79 (m, 2H), 7.74-7.59 (m, 5H), 4.73 (br s, 1H), 4.54 (br s, 2H), 3.94 (m, 2H), 3.76 (br s, 2H), 3.61 (br s, 1H), 3.20 (br s, 2H), 3.16 (s, 3H), 2.39-1.96 (m, 10H), 1.79 (m, 1H).

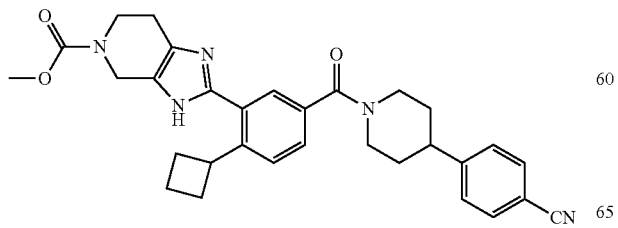

Compound 419. Methyl 2-(5-(4-(4-cyanophenyl)piperidine-1-carbonyl)-2-cyclobutylphenyl)-6,7-dihydro-3H-imidazo[4,5-c]pyridine-5(4H)-carboxylate The title compound was prepared using standard chemical manipulations and procedures similar to those used for the preparation of compound 409, except compound 413.1 was used in place of compound 230.1. m/z (ES+) 524 (M+H).

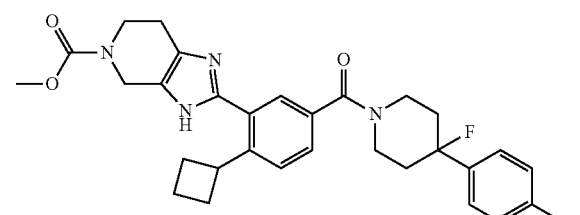

Compound 420. Methyl 2-(5-(4-(4-cyanophenyl)-4-fluoropiperidine-1-carbonyl)-2-cyclobutylphenyl)-6,7-dihydro-3H-imidazo[4,5-c]pyridine-5(4H)-carboxylate The title compound was prepared using standard chemical manipulations and procedures similar to those used for the preparation of compound 409, except compounds 413.1 and 11.2 were used in place of compounds 230.1 and 1.5 respectively. m/z (ES+) 542 (M+H).

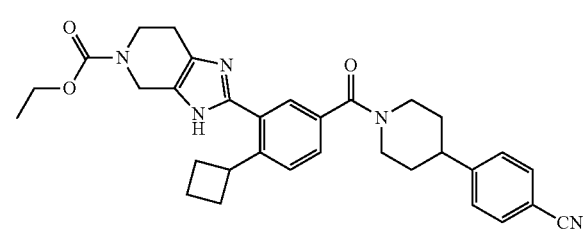 [SMILES: CCOC(=O)N1CCc2nc(-c3cc(C(=O)N4CCC(c5ccc(C#N)cc5)CC4)ccc3C3CCC3)[nH]c2C1]

Compound 421. Ethyl 2-(5-(4-(4-cyanophenyl)piperidine-1-carbonyl)-2-cyclobutylphenyl)-6,7-dihydro-3H-imidazo[4,5-c]pyridine-5(4H)-carboxylate The title compound was prepared using standard chemical manipulations and procedures similar to those used for the preparation of compound 409, except compound 413.1 and diethyl dicarbonate were used in place of compound 230.1 and dimethyl dicarbonate respectively. m/z (ES+) 538 (M+H).

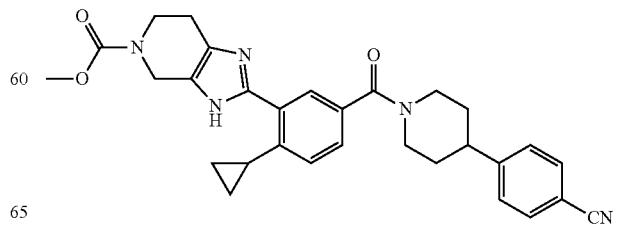

Compound 422. Methyl 2-(5-(4-(4-cyanophenyl)
piperidine-1-carbonyl)-2-cyclopropylphenyl)-6,7-
dihydro-3H-imidazo[4,5-c]pyridine-5(4H)-carboxy-
late The title compound was prepared using standard chemical manipulations and procedures similar to those used for the preparation of compound 421, except bromo(cyclopropyl)magnesium and dimethyl diethyl Bicarbonate were used in place of bromo(cyclobutyl)magnesium and diethyl dicarbonate respectively. m/z (ES+) 510 (M+H).

Compound 423. 4-(1-(2,4-Dimethyl-5-(5-(oxetan-3-yl)-4,5,6,7-tetrahydro-1H-imidazo[4,5-c]pyridin-2-yl)benzoyl)piperidin-4-yl)benzonitrile A mixture of 4-(1-(2,4-dimethyl-5-(4,5,6,7-tetrahydro-1H-imidazo[4,5-c]pyridin-2-yl)benzoyl)piperidin-4-yl)benzonitrile (compound 2.9, 62 mg), oxetan-3-one (18 μl), sodium cyanotrihydroborate (18 mg), and acetic acid (80 μl) in MeOH/THF (1:1 v/v) was stirred for 16 hours. The reaction was then diluted with dichloromethane, washed with saturated sodium bicarbonate solution followed by brine. The organic layer was dried (MgSO₄) and concentrated. The residue was purified by preparative TLC at 8% MeOH in DCM to give 42 mg white solid (60%). m/z (ES+) 496 (M+H)⁺. ¹H NMR (400 MHz, Chloroform-d) δ 7.63 (d, 2H), 7.32 (d, 2H), 7.27 and 7.20 (2 singlet, amide rotamers, 1H), 7.02 (s, 1H), 4.96 (s, 1H), 4.74 (m, 4H), 3.88-3.77 (m, 1H), 3.63 (d, 1H), 3.49 (d, 2H), 3.08 (t, 1H), 2.97-2.62 (m, 6H), 2.45 (d, 3H), 2.31 and 2.22 (2 singlets, amide rotamers, 3H), 2.11-1.40 (m, 4H).

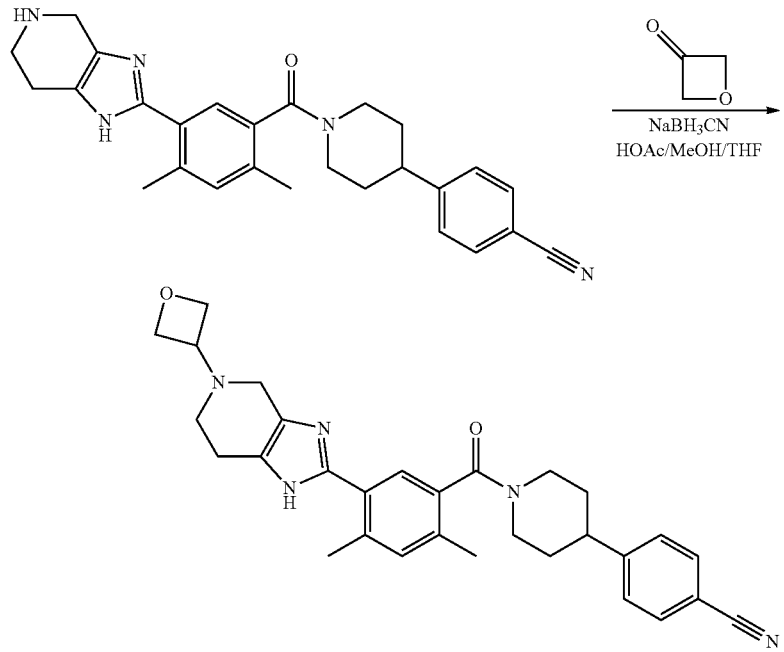

Compound 424. 4-(1-(5-(5-Cyclopropyl-4,5,6,7-tetrahydro-1H-imidazo[4,5-c]pyridin-2-yl)-2,4-dimethylbenzoyl)piperidin-4-yl)benzonitrile The title compound was prepared using standard chemical manipulations and procedures similar to those used for preparation of compound 423. m/z (ES+) 480 (M+H)⁺. ¹H NMR (400 MHz, Chloroform-d) δ 10.58, 7.61 (d, 2H), 7.33 (d, 2H), 7.23 and 7.15 (2 singlet, amide rotamers, 1H), 6.97 (s, 1H), 4.93 (s, 1H), 3.80-3.66 (m, 2H), 3.64-3.49 (m, 1H), 3.02 (m, 3H), 2.91-2.64 (m, 4H), 2.41 (d, 3H), 2.28 and 2.18

(2 singles, amide rotamers, 3H), 2.07-1.86 (m, 2H), 1.84-1.37 (m, 2H), 0.66-0.40 (m, 4H).

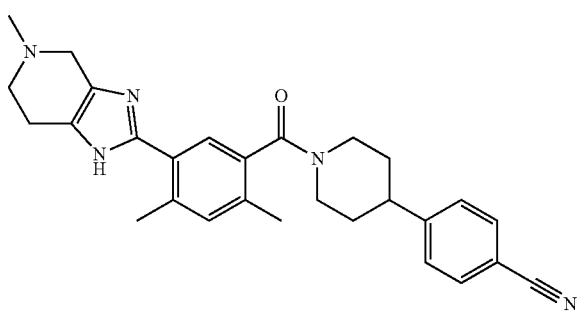 [SMILES: Cc1cc(C)c(-c2nc3c([nH]2)CCN(C)C3)cc1C(=O)N1CCC(c2ccc(C#N)cc2)CC1]

Compound 425. 4-(1-(2,4-Dimethyl-5-(5-methyl-4,5,6,7-tetrahydro-1H-imidazo[4,5-c]pyridin-2-yl)benzoyl)piperidin-4-yl)benzonitrile The title compound was prepared using standard chemical manipulations and procedures similar to those used for preparation of compound 406 but using compound 2.9 in place of compound 406.3. m/z (ES+) 454 (M+H)+.

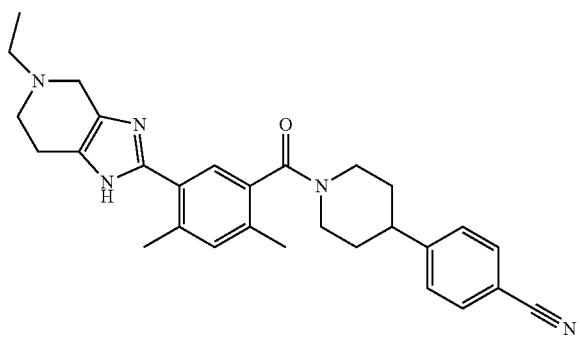 [SMILES: CCN1CCc2[nH]c(-c3cc(C(=O)N4CCC(c5ccc(C#N)cc5)CC4)c(C)cc3C)nc2C1]

Compound 426. 4-(1-(5-(5-Ethyl-4,5,6,7-tetrahydro-1H-imidazo[4,5-c]pyridin-2-yl)-2,4-dimethylbenzoyl)piperidin-4-yl)benzonitrile The title compound was prepared using standard chemical manipulations and procedures similar to those used for preparation of compound 423. m/z (ES+) 468 (M+H)+. $^1$H NMR (400 MHz, Chloroform-d) δ 7.63 (d, 2H), 7.40-7.19 (m, 3H), 7.04 (s, 1H), 4.95 (s, 1H), 3.75-3.51 (m, 3H), 3.09 (m, 1H), 2.95-2.77 (m, 6H), 2.71 (m, 2H), 2.46 (s, 3H), 2.30 and 2.21 (2 singlets, amide rotamers, 3H), 2.12-1.89 (m, 1H), 1.85-1.43 (m, 3H), 1.22 (m, 3H).

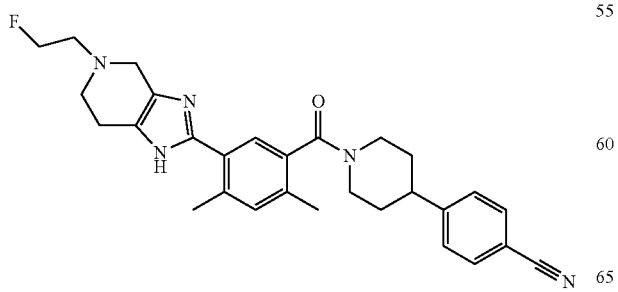

Compound 427. 4-(1-(5-(5-(2-Fluoroethyl)-4,5,6,7-tetrahydro-1H-imidazo[4,5-c]pyridin-2-yl)-2,4-dimethylbenzoyl)piperidin-4-yl)benzonitrile A mixture of 4-(1-(2,4-dimethyl-5-(4,5,6,7-tetrahydro-1H-imidazo[4,5-c]pyridin-2-yl)benzoyl)piperidin-4-yl)benzonitrile (compound 2.9, 88 mg), 1-bromo-2-fluoroethane (150 μl), potassium iodide (50 mg), and triethyl amine (140 μl) in DMF (2 ml) was stirred for 48 hours. The reaction mixture was then diluted with dichloromethane and washed with brine. The organic layer was dried (MgSO$_4$) and concentrated. The residue was purified by prep. TLC using 8% MeOH in DCM to give 51 mg of a white solid (52%). m/z (ES+) 486 (M+H)+. $^1$H NMR (400 MHz, Chloroform-d) 7.63 (d, 2H), 7.32 (d, 2H), 7.28 and 7.20 (2 singlets, amide rotamers, 1H), 7.00 (s, 1H), 4.93 (m, 1H), 4.67 (dt, J$_1$=47.6 Hz, J$_2$=4.9 Hz, 2H), 3.71 (d, 2H), 3.62 (d, 1H), 3.03-2.71 (m, 8H), 2.43 (d, 3H), 2.29 and 2.19 (2 singlets, amide rotamers, 3H), 2.08-1.89 (m, 2H), 1.85-1.49 (m, 2H), 3.18-3.05 (m, 1H).

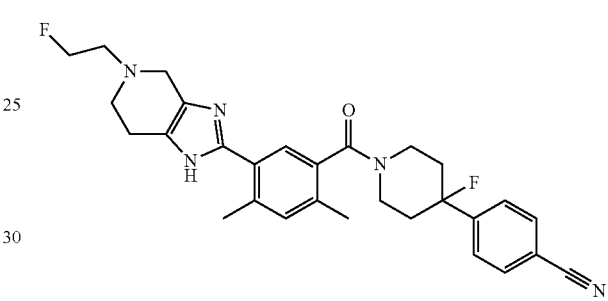

Compound 428. 4-(4-Fluoro-1-(5-(5-(2-fluoroethyl)-4,5,6,7-tetrahydro-1H-imidazo[4,5-c]pyridin-2-yl)-2,4-dimethylbenzoyl)piperidin-4-yl)benzonitrile The title compound was prepared using standard chemical manipulations and procedures similar to those used for preparation of compound 427 but using compound 11.2 HCl salt instead of compound 1.5. m/z (ES+) 504 (M+H)+. $^1$H NMR (400 MHz, Chloroform-d) δ 7.70 (d, 2H), 7.50 (d, 2H), 7.28 and 7.21 (2 singlet, amide rotamers, 1H), 7.00 (s, 1H), 4.92-4.77 (m, 1H), 4.66 (dt, J$_1$=47.7 Hz, J$_2$=4.8 Hz, 2H), 3.68 (d, 2H), 3.58-3.35 (m, 2H), 3.33-3.11 (m, 1H), 2.95 (dt, 4H), 2.76 (d, 2H), 2.42 (s, 3H), 2.28 and 2.20 (2 singlets, amide rotamers, 3H), 2.16-1.72 (m, 4H).

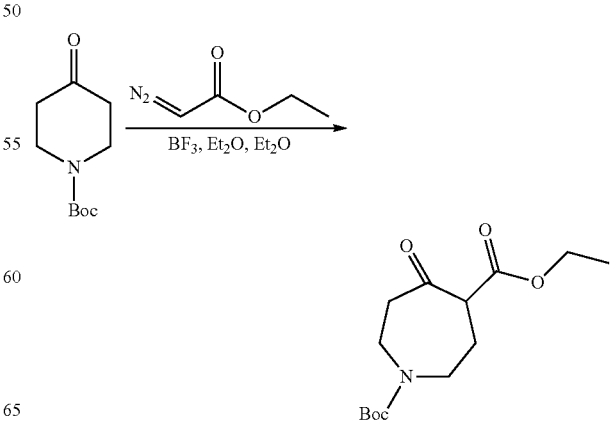

Compound 429.1. 1-tert-Butyl 4-ethyl 5-oxoazepane-1,4-dicarboxylate

To a solution of tert-butyl 4-oxopiperidine-1-carboxylate (20.0 g, 100 mmol, 1.00 equiv) in ether (60 mL) −30° C. was added dropwise a solution of BF$_3$.Et$_2$O (16.0 mL, 1.30 equiv) in ether (20 mL). After stirring 30 min at −30° C., a solution of ethyl 2-diazoacetate (16.0 g, 140 mmol, 1.30 equiv) in ether (20 mL) was added dropwise to the reaction at −30° C. The resulting solution was stirred for 1 h at −30° C., then warmed to 25° C. and stirred for 2 h. The reaction was then quenched with 100 mL of 30% aqueous potassium carbonate. The resulting mixture was extracted with 2×250 mL of ethyl acetate, and the combined organic layers were washed with 2×50 mL of brine, dried over anhydrous sodium sulfate, and concentrated under reduced pressure. The residue was purified by silica gel chromatography with ethyl acetate/petroleum ether (1/10) as eluent to furnish 19.0 g (66%) of the title compound as a light yellow oil.

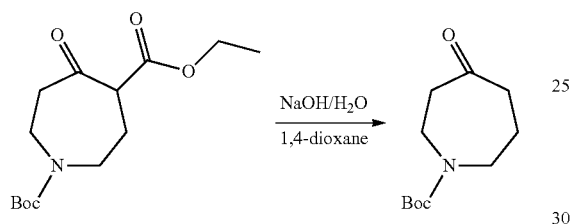

Compound 429.2. tert-Butyl 4-oxoazepane-1-carboxylate

To a solution 1-tert-butyl 4-ethyl 5-oxoazepane-1,4-dicarboxylate (429.1, 19.0 g, 66.6 mmol, 1.00 equiv) in 1,4-dioxane (190 mL) was added dropwise sodium hydroxide (4.00 g, 100 mmol, 1.50 equiv) in water (100 mL). The resulting mixture was stirred at room temperature overnight. The pH was then adjusted to 4-5 with hydrogen chloride (aq. 3 M) and the resulting solution was extracted with 2×50 mL of ethyl acetate. The combined organic layers were washed with 2×10 mL of brine, dried over anhydrous sodium sulfate, and concentrated under reduced pressure. The crude residue was purified by silica gel chromatography using ethyl acetate/petroleum ether (1:3) as eluent to furnish 11.0 g (77%) of the title compound as a yellow oil.

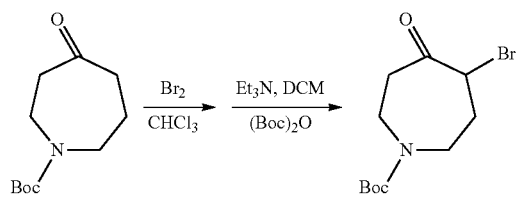

Compound 429.3. tert-Butyl 4-bromo-5-oxoazepane-1-carboxylate

To a solution tert-butyl 4-oxoazepane-1-carboxylate (429.2, 11.0 g, 51.6 mmol, 1.00 equiv) in chloroform (220 mL) 0° C. was added dropwise solution of Br$_2$ (12.4 g, 77.6 mmol, 1.50 equiv) in chloroform (110 mL). The resulting mixture was stirred at room temperature overnight. The formed solids were collected by filtration and taken up in 200 mL of dichloromethane. Et$_3$N (12.2 g) and (Boc)$_2$O (8.70 g, 40.3 mmol, 1.00 equiv) were added to the mixture at 0° C. The resulting solution was stirred for 3 h at room temperature, and then concentrated under pressure. The crude residue was purified by silica gel chromatography using ethyl acetate/petroleum ether (1:10) as eluent to give 4.00 g (27%) of the title compound as a yellow oil.

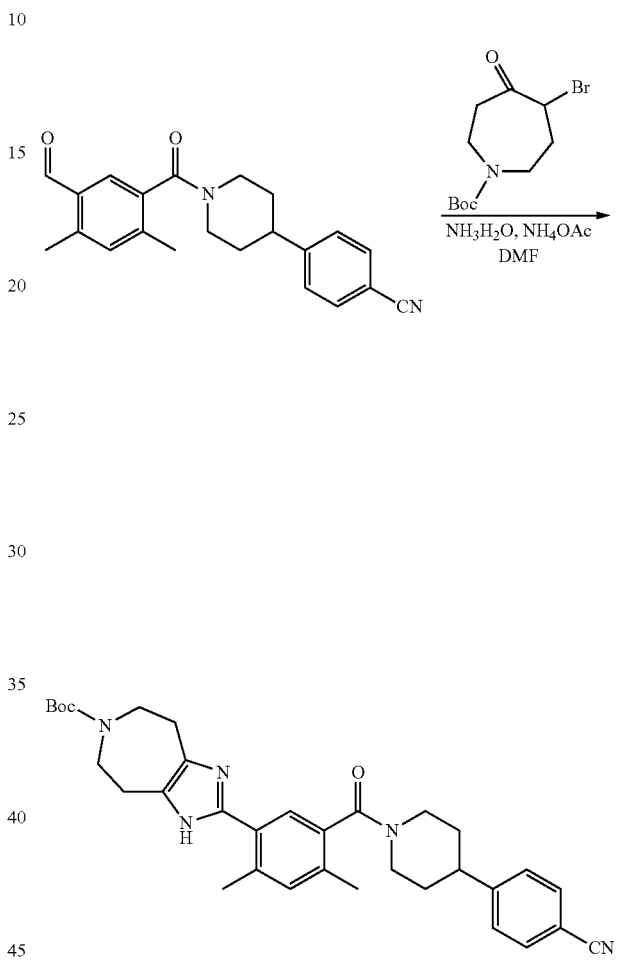

Compound 429.4. tert-Butyl 2-(5-(4-(4-cyanophenyl)piperidine-1-carbonyl)-2,4-dimethylphenyl)-4,5,7,8-tetrahydroimidazo[4,5-d]azepine-6(1H)-carboxylate To a solution of tert-butyl 4-bromo-5-oxoazepane-1-carboxylate (429.3, 844 mg, 2.89 mmol, 2.00 equiv) in N,N-dimethylformamide (5 mL) were added compound 16.4 (500 mg, 1.44 mmol, 1.00 equiv), NH$_4$OH (606 mg, 4.33 mmol, 3.00 equiv, 25%), and NH$_4$OAc (500 mg, 6.49 mmol, 4.50 equiv). The resulting mixture was stirred overnight at 130° C. under nitrogen. After cooling to ambient temperature, 30 mL of ethyl acetate was added. The resulting mixture was washed with 3×20 mL of brine, dried over anhydrous sodium sulfate, and concentrated under reduced pressure. The residue was purified by silica gel chromatography with ethyl acetate as eluent to yield 343 mg (43%) of the title compound as a brown solid.

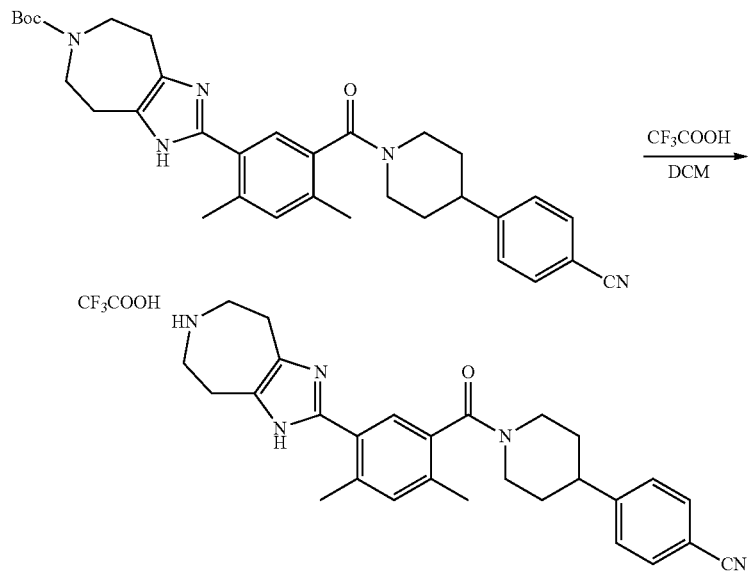

Compound 429.5. 4-(1-(5-(1,4,5,6,7,8-Hexahydroimidazo[4,5-d]azepin-2-yl)-2,4-dimethylbenzoyl)piperidin-4-yl)benzonitrile trifluoroacetate To a solution of compound 429.4 (550 mg, 0.990 mmol, 1.00 equiv) in DCM (3 mL) was added trifluoroacetic acid (1.3 mL). After stirring at 25° C. for 4 h, the mixture was concentrated under reduced pressure and dried to yield 400 mg (71%) of the title compound as a brown solid.

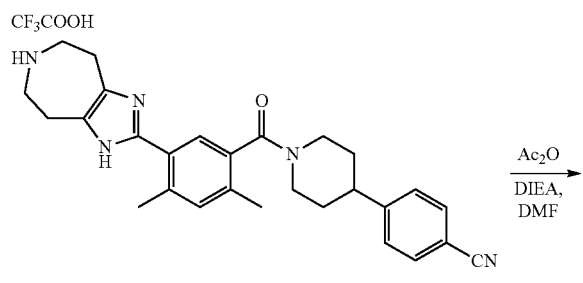

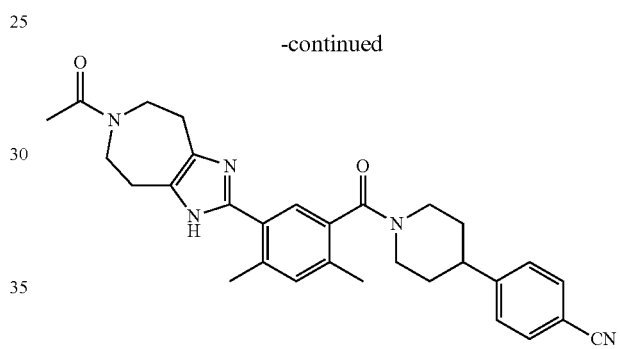

Compound 429. 4-(1-(5-(6-Acetyl-1,4,5,6,7,8-hexahydroimidazo[4,5-d]azepin-2-yl)-2,4-dimethylbenzoyl)piperidin-4-yl)benzonitrile The title compound was prepared using standard chemical manipulations and procedures similar to those used for the preparation of compound 2, except compound 429.5 was used in place of compound 2.9. m/z (ES+) 496 (M+H)$^+$. $^1$H NMR (300 MHz, CD$_3$OD) δ 7.65 (d, J=8.1 Hz, 2H), 7.44-7.32 (m, 4H), 4.90 (m, 1H), 3.86 (m, 2H), 3.60 (m, 1H), 3.20 (m, 2H), 3.00 (m, 6H), 2.40-2.31 (m, 6H), 2.20 (s, 3H), 2.00-1.60 (m, 5H).

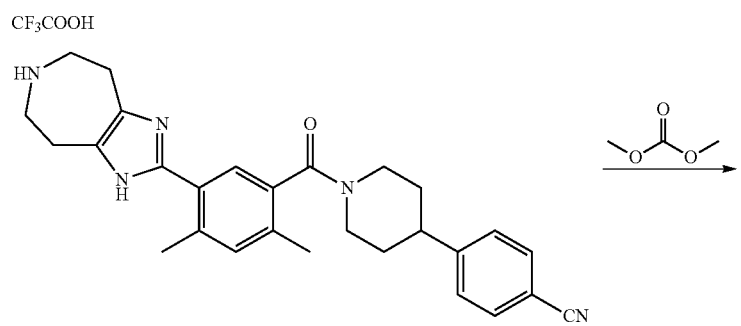

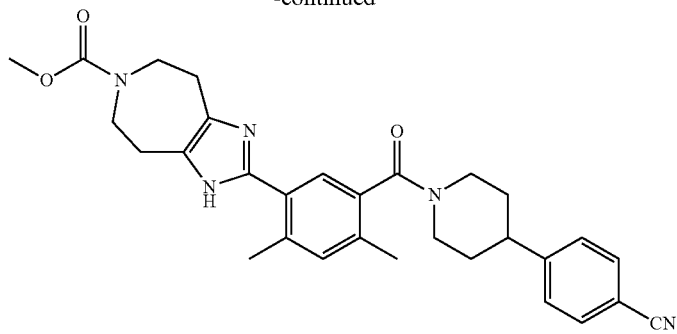

Compound 430. Methyl 2-(5-(4-(4-cyanophenyl)piperidine-1-carbonyl)-2,4-dimethylphenyl)-4,5,7,8-tetrahydroimidazo[4,5-d]azepine-6(1H)-carboxylate The title compound was prepared using standard chemical manipulations and procedures similar to those used for the preparation of compound 409, except compound 429.5 was used in place of compound 406.3. m/z (ES+) 496 (M+H)+.

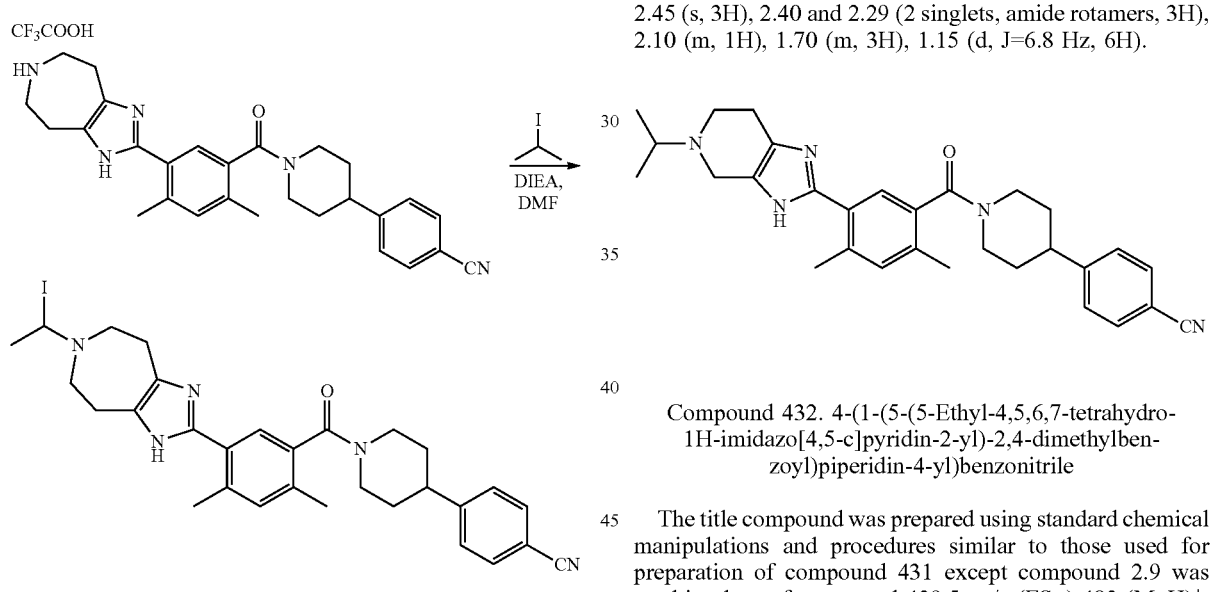

Compound 431. 4-(1-(5-(6-isopropyl-1,4,5,6,7,8-hexahydroimidazo[4,5-d]azepin-2-yl)-2,4-dimethylbenzoyl)piperidin-4-yl)benzonitrile To a solution of 4-(1-(5-(1,4,5,6,7,8-hexahydroimidazo[4,5-d]azepin-2-yl)-2,4-dimethylbenzoyl)piperidin-4-yl)benzonitrile trifluoroacetate (429.5, 80.0 mg, 0.140 mmol, 1.00 equiv) in N,N-dimethylformamide (5 mL) were added 2-iodopropane (270 mg, 1.59 mmol, 9.00 equiv) and DIEA (205 mg, 1.59 mmol, 9.00 equiv). The resulting solution was stirred overnight at 80° C. in an oil bath. After cooling to ambient temperature, the mixture was diluted with 50 mL of ethyl acetate, washed with 3×20 mL of brine, dried (Na$_2$SO$_4$), and concentrated. The residue was purified using silica gel column chromatography with ethyl acetate/petroleum ether (1:10) as eluent. The product (50 mg) was further purified by Prep-HPLC with the following conditions (1#-Pre-HPLC-001(SHIMADZU)): Column, Xbridge Prep C18, 5 um, 19*1.50 mm; mobile phase, water with 0.03% NH$_3$H$_2$O and CH$_3$CN (38.0% CH$_3$CN up to 51.0% in 8 min, up to 100.0% in 2 min, down to 38.0% in 1 min); Detector, Waters 2489 254 & 220 nm. The fractions containing pure compound were combined and lyophilized to yield 15.0 mg (21%) of the title compound as a white solid. m/z (ES+) 496 (M+H)+. $^1$H NMR (400 MHz, CD$_3$OD) δ 7.69 (d, J=8.0 Hz, 2H), 7.49 (m, 2H), 7.33-7.23 (m, 2H), 4.86 (m, 1H), 3.65 (m, 1H), 3.30 (m, 1H), 3.15 (m, 1H), 2.99 (m, 6H), 2.80 (m, 4H), 2.45 (s, 3H), 2.40 and 2.29 (2 singlets, amide rotamers, 3H), 2.10 (m, 1H), 1.70 (m, 3H), 1.15 (d, J=6.8 Hz, 6H).

Compound 432. 4-(1-(5-(5-Ethyl-4,5,6,7-tetrahydro-1H-imidazo[4,5-c]pyridin-2-yl)-2,4-dimethylbenzoyl)piperidin-4-yl)benzonitrile The title compound was prepared using standard chemical manipulations and procedures similar to those used for preparation of compound 431 except compound 2.9 was used in place of compound 429.5. m/z (ES+) 482 (M+H)+.

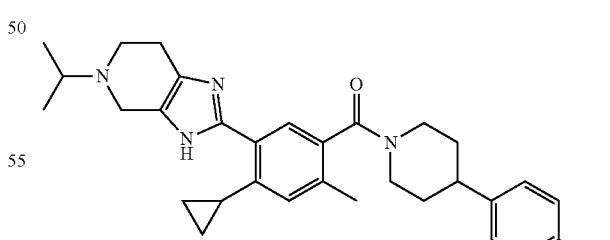

Compound 433. 4-(1-(4-Cyclopropyl-5-(5-isopropyl-4,5,6,7-tetrahydro-3H-imidazo[4,5-c]pyridin-2-yl)-2-methylbenzoyl)piperidin-4-yl)benzonitrile The title compound was prepared using standard chemical manipulations and procedures similar to those used for the preparation of compound 431, except compound 142.2 and tort-butyl 3-bromo-4-oxopiperidine-1-carboxylate were used in place of compound 152.3 and tert-butyl 4-ethyl 5-oxoazepane-1,4-dicarboxylate (429.2) respectively. m/z (ES+) 508 (M+H)+.

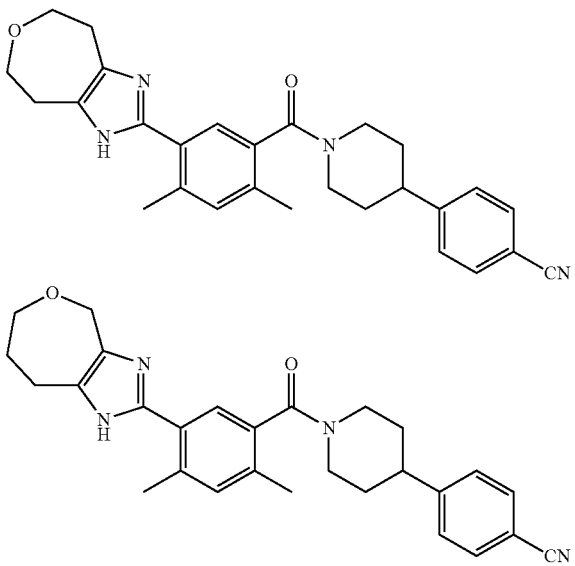

Compounds 434 and 435. 4-(1-(2,4-Dimethyl-5-(4,5,7,8-tetrahydro-1H-oxepino[4,5-d]imidazol-2-yl)benzoyl)piperidin-4-yl)benzonitrile and 4-(1-(2,4-dimethyl-5-(4,6,7,8-tetrahydro-1H-oxepino[3,4-d]imidazol-2-yl)benzoyl)piperidin-4-yl)benzonitrile The title compounds were prepared as a separable mixture using standard chemical manipulations and procedures similar to those used for the preparation of compound 429, except oxepan-4-one was used in place of compound tert-butyl 4-oxoazepane-1-carboxylate (429.2). 434: m/z (ES+) 455 (M+H)+. 435: m/z (ES+) 455 (M+H)+.

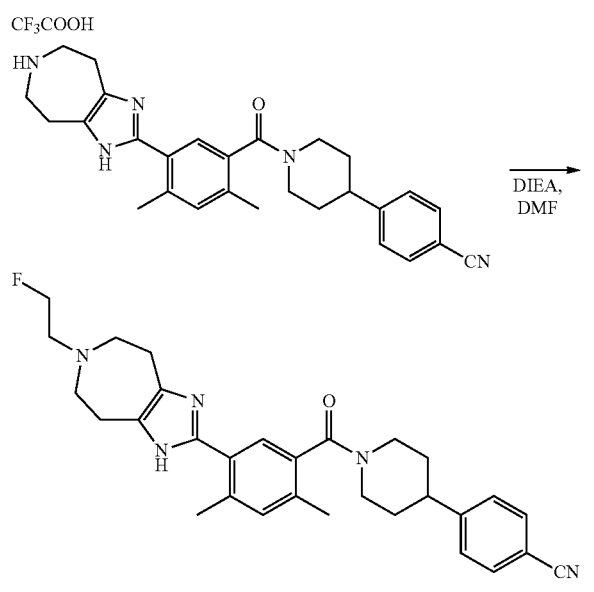

Compound 436. 4-(1-(5-(6-(2-Fluoroethyl)-1,4,5,6,7,8-hexahydroimidazo[4,5-d]azepin-2-yl)-2,4-dimethylbenzoyl)piperidin-4-yl)benzonitrile The title compound was prepared using standard chemical manipulations and procedures similar to those used for the preparation of compound 427, except compound 429.5 was used in place of compound 2.9. m/z (ES+) 500 (M+H)+. 1H NMR (400 MHz, CD3OD) δ 7.64 (d, J=8.1 Hz, 2H), 7.43 (m, 2H), 7.28-7.20 (m, 2H), 4.86 (m, 1H), 4.60 (dt, J1=47.7 Hz, J2=4.8 Hz, 2H), 3.60 (m, 1H), 3.20 (m, 1H), 3.00 (m, 8H), 2.80 (m, 4H), 2.40 (s, 3H), 2.35 and 2.24 (2 singlets, amide rotamers, 3H), 1.99 (m, 1H), 1.70 (m, 3H).

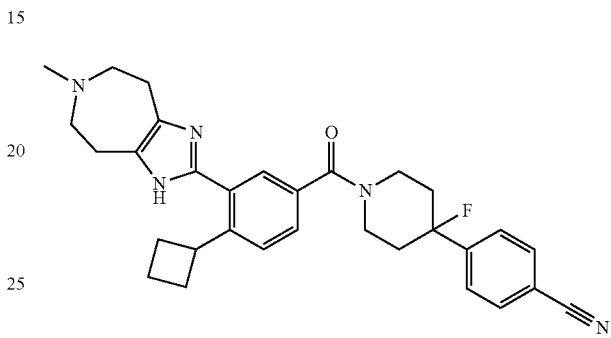

Compound 437. 4-(1-(4-Cyclobutyl-3-(6-methyl-1,4,5,6,7,8-hexahydroimidazo[4,5-d]azepin-2-yl)benzoyl)-4-fluoropiperidin-4-yl)benzonitrile The title compound was prepared using standard chemical manipulations and procedures similar to those used for the preparation of compound 418, except compound 429.3 was used in place of compound tert-butyl 3-bromo-4-oxopiperidine-1-carboxylate. m/z (ES+) 512 (M+H)+.

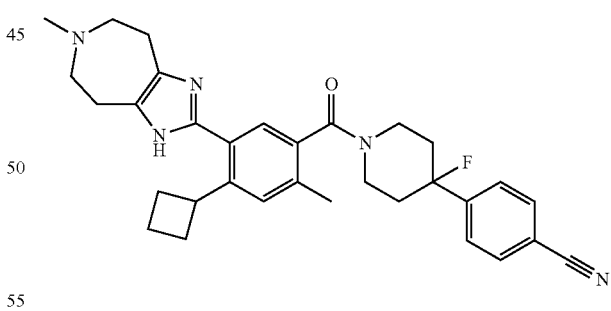

Compound 438. 4-(1-(4-Cyclobutyl-2-methyl-5-(6-methyl-1,4,5,6,7,8-hexahydroimidazo[4,5-d]azepin-2-yl)benzoyl)-4-fluoropiperidin-4-yl)benzonitrile The title compound was prepared using standard chemical manipulations and procedures similar to those used for the preparation of compound 407, except compound 429.3 was used in place of compound tert-butyl 3-bromo-4-oxopiperidine-1-carboxylate. m/z (ES+) 526 (M+H)+.

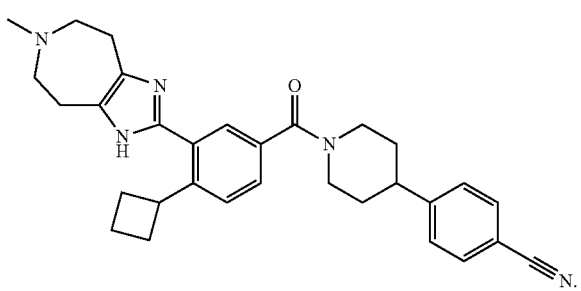 [SMILES: CN1CCc2nc(-c3cc(C(=O)N4CCC(c5ccc(C#N)cc5)CC4)ccc3C3CCC3)[nH]c2CC1]

Compound 439. 4-(1-(4-Cyclobutyl-3-(6-methyl-1,4,5,6,7,8-hexahydroimidazo[4,5-d]azepin-2-yl)benzoyl)piperidin-4-yl)benzonitrile The title compound was prepared using standard chemical manipulations and procedures similar to those used for the preparation of compound 417, except compound 429.3 was used in place of compound tert-butyl 3-bromo-4-oxopiperidine-1-carboxylate. m/z (ES+) 494 (M+H)+.

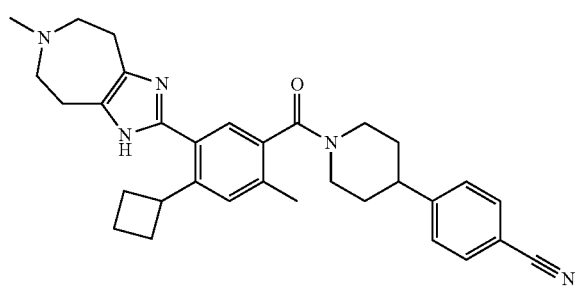 [SMILES: Cc1cc(C2CCC2)c(-c2nc3c([nH]2)CCN(C)CC3)cc1C(=O)N1CCC(c2ccc(C#N)cc2)CC1]

Compound 440. 4-(1-(4-Cyclobutyl-2-methyl-5-(6-methyl-1,4,5,6,7,8-hexahydroimidazo[4,5-d]azepin-2-yl)benzoyl)piperidin-4-yl)benzonitrile The title compound was prepared using standard chemical manipulations and procedures similar to those used for the preparation of compound 406, except compound 429.3 was used in place of compound tert-butyl 3-bromo-4-oxopiperidine-1-carboxylate. m/z (ES+) 508 (M+H)+.

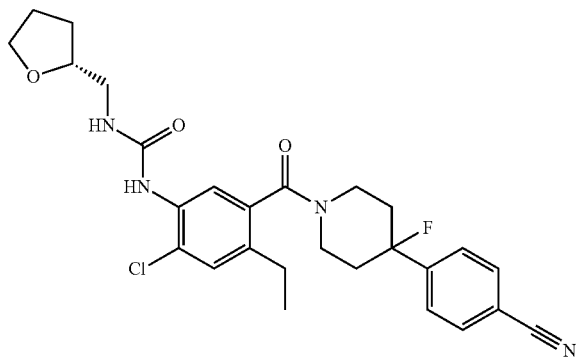 [SMILES: CCc1cc(Cl)c(NC(=O)NC[C@H]2CCCO2)cc1C(=O)N1CCC(F)(c2ccc(C#N)cc2)CC1]

Compound 441. (R)-1-(2-Chloro-5-(4-(4-cyanophenyl)-4-fluoropiperidine-1-carbonyl)-4-ethylphenyl)-3-((tetrahydrofuran-2-yl)methyl)urea The title compound was prepared using readily available reagents and procedures similar to those used for the preparation of compound 67 and using compound 178.2 in place of compound 48.1. m/z (ES+) 513 (M+H)+.

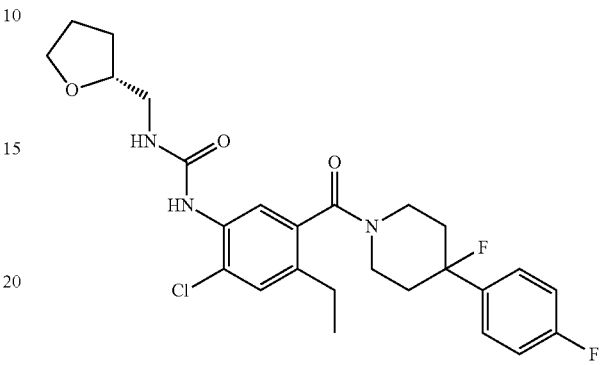

Compound 442. (R)-1-(2-Chloro-4-ethyl-5-(4-fluoro-4-(4-fluorophenyl)piperidine-1-carbonyl)phenyl)-3-((tetrahydrofuran-2-yl)methyl)urea The title compound was prepared using readily available reagents and procedures similar to those used for the preparation of compound 67 and using compound 178.2 in place of compound 48.1. m/z (ES+) 506 (M+H)+.

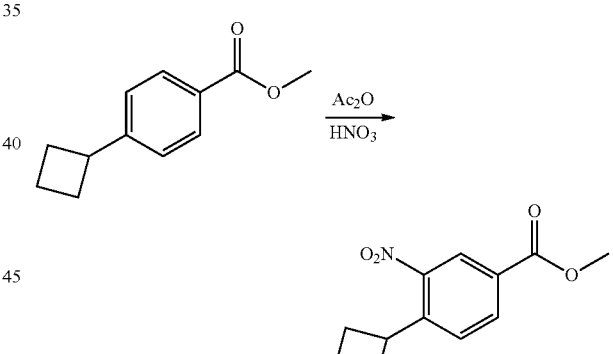

Compound 443.1. Methyl 4-cyclobutyl-3-nitrobenzoate

To a solution of methyl 4-cyclobutylbenzoate (compound 168.1, 3.80 g, 20.0 mmol, 1.00 equiv) in acetic anhydride (12 mL) 0° C. was added dropwise fuming HNO$_3$ (5 mL, 97%). The resulting mixture was stirred at 30° C. in an oil bath. After 2 h, 30 mL of water was carefully added and the mixture was extracted with 2×30 mL of ethyl acetate. The combined organic layers were washed with aqueous saturated NaHCO$_3$ (note: gas evolution), dried over anhydrous sodium sulfate, and concentrated under reduced pressure. The residue was purified using silica gel column chromatography with ethyl acetate/petroleum ether (1:25) as eluent to furnish 3.00 g (64%) of the title compound as a light yellow oil.

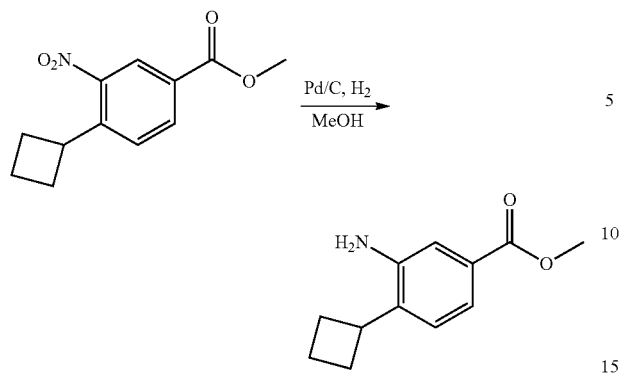

Compound 443.2. Methyl 3-amino-4-cyclobutylbenzoate

A flask containing a solution of methyl 4-cyclobutyl-3-nitrobenzoate (compound 443.1, 2.50 g, 10.6 mmol, 1.00 equiv) in methanol (30 mL) was purged with nitrogen. Palladium on carbon (10%, 60% water, 1.2 g) was added and the flask was carefully purged further with nitrogen. The atmosphere was then changed to hydrogen and the mixture was stirred overnight at 20° C. After purging the system with nitrogen, the solids were then removed by filtration and the filtrate was concentrated under reduced pressure. The residue was purified using silica gel column chromatography with ethyl acetate/petroleum ether (1:5) as eluent to yield 1.60 g (73%) of the title compound as a white solid.

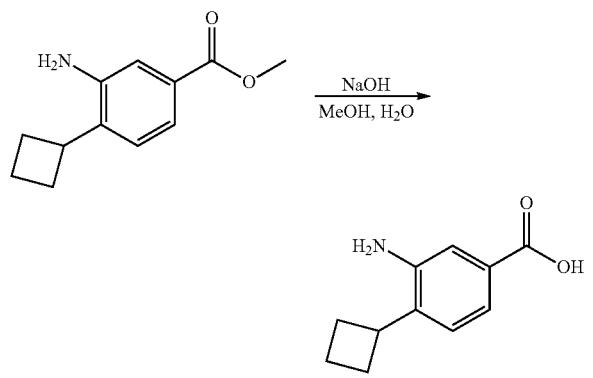

Compound 443.3. 3-Amino-4-cyclobutylbenzoic acid

Into around-bottom flask, was placed a solution of methyl 3-amino-4-cyclobutylbenzoate (1.00 g, 4.87 mmol, 1.00 equiv) and sodium hydroxide (compound 443.2, 800 mg, 20.0 mmol, 4.00 equiv) in a solvent mixture of methanol and H$_2$O (20/10 mL). The resulting solution was stirred for 8 h at 20° C. After cooling to ambient temperature, the organic solvent was removed under reduced pressure. The pH of the remaining aqueous layer was adjusted to ~4-5 with HCl (aqueous, 1 M). The resulting precipitate was then collected by filtration and dried to furnish 500 mg (54%) of the title compound as a white solid.

Compound 443.4. 4-(1-(3-Amino-4-cyclobutylbenzoyl)-4-fluoropiperidin-4-yl)benzonitrile The title compound was prepared using a procedure similar to that used for the preparation of compound 42.2, but using compound 443.3 in place of compound 42.1.

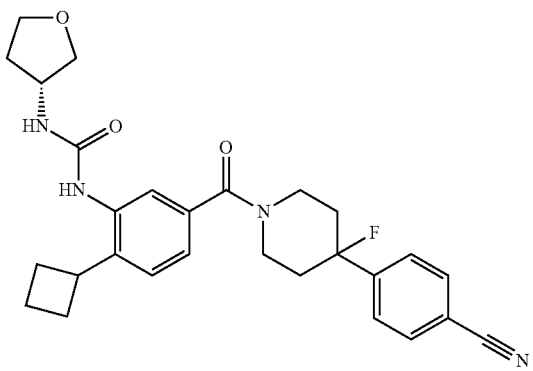 [SMILES: N#Cc1ccc(C2(F)CCN(C(=O)c3ccc(C4CCC4)c(NC(=O)N[C@@H]4CCOC4)c3)CC2)cc1]

Compound 443. (R)-1-(5-(4-(4-Cyanophenyl)-4-fluoropiperidine-1-carbonyl)-2-cyclobutylphenyl)-3-(tetrahydrofuran-3-yl)urea The title compound was prepared using standard chemical manipulations and procedures similar to those used for the preparation of compound 64, using compound 443.4 and (R)-tetrahydrofuran-3-amine in place of compound 42.2 and (R)-(tetrahydrofuran-2-yl)methanamine respectively. m/z (ES+) 491 (M+H)$^+$.

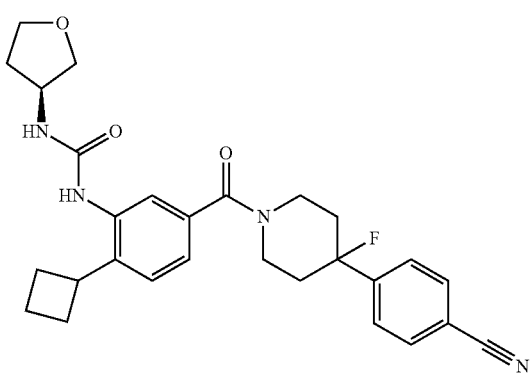 [SMILES: N#Cc1ccc(C2(F)CCN(C(=O)c3ccc(C4CCC4)c(NC(=O)N[C@H]4CCOC4)c3)CC2)cc1]

Compound 444. (S)-1-(5-(4-(4-Cyanophenyl)-4-fluoropiperidine-1-carbonyl)-2-cyclobutylphenyl)-3-(tetrahydrofuran-3-yl)urea The title compound was prepared using standard chemical manipulations and procedures similar to those used for the preparation of compound 443, using (S)-tetrahydrofuran-3-amine in place of (R)-tetrahydrofuran-3-amine. m/z (ES+) 491 (M+H)+. $^1$H NMR (300 MHz, CD$_3$OD): δ 7.83-7.77 (m, 3H), 7.69 (d, J=8.4 Hz, 2H), 7.38 (d, J=8.1 Hz, 1H), 7.22 (dd, J=7.8 Hz, J=1.5 Hz, 1H), 4.80-4.62 (m, 1H), 4.39-4.31 (m, 1H), 4.02-3.78 (m, 4H), 3.72-3.49 (m, 3H), ~3.3 (1H partially obscured by methanol solvent peak), 2.50-2.37 (m, 2H), 2.37-1.78 (m, 10H).

Compound 445.2. Methyl 4-cyclobutyl-5-(5-ethyl-1H-pyrazol-3-yl)-2-methylbenzoate To a solution of methyl 4-cyclobutyl-2-methyl-5-(3-oxopentanoyl)benzoate (compound 445.1, 300 mg, 0.990 mmol, 1.00 equiv) in methanol (15 mL) was added NH$_2$NH$_2$.H$_2$O. The resulting solution was stirred for 1.5 h at 80° C. in an oil bath, and then concentrated under reduced pressure. The residue was diluted with 100 mL of ethyl acetate, then washed with 3×100 mL of brine, dried over anhydrous sodium sulfate and concentrated under reduced pressure. The residue was purified using silica gel column chromatography with ethyl acetate/petroleum ether (1:5) as eluent to yield 188 mg (64%) of the title compound as a yellow oil.

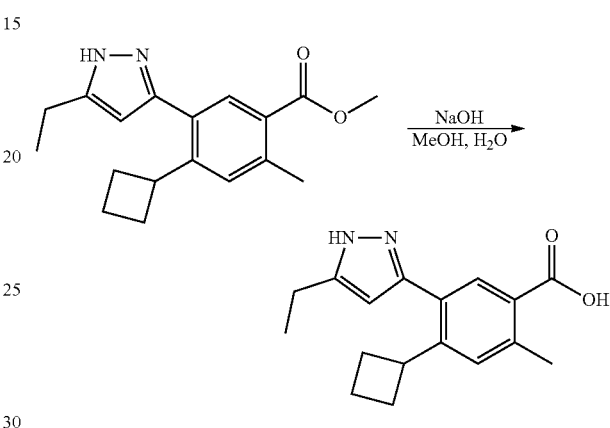

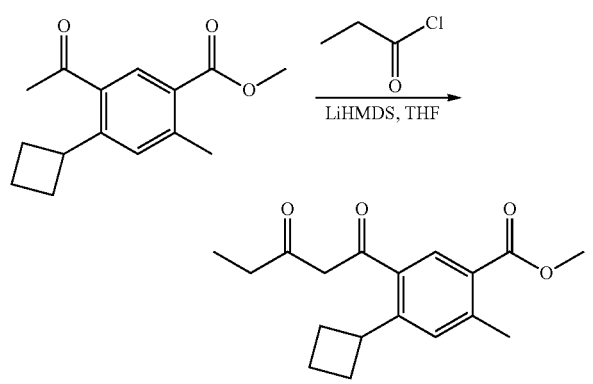

Compound 445.1. Methyl 4-cyclobutyl-2-methyl-5-(3-oxopentanoyl)benzoate

To a solution of methyl 5-acetyl-4-cyclobutyl-2-methylbenzoate (compound 238.1, 500 mg, 2.03 mmol, 1.00 equiv) in tetrahydrofuran (15 mL) at 0° C. was added dropwise a solution of LiHMDS (680 mg, 4.06 mmol, 2.00 equiv) in tetrahydrofuran (5 mL). After 30 min of stirring at 0° C., a solution of propanoyl chloride (280 mg, 3.03 mmol, 1.50 equiv) in tetrahydrofuran (5 mL) was added dropwise. The resulting mixture was stirred for 3 h at 15° C., and then concentrated under reduced pressure. The residue was diluted with 40 mL of ethyl acetate, washed with of brine (3×40 mL), dried (Na$_2$SO$_4$), and concentrated under reduced pressure. This resulted in 500 mg (crude) of the title compound as a brown oil.

Compound 445.3. 4-Cyclobutyl-5-(5-ethyl-1H-pyrazol-3-yl)-2-methylbenzoic acid To a solution of methyl 4-cyclobutyl-5-(5-ethyl-1H-pyrazol-3-yl)-2-methylbenzoate (compound 445.2, 188 mg, 0.630 mmol, 1.00 equiv) in methanol (6 mL) was added aqueous sodium hydroxide (76.0 mg, 1.90 mmol, 3.00 equiv in 3 mL water). The resulting solution was stirred for 2 h at 70° C. in an oil bath. After cooling to ambient temperature, the mixture was concentrated under reduced pressure. The residue was diluted with 20 mL of H$_2$O. The pH of the mixture was adjusted to ~4 with aqueous HCl (2 M). The mixture was then extracted with 3×20 mL of ethyl acetate. The combined organic layers were washed with 3×20 mL of brine, dried (Na$_2$SO$_4$), and concentrated under reduced pressure. This resulted in 0.180 g (crude) of the title compound as a yellow oil.

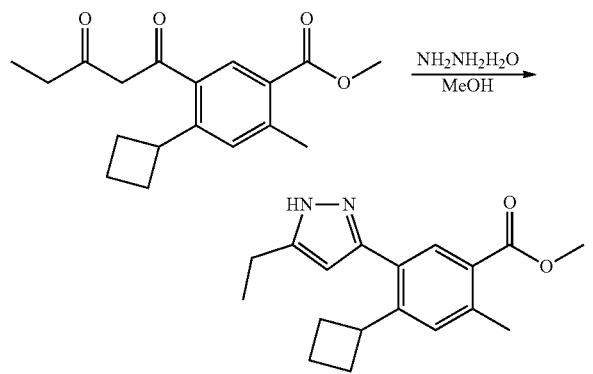

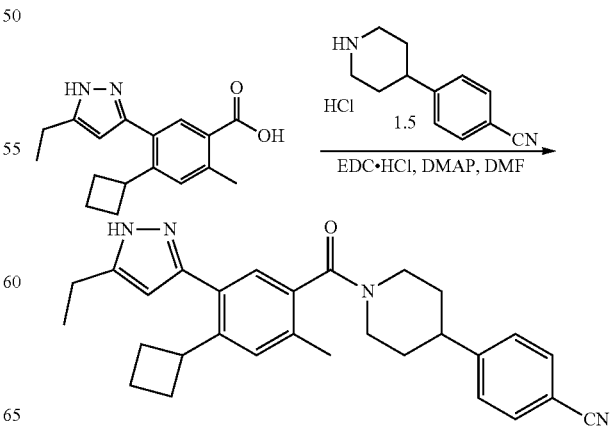

Compound 445. 4-(1-(4-Cyclobutyl-5-(5-ethyl-1H-pyrazol-3-yl)-2-methylbenzoyl)piperidin-4-yl)benzonitrile To a solution of 4-cyclobutyl-5-(5-ethyl-1H-pyrazol-3-yl)-2-methylbenzoic acid (compound 445.3, 130 mg, 0.460 mmol, 1.00 equiv) in N,N-dimethylformamide (5 mL) were added 4-(Piperidin-4-yl)benzonitrile hydrochloride (1.5, 102 mg, 0.460 mmol, 1.00 equiv), EDCI (176 mg, 0.920 mmol, 2.00 equiv), and 4-dimethylaminopyridine (112 mg, 0.920 mmol, 2.00 equiv). The resulting solution was stirred for 2 h at 30° C., and then diluted with 40 mL of ethyl acetate. The mixture was washed with 3×40 mL of brine, dried (Na₂SO₄), and concentrated under reduced pressure. The crude product was purified by Prep-HPLC with the following conditions (1#-Pre-HPLC-001(SHIMADZU)): Column, SunFire Prep C18, 19*150 mm 5 um; mobile phase, water with 0.05% TFA and CH₃CN (59.0% CH₃CN up to 73.0% in 6 min, up to 100.0% in 7 min, down to 59.0% in 1 min); Detector, Waters 2489 254 & 220 nm. The fractions containing pure compound were combined and lyophilized to yield 150 mg (72%) of the title compound as a white solid. m/z (ES+) 453 (M+H)⁺.

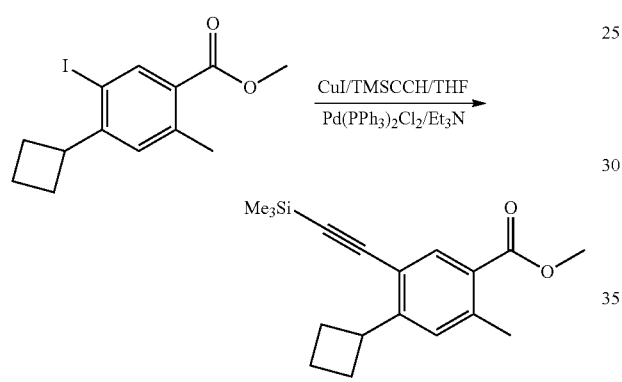

Compound 446.1 Methyl 4-cyclobutyl-2-methyl-5-((trimethylsilyl)ethynyl)benzoate

A mixture of methyl 4-cyclobutyl-5-iodo-2-methylbenzoate (compound 152.3, 1.32 g, 4 mmol), trimethylsilylacetylene (663 μl, 4.8 mmol), Pd(PPh₃)₂Cl₂ (85 mg, 0.12 mmol) and copper iodide (CuI, 46 mg, 0.24 mmol) in THF (8 ml) and triethylamine (2 ml) was degassed and then heated to 80° C. for 1.5 hours under nitrogen. After cooling to ambient temperature, the reaction was filtered through celite and concentrated. The residue was dissolved in ethyl acetate (EtOAc), washed with brine, dried over MgSO₄ and concentrated. The residue was purified by flash chromatography (SiO₂; 3% EtOAc in Hexane) to give 1.17 g (97%) of the title compound as a liquid. ¹HNMR (400 MHz, CDCl₃) δ 8.01 (s, 1H), 7.15 (s, 1H), 4.01-3.75 (m, 4H), 2.63 (s, 3H), 2.54-2.31 (m, 2H), 2.27-2.12 (m, 2H), 2.12-1.98 (m, 1H), 1.94-1.80 (m, 1H), 0.28 (s, 9H).

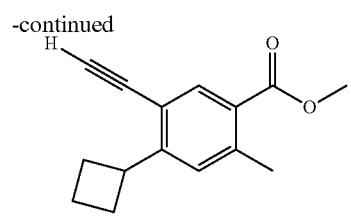

Compound 446.2. Methyl 4-cyclobutyl-5-ethynyl-2-methylbenzoate

To a solution of compound 446.1 (1.17 g, 3.9 mmol) in THF (6 ml) at −20° C. was added 4.1 ml TBAF (1.0 M in THF). The mixture was stirred for 30 minutes at this temperature and was then diluted with water (15 ml) and extracted with EtOAc twice. The combined organic phases were washed with brine, dried (MgSO₄), and concentrated. The residue was purified by flash chromatography (SiO₂; 2% EtOAc in Hexane) to give 816 mg (91%) of the title compound as a liquid. m/z (ES−) 227 (M−H)⁺. ¹H NMR (400 MHz, CDCl₃) δ 8.05 (s, 1H), 7.20 (s, 1H), 4.02-3.80 (m, 4H), 3.25 (s, 1H), 2.64 (s, 3H), 2.52-2.38 (m, 2H), 2.29-2.13 (m, 2H), 2.12-1.98 (m, 1H), 1.93-1.79 (m, 1H).

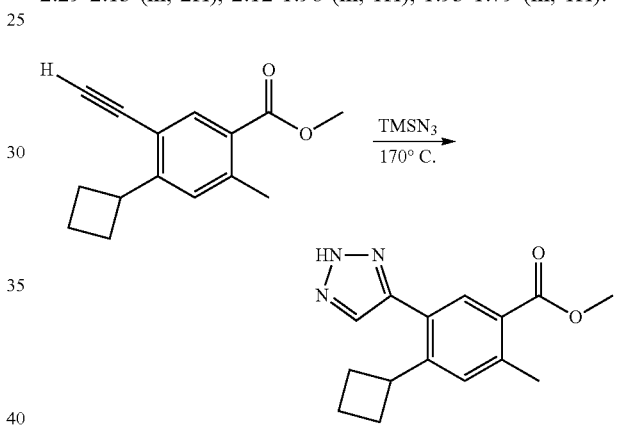

Compound 446.3. Methyl 4-cyclobutyl-2-methyl-5-(2H-1,2,3-triazol-4-yl) benzoate

Methyl 4-cyclobutyl-5-ethynyl-2-methylbenzoate (compound 446.2, 180 mg, 0.69 mmol) was dissolved in TMSN₃ (1 ml) in sealed tube. The reaction was heated to 170° C. for 24 hours behind a blast shield then cooled down to 0° C. EtOAc (10 ml) and water (20 ml) were added. The resulting mixture was stirred at RT for 1 hr. The organic phase was then washed with brine, dried (MgSO₄), and concentrated. The residue was purified by flash chromatography (SiO₂; 0-30% EtOAc in Hexane) to give 92 mg (49%) of the title compound as a liquid. m/z (ES+) (272) (M+H)⁺. ¹H NMR (400 MHz, CDCl₃) δ 8.04 (s, 1H), 7.83 (s, 1H), 7.35 (s, 1H), 3.90 (s, 4H), 2.69 (s, 3H), 2.27-2.15 (m, 2H), 2.13-2.03 (m, 2H), 1.99-1.90 (m, 1H), 1.86-1.76 (m, 1H).

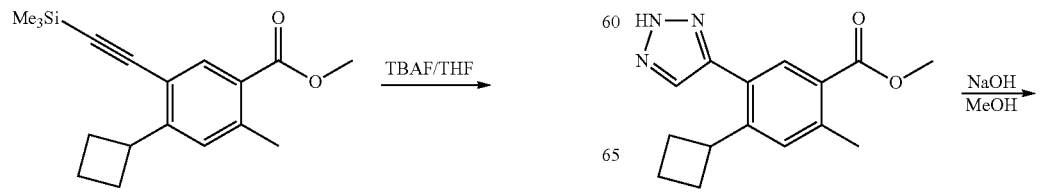

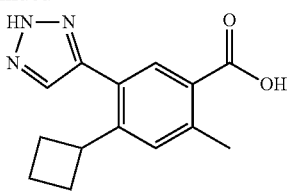

Compound 446.4. 4-Cyclobutyl-2-methyl-5-(2H-1,2,3-triazol-4-yl) benzoic acid

A solution of methyl 4-cyclobutyl-2-methyl-5-(2H-1, 2, 3-triazol-4-yl)benzoate (compound 446.3, 92 mg, 0.34 M) in 2N NaOH (1.5 ml) and methanol (MeOH) (4 ml) was heated at 50° C. for 16 hours. After cooling to room temperature, the methanol was removed under reduced pressure. The residue was neutralized with 2N HCl to pH 3-4 and extracted with EtOAc. The organic phase was then washed with brine, dried (MgSO$_4$), and concentrated to yield 83 mg of a white solid that was used without further purification. m/z (ES−) 256 (M−H)$^+$.

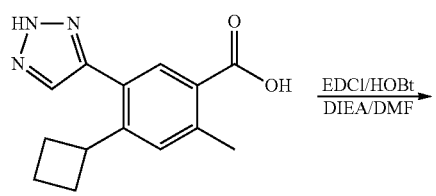

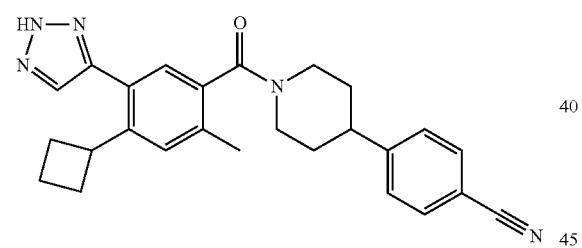

Compound 446. 4-(1-(4-Cyclobutyl-2-methyl-5-(2H-1,2,3-triazol-4-yl) benzoyl) piperidin-4-yl) benzonitrile A mixture of the above acid (compound 446.4, 44 mg, 0.17 mmol), compound 1.5 (42 mg, 0.19 M), EDCI (49 mg, 0.26 mmol), HOBt (33 mg, 0.19 mmol) and DIEA (120 □l, 0.68 mmol) in DMF (1 ml) was stirred at room temperature for 2.5 hours. The reaction was then diluted with water and extracted with EtOAc. The organic layer was washed with brine, dried over MgSO$_4$, and concentrated. The residue was purified by flash chromatography (SiO$_2$; 8% Methanol in dichloromethane) and to yield 46 mg foam of the title compound (70%). m/z (ES+) 426 (M+H)$^+$. $^1$H NMR (400 MHz, CDCl$_3$) δ 12.20 (s, 1H), 7.70 (d, 1H), 7.66-7.49 (m, 2H), 7.44-7.21 (m, 4H), 5.01 (d, 1H), 3.83 (p, 1H), 3.72 (d, 1H), 3.27-3.06 (m, 1H), 2.91 (m, 2H), 2.46 (2 singlets, amide rotamers, 3H), 2.27-1.89 (m, 3H), 1.86-1.43 (m, 7H).

Compound 447. 4-(1-(4-Cyclobutyl-2-methyl-5-(2H-1,2,3-triazol-4-yl)benzoyl)-4-fluoropiperidin-4-yl)benzonitrile The title compound was prepared using procedures similar to those used for preparation of compound 446 and using compound 11.2 HCl salt in place of compound 1.5. m/z (ES+) (444) (M+H)$^+$. $^1$H NMR (400 MHz, CDCl$_3$) δ 12.00 (s, 1H), 7.77 (s, 1H), 7.67 (m, 2H), 7.49 (d, 2H), 7.37 (m, 2H), 4.92 (d, 1H), 3.85 (t, 1H), 3.61 (m, 1H), 3.52 (m, 1H), 3.25 (m, 1H), 2.45 (2 singlets, amide rotamers, 3H), 2.28-1.89 (m, 8H), 1.85 (m, 2H).

Compound 448.1. Methyl 5-(6,7-dihydro-4H-pyrano[4,3-d]thiazol-2-yl)-2,4-dimethylbenzoate To a solution of methyl 5-carbamothioyl-2,4-dimethylbenzoate (compound 130.1, 500 mg, 2.24 mmol, 1.00 equiv) in ethanol (5 mL) was added sodium bicarbonate (396 mg, 4.71 mmol, 1.00 equiv) and 3-bromodihydro-2H-pyran-4 (3H)-one (compound 1.10.1, 186 mg, 1.04 mmol, 1.00 equiv). The resulting solution was stirred overnight at 80° C. under nitrogen. After cooling to room temperature the mixture was concentrated under reduced pressure. The residue was taken up 10 mL of water and ethyl acetate. The aqueous phase was extracted with 2×20 mL of ethyl acetate and the combined organic layers were dried (MgSO$_4$), and concentrated under reduced pressure to yield 400 mg (56%) of the title compound as a yellow solid.

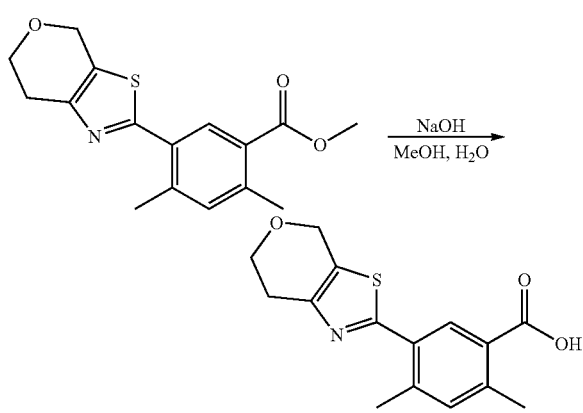

Compound 448.2. 5-(6,7-Dihydro-4H-pyrano[4,3-d]thiazol-2-yl)-2,4-dimethylbenzoic acid A solution of compound 448.1 (304 mg, 1.00 mmol) and sodium hydroxide (aqueous, 280 mg, 7.00 mmol in 3 mL water) in methanol (5 mL) was stirred for 1 h at 56° C. in an oil bath. After cooling to ambient temperature, the methanol was removed under reduced pressure. The pH of the remaining aqueous layer was adjusted to 3~4 with hydrogen chloride (aq., 2 M). The resulting precipitate was collected by filtration and dried in an oven under reduced pressure to yield 230 mg (79%) of the title compound as a yellow solid.

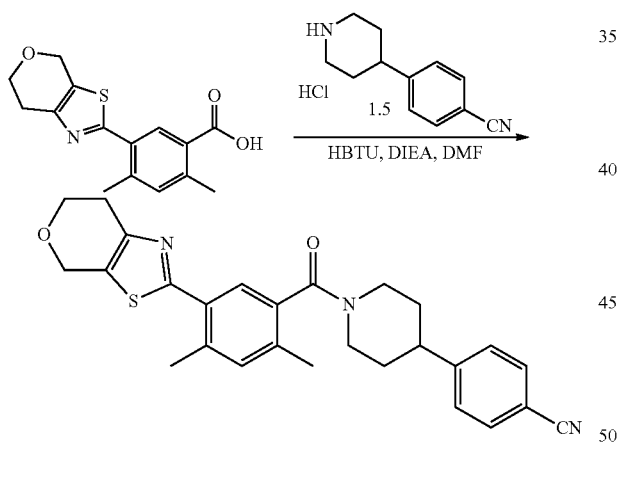

Compound 448. 4-(1-(5-(6,7-Dihydro-4H-pyrano[4,3-d]thiazol-2-yl)-2,4-dimethylbenzoyl)piperidin-4-yl)benzonitrile A solution of compound 448.2 (100 mg, 0.35 mmol, 1.00 equiv) in N,N-dimethylformamide (3 mL), DIEA (140 mg, 1.08 mmol, 3.00 equiv), and HBTU (197 mg, 0.52 mmol, 1.50 equiv) was stirred for 0.5 h at 25° C. A solution of 4-(piperidin-4-yl)benzonitrile hydrochloride (compound 1.5, 92.2 mg, 0.41 mmol, 1.10 equiv) in DIEA (1 mL) was added dropwise. The resulting solution was stirred for 0.5 h at 25° C., then quenched with 10 mL of water. The aqueous phase was extracted with 2×20 mL of ethyl acetate and the combined organic layers were washed with 1×20 mL of water, 1×20 mL of brine, dried over anhydrous sodium sulfate and concentrated under reduced pressure. The residue was purified using silica gel column chromatography with ethyl acetate/petroleum ether (1:1) as eluent. The product was further purified by Prep-HPLC using the following conditions (1#-Pre-HPLC-001 (SHIMADZU)): Column, SunFire Prep C18, 19*150 min 5 um; mobile phase, water with 0.05% TFA and CH$_3$CN (25% CH$_3$CN up to 80% in 7 min, up to 100% in 1 min, down to 25% in 1 min); Detector, Waters 2489 254 & 220 nm. The fractions containing pure compound were combined and lyophilized to yield 134.9 mg (85%) of the title compound as a white solid. m/z (ES+) 458 (M+H)$^+$.

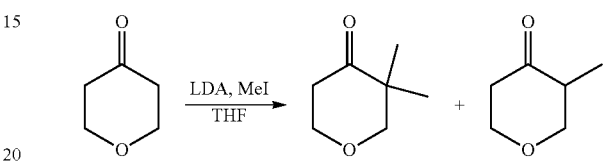

Compound 449.1 and Compound 400.1. 3,3-Dimethyldihydro-2H-pyran-4(3H)-one (compound 449.1) and 3-methyldihydro-2H-pyran-4(3H)-one (compound 400.1)

To a solution of LDA (2.0 M in heptanes/THF/ethylbenzene) (28 mL, 55 mmol) was added dihydro-2H-pyran-4(3H)-one (4.612 g, 46 mmol) in THF (50 mL) drop-wise under argon at −78° C. The mixture was stirred at −78° C. for 5 minutes, then iodomethane (14 mL, 225 mmol) in THF (500 ml) was added. The resulting mixture was allowed to warm to 0° C. and stirred for 2 hours at 0° C. The reaction was allowed to warm to room temperature for 5 min, then cooled back to 0° C. and quenched with saturated ammonium chloride (30 mL) and the mixture was extracted with ether (2×50 mL). The combined organics was washed with brine (50 mL), dried (MgSO$_4$), filtered and concentrated in vacuo. The residue was purified by silica gel chromatography (15% ethyl acetate in hexanes) to yield 3,3-dimethyldihydro-2H-pyran-4(3H)-one (compound 449.1) as an oil (694 mg, 13%) and 3-methyldihydro-2H-pyran-4(3H)-one (compound 400.1) as an oil (860 mg, 16%).

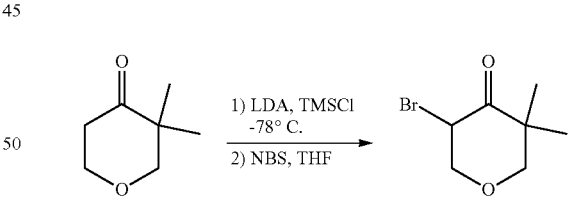

Compound 449.2. 5-Bromo-3,3-dimethyldihydro-2H-pyran-4(3H)-one

A solution of lithium diisopropylamine (2.0 M in heptanes/THF/ethylbenzene) (2.5 ml, 5.1 mmol) diluted with THF (10 mL) under argon was cooled to −78° C. Chlorotrimethylsilane (2.5 mL, 19.5 mmol) was added followed by 3,3-dimethyldihydro-2H-pyran-4(3H)-one (compound 449.1, 500 mg, 3.9 mmol) in THF (5 mL) and triethylamine (8.0 mL, 57 mmol). The resulting mixture was stirred at −78° C. for 5 minutes and then quenched with saturated NaHCO$_3$ (20 mL). The mixture was extracted with ether (30 mL) and the organics was washed with 1M citric acid (50 mL), dried (K₂CO₃), filtered and concentrated in vacuo. The residue was dissolved in THF (5 mL) and cooled to 0° C. N-Bromosuccinimide (694 mg, 3.9 mmol) was added and the resulting mixture was stirred at room temperature for 2 hrs and then quenched with saturated NaHCO₃ (10 mL). The mixture was extracted with ether (2×20 mL) and the organics was washed with brine, dried (MgSO₄), filtered and concentrated in vacuo. The residue was purified by silica gel chromatography (8% ethyl acetate in hexane) to yield the title compound as an oil (150 mg, 18 N.

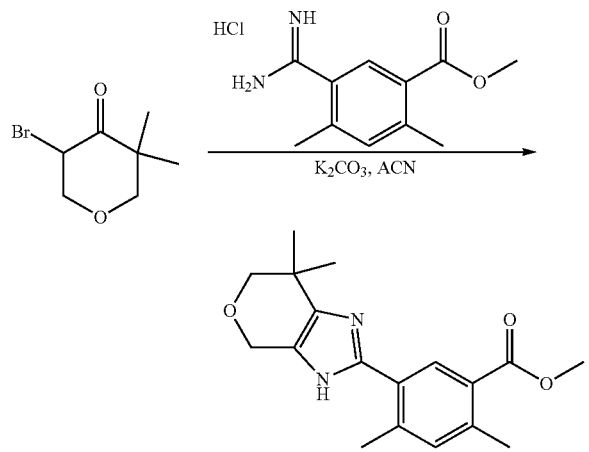

Compound 449.3. Methyl 5-(7,7-dimethyl-3,4,6,7-tetrahydropyrano[3,4-d]imidazol-2-yl)-2,4-dimethylbenzoate A mixture of 5-bromo-3,3-dimethyldihydro-2H-pyran-4(3H)-one (compound 449.2, 150 mg, 0.72 mmol), methyl 5-carbamimidoyl-2,4-dimethylbenzoate hydrochloride (compound 2.5, 135 mg, 0.55 mmol), and potassium carbonate (228 mg, 1.65 mmol) in acetonitrile (8 mL) was heated at 100° C. for 48 hrs. The mixture was concentrated in vacuo and the residue was dissolved in ethyl acetate (10 mL) and washed with brine (20 mL), dried (MgSO₄), filtered and concentrated in vacuo. The residue was purified by silica gel chromatography (50% ethyl acetate in hexanes) to yield the title compound as a white solid (27 mg, 15%).

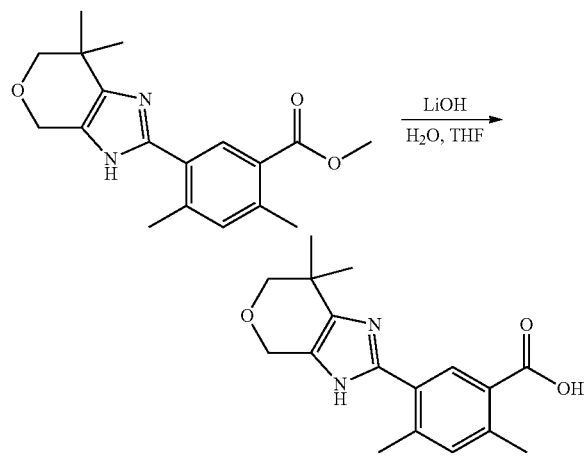

Compound 449.4. 5-(7,7-Dimethyl-3,4,6,7-tetrahydropyrano[3,4-d]imidazol-2-yl)-2,4-dimethylbenzoic acid To methyl 5-(7,7-dimethyl-3,4,6,7-tetrahydropyrano[3,4-d]imidazol-2-yl)-2,4-dimethylbenzoate (compound 449.3, 27 mg, 0.086 mmol) in THF (3 mL) was added 2 M lithium hydroxide (430 ul, 0.86 mmol) and the mixture was heated at 50° C. for 16 hrs. The volatile solvents were removed in vacuo and the resulting residue was neutralized with 2M HCl to pH=3 and concentrated in vacuo to give a white solid and used in the next reaction without doing further purification. m/z (ES−) 299 (M−H)⁻.

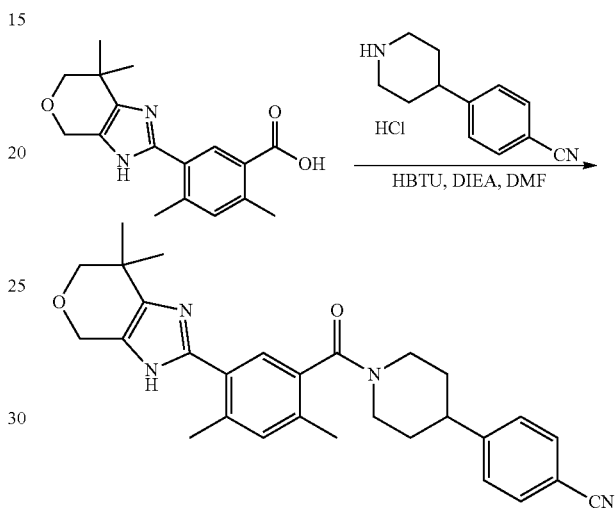

Compound 449. 4-(1-(5-(7,7-Dimethyl-3,4,6,7-tetrahydropyrano[3,4-d]imidazol-2-yl)-2,4-dimethylbenzoyl)piperidin-4-yl)benzonitrile Crude 5-(7,7-Dimethyl-3,4,6,7-tetrahydropyrano[3,4-d]imidazol-2-yl)-2,4-dimethylbenzoic acid (compound 449.4, 0.086 mmol) was dissolved in DMF (1 mL). 4-(Piperidin-4-yl)benzonitrile hydrochloride (compound 1.5, 19 mg, 0.086 mmol), 2-(1H-benzo[1,2,3]triazol-1-yl)-1,1,3,3-tetramethyluronium hexafluorophosphate(V) (HBTU) (65 mg, 0.17 mmol) and DIEA (45 µl, 0.26 mmol) were added and the mixture was stirred at room temperature for 16 hrs. The mixture was then diluted with ethyl acetate (10 mL) and washed with brine (10 mL), dried (MgSO₄), filtered and concentrated in metro. The residue was purified by silica gel chromatography (ethyl acetate) to obtain the title compound as a solid foam (15 mg, 30%). m/z (ES+) 469 (M+H)⁺.

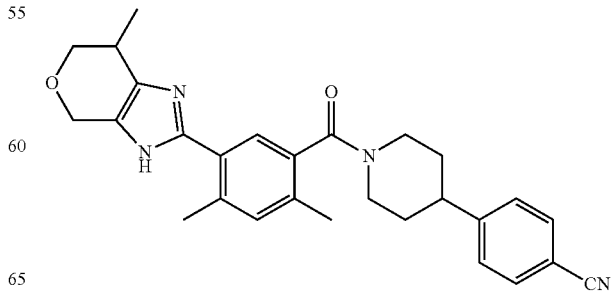

Compound 450. 4-(1-(2,4-Dimethyl-5-(7-methyl-3,4,6,7-tetrahydropyrano[3,4-d]imidazol-2-yl)benzoyl)piperidin-4-yl)benzonitrile The title compound was prepared using standard chemical manipulations and procedures similar to those used for preparation of compound 449, except 3-methyldihydro-2H-pyran-4(3H)-one (compound 400.1) was used in place of 3,3-dimethyldihydro-2H-pyran-4(3H)-one (compound 449.1). m/z (ES+) 455 (M+H)$^+$.

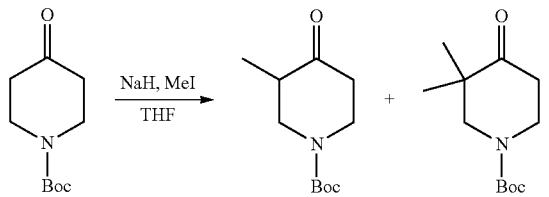 [SMILES: CC(C)(C)OC(=O)N1CCC(=O)CC1 ; CC1CN(C(=O)OC(C)(C)C)CCC1=O ; CC(C)(C)OC(=O)N1CCC(=O)C(C)(C)C1 ; "THF"]

Compound 451.1 and compound 451.2. tert-Butyl 3-methyl-4-oxopiperidine-1-carboxylate and tert-butyl 3,3-dimethyl-4-oxopiperidine-1-carboxylate Sodium hydride (60% in mineral oil)(1.27 g, 31.8 mmoL), was suspended in THF (80 mL) under an atmosphere of nitrogen. tert-Butyl 4-oxopiperidine-1-carboxylate (6.0 g, 30 mmol) was added portion-wise at room temperature. The mixture was stirred at room temperature for 1.5 hours and then methyl iodide (3.8 mL, 6.1 mmol) was added. The mixture was stirred at room temperature overnight and then cooled to 0° C. and carefully quenched with water (20 mL). The mixture was extracted with ethyl acetate (100 mL), dried (Na$_2$SO$_4$), filtered and concentrated in vacuo. The crude product was purified by silica gel chromatography (10:1 hexane/ethyl acetate) to obtain compound 451.1 as a clear oil (1.7 g, 27%) and compound 451.2 as a crystalline solid (963 mg, 14%).

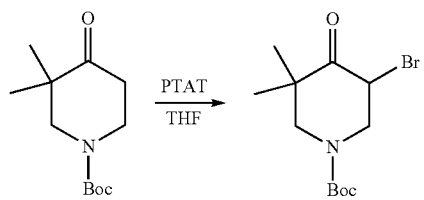

Compound 451.3. tert-Butyl 5-bromo-3,3-dimethyl-4-oxopiperidine-1-carboxylate tert-Butyl 3,3-dimethyl-4-oxopiperidine-1-carboxylate (0.963 g, 4.24 mmol) as dissolved in THF (10 mL) and then phenyltrimethylammonium tribromide (PTAT) (1.59 g, 4.24 mmol) was added. The mixture was stirred at room temperature for 2 hours then water (20 mL) was added and mixture was extracted with ethyl acetate (100 mL). The organics was dried (Na$_2$SO$_4$), filtered and concentrated in vacuo. The crude product was purified by silica gel chromatography (10:1 hexane/ethyl acetate) to obtain compound 451.3 as a white crystalline solid (0.94 g, 73%).

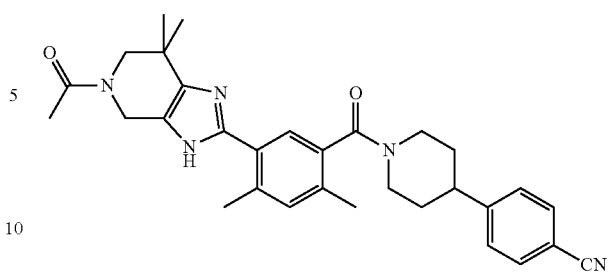

Compound 451. 4-(4-(5-(5-Acetyl-7,7-dimethyl-4,5,6,7-tetrahydro-3H-imidazo[4,5-c]pyridin-2-yl)-2,4-dimethylbenzoyl)cyclohexyl)benzonitrile The title compound was prepared using standard chemical manipulations and procedures similar to those used for the preparation of compound 2, except tert-butyl 5-bromo-3,3-dimethyl-4-oxopiperidine-1-carboxylate (compound 451.3) was used in place of tert-butyl 3-bromo-4-oxopiperidine-1-carboxylate. m/z (ES+) 510 (M+H)$^+$.

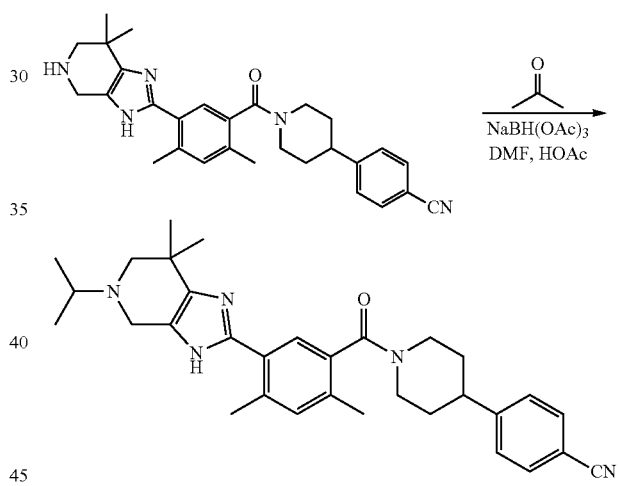

Compound 452. 4-(1-(5-(5-Isopropyl-7,7-dimethyl-4,5,6,7-tetrahydro-3H-imidazo[4,5-c]pyridin-2-yl)-2,4-dimethylbenzoyl)piperidin-4-yl)benzonitrile 4-(1-(5-(7,7-Dimethyl-4,5,6,7-tetrahydro-3H-imidazo[4,5-c]pyridin-2-yl)-2,4-dimethylbenzoyl)piperidin-4-yl)benzonitrile (0.12 g, 0.26 mmol) (intermediate prepared in the synthesis of compound 451), DMF (4 mL), acetic acid (69 µL, 1.21 mmol), sodium triacetoxyborohydide (0.11 g, 0.52 mmol) and acetone (0.50 mL, 6.8 mmol) were mixed and stirred at room temperature for 2 hours. The reaction was carefully quenched with water (10 mL) and the mixture was extracted with ethyl acetate (60 mL) and the organics was dried (Na$_2$SO$_4$), filtered and concentrated in vacuo. The crude product was purified by preparative TLC (DCM/10% MeOH) followed by a second preparative TLC (ethyl acetate/5% MeOH) to obtain the title compound as a white powder (4.1 mg, 8.1%). m/z (ES+) 510 (M+H)$^-$.

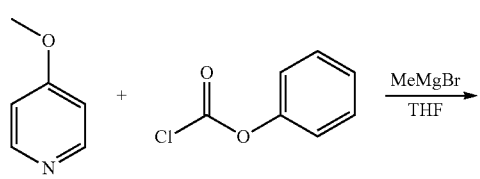

Compound 454.1. Phenyl 4-methoxy-2-methylpyridine-1(2H)-carboxylate

A 3-L four neck round-bottom flask was purged and maintained with a nitrogen atmosphere and a solution of 4-methoxypyridine (30.0 g, 275 mmol, 1.00 equiv) in tetrahydrofuran (1.2 L) was added. The mixture was cooled to −40° C. and phenyl chloroformate (45.0 g, 287 mmol, 1.05 equiv) was added dropwise. The resulting solution was stirred for 1 h at −40° C., then methylmagnesium bromide (3M, 110 mL, 1.20 equiv) was added to the reaction mixture while maintaining the temperature at −40° C. The resulting solution was warmed slowly to 5-10° C. and stirred for 2 h, then carefully quenched with ice water (100 mL). The resulting mixture was extracted with ethyl acetate (2×1 L) and the combined organics was washed with brine (1×300 mL), dried (Na$_2$SO$_4$), filtered and concentrated in vacuo to yield the title compound as a light brown oil (71.0 g, >theoretical).

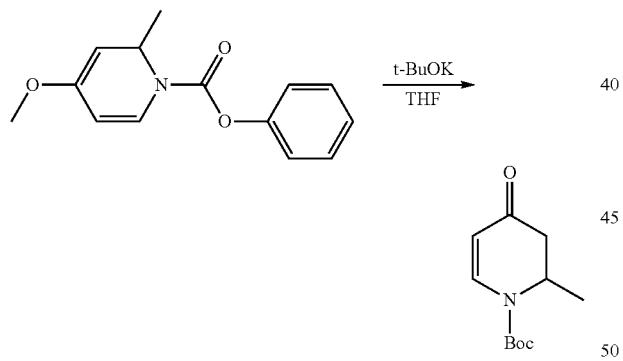

Compound 454.2. tert-Butyl 2-methyl-4-oxo-3,4-dihydropyridine-1(2H)-carboxylate A 3-L four neck round-bottom flask was purged and maintained with a nitrogen atmosphere and a solution of phenyl 4-methoxy-2-methylpyridine-1(2H)-carboxylate (454.1, 70.0 g, 285 mmol, 1.00 equiv) in tetrahydrofuran (1.2 L) was added. The solution was cooled to −78° C. then potassium tert-butoxide (128 g, 1.14 mol, 4.00 equiv) was added portion-wise. The resulting mixture was stirred at 10-15° C. for 20 h then concentrated in vacuo. The residue was dissolved in EtOAc (1.5 L), then carefully quenched with ice water (200 mL). The layers were separated and the aqueous was extracted with additional ethyl acetate (100 mL). The combined organics was washed with aqueous sodium hydroxide (1.5 M, 3×100 mL), aqueous hydrochloric acid (1 M, 2×100 mL), and brine (200 mL), dried (Na$_2$SO$_4$), filtered and concentrated in vacuo. The residue was purified by silica gel chromatography (ethyl acetate/petroleum ether, 1:200-1:20) as the eluent to obtain the title compound as a light yellow oil (31.0 g, 51%).

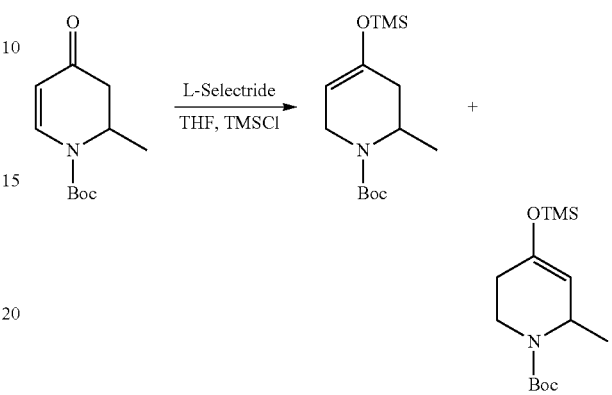

Compound 453.1 and compound 454.3. tert-Butyl 6-methyl-4-((trimethylsilyl)oxy)-5,6-dihydropyridine-1(2H)-carboxylate (453.1) and tert-butyl 2-methyl-4-((trimethylsilyl)oxy)-5,6-dihydropyridine-1(2H)-carboxylate (454.3)

A 500-mL three neck round-bottom flask was purged and maintained with a nitrogen atmosphere and a solution of tert-butyl 2-methyl-4-oxo-3,4-dihydropyridine-1(2H)-carboxylate (compound 454.2, 10.5 g, 49.5 mmol, 1.00 equiv) in tetrahydrofuran (300 mL) was added. The solution was cooled to −78° C. and L-Selectride (1 Min THF, 60 mL, 1.20 equiv) was added drop-wise. The resulting solution was stirred for 2 h at −78° C. then chlorotrimethylsilane (6.96 g, 64.1 mmol, 1.30 equiv) was added drop-wise with stirring. The resulting solution was stirred for 16 h at 10-15° C., and then concentrated in vacuo. The residue was diluted with n-hexane (500 mL) and the solids were filtered away. The filtrate was concentrated in vacuo and the residue purified by silica gel chromatography ethyl acetate/petroleum ether (1:100-1:20) as the eluent to obtain a mixture of the title compounds as a light yellow solid (10.0 g, 71%).

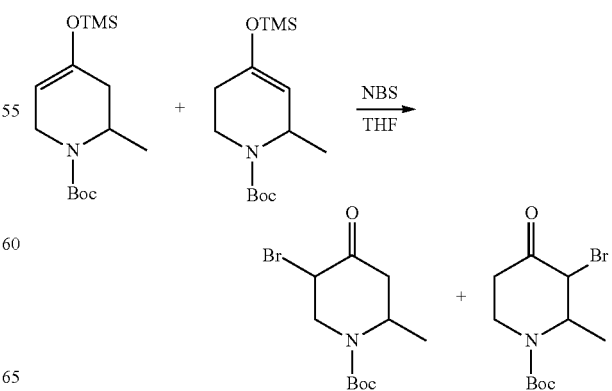

Compound 453.2 and compound 454.4. tert-Butyl 5-bromo-2-methyl-4-oxopiperidine-1-carboxylate (453.2) and tert-butyl 3-bromo-2-methyl-4-oxopiperidine-1-carboxylate (454.4)

Into a round-bottom flask, was placed a solution of a mixture of tell-butyl 6-methyl-4-((trimethylsilyl)oxy)-5,6-dihydropyridine-1(2H)-carboxylate and tert-butyl 2-methyl-4-((trimethylsilyl)oxy)-5,6-dihydropyridine-1(2H)-carboxylate (compound 453.1 and compound 454.2, 4.00 g, 12.5 mmol, 1.00 equiv, 89% combined purity) in tetrahydrofuran (250 mL). The mixture was cooled to 0-5° C. and N-bromosuccinimide (4.97 g, 27.9 mmol, 2.2 equiv) was added to the reaction mixture in portions. The resulting mixture was stirred at 25° C. for 2 h, then concentrated in vacuo. The residue was purified by silica gel chromatography with ethyl acetate/petroleum ether (1:100-1:10) as the eluent to obtain a mixture of the title compounds as a yellow oil (2.50 g, 69%).

(1.90 g, 24.7 mmol, 4.50 equiv), and ammonium hydroxide (2.88 g, 16.4 mmol, 3.00 equiv, 20%) were added and the resulting mixture was stirred for 2 h at 130° C. The mixture was cooled to 10-15° C. then quenched with ice water (50 mL). The resulting solution was extracted with ethyl acetate (2×50 mL) and the organics were combined. The pH of the aqueous was adjusted to 6 with hydrogen chloride (2 M) and extracted with ethyl acetate (2×150 mL) and all organic extracts were combined, dried ($Na_2SO_4$), filtered and concentrated in vacuo. The residue was purified by silica gel chromatography with ethyl acetate/petroleum ether (1:4-2:1) as the eluent to obtain a mixture of the title compounds as a light yellow oil (480 mg, 23%).

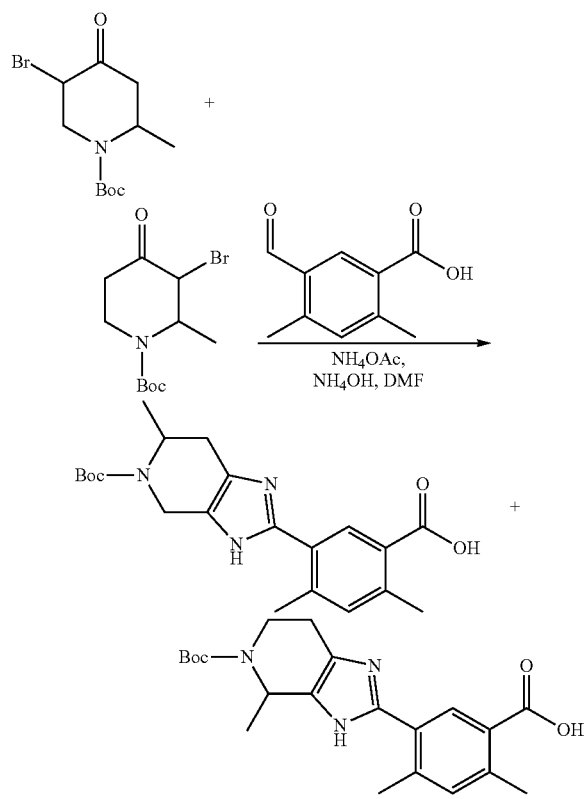

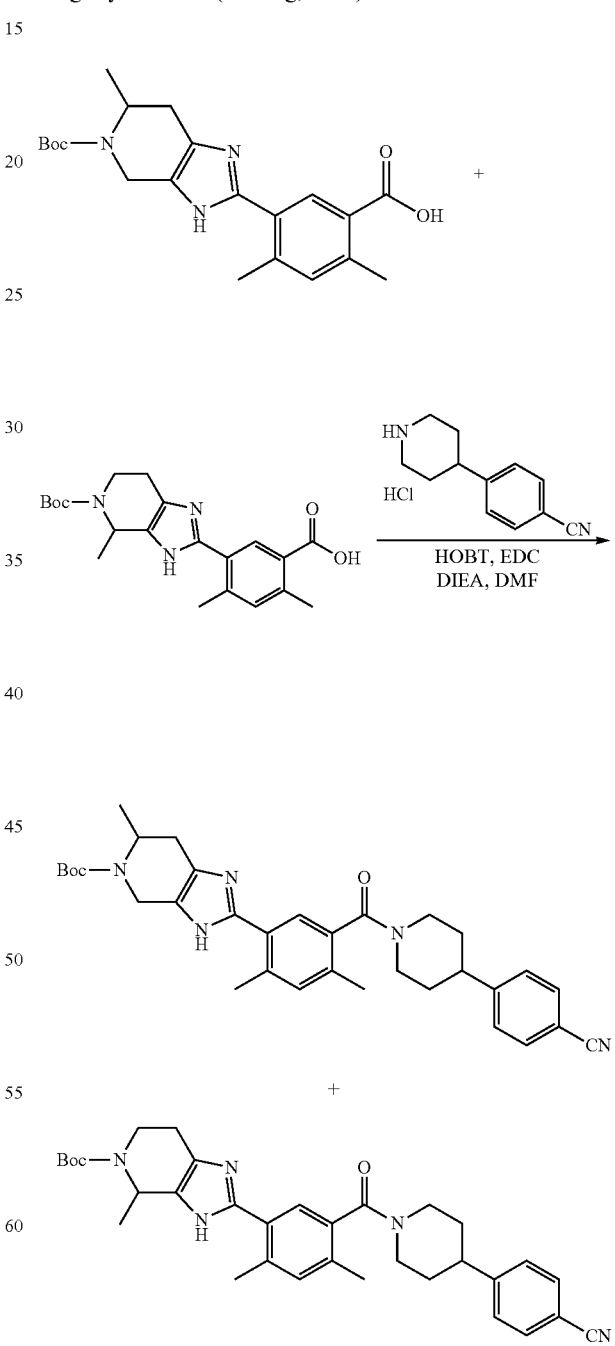

Compound 453.3 and compound 454.5. 5-(5-(tert-Butoxycarbonyl)-6-methyl-4,5,6,7-tetrahydro-3H-imidazo[4,5-c]pyridin-2-yl)-2,4-dimethylbenzoic acid (453.3) and 5-(5-(tert-butoxycarbonyl)-4-methyl-4,5,6,7-tetrahydro-3H-imidazo[4,5-c]pyridin-2-yl)-2,4-dimethylbenzoic acid (454.5)

Into a 50-mL sealed tube, was placed a solution of a mixture of tert-Butyl 5-bromo-2-methyl-4-oxopiperidine-1-carboxylate and tert-butyl 3-bromo-2-methyl-4-oxopiperidine-1-carboxylate (compound 453.2 and compound 454.4, 1.60 g, 5.48 mmol, 1.00 equiv) in N,N-dimethylformamide (10 mL). 5-Formyl-2,4-dimethylbenzoic acid (compound 16.3, 978 mg, 5.49 mmol, 1.00 equiv), ammonium acetate Compound 453.4 and compound 454.6. tert-Butyl 2-(5-(4-(4-cyanophenyl)piperidine-1-carbonyl)-2,4-dimethylphenyl)-6-methyl-6,7-dihydro-3H-imidazo[4,5-c]pyridine-5(4H)-carboxylate (compound 453.4) and tert-butyl 2-(5-(4-(4-cyanophenyl)piperidine-1-carbonyl)-2,4-dimethylphenyl)-4-methyl-6,7-dihydro-3H-imidazo[4,5-c]pyridine-5(4H)-carboxylate (compound 454.6)

Into around-bottom flask, was placed a solution of a mixture of 5-(5-(tert-butoxycarbonyl)-6-methyl-4,5,6,7-tetrahydro-3H-imidazo[4,5-c]pyridin-2-yl)-2,4-dimethylbenzoic acid and 5-(5-(tert-butoxycarbonyl)-4-methyl-4,5,6,7-tetrahydro-3H-imidazo[4,5-c]pyridin-2-yl)-2,4-dimethylbenzoic acid (compound 453.3 and compound 454.5, 480 mg, 1.25 mmol, 1.00 equiv) in N,N-dimethylformamide (10 mL). DIEA (643 mg, 4.98 mmol, 4.00 equiv), EDC (476 mg, 2.48 mmol, 2.00 equiv), and 1-hydroxybenzotrizole (337 mg, 2.50 mmol, 2.00 equiv) were added and the resulting solution was stirred at 25° C. for 20 min. 4-(Piperidin-4-yl)benzonitrile hydrochloride (compound 1.5, 276 mg, 1.24 mmol, 1.00 equiv) was then added in portions at 0° C. The resulting solution was stirred at 25° C. for 16 h, and then quenched with of ice water (40 mL). The resulting solids were collected by filtration, and then dissolved in ethyl acetate (100 mL). The resulting organics was washed with brine (2×30 mL), dried (Na₂SO₄), filtered and concentrated in mow to obtain a mixture of the title compounds as a light yellow oil (440 mg, 64%).

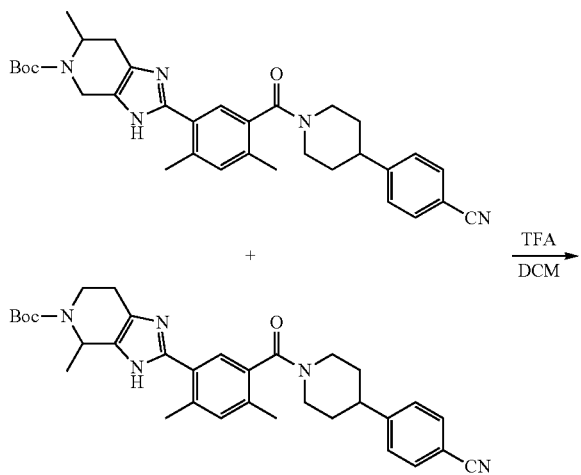

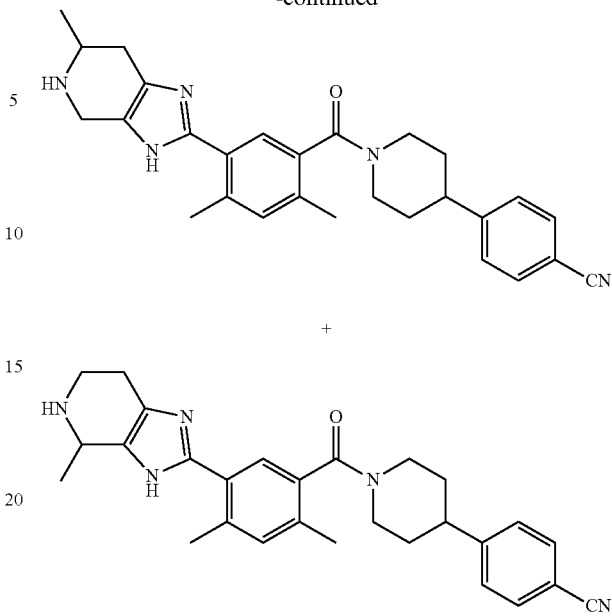

Compound 453.5 and compound 454.7. 4-(1-(2,4-Dimethyl-5-(6-methyl-4,5,6,7-tetrahydro-3H-imidazo[4,5-c]pyridin-2-yl)benzoyl)piperidin-4-yl)benzonitrile 2,2,2-trifluoroacetate (compound 453.5) and 4-(1-(2,4-dimethyl-5-(4-methyl-4,5,6,7-tetrahydro-3H-imidazo[4,5-c]pyridin-2-yl)benzoyl)piperidin-4-yl)benzonitrile 2,2,2-trifluoroacetate (compound 454.7)

Into around-bottom flask, was placed a solution of a mixture of tert-butyl 2-(5-(4-(4-cyanophenyl)piperidine-1-carbonyl)-2,4-dimethylphenyl)-6-methyl-6,7-dihydro-3H-imidazo[4,5-c]pyridine-5(4H)-carboxylate and tert-butyl 2-(5-(4-(4-cyanophenyl)piperidine-1-carbonyl)-2,4-dimethylphenyl)-4-methyl-6,7-dihydro-3H-imidazo[4,5-c]pyridine-5(4H)-carboxylate (compound 453.4 and compound 454.6, 440 mg, 0.790 mmol, 1.00 equiv) in dichloromethane (10 mL) and trifluoroacetic acid (3 mL). The resulting solution was stirred at 25° C. for 20 h, then concentrated in vacuo to obtain a mixture of the title compounds as a yellow oil (450 mg, 99%).

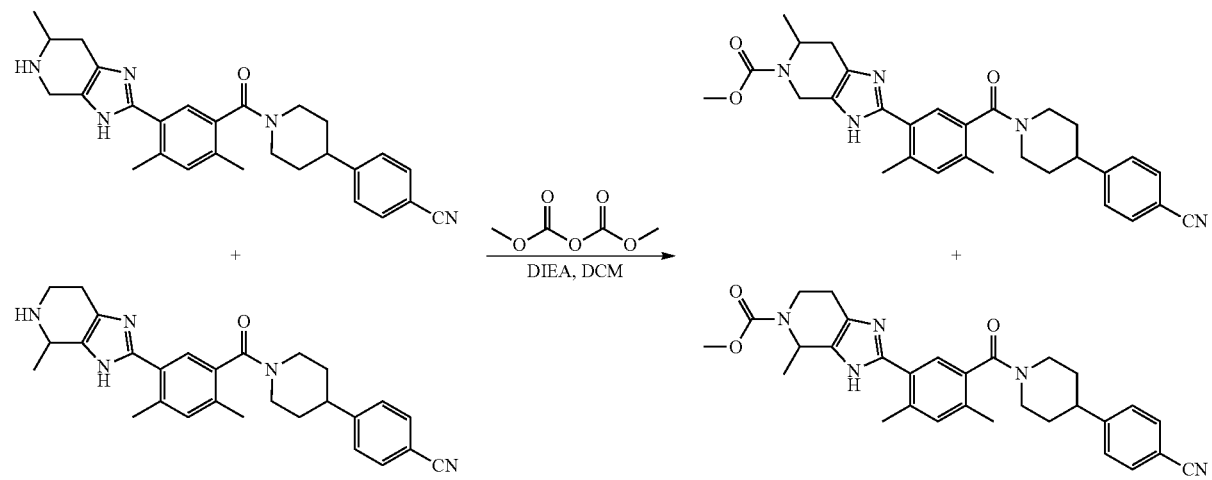

Compounds 453 and 454. Methyl 2-(5-(4-(4-cyanophenyl)piperidine-1-carbonyl)-2,4-dimethylphenyl)-6-methyl-6,7-dihydro-3H-imidazo[4,5-c]pyridine-5(4H)-carboxylate (compound 453) and methyl 2-(5-(4-(4-cyanophenyl)piperidine-1-carbonyl)-2,4-dimethylphenyl)-4-methyl-6,7-dihydro-3H-imidazo[4,5-c]pyridine-5(4H)-carboxylate (compound 454)

Into an 8-mL sealed tube, was placed a mixture of 4-(1-(2,4-dimethyl-5-(6-methyl-4,5,6,7-tetrahydro-3H-imidazo[4,5-c]pyridin-2-yl)benzoyl)piperidin-4-yl)benzonitrile 2,2,2-trifluoroacetate and 4-(1-(2,4-dimethyl-5-(4-methyl-4,5,6,7-tetrahydro-3H-imidazo[4,5-c]pyridin-2-yl)benzoyl)piperidin-4-yl)benzonitrile 2,2,2-trifluoroacetate (compound 453.5 and compound 454.7, 100 mg, 0.176 mmol, 1.00 equiv) in dichloromethane (6 mL). DIEA (114 mg, 0.880 mmol, 5.00 equiv) was added and the mixture was cooled to 0° C. Dimethyl dicarbonate (29.6 mg, 0.220 mmol, 1.25 equiv) was added drop-wise with stirring at 0° C., and then the resulting solution was stirred for 2.5 h at 0-5° C. The resulting mixture was concentrated in vacuo and the residue was purified by prep-HPLC (1#-Pre-HPLC-001(SHIMADZU)): Column, Xbridge Prep C18, 5um, 19*150 mm; mobile phase, water with 0.03% $NH_3H_2O$ and $CH_3CN$ (39.0% $CH_3CN$ up to 52.0% in 7 min, up to 100.0% in 1 min, down to 39.0% in 1 min); Detector, Waters 2489 254 & 220 nm. The title compounds were obtained from the prep-HPLC as a mixture of isomers (30 mg). The isomeric mixture was purified by chiral-prep-HPLC (2#-Gilson Gx 281 (HPLC-09)): Column, Chiralpak IA, 2*25 cm, 5 um; mobile phase, Hex (0.1% DEA) and ethanol (0.2% TEA) (hold 50.0% ethanol (0.2% TEA) in 10 min); Detector, UV 220/254 nm. The chiral-prep-HPLC fractions containing pure, separated products were appropriately combined and lyophilized to obtain methyl 2-(5-(4-(4-cyanophenyl)piperidine-1-carbonyl)-2,4-dimethylphenyl)-6-methyl-6,7-dihydro-3H-imidazo[4,5-c]pyridine-5(4H)-carboxylate (compound 453) as a white solid (14.2 mg, 13%) and methyl 2-(5-(4-(4-cyanophenyl)piperidine-1-carbonyl)-2,4-dimethylphenyl)-4-methyl-6,7-dihydro-3H-imidazo[4,5-c]pyridine-5(4H)-carboxylate (compound 454) as white solid (11.8 mg, 10%). Compound 453: m/z (ES+) 512 (M+H)$^+$. Compound 454: m/z (ES+) 512 (M+H)$^+$.

Compounds 455 & 456. 4-(1-(5-(5,6-Dimethyl-4,5,6,7-tetrahydro-3H-imidazo[4,5-c]pyridin-2-yl)-2,4-dimethylbenzoyl)piperidin-4-yl)benzonitrile (compound 455) and 4-(1-(5-(4,5-dimethyl-4,5,6,7-tetrahydro-3H-imidazo[4,5-c]pyridin-2-yl)-2,4-dimethylbenzoyl)piperidin-4-yl)benzonitrile (compound 456)

Into a 10-mL sealed tube, was placed a solution of a mixture of 4-(1-(2,4-dimethyl-5-(6-methyl-4,5,6,7-tetrahydro-3H-imidazo[4,5-c]pyridin-2-yl)benzoyl)piperidin-4-yl)benzonitrile trifluoroacetate and 4-(1-(2,4-dimethyl-5-(4-methyl-4,5,6,7-tetrahydro-3H-imidazo[4,5-c]pyridin-2-yl)benzoyl)piperidin-4-yl)benzonitrile trifluoroacetate (compound 453.5 and compound 454.7, (100 mg, 0.22 mmol, 1.00 equiv) in tetrahydrofuran (5 mL). Formaldehyde (1 mL, 37 wt %) and sodium triacetoxyborohydride (162 mg, 0.760 mmol, 3.5 equiv) were added to the mixture and stirred for 2.5 h at 40° C. The mixture was concentrated in vacuo and the residue was purified by Prep-HPLC with the following conditions (1#-Pre-HPLC-001(SHIMADZU)): Column, Xbridge Prep C18, 5 um, 19*150 mm; mobile phase, water with 0.03% NH3H2O and CH3CN (32% CH3CN up to 42% in 8 min, up to 100% in 2 min, down to 32% in 1 min); Detector, Waters 2489 254 nm & 220 nm. The title compounds were obtained from the prep-HPLC as a mixture of isomers (50 mg). The isomeric mixture was purified by chiral-prep-HPLC with the following conditions (2#-Gilson Gx 281 (HPLC-09)): Column, Chiralpak IC, 2*25 cm, 5um; mobile phase, Hex (0.2% TEA) and ethanol (0.2% TEA) (hold 50.0% ethanol (0.2% TEA) in 27 min); Detector, UV 220/254 nm. The chiral-prep-HPLC fractions containing pure, separated products were appropriately combined and lyophilized to obtain 4-(1-(5-(5,6-dimethyl-4,5,6,7-tetrahydro-3H-imidazo[4,5-c]pyridin-2-yl)-2,4-dimethylbenzoyl)piperidin-4-yl)benzonitrile (compound 455) as a white solid (13.5 mg, 13%) and 4-(1-(5-(4,5-dimethyl-4,5,6,7-tetrahydro-3H-imidazo[4,5-c]pyridin-2-yl)-2,4-dimethylbenzoyl)piperidin-4-yl)benzonitrile (compound 456) as a white solid (6.8 mg, 7%). Compound 455: m/z (ES+) 468 (M+H)$^+$. Compound 456: m/z (ES+) 468 (M+H)$^+$.

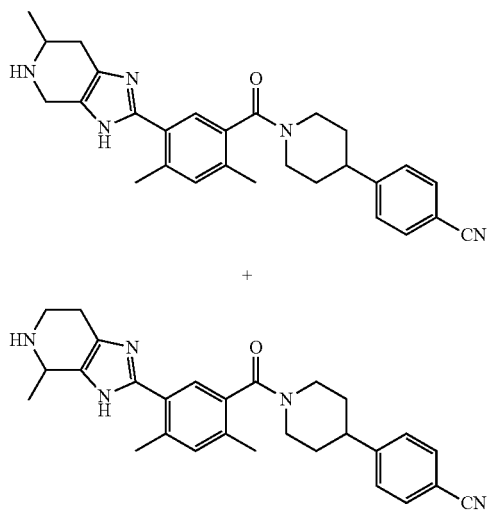

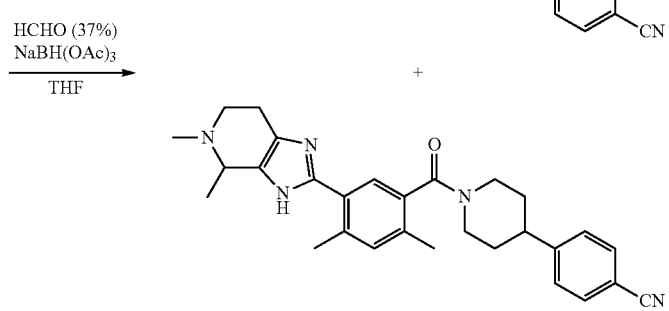

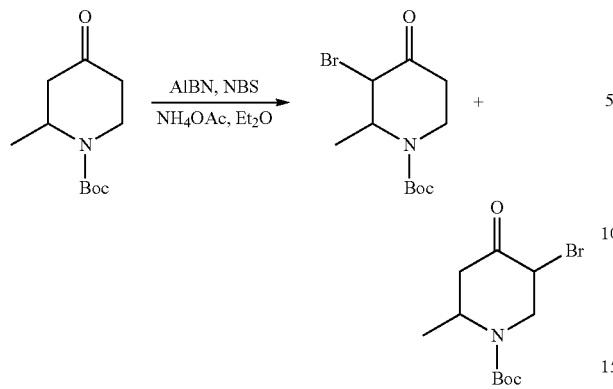

Compound 457.1 and compound 457.2. tert-Butyl 3-bromo-2-methyl-4-oxopiperidine-1-carboxylate (compound 457.1) and tert-butyl 5-bromo-2-methyl-4-oxopiperidine-1-carboxylate (compound 457.2)

Into a 1-L four neck round-bottom flask, which was purged and maintained with an inert atmosphere of nitrogen, was placed a solution of tert-butyl 2-methyl-4-oxopiperidine-1-carboxylate (5.00 g, 23.4 mmol, 1.00 equiv) in ether (700 mL). Ammonium acetate (904 mg, 11.7 mmol, 0.50 equiv) and azobisisobutyronitrile (AIBN) (192 mg, 1.17 mmol, 0.05 equiv) were added. The mixture was cooled to 0° C., then N-bromosuccinimide (4.15 g, 23.5 mmol, 1.00 equiv) was added in portions. The resulting mixture was stirred for 4 h at 25° C., then concentrated in vacuo. The residue was purified by silica gel chromatography with ethyl acetate/petroleum ether (1:100-1:10) as the eluent to obtain a mixture of the title compounds as a light yellow oil (4.10 g, 60%).

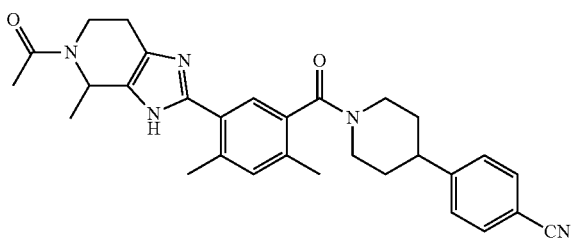 [SMILES: CC(=O)N1CCc2nc(-c3cc(C(=O)N4CCC(c5ccc(C#N)cc5)CC4)c(C)cc3C)[nH]c2C1C]

Compound 457. 4-(1-(5-(5-Acetyl-4-methyl-4,5,6,7-tetrahydro-3H-imidazo[4,5-c]pyridin-2-yl)-2,4-dimethylbenzoyl)piperidin-4-yl)benzonitrile The title compound was prepared using standard chemical manipulations and procedures similar to those used for the preparation of compound 400 and compound 2, except a mixture of tert-butyl 3-bromo-2-methyl-4-oxopiperidine-1-carboxylate (compound 457.1) and tert-butyl 5-bromo-2-methyl-4-oxopiperidine-1-carboxylate (compound 457.2) was used in place of 3-bromo-5-methyldihydro-2H-pyran-4(3H)-one (compound 400.2). The product contains about 10% of the other methyl regioisomer 4-(1-(5-(5-acetyl-6-methyl-4,5,6,7-tetrahydro-3H-imidazo[4,5-c]pyridin-2-yl)-2,4-dimethylbenzoyl)piperidin-4-yl)benzonitrile. m/z (ES+) 496 (M+H)+.

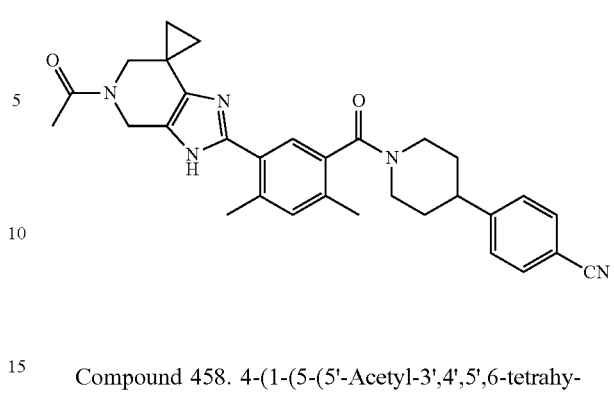

Compound 458. 4-(1-(5-(5'-Acetyl-3',4',5',6-tetrahydrospiro[cyclopropane-1,7'-imidazo[4,5-c]pyridin]-2'-yl)-2,4-dimethylbenzoyl)piperidin-4-yl)benzonitrile The title compound was prepared using standard chemical manipulations and procedures similar to those used for the preparation of compound 449 and compound 2, except tert-butyl 8-oxo-5-azaspiro[2.5]octane-5-carboxylate (Remen, L. et al. *Bioorg. and Med. Chem. Lett.,* 2009, 32, 351-357) was used in place of 3,3-dimethyldihydro-2H-pyran-4(3H)-one (compound 449.1). m/z (ES+) 508 (M+H)+. 1H-NMR (300 MHz, CD3OD): δ 7.71 (d, J=8.1 Hz, 2H), 7.47 (d, J=7.8 Hz, 2H), 7.37-7.20 (m, 2H), 4.77 and 4.71 (2 singlets, acetyl amide rotamers, CH2, 2H), 3.77 and 3.72 ((2 singlets, acetyl amide rotamers, CH2, 2H), 3.71-3.67 (m, 1H), 3.30-3.18 (m, 1H), 2.99 (t, J=11.6 Hz, 2H), 2.48-2.27 (m, 6H), 2.24 and 2.21 (2 singlets, acetyl amide rotamers, acetyl CH3, 3H), 2.10-1.95 (m, 1H), 1.92-1.52 (m, 3H), 1.18-0.96 (m, 4H).

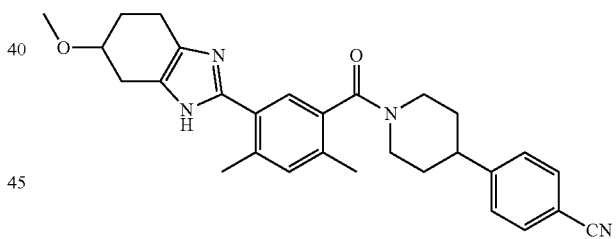

Compound 459. 4-(1-(5-(6-Methoxy-4,5,6,7-tetrahydro-1H-benzo[d]imidazol-2-yl)-2,4-dimethylbenzoyl)piperidin-4-yl)benzonitrile The title compound was prepared using standard chemical manipulations and procedures similar to those used for the preparation of compound 449, except 4-methoxycyclohexanone (Kaiho, T. et al. *J. Med. Chem.,* 1989, 32, 351-357) was used in place of 3,3-dimethyldihydro-2H-pyran-4(3H)-one (compound 449.1). m/z (ES+) 469 (M+H)+. 1H-NMR (300 MHz, CD3OD): δ 7.69 (d, J=8.1 Hz, 2H), 7.53-7.44 (m, 2H), 7.37-7.21 (m, 2H), one proton estimated under methanol (1H), 3.84-3.75 (m, 1H), 3.73-3.57 (m, 1H), 3.45 (s, 3H), 3.27-3.19 (m, 1H), 3.05-2.91 (m, 3H), 2.79-2.58 (m, 3H), 2.46 (s, 3H), 2.40 and 2.29 (2 singlets, amide rotamers, 3H), 2.17-1.92 (m, 3H), 1.92-1.67 (m, 3H).

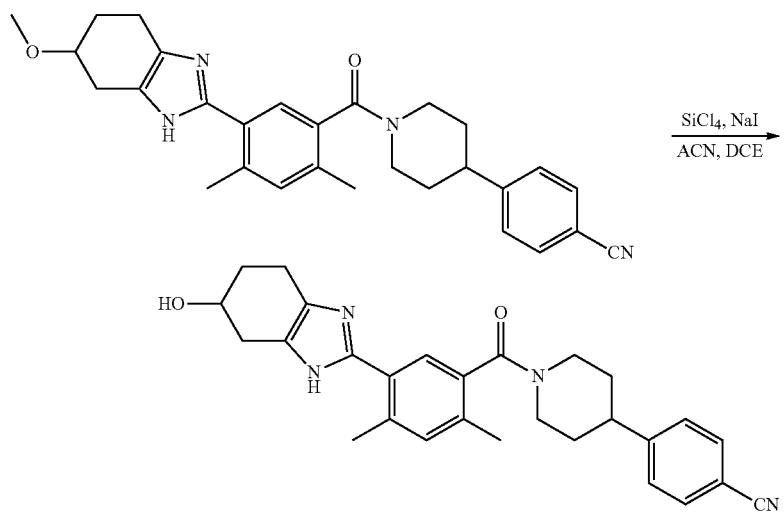

Compound 460. 4-(1-(5-(6-Hydroxy-4,5,6,7-tetrahydro-1H-benzo[d]imidazol-2-yl)-2,4-dimethylbenzoyl)piperidin-4-yl)benzonitrile Into around-bottom flask, was placed a solution of 4-(1-(5-(6-methoxy-4,5,6,7-tetrahydro-1H-benzo[d]imidazol-2-yl)-2,4-dimethylbenzoyl)piperidin-4-yl)benzonitrile (compound 459, 80 mg, 0.17 mmol, 1.0 equiv) in a solvent mixture of acetonitrile and dichloromethane (10/10 mL). Tetrachlorosilane (32 mg, 0.19 mmol, 1.1 equiv) and sodium iodide (28 mg, 0.19 mmol, 1.1 equiv) were added to the reaction and the resulting mixture was stirred overnight at 20° C. The reaction was quenched with aqueous sodium bicarbonate (10 mL) and the aqueous was extracted with ethyl acetate (3×10 mL). The combined organics was dried ($NaSO_4$), filtered and concentrated in vacuo and the residue was purified by silica gel chromatography with ethyl acetate as the eluent to obtain the title compound as a yellow solid (7.1 mg, 9%). m/z (ES+) 455 (M+H)$^+$.

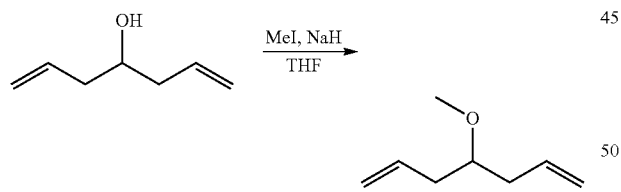

Compound 461.1. 4-Methoxyhepta-1,6-diene

Into a round-bottom flask, was placed a solution of hepta-1,6-dien-4-ol (2.00 g, 17.8 mmol, 1.00 equiv) and iodomethane (5.00 g, 35.2 mmol, 2.00 equiv) in tetrahydrofuran (30 mL). The solution was cooled to 0° C. and sodium hydride (1.00 g, 25.0 mmol, 1.50 equiv, 60% in mineral oil) was added to the reaction in portions. The resulting mixture was stirred overnight at room temperature, then carefully quenched with water (5 mL) and diluted with of ether (30 mL). The organics was washed with brine (2×20 mL), dried ($Na_2SO_4$), filtered and concentrated in vacuo to obtain the title compound as a colorless oil (2.00 g, 84%).

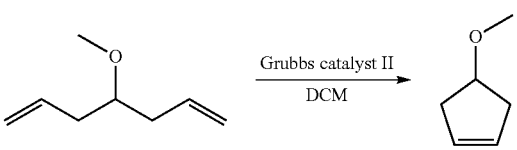

Compound 461.2. 4-Methoxycyclopent-1-ene

Into around-bottom flask, which was purged and maintained with an inert atmosphere of nitrogen, was placed a solution of 4-methoxyhepta-1,6-diene (compound 461.1, 200 mg, 1.43 mmol, 1.00 equiv, 90%) in dichloromethane (25 mL). Grubbs II catalyst (55 mg, 0.06 mmol, 0.04 equiv) was added and the resulting solution was stirred overnight at room temperature. The mixture was concentrated in vacuo to obtain the title compound as a colorless oil (100 mg, 57%).

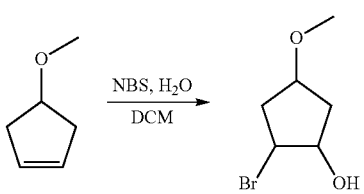

Compound 461.3.
2-Bromo-4-methoxycyclopentanol

Into a round-bottom flask, was added a solution of 4-methoxycyclopent-1-ene (compound 461.2, 1.00 g, 8.66 mmol, 1.00 equiv, 85%) in dichloromethane (100 mL) and a solution of N-bromosuccimide (2.00 g, 11.3 mmol, 1.00 equiv) in water (20 mL). The reaction mixture was stirred at room temperature for 3 hours and then the resulting mixture was washed with water (20 mL), dried ($Na_2SO_4$), filtered and concentrated in vacuo to obtain the title compound as a colorless oil (1.00 g, 36%).

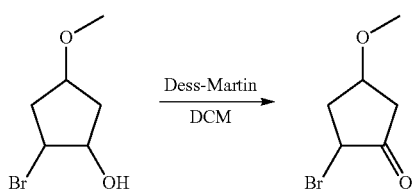

Compound 461.4.
2-Bromo-4-methoxycyclopentanone

Into a round-bottom flask, was placed a solution of 2-Bromo-4-methoxycyclopentanol (compound 461.3, 1.00 g, 3.08 mmol, 1.00 equiv, 60%) in dichloromethane (100 mL). Dess-Martin periodinane (2.00 g, 4.72 mmol, 1.10 equiv) was added in portions and the mixture was stirred overnight at room temperature. The mixture was then diluted with water (20 mL) and quenched with $Na_2SO_4$ (4 g). The aqueous was extracted with dichloromethane (100 mL) and the combined organics was washed with brine (30 mL), dried ($Na_7SO_4$), filtered and concentrated in vacuo to obtain the title compound as a brown oil (800 mg, 81%).

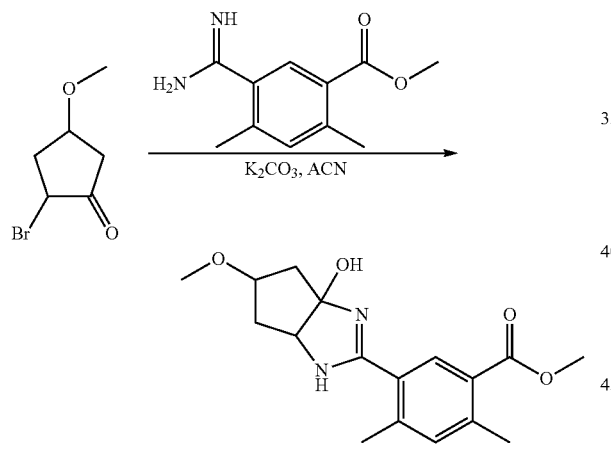

Compound 461.5. Methyl 5-(3a-hydroxy-5-methoxy-1,3a,4,5,6,6a-hexahydrocyclopenta[d]imidazol-2-yl)-2,4-dimethylbenzoate Into around-bottom flask, was placed a solution of 2-bromo-4-methoxycyclopentanone (compound 461.4, 600 mg, 1.86 mmol, 60%) in ACN (15 mL). Methyl 5-carbamimidoyl-2,4-dimethylbenzoate hydrochloride (compound 2.5, 320 mg) and potassium carbonate (430 mg, 3.11 mmol) were added and the mixture was stirred overnight at 80° C. The mixture was concentrated in vacuo and the residue was diluted with ethyl acetate (50 mL) and then washed with brine (2×20 mL), dried ($Na_2SO_4$), filtered and concentrated in vacuo. The residue was purified by silica gel chromatography with dichloromethane/methanol (10:1) as the eluent to obtain the title compound as a brown oil (200 mg, 27%).

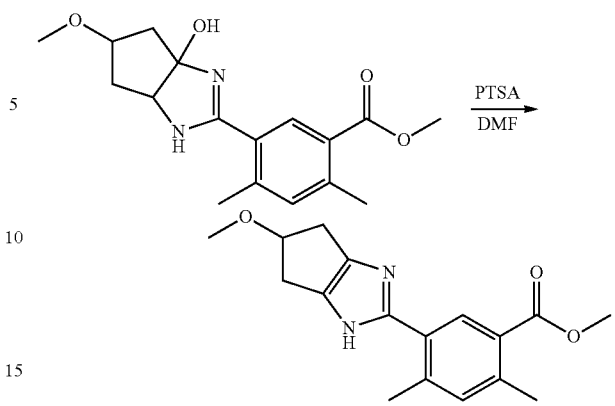

Compound 461.6. Methyl 5-(5-methoxy-1,4,5,6-tetrahydrocyclopenta[d]imidazol-2-yl)-2,4-dimethylbenzoate Into around-bottom flask, was placed a solution of methyl 5-(3a-hydroxy-5-methoxy-1,3a 4,5,6,6a-hexahydrocyclopenta[d]imidazol-2-yl)-2,4-dimethylbenzoate (compound 461.5, 200 mg, 0.38 mmol, 1.00 equiv, 60%) in N,N-dimethylformamide (mL). p-Toluenesulfonic acid (20 mg, 0.12 mmol, 0.18 equiv) was added and the resulting solution was stirred overnight at 80° C., then concentrated in vacuo. The residue was purified by silica gel chromatography with dichloromethane/methanol (10:1) as the eluent to obtain the title compound as a brown oil (100 mg, 66%).

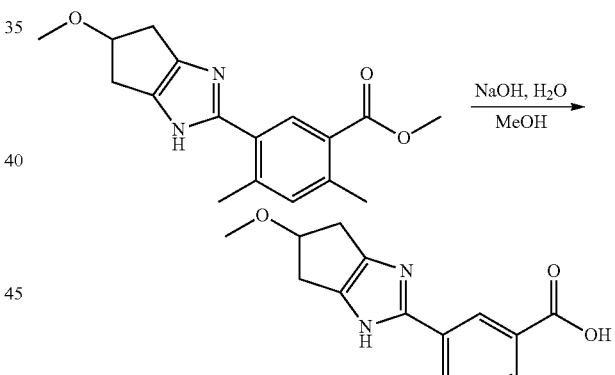

Compound 461.7. 5-(5-Methoxy-1,4,5,6-tetrahydrocyclopenta[d]imidazol-2-yl)-2,4-dimethylbenzoic acid Into around-bottom flask, was placed a solution of methyl 5-(5-methoxy-1,4,5,6-tetrahydrocyclopenta[d]imidazol-2-yl)-2,4-dimethylbenzoate (compound 461.6, 100 mg, 0.270 mmol, 1.00 equiv, 80%) in methanol (3 mL). A solution of sodium hydroxide (67.0 mg, 1.68 mmol, 5.00 equiv) in water (3 mL) was added and the resulting mixture was stirred overnight at 70° C., then concentrated in vacuo. The residue was diluted with water (3 mL) and the pH of the solution was adjusted to 2-3 with aqueous hydrogen chloride (12 M). The mixture was extracted ethyl acetate (3×10 mL), and the combined organics was concentrated in vacuo to obtain the title compound as a brown solid (80 mg, 84%).

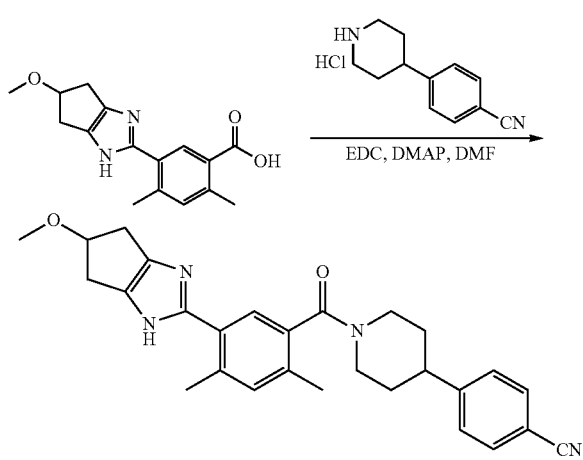

Compound 461. 4-(1-(5-(5-Methoxy-1,4,5,6-tetrahydrocyclopenta[d]imidazol-2-yl)-2,4-dimethylbenzoyl)piperidin-4-yl)benzonitrile Into around-bottom flask, was placed a solution of 5-(5-Methoxy-1,4,5,6-tetrahydrocyclopenta[d]imidazol-2-yl)-2,4-dimethylbenzoic acid (compound 461.7, 60 mg, 0.17 mmol, 1.00 equiv, 80%) in N,N-dimethylformamide (4 mL). 4-(Piperidin-4-yl)benzonitrile hydrochloride (compound 1.5, 46 mg, 0.20 mmol, 1.00 equiv), 4-dimethylaminopyridine (52 mg, 0.43 mmol, 2.00 equiv), and EDC.HCl (80 mg, 0.42 mmol, 2.00 equiv) were added and the mixture was stirred overnight at room temperature. The resulting solution was diluted with ethyl acetate (30 mL) and washed with brine (3×10 mL), dried ($Na_2SO_4$), filtered and concentrated in vacuo. The residue (40 mg) was purified by preparative-HPLC with the following conditions (1#-Pre-HPLC-001 (SHIMADZU)): Column, SunFire Prep C18, 19*150 mm 5 um; mobile phase, water with 0.05% TFA and $CH_3CN$ (15.0% $CH_3CN$ up to 55.0% in 7 min, up to 100.0% in 1 min, down to 15.0% in 1 min); Detector, Waters 2489 254 & 220 nm. The fractions containing pure product were combined and lyophilized to obtain the title compound as a white solid (8.9 mg, 11%). m/z (ES+) 455 (M+H)+.

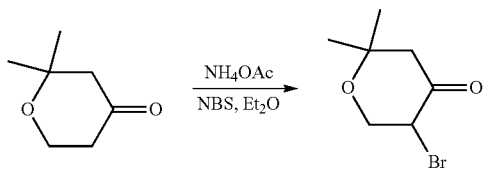

Compound 462.1. 5-Bromo-2,2-dimethyldihydro-2H-pyran-4(3H)-one

Into around-bottom flask, was placed a solution of 2,2-dimethyloxan-4-one (1.00 g, 7.80 mmol, 1.00 equiv) in ether (20 mL). N-Bromosuccinimide (1.50 g, 25.5 mmol, 3.26 equiv) was added in portions, followed by the addition of ammonium acetate (60.0 mg, 0.78 mmol, 0.10 equiv). The resulting mixture was stirred overnight at 25° C., then diluted with ethyl acetate (20 mL). The resulting mixture was washed brine (2×40 mL), dried ($Na_2SO_4$), filtered and concentrated in vacuo. The residue was purified by silica gel chromatography with ethyl acetate/petroleum ether (1:30) as the eluent to obtain the title compound as a yellow oil (508 mg, 31%).

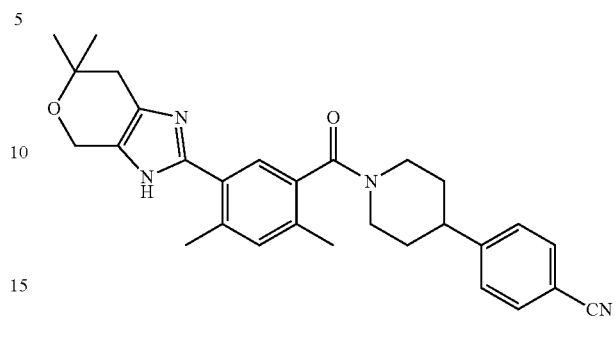

Compound 462. 4-(1-(5-(6,6-Dimethyl-3,4,6,7-tetrahydropyrano[3,4-d]imidazol-2-yl)-2,4-dimethylbenzoyl)piperidin-4-yl)benzonitrile The title compound was prepared using standard chemical manipulations and procedures similar to those used for the preparation of compound 461, except 5-bromo-2,2-dimethyldihydro-2H-pyran-4(3H)-one (compound 462.1) was used in place of 2-bromo-4-methoxycyclopentanone (compound 461.4). m/z (ES+) 469 (M+H)+.

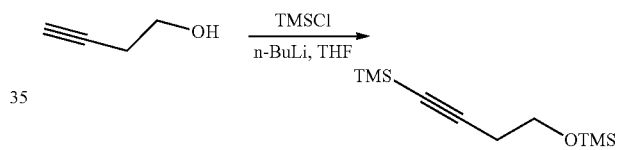

Compound 463.1. Trimethyl((4-(trimethylsilyl)but-3-yn-1-yl)oxy)silane

Into a 1-L three neck round-bottom flask, was placed a solution of but-3-yn-1-ol (20.0 g, 285 mmol, 1.00 equiv) in tetrahydrofuran (300 mL) and the mixture was purged with nitrogen. The mixture was cooled to −78° C., then n-butyllithium (2.5 M in THF) (270 mL, 2.40 equiv) was added drop-wise followed by the addition of chlorotrimethylsilane (67.9 g, 625 mmol, 2.20 equiv). The resulting mixture was then stirred for 1 h at 25° C., then carefully quenched with aqueous sodium bicarbonate (250 mL). The aqueous was extracted with ether (3×100 mL) and the combined organics was dried ($Na_2SO_4$), filtered and concentrated in vacuo. The residue was purified by silica gel chromatography with ether/petroleum ether (1:10-1:1) as the eluent to obtain the title compound as a colorless oil (10.0 g, 16%).

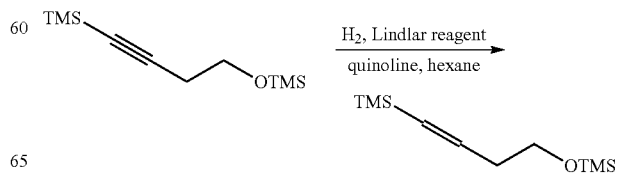

Compound 463.2. Trimethyl((4-(trimethylsilyl)but-3-en-1-yl)oxy)silane

Into a round-bottom flask, was placed a solution of compound 463.1, 2.00 g, 7.46 mmol, 1.00 equiv, 80%) in hexane (30 mL). The system was purged with nitrogen. Quinoline (0.1 mL, 0.10 equiv) and Lindlar reagent (poisoned by Pb) (0.2 g, 0.10 equiv, 5%) were added to the mixture. The resulting mixture was hydrogenated overnight at room temperature under atmosphere pressure of hydrogen. After completion of the reaction, the system was purged with nitrogen and the solids were removed by filtration. The filtrate was concentrated in vacuo and the residue was purified by silica gel chromatography with hexane/ether (20:1) as the eluent to obtain the title compound as a colorless oil (1.50 g, 74%).

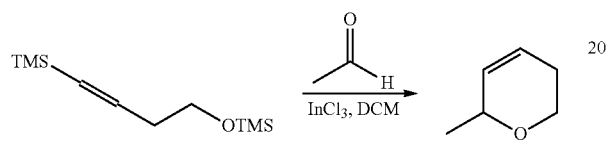

Compound 463.3. 6-Methyl-3,6-dihydro-2H-pyran

Into around-bottom flask, was placed a mixture of trimethyl((4-(trimethylsilyl)but-3-en-1-yl)oxy)silane (compound 463.2, 1.50 g, 6.93 mmol, 1.00 equiv), acetaldehyde (900 mg, 20.4 mmol, 3.00 equiv), and indium(III) chloride (1.50 g, 1.00 equiv) iii dichloromethane (15 mL). The resulting mixture was stirred overnight at 25° C., then diluted with DCM (50 mL). The organics was washed with brine (3×20 mL), dried (Na$_2$SO$_4$), filtered and concentrated in vacuo to obtain the title compound as a brown oil (0.600 g, 88%).

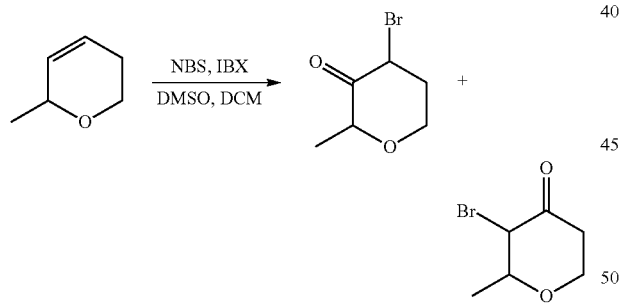

Compound 463.4 and compound 463.5. 4-Bromo-2-methyldihydro-2H-pyran-3(4H)-one (compound 463.4) and 3-bromo-2-methyldihydro-2H-pyran-4(3H)-one (compound 463.5)

Into a round-bottom flask, was placed a solution of o-iodoxybenzoic acid (IBX) (3.42 g, 6.11 mmol, 2.00 equiv) in DMSO (12 mL). The mixture was stirred for 30 min at 25° C. then a solution of 6-methyl-3,6-dihydro-2H-pyran (compound 463.3, 600 mg, 4.28 mmol, 1.00 equiv, 70%) in dichloromethane (30 mL) was added drop-wise. The mixture was cooled to 0-5° C., then N-bromosuccinimide (1.20 g, 6.74 mmol, 1.10 equiv) was added portion-wise. The resulting mixture was stirred overnight at 25° C., then the solids were removed by filtration. The filtrate was diluted with dichloromethane (50 mL) and washed with brine (3×20 mL). The mixture was dried (Na$_2$SO$_4$), filtered and concentrated in vacuo. The residue was purified by silica gel chromatography with ethyl acetate/petroleum ether (1:20) as the eluent to obtain a mixture of the title compounds as a brown oil (600 mg, 73%).

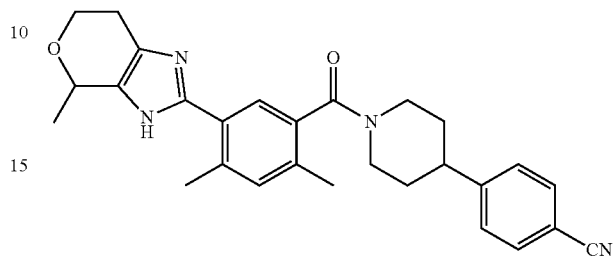

Compound 463. 4-(1-(2,4-Dimethyl-5-(4-methyl-3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 461, except a mixture of 4-bromo-2-methyldihydro-2H-pyran-3(4H)-one (compound 463.4) and 3-bromo-2-methyldihydro-2H-pyran-4(3H)-one (compound 463.5) was used in place of 2-bromo-4-methoxycyclopentanone (compound 461.4). m/z (ES+) 455 (M+H)$^+$.

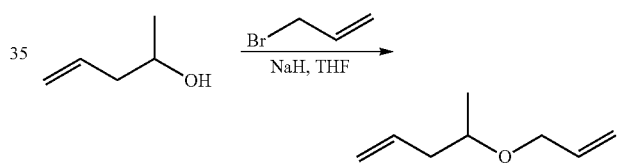

Compound 464.1. 4-(Allyloxy)pent-1-ene

A 500-mL four neck round-bottom flask was purged and maintained with an inert atmosphere of nitrogen, then a suspension of sodium hydride (14.0 g, 350 mmol, 2.01 equiv, 60%) in N,N-dimethylformamide (100 mL) was added. The mixture was cooled to 0° C., then a solution of pent-4-en-2-ol (15.0 g, 174 mmol, 1.00 equiv) in N,N-dimethylformamide (100 mL) was added drop-wise and the mixture was stirred for 20 min at 0° C. The mixture was cooled to −20° C. and a solution of 3-bromoprop-1-ene (20.9 g, 172 mmol, 0.99 equiv) in N,N-dimethylformamide (100 mL) was added. The resulting mixture was allowed to warm to room temperature and stirred overnight, then carefully quenched with H$_2$O (500 mL). The aqueous was extracted with ethyl acetate (4×100 mL) and the combined organics was washed with brine (2×200 mL), dried (Na$_2$SO$_4$), filtered and concentrated in vacuo to obtain the title compound as a yellow oil (13.3 g, 61%).

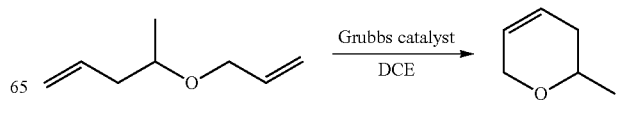

Compound 464.2. 2-Methyl-3,6-dihydro-2H-pyran

A 500-mL three neck round-bottom flask was purged and maintained with an inert atmosphere of nitrogen, then a solution of 4-(allyloxy)pent-1-ene (compound 464.1, 3.00 g, 23.8 mmol, 1.00 equiv) in DCE (200 mL) was added. Grubbs catalyst was added (810 mg, 0.950 mmol, 0.04 equiv) and the mixture was stirred at 60° C. for 4 h. The mixture was then concentrated in vacuo at 20° C. to obtain the title compound as a colorless oil (2.00 g, 86%).

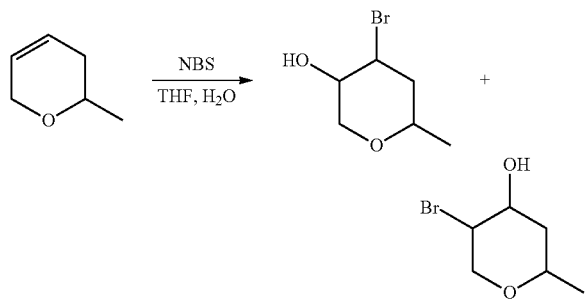

Compound 464.3 and 464.4. 4-Bromo-6-methyltetrahydro-2H-pyran-3-ol and 5-bromo-2-methyltetrahydro-2H-pyran-4-ol Into a round-bottom flask, was placed a solution of methyl-3,6-dihydro-2H-pyran (compound 464.2, 2.00 g, 20.4 mmol, 1.00 equiv) in a mixture of tetrahydrofuran and $H_2O$ (20/20 mL). N-Bromosuccinimide (3.60 g, 20.3 mmol, 1.00 equiv) was added and the resulting mixture was stirred at room temperature overnight. The mixture was extracted with dichloromethane (2×20 mL) and the combined organics were washed with brine (2×20 mL), dried ($Na_2SO_4$), filtered and concentrated in vacuo to obtain a mixture of the title compounds as a yellow oil (1.10 g, crude).

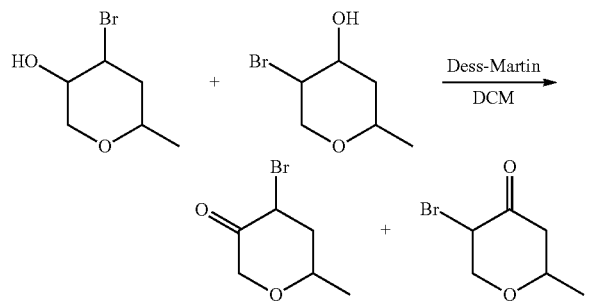

Compound 464.5 and 464.6. 4-Bromo-6-methyldihydro-2H-pyran-3(4H)-one and 5-bromo-2-methyldihydro-2H-pyran-4(3H)-one Into around-bottom flask, was placed a mixture of 4-bromo-6-methyltetrahydro-2H-pyran-3-ol (compound 464.3) and 5-bromo-2-methyltetrahydro-2H-pyran-4-ol (compound 464.4) (1.10 g, 5.64 mmol, 1.00 equiv) as a solution in dichloromethane (30 mL). Dess-Martin periodinane (2.90 g, 6.84 mmol, 1.21 equiv) was added and the resulting solution was stirred overnight at room temperature, then quenched with water (20 mL). The aqueous was extracted with dichloromethane (2×20 mL) and the combined organics were washed with brine (2×50 mL), dried ($Na_2SO_4$), filtered and concentrated in vacuo to obtain a mixture of the title compounds as a yellow oil (0.7 g).

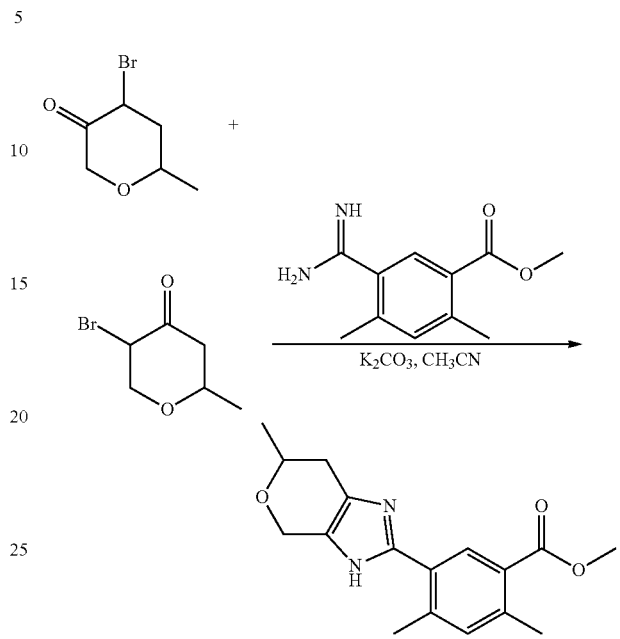

Compound 464.7. Methyl 2,4-dimethyl-5-(6-methyl-3,4,6,7-tetrahydropyrano[3,4-d]imidazol-2-yl)benzoate Into around-bottom flask, was placed a mixture of 4-bromo-6-methyldihydro-2H-pyran-3(4H)-one (compound 464.5) and 5-bromo-2-methyldihydro-2H-pyran-4(3H)-one (Compound 464.6) (700 mg, 3.63 mmol) as a solution in acetonitrile (20 mL). Methyl 5-carbamimidoyl-2,4-dimethylbenzoate hydrochloride (compound 2.5, 750 mg) and potassium carbonate (1.00 g, 7.25 mmol) were added and the mixture was stirred overnight at 75° C. under nitrogen. The mixture was cooled and the solids were removed by filtration. The filtrate was concentrated in vacuo and the residue was purified by silica gel chromatography with ethyl acetate/petroleum ether (1:1) as the eluent to obtain the title compound as a yellow solid (100 mg, 9%).

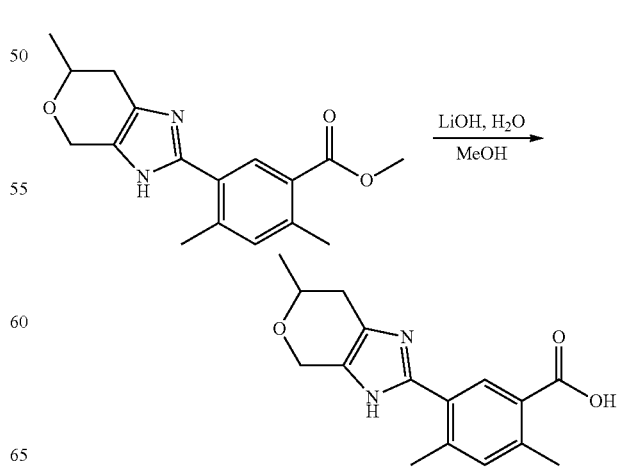

Compound 464.8. 2,4-Dimethyl-5-(6-methyl-3,4,6,7-tetrahydropyrano[3,4-d]imidazol-2-yl)benzoic acid Into around-bottom flask, was placed a solution of methyl 2,4-dimethyl-5-(6-methyl-3,4,6,7-tetrahydropyrano[3,4-d]imidazol-2-yl)benzoate (compound 464.7, 100 mg, 0.330 mmol, 1.00 equiv) in methanol (10 mL). A solution of lithium hydroxide (76 mg, 3.17 mmol, 10.0 equiv) in water (10 mL) was added and the resulting solution was stirred for 4 h at room temperature. The mixture was concentrated in vacuo and then aqueous HCl was added until the pH was 5-6. The mixture was adjusted to pH 5-6 with aqueous HCl and then the resulting mixture was concentrated in vacuo. MeOH (5 mL) was added to the residue and the solids were removed by filtration. The filtrate was concentrated in vacuo to obtain the title compound as a yellow solid (60 ma. 63%1.

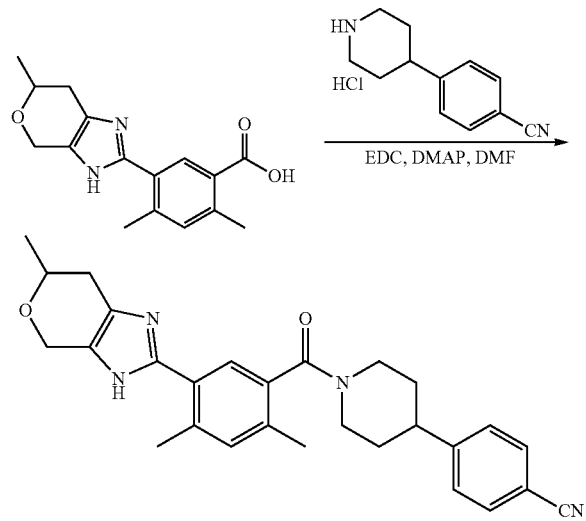

Compound 464. 4-(1-(2,4-Dimethyl-5-(6-methyl-3,4,6,7-tetrahydropyrano[3,4-d]imidazol-2-yl)benzoyl)piperidin-4-yl)benzonitrile Into around-bottom flask, was placed a solution of 2,4-dimethyl-5-[6-methyl-3H,4H,6H,7H-pyrano[3,4-d]imidazol-2-yl]benzoic acid (50 mg, 0.17 mmol, 1.00 equiv) in N,N-dimethylformamide (10 mL). EDC.HCl (67 mg, 0.35 mmol, 2.00 equiv), 4-dimethylaminopyridine (64 mg, 0.52 mmol, 3.00 equiv), and 4-(piperidin-4-yl)benzonitrile hydrochloride (compound 1.5, 39 mg, 0.18 mmol, 1.00 equiv) were added and the solution was stirred for 2 h at room temperature. The reaction was quenched with water (20 mL) and the aqueous was extracted with ethyl acetate (2×20 mL). The combined organics was dried (Na$_2$SO$_4$), filtered and concentrated in vacuo. The residue was purified by silica gel chromatography with ethyl acetate/petroleum ether (1:1) as the eluent. The crude product (20 mg) was purified by Prep-HPLC with the following conditions (1#-Pre-HPLC-001 (SHIMADZU)): Column, Xbridge Prep Phenyl, 5 um, 19*150 mm; mobile phase, water with 0.03% NH$_3$H$_2$O and CH$_3$CN (30% CH$_3$CN up to 60% in 9 min, up to 100% in 1 min, down to 30% in 1 min); Detector, Waters 2489 254 nm & 220 nm. The fractions containing pure product were combined and lyophilized to obtain the title compound as a white solid (8.0 mg, 10%). m/z (ES+) 455 (M+H)$^+$.

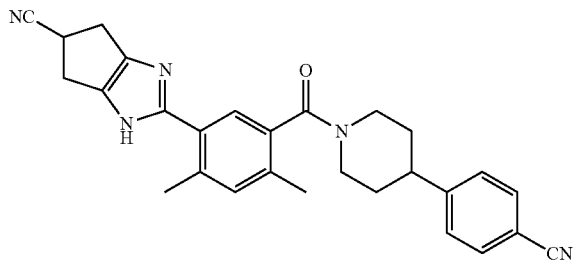 [SMILES: Cc1cc(C)c(-c2nc3c([nH]2)CC(C#N)C3)cc1C(=O)N1CCC(c2ccc(C#N)cc2)CC1]

Compound 465. 2-(5-(4-(4-Cyanophenyl)piperidine-1-carbonyl)-2,4-dimethylphenyl)-1,4,5,6-tetrahydrocyclopenta[d]imidazole-5-carbonitrile The title compound was prepared using standard chemical manipulations and procedures similar to those used for the preparation of compound 461, except cyclopent-3-enecarbonitrile (Johnson, C. R. et al. *J. Org. Chem,* 1969, 34, 860-864) was used in place of 4-methoxycyclopent-1-ene (compound 461.2). m/z (ES+) 450 (M+H)$^+$.

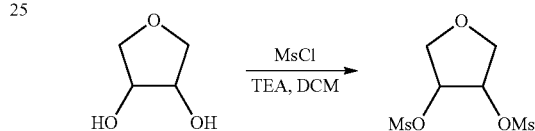

Compound 466.1. Tetrahydrofuran-3,4-diyl dimethanesulfonate

Into a round-bottom flask, was placed a solution of tetrahydrofuran-3,4-diol (500 mg, 4.80 mmol, 1.00 equiv) and triethylamine (1.45 g, 14.3 mmol, 3.00 equiv) in dichloromethane (8 mL). The mixture was cooled to 0-5° C. and a solution of methanesulfonyl chloride (1.40 g, 12.2 mmol, 2.50 equiv) in dichloromethane (2 mL) was added dropwise. The solution was stirred at room temperature for 2 h, and then diluted with dichloromethane (100 mL). The solution was washed with aqueous NH$_4$Cl (2×30 mL) then brine (30 mL), dried (Na$_2$SO$_4$), filtered and concentrated in vacuum to obtain the title compound as a brown solid (1.00 g, 72%).

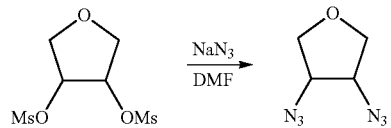

Compound 466.2. 3,4-Diazidotetrahydrofuran

Into a round-bottom flask, was placed a mixture of tetrahydrofuran-3,4-diyl dimethanesulfonate (compound 466.1, 2.00 g, 7.30 mmol, 1.00 equiv, 95%) and sodium azide (4.00 g, 61.5 mmol, 8.00 equiv) in N,N-dimethylformamide (20 mL). The resulting mixture was stirred overnight at 100° C. behind a blast shield, then cooled and diluted with ether (100 mL). The mixture was washed with brine (5×20 mL), dried (Na$_2$SO$_4$), filtered and concentrated in vacuo to obtain the title compound as a colorless oil (1.00 g, 80%).

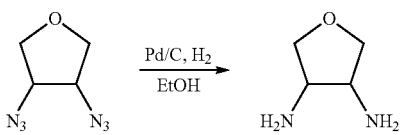

Compound 466.3. Tetrahydrofuran-3,4-diamine

Into around-bottom flask, was placed a solution of 3,4-diazidotetrahydrofuran (compound 466.2, 900 mg, 5.26 mmol, 1.00 equiv, 90%) in ethanol (10 mL). The system was purged with nitrogen and palladium on carbon (10 wt % Pd) (900 mg) was added. After further purging the system with nitrogen, the atmosphere was changed to hydrogen and the resulting suspension was stirred overnight at room temperature under an atmosphere of hydrogen. After purging the system with nitrogen, the solids were removed by filtration and the filtrate was concentrated in vacuo to obtain the title compound as a colorless oil (600 mg, 98%).

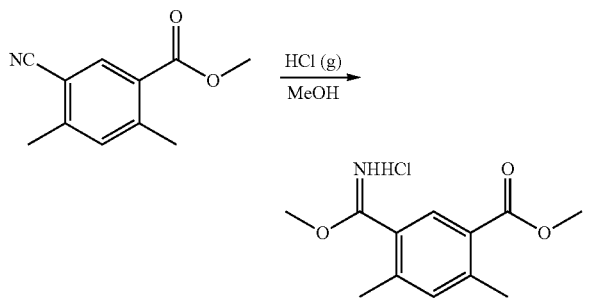

Compound 466.4. Methyl 5-(imino(methoxy)methyl)-2,4-dimethylbenzoate hydrochloride Into a 50-mL three neck round-bottom flask, was placed a solution of methyl 5-cyano-2,4-dimethylbenzoate (compound 2.3, 900 mg, 4.28 mmol, 1.00 equiv, 90%) in methanol (20 mL). Hydrogen chloride gas was introduced by bubbling through the solution for 0.5 hr. The reaction mixture was then transferred into a 30-mL sealed tube and stirred overnight at room temperature. The mixture was concentrated under vacuum and the residue was diluted with ethyl acetate (30 mL) and extracted with water (10 mL). The aqueous was concentrated in vacuo to obtain the title compound as a white solid (200 mg, 15%).

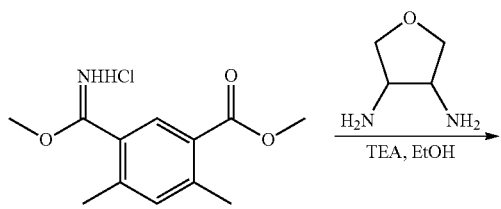

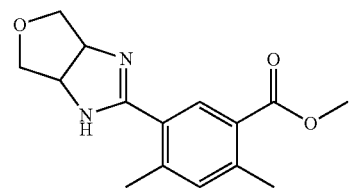

Compound 466.5. Methyl 2,4-dimethyl-5-(3a,4,6,6a-tetrahydro-1H-furo[3,4-d]imidazol-2-yl)benzoate Into around-bottom flask, was placed a solution of tetrahydrofuran-3,4-diamine (compound 466.3, 140 mg, 1.17 mmol, 1.00 equiv, 85%) in ethanol (6 mL). Methyl 5-(imino(methoxy)methyl)-2,4-dimethylbenzoate hydrochloride (compound 466.4, 300 mg, 0.930 mmol, 1.00 equiv) and triethylamine (140 mg, 1.38 mmol, 1.00 equiv) were added and the resulting solution was stirred overnight at 80° C., then concentrated in vacuo. The residue was purified by silica gel chromatography with dichloromethane/methanol (10:1) as the eluent to obtain the title compound as a brown oil (120 mg, 34%).

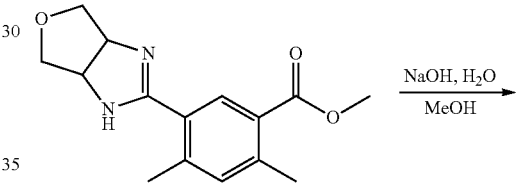

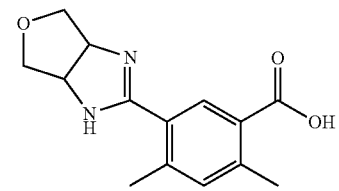

Compound 466.5. 2,4-Dimethyl-5-(3a,4,6,6a-tetrahydro-1H-furo[3,4-d]imidazol-2-yl)benzoic acid Into around-bottom flask, was placed a solution of methyl 2,4-dimethyl-5-(3a,4,6,6a-tetrahydro-1H-furo[3,4-d]imidazol-2-yl)benzoate (compound 466.5, 100 mg, 0.330 mmol, 1.00 equiv, 90%) and sodium hydroxide (73 mg, 1.82 mmol, 5.00 equiv) in methanol/H$_2$O (3/3 mL). The resulting solution was stirred overnight at 70° C., then concentrated in vacuum. The residue was diluted with H$_2$O (5 mL) and the pH of the solution was adjusted to 2-3 with hydrogen chloride (12 N), then extracted with ethyl acetate (3×10 mL). The combined organics was concentrated in vacuo to obtain the title compound as a yellow solid (80.0 mg, 84%).

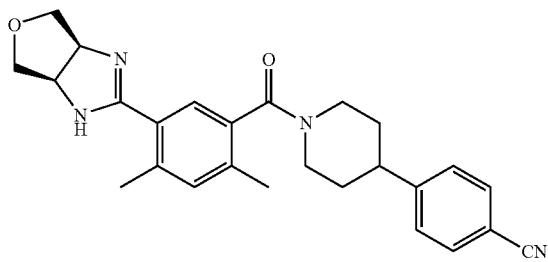 [SMILES: Cc1cc(C)c(C2=N[C@@H]3COC[C@@H]3N2)cc1C(=O)N1CCC(c2ccc(C#N)cc2)CC1]

Compound 466. 4-(1-(2,4-Dimethyl-5-(-3a,4,6,6a-tetrahydro-1H-furo[3,4-d]imidazol-2-yl)benzoyl)piperidin-4-yl)benzonitrile Into around-bottom flask, was placed a solution of 2,4-dimethyl-5-(3a,4,6,6a-tetrahydro-1H-furo[3,4-d]imidazol-2-yl)benzoic acid (compound 466.5, 80.0 mg, 0.250 mmol, 1.00 equiv, 80%) in N,N-dimethylformamide (4 mL). 4-(Piperidin-4-yl)benzonitrile hydrochloride (compound 1.5, 82.0 mg, 0.350 mmol, 1.20 equiv), 4-dimethylaminopyridine (76.0 mg, 0.620 mmol, 2.00 equiv), and EDC.HCl (116 mg, 0.610 mmol, 2.00 equiv) were added and the resulting solution was stirred overnight at room temperature. The mixture was diluted with ethyl acetate (30 mL) and washed with brine (3×15 mL), dried (Na₂SO₄), filtered and concentrated in vacuo. The crude product (50 mg) was purified by Prep-HPLC with the following conditions (1#-Pre-HPLC-001 (SHIMADZU)): Column, Xbridge Prep C18, 5 um, 19*150 mm; mobile phase, water with 0.05% TFA and CH₃CN (15% CH₃CN up to 50% in 9 min, up to 100% in 1 min, down to 15% in 1 min); Detector, Waters 2489 254 nm & 220 nm. The fractions containing pure product were combined and lyophilized to obtain the title compound as a white solid (13 mg, 12%). m/z (ES+) 429 (M+H)⁺. ¹H-NMR (300 MHz, CD₃OD): δ 7.70 (d, 2H), 7.53-7.36 (m, 4H), 5.09 (s, 2H), 4.17 (d, J=10.8 Hz, 2H), 3.77 (d, J=10.5 Hz, 2H), 3.60-3.44 (m, 1H), ~3.3 (m, partially overlapped with water, 1H), 3.10-2.92 (m, 2H), 2.48 (s, 3H), 2.45 and 2.35 (2 singlets, amide rotamers, Ar—CH₃, 3H), 2.10-1.97 (m, 1H), 1.92-1.52 (m, 3H).

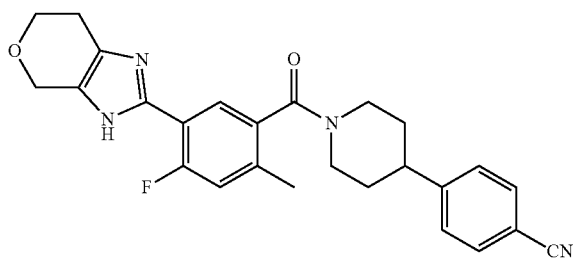

Compound 467. 4-(1-(4-Fluoro-2-methyl-5-(3,4,6,7-tetrahydropyrano[3,4-d]imidazol-2-yl)benzoyl)piperidin-4-yl)benzonitrile The title compound was prepared using standard chemical manipulations and procedures similar to those used for the preparation of compound 1 and compound 2, except 4-fluoro-2-methylbenzoic acid was used in place of 2,4 dimethylbenzoic acid. m/z (ES+) 445 (M+H)⁺.

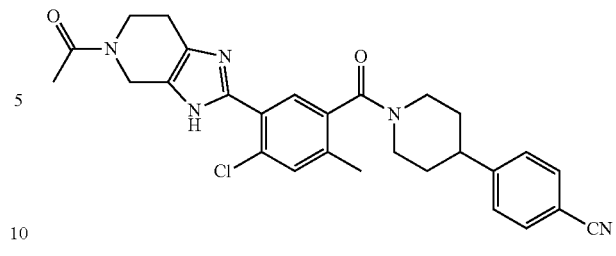

Compound 468. 4-(1-(5-(5-Acetyl-4,5,6,7-tetrahydro-3H-imidazo[4,5-c]pyridin-2-yl)-4-chloro-2-methylbenzoyl)piperidin-4-yl)benzonitrile The title compound was prepared using standard chemical manipulations and procedures similar to those used for the preparation of compound 2, except 4-chloro-2-methylbenzoic acid was used in place of 2,4 dimethylbenzoic acid. m/z (ES+) 502 (M+H)⁺.

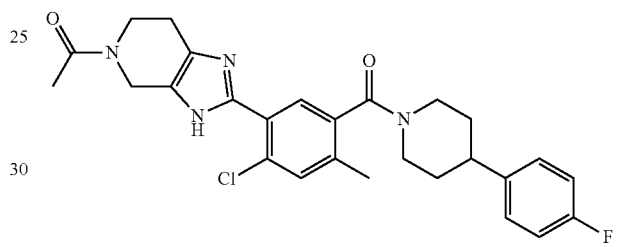

Compound 469. 1-(2-(2-Chloro-5-(4-(4-fluorophenyl)piperidine-1-carbonyl)-4-methylphenyl)-6,7-dihydro-3H-imidazo[4,5-c]pyridin-5(4H)-yl)ethanone The title compound was prepared using standard chemical manipulations and procedures similar to those used for the preparation of compound 2 and compound 468. m/z (ES+) 495 (M+H)⁺.

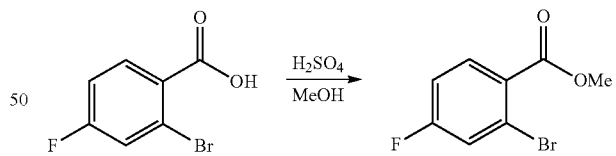

Compound 470.1. Methyl 2-bromo-4-fluorobenzoate

Into a round-bottom flask, was placed a solution of 2-bromo-4-fluorobenzoic acid (21.8 g, 99.5 mmol, 1.00 equiv) in a solvent mixture of sulfuric acid (20 mL) and methanol (20 mL). The resulting solution was stirred for 5 h at 85° C., then cooled and cooled and concentrated in vacuo. The residue was diluted with ethyl acetate (200 mL) and washed with brine (200 mL) then aqueous NaHCO₃ (100 mL. Note: gas evolution), dried (Na₂SO₄), filtered and concentrated in vacuo to obtain the title compound as a light yellow oil (22.0 g, 95%).

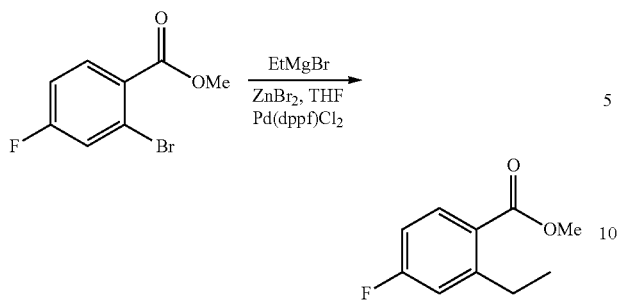

Compound 470.1. Methyl 2-ethyl-4-fluorobenzoate

The title compound (colorless oil, 14.5 g, 93%) was prepared using a procedure similar to that used for the preparation of compound 48.1 and using of methyl 2-bromo-4-fluorobenzoate (compound 470.1, 20.0 g) in place of methyl 2-bromo-4-methylbenzoate.

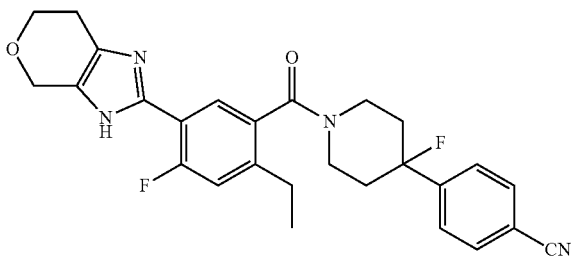 [SMILES: CCc1cc(F)c(-c2nc3c([nH]2)COCC3)cc1C(=O)N1CCC(F)(c2ccc(C#N)cc2)CC1]

Compound 470. 4-(1-(2-Ethyl-4-fluoro-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 1 and compound 2, except methyl 2-ethyl-4-fluorobenzoate (compound 470.1) was used in place of 2,4-dimethylbenzoic acid, and 4-(4-fluoropiperidin-4-yl)benzonitrile hydrochloride (compound 11.2) was used in place of 4-(piperidin-4-yl)benzonitrile hydrochloride (compound 1.5). m/z (ES+) 477 (M+H)+.

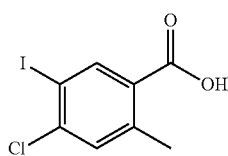

Compound 471.1. 4-Chloro-5-iodo-2-methylbenzoic acid

The title compound was prepared using standard chemical manipulations and procedures similar to those used for the preparation of compound 2.1, except 4-chloro-2-methylbenzoic acid was used in place of 2,4-dimethylbenzoic acid.

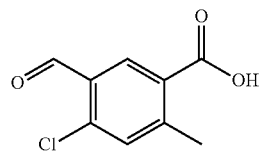

Compound 471.2. 4-Chloro-5-formyl-2-methylbenzoic acid

The title compound was prepared using standard chemical manipulations and procedures similar to those used for the preparation of compound 392.2, except 4-chloro-5-iodo-2-methylbenzoic acid (compound 471.1) was used in place of 4-cyclobutyl-5-iodo-2-methylbenzoic acid (compound 392.1).

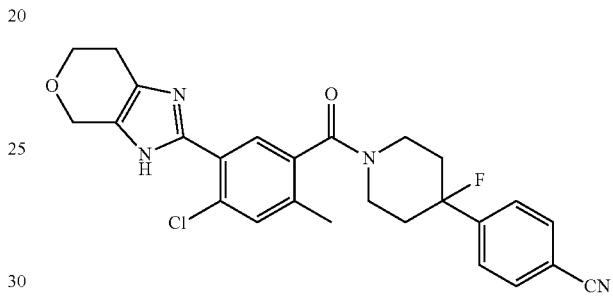

Compound 471. 4-(1-(4-Chloro-2-methyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 400, except 4-chloro-5-formyl-2-methylbenzoic acid (compound 471.2) was used in place of 2-ethyl-5-formyl-4-methylbenzoic acid (compound 211.4), 3-bromodihydro-2H-pyran-4(3H)-one was used in place of 3-bromo-5-methyldihydro-2H-pyran-4(3H)-one (compound 400.2) and 4-(4-fluoropiperidin-4-yl)benzonitrile hydrochloride (compound 11.2) was used in place of 4-(piperidin-4-yl)benzonitrile hydrochloride (compound 1.5). m/z (ES+) 479 (M+H)+.

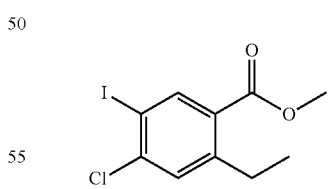

Compound 472.1. Methyl 4-chloro-2-ethyl-5-iodobenzoate

The title compound was prepared using standard chemical manipulations and procedures similar to those used for the preparation of compound 211.2, except methyl 4-chloro-2-ethylbenzoate (compound 178.2) was used in place of methyl 2-ethyl-4-methylbenzoate (compound 48.1).

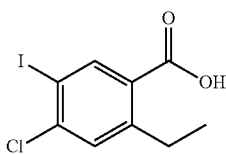

Compound 472.2. 4-Chloro-2-ethyl-5-iodobenzoic acid

The title compound was prepared using standard chemical manipulations and procedures similar to those used for the preparation of compound 211.3, except methyl 4-chloro-2-ethyl-5-iodobenzoate (compound 472.1) was used in place of 2-ethyl-5-iodo-4-methylbenzoate (compound 211.2).

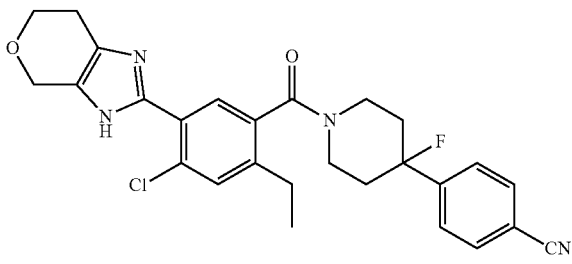 [SMILES: CCc1cc(Cl)c(-c2nc3c([nH]2)COCC3)cc1C(=O)N1CCC(F)(c2ccc(C#N)cc2)CC1]

Compound 472. 4-(1-(4-Chloro-2-ethyl-5-(3,4,6,7-tetrahydropyrano[3,4-d]imidazol-2-yl)benzoyl)-4-fluoropiperidin-4-yl)benzonitrile The title compound was prepared using standard chemical manipulations and procedures similar to those used for the preparation of compound 400, except 4-chloro-2-ethyl-5-iodobenzoic acid (compound 472.2) was used in place of 2-ethyl-5-formyl-4-methylbenzoic acid (211.4), 3-bromodihydro-2H-pyran-4(3H)-one was used in place of 3-bromo-5-methyldihydro-2H-pyran-4(3H)-one (compound 400.2) and 4-(4-fluoropiperidin-4-yl)benzonitrile hydrochloride (compound 11.2) was used in place of 4-(piperidin-4-yl)benzonitrile hydrochloride (compound 1.5). m/z (ES+) 493 (M+H)+.

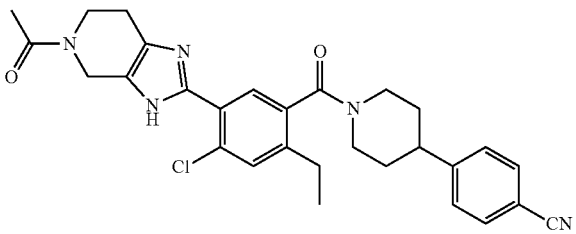 [SMILES: CCc1cc(Cl)c(-c2nc3c([nH]2)CN(C(C)=O)CC3)cc1C(=O)N1CCC(c2ccc(C#N)cc2)CC1]

Compound 473. 4-(1-(5-(5-Acetyl-4,5,6,7-tetrahydro-3H-imidazo[4,5-c]pyridin-2-yl)-4-chloro-2-ethylbenzoyl)piperidin-4-yl)benzonitrile The title compound was prepared using standard chemical manipulations and procedures similar to those used for the preparation of compound 2, except methyl 4-chloro-2-ethyl-5-iodobenzoate (compound 472.1) was used in place of methyl 5-iodo-2,4-dimethylbenzoate (compound 2.2). m/z (ES+) 516 (M+H)+. 1H-NMR (300 MHz, CD3OD): δ 7.73-7.54 (m, 4H), 7.53-7.42 (m, 2H), 4.75 and 4.70 (2 singlets, acetyl amide rotamers, CH2, 2H), 4.02-3.88 (m, 2H), 3.68-3.52 (m, 1H), 3.32-3.20 (m, 1H), 3.07-2.88 (m, 3H), 2.88-2.58 (m, 3H), 2.25 and 2.22 (2 singlets, acetyl amide rotamers, acetyl CH3, 3H), 2.11-1.98 (m, 1H), 1.93-1.53 (m, 3H), 1.39-1.22 (m, 3H).

Additional example compounds are found in Table 1. Table 1 begins on page 460.

Example 1—FASN Inhibition by Compounds of the Present Disclosure

Determination of FASN biochemical activity: The FASN enzyme was isolated from SKBr3 cells. SKBr3 is a human breast cancer cell-line with high levels of FASN expression. It is estimated that FASN comprises about 25% of the cytosolic proteins in this cell line. SKBr3 cells were homogenized in a dounce homogenizer then centrifuged for 15 minutes at 4° C. to remove particulate matter. The supernatant was then analyzed for protein content, diluted to the appropriate concentration, and used to measure FASN activity. The presence of FASN was confirmed by western blot analysis. A similar method for isolation of FASN from SKBr3 cells is described in Teresa, P. et al. (*Clin. Cancer Res.* 2009; 15(24), 7608-7615).

FASN activity of the SKBr3 cell extract was determined by measuring either NADPH oxidation or the amount of thiol-containing coenzyme A (CoA) released during the fatty acid synthase reaction. The dye CPM (7-diethylamino-3-(4'-maleimidyl-phenyl)-4-methylcoumarin) contains a thiol reactive group that increases its fluorescence emission on reaction with the sulfhydryl group of CoA. The biochemical activities shown in Table 1 were determined using the fluorescence measurement of CoA release via a procedure described in Chung C. C. et al. (*Assay and Drug Development Technologies,* 2008, 6(3), 361-374).

Example 2—Antiviral Activity

The antiviral activity of Structure (I-Z) was assessed using the HCV1b replicon system:

(I-Z)

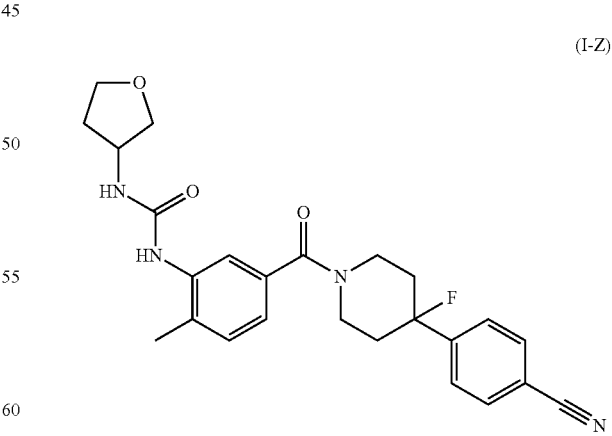

The replicon was constructed using the ET (luc-ubi-neo/ET) cell line, a Huh7 human hepatoma cell line harboring an HCV replicon with a stable luciferase (Luc) reporter and three cell culture-adaptive mutations (Pietschmann, et al (2002) *J. Virol.* 76:4008-4021). The HCV replicon antiviral evaluation assay examined the effects of compounds at six half-log concentrations. Human interferon alpha-2b was included in each run as a positive control compound. Sub-confluent cultures of the ET line were plated out into 96-well plates that are dedicated for the analysis of cell numbers (cytotoxicity) or antiviral activity and the next day drugs were added to the appropriate wells. Cells were processed 72 hr later when the cells were still sub-confluent. $EC_{50}$ (concentrations inhibiting the replicon by 50% and 90%, respectively), $IC_{50}$ (concentration decreasing cell viability by 50%) and SI (selective index: $IC_{50}/EC_{50}$) values were determined. HCV RNA replicon levels were assessed as either HCV RNA replicon-derived Luc activity or as HCV RNA by TaqMan RT-PCR. Two methods were used to estimate cell counts (cytotoxicity). When the Luc assay system was employed, the colorimetric CytoTox-1 cell proliferation assay (Promega) was used to estimate cell numbers, while ribosomal RNA (rRNA) levels determined via TaqMan RT-PCR were used as an indication of cell numbers in the RNA-based assay. A summary of the results is listed below in Table 2.

TABLE 2

| Method | Replicon EC50 (µM) | Cell IC50 (µM) | Selectivity Index |
|---|---|---|---|
| Luciferase activity | 0.017 | >32 | >1882 |
| TaqMan RT-PCR | 0.105 | >100 | >952 |

Example 3—FASN Inhibition Correlates to HCV Inhibition

The antiviral activities of 15 compounds of the present disclosure (numbers correlate to the compounds in Table 1) were measured using the HCV replicon system. Replicon cell line 1b (HCV 1b/Luc-Neo replicon (1b Con1 with Firefly gene integrated)) was established following published methods (Lohmann et al. (1999) *Science* 285(5424): 110-113, Lohmann et al. (2001) *J. Virol.* 75(3):1437-1449 and Qi et al. (2009) *Antiviral Res.* 81(2):166-173) using Huh7 by G418 selection. The replicon was assembled using synthetic gene fragments. The Glib line has PV-EKT and harbors 3 adaptive mutations E1202G(NS3), T1280I(NS3), K1846T(NS4B) and the backbone is Con1. The culture medium was:
a) DMEM supplement with 10% FBS, G418 (250 µg/ml), streptomycin (100 µg/ml)/penicillin (100 U/ml), L-glutamine (100×), NEAA (100×)
b) Media prepared as follows:
  i) 500 ml DMEM media (Gibco, Cat#11960-077)
  ii) 57 ml Fetal Bovine Serum (Gibco, Cat#16140-071)
  iii) 5.7 ml Penicillin-Streptomycin (Gibco, Cat#15140-122)
  iv) 5.7 ml MEM non-essential amino acids (Gibco, Cat#111140-050)
  v) 5.7 ml L-glutamine (Gibco, Cat#125030-081)
  vi) 574.1 ml media+2.87 ml 50 mg/ml G418 [final 0.25 mg/ml] (Gibco, Cat#10131-027)

Compounds were dissolved in DMSO to provide a 10 mM stock or used from stock DMSO solutions. Compounds were diluted to generate 10-point half log (3.16-fold) serial dilutions for assay in 384-well plates (Echo qualified 384-well PP (Labcyte Cat#P-05525)) plus DMSO in duplicate. This experiment was repeated three times on three different days.

Cells were harvested when confluency reached 90%-100%. Cell concentrations were adjusted to $8 \times 10^4$ cells/ml and added to 384-well white assay microplates (tissue-culture treated—Greiner Cat#781080) to reach a final cell density of 2,000 cells/well. Plates were incubated at 5% $CO_2$ and 37° C. for 72 hours.

After 72 hours of incubation Bright-Glo Luciferase reagent (Promega, cat# E2650) and Cell Titer Flo (Promega, cat#G6080/1/2) were prepared and stored in the dark while equilibrating to room temperature. Treated cells were likewise equilibrated to room temperature. 10 µL of Cell Titer Flo was added to each well of compound-treated cells and incubated in microtiter plates for approx. 0.5 hours. Cell viability was measured using an Envision reader (available from Perkin Elmer) to estimate cytotoxicity. 30 µL of firefly luciferase substrate were added to each well and chemiluminescence was measured as an indicator of the extent of HCV replication.

The anti-replicon activity (% inhibition) is calculated using the equation:

$$\% \text{ Inhibition} = \left(1 - \frac{Cmpd - \text{Control}}{DMSO - \text{Control}}\right) \times 100.$$

Cytotoxicity is calculated using the equation:

$$\% \text{ Cytotoxicity} = \left(1 - \frac{Cmpd - \text{Background}}{DMSO - \text{Background}}\right) \times 100.$$

There was determined to be a correlation between potency of FASN inhibition and antiviral activity as illustrated in Table 3 below and FIG. 1. It is noted that none of the compounds caused significant cytotoxicity.

TABLE 3

| Molecule | Biochemical IC50 (µM) | Antiviral EC50 (µM) |
|---|---|---|
| 1 | 0.230 | 0.425 |
| 2 | 0.065 | 0.192 |
| 12 | 0.370 | 1.003 |
| 14 | 0.263 | 0.260 |
| 20 | 0.022 | 0.011 |
| 27 | 0.107 | 0.153 |
| 43 | 0.110 | 0.154 |
| 55 | 0.035 | 0.034 |
| 58 | 0.025 | 0.078 |
| 67 | 0.090 | 0.270 |
| 68 | 0.100 | 0.301 |
| 70 | 0.037 | 0.099 |
| 73 | 0.040 | 0.117 |
| 152 | 0.052 | 0.072 |
| 343 | 0.600 | 0.624 |

Example 4—FASN Inhibitors Retain Activity Against HCV Mutants that Confer Resistance to Direct-Acting Antiviral Agents One of the major challenges in treating hepatitis C is the rapid emergence of resistance in response to direct-acting antiviral agents. Resistance typically results when the virus generates a point mutant that supports essential viral functions but prevents antiviral agents from binding. Three FASN inhibitors (compounds 55, 20, and 70) were tested for their ability to inhibit mutants of HCV that confer resistance to representative antiviral agents. Each of these mutants was introduced into a GT1b construct based on a Con1 backbone containing the PVIRES-Luciferase Ubi-Neo gene and harboring 1 adaptive mutation (S2204I). (Lohmann et al. (1999) *Science* 285(5424):110-113, Lohmann et al. (2001) *J. Virol.* 75(3):1437-1449 and Qi et al. (2009) *Antiviral Res.* 81(2): 166-173). Antiviral activities were measured by the method described in Example 3.

The studied mutations are shown in Table 4 below.

TABLE 4

| Studied Mutations | |
|---|---|
| Mutant | Reference |
| NS3 A156T | Susser et al *J. Clin. Virol.* 52(4), 321-327 (2011) and references therein |
| NS3 R155K | Susser et al *J. Clin. Virol.* 52(4), 321-327 (2011) and references therein |
| NS4B H94R | Rai et al. *Antiviral Res.* 90, 93-101 (2011) |

TABLE 4-continued

| Studied Mutations | |
|---|---|
| Mutant | Reference |
| NS5AY393H | Fridell et a.l *Antimicrob. Agents Chemother.* 54(9), 3641-3650 (2010) |
| NS5B M423I | (non-nucleoside site) Troke et al. *Antimicrob. Agents Chemother.* 56(3), 1331-1341 (2012) |
| NS5B S282T | (nucleoside site) Dutartre et al. *Antimicrob. Agents Chemother.* 50(12), 4161-4169 (2006) |

A known NS4B allosteric inhibitor (Compound A), a known NSSA inhibitor (Compound B), a known non-nucleoside NS5B inhibitor (Compound C), a known NS3/NS4A protease inhibitor (Compound D) and a known nucleoside NS5B inhibitor (Compound E) were tested in parallel with the FASN inhibitors of the present disclosure to confirm the performance of the resistance mutations.

Antiviral $EC_{50}$'s for the various compounds against the panel of mutants, along with the relative shift in $EC_{50}$ relative to the GT1b wild-type replicon are shown below. Normal assay variation is ±3-4 fold. $EC_{50}$ shifts outside this range imply resistance and are indicated in bold. The 3 FASN inhibitors retain activity across the panel of mutants, whereas the direct-acting antiviral agents display resistance against mutations in their respective binding sites.

TABLE 5

Antiviral $EC_{50}$'s.

| | $EC_{50}$ (nM) | | | | | | |
|---|---|---|---|---|---|---|---|
| Compound | 1b Wild Type | NS3 A156T | NS3 R155K | NS4B H94R | NS5A Y93H | NS5B M423I | NS5B S282T |
| 55 | 49.63 | 143.00 | 156.10 | 67.31 | 109.40 | 19.22 | 73.30 |
| 20 | 16.71 | 44.06 | 25.46 | 17.02 | 32.00 | 19.70 | 25.60 |
| 70 | 39.18 | 49.97 | 43.91 | 36.00 | 108.90 | 58.69 | 56.90 |
| Compound A | 261.00 | 232.20 | 209.60 | 2813.00 | n.t. | 126.60 | n.t. |
| Compound B | 0.01 | 0.01 | n.t. | n.t. | 0.28 | 0.01 | 0.01 |
| Compound D | 0.67 | 105.00 | 236.60 | 0.39 | n.t. | 1.54 | n.t. |
| Compound C | 4.27 | 4.57 | 8.43 | 4.61 | 3.00 | 34.09 | 3.00 |
| Compound E | 583.70 | 890.90 | n.t. | n.t. | 1069.0 | 159.30 | 15650.0 |

TABLE 6

Fold shift in EC50 relative to wild-type

| | HCV | Fold shift in EC50 relative to wild-type | | | | | |
|---|---|---|---|---|---|---|---|
| Compound | Binding Site | NS3 A156T | NS3 R155K | NS4B H94R | NS5A Y93H | NS5B M423I | NS5B S282T |
| 55 | | 2.88 | 3.15 | 1.36 | 2.20 | 0.39 | 1.48 |
| 20 | | 2.64 | 1.52 | 1.02 | 1.92 | 1.18 | 1.53 |
| 70 | | 1.28 | 1.12 | 0.92 | 2.78 | 1.50 | 1.45 |
| Compound A | NS4B | 0.89 | 0.80 | 10.78 | n.t. | 0.49 | n.t. |
| Compound B | NS5A | 1.00 | n.t. | n.t. | 35.13 | 0.75 | 0.88 |
| Compound D | NS3/4A | 156.46 | 352.56 | 0.58 | n.t. | 2.29 | n.t. |
| Compound C | NS5B (non-nuc) | 1.07 | 1.98 | 1.08 | 0.70 | 7.99 | 0.70 |
| Compound E | NS5B (nuc) | 1.53 | n.t. | n.t. | 1.83 | 0.27 | 26.81 |

Example 5—FASN Inhibitors Useful in Combination Therapies

This example describes the in vitro antiviral activity and cytotoxicity of the compound of Structure (V-K) in combination with IFN-α, Ribavirin, Compounds B, C, D and E against an HCV GT1b replicon cell line.

(V-K)

Materials:
Virus:
The GT1b replicon plasmid was assembled using synthetic gene fragments. The replicon genome contains PVI-RES-Luciferase Ubi-Neo gene segments and harbors 1 adaptive mutation (S22041), and the backbone is Con1. The replicon GT1b cell line was established by the following published methods.

Medium and Reagents:
Table 7 below provides details regarding the culture medium reagents used in this example.

TABLE 7

List of culture medium regents

| Reagent | Vendor | Catalogue Number |
|---|---|---|
| Dimethyl sulfoxide (DMSO) | Sigma | Cat #34869-100ML |
| DMEM | Invitrogen | Cat #11960-044 |
| Fetal Bovine Serum (FBS) | Gibco | Cat #16140 |
| Pen-Strep | Invitrogen | Cat #15140-122 |
| MEM non-essential amino acids | Invitrogen | Cat #11140-050 |
| L-Glutamin | Invitrogen | Cat #25030-081 |
| G418 (geneticin) | Gibco | Cat #10131-027 |
| Trypsin/EDTA | Invitrogen | Cat #25200-072 |
| DPBS/Modified | Hyclone | SH30028.01B |
| 96-well cell plate | Greiner | Cat #655090 |
| Cell titer fluro | Promega | Cat #G6082 |
| Bright-Glo | Promega | Cat #E264B |

Analytical Instruments:
The following analytical instruments were used to perform the assays of this example:
POD-810
Topcount (PE)
Envision (PE)
Multidrop (Thermo)

Methods:
Preparation of Compound Plates for Single Compound Testing:
Compounds were supplied as dry powders and were reconstituted in DMSO to generate stock solutions. The POD-810 system was used to generate 10-point half log (3.16-fold) serial dilutions for the assay in 96-well plates. The highest test concentrations are detailed for each compound in Table 8.

Assay Protocol (Single Compounds):
Each compound was assayed with 3.16-fold (half log) serial dilutions for 10 concentrations plus DMSO in duplicate. HCV replicon GT1b cells were harvested and adjusted to a cell concentration of 8E+04 cells/ml. A Multidrop was used to plate 100 µL/well into 96 assay microplates to reach a final cell density of 8,000 cells/well. Plates were incubated at 5% $CO_2$, 37° C. for 72 hours.

At the end of the 72 hour incubation, antiviral activity and cytotoxicity were measured. Bright-Glo Luiferase reagent and Cell Titer Flo were prepared and stored in dark while equilibrating to room temperature. The cell plates were allowed to equilibrate to room temperature as well. A Multidrop was used to add 20 µL Cell Titer Flo to each well of compound-treated and compound-free cells. The plates are incubated for 1 hour, and cell viability is measured on an Envision reader for cytoxicity calculation. Fifty microliters of firefly luciferase substrate are added to each well, incubated for 2 minutes, and chemiluminescence is measured for $EC_{50}$ calculation.

The anti-replicon activity (% inhibition) was calculated using the following equation:

% Inhibition=[1−((Compound-background)/(DMSO-background))×100].

Test Compounds and Assay Setup for Two-Compound Combination Studies:

The DMSO stocks of the compounds used in the single compound testing were also used in this analysis. Combination dilution matrixes were generated by POD-810 in 96-well assay microplates. The POD-810 system was used to generate 7-point, 2-fold serial dilutions in a matrix format. The maximum concentration tested for each compound is detailed below.

TABLE 8

Expected activities and upper concentrations of compounds tested in single-agent and combination studies

| Compound | Expected GT1b EC50 (µM) | Highest concentration for single-agent testing (µM) | Highest concentration for combination testing (µM) |
|---|---|---|---|
| (V-K) | 0.060 | 10.0 | 0.100 |
| Compound D | 0.0014 | 0.032 | 0.0032 |
| Compound C | 0.018 | 10.0 | 0.032 |
| Compound B | 0.000009 | 0.001 | 0.000032 |
| Compound E | 4.030 | 100.0 | 10.0 |
| IFN | 64.94 IU/ml | 1000 IU/ml | 10.0 IU/ml |
| Ribavirin | 26.830 | 320.0 | 100.0 |

The compound of Structure (V-K) was tested alone and in combination with compounds detailed in Table 9. Each compound was also tested alone as a single agent.

TABLE 9

Combinations of compounds for in vitro evaluation.

| Regimen | Combination |
|---|---|
| 1 | (V-K) + Compound D |
| 2 | (V-K) + Compound C |
| 3 | (V-K) + Compound B |
| 5 | (V-K) + Compound E |

TABLE 9-continued

Combinations of compounds for in vitro evaluation.

| Regimen | Combination |
|---|---|
| 6 | (V-K) + IFN-α |
| 7 | (V-K) + RBV |

Assay Setup (Two-Drug Combinations):

Each compound was assayed with 2-fold serial dilutions for 7 concentrations in matrix format plus each drug alone. HCV replicon GT1b cells were harvested and adjusted to a cell concentration of 8E+04 cells/ml. A Multidrop was used to plate 100 μL into 96 assay microplates to reach a final cell density of 8,000 cells/well. Plates were incubated at 5% $CO_2$, 37° C. for 72 hours.

At the end of the 72 hour incubation, antiviral activity and cytotoxicity were measured. Bright-Glo Luiferase reagent and Cell Titer Flo were prepared and store in dark while allowing to equilibrate to room temperature. The cells plates were allowed to equilibrate to room temperature as well. A Multidrop was used to add 20 μL Cell Titer Flo to each well of compound-treated and compound-free cells. The plates were incubated for 1 hour, and cell viability was measured on an Envision reader for cytotoxicity calculation. The liquid was then removed from the plates, after which 50 μL PBS and 50 μL firefly luciferase substrate solution were added to each well, after a 2-minute incubation period, chemiluminescence (for HCV replication calculation) was measured. The data were analyzed using MacSynergy™ II.

Assay Results:

Activity and Cytotoxicity of the Compounds.

The $EC_{50}$ and $CC_{50}$ values are summarized below in Table 10.

TABLE 10

$EC_{50}$ and $CC_{50}$ of Each Test Compound

| | GT1b | | |
|---|---|---|---|
| Compound | $EC_{50}$ (μM) | Expected $EC_{50}$ (μM) | $CC_{50}$ (μM) |
| (V-K) | 0.04 | 0.06 | >10 |
| Compound D | 0.0021 | 0.0014 | >0.032 |
| Compound C | 0.006 | 0.018 | >10 |
| Compound B | 0.000012 | 0.000009 | >0.001 |
| Compound E | 2.41 | 4.03 | >100 |
| IFN-α (IU/mL) | 1.34 | 1 | >1000 |
| RBV | 32.75 | 26.83 | 239 |

Combination Effect.

The combination effect of the compound pairs was calculated using MacSynergy™ II and those results are summarized in Table 11 below.

TABLE 11

Summary of the combination effects of the compound pairs

| | | MacSynergy ™ II SYNERGY PLOT (95%) | | | |
|---|---|---|---|---|---|
| Compd 1 (top conc) | Compd 2 (top conc) | SYNERGY | Log volume | ANTAG-ONISM | Log volume |
| (V-K) | Compound D | 16.7 | 1.51 | −13.03 | −1.18 |
| | Compound C | 2.93 | 0.27 | −9.2 | −0.83 |
| | Compound B | 6.75 | 0.61 | −7.11 | −0.64 |
| | Compound E | 1.08 | 0.1 | −7.81 | −0.73 |

TABLE 11-continued

Summary of the combination effects of the compound pairs

| | | MacSynergy ™ II SYNERGY PLOT (95%) | | | |
|---|---|---|---|---|---|
| Compd 1 (top conc) | Compd 2 (top conc) | SYNERGY | Log volume | ANTAG-ONISM | Log volume |
| | IFN-α | 5.44 | 0.49 | −24.88 | −2.25 |
| | RBV | 1.64 | 0.15 | −3.52 | −0.32 |

*None of the combinations cause cytotoxicity.

Conclusions

The Z factors of the compound pairs summarized in Table 12 indicate that the assay quality is better than the QC standard.

TABLE 12

Summary of the Z factor of compound pairs

| | Z factor | | |
|---|---|---|---|
| Drug Pairs | Plate-1 | Plate-2 | Plate-3 |
| (V-K) + Compound D | 0.68 | 0.86 | 0.83 |
| (V-K) + Compound C | 0.66 | 0.78 | 0.65 |
| (V-K) + Compound B | 0.70 | 0.83 | 0.84 |
| (V-K) + Compound E | 0.72 | 0.76 | 0.74 |
| (V-K) + IFN-α | 0.75 | 0.70 | 0.66 |
| (V-K) + RBV | 0.78 | 0.78 | 0.72 |

The $EC_{50}$ values of the individual compounds in the combination matrix (summarized in Table 13) are consistent with the $EC_{50}$ data in obtained for single-compound inhibition Table 10.

TABLE 13

Summary of $EC_{50}$ of single dose in compound combination

| | GT1b | |
|---|---|---|
| Compound | $EC_{50}$ (μM) in dose ranging assay | $EC_{50}$ (μM) of single dose in drug combination |
| (V-K) | 0.04 | 0.07 |
| Compound D | 0.0021 | 0.0017 |
| Compound C | 0.006 | 0.009 |
| Compound B | 0.000012 | 0.000009 |
| Compound E | 2.41 | 1.79 |
| IFN-α(IU/mL) | 1.34 | 3.43 |
| RBV | 32.75 | 31.63 |

The compound of Structure (V-K) was demonstrated to have additive antiviral activity without enhanced cytotoxicity in combination with agents representing a variety of mechanisms. These results are summarized in Table 14 below.

TABLE 14

Summary of antiviral mechanisms that are additive with the compound of Structure (V-K). The term "direct-acting antiviral" ("DAA") refers to a compound that binds to and inhibits a viral protein, rather than a host protein.

| Molecule | Mechanism | Class |
|---|---|---|
| IFN-α | Cellular defense | Host |
| RBV | Multiple | Host |
| Compound D | HCV Protease | DAA |
| Compound B | NS5A Inhibitor | DAA |
| Compound C | NS5B Inhibitor | DAA |
| Compound E | NS5B Inhibitor | DAA |

IFN-α and RBV represent current standard-of-care for treating Hepatitis C infection, and the HCV protease inhibitors Telaprevir and Boceprivir have recently been approved. The additive antiviral activity and lack of enhanced cytotoxicity in combination with IFN-α and RBV further suggest that compounds of this invention will not interfere with critical host processes such as cellular defense (IFN-α) or guanidine nucleotide biosynthesis (RBV). Compounds of this invention such as the compound of Structure (V-K) should therefore be therapeutically useful if administered in combination regimens with current standard of care. Moreover, the additive antiviral activities observed with Compound B, Compound C, and Compound E suggest that molecules of this invention such as the compound of Structure (V-K) can be productively combined with agents currently in development that target newer mechanisms (e.g., NS5A and NS5B inhibitors).

Example 6—Anti-Tumor Activity—Multiplexed Cytotoxicity Assay

Cells were grown in RPMI1640, 10% FBS, 2 mM L-alanyl-L-Glutamine, 1 mM Na pyruvate or a special medium in a humidified atmosphere of 5% $CO_2$ at 37° C. Cells were seeded into 384-well plates and incubated in a humidified atmosphere of 5% $CO_2$ at 37° C. Compounds were added 24 hours post cell seeding. At the same time, a time zero untreated cell plate was generated.

After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody.

Compounds were serially diluted in half-log (3.16-fold) increments and assayed over 10 concentrations in a final assay concentration of 0.1% DMSO from the highest test concentration specified in the sample information chapter. Automated fluorescence microscopy was carried out using a GE Healthcare IN Cell Analyzer 1000, and images were collected with a 4× objective.

Twelve bit tiff images were acquired using the InCell Analyzer 1000 3.2 and analyzed with Developer Toolbox 1.6 software. $EC_{50}$ and $IC_{50}$ values were calculated using non-linear regression to fit data to a sigmoidal 4 point, 4 parameter One-Site dose response model, where: y (fit)=A+ [(B−A)/(1+((C/x)^D))]. Curve-fitting, $EC_{50}/IC_{50}$ calculations and report generation are performed using a custom data reduction engine MathIQ based software (AIM).

The multiplexed cytotoxicity assay uses a cell image based analysis technique where cells are fixed and stained with fluorescently labeled antibodies and nuclear dye to visualize nuclei, and apoptotic and mitotic cells. Apoptotic cells are detected using an anti-active caspase-3 antibody. Mitotic cells are detected using an anti phospho-histone-3 antibody.

Cell proliferation is measured by the signal intensity of the incorporated nuclear dye. The cell proliferation assay output is referred to as the relative cell count. To determine the cell proliferation end point, the cell proliferation data output is transformed to percent of control (POC) using the following formula:

POC=relative cell count (compound wells)/relative cell count (vehicle wells)×100

Time zero non-treated plate is used to determine number of doublings in 72 hour assay period: Number of doublings in 72 hours=LN[Cell number (72 hrs end point)*Cell number (time zero)]/LN(2). The output of each biomarker is fold increase over vehicle background normalized to the relative cell count in each well.

The activated caspase-3 marker labels cells from early to late stage apoptosis. The output is shown as a fold increase of apoptotic cells over vehicle background normalized to the relative cell count in each well. Concentrations of test compound that cause a 5-fold induction in the caspase-3 signal indicates significant apoptosis induction. Wells with concentrations higher than the relative cell count $IC_{95}$ are eliminated from the caspase3 induction analysis.

The phospho-histone-3 marker labels mitotic cells. The output is shown as a fold induction of mitotic cells over vehicle background normalized to the relative cell count in each well. When the fold induction of mitotic cell signal over background is ~1, there is "no effect" on the cell cycle. Two or more fold increase in phospho-histone-3 signal over vehicle background indicates significant test compound induction of mitotic block.

Two or more fold decrease in the phospho-histone-3 signal may indicate G1/S block only when cytotoxicity levels are below the measured relative cell count $IC_{95}$. When 2 or more fold decrease in the phospho-histone-3 signal are observed at concentrations higher than the relative cell count $IC_{95}$, the decrease in mitotic cell counts are most likely due to a more general cytotoxicity effect rather than a true G1/S phase block. Wells with concentrations higher than the relative cell count $IC_{95}$ are eliminated from the phospho-histone-3 analysis.

Cell proliferation measured by relative cell counts were the criteria for positive response.

Apoptosis:
>5-fold increase in activated caspase-3 signal indicates an apoptotic response Mitosis:
>2-fold increase in phospho-histone-3 indicates mitotic block
<2-fold decrease in phospho-histone-3 indicates G1/S block

TABLE 15

Results

| Compound | Biochemical $IC_{50}$ (µM) | G1/S cell cycle block (µM) | Max G2/M cell cycle block | Max Apoptosis Fold Induction |
|---|---|---|---|---|
| 205 | 0.220 | 0.160 | 1.36 | 2.39 |
| 95 | 0.030 | 0.012 | 0.94 | 2.45 |
| 142 | 0.140 | 0.031 | 1.28 | 2.34 |
| 153 | 0.060 | 0.014 | 1.17 | 2.55 |
| 427 | 0.080 | 0.019 | 1.00 | 2.39 |
| 42 | 0.070 | 0.013 | 1.09 | 2.20 |

TABLE 15-continued

Results

| Compound | Biochemical IC$_{50}$ (μM) | G1/S cell cycle block (μM) | Max G2/M cell cycle block | Max Apoptosis Fold Induction |
|---|---|---|---|---|
| 48 | 0.170 | 0.027 | 1.27 | 2.20 |
| 156 | 0.030 | 0.031 | 1.28 | 2.59 |
| 182 | 0.150 | 0.030 | 1.54 | 2.07 |
| 183 | 0.170 | 0.031 | 1.00 | 2.40 |

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

All publications and patent applications cited in this specification are herein incorporated by reference as if each individual publication or patent application were specifically and individually indicated to be incorporated by reference.

TABLE 1

| ID | Structure | FASN IC50 (μM) |
|---|---|---|
| 1 | 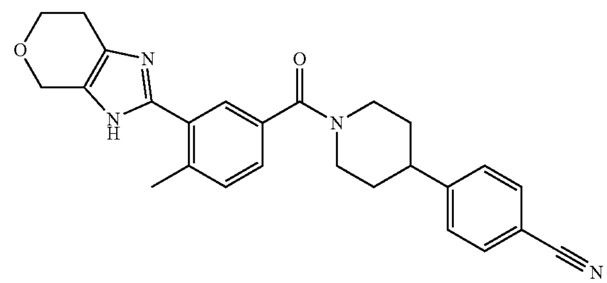 [SMILES: Cc1ccc(C(=O)N2CCC(c3ccc(C#N)cc3)CC2)cc1-c1nc2c([nH]1)COCC2] | 0.230 |
| 2 | 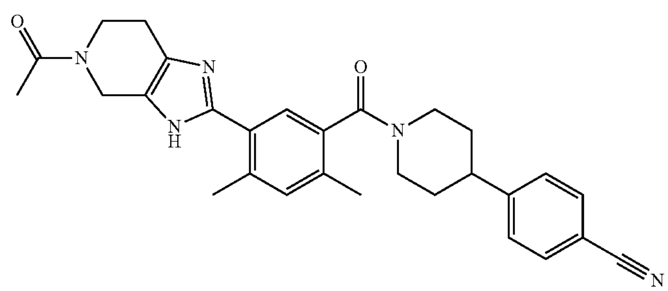 [SMILES: CC(=O)N1CCc2nc(-c3cc(C(=O)N4CCC(c5ccc(C#N)cc5)CC4)c(C)cc3C)[nH]c2C1] | 0.065 |
| 2.9 | 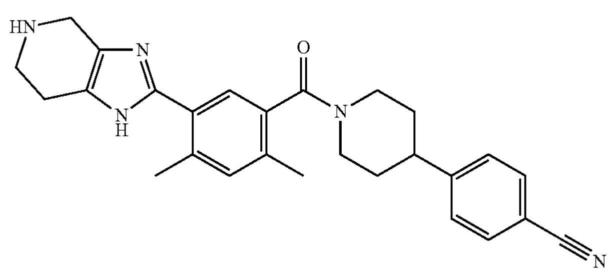 [SMILES: Cc1cc(C)c(-c2nc3c([nH]2)CCNC3)cc1C(=O)N1CCC(c2ccc(C#N)cc2)CC1] | 0.060 |
| 3 | 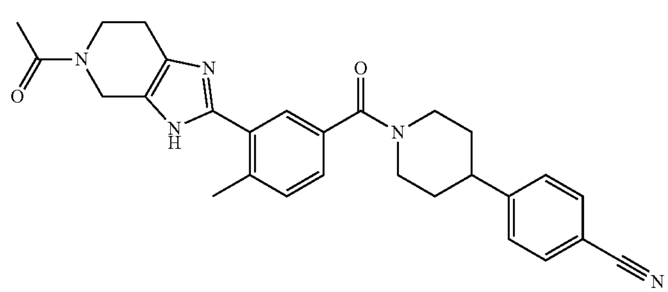 [SMILES: CC(=O)N1CCc2nc(-c3cc(C(=O)N4CCC(c5ccc(C#N)cc5)CC4)ccc3C)[nH]c2C1] | 0.146 |

TABLE 1-continued

| ID | Structure | FASN IC50 (μM) |
|---|---|---|
| 4 | 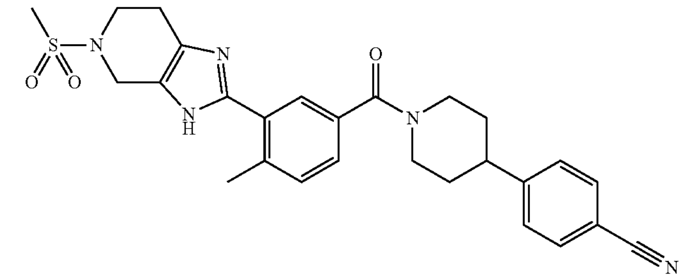 [SMILES: Cc1ccc(C(=O)N2CCC(c3ccc(C#N)cc3)CC2)cc1-c1nc2c([nH]1)CN(S(C)(=O)=O)CC2] | 0.200 |
| 5 | 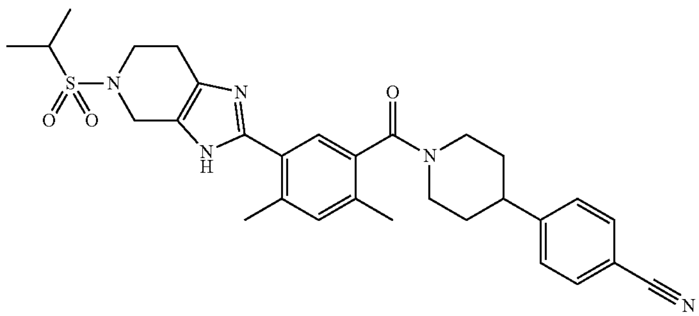 | 0.055 |
| 6 | 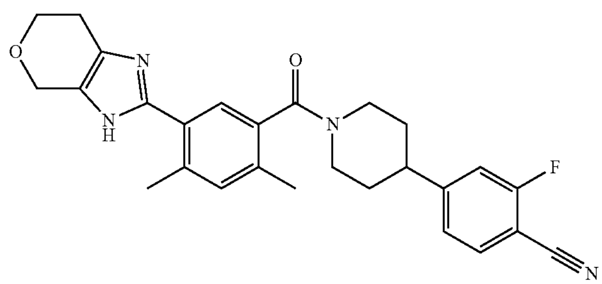 [SMILES: Cc1cc(C)c(-c2nc3c([nH]2)COCC3)cc1C(=O)N1CCC(c2ccc(C#N)c(F)c2)CC1] | 0.360 |
| 7 | 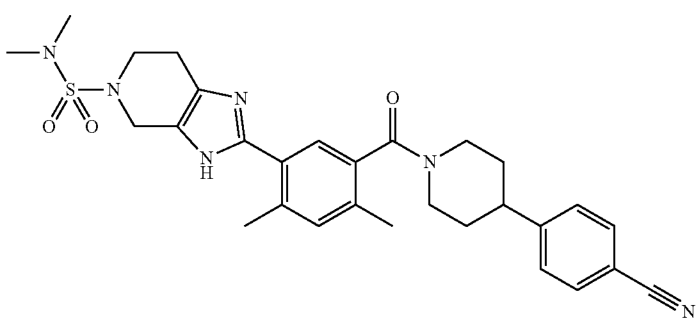 [SMILES: Cc1cc(C)c(-c2nc3c([nH]2)CN(S(=O)(=O)N(C)C)CC3)cc1C(=O)N1CCC(c2ccc(C#N)cc2)CC1] | 0.050 |
| 8 | 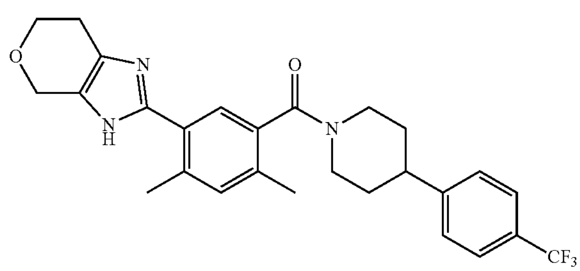 [SMILES: Cc1cc(C)c(-c2nc3c([nH]2)COCC3)cc1C(=O)N1CCC(c2ccc(C(F)(F)F)cc2)CC1] | 0.125 |

TABLE 1-continued

| ID | Structure | FASN IC50 (µM) |
|---|---|---|
| 9 | 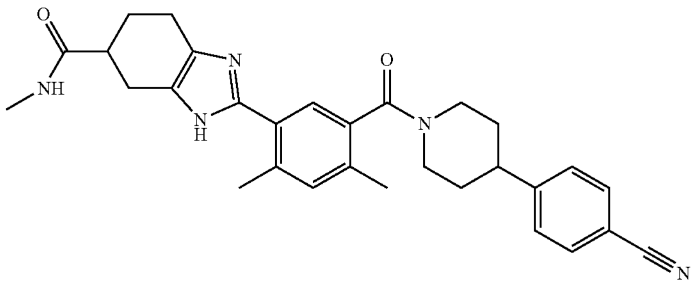 [SMILES: CNC(=O)C1CCc2nc(-c3cc(C(=O)N4CCC(c5ccc(C#N)cc5)CC4)c(C)cc3C)[nH]c2C1] | 0.040 |
| 11 | 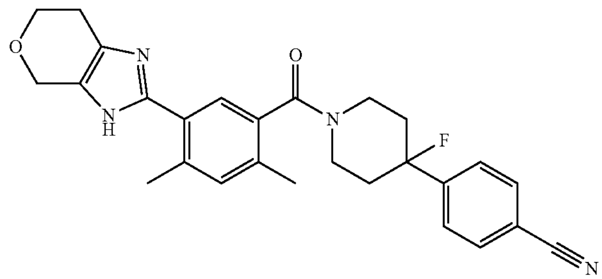 [SMILES: Cc1cc(C)c(-c2nc3c([nH]2)COCC3)cc1C(=O)N1CCC(F)(c2ccc(C#N)cc2)CC1] | 0.170 |
| 12 | 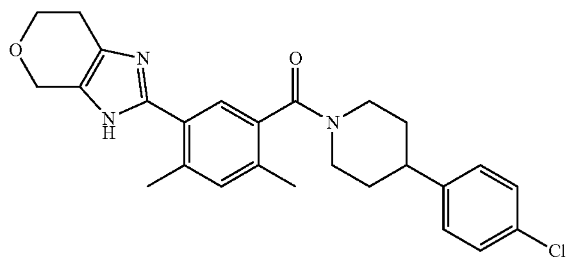 [SMILES: Cc1cc(C)c(-c2nc3c([nH]2)COCC3)cc1C(=O)N1CCC(c2ccc(Cl)cc2)CC1] | 0.370 |
| 13 | 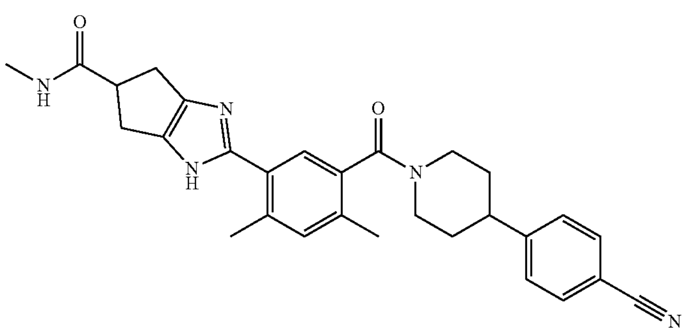 [SMILES: CNC(=O)C1Cc2nc(-c3cc(C(=O)N4CCC(c5ccc(C#N)cc5)CC4)c(C)cc3C)[nH]c2C1] | 0.260 |
| 14 | 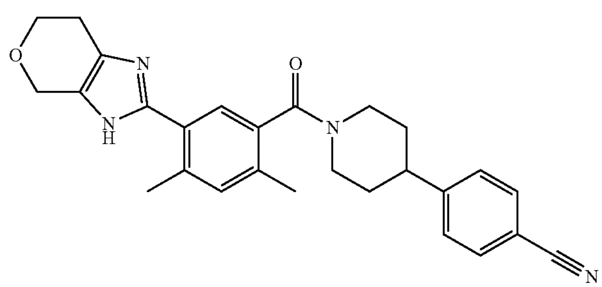 [SMILES: Cc1cc(C)c(-c2nc3c([nH]2)COCC3)cc1C(=O)N1CCC(c2ccc(C#N)cc2)CC1] | 0.263 |

TABLE 1-continued

| ID | Structure | FASN IC50 (μM) |
|---|---|---|
| 15 | 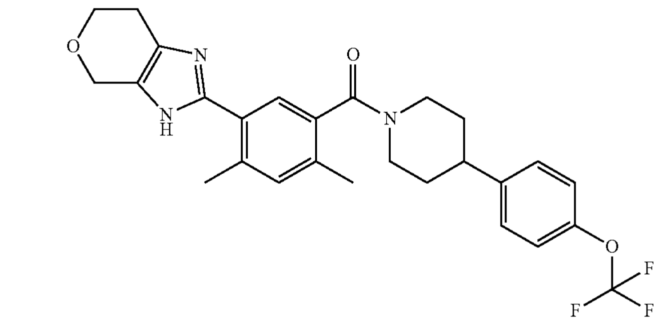 [SMILES: Cc1cc(C)c(-c2nc3c([nH]2)COCC3)cc1C(=O)N1CCC(c2ccc(OC(F)(F)F)cc2)CC1] | 0.180 |
| 16 | 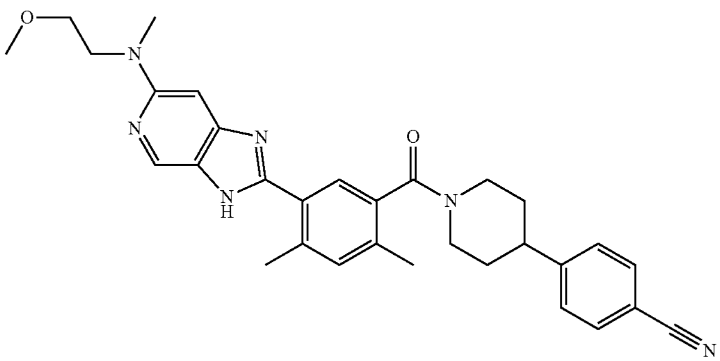 [SMILES: COCCN(C)c1cc2nc(-c3cc(C(=O)N4CCC(c5ccc(C#N)cc5)CC4)c(C)cc3C)[nH]c2cn1] | 0.058 |
| 17 | 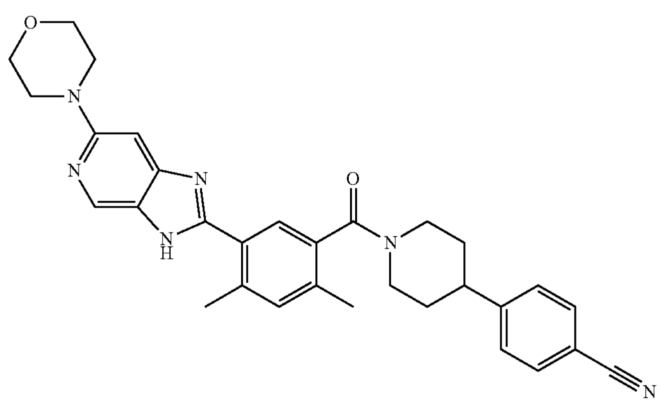 [SMILES: Cc1cc(C)c(-c2nc3cc(N4CCOCC4)ncc3[nH]2)cc1C(=O)N1CCC(c2ccc(C#N)cc2)CC1] | 0.073 |
| 18 | 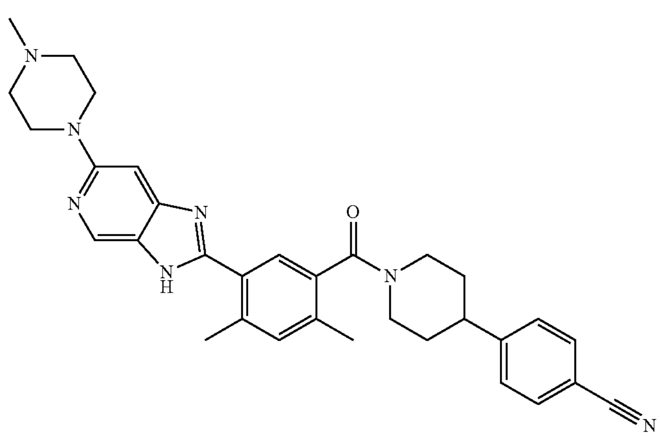 [SMILES: Cc1cc(C)c(-c2nc3cc(N4CCN(C)CC4)ncc3[nH]2)cc1C(=O)N1CCC(c2ccc(C#N)cc2)CC1] | 0.990 |

TABLE 1-continued
| ID | Structure | FASN IC50 (μM) |
|---|---|---|
| 19 | 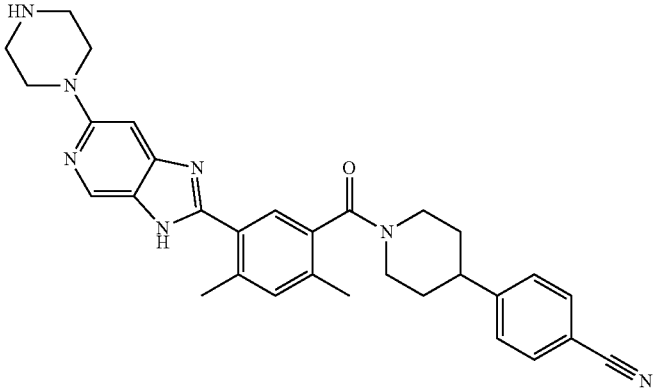 [SMILES: Cc1cc(C)c(-c2nc3cc(N4CCNCC4)ncc3[nH]2)cc1C(=O)N1CCC(c2ccc(C#N)cc2)CC1] | 0.870 |
| 20 | 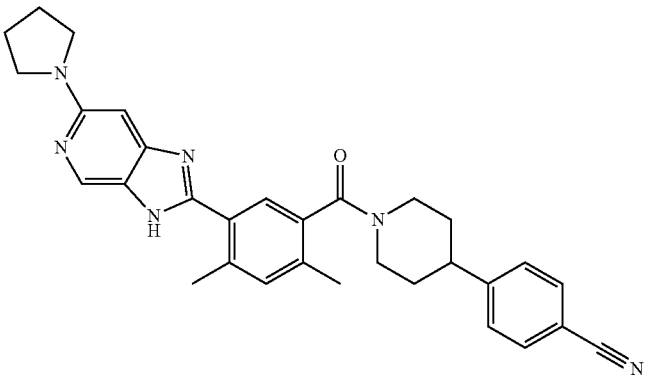 [SMILES: Cc1cc(C)c(-c2nc3cc(N4CCCC4)ncc3[nH]2)cc1C(=O)N1CCC(c2ccc(C#N)cc2)CC1] | 0.022 |
| 21 | 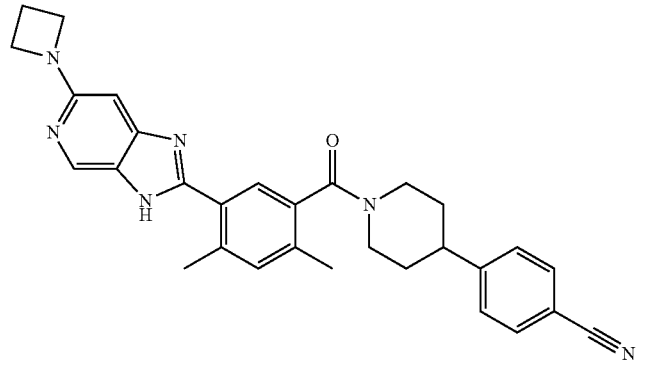 [SMILES: Cc1cc(C)c(-c2nc3cc(N4CCC4)ncc3[nH]2)cc1C(=O)N1CCC(c2ccc(C#N)cc2)CC1] | 0.045 |
| 22 | 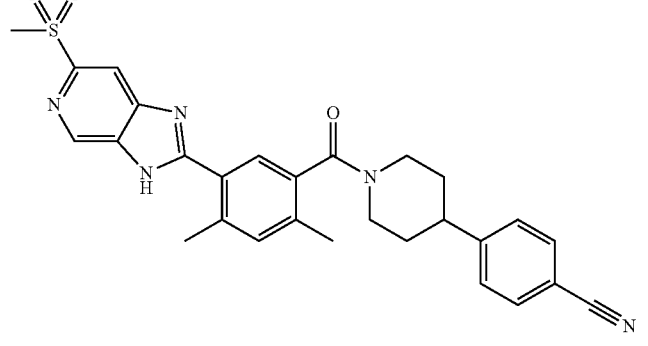 | 0.085 |

TABLE 1-continued

| ID | Structure | FASN IC50 (μM) |
|---|---|---|
| 23 | 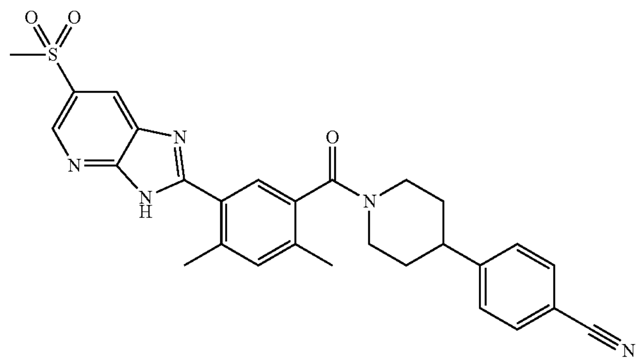 [SMILES: Cc1cc(C)c(-c2nc3cc(S(C)(=O)=O)cnc3[nH]2)cc1C(=O)N1CCC(c2ccc(C#N)cc2)CC1] | 0.070 |
| 24 | 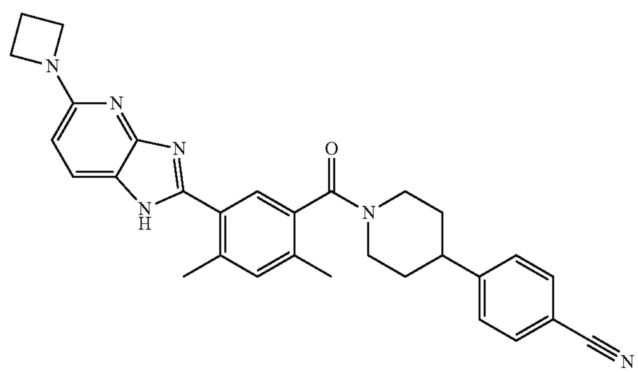 [SMILES: Cc1cc(C)c(-c2nc3nc(N4CCC4)ccc3[nH]2)cc1C(=O)N1CCC(c2ccc(C#N)cc2)CC1] | 0.070 |
| 25 | 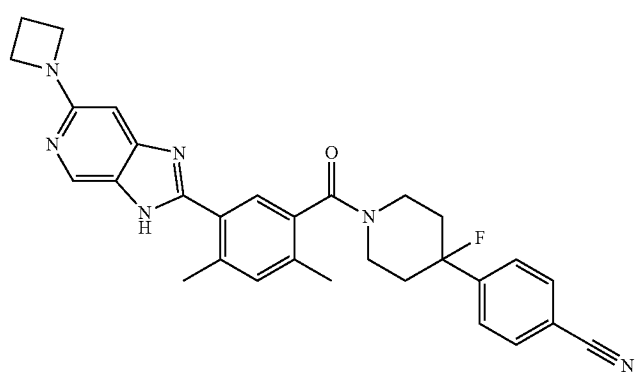 [SMILES: Cc1cc(C)c(-c2nc3cc(N4CCC4)ncc3[nH]2)cc1C(=O)N1CCC(F)(c2ccc(C#N)cc2)CC1] | 0.150 |
| 26 | 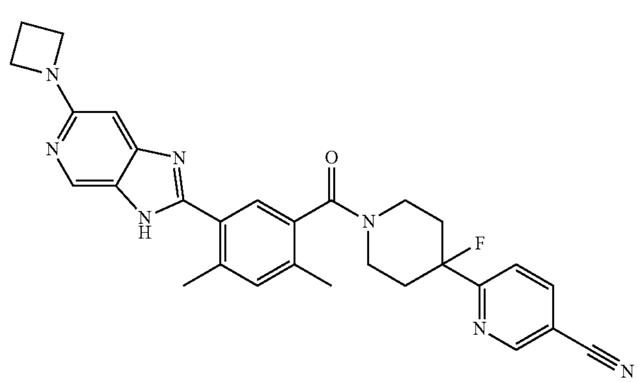 [SMILES: Cc1cc(C)c(-c2nc3cc(N4CCC4)ncc3[nH]2)cc1C(=O)N1CCC(F)(c2ccc(C#N)cn2)CC1] | 7.195 |

TABLE 1-continued

| ID | Structure | FASN IC50 (μM) |
|---|---|---|
| 27 | 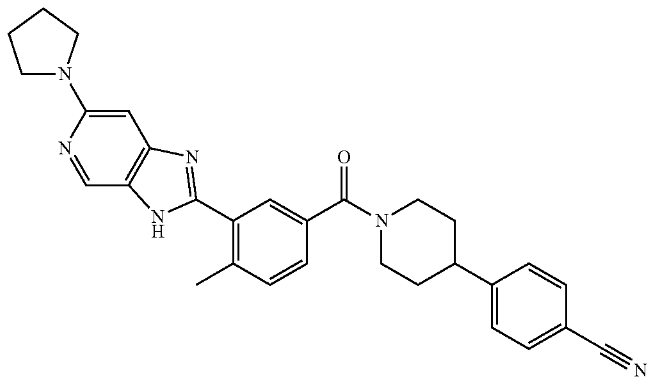 [SMILES: Cc1ccc(C(=O)N2CCC(c3ccc(C#N)cc3)CC2)cc1-c1nc2cc(N3CCCC3)ncc2[nH]1] | 0.107 |
| 28 | 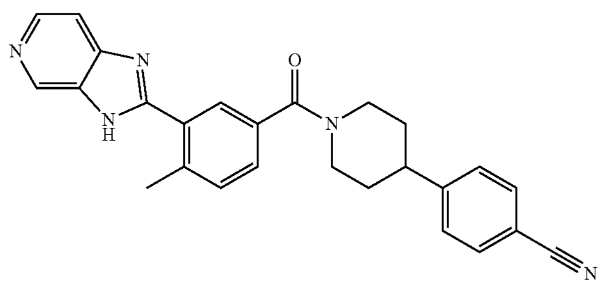 [SMILES: Cc1ccc(C(=O)N2CCC(c3ccc(C#N)cc3)CC2)cc1-c1nc2ccncc2[nH]1] | 0.490 |
| 29 | 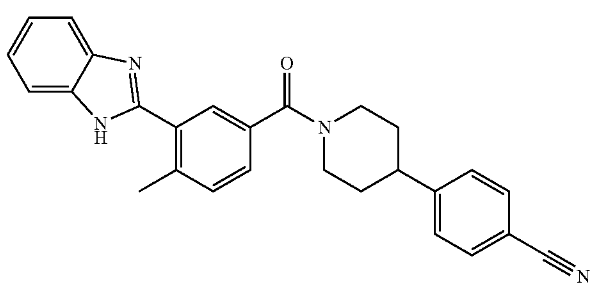 [SMILES: Cc1ccc(C(=O)N2CCC(c3ccc(C#N)cc3)CC2)cc1-c1nc2ccccc2[nH]1] | 0.980 |
| 30 | 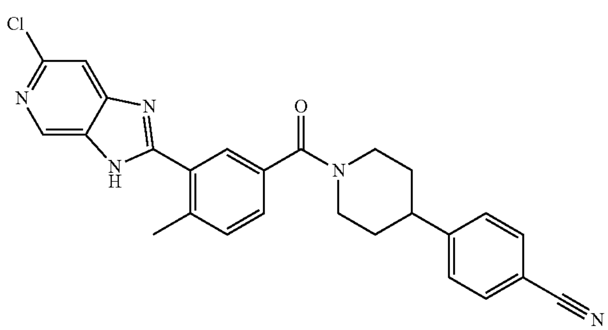 [SMILES: Cc1ccc(C(=O)N2CCC(c3ccc(C#N)cc3)CC2)cc1-c1nc2cc(Cl)ncc2[nH]1] | 0.320 |

TABLE 1-continued

| ID | Structure | FASN IC50 (μM) |
|----|-----------|----------------|
| 31 | 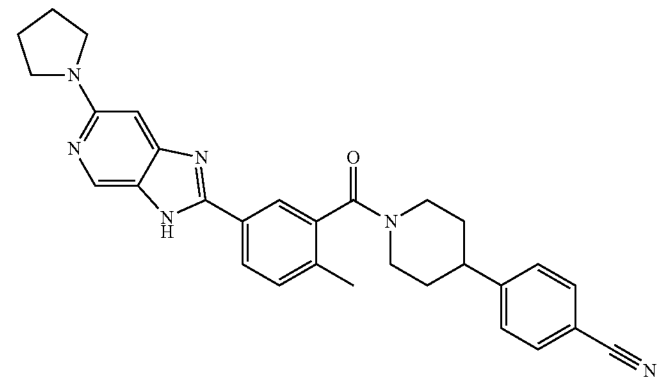 [SMILES: Cc1ccc(-c2nc3cc(N4CCCC4)ncc3[nH]2)cc1C(=O)N1CCC(c2ccc(C#N)cc2)CC1] | 0.060 |
| 32 | 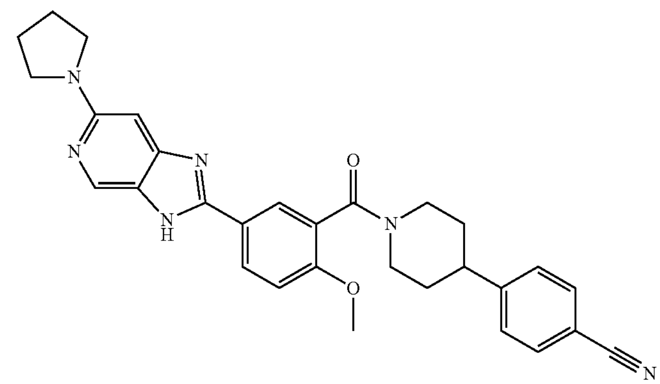 [SMILES: COc1ccc(-c2nc3cc(N4CCCC4)ncc3[nH]2)cc1C(=O)N1CCC(c2ccc(C#N)cc2)CC1] | 0.215 |
| 33 | 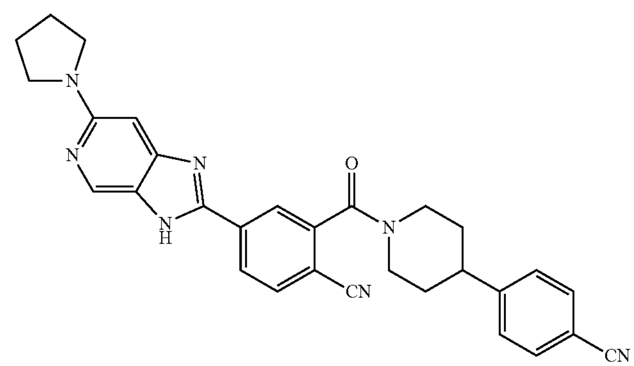 [SMILES: N#Cc1ccc(C2CCN(C(=O)c3cc(-c4nc5cc(N6CCCC6)ncc5[nH]4)ccc3C#N)CC2)cc1] | 7.500 |
| 34 | 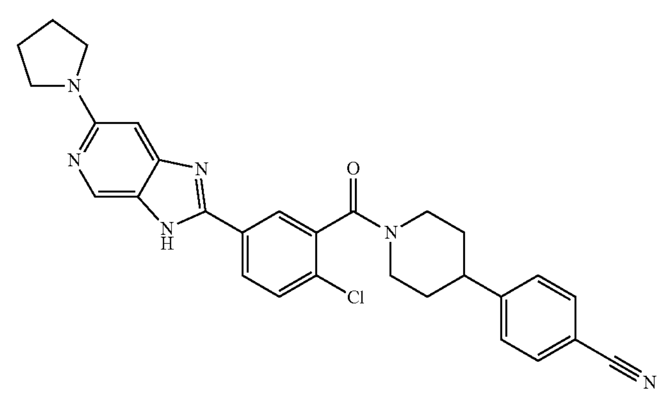 [SMILES: N#Cc1ccc(C2CCN(C(=O)c3cc(-c4nc5cc(N6CCCC6)ncc5[nH]4)ccc3Cl)CC2)cc1] | 0.080 |

TABLE 1-continued

| ID | Structure | FASN IC50 (μM) |
|---|---|---|
| 35 | 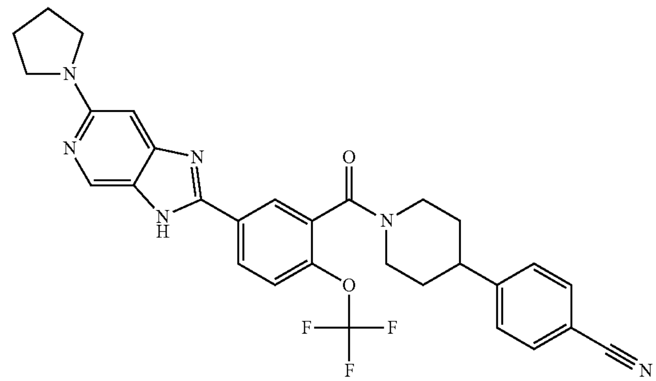 [SMILES: N#Cc1ccc(C2CCN(C(=O)c3cc(-c4nc5cc(N6CCCC6)ncc5[nH]4)ccc3OC(F)(F)F)CC2)cc1] | 25.083 |
| 36 | 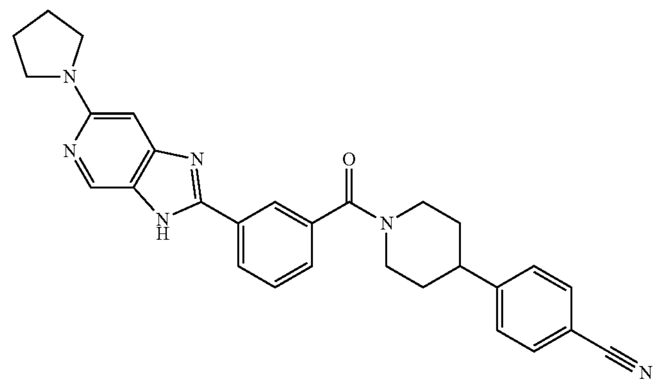 [SMILES: N#Cc1ccc(C2CCN(C(=O)c3cccc(-c4nc5cc(N6CCCC6)ncc5[nH]4)c3)CC2)cc1] | 0.130 |
| 37 | 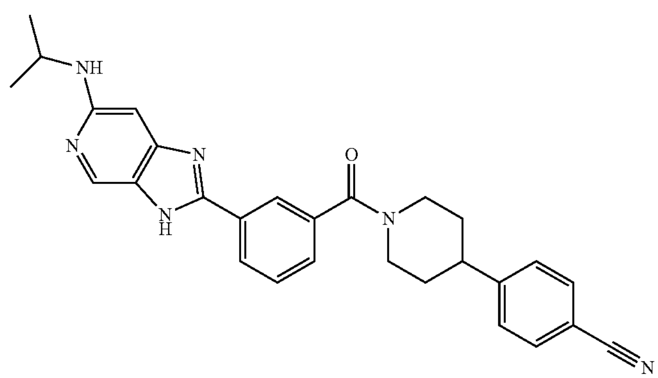 [SMILES: CC(C)Nc1cc2nc(-c3cccc(C(=O)N4CCC(c5ccc(C#N)cc5)CC4)c3)[nH]c2cn1] | 0.675 |
| 38 | 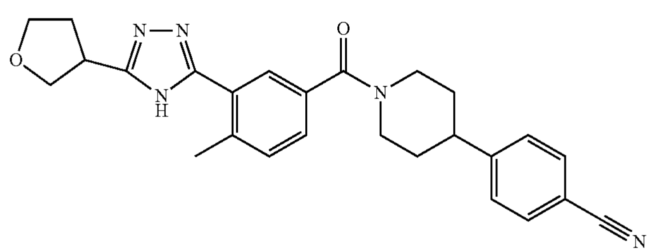 [SMILES: Cc1ccc(C(=O)N2CCC(c3ccc(C#N)cc3)CC2)cc1-c1nnc(C2CCOC2)[nH]1] | 2.345 |

TABLE 1-continued

| ID | Structure | FASN IC50 (μM) |
|---|---|---|
| 39 | 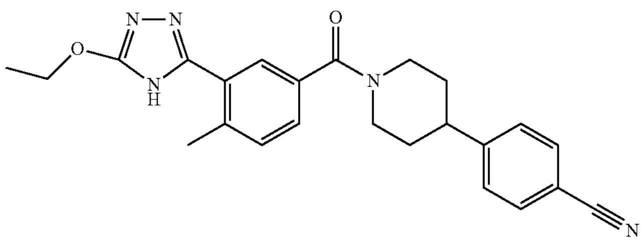 [SMILES: CCOc1nnc(-c2cc(C(=O)N3CCC(c4ccc(C#N)cc4)CC3)ccc2C)[nH]1] | 1.710 |
| 40 | 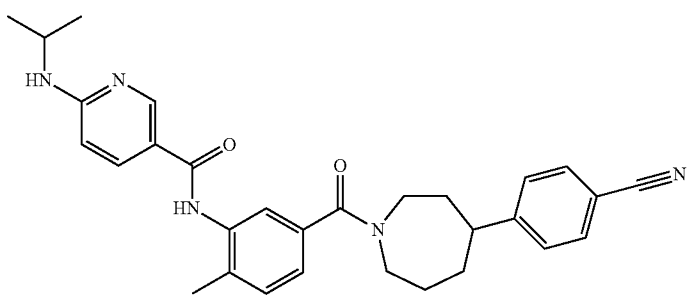 [SMILES: Cc1ccc(C(=O)N2CCCC(c3ccc(C#N)cc3)CC2)cc1NC(=O)c1ccc(NC(C)C)nc1] | 0.050 |
| 41 | 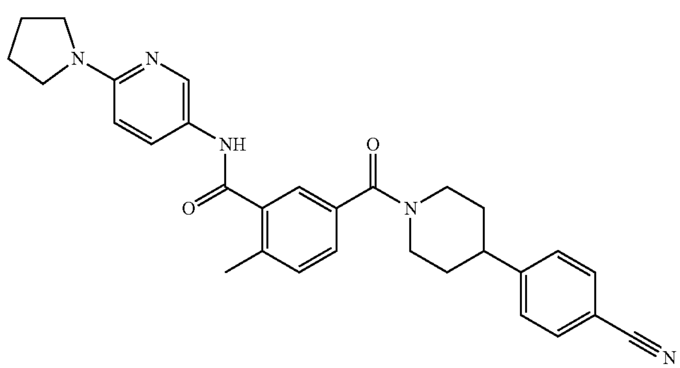 [SMILES: Cc1ccc(C(=O)N2CCC(c3ccc(C#N)cc3)CC2)cc1C(=O)Nc1ccc(N2CCCC2)nc1] | 0.035 |
| 42 | 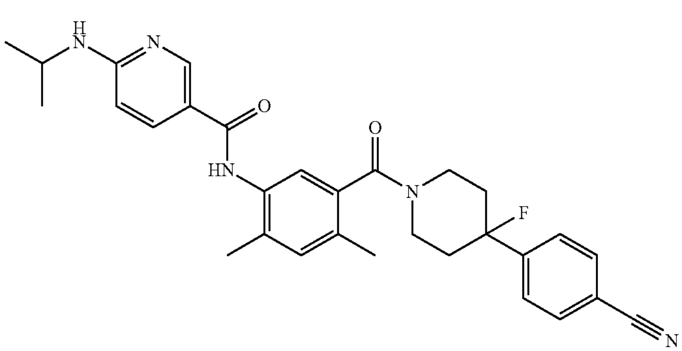 [SMILES: Cc1cc(C)c(C(=O)N2CCC(F)(c3ccc(C#N)cc3)CC2)cc1NC(=O)c1ccc(NC(C)C)nc1] | 0.067 |

TABLE 1-continued

| ID | Structure | FASN IC50 (μM) |
|---|---|---|
| 43 | 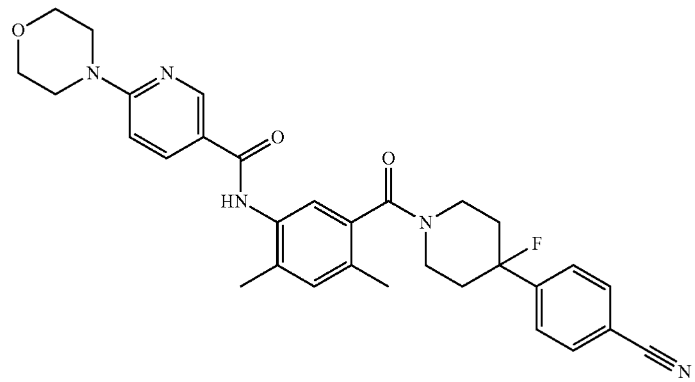 | 0.110 |
| 44 | 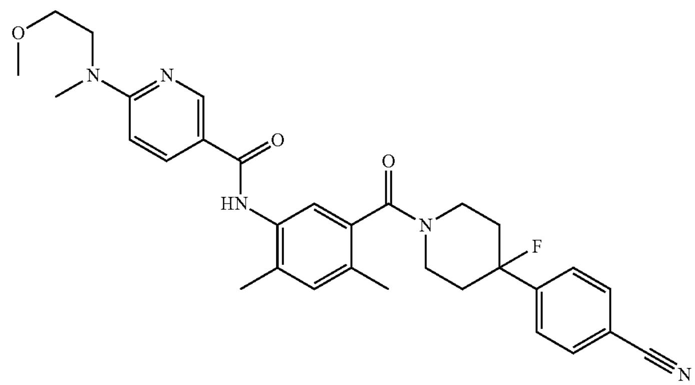 [SMILES: COCCN(C)c1ccc(C(=O)Nc2cc(C(=O)N3CCC(F)(c4ccc(C#N)cc4)CC3)c(C)cc2C)cn1] | 0.180 |
| 45 | 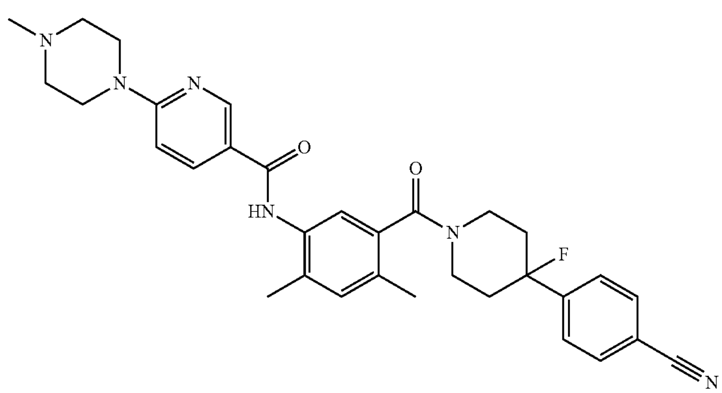 [SMILES: Cc1cc(C)c(C(=O)N2CCC(F)(c3ccc(C#N)cc3)CC2)cc1NC(=O)c1ccc(N2CCN(C)CC2)nc1] | 0.147 |
| 46 | 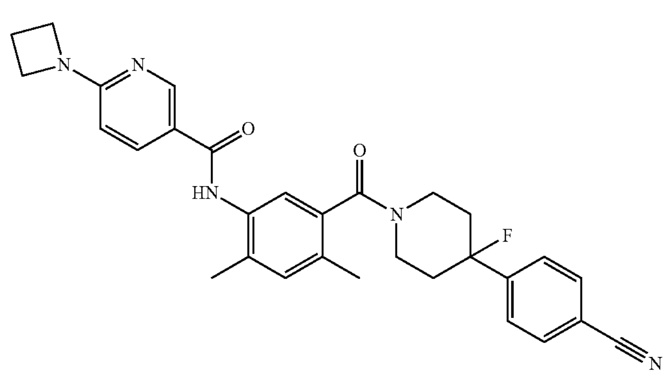 [SMILES: Cc1cc(C)c(C(=O)N2CCC(F)(c3ccc(C#N)cc3)CC2)cc1NC(=O)c1ccc(N2CCC2)nc1] | 0.050 |

TABLE 1-continued
| ID | Structure | FASN IC50 (μM) |
|---|---|---|
| 47 | 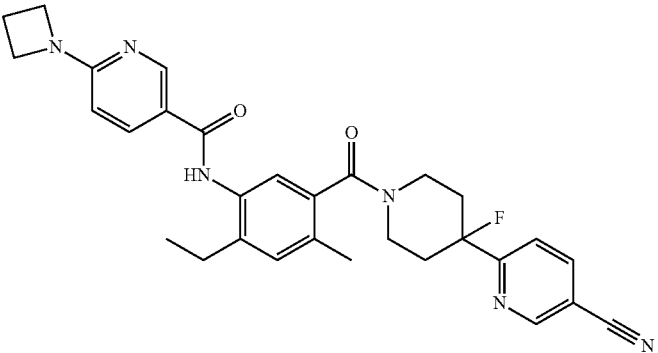 [SMILES: CCc1cc(C)c(C(=O)N2CCC(F)(c3ccc(C#N)cn3)CC2)cc1NC(=O)c1ccc(N2CCC2)nc1] | 0.230 |
| 48 | 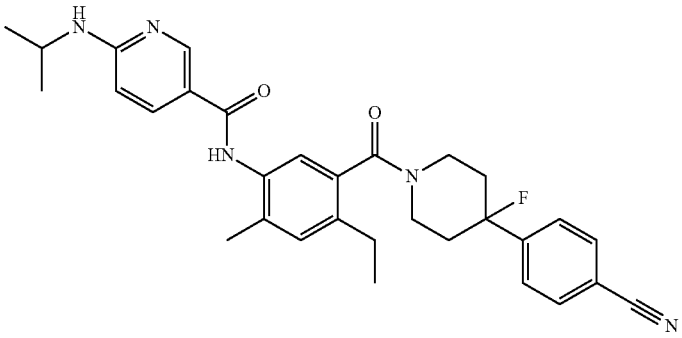 [SMILES: CCc1cc(C)c(NC(=O)c2ccc(NC(C)C)nc2)cc1C(=O)N1CCC(F)(c2ccc(C#N)cc2)CC1] | 0.170 |
| 49 | 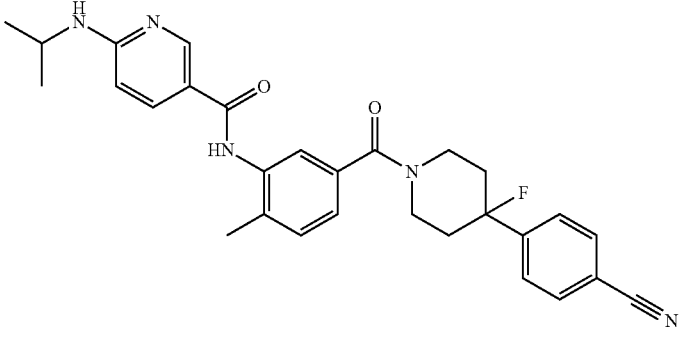 | 0.040 |
| 50 | 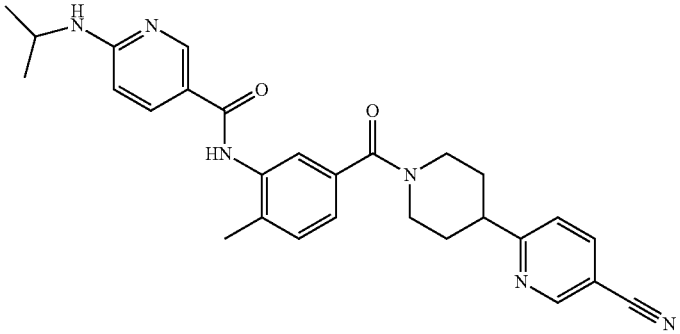 | 0.520 |

TABLE 1-continued

| ID | Structure | FASN IC50 (μM) |
|---|---|---|
| 51 | 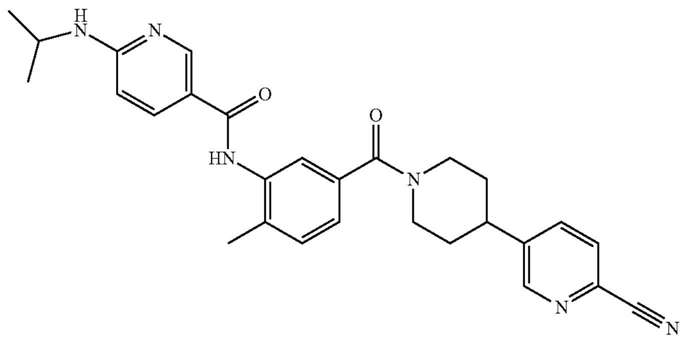 [SMILES: Cc1ccc(C(=O)N2CCC(c3ccc(C#N)nc3)CC2)cc1NC(=O)c1ccc(NC(C)C)nc1] | 1.700 |
| 52 | 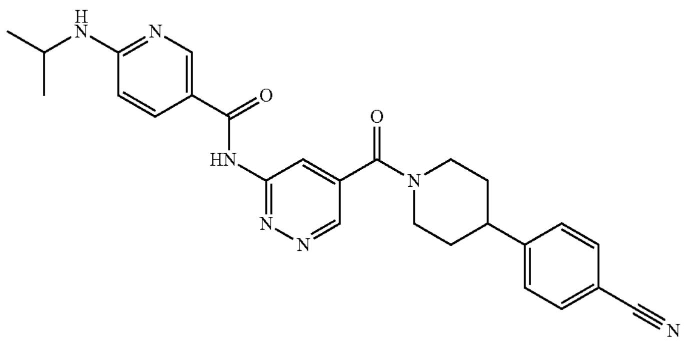 [SMILES: CC(C)Nc1ccc(C(=O)Nc2cc(C(=O)N3CCC(c4ccc(C#N)cc4)CC3)cnn2)cn1] | 31.650 |
| 53 | 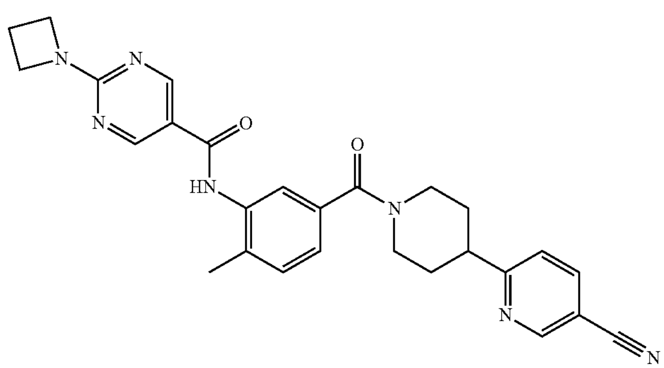 [SMILES: Cc1ccc(C(=O)N2CCC(c3ccc(C#N)cn3)CC2)cc1NC(=O)c1cnc(N2CCC2)nc1] | 1.970 |
| 54 | 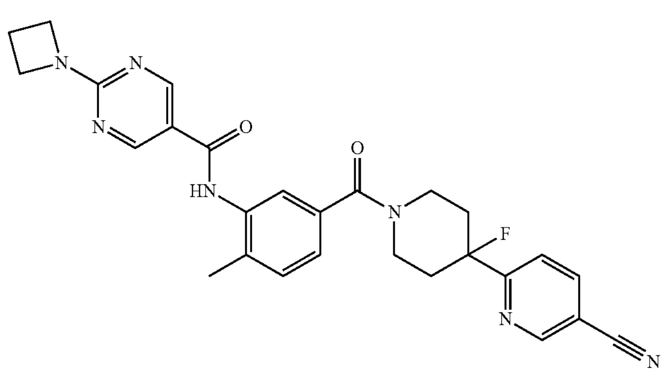 [SMILES: Cc1ccc(C(=O)N2CCC(F)(c3ccc(C#N)cn3)CC2)cc1NC(=O)c1cnc(N2CCC2)nc1] | 0.310 |

TABLE 1-continued
| ID | Structure | FASN IC50 (μM) |
|---|---|---|
| 55 | 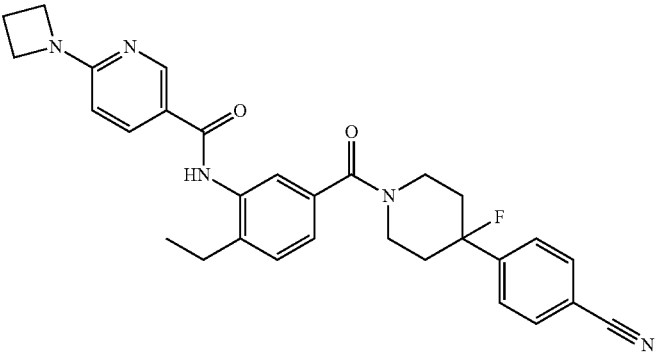 | 0.035 |
| 56 | 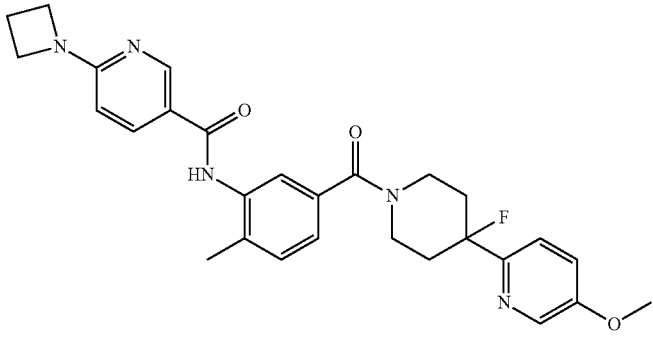 [SMILES: COc1ccc(C2(F)CCN(C(=O)c3ccc(C)c(NC(=O)c4ccc(N5CCC5)nc4)c3)CC2)nc1] | 2.800 |
| 57 | 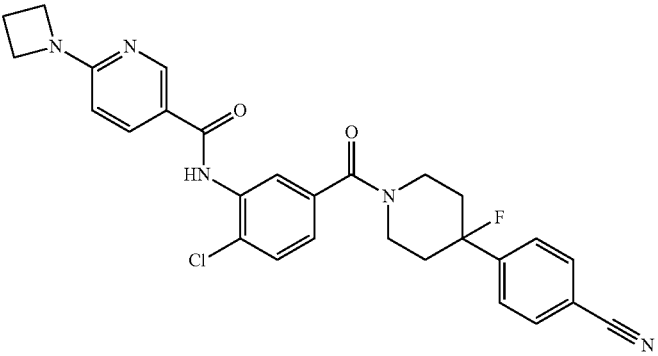 [SMILES: N#Cc1ccc(C2(F)CCN(C(=O)c3ccc(Cl)c(NC(=O)c4ccc(N5CCC5)nc4)c3)CC2)cc1] | 0.030 |
| 58 | 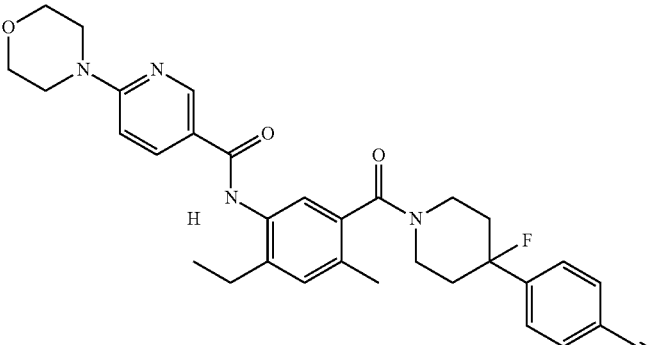 | 0.025 |

TABLE 1-continued
| ID | Structure | FASN IC50 (μM) |
|---|---|---|
| 60 | 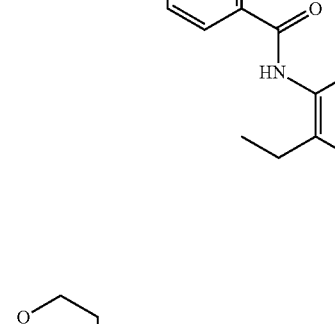 | 0.045 |
| 61 | 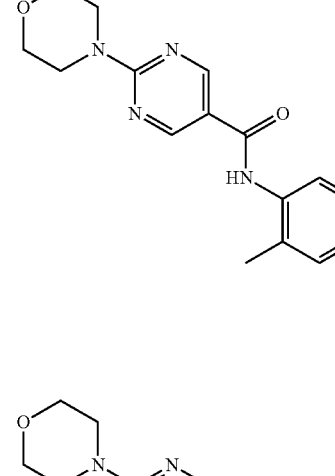 | 0.230 |
| 62 | 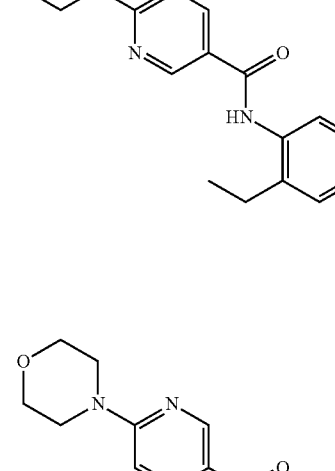 | 0.093 |
| 63 | 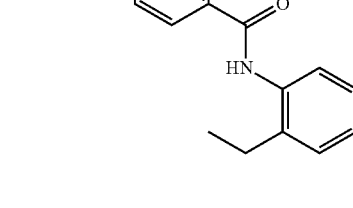 | 0.510 |

TABLE 1-continued

| ID | Structure | FASN IC50 (μM) |
|---|---|---|
| 64 | 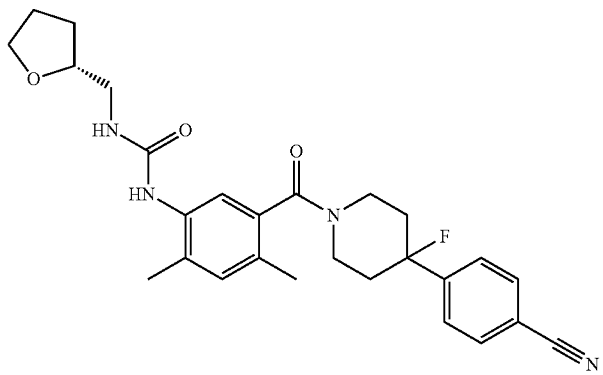 [SMILES: Cc1cc(C)c(C(=O)N2CCC(F)(c3ccc(C#N)cc3)CC2)cc1NC(=O)NC[C@H]1CCCO1] | 0.170 |
| 65 | 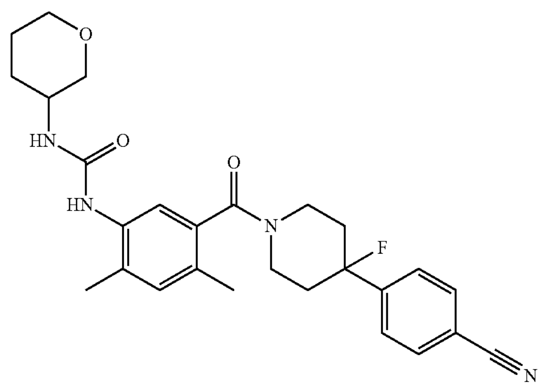 [SMILES: Cc1cc(C)c(C(=O)N2CCC(F)(c3ccc(C#N)cc3)CC2)cc1NC(=O)NC1CCCOC1] | 0.090 |
| 66 | 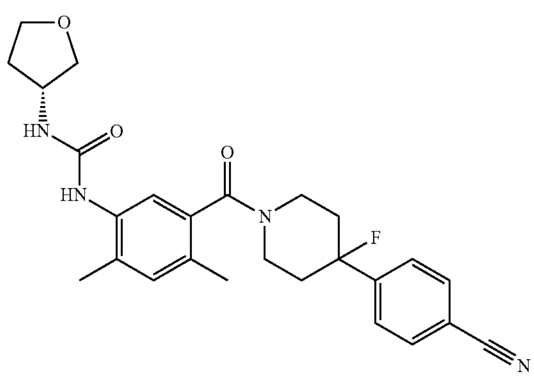 [SMILES: Cc1cc(C)c(C(=O)N2CCC(F)(c3ccc(C#N)cc3)CC2)cc1NC(=O)N[C@@H]1CCOC1] | 0.230 |
| 67 | 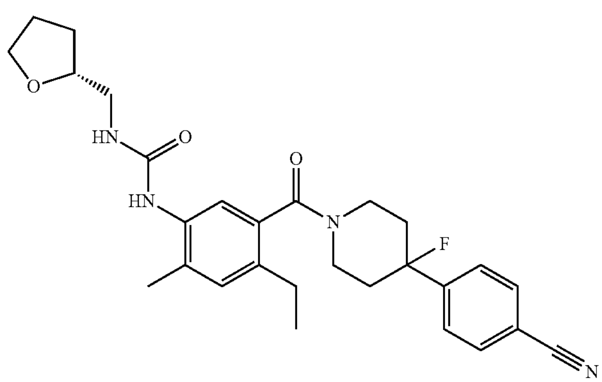 [SMILES: CCc1cc(C)c(NC(=O)NC[C@H]2CCCO2)cc1C(=O)N1CCC(F)(c2ccc(C#N)cc2)CC1] | 0.090 |

TABLE 1-continued
| ID | Structure | FASN IC50 (μM) |
|---|---|---|
| 68 | 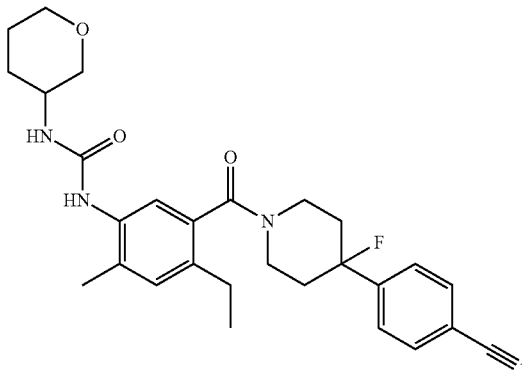 | 0.100 |
| 69 | 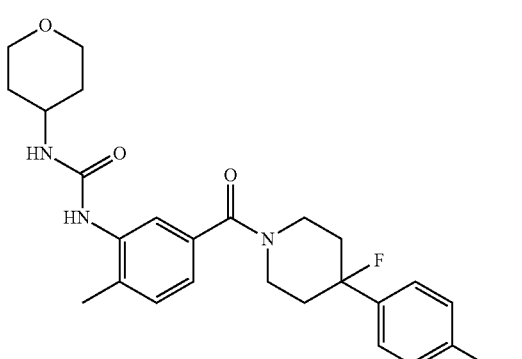 | 0.065 |
| 70 | 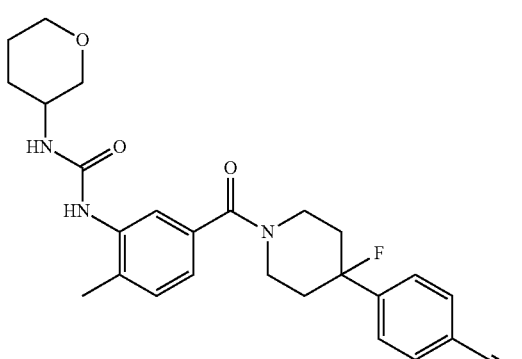 | 0.037 |
| 71 | 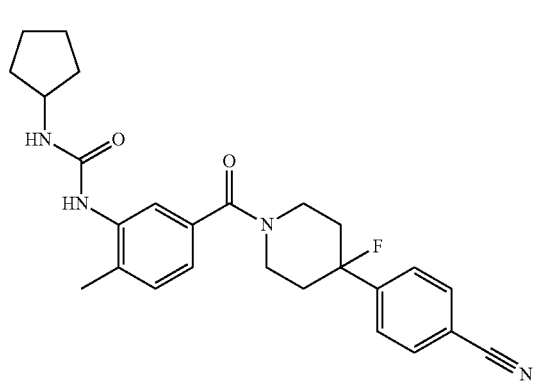 [SMILES: Cc1ccc(C(=O)N2CCC(F)(c3ccc(C#N)cc3)CC2)cc1NC(=O)NC1CCCC1] | 0.030 |

TABLE 1-continued
| ID | Structure | FASN IC50 (μM) |
|---|---|---|
| 72 | 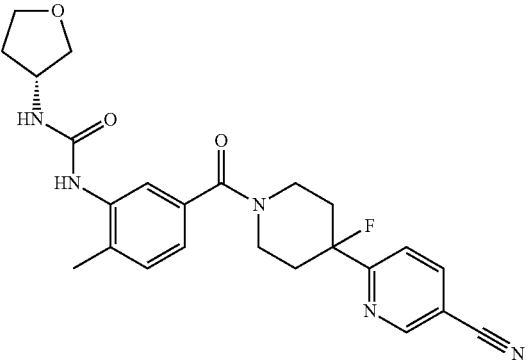 | 0.200 |
| 73 | 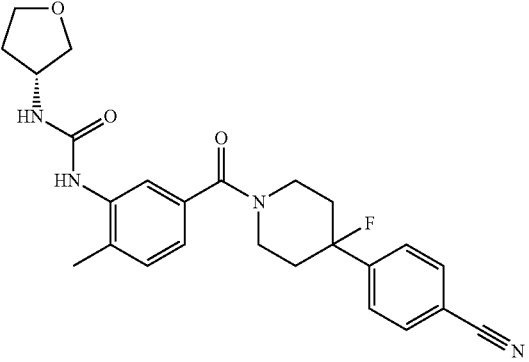 | 0.040 |
| 74 | 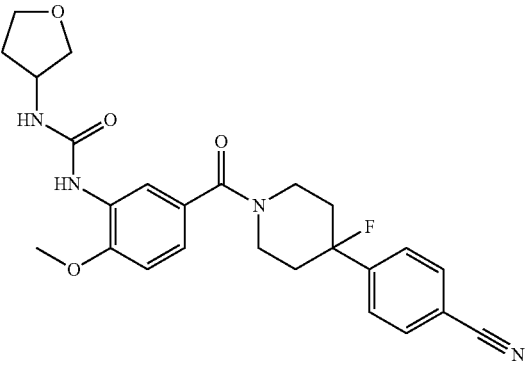 [SMILES: COc1ccc(C(=O)N2CCC(F)(c3ccc(C#N)cc3)CC2)cc1NC(=O)NC1CCOC1] | 0.120 |
| 75 | 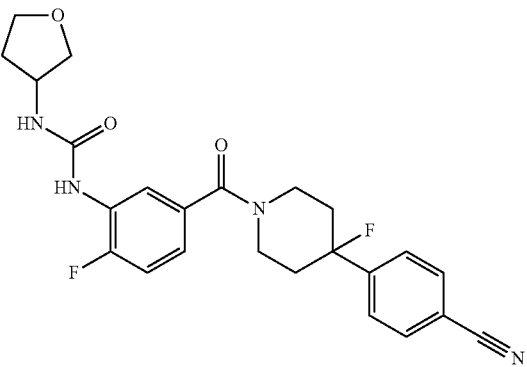 | 0.130 |

TABLE 1-continued
| ID | Structure | FASN IC50 (μM) |
|---|---|---|
| 76 | 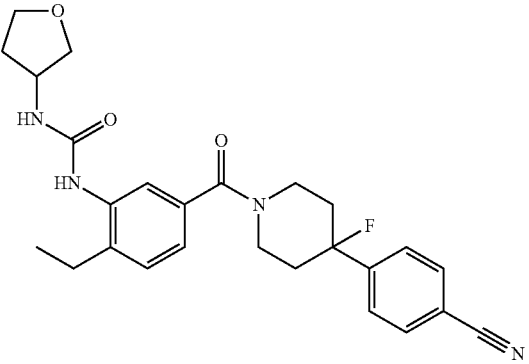 [SMILES: CCc1ccc(C(=O)N2CCC(F)(c3ccc(C#N)cc3)CC2)cc1NC(=O)NC1CCOC1] | 0.035 |
| 77 | 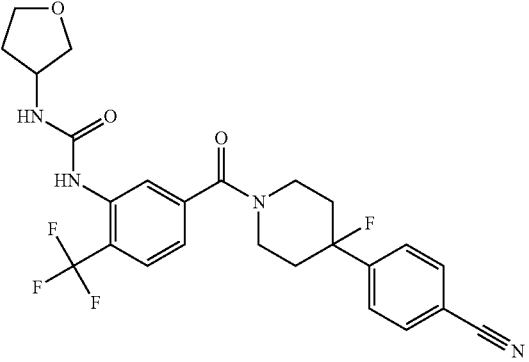 [SMILES: N#Cc1ccc(C2(F)CCN(C(=O)c3ccc(C(F)(F)F)c(NC(=O)NC4CCOC4)c3)CC2)cc1] | 0.080 |
| 78 | 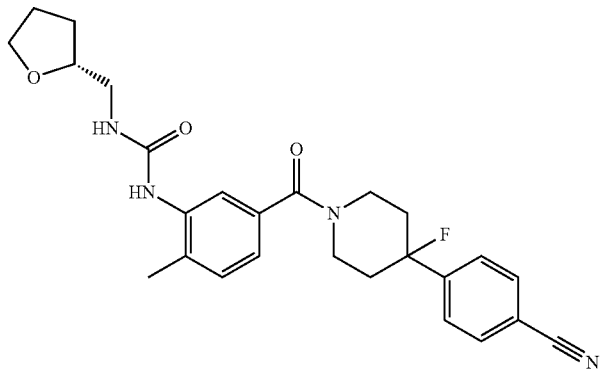 [SMILES: Cc1ccc(C(=O)N2CCC(F)(c3ccc(C#N)cc3)CC2)cc1NC(=O)NC[C@H]1CCCO1] | 0.035 |
| 79 | 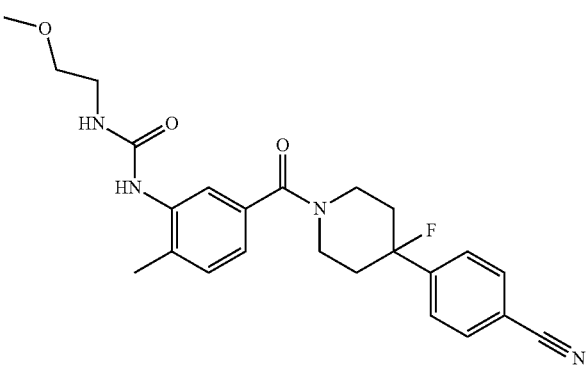 [SMILES: COCCNC(=O)Nc1cc(C(=O)N2CCC(F)(c3ccc(C#N)cc3)CC2)ccc1C] | 0.045 |

TABLE 1-continued
| ID | Structure | FASN IC50 (μM) |
|---|---|---|
| 80 | 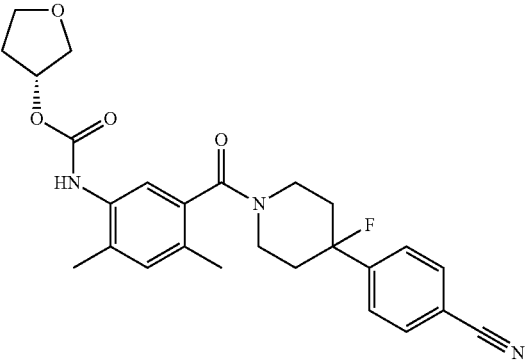 [SMILES: Cc1cc(C)c(C(=O)N2CCC(F)(c3ccc(C#N)cc3)CC2)cc1NC(=O)O[C@@H]1CCOC1] | 0.400 |
| 81 | 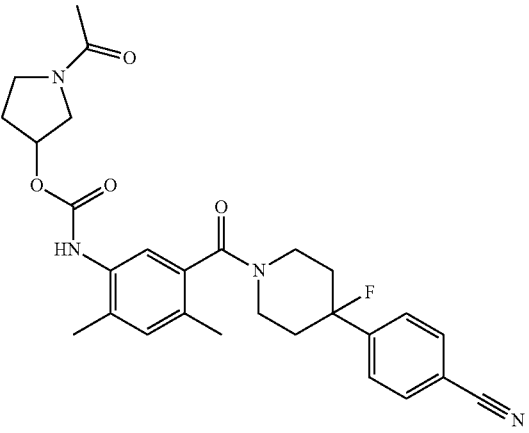 [SMILES: CC(=O)N1CCC(OC(=O)Nc2cc(C(=O)N3CCC(F)(c4ccc(C#N)cc4)CC3)c(C)cc2C)C1] | 0.200 |
| 82 | 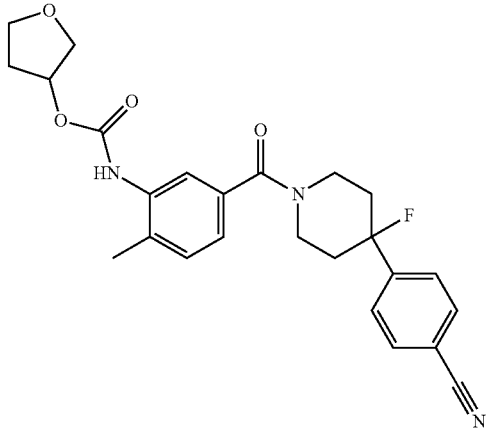 [SMILES: Cc1ccc(C(=O)N2CCC(F)(c3ccc(C#N)cc3)CC2)cc1NC(=O)OC1CCOC1] | 0.077 |
| 83 | 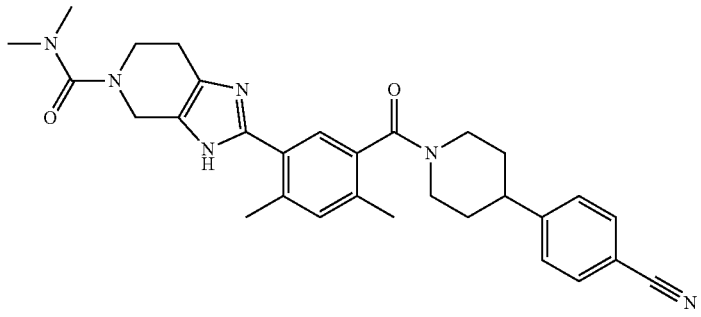 [SMILES: Cc1cc(C)c(-c2nc3c([nH]2)CN(C(=O)N(C)C)CC3)cc1C(=O)N1CCC(c2ccc(C#N)cc2)CC1] | 0.090 |

| ID | Structure | FASN IC50 (μM) |
|---|---|---|
| 84 | 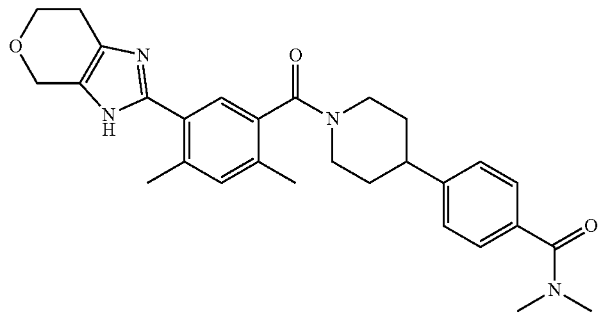 [SMILES: Cc1cc(C)c(-c2nc3c([nH]2)COCC3)cc1C(=O)N1CCC(c2ccc(C(=O)N(C)C)cc2)CC1] | 5.320 |
| 85 | 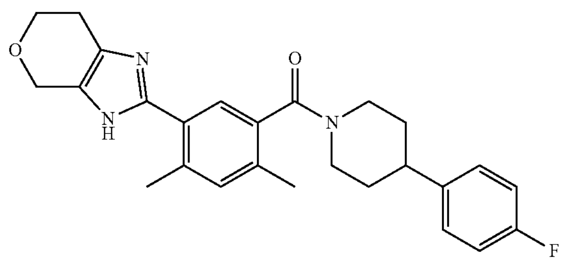 [SMILES: Cc1cc(C)c(-c2nc3c([nH]2)COCC3)cc1C(=O)N1CCC(c2ccc(F)cc2)CC1] | 1.450 |
| 86 | 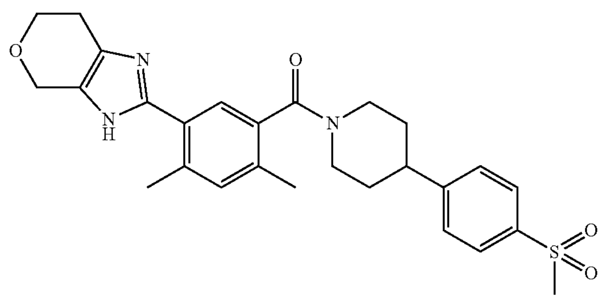 [SMILES: Cc1cc(C)c(-c2nc3c([nH]2)COCC3)cc1C(=O)N1CCC(c2ccc(S(C)(=O)=O)cc2)CC1] | 5.420 |
| 87 | 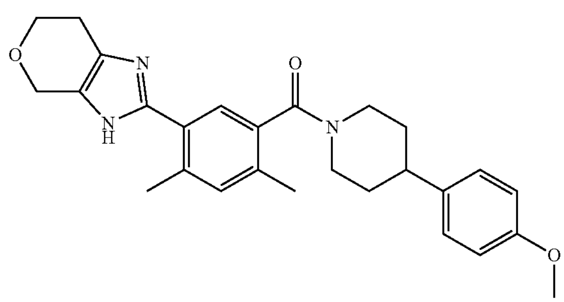 [SMILES: COc1ccc(C2CCN(C(=O)c3cc(-c4nc5c([nH]4)COCC5)c(C)cc3C)CC2)cc1] | 0.310 |
| 88 | 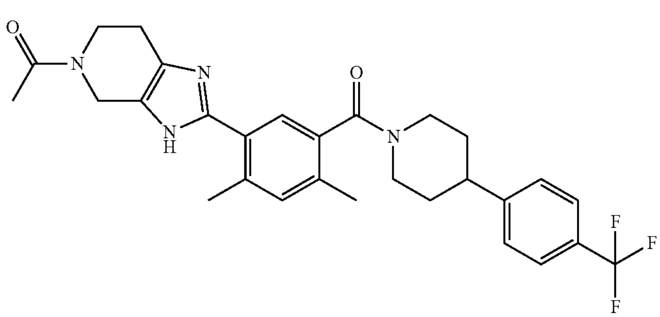 [SMILES: CC(=O)N1CCc2nc(-c3cc(C(=O)N4CCC(c5ccc(C(F)(F)F)cc5)CC4)c(C)cc3C)[nH]c2C1] | 0.040 |

TABLE 1-continued

| ID | Structure | FASN IC50 (µM) |
|----|-----------|----------------|
| 89 | 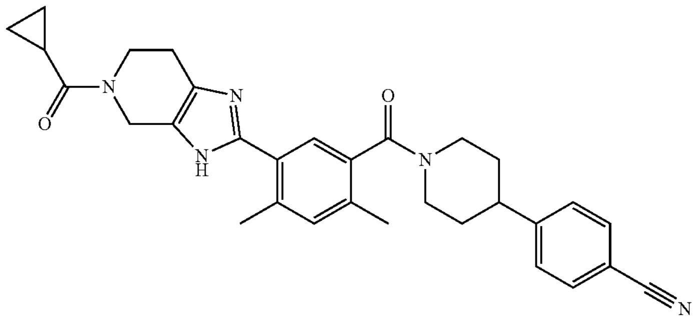 [SMILES: Cc1cc(C)c(-c2nc3c([nH]2)CN(C(=O)C2CC2)CC3)cc1C(=O)N1CCC(c2ccc(C#N)cc2)CC1] | 0.030 |
| 90 | 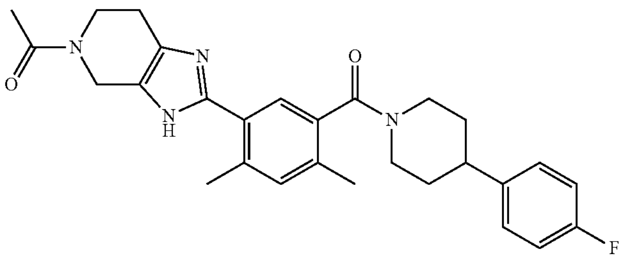 [SMILES: CC(=O)N1CCc2nc(-c3cc(C(=O)N4CCC(c5ccc(F)cc5)CC4)c(C)cc3C)[nH]c2C1] | 0.380 |
| 91 | 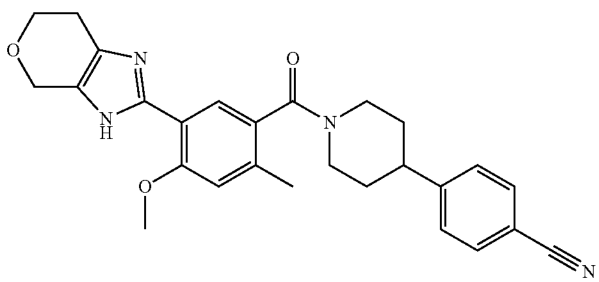 [SMILES: COc1cc(C)c(C(=O)N2CCC(c3ccc(C#N)cc3)CC2)cc1-c1nc2c([nH]1)COCC2] | 2.210 |
| 92 | 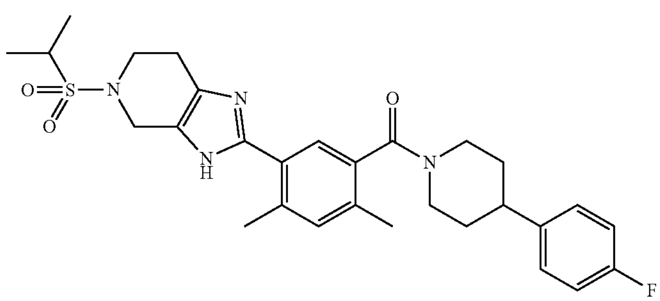 [SMILES: Cc1cc(C)c(-c2nc3c([nH]2)CN(S(=O)(=O)C(C)C)CC3)cc1C(=O)N1CCC(c2ccc(F)cc2)CC1] | 0.940 |
| 93 | 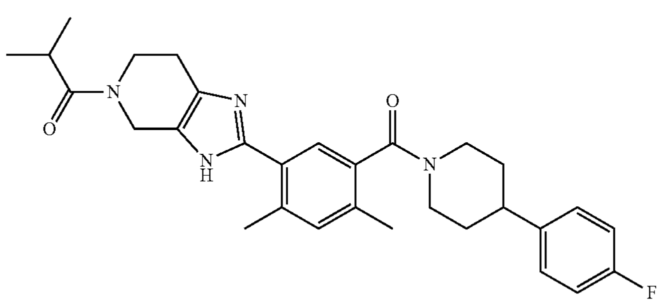 [SMILES: Cc1cc(C)c(-c2nc3c([nH]2)CN(C(=O)C(C)C)CC3)cc1C(=O)N1CCC(c2ccc(F)cc2)CC1] | 0.550 |

TABLE 1-continued

| ID | Structure | FASN IC50 (μM) |
|---|---|---|
| 94 | 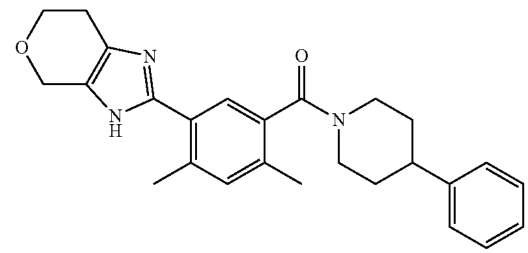 [SMILES: Cc1cc(C)c(-c2nc3c([nH]2)COCC3)cc1C(=O)N1CCC(c2ccccc2)CC1] | 5.260 |
| 95 | 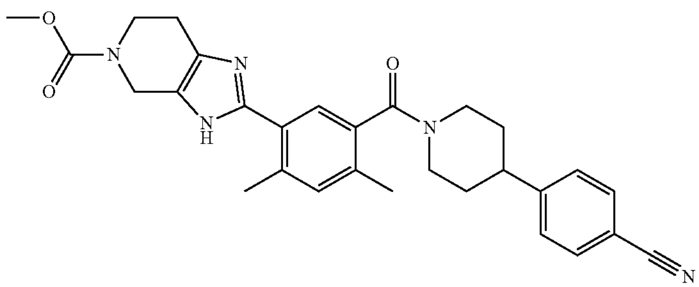 [SMILES: COC(=O)N1CCc2nc(-c3cc(C(=O)N4CCC(c5ccc(C#N)cc5)CC4)c(C)cc3C)[nH]c2C1] | 0.030 |
| 96 | 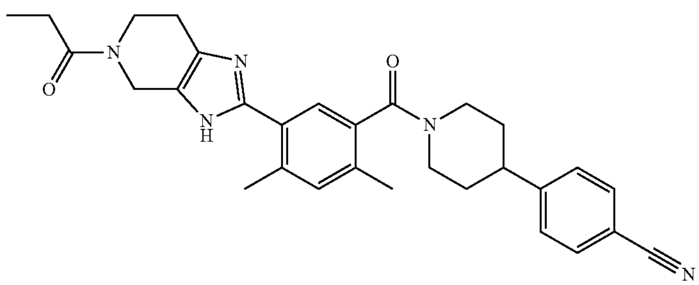 [SMILES: CCC(=O)N1CCc2nc(-c3cc(C(=O)N4CCC(c5ccc(C#N)cc5)CC4)c(C)cc3C)[nH]c2C1] | 0.030 |
| 97 | 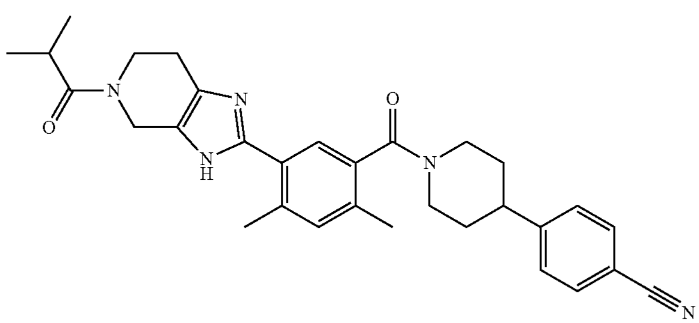 [SMILES: Cc1cc(C)c(-c2nc3c([nH]2)CN(C(=O)C(C)C)CC3)cc1C(=O)N1CCC(c2ccc(C#N)cc2)CC1] | 0.025 |
| 98 | 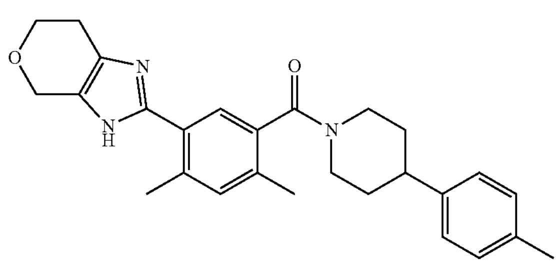 [SMILES: Cc1ccc(C2CCN(C(=O)c3cc(-c4nc5c([nH]4)COCC5)c(C)cc3C)CC2)cc1] | 0.900 |

TABLE 1-continued

| ID | Structure | FASN IC50 (μM) |
|---|---|---|
| 99 | 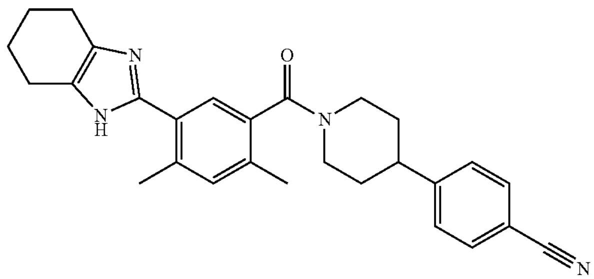 [SMILES: Cc1cc(C)c(-c2nc3c([nH]2)CCCC3)cc1C(=O)N1CCC(c2ccc(C#N)cc2)CC1] | 0.220 |
| 100 | 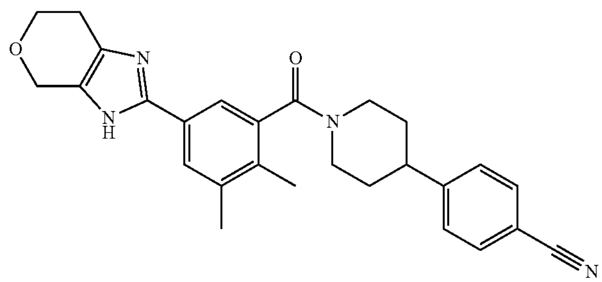 [SMILES: Cc1cc(-c2nc3c([nH]2)COCC3)cc(C(=O)N2CCC(c3ccc(C#N)cc3)CC2)c1C] | >50 |
| 101 | 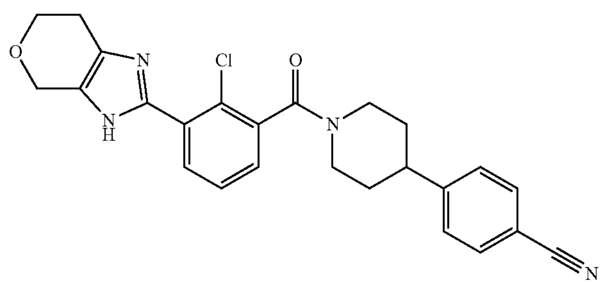 [SMILES: N#Cc1ccc(C2CCN(C(=O)c3cccc(-c4nc5c([nH]4)COCC5)c3Cl)CC2)cc1] | >50 |
| 102 | 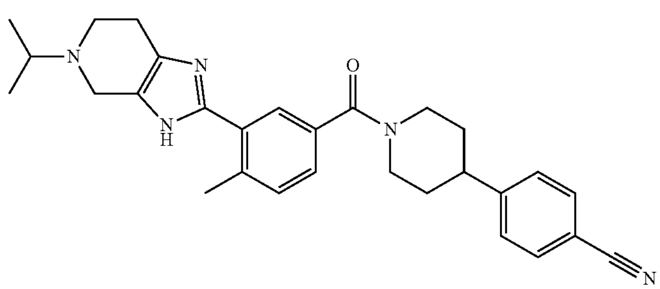 [SMILES: Cc1ccc(C(=O)N2CCC(c3ccc(C#N)cc3)CC2)cc1-c1nc2c([nH]1)CN(C(C)C)CC2] | 0.085 |
| 103 | 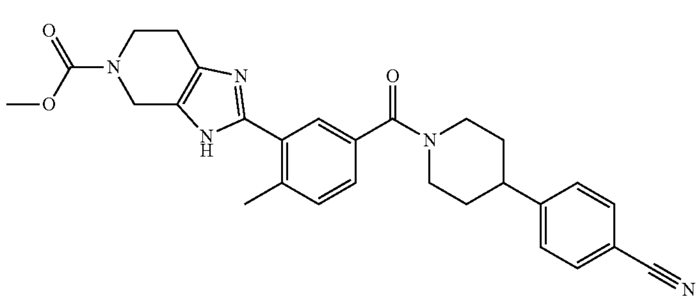 [SMILES: COC(=O)N1CCc2nc(-c3cc(C(=O)N4CCC(c5ccc(C#N)cc5)CC4)ccc3C)[nH]c2C1] | 0.035 |

TABLE 1-continued

| ID | Structure | FASN IC50 (μM) |
|---|---|---|
| 104 | 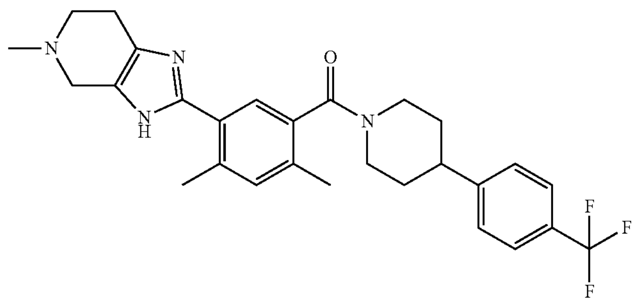 [SMILES: Cc1cc(C)c(-c2nc3c([nH]2)CN(C)CC3)cc1C(=O)N1CCC(c2ccc(C(F)(F)F)cc2)CC1] | 0.130 |
| 105 | 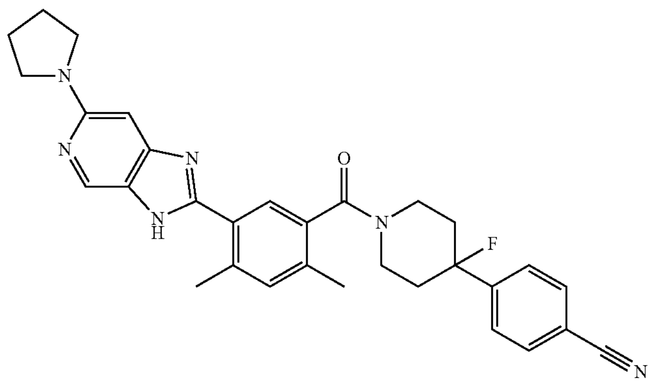 [SMILES: Cc1cc(C)c(-c2nc3cc(N4CCCC4)ncc3[nH]2)cc1C(=O)N1CCC(F)(c2ccc(C#N)cc2)CC1] | 0.015 |
| 106 | 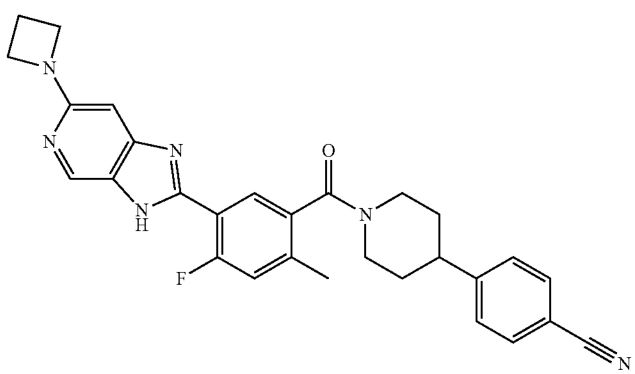 [SMILES: Cc1cc(F)c(-c2nc3cc(N4CCC4)ncc3[nH]2)cc1C(=O)N1CCC(c2ccc(C#N)cc2)CC1] | 0.900 |
| 107 | 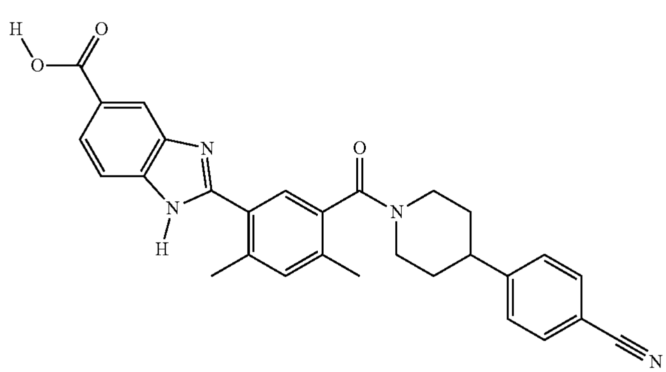 [SMILES: Cc1cc(C)c(-c2nc3cc(C(=O)O)ccc3[nH]2)cc1C(=O)N1CCC(c2ccc(C#N)cc2)CC1] | 1.490 |

TABLE 1-continued

| ID | Structure | FASN IC50 (μM) |
|---|---|---|
| 108 | 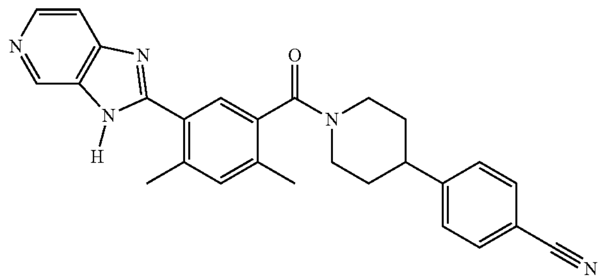 [SMILES: Cc1cc(C)c(-c2nc3ccncc3[nH]2)cc1C(=O)N1CCC(c2ccc(C#N)cc2)CC1] | 1.050 |
| 109 | 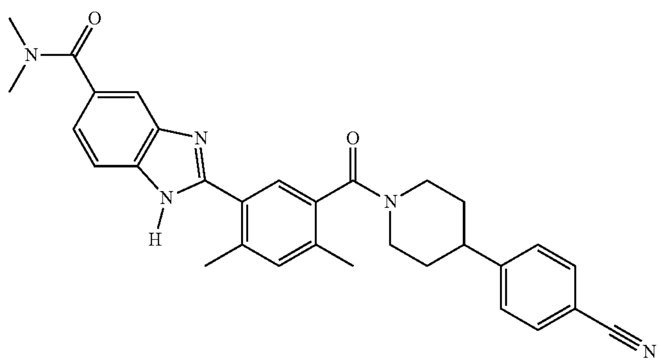 [SMILES: Cc1cc(C)c(-c2nc3cc(C(=O)N(C)C)ccc3[nH]2)cc1C(=O)N1CCC(c2ccc(C#N)cc2)CC1] | 0.250 |
| 110 | 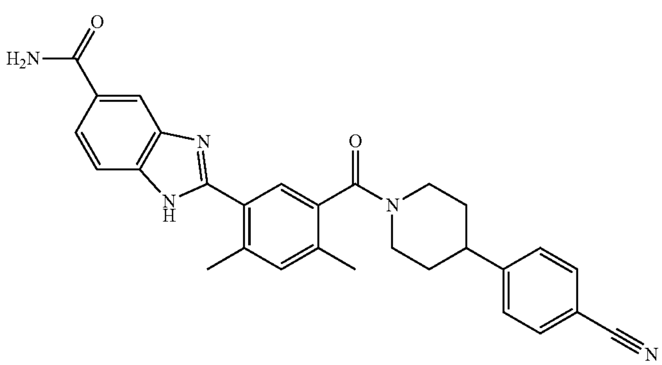 [SMILES: Cc1cc(C)c(-c2nc3cc(C(N)=O)ccc3[nH]2)cc1C(=O)N1CCC(c2ccc(C#N)cc2)CC1] | 0.280 |
| 111 | 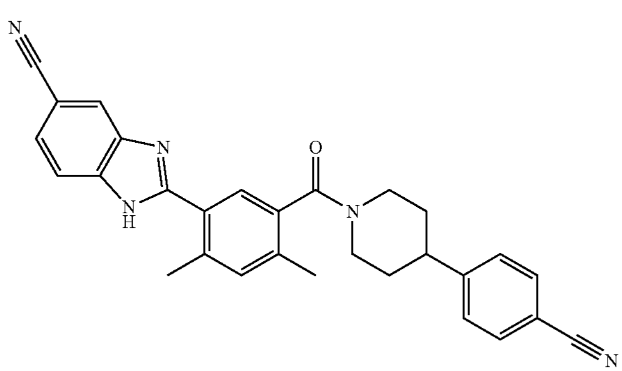 [SMILES: Cc1cc(C)c(-c2nc3cc(C#N)ccc3[nH]2)cc1C(=O)N1CCC(c2ccc(C#N)cc2)CC1] | 0.135 |

TABLE 1-continued

| ID | Structure | FASN IC50 (μM) |
|---|---|---|
| 112 | 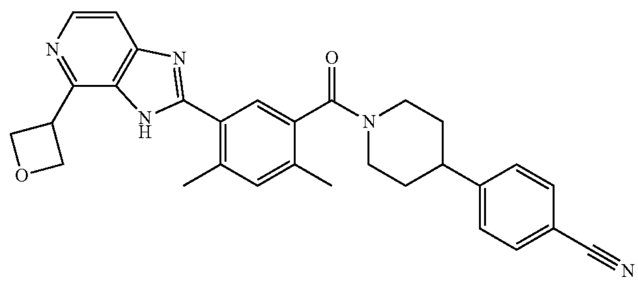 [SMILES: Cc1cc(C)c(-c2nc3ccnc(C4COC4)c3[nH]2)cc1C(=O)N1CCC(c2ccc(C#N)cc2)CC1] | 1.295 |
| 113 | 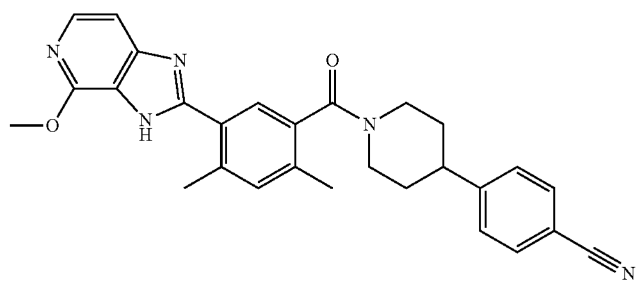 [SMILES: COc1nccc2nc(-c3cc(C(=O)N4CCC(c5ccc(C#N)cc5)CC4)c(C)cc3C)[nH]c12] | 0.130 |
| 114 | 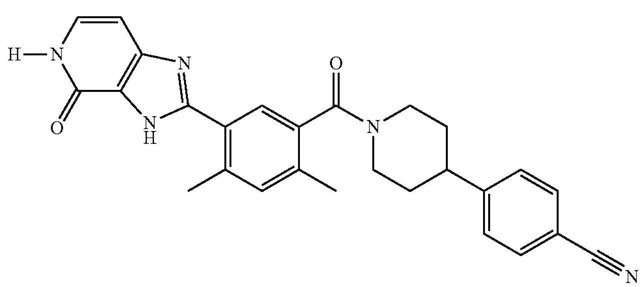 [SMILES: Cc1cc(C)c(-c2nc3cc[nH]c(=O)c3[nH]2)cc1C(=O)N1CCC(c2ccc(C#N)cc2)CC1] | 0.245 |
| 115 | 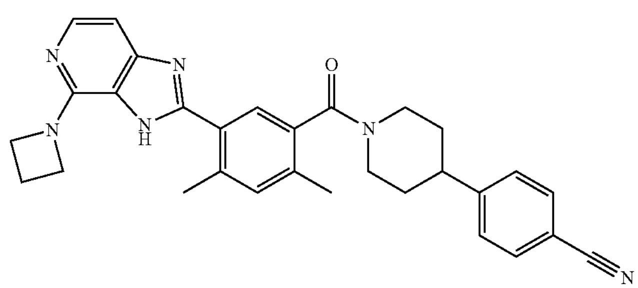 [SMILES: Cc1cc(C)c(-c2nc3ccnc(N4CCC4)c3[nH]2)cc1C(=O)N1CCC(c2ccc(C#N)cc2)CC1] | 0.480 |
| 116 | 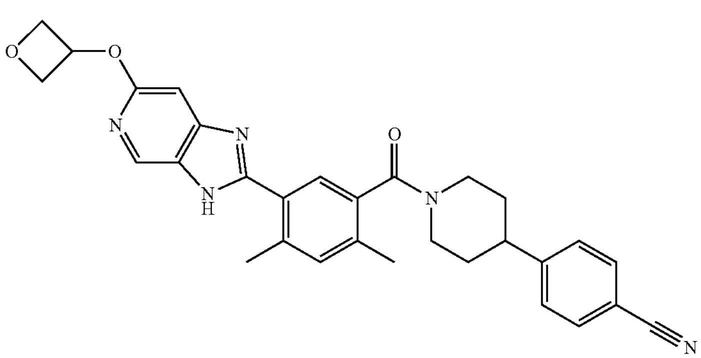 [SMILES: Cc1cc(C)c(-c2nc3cc(OC4COC4)ncc3[nH]2)cc1C(=O)N1CCC(c2ccc(C#N)cc2)CC1] | 0.090 |

TABLE 1-continued

| ID | Structure | FASN IC50 (μM) |
|---|---|---|
| 117 | 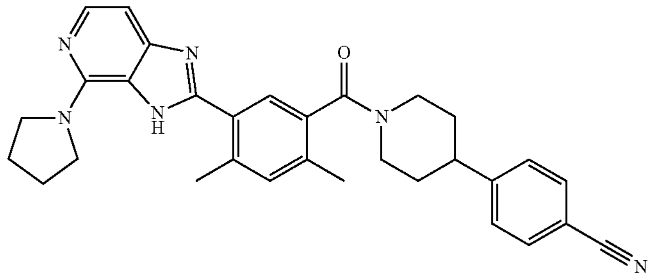 [SMILES: Cc1cc(C)c(-c2nc3ccnc(N4CCCC4)c3[nH]2)cc1C(=O)N1CCC(c2ccc(C#N)cc2)CC1] | 0.090 |
| 118 | 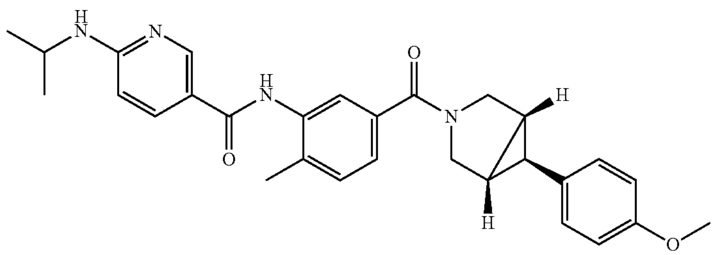 [SMILES: COc1ccc([C@H]2[C@@H]3CN(C(=O)c4ccc(C)c(NC(=O)c5ccc(NC(C)C)nc5)c4)C[C@@H]32)cc1] | 0.350 |
| 119 | 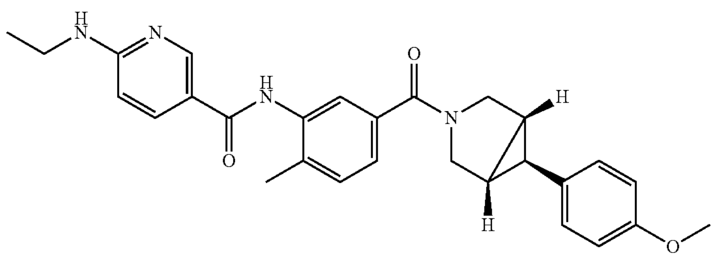 [SMILES: CCNc1ccc(C(=O)Nc2cc(C(=O)N3C[C@@H]4[C@H](C3)[C@H]4c3ccc(OC)cc3)ccc2C)cn1] | 0.460 |
| 120 | 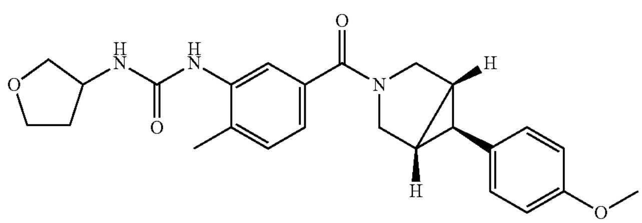 [SMILES: COc1ccc([C@H]2[C@@H]3CN(C(=O)c4ccc(C)c(NC(=O)NC5CCOC5)c4)C[C@@H]32)cc1] | 0.460 |
| 121 | 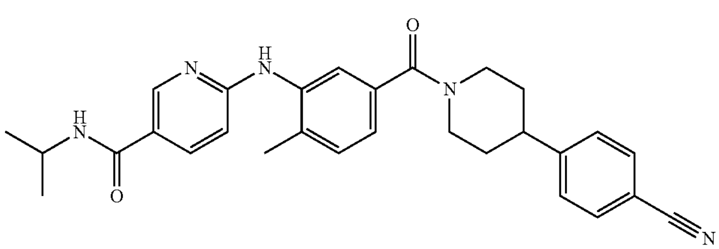 [SMILES: Cc1ccc(C(=O)N2CCC(c3ccc(C#N)cc3)CC2)cc1Nc1ccc(C(=O)NC(C)C)cn1] | 2.300 |
| 122 | 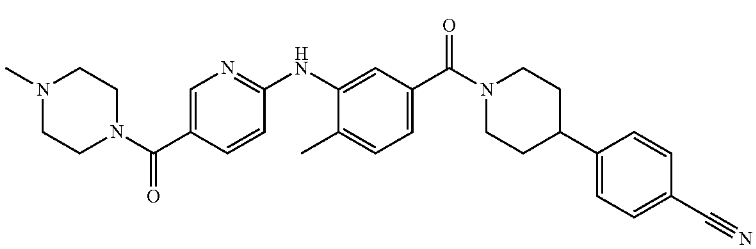 [SMILES: Cc1ccc(C(=O)N2CCC(c3ccc(C#N)cc3)CC2)cc1Nc1ccc(C(=O)N2CCN(C)CC2)cn1] | 0.890 |

TABLE 1-continued
| ID | Structure | FASN IC50 (μM) |
|---|---|---|
| 123 | 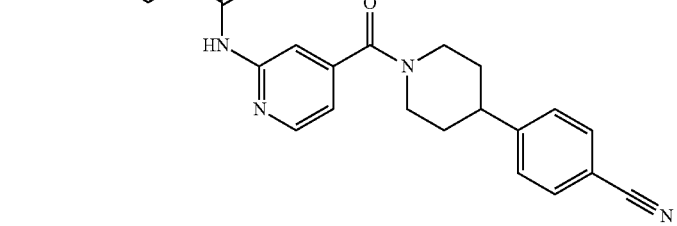 | 0.690 |
| 124 | 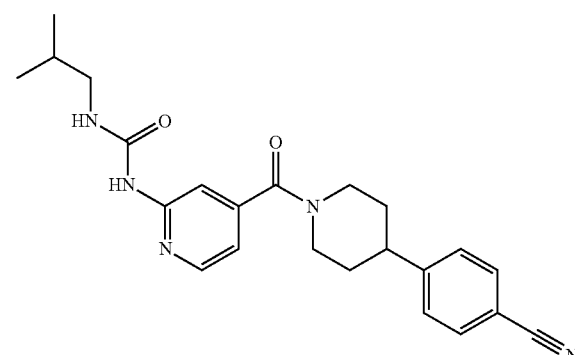 | 32.880 |
| 125 | 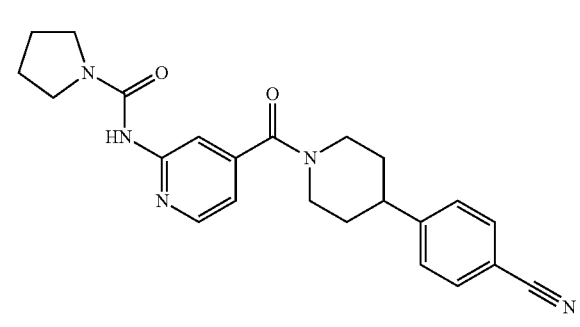 [SMILES: N#Cc1ccc(C2CCN(C(=O)c3ccnc(NC(=O)N4CCCC4)c3)CC2)cc1] | >50 |
| 126 | 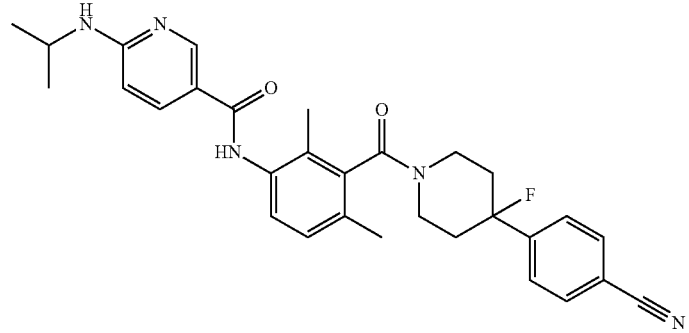 [SMILES: Cc1ccc(NC(=O)c2ccc(NC(C)C)nc2)c(C)c1C(=O)N1CCC(F)(c2ccc(C#N)cc2)CC1] | >50 |
| 127 | 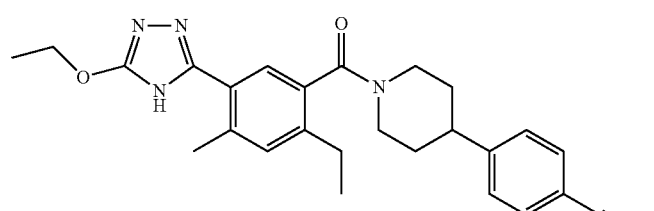 | 0.730 |

TABLE 1-continued

| ID | Structure | FASN IC50 (μM) |
|---|---|---|
| 128 | 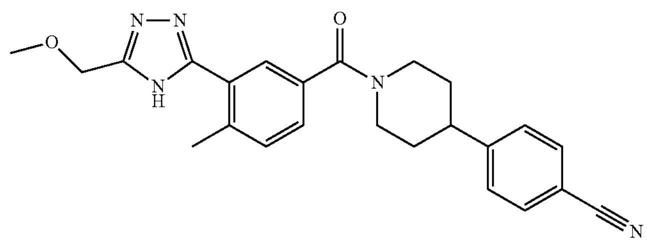 [SMILES: COCc1nnc(-c2cc(C(=O)N3CCC(c4ccc(C#N)cc4)CC3)ccc2C)[nH]1] | 2.260 |
| 129 | 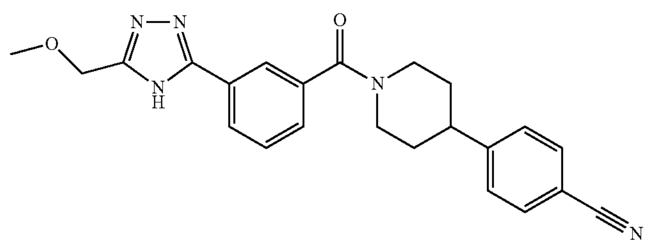 [SMILES: COCc1nnc(-c2cccc(C(=O)N3CCC(c4ccc(C#N)cc4)CC3)c2)[nH]1] | >50 |
| 130 | 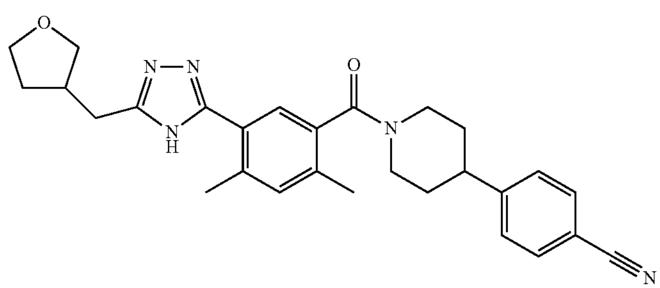 [SMILES: Cc1cc(C)c(-c2nnc(CC3CCOC3)[nH]2)cc1C(=O)N1CCC(c2ccc(C#N)cc2)CC1] | 0.300 |
| 131 | 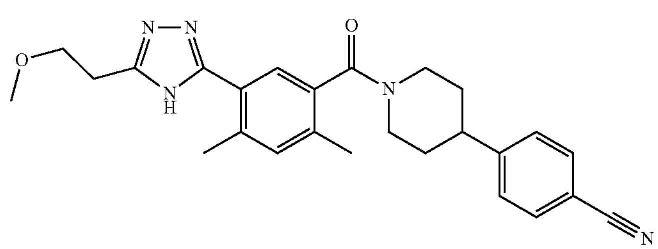 [SMILES: COCCc1nnc(-c2cc(C(=O)N3CCC(c4ccc(C#N)cc4)CC3)c(C)cc2C)[nH]1] | 0.220 |
| 132 | 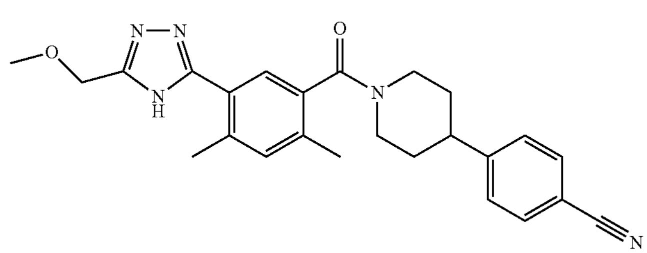 | 0.450 |
| 133 | Abs | 0.790 |

TABLE 1-continued

| ID | Structure | FASN IC50 (μM) |
|---|---|---|
| 134 | 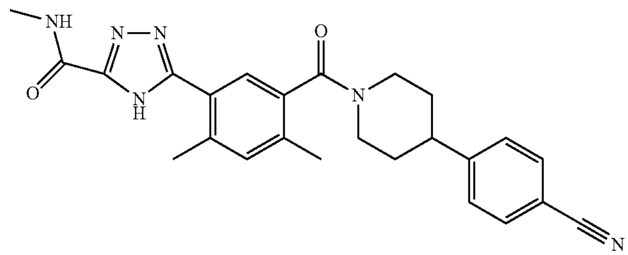 [SMILES: CNC(=O)c1nnc(-c2cc(C(=O)N3CCC(c4ccc(C#N)cc4)CC3)c(C)cc2C)[nH]1] | 1.330 |
| 135 | 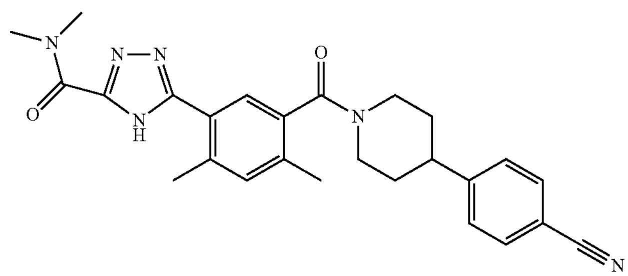 [SMILES: Cc1cc(C)c(-c2nnc(C(=O)N(C)C)[nH]2)cc1C(=O)N1CCC(c2ccc(C#N)cc2)CC1] | 2.040 |
| 136 | (Abs) | 0.240 |
| 137 | 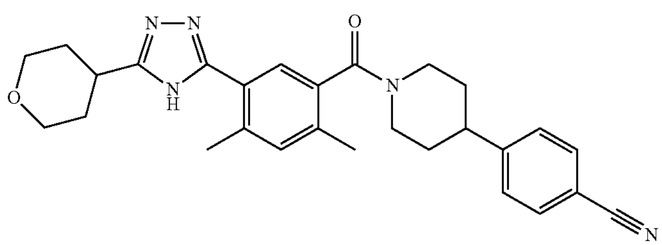 | 0.500 |
| 138 | 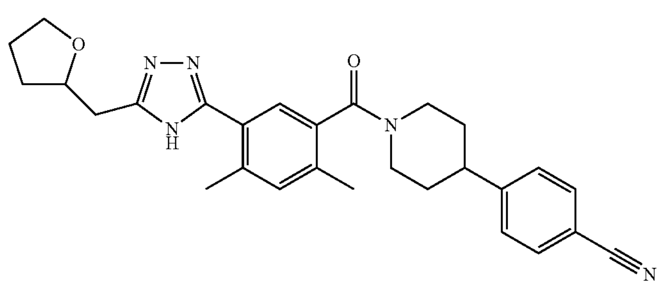 [SMILES: Cc1cc(C)c(-c2nnc(CC3CCCO3)[nH]2)cc1C(=O)N1CCC(c2ccc(C#N)cc2)CC1] | 0.640 |
| 139 | 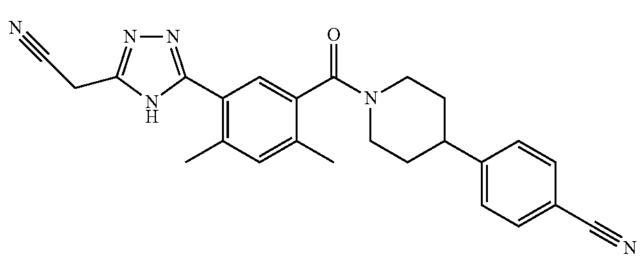 [SMILES: Cc1cc(C)c(-c2nnc(CC#N)[nH]2)cc1C(=O)N1CCC(c2ccc(C#N)cc2)CC1] | 1.210 |

TABLE 1-continued

| ID | Structure | FASN IC50 (μM) |
|----|-----------|----------------|
| 140 | 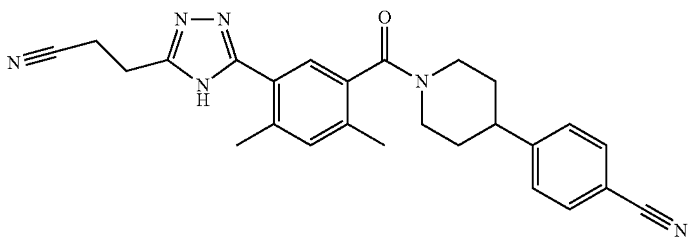 [SMILES: Cc1cc(C)c(-c2nnc(CCC#N)[nH]2)cc1C(=O)N1CCC(c2ccc(C#N)cc2)CC1] | 0.380 |
| 141 | 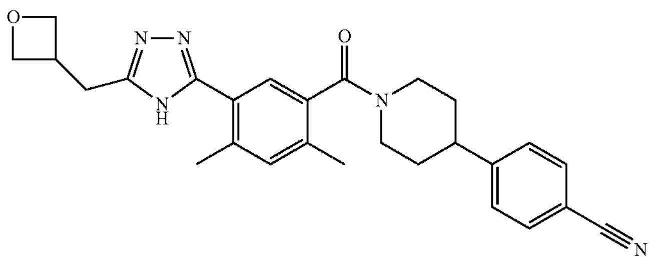 [SMILES: Cc1cc(C)c(-c2nnc(CC3COC3)[nH]2)cc1C(=O)N1CCC(c2ccc(C#N)cc2)CC1] | >50 |
| 142 | 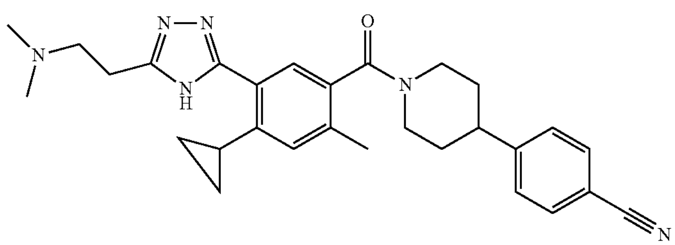 [SMILES: Cc1cc(C2CC2)c(-c2nnc(CCN(C)C)[nH]2)cc1C(=O)N1CCC(c2ccc(C#N)cc2)CC1] | 0.175 |
| 143 | 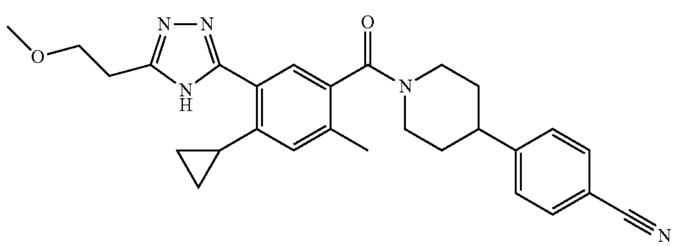 [SMILES: COCCc1nnc(-c2cc(C(=O)N3CCC(c4ccc(C#N)cc4)CC3)c(C)cc2C2CC2)[nH]1] | 0.140 |
| 144 | 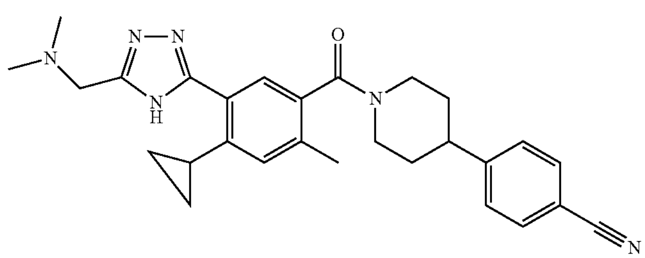 [SMILES: Cc1cc(C2CC2)c(-c2nnc(CN(C)C)[nH]2)cc1C(=O)N1CCC(c2ccc(C#N)cc2)CC1] | 0.320 |
| 145 | 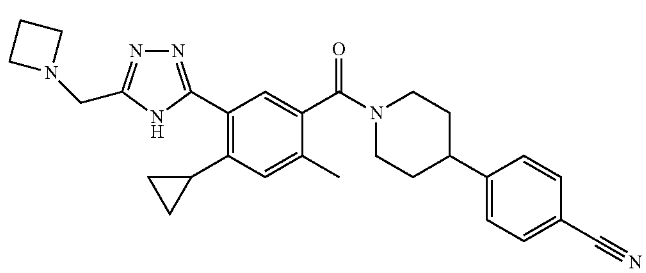 [SMILES: Cc1cc(C2CC2)c(-c2nnc(CN3CCC3)[nH]2)cc1C(=O)N1CCC(c2ccc(C#N)cc2)CC1] | 0.820 |

TABLE 1-continued

| ID | Structure | FASN IC50 (μM) |
|---|---|---|
| 146 | 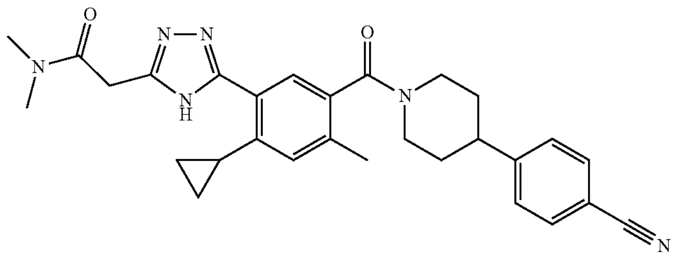 [SMILES: Cc1cc(C2CC2)c(-c2nnc(CC(=O)N(C)C)[nH]2)cc1C(=O)N1CCC(c2ccc(C#N)cc2)CC1] | 0.260 |
| 147 | 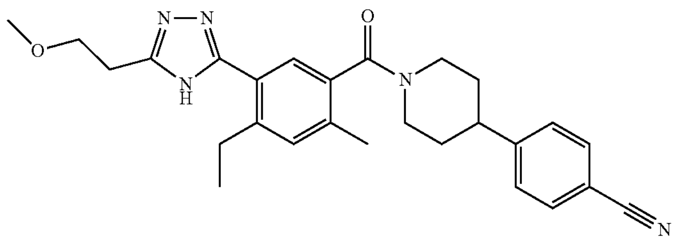 [SMILES: CCc1cc(C)c(C(=O)N2CCC(c3ccc(C#N)cc3)CC2)cc1-c1nnc(CCOC)[nH]1] | 0.250 |
| 148 | 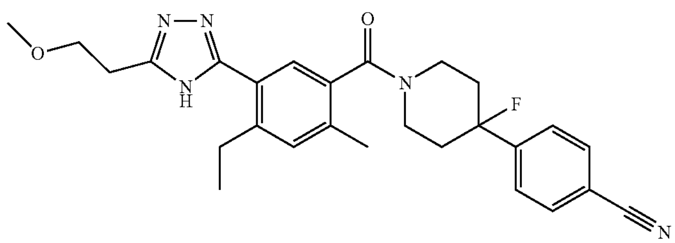 [SMILES: CCc1cc(C)c(C(=O)N2CCC(F)(c3ccc(C#N)cc3)CC2)cc1-c1nnc(CCOC)[nH]1] | 0.180 |
| 149 | 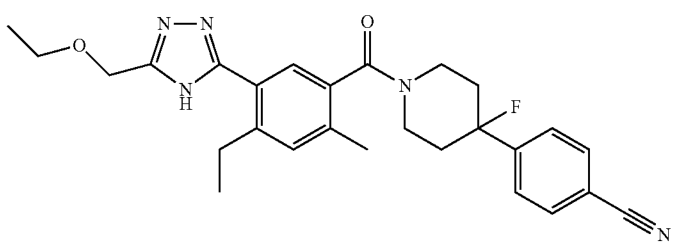 [SMILES: CCOCc1nnc(-c2cc(C(=O)N3CCC(F)(c4ccc(C#N)cc4)CC3)c(C)cc2CC)[nH]1] | 0.240 |
| 150 | 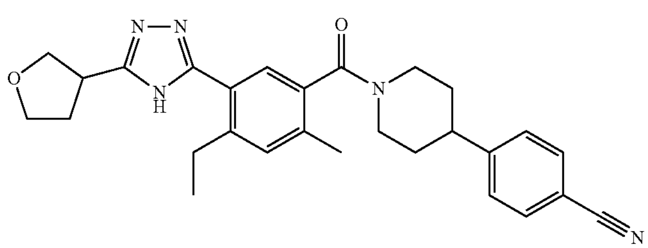 [SMILES: CCc1cc(C)c(C(=O)N2CCC(c3ccc(C#N)cc3)CC2)cc1-c1nnc(C2CCOC2)[nH]1] | 0.300 |
| 151 | 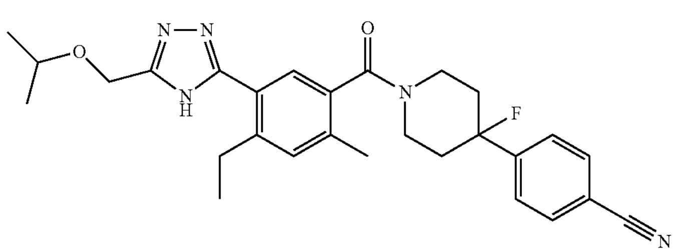 [SMILES: CCc1cc(C)c(C(=O)N2CCC(F)(c3ccc(C#N)cc3)CC2)cc1-c1nnc(COC(C)C)[nH]1] | 0.420 |

TABLE 1-continued

| ID | Structure | FASN IC50 (μM) |
|---|---|---|
| 152 | 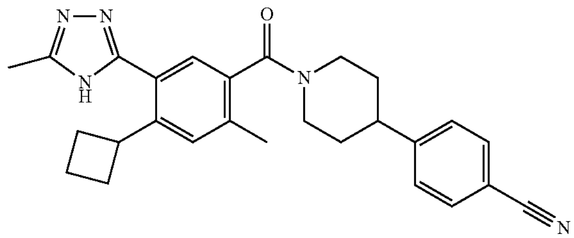 [SMILES: Cc1nnc(-c2cc(C(=O)N3CCC(c4ccc(C#N)cc4)CC3)c(C)cc2C2CCC2)[nH]1] | 0.052 |
| 153 | 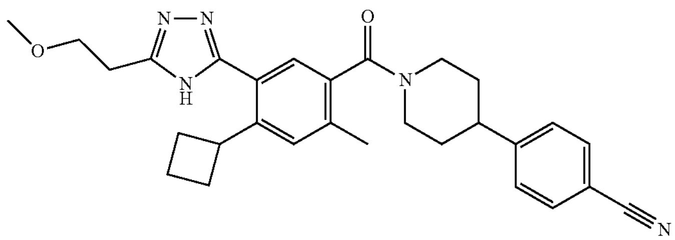 [SMILES: COCCc1nnc(-c2cc(C(=O)N3CCC(c4ccc(C#N)cc4)CC3)c(C)cc2C2CCC2)[nH]1] | 0.055 |
| 154 | 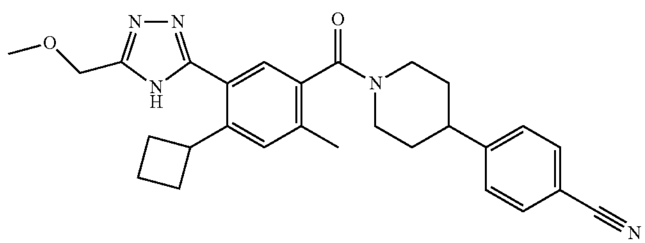 [SMILES: COCc1nnc(-c2cc(C(=O)N3CCC(c4ccc(C#N)cc4)CC3)c(C)cc2C2CCC2)[nH]1] | 0.105 |
| 155 | 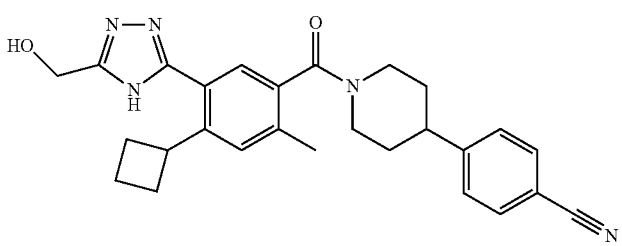 [SMILES: Cc1cc(C2CCC2)c(-c2nnc(CO)[nH]2)cc1C(=O)N1CCC(c2ccc(C#N)cc2)CC1] | 0.020 |
| 156 | 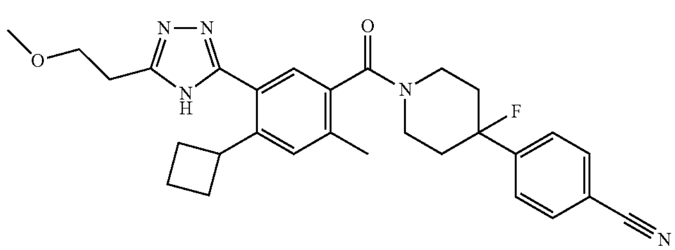 [SMILES: COCCc1nnc(-c2cc(C(=O)N3CCC(F)(c4ccc(C#N)cc4)CC3)c(C)cc2C2CCC2)[nH]1] | 0.030 |
| 157 | 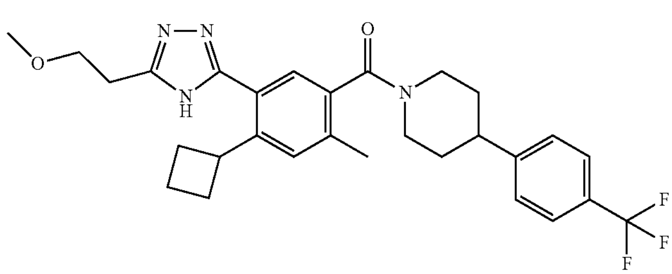 [SMILES: COCCc1nnc(-c2cc(C(=O)N3CCC(c4ccc(C(F)(F)F)cc4)CC3)c(C)cc2C2CCC2)[nH]1] | 0.090 |

TABLE 1-continued

| ID | Structure | FASN IC50 (μM) |
|---|---|---|
| 158 | 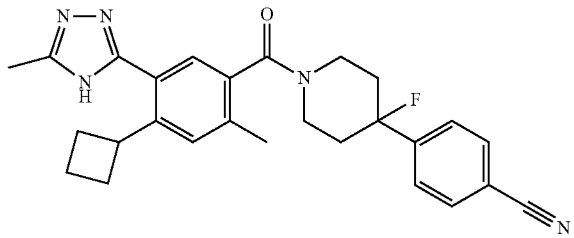 [SMILES: Cc1nnc(-c2cc(C(=O)N3CCC(F)(c4ccc(C#N)cc4)CC3)c(C)cc2C2CCC2)[nH]1] | 0.057 |
| 159 | 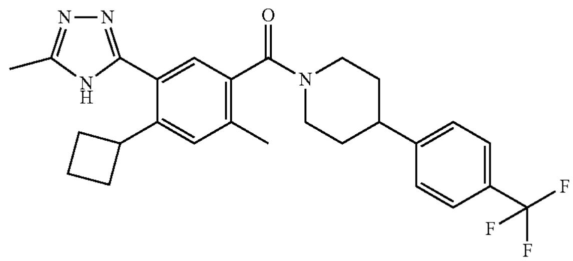 [SMILES: Cc1nnc(-c2cc(C(=O)N3CCC(c4ccc(C(F)(F)F)cc4)CC3)c(C)cc2C2CCC2)[nH]1] | 0.070 |
| 160 | 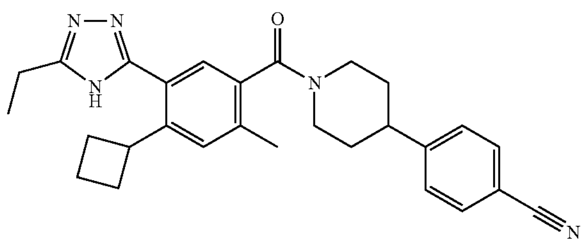 [SMILES: CCc1nnc(-c2cc(C(=O)N3CCC(c4ccc(C#N)cc4)CC3)c(C)cc2C2CCC2)[nH]1] | 0.055 |
| 161 | 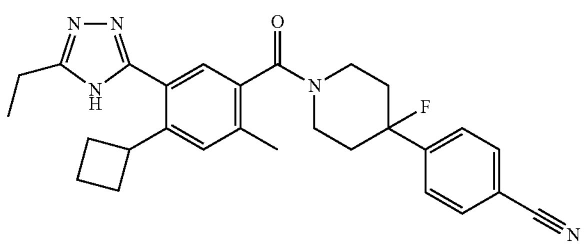 [SMILES: CCc1nnc(-c2cc(C(=O)N3CCC(F)(c4ccc(C#N)cc4)CC3)c(C)cc2C2CCC2)[nH]1] | 0.040 |
| 162 | 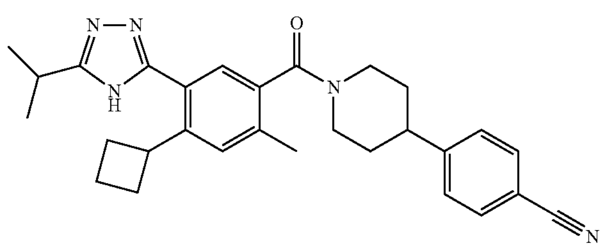 [SMILES: Cc1cc(C2CCC2)c(-c2nnc(C(C)C)[nH]2)cc1C(=O)N1CCC(c2ccc(C#N)cc2)CC1] | 0.115 |
| 163 | 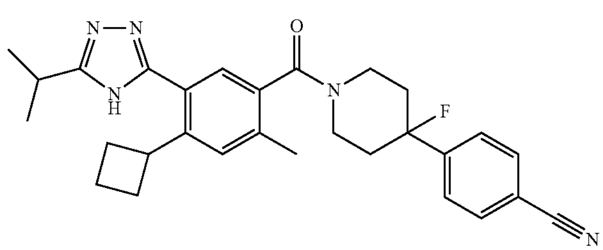 [SMILES: Cc1cc(C2CCC2)c(-c2nnc(C(C)C)[nH]2)cc1C(=O)N1CCC(F)(c2ccc(C#N)cc2)CC1] | 0.135 |

TABLE 1-continued
| ID | Structure | FASN IC50 (μM) |
|---|---|---|
| 164 | 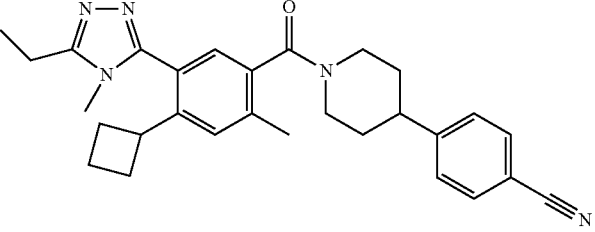 [SMILES: CCc1nnc(-c2cc(C(=O)N3CCC(c4ccc(C#N)cc4)CC3)c(C)cc2C2CCC2)n1C] | >50 |
| 165 | 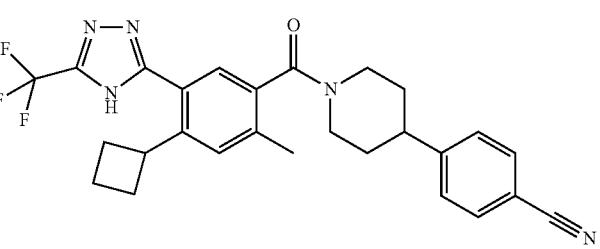 | 1.000 |
| 166 | 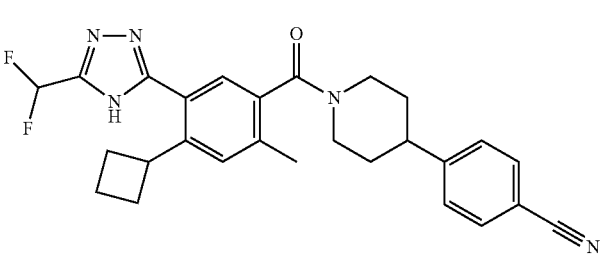 [SMILES: Cc1cc(C2CCC2)c(-c2nnc(C(F)F)[nH]2)cc1C(=O)N1CCC(c2ccc(C#N)cc2)CC1] | 0.160 |
| 167 | 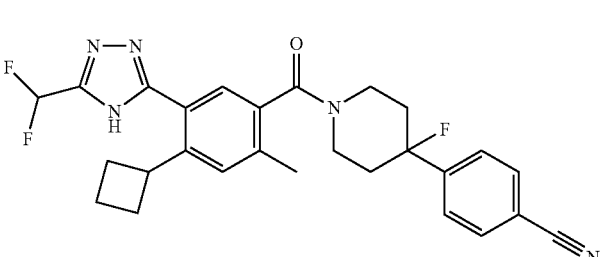 | 0.125 |
| 168 | 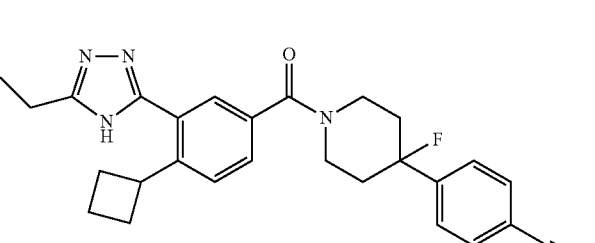 | 0.060 |
| 169 | 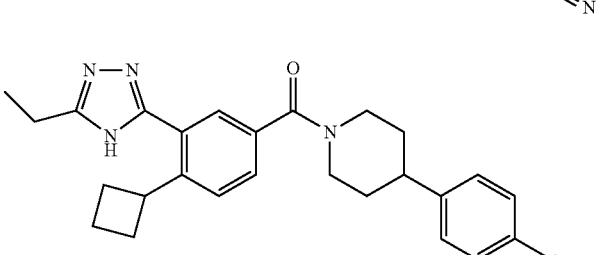 | 0.090 |

TABLE 1-continued
| ID | Structure | FASN IC50 (μM) |
|---|---|---|
| 170 | 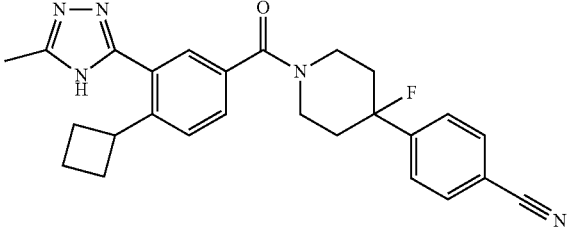 [SMILES: Cc1nnc(-c2cc(C(=O)N3CCC(F)(c4ccc(C#N)cc4)CC3)ccc2C2CCC2)[nH]1] | 0.090 |
| 171 | 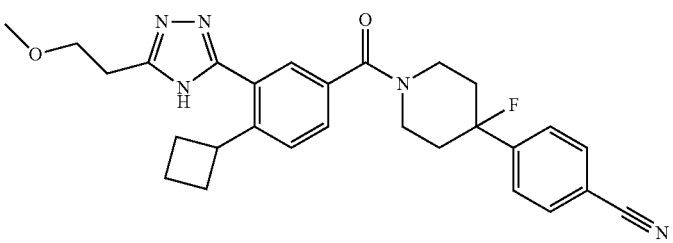 [SMILES: COCCc1nnc(-c2cc(C(=O)N3CCC(F)(c4ccc(C#N)cc4)CC3)ccc2C2CCC2)[nH]1] | 0.070 |
| 172 | [Abs] 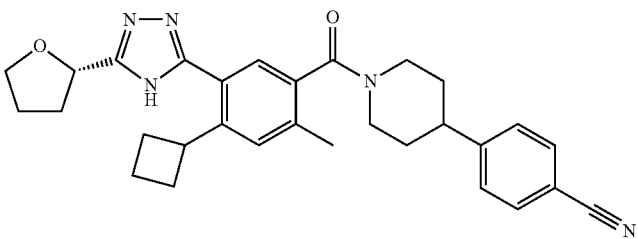 | 0.140 |
| 173 | [Abs] 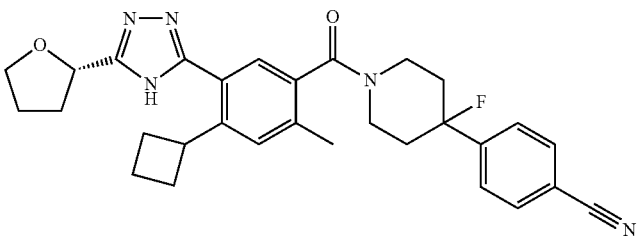 | 0.240 |
| 174 | [Abs] 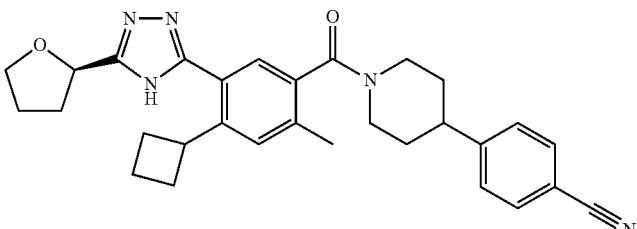 | 0.200 |
| 175 | 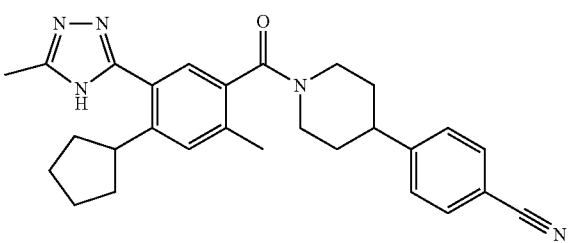 [SMILES: Cc1nnc(-c2cc(C(=O)N3CCC(c4ccc(C#N)cc4)CC3)c(C)cc2C2CCCC2)[nH]1] | 0.310 |

US 9,809,591 B2
607                                                                 608
TABLE 1-continued
| ID | Structure | FASN IC50 (μM) |
|----|-----------|----------------|
| 176 | 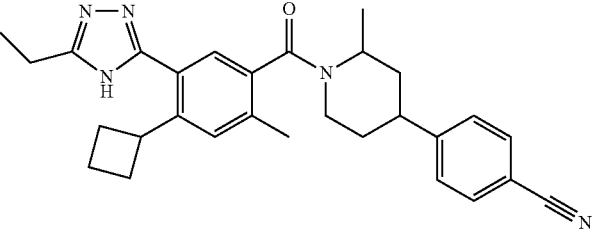 [SMILES: CCc1nnc(-c2cc(C(=O)N3CCC(c4ccc(C#N)cc4)CC3C)c(C)cc2C2CCC2)[nH]1] | 5.990 |
| 177 | 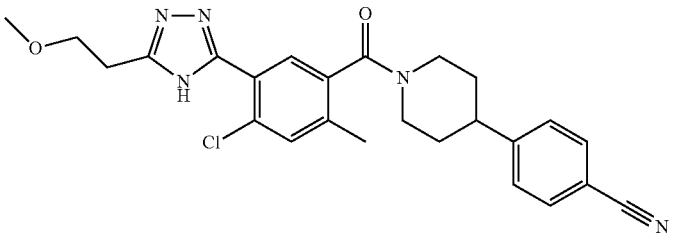 [SMILES: COCCc1nnc(-c2cc(C(=O)N3CCC(c4ccc(C#N)cc4)CC3)c(C)cc2Cl)[nH]1] | 2.110 |
| 178 | 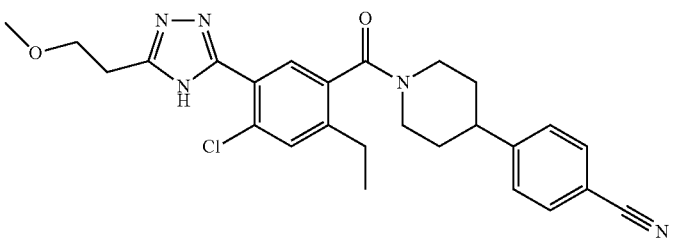 [SMILES: CCc1cc(Cl)c(-c2nnc(CCOC)[nH]2)cc1C(=O)N1CCC(c2ccc(C#N)cc2)CC1] | 0.555 |
| 179 | 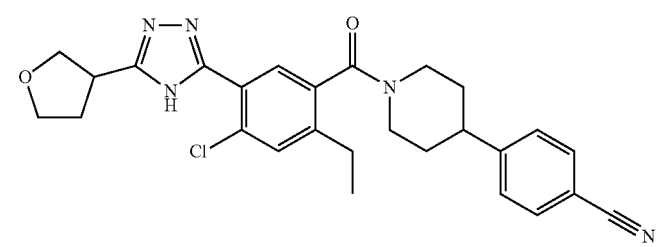 [SMILES: CCc1cc(Cl)c(-c2nnc(C3CCOC3)[nH]2)cc1C(=O)N1CCC(c2ccc(C#N)cc2)CC1] | 1.260 |
| 180 | 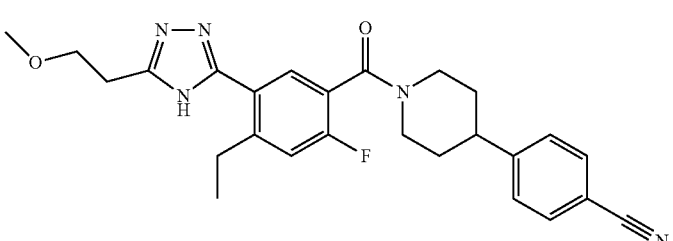 | 8.230 |
| 181 | 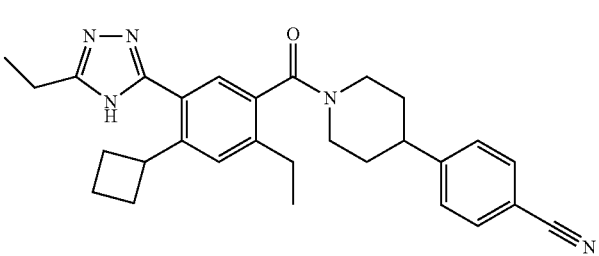 [SMILES: CCc1nnc(-c2cc(C(=O)N3CCC(c4ccc(C#N)cc4)CC3)c(CC)cc2C2CCC2)[nH]1] | 0.115 |

TABLE 1-continued

| ID | Structure | FASN IC50 (μM) |
|---|---|---|
| 182 | 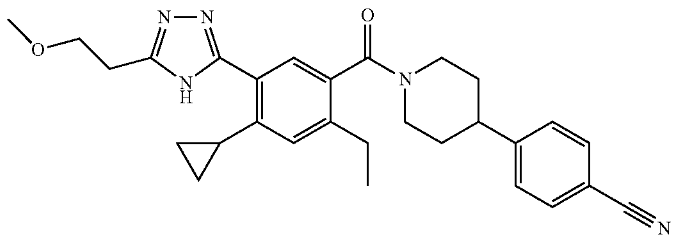 [SMILES: CCc1cc(C2CC2)c(-c2nnc(CCOC)[nH]2)cc1C(=O)N1CCC(c2ccc(C#N)cc2)CC1] | 0.145 |
| 183 | 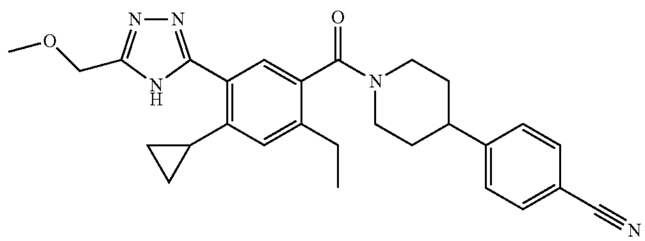 [SMILES: CCc1cc(C2CC2)c(-c2nnc(COC)[nH]2)cc1C(=O)N1CCC(c2ccc(C#N)cc2)CC1] | 0.170 |
| 184 | 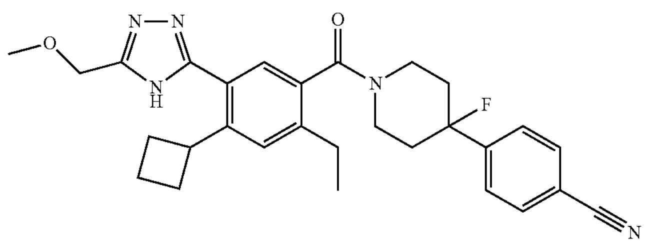 [SMILES: CCc1cc(C2CCC2)c(-c2nnc(COC)[nH]2)cc1C(=O)N1CCC(F)(c2ccc(C#N)cc2)CC1] | 0.085 |
| 185 | 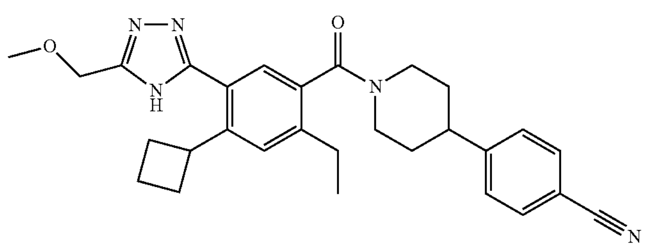 [SMILES: CCc1cc(C2CCC2)c(-c2nnc(COC)[nH]2)cc1C(=O)N1CCC(c2ccc(C#N)cc2)CC1] | 0.080 |
| 186 | 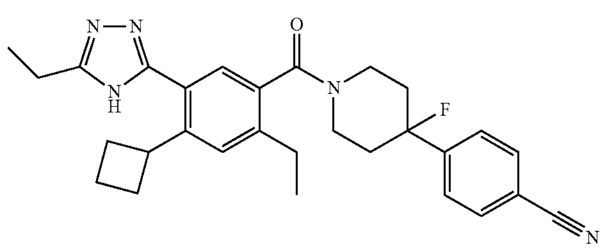 [SMILES: CCc1nnc(-c2cc(C(=O)N3CCC(F)(c4ccc(C#N)cc4)CC3)c(CC)cc2C2CCC2)[nH]1] | 0.055 |
| 187 | 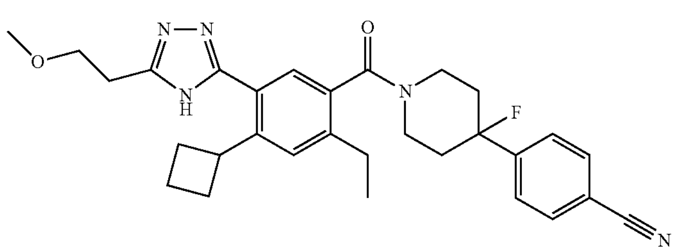 [SMILES: CCc1cc(C2CCC2)c(-c2nnc(CCOC)[nH]2)cc1C(=O)N1CCC(F)(c2ccc(C#N)cc2)CC1] | 0.065 |

TABLE 1-continued

| ID | Structure | FASN IC50 (μM) |
|---|---|---|
| 188 | 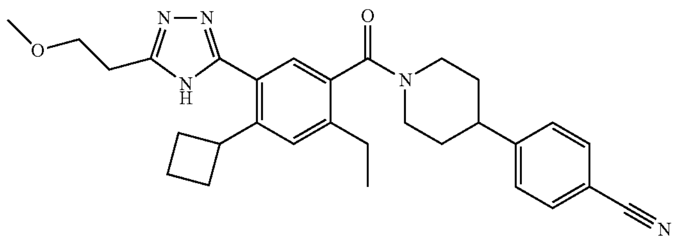 [SMILES: CCc1cc(C2CCC2)c(-c2nnc(CCOC)[nH]2)cc1C(=O)N1CCC(c2ccc(C#N)cc2)CC1] | 0.070 |
| 189 | 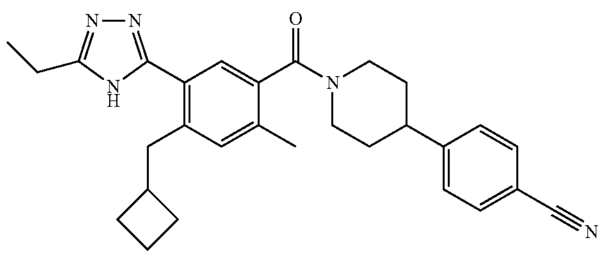 [SMILES: CCc1nnc(-c2cc(C(=O)N3CCC(c4ccc(C#N)cc4)CC3)c(C)cc2CC2CCC2)[nH]1] | 0.270 |
| 190 | 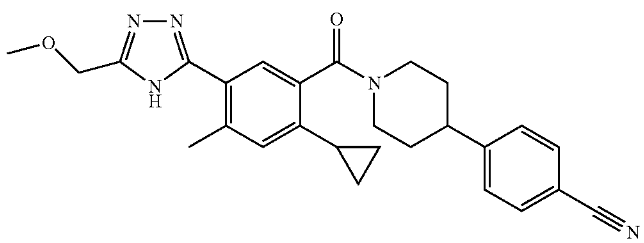 [SMILES: COCc1nnc(-c2cc(C(=O)N3CCC(c4ccc(C#N)cc4)CC3)c(C3CC3)cc2C)[nH]1] | 5.060 |
| 191 | 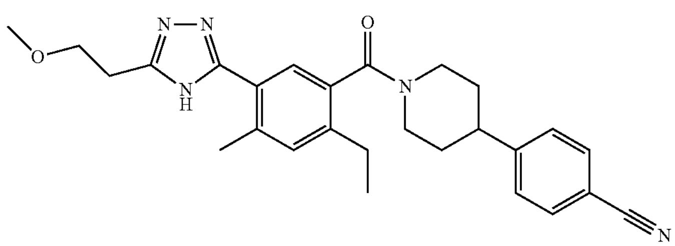 [SMILES: CCc1cc(C)c(-c2nnc(CCOC)[nH]2)cc1C(=O)N1CCC(c2ccc(C#N)cc2)CC1] | 0.200 |
| 192 | 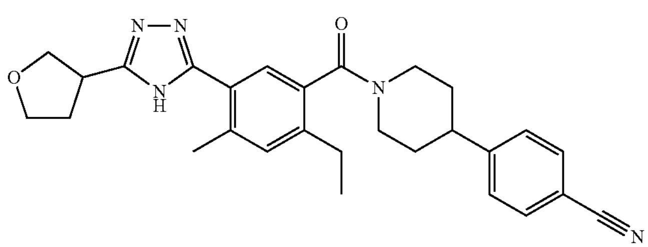 [SMILES: CCc1cc(C)c(-c2nnc(C3CCOC3)[nH]2)cc1C(=O)N1CCC(c2ccc(C#N)cc2)CC1] | 0.300 |
| 193 | 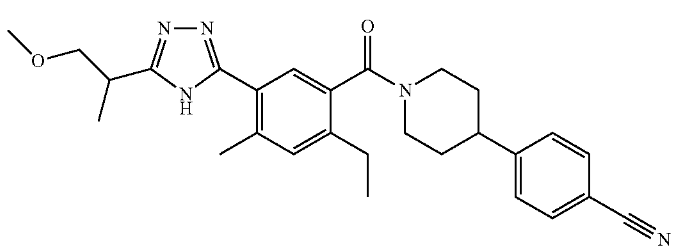 [SMILES: CCc1cc(C)c(-c2nnc(C(C)COC)[nH]2)cc1C(=O)N1CCC(c2ccc(C#N)cc2)CC1] | 0.440 |

TABLE 1-continued
| ID | Structure | FASN IC50 (μM) |
|---|---|---|
| 194 | 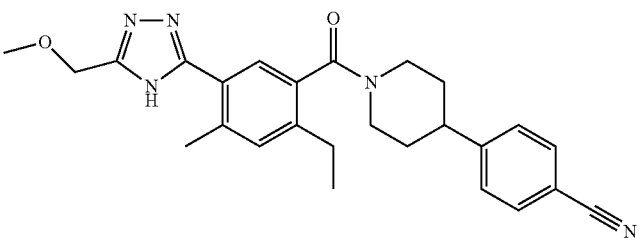 [SMILES: CCc1cc(C)c(-c2nnc(COC)[nH]2)cc1C(=O)N1CCC(c2ccc(C#N)cc2)CC1] | 0.400 |
| 195 | 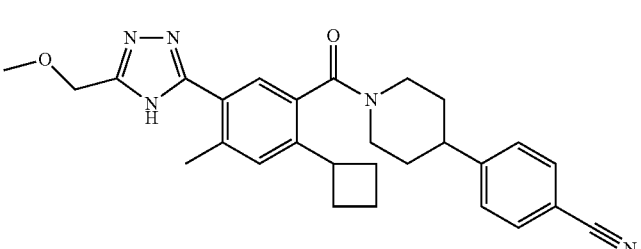 | >50 |
| 196 | 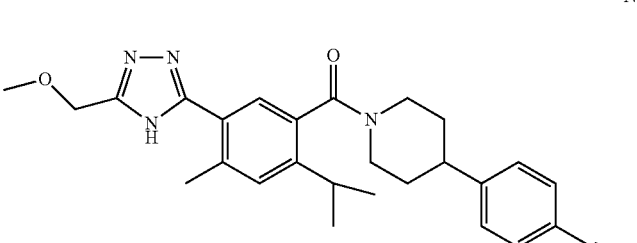 | >50 |
| 197 | 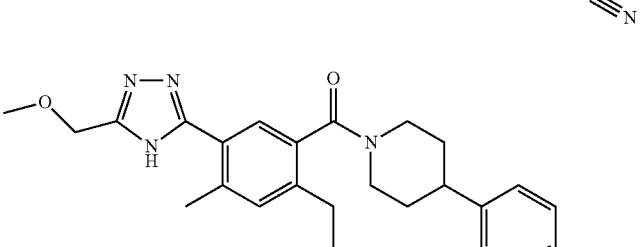 | 11.105 |
| 198 | 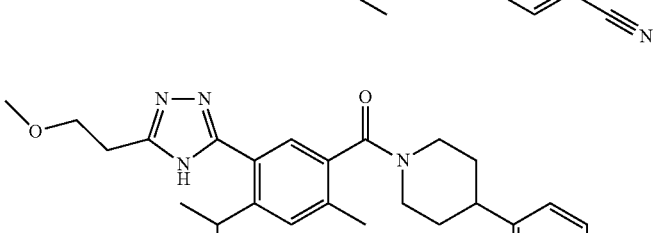 | 0.705 |
| 199 | 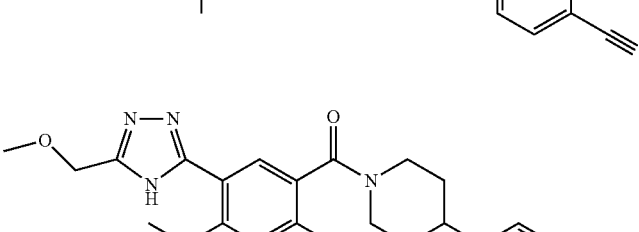 | 1.060 |

TABLE 1-continued

| ID | Structure | FASN IC50 (μM) |
|----|-----------|----------------|
| 200 | 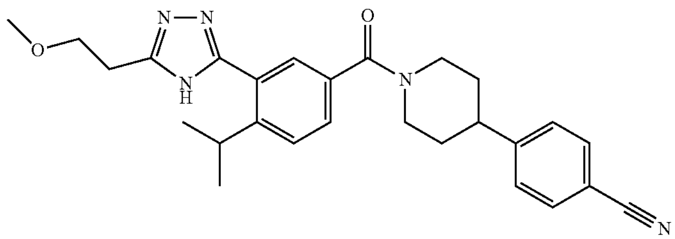 [SMILES: COCCc1nnc(-c2cc(C(=O)N3CCC(c4ccc(C#N)cc4)CC3)ccc2C(C)C)[nH]1] | 13.520 |
| 201 | 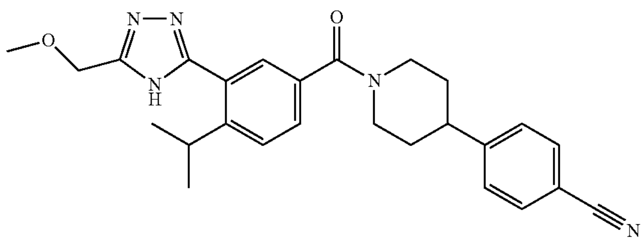 [SMILES: COCc1nnc(-c2cc(C(=O)N3CCC(c4ccc(C#N)cc4)CC3)ccc2C(C)C)[nH]1] | 23.140 |
| 202 | 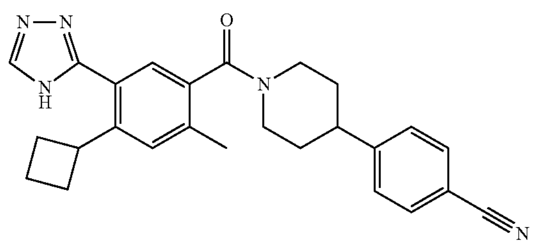 [SMILES: Cc1cc(C2CCC2)c(-c2nnc[nH]2)cc1C(=O)N1CCC(c2ccc(C#N)cc2)CC1] | 0.055 |
| 203 | 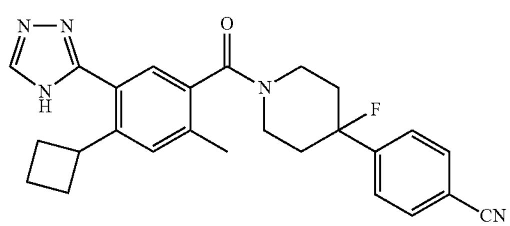 [SMILES: Cc1cc(C2CCC2)c(-c2nnc[nH]2)cc1C(=O)N1CCC(F)(c2ccc(C#N)cc2)CC1] | 0.045 |
| 204 | 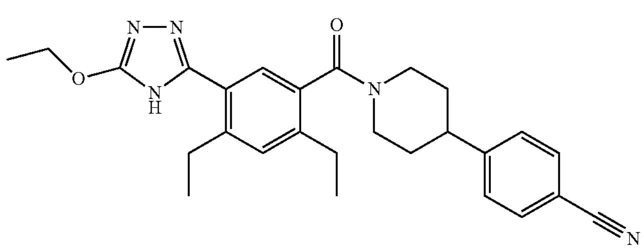 [SMILES: CCOc1nnc(-c2cc(C(=O)N3CCC(c4ccc(C#N)cc4)CC3)c(CC)cc2CC)[nH]1] | 0.195 |
| 205 | 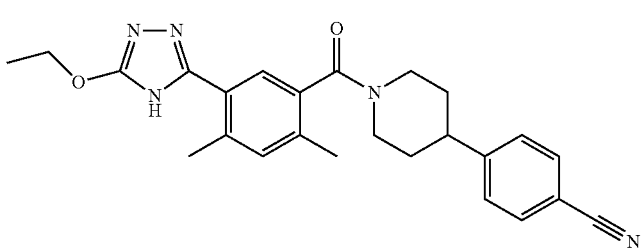 [SMILES: CCOc1nnc(-c2cc(C(=O)N3CCC(c4ccc(C#N)cc4)CC3)c(C)cc2C)[nH]1] | 0.220 |

TABLE 1-continued

| ID | Structure | FASN IC50 (μM) |
|---|---|---|
| 206 | 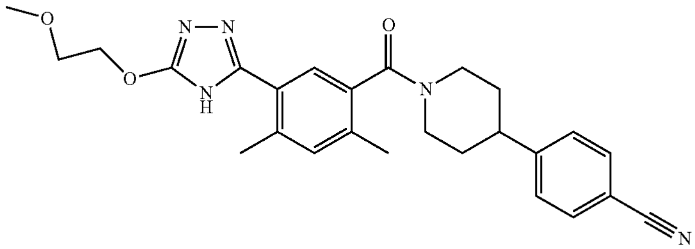 [SMILES: COCCOc1nnc(-c2cc(C(=O)N3CCC(c4ccc(C#N)cc4)CC3)c(C)cc2C)[nH]1] | 0.320 |
| 207 | 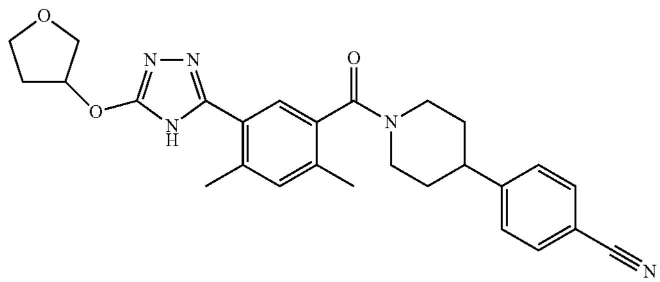 | 0.300 |
| 208 | 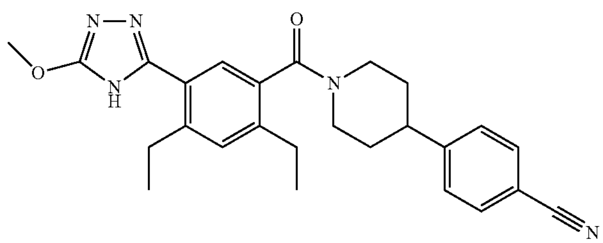 [SMILES: CCc1cc(CC)c(-c2nnc(OC)[nH]2)cc1C(=O)N1CCC(c2ccc(C#N)cc2)CC1] | 0.100 |
| 209 | 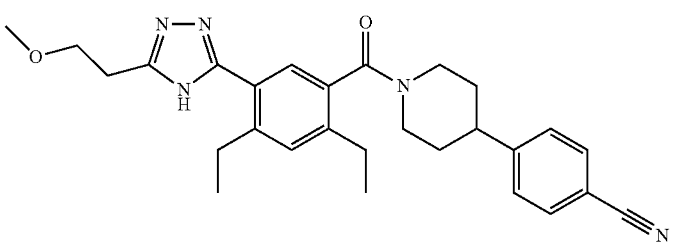 [SMILES: CCc1cc(CC)c(-c2nnc(CCOC)[nH]2)cc1C(=O)N1CCC(c2ccc(C#N)cc2)CC1] | 0.105 |
| 210 | 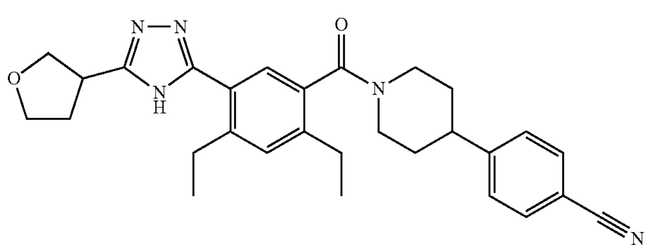 [SMILES: CCc1cc(CC)c(-c2nnc(C3CCOC3)[nH]2)cc1C(=O)N1CCC(c2ccc(C#N)cc2)CC1] | 0.310 |
| 211 | 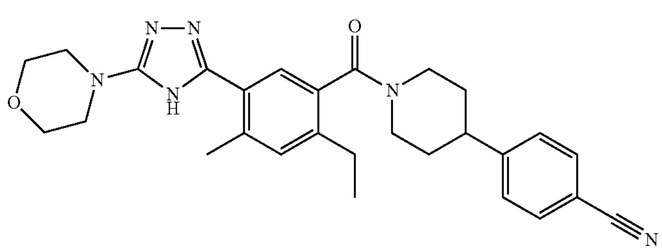 [SMILES: CCc1cc(C)c(-c2nnc(N3CCOCC3)[nH]2)cc1C(=O)N1CCC(c2ccc(C#N)cc2)CC1] | 0.830 |

TABLE 1-continued
| ID | Structure | FASN IC50 (μM) |
|---|---|---|
| 212 | 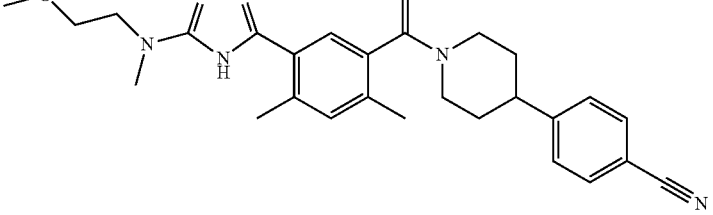 | 7.190 |
| 213 | 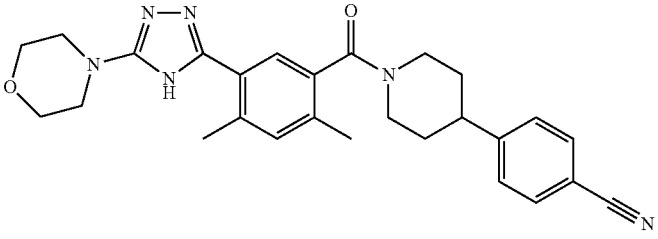 [SMILES: Cc1cc(C)c(-c2nnc(N3CCOCC3)[nH]2)cc1C(=O)N1CCC(c2ccc(C#N)cc2)CC1] | 0.790 |
| 214 | 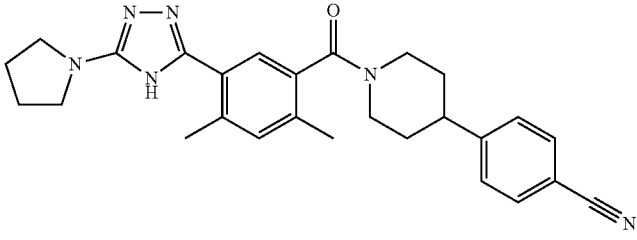 [SMILES: Cc1cc(C)c(-c2nnc(N3CCCC3)[nH]2)cc1C(=O)N1CCC(c2ccc(C#N)cc2)CC1] | 28.760 |
| 215 | 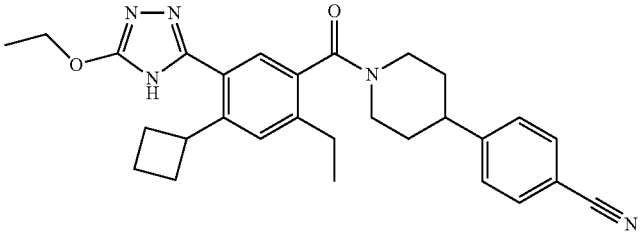 [SMILES: CCOc1nnc(-c2cc(C(=O)N3CCC(c4ccc(C#N)cc4)CC3)c(CC)cc2C2CCC2)[nH]1] | 0.080 |
| 216 | 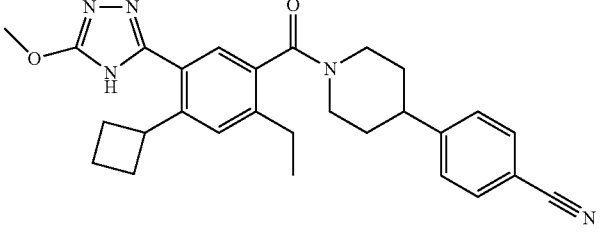 [SMILES: CCc1cc(C2CCC2)c(-c2nnc(OC)[nH]2)cc1C(=O)N1CCC(c2ccc(C#N)cc2)CC1] | 0.090 |
| 217 | 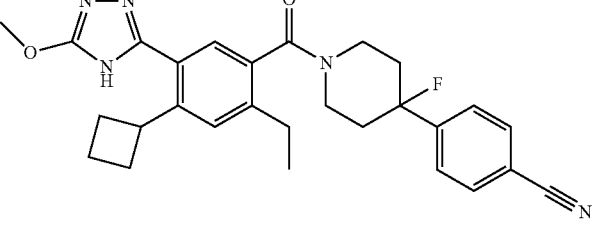 | 0.100 |

TABLE 1-continued

| ID | Structure | FASN IC50 (μM) |
|---|---|---|
| 218 | 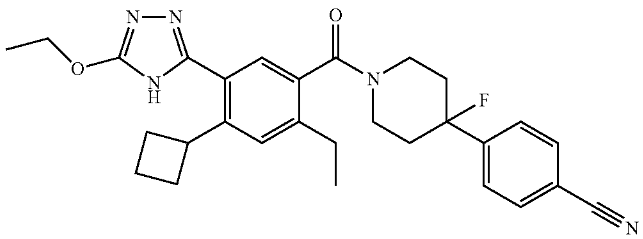 | 0.170 |
| 219 | 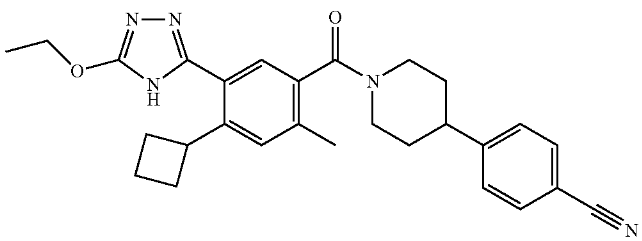 [SMILES: CCOc1nnc(-c2cc(C(=O)N3CCC(c4ccc(C#N)cc4)CC3)c(C)cc2C2CCC2)[nH]1] | 0.085 |
| 220 | 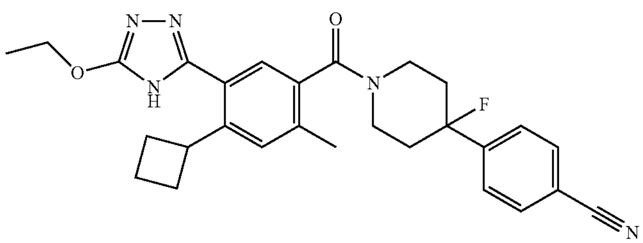 [SMILES: CCOc1nnc(-c2cc(C(=O)N3CCC(F)(c4ccc(C#N)cc4)CC3)c(C)cc2C2CCC2)[nH]1] | 0.055 |
| 221 | 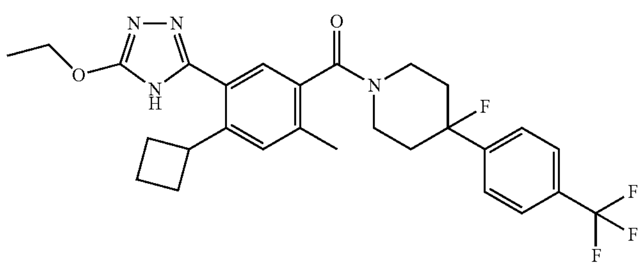 [SMILES: CCOc1nnc(-c2cc(C(=O)N3CCC(F)(c4ccc(C(F)(F)F)cc4)CC3)c(C)cc2C2CCC2)[nH]1] | 0.250 |
| 222 | 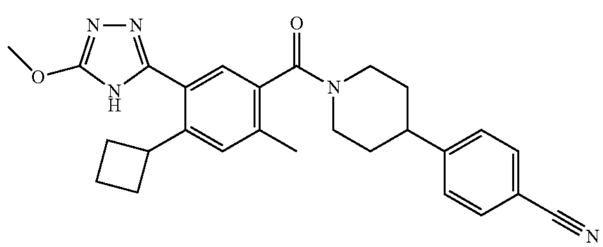 [SMILES: COc1nnc(-c2cc(C(=O)N3CCC(c4ccc(C#N)cc4)CC3)c(C)cc2C2CCC2)[nH]1] | 0.065 |
| 223 | 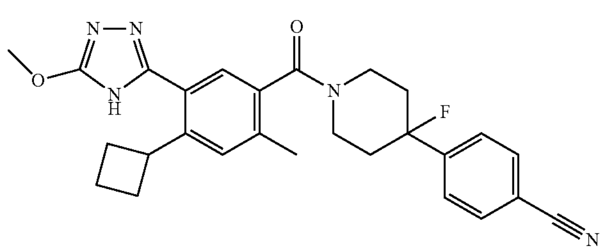 [SMILES: COc1nnc(-c2cc(C(=O)N3CCC(F)(c4ccc(C#N)cc4)CC3)c(C)cc2C2CCC2)[nH]1] | 0.030 |

TABLE 1-continued

| ID | Structure | FASN IC50 (μM) |
|---|---|---|
| 224 | 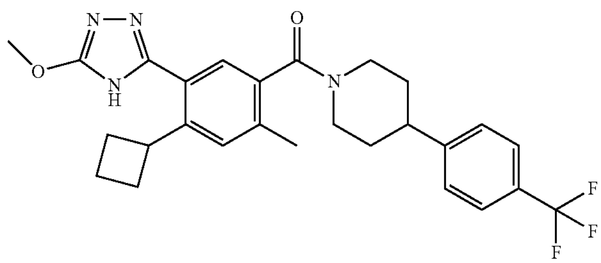 [SMILES: COc1nnc(-c2cc(C(=O)N3CCC(c4ccc(C(F)(F)F)cc4)CC3)c(C)cc2C2CCC2)[nH]1] | 0.160 |
| 225 | 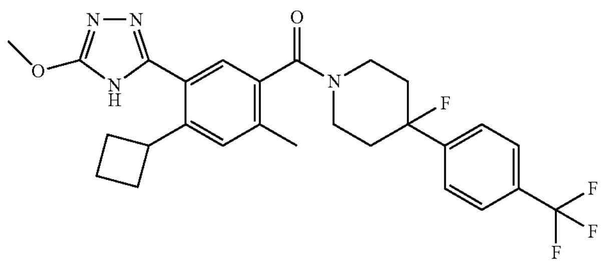 [SMILES: COc1nnc(-c2cc(C(=O)N3CCC(F)(c4ccc(C(F)(F)F)cc4)CC3)c(C)cc2C2CCC2)[nH]1] | 0.140 |
| 226 | 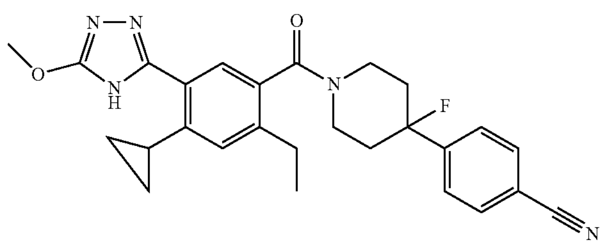 [SMILES: CCc1cc(C2CC2)c(-c2nnc(OC)[nH]2)cc1C(=O)N1CCC(F)(c2ccc(C#N)cc2)CC1] | 0.055 |
| 227 | 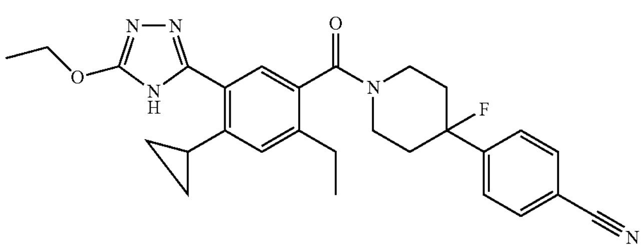 [SMILES: CCOc1nnc(-c2cc(C(=O)N3CCC(F)(c4ccc(C#N)cc4)CC3)c(CC)cc2C2CC2)[nH]1] | 0.070 |
| 228 | 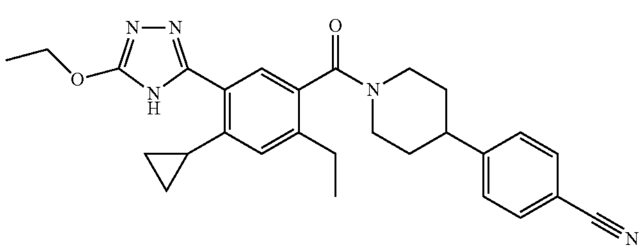 | 0.110 |
| 229 | 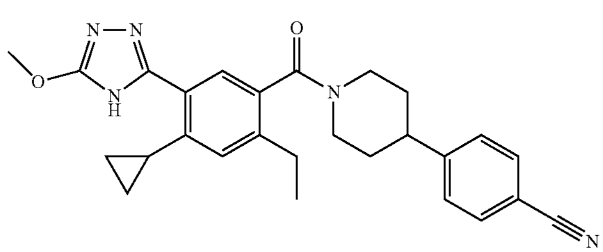 [SMILES: CCc1cc(C2CC2)c(-c2nnc(OC)[nH]2)cc1C(=O)N1CCC(c2ccc(C#N)cc2)CC1] | 0.090 |

TABLE 1-continued

| ID | Structure | FASN IC50 (μM) |
|---|---|---|
| 230 | 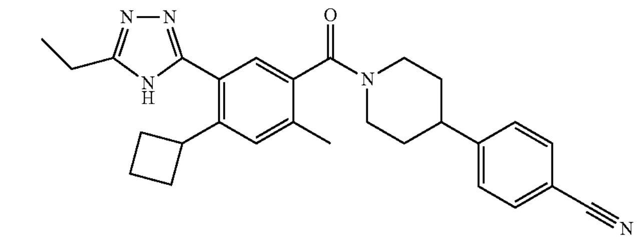 | 30.990 |
| 231 | 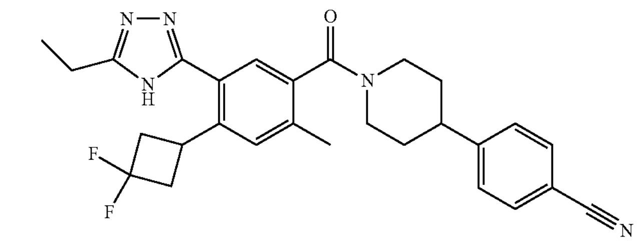 [SMILES: CCc1nnc(-c2cc(C(=O)N3CCC(c4ccc(C#N)cc4)CC3)c(C)cc2C2CC(F)(F)C2)[nH]1] | 0.300 |
| 232 | 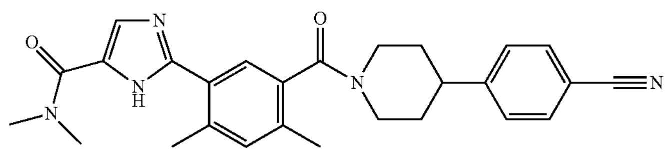 [SMILES: Cc1cc(C)c(-c2ncc(C(=O)N(C)C)[nH]2)cc1C(=O)N1CCC(c2ccc(C#N)cc2)CC1] | 0.650 |
| 233 | 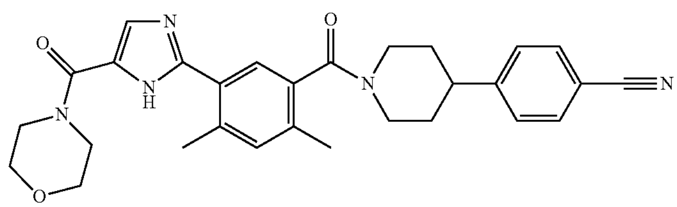 [SMILES: Cc1cc(C)c(-c2ncc(C(=O)N3CCOCC3)[nH]2)cc1C(=O)N1CCC(c2ccc(C#N)cc2)CC1] | 1.630 |
| 234 | 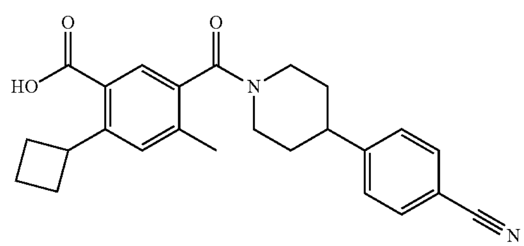 [SMILES: Cc1cc(C2CCC2)c(C(=O)O)cc1C(=O)N1CCC(c2ccc(C#N)cc2)CC1] | >50 |
| 235 | 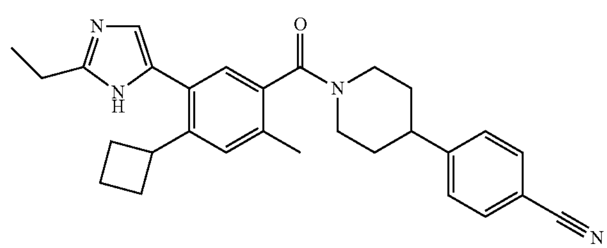 [SMILES: CCc1ncc(-c2cc(C(=O)N3CCC(c4ccc(C#N)cc4)CC3)c(C)cc2C2CCC2)[nH]1] | 0.030 |
| 236 | 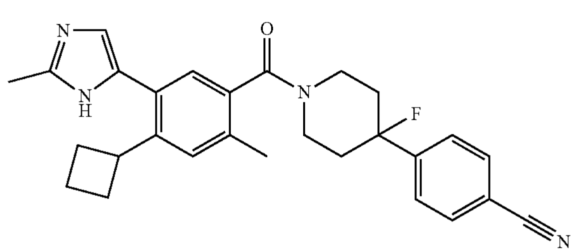 [SMILES: Cc1ncc(-c2cc(C(=O)N3CCC(F)(c4ccc(C#N)cc4)CC3)c(C)cc2C2CCC2)[nH]1] | 0.060 |

TABLE 1-continued

| ID | Structure | FASN IC50 (μM) |
|---|---|---|
| 237 | 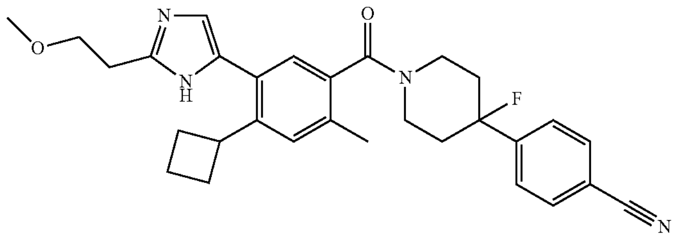 [SMILES: COCCc1ncc(-c2cc(C(=O)N3CCC(F)(c4ccc(C#N)cc4)CC3)c(C)cc2C2CCC2)[nH]1] | 0.080 |
| 238 | 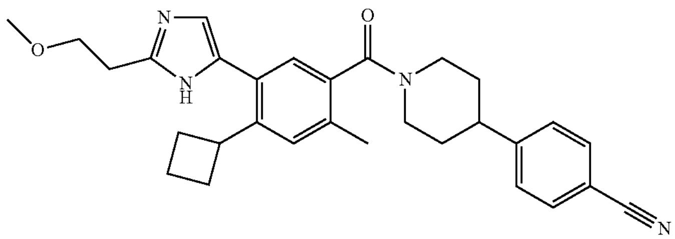 [SMILES: COCCc1ncc(-c2cc(C(=O)N3CCC(c4ccc(C#N)cc4)CC3)c(C)cc2C2CCC2)[nH]1] | 0.100 |
| 239 | 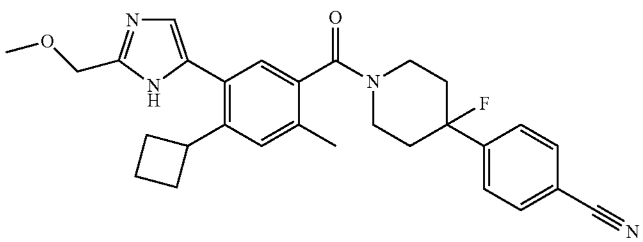 [SMILES: COCc1ncc(-c2cc(C(=O)N3CCC(F)(c4ccc(C#N)cc4)CC3)c(C)cc2C2CCC2)[nH]1] | 0.050 |
| 240 | 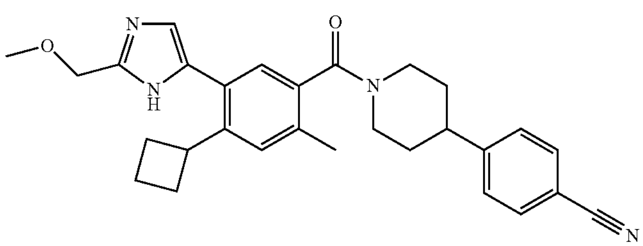 [SMILES: COCc1ncc(-c2cc(C(=O)N3CCC(c4ccc(C#N)cc4)CC3)c(C)cc2C2CCC2)[nH]1] | 0.050 |
| 241 | 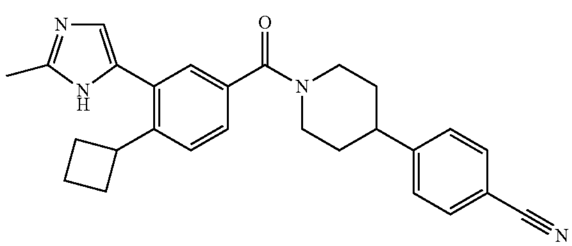 [SMILES: Cc1ncc(-c2cc(C(=O)N3CCC(c4ccc(C#N)cc4)CC3)ccc2C2CCC2)[nH]1] | 0.120 |
| 242 | 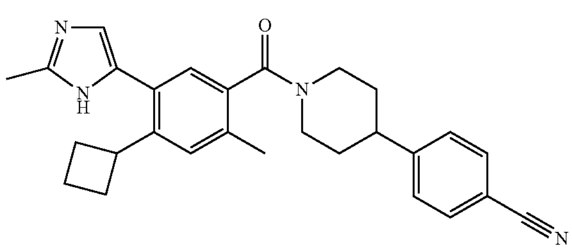 [SMILES: Cc1ncc(-c2cc(C(=O)N3CCC(c4ccc(C#N)cc4)CC3)c(C)cc2C2CCC2)[nH]1] | 0.050 |

TABLE 1-continued

| ID | Structure | FASN IC50 (μM) |
|---|---|---|
| 243 | 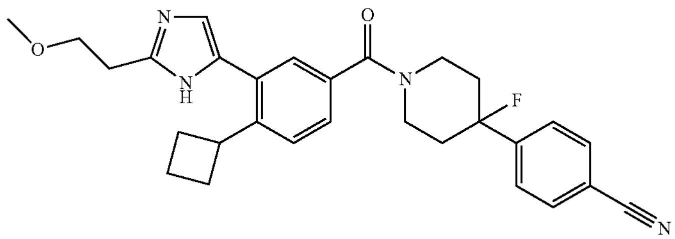 | 0.120 |
| 244 | 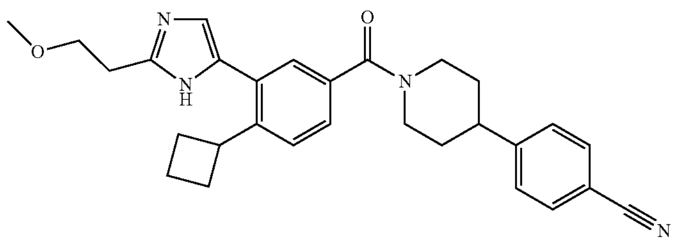 [SMILES: COCCc1ncc(-c2cc(C(=O)N3CCC(c4ccc(C#N)cc4)CC3)ccc2C2CCC2)[nH]1] | 0.220 |
| 245 | 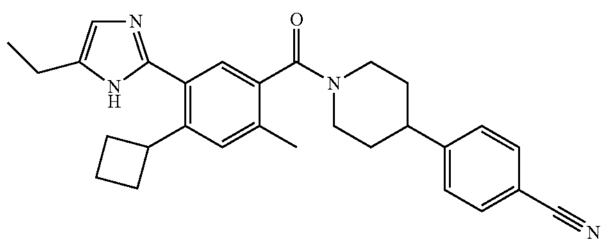 [SMILES: CCc1cnc(-c2cc(C(=O)N3CCC(c4ccc(C#N)cc4)CC3)c(C)cc2C2CCC2)[nH]1] | 0.020 |
| 246 | 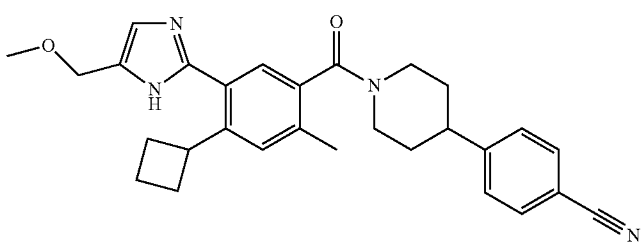 [SMILES: COCc1cnc(-c2cc(C(=O)N3CCC(c4ccc(C#N)cc4)CC3)c(C)cc2C2CCC2)[nH]1] | 0.050 |
| 247 | 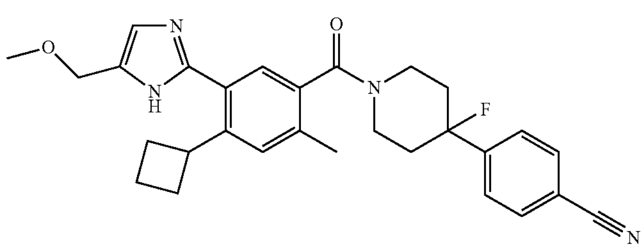 [SMILES: COCc1cnc(-c2cc(C(=O)N3CCC(F)(c4ccc(C#N)cc4)CC3)c(C)cc2C2CCC2)[nH]1] | 0.020 |
| 248 | 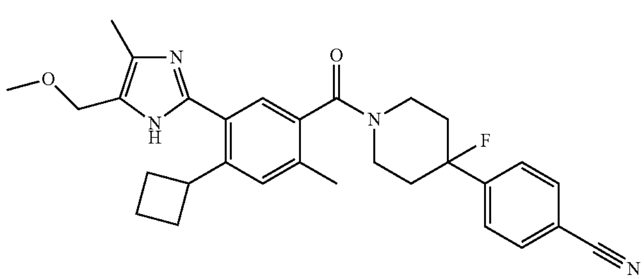 [SMILES: COCc1[nH]c(-c2cc(C(=O)N3CCC(F)(c4ccc(C#N)cc4)CC3)c(C)cc2C2CCC2)nc1C] | 0.060 |

TABLE 1-continued
| ID | Structure | FASN IC50 (μM) |
|---|---|---|
| 249 | 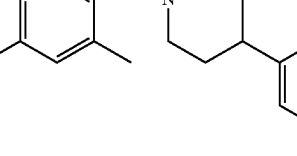 | 0.070 |
| 250 | 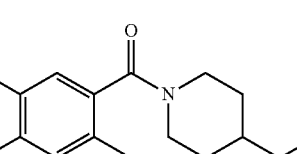 | 0.030 |
| 251 | 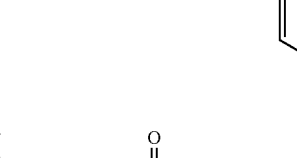 | 0.580 |
| 252 | 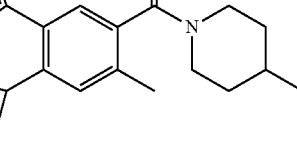 | 0.180 |
| 253 | 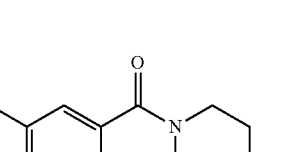 | 0.090 |
| 254 | 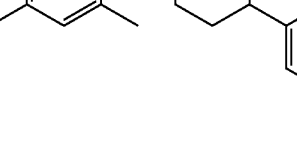 | 0.090 |

TABLE 1-continued

| ID | Structure | FASN IC50 (μM) |
|---|---|---|
| 255 | 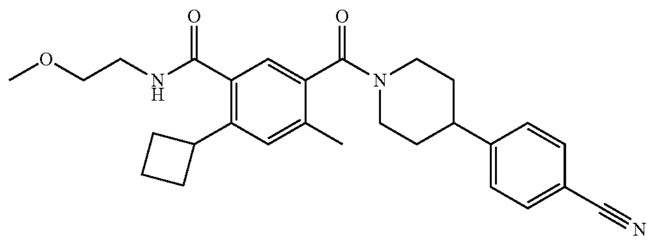 [SMILES: COCCNC(=O)c1cc(C(=O)N2CCC(c3ccc(C#N)cc3)CC2)c(C)cc1C1CCC1] | 0.410 |
| 256 | 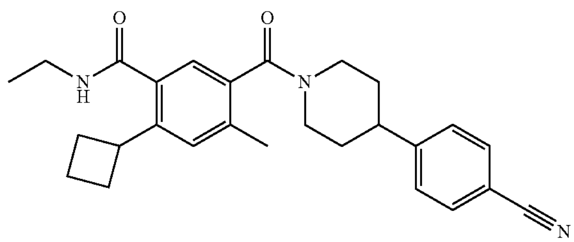 [SMILES: CCNC(=O)c1cc(C(=O)N2CCC(c3ccc(C#N)cc3)CC2)c(C)cc1C1CCC1] | 0.090 |
| 257 | Abs | 0.580 |
| 258 | 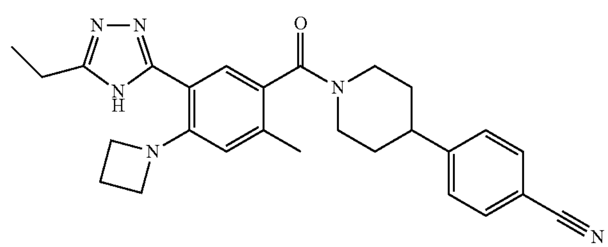 [SMILES: CCc1nnc(-c2cc(C(=O)N3CCC(c4ccc(C#N)cc4)CC3)c(C)cc2N2CCC2)[nH]1] | 0.150 |
| 259 | 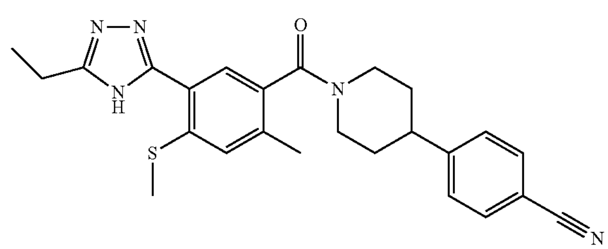 [SMILES: CCc1nnc(-c2cc(C(=O)N3CCC(c4ccc(C#N)cc4)CC3)c(C)cc2SC)[nH]1] | 1.330 |
| 260 | 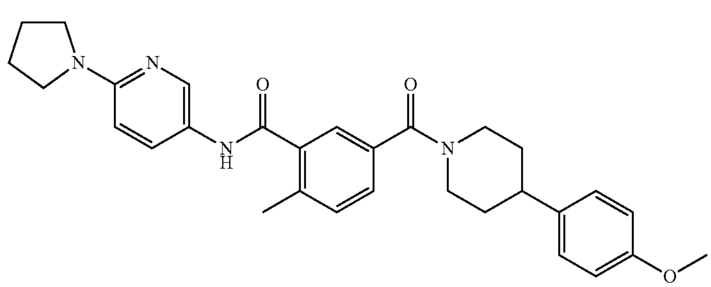 [SMILES: COc1ccc(C2CCN(C(=O)c3ccc(C)c(C(=O)Nc4ccc(N5CCCC5)nc4)c3)CC2)cc1] | 3.500 |

TABLE 1-continued

| ID | Structure | FASN IC50 (μM) |
|---|---|---|
| 261 | 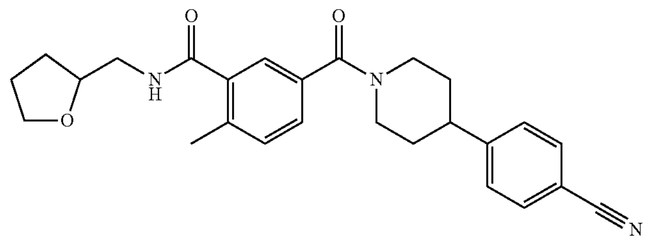 [SMILES: Cc1ccc(C(=O)N2CCC(c3ccc(C#N)cc3)CC2)cc1C(=O)NCC1CCCO1] | 21.750 |
| 262 | 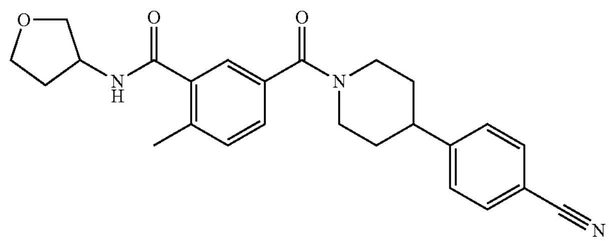 [SMILES: Cc1ccc(C(=O)N2CCC(c3ccc(C#N)cc3)CC2)cc1C(=O)NC1CCOC1] | 5.343 |
| 263 | 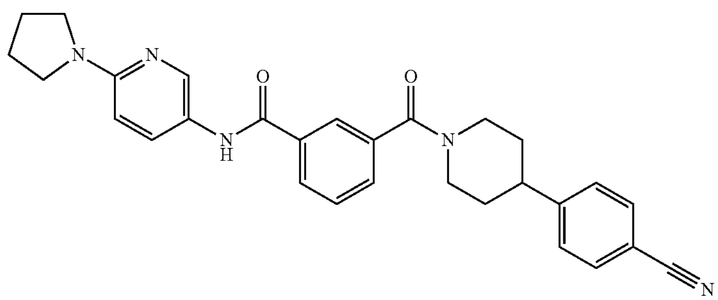 [SMILES: N#Cc1ccc(C2CCN(C(=O)c3cccc(C(=O)Nc4ccc(N5CCCC5)nc4)c3)CC2)cc1] | 0.250 |
| 264 | 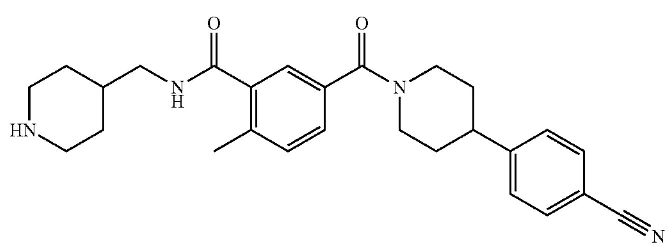 [SMILES: Cc1ccc(C(=O)N2CCC(c3ccc(C#N)cc3)CC2)cc1C(=O)NCC1CCNCC1] | >50 |
| 265 | 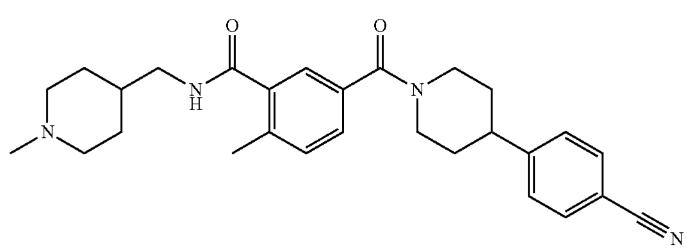 [SMILES: Cc1ccc(C(=O)N2CCC(c3ccc(C#N)cc3)CC2)cc1C(=O)NCC1CCN(C)CC1] | >50 |
| 266 | 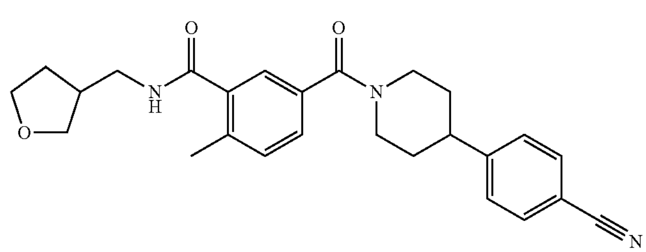 [SMILES: Cc1ccc(C(=O)N2CCC(c3ccc(C#N)cc3)CC2)cc1C(=O)NCC1CCOC1] | >50 |

TABLE 1-continued

| ID | Structure | FASN IC50 (μM) |
|---|---|---|
| 267 | 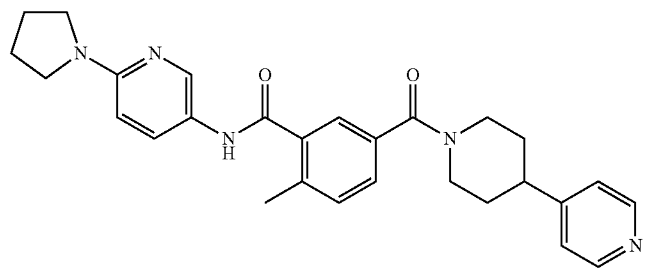 [SMILES: Cc1ccc(C(=O)N2CCC(c3ccncc3)CC2)cc1C(=O)Nc1ccc(N2CCCC2)nc1] | 30.260 |
| 268 | 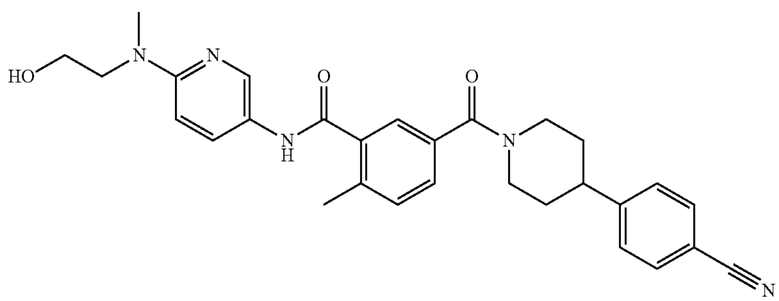 [SMILES: Cc1ccc(C(=O)N2CCC(c3ccc(C#N)cc3)CC2)cc1C(=O)Nc1ccc(N(C)CCO)nc1] | 0.390 |
| 269 | 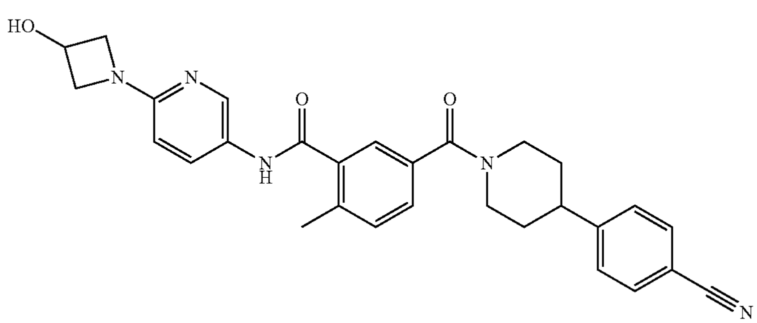 [SMILES: Cc1ccc(C(=O)N2CCC(c3ccc(C#N)cc3)CC2)cc1C(=O)Nc1ccc(N2CC(O)C2)nc1] | 1.350 |
| 270 | 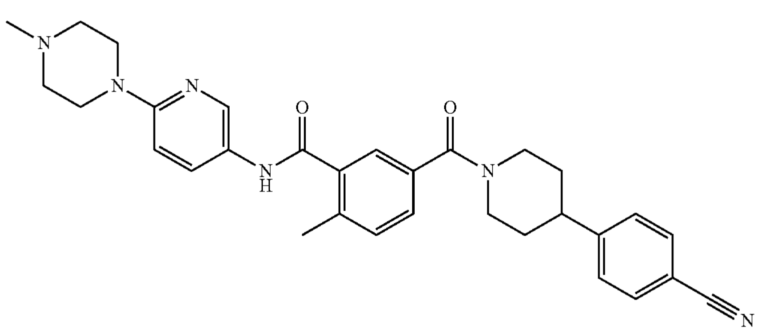 [SMILES: Cc1ccc(C(=O)N2CCC(c3ccc(C#N)cc3)CC2)cc1C(=O)Nc1ccc(N2CCN(C)CC2)nc1] | 1.980 |

TABLE 1-continued

| ID | Structure | FASN IC50 (μM) |
|----|-----------|----------------|
| 271 | 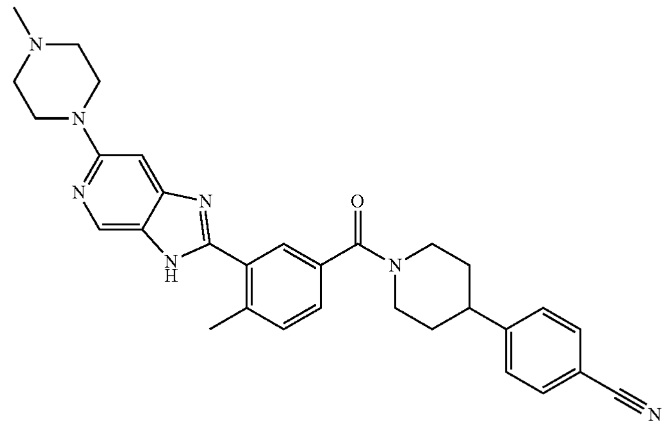 [SMILES: Cc1ccc(C(=O)N2CCC(c3ccc(C#N)cc3)CC2)cc1-c1nc2cc(N3CCN(C)CC3)ncc2[nH]1] | 0.520 |
| 272 | 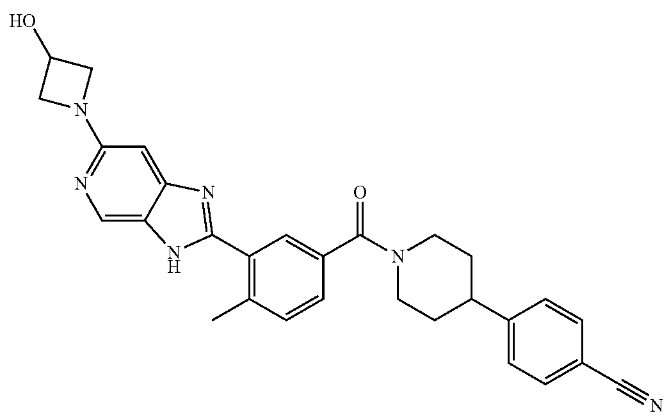 [SMILES: Cc1ccc(C(=O)N2CCC(c3ccc(C#N)cc3)CC2)cc1-c1nc2cc(N3CC(O)C3)ncc2[nH]1] | 0.300 |
| 273 | 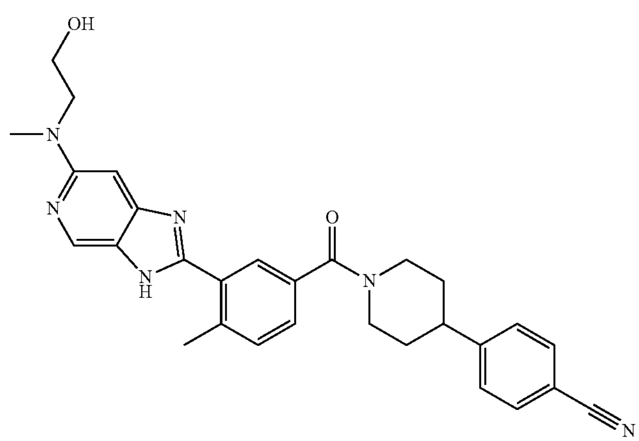 [SMILES: Cc1ccc(C(=O)N2CCC(c3ccc(C#N)cc3)CC2)cc1-c1nc2cc(N(C)CCO)ncc2[nH]1] | 0.060 |
| 274 | 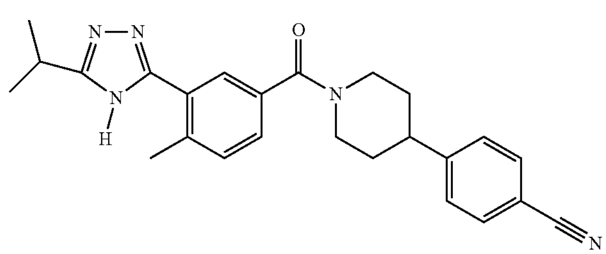 [SMILES: Cc1ccc(C(=O)N2CCC(c3ccc(C#N)cc3)CC2)cc1-c1nnc(C(C)C)[nH]1] | 2.345 |

TABLE 1-continued
| ID | Structure | FASN IC50 (μM) |
|---|---|---|
| 275 | 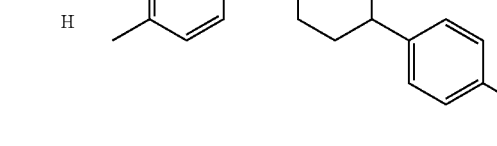 | 2.245 |
| 276 |  Abs | 9.060 |
| 277 | 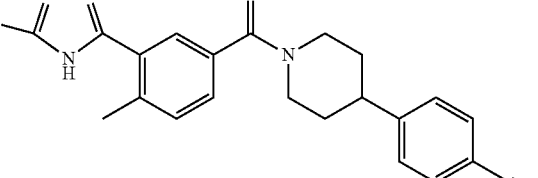 Abs | 11.680 |
| 278 | 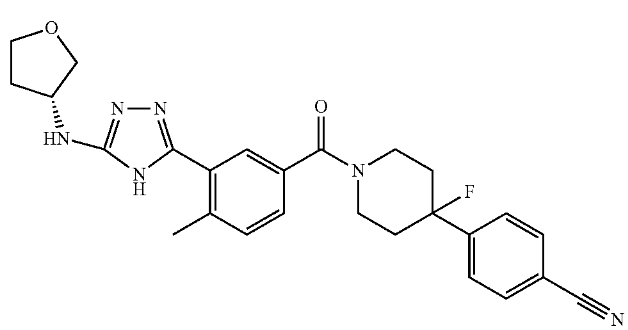 [SMILES: Cc1ccc(C(=O)N2CCC(F)(c3ccc(C#N)cc3)CC2)cc1-c1nnc(N[C@@H]2CCOC2)[nH]1] | 1.750 |

TABLE 1-continued

| ID | Structure | FASN IC50 (μM) |
|---|---|---|
| 279 | 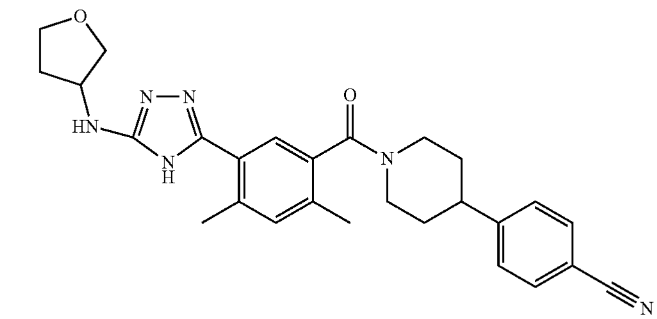 [SMILES: Cc1cc(C)c(-c2nnc(NC3CCOC3)[nH]2)cc1C(=O)N1CCC(c2ccc(C#N)cc2)CC1] | 0.330 |
| 280 | 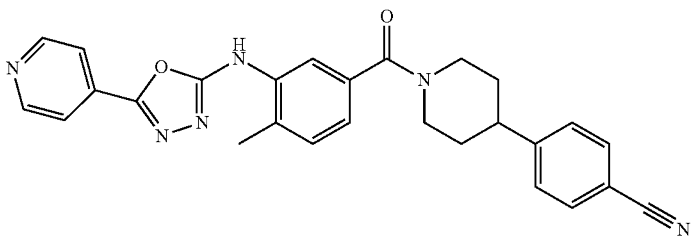 [SMILES: Cc1ccc(C(=O)N2CCC(c3ccc(C#N)cc3)CC2)cc1Nc1nnc(-c2ccncc2)o1] | 0.700 |
| 281 | 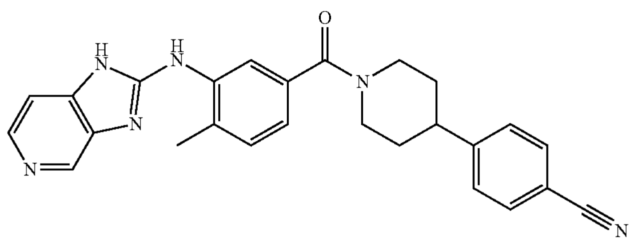 [SMILES: Cc1ccc(C(=O)N2CCC(c3ccc(C#N)cc3)CC2)cc1Nc1nc2cnccc2[nH]1] | 42.300 |
| 282 | 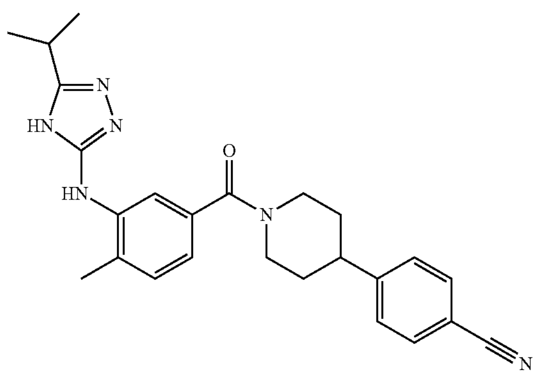 [SMILES: Cc1ccc(C(=O)N2CCC(c3ccc(C#N)cc3)CC2)cc1Nc1nnc(C(C)C)[nH]1] | 30.090 |
| 283 | 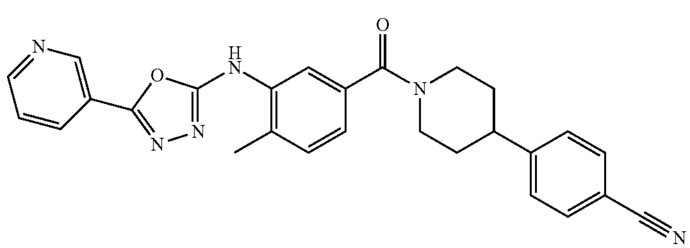 [SMILES: Cc1ccc(C(=O)N2CCC(c3ccc(C#N)cc3)CC2)cc1Nc1nnc(-c2cccnc2)o1] | 1.000 |

TABLE 1-continued

| ID | Structure | FASN IC50 (μM) |
|---|---|---|
| 284 | 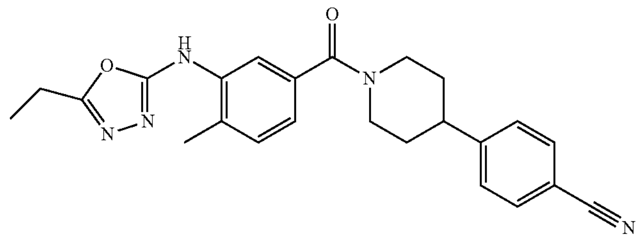 [SMILES: CCc1nnc(Nc2cc(C(=O)N3CCC(c4ccc(C#N)cc4)CC3)ccc2C)o1] | 1.005 |
| 285 | 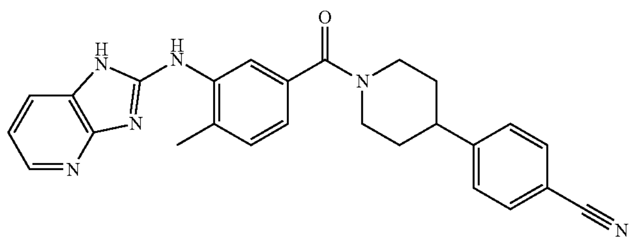 [SMILES: Cc1ccc(C(=O)N2CCC(c3ccc(C#N)cc3)CC2)cc1Nc1nc2ncccc2[nH]1] | >50 |
| 286 | 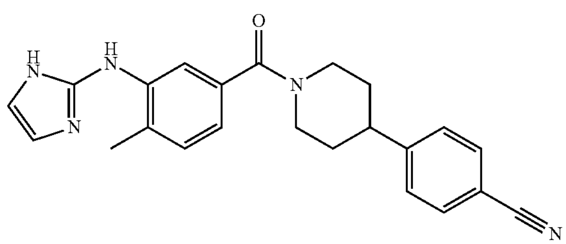 [SMILES: Cc1ccc(C(=O)N2CCC(c3ccc(C#N)cc3)CC2)cc1Nc1ncc[nH]1] | >50 |
| 287 | 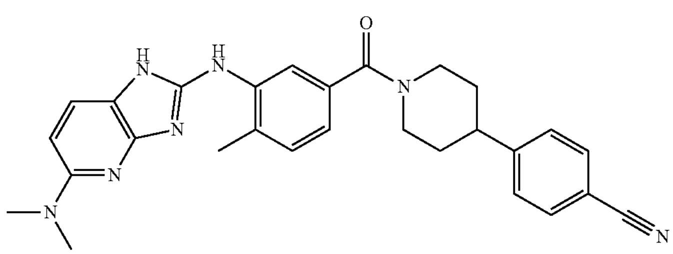 [SMILES: Cc1ccc(C(=O)N2CCC(c3ccc(C#N)cc3)CC2)cc1Nc1nc2nc(N(C)C)ccc2[nH]1] | >50 |
| 288 | 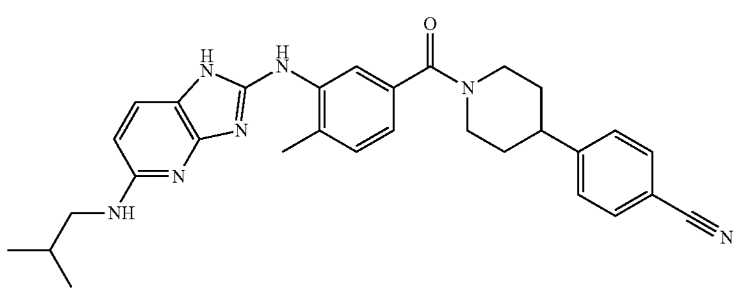 [SMILES: Cc1ccc(C(=O)N2CCC(c3ccc(C#N)cc3)CC2)cc1Nc1nc2nc(NCC(C)C)ccc2[nH]1] | |
| 289 | 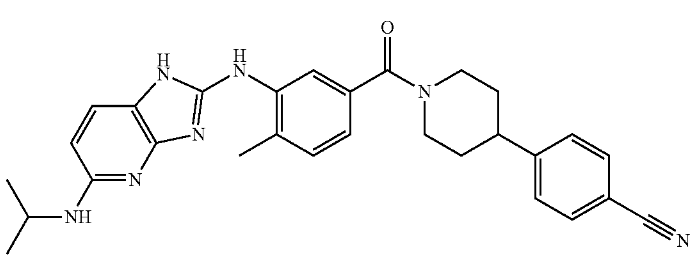 [SMILES: Cc1ccc(C(=O)N2CCC(c3ccc(C#N)cc3)CC2)cc1Nc1nc2nc(NC(C)C)ccc2[nH]1] | 32.733 |

| ID | Structure | FASN IC50 (μM) |
|---|---|---|
| 290 | 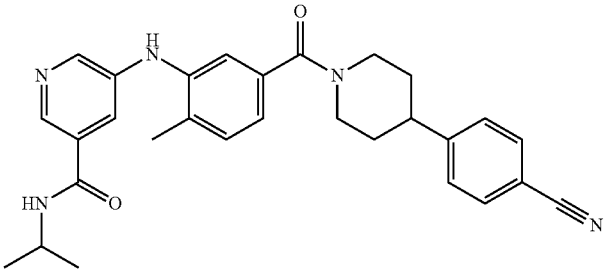 [SMILES: Cc1ccc(C(=O)N2CCC(c3ccc(C#N)cc3)CC2)cc1Nc1cncc(C(=O)NC(C)C)c1] | 0.470 |
| 291 | 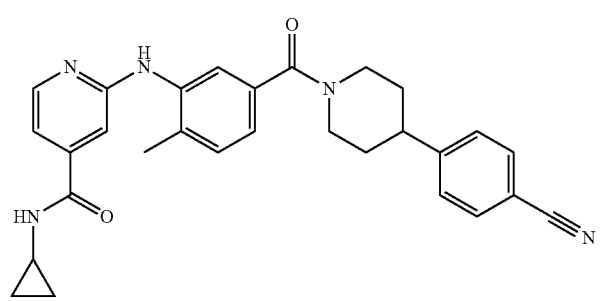 [SMILES: Cc1ccc(C(=O)N2CCC(c3ccc(C#N)cc3)CC2)cc1Nc1cc(C(=O)NC2CC2)ccn1] | 0.370 |
| 292 | 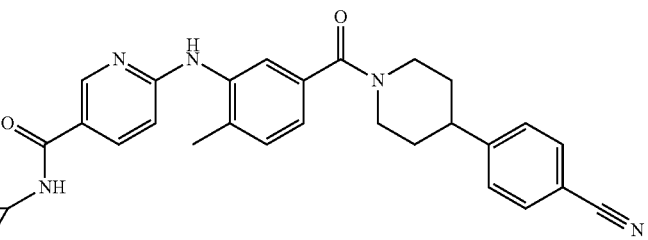 | 0.270 |
| 293 | 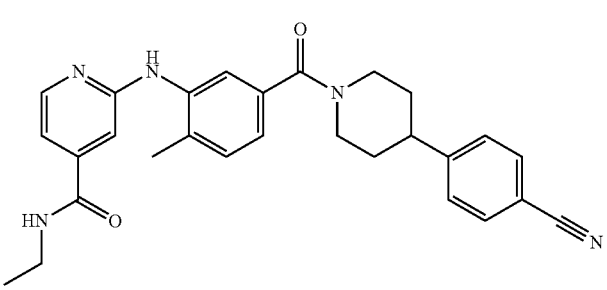 [SMILES: CCNC(=O)c1ccnc(Nc2cc(C(=O)N3CCC(c4ccc(C#N)cc4)CC3)ccc2C)c1] | 1.080 |
| 294 | 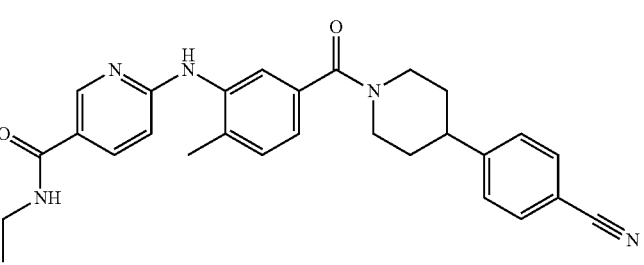 [SMILES: CCNC(=O)c1ccc(Nc2cc(C(=O)N3CCC(c4ccc(C#N)cc4)CC3)ccc2C)nc1] | — |

TABLE 1-continued

| ID | Structure | FASN IC50 (μM) |
|---|---|---|
| 295 | 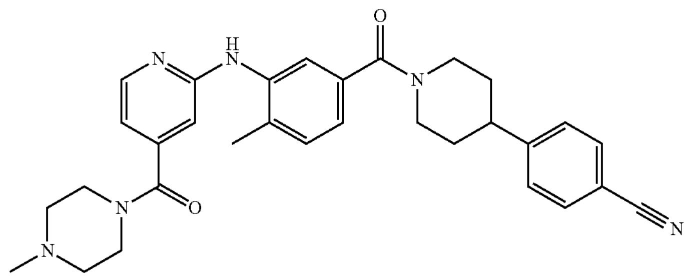 [SMILES: Cc1ccc(C(=O)N2CCC(c3ccc(C#N)cc3)CC2)cc1Nc1cc(C(=O)N2CCN(C)CC2)ccn1] | 3.820 |
| 296 | 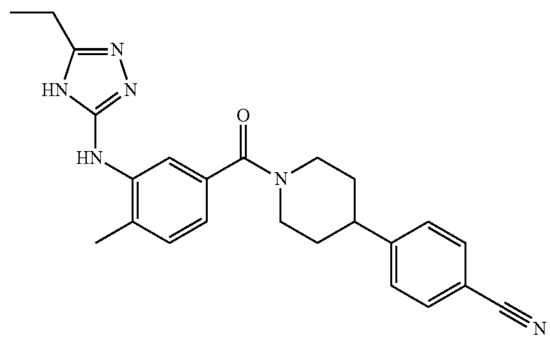 [SMILES: CCc1nnc(Nc2cc(C(=O)N3CCC(c4ccc(C#N)cc4)CC3)ccc2C)[nH]1] | 3.250 |
| 297 | 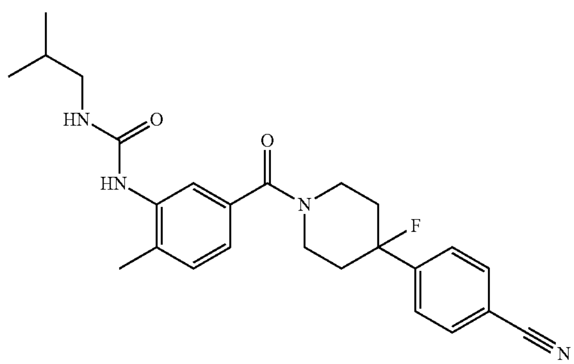 [SMILES: Cc1ccc(C(=O)N2CCC(F)(c3ccc(C#N)cc3)CC2)cc1NC(=O)NCC(C)C] | 0.025 |
| 298 | 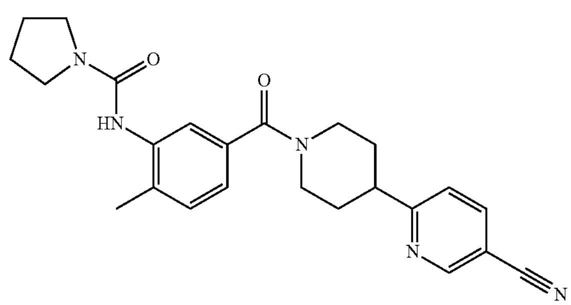 [SMILES: Cc1ccc(C(=O)N2CCC(c3ccc(C#N)cn3)CC2)cc1NC(=O)N1CCCC1] | |
| 299 | 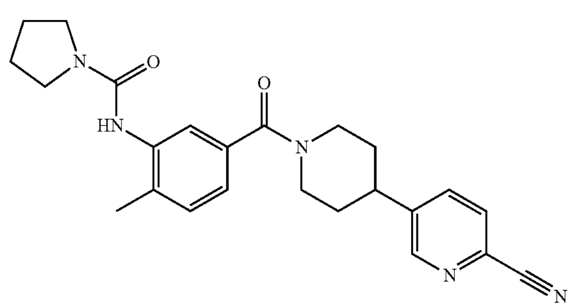 [SMILES: Cc1ccc(C(=O)N2CCC(c3ccc(C#N)nc3)CC2)cc1NC(=O)N1CCCC1] | |

TABLE 1-continued

| ID | Structure | FASN IC50 (μM) |
|---|---|---|
| 300 | 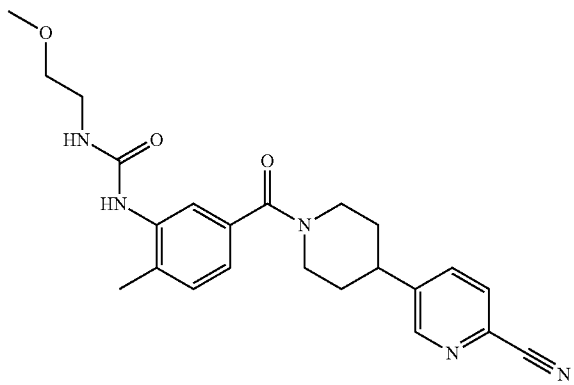 [SMILES: COCCNC(=O)Nc1cc(C(=O)N2CCC(c3ccc(C#N)nc3)CC2)ccc1C] | |
| 301 | 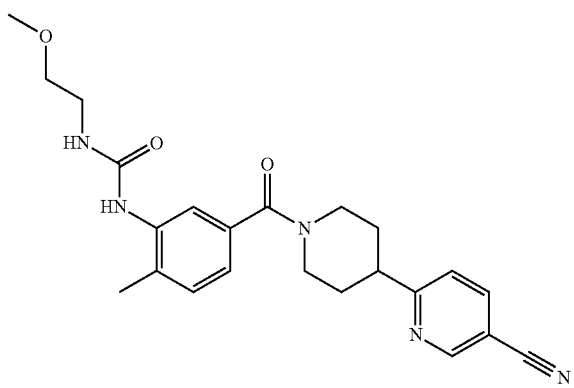 [SMILES: COCCNC(=O)Nc1cc(C(=O)N2CCC(c3ccc(C#N)cn3)CC2)ccc1C] | |
| 302 | 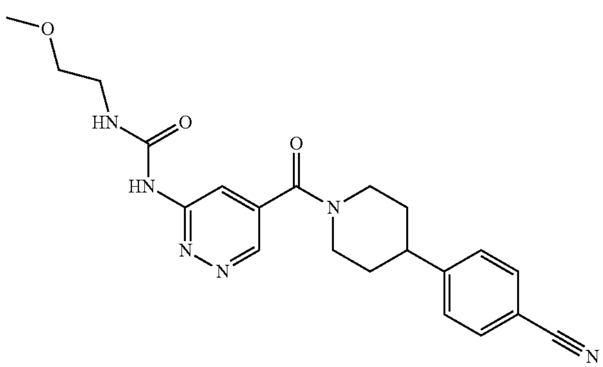 [SMILES: COCCNC(=O)Nc1cc(C(=O)N2CCC(c3ccc(C#N)cc3)CC2)cnn1] | >50 |
| 303 | 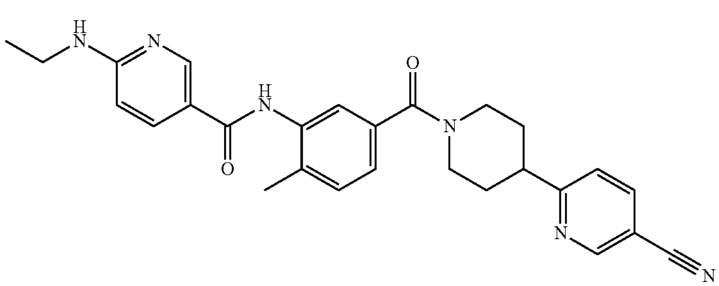 [SMILES: CCNc1ccc(C(=O)Nc2cc(C(=O)N3CCC(c4ccc(C#N)cn4)CC3)ccc2C)cn1] | |

US 9,809,591 B2
653 654
TABLE 1-continued
| ID | Structure | FASN IC50 (μM) |
|---|---|---|
| 304 | 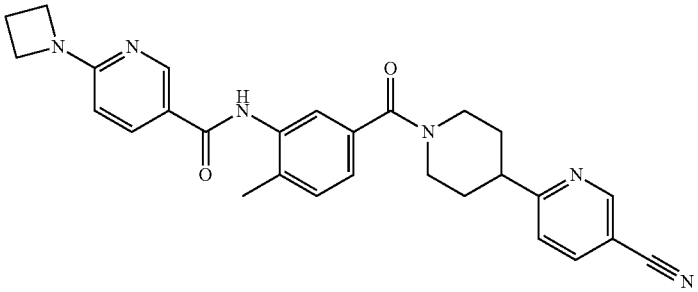 [SMILES: Cc1ccc(C(=O)N2CCC(c3ccc(C#N)cn3)CC2)cc1NC(=O)c1ccc(N2CCC2)nc1] | 0.680 |
| 305 | 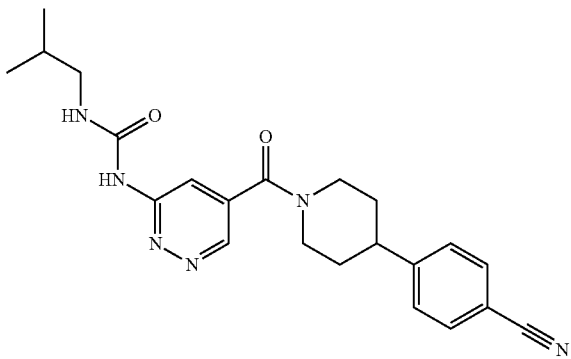 [SMILES: CC(C)CNC(=O)Nc1cc(C(=O)N2CCC(c3ccc(C#N)cc3)CC2)cnn1] | >50 |
| 306 | 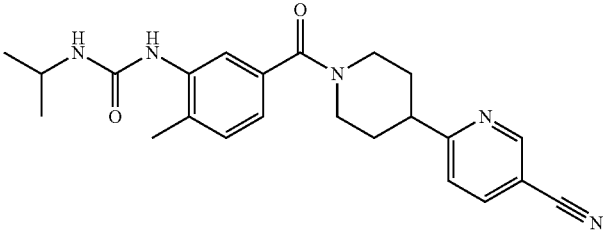 [SMILES: Cc1ccc(C(=O)N2CCC(c3ccc(C#N)cn3)CC2)cc1NC(=O)NC(C)C] | 2.900 |
| 307 | 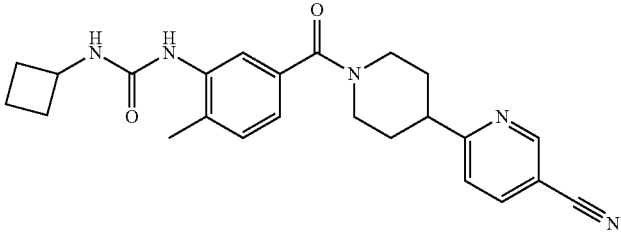 [SMILES: Cc1ccc(C(=O)N2CCC(c3ccc(C#N)cn3)CC2)cc1NC(=O)NC1CCC1] | 5.360 |
| 308 | 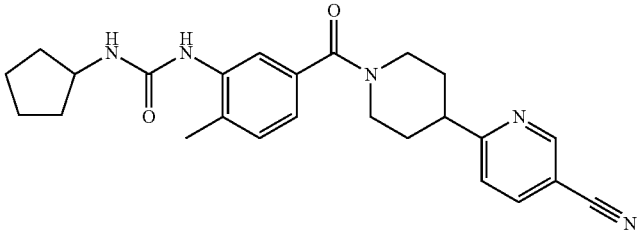 [SMILES: Cc1ccc(C(=O)N2CCC(c3ccc(C#N)cn3)CC2)cc1NC(=O)NC1CCCC1] | 2.750 |

TABLE 1-continued

| ID | Structure | FASN IC50 (μM) |
|---|---|---|
| 309 | 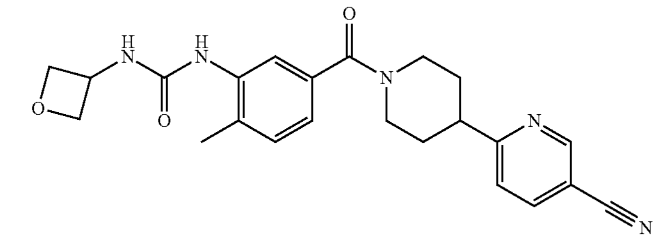 [SMILES: Cc1ccc(C(=O)N2CCC(c3ccc(C#N)cn3)CC2)cc1NC(=O)NC1COC1] | |
| 310 | 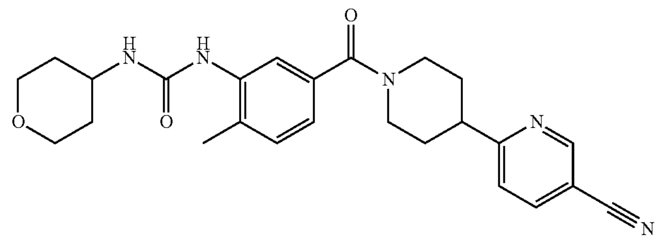 [SMILES: Cc1ccc(C(=O)N2CCC(c3ccc(C#N)cn3)CC2)cc1NC(=O)NC1CCOCC1] | 8.780 |
| 311 | 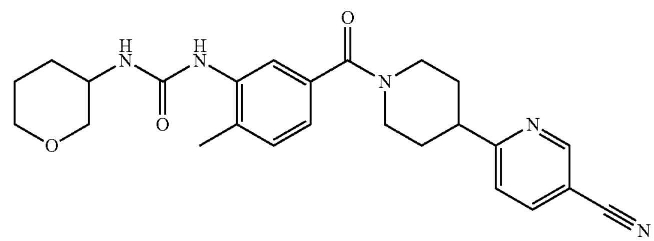 [SMILES: Cc1ccc(C(=O)N2CCC(c3ccc(C#N)cn3)CC2)cc1NC(=O)NC1CCCOC1] | |
| 312 | 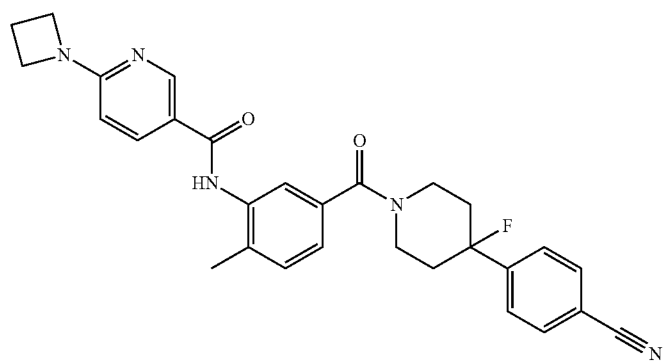 [SMILES: Cc1ccc(C(=O)N2CCC(F)(c3ccc(C#N)cc3)CC2)cc1NC(=O)c1ccc(N2CCC2)nc1] | 0.025 |
| 313 | 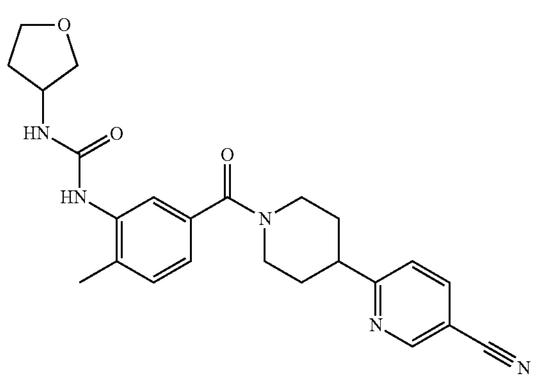 [SMILES: Cc1ccc(C(=O)N2CCC(c3ccc(C#N)cn3)CC2)cc1NC(=O)NC1CCOC1] | 1.630 |

TABLE 1-continued

| ID | Structure | FASN IC50 (μM) |
|---|---|---|
| 314 | 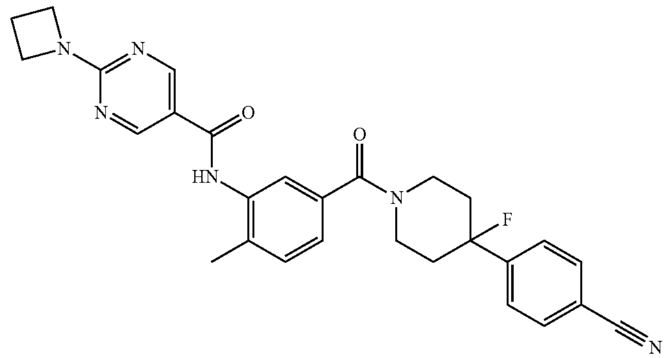 [SMILES: Cc1ccc(C(=O)N2CCC(F)(c3ccc(C#N)cc3)CC2)cc1NC(=O)c1cnc(N2CCC2)nc1] | 0.047 |
| 315 | 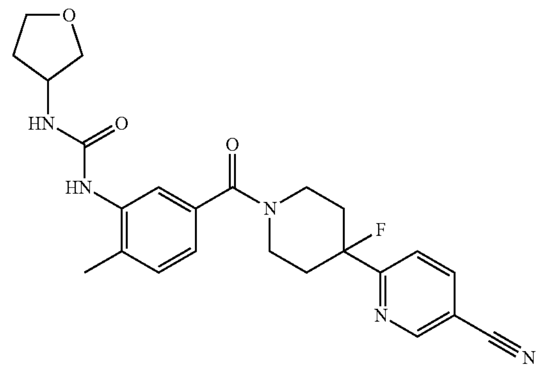 [SMILES: Cc1ccc(C(=O)N2CCC(F)(c3ccc(C#N)cn3)CC2)cc1NC(=O)NC1CCOC1] | 0.267 |
| 316 | (Abs) | 0.690 |
| 317 | 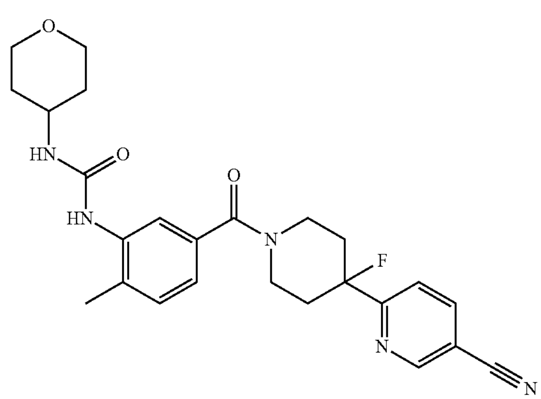 | 1.170 |

TABLE 1-continued

| ID | Structure | FASN IC50 (μM) |
|---|---|---|
| 318 | 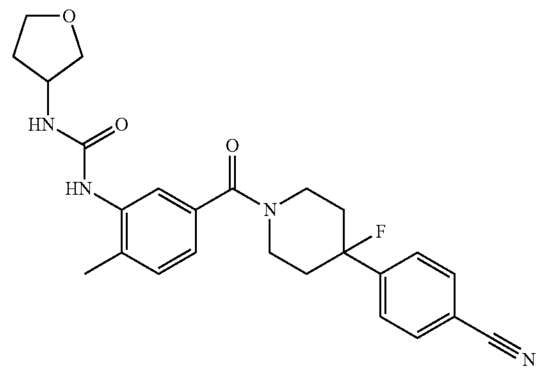 [SMILES: Cc1ccc(C(=O)N2CCC(F)(c3ccc(C#N)cc3)CC2)cc1NC(=O)NC1CCOC1] | 0.037 |
| 319 | 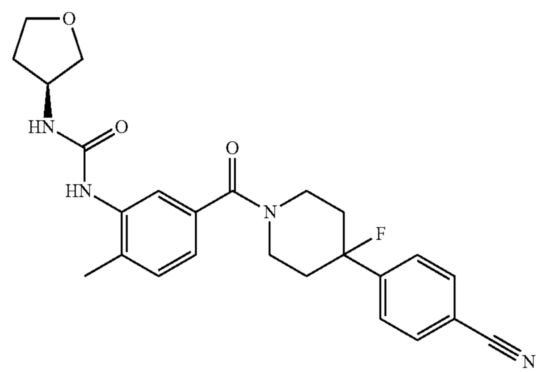 [SMILES: Cc1ccc(C(=O)N2CCC(F)(c3ccc(C#N)cc3)CC2)cc1NC(=O)N[C@H]1CCOC1] | 0.195 |
| 320 | 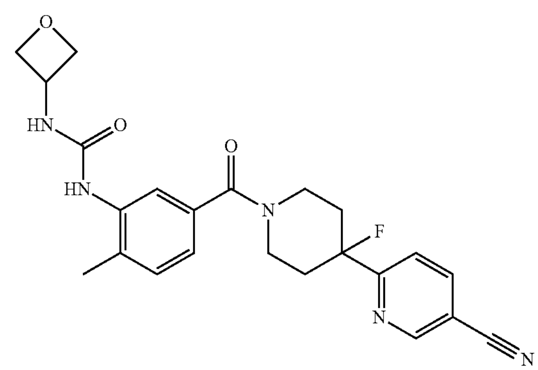 | 1.020 |
| 321 | 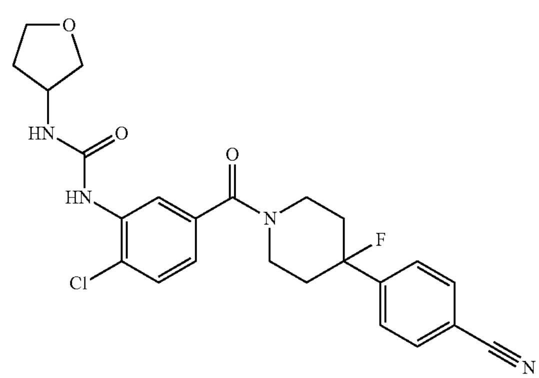 [SMILES: N#Cc1ccc(C2(F)CCN(C(=O)c3ccc(Cl)c(NC(=O)NC4CCOC4)c3)CC2)cc1] | 0.030 |

TABLE 1-continued
| ID | Structure | FASN IC50 (μM) |
|---|---|---|
| 322 | 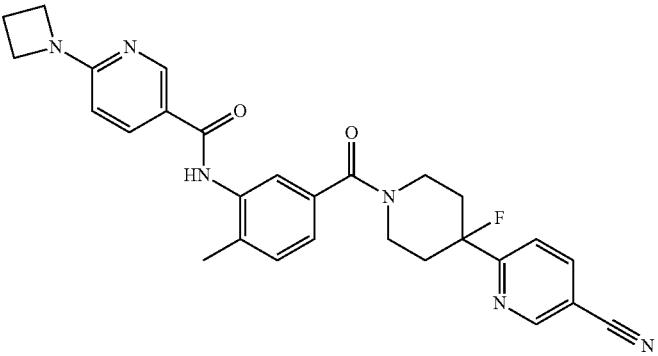 [SMILES: Cc1ccc(C(=O)N2CCC(F)(c3ccc(C#N)cn3)CC2)cc1NC(=O)c1ccc(N2CCC2)nc1] | 0.180 |
| 323 | 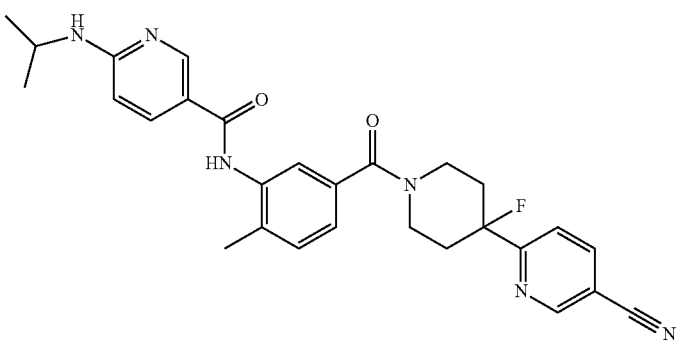 [SMILES: Cc1ccc(C(=O)N2CCC(F)(c3ccc(C#N)cn3)CC2)cc1NC(=O)c1ccc(NC(C)C)nc1] | 0.360 |
| 324 | 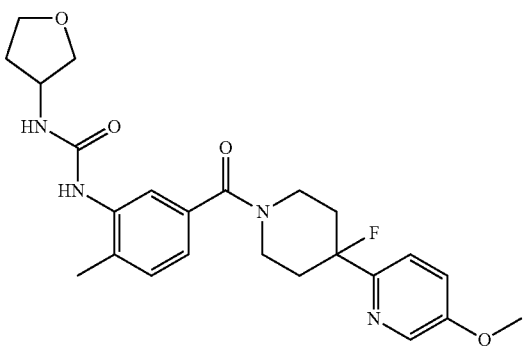 [SMILES: COc1ccc(C2(F)CCN(C(=O)c3ccc(C)c(NC(=O)NC4CCOC4)c3)CC2)nc1] | 1.175 |
| 325 | 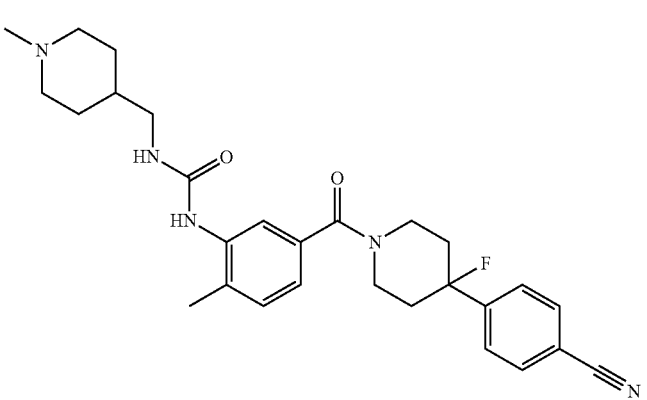 [SMILES: Cc1ccc(C(=O)N2CCC(F)(c3ccc(C#N)cc3)CC2)cc1NC(=O)NCC1CCN(C)CC1] | 0.340 |

TABLE 1-continued
| ID | Structure | FASN IC50 (μM) |
|---|---|---|
| 326 | 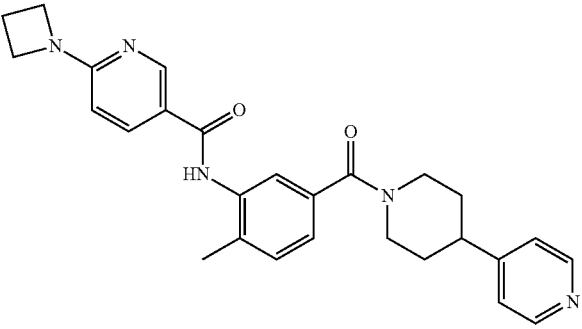 [SMILES: Cc1ccc(C(=O)N2CCC(c3ccncc3)CC2)cc1NC(=O)c1ccc(N2CCC2)nc1] | 2.750 |
| 327 | 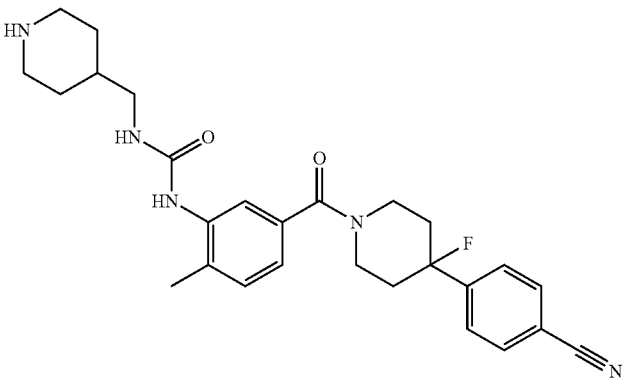 [SMILES: Cc1ccc(C(=O)N2CCC(F)(c3ccc(C#N)cc3)CC2)cc1NC(=O)NCC1CCNCC1] | 0.610 |
| 328 | 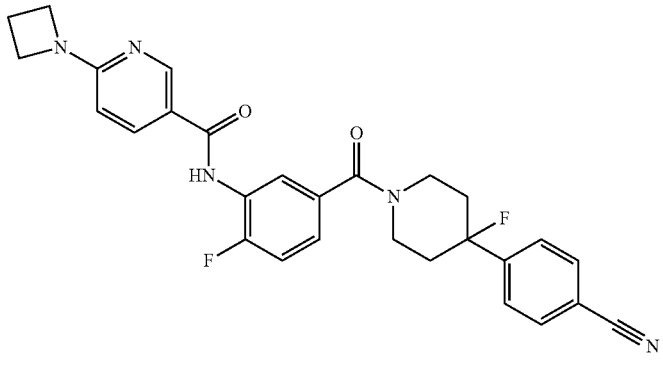 | 0.220 |
| 329 | 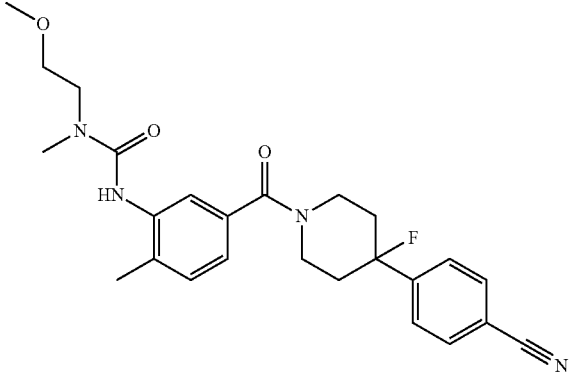 [SMILES: COCCN(C)C(=O)Nc1cc(C(=O)N2CCC(F)(c3ccc(C#N)cc3)CC2)ccc1C] | 8.870 |

TABLE 1-continued
| ID | Structure | FASN IC50 (μM) |
|---|---|---|
| 330 | 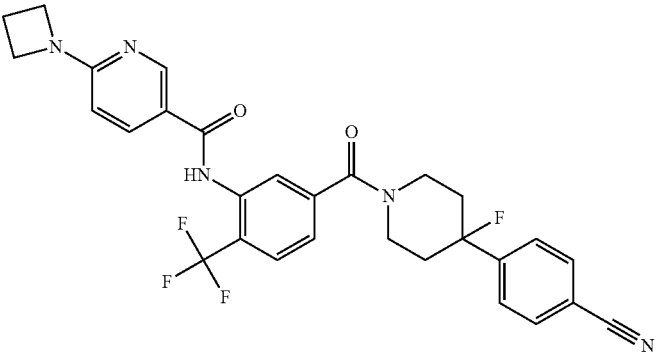 [SMILES: N#Cc1ccc(C2(F)CCN(C(=O)c3ccc(C(F)(F)F)c(NC(=O)c4ccc(N5CCC5)nc4)c3)CC2)cc1] | 0.120 |
| 331 | 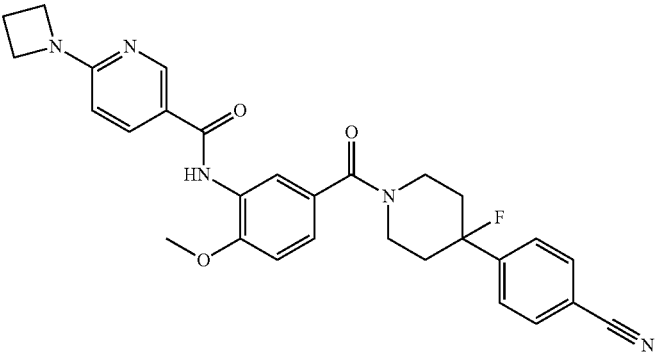 | 0.085 |
| 332 | 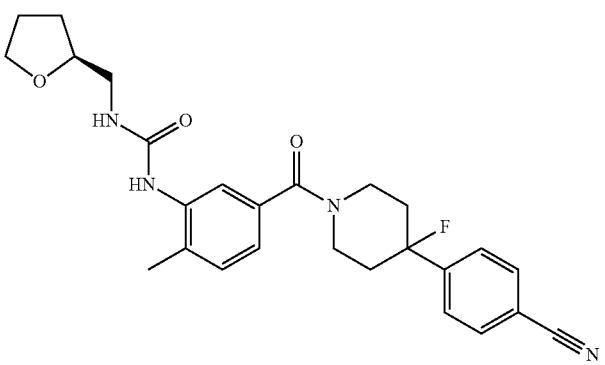 [Abs] | 0.050 |
| 333 | 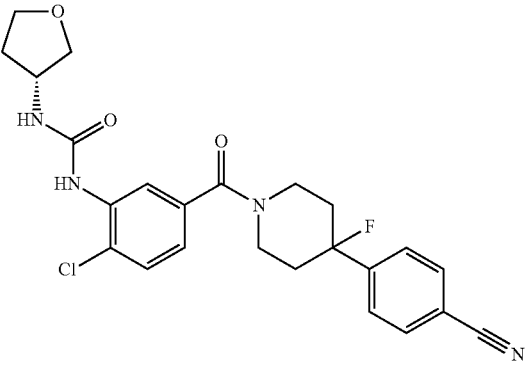 [SMILES: N#Cc1ccc(C2(F)CCN(C(=O)c3ccc(Cl)c(NC(=O)N[C@@H]4CCOC4)c3)CC2)cc1] | |

TABLE 1-continued
| ID | Structure | FASN IC50 (μM) |
|---|---|---|
| 334 | 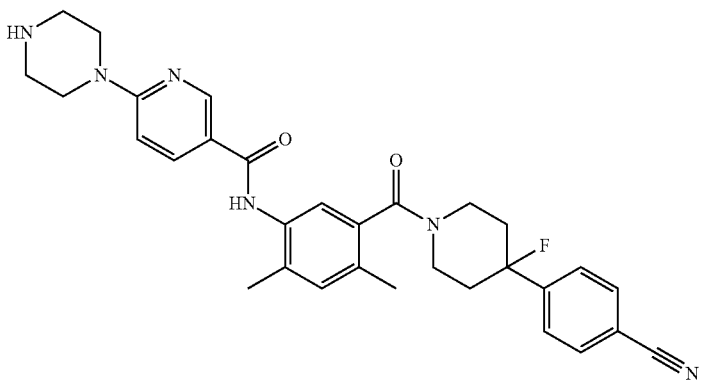 [SMILES: Cc1cc(C)c(C(=O)N2CCC(F)(c3ccc(C#N)cc3)CC2)cc1NC(=O)c1ccc(N2CCNCC2)nc1] | 0.140 |
| 335 | 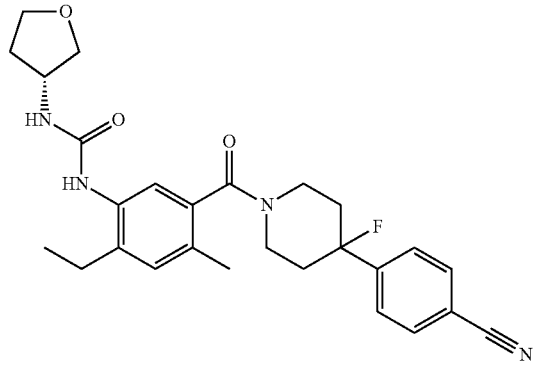 [SMILES: CCc1cc(C)c(C(=O)N2CCC(F)(c3ccc(C#N)cc3)CC2)cc1NC(=O)N[C@@H]1CCOC1] | 0.490 |
| 336 | 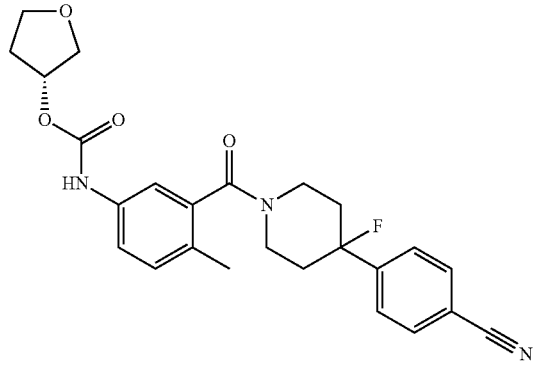 [SMILES: Cc1ccc(NC(=O)O[C@@H]2CCOC2)cc1C(=O)N1CCC(F)(c2ccc(C#N)cc2)CC1] | 0.420 |
| 337 | 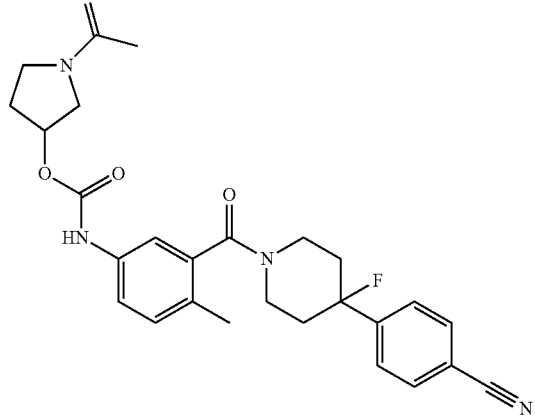 | 0.165 |

TABLE 1-continued

| ID | Structure | FASN IC50 (μM) |
|----|-----------|----------------|
| 338 | Abs | 0.035 |
| 339 | Abs | 0.093 |
| 340 | 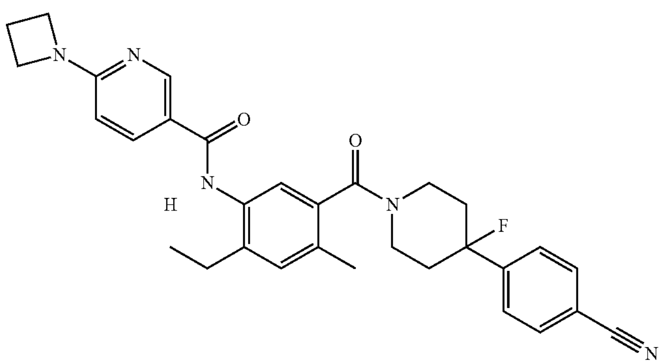 | 0.080 |
| 341 | 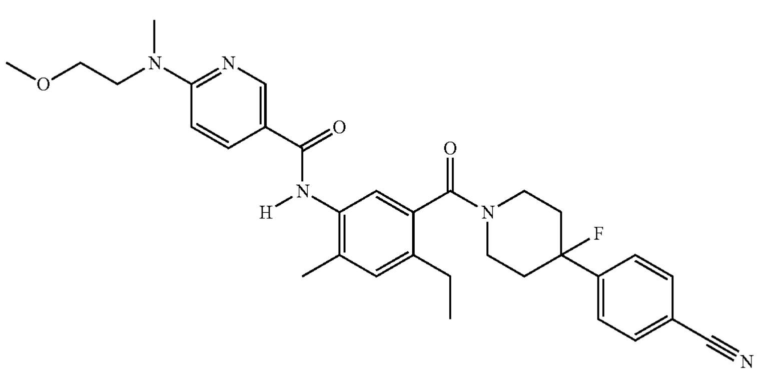 [SMILES: CCc1cc(C)c(NC(=O)c2ccc(N(C)CCOC)nc2)cc1C(=O)N1CCC(F)(c2ccc(C#N)cc2)CC1] | 0.085 |

TABLE 1-continued

| ID | Structure | FASN IC50 (μM) |
|---|---|---|
| 342 | 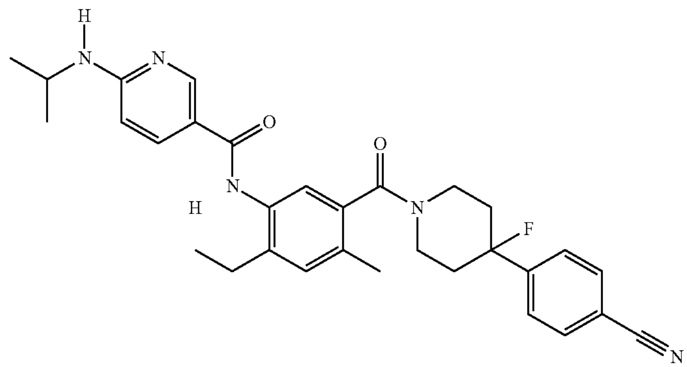 | 0.090 |
| 343 | 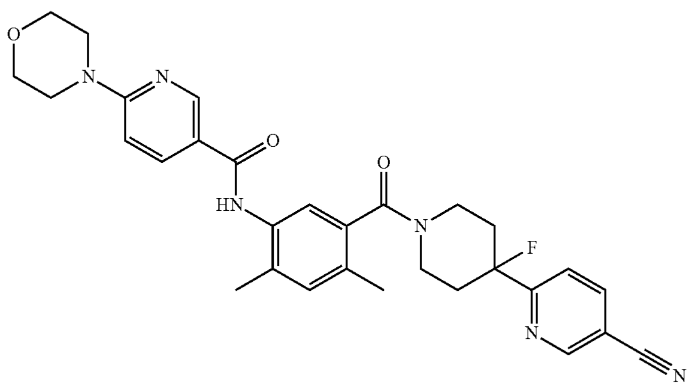 [SMILES: Cc1cc(C)c(C(=O)N2CCC(F)(c3ccc(C#N)cn3)CC2)cc1NC(=O)c1ccc(N2CCOCC2)nc1] | 0.600 |
| 344 | (Abs) | 0.250 |
| 345 | (Abs) | 0.140 |

TABLE 1-continued

| ID | Structure | FASN IC50 (μM) |
|---|---|---|
| 346 | 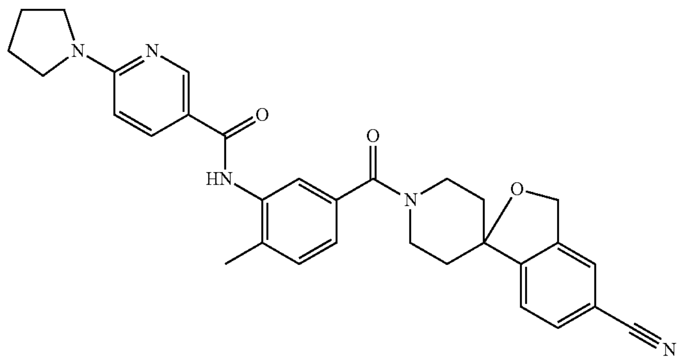 [SMILES: Cc1ccc(C(=O)N2CCC3(CC2)OCc2cc(C#N)ccc23)cc1NC(=O)c1ccc(N2CCCC2)nc1] | 0.330 |
| 347 | 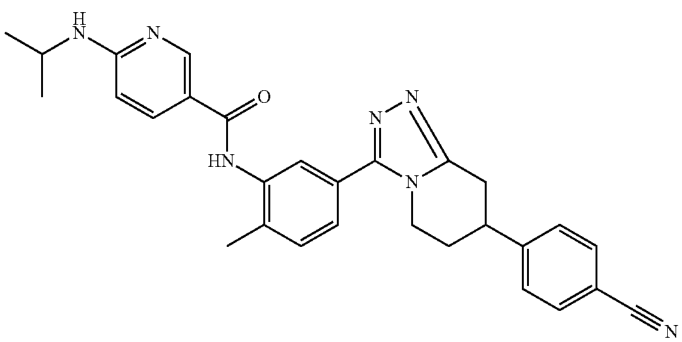 [SMILES: Cc1ccc(-c2nnc3n2CCC(c2ccc(C#N)cc2)C3)cc1NC(=O)c1ccc(NC(C)C)nc1] | 0.300 |
| 348 | 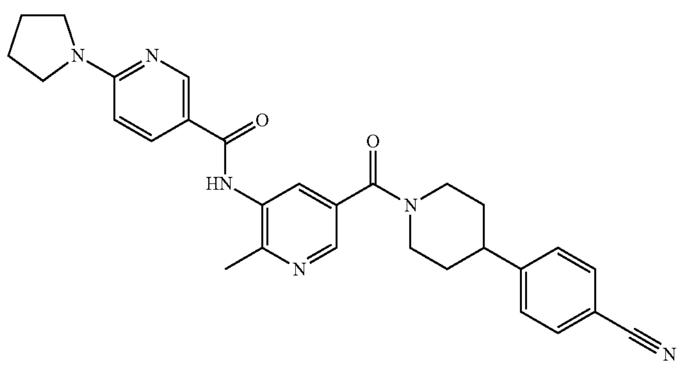 [SMILES: Cc1ncc(C(=O)N2CCC(c3ccc(C#N)cc3)CC2)cc1NC(=O)c1ccc(N2CCCC2)nc1] | 0.455 |
| 349 | 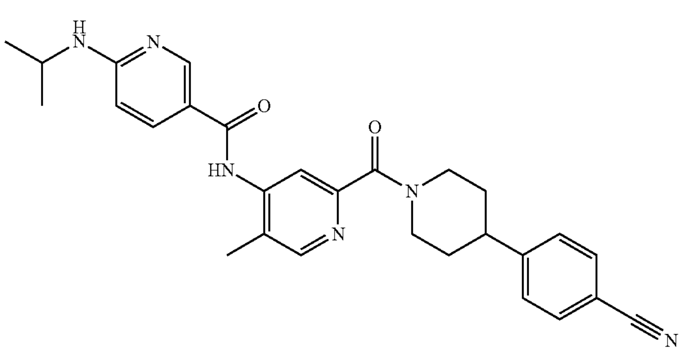 [SMILES: Cc1cnc(C(=O)N2CCC(c3ccc(C#N)cc3)CC2)cc1NC(=O)c1ccc(NC(C)C)nc1] | >50 |

TABLE 1-continued

| ID | Structure | FASN IC50 (μM) |
|---|---|---|
| 350 | 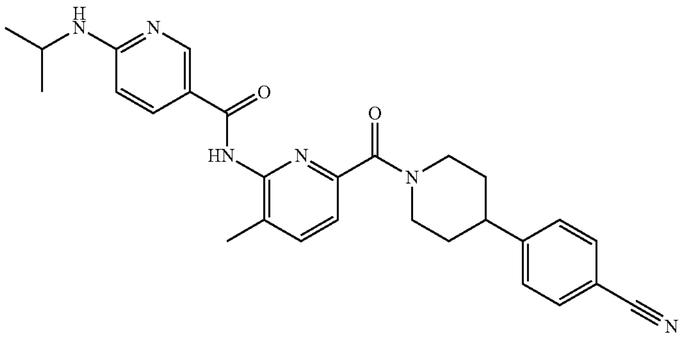 [SMILES: Cc1ccc(C(=O)N2CCC(c3ccc(C#N)cc3)CC2)nc1NC(=O)c1ccc(NC(C)C)nc1] | 32.600 |
| 351 | 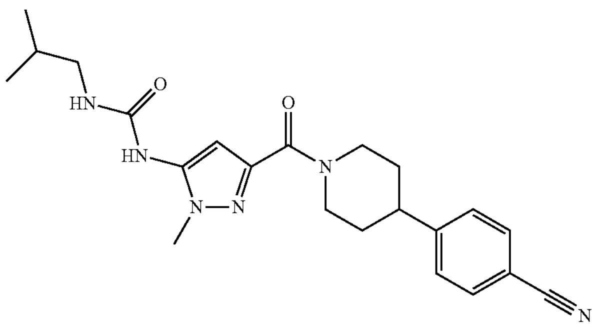 [SMILES: CC(C)CNC(=O)Nc1cc(C(=O)N2CCC(c3ccc(C#N)cc3)CC2)nn1C] | >50 |
| 352 | 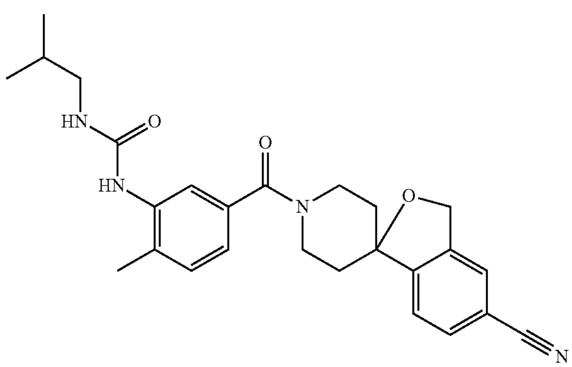 [SMILES: Cc1ccc(C(=O)N2CCC3(CC2)OCc2cc(C#N)ccc23)cc1NC(=O)NCC(C)C] | 0.880 |
| 353 | 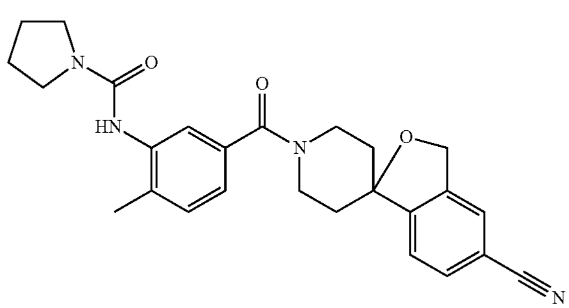 [SMILES: Cc1ccc(C(=O)N2CCC3(CC2)OCc2cc(C#N)ccc23)cc1NC(=O)N1CCCC1] | 18.500 |

TABLE 1-continued
| ID | Structure | FASN IC50 (μM) |
|---|---|---|
| 354 | 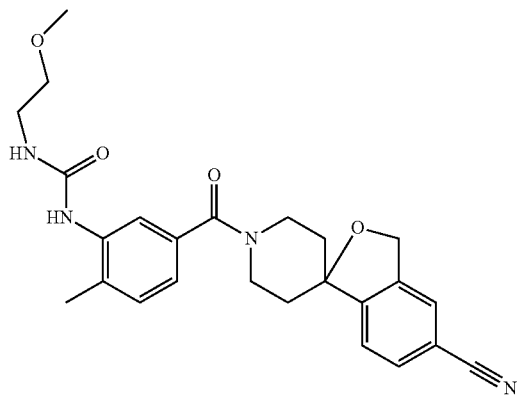 [SMILES: COCCNC(=O)Nc1cc(C(=O)N2CCC3(CC2)OCc2cc(C#N)ccc23)ccc1C] | 0.380 |
| 355 | 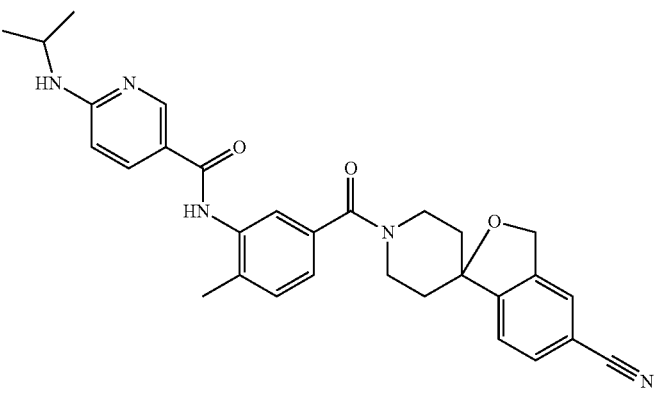 [SMILES: Cc1ccc(C(=O)N2CCC3(CC2)OCc2cc(C#N)ccc23)cc1NC(=O)c1ccc(NC(C)C)nc1] | 0.140 |
| 356 | 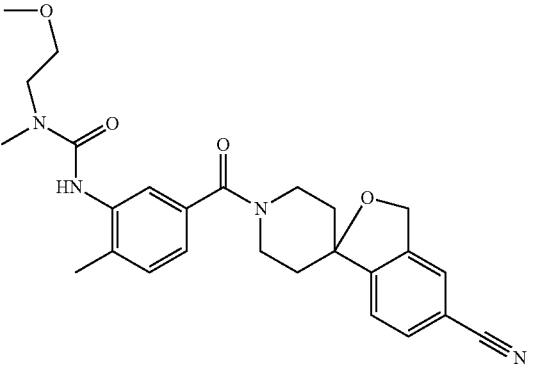 [SMILES: COCCN(C)C(=O)Nc1cc(C(=O)N2CCC3(CC2)OCc2cc(C#N)ccc23)ccc1C] | >50 |
| 357 | 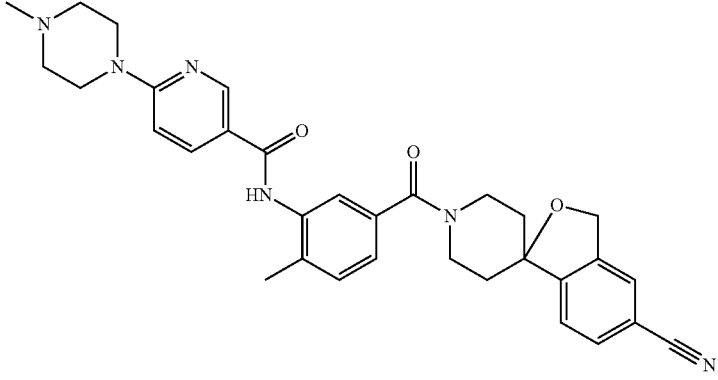 [SMILES: Cc1ccc(C(=O)N2CCC3(CC2)OCc2cc(C#N)ccc23)cc1NC(=O)c1ccc(N2CCN(C)CC2)nc1] | 0.230 |

TABLE 1-continued

| ID | Structure | FASN IC50 (μM) |
|---|---|---|
| 358 | 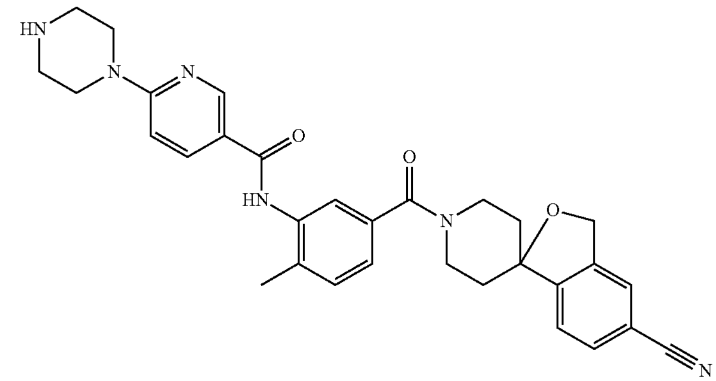 [SMILES: Cc1ccc(C(=O)N2CCC3(CC2)OCc2cc(C#N)ccc23)cc1NC(=O)c1ccc(N2CCNCC2)nc1] | 0.805 |
| 359 | 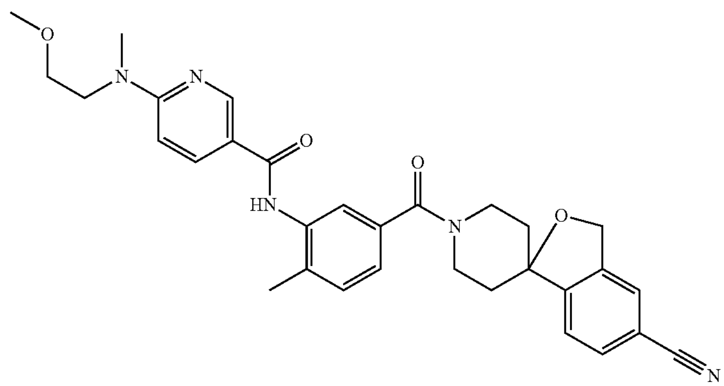 [SMILES: COCCN(C)c1ccc(C(=O)Nc2cc(C(=O)N3CCC4(CC3)OCc3cc(C#N)ccc34)ccc2C)cn1] | 0.105 |
| 360 | 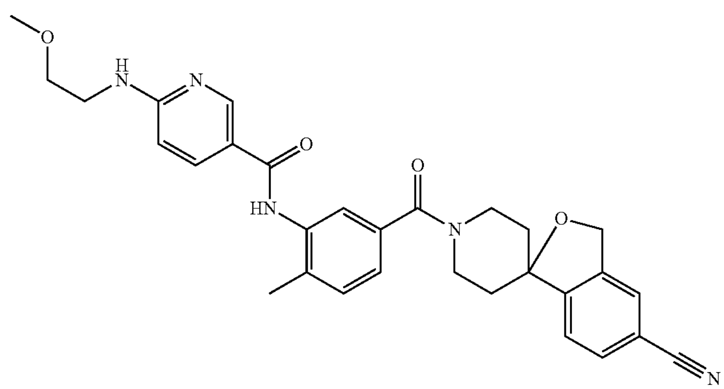 [SMILES: COCCNc1ccc(C(=O)Nc2cc(C(=O)N3CCC4(CC3)OCc3cc(C#N)ccc34)ccc2C)cn1] | 0.280 |
| 361 | 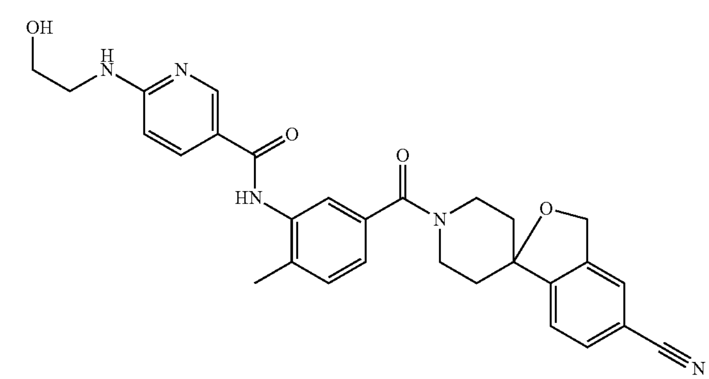 [SMILES: Cc1ccc(C(=O)N2CCC3(CC2)OCc2cc(C#N)ccc23)cc1NC(=O)c1ccc(NCCO)nc1] | 0.360 |

TABLE 1-continued

| ID | Structure | FASN IC50 (μM) |
|---|---|---|
| 362 | 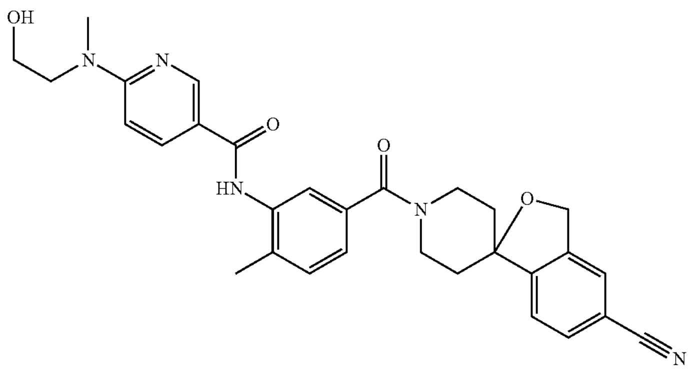 [SMILES: Cc1ccc(C(=O)N2CCC3(CC2)OCc2cc(C#N)ccc23)cc1NC(=O)c1ccc(N(C)CCO)nc1] | 0.247 |
| 363 | 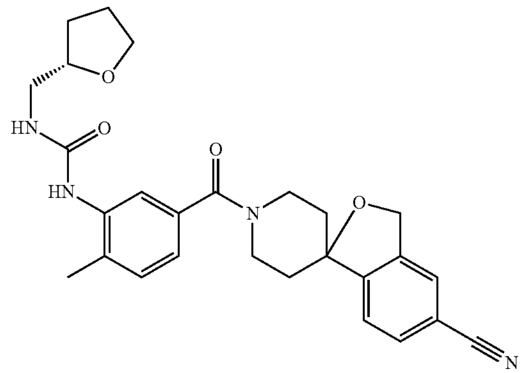 [SMILES: Cc1ccc(C(=O)N2CCC3(CC2)OCc2cc(C#N)ccc23)cc1NC(=O)NC[C@@H]1CCCO1] | 0.050 |
| 364 | 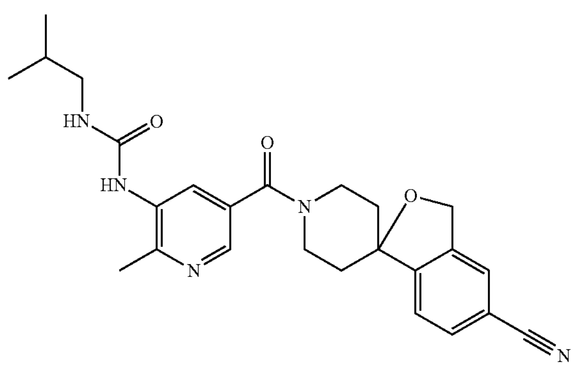 [SMILES: Cc1ncc(C(=O)N2CCC3(CC2)OCc2cc(C#N)ccc23)cc1NC(=O)NCC(C)C] | 37.000 |
| 365 | 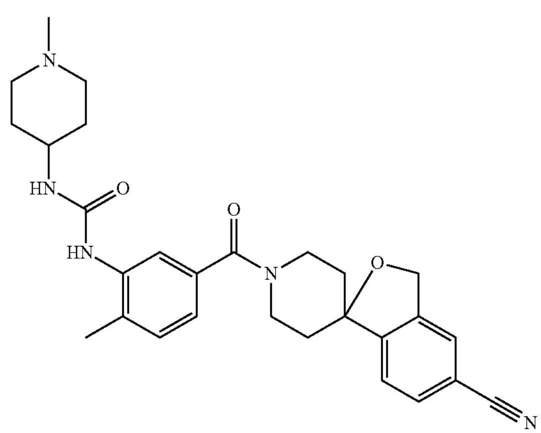 [SMILES: Cc1ccc(C(=O)N2CCC3(CC2)OCc2cc(C#N)ccc23)cc1NC(=O)NC1CCN(C)CC1] | 0.310 |

TABLE 1-continued
| ID | Structure | FASN IC50 (μM) |
|---|---|---|
| 366 | 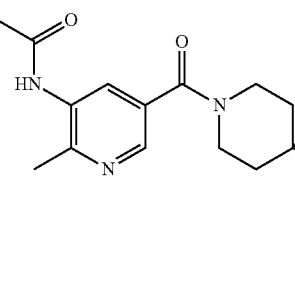 | 1.100 |
| 367 | 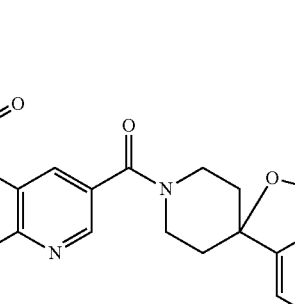 | — |
| 368 | 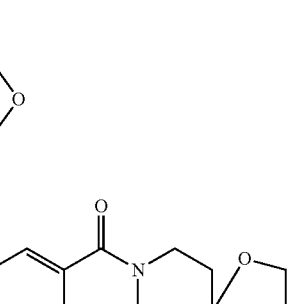 | 0.310 |
| 369 | 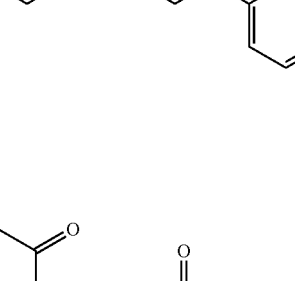 | 7.150 |

TABLE 1-continued
| ID | Structure | FASN IC50 (μM) |
370 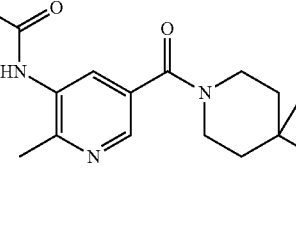
371 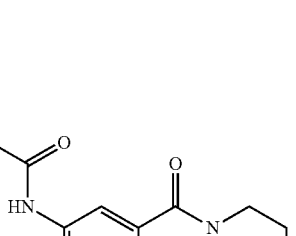
372 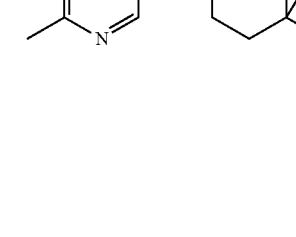
373 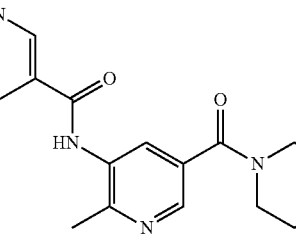 >50

TABLE 1-continued
| ID | Structure | FASN IC50 (μM) |
|---|---|---|
| 374 | 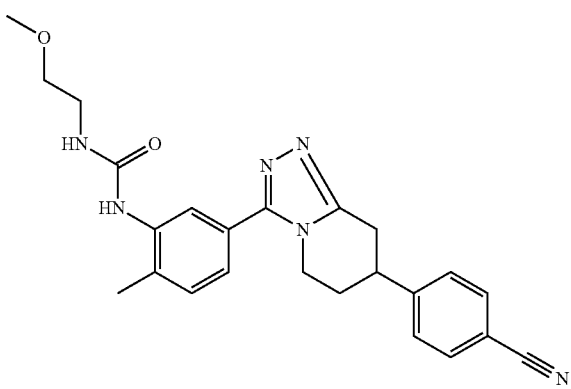 [SMILES: COCCNC(=O)Nc1cc(-c2nnc3n2CCC(c2ccc(C#N)cc2)C3)ccc1C] | 3.580 |
| 375 | 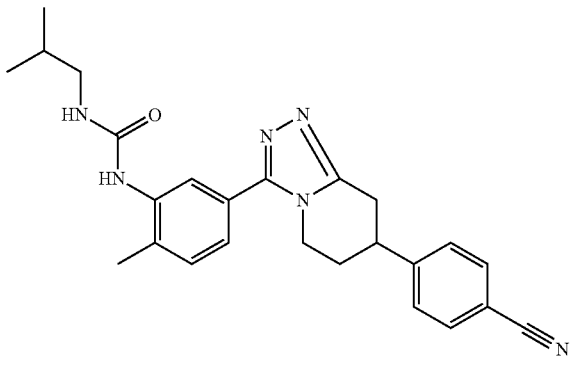 [SMILES: Cc1ccc(-c2nnc3n2CCC(c2ccc(C#N)cc2)C3)cc1NC(=O)NCC(C)C] | 6.360 |
| 376 | 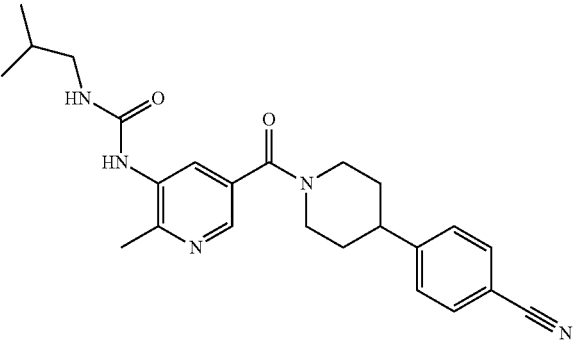 [SMILES: Cc1ncc(C(=O)N2CCC(c3ccc(C#N)cc3)CC2)cc1NC(=O)NCC(C)C] | 6.070 |
| 377 | 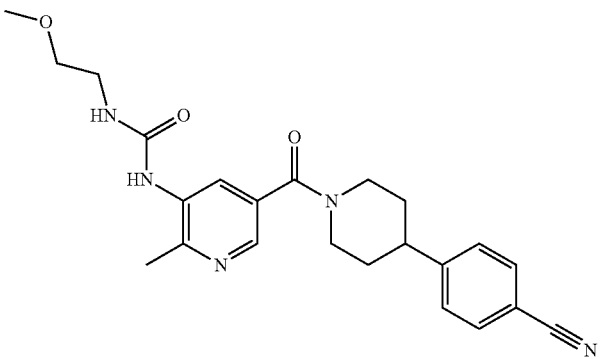 [SMILES: COCCNC(=O)Nc1cc(C(=O)N2CCC(c3ccc(C#N)cc3)CC2)cnc1C] | 2.550 |

TABLE 1-continued

| ID | Structure | FASN IC50 (μM) |
|---|---|---|
| 378 | 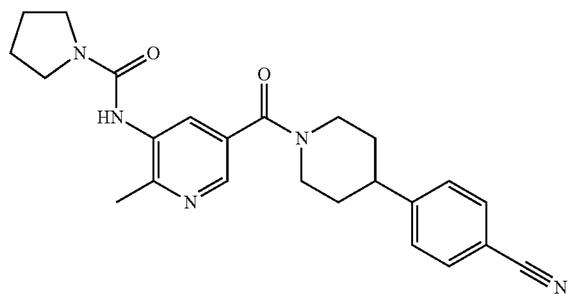 [SMILES: Cc1ncc(C(=O)N2CCC(c3ccc(C#N)cc3)CC2)cc1NC(=O)N1CCCC1] | |
| 379 | 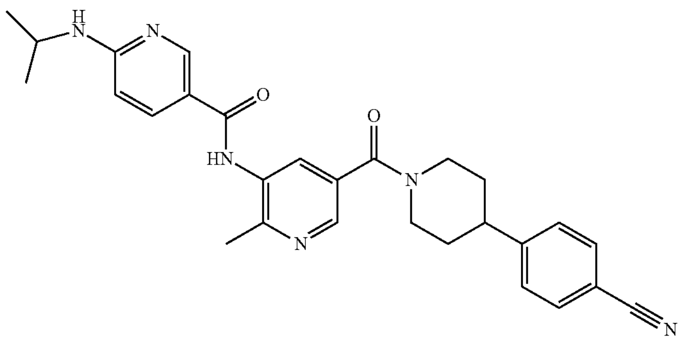 | 0.705 |
| 380 | 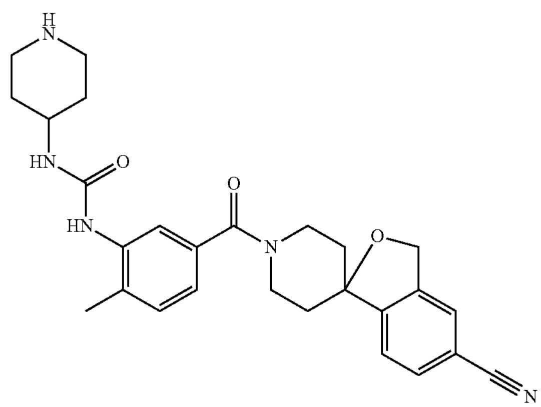 [SMILES: Cc1ccc(C(=O)N2CCC3(CC2)OCc2cc(C#N)ccc23)cc1NC(=O)NC1CCNCC1] | 0.420 |
| 381 | 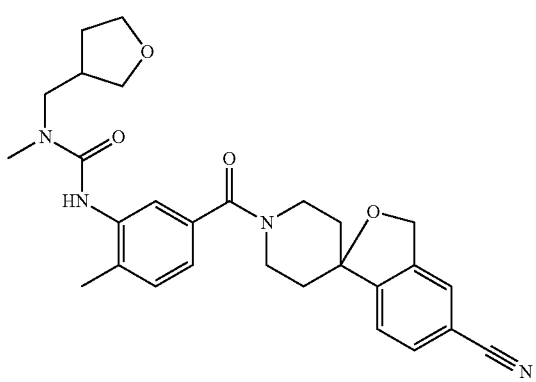 [SMILES: Cc1ccc(C(=O)N2CCC3(CC2)OCc2cc(C#N)ccc23)cc1NC(=O)N(C)CC1CCOC1] | >50 |

TABLE 1-continued
| ID | Structure | FASN IC50 (μM) |
|---|---|---|
| 382 | 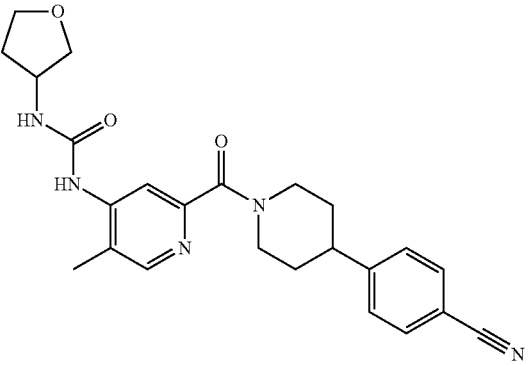 [SMILES: Cc1cnc(C(=O)N2CCC(c3ccc(C#N)cc3)CC2)cc1NC(=O)NC1CCOC1] | >50 |
| 383 | 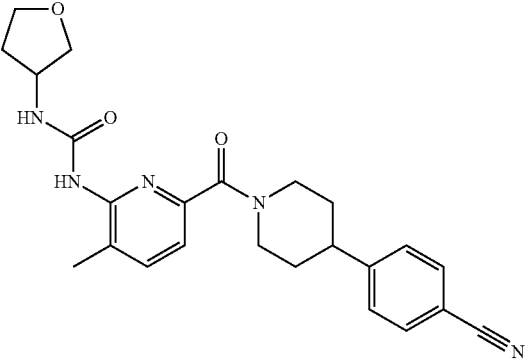 [SMILES: Cc1ccc(C(=O)N2CCC(c3ccc(C#N)cc3)CC2)nc1NC(=O)NC1CCOC1] | >50 |
| 384 | 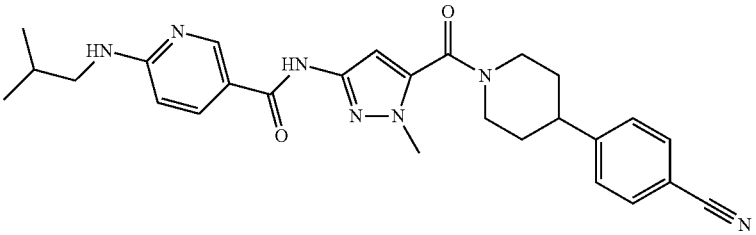 [SMILES: CC(C)CNc1ccc(C(=O)Nc2cc(C(=O)N3CCC(c4ccc(C#N)cc4)CC3)n(C)n2)cn1] | >50 |
| 385 | 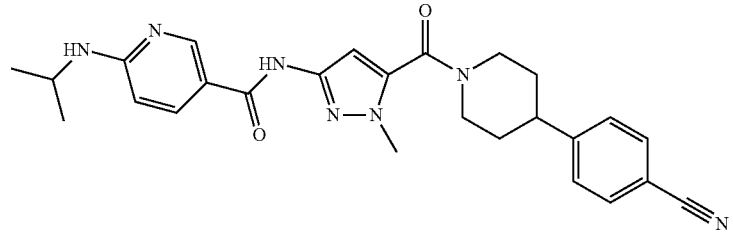 [SMILES: CC(C)Nc1ccc(C(=O)Nc2cc(C(=O)N3CCC(c4ccc(C#N)cc4)CC3)n(C)n2)cn1] | 8.867 |
| 386 | 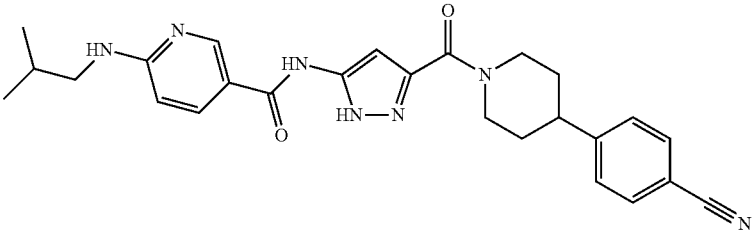 [SMILES: CC(C)CNc1ccc(C(=O)Nc2cc(C(=O)N3CCC(c4ccc(C#N)cc4)CC3)n[nH]2)cn1] | |

TABLE 1-continued

| ID | Structure | FASN IC50 (μM) |
|---|---|---|
| 387 | 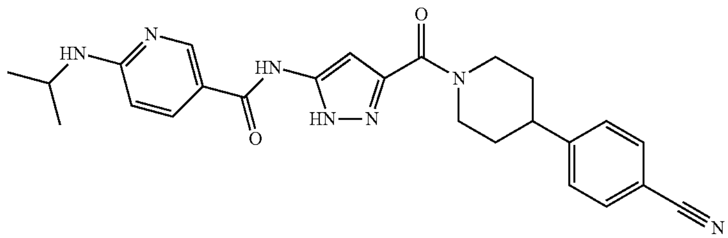 [SMILES: CC(C)Nc1ccc(C(=O)Nc2cc(C(=O)N3CCC(c4ccc(C#N)cc4)CC3)n[nH]2)cn1] | >50 |
| 388 | 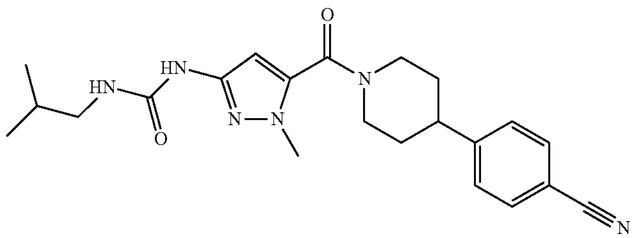 [SMILES: CC(C)CNC(=O)Nc1cc(C(=O)N2CCC(c3ccc(C#N)cc3)CC2)n(C)n1] | 13.380 |
| 389 | 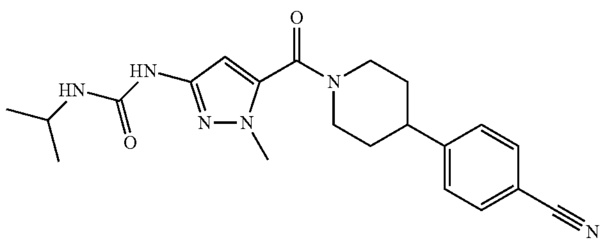 [SMILES: CC(C)NC(=O)Nc1cc(C(=O)N2CCC(c3ccc(C#N)cc3)CC2)n(C)n1] | 16.600 |
| 390 | 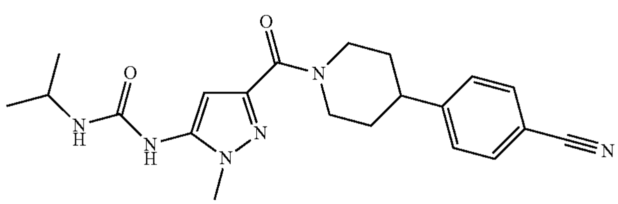 [SMILES: CC(C)NC(=O)Nc1cc(C(=O)N2CCC(c3ccc(C#N)cc3)CC2)nn1C] | >50 |
| 391 | 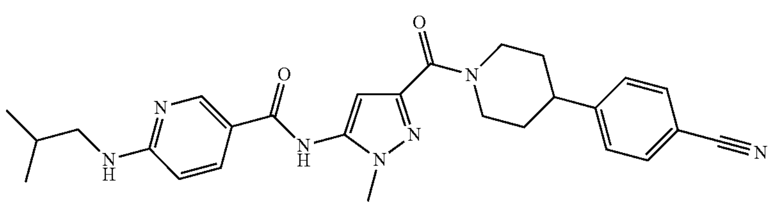 [SMILES: CC(C)CNc1ccc(C(=O)Nc2cc(C(=O)N3CCC(c4ccc(C#N)cc4)CC3)nn2C)cn1] | >50 |
| 392 | 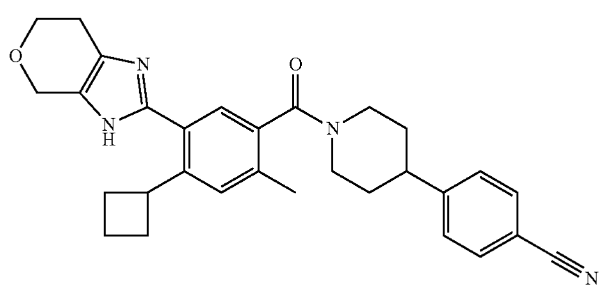 [SMILES: Cc1cc(C2CCC2)c(-c2nc3c([nH]2)COCC3)cc1C(=O)N1CCC(c2ccc(C#N)cc2)CC1] | 0.025 |

TABLE 1-continued

| ID | Structure | FASN IC50 (μM) |
|---|---|---|
| 393 | 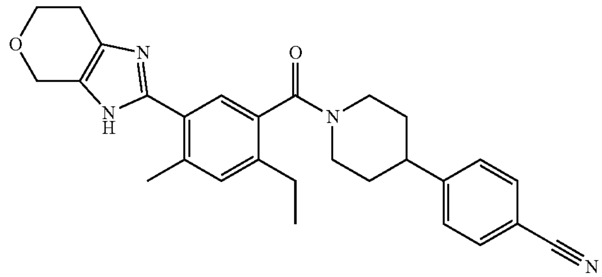 [SMILES: CCc1cc(C)c(-c2nc3c([nH]2)COCC3)cc1C(=O)N1CCC(c2ccc(C#N)cc2)CC1] | 0.065 |
| 394 | 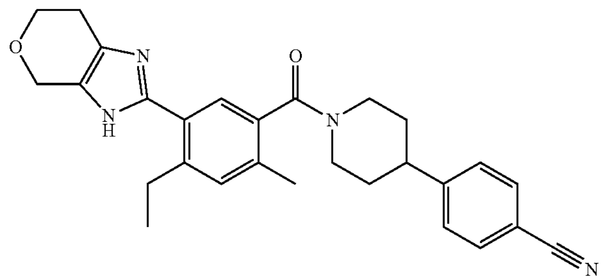 [SMILES: CCc1cc(C)c(C(=O)N2CCC(c3ccc(C#N)cc3)CC2)cc1-c1nc2c([nH]1)COCC2] | 0.135 |
| 395 | 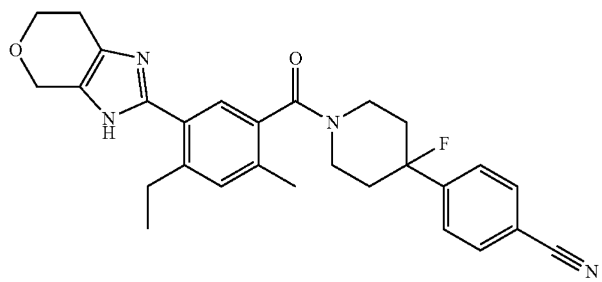 [SMILES: CCc1cc(C)c(C(=O)N2CCC(F)(c3ccc(C#N)cc3)CC2)cc1-c1nc2c([nH]1)COCC2] | 0.260 |
| 396 | 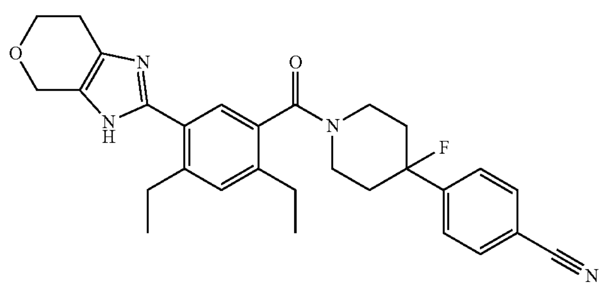 [SMILES: CCc1cc(CC)c(-c2nc3c([nH]2)COCC3)cc1C(=O)N1CCC(F)(c2ccc(C#N)cc2)CC1] | 0.050 |
| 397 | 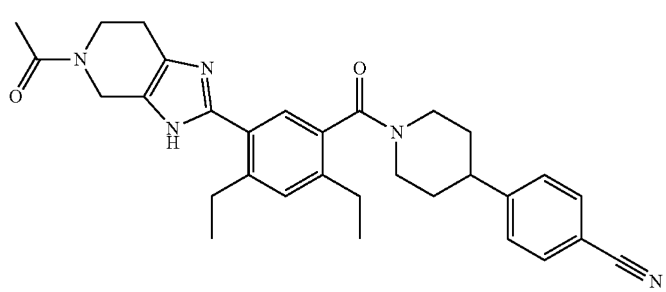 [SMILES: CCc1cc(CC)c(-c2nc3c([nH]2)CN(C(C)=O)CC3)cc1C(=O)N1CCC(c2ccc(C#N)cc2)CC1] | 0.040 |

TABLE 1-continued

| ID | Structure | FASN IC50 (μM) |
|---|---|---|
| 398 | 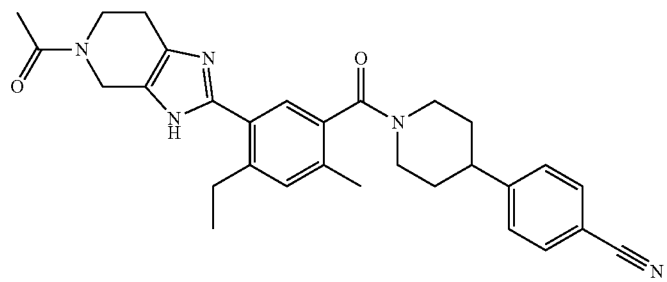 [SMILES: CCc1cc(C)c(C(=O)N2CCC(c3ccc(C#N)cc3)CC2)cc1-c1nc2c([nH]1)CN(C(C)=O)CC2] | 0.035 |
| 399 | 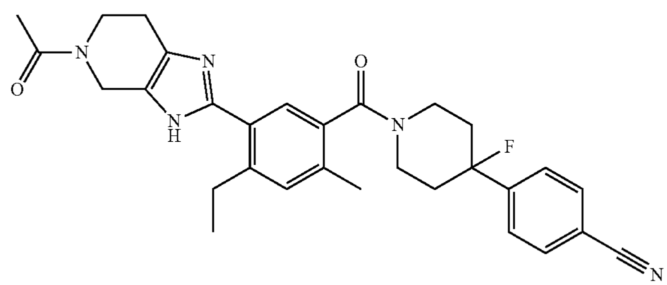 [SMILES: CCc1cc(C)c(C(=O)N2CCC(F)(c3ccc(C#N)cc3)CC2)cc1-c1nc2c([nH]1)CN(C(C)=O)CC2] | 0.030 |
| 400 | 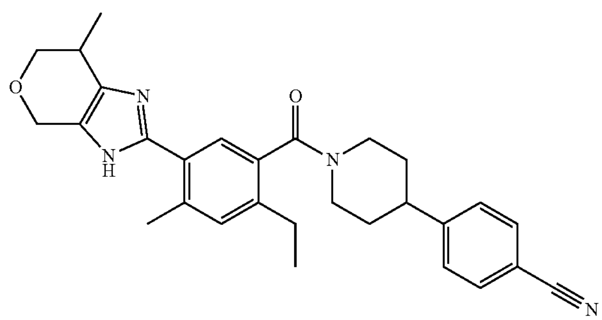 [SMILES: CCc1cc(C)c(-c2nc3c([nH]2)COCC3C)cc1C(=O)N1CCC(c2ccc(C#N)cc2)CC1] | 0.260 |
| 401 | 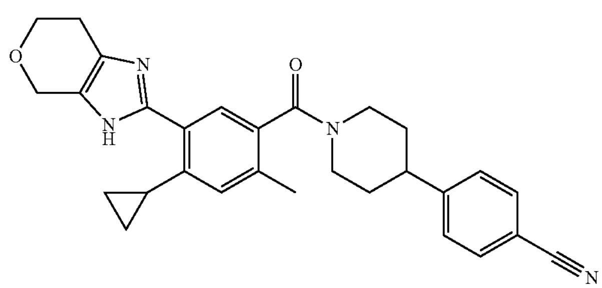 [SMILES: Cc1cc(C2CC2)c(-c2nc3c([nH]2)COCC3)cc1C(=O)N1CCC(c2ccc(C#N)cc2)CC1] | 0.065 |
| 402 | 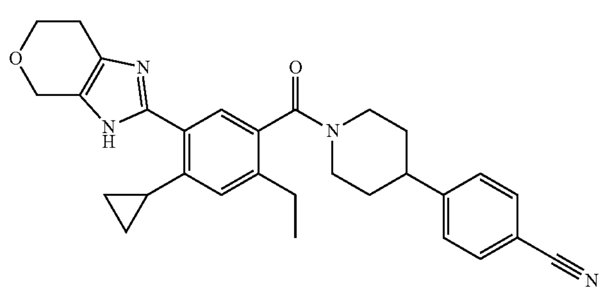 [SMILES: CCc1cc(C2CC2)c(-c2nc3c([nH]2)COCC3)cc1C(=O)N1CCC(c2ccc(C#N)cc2)CC1] | 0.077 |

TABLE 1-continued

| ID | Structure | FASN IC50 (μM) |
|---|---|---|
| 403 | 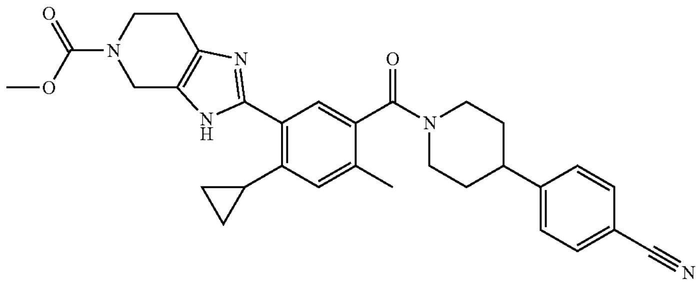 [SMILES: COC(=O)N1CCc2nc(-c3cc(C(=O)N4CCC(c5ccc(C#N)cc5)CC4)c(C)cc3C3CC3)[nH]c2C1] | 0.045 |
| 404 | 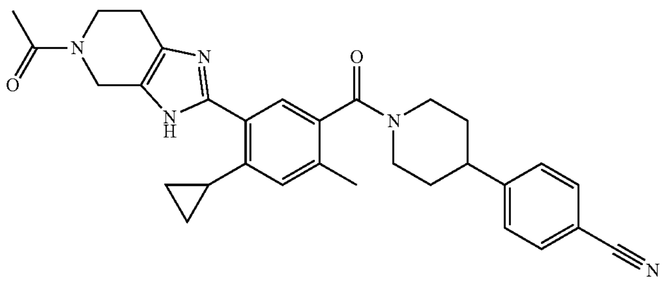 [SMILES: CC(=O)N1CCc2nc(-c3cc(C(=O)N4CCC(c5ccc(C#N)cc5)CC4)c(C)cc3C3CC3)[nH]c2C1] | 0.040 |
| 405 | 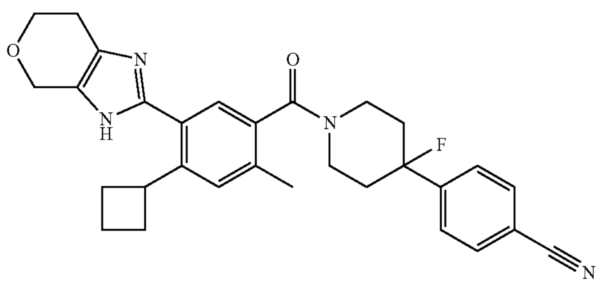 [SMILES: Cc1cc(C2CCC2)c(-c2nc3c([nH]2)COCC3)cc1C(=O)N1CCC(F)(c2ccc(C#N)cc2)CC1] | 0.010 |
| 406 | 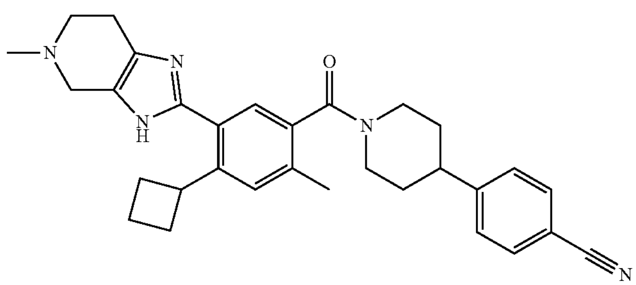 [SMILES: Cc1cc(C2CCC2)c(-c2nc3c([nH]2)CN(C)CC3)cc1C(=O)N1CCC(c2ccc(C#N)cc2)CC1] | 0.020 |
| 407 | 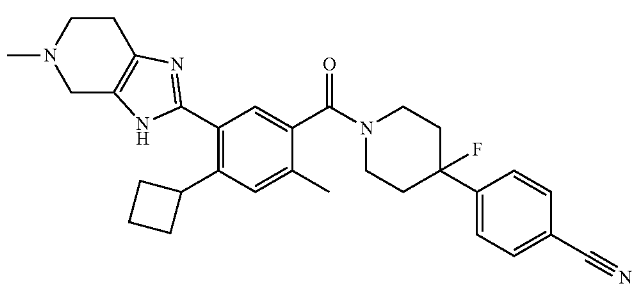 [SMILES: Cc1cc(C2CCC2)c(-c2nc3c([nH]2)CN(C)CC3)cc1C(=O)N1CCC(F)(c2ccc(C#N)cc2)CC1] | 0.040 |

TABLE 1-continued

| ID | Structure | FASN IC50 (μM) |
|----|-----------|----------------|
| 408 | 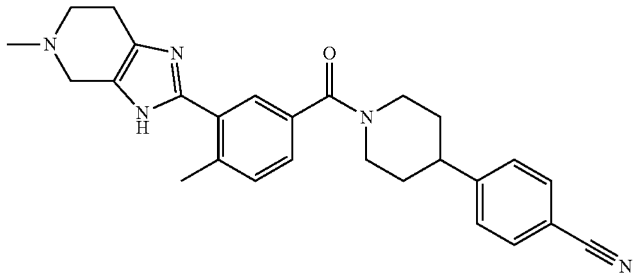 [SMILES: Cc1ccc(C(=O)N2CCC(c3ccc(C#N)cc3)CC2)cc1-c1nc2c([nH]1)CN(C)CC2] | 0.145 |
| 409 | 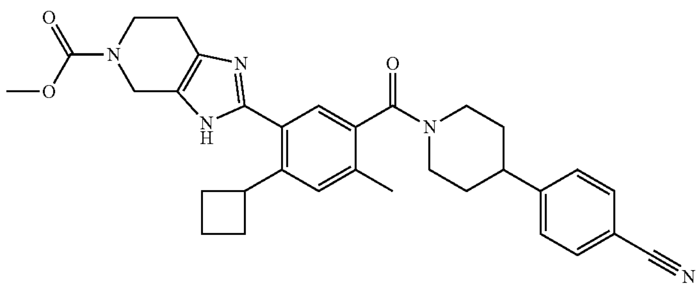 [SMILES: COC(=O)N1CCc2nc(-c3cc(C(=O)N4CCC(c5ccc(C#N)cc5)CC4)c(C)cc3C3CCC3)[nH]c2C1] | 0.020 |
| 410 | 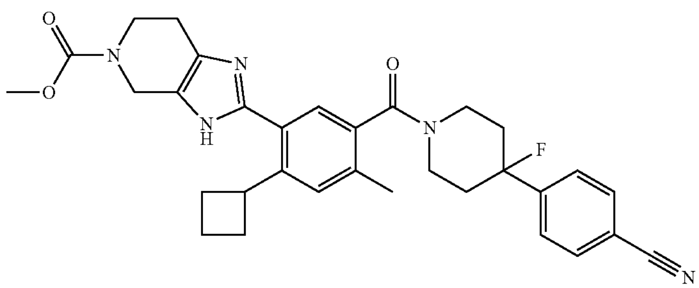 [SMILES: COC(=O)N1CCc2nc(-c3cc(C(=O)N4CCC(F)(c5ccc(C#N)cc5)CC4)c(C)cc3C3CCC3)[nH]c2C1] | 0.010 |
| 411 | 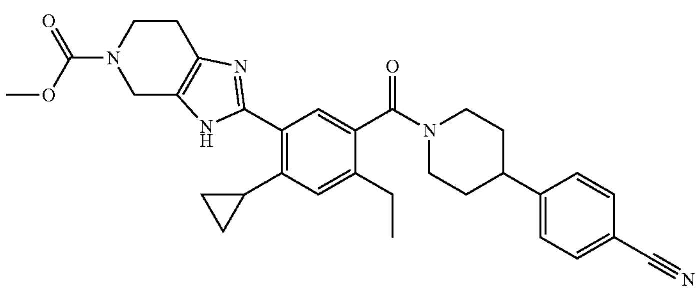 [SMILES: CCc1cc(C2CC2)c(-c2nc3c([nH]2)CN(C(=O)OC)CC3)cc1C(=O)N1CCC(c2ccc(C#N)cc2)CC1] | 0.035 |
| 412 | 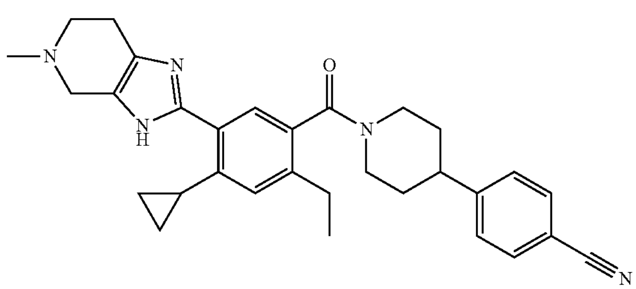 [SMILES: CCc1cc(C2CC2)c(-c2nc3c([nH]2)CN(C)CC3)cc1C(=O)N1CCC(c2ccc(C#N)cc2)CC1] | 0.035 |

TABLE 1-continued

| ID | Structure | FASN IC50 (μM) |
|---|---|---|
| 413 | 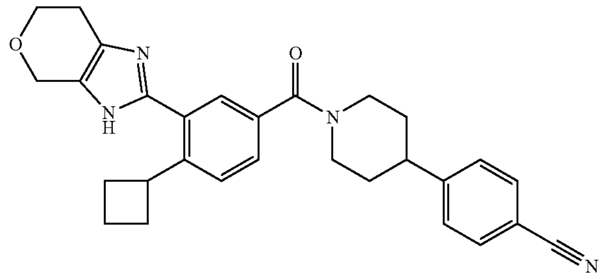 [SMILES: N#Cc1ccc(C2CCN(C(=O)c3ccc(C4CCC4)c(-c4nc5c([nH]4)COCC5)c3)CC2)cc1] | 0.065 |
| 414 | 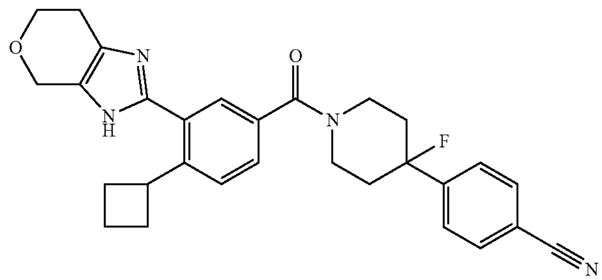 [SMILES: N#Cc1ccc(C2(F)CCN(C(=O)c3ccc(C4CCC4)c(-c4nc5c([nH]4)COCC5)c3)CC2)cc1] | 0.033 |
| 415 | 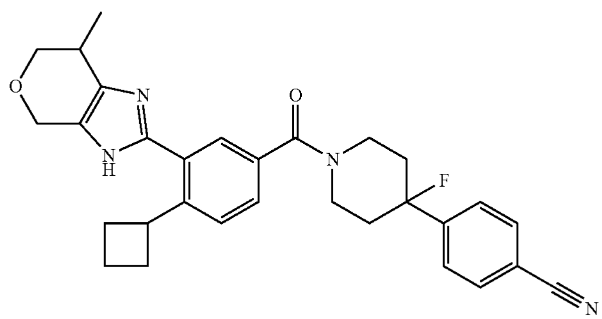 [SMILES: CC1COCc2[nH]c(-c3cc(C(=O)N4CCC(F)(c5ccc(C#N)cc5)CC4)ccc3C3CCC3)nc21] | 0.040 |
| 416 | 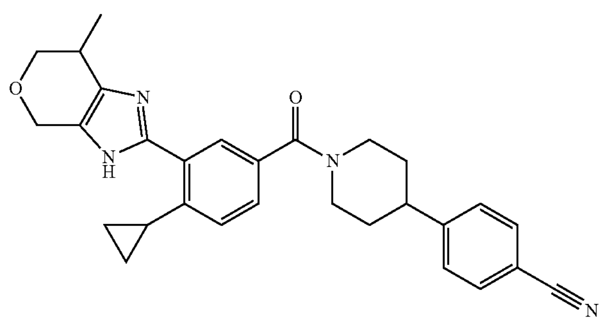 [SMILES: CC1COCc2[nH]c(-c3cc(C(=O)N4CCC(c5ccc(C#N)cc5)CC4)ccc3C3CC3)nc21] | 0.055 |
| 417 | 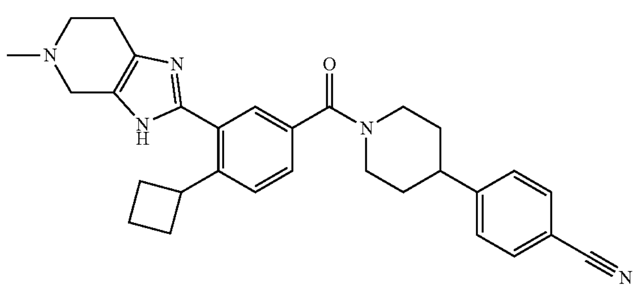 [SMILES: CN1CCc2nc(-c3cc(C(=O)N4CCC(c5ccc(C#N)cc5)CC4)ccc3C3CCC3)[nH]c2C1] | 0.020 |

TABLE 1-continued

| ID | Structure | FASN IC50 (μM) |
|---|---|---|
| 418 | 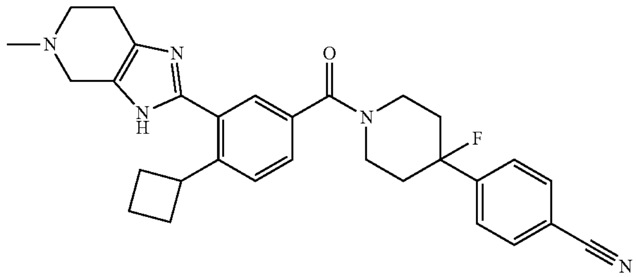 [SMILES: CN1CCc2nc(-c3cc(C(=O)N4CCC(F)(c5ccc(C#N)cc5)CC4)ccc3C3CCC3)[nH]c2C1] | 0.050 |
| 419 | 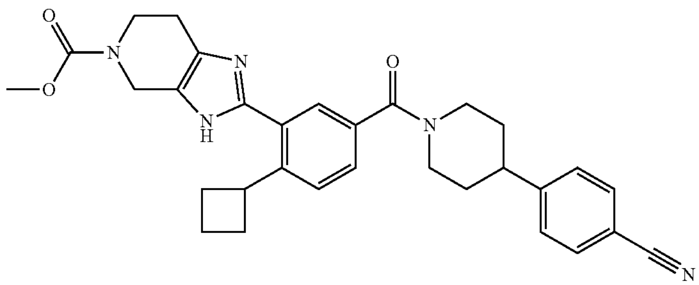 [SMILES: COC(=O)N1CCc2nc(-c3cc(C(=O)N4CCC(c5ccc(C#N)cc5)CC4)ccc3C3CCC3)[nH]c2C1] | 0.010 |
| 420 | 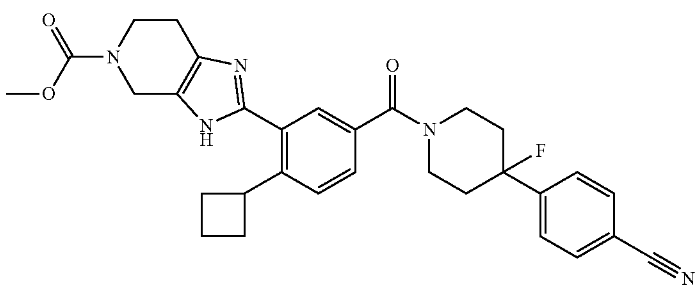 [SMILES: COC(=O)N1CCc2nc(-c3cc(C(=O)N4CCC(F)(c5ccc(C#N)cc5)CC4)ccc3C3CCC3)[nH]c2C1] | 0.020 |
| 421 | 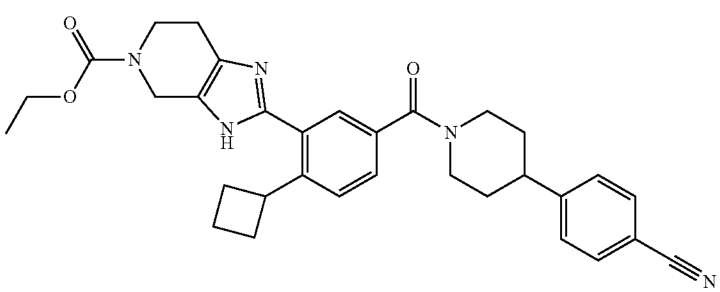 [SMILES: CCOC(=O)N1CCc2nc(-c3cc(C(=O)N4CCC(c5ccc(C#N)cc5)CC4)ccc3C3CCC3)[nH]c2C1] | 0.050 |
| 422 | 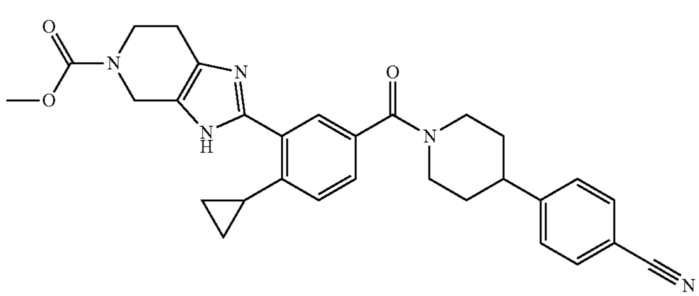 [SMILES: COC(=O)N1CCc2nc(-c3cc(C(=O)N4CCC(c5ccc(C#N)cc5)CC4)ccc3C3CC3)[nH]c2C1] | 0.020 |

TABLE 1-continued

| ID | Structure | FASN IC50 (μM) |
|---|---|---|
| 423 | 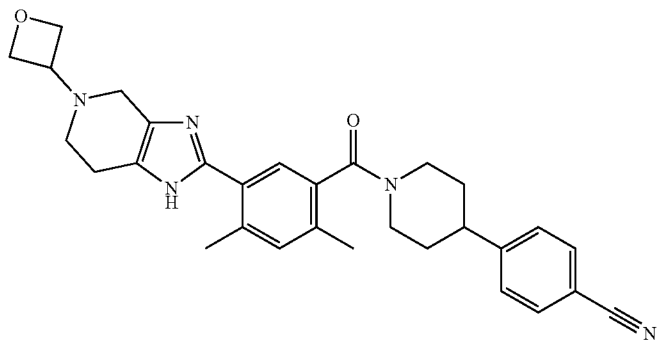 [SMILES: Cc1cc(C)c(-c2nc3c([nH]2)CCN(C2COC2)C3)cc1C(=O)N1CCC(c2ccc(C#N)cc2)CC1] | 0.175 |
| 424 | 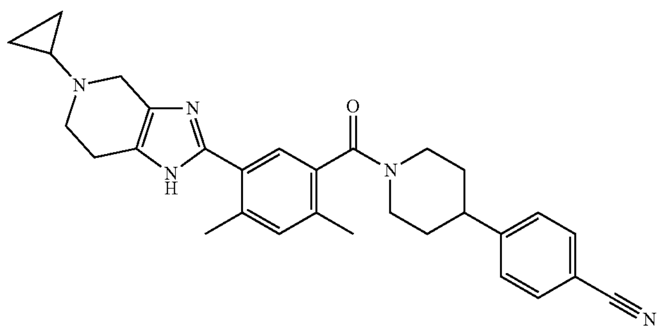 [SMILES: Cc1cc(C)c(-c2nc3c([nH]2)CCN(C2CC2)C3)cc1C(=O)N1CCC(c2ccc(C#N)cc2)CC1] | 0.165 |
| 425 | 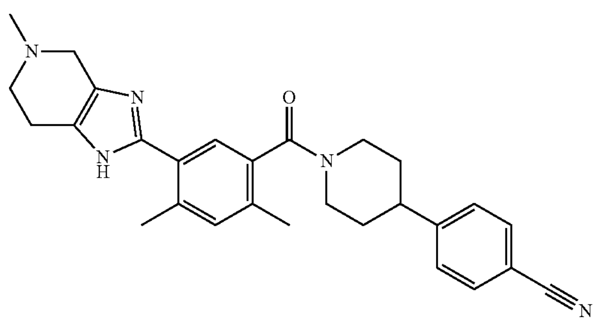 [SMILES: Cc1cc(C)c(-c2nc3c([nH]2)CCN(C)C3)cc1C(=O)N1CCC(c2ccc(C#N)cc2)CC1] | 0.075 |
| 426 | 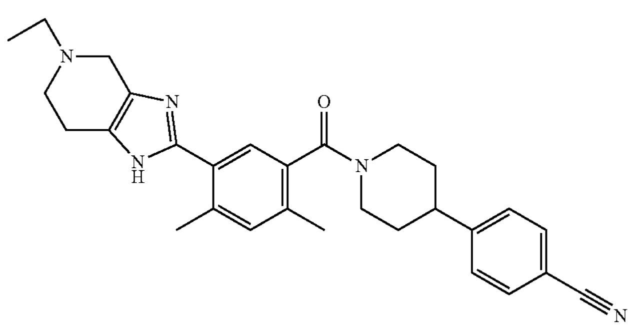 [SMILES: CCN1CCc2[nH]c(-c3cc(C(=O)N4CCC(c5ccc(C#N)cc5)CC4)c(C)cc3C)nc2C1] | 0.060 |

TABLE 1-continued

| ID | Structure | FASN IC50 (μM) |
|---|---|---|
| 427 | 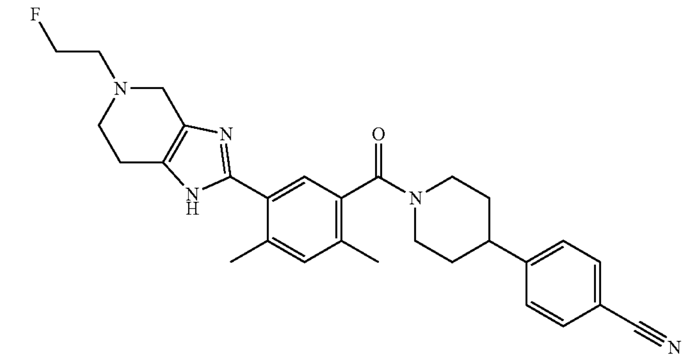 [SMILES: Cc1cc(C)c(-c2nc3c([nH]2)CCN(CCF)C3)cc1C(=O)N1CCC(c2ccc(C#N)cc2)CC1] | 0.080 |
| 428 | 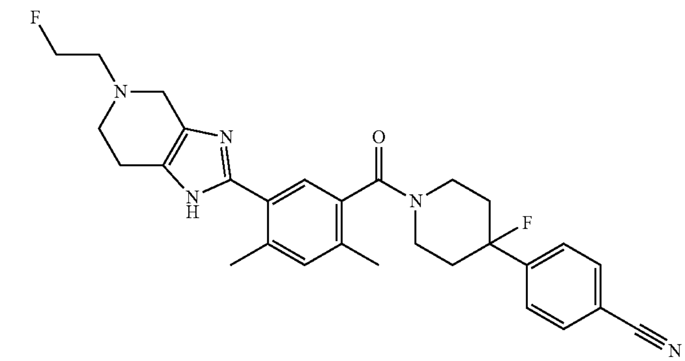 [SMILES: Cc1cc(C)c(-c2nc3c([nH]2)CCN(CCF)C3)cc1C(=O)N1CCC(F)(c2ccc(C#N)cc2)CC1] | 0.040 |
| 429 | 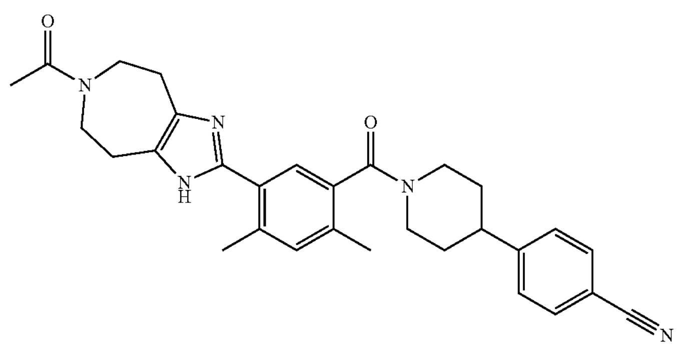 [SMILES: CC(=O)N1CCc2nc(-c3cc(C(=O)N4CCC(c5ccc(C#N)cc5)CC4)c(C)cc3C)[nH]c2CC1] | 0.060 |
| 430 | 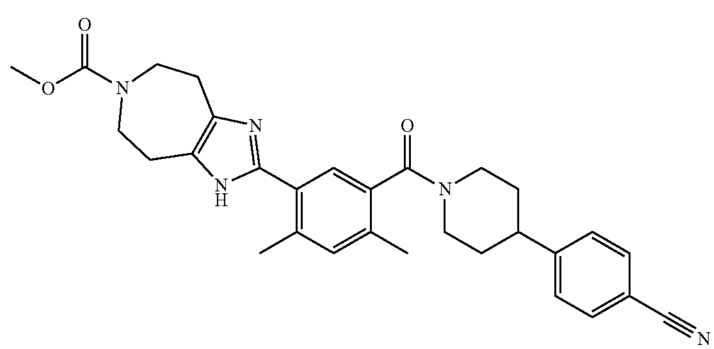 [SMILES: COC(=O)N1CCc2nc(-c3cc(C(=O)N4CCC(c5ccc(C#N)cc5)CC4)c(C)cc3C)[nH]c2CC1] | 0.035 |

| ID | Structure | FASN IC50 (µM) |
|---|---|---|
| 431 | 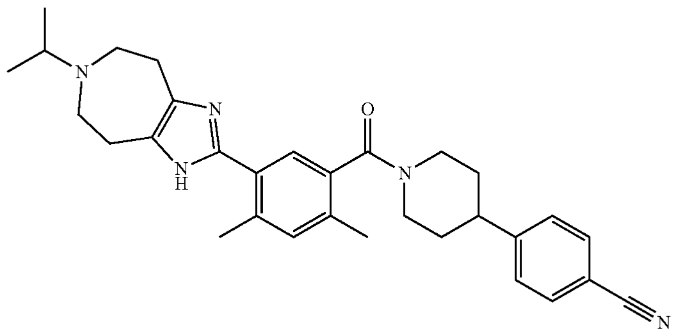 [SMILES: Cc1cc(C)c(-c2nc3c([nH]2)CCN(C(C)C)CC3)cc1C(=O)N1CCC(c2ccc(C#N)cc2)CC1] | 0.025 |
| 432 | 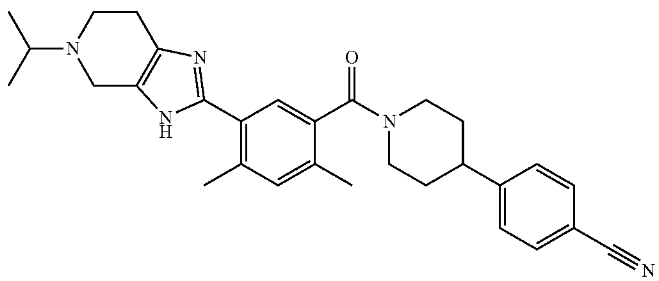 [SMILES: Cc1cc(C)c(-c2nc3c([nH]2)CN(C(C)C)CC3)cc1C(=O)N1CCC(c2ccc(C#N)cc2)CC1] | 0.065 |
| 433 | 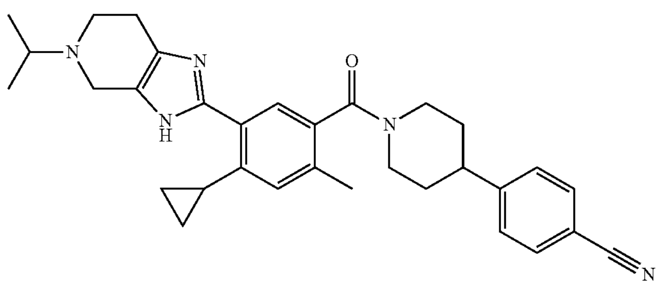 [SMILES: Cc1cc(C2CC2)c(-c2nc3c([nH]2)CN(C(C)C)CC3)cc1C(=O)N1CCC(c2ccc(C#N)cc2)CC1] | 0.040 |
| 434 | 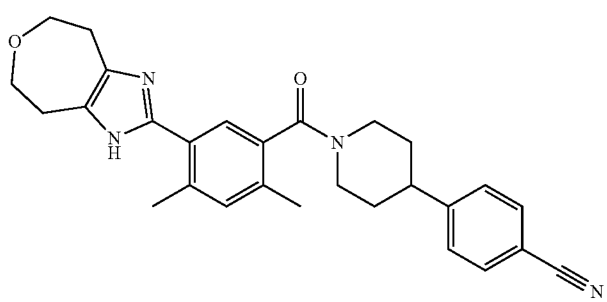 [SMILES: Cc1cc(C)c(-c2nc3c([nH]2)CCOCC3)cc1C(=O)N1CCC(c2ccc(C#N)cc2)CC1] | 0.470 |
| 435 | 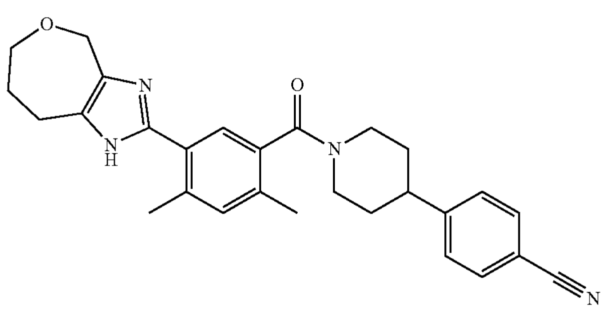 [SMILES: Cc1cc(C)c(-c2nc3c([nH]2)CCCOC3)cc1C(=O)N1CCC(c2ccc(C#N)cc2)CC1] | 0.365 |

TABLE 1-continued
| ID | Structure | FASN IC50 (μM) |
|---|---|---|
| 436 | 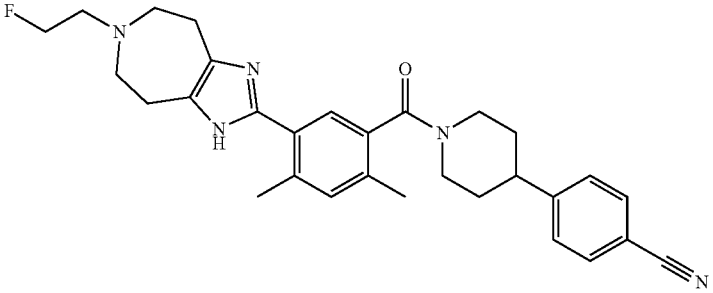 [SMILES: Cc1cc(C)c(-c2nc3c([nH]2)CCN(CCF)CC3)cc1C(=O)N1CCC(c2ccc(C#N)cc2)CC1] | 0.040 |
| 437 | 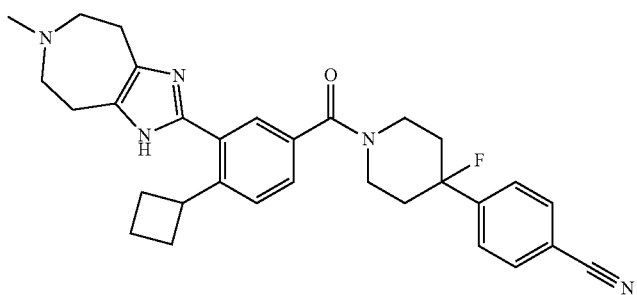 [SMILES: CN1CCc2nc(-c3cc(C(=O)N4CCC(F)(c5ccc(C#N)cc5)CC4)ccc3C3CCC3)[nH]c2CC1] | 0.050 |
| 438 | 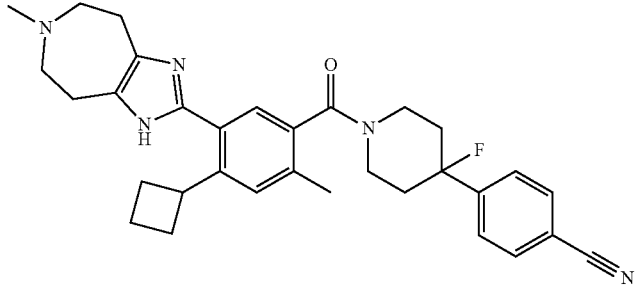 [SMILES: Cc1cc(C2CCC2)c(-c2nc3c([nH]2)CCN(C)CC3)cc1C(=O)N1CCC(F)(c2ccc(C#N)cc2)CC1] | 0.060 |
| 439 | 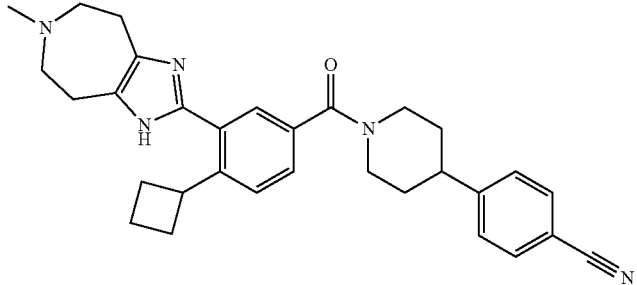 [SMILES: CN1CCc2nc(-c3cc(C(=O)N4CCC(c5ccc(C#N)cc5)CC4)ccc3C3CCC3)[nH]c2CC1] | 0.110 |
| 440 | 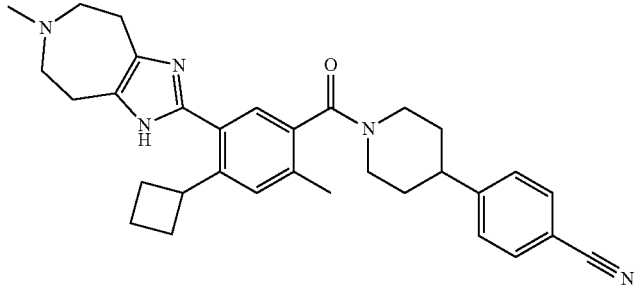 [SMILES: Cc1cc(C2CCC2)c(-c2nc3c([nH]2)CCN(C)CC3)cc1C(=O)N1CCC(c2ccc(C#N)cc2)CC1] | 0.050 |

TABLE 1-continued
| ID | Structure | FASN IC50 (μM) |
|---|---|---|
| 441 | 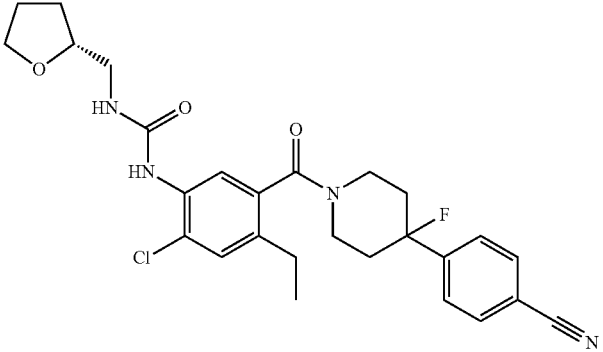 | 0.140 |
| 442 | 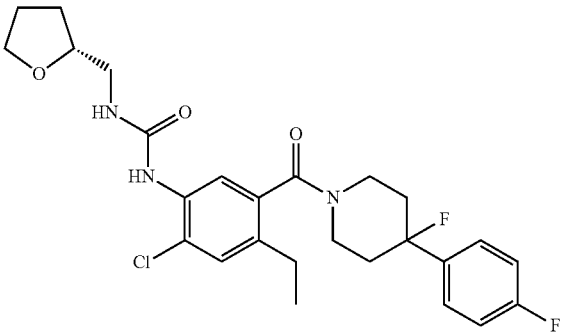 | 12.480 |
| 443 | 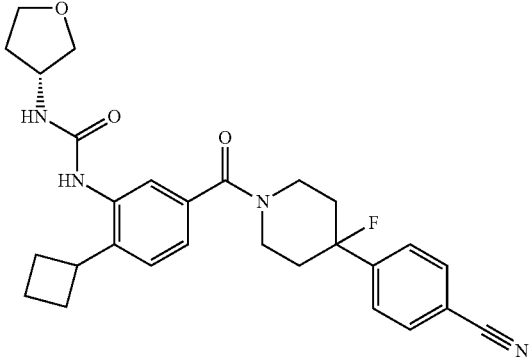 | 0.060 |
| 444 | 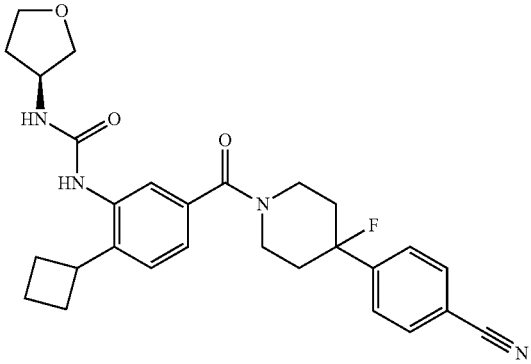 | 0.040 |

TABLE 1-continued

| ID | Structure | FASN IC50 (μM) |
|---|---|---|
| 445 | 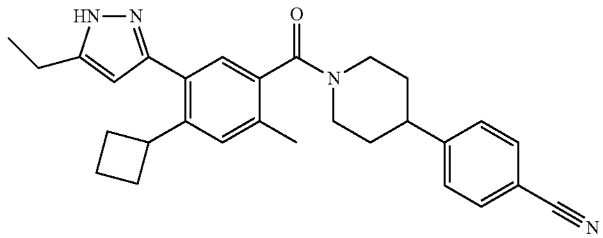 [SMILES: CCc1cc(-c2cc(C(=O)N3CCC(c4ccc(C#N)cc4)CC3)c(C)cc2C2CCC2)n[nH]1] | 0.490 |
| 446 | 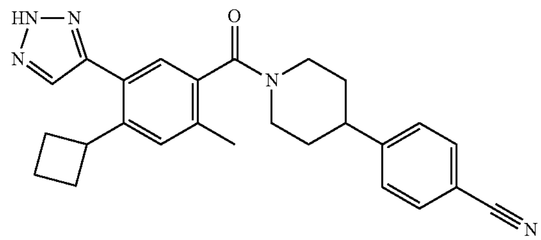 [SMILES: Cc1cc(C2CCC2)c(-c2cn[nH]n2)cc1C(=O)N1CCC(c2ccc(C#N)cc2)CC1] | 0.390 |
| 447 | 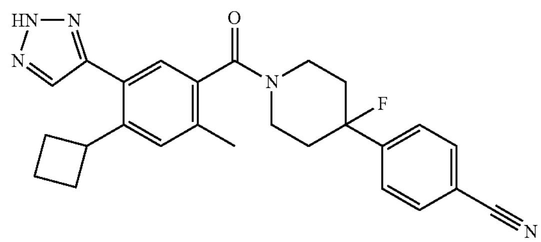 [SMILES: Cc1cc(C2CCC2)c(-c2cn[nH]n2)cc1C(=O)N1CCC(F)(c2ccc(C#N)cc2)CC1] | |
| 448 | 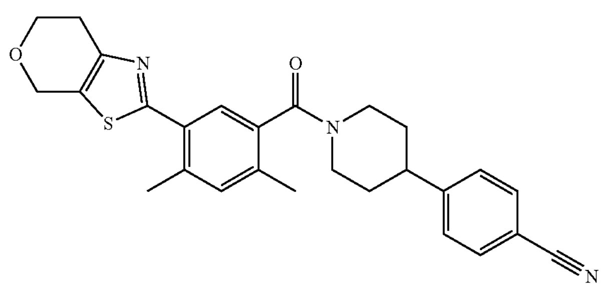 [SMILES: Cc1cc(C)c(-c2nc3c(s2)COCC3)cc1C(=O)N1CCC(c2ccc(C#N)cc2)CC1] | 10.610 |
| 449 | 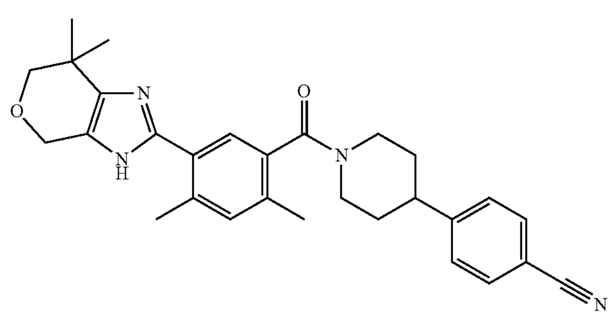 [SMILES: Cc1cc(C)c(-c2nc3c([nH]2)COCC3(C)C)cc1C(=O)N1CCC(c2ccc(C#N)cc2)CC1] | 0.135 |

TABLE 1-continued
| ID | Structure | FASN IC50 (μM) |
|---|---|---|
| 450 | 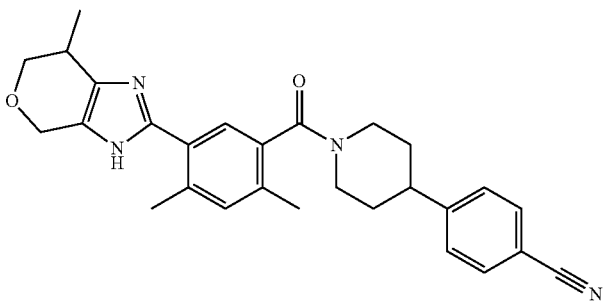 [SMILES: Cc1cc(C)c(-c2nc3c([nH]2)COCC3C)cc1C(=O)N1CCC(c2ccc(C#N)cc2)CC1] | 0.105 |
| 451 | 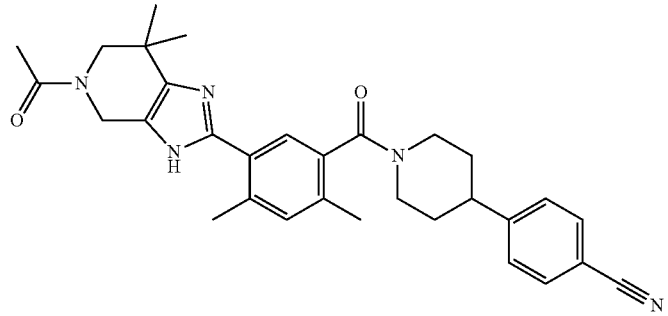 [SMILES: CC(=O)N1Cc2[nH]c(-c3cc(C(=O)N4CCC(c5ccc(C#N)cc5)CC4)c(C)cc3C)nc2C(C)(C)C1] | 0.070 |
| 452 | 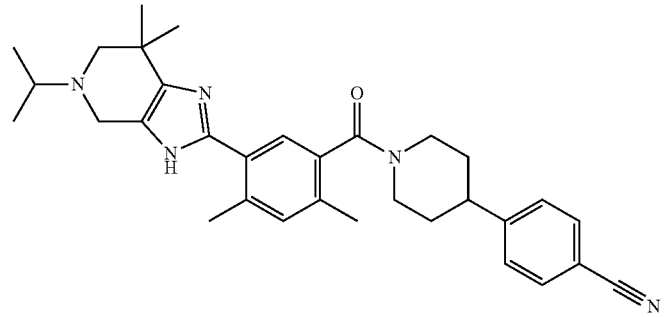 [SMILES: Cc1cc(C)c(-c2nc3c([nH]2)CN(C(C)C)CC3(C)C)cc1C(=O)N1CCC(c2ccc(C#N)cc2)CC1] | 0.130 |
| 453 | 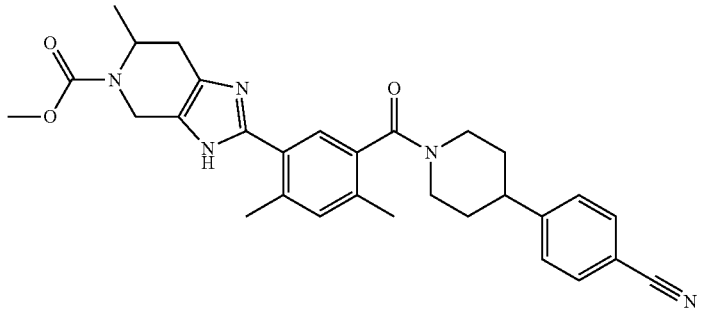 [SMILES: COC(=O)N1Cc2[nH]c(-c3cc(C(=O)N4CCC(c5ccc(C#N)cc5)CC4)c(C)cc3C)nc2CC1C] | 0.070 |
| 454 | 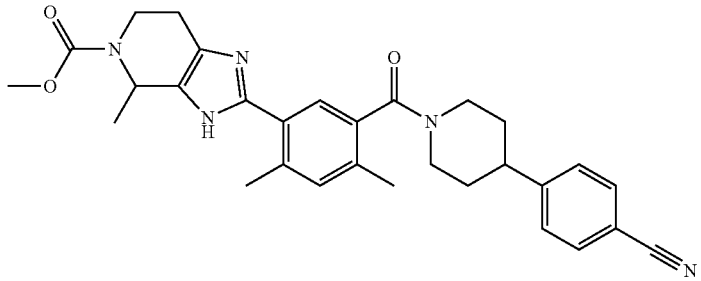 [SMILES: COC(=O)N1CCc2nc(-c3cc(C(=O)N4CCC(c5ccc(C#N)cc5)CC4)c(C)cc3C)[nH]c2C1C] | 0.077 |

TABLE 1-continued
| ID | Structure | FASN IC50 (μM) |
|---|---|---|
| 455 | 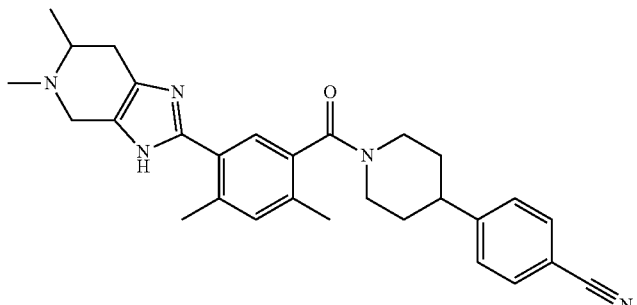 | 0.130 |
| 456 | 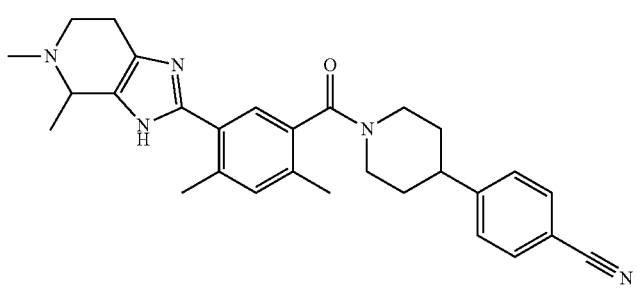 [SMILES: Cc1cc(C)c(-c2nc3c([nH]2)C(C)N(C)CC3)cc1C(=O)N1CCC(c2ccc(C#N)cc2)CC1] | 0.135 |
| 457 | 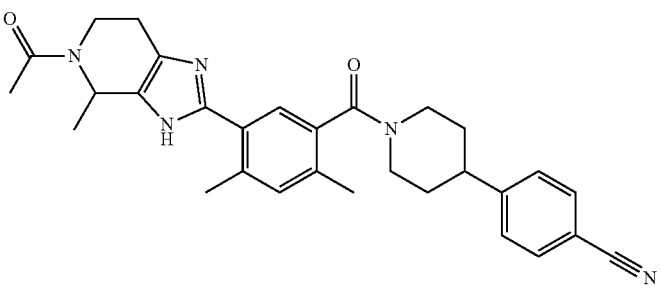 [SMILES: CC(=O)N1CCc2nc(-c3cc(C(=O)N4CCC(c5ccc(C#N)cc5)CC4)c(C)cc3C)[nH]c2C1C] | 0.080 |
| 458 | 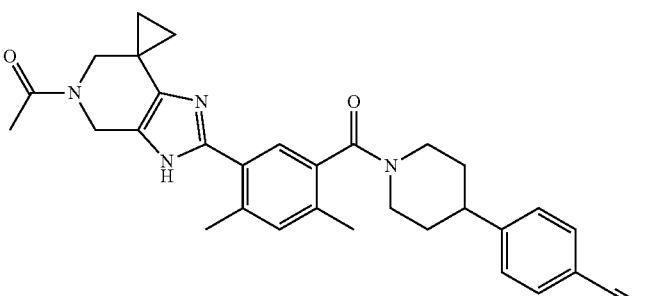 | 0.130 |
| 459 | 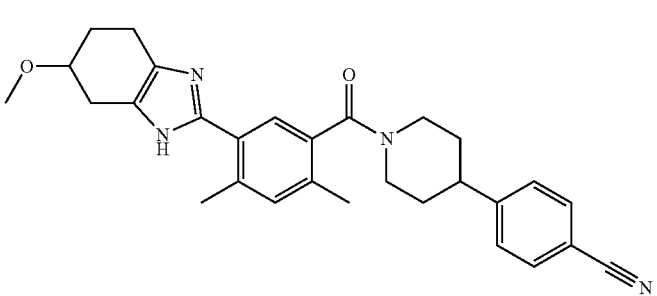 [SMILES: COC1CCc2nc(-c3cc(C(=O)N4CCC(c5ccc(C#N)cc5)CC4)c(C)cc3C)[nH]c2C1] | 0.310 |

TABLE 1-continued

| ID | Structure | FASN IC50 (μM) |
|---|---|---|
| 460 | 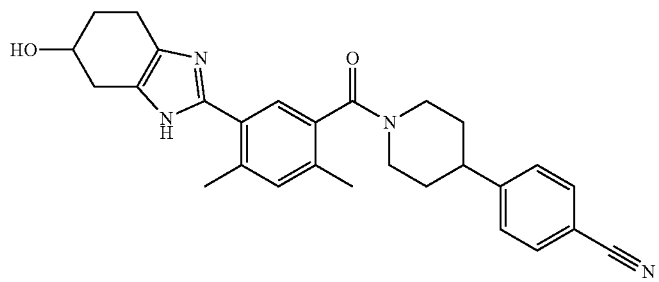 [SMILES: Cc1cc(C)c(-c2nc3c([nH]2)CC(O)CC3)cc1C(=O)N1CCC(c2ccc(C#N)cc2)CC1] | 0.090 |
| 461 | 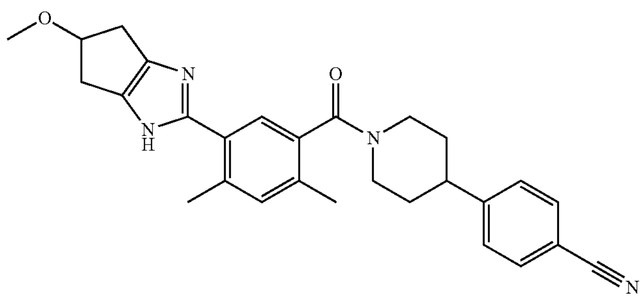 [SMILES: COC1Cc2nc(-c3cc(C(=O)N4CCC(c5ccc(C#N)cc5)CC4)c(C)cc3C)[nH]c2C1] | 0.105 |
| 462 | 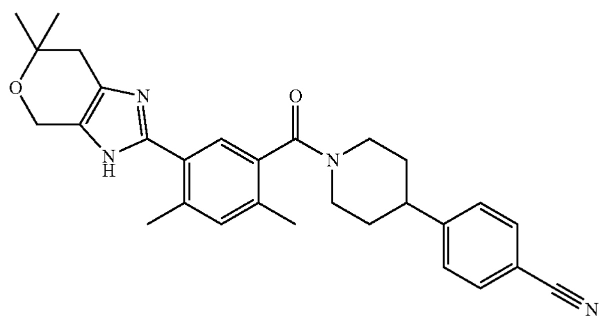 [SMILES: Cc1cc(C)c(-c2nc3c([nH]2)COC(C)(C)C3)cc1C(=O)N1CCC(c2ccc(C#N)cc2)CC1] | 0.780 |
| 463 | 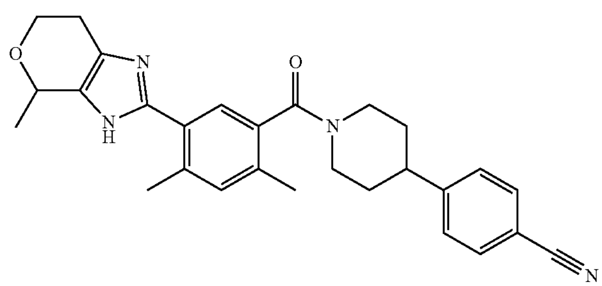 [SMILES: Cc1cc(C)c(-c2nc3c([nH]2)C(C)OCC3)cc1C(=O)N1CCC(c2ccc(C#N)cc2)CC1] | 0.440 |
| 464 | 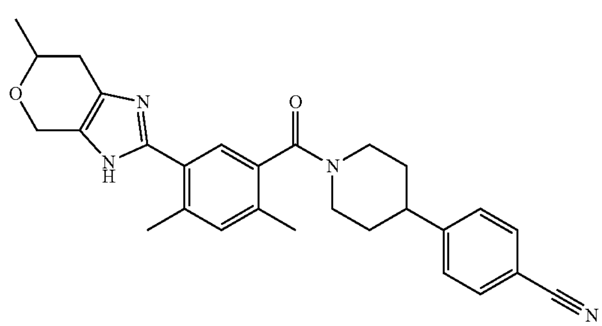 [SMILES: Cc1cc(C)c(-c2nc3c([nH]2)COC(C)C3)cc1C(=O)N1CCC(c2ccc(C#N)cc2)CC1] | 0.065 |

TABLE 1-continued

| ID | Structure | FASN IC50 (μM) |
|----|-----------|----------------|
| 465 | 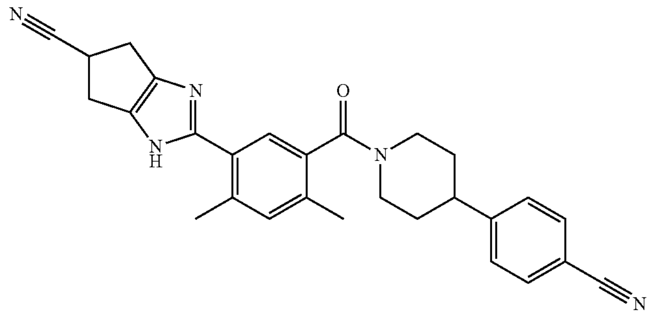 [SMILES: Cc1cc(C)c(-c2nc3c([nH]2)CC(C#N)C3)cc1C(=O)N1CCC(c2ccc(C#N)cc2)CC1] | 0.050 |
| 466 | Abs | 34.670 |
| 467 | 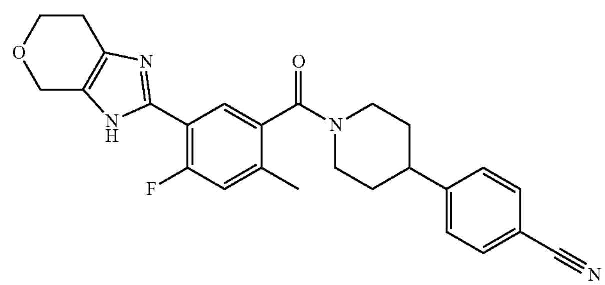 | 1.810 |
| 468 | 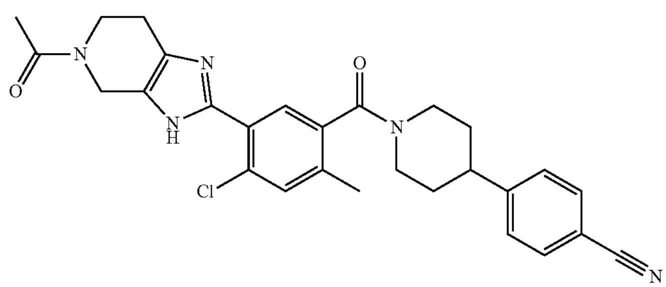 [SMILES: CC(=O)N1CCc2nc(-c3cc(C(=O)N4CCC(c5ccc(C#N)cc5)CC4)c(C)cc3Cl)[nH]c2C1] | 0.170 |
| 469 | 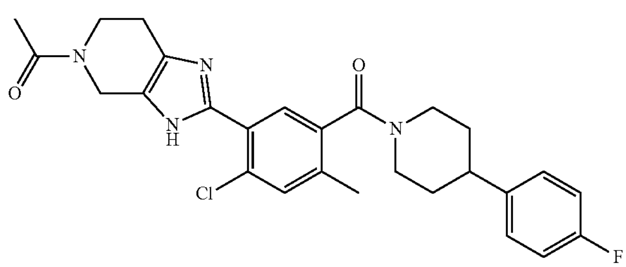 | 2.100 |

TABLE 1-continued

| ID | Structure | FASN IC50 (μM) |
|---|---|---|
| 470 | 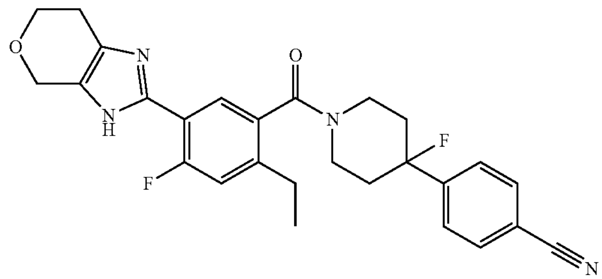 [SMILES: CCc1cc(F)c(-c2nc3c([nH]2)COCC3)cc1C(=O)N1CCC(F)(c2ccc(C#N)cc2)CC1] | 1.130 |
| 471 | 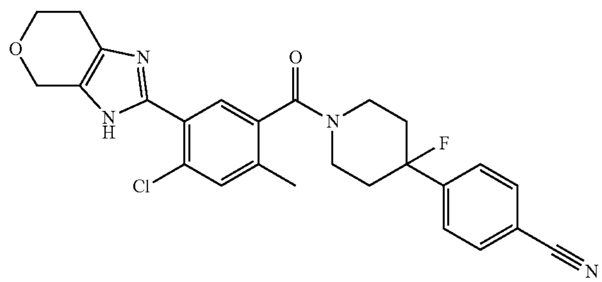 [SMILES: Cc1cc(Cl)c(-c2nc3c([nH]2)COCC3)cc1C(=O)N1CCC(F)(c2ccc(C#N)cc2)CC1] | 0.450 |
| 472 | 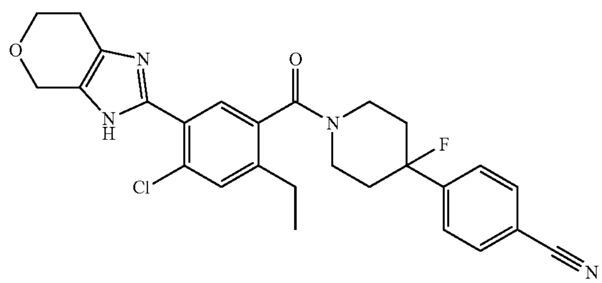 [SMILES: CCc1cc(Cl)c(-c2nc3c([nH]2)COCC3)cc1C(=O)N1CCC(F)(c2ccc(C#N)cc2)CC1] | 0.230 |
| 473 | 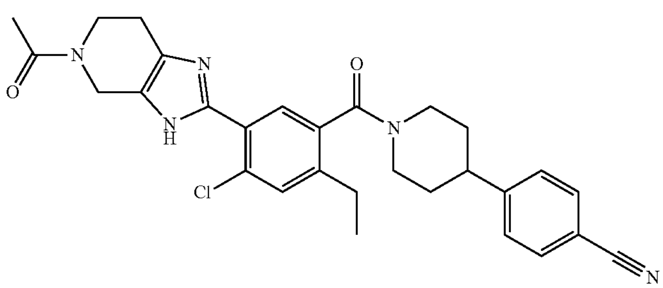 [SMILES: CCc1cc(Cl)c(-c2nc3c([nH]2)CN(C(C)=O)CC3)cc1C(=O)N1CCC(c2ccc(C#N)cc2)CC1] | 0.110 |
| 474 | 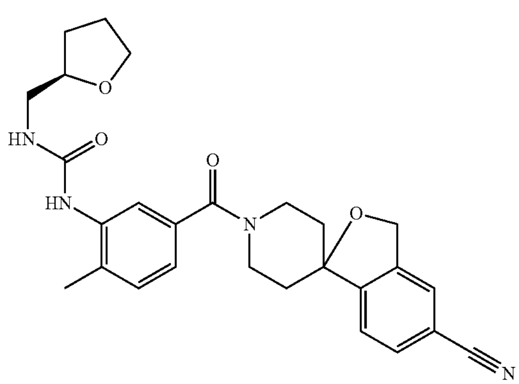 [SMILES: Cc1ccc(C(=O)N2CCC3(CC2)OCc2cc(C#N)ccc23)cc1NC(=O)NC[C@H]1CCCO1] | 0.180 |

TABLE 1-continued
| ID | Structure | FASN IC50 (μM) |
|---|---|---|
| 475 | 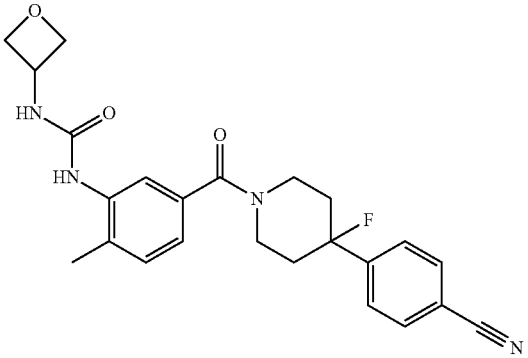 [SMILES: Cc1ccc(C(=O)N2CCC(F)(c3ccc(C#N)cc3)CC2)cc1NC(=O)NC1COC1] | 0.050 |
| 476 | 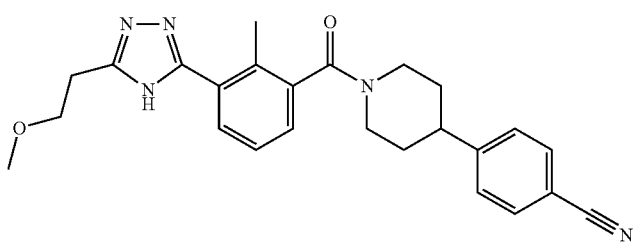 [SMILES: COCCc1nnc(-c2cccc(C(=O)N3CCC(c4ccc(C#N)cc4)CC3)c2C)[nH]1] | >50 |
| 477 | 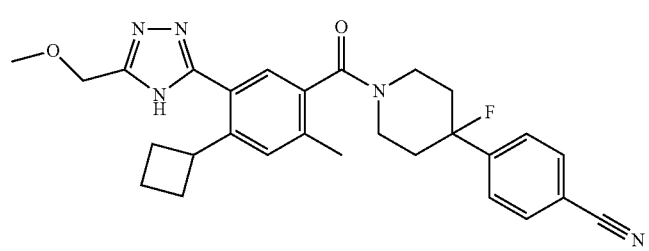 [SMILES: COCc1nnc(-c2cc(C(=O)N3CCC(F)(c4ccc(C#N)cc4)CC3)c(C)cc2C2CCC2)[nH]1] | 0.130 |
| 478 | 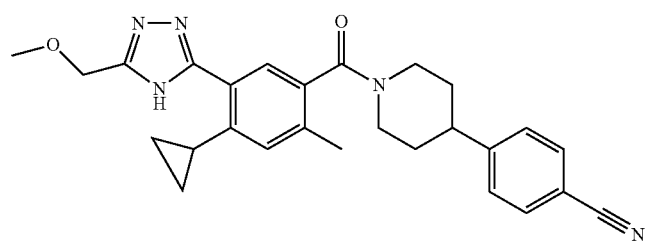 [SMILES: COCc1nnc(-c2cc(C(=O)N3CCC(c4ccc(C#N)cc4)CC3)c(C)cc2C2CC2)[nH]1] | 0.420 |
| 479 | 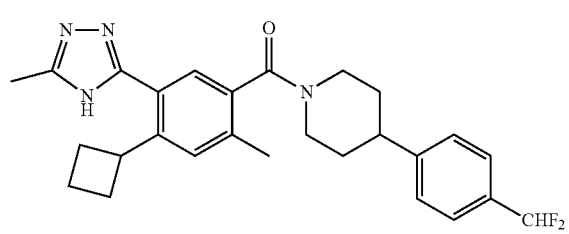 [SMILES: Cc1nnc(-c2cc(C(=O)N3CCC(c4ccc(C(F)F)cc4)CC3)c(C)cc2C2CCC2)[nH]1] | 0.110 |
| 480 | 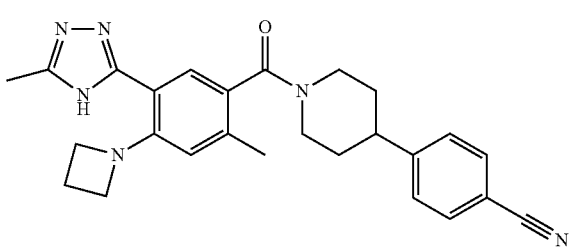 [SMILES: Cc1nnc(-c2cc(C(=O)N3CCC(c4ccc(C#N)cc4)CC3)c(C)cc2N2CCC2)[nH]1] | 0.180 |

TABLE 1-continued

| ID | Structure | FASN IC50 (μM) |
|---|---|---|
| 481 | 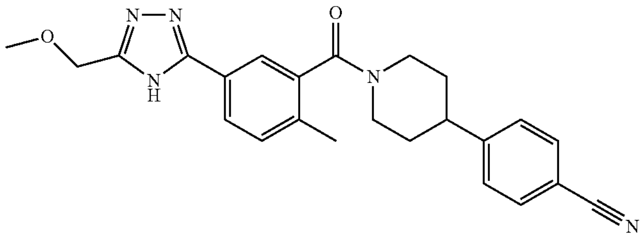 [SMILES: COCc1nnc(-c2ccc(C)c(C(=O)N3CCC(c4ccc(C#N)cc4)CC3)c2)[nH]1] | 21.240 |
| 482 | 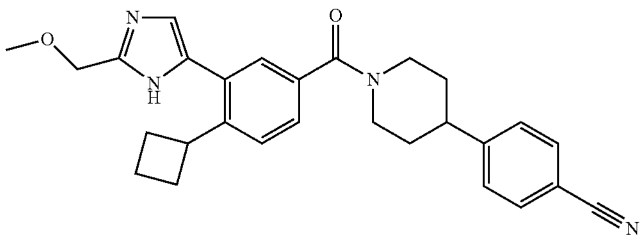 [SMILES: COCc1ncc(-c2cc(C(=O)N3CCC(c4ccc(C#N)cc4)CC3)ccc2C2CCC2)[nH]1] | 0.240 |
| 483 | 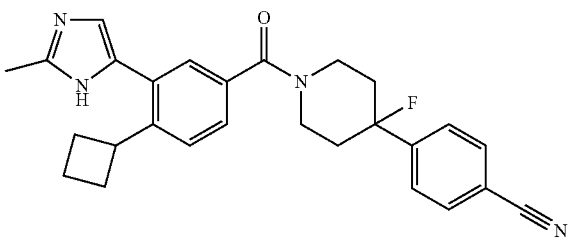 [SMILES: Cc1ncc(-c2cc(C(=O)N3CCC(F)(c4ccc(C#N)cc4)CC3)ccc2C2CCC2)[nH]1] | 0.100 |
| 484 | 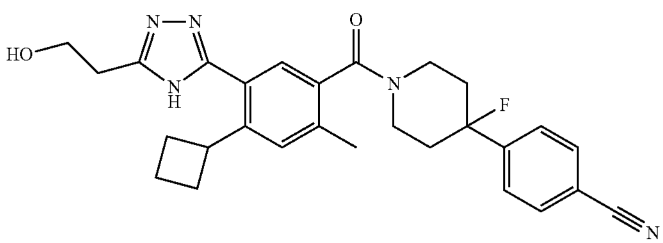 [SMILES: Cc1cc(C2CCC2)c(-c2nnc(CCO)[nH]2)cc1C(=O)N1CCC(F)(c2ccc(C#N)cc2)CC1] | 0.070 |
| 485 | 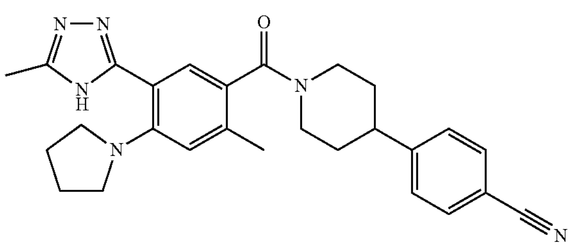 [SMILES: Cc1nnc(-c2cc(C(=O)N3CCC(c4ccc(C#N)cc4)CC3)c(C)cc2N2CCCC2)[nH]1] | 0.130 |
| 486 | 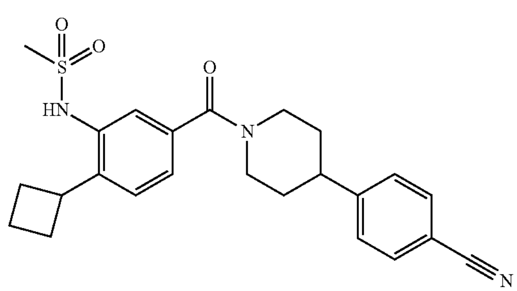 [SMILES: CS(=O)(=O)Nc1cc(C(=O)N2CCC(c3ccc(C#N)cc3)CC2)ccc1C1CCC1] | 0.540 |

TABLE 1-continued

| ID | Structure | FASN IC50 (μM) |
|---|---|---|
| 487 | 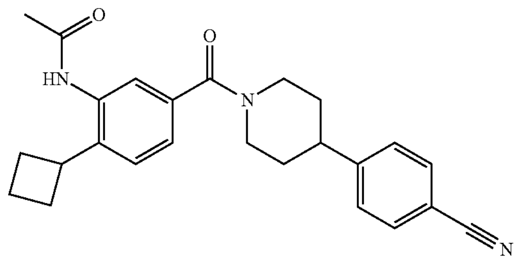 [SMILES: CC(=O)Nc1cc(C(=O)N2CCC(c3ccc(C#N)cc3)CC2)ccc1C1CCC1] | 0.380 |
| 488 | [Abs] | 0.030 |
| 489 | 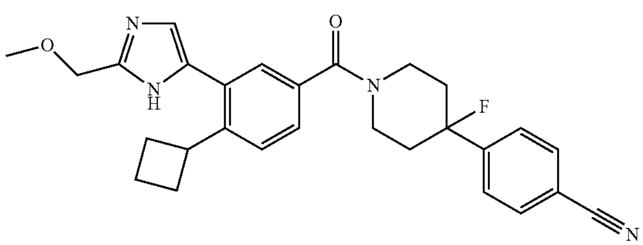 [SMILES: COCc1ncc(-c2cc(C(=O)N3CCC(F)(c4ccc(C#N)cc4)CC3)ccc2C2CCC2)[nH]1] | 0.180 |
| 490 | [Abs] | 0.090 |

TABLE 1-continued
| ID | Structure | FASN IC50 (μM) |
|---|---|---|
| 491 | 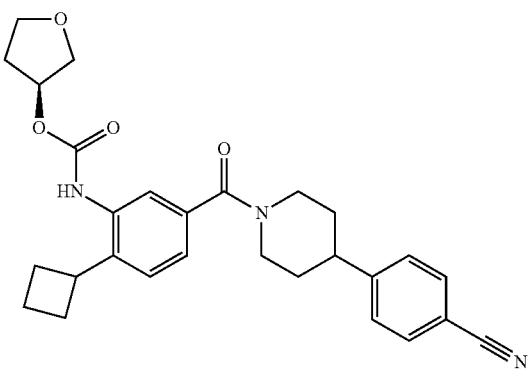 Abs | 0.070 |
| 492 | 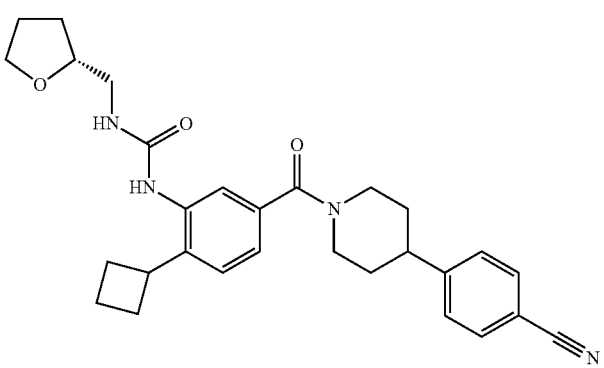 Abs | 0.030 |
| 493 | 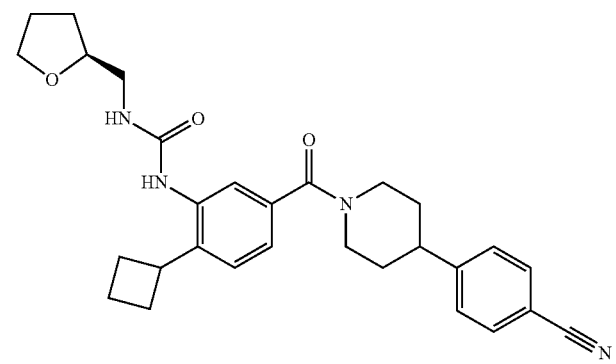 Abs | 0.090 |
| 494 | 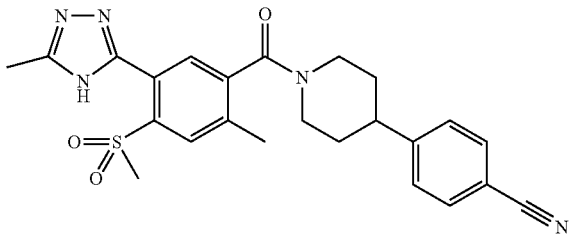 [SMILES: Cc1nnc(-c2cc(C(=O)N3CCC(c4ccc(C#N)cc4)CC3)c(C)cc2S(C)(=O)=O)[nH]1] | >50 |

The invention claimed is:
1. A compound of Formula (IX):

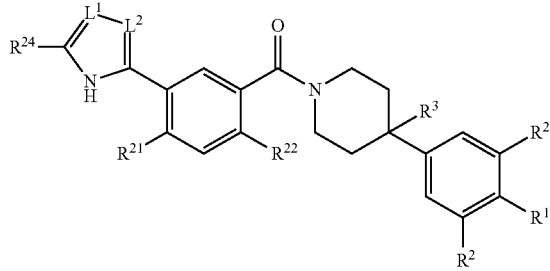

or a pharmaceutically acceptable salt thereof, wherein:
$R^1$ is H, —CN, halogen, $C_1$-$C_4$ straight or branched alkyl, —O—($C_3$-$C_5$ cycloalkyl), —O—($C_1$-$C_4$ straight or branched alkyl) wherein:
  $C_3$-$C_5$ cycloalkyl optionally includes an oxygen or nitrogen heteroatom; and
  when $R^1$ is not H, —CN or halogen, it is optionally substituted with one or more halogens;
each $R^2$ is independently hydrogen, halogen or $C_1$-$C_4$ straight or branched alkyl;
$R^3$ is H, —OH, or halogen;
$R^{21}$ is H, halogen, $C_1$-$C_4$ straight or branched alkyl, $C_3$-$C_5$ cycloalkyl wherein the $C_3$-$C_5$ cycloalkyl optionally includes an oxygen or nitrogen heteroatom;
$R^{22}$ is H, halogen, or $C_1$-$C_2$ alkyl;
$R^{24}$ is H, $C_1$-$C_4$ straight or branched alkyl, —($C_1$-$C_4$ alkyl)$_t$-OH,
  —($C_1$-$C_4$ alkyl)$_t$-O$_t$—($C_3$-$C_5$ cycloalkyl), or
  —($C_1$-$C_4$ alkyl)$_t$-O—($C_1$-$C_4$ straight or branched alkyl)
  wherein:
    t is 0 or 1;
    the $C_3$-$C_5$ cycloalkyl optionally includes an oxygen or nitrogen heteroatom;
$L^1$ is $CR^{23}$ and $L^2$ is N, or
$L^1$ is N and $L^2$ is CH; and
$R^{23}$ is H or $C_1$-$C_4$ straight or branched alkyl.
2. The compound of claim 1, wherein $R^{24}$ is $C_1$-$C_4$ straight or branched alkyl or —($C_1$-$C_4$ alkyl)$_t$-O—($C_1$-$C_4$ straight or branched alkyl) wherein t is 0 or 1.
3. The compound of claim 1, wherein $R^{21}$ is halogen, $C_1$-$C_4$ straight or branched alkyl or $C_3$-$C_5$ cycloalkyl wherein the $C_3$-$C_5$ cycloalkyl optionally includes an oxygen or nitrogen heteroatom.
4. The compound of claim 1, wherein $R^3$ is H or halogen.
5. The compound of claim 1, wherein $R^1$ is halogen, —CN or $C_1$-$C_2$ haloalkyl.
6. The compound of claim 1, wherein $R^{22}$ is H, methyl, or ethyl.
7. The compound of claim 1, wherein $R^1$ is —CN, each $R^2$ is H, $R^3$ is H or F, $R^{21}$ is $C_3$-$C_4$ cycloalkyl, $R^{22}$ is methyl, $L^1$ is $CR^{23}$, $L^2$ is N, and $R^{24}$ is methyl, ethyl, hydroxymethyl, methoxymethyl, or 2-methoxyethyl.
8. The compound of claim 1, wherein $R^1$ is —CN, each $R^2$ is H, $R^3$ is H or F, $R^{21}$ is $C_3$-$C_4$ cycloalkyl, $R^{22}$ is methyl, $L^1$ is N, $L^2$ is CH, and $R^{24}$ is methyl, ethyl, hydroxymethyl, methoxymethyl, or 2-methoxyethyl.
9. The compound of claim 1, having the following formula:

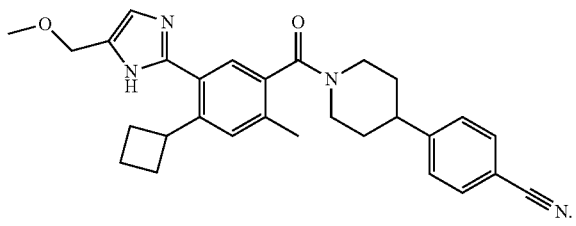 [SMILES: COCc1cnc(-c2cc(C(=O)N3CCC(c4ccc(C#N)cc4)CC3)c(C)cc2C2CCC2)[nH]1]

10. A pharmaceutical composition comprising the compound of claim 1 and a pharmaceutically acceptable carrier, excipient, or diluent.

* * * * *

UNITED STATES PATENT AND TRADEMARK OFFICE
CERTIFICATE OF CORRECTION

PATENT NO. : 9,809,591 B2  
APPLICATION NO. : 14/874961  
DATED : November 7, 2017  
INVENTOR(S) : Johan D. Oslob et al.

Page 1 of 1

It is certified that error appears in the above-identified patent and that said Letters Patent is hereby corrected as shown below:

In the Claims

At Column 737, Claim number 1, Line number 20:
"-O-($C_3$-$C_5$ cycloalkyl), -O-($C_1$-$C_4$ straight or"
Should read:
-- -O-($C_3$-$C_5$ cycloalkyl), or -O-($C_1$-$C_4$ straight or --

At Column 737, Claim number 1, Line number 29:
"$R^{21}$ is H, halogen, $C_1$-$C_4$ straight or branched alkyl, $C_3$-$C_5$"
Should read:
-- $R^{21}$ is H, halogen, $C_1$-$C_4$ straight or branched alkyl, or $C_3$-$C_5$ --

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*